US009512139B2

(12) United States Patent
Obrecht et al.

(10) Patent No.: US 9,512,139 B2

(45) Date of Patent: Dec. 6, 2016

(54) CONFORMATIONALLY CONSTRAINED, FULLY SYNTHETIC MACROCYCLIC COMPOUNDS

(75) Inventors: Daniel Obrecht, Bättwil (CH); Philipp Ermert, Allschwil (CH); Said Oumouch, Mulhouse (FR); Franck Lach, Les Grandes Loges (FR); Anatol Luther, Binzen (DE); Karsten Marx, Basel (CH); Kerstin Möhle, Wettswil (CH)

(73) Assignee: POLYPHOR AG, Allschwil (CH)

( * ) Notice: Subject to any disclaimer, the term of this patent is extended or adjusted under 35 U.S.C. 154(b) by 137 days.

(21) Appl. No.: 13/508,531

(22) PCT Filed: Aug. 3, 2010

(86) PCT No.: PCT/CH2010/000191

§ 371 (c)(1),
(2), (4) Date: Jul. 11, 2012

(87) PCT Pub. No.: WO2011/014973

PCT Pub. Date: Feb. 10, 2011

(65) Prior Publication Data

US 2012/0270881 A1 Oct. 25, 2012

(30) Foreign Application Priority Data

Aug. 5, 2009 (WO) ................ PCT/EP2009/060168

(51) Int. Cl.

| | |
|---|---|
| *C07D 273/02* | (2006.01) |
| *A61K 31/407* | (2006.01) |
| *C07D 273/00* | (2006.01) |
| *A61K 31/4985* | (2006.01) |
| *A61K 31/437* | (2006.01) |
| *A61P 1/00* | (2006.01) |
| *A61P 25/06* | (2006.01) |
| *A61P 25/18* | (2006.01) |
| *A61P 25/24* | (2006.01) |
| *A61P 25/28* | (2006.01) |
| *A61P 27/02* | (2006.01) |
| *A61P 29/00* | (2006.01) |
| *A61P 35/00* | (2006.01) |
| *A61P 19/00* | (2006.01) |
| *C07D 498/04* | (2006.01) |
| *C07D 497/18* | (2006.01) |
| *C07D 498/18* | (2006.01) |

(52) U.S. Cl.

CPC .......... *C07D 498/04* (2013.01); *C07D 497/18* (2013.01); *C07D 498/18* (2013.01)

(58) Field of Classification Search

None

See application file for complete search history.

(56) References Cited

PUBLICATIONS

Lutz et al. In Tetrahedron Letters (2008), 49(34), 5003-5005.*
Wessjohann et al. In Mol. Divers. 2005, 9, 171-186.*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Chen et al. in J. Med. Chem. 2006, 49, 995-1005.*

* cited by examiner

*Primary Examiner* — Dennis Heyer

(74) *Attorney, Agent, or Firm* — Birch, Stewart, Kolasch & Birch, LLP

(57) ABSTRACT

Conformationally restricted, spatially defined 12-30 membered macrocyclic ring systems of formulae Ia and Ib are constituted by three distinct molecular parts: Template A, conformation Modulator B and Bridge C. These macrocycles Ia and Ib are readily manufactured by parallel synthesis or combinatorial chemistry in solution or on solid phase. They are designed to interact with a variety of specific biological target classes, examples being the agonistic or antagonistic activity on G-protein coupled receptors (GPCRs), ion channels and signal transduction pathways. In particular, these macrocycles act as antagonists of the motilin receptor, the FP receptor and the purinergic receptors $P2Y_1$, as modulators of the serotonin receptor of subtype $5\text{-}HT_{2B}$, as blockers of the voltage-gated potassium channel $K_v1.3$ and as inhibitors of the β-catenin-dependent "canonical" Wnt pathway. Thus they are showing great potential as medicaments for a variety of diseases.

Ia

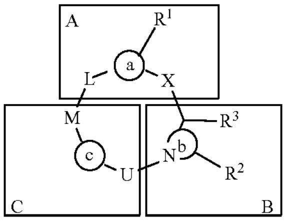

Ib

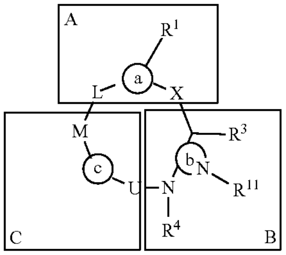

11 Claims, 2 Drawing Sheets

Figure 1: Macrocycles of Type Ia/Ib
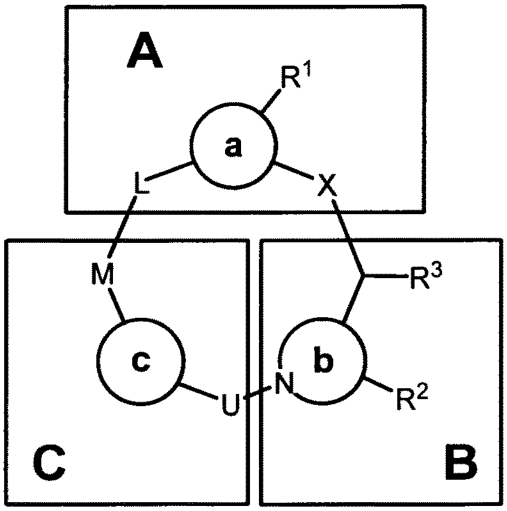
Ia
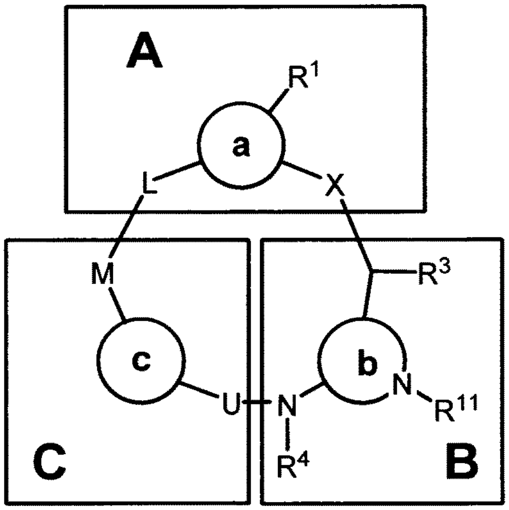
Ib

Figure 2: building block A "Template":
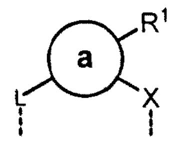
building block B "Modulator":
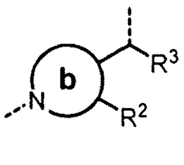
or
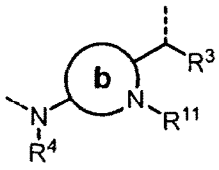
building block C "Bridge":
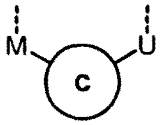
respectively
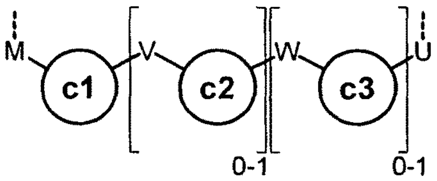
Figure 3: Connectivities of macrocycle Ia/Ib
M =
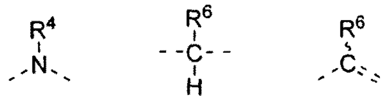
M—L =
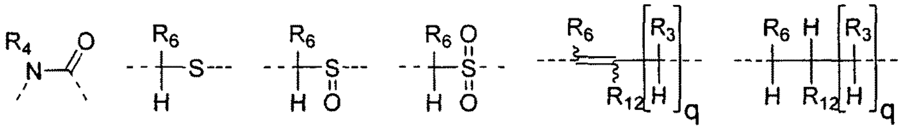
U =
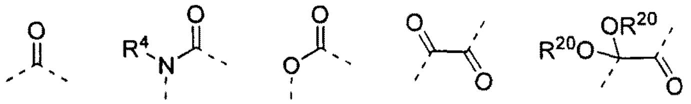
V, W =
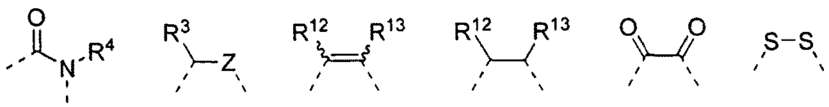
X =
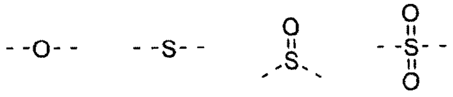

CONFORMATIONALLY CONSTRAINED, FULLY SYNTHETIC MACROCYCLIC COMPOUNDS

Macrocyclic natural and synthetic products have played a crucial role in the development of new drugs, especially as anti-infectives (F. von Nussbaum, M. Brands, B. Hinzen, S. Weigand, D. Häbich, *Angew. Chem. Int. Ed. Engl.* 2006, 45, 5072-5129; D. Obrecht, J. A. Robinson, F. Bernardini, C. Bisang, S. J. DeMarco, K. Moehle, F. O. Gombert, *Curr. Med. Chem.* 2009, 16, 42-65), as anti-cancer drugs and in other therapeutic areas (C. E. Ballard, H. Yu, B. Wang, *Curr. Med. Chem.* 2002, 9, 471-498; F. Sarabia, S. Chammaa, A. S. Ruiz, L. M. Ortiz, F. J. Herrera, *Curr. Med. Chem.* 2004, 11, 1309-1332). They often display remarkable biological activities, and many macrocycles or their derivatives have been successfully developed into drugs (L. A. Wessjohann, E. Ruijter, D. Garcia-Rivera, W. Brandt, *Mol. Divers.* 2005, 9, 171-186; D. J. Newman, G. M. Gragg, K. M. Snader, *J. Nat. Prod.* 2003, 66, 1022-1037). The chemical diversity of macrocyclic natural products is immense and provides a tremendous source of inspiration for drug design.

Macrocyclic natural and synthetic products generally exhibit semi-rigid backbone conformations placing appended substituents into well-defined spatial orientation. Certain ring sizes are preferred (L. A. Wessjohann, E. Ruijter, D. Garcia-Rivera, W. Brandt, *Mol. Divers.* 2005, 9, 171-186), e.g. 16-membered rings are frequently found in oxygen-containing macrocycles, such as polyketides (M. Q. Zhang, B. Wilkinson, *Curr. Opin. Biotechnol.* 2007, 18, 478-488). It is hypothesized that semi-rigid scaffolds possess some of the favorable binding properties of rigid molecules (entropy), yet still retaining enough flexibility to adapt suitable conformations in the binding event (induced fit).

Macrocyclic natural and synthetic products are generally classified according to the chemical nature of the backbone, e.g. cyclic peptides (Y. Hamady, T. Shioiri, *Chem. Rev.* 2005, 105, 4441-4482; N.-H. Tan, J. Zhou, *Chem. Rev.* 2006, 106, 840-895); cyclic depsipeptides (F. Sarabia, S. Chammaa, A. S. Ruiz, L. M. Ortiz, F. J. Herrera, *Curr. Med. Chem.* 2004, 11, 1309-1332); macrocyclic lactones (macrolactones) and macrolides; macrocyclic lactams (macrolactams), macrocyclic amines, macrocyclic ethers, macrocyclic ureas and urethanes, and others. The conformational, physico-chemical, pharmacological and pharmacodynamic properties of macrocyclic natural and synthetic compounds depend largely on the ring size, the chemical nature of the backbone, and of appended groups (L. A. Wessjohann, E. Ruijter, D. Garcia-Rivera, W. Brandt, *Mol. Divers.* 2005, 9, 171-186). By modifying these three parameters nature has created a virtually unlimited repertoire of molecular diversity. Despite their undisputed interesting biological properties, many natural products show limitations for drug development, such as:

- High structural complexity
- Low metabolic stability
- Low oral bioavailability
- Low membrane permeability; i.e. intracellular targets not amenable
- Low tissue penetration
- Short half-life
- Chemical synthesis often complex and lengthy
- Often accessible only by fermentation or recombinant methods
- High production costs
- Complex quality control and development processes.

BRIEF DESCRIPTION OF THE DRAWINGS

FIG. 1 depicts macrocyclic natural product-like molecules of Type Ia/Ib, which can be synthesized in a modular approach by connecting suitably protected building blocks A, B, and C to a linear precursor followed by subsequent cyclization.

FIG. 2 shows building blocks A, B and C. Building block A serves as conformation-inducing template ("Template") and is based on appropriately substituted and protected divalent phenol or thiophenol derivatives. Building block B serves as a conformational modulator ("Modulator") by influencing the conformation of the macrocycle, e.g. through cis/trans-isomerization of amides. Building block C connects building blocks A and B ("Bridge"), which can be constituted by one to three appropriately and independently substituted subunits c1, c2 and c3 derived from suitably substituted and protected precursors, most often from, but not limited to, appropriately substituted and protected amino acid or amine derivatives.

FIG. 3 shows the connectivities of macrocycle Ia/Ib.

The present invention describes now novel, fully synthetic, macrocyclic natural product-like molecules of type Ia/Ib (FIG. 1), which can be synthesized in a modular approach by connecting suitably protected building blocks A, B, and C to a linear precursor followed by subsequent cyclization.

Building blocks A (FIG. 2) serve as conformation-inducing templates ("Template") and are based on appropriately substituted and protected divalent phenol or thiophenol derivatives.

Building blocks B (FIG. 2) are corresponding to appropriately substituted and protected tertiary amins.

Building blocks B serve as a conformational modulator ("Modulator") by influencing the conformation of the macrocycle, e.g. through cis/trans-isomerization of amides.

In macrocycles of type Ia/Ib the building blocks A and B are connected via the "Bridge" C (FIG. 2), which can be constituted by one to three appropriately and independently substituted subunits c1, c2 and c3 derived from suitably substituted and protected precursors, most often from, but not limited to, appropriately substituted and protected amino acid or amine derivatives.

The connection of building block A to building block B occurs via an ether (X═O) or thioether (X═S) bond and to building block C via M-L as detailed below. The sulfur atom of a thioether linkage can easily and selectively be oxidized to the corresponding sulfoxide (S═O) or sulfone ($S({=}O)_2$) both of which are therefore a part of the invention (FIG. 3).

The functional moiety U connects the bridge C with the nitrogen atom of modulator B. In most cases this is realized by an amide bond (secondary or tertiary), in which case the moiety U corresponds to a carbonyl group (—C(═O)—). Alternatively, U can be defined as a carbamoyl moiety ($—NR^4—C(═O)—$) which corresponds to a urea moiety (including the N-atom of B) as functional connection between B and C. Similarly a carboxyl group (—O—C(═O)—) as U describes a carbamate linkage between B and C. In addition, U can represent an oxalyl group (—C(═O)—C(═O)—) or the corresponding acetal ($—C(—OR^{20})_2—C(═O)—$).

Importantly, in case that $R^2$ of building block B constitutes an amine substituent, two alternatives for linking building block B with building block C is possible: Either the standard link via the heterocyclic nitrogen atom or, alternatively, the exocyclic amine functionality. This is reflected either by formula Ia or formula Ib, respectively, which are both integral part of this invention sharing equally common technical features.

The connectivity between C and A is described in a generic way with the functional unit M-L, which corresponds in most cases to a secondary or tertiary amide bond (M-L=-$NR^4$—C(═O)—). Alternative connections of M-L are thioethers (—$CHR^6$—S—) and its oxidation products, i.e. sulfoxides (—$CHR^6$—S(═O)—) or sulfones (—$CHR^6$—$S(═O)_2$—), as well as olefinic moieties (—$CR^6$═$CR^{12}$—$(CHR^3)_q$—) and their reduced forms, the aliphatic groups (—$CHR^6$—$CHR^{12}$—$(CHR^3)_q$—).

As already mentioned, the bridge C in turn can be constituted by one to three appropriately and independently substituted subunits c1, c2 and c3. These subunits c1 to c3 are independently connected to each other by the generic groups V and W which can correspond to an amide bond (—C(═O)$NR^4$—), a methylene-heteroatom linkage (—$CHR^3$—Z—), an alkene[1,2]diyl moiety (—$CHR^{12}$═$CHR^{13}$—), introduced by olefin metathesis, an alkane[1,2]diyl spacer (—$CHR^{12}$—$CHR^{13}$—), accessible from the metathesis product by hydrogenation, an oxalyl group (—C(═O)—C(═O)—) or a disulfide bridge (—S—S—).

The spatial orientation of the substituents in macrocycles of type Ia/Ib is modulated by the ring size and the stereochemical connectivity within building blocks A, B and C. Both, the macrocyclic backbone and the substituents can contribute to the biological activity of compounds of type Ia/Ib.

For most examples the backbone of macrocycles Ia/Ib contains an aromatic ether/thioether linkage and one or more tertiary amide bonds; in other cases a secondary amide bond, an aliphatic ether linkage, an ethylidene or an ethylene moiety may be part of the backbone as defined above. Ether linkages in macrocyclic molecules have been shown to be beneficial by favorably influencing physico-chemical and pharmacological properties, such as solubility in aqueous solutions, metabolic stability against proteolytic degradation, cell permeability and oral absorption (K. X. Chen et al., *J. Med. Chem.* 2006, 49, 995-1005). In addition, tertiary amide containing macrocycles show increased proteolytic stability, cell permeability and oral bioavailability compared to the parent molecules with secondary amide bonds (E. Biron, J. Chatterjee, O. Ovadia, D. Langenegger, J. Brueggen, D. Hoyer, H. A. Schmid, R. Jelinek, C. Gilon, A. Hoffmann, H. Kessler, *Angew. Chem. Int. Ed.* 2008, 47, 1-6; J. Chatterjee, O. Ovadia, G. Zahn, L. Marinelli, A. Hoffmann, C. Gilon, H. Kessler, *J. Med. Chem.* 2007, 50, 5878-5881). For example, the cyclic undecapeptide cyclosporin A (INN: Ciclosporin), which is used as immunosuppressant in organ transplants, contains seven N-methylated amino acids and possesses good oral bioavailability when formulated appropriately (P. R. Beauchesne, N. S. C. Chung, K. M. Wasan, *Drug Develop. Ind. Pharm.* 2007, 33, 211-220). Peptidyl cis/trans isomerization of proline or pipecolic acid containing polypeptides and proteins is a well known process in protein folding events. In vivo, this process can be mediated by peptidyl prolyl cis/trans isomerases such as the cyclophilins, the FK506-binding proteins and the parvulins (A. Bell, P. Monaghan, A. P. Page, Int. J. Parasitol. 2006, 36, 261-276). Besides their role in protein folding and in the immune system, peptidyl prolyl cis/trans isomerases have been implicated in cell cycle control (P. E. Shaw, *EMBO Reports* 2002, 3, 521-526) and therefore constitute interesting pharmaceutical targets. FK506 and cyclosporin A which bind to the FK506-binding protein and cyclophilins, respectively, are both macrocyclic natural products, with the former one containing a pipecolic acid residue.

For many existing and emerging biological targets it is difficult to find classical small molecule hits as starting points for drug development (J. A. Robinson, S. DeMarco, F. Gombert, K. Moehle, D. Obrecht, *Drug Disc. Today* 2008, 13, 944-951). Many of these extra- and intracellular "difficult targets" involve protein-protein interactions, such as receptor tyrosine kinases, growth factor receptors, transcription modulators, chaperones, and others. For several of them macrocyclic natural and synthetic compounds have been described as good starting points for drug discovery programs (e.g. D. Obrecht, J. A. Robinson, F. Bernardini, C. Bisang, S. J. DeMarco, K. Moehle, F. O. Gombert, *Curr. Med. Chem.* 2009, 16, 42-65).

The novel and fully synthetic macrocyclic compounds of type Ia/Ib described in the embodiments of this invention combine unique features of macrocyclic natural products with beneficial physico-chemical and pharmacological properties of small molecules, like:

Natural product-like structural complexity
Good solubility
High metabolic stability
Improved oral bioavailability
Improved membrane permeability
Extra- and intracellular targets amenable
Improved tissue penetration
Small molecule-like pharmacokinetics
Modular chemical synthesis
Synthesis process well suited for parallelization
Reasonable production costs
Small molecule-like QC and development processes The main embodiment of the current invention of novel and fully synthetic macrocyclic compounds of type Ia/Ib according FIG. 1 (detailed in FIGS. 2 and 3) is defined by groups of selected building blocks A, B and C as shown in Table 1 to 3 and by the appending substituents $R^1$-$R^{53}$ as detailed below.

Building block A is a bivalent radical selected from the group of Table 1.

As mentioned hereinabove, building blocks of type A act as templates and exert an important conformational constraint on products of type Ia/Ib. The structural effects of building blocks of type A depend largely on the relative orientation of the attachment vectors of —X— and -L- and on the spatial distance between these groups. Molecular modeling, performed on the prevalent examples wherein -L- is —C(═O)—, clearly indicates that distances (typically between 2.5 and 7.5 Å) and vector arrangements for —X— and —C(═O)— in A1-A683 vary considerably, thus strongly influencing the conformations of macrocycles of type Ia/Ib.

TABLE 1

Radicals A1-A683

A1

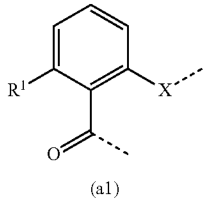

(a1)

TABLE 1-continued
Radicals A1-A683
A2
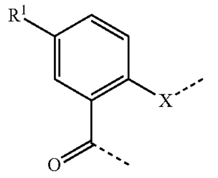
(a1)
A3
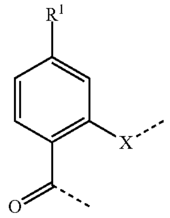
(a1)
A4
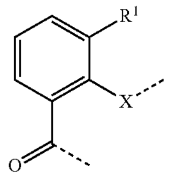
(a1)
A5
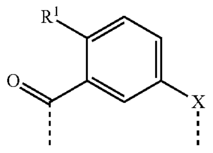
(a1)
A6
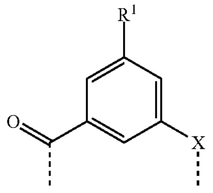
(a1)
A7
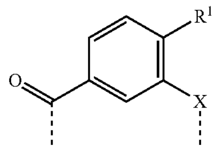
(a1)
A8
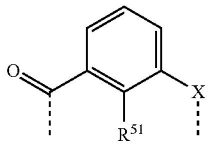
(a1)
TABLE 1-continued
Radicals A1-A683
A9
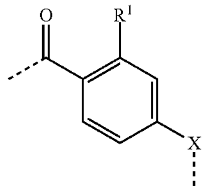
(a1)
A10
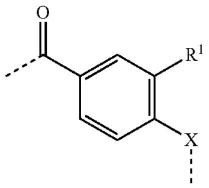
(a1)
A11
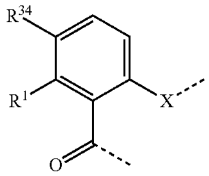
(a1)
A12
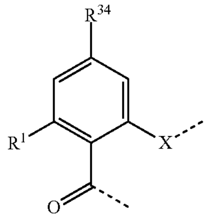
(a1)
A13
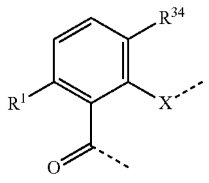
(a1)
A14
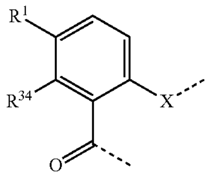
(a1)

TABLE 1-continued
Radicals A1-A683
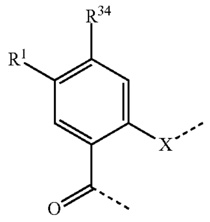
A15
(a1)
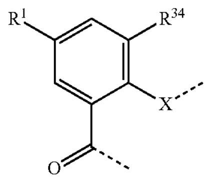
A16
(a1)
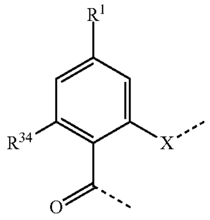
A17
(a1)
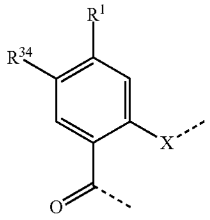
A18
(a1)
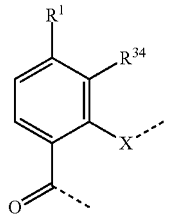
A19
(a1)
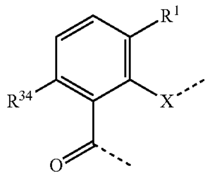
A20
(a1)
TABLE 1-continued
Radicals A1-A683
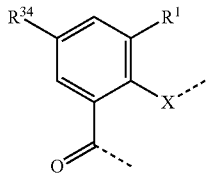
A21
(a1)
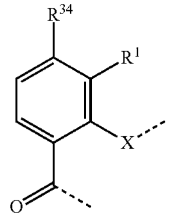
A22
(a1)
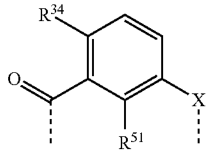
A23
(a1)
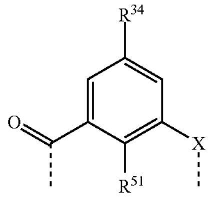
A24
(a1)
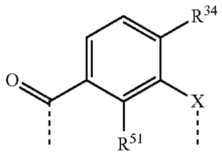
A25
(a1)
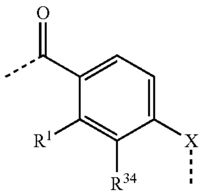
A26
(a1)

TABLE 1-continued
Radicals A1-A683
A27
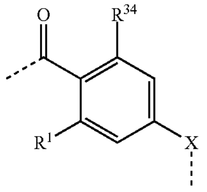
(a1)
A28
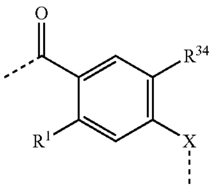
(a1)
A29
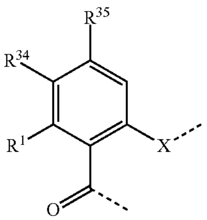
(a1)
A30
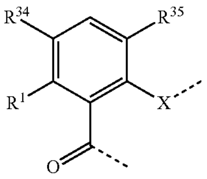
(a1)
A31
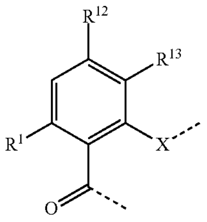
(a1)
A32
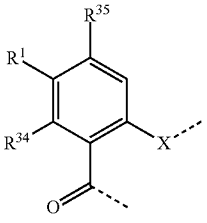
(a1)
TABLE 1-continued
Radicals A1-A683
A33
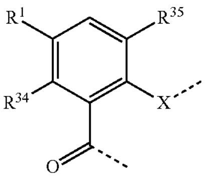
(a1)
A34
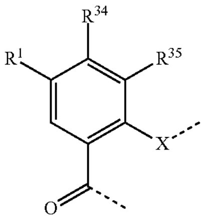
(a1)
A35
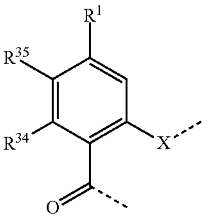
(a1)
A36
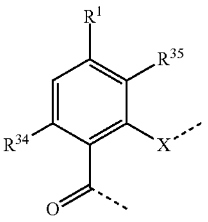
(a1)
A37
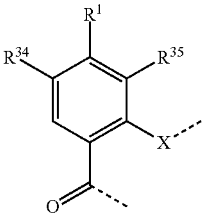
(a1)
A38
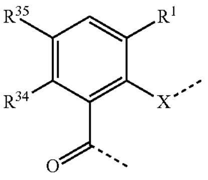
(a1)

TABLE 1-continued
Radicals A1-A683
A39
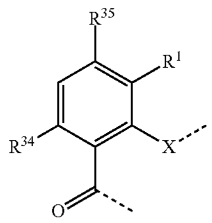
(a1)
A40
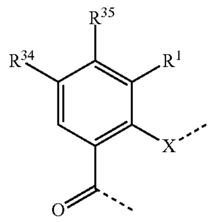
(a1)
A41
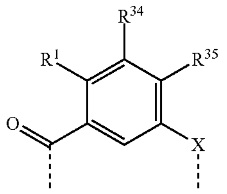
(a1)
A42
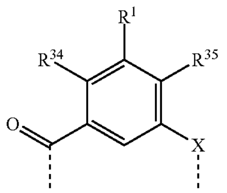
(a1)
A43
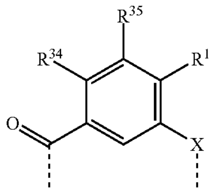
(a1)
A44
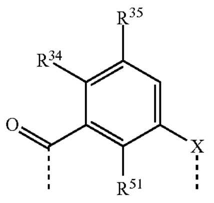
(a1)
TABLE 1-continued
Radicals A1-A683
A45
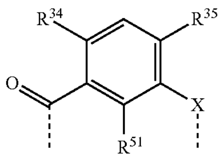
(a1)
A46
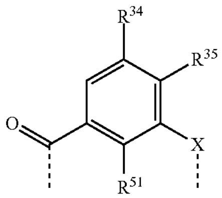
(a1)
A47
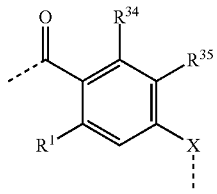
(a1)
A48
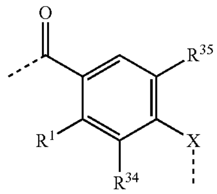
(a1)
A49
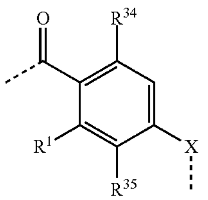
(a1)
A50
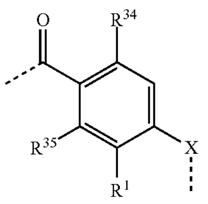
(a1)

TABLE 1-continued
Radicals A1-A683
A51
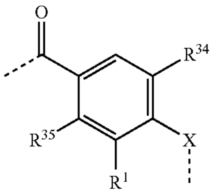
(a1)
A52
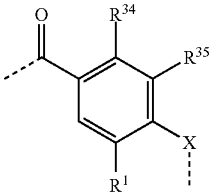
(a1)
A53
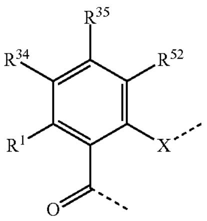
(a1)
A54
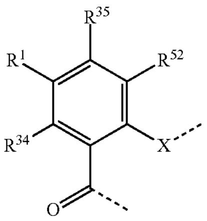
(a1)
A55
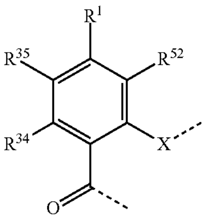
(a1)
A56
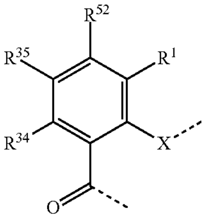
(a1)
TABLE 1-continued
Radicals A1-A683
A57
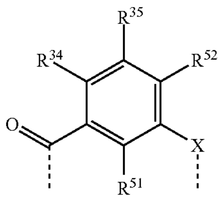
(a1)
A58
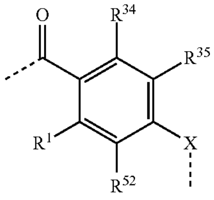
(a1)
A59
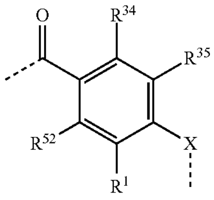
(a1)
A60
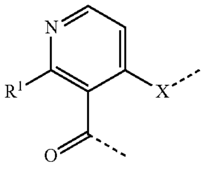
(a2)
A61
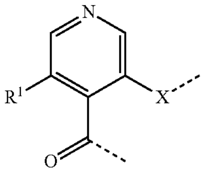
(a2)
A62
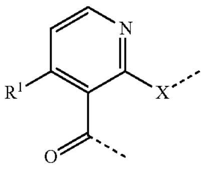
(a2)
A63
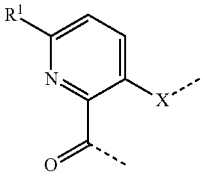
(a2)

TABLE 1-continued
Radicals A1-A683
A64
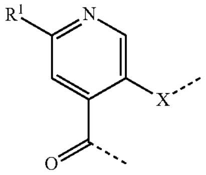
(a2)
A65
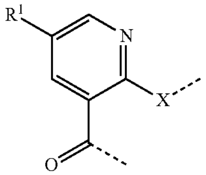
(a2)
A66
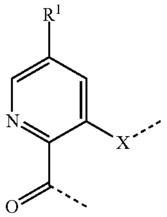
(a2)
A67
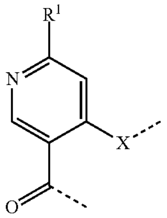
(a2)
A68
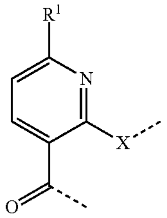
(a2)
A69
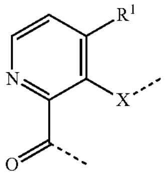
(a2)
TABLE 1-continued
Radicals A1-A683
A70
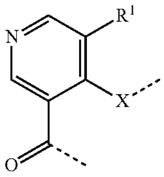
(a2)
A71
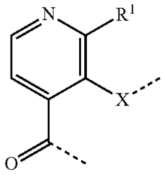
(a2)
A72
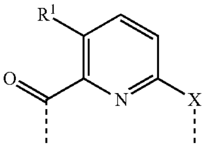
(a2)
A73
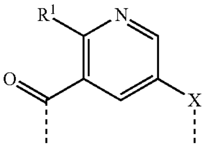
(a2)
A74
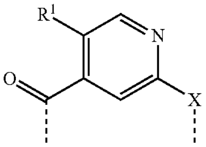
(a2)
A75
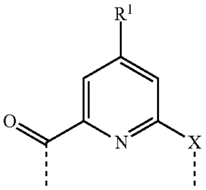
(a2)
A76
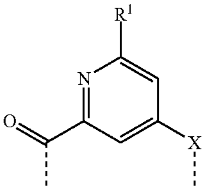
(a2)

TABLE 1-continued
| Radicals A1-A683 | |
|---|---|
| 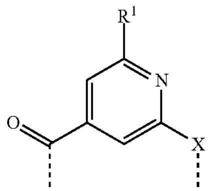 (a2) | A77 |
| 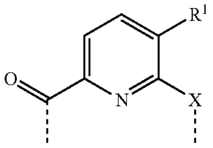 (a2) | A78 |
| 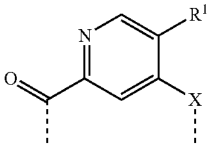 (a2) | A79 |
| 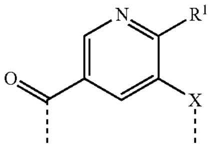 (a2) | A80 |
| 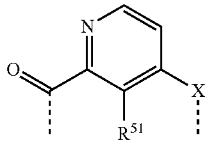 (a2) | A81 |
| 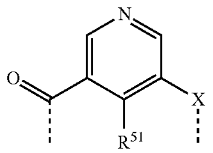 (a2) | A82 |
| 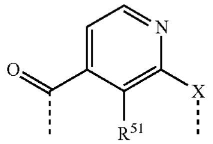 (a2) | A83 |
TABLE 1-continued
| Radicals A1-A683 | |
|---|---|
| 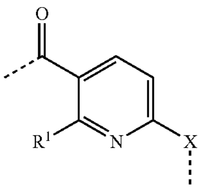 (a2) | A84 |
| 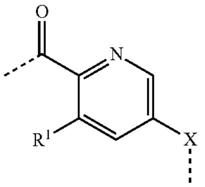 (a2) | A85 |
| 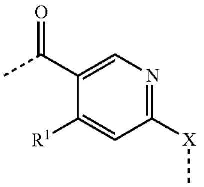 (a2) | A86 |
| 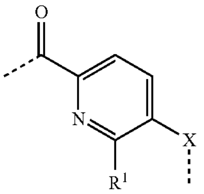 (a2) | A87 |
| 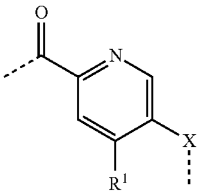 (a2) | A88 |
| 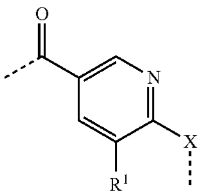 (a2) | A89 |

TABLE 1-continued
Radicals A1-A683
A90
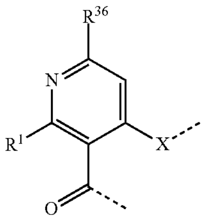
(a2)
A91
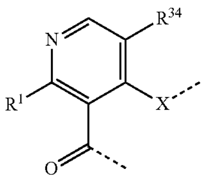
(a2)
A92
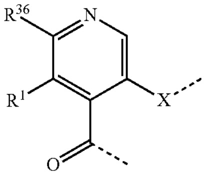
(a2)
A93
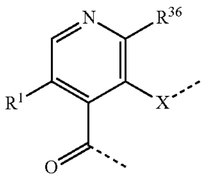
(a2)
A94
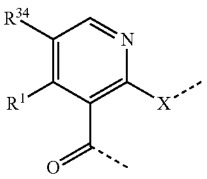
(a2)
A95
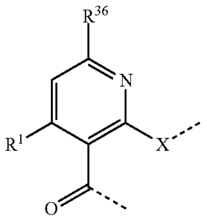
(a2)
TABLE 1-continued
Radicals A1-A683
A96
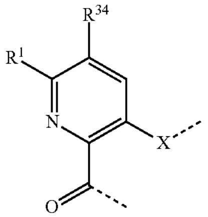
(a2)
A97
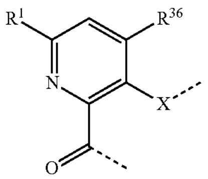
(a2)
A98
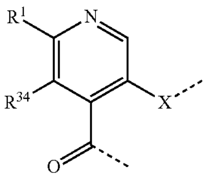
(a2)
A99
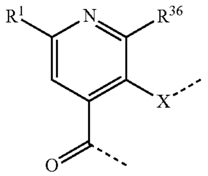
(a2)
A100
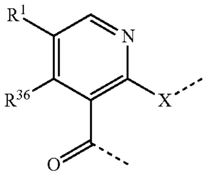
(a2)
A101
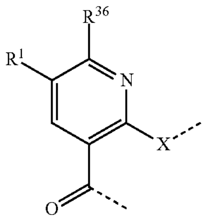
(a2)

TABLE 1-continued
Radicals A1-A683
A102
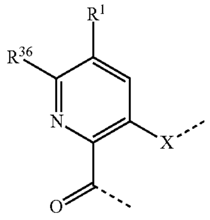
(a2)
A103
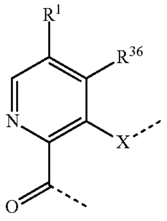
(a2)
A104
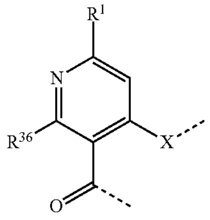
(a2)
A105
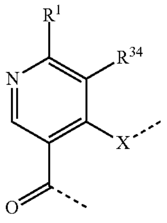
(a2)
A106
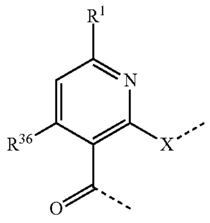
(a2)
A107
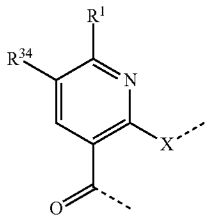
(a2)
TABLE 1-continued
Radicals A1-A683
A108
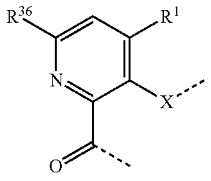
(a2)
A109
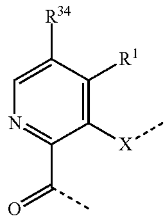
(a2)
A110
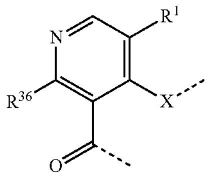
(a2)
A111
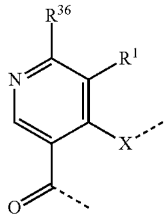
(a2)
A112
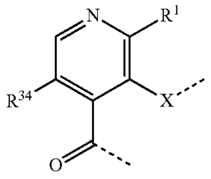
(a2)
A113
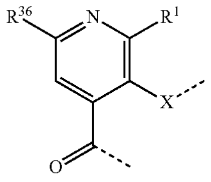
(a2)

TABLE 1-continued
Radicals A1-A683
A114
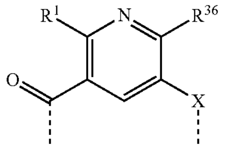
(a2)
A115
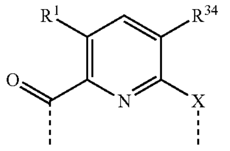
(a2)
A116
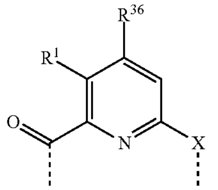
(a2)
A117
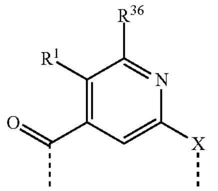
(a2)
A118
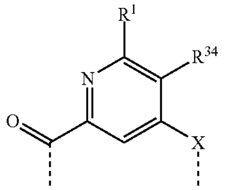
(a2)
A119
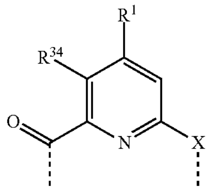
(a2)
A120
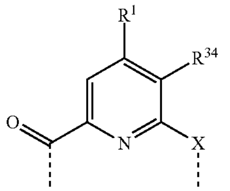
(a2)
TABLE 1-continued
Radicals A1-A683
A121
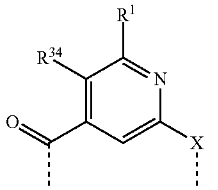
(a2)
A122
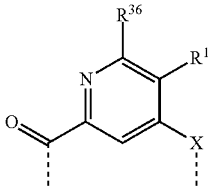
(a2)
A123
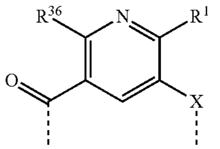
(a2)
A124
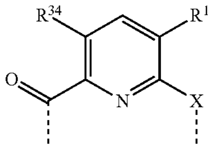
(a2)
A125
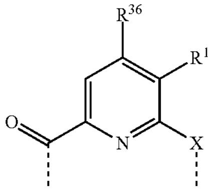
(a2)
A126
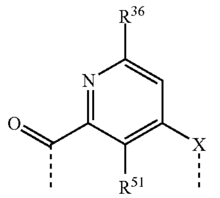
(a2)
A127
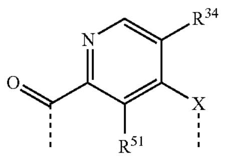
(a2)

TABLE 1-continued
| Radicals A1-A683 | |
|---|---|
| 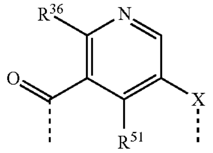 (a2) | A128 |
| 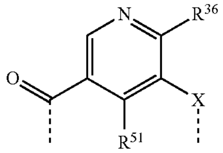 (a2) | A129 |
| 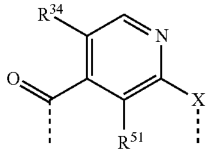 (a2) | A130 |
| 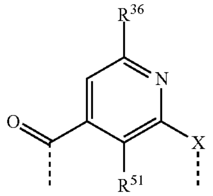 (a2) | A131 |
| 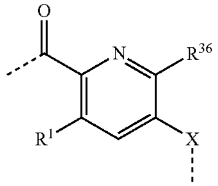 (a2) | A132 |
| 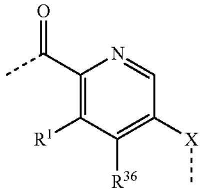 (a2) | A133 |
| 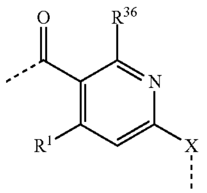 (a2) | A134 |
| 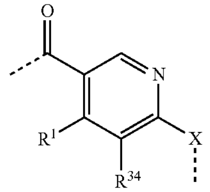 (a2) | A135 |
| 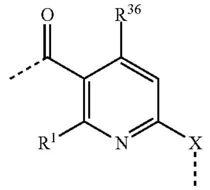 (a2) | A136 |
| 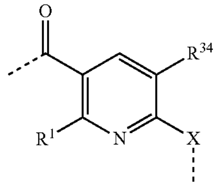 (a2) | A137 |
| 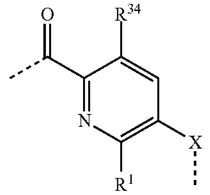 (a2) | A138 |
| 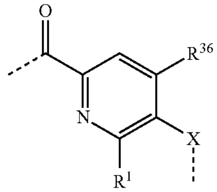 (a2) | A139 |
| 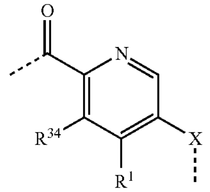 (a2) | A140 |

TABLE 1-continued
Radicals A1-A683
A141
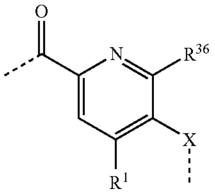
(a2)
A142
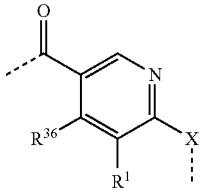
(a2)
A143
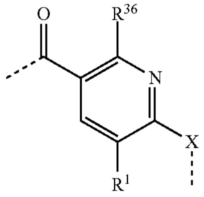
(a2)
A144
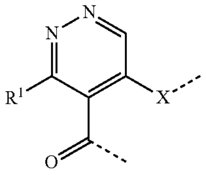
(a3)
A145
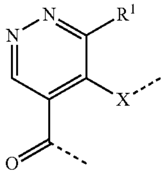
(a3)
A146
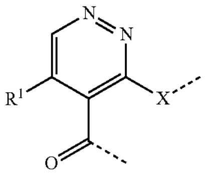
(a3)
TABLE 1-continued
Radicals A1-A683
A147
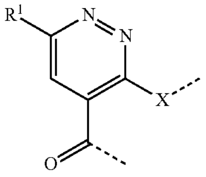
(a3)
A148
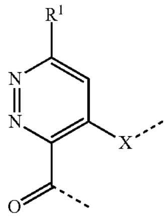
(a3)
A149
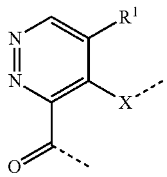
(a3)
A150
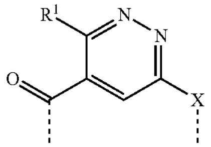
(a3)
A151
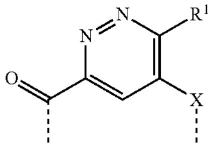
(a3)
A152
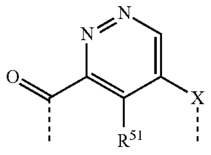
(a3)
A153
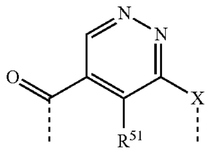
(a3)

TABLE 1-continued
Radicals A1-A683
A154
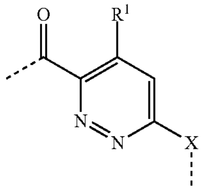
(a3)
A155
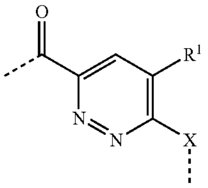
(a3)
A156
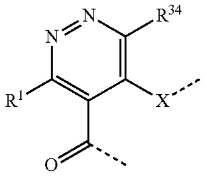
(a3)
A157
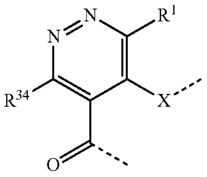
(a3)
A158
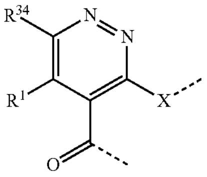
(a3)
A159
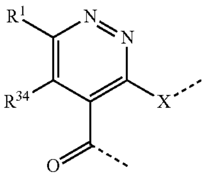
(a3)
TABLE 1-continued
Radicals A1-A683
A160
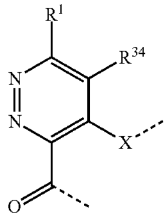
(a3)
A161
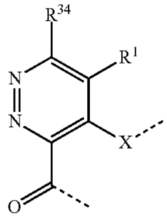
(a3)
A162
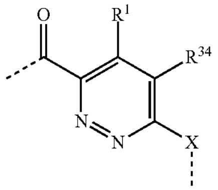
(a3)
A163
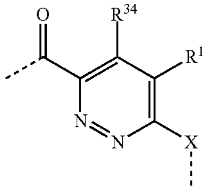
(a3)
A164
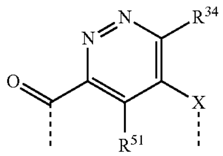
(a3)
A165
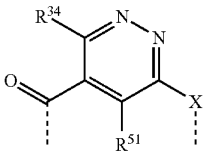
(a3)

TABLE 1-continued
| Radicals A1-A683 | |
|---|---|
| 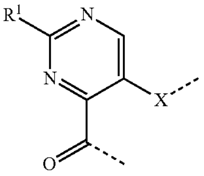<br>(a4) | A166 |
| 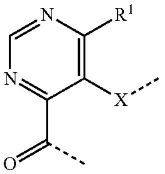<br>(a4) | A167 |
| 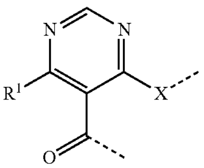<br>(a4) | A168 |
| 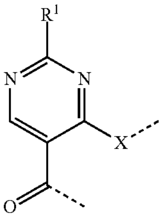<br>(a4) | A169 |
| 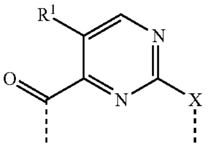<br>(a4) | A170 |
| 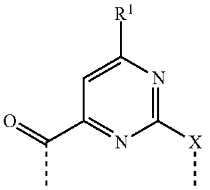<br>(a4) | A171 |
| 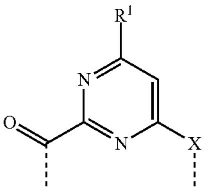<br>(a4) | A172 |
| 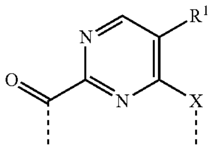<br>(a4) | A173 |
| 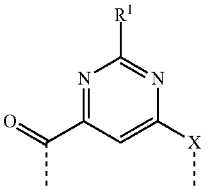<br>(a4) | A174 |
| 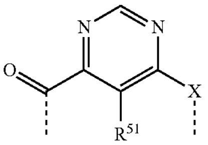<br>(a4) | A175 |
| 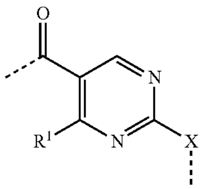<br>(a4) | A176 |
| 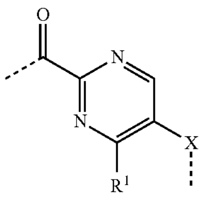<br>(a4) | A177 |
| 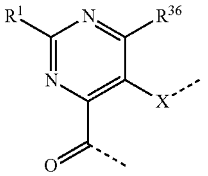<br>(a4) | A178 |

TABLE 1-continued
Radicals A1-A683
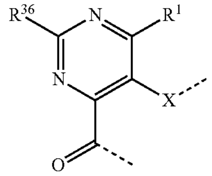
A179
(a4)
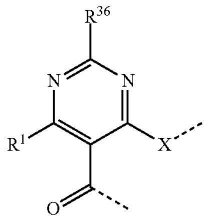
A180
(a4)
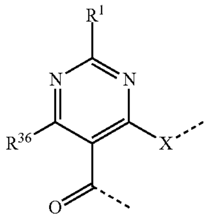
A181
(a4)
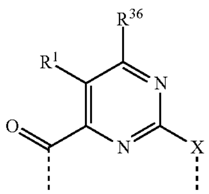
A182
(a4)
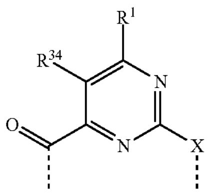
A183
(a4)
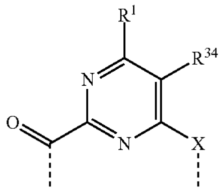
A184
(a4)
TABLE 1-continued
Radicals A1-A683
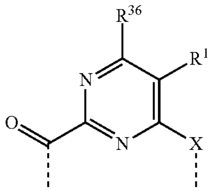
A185
(a4)
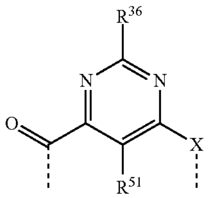
A186
(a4)
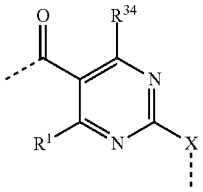
A187
(a4)
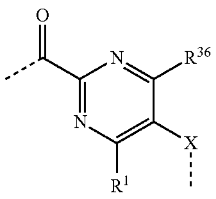
A188
(a4)
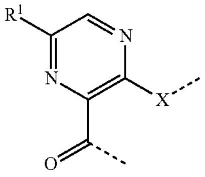
A189
(a5)
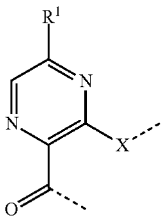
A190
(a5)

TABLE 1-continued
Radicals A1-A683
A191
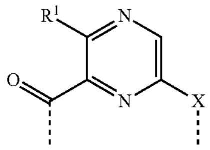
(a5)
A192
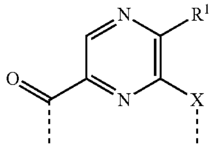
(a5)
A193
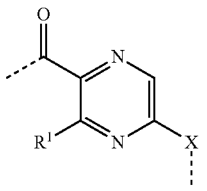
(a5)
A194
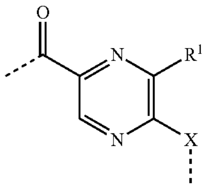
(a5)
A195
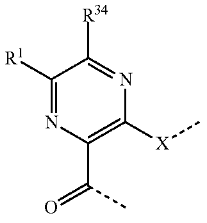
(a5)
A196
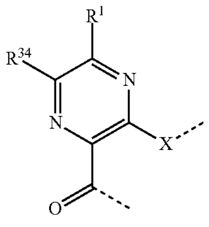
(a5)
A197
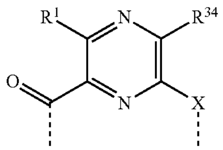
(a5)
TABLE 1-continued
Radicals A1-A683
A198
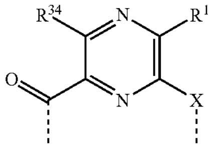
(a5)
A199
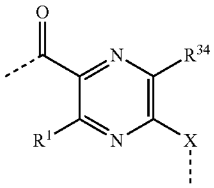
(a5)
A200
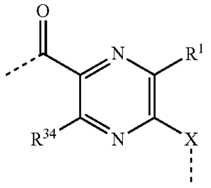
(a5)
A201
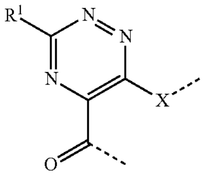
(a6)
A202
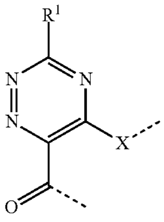
(a6)
A203
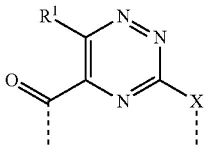
(a6)
A204
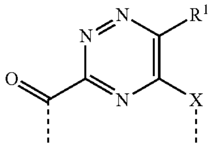
(a6)

TABLE 1-continued
Radicals A1-A683
A205
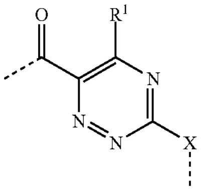
(a6)
A206
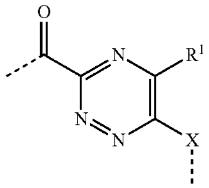
(a6)
A207
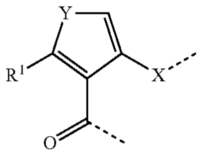
(a7)
A208
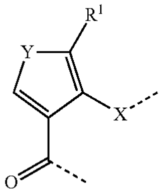
(a7)
A209
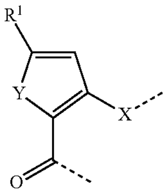
(a7)
A210
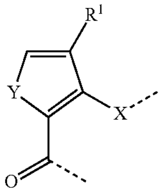
(a7)
A211
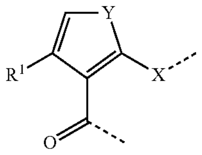
(a7)
TABLE 1-continued
Radicals A1-A683
A212
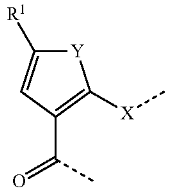
(a7)
A213
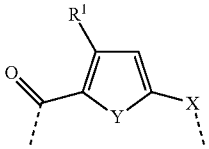
(a7)
A214
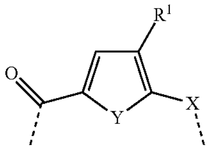
(a7)
A215
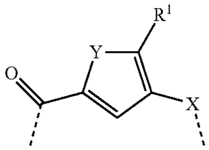
(a7)
A216
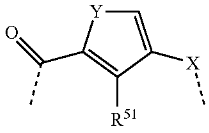
(a7)
A217
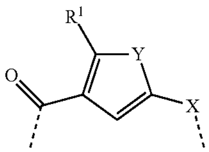
(a7)
A218
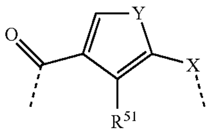
(a7)

TABLE 1-continued
Radicals A1-A683
A219
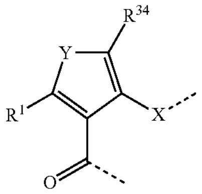
(a7)
A220
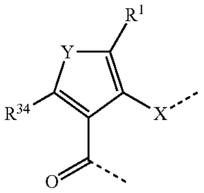
(a7)
A221
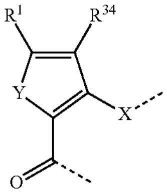
(a7)
A222
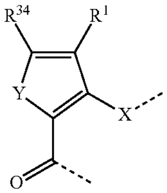
(a7)
A223
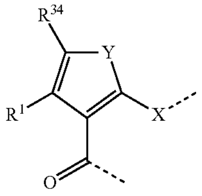
(a7)
A224
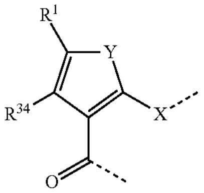
(a7)
TABLE 1-continued
Radicals A1-A683
A225
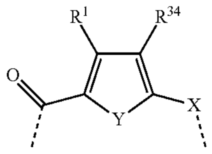
(a7)
A226
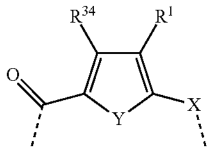
(a7)
A227
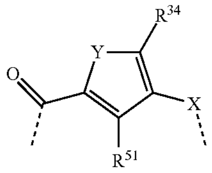
(a7)
A228
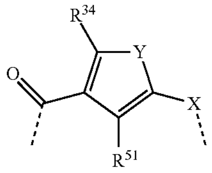
(a7)
A229
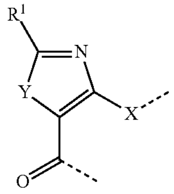
(a8)
A230
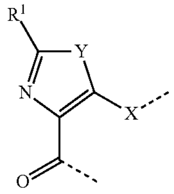
(a8)
A231
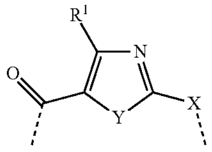
(a8)

TABLE 1-continued
| Radicals A1-A683 |
|---|
A232
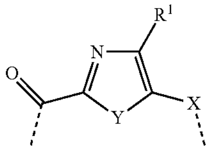
(a8)
A233
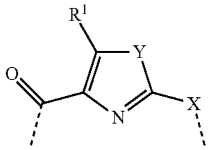
(a8)
A234
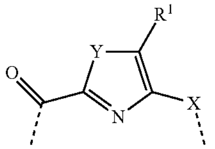
(a8)
A235
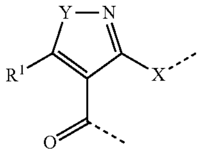
(a8)
A236
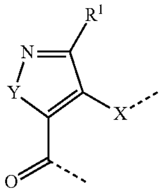
(a9)
A237
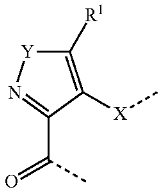
(a9)
A238
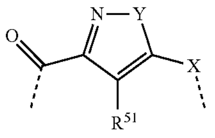
(a9)
TABLE 1-continued
| Radicals A1-A683 |
|---|
A239
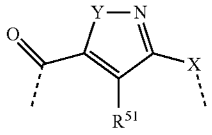
(a9)
A240
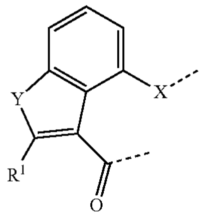
(a10)
A241
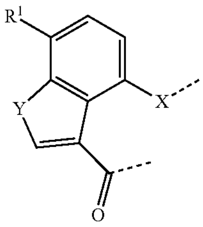
(a10)
A242
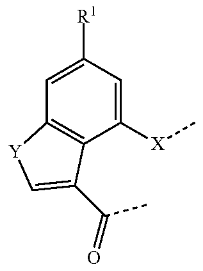
(a10)
A243
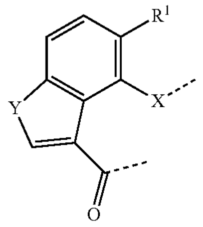
(a10)
A244
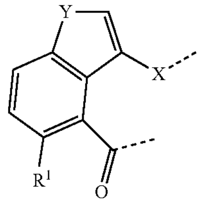
(a10)

TABLE 1-continued
Radicals A1-A683
A245
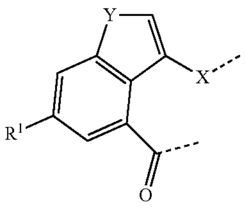
(a10)
A246
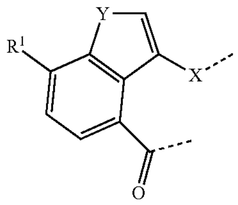
(a10)
A247
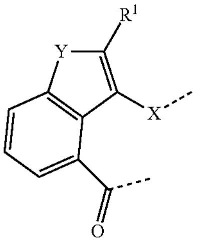
(a10)
A248
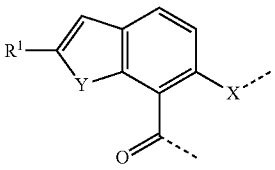
(a10)
A249
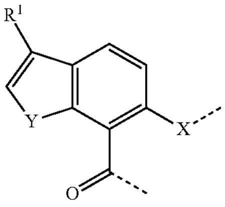
(a10)
A250
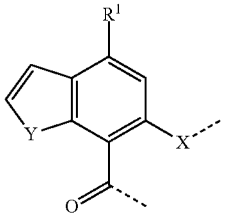
(a10)
TABLE 1-continued
Radicals A1-A683
A251
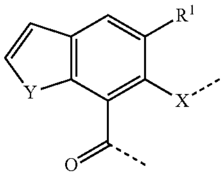
(a10)
A252
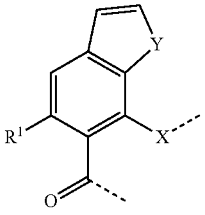
(a10)
A253
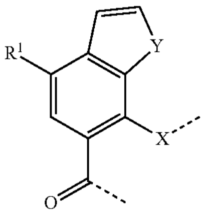
(a10)
A254
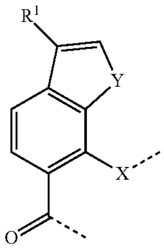
(a10)
A255
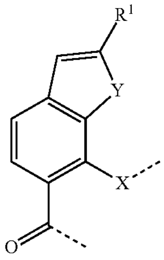
(a10)
A256
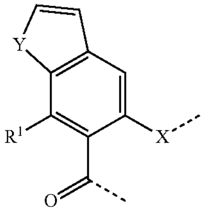
(a10)

TABLE 1-continued
Radicals A1-A683
A257
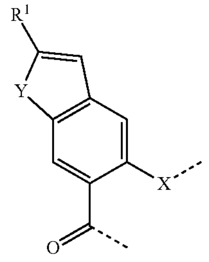
(a10)
A258
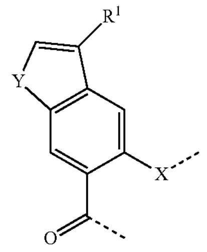
(a10)
A259
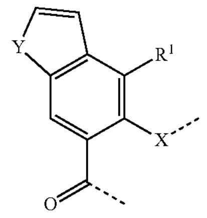
(a10)
A260
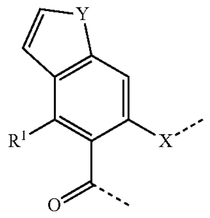
(a10)
A261
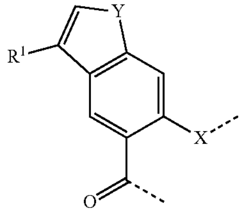
(a10)
TABLE 1-continued
Radicals A1-A683
A262
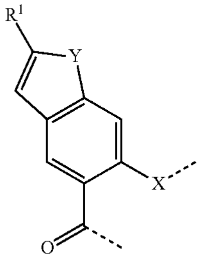
(a10)
A263
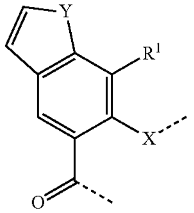
(a10)
A264
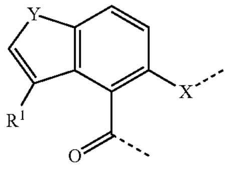
(a10)
A265
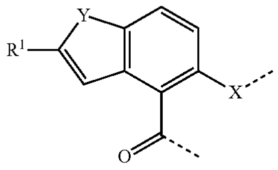
(a10)
A266
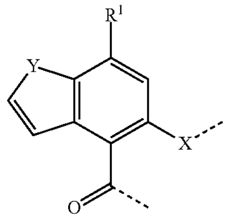
(a10)
A267
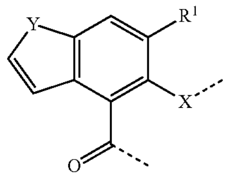
(a10)

TABLE 1-continued
Radicals A1-A683
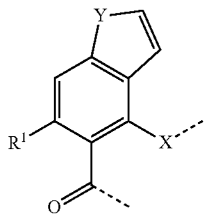
A268
(a10)
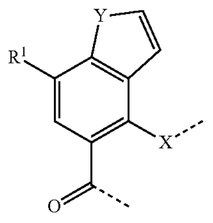
A269
(a10)
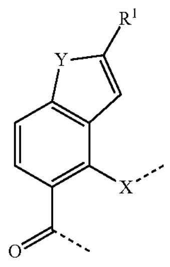
A270
(a10)
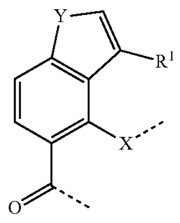
A271
(a10)
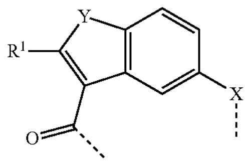
A272
(a10)
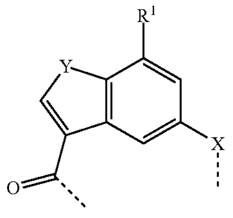
A273
(a10)
TABLE 1-continued
Radicals A1-A683
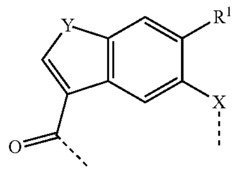
A274
(a10)
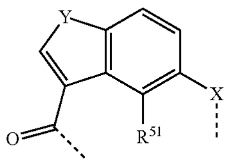
A275
(a10)
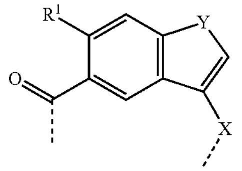
A276
(a10)
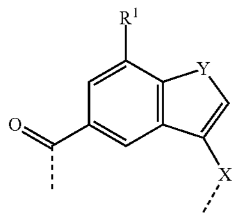
A277
(a10)
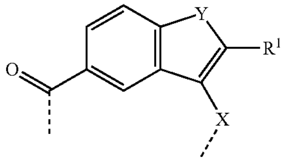
A278
(a10)
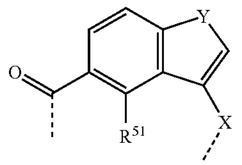
A279
(a10)

TABLE 1-continued
| Radicals A1-A683 | |
|---|---|
| 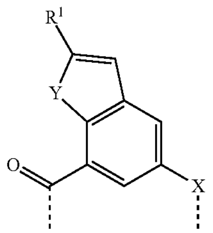 (a10) | A280 |
| 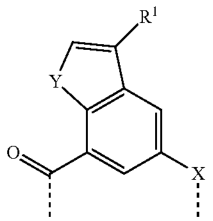 (a10) | A281 |
| 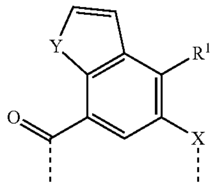 (a10) | A282 |
| 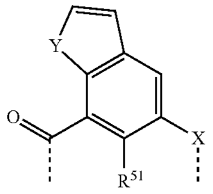 (a10) | A283 |
| 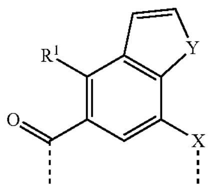 (a10) | A284 |
| 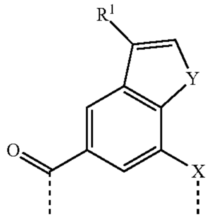 (a10) | A285 |
TABLE 1-continued
| Radicals A1-A683 | |
|---|---|
| 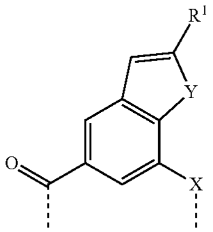 (a10) | A286 |
| 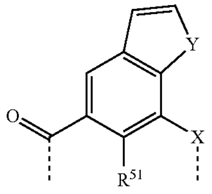 (a10) | A287 |
| 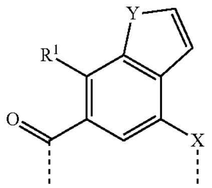 (a10) | A288 |
| 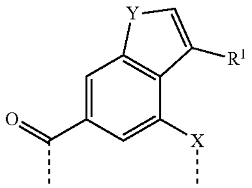 (a10) | A289 |
| 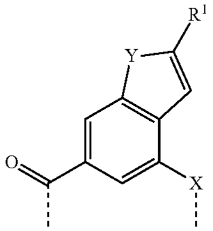 (a10) | A290 |
| 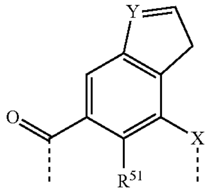 (a10) | A291 |

TABLE 1-continued
| Radicals A1-A683 | |
|---|---|
| 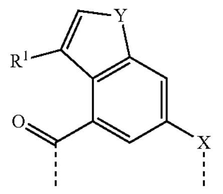 (a10) | A292 |
| 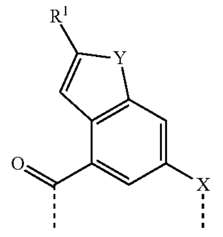 (a10) | A293 |
| 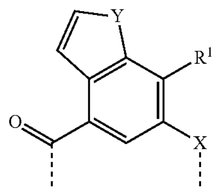 (a10) | A294 |
| 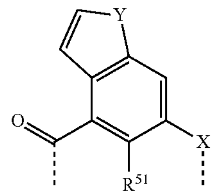 (a10) | A295 |
| 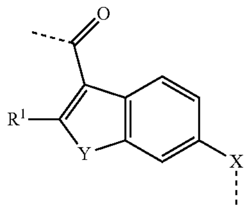 (a10) | A296 |
| 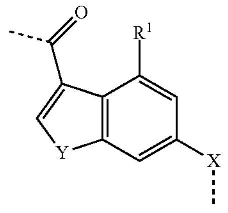 (a10) | A297 |
TABLE 1-continued
| Radicals A1-A683 | |
|---|---|
| 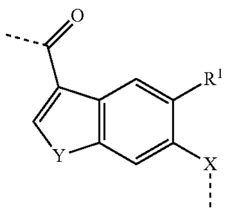 (a10) | A298 |
| 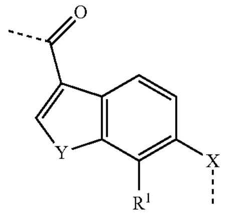 (a10) | A299 |
| 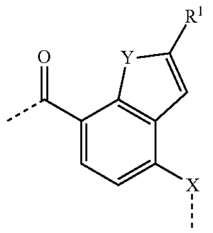 (a10) | A300 |
| 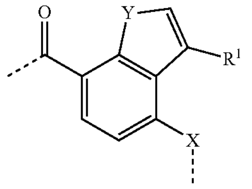 (a10) | A301 |
| 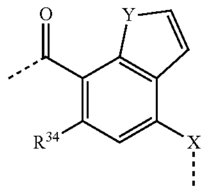 (a10) | A302 |
| 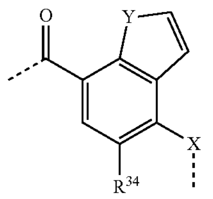 (a10) | A303 |

TABLE 1-continued
| Radicals A1-A683 | |
|---|---|
| 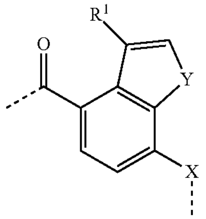 (a10) | A304 |
| 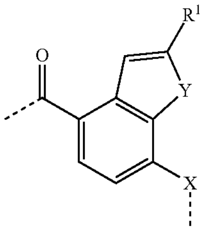 (a10) | A305 |
| 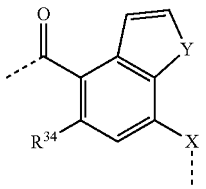 (a10) | A306 |
| 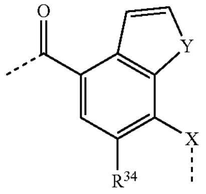 (a10) | A307 |
| 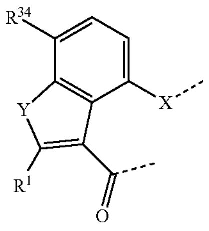 (a10) | A308 |
| 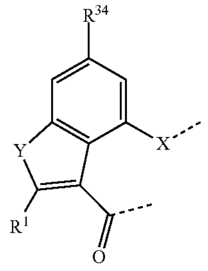 (a10) | A309 |
TABLE 1-continued
| Radicals A1-A683 | |
|---|---|
| 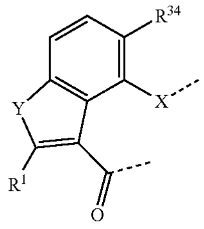 (a10) | A310 |
| 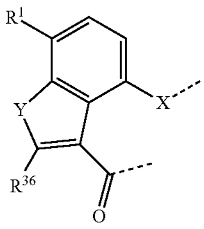 (a10) | A311 |
| 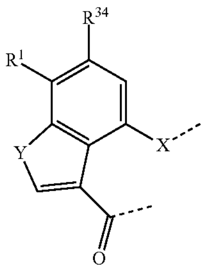 (a10) | A312 |
| 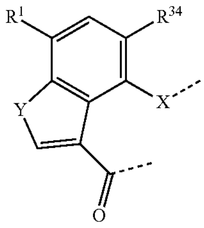 (a10) | A313 |
| 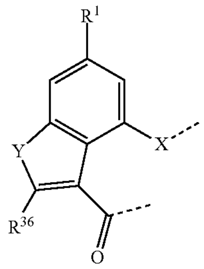 (a10) | A314 |

TABLE 1-continued
Radicals A1-A683
A315
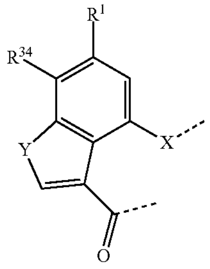
(a10)
A316
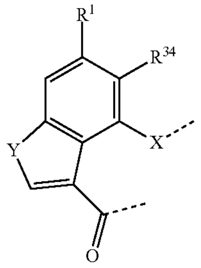
(a10)
A317
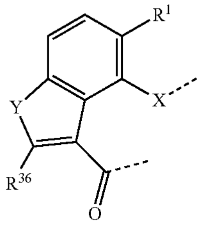
(a10)
A318
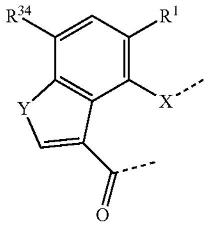
(a10)
A319
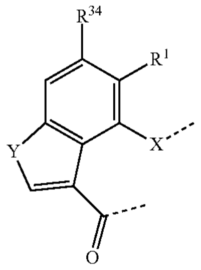
(a10)
TABLE 1-continued
Radicals A1-A683
A320
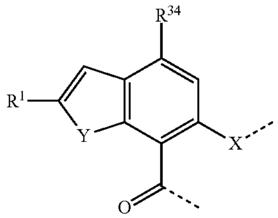
(a10)
A321
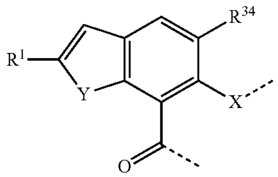
(a10)
A322
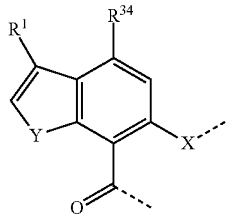
(a10)
A323
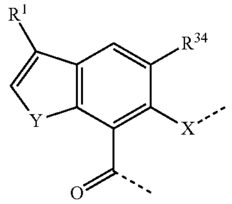
(a10)
A324
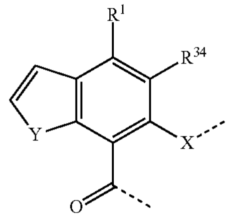
(a10)
A325
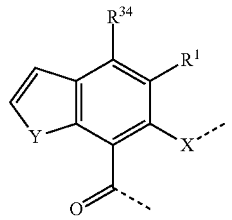
(a10)

TABLE 1-continued
Radicals A1-A683
A326
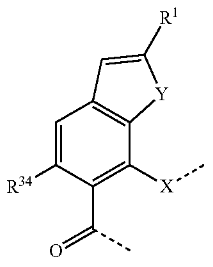
(a10)
A327
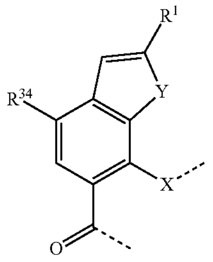
(a10)
A328
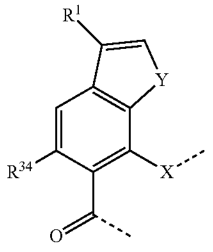
(a10)
A329
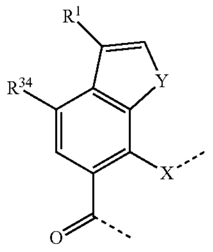
(a10)
A330
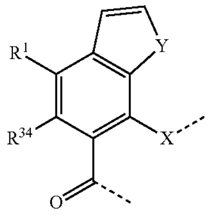
(a10)
A331
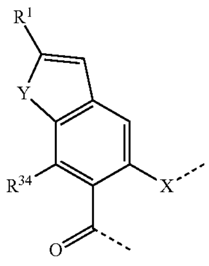
(a10)
A332
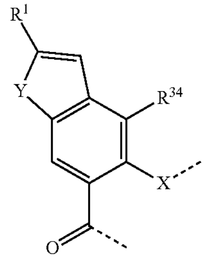
(a10)
A333
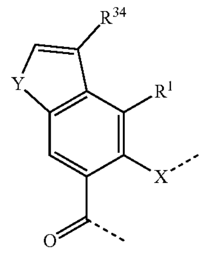
(a10)
A334
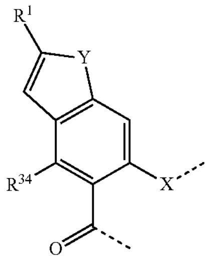
(a10)
A335
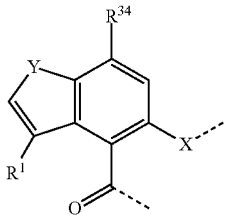
(a10)

TABLE 1-continued
Radicals A1-A683
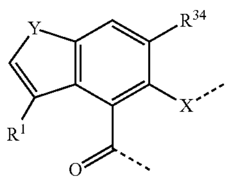
A336
(a10)
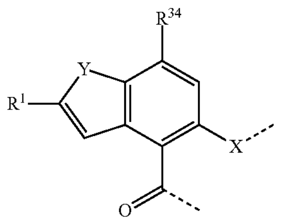
A337
(a10)
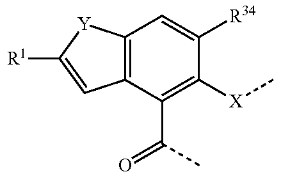
A338
(a10)
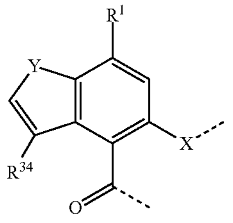
A339
(a10)
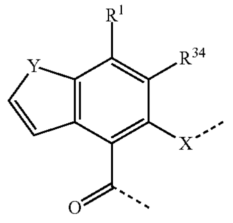
A340
(a10)
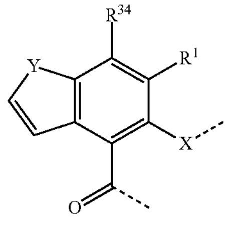
A341
(a10)
TABLE 1-continued
Radicals A1-A683
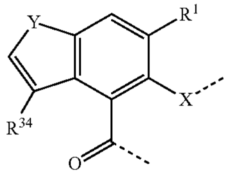
A342
(a10)
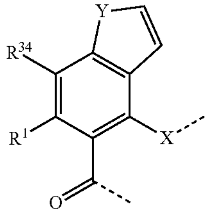
A343
(a10)
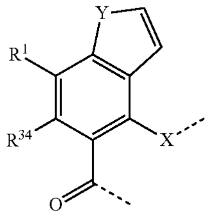
A344
(a10)
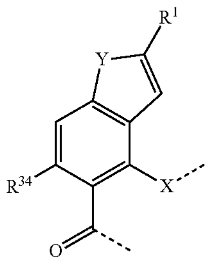
A345
(a10)
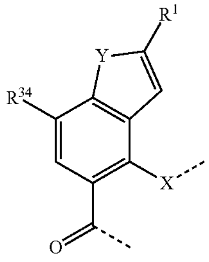
A346
(a10)
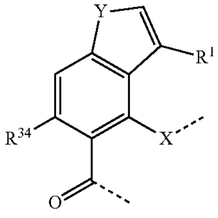
A347
(a10)

TABLE 1-continued
Radicals A1-A683
A348
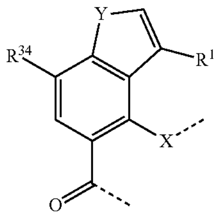
(a10)
A349
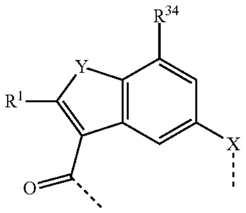
(a10)
A350
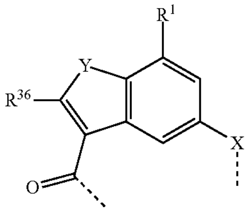
(a10)
A351
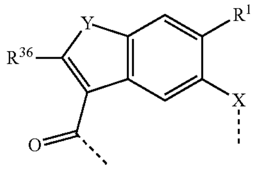
(a10)
A352
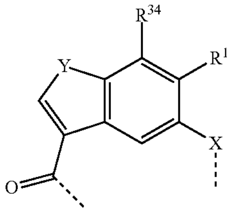
(a10)
A353
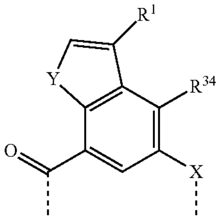
(a10)
TABLE 1-continued
Radicals A1-A683
A354
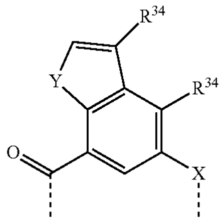
(a10)
A355
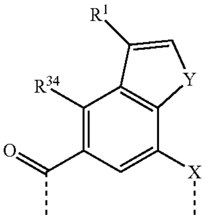
(a10)
A356
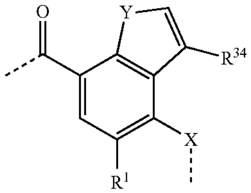
(a10)
A357
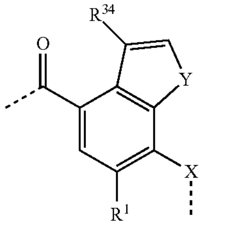
(a10)
A358
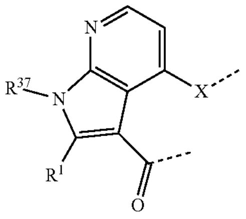
(a11)

TABLE 1-continued
Radicals A1-A683
A359
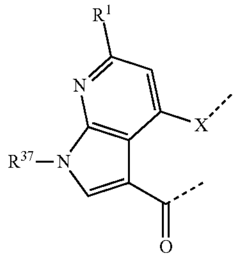
(a11)
A360
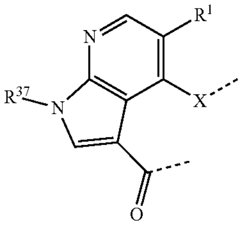
(a11)
A361
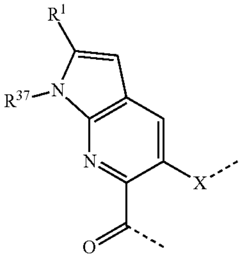
(a11)
A362
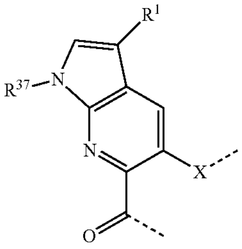
(a11)
A363
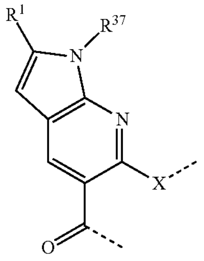
(a11)
TABLE 1-continued
Radicals A1-A683
A364
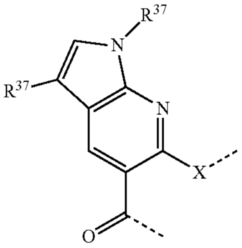
(a11)
A365
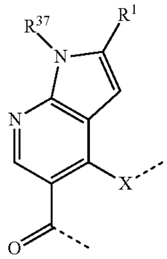
(a11)
A366
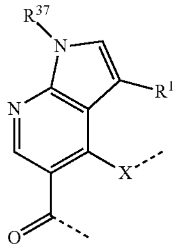
(a11)
A367
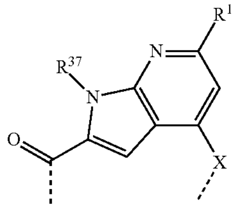
(a11)
A368
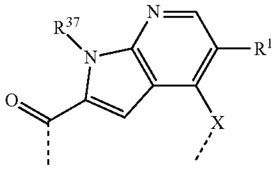
(a11)
A369
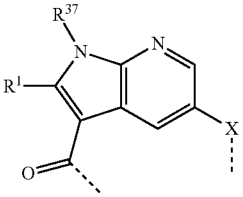
(a11)

TABLE 1-continued
Radicals A1-A683
A370
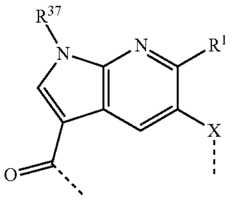
(a11)
A371
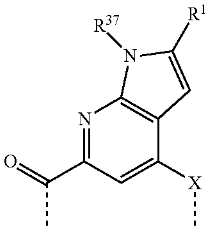
(a11)
A372
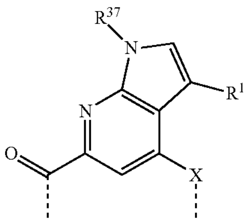
(a11)
A373
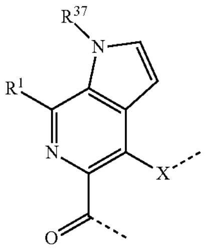
(a12)
A374
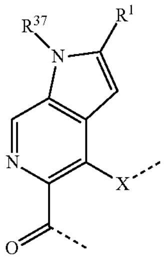
(a12)
TABLE 1-continued
Radicals A1-A683
A375
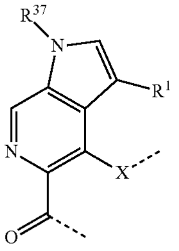
(a12)
A376
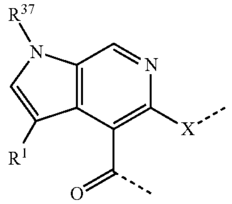
(a12)
A377
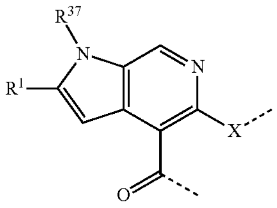
(a12)
A378
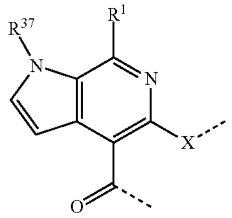
(a12)
A379
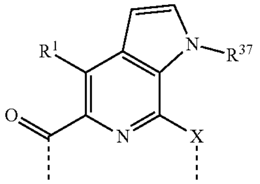
(a12)
A380
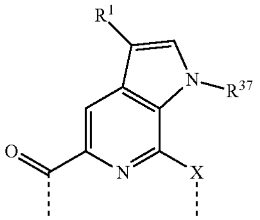
(a12)

TABLE 1-continued
Radicals A1-A683
A381
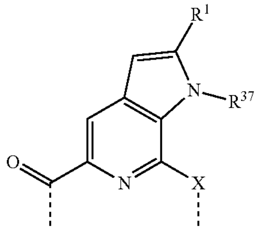
(a12)
A382
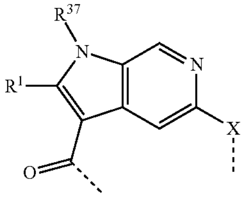
(a12)
A383
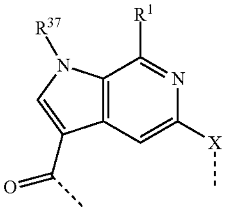
(a12)
A384
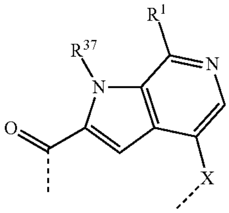
(a12)
A385
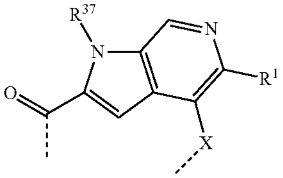
(a12)
A386
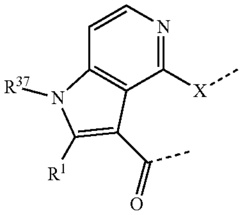
(a13)
TABLE 1-continued
Radicals A1-A683
A387
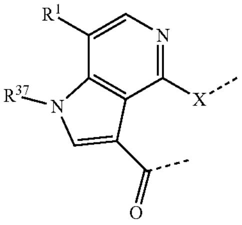
(a13)
A388
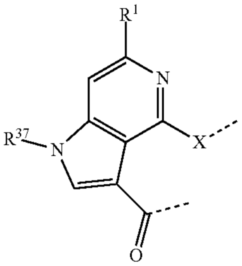
(a13)
A389
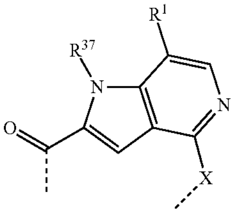
(a13)
A390
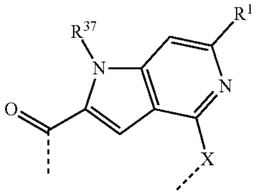
(a13)
A391
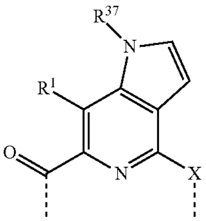
(a13)

Radicals A1-A683
A392
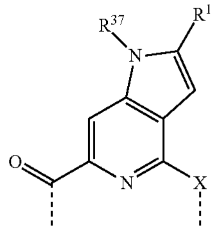
(a13)
A393
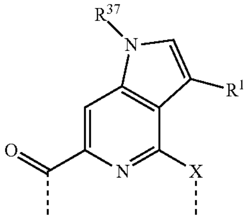
(a13)
A394
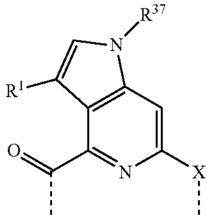
(a13)
A395
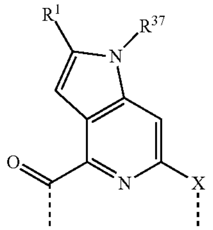
(a13)
A396
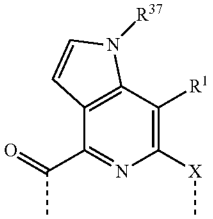
(a13)
Radicals A1-A683
A397
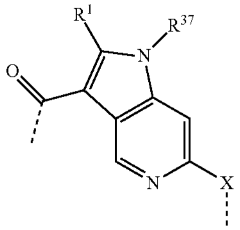
(a13)
A398
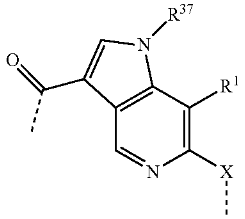
(a13)
A399
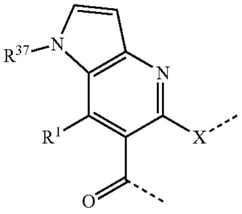
(a14)
A400
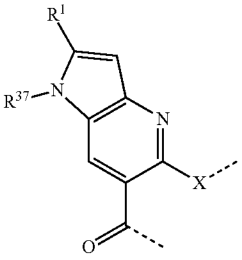
(a14)
A401
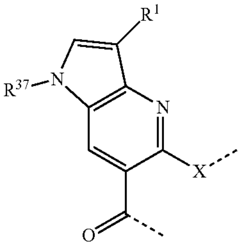
(a14)

TABLE 1-continued
Radicals A1-A683
A402
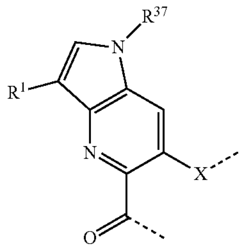
(a14)
A403
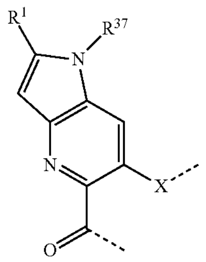
(a14)
A404
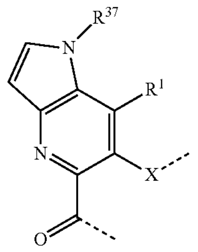
(a14)
A405
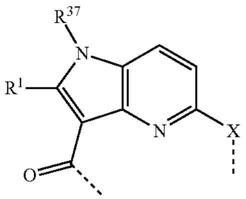
(a14)
A406
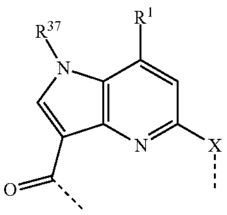
(a14)
TABLE 1-continued
Radicals A1-A683
A407
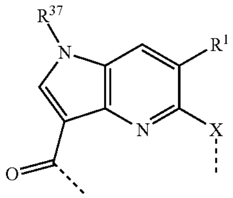
(a14)
A408
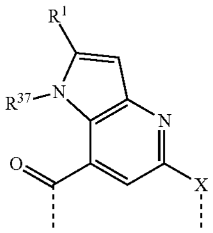
(A14)
A409
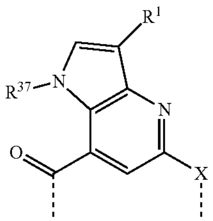
(A14)
A410
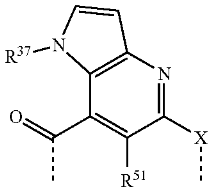
(A14)
A411
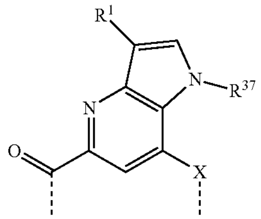
(a14)
A412
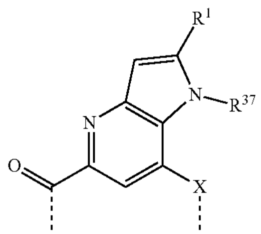
(a14)

TABLE 1-continued
Radicals A1-A683
A413
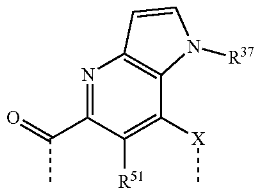
(a14)
A414
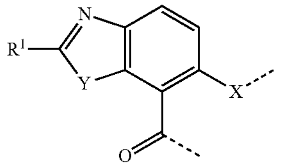
(a15)
A415
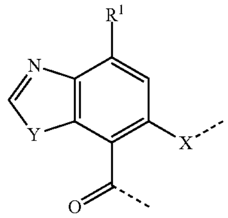
(a15)
A416
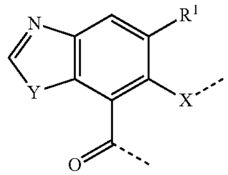
(a15)
A417
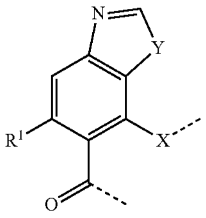
(a15)
A418
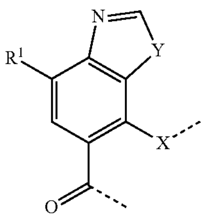
(a15)
TABLE 1-continued
Radicals A1-A683
A419
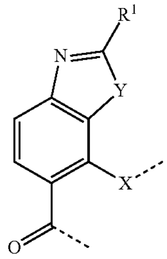
(a15)
A420
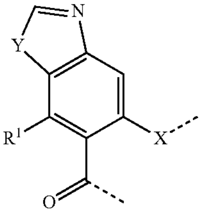
(a15)
A421
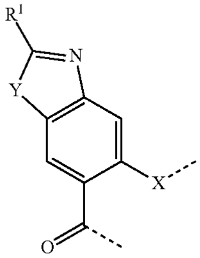
(a15)
A422
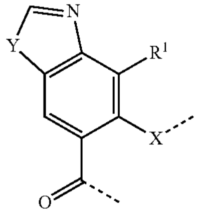
(a15)
A423
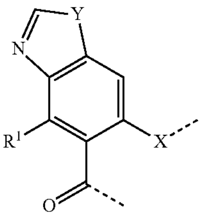
(a15)

TABLE 1-continued
Radicals A1-A683
A424
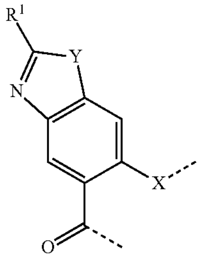
(a15)
A425
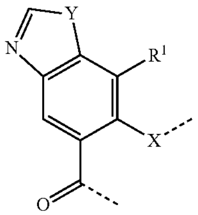
(a15)
A426
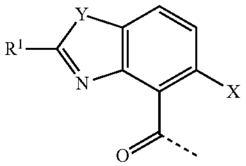
(a15)
A427
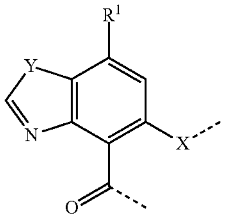
(a15)
A428
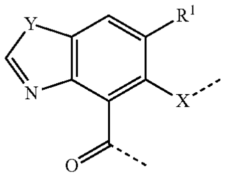
(a15)
A429
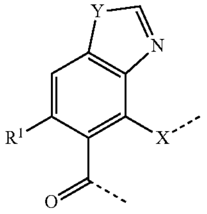
(a15)
TABLE 1-continued
Radicals A1-A683
A430
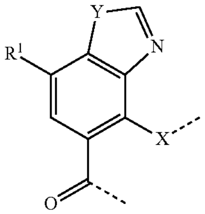
(a15)
A431
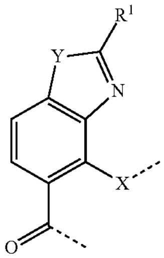
(a15)
A432
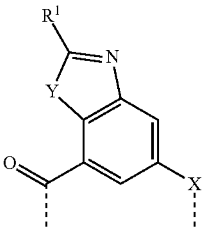
(a15)
A433
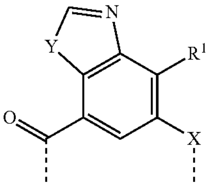
(a15)
A434
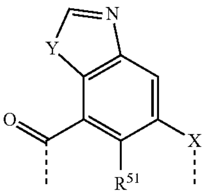
(a15)
A435
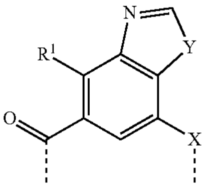
(a15)

TABLE 1-continued
| Radicals A1-A683 | |
|---|---|
| 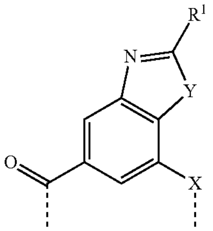<br>(a15) | A436 |
| 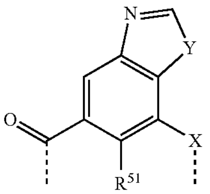<br>(a15) | A437 |
| 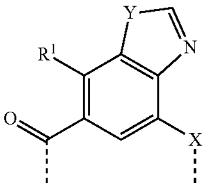<br>(a15) | A438 |
| 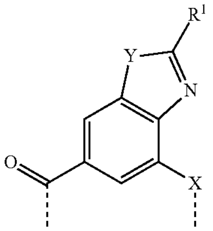<br>(a15) | A439 |
| 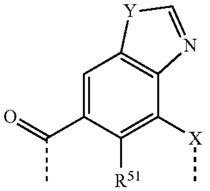<br>(a15) | A440 |
| 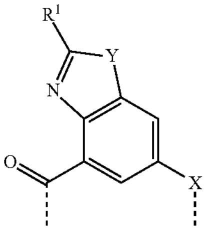<br>(a15) | A441 |
TABLE 1-continued
| Radicals A1-A683 | |
|---|---|
| 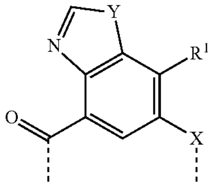<br>(a15) | A442 |
| 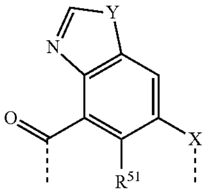<br>(a15) | A443 |
| 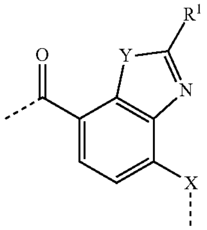<br>(a15) | A444 |
| 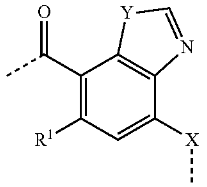<br>(a15) | A445 |
| 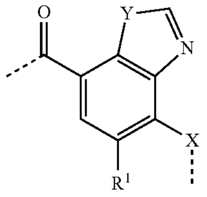<br>(a15) | A446 |
| 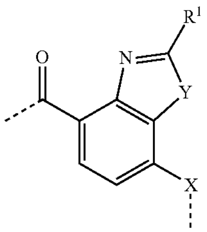<br>(a15) | A447 |

TABLE 1-continued
Radicals A1-A683
A448
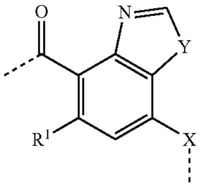
(a15)
A449
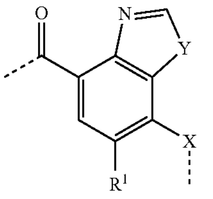
(a15)
A450
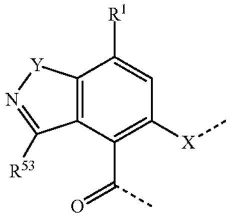
(a16)
A451
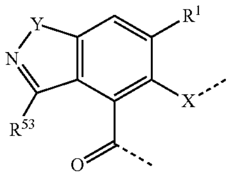
(a16)
A452
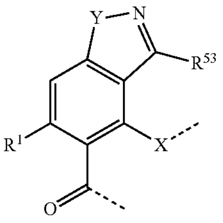
(a16)
A453
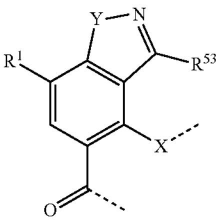
(a16)
TABLE 1-continued
Radicals A1-A683
A454
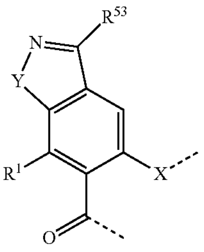
(a16)
A455
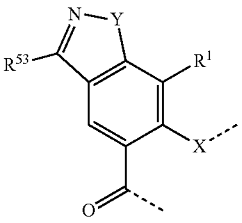
(a16)
A456
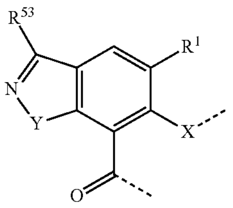
(a16)
A457
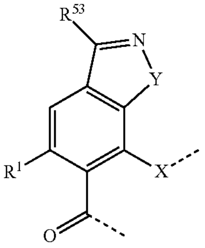
(a16)
A458
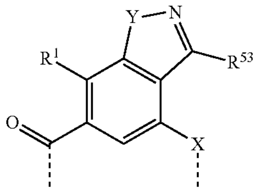
(a16)
A459
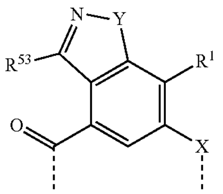
(a16)

TABLE 1-continued
| Radicals A1-A683 |
|---|
| 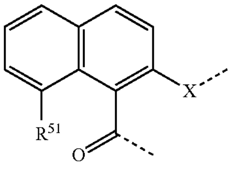 A460 |
| (a17) |
| 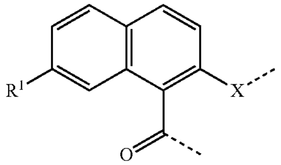 A461 |
| (a17) |
| 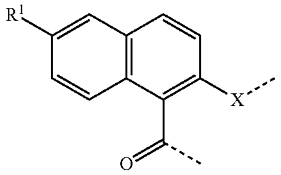 A462 |
| (a17) |
| 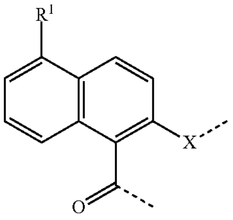 A463 |
| (a17) |
| 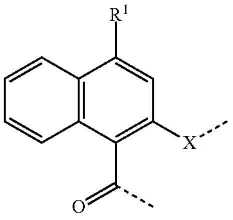 A464 |
| (a17) |
| 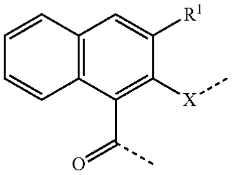 A465 |
| (a17) |
TABLE 1-continued
| Radicals A1-A683 |
|---|
| 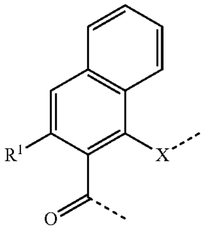 A466 |
| (a17) |
| 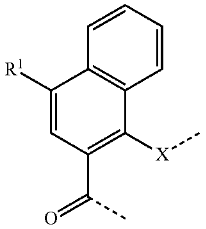 A467 |
| (a17) |
| 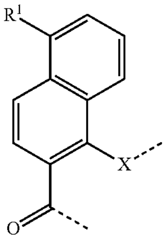 A468 |
| (a17) |
| 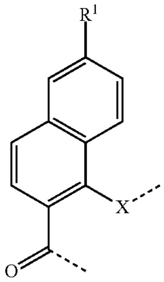 A469 |
| (a17) |
| 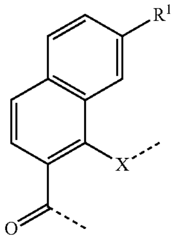 A470 |
| (a17) |

TABLE 1-continued
Radicals A1-A683
A471
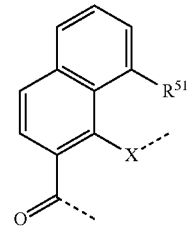
(a17)
A472
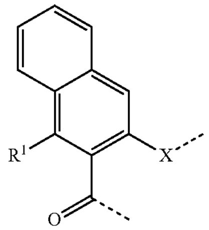
(a17)
A473
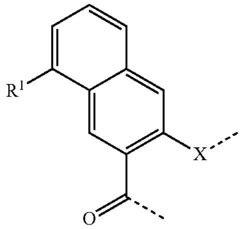
(a17)
A474
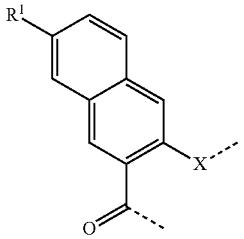
(a17)
A475
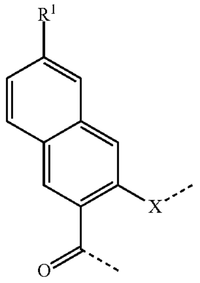
(a17)
TABLE 1-continued
Radicals A1-A683
A476
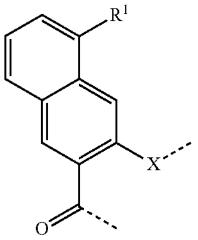
(a17)
A477
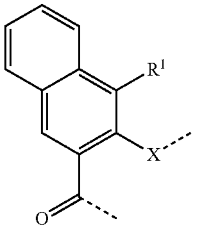
(a17)
A478
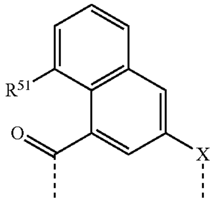
(a17)
A479
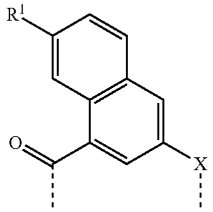
(a17)
A480
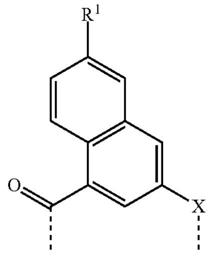
(a17)

TABLE 1-continued
Radicals A1-A683
A481
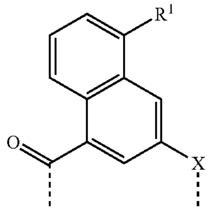
(a17)
A482
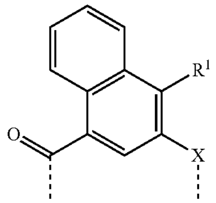
(a17)
A483
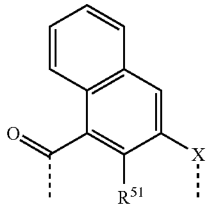
(a17)
A484
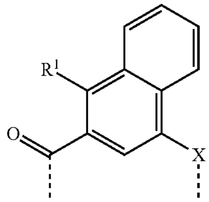
(a17)
A485
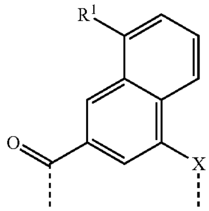
(a17)
A486
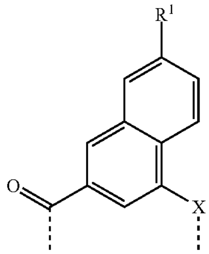
(a17)
TABLE 1-continued
Radicals A1-A683
A487
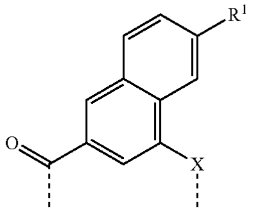
(a17)
A488
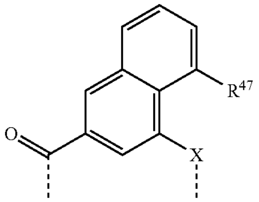
(a17)
A489
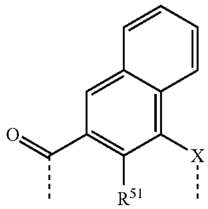
(a17)
A490
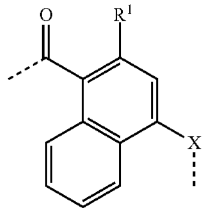
(a17)
A491
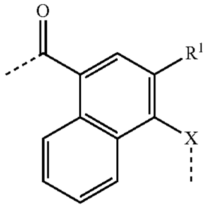
(a17)
A492
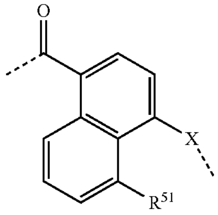
(a17)

TABLE 1-continued
| Radicals A1-A683 | |
|---|---|
| 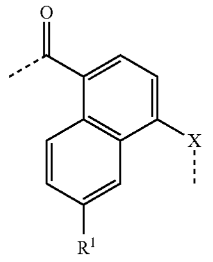 (a17) | A493 |
| 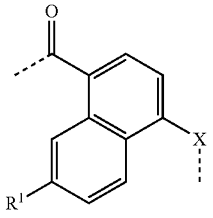 (a17) | A494 |
| 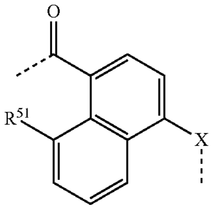 (a17) | A495 |
| 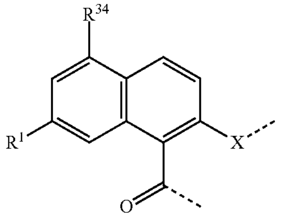 (a17) | A496 |
| 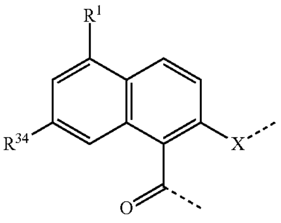 (a17) | A497 |
TABLE 1-continued
| Radicals A1-A683 | |
|---|---|
| 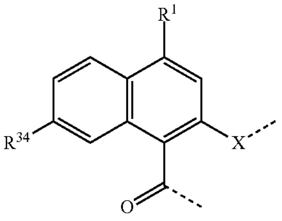 (a17) | A498 |
| 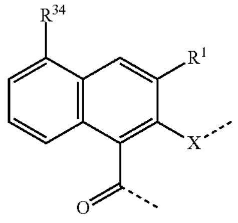 (a17) | A499 |
| 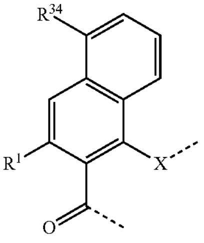 (a17) | A500 |
| 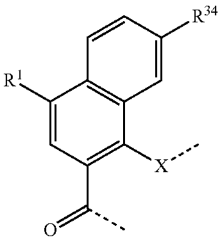 (a17) | A501 |
| 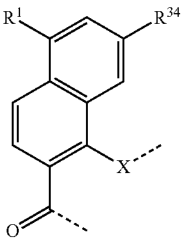 (a17) | A502 |

TABLE 1-continued
| Radicals A1-A683 |
| --- |
A503
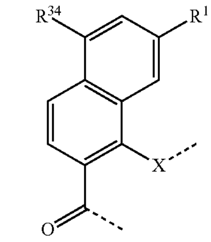
(a17)
A504
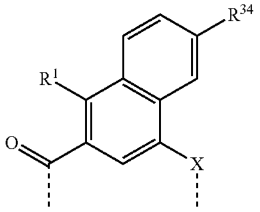
(a17)
A505
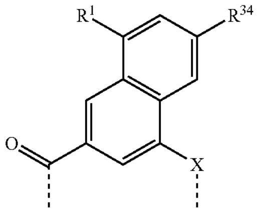
(a17)
A506
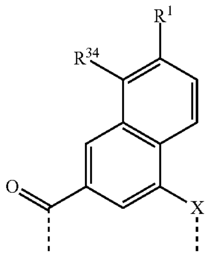
(a17)
A507
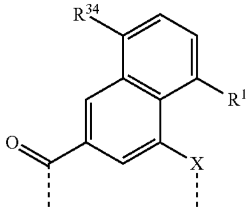
(a17)
A508
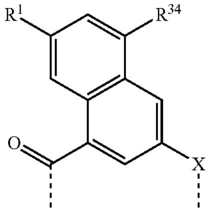
(a17)
TABLE 1-continued
| Radicals A1-A683 |
| --- |
A509
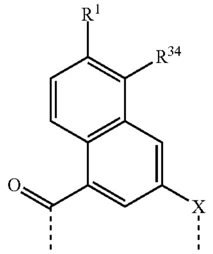
(a17)
A510
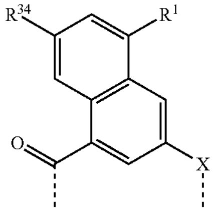
(a17)
A511
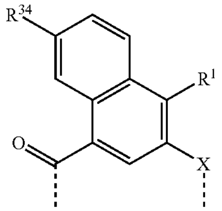
(a17)
A512
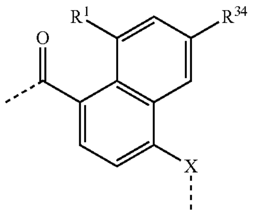
(a17)
A513
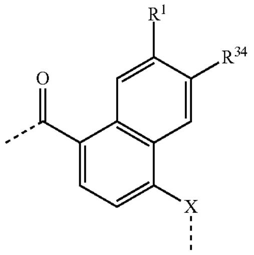
(a17)

TABLE 1-continued
| Radicals A1-A683 |
|---|
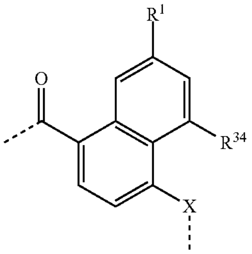
A514
(a17)
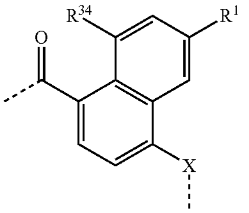
A515
(a17)
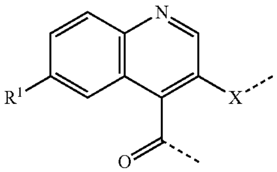
A516
(a18)
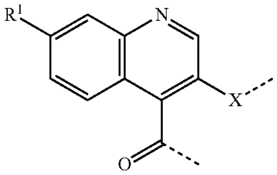
A517
(a18)
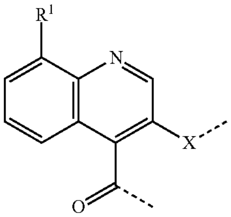
A518
(a18)
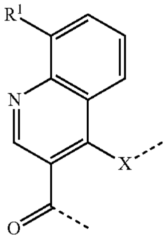
A519
(a18)
TABLE 1-continued
| Radicals A1-A683 |
|---|
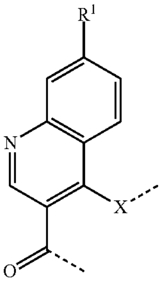
A520
(a18)
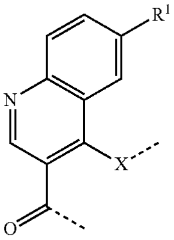
A521
(a18)
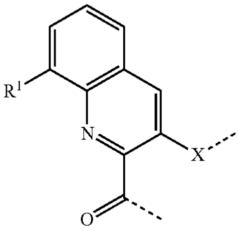
A522
(a18)
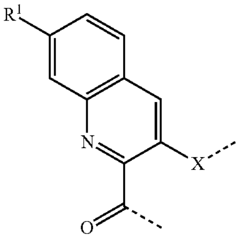
A523
(a18)
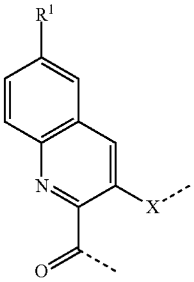
A524
(a18)

TABLE 1-continued
Radicals A1-A683
A525
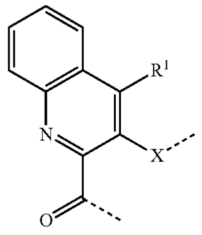
(a18)
A526
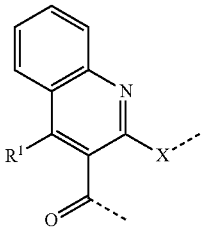
(a18)
A527
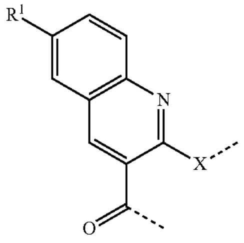
(a18)
A528
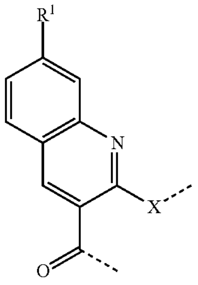
(a18)
A529
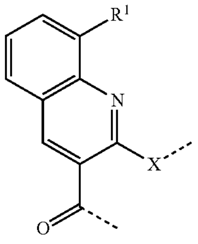
(a18)
TABLE 1-continued
Radicals A1-A683
A530
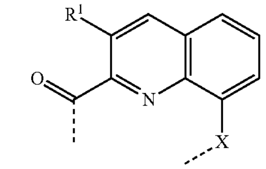
(a18)
A531
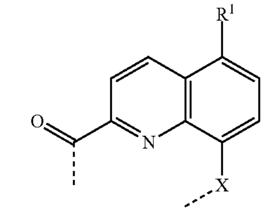
(a18)
A532
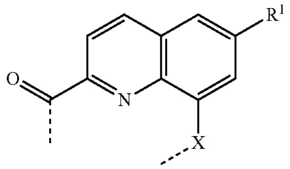
(a18)
A533
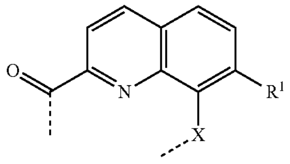
(a18)
A534
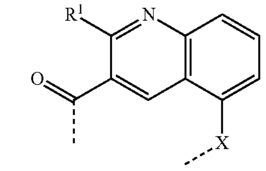
(a18)
A535
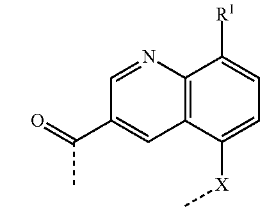
(a18)
A536
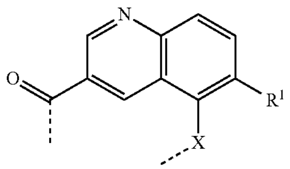
(a18)

TABLE 1-continued
Radicals A1-A683
A537
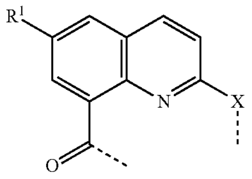
(a18)
A538
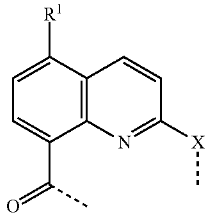
(a18)
A539
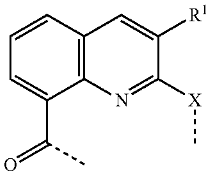
(a18)
A540
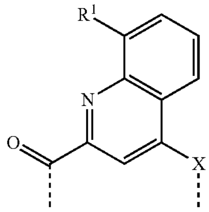
(a18)
A541
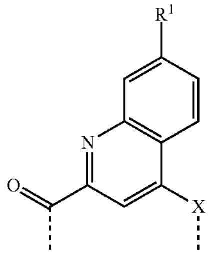
(a18)
A542
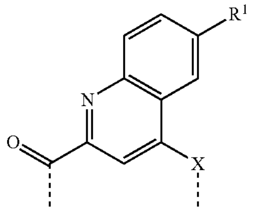
(a18)
TABLE 1-continued
Radicals A1-A683
A543
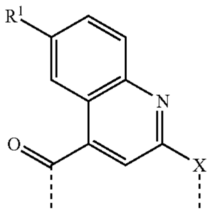
(a18)
A544
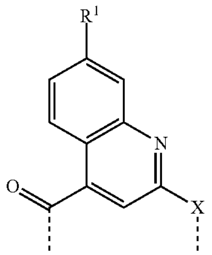
(a18)
A545
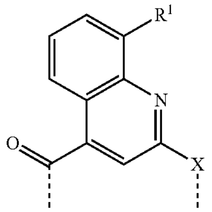
(a18)
A546
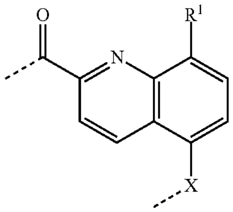
(a18)
A547
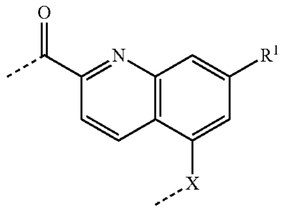
(a18)
A548
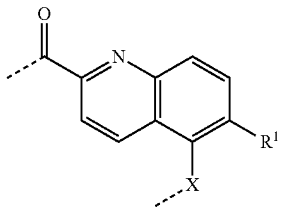
(a18)

TABLE 1-continued
| Radicals A1-A683 |
|---|
A549
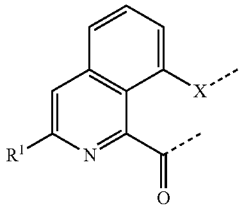
(a19)
A550
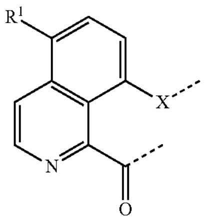
(a19)
A551
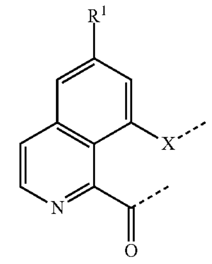
(a19)
A552
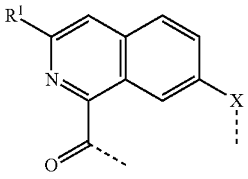
(a19)
A553
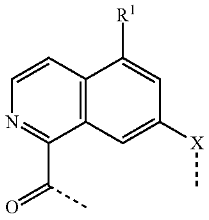
(a19)
A554
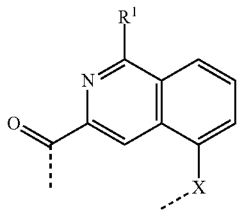
(a19)
TABLE 1-continued
| Radicals A1-A683 |
|---|
A555
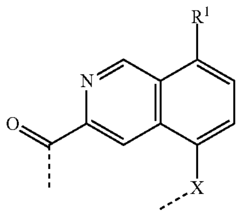
(a19)
A556
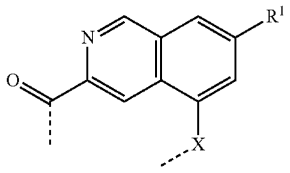
(a19)
A557
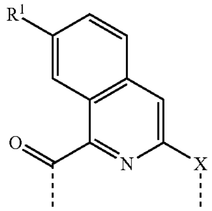
(a19)
A558
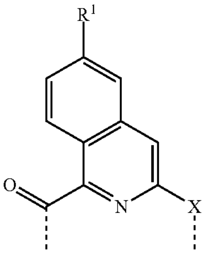
(a19)
A559
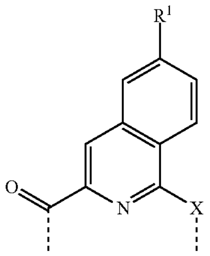
(a19)
A560
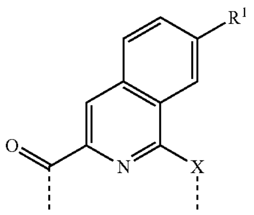
(a19)

TABLE 1-continued
| Radicals A1-A683 | |
|---|---|
| 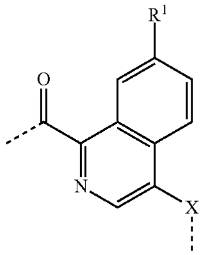<br>(a19) | A561 |
| 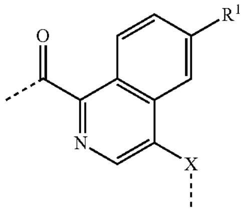<br>(a19) | A562 |
| 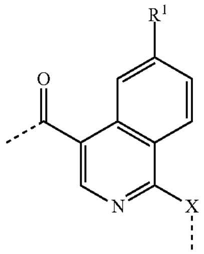<br>(a19) | A563 |
| 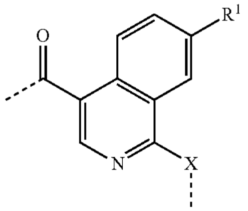<br>(a19) | A564 |
| 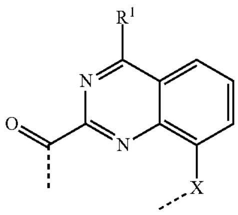<br>(a20) | A565 |
| 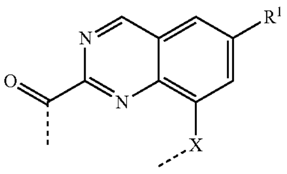<br>(a20) | A566 |
TABLE 1-continued
| Radicals A1-A683 | |
|---|---|
| 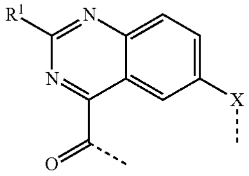<br>(a20) | A567 |
| 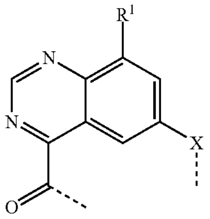<br>(a20) | A568 |
| 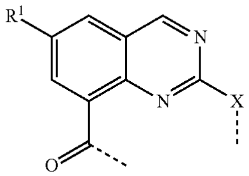<br>(a20) | A569 |
| 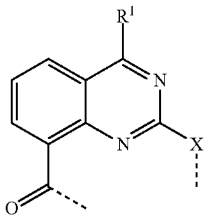<br>(a20) | A570 |
| 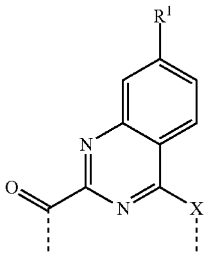<br>(a20) | A571 |
| 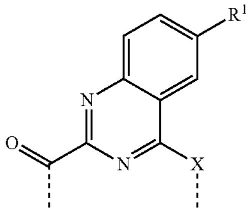<br>(a20) | A572 |

TABLE 1-continued
Radicals A1-A683
A573
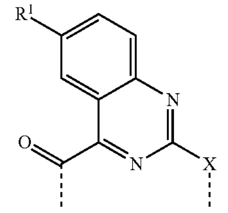
(a20)
A574
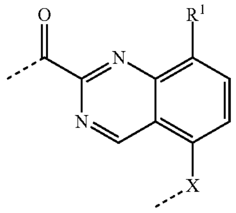
(a20)
A575
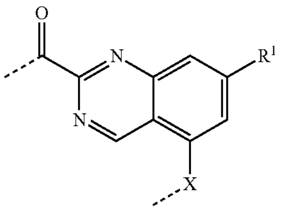
(a20)
A576
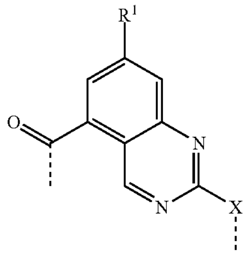
(a20)
A577
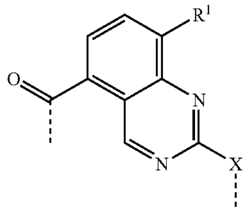
(a20)
A578
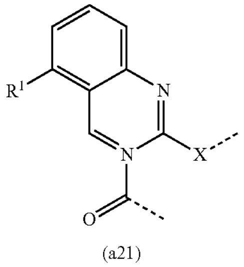
(a21)
TABLE 1-continued
Radicals A1-A683
A579
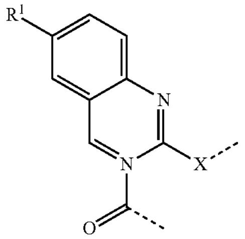
(a21)
A580
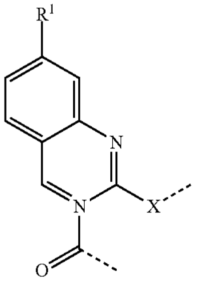
(a21)
A581
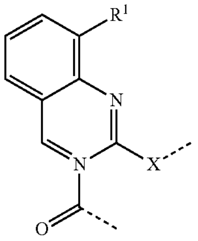
(a21)
A582
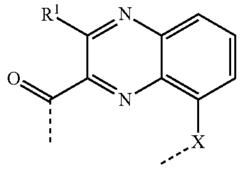
(a21)
A583
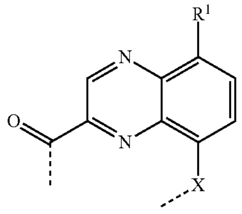
(a21)

TABLE 1-continued
| Radicals A1-A683 | |
|---|---|
| 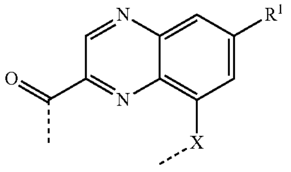<br>(a21) | A584 |
| 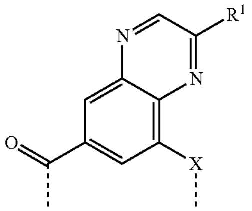<br>(a21) | A585 |
| 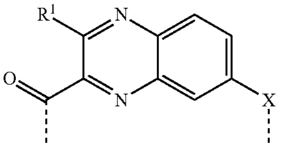<br>(a21) | A586 |
| 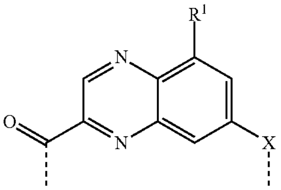<br>(a21) | A587 |
| 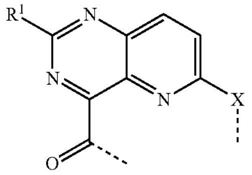<br>(a22) | A588 |
| 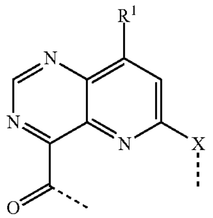<br>(a22) | A589 |
TABLE 1-continued
| Radicals A1-A683 | |
|---|---|
| 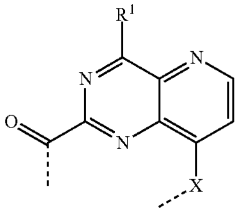<br>(a22) | A590 |
| 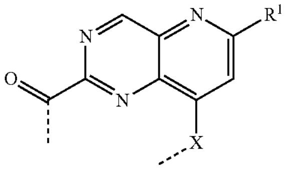<br>(a22) | A591 |
| 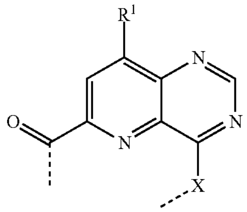<br>(a22) | A592 |
| 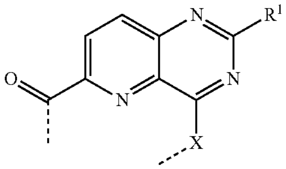<br>(a22) | A593 |
| 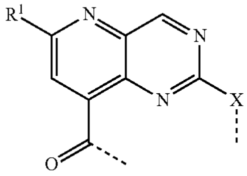<br>(a22) | A594 |
| 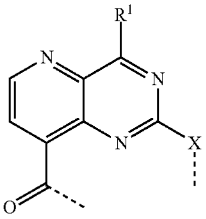<br>(a22) | A595 |

TABLE 1-continued
| Radicals A1-A683 | |
|---|---|
| 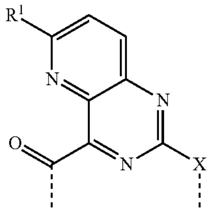<br>(a22) | A596 |
| 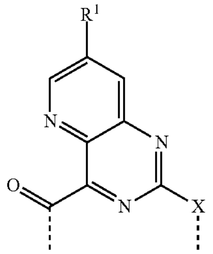<br>(a22) | A597 |
| 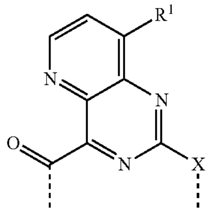<br>(a22) | A598 |
| 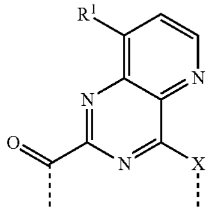<br>(a22) | A599 |
| 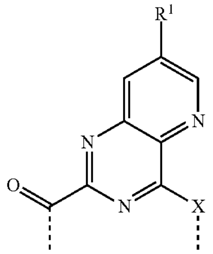<br>(a22) | A600 |
TABLE 1-continued
| Radicals A1-A683 | |
|---|---|
| 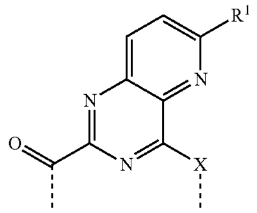<br>(a22) | A601 |
| 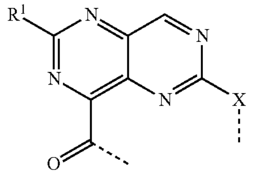<br>(a23) | A602 |
| 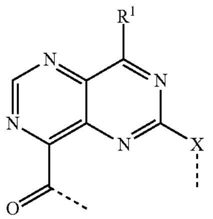<br>(a23) | A603 |
| 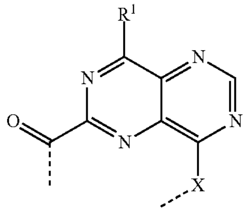<br>(a23) | A604 |
| 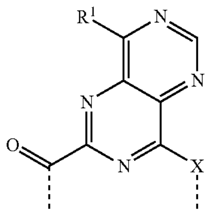<br>(a23) | A605 |
| 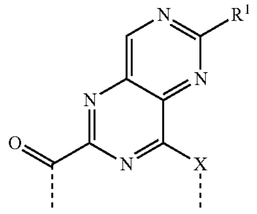<br>(a23) | A606 |

TABLE 1-continued
Radicals A1-A683
A607
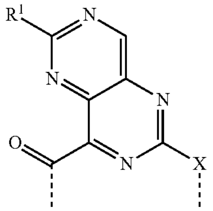
(a23)
A608
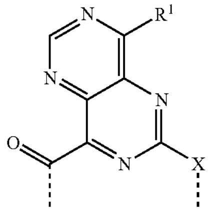
(a23)
A609
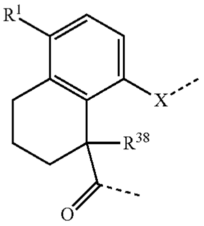
(a24)
A610
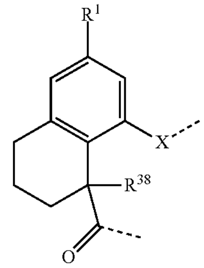
(a24)
A611
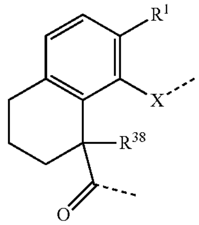
(a24)
TABLE 1-continued
Radicals A1-A683
A612
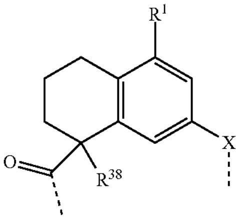
(a24)
A613
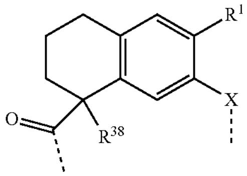
(a24)
A614
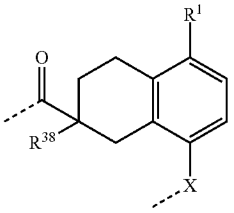
(a24)
A615
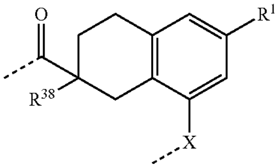
(a24)
A616
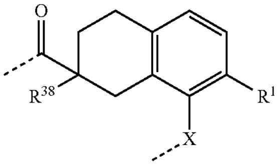
(a24)
A617
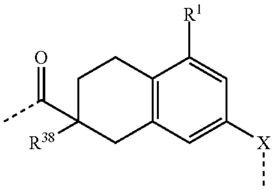
(a24)

TABLE 1-continued
| Radicals A1-A683 | |
|---|---|
| 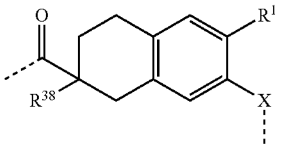 (a24) | A618 |
| 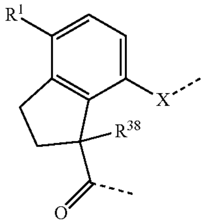 (a25) | A619 |
| 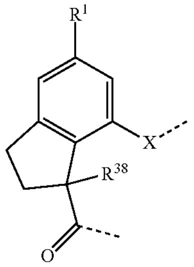 (a25) | A620 |
| 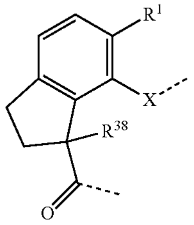 (a25) | A621 |
| 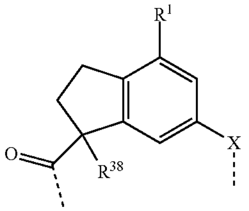 (a25) | A622 |
| 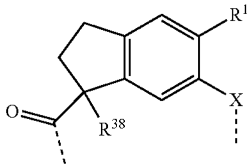 (a25) | A623 |
TABLE 1-continued
| Radicals A1-A683 | |
|---|---|
| 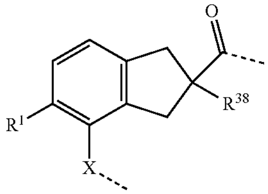 (a25) | A624 |
| 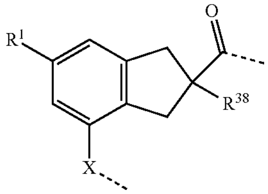 (a25) | A625 |
| 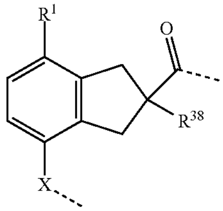 (a25) | A626 |
| 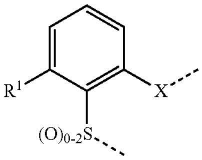 (a1) | A627 |
| 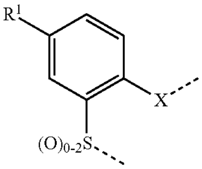 (a1) | A628 |
| 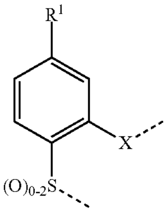 (a1) | A629 |

TABLE 1-continued
Radicals A1-A683
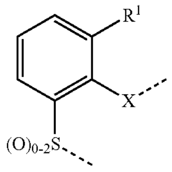
(a1)
A630
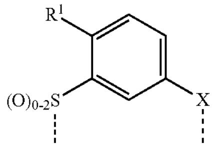
(a1)
A631
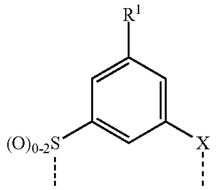
(a1)
A632
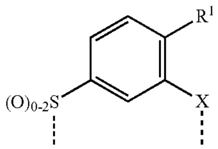
(a1)
A633
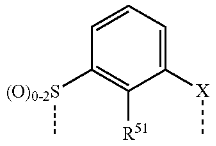
(a1)
A634
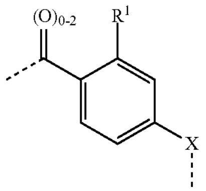
(a1)
A635
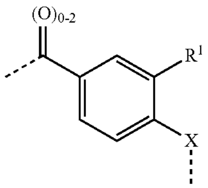
(a1)
A636
TABLE 1-continued
Radicals A1-A683
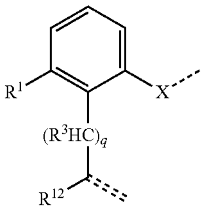
(a1)
A637
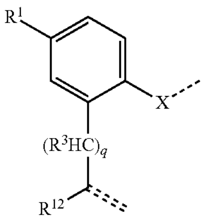
(a1)
A638
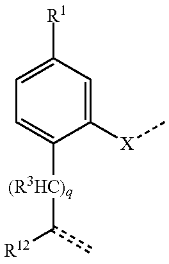
(a1)
A639
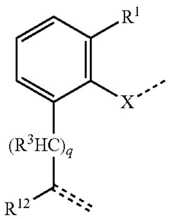
(a1)
A640
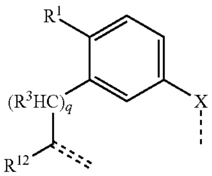
(a1)
A641
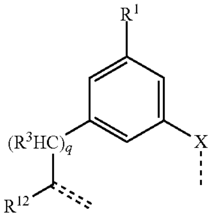
(a1)
A642

TABLE 1-continued
Radicals A1-A683
A643
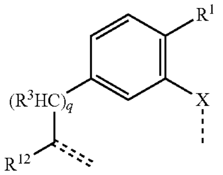
(a1)
A644
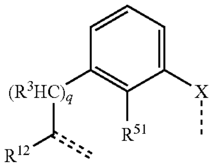
(a1)
A645
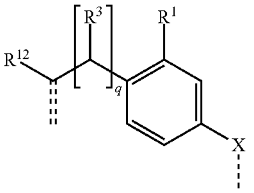
(a1)
A646
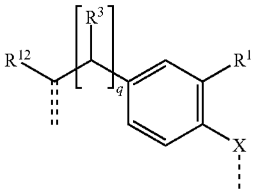
(a1)
A647
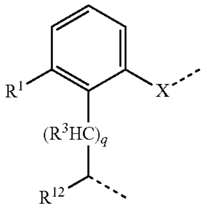
(a1)
A648
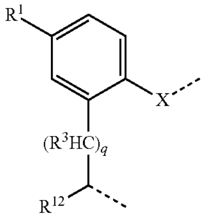
(a1)
TABLE 1-continued
Radicals A1-A683
A649
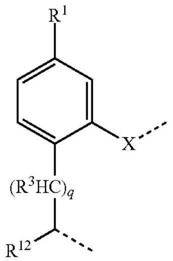
(a1)
A650
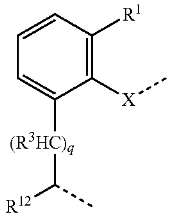
(a1)
A651
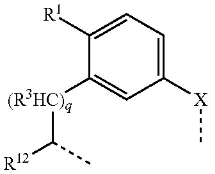
(a1)
A652
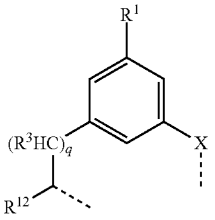
(a1)
A653
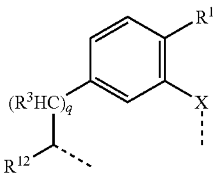
(a1)
A654
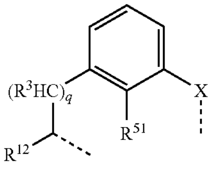
(a1)

TABLE 1-continued
Radicals A1-A683
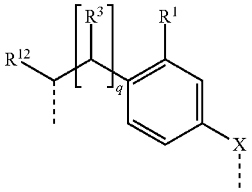
(a1) A655
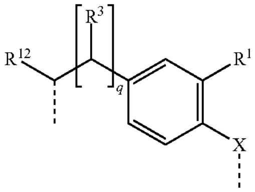
(a1) A656
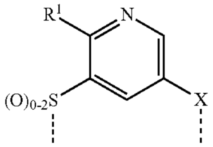
(a2) A657
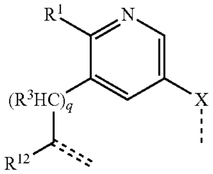
(a2) A658
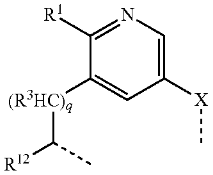
(a2) A659
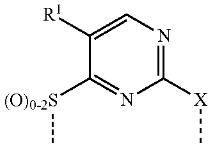
(a4) A660
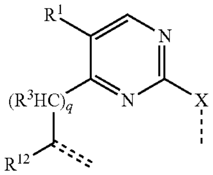
(a4) A661
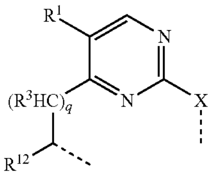
(a4) A662
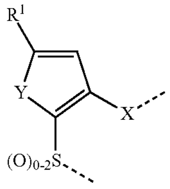
(a7) A663
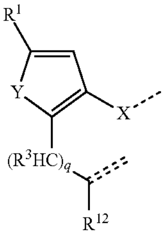
(a7) A664
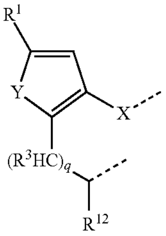
(a7) A665
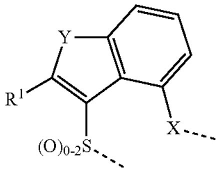
(a10) A666
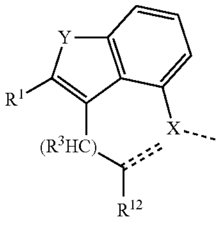
(a10) A667

TABLE 1-continued
Radicals A1-A683
A668
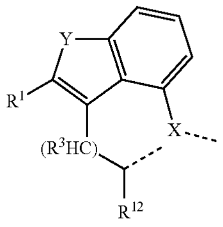
(a10)
A669
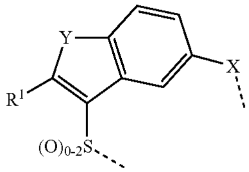
(a10)
A670
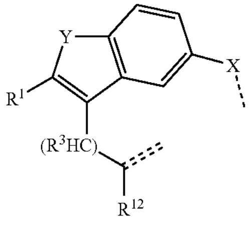
(a10)
A671
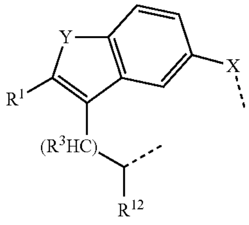
(a10)
A672
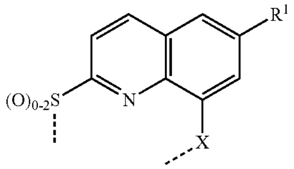
(a18)
A673
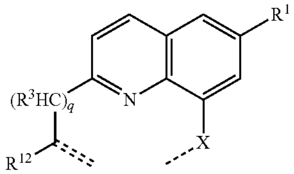
(a18)
TABLE 1-continued
Radicals A1-A683
A674
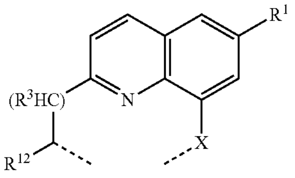
(a18)
A675
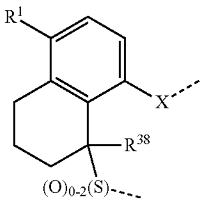
(a24)
A676
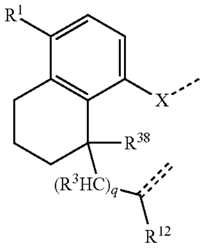
(a24)
A677
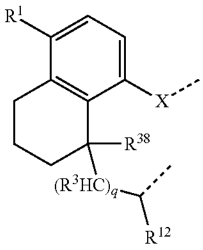
(a24)
A678
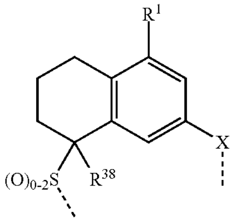
(a24)

TABLE 1-continued

| Radicals A1-A683 | |
|---|---|
| 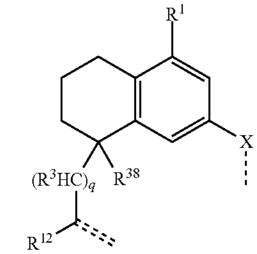 (a24) | A679 |
| 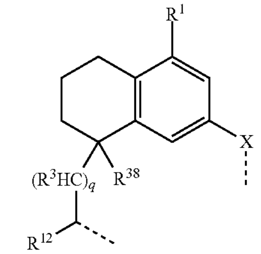 (a24) | A680 |
| 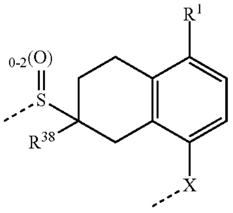 (a24) | A681 |
| 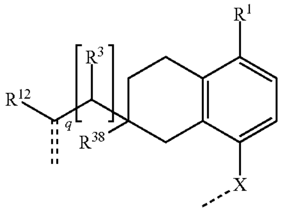 (a24) | A682 |
| 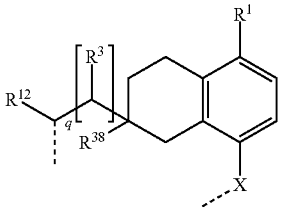 (a24) | A683 |

Building block B is a bivalent radical selected from the group of Table 2.

B1-B22 are optionally substituted cyclic secondary amines carrying a moiety of type —$CHR^3$-LG, wherein LG is a suitable leaving group that can be replaced by the nucleophilic groups of building blocks A forming an ether (—O—) or a thioether (—S—) linkage (or their oxidized forms) between building blocks of type A and B.

Appropriate LGs are for example —OH being transformed into the active LG in situ during a Mitsunobu reactions, or halogens like —Br or —I amenable to $S_N$ reactions.

In most examples of type Ia/Ib, the secondary amine nitrogen of building block B forms a tertiary amide bond with a carboxyl group of building blocks of type C. In case suitable exocyclic amine functionality is present, it can be, instead of the ring-nitrogen, involved in the formation of a secondary or preferably tertiary amide connection. Such an alternative binding mode according formula Ib is realized with e.g. B10.

By virtue of inducing peptidyl cis-trans isomerizations or stabilizing cis amide bonds, building blocks of type B can function as conformational modulators in macrocycles of type Ia/Ib.

TABLE 2

| Radicals B1-B22 |
|---|
| 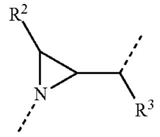 B1 (b1) |
| 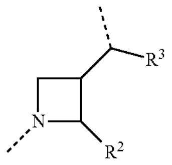 B2 (b2) |
| 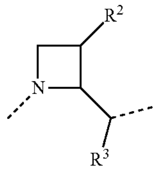 B3 (b2) |
| 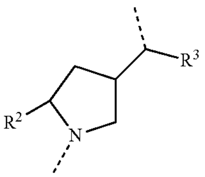 B4 (b3) |
| 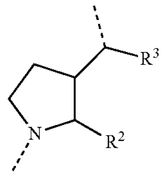 B5 (b3) |

TABLE 2-continued
| Radicals B1-B22 |
| --- |
| 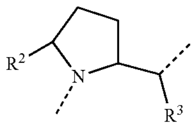<br>B6 (b3) |
| 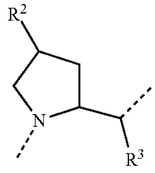<br>B7 (b3) |
| 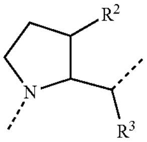<br>B8 (b3) |
| 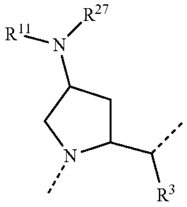<br>B9 (b3) |
| 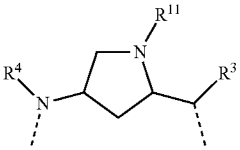<br>B10 (b3) |
| 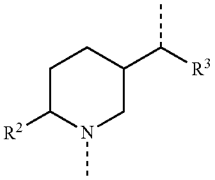<br>B11 (b4) |
| 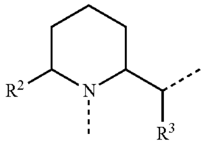<br>B12 (b4) |
TABLE 2-continued
| Radicals B1-B22 |
| --- |
| 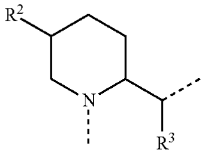<br>B13 (b4) |
| 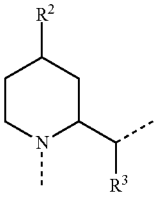<br>B14 (b4) |
| 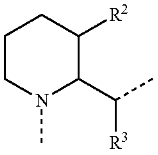<br>B15 (b4) |
| 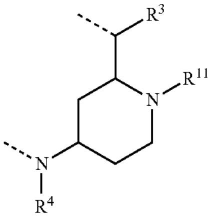<br>B16 (b4) |
| 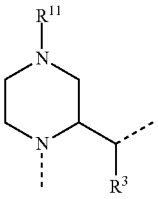<br>B17 (b5) |
| 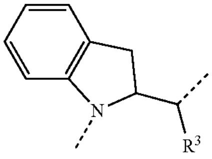<br>B18 (b8) |
| 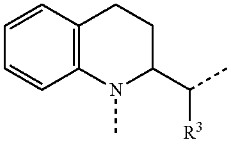<br>B19 (b10) |

TABLE 2-continued

Radicals B1-B22

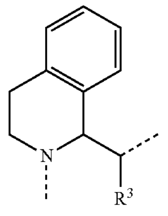

B20 (b11)

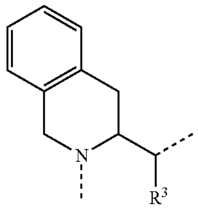

B21 (b11)

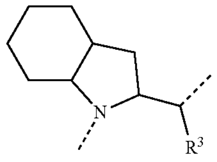

B22 (b12)

Building block C is a bivalent radical selected from the group of Table 3.

As mentioned before the divalent moiety C may consist of one to three subunits c1 to c3. As a consequence it directly influences the ring size of the macrocycle and can be regarded as spacer or linker. This linker ensemble C is joined to building block A via its M-terminus (i.e. N-terminus in case of an amino acid) and to building block B via its U-terminus (i.e. C-terminus in case of an amino acid) to form the macrocyclic ring of type Ia/Ib. As detailed above linker C contributes with the four groups M, U, V and W (cf. FIGS. 2 and 3) to the backbone of macrocycle Ia/Ib. For example, in case M is —$NR^4$—, C1 represents a linker moiety constituted of one to three α-amino acid derivatives connected along their main chains, while C7-C10 are equivalent to moieties containing β-amino acids. The simplest situation in which at least one connection between the subunits c1 to c3 is realized by a non-amidic group are C2-C5. Finally C58-C101 depict cases in which longer carbon chains (>3 C-atoms) separate at least one pair of the generic groups M, V, W, U.

TABLE 3

Representations of Linker C

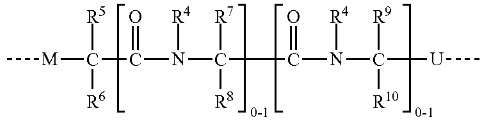

C1

TABLE 3-continued

Representations of Linker C

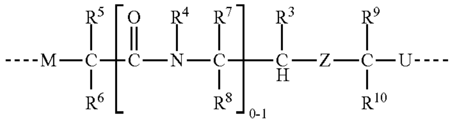

C2

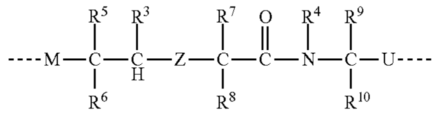

C3

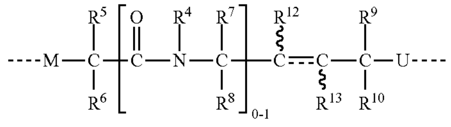

C4

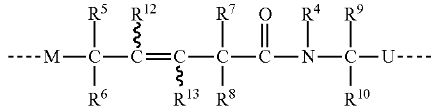

C5

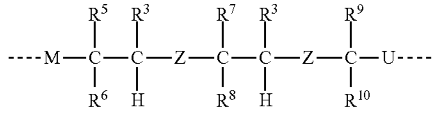

C6

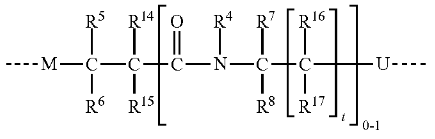

C7

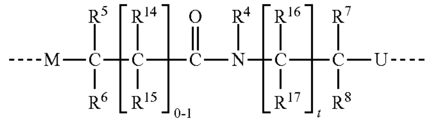

C8

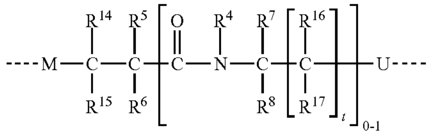

C9

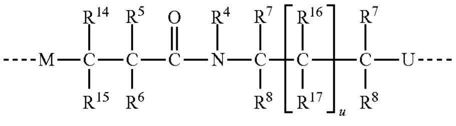

C10

TABLE 3-continued
Representations of Linker C
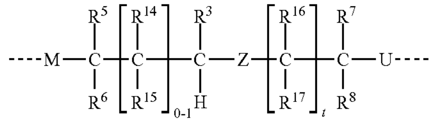
C11
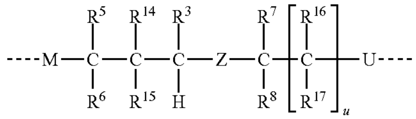
C12
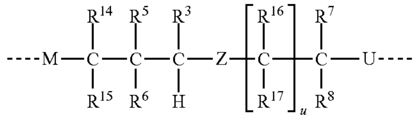
C13
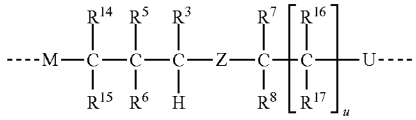
C14
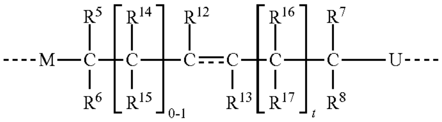
C15
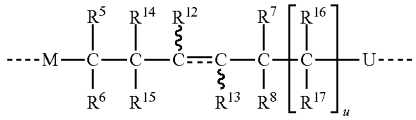
C16
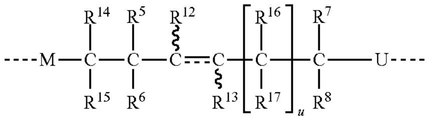
C17
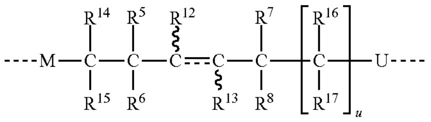
C18
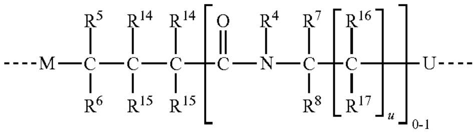
C19
TABLE 3-continued
Representations of Linker C
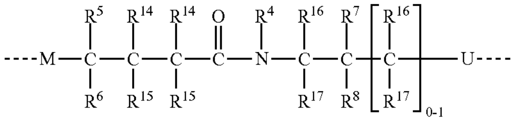
C20
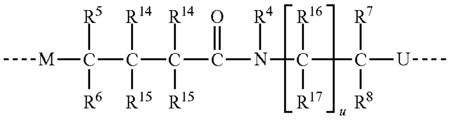
C21
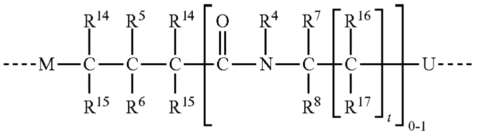
C22
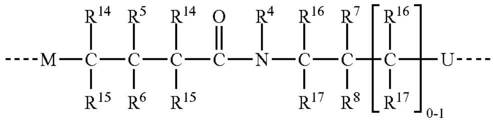
C23
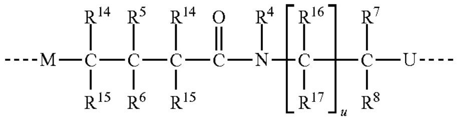
C24
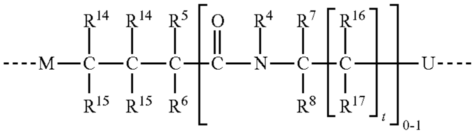
C25
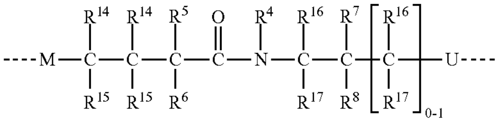
C26
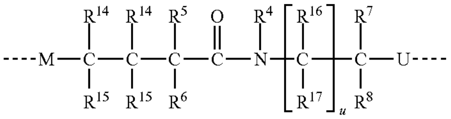
C27
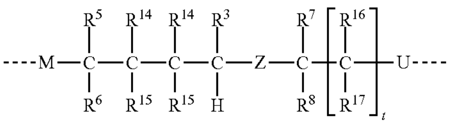
C28

TABLE 3-continued
| Representations of Linker C |
| --- |
| 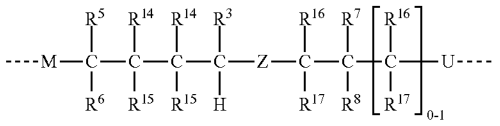 |
| C29 |
| 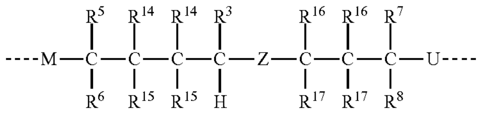 |
| C30 |
| 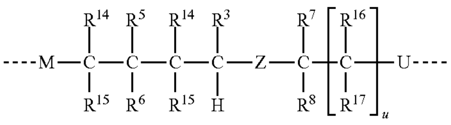 |
| C31 |
| 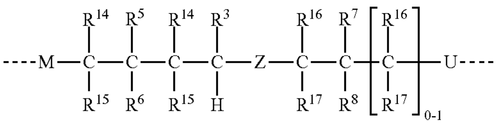 |
| C32 |
| 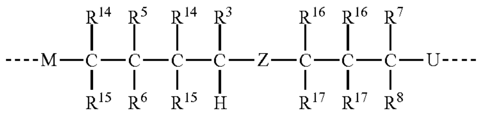 |
| C33 |
| 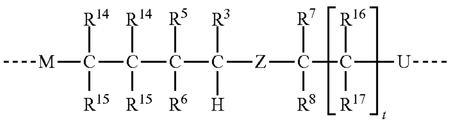 |
| C34 |
| 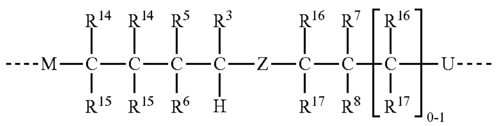 |
| C35 |
| 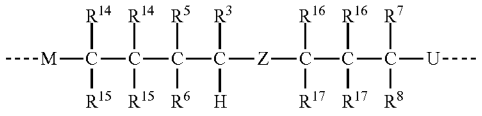 |
| C36 |
| 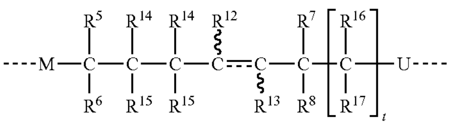 |
| C37 |
TABLE 3-continued
| Representations of Linker C |
| --- |
| 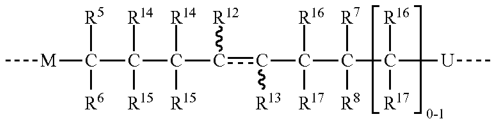 |
| C38 |
| 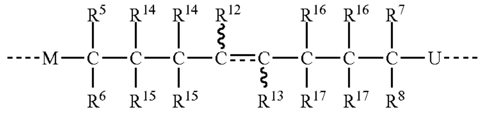 |
| C39 |
| 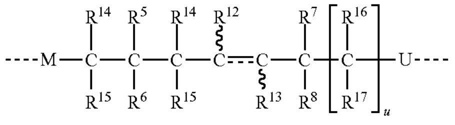 |
| C40 |
| 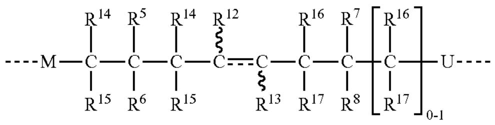 |
| C41 |
| 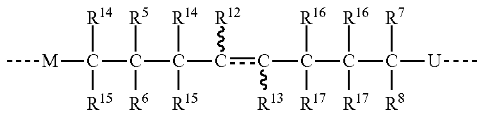 |
| C42 |
| 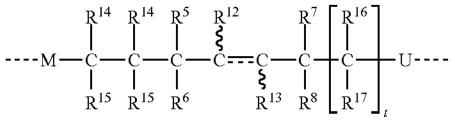 |
| C43 |
| 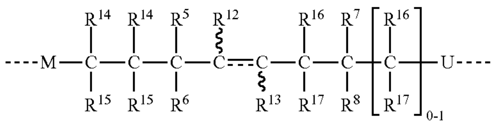 |
| C44 |
| 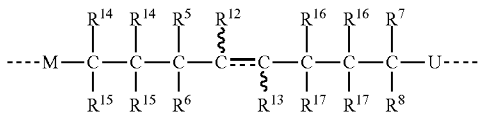 |
| C45 |
| 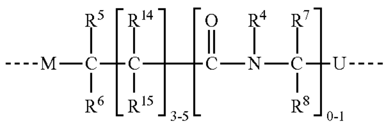 |
| C46 |

TABLE 3-continued
Representations of Linker C
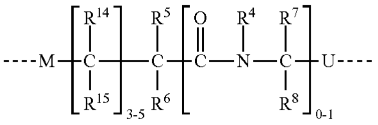
C47
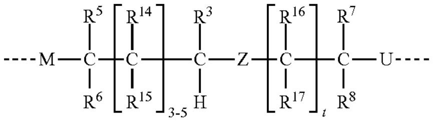
C48
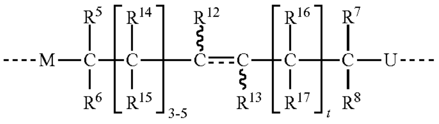
C49
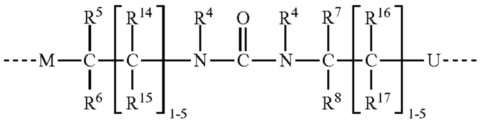
C50
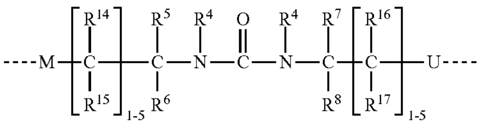
C51
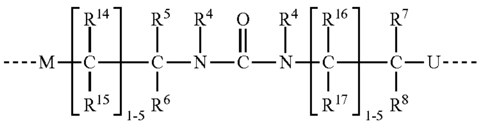
C52
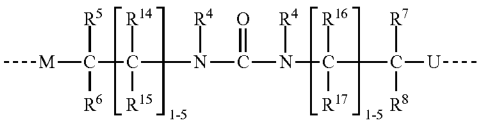
C53
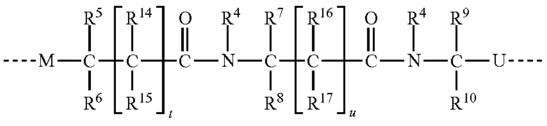
C54
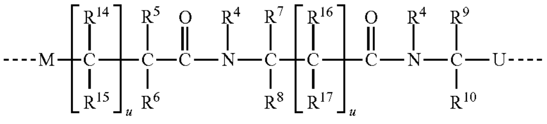
C55
TABLE 3-continued
Representations of Linker C
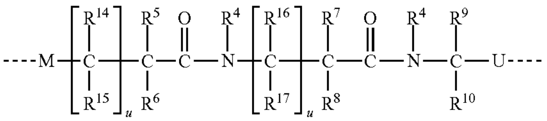
C56
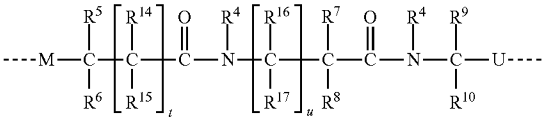
C57
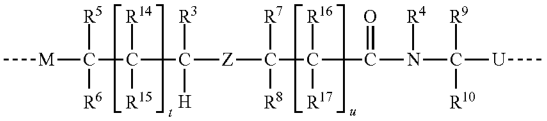
C58
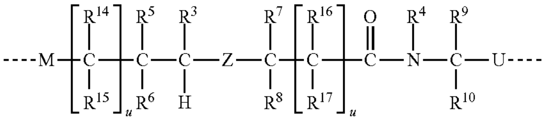
C59
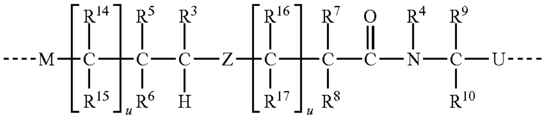
C60
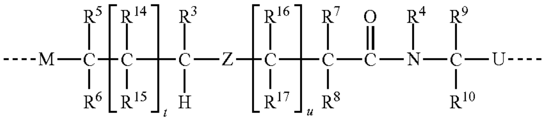
C61
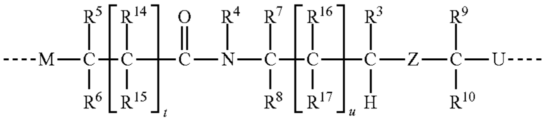
C62
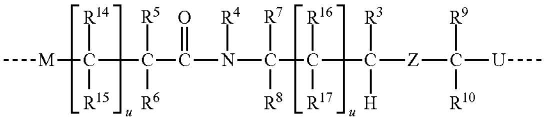
C63
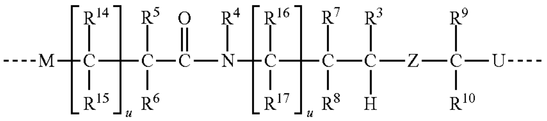
C64

TABLE 3-continued
Representations of Linker C
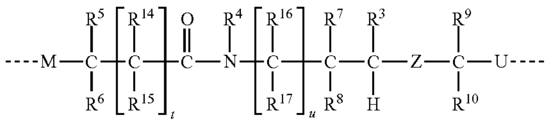
C65
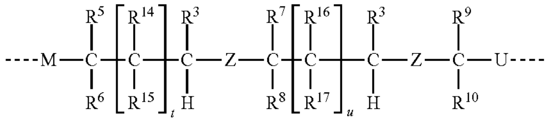
C66
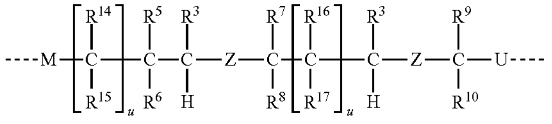
C67
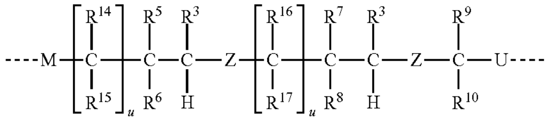
C68
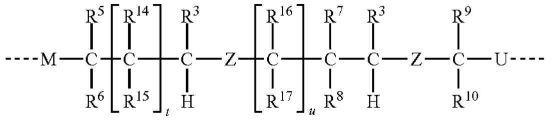
C69
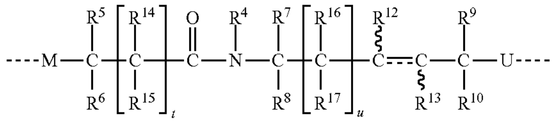
C70
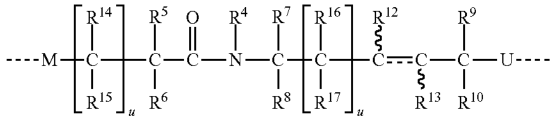
C71
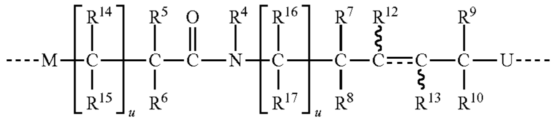
C72
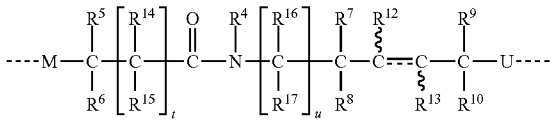
C73
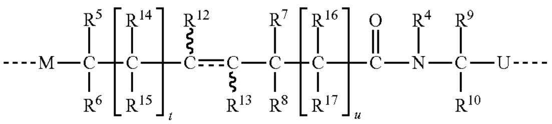
C74
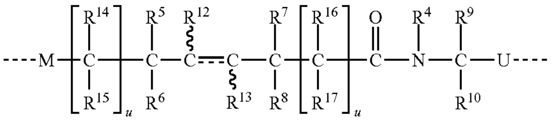
C75
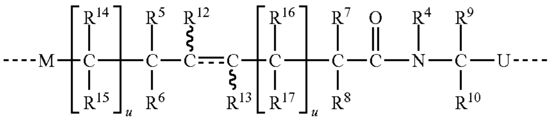
C76
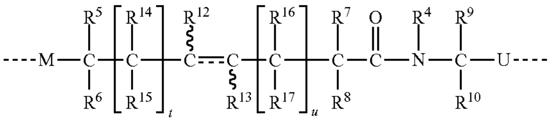
C77
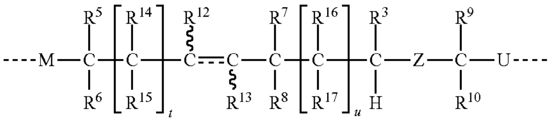
C78
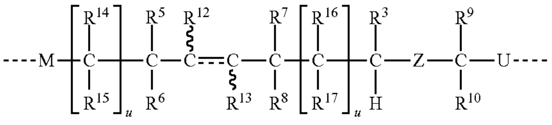
C79
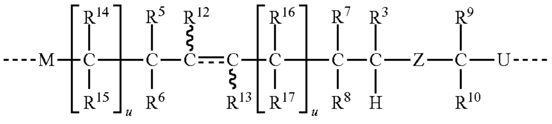
C80
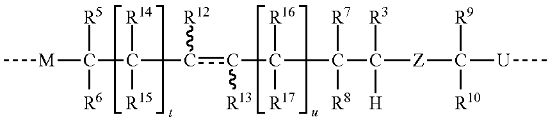
C81
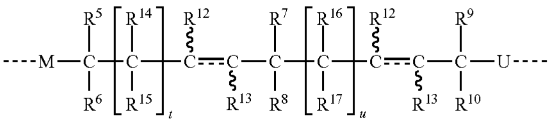
C82

TABLE 3-continued
Representations of Linker C
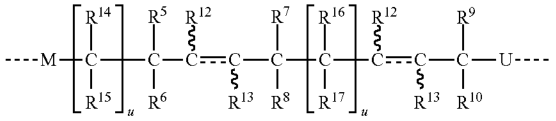
C83
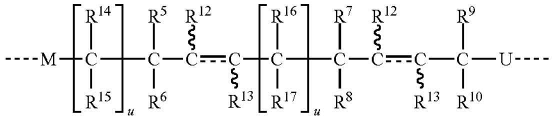
C84
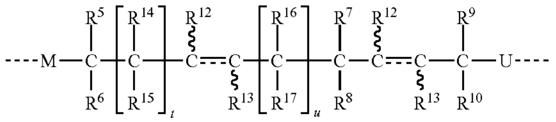
C85
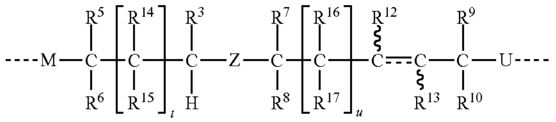
C86
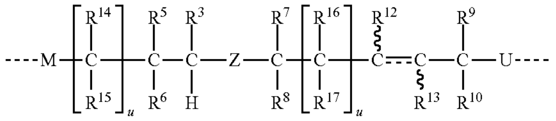
C87
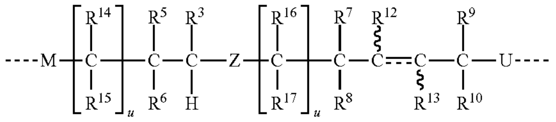
C88
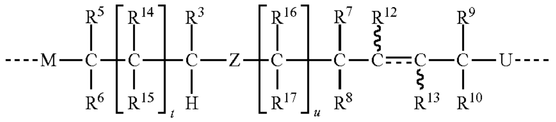
C89
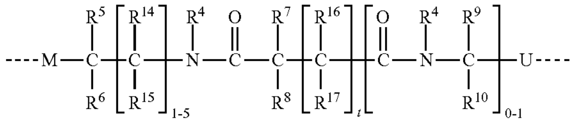
C90
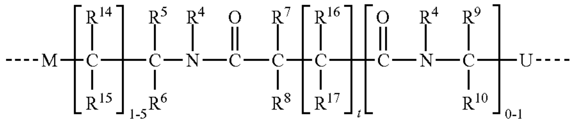
C91
TABLE 3-continued
Representations of Linker C
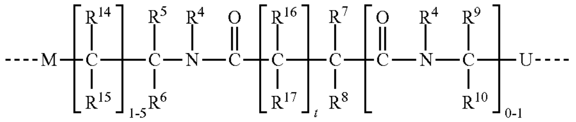
C92
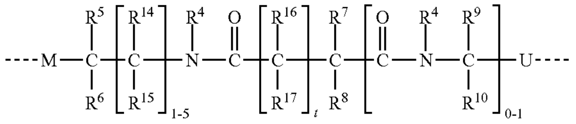
C93
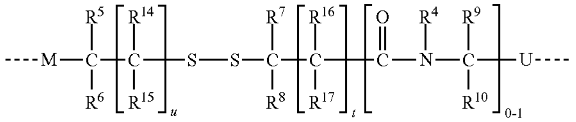
C94
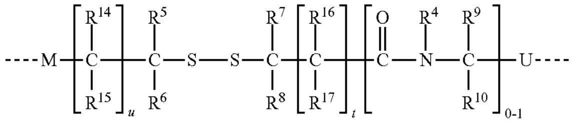
C95
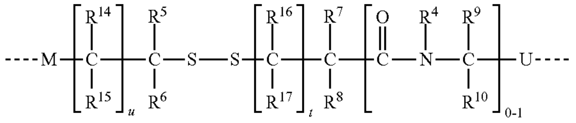
C96
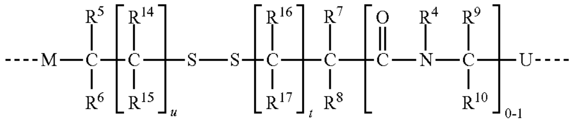
C97
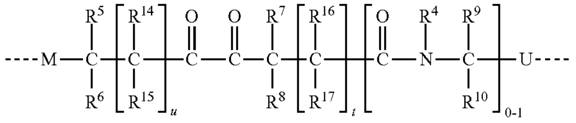
C98
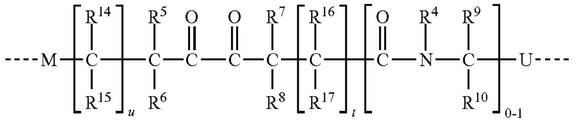
C99
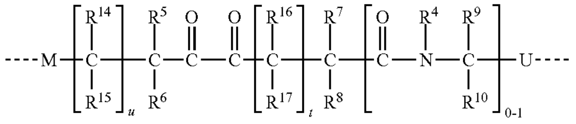
C100

TABLE 3-continued

Representations of Linker C

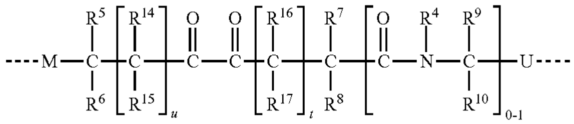

C101

According to the preceding definitions, macrocycles of type Ia/Ib contain at least one amide bond or isosteric surrogates thereof. As mentioned in the introduction, tertiary amide containing products generally show various ratios of cis and trans amide bond conformations in solution; this preference is in contrast to secondary amides that strongly prefer trans conformations. The occurrence of cis and/or trans conformations in macrocyclic natural products containing tertiary amide groups is well documented. In some cases a rapid equilibration between the cis and trans amide bonds, a so-called "peptidyl cis/trans isomerization", is observed; whereas in other cases discrete cis and trans tertiary amide bonds are detected as two stable conformers in solution at room temperature.

Consequently all possible stereoisomers (explicitly including atropisomers), conformers or rotamers of macrocycles Ia/Ib are part of this invention.

The substituents mentioned in formulae Ia and Ib, respectively in the above description of the building blocks A, B or C are defined in detail with the following terms:

$R^1$ is H; F; Cl; Br; I; $CF_3$; $OCF_3$; $OCHF_2$; $NO_2$; CN; alkyl; alkenyl; alkynyl; cycloalkyl; heterocycloalkyl; aryl; heteroaryl; arylalkyl; heteroarylalkyl; $—(CR^{18}R^{19})_qOR^{20}$; $—(CR^{18}R^{19})_qSR^{20}$; $—(CR^{18}R^{19})_qNR^4R^{11}$; $—(CR^{18}R^{19})_qOCONR^4R^{11}$; $—(CR^{18}R^{19})_qOCOOR^{21}$; $—(CR^{18}R^{19})_qNR^4COOR^{21}$; $—(CR^{18}R^{19})_qNR^4COR^{22}$; $—(CR^{18}R^{19})_qNR^4CONR^4R^{11}$; $—(CR^{18}R^{19})_qNR^4SO_2R^{23}$; $—(CR^{18}R^{19})_qNR^4SO_2NR^4R^{11}$; $—(CR^{18}R^{19})_qCOOR^{21}$; $—(CR^{18}R^{19})_qCONR^4R^{11}$; $—(CR^{18}R^{19})_qSO_2NR^4R^{11}$; $—(CR^{18}R^{19})_qPO(OR^{21})_2$; $—(CR^{18}R^{19})_qOPO(OR^{21})_2$; $—(CR^{18}R^{19})_qCOR^{22}$; $—(CR^{18}R^{19})_qSO_2R^{23}$; $—(CR^{18}R^{19})_qOSO_3R^{21}$; $—(CR^{18}R^{19})_qR^{24}$; $—(CR^{18}R^{19})_qR^{25}$; or $—(CR^{18}R^{19})_qR^{26}$;

$R^2$ is H; $CF_3$; alkyl; alkenyl; cycloalkyl; heterocycloalkyl; aryl; heteroaryl; arylalkyl; heteroarylalkyl; $—(CR^{18}R^{19})_qOR^{20}$; $—(CR^{18}R^{19})_qSR^{20}$; $—(CR^{18}R^{19})_qNR^4R^{11}$; $—(CR^{18}R^{19})_qOCONR^4R^{11}$; $—(CR^{18}R^{19})_qOCOOR^{21}$; $—(CR^{18}R^{19})_qNR^4COOR^{21}$; $—(CR^{18}R^{19})_qNR^4COR^{22}$; $—(CR^{18}R^{19})_qNR^4CONR^4R^{11}$; $—(CR^{18}R^{19})_qNR^4SO_2R^{23}$; $—(CR^{19}R^{19})_qNR^4SO_2NR^4R^{11}$; $—(CR^{18}R^{19})_qCOOR^{21}$; $—(CR^{18}R^{19})_qCONR^4R^{11}$; $—(CR^{18}R^{19})_qSO_2NR^4R^{11}$; $—(CR^{18}R^{19})_qPO(OR^{21})_2$; $—(CR^{18}R^{19})_qCOR^{22}$; $—(CR^{18}R^{19})_qSO_2R^{23}$; $—(CR^{18}R^{19})_qR^{24}$; $—(CR^{18}R^{19})_qR^{25}$; or $—(CR^{18}R^{19})_qR^{26}$;

$R^3$ is H; $CF_3$; alkyl; cycloalkyl; heterocycloalkyl; aryl; heteroaryl; arylalkyl; or heteroarylalkyl;

$R^4$ is H; alkyl; alkenyl; cycloalkyl; heterocycloalkyl; aryl; heteroaryl; arylalkyl; heteroarylalkyl; or a suitable N-protecting group;

$R^5$, $R^7$ and $R^9$ are independently defined as is H; F; $CF_3$; alkyl; alkenyl; cycloalkyl; heterocycloalkyl; aryl; heteroaryl; arylalkyl; heteroarylalkyl; $—(CR^{18}R^{19})_qOR^{20}$; $—(CR^{18}R^{19})_qSR^{20}$; $—(CR^{18}R^{19})_qNR^4R^{11}$; $—(CR^{18}R^{19})_qOCONR^4R^{11}$; $—(CR^{18}R^{19})_qOCOOR^{21}$; $—(CR^{18}R^{19})_qNR^4COOR^{21}$; $—(CR^{18}R^{19})_qNR^4COR^{22}$; $—(CR^{18}R^{19})_qNR^4CONR^4R^{11}$; $—(CR^{18}R^{19})_qNR^4SO_2R^{23}$; $—(CR^{18}R^{19})_qNR^4SO_2NR^4R^{11}$; $—(CR^{18}R^{19})_qCOOR^{21}$; $—(CR^{18}R^{19})_qCONR^4R^{11}$; $—(CR^{18}R^{19})_qSO_2NR^4R^{11}$; $—(CR^{18}R^{19})_qPO(OR^{21})_2$; $—(CR^{18}R^{19})_qCOR^{22}$; $—(CR^{18}R^{19})_qSO_2R^{23}$; $—(CR^{18}R^{19})_qR^{24}$; $—(CR^{18}R^{19})_qR^{25}$; or $—(CR^{18}R^{19})_qR^{26}$;

$R^6$, $R^8$ and $R^{10}$ are independently defined as H; F; $CF_3$; alkyl; alkenyl; cycloalkyl; heterocycloalkyl; aryl; heteroaryl; arylalkyl; or heteroarylalkyl;

$R^{11}$ is H; alkyl; alkenyl; cycloalkyl; heterocycloalkyl; aryl; heteroaryl; arylalkyl; heteroarylalkyl; a suitable protecting group; $—(CR^{18}R^{19})_rOR^{20}$; $—(CR^{18}R^{19})_rSR^{20}$; $—(CR^{18}R^{19})_rNR^4R^{27}$; $—(CR^{18}R^{19})_rOCONR^4R^{27}$; $—(CR^{18}R^{19})_rOCOOR^{21}$; $—(CR^{18}R^{19})_rNR^4COOR^{21}$; $—(CR^{18}R^{19})_rNR^4CONR^4R^{27}$; $—(CR^{18}R^{19})_rNR^4SO_2R^{23}$; $—(CR^{18}R^{19})_rNR^4SO_2NR^4R^{27}$; $—(CR^{18}R^{19})_qCOOR^{21}$; $—(CR^{18}R^{19})_qCONR^4R^{27}$; $—(CR^{18}R^{19})_qCOR^{22}$; $—(CR^{18}R^{19})_qSO_2R^{23}$; $—(CR^{18}R^{19})_qSO_2NR^4R^{27}$; $—(CR^{18}R^{19})_qR^{24}$; $—(CR^{18}R^{19})_sR^{25}$; $—(CR^{18}R^{19})_qR^{26}$; or $—(CR^{18}R^{19})_qR^{31}$;

$R^{12}$ and $R^{13}$ are independently defined as H; or alkyl.

$R^{14}$ and $R^{16}$ are independently defined as H; F; $CF_3$; alkyl; alkenyl; cycloalkyl; heterocycloalkyl; aryl; heteroaryl; arylalkyl; heteroarylalkyl; $—(CR^{18}R^{19})_qOR^{20}$; $—(CR^{18}R^{19})_qNR^4R^{11}$; $—(CR^{18}R^{19})_qNR^4COOR^{21}$; $—(CR^{18}R^{19})_qNR^4COR^{22}$; $—(CR^{18}R^{19})_qNR^4CONR^4R^{11}$; $—(CR^{18}R^{19})_qNR^4SO_2R^{23}$; $—(CR^{18}R^{19})_qNR^4SO_2NR^4R^{11}$; $—(CR^{18}R^{19})_qCOOR^{21}$; $—(CR^{18}R^{19})_qCONR^4R^{11}$; $—(CR^{18}R^{19})_qSO_2NR^4R^{11}$; or $—(CR^{18}R^{19})_qCOR^{22}$;

$R^{15}$ and $R^{17}$ are independently defined as H; F; $CF_3$; alkyl; alkenyl; cycloalkyl; heterocycloalkyl; aryl; heteroaryl; arylalkyl; or heteroarylalkyl;

$R^{18}$ is H; F; $CF_3$; alkyl; alkenyl; cycloalkyl; heterocycloalkyl; aryl; heteroaryl; arylalkyl; heteroarylalkyl; $—(CR^{29}R^{30})_sOR^{31}$; $—(CR^{29}R^{30})_sSR^{31}$; $—(CR^{29}R^{30})_sNR^{28}R^{31}$; $—(CR^{29}R^{30})_sOCONR^{28}R^{31}$; $—(CR^{29}R^{30})_sOCOOR^{21}$; $—(CR^{29}R^{30})_sNR^{28}COOR^{21}$; $—(CR^{29}R^{30})_sNR^{28}COR^{31}$; $—(CR^{29}R^{30})_sNR^{28}CONR^{28}R^{31}$; $—(CR^{29}R^{30})_sNR^{28}SO_2R^{23}$; $—(CR^{29}R^{30})_sNR^{28}SO_2NR^{28}R^{31}$; $—(CR^{29}R^{30})_qCOOR^{21}$; $—(CR^{29}R^{30})_qCONR^{28}R^{31}$; $—(CR^{29}R^{30})_qSO_2NR^{28}R^{31}$; $—(CR^{29}R^{30})_qPO(OR^{21})_2$; $—(CR^{29}R^{30})_qCOR^{31}$; $—(CR^{29}R^{30})_qSO_2R^{23}$; $—(CR^{29}R^{30})_qR^{24}$; $—(CR^{29}R^{30})_qR^{25}$; or $—(CR^{29}R^{30})_qR^{26}$;

$R^{19}$ is H; $CF_3$; alkyl; alkenyl; cycloalkyl; heterocycloalkyl; aryl; heteroaryl; arylalkyl; or heteroarylalkyl;

$R^{20}$ is H; alkyl; alkenyl; cycloalkyl; heterocycloalkyl; aryl; heteroaryl; arylalkyl; heteroarylalkyl; $—(CR^{29}R^{30})_rOR^{31}$; $—(CR^{29}R^{30})_rSR^{31}$; $—(CR^{29}R^{30})_rNR^{28}R^{31}$; $—(CR^{29}R^{30})_rOCONR^{28}R^{31}$; $—(CR^{29}R^{30})_rNR^{28}COOR^{21}$; $—(CR^{29}R^{30})_rNR^{28}COR^{31}$; $—(CR^{29}R^{30})_rNR^{28}CONR^{28}R^{31}$; $—(CR^{29}R^{30})_rNR^{28}SO_2R^{23}$; $—(CR^{29}R^{30})_rNR^{28}SO_2NR^{28}R^{31}$; $—(CR^{29}R^{30})_qCOOR^{21}$; $—(CR^{29}R^{30})_qCONR^{28}R^{31}$; $—(CR^{29}R^{30})_qSO_2NR^{28}R^{31}$; $—(CR^{29}R^{30})_qCOR^{31}$; $—(CR^{29}R^{30})_qSO_2R^{23}$; $—(CR^{29}R^{30})_qR^{24}$; $—(CR^{29}R^{30})_qR^{25}$; $—(CR^{29}R^{30})_qR^{26}$; or $—(CR^{29}R^{30})_qR^{31}$;

$R^{21}$ is H; alkyl; alkenyl; cycloalkyl; heterocycloalkyl; aryl; heteroaryl; arylalkyl; heteroarylalkyl; or a suitable O-protecting group;

$R^{22}$ is alkyl; alkenyl; cycloalkyl; heterocycloalkyl; aryl; heteroaryl; arylalkyl; heteroarylalkyl; $—(CR^{29}R^{30})_sOR^{31}$; $—(CR^{29}R^{30})_sSR^{31}$; $—(CR^{29}R^{30})_sNR^{28}R^{31}$; $—(CR^{29}R^{30})_sOCONR^{28}R^{31}$; $—(CR^{29}R^{30})_sNR^{28}COOR^{21}$; $—(CR^{29}R^{30})_sNR^{28}COR^{31}$;

$-(CR^{29}R^{30})_sNR^{28}CONR^{28}R^{31}$; $-(CR^{29}R^{30})_sNR^{28}SO_2NR^{23}$; $-(CR^{29}R^{30})_sNR^{28}SO_2NR^{28}R^{31}$; $-(CR^{29}R^{30})_sCOOR^{21}$; $-(CR^{29}R^{30})_sCONR^{28}R^{31}$; $-(CR^{29}R^{30})_sSO_2NR^{28}R^{31}$; $-(CR^{29}R^{30})_tCOR^{31}$; $-(CR^{29}R^{30})_sSO_2R^{23}$; $-(CR^{29}R^{30})_tR^{24}$; $-(CR^{29}R^{30})_rR^{25}$; $-(CR^{29}R^{30})_rR^{26}$; or $-(CR^{29}R^{30})_6R^{31}$;

$R^{23}$ is H; alkyl; alkenyl; cycloalkyl; heterocycloalkyl; aryl; heteroaryl; arylalkyl; heteroarylalkyl; or $-(CR^{32}R^{33})_tR^{24}$;

$R^{24}$ is aryl; heteroaryl; $-C_6H_2R^{34}R^{35}R^{31}$; or a group of one of the formulae H1-H34 listed in Table 4.

TABLE 4

Groups of Formulae H1-H34

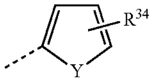
H1

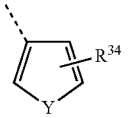
H2

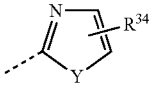
H3

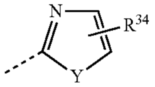
H4

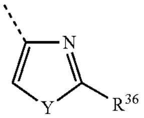
H5

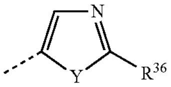
H6

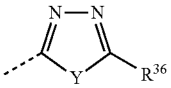
H7

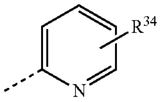
H8

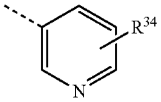
H9

TABLE 4-continued

Groups of Formulae H1-H34

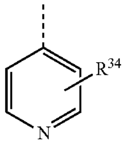
H10

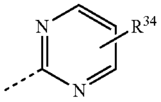
H11

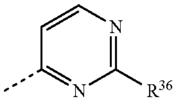
H12

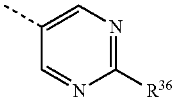
H13

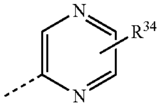
H14

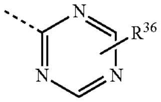
H15

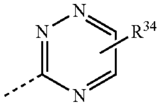
H16

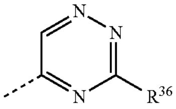
H17

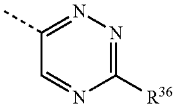
H18

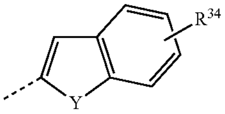
H19

TABLE 4-continued
Groups of Formulae H1-H34
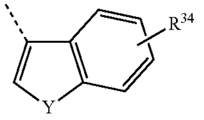
H20
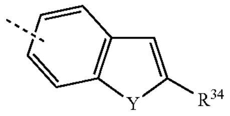
H21
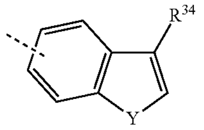
H22
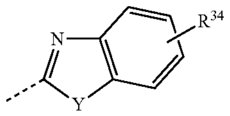
H23
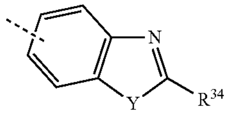
H24
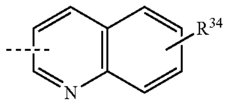
H25
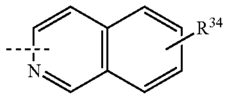
H26
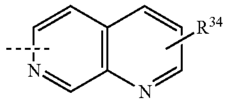
H27
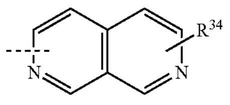
H28
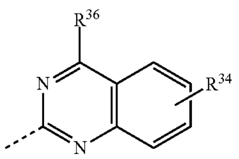
H29
TABLE 4-continued
Groups of Formulae H1-H34
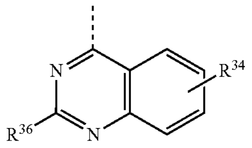
H30
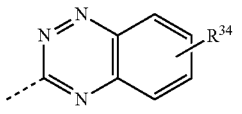
H31
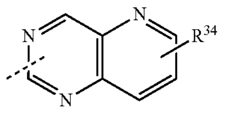
H32
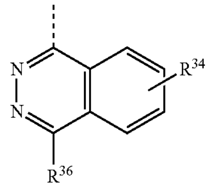
H33
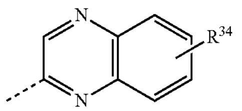
H34
$R^{25}$ is a group of one of formulae H35-H41 as shown in Table 5 below.
TABLE 5
Radicals of Formulae H35-H41
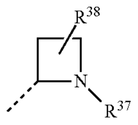
H35
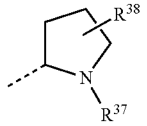
H36
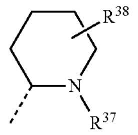
H37

TABLE 5-continued

| Radicals of Formulae H35-H41 |
|---|
| 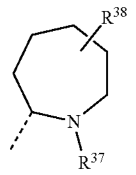 |
| H38 |
| 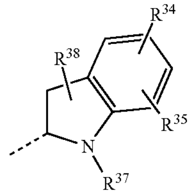 |
| H39 |
| 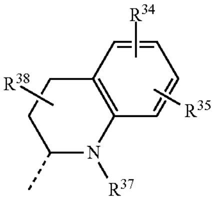 |
| H40 |
| 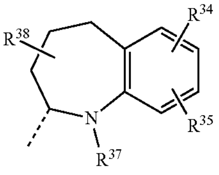 |
| H41 |

$R^{26}$ is a group of one of formulae H42-H50 as shown in Table 6 below.

Table 6

| Groups of Formulae H42-H50 |
|---|
| 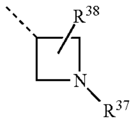 |
| H42 |
| 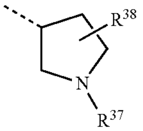 |
| H43 |
| 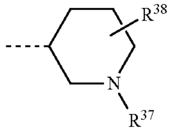 |
| H44 |

Table 6-continued

| Groups of Formulae H42-H50 |
|---|
| 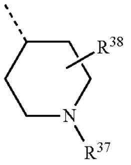 |
| H45 |
| 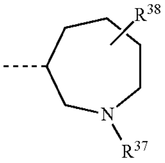 |
| H46 |
| 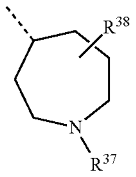 |
| H47 |
| 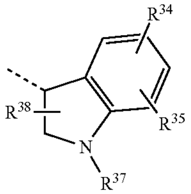 |
| H48 |
| 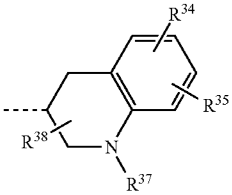 |
| H49 |
| 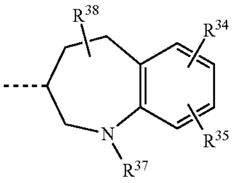 |
| H50 |

$R^{27}$ is H; alkyl; lower alkenyl; cycloalkyl; heterocycloalkyl; aryl; heteroaryl; lower arylalkyl; lower heteroarylalkyl; a suitable protecting group; or $—(CR^{29}R^{30})_qR^{24}$;

$R^{28}$ is H; alkyl; lower alkenyl; cycloalkyl; heterocycloalkyl; aryl; heteroaryl; lower arylalkyl; lower heteroarylalkyl; a suitable N-protecting group; $—(CR^{32}R^{33})_sOR^{21}$; $—(CR^{32}R^{33})_sNR^{43}R^{42}$;

$-(CR^{32}R^{33})_sNR^{42}CONR^{43}R^{42}$; $-(CR^{32}R^{33})_sNR^{42}COR^{21}$; $-(CR^{32}R^{33})_sNR^{42}SO_2NR^{21}$; $-(CR^{32}R^{33})_qCOOR^{21}$; $-(CR^{32}R^{33})_qCOR^{23}$; or $-(CR^{32}R^{33})_qSO_2R^{21}$;

$R^{29}$ is H; F; $CF_3$; alkyl; alkenyl; cycloalkyl; heterocycloalkyl; aryl; heteroaryl; arylalkyl; heteroarylalkyl; $-(CR^{32}R^{33})_sOR^{31}$; $-(CR^{32}R^{33})_sSR^{31}$; $-(CR^{32}R^{33})_sNR^{28}R^{31}$; $-(CR^{32}R^{33})_sOCONR^{28}R^{31}$; $-(CR^{32}R^{33})_sOCOOR^{21}$; $-(CR^{32}R^{33})_sNR^{28}COOR^{21}$; $-(CR^{32}R^{33})_sNR^{28}COR^{31}$; $-(CR^{32}R^{33})_sNR^{28}CONR^{28}R^{31}$; $-(CR^{32}R^{33})_sNR^{28}SO_2R^{23}$; $-(CR^{32}R^{33})_sNR^{28}SO_2NR^{28}R^{31}$; $-(CR^{32}R^{33})_qCONR^{21}$; $-(CR^{32}R^{33})_qCONR^{28}R^{31}$; $-(CR^{32}R^{33})_qSO_2NR^{28}R^{31}$; $-(CR^{32}R^{33})_qPO(OR^{21})_2$; $-(CR^{32}R^{33})_qCOR^{31}$; $-(CR^{32}R^{33})_qSO_2R^{23}$; or $-(CR^{32}R^{33})_qR^{31}$;

$R^{30}$ is H; F; $CF_3$; alkyl; alkenyl; cycloalkyl; heterocycloalkyl; aryl; heteroaryl; arylalkyl; or heteroarylalkyl;

$R^{31}$ is H; alkyl; alkenyl; cycloalkyl; heterocycloalkyl; aryl; heteroaryl; arylalkyl; heteroarylalkyl; or a group of one of the formulae H51-H55 as shown in Table 7 below.

TABLE 7

Groups of Formulae H51-H55

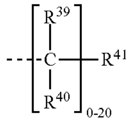

H51

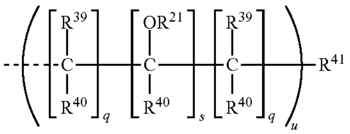

H52

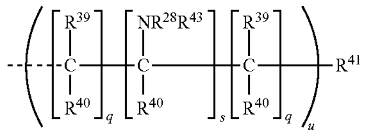

H53

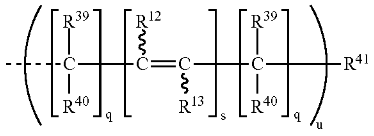

H54

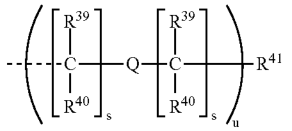

H55

$R^{32}$ and $R^{33}$ are independently defined as H; F; $CF_3$; alkyl; alkenyl; cycloalkyl; heterocycloalkyl; aryl; heteroaryl; arylalkyl; or heteroarylalkyl;

$R^{34}$ and $R^{35}$ are independently defined as H; F; Cl; $CF_3$; $OCF_3$; $OCHF_2$; $NO_2$; CN; alkyl; alkenyl; alkynyl; cycloalkyl; heterocycloalkyl; aryl; heteroaryl; arylalkyl; heteroarylalkyl; $-(CR^{29}R^{30})_qOR^{31}$; $-(CR^{29}R^{30})_qSR^{31}$; $-(CR^{29}R^{30})_qNR^{28}R^{31}$; $-(CR^{29}R^{30})_qOCONR^{28}R^{31}$; $-(CR^{29}R^{30})_qNR^{28}COOR^{21}$; $-(CR^{29}R^{30})_qNR^{28}COR^{31}$; $-(CR^{29}R^{30})_qNR^{28}CONR^{28}R^{31}$; $-(CR^{29}R^{30})_qNR^{28}R^{23}$; $-(CR^{29}R^{30})_qSO_2NR^{28}R^{31}$; $-(CR^{29}R^{30})_qCOOR^{21}$; $-(CR^{29}R^{30})_qCONR^{28}R^{31}$; $-(CR^{29}R^{30})_qSO_2NR^{28}R^{31}$; $-(CR^{29}R^{30})_qCOR^{31}$; $-(CR^{29}R^{30})_qSO_2R^{23}$; or $-(CR^{29}R^{30})_qR^{31}$;

$R^{36}$ is H; alkyl; alkenyl; alkynyl; cycloalkyl; heterocycloalkyl; aryl; heteroaryl; arylalkyl; heteroarylalkyl; or $-NR^{28}R^{31}$;

$R^{37}$ is H; alkyl; alkenyl; cycloalkyl; heterocycloalkyl; aryl; heteroaryl; arylalkyl; heteroarylalkyl; a suitable N-protecting group; $-(CR^{29}R^{30})_rOR^{31}$; $-(CR^{29}R^{30})_rSR^{31}$; $-(CR^{29}R^{30})_rNR^{28}R^{31}$; $-(CR^{29}R^{30})_rOCONR^{28}R^{31}$; $-(CR^{29}R^{30})_rNR^{28}COOR^{21}$; $-(CR^{29}R^{30})_rNR^{28}COR^{31}$; $-(CR^{29}R^{30})_rNR^{28}CONR^{28}R^{31}$; $-(CR^{29}R^{30})_rNR^{28}SO_2R^{23}$; $-(CR^{29}R^{30})_rNR^{28}SO_2NR^{28}R^{31}$; $-(CR^{29}R^{30})_qCOOR^{21}$; $-(CR^{29}R^{30})_qCONR^{28}R^{31}$; $-(CR^{29}R^{30})_rSO_2NR^{28}R^{31}$; $-(CR^{29}R^{30})_qCOR^{31}$; $-(CR^{29}R^{30})_qSO_2R^{23}$; or $-(CR^{29}R^{30})_qR^{31}$;

$R^{38}$ is H; alkyl; alkenyl; cycloalkyl; heterocycloalkyl; aryl; heteroaryl; arylalkyl; heteroarylalkyl; $-(CR^{29}R^{30})_qOR^{31}$; $-(CR^{29}R^{30})_qSR^{31}$; $-(CR^{29}R^{30})_qNR^{28}R^{31}$; $-(CR^{29}R^{30})_qNR^{28}COOR^{21}$; $-(CR^{29}R^{30})_qNR^{28}COR^{31}$; $-(CR^{29}R^{30})_qNR^{28}CONR^{28}R^{31}$; $-(CR^{29}R^{30})_qCOOR^{21}$; $-(CR^{29}R^{30})_qCONR^{28}R^{31}$; $-(CR^{29}R^{30})_qCOR^{31}$; or $-(CR^{29}R^{30})_qR^{31}$;

$R^{39}$ is H; F; $CF_3$; alkyl; alkenyl; cycloalkyl; heterocycloalkyl; aryl; heteroaryl; arylalkyl; heteroarylalkyl; $-(CR^{32}R^{33})_uOR^{21}$; $-(CR^{32}R^{33})_uNR^{28}R^{43}$; $-(CR^{32}R^{33})_tCOOR^{21}$; or $-(CR^{32}R^{33})_tCONR^{28}R^{43}$;

$R^{40}$ is H; F; $CF_3$; alkyl; alkenyl; cycloalkyl; heterocycloalkyl; aryl; heteroaryl; arylalkyl; heteroarylalkyl; $-(CR^{32}R^{33})_uOR^{21}$; $-(CR^{32}R^{33})_uNR^{28}R^{43}$; $-(CR^{32}R^{33})_tCOOR^{21}$; or $-(CR^{32}R^{33})_tCONR^{28}R^{43}$;

$R^{41}$ is H; $CF_3$; alkyl; alkenyl; cycloalkyl; heterocycloalkyl; aryl; heteroaryl; arylalkyl; heteroarylalkyl; $-OR^{21}$; $-NR^{28}R^{43}$; $-NR^{28}COR^{23}$; $-NR^{28}COOR^{21}$; $-NR^{28}SO_2R^{23}$; $-NR^{28}CONR^{28}R^{43}$; $-COOR^{21}$; $-CONR^{28}R^{43}$; $-C(=NR^{43})NR^{28}R^{43}$; $-NR^{28}C(=NR^{43})NR^{28}R^{43}$; or a group of one of the formulae H56-H110 as shown in Table 8 below.

TABLE 8

Groups of Formulae H56-H110

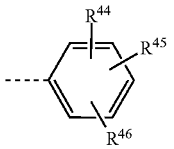

H56

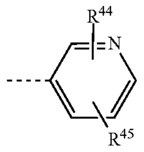

H57

TABLE 8-continued
| Groups of Formulae H56-H110 |
| --- |
| 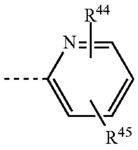 H58 |
| 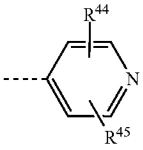 H59 |
| 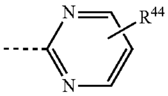 H60 |
| 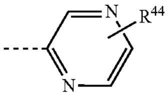 H61 |
| 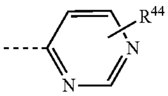 H62 |
| 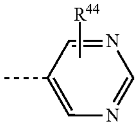 H63 |
| 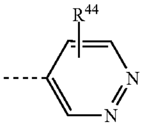 H64 |
| 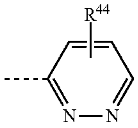 H65 |
| 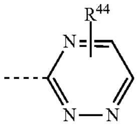 H66 |
TABLE 8-continued
| Groups of Formulae H56-H110 |
| --- |
| 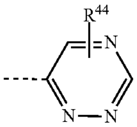 H67 |
| 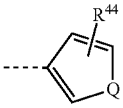 H68 |
| 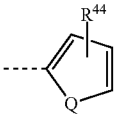 H69 |
| 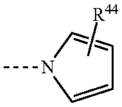 H70 |
| 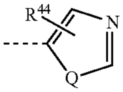 H71 |
| 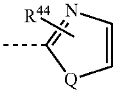 H72 |
| 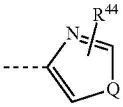 H73 |
| 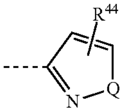 H74 |
| 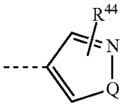 H75 |
| 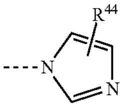 H76 |

TABLE 8-continued
Groups of Formulae H56-H110
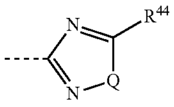
H77
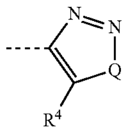
H78
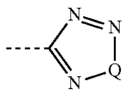
H79
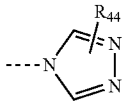
H80
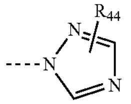
H81
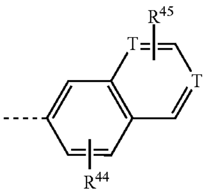
H82
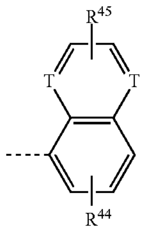
H83
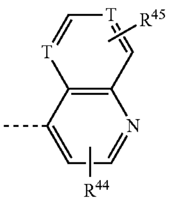
H84
TABLE 8-continued
Groups of Formulae H56-H110
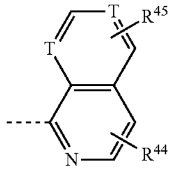
H85
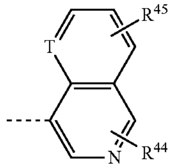
H86
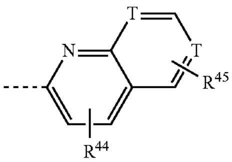
H87
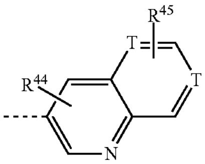
H88
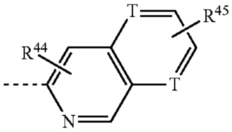
H89
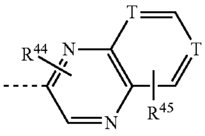
H90
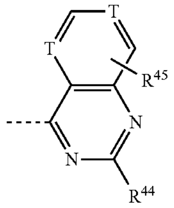
H91

TABLE 8-continued
| Groups of Formulae H56-H110 |
|---|
| 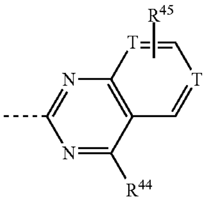 H92 |
| 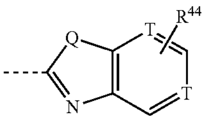 H93 |
| 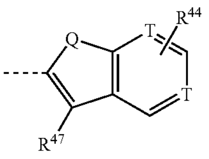 H94 |
| 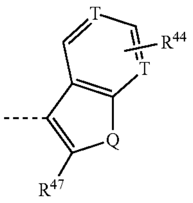 H95 |
| 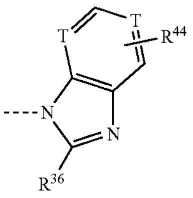 H96 |
| 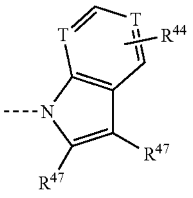 H97 |
| 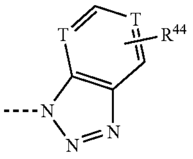 H98 |
TABLE 8-continued
| Groups of Formulae H56-H110 |
|---|
| 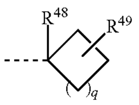 H99 |
| 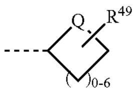 H100 |
| 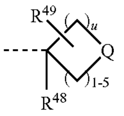 H101 |
| 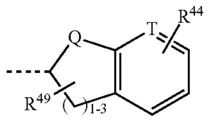 H102 |
| 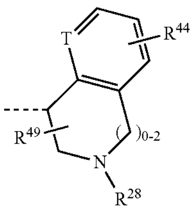 H103 |
| 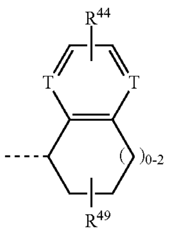 H104 |
| 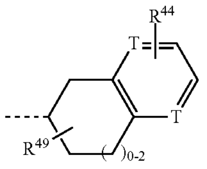 H105 |
| 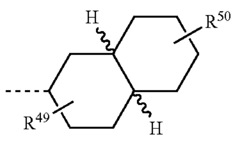 H106 |

TABLE 8-continued

| Groups of Formulae H56-H110 |
|---|
| 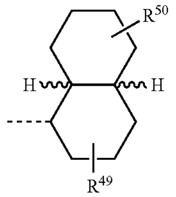 |
| H107 |
| 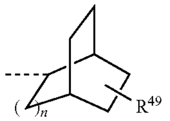 |
| H108 |
| 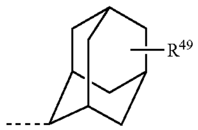 |
| H109 |
| 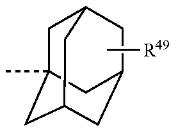 |
| H110 |

$R^{42}$ is H; alkyl; alkenyl; cycloalkyl; cycloheteroalkyl; aryl; heteroaryl; $—(CR^{23}R^{33})_sOR^{21}$; $—(CR^{23}R^{33})_sNR^4R^{43}$; $—(CR^{23}R^{33})_qCOOR^{21}$; or $—(CR^{23}R^{33})_qCONR^4R^{43}$;

$R^{43}$ is H; alkyl; alkenyl; cycloalkyl; heterocycloalkyl; aryl; heteroaryl; arylalkyl; heteroarylalkyl; or a suitable N-protecting group;

$R^{44}$, $R^{45}$ and $R^{46}$ are independently defined as H; F; $CF_3$; $OCF_3$; $OCHF_2$; $NO_2$; CN; alkyl; alkenyl; alkynyl; cycloalkyl; heterocycloalkyl; aryl; heteroaryl; arylalkyl; heteroarylalkyl; $—OR^{23}$; $—NR^{28}R^{43}$; $—NR^{28}COR^{23}$; $—NR^{28}SO_2R^{23}$; $—NR^{28}CONR^{28}R^{43}$; $—COR^{23}$; or $—SO_2R^{23}$;

$R^{47}$ is H; $CF_3$; alkyl; alkenyl; alkynyl; cycloalkyl; heterocycloalkyl; aryl; heteroaryl; arylalkyl; heteroarylalkyl; $—COOR^{21}$; or $—CONR^{28}R^{43}$;

$R^{48}$ is H; F; $CF_3$; alkyl; alkenyl; cycloalkyl; cycloheteroalkyl; aryl; heteroaryl; $—(CR^{23}R^{33})_tOR^1$; $—(CR^{23}R^{33})_tNR^{28}R^{43}$; $—(CR^{23}R^{33})_tCOOR^{21}$; or $—(CR^{23}R^{33})_tCONR^{21}R^{43}$ $R^{49}$ and $R^{50}$ are independently defined as H; F; $CF_3$; alkyl; alkenyl; cycloalkyl; heterocycloalkyl; aryl; heteroaryl; arylalkyl; heteroarylalkyl; $—(CR^{32}R^{33})_qOR^{21}$; $—(CR^{32}R^{33})_qNR^{28}R^{43}$; $—(CR^{32}R^{33})_qCOOR^{21}$; or $—(CR^{32}R^{33})_qCONR^{28}R^{43}$;

$R^{51}$ is H; F; Cl; $CF_3$; $OCF_3$; or lower alkyl;

$R^{52}$ is H; F; Cl; $CF_3$; $OCF_3$; $OCHF_2$; $NO_2$; CN; lower alkyl; lower alkenyl; lower alkynyl; lower cycloalkyl; lower heterocycloalkyl; aryl; heteroaryl; lower arylalkyl; or lower heteroarylalkyl;

$R^{53}$ is $CF_3$; $OCF_3$; CN; lower alkyl; lower cycloalkyl; aryl; lower alkoxy; or aryloxy.

Taken together, the following pairs of said substituents can define cyclic structural elements:

Taken together ($R^4$ and $R^{11}$); ($R^4$ and $R^{27}$); ($R^5$ and $R^6$); ($R^5$ and $R^7$); ($R^5$ and $R^9$); ($R^5$ and $R^{14}$); ($R^5$ and $R^{16}$); ($R^7$ and $R^8$); ($R^7$ and $R^9$); ($R^7$ and $R^{16}$); ($R^9$ and $R^{10}$); ($R^{14}$ and $R^{15}$); ($R^{16}$ and $R^{17}$); ($R^{18}$ and $R^{19}$); ($R^{27}$ and $R^{28}$); ($R^{28}$ and $R^{31}$); ($R^{28}$ and $R^{43}$); ($R^{29}$ and $R^{30}$); ($R^{32}$ and $R^{33}$); ($R^{34}$ and $R^{35}$); ($R^{37}$ and $R^{38}$); ($R^{39}$ and $R^{40}$); ($R^{39}$ and $R^{41}$); ($R^{39}$ and $R^{49}$); ($R^{42}$ and $R^{43}$); ($R^{44}$ and $R^{45}$); or ($R^{44}$ and $R^{46}$) can form optionally substituted cycloalkyl or heterocycloalkyl moieties.

In addition, the structural elements $—NR^4R^{11}$; $—NR^{11}R^{27}$; $—NR^{27}R^{28}$; $—NR^{28}R^{31}$ or $—NR^{28}R^{43}$ can form one of the groups of formulae H111-H118 as shown in Table 9 below.

TABLE 9

| Heterocyclic Groups Defined by Linking the Residues of the Disubstituted Amino Groups $—NR^4R^{11}$; $—NR^{11}R^{27}$; $—NR^{27}R^{28}$; $—NR^{28}R^{31}$ or $—NR^{28}R^{43}$. |
|---|
| 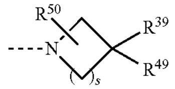 |
| H111 |
| 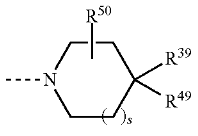 |
| H112 |
| 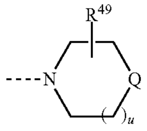 |
| H113 |
| 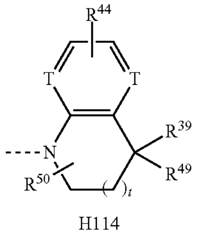 |
| H114 |
| 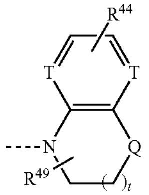 |
| H115 |
| 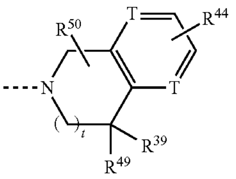 |
| H116 |

TABLE 9-continued

Heterocyclic Groups Defined by Linking the Residues of the Disubstituted Amino Groups $—NR^4R^{11}$; $—NR^{11}R^{27}$; $—NR^{27}R^{28}$; $—NR^{28}R^{31}$ or $—NR^{28}R^{43}$.

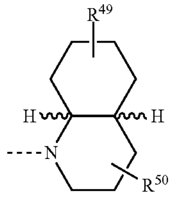

H117

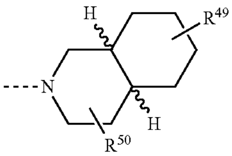

H118

Variable heteroatoms and connector groups in the aforementioned structures are:

Z is O; S; S(═O); $S(═O)_2$; or $NR^{28}$;

Y is O; S; or $NR^4$;

Q is O; S; or $NR^{28}$;

T is $CR^{46}$ or N; in case T occurs several times in the same ring structure each T is defined independently of the other.

The indices in the aforementioned structures are defined as:

q is an integer of 0-4;

is an integer of 2-4;

s is an integer of 1-4;

t is an integer of 0-2;

u is an integer of 1-2.

Some of the aforementioned substituents can occur several times within the same molecular entity, for example, but not limited to $R^{14}$, $R^{15}$, $R^{16}$, $R^{17}$, $R^{18}$, $R^{19}$, $R^{28}$, $R^{29}$, $R^{30}$, $R^{31}$, $R^{32}$, $R^{33}$, $R^{39}$, $R^{40}$, $R^{41}$, $R^{42}$, $R^{43}$, $R^{44}$, $R^{45}$, $R^{46}$, and $R^{50}$. Each one of such substituents shall be selected independently from the other radicals of the same type and within the scope of the definition of the respective group.

"Salts" as understood herein are especially, but not limited to, the pharmaceutically acceptable salts of compounds of formula Ia/Ib. Such salts are formed, for example, as acid addition salts, preferably with organic or inorganic acids, from compounds of type Ia/Ib with a basic nitrogen atom. Suitable inorganic acids are, for example, halogen acids, such as hydrochloric acid, sulfuric acid, or phosphoric acid. Suitable organic acids are, for example, carboxylic, phosphonic, sulfonic or sulfamic acids; like acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantinecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

As used in this description, the term "alkyl", taken alone or in combinations (i.e. as part of another group, such as "arylalkyl") designates saturated, straight-chain or branched hydrocarbon radicals having up to 24, preferably up to 12, carbon atoms. Most preferred in the present invention, "alkyl" is "lower alkyl" which designates alkyl groups having up to 6 carbon atoms.

The term "alkenyl", taken alone or in combinations, designates straight chain or branched hydrocarbon radicals having up to 24, preferably up to 12, carbon atoms and containing at least one or, depending on the chain length, up to four olefinic double bonds. Such alkenyl moieties can exist as E or Z configurations, both of which are part of the invention.

The term "alkynyl", taken alone or in combinations, refers to an aliphatic hydrocarbon chain and includes, but is not limited to, straight and branched chains having 2 to 10 carbon atoms (unless explicitly specified otherwise) and containing at least one triple bond.

The term "cycloalkyl", taken alone or in combinations, refers to a saturated alicyclic moiety having from three to ten carbon atoms.

The term "heterocycloalkyl", taken alone or in combinations, describes a saturated or partially unsaturated heterocyclic moiety having from three to seven ring carbon atoms and one or more ring heteroatoms selected from nitrogen, oxygen and sulphur. This term includes, for example, azetidinyl, pyrrolidinyl, tetrahydrofuranyl, piperidinyl and the like.

The term "aryl", taken alone or in combinations, designates aromatic carbocyclic hydrocarbon radicals containing one or two six-membered rings, such as phenyl or naphthyl, which may be substituted by up to three substituents such as F, Cl, Br, $CF_3$, $NO_2$, lower alkyl or lower alkenyl.

The term "heteroaryl", taken alone or in combinations, designates aromatic heterocyclic radicals containing one or two five- and/or six-membered rings, at least one of them containing up to three heteroatoms selected from the group consisting of O, S and N and whereby the heteroaryl radicals or tautomeric forms thereof may be attached via any suitable atom. Said heteroaryl ring(s) are optionally substituted, e.g. as indicated above for "aryl".

The term "arylalkyl", as used herein, whether used alone or as part of another group, refers to the group $—R^a—R^b$, where $R^a$ is an alkyl group as defined above, substituted by $R^b$, an aryl group, as defined above. Examples of arylalkyl moieties include, but are not limited to, benzyl, 1-phenylethyl, 2-phenylethyl, 3-phenylpropyl, 2-phenylpropyl and the like. Similarly, the term "lower arylalkyl", refers to the above moiety $—R^a—R^b$ wherein $R^a$ is a lower alkyl group.

The term "heteroarylalkyl", whether used alone or as part of another group, refers to the group $—R^a—R^c$, where $R^a$ is an alkyl group as defined above, substituted by $R^c$, a heteroaryl group, as defined above. Analogously the term "lower heteroarylalkyl", refers to the above moiety $—R^a—R^c$ but wherein $R^a$ is a lower alkyl group.

The terms "alkoxy" and "aryloxy", taken alone or in combinations, refer to the group $—O—R^a$, wherein $R^a$, is an alkyl group or an aryl group as defined above.

"Amino" designates primary, secondary or tertiary amines. Particular secondary and tertiary amines are alkylamines, dialkylamines, arylamines, diarylamines, arylalkylamines and diarylamines wherein the alkyl or aryl is as herein defined and optionally substituted.

The term "optionally substituted" is intended to mean that a group, such as but not limited to alkyl, alkenyl, alkynyl, cycloalkyl, aryl, heteroaryl, heterocycloalkyl, alkoxy and aryloxy may be substituted with one or more substituents independently selected from, e.g., halogen (F, Cl, Br, I), cyano (—CN), nitro (—$NO_2$), —$SR^a$, —$S(O)R^a$, —$S(O)_2R^a$, —$R^a$, —$C(O)R^a$, —$C(O)OR^a$, —$C(O)NR^bR^c$, —$C(=NR^a)NR^bR^c$, —$OR^a$, —$OC(O)R^a$, —$OC(O)OR^a$, —$OC(O)NR^bR^c$, —$OS(O)R^a$, —$OS(O)_2R^a$, —$OS(O)NR^bR^c$, —$OS(O)_2NR^bR^c$, —$NR^bR^c$, —$NR^aC(O)R^b$, —$NR^aC(O)OR^b$, —$NR^aC(O)NR^bR^c$, —$NR^aC(=NR^d)NR^bR^c$, —$NR^aS(O)R^b$, —$NR^aS(O)_2R^b$, wherein $R^a$, $R^b$, $R^c$, and $R^d$ are each independently, e.g., hydrogen, alkyl, alkenyl, alkynyl, cycloalkyl, aryl, heteroaryl, or heterocycloalkyl as described herein; or $R^b$ and $R^c$ may be taken together with the N-atom to which they are attached forming heterocycloalkyl or heteroaryl. These groups in turn can be substituted with any described moiety, including, but not limited to, one or more moieties selected from the group consisting of halogen (F, Cl, Br, or I), hydroxyl, amino, alkylamino (e.g., monoalkylamino, dialkylamino, or trialkylamino), arylamino (e.g. monoarylamino, diarylamino, or triarylamino), hydroxy, carboxy, alkoxy, aryloxy, nitro, cyano, sulfonic acid, sulfate, phosphonic acid, phosphate, or phosphonate.

Said groups, especially but not limited to hydroxy, amino and carboxyl, may be either unprotected or protected, if necessary, as well-known to those skilled in the art. Examples of suitable protecting groups are as detailed in P. G. M. Wuts, T. W. Greene, *Greene's Protective Groups in Organic Synthesis*, John Wiley and Sons, 4th Edition, 2006.

As used herein, all groups that can be substituted in one embodiment are indicated to be "optionally substituted", unless otherwise specified.

As mentioned earlier herein, the term "lower" designates radicals and compounds having up to 6 carbon atoms. Thus, for example, the term "lower alkyl" designates saturated, straight-chain, or branched hydrocarbon radicals having up to 6 carbon atoms, such as methyl, ethyl, n-propyl, isopropyl, n-butyl, s-butyl, isobutyl, t-butyl, and the like. Similarly, the term "lower cycloalkyl" designates saturated cyclic hydrocarbon radicals having up to 6 carbon atoms, such as cyclopropyl, cyclobutyl, cyclopentyl, cyclohexyl and the like.

The embodiments of the present invention shall include so-called "prodrugs" of the compounds of this invention. In general, such prodrugs will be functional derivatives of the compounds, which in vivo are readily convertible into the required compound. Conventional procedures for the selection and preparation of suitable prodrug derivatives are described, for example, in Hans Bundgaard, *Design of Prodrugs*, Elsevier, 1985; and in Valentino J. Stella et al., *Prodrugs: Challenges and Rewards*, Springer, 1st ed., 2007.

The term "isomer" comprises species of identical chemical formula, constitution and thus molecular mass, such as but not limited to C═C-double bond or amide cis/trans isomers, rotamers, conformers, diastereomers.

All possible stereoisomers (explicitly including atropisomers), conformers and rotamers as well as salts, solvates, clathrates, N-oxides, or isotopically enriched or enantiomerically enriched versions of macrocycles of type Ia/Ib are part of this invention.

In another embodiment of this invention, the macrocycles of type Ia/Ib are defined as above but wherein M is —$N(R^4)$— and wherein all possible stereoisomers of such compounds or pharmaceutical acceptable salts thereof are included.

In a preferred embodiment of this invention, the macrocycles of type Ia/Ib are defined by groups of selected building blocks A, B and C and substituents $R^1$-$R^{53}$ as detailed below:

The building block of type A is selected from

A1(a1); A2(a1); A3(a1); A4(a1); A5(a1); A6(a1); A7(a1); A9(a1); A10(a1); A73(a2); A80(a2); A170(a4); A171(a4); A209(a7); A210(a7); A240(a10); A241(a10); A242(a10); A243(a10); A272(a10); A530(a18); A531(a18); A532(a18); A533(a18); A609(a24); A610(a24); A611(a24); A612(a24); A613(a24); A614(a24); A615(a24); A631(a1); A632(a1); A633(a1); A641(a1); A642(a1); A643(a1); A651(a1); A652(a1); or A653(a1);

the building block of type B is selected from

B4(b3); B5(b3); B6(b3); B7(b3); B8(b3); B9(b3); B10(b3); B12(b4); B13(b4); B14(b4); B15(b4); B16(b4) or B17(b5);

the building block of type C is selected from

C1; C2; C3; C4; C5; C6; C7; C8; C9; C10; C11; C12; C13; C14; C15; C16; C17; C18; C19; C20; C21; C25; C26; C27; C28; C29; C30; C34; C35; C36; C37; C38; C39; C43; C44; C45; C46; C47; C48; C49; C50; C51; C52; C53; C54; C55; C56; C57; C58; C59; C60; C61; C62; C63; C64; C65; C66; C67; C68; C69; C70; C71; C72; C73; C74; C75; C76; C77; C78; C79; C80; C81; C86; C87; C88; C89; C90; C91; C92; or C93;

and wherein $R^1$ is H; F; Cl; Br; I; $CF_3$; $OCF_3$; $OCHF_2$; $NO_2$; CN; lower alkyl; lower alkenyl; lower alkynyl; lower cycloalkyl; lower heterocycloalkyl; aryl; heteroaryl; lower arylalkyl; lower heteroarylalkyl; —$(CR^{18}R^{19})_qOR^{20}$; —$(CR^{18}R^{19})_qNR^4R^{11}$; —$(CR^{18}R^{19})_qNR^4COOR^{21}$; —$(CR^{18}R^{19})_qNR^4COR^{22}$; —$(CR^{18}R^{19})_qNR^4CONR^4R^{11}$; —$(CR^{18}R^{19})_qNR^4SO_2R^{23}$; —$(CR^{18}R^{19})_qNR^4SO_2NR^4R^{11}$; —$(CR^{18}R^{19})_qCOOR^{21}$; —$(CR^{18}R^{19})_qCONR^4R^{11}$; —$(CR^{18}R^{19})_qSO_2NR^4R^{11}$; —$(CR^{18}R^{19})_qPO(OR^{21})_2$; —$(CR^{18}R^{19})_qCOR^{22}$; —$(CR^{18}R^{19})_qSO_2R^{23}$; —$(CR^{18}R^{19})_qOSO_3R^{21}$; —$(CR^{18}R^{19})_1R^{24}$; —$(CR^{18}R^{19})_qR^{25}$; or —$(CR^{18}R^{19})_qR^{26}$;

$R^2$ is H; $CF_3$; lower alkyl; lower alkenyl; cycloalkyl; heterocycloalkyl; aryl; heteroaryl; lower arylalkyl; lower heteroarylalkyl; —$(CR^{18}R^{19})_qOR^{20}$; —$(CR^{18}R^{19})_qNR^4R^{11}$; —$(CR^{18}R^{19})_qNR^4COOR^{21}$; —$(CR^{18}R^{19})_qNR^4COR^{22}$; —$(CR^{18}R^{19})_qNR^4CONR^4R^{11}$; —$(CR^{18}R^{19})_qNR^4SO_2R^{23}$; —$(CR^{18}R^{19})_qNR^4SO_2NR^4R^{11}$; —$(CR^{18}R^{19})_qCOOR^{21}$; —$(CR^{18}R^{19})_qCONR^4R^{11}$; —$(CR^{18}R^{19})_qSO_2NR^4R^{11}$; —$(CR^{18}R^{19})_qPO(OR^{21})_2$; —$(CR^{18}R^{19})_qCOR^{22}$; —$(CR^{18}R^{19})_qSO_2R^{23}$; —$(CR^{18}R^{19})_qR^{24}$; —$(CR^{18}R^{19})_qR^{25}$; or —$(CR^{18}R^{19})_qR^{26}$;

$R^4$ is H; lower alkyl; lower alkenyl; lower cycloalkyl; lower heterocycloalkyl; or a suitable N-protecting group;

$R^5$, $R^7$ and $R^9$ are independently defined as H; F; $CF_3$; lower alkyl; lower alkenyl; lower cycloalkyl; lower heterocycloalkyl; aryl; heteroaryl; lower arylalkyl; lower heteroarylalkyl; —$(CR^{18}R^{19})_qOR^{20}$; —$(CR^{18}R^{19})_qNR^4R^{11}$; —$(CR^{18}R^{19})_qNR^4COOR^{21}$; —$(CR^{18}R^{19})_qNR^4COR^{22}$; —$(CR^{18}R^{19})_qNR^4CONR^{11}$; —$(CR^{18}R^{19})_qNR^4SO_2R^{23}$; —$(CR^{18}R^{19})_qNR^4SO_2NR^4R^{11}$; —$(CR^{18}R^{19})_qPO(OR^{21})_2$; —$(CR^{18}R^{19})_qCONR^4R^{11}$; —$(CR^{18}R^{19})_qSO_2NR^4R^{11}$; —$(CR^{18}R^{19})_qPO(OR^{21})_2$; —$(CR^{18}R^{19})_qCOR^{22}$; —$(CR^{18}R^{19})_qSO_2R^{23}$; —$(CR^{18}R^{19})_qR^{24}$; —$(CR^{18}R^{19})_qR^{25}$; or —$(CR^{18}R^{19})_qR^{26}$;

$R^6$, $R^8$ and $R^{10}$ are independently defined as H; $CF_3$; or lower alkyl;

$R^{11}$ is H; alkyl; alkenyl; cycloalkyl; lower heterocycloalkyl; aryl; heteroaryl; lower arylalkyl; lower heteroarylalkyl; a suitable protecting group; $-(CR^{18}R^{19})_rOR^{20}$; $-(CR^{18}R^{19})_rNR^4R^{27}$; $-(CR^{18}R^{19})_rNR^4COOR^{21}$; $-(CR^{18}R^{19})_rNR^4CONR^4R^{27}$; $-(CR^{18}R^{19})_rNR^4SO_2R^{23}$; $-(CR^{18}R^{19})_rNR^4SO_2NR^4R^{27}$; $-(CR^{18}R^{19})_qCOOR^{21}$; $-(CR^{18}R^{19})_qCONR^4R^{27}$; $-(CR^{18}R^{19})_qCOR^{22}$; $-(CR^{18}R^{19})_qSO_2R^{23}$; $-(CR^{18}R^{19})_qSO_2NR^4R^{27}$; $-(CR^{18}R^{19})_qR^{24}$; $-(CR^{18}R^{19})_sR^{25}$; $-(CR^{18}R^{19})_qR^{26}$; or $-(CR^{18}R^{19})_qR^{31}$;

$R^{12}$ and $R^{13}$ are independently defined as H; or lower alkyl.

$R^{14}$ and $R^{16}$ are independently defined as H; F; $CF_3$; lower alkyl; lower alkenyl; lower cycloalkyl; lower heterocycloalkyl; aryl; heteroaryl; lower arylalkyl; lower heteroarylalkyl; $-(CR^{18}R^{19})_qOR^{20}$; $-(CR^{18}R^{19})_qNR^4R^{11}$; $-(CR^{18}R^{19})_qNR^4COOR^{21}$; $-(CR^{18}R^{19})_qNR^4COR^{22}$; $-(CR^{18}R^{19})_qNR^4CONR^4R^{11}$; $-(CR^{18}R^{19})_qNR^4SO_2R^{23}$; $-(CR^{18}R^{19})_qCOOR^{21}$; $-(CR^{18}R^{19})_qCONR^4R^{11}$; or $-(CR^{18}R^{19})_qCOR^{22}$;

$R^{15}$ and $R^{17}$ are independently defined as H; $CF_3$; or lower alkyl;

$R^{18}$ is H; F; $CF_3$; lower alkyl; lower alkenyl; lower cycloalkyl; lower heterocycloalkyl; aryl; heteroaryl; lower arylalkyl; lower heteroarylalkyl; $-(CR^{29}R^{30})_sOR^{31}$; $-(CR^{29}R^{30})_sNR^{28}R^{31}$; $-(CR^{29}R^{30})_sNR^{28}COOR^{21}$; $-(CR^{29}R^{30})_sNR^{28}COR^{31}$; $-(CR^{29}R^{30})_sNR^{28}CONR^{28}R^{31}$; $-(CR^{29}R^{30})_sNR^{28}SO_2R^{23}$; $-(CR^{29}R^{30})_sNR^{28}SO_2NR^{28}R^{31}$; $-(CR^{29}R^{30})_qCOOR^{21}$; $-(CR^{29}R^{30})_qCONR^{28}R^{31}$; $-(CR^{29}R^{30})_qSO_2NR^{28}R^{31}$; $-(CR^{29}R^{30})_qPO(OR^{21})_2$; $-(CR^{29}R^{30})_qCOR^{31}$; $-(CR^{29}R^{30})_qSO_2R^{23}$; $-(CR^{29}R^{30})_qR^{24}$; $-(CR^{29}R^{30})_qR^{25}$; or $-(CR^{29}R^{30})_qR^{26}$;

$R^{19}$ is H; $CF_3$; or lower alkyl;

$R^{20}$ is H; lower alkyl; lower alkenyl; lower cycloalkyl; lower heterocycloalkyl; aryl; heteroaryl; lower arylalkyl; lower heteroarylalkyl; $-(CR^{29}R^{30})_rOR^{31}$; $-(CR^{29}R^{30})_rNR^{28}R^{31}$; $-(CR^{29}R^{30})_rNR^{28}COOR^{21}$; $-(CR^{29}R^{30})_rNR^{28}COR^{31}$; $-(CR^{29}R^{30})_rNR^{28}CONR^{28}R^{31}$; $-(CR^{29}R^{30})_rNR^{28}SO_2R^{23}$; $-(CR^{29}R^{30})_qCOOR^{21}$; $-(CR^{29}R^{30})_qCONR^{28}R^{31}$; $-(CR^{29}R^{30})_qSO_2NR^{28}R^{31}$; $-(CR^{29}R^{30})_qCOR^{31}$; $-(CR^{29}R^{30})_qSO_2R^{23}$; $-(CR^{29}R^{30})_qR^{24}$; $-(CR^{29}R^{30})_qR^{25}$; $-(CR^{29}R^{30})_qR^{26}$; or $-(CR^{29}R^{30})_qR^{31}$;

$R^{22}$ is lower alkyl; lower alkenyl; lower cycloalkyl; lower heterocycloalkyl; aryl; heteroaryl; lower arylalkyl; lower heteroarylalkyl; $-(CR^{29}R^{30})_sOR^{31}$; $-(CR^{29}R^{30})_sNR^{28}R^{31}$; $-(CR^{29}R^{30})_sNR^{28}COOR^{21}$; $-(CR^{29}R^{30})_sNR^{28}COR^{31}$; $-(CR^{29}R^{30})_sNR^{28}CONR^{28}R^{31}$; $-(CR^{29}R^{30})_sNR^{28}SO_2R^{23}$; $-(CR^{29}R^{30})_sCOOR^{21}$; $-(CR^{29}R^{30})_sCONR^{28}R^{31}$; $-(CR^{29}R^{30})_sSO_2NR^{28}R^{31}$; $-(CR^{29}R^{30})_tCOR^{31}$; $-(CR^{29}R^{30})_sSO_2R^{23}$; $-(CR^{29}R^{30})_tR^{24}$; $-(CR^{29}R^{30})_tR^{25}$; or $-(CR^{29}R^{30})_tR^{31}$;

$R^{29}$ is H; F; $CF_3$; lower alkyl; lower alkenyl; lower cycloalkyl; lower heterocycloalkyl; aryl; heteroaryl; lower arylalkyl; lower heteroarylalkyl; $-(CR^{32}R^{33})_sOR^{31}$; $-(CR^{32}R^{33})_sNR^{28}R^{31}$; $-(CR^{32}R^{33})_sNR^{28}COOR^{21}$; $-(CR^{32}R^{33})_sNR^{28}COR^{31}$; $-(CR^{32}R^{33})_sNR^{28}CONR^{28}R^{31}$; $-(CR^{32}R^{33})_sNR^{28}SO_2R^{23}$; $-(CR^{32}R^{33})_qCOOR^{21}$; $-(CR^{32}R^{33})_qCONR^{28}R^{31}$; $-(CR^{32}R^{33})_qSO_2NR^{28}R^{31}$; $-(CR^{32}R^{33})_qPO(OR^{21})_2$; $-(CR^{32}R^{33})_qCOR^{31}$; $-(CR^{32}R^{33})_qSO_2R^{23}$; or $-(CR^{32}R^{33})_qR^{31}$;

$R^{30}$ and $R^{33}$ are independently defined as H; $CF_3$; or lower alkyl;

$R^{34}$ and $R^{35}$ are independently defined as H; F; Cl; $CF_3$; $OCF_3$; $OCHF_2$; $NO_2$; CN; lower alkyl; lower alkenyl; lower alkynyl; lower cycloalkyl; lower heterocycloalkyl; aryl; heteroaryl; lower arylalkyl; lower heteroarylalkyl; $-(CR^{29}R^{30})_qOR^{31}$; $-(CR^{29}R^{30})_qNR^{28}R^{31}$; $-(CR^{29}R^{30})_qNR^{28}COOR^{21}$; $-(CR^{29}R^{30})_qNR^{28}COR^{31}$; $-(CR^{29}R^{30})_qNR^{28}CONR^{28}R^{31}$; $-(CR^{29}R^{30})_qNR^{28}SO_2R^{23}$; $-(CR^{29}R^{30})_qCOOR^{21}$; $-(CR^{29}R^{30})_qCONR^{28}R^{31}$; $-(CR^{29}R^{30})_qSO_2NR^{28}R^{23}$; $-(CR^{29}R^{30})_qCOR^{31}$; $-(CR^{29}R^{30})_qSO_2R^{23}$; or $-(CR^{29}R^{30})_qR^{31}$;

$R^{37}$ is H; lower alkyl; lower alkenyl; lower cycloalkyl; lower heterocycloalkyl; aryl; heteroaryl; lower arylalkyl; lower heteroarylalkyl; a suitable N-protecting group; $-(CR^{29}R^{30})_rOR^{31}$; $-(CR^{29}R^{30})_rNR^{28}R^{31}$; $-(CR^{29}R^{30})_rNR^{28}COOR^{21}$; $-(CR^{29}R^{30})_rNR^{28}COR^{31}$; $-(CR^{29}R^{30})_rNR^{28}CONR^{28}R^{31}$; $-(CR^{29}R^{30})_rNR^{28}SO_2R^{23}$; $-(CR^{29}R^{30})_qCOOR^{21}$; $-(CR^{29}R^{30})_qCONR^{28}R^{31}$; $-(CR^{29}R^{30})_rSO_2NR^{28}R^{31}$; $-(CR^{29}R^{30})_qCOR^{31}$; $-(CR^{29}R^{30})_qSO_2R^{23}$; or $-(CR^{29}R^{30})_qR^{31}$;

$R^{38}$ is H; lower alkyl; lower alkenyl; lower cycloalkyl; lower heterocycloalkyl; aryl; heteroaryl; lower arylalkyl; lower heteroarylalkyl; $-(CR^{29}R^{30})_qOR^{31}$; $-(CR^{29}R^{30})_qNR^{28}R^{31}$; $-(CR^{29}R^{30})_qNR^{28}COOR^{21}$; $-(CR^{29}R^{30})_qNR^{28}COR^{31}$; $-(CR^{29}R^{30})_qNR^{28}CONR^{28}R^{31}$; $-(CR^{29}R^{30})_qCOOR^{21}-$; $-(CR^{29}R^{30})_qCONR^{28}R^{31}$; $-(CR^{29}R^{30})_qCOR^{31}$; or $-(CR^{29}R^{30})_qR^{31}$;

Z is O; S; S(=O); or $S(=O)_2$;

U is $-C(=O)-$; $-NR^4-C(=O)-$; $-C(=O)-C(=O)-$; or $-C(-OR^{20})_2-C(=O)-$.

In a further preferred embodiment of this invention, the macrocycles of type Ia/Ib are defined by groups of selected building blocks A, B and C and substituents $R^1$-$R^{53}$ as detailed below:

The building block of type A is selected from

A1(a1); A2(a1); A3(a1); A4(a1); A5(a1); A6(a1); A7(a1); A9(a1); A10(a1); A73(a2); A170(a4); A209(a7); A240(a10); A272(a10); A532(a18); A614(a24); A631(a1); A632(a1); A633(a1); A641(a1); A642(a1); A643(a1); A651(a1); A652(a1); or A653(a1);

the building block of type B is selected from

B7(b3); B8(b3); B9(b3); B10(b3); or B17(b5);

the building block of type C is selected from

C1; C2; C4; C7; C8; C9; C10; C11; C12; C13; C14; C15; C16; C17; C18; C19; C20; C21; C25; C26; C27; C28; C29; C30; C34; C35; C36; C37; C38; C39; C43; C44; C45; C46; C47; C48; C49; C90; C91; C92; or C93;

and wherein $R^1$ is H; F; Cl; $CF_3$; $OCF_3$; $OCHF_2$; $NO_2$; CN; lower alkyl; lower alkenyl; lower alkynyl; lower cycloalkyl; lower heterocycloalkyl; aryl; heteroaryl; lower arylalkyl; lower heteroarylalkyl; $-(CR^{18}R^{19})_qOR^{20}$; $-(CR^{18}R^{19})_qNR^4R^{11}$; $-(CR^{18}R^{19})_qNR^4COR^{22}$; $-(CR^{18}R^{19})_qNR^4CONR^4R^{11}$; $-(CR^{18}R^{19})_qNR^4SO_2R^{23}$; $-(CR^{18}R^{19})_qNR^4SO_2NR^4R^{11}$; $-(CR^{18}R^{19})_qCOOR^{21}$; $-(CR^{18}R^{19})_qCONR^4R^{11}$; $-(CR^{18}R^{19})_qSO_2NR^4R^{11}$; $-(CR^{18}R^{19})_qCOR^{22}$; $-(CR^{18}R^{19})_qSO_2R^{23}$; $-(CR^{18}R^{19})_qR^{24}$; $-(CR^{18}R^{19})_qR^{25}$; or $-(CR^{18}R^{19})_qR^{26}$;

$R^2$ is H; $CF_3$; lower alkyl; lower alkenyl; cycloalkyl; heterocycloalkyl; aryl; heteroaryl; lower arylalkyl;

lower heteroarylalkyl; $-(CR^{18}R^{19})_qOR^{20}$; $-(CR^{18}R^{19})_qNR^4R^{11}$; $-(CR^{18}R^{19})_qNR^4COR^{22}$; $-(CR^{18}R^{19})_qNR^4CONR^4R^{11}$; $-(CR^{18}R^{19})_qNR^4SO_2R^{23}$; $-(CR^{18}R^{19})_qNR^4SO_2NR^4R^{11}$; $-(CR^{18}R^{19})_qCOOR^{21}$; $-(CR^{18}R^{19})_qCONR^4R^{11}$; $-(CR^{18}R^{19})_qSO_2NR^4R^{11}$; $-(CR^{18}R^{19})_qCOR^{22}$; $-(CR^{18}R^{19})_qSO_2R^{23}$; $-(CR^{18}R^{19})_qR^{24}$; $-(CR^{18}R^{19})R^{25}$; or $-(CR^{18}R^{19})_qR^{26}$;

$R^4$ is H; lower alkyl; lower alkenyl; or a suitable N-protecting group;

$R^5$, $R^7$ and $R^9$ are independently defined as H; $CF_3$; lower alkyl; lower alkenyl; lower cycloalkyl; lower heterocycloalkyl; aryl; heteroaryl; lower arylalkyl; lower heteroarylalkyl; $-(CR^{18}R^{19})_qOR^{20}$; $-(CR^{18}R^{19})_qNR^4R^{11}$; $-(CR^{18}R^{19})_qNR^4COR^{22}$; $-(CR^{18}R^{19})_qNR^4CONR^{11}$, $-(CR^{18}R^{19})_qNR^4SO_2R^{23}$; $-(CR^{18}R^{19})_qCOOR^{21}$; $-(CR^{18}R^{19})_qCONR^4R^{11}$; $-(CR^{18}R^{19})_qSO_2NR^4R^{11}$; $-(CR^{18}R^{19})_qCOR^{22}$; $-(CR^{18}R^{19})_qSO_2R^{23}$; $-(CR^{18}R^{19})_qR^{24}$; $-(CR^{18}R^{19})_qR^{25}$; or $-(CR^{18}R^{19})_qR^{26}$;

$R^6$, $R^8$ and $R^{10}$ are independently defined as H; $CF_3$; or $CH_3$;

$R^{11}$ is H; alkyl; alkenyl; cycloalkyl; lower heterocycloalkyl; aryl; heteroaryl; lower arylalkyl; lower heteroarylalkyl; a suitable protecting group; $-(CR^{18}R^{19})_rOR^{20}$; $-(CR^{18}R^{19})_rNR^4R^{27}$; $-(CR^{18}R^{19})_rNR^4CONR^4R^{27}$; $-(CR^{18}R^{19})_rNR^4SO_2R^{23}$; $-(CR^{18}R^{19})_qCOOR^{21}$; $-(CR^{18}R^{19})_qCONR^4R^{27}$; $-(CR^{18}R^{19})_qCOR^{22}$; $-(CR^{18}R^{19})_qR^{24}$; $-(CR^{18}R^{19})_sR^{25}$; $-(CR^{18}R^{19})_qR^{26}$; or $-(CR^{18}R^{19})_qR^{31}$;

$R^{12}$ and $R^{13}$ are independently defined as H; or lower alkyl.

$R^{14}$ and $R^{16}$ are independently defined as H; F; $CF_3$; lower alkyl; lower alkenyl; lower cycloalkyl; lower heterocycloalkyl; aryl; heteroaryl; lower arylalkyl; lower heteroarylalkyl; $-(CR^{18}R^{19})_qOR^{20}$; $-(CR^{18}R^{19})_qNR^4R^{11}$; $-(CR^{18}R^{19})_qNR^4COR^{22}$; $-(CR^{18}R^{19})_qCOOR^{21}$; or $-(CR^{18}R^{19})_qCONR^4R^{11}$;

$R^{15}$ and $R^{17}$ are independently defined as H; $CF_3$; or $CH_3$;

$R^{18}$ is H; F; $CF_3$; lower alkyl; lower alkenyl; lower cycloalkyl; lower heterocycloalkyl; aryl; heteroaryl; lower arylalkyl; lower heteroarylalkyl; $-(CR^{29}R^{30})_sOR^{31}$; $-(CR^{18}R^{19})_sNR^{28}R^{31}$; $-(CR^{29}R^{30})_sNR^{28}COR^{31}$; $-(CR^{29}R^{30})_sNR^{28}CONR^{28}R^{31}$; $-(CR^{29}R^{30})_sNR^{28}SO_2R^{23}$; $-(CR^{29}R^{30})_qCOOR^{21}$; $-(CR^{29}R^{30})_qCONR^{28}R^{31}$; $-(CR^{29}R^{30})_qSO_2NR^{28}R^{31}$; $-(CR^{29}R^{30})_qCOR^{31}$; $-(CR^{29}R^{30})_qSO_2R^{23}$; $-(CR^{29}R^{30})_qR^{24}$; $-(CR^{29}R^{30})_qR^{25}$; or $-(CR^{29}R^{30})_qR^{26}$;

$R^{19}$ is H; $CF_3$; or $CH_3$;

$R^{20}$ is H; lower alkyl; lower alkenyl; lower cycloalkyl; lower heterocycloalkyl; aryl; heteroaryl; lower arylalkyl; lower heteroarylalkyl; $-(CR^{29}R^{30})_rOR^{31}$; $-(CR^{29}R^{30})_rNR^{28}R^{31}$; $-(CR^{29}R^{30})_rNR^{28}COR^{31}$; $-(CR^{29}R^{30})_rNR^{28}CONR^{28}R^{31}$; $-(CR^{29}R^{30})_rNR^{28}SO_2R^{23}$; $-(CR^{29}R^{30})_qCOOR^{21}$; $-(CR^{29}R^{30})_qCONR^{28}R^{31}$; $-(CR^{29}R^{30})_qSO_2NR^{28}R^{31}$; $-(CR^{29}R^{30})_qCOR^{31}$; $-(CR^{29}R^{30})_qSO_2R^{23}$; $-(CR^{29}R^{30})_qR^{24}$; $-(CR^{29}R^{30})_qR^{25}$; $-(CR^{18}R^{19})_qR^{26}$, or $-(CR^{29}R^{30})_qR^{31}$;

$R^{22}$ is lower alkyl; lower alkenyl; lower cycloalkyl; lower heterocycloalkyl; aryl; heteroaryl; lower arylalkyl; lower heteroarylalkyl; $-(CR^{29}R^{30})_sOR^{31}$; $-(CR^{29}R^{30})_sNR^{28}R^{31}$; $-(CR^{29}R^{30})_sNR^{28}COR^{31}$; $-(CR^{29}R^{30})_sNR^{28}CONR^{28}R^{31}$; $-(CR^{29}R^{30})_sNR^{28}SO_2R^{23}$; $-(CR^{29}R^{30})_sCOOR^{21}$; $-(CR^{29}R^{30})_sCONR^{28}R^{31}$; $-(CR^{29}R^{30})_sSO_2NR^{28}R^{31}$; $-(CR^{29}R^{30})_tCOR^{31}$; $-(CR^{29}R^{30})_sSO_2R^{23}$; $-(CR^{29}R^{30})_tR^{24}$; $-(CR^{29}R^{30})_tR^{25}$; $-(CR^{29}R^{30})_tR^{26}$; or $-(CR^{29}R^{30})_tR^{31}$;

$R^{29}$ is H; F; $CF_3$; lower alkyl; lower alkenyl; lower cycloalkyl; lower heterocycloalkyl; aryl; heteroaryl; lower arylalkyl; lower heteroarylalkyl; $-(CR^{32}R^{33})_sOR^{31}$; $-(CR^{32}R^{33})_sNR^{28}R^{31}$; $-(CR^{32}R^{33})_sNR^{28}COR^{31}$; $-(CR^{32}R^{33})_sNR^{28}CONR^{28}R^{31}$; $-(CR^{32}R^{33})_qCOOR^{21}$; $-(CR^{32}R^{33})_qCONR^{28}R^{31}$; $-(CR^{32}R^{33})_qCOR^{31}$; or $-(CR^{32}R^{33})_qR^{31}$;

$R^{30}$ and $R^{33}$ are independently defined as H; $CF_3$; or $CH_3$;

$R^{34}$ and $R^{35}$ are independently defined as H; F; Cl; $CF_3$; $OCF_3$; $OCHF_2$; lower alkyl; lower alkenyl; lower alkynyl; lower cycloalkyl; lower heterocycloalkyl; aryl; heteroaryl; lower arylalkyl; lower heteroarylalkyl; $-(CR^{29}R^{30})_qOR^{31}$; $-(CR^{29}R^{30})_qNR^{28}R^{31}$; $-(CR^{29}R^{30})_qNR^{28}COR^{31}$; $-(CR^{29}R^{30})_qNR^{28}CONR^{28}R^{31}$; $-(CR^{29}R^{30})_qNR^{28}SO_2R^{23}$; $-(CR^{29}R^{30})_qCOOR^{21}$; $-(CR^{29}R^{30})_qCONR^{28}R^{31}$; $-(CR^{29}R^{30})_qSO_2NR^{28}R^{31}$; $-(CR^{29}R^{30})_qCOR^{31}$; $-(CR^{29}R^{30})_qSO_2R^{23}$; or $-(CR^{29}R^{30})_qR^{31}$;

$R^{37}$ is H; lower alkyl; lower alkenyl; lower cycloalkyl; lower heterocycloalkyl; aryl; heteroaryl; lower arylalkyl; lower heteroarylalkyl; a suitable N-protecting group; $-(CR^{29}R^{30})_rOR^{31}$; $-(CR^{29}R^{30})_rNR^{28}R^{31}$; $-(CR^{29}R^{30})_rNR^{28}COOR^{21}$; $-(CR^{29}R^{30})_rNR^{28}COR^{31}$; $-(CR^{29}R^{30})_rNR^{28}CONR^{28}R^{31}$; $-(CR^{29}R^{30})_qCOOR^{21}$; $-(CR^{29}R^{30})_qCONR^{28}R^{31}$; $-(CR^{29}R^{30})_qCOR^{31}$; or $-(CR^{29}R^{30})_qR^{31}$;

$R^{38}$ is H; lower alkyl; lower alkenyl; lower cycloalkyl; lower heterocycloalkyl; aryl; heteroaryl; lower arylalkyl; lower heteroarylalkyl; $-(CR^{29}R^{30})_qOR^{31}$; $-(CR^{29}R^{30})_qNR^{28}R^{31}$; $-(CR^{29}R^{30})_qNR^{28}COR^{31}$; $-(CR^{29}R^{30})_qNR^{28}CONR^{28}R^{31}$; $-(CR^{29}R^{30})_qCOOR^{21}$; $-(CR^{29}R^{30})_qCONR^{28}R^{31}$; $-(CR^{29}R^{30})_qCOR^{31}$; or $-(CR^{29}R^{30})_qR^{31}$;

Z is O; S or $S(=O)_2$;

U is $-C(=O)-$; $-NR^4-C(=O)-$; or $-C(=O)-C(=O)-$.

In a particularly preferred embodiment of this invention, the macrocycles of type Ia/Ib are defined by groups of selected building blocks A, B and C and substituents $R^1$-$R^{53}$ as detailed below:

The building block of type A is selected from

A1(a1); A2(a1); A3(a1); A4(a1); A5(a1); A6(a1); A7(a1); A9(a1); A10(a1); A73(a2); A170(a4); A209(a7); A240 (a10); A272(a10); A532(a18); A614(a24); A631(a1); A632(a1); A633(a1); A641(a1); A642(a1); A643(a1); A651(a1); A652(a1); or A653(a1).

The building block of type B is selected from

B7 (b3); B8 (b3); B9(b3); B10 (b3); or B17(b5).

The building block of type C is selected from

C1; C8; C9; C11; C12; C15; C17; C19; C20; C25; or C47;

and wherein $R^1$ is H; F; Cl; Br; $CF_3$; $OCF_3$; $OCHF_2$; CN; lower alkyl; lower alkenyl; cycloalkyl; heterocycloalkyl; aryl; heteroaryl; lower arylalkyl; lower heteroarylalkyl; $-(CR^{29}R^{30})_qOR^{20}$; $-(CR^{29}R^{30})_qNR^4R^{11}$; $-(CR^{29}R^{30})_qNR^4COR^{22}$; $-(CR^{29}R^{30})_qNR^4CONR^4R^{11}$; $-(CR^{29}R^{30})_qNR^4SO_2R^{23}$; $-(CR^{29}R^{30})_qCOOR^{21}$; $-(CR^{29}R^{30})_qCONR^4R^{11}$; $-(CR^{29}R^{30})_qSO_2NR^4R^{11}$; $-(CR^{29}R^{30})_qCOR^{22}$; $-(CR^{29}R^{30})_qSO_2R^{23}$; $-(CR^{29}R^{30})_qR^{24}$; $-(CR^{29}R^{30})_qR^{25}$; or $-(CR^{29}R^{30})_qR^{26}$;

$R^2$ is H; $CF_3$; lower alkyl; lower alkenyl; lower cycloalkyl; lower heterocycloalkyl; aryl; heteroaryl;

lower arylalkyl; lower heteroarylalkyl; $—(CR^{29}R^{30})_qOR^{20}$; $—(CR^{29}R^{30})_qNR^4R^{11}$; $—(CR^{29}R^{30})_qNR^4COR^{22}$; $—(CR^{29}R^{30})_qNR^4CONR^4R^{11}$; $—(CR^{29}R^{30})_qNR^4SO_2R^{23}$; $—(CR^{29}R^{30})_qCOOR^{21}$; $—(CR^{29}R^{30})_qCONR^4R^{11}$; $—(CR^{29}R^{30})_qSO_2NR^4R^{11}$; $—(CR^{29}R^{30})_qCOR^{22}$; $—(CR^{29}R^{30})_qSO_2R^{23}$; $—(CR^{29}R^{30})_qR^{24}$; $—(CR^{29}R^{30})_qR^{25}$; or $—(CR^{29}R^{30})_qR^{26}$;

$R^4$ is H; acetyl; lower alkyl; lower alkenyl; or a suitable N-protecting group;

$R^5$, $R^7$ and $R^9$ are independently defined as H; $CF_3$; lower alkyl; lower alkenyl; lower cycloalkyl; lower heterocycloalkyl; aryl; heteroaryl; lower arylalkyl; lower heteroarylalkyl; $—(CR^{18}R^{19})_qOR^{20}$; $—(CR^{18}R^{19})_qNR^4R^{11}$; $—(CR^{18}R^{19})_qNR^4COR^{22}$; $—(CR^{18}R^{19})_qNR^4CONR^4R^{11}$; $—(CR^{18}R^{19})_qNR^4SO_2R^{23}$; $—(CR^{18}R^{19})_qCOOR^{21}$; $—(CR^{18}R^{19})_qCONR^4R^{11}$; $—(CR^{18}R^{19})_qNR^4R^{11}$; $—(CR^{18}R^{19})_qCOR^{22}$; $—(CR^{29}R^{30})_qSO_2R^{23}$; $—(CR^{18}R^{19})_qR^{24}$; $—(CR^{18}R^{19})_qR^{25}$; or $—(CR^{18}R^{19})_qR^{26}$;

$R^6$, $R^8$ and $R^{10}$ are independently defined as H; $CF_3$; $CH_3$; or benzyl;

$R^{11}$ is H; alkyl; alkenyl; cycloalkyl; lower heterocycloalkyl; aryl; heteroaryl; lower arylalkyl; lower heteroarylalkyl; a suitable protecting group; $—(CR^{18}R^{19})_rOR^{20}$; $—(CR^{18}R^{19})_rNR^4R^{27}$; $—(CR^{18}R^{19})_rNR^4CONR^4R^{27}$; $—(CR^{18}R^{19})_rNR^4SO_2R^{23}$; $—(CR^{18}R^{19})_qCOOR^{21}$; $—(CR^{18}R^{19})_qCONR^4R^{27}$; $—(CR^{18}R^{19})_qCOR^{22}$; $—(CR^{18}R^{19})_qR^{24}$; $—(CR^{18}R^{19})_sR^{25}$; $—(CR^{18}R^{19})_qR^{26}$; or $—(CR^{18}R^{19})_qR^{31}$;

$R^{12}$ and $R^{13}$ are independently defined as H; or lower alkyl.

$R^{14}$ and $R^{16}$ are independently defined as H; F; $CF_3$; lower alkyl; lower alkenyl; lower cycloalkyl; lower heterocycloalkyl; aryl; heteroaryl; lower arylalkyl; lower heteroarylalkyl; $—(CR^{29}R^{30})_qOR^{20}$; $—(CR^{29}R^{30})_qNR^4R^{11}$; $—(CR^{29}R^{30})_qNR^4COR^{22}$; $—(CR^{29}R^{30})_qCOOR^{21}$; or $—(CR^{29}R^{30})_qCONR^4R^{11}$;

$R^{15}$ and $R^{17}$ are independently defined as H; $CF_3$; or $CH_3$;

$R^{18}$ is H; F; $CF_3$; lower alkyl; lower alkenyl; lower cycloalkyl; lower heterocycloalkyl; aryl; heteroaryl; lower arylalkyl; lower heteroarylalkyl; $—(CR^{29}R^{30})_sOR^{31}$; $—(CR^{29}R^{30})_sNR^{28}R^{31}$; $—(CR^{29}R^{30})_sNR^{28}COR^{31}$; $—(CR^{29}R^{30})_sNR^{28}CONR^{28}R^{31}$; $—(CR^{29}R^{30})_sNR^{28}SO_2R^{23}$; $—(CR^{29}R^{30})_qCOOR^{21}$; $—(CR^{29}R^{30})_qCONR^{28}R^{31}$; $—(CR^{29}R^{30})_qSO_2NR^{28}R^{31}$; $—(CR^{29}R^{30})_qCOR^{31}$; $—(CR^{29}R^{30})_qSO_2R^{23}$; $—(CR^{29}R^{30})_qR^{24}$; $—(CR^{29}R^{30})_qR^{25}$; or $—(CR^{29}R^{30})_qR^{26}$;

$R^{19}$ is H; $CF_3$; or $CH_3$;

$R^{20}$ is H; lower alkyl; lower alkenyl; lower cycloalkyl; lower heterocycloalkyl; aryl; heteroaryl; lower arylalkyl; lower heteroarylalkyl; $—(CR^{29}R^{30})_rOR^{31}$; $—(CR^{29}R^{30})_rNR^{28}R^{31}$; $—(CR^{29}R^{30})_rNR^{28}COR^{31}$; $—(CR^{29}R^{30})_rNR^{28}CONR^{28}R^{31}$; $—(CR^{29}R^{30})_rNR^{28}SO_2R^{23}$; $—(CR^{29}R^{30})_qCOOR^{21}$; $—(CR^{29}R^{30})_qCONR^{28}R^{31}$; $—(CR^{29}R^{30})_qSO_2NR^{28}R^{31}$; $—(CR^{29}R^{30})_qCOR^{31}$; $—(CR^{29}R^{30})_qSO_2R^{23}$; $—(CR^{29}R^{30})_qR^{24}$; $—(CR^{29}R^{30})_qR^{25}$; $—(CR^{29}R^{30})_qR^{26}$; or $—(CR^{29}R^{30})_qR^{31}$;

$R^{22}$ is lower alkyl; lower alkenyl; lower cycloalkyl; lower heterocycloalkyl; aryl; heteroaryl; lower arylalkyl; lower heteroarylalkyl; $—(CR^{29}R^{30})_sOR^{31}$; $—(CR^{29}R^{30})_sNR^{28}R^{31}$; $—(CR^{29}R^{30})_sNR^{28}COR^{31}$; $—(CR^{29}R^{30})_sNR^{28}CONR^{28}R^{31}$; $—(CR^{29}R^{30})_sNR^{28}SO_2R^{23}$; $—(CR^{29}R^{30})_sCOOR^{21}$; $—(CR^{29}R^{30})_sCONR^{28}R^{31}$; $—(CR^{29}R^{30})_sSO_2NR^{28}R^{31}$; $—(CR^{29}R^{30})_tCOR^{31}$; $—(CR^{29}R^{30})_sSO_2R^{23}$; $—(CR^{29}R^{30})_tR^{24}$; $—(CR^{29}R^{30})_tR^{25}$; $—(CR^{29}R^{30})_tR^{26}$; or $—(CR^{29}R^{30})_tR^{31}$;

$R^{24}$ is aryl; heteroaryl; or $—C_6H_2R^{34}R^{35}R^{31}$;

$R^{25}$ and $R^{26}$ are independently defined as heterocycloalkyl;

$R^{27}$ is H; lower alkyl; lower alkenyl; lower cycloalkyl; lower heterocycloalkyl; aryl; heteroaryl; lower arylalkyl; lower heteroarylalkyl; a suitable protecting group; or $—(CR^{29}R^{30})_qR^{24}$;

$R^{28}$ is H; $—(CR^{32}R^{33})_sOR^{21}$; or $—(CR^{32}R^{33})_sNR^{43}R^{42}$;

$R^{29}$ is H; F; $CF_3$; lower alkyl; lower alkenyl; lower cycloalkyl; lower heterocycloalkyl; aryl; heteroaryl; lower arylalkyl; lower heteroarylalkyl; $—(CR^{32}R^{33})_sOR^{31}$; $—(CR^{32}R^{33})_sNR^{28}R^{31}$; $—(CR^{32}R^{33})_sNR^{28}COR^{31}$; $—(CR^{32}R^{33})_sNR^{28}CONR^{28}R^{31}$; $—(CR^{32}R^{33})_qCOOR^{21}$; $—(CR^{32}R^{33})_qCONR^{28}R^{31}$; $—(CR^{32}R^{33})_qCOR^{31}$; or $—(CR^{32}R^{33})_qR^{31}$;

$R^{30}$ and $R^{33}$ are independently defined as H; F; $CF_3$; or $CH_3$;

$R^{31}$ is H; alkyl; alkenyl; cycloalkyl; heterocycloalkyl; aryl; heteroaryl; arylalkyl; or heteroarylalkyl;

$R^{32}$ is H; F; $CF_3$; lower alkyl; lower alkenyl; lower cycloalkyl; lower heterocycloalkyl; aryl; heteroaryl; lower arylalkyl; or lower heteroarylalkyl;

$R^{34}$ and $R^{35}$ are independently defined as H; F; Cl; $CF_3$; lower alkyl; lower alkenyl; lower cycloalkyl; lower heterocycloalkyl; aryl; heteroaryl; lower arylalkyl; lower heteroarylalkyl; $—(CR^{29}R^{30})_qOR^{31}$; $—(CR^{29}R^{30})_qNR^{28}R^{31}$; $—(CR^{29}R^{30})_qNR^{28}COR^{31}$; $—(CR^{29}R^{30})_qNR^{28}CONR^{28}R^{31}$; $—(CR^{29}R^{30})_qNR^{28}SO_2R^{23}$; $—(CR^{29}R^{30})_qCOOR^{21}$; $—(CR^{29}R^{30})_qCONR^{28}R^{31}$; $—(CR^{29}R^{30})_qSO_2NR^{28}R^{31}$; $—(CR^{29}R^{30})_qCOR^{31}$; $—(CR^{29}R^{30})_qSO_2R^{23}$; or $—(CR^{29}R^{30})_qR^{31}$;

$R^{38}$ is H; lower alkyl; lower alkenyl; lower cycloalkyl; lower heterocycloalkyl; aryl; heteroaryl; lower arylalkyl; lower heteroarylalkyl; $—(CR^{29}R^{30})_qOR^{31}$; $—(CR^{29}R^{30})_qNR^{28}R^{31}$; $—(CR^{29}R^{30})_qNR^{28}COR^{31}$; $—(CR^{29}R^{30})_qNR^{28}CONR^{28}R^{31}$; $—(CR^{29}R^{30})_qCOOR^{21}$; $—(CR^{29}R^{30})_qCONR^{28}R^{31}$; $—(CR^{29}R^{30})_qCOR^{31}$; or $—(CR^{29}R^{30})_qR^{31}$;

$R^{42}$ and $R^{43}$ are independently defined as H; lower alkyl; lower alkenyl; lower cycloalkyl; lower heterocycloalkyl; aryl; heteroaryl; lower arylalkyl; lower heteroarylalkyl; or a suitable N-protecting group;

X is O; S; S(═O); or $S(═O)_2$;

Y is O; S; or $NR^4$;

Z is O; S or $S(═O)_2$;

U is —C(═O)—; $—NR^4—C(═O)—$; or —C(═O)—C(═O)—;

This particularly preferred embodiment includes all possible stereoisomers (explicitly including atropisomers), conformers and rotamers as well as pharmaceutically acceptable salts, solvates, clathrates, isotopically enriched or enantiomerically enriched versions of above macrocyclic compounds.

In a further particularly preferred embodiment of this invention, the macrocycles of type Ia/Ib are defined by groups of selected building blocks A, B and C and substituents $R^1$-$R^{53}$ as detailed below:

The building block of type A is selected from

A2(a1); A5(a1); A9(a1); A73(a2); A209(a7); A272(a10); A532(a18); A614(a24); A641(a1); or A651(a1);

the building block of type B is selected from

B7; B9; B10 or B17;

the building block of type C is selected from

C1; C8; C9; C11; C15; C17; C19; C20; C25; or C47;

and wherein $R^1$ is H; F; Cl; Br; $CH_3$; $OCH_3$; OH; or aryl;

$R^2$ is H; $CH_3$; heterocycloalkyl; aryl; benzyl; heteroaryl; —$OR^{20}$; —$NR^4R^{11}$; —$NR^4COOR^{21}$; —$NR^4COR^{22}$; —$NR^4CONR^4R^{11}$; or —$NR^4SO_2R^{23}$;

$R^3$ is H;

$R^4$ is H; acetyl; lower alkyl; lower alkenyl; or a suitable N-protecting group;

$R^5$, $R^7$ and $R^9$ are independently defined as H; $CF_3$; lower alkyl; lower alkenyl; lower cycloalkyl; lower heterocycloalkyl; aryl; heteroaryl; lower arylalkyl; lower heteroarylalkyl; —$OR^{20}$; —$NR^4R^{11}$; —$NR^4COR^{22}$, —$NR^4CONR^4R^{11}$; —$NR^4SO_2R^{23}$; —$COOR^{21}$; —$CONR^4R^{11}$; or —$COR^{22}$;

$R^6$, $R^8$ and $R^{10}$ are defined as H;

$R^{11}$ is H; alkyl; aryl; heteroaryl; lower arylalkyl; lower heteroarylalkyl; —$(CR^{18}R^{19})_rOR^{20}$; —$(CR^{18}R^{19})_rNR^4R^{27}$; —$(CR^{18}R^{19})_qCOOR^{21}$; —$COR^{22}$; —$(CR^{18}R^{19})_qR^{24}$; or —$(CR^{18}R^{19})_qR^{31}$;

$R^{12}$ and $R^{13}$ are defined as H;

$R^{14}$ and $R^{16}$ are independently defined as H; lower alkyl; or lower arylalkyl;

$R^{15}$ and $R^{17}$ are defined as H;

$R^{18}$ and $R^{19}$ are defined as H;

$R^{20}$ is H; aryl; heteroaryl; lower arylalkyl; lower heteroarylalkyl; or —$(CR^{29}R^{30})_qR^{24}$;

$R^{21}$ is H; lower alkyl; lower arylalkyl; or a suitable O-protecting group;

$R^{22}$ is lower alkyl; lower alkenyl; aryl; heteroaryl; lower arylalkyl; lower heteroarylalkyl; —$(CR^{29}R^{30})_sOR^{31}$; —$(CR^{29}R^{30})_sNR^{28}R^{31}$; —$(CR^{29}R^{30})_sCOOR^{21}$; —$(CR^{29}R^{30})_rR^{24}$; or —$(CR^{29}R^{30})_rR^{31}$;

$R^{23}$ is H; lower alkyl; aryl; heteroaryl; or —$R^{24}$;

$R^{24}$ is aryl; heteroaryl; or —$C_6H_2R^{34}R^{35}R^{31}$;

$R^{27}$ is H; acetyl; $CH_3$; or —$(CH_2)_qR^{24}$;

$R^{28}$ is H; —$(CR^{32}R^{33})_sOR^{21}$; or —$(CR^{32}R^{33})_sNR^{43}R^{42}$;

$R^{29}$ is H; lower alkyl; aryl; or heteroaryl;

$R^{30}$, $R^{32}$ and $R^{33}$ are independently defined as H; $CF_3$; or $CH_3$;

$R^{31}$ is H; alkyl; cycloalkyl; heterocycloalkyl; aryl; heteroaryl; arylalkyl; or heteroarylalkyl;

$R^{34}$ and $R^{35}$ are independently defined as H; heterocycloalkyl; —$OR^{31}$; or —$NR^{28}R^{31}$;

$R^{38}$ is H; —$NR^{28}R^{31}$; —$NR^{28}COR^{31}$; or —$NR^{28}COOR^{31}$;

$R^{42}$ and $R^{43}$ are independently defined as H; $CH_3$; or benzyl;

X is O; S; S(=O); or $S(=O)_2$;

Y is O; S; or $NR^4$;

Z is O; S or $S(=O)_2$;

U is —C(=O)—; —$NR^4$—C(=O)—; or —C(=O)—C(=O)—.

This further particularly preferred embodiment includes all possible stereoisomers (explicitly including atropisomers), conformers and rotamers as well as pharmaceutically acceptable salts, solvates, clathrates, isotopically enriched or enantiomerically enriched versions of above macrocyclic compounds.

In another preferred embodiment of this invention, the macrocycles of formulae Ia and Ib as described in the main embodiment can contain as a "Linker" the building block C which is represented by the formula $$--[-C_{AA}-]_{1-3}--$$

Examples of readily accessible amino acids defining possible subunits $C_{AA}$ of the linker C are listed in Table 10 below. Only one stereoisomer of enantiomeric amino acids is cited, usually the L-enantiomer; it is understood that the complementary enantiomer is also part to the embodiment. Also not mentioned explicitly but naturally part of the embodiment are the simple N-Methyl derivatives of the listed amino acids.

TABLE 10

Substances Representing Subunits of "Linkers" C
(continued on the following pages)

| Code | Chemical Name |
|---|---|
| Ala | L-Alanine |
| Arg | L-Arginine |
| Asn | L-Asparagine |
| Asp | L-Aspartic acid |
| Cys | L-Cysteine |
| Glu | L-Glutamic acid |
| Gln | L-Glutamine |
| Gly | Glycine |
| His | L-Histidine |
| Ile | L-Isoleucine |
| Leu | L-Leucine |
| Lys | L-Lysine |
| Met | L-Methionine |
| Phe | L-Phenylalanine |
| Pro | L-Proline |
| Ser | L-Serine |
| Thr | L-Threonine |
| Trp | L-Tryptophan |
| Tyr | L-Tyrosine |
| Val | L-Valine |
| Apa | 3-Amino-propanoic acid |
| H-$\beta^3$-HAla-OH | (3S)-3-Amino-butyric acid |
| H-$\beta^3$-HVal-OH | (3R)-3-Amino-4-methyl-valeric acid |
| H-$\beta^3$-HIle-OH | (3R,4S)-3-Amino-4-methyl-hexanoic acid |
| H-$\beta^3$-HLeu-OH | (3S)-3-Amino-5-methyl-hexanoic acid |

TABLE 10-continued

Substances Representing Subunits of "Linkers" C
(continued on the following pages)

| Code | Chemical Name |
|---|---|
| H-$\beta^3$-HMet-OH | (3S)-3-Amino-5-methylthio pentanoic acid |
| H-$\beta^3$-HTyr-OH | (3S)-3-Amino-4-(4'-hydroxyphenyl)-butyric acid |
| H-$\beta^3$-HHis-OH | (3S)-3-Amino-4-(imidazole-4'-yl)-butyric acid |
| H-$\beta^3$-HPhe-OH | (3S)-3-Amino-4-phenyl butyric acid |
| H-$\beta^3$-HTrp-OH | (3S)-3-Amino-4-(indol-3'-yl)-butyric acid |
| H-$\beta^3$-HSer-OH | (3R)-3-Amino-4-hydroxy-butyric acid |
| H-$\beta^3$-HAsp-OH | 3-Amino-pentanedioic acid |
| H-$\beta^3$-HGlu-OH | (3S)-3-Amino-hexanedioic acid |
| H-$\beta^3$-HLys-OH | (3S)-3,7-Diamino-heptanoic acid |
| H-$\beta^3$-HArg-OH | (3S)-3-Amino-6-guanidino-hexanoic-acid |
| H-$\beta^3$-HCys-OH | (3R)-3-Amino-4-mercapto-butyric acid |
| H-$\beta^3$-HAsn-OH | (3S)-3-Amino-4-carbamoyl-butyric acid |
| H-$\beta^3$-HGln-OH | (3S)-3-Amino-5-carbamoyl-pentanoic acid |
| H-$\beta^3$-HThr-OH | (3R,4R)-3-Amino-4-hydroxy-pentanoic acid |
| Gaba | 4-Amino-butyric acid |
| H-$\gamma^4$-DiHAla-OH | (4S)-4-Amino-pentanoic acid |
| H-$\gamma^4$-DiHVal-OH | (4R)-4-Amino-5-methyl-hexanoic acid |
| H-$\gamma^4$-DiHIle-OH | (4R,5S)-4-Amino-5-methyl-heptanoic acid |
| H-$\gamma^4$-DiHLeu-OH | (4R)-4-Amino-6-methyl-heptanoic acid |
| H-$\gamma^4$-DiHMet-OH | (4R)-4-Amino-6-methylthio-hexanoic acid |
| H-$\gamma^4$-DiHTyr-OH | (4R)-4-Amino-5-(4'-hydroxyphenyl)-pentanoic acid |
| H-$\gamma^4$-DiHHis-OH | (4R)-4-Amino-5-(imidazole-4'-yl)-pentanoic acid |
| H-$\gamma^4$-DiHPhe-OH | (4R)-4-Amino-5-phenyl-pentanoic acid |
| H-$\gamma^4$-DiHTrp-OH | (4R)-4-Amino-5-(indol-3'-yl)-pentanoic acid |
| H-$\gamma^4$-DiHSer-OH | (4R)-4-Amino-5-hydroxy-pentanoic acid |
| H-$\gamma^4$-DiHAsp-OH | (4R)-4-Amino-hexanedioic acid |
| H-$\gamma^4$-DiHGlu-OH | 4-Amino-heptanedioic acid |
| H-$\gamma^4$-DiHLys-OH | (4S)-4,8-Diamino-octanoic acid |
| H-$\gamma^4$-DiHArg-OH | (4S)-4-Amino-7-guanidino-heptanoic-acid |
| H-$\gamma^4$-DiHCys-OH | (4R)-4-Amino-5-mercapto-pentanoic acid |
| H-$\gamma^4$-DiHAsn-OH | (4R)-4-Amino-5-carbamoyl-pentanoic acid |
| H-$\gamma^4$-DiHGln-OH | (3S)-3-Amino-5-carbamoyl-hexanoic acid |
| H-$\gamma^4$-DiHThr-OH | (4R,5R)-4-Amino-5-hydroxy-hexanoic acid |
| Cit | L-Citrulline |
| Orn | L-Ornithine |
| tBuA | L-t-Butylalanine |
| Sar | Sarcosine |
| Pen | L-Penicillamine |
| tBuG | L-tert.-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC($NH_2$)═NH) | L-meta-Amidinophenylalanine |
| Phe(pC($NH_2$)═NH) | L-para-Amidinophenylalanine |
| Phe(mNHC($NH_2$)═NH) | L-meta-Guanidinophenylalanine |
| Phe(pNHC($NH_2$)═NH) | L-para-Guanidinophenylalanine |
| 2Pal | (2S)-2-Amino-3-(pyridine-2'-yl)-propionic acid |
| 4Pal | (2S)-2-Amino-3-(pyridine-4'-yl)-propionic acid |
| Phg | L-Phenylglycine |
| Cha | L-Cyclohexylalanine |
| $C_4$al | L-3-Cyclobutylalanine |
| $C_5$al | L-3-Cyclopentylalanine |
| Nle | L-Norleucine |
| 2-Nal | L-2-Naphthylalanine |
| 1-Nal | L-1-Naphthylalanine |
| 4ClPhe | L-4-Chlorophenylalanine |
| 3ClPhe | L-3-Chlorophenylalanine |
| 2ClPhe | L-2-Chlorophenylalanine |
| 3,4$Cl_2$Phe | L-3,4-Dichlorophenylalanine |
| 4FPhe | L-4-Fluorophenylalanine |
| 3FPhe | L-3-Fluorophenylalanine |
| 2FPhe | L-2-Fluorophenylalanine |
| Thi | L-β-2-Thienylalanine |
| Tza | L-2-Thiazolylalanine |
| Mso | L-Methionine sulfoxide |
| AcLys | N-Acetyllysine |
| Dap | 2,3-Diaminopropionic acid |
| Dab | 2,4-Diaminobutyric acid |

TABLE 10-continued

| Substances Representing Subunits of “Linkers” C (continued on the following pages) | |
|---|---|
| Code | Chemical Name |
| Dbu | (2S)-2,3-Diamino-butyric acid |
| Abu | γ-Aminobutyric acid (GABA) |
| Aha | ε-Aminohexanoic acid |
| Aib | α-Aminoisobutyric acid |
| ACC | 1-Amino cyclopropane carboxylic acid |
| ACBC | 1-Amino cyclobutane carboxylic acid |
| ACPC | 1-Amino cyclopentane carboxylic acid |
| ACHC | 1-Amino cyclohexane carboxylic acid |
| Y(Bzl) | L-O-Benzyltyrosine |
| H(Bzl) | (3S)-2-Amino-3-(1'-benzylimidazole-4'-yl)-propionic acid |
| Bip | L-(4-phenyl)phenylalanine |
| S(Bzl) | L-O-Benzylserine |
| T(Bzl) | L-O-Benzylthreonine |
| alloT | (2S,3S)-2-Amino-3-hydroxy-butyric acid |
| Leu3OH | (2S,3R)-2-Amino-3-hydroxy-4-methyl-pentanoic acid |
| hAla | L-Homo-alanine |
| hArg | L-Homo-arginine |
| hCys | L-Homo-cysteine |
| hGlu | L-Homo-glutamic acid |
| hGln | L-Homo-glutamine |
| hHis | L-Homo-histidine |
| hIle | L-Homo-isoleucine |
| hLeu | L-Homo-leucine |
| hNle | L-Homo-norleucine |
| hLys | L-Homo-lysine |
| hMet | L-Homo-Methionine |
| hPhe | L-Homo-phenylalanine |
| hSer | L-Homo-serine |
| hThr | L-Homo-threonine |
| hTrp | L-Homo-tryptophan |
| hTyr | L-Homo-tyrosine |
| hVal | L-Homo-valine |
| hCha | L-Homo-cyclohexylalanine |
| Bpa | L-4-Benzoylphenylalanine |
| OctG | L-Octylglycine |
| Tic | (3S)-1,2,3,4-Tetrahydroisoquinoline-3-carboxylic acid |
| Tiq | (1S)-1,2,3,4-Tetrahydroisoquinoline-1-carboxylic acid |
| Oic | (2S,3aS,7aS)-1-Octahydro-1H-indole-2-carboxylic acid |
| 4AmPyrr1 | (2S,4S)-4-Amino-pyrrolidine-2-carboxylic acid |
| 4AmPyrr2 | (2S,4R)-4-Amino-pyrrolidine-2-carboxylic acid |
| 4PhePyrr1 | (2S,4R)-4-Phenyl-pyrrolidine-2-carboxylic acid |
| 4PhePyrr2 | (2S,4S)-4-Phenyl-pyrrolidine-2-carboxylic acid |
| 5PhePyrr1 | (2S,5R)-5-Phenyl-pyrrolidine-2-carboxylic acid |
| 5PhePyrr2 | (2S,5S)-5-Phenyl-pyrrolidine-2-carboxylic acid |
| 4Hyp1 | (4S)-L-Hydroxyproline |
| 4Hyp2 | (4R)-L-Hydroxyproline |
| 4Mp1 | (4S)-L-Mercaptoproline |
| 4Mp2 | (4R)-L-Mercaptoproline |
| Pip | L-Pipecolic acid |
| H-$\beta^3$-HCit-OH | (3S)-3-Amino-6-carbamidyl-hexanoic acid |
| H-$\beta^3$-HOrn-OH | (3S)-3,6-Diamino-hexanoic acid |
| H-$\beta^3$-HtBuA-OH | (3S)-3-Amino-5,5-dimethyl-hexanoic acid |
| H-$\beta^3$-HSar-OH | N-Methyl-3-amino-propionic acid |
| H-$\beta^3$-HPen-OH | (3R)-3-Amino-4-methyl-4-mercapto-pentanoic acid |
| H-$\beta^3$-HtBuG-OH | (3R)-3-Amino-4,4-dimethyl-pentanoic acid |
| H-$\beta^3$-H4AmPhe-OH | (3S)-3-Amino-4-(4'-aminophenyl)-butyric acid |
| H-$\beta^3$-H3AmPhe-OH | (3S)-3-Amino-4-(3'-aminophenyl)-butyric acid |
| H-$\beta^3$-H2AmPhe-OH | (3S)-3-Amino-4-(2'-aminophenyl)-butyric acid |
| H-$\beta^3$-HPhe(mC(NH$_2$)=NH)—OH | (3S)-3-Amino-4-(3'-amidinophenyl)-butyric acid |

TABLE 10-continued

Substances Representing Subunits of "Linkers" C
(continued on the following pages)

| Code | Chemical Name |
|---|---|
| H-$\beta^3$-HPhe(pC($NH_2$)=NH)—OH | (3S)-3-Amino-4-(4'-amidinophenyl)-butyric acid |
| H-$\beta^3$-HPhe(mNHC($NH_2$)=NH)—OH | (3S)-3-Amino-4-(3'-guanidinophenyl)-butyric acid |
| H-$\beta^3$-HPhe(pNHC($NH_2$)=NH)—OH | (3S)-3-Amino-4-(4'-guanidino-phenyl)-butyric acid |
| H-$\beta^3$-H2Pal-OH | (3S)-3-Amino-4-(pyridine-2'-yl)-butyric acid |
| H-$\beta^3$-H4Pal-OH | (3S)-3-Amino-4-(pyridine-4'-yl)-butyric acid |
| H-$\beta^3$-HPhg-OH | (3R)-3-Amino-3-phenyl-propionic acid |
| H-$\beta^3$-HCha-OH | (3S)-3-Amino-4-cyclohexyl-butyric acid |
| H-$\beta^3$-H$C_4$al-OH | (3S)-3-Amino-4-cyclobutyl-butyric acid |
| H-$\beta^3$-H$C_5$al-OH | (3S)-3-Amino-4-cyclopentyl-butyric acid |
| H-$\beta^3$-HNle-OH | (3S)-3-Amino-heptanoic acid |
| H-$\beta^3$-H2Nal-OH | (3S)-3-Amino-4-(2'-naphthyl)-butyric acid |
| H-$\beta^3$-H1Nal-OH | (3S)-3-Amino-4-(1'-naphthyl)-butyric acid |
| H-$\beta^3$-H4ClPhe-OH | (3S)-3-Amino-4-(4'-chlorophenyl)-butyric acid |
| H-$\beta^3$-H3ClPhe-OH | (3S)-3-Amino-4-(3'-chlorophenyl)-butyric acid |
| H-$\beta^3$-H2ClPhe-OH | (3S)-3-Amino-4-(2'-chlorophenyl)-butyric acid |
| H-$\beta^3$-H3,4$Cl_2$Phe-OH | (3S)-3-Amino-4-(3',4'-dichlorophenyl)-butyric acid |
| H-$\beta^3$-H4FPhe-OH | (3S)-3-Amino-4-(4'-fluorophenyl)-butyric acid |
| H-$\beta^3$-H3FPhe-OH | (3S)-3-Amino-4-(3'-fluorophenyl)-butyric acid |
| H-$\beta^3$-H2FPhe-OH | (3S)-3-Amino-4-(2'-fluorophenyl)-butyric acid |
| H-$\beta^3$-HThi-OH | (3R)-3-Amino-4-(2'-thienyl)-butyric acid |
| H-$\beta^3$-HTza-OH | (3R)-3-Amino-4-(2'-thiazolyl)-butyric acid |
| H-$\beta^3$-HMso-OH | (3R)-3-Amino-4-methylsulfoxyl-butyric acid |
| H-$\beta^3$-HAcLys-OH | (3S)-7-Acetylamino-3-amino-heptanoic acid |
| H-$\beta^3$-HDpr-OH | (3R)-3,4-diamino-butyric acid |
| H-$\beta^3$-H$A_2$Bu—OH | (3S)-3,5-Diamino-pentanoic acid |
| H-$\beta^3$-HDbu-OH | (3R)-3,4-Diamino-pentanoic acid |
| H-$\beta^3$-HAib-OH | Amino-dimethyl acetic acid |
| H-$\beta^3$-HCyp-OH | 1-Amino-cyclopentane-1-yl-acetic acid |
| H-$\beta^3$-HY(Bzl)-OH | (3S)-3-Amino-4-(4'-benzyloxyphenyl)-butyric acid |
| H-$\beta^3$-HH(Bzl)-OH | (3S)-3-Amino-4-(1'-benzylimidazole-4'-yl)-butyric acid |
| H-$\beta^3$-HBip-OH | (3S)-3-Amino-4-biphenylyl-butyric acid |
| H-$\beta^3$-HS(Bzl)-OH | (3S)-3-Amino-4-(benzyloxy)-butyric acid |
| H-$\beta^3$-HT(Bzl)-OH | (3R,4R)-3-Amino-4-benzyloxy-pentanoic acid |
| H-$\beta^3$-HalloT-OH | (3R,4S)-3-Amino-4-hydroxy-pentanoic acid |
| H-$\beta^3$-HLeu3OH—OH | (3R,4R)-3-Amino-4-hydroxy-5-methyl-hexanoic acid |
| H-$\beta^3$-HhAla-OH | (3S)-3-Amino-pentanoic acid |
| H-$\beta^3$-HhArg-OH | (3S)-3-Amino-7-guanidino-heptanoic acid |
| H-$\beta^3$-HhCys-OH | (3R)-Amino-5-mercapto-pentanoic acid |
| H-$\beta^3$-HhGlu-OH | (3S)-3-Amino-heptanedioic acid |
| H-$\beta^3$-HhGln-OH | (3S)-3-Amino-6-carbamoyl hexanoic acid |
| H-$\beta^3$-HhHis-OH | (3S)-3-Amino-5-(imidazole-4'-yl)-pentanoic acid |
| H-$\beta^3$-HhIle-OH | (3S,5S)-3-Amino-5-methyl-heptanoic acid |
| H-$\beta^3$-HhLeu-OH | (3S)-3-Amino-6-methyl-heptanoic acid |
| H-$\beta^3$-HhNle-OH | (3S)-3-Amino-octanoic acid |
| H-$\beta^3$-DiAoc-OH | (3S)-3,8-Diamino-octanoic acid |
| H-$\beta^3$-HhMet-OH | (3S)-3-Amino-6-methylthio-hexanoic acid |
| H-$\beta^3$-HhPe-OH | (3S)-3-Amino-5-phenyl-pentanoic acid |
| H-$\beta^3$-HhSer-OH | (3S)-3-Amino-5-hydroxy-pentanoic acid |
| H-$\beta^3$-HhThr-OH | (3S,5R)-3-Amino-5-hydroxy-hexanoic acid |
| H-$\beta^3$-HhTrp-OH | (3S)-3-Amino-5-(indol-3'-yl)-pentanoic acid |
| H-$\beta^3$-HhThr-OH | (3S)-3-Amino-5-(4'-hydroxyphenyl)-pentanoic acid |
| H-$\beta^3$-HhCha-OH | (3S)-3-Amino-5-cyclohexyl-pentanoic acid |
| H-$\beta^3$-HBpa-OH | (3S)-3-Amino-4-(4'-benzoylphenyl)-butyric acid |

TABLE 10-continued

| Substances Representing Subunits of “Linkers” C (continued on the following pages) | |
|---|---|
| Code | Chemical Name |
| H-$\beta^3$-HOctG-OH | (3S)-3-Amino-undecanoic acid |
| H-$\beta^3$-HNle-OH | (3S)-3-Amino-heptanoic acid |
| H-$\beta^3$-HTic-OH | (3S)-1,2,3,4-Tetrahydroisoquinoline-3-yl-acetic acid |
| H-$\beta^3$-HTiq-OH | (1S)-1,2,3,4-Tetrahydroisoquinoline-1-acetic acid |
| H-$\beta^3$-HOic-OH | (2S,3aS,7aS)-1-Octahydro-1H-indole-2-yl-acetic acid |
| H-$\beta^3$-H4AmPyrr1-OH | (2S,4S)-4-Amino-pyrrolidine-2-acetic acid |
| H-$\beta^3$-H4AmPyrr2-OH | (2S,4R)-4-Amino-pyrrolidine-2-acetic acid |
| H-$\beta^3$-H4PhePyrr1-OH | (2S,4R)-4-Phenyl-pyrrolidine-2-acetic acid |
| H-$\beta^3$-H4PhePyrr2-OH | (2S,4S)-4-Phenyl-pyrrolidine-2-acetic acid |
| H-$\beta^3$-H5PhePyrr1-OH | (2S,5R)-5-Phenyl-pyrrolidine-2-acetic acid |
| H-$\beta^3$-H5PhePyrr2-OH | (2S,5S)-5-Phenyl-pyrrolidine-2-acetic acid |
| H-$\beta^3$-H4Hyp1-OH | (2S,4S)-4-Hydroxy-pyrrolidine-2-acetic acid |
| H-$\beta^3$-H4Hyp2-OH | (2S,4R)-4-Hydroxy-pyrrolidine-2-acetic acid |
| H-$\beta^3$-H4Mp1-OH | (2R,4S)-4-Mercapto-pyrrolidine-2-acetic acid |
| H-$\beta^3$-H4Mp2-OH | (2R,4R)-4-Mercapto-pyrrolidine-2-acetic acid |
| H-$\beta^3$-HPip-OH | (2S)-Piperidine-2-acetic acid |
| H-$\beta^3$-HPro-OH | (2S)-Pyrrolidine-2-acetic acid |
| Ahb | 4-Amino-2-hydroxy butyric acid |
| H-$\gamma^4$-DiHCit-OH | (4S)-4-Amino-7-carbamidyl-heptanoic acid |
| H-$\gamma^4$-DiHOrn-OH | (4S)-4,7-Diamino-heptanoic acid |
| H-$\gamma^4$-DiHtBuA-OH | (4R)-4-Amino-6,6-dimethyl-heptanoic acid |
| H-$\gamma^4$-DiHSar-OH | N-Methyl-4-amino-butyric acid |
| H-$\gamma^4$-DiHPen-OH | (4R)-4-Amino-5-methyl-5-mercapto-hexanoic acid |
| H-$\gamma^4$-DiHtBuG-OH | (4R)-4-Amino-5,5-dimethyl-hexanoic acid |
| H-$\gamma^4$-DiH4AmPhe-OH | (4R)-4-Amino-5-(4'-aminophenyl)-pentanoic acid |
| H-$\gamma^4$-DiH3AmPhe-OH | (4R)-4-Amino-5-(3'-aminophenyl)-pentanoic acid |
| H-$\gamma^4$-DiH2AmPhe-OH | (4R)-4-Amino-5-(2'-aminophenyl)-pentanoic acid |
| H-$\gamma^4$-DiHPhe(mC($NH_2$)═NH)—OH | (4R)-4-Amino-5-(3'-amidinophenyl)-pentanoic acid |
| H-$\gamma^4$-DiHPhe(pC($NH_2$)═NH)—OH | (4R)-4-Amino-5-(4'-amidinophenyl)-pentanoic acid |
| H-$\gamma^4$-DiHPhe(mNHC($NH_2$)═NH)—OH | (4R)-4-Amino-5-(3'-guanidino-phenyl)-pentanoic acid |
| H-$\gamma^4$-DiHPhe(pNHC($NH_2$)═NH)—OH | (4R)-4-Amino-5-(4'-guanidino-phenyl)-pentanoic acid |
| H-$\gamma^4$-DiH2Pal-OH | (4R)-4-Amino-5-(pyridine-4'-yl)-pentanoic acid |
| H-$\gamma^4$-DiH4Pal-OH | (4R)-4-Amino-5-(pyridine-4'-yl)-pentanoic acid |
| H-$\gamma^4$-DiHPhg-OH | (4R)-4-Amino-4-phenyl-butyric acid |
| H-$\gamma^4$-DiHCha-OH | (4R)-4-Amino-5-cyclohexyl-pentanoic acid |
| H-$\gamma^4$-DiH$C_4$al-OH | (4R)-4-Amino-5-cyclobutyl-pentanoic acid |
| H-$\gamma^4$-DiH$C_5$al-OH | (4R)-4-Amino-5-cyclopentyl-pentanoic acid |
| H-$\gamma^4$-DiHNle-OH | (4S)-4-Amino-octanoic acid |
| H-$\gamma^4$-DiH2Nal-OH | (4S)-4-Amino-5-(2'-naphthyl)-pentanoic acid |
| H-$\gamma^4$-DiH1Nal-OH | (4S)-4-Amino-5-(1'-naphthyl)-pentanoic acid |
| H-$\gamma^4$-DiH4ClPhe-OH | (4R)-4-Amino-5-(4'-chlorophenyl)-pentanoic acid |
| H-$\gamma^4$-DiH3ClPhe-OH | (4R)-4-Amino-5-(3'-chlorophenyl)-pentanoic acid |
| H-$\gamma^4$-DiH2ClPhe-OH | (4R)-4-Amino-5-(2'-chlorophenyl)-pentanoic acid |
| H-$\gamma^4$-DiH3,4$Cl_2$Phe-OH | (4R)-4-Amino-5-(3',4'-dichloro-phenyl)-pentanoic acid |
| H-$\gamma^4$-DiH4FPhe-OH | (4R)-4-Amino-5-(4'-fluorophenyl)-pentanoic acid |

TABLE 10-continued

| Substances Representing Subunits of “Linkers” C (continued on the following pages) | |
|---|---|
| Code | Chemical Name |
| H-$\gamma^4$-DiH3FPhe-OH | (4R)-4-Amino-5-(3'-fluorophenyl)-pentanoic acid |
| H-$\gamma^4$-DiH2FPhe-OH | (4R)-4-Amino-5-(2'-fluorophenyl)-pentanoic acid |
| H-$\gamma^4$-DiHThi-OH | (4R)-4-Amino-5-(2'-thienyl)-pentanoic acid |
| H-$\gamma^4$-DiHTza-OH | (4R)-4-Amino-5-(2'-thiazolyl)-pentanoic acid |
| H-$\gamma^4$-DiHMso-OH | (4R)-4-Amino-5-methylsulfoxyl-pentanoic acid |
| H-$\gamma^4$-DiHAcLys-OH | (4S)-8-Acetylamino-4-amino-ocatanoic acid |
| H-$\gamma^4$-DiHDpr-OH | (4R)-4,5-diamino-pentanoic acid |
| H-$\gamma^4$-DiH$A_2$Bu—OH | (4R)-4,5-Diamino-hexanoic acid |
| H-$\gamma^4$-DiHDbu-OH | (4R)-4,5-Diamion-hexanoic acid |
| H-$\gamma^4$-DiHAib-OH | 3-Amino-3,3-dimethyl propionic acid |
| H-$\gamma^4$-DiHCyp-OH | (1'-Amino-cyclopentane-1'-yl)-3-propionic acid |
| H-$\gamma^4$-DiHY(Bzl)-OH | (4R)-4-Amino-5-(4'-benzyloxyphenyl)-pentanoic acid |
| H-$\gamma^4$-DiHH(Bzl)-OH | (4R)-4-Amino-5-(1'-benzylimidazole-4'-yl)-pentanoic acid |
| H-$\gamma^4$-DiHBip-OH | (4R)-4-Amino-5-biphenylyl-pentanoic acid |
| H-$\gamma^4$-DiHS(Bzl)-OH | (4S)-4-Amino-5-(benzyloxy)-pentanoic acid |
| H-$\gamma^4$-DiHT(Bzl)-OH | (4R,5R)-4-Amino-5-benzyloxy-hexanoic acid |
| H-$\gamma^4$-DiHalloT-OH | (4R,5S)-4-Amino-5-hydroxy-hexanoic acid |
| H-$\gamma^4$-DiHLeu3OH—OH | (4R,5R)-4-Amino-5-hydroxy-6-methyl-heptanoic acid |
| H-$\gamma^4$-DiHhAla-OH | (4S)-4-Amino-hexanoic acid |
| H-$\gamma^4$-DiHhArg-OH | (4S)-4-Amino-8-guanidino-octanoic acid |
| H-$\gamma^4$-DiHhCys-OH | (4R)-Amino-6-mercapto-hexanoic acid |
| H-$\gamma^4$-DiHhGlu-OH | (4S)-4-Amino-ocatanedioic acid |
| H-$\gamma^4$-DiHhGln-OH | (4S)-4-Amino-7-carbamoyl-heptanoic acid |
| H-$\gamma^4$-DiHhHis-OH | (4S)-4-Amino-6-(imidazole-4'-yl)-hexanoic acid |
| H-$\gamma^4$-DiHhIle-OH | (4S,6S)-4-Amino-6-methyl-octanoic acid |
| H-$\gamma^4$-DiHhLeu-OH | (4S)-4-Amino-7-methyl-ocatanoic acid |
| H-$\gamma^4$-DiHhNle-OH | (4S)-4-Amino-nonanoic acid |
| H-$\gamma^4$-DiHhLys-OH | (4S)-4,9-Diamino-nonanoic acid |
| H-$\gamma^4$-DiHhMet-OH | (4R)-4-Amino-7-methylthioheptanoic acid |
| H-$\gamma^4$-DiHhPhe-OH | (4S)-4-Amino-6-phenyl-hexanoic acid |
| H-$\gamma^4$-DiHhSer-OH | (4R)-4-Amino-6-hydroxy-hexanoic acid |
| H-$\gamma^4$-DiHhThr-OH | (4R,6R)-4-Amino-6-hydroxy-heptanoic acid |
| H-$\gamma^4$-DiHhTrp-OH | (4S)-4-Amino-6-(indol-3'-yl)-hexanoicacid |
| H-$\gamma^4$-DiHhTyr-OH | (4S)-4-Amino-6-(4'-hydroxyphenyl)-hexanoic acid |
| H-$\gamma^4$-DiHhCha-OH | (4R)-4-Amino-5-cyclohexyl-pentanoic acid |
| H-$\gamma^4$-DihBpa-OH | (4R)-4-Amino-5-(4'-benzoylphenyl)-pentanoic acid |
| H-$\gamma^4$-DiHOctG-OH | (4S)-4-Amino-dodecanoic acid |
| H-$\gamma^4$-DiHNle-OH | (4S)-4-Amino-octanoic acid |
| H-$\gamma^4$-DiHTic-OH | (3R)-1',2',3',4'-Tetrahydroisoquinoline-3'-yl-3-propionic acid |
| H-$\gamma^4$-DiHTiq-OH | (1'R)-1',2',3',4'-Tetrahydroisoquinoline-1'-yl-3-propionic acid |
| H-$\gamma^4$-DiHOic-OH | (2'S,3'aS,7'aS)-1'-Octahydro-1H-indole-2'-yl-3-propionic acid |
| H-$\gamma^4$-DiH4AmPyrr1-OH | (2'R,4'S)-4'-Amino-pyrrolidine-2'-yl-3-propionic acid |
| H-$\gamma^4$-DiH4AmPyrr2-OH | (2'R,4'R)-4'-Amino-pyrrolidine-2'-yl-3-propionic acid |
| H-$\gamma^4$-DiH4PhePyrr1-OH | (2'R,4'R)-4'-Phenyl-pyrrolidine-2'-yl-3-propionic acid |
| H-$\gamma^4$-DiH4PhePyrr2-OH | (2'R,4'S)-4'-Phenyl-pyrrolidine-2'-yl-3-propionic acid |
| H-$\gamma^4$-DiH5PhePyrr1-OH | (2'S,5'R)-5'-Phenyl-pyrrolidine-2'-yl-3-propionic acid |
| H-$\gamma^4$-DiH5PhePyrr2-OH | (2'S,5'S)-5'-Phenyl-pyrrolidine-2'-yl-3-propionic acid |
| H-$\gamma^4$-DiH4Hyp1-OH | (2'R,4'S)-4'-Hydroxy-pyrrolidine-2'-yl-2-propionic acid |
| H-$\gamma^4$-DiH4Hyp2-OH | (2'R,4'R)-4'-Hydroxy-pyrrolidine-2'-yl-3-propionic acid |
| H-$\gamma^4$-DiH4Mp1-OH | (2'R,4'S)-4'-Mercapto-pyrrolidine-2'-yl-3-propionic acid |

TABLE 10-continued

| Substances Representing Subunits of "Linkers" C (continued on the following pages) | |
|---|---|
| Code | Chemical Name |
| H-$\gamma^4$-DiH4Mp2-OH | (2'R,4'R)-4'-Mercapto-pyrrolidine-2'-yl-3-propionic acid |
| H-$\gamma^4$-DiHPip-OH | (2'S)-Piperidine-2'-yl-3-propionic acid |
| H-$\gamma^4$-DiHPro-OH | (2'S)-Pyrrolidine-2'-yl-3-propionic acid |
| (AEt)G | N-(2-Aminoethyl)glycine |
| (APr)G | N-(3-Amino-n-propyl)glycine |
| (ABu)G | N-(4-Amino-n-butyl)glycine |
| (APe)G | N-(5-Amino-n-pentyl)glycine |
| (GuEt)G | N-(2-Guanidinoethyl)glycine |
| (GuPr)G | N-(3-Guanidino-n-propyl)glycine |
| (GuBu)G | N-(4-Guanidino-n-butyl)glycine |
| (GuPe)G | N-(5-Guanidino-n-pentyl)glycine |
| ($PEG_3$-$NH_2$)G | N—[$H_2N$—$(CH_2)_3$—$(OCH_2$—$CH_2)_2$—$O(CH_2)_3$]glycine |
| (Me)G | N-Methylglycine |
| (Et)G | N-Ethylglycine |
| (Bu)G | N-Butylglycine |
| (Pe)G | N-Pentylglycine |
| (Ip)G | N-Isopropylglycine |
| (2MePr)G | N-(2-Methylpropyl)glycine |
| (3MeBu)G | N-(3-Methylbutyl)glycine |
| (1MePr)G | (1S)-N-(1-Methylpropyl)glycine |
| (2MeBu)G | (2S)-N-(2-Methylbutyl)glycine |
| (MthEt)G | N-(Methylthioethyl)glycine |
| (MthPr)G | N-(Methylthiopropyl)glycine |
| (Ben)G | N-(Benzyl)glycine |
| (PhEt)G | N-(2-Phenylethyl)glycine |
| (HphMe)G | N-([4'-hydroxyphenyl]methyl)glycine |
| (HphEt)G | N-(2-[4'-hydroxyphenyl]ethyl)glycine |
| (ImMe)G | N-(Imidazol-5-yl-methyl)glycine |
| (ImEt)G | N-(2-(Imidazol-5'-yl)ethyl)glycine |
| (InMe)G | N-(Indol-2-yl-methyl)glycine |
| (InEt)G | N-(2-(Indol-2'-yl)ethyl)glycine |
| (CboMe)G | N-(Carboxymethyl)glycine |
| (CboEt)G | N-(2-Carboxyethyl)glycine |
| (CboPr)G | N-(3-Carboxypropyl)glycine |
| (CbaMe)G | N-(Carbamoylmethyl)glycine |
| (CbaEt)G | N-(2-Carbamoylethyl)glycine |
| (CbaPr)G | N-(3-Carbamoylpropyl)glycine |
| (HyEt)G | N-(2-Hydroxyethyl)glycine |
| (HyPr)G | (2R)-N-(2-Hydroxypropyl)glycine |
| (Mcet)G | N-(2-Mercaptoethyl)glycine |

In a specific preferred embodiment of this invention, the macrocycles of type Ia/Ib are selected from the following list:

(2S,11S,19aS)—N-[2-(dimethylamino)ethyl]-15-fluoro-7,12-dimethyl-2-{[(1-naphthylamino)carbonyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide; (2S,11S,19aS)—N-(2-aminoethyl)-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)—N-(2-{[amino(imino)methyl]amino}ethyl)-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)-15-fluoro-7,12-dimethyl-2-{[2-(1-naphthyl)-acetyl]amino}-5,8,13-trioxo-N-[2-(2-pyridinylamino)ethyl]-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)—N-[2-(dimethylamino)ethyl]-15-fluoro-7,12-dimethyl-2-{[2-(1-naphthyl)ethyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)—N-[2-(acetylamino)ethyl]-15-fluoro-7,12-dimethyl-2-[2-(1-naphthyl)acetyl]amino-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)—N-[2-(dimethylamino)ethyl]-15-fluoro-7,12-dimethyl-2-{[2-(2-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)—N-[2-(dimethylamino)ethyl]-15-fluoro-7,12-dimethyl-5,8,13-trioxo-2-(2-[3-(trifluoromethyl)phenyl]-acetylamino)-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)—N-[2-(dimethylamino)ethyl]-15-fluoro-2-[2-(3-methoxyphenyl)acetyl]amino-7,12-dimethyl-5,8,13-trioxo-2,3,6,7, 8, 9, 10, 11, 12, 13, 19,19a-dodecahydro-1H,5H-pyrrolo[2,1-c][1,4,7,12]benzoxatriazacyclopentadecine-11-carboxamide;

(2S,11S,19aS)—N-[3-(dimethylamino)propyl]-15-fluoro-7,12-dimethyl-2-[2-(1-naphthyl)acetyl]amino-5,8,13-trioxo-2,3,6,7,8,9,10,11,12,13,19,19a-dodecahydro-1H,5H-pyrrolo[2,1-c]-[1,4,7,12]benzoxatriazacyclopentadecine-11-carboxamide;

(2S,11S,19aS)-15-fluoro-7,12-dimethyl-2-[2-(1-naphthyl)-acetyl]amino-5,8,13-trioxo-N-(3-pyridinylmethyl)-2,3,6,7,8,9,10,11,12,13,19,19a-dodecahydro-1H,5H-pyrrolo[2,1-c][1,4,7,12]-benzoxatriazacyclopentadecine-11-carboxamide;

N-[(4S,6S,10S)-14-methyl-6-[2-(2-naphthyl)acetyl]amino-9,15-dioxo-2-oxa-8,14-diazatricyclo[14.3.1.$0^{4,8}$]icosa-1(20),16,18-trien-10-yl]decanamide;

N-[(4S,6S,10S)-14-methyl-10-{[2-(2-naphthyl)acetyl]amino}-9,15-dioxo-2-oxa-8,14-diazatricyclo[14.3.1.$0^{4,8}$]icosa-1(20),16,18-trien-6-yl]-2-(2-naphthyl)acetamide;

N-[(4S,6S,10S)-14-methyl-6-[2-(2-naphthyl)acetyl]amino-9,15-dioxo-2-oxa-8,14-diazatricyclo[14.3.1.$0^{4,8}$]icosa-1(20),16,18-trien-10-yl]-2-(1-naphthyl)acetamide;

N-[(4S,6S,10S)-14-methyl-9,15-dioxo-10-[(3-toluidinocarbonyl)-amino]-2-oxa-8,14-diazatricyclo[14.3.1.$0^{4,8}$]icosa-1(20),16,18-trien-6-yl]-2-(2-naphthyl)acetamide;

N-[(4S,6S,10S)-10-([3-(dimethylamino)anilino]carbonylamino)-14-methyl-9,15-dioxo-2-oxa-8,14-diazatricyclo[14.3.1.$0^{4,8}$]icosa-1(20),16,18-trien-6-yl]-2-(2-naphthyl)acetamide;

N-[(4S,6S,10S)-6-({[3-(dimethylamino)anilino]carbonyl}amino)-14-methyl-9,15-dioxo-2-oxa-8,14-diazatricyclo[14.3.1.$0^{4,8}$]icosa-1(20),16,18-trien-10-yl]-2-(2-naphthyl)acetamide;

N-[(4S,6S,10S)-14-methyl-9,15-dioxo-6-[(3-phenylpropanoyl)-amino]-2-oxa-8,14-diazatricyclo[14.3.1.$0^{4,8}$]icosa-1(20),16,18-trien-10-yl]decanamide;

N-[(4S,6S,10S)-14-methyl-6-[(3-morpholinobenzoyl)amino]-9,15-dioxo-2-oxa-8,14-diazatricyclo[14.3.1.$0^{4,8}$]icosa-1(20),16,18-trien-10-yl]decanamide;

N-[(4S,6S,10S)-6-({[3-(dimethylamino)anilino]carbonyl}amino)-14-methyl-9,15-dioxo-2-oxa-8,14-diazatricyclo[14.3.1.$0^{4,8}$]icosa-1(20),16,18-trien-10-yl]decanamide;

N-[(4S,6S,10S)-6-({[3-(dimethylamino)anilino]carbonyl}amino)-14-methyl-9,15-dioxo-2-oxa-8,14-diazatricyclo[14.3.1.$0^{4,8}$]icosa-1(20),16,18-trien-10-yl]-2-(1-naphthyl)acetamide;

N-[(4S,6S,10S)-6-({[(3-methoxyanilino)carbonyl]amino}-14-methyl-9,15-dioxo-2-oxa-8,14-diazatricyclo[14.3.1.$0^{4,8}$]icosa-1(20),16,18-trien-10-yl]-2-(2-naphthyl)acetamide;

N-[(4S,6S,10S)-14-methyl-9,15-dioxo-6-{[2-(3-phenoxyphenyl)-acetyl]amino}-2-oxa-8,14-diazatricyclo[14.3.1.$0^{4,8}$]icosa-1(20),16,18-trien-10-yl]decanamide;

N-[(4S,6S,10S)-14-methyl-6-{[2-(2-naphthyl)acetyl]amino}-9,15-dioxo-2-oxa-8,14-diazatricyclo[14.3.1.$0^{4,8}$]icosa-1(20),16,18-trien-10-yl]-6-phenylhexanamide;

N-[(4S,6S,10S)-14-methyl-6-{[2-(2-naphthyl)acetyl]amino}-9,15-dioxo-2-oxa-8,14-diazatricyclo[14.3.1.$0^{4,8}$]icosa-1(20),16,18-trien-10-yl]-5-phenoxypentanamide;

(E)-N-[(4S,6S,10S)-14-methyl-6-[2-(2-naphthyl)acetyl]amino-9,15-dioxo-2-oxa-8,14-diazatricyclo[14.3.1.$0^{4,8}$]icosa-1(20),16,18-trien-10-yl]-3-decenamide;

N-[(4S,6S,10S)-14-methyl-6-{[2-(1-naphthyl)acetyl]amino}-9,15-dioxo-2-oxa-8,14-diazatricyclo[14.3.1.$0^{4,8}$]icosa-1(20),16,18-trien-10-yl]decanamide;

6-(benzyloxy)-N-[(4S,6S,10S)-14-methyl-6-[2-(2-naphthyl)-acetyl]amino-9,15-dioxo-2-oxa-8,14-diazatricyclo[14.3.1.$0^{4,8}$]-icosa-1(20),16,18-trien-10-yl]hexanamide;

2-[1,1'-biphenyl]-4-yl-N-[(4S,6S,10S)-14-methyl-6-{[2-(2-naphthyl)acetyl]amino}-9,15-dioxo-2-oxa-8,14-diazatricyclo-[14.3.1.$0^{4,8}$]icosa-1(20),16,18-trien-10-yl]acetamide;

N-[(4S,6S,10S)-14-methyl-6-{[2-(2-naphthyl)acetyl]amino}-9,15-dioxo-2-oxa-8,14-diazatricyclo[14.3.1.$0^{4,8}$]icosa-1(20),16,18-trien-10-yl]-3,3-diphenylpropanamide;

6-(benzyloxy)-N-[(4S,6S,10S)-14-methyl-9,15-dioxo-10-[(6-phenylhexanoyl)amino]-2-oxa-8,14-diazatricyclo[14.3.1.$0^{4,8}$]-icosa-1(20),16,18-trien-6-yl]hexanamide;

2-[1,1'-biphenyl]-3-yl-N-[(4S,6S,10S)-6-([3-(dimethylamino)-anilino]carbonylamino)-14-methyl-9,15-dioxo-2-oxa-8,14-diazatricyclo[14.3.1.$0^{4,8}$]icosa-1(20),16,18-trien-10-yl]-acetamide;

2-[1,1'-biphenyl]-4-yl-N-[(4S,6S,10S)-6-([3-(dimethylamino)-anilino]carbonylamino)-14-methyl-9,15-dioxo-2-oxa-8,14-diazatricyclo[14.3.1.$0^{4,8}$]icosa-1(20),16,18-trien-10-yl]-acetamide;

N-[(4S,6S,10S)-10-[([1,1'-biphenyl]-4-ylsulfonyl)amino]-14-methyl-9,15-dioxo-2-oxa-8,14-diazatricyclo[14.3.1.$0^{4,8}$]icosa-1(20),16,18-trien-6-yl]-2-(2-naphthyl)acetamide;

N-[(4S,6S,10S)-6-{[(3-fluoroanilino)carbonyl]amino}-14-methyl-9,15-dioxo-2-oxa-8,14-diazatricyclo[14.3.1.$0^{4,8}$]icosa-1(20), 16,18-trien-10-yl]-2-(2-naphthyl)acetamide;

N-[(4S,6S,10S)-6-({[4-(dimethylamino)anilino]carbonyl}amino)-14-methyl-9,15-dioxo-2-oxa-8,14-diazatricyclo[14.3.1.$0^{4,8}$]icosa-1(20),16,18-trien-10-yl]-2-(2-naphthyl)acetamide;

phenyl N-[(4S,6S,10S)-14-methyl-10-{[2-(2-naphthyl)acetyl]-amino}-9,15-dioxo-2-oxa-8,14-diazatricyclo[14.3.1.$0^{4,8}$]icosa-1(20),16,18-trien-6-yl]carbamate;

N-[(4S,6S,10S)-14-methyl-9,15-dioxo-6-[2-(7-quinolinyl)acetyl]-amino-2-oxa-8,14-diazatricyclo[14.3.1.$0^{4,8}$]icosa-1(20),16,18-trien-10-yl]-2-(2-naphthyl)acetamide;

N-[(4S,6S,10S)-14-methyl-9,15-dioxo-6-{[2-(3-phenoxyphenyl)-acetyl]amino}-2-oxa-8,14-diazatricyclo[14.3.1.$0^{4,8}$]icosa-1(20),16,18-trien-10-yl]-2-(2-naphthyl)acetamide;

N-[(4S,6S,10S)-14-methyl-10-{[2-(2-naphthyl)acetyl]amino}-9,15-dioxo-2-oxa-8,14-diazatricyclo[14.3.1.$0^{4,8}$]icosa-1(20),16,18-trien-6-yl]decanamide;

N-[(4S,6S,10S)-14-methyl-10-{[2-(1-naphthyl)acetyl]amino}-9,15-dioxo-2-oxa-8,14-diazatricyclo[14.3.1.$0^{4,8}$]icosa-1(20),16,18-trien-6-yl]decanamide;

N-[(4S,6S,10S)-14-methyl-10-{[2-(1-naphthyl)acetyl]amino}-9,15-dioxo-2-oxa-8,14-diazatricyclo[14.3.1.$0^{4,8}$]icosa-1(20),16,18-trien-6-yl]hexanamide;

2-[1,1'-biphenyl]-4-yl-N-[(4S,6S,10S)-14-methyl-10-{[2-(1-naphthyl)acetyl]amino}-9,15-dioxo-2-oxa-8,14-diazatricyclo-[14.3.1.$0^{4,8}$]icosa-1(20),16,18-trien-6-yl]acetamide;

N-[(4S,6S,10S)-10-[(2-[1,1'-biphenyl]-4-ylacetyl)amino]-14-methyl-9,15-dioxo-2-oxa-8,14-diazatricyclo[14.3.1.$0^{4,8}$]icosa-1(20),16,18-trien-6-yl]-2,2-diphenylacetamide;

N-[(4S,6S,10S)-6-[(2-[1,1'-biphenyl]-4-ylacetyl)amino]-14-methyl-9,15-dioxo-2-oxa-8,14-diazatricyclo[14.3.1.$0^{4,8}$]icosa-1(20),16,18-trien-10-yl]-2,2-diphenylacetamide;

N-[(4S,6S,10S)-6-[(2,2-diphenylacetyl)amino]-14-methyl-9,15-dioxo-2-oxa-8,14-diazatricyclo[14.3.1.$0^{4,8}$]icosa-1(20),16,18-trien-10-yl]decanamide;

N-[(4S,6S,10S)-14-methyl-10-{[2-(1-naphthyl)acetyl]amino}-9,15-dioxo-2-oxa-8,14-diazatricyclo[14.3.1.$0^{4,8}$]icosa-1(20),16,18-trien-6-yl]-2,2-diphenylacetamide;

N-[(4S,6S,10S)-6-[(3,3-diphenylpropanoyl)amino]-14-methyl-9,15-dioxo-2-oxa-8,14-diazatricyclo[14.3.1.$0^{4,8}$]icosa-1(20),16,18-trien-10-yl]decanamide;

2-[1,1'-biphenyl]-4-yl-N-[(4S,6S,10S)-10-[(2-[1,1'-biphenyl]-4-ylacetyl)amino]-14-methyl-9,15-dioxo-2-oxa-8,14-diazatricyclo-[14.3.1.$0^{4,8}$]icosa-1(20),16,18-trien-6-yl]acetamide;

N-[(4S,6S,10S)-6-({[3-(dimethylamino)anilino]carbonyl}amino)-14-methyl-9,15-dioxo-2-oxa-8,14-diazatricyclo[14.3.1.$0^{4,8}$]icosa-1(20),16,18-trien-10-yl]-3,3-dimethylbutanamide;

N-[(4S,6S,10S)-6-({[3-(dimethylamino)anilino]carbonyl}amino)-9,15-dioxo-2-oxa-8,14-diazatricyclo[14.3.1.$0^{4,8}$]icosa-1(20), 16,18-trien-10-yl]-2-(2-naphthyl)acetamide;

benzyl N-[(4S,6S,10S)-6-{[2-(2-naphthyl)acetyl]amino}-9,15-dioxo-2-oxa-8,14-diazatricyclo[14.3.1.$0^{4,8}$]icosa-1(20),16,18-trien-10-yl]carbamate;

N-[(4S,6S,10S)-6-{[2-(2-naphthyl)acetyl]amino}-9,15-dioxo-2-oxa-8,14-diazatricyclo[14.3.1.$0^{4,8}$]icosa-1(20),16,18-trien-10-yl]decanamide;

(4S,6R,15S)-11,16-dimethyl-N-(2-naphthylmethyl)-9,12,17-trioxo-6-{[3-(4-pyridinyl)propanoyl]amino}-2-thia-8,11,16-triazatricyclo[16.3.1.$0^{4,8}$]docosa-1(22),18,20-triene-15-carboxamide;

tert-butyl N-[(4S,6R,15S)-11,16-dimethyl-15-{[(2-naphthylmethyl)amino]carbonyl}-9,12,17-trioxo-2-thia-8,11,16-triazatricyclo[16.3.1.$0^{4,8}$]docosa-1(22),18,20-trien-6-yl]carbamate;

(4S,6R,15S)-11,16-dimethyl-N-(2-naphthylmethyl)-9,12,17-trioxo-6-(pentanoylamino)-2-thia-8,11,16-triazatricyclo[16.3.1.$0^{4,8}$]-docosa-1(22),18,20-triene-15-carboxamide;

(4S,6R,15S)-6-(acetylamino)-11,16-dimethyl-N-(2-naphthylmethyl)-9,12,17-trioxo-2-thia-8,11,16-triazatricyclo-[16.3.1.$0^{4,8}$]docosa-1(22),18,20-triene-15-carboxamide;

(2S,11S,19aS)-15-fluoro-7,12-dimethyl-2-(1-naphthoylamino)-N-(2-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)-15-fluoro-7,12-dimethyl-2-[2-(2-naphthyl)acetyl]-amino-N-(1-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)-2-[(3-chlorobenzoyl)amino]-15-fluoro-7,12-dimethyl-N-(1-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide.

In another specific preferred embodiment of this invention, the macrocycles of type Ia/Ib are selected from the following list:

(2S,11S,19aS)-2-(acetylamino)-15-fluoro-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)—N-[2-(dimethylamino)ethyl]-15-fluoro-2-{[2-(1H-indol-3-yl)acetyl]amino}-7,12-dimethyl-5,8,13-trioxo-2,3,6,7,8,9,10,11,12,13,19,19a-dodecahydro-1H,5H-pyrrolo[2,1-c]-[1,4,7,12]benzoxatriazacyclopentadecine-11-carboxamide;

(2S,11S,19aS)-15-fluoro-2-{[2-(1H-indol-3-yl)acetyl]amino}-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c]-[1,4,7,12]benzoxatriazacyclopentadecine-11-carboxamide;

(2S,11S,19aS)-2-{[2-(dimethylamino)acetyl]amino}-15-fluoro-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c]-[1,4,7,12]benzoxatriazacyclopentadecine-11-carboxamide;

tert-butyl N-[(2S,11S,19aS)-15-fluoro-11-({[2-(1H-indol-3-yl)ethyl]amino}carbonyl)-7,12-dimethyl-5,8,13-trioxo-2,3,6,7,8,9,10,11,12,13,19,19a-dodecahydro-1H,5H-pyrrolo[2,1-c]-[1,4,7,12]benzoxatriazacyclopentadecin-2-yl]carbamate;

(2S,11S,19aS)—N-[2-(dimethylamino)ethyl]-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c]-[1,4,7,12]benzoxatriazacyclopentadecine-11-carboxamide;

benzyl N-[(4S,6S,10S)-14-methyl-6-{[2-(2-naphthyl)acetyl]-amino}-9,15-dioxo-2-oxa-8,14-diazatricyclo[14.3.1.$0^{4,8}$]icosa-1(20),16,18-trien-10-yl]carbamate;

benzyl N-[(4S,6S,13S)-6-{[2-(1H-indol-3-yl)acetyl]amino}-11,15-dimethyl-9,12,16-trioxo-2-oxa-8,11,15-triazatricyclo-[15.3.1.$0^{4,8}$]henicosa-1(21),17,19-trien-13-yl]carbamate;

N-[(4S,6S,13S)-6-{[2-(1H-indol-3-yl)acetyl]amino}-11,15-dimethyl-9,12,16-trioxo-2-oxa-8,11,15-triazatricyclo-[15.3.1.$0^{4,8}$]henicosa-1(21),17,19-trien-13-yl]decanamide.

Synthesis of the Building Blocks

Readily available examples of amino acids representing subunits of the Bridge C are detailed to the level of fully-defined structures in Table 10. Additional analogs can be accessed smoothly, and a plethora of literature precedents are published. Therefore this section focuses on synthetic approaches towards building blocks of the Template A and the Modulator B.

Functional groups not involved in ring connections of the macrocyclic backbone can be diversified by standard methods of organic synthesis, preferably by parallel/combinatorial chemistry introducing so-called high variation substituents. These derivatization methods are well-known to those skilled in the art and do not require further exemplification (selected references: A. R. Katritzky et al. (eds), *Comprehensive Functional Group Transformations*, Pergamon, 1995; S. Patai, Z. Rappoport (eds), *Chemistry of Functional Groups*, Wiley, 1999; J. March, *Advanced Organic Chemistry,* 4 ed., Wiley, 1992; D. Obrecht, J. M. Villalgordo (eds), *Solid-Supported Combinatorial and Parallel Synthesis of Small-Molecular-Weight Compound Libraries*, Pergamon, 1998; W. Bannwarth et al. (eds), *Combinatorial Chemistry: From Theory to Application,* 2 ed., Wiley-VCH 2006).

Synthesis of Template A Building Blocks

A) General Transformations

The majority of the building blocks of type A are based on readily available substances carrying a carboxylic acid group and either an aromatic or heteroaromatic hydroxy (Ar/Hetar-OH) or thiol moiety (Ar/Hetar-SH). The —COOH group may be attached to the same ring as the —OH/—SH group or to an annelated ring which in turn may be aromatic or partially unsaturated. In one subset of building blocks the —COOH group is replaced by a sulfanyl group (—SH) leading to sulfanyl phenols (mercapto phenols) and sulfanyl thiophenols (mercapto thiophenols) as building blocks. Yet another small subset carries instead of the —COOH an alkenyl group (—$(CHR^3)_q$—$CR^{12}$═$CH_2$; q=0-4).

In general phenol derivatives are more abundantly described in the literature than the corresponding thiophenols. However, transformations of phenols into thiophenols are well established. Therefore the phenolic systems can be regarded as precursors towards their thio-analogs. Alternatively thiophenols might be derived from the corresponding aryl halides or diazonium salts.

Selected examples of general scope for transformations introducing a sulfanyl group (—SH), i.e. Ar/Hetar-X→Ar/Hetar-SH (X═OH, F, Cl, Br, I, $N_2^+$), are the following T-I to T-VII:

T-I: A sequence of broad applicability is the transformation of a phenol into a thiocarbamate with N,N-dimethylthiocarbamoyl chloride, followed by Newman-Kwart rearrangement and subsequent hydrolysis (A. Gallardo-Godoy et al., *J. Med. Chem.* 2005, 48, 2407-2419; P. Beaulieu et al., *Bioorg. Med. Chem. Lett.* 2006, 16, 4987-4993; H. Sugiyama et al., *Chem. Pharm. Bull.* 2007, 55, 613-624; S. Lin et al., *Org. Prep. Proced. Int.* 2000; 547-556).

T-II: The direct transformation of an —OH adjacent to a pyridinic nitrogen (i.e. equivalent to the pyridone tautomer) can be accomplished by heating with $P_2S_5$ (K. Hirai et al., *Heterocycles* 1994, 38, 277-280).

T-III: As an alternative to phenols, halogen-substituted (esp. with F or Cl) aromatic ring systems might serve as precursors. In case the halogen is in a position activated by an electron withdrawing group in ortho- or para-position the —SH moiety or a protected surrogate can be introduced under mild conditions by nucleophilic aromatic substitution reactions ($S_NAr$) (G. J. Atwell et al., *J. Med. Chem.* 1994, 37, 371-380). Especially in the field of heterocyclic compounds, where the electron withdrawing effect is exerted by pyridine-like nitrogen atoms, this type of substitution is often utilized (S. McCombie et al., *Heterocycles,* 1993, 35, 93-97).

T-IV: Similarly, in Sandmeyer-type reactions a diazonium group (—$N_2^+$) is replaced (C. Mukherjee, E. Biehl, *Heterocycles* 2004, 63, 2309-2318).

T-V: In positions not activated for an $S_NAr$ the substitution of halogen atoms (esp. Br or I) can be accomplished via the corresponding organolithium or Grignard reagents (J. L. Kice, A. G. Kutateladze, *J. Org. Chem.* 1993, 58, 917-923; P. C. Kearney et al., *J. Am. Chem. Soc.* 1993, 115, 9907-9919). Alternatively, transition metal-catalyzed transformations are feasible for this type of reaction, e.g. Cu-catalyzed substitution with benzothioic S-acid (N. Sawada et al., *Tetrahedron Lett.* 2006, 47, 6595-6597), or Pd-catalyzed substitution with KS—Si(i-Pr)$_3$ followed by desilylation of the introduced —SSi(i-Pr)$_3$ group (A. M. Rane et al., *Tetrahedron Lett.* 1994, 35, 3225-3226).

The thus introduced —SH moieties constitute a thia-bridge —S— in the later macrocyclic products and can be selectively transformed into higher oxidation states. Therefore the building blocks with sulfanyl moieties are also regarded as building blocks for the introduction of sulfinyl (—S(═O)—; i.e. sulfoxide) and sulfonyl (—S(═O)$_2$—; i.e. sulfone) moieties. Suitable oxidation methods are:

T-VI: The selective oxidation of a thioether (—S—) to a sulfoxide (—S(═O)—) can be highly selectively and mildly achieved with hexamethylenetetramine-bromine HMTAB (K. Choudhary et al.; *J. Phys. Org. Chem.* 2000, 13, 283-292); under these conditions primary hydroxyl groups for example are not affected. In a number of related reactions chlorotrimethylsilane showed high selectivity, too (Y.-J. Chen et al., *Tetrahedron Lett.* 2000, 41, 5233-5236).

T-VII: Stronger oxidants directly transfer the sulfanyl (—S—) into the sulfonyl group (—S(═O)$_2$—). Among the many reagents mentioned in literature the system periodic acid/chromium(VI)oxide for example can be applied in the presence of C═C-double bonds (US2007/293548 A1).

Hydroxyl groups attached to aromatic rings (Ar—OH or Hetar-OH) in turn, if not already part of a commercially available substance, can be introduced by various methods, e.g. H-I to H-IV:

H-I: Analogously to T-III) the hydroxy group or its surrogate can be introduced by an $S_NAr$ reaction of halogen atoms, esp. Cl or F, ortho or para to an electron withdrawing substituent (W. Cantrell, *Tetrahedron Lett.* 2006, 47, 4249-4251) or to a pyridinic nitrogen atom (S. D. Taylor et al., *J. Org. Chem.* 2006, 71, 9420-9430).

H-II: Sandmeyer-type hydroxylations of aromatic amines via intermediate diazonium salts (P. Madsen et al., *J. Med. Chem.* 2002, 45, 5755-5775).

H-III: The substitution of halogen atoms (esp. Br and I), which not activated for an $S_NAr$, can be achieved by transition metal-catalyzed C—O-couplings. Predominant are Pd-catalysts (K. W. Anderson et al., *J. Am. Chem. Soc.* 2006, 128, 10694-10695; B. J. Gallon et al., *Angew. Chem., Int. Ed.* 2007, 46, 7251-7254), but also others find application, like Cu-catalysts (J. E. Ellis, S. R. Lenger, *Synth. Commun.* 1998, 28, 1517-1524).

H-IV: Of broad scope is also a two-step process which first transforms halogen atoms (Cl, Br and I) into a boronate and then oxidatively cleaves the carbon-boron bond to the phenol (J. R. Vyvyan et al., *J. Org. Chem.* 2004, 69, 2461-2468).

The carboxylic acid group of template A building blocks, if not already present in commercially available substances, can be introduced by standard procedures like C-I to C-IV:

C-I: The oxidation of functional groups like hydroxymethyl (—$CH_2$—OH) or aldehyde (—C(═O)H) is achieved under mild conditions (G. V. M. Sharma et al., *Synth. Commun.* 2000, 30, 397-406; C. Wiles et al., *Tetrahedron Lett.* 2006, 47, 5261-5264). Also methyl groups on benzene rings can be oxidized; however, as harsh reaction conditions are usually required, its applicability is limited. In contrast, the relatively acidic methyl groups ortho or para to a pyridine nitrogen can be oxidized under milder conditions; making this the method of choice for many pyridine analogs (T. R. Kelly, F. Lang, *J. Org. Chem.* 1996, 61, 4623-4633).

C-II: Halogen atoms can easily be replaced by a carboxyl group or surrogate thereof, e.g. by halogen metal exchange and subsequent carboxylation of the intermediate Grignard or organolithium species (C. G. Screttas, B. R. Steele, *J. Org. Chem.* 1989, 54, 1013-1017), or by utilizing Mander's reagent (methyl cyanoformate)(A. Lepretre et al., *Tetrahedron* 2000, 56, 265-274).

C-III: In the case that acidified ring positions are to be carboxylated, a viable method is deprotonation with a strong base (usually tert-butyl lithium) followed by carboxylation of the intermediate organolithium species in analogy to C-II).

C-IV: Hydrolysis of ester, amide or nitrile groups. The CN group in turn can easily be introduced by treating organic halides with CuCN (Rosenmund-von Braun reaction: C. F. Koelsch, A. G. Whitney, *J. Org. Chem.,* 1941, 6, 795-803).

Applied to commercially available starting materials these general transformations offer a tool box for accessing a huge variety of Templates A. Additional literature examples are cited below within the sections on specific derivatives.

B) Specific Transformations

Selected transformations of broad applicability leading to specific building block categories of hydroxy-aryl or hydroxy-heteroaryl derivatives are described below:

A1-A59 and A627-A656 Phenyl Derivatives

A plethora of hydroxy benzoic acids with diverse substitution patterns are commercially available and can be directly utilized for constructing the macrocyclic backbone. Even not so common tetrasubstituted hydroxy benzoic acids (A53-A59) can be constructed by processes relying on the general procedures mentioned above, e.g. carboxylation of pentasubstituted phenol derivatives (K. Sung, R. J. Lagow, *J. Mater. Chem.* 1996, 6, 917-918; E. Marzi, M. Schlosser, *Tetrahedron* 2005, 61, 3393-3402; K. C. Nicolaou et al., *Angew. Chem., Int. Ed.* 1999, 38, 3334-3339). Alternative approaches to tetrasubstituted hydroxy benzoic acids involve, for example, the oxidation of benzaldehydes followed by the introduction of substituents into the remaining free positions (K. C. Nicolaou et al., *Chem. Eur. J.* 2000, 6, 3095-3115).

In the sulfanyl thiophenol (mercapto thiophenol) series A627-A636 simpler derivatives are commercially available. The synthesis of more advanced ones can be achieved by subjecting suitable precursors to the general procedures T-I to T-V. Once incorporated in the macrocycle Ia/Ib the thioether (sulfanyl group; —S—) can be easily and selectively oxidized to the sulfoxide or sulfone by applying the general procedures T-VI and T-VII. Therefore A627-A636 should also be regarded as building blocks for inserting a sulfinyl (—S(═O)—) or sulfonyl (—$S(=O)_2$—) group into macrocycle Ia/Ib.

A C═C-double bond connectivity between Template A and Bridge C is conveniently introduced by metathesis or ring closing metathesis reactions. The corresponding building blocks A are based on phenol/thiophenol derivatives carrying a vinyl or alkenyl substituent (—$(CHR^3)_q$—$CR^{12}$═$CH_2$; q=0-4). A number of vinyl (q=0) or allyl (q=1) analogs are commercially available. Depending on the length q of the methylene tether, different approaches are feasible. Vinyl (q=0) and allyl (q=1) can be easily obtained by cross coupling reactions of the corresponding halo-substituted (Cl, Br, I) phenols/thiophenols, e.g. by Heck, Suzuki or Stille reaction (L. Joucla et al., *Tetrahedron Lett.* 2008, 49, 4738-4741; B. Soederberg et al., *J. Org. Chem.* 1997, 62, 5838-5845; Y. Yamamoto et al., *Chem. Lett.* 2006, 35, 704-705). Very versatile is the mild Negishi coupling which is not only useful for introducing vinyl (T. Yamamoto, T. Yamakawa, *J. Org. Chem.* 2009, 74, 3603-3605) or allyl substituents (F. Kneisel et al., *Synthesis* 2005, 2625-2629) but is also suitable for longer side chains with terminal olefin group (q=2-4; e.g. N. Kurono, *Tetrahedron* 1999, 55, 6097-6108). Additional approaches involve, e.g.: a) the synthesis of ortho-allyl phenols by Claisen rearrangement (W. A. L. Otterlo et al., *Tetrahedron* 2005, 61, 7746-7755) or b) the chain elongation of benzaldehydes or phenyl acetaldehydes by addition of vinyl or allyl Grignard reagents followed by reduction of the thus obtained secondary alcohols to the corresponding methylene compounds with trimethylsilane/TFA (B. Dahl et al., *Tetrahedron Lett.* 2004, 45, 9599-9602).

Double bonds in the macrocyclic backbone can be easily hydrogenated and should therefore be regarded as building blocks for introducing optionally substituted methylene linkers (—$(CHR^3)_q$—$CR^{12}$—) as well.

A60-A143 and A657-A659 Pyridine Derivatives

As with the previous class of compounds, also for pyridines a large number of substances is commercially available and can be incorporated into the macrocycle directly or easily transferred into suitably substituted pyridines by the general methods mentioned above. Selected literature examples are available for transformations of type C-III (M. Shimano et al. *Tetrahedron Lett.* 1998, 39; 4363-4366), H-II (L. Carpino et al., *J. Org. Chem.* 2004, 69; 54-61), C—I (T. R. Kelly, F. Lang, *Tetrahedron Lett.* 1995, 36, 5319-5322), or C-IV (J. L. LaMattina, R. L. Taylor, *J. Org. Chem.* 1981, 46, 4179-4182). For the related sulfanyl/sulfinyl/sulfonyl pyridines A657 and alkenyl/alkyl pyridines A658/A659 compare the section about the corresponding phenyl derivatives above.

A144-A165 Pyridazine Derivatives

In analogy to general transformation C-I, readily available, methylpyridazines can be oxidized to the corresponding 3- or 4-carboxylic acids (M. Morishita et al., *Chem. Pharm. Bull.* 1994, 42, 371-372; M. Winn et al., *J. Med. Chem.* 1993, 36, 2676-2688). Of equally broad scope is the hydrolysis of the corresponding nitriles under chemical (G. Heinisch, D. Lassnigg, *Arch. Pharm.* (*Weinheim, Ger.*) 1987, 320, 1222-1226) or enzymatic conditions (nitrilase from *Rhodococcus* sp.: N. Klempier et al., *Tetrahedron Lett.* 1991, 32, 341-344).

In addition, the pyridazine core can be built up from β-keto-esters which are subjected to a Staudinger reaction followed by an aza-Wittig-cyclization of the intermediate azide (S. V. Galiullina et al., *Russ. J. Org. Chem.* 2007, 43, 607-614; M. Guillaume et al., *Synthesis* 1995, 8, 920-922). In another approach β-ketoesters are cyclocondensed with the monohydrazone of α,β-diketones (E. E. Schweizer, K.-J. Lee, *J. Org. Chem.* 1982, 47, 2768-2773).

A166-A188 and A660-A662 Pyrimidine Derivatives

As for pyridines, a large number of suitable building blocks are commercially available and can be directly used or easily transferred into the targeted compounds by the standard procedures mentioned above, including transformations of type C-I (Y. Honma et al., *Chem. Pharm. Bull.* 1982, 30, 4314-4324), or C-IV (I. V. Oleinik, O. A. Zagulyaeva, *Chem. Heterocycl. Compd.* 1993, 29, 427-431). In addition, the pyrimidine 2-carboxylic acid core can be constructed by cyclocondensation of oxalates with malonamidine derivatives (G. A. Howard et al., *J. Chem. Soc.* 1944, 476-477). Different substitution patterns are accessible by reacting malonates with amidines (M. Otsuka et al., *Chem. Pharm. Bull.* 1985, 33, 515-519).

For the related sulfanyl/sulfinyl/sulfonyl pyrimidines A660 and alkenyl/alkyl pyrimidines A661/A662 compare the section about the corresponding phenyl derivatives above.

A189-A200 Pyrazine Derivatives

Pyrazine carboxylic acids are easily obtained by cyclocondensation of α,β-diaminopropionic acid with α,β-dicarbonyl derivatives (J. Bostroem et al., *Bioorg. Med. Chem.* 2007, 15, 4077-4084). Selected standard protocol examples are cited for C-I (J. R. Young et al., *Bioorg. Med. Chem. Lett.* 2000, 10, 1723-1728), for C-III (N. Ple et al., *Tetrahedron* 1998, 54, 9701-9710), and for C-II (A. P. Krapcho et al., *J. Heterocycl. Chem.* 1997, 34, 27-32). Highly chemoselective oxidations of type C-I can also be achieved by biotransformation with *Pseudomonas putida* (A. Kiener, *Angew. Chem.* 1992, 104, 748-749).

A201-A206 Triazine Derivatives

A possible route to suitably substituted precursors of bifunctional triazines is the cyclocondensation of amidrazones with α,β-diketones or α,β-diketoesters (M. Sagi et al., Heterocycles 1990, 30, 1009-1021). In addition, α,γ-diketoesters are described as suitable starting material, in which case a multi-step reaction sequence proceeds via intermediate 4-nitrosopyrazoles (R. Fusco, S. Rossi, *Tetrahedron* 1958, 3, 209-224).

A207-A228 and A663-A665 Derivatives of Furan, Thiophene and Pyrrole

Furan-3-carboxylic acids of type A207/208 can be synthesized from 2-carbonyl-3-oxo-butanoates by bromination and subsequent cyclization (A. Becker, *Helv. Chim. Acta* 1949, 32, 1114-1122; R. Richter, *Helv. Chim. Acta* 1949, 32, 1123-1136). The analogous thiophenes A207/208 can be prepared from 3-methoxycarbonyl-tetrahydrothiophene-4-one by oxidation (M. R. Banks et al., *J. Chem. Res.* (*M*) 1984, 369-389) or by condensation with aldehydes and subsequent isomerization (R. Jaunin, *Helv. Chim. Acta* 1980, 63, 1542-1553). Pyrroles A207/208 can be obtained from suitably substituted N-protected 3-amino-acrylates by treatment with 2-chloro-acetyl chloride followed by cyclization (E. Benary, R. Konrad, *Chem. Ber.* 1923, 56, 44-52).

Furans A209/210 are accessible in multi-step reactions starting from methylenephosphoranes and aldehydes (H. H. Wasserman, G. M. Lee, *Tetrahedron Lett.* 1994, 35, 9783-9786). Thiophenes A209/210 can be prepared from 2-mercaptoacetate and acetylene carboxylates (H. Fiesselmann, G. Pfeiffer, *Chem. Ber.* 1954, 87, 848-856).

The pyrroles A209/210 are obtained by condensing β-alanine esters with 2,3-dioxo-pent-4-enoates (H. H. Wasserman et al., Tetrahedron Lett. 1989, 30, 1721-1724) or by reacting 3-oxo-propanoates with glycine esters (A. Treibs, A. Ohorodnik, *Liebigs Ann. Chem.* 1958, 611, 139-149).

Furan carboxylic acids of type A211/212 can be synthesized from diazomalonates and suitably substituted alkynes in a two-step-procedure catalyzed by Rh(II)-acetate (P. Müller, C. Gränicher, *Helv. Chim. Acta* 1993, 76, 521-534). The corresponding thiophenes A211-214 are accessible by carboxylation method C-III (J. Sicé, *J. Am. Chem. Soc.* 1953, 75, 3697-3700), which is also applied for the synthesis of furans A213/214 (D. G. Manly, E. D. Amstutz, *J. Org. Chem.* 1956, 21, 516-519).

Pyrroles A211/212 can be prepared from suitably substituted 2-chloroethylidene-malonates by a tandem Staudinger reaction/aza-Wittig protocol (F.-P. Montforts et al., *Liebigs Ann. Chem.* 1990, 1037-1043). Pyrroles A213/214 can be obtained from N-protected glutamate, which is transformed into the didehydro derivative and cyclized in the presence of $LiCuMe_2$ (M. M. Paz, F. J. Sardina, *J. Org. Chem.* 1993, 58, 6990-6995).

Thiophenes A215/216 are available from 3-bromo-thiophenes in a multi-step sequence involving general reactions T-IV and C-II (E. C. Taylor, D. E. Vogel, *J. Org. Chem.* 1985, 50, 1002-1004).

Pyrroles A215/216 can be prepared from amino-oxoacetate and oxalyl chloride, alcoholysis of the isocyanate and reaction with 3-bromoacetonyl)triphenylphosphonium bromide (J. P. Bazureau et al., *Tetrahedron Lett.* 1988, 29, 1921-1922), or from N-Pfp-protected 3-oxo-prolinates (F.-A. Marcotte, W. D. Lubell, *Org. Lett.* 2002, 4, 2601-2603).

Furans A217/218 can be obtained from acetylene carboxylates by reaction with ethoxyvinylidene-tetracarbonyl-ferrocene complexes (Atiq-ur-Rehman et al., *J. Am. Chem. Soc.* 1993, 115, 9848-9849). Thiophenes A217/218 are accessible from formylsuccinates by cyclization in the presence of methanol, hydrogen chloride and hydrogen sulfide (S. Mitra et al., *J. Chem. Soc.* 1939, 1116-1117), or from 2,4-dibromothiophenes by carboxylation of type C-II (D. Spinelli et al., *J. Chem. Res.* (*M*) 1993, 8, 1873-1890). Pyrroles A217/218 (keto-tautomer) can be obtained from suitably substituted aminomethylene succinates by base-induced cyclization (C. A. Grob, P. Ankli, *Helv. Chim. Acta* 1949, 32, 2023-2038).

For the related sulfanyl/sulfinyl/sulfonyl analogs A663 and alkenyl/alkyl analogs A664/A665 compare the section about the corresponding phenyl derivatives above.

A229-A234 Oxazole, Thiazole and Imidazole Derivatives

Oxazoles of type A229 are obtained by reaction of acetyl isocyanates and diazoacetate followed by cyclization (O. Tsuge et al., *Tetrahedron* 1973, 29, 1983-1990), whereas the thiazoles A229 can be synthesized from bromomalonates and thioamides (F. A. J. Kerdesky et al., *J. Med. Chem.* 1991, 34, 2158-2165), and the imidazoles A229 from aminomalonate and acetimidates (M. S. Poonian, E. F. Nowoswiat, *J. Org. Chem.* 1980, 45, 203-208). The oxazoles and thiazoles of type A230 are accessible by cyclizing monoethyl acetamidomalonate in the presence of trifluoroacetic anhydride (J. Morgan et al., *J. Chem. Soc., Perkin Trans.* 1, 1997, 5, 613-620) or phosphorus pentasulfide (A. G. Long, A. Tulley, *J. Chem. Soc.* 1964, 1190-1192). The imidazoles A230 can be obtained from aminomalonate by reaction with trimethylorthoformate and subsequent cyclization (R. S. Hosmane, B. B. Lim, *Tetrahedron Lett.* 1985, 26, 1915-1918). Oxazoles of type A231 might be accessed from hydroxyacetaldehyde dimer (C. M. Shafer, T. F. Molinski, *J. Org. Chem.* 1998, 63, 551-555), and the corresponding thiazoles A231 from β-ketoesters (P.-F. Zhang, Z.-C. Chen, *Synth. Comm.* 2001, 31, 415-420). Imidazoles A231 can be prepared from N-protected glycines in a multi-step reaction sequence (G. van Lommen et al., *Bioorg. Med. Chem. Lett.* 2005, 15, 497-500; J. Singh et al., *Tetrahedron Lett.* 1993, 34, 211-214).

Oxazoles of type A232 can be synthesized from diazoacetates by rhodium-catalyzed reaction with cyanoformate (G. Shi et al., *J. Fluorine Chem.* 1991, 52, 149-157). Oxazoles of type A233 can be obtained by heating acetylene carboxylates with diazoacetates (R. Huisgen, H. Blaschke, *Chem. Ber.* 1965, 98, 2985-2997).

Thiazoles A233 are available from suitably substituted cysteine esters by reaction with diphosgene followed by bromination/elimination (G. Serra et al., *Heterocycles* 1995, 41, 2701-2711). Oxazoles A234 can be obtained from suitably substituted hydroxyacetonitriles and oxalyl chloride (K. van Aken, G. Hoornaert, *J. Chem. Soc., Chem. Comm.* 1992, 12, 895-896), and the thiazoles A234 from 2-mercaptoacetate and cyanoformate (G. Satzinger, *Liebigs Ann. Chem.* 1978, 473-511).

A235-A239 Isoxazole, Isothiazole and Pyrazole Derivatives

Isoxazoles and pyrazoles of type A235 can be synthesized from (2-methoxymethylene)-malonates by reaction with hydroxylamine (K. Bowden et al., *J. Chem. Soc. C* 1968, 172-185) or hydrazine (T. M. Willson et al., *Bioorg. Med. Chem. Lett.* 1996, 6, 1047-1050).

The isothiazoles A236 can be obtained from suitably substituted O-toluenesulfonyloxyiminoacetates by reacting with thioglycollates (B. Rezessy et al., *Tetrahedron Lett.* 1992, 33, 6523-6526); and the corresponding pyrazoles A236 can be prepared either from suitably substituted 2-oxopropionates and hydrazinoacetates (R. N. Comber et al., *Carbohyd. Res.* 1992, 216, 441-452) or from 3-oxopropionates by 2-diazotation and subsequent cyclization (F. J. L. Herrera, C. U. Baelo, *Carbohyd. Res.* 1985, 143, 161-174).

The isoxazoles A237 are accessible by treatment of 4-chloro-3-oxo-butanoates with isopentylnitrite (G. Hesse, G. Krehbiel, *Chem. Ber.* 1955, 88, 130-133). The pyrazoles A237 can be obtained from malonates and diazoacetate (A.

Bertho, H. Nüssel, *Liebigs Ann. Chem.* 1927, 457, 278-307). Pyrazoles of type A238 (keto-isomers) can be synthesized from ketosuccinic acids and hydrazines (K. J. Duffy et al., *J. Med. Chem.* 2001, 44, 3730-3745).

Isoxazoles of type A239 can be synthesized from 3-substituted 2-bromomaleic acids by esterification and subsequent reaction with hydroxyurea (C. Bennouna et al., *Bull. Soc. Chim. Fr.* 1980, 2, 478-480). Isothiazoles A239 can be prepared from 3-substituted 2-aminofumaramides by reaction with hydrogen sulfide and hydrolysis of the formed amides (J. Lykkeberg, P. Krogsgaard-Larsen, *Acta Chem. Scand. B* 1976, 30, 781-785). The corresponding pyrazoles are accessible by cyclocondensation of maleates with hydrazines followed by oxidation (G. P. Lahm et al., *Bioorg. Med. Chem. Lett.* 2007, 17, 6274-6279).

A240-A357 and A666-A671 Benzofuran, Benzothiophene and Indole Derivatives

Benzothiophenes A240 can be prepared in a multi-step sequence transforming 2-hydroxy-benzaldehydes into the 3-isopropoxy-2,3-dihydrobenzothiophen-2-ones and carboxylating the 3-position (A. V. Kalinin et al., *J. Org. Chem.* 2003, 68, 5992-5999). A possible route to benzofurans of type A241-A243 involves condensation of suitably substituted cyclohexane-1,3-diones and 3-bromo-2-oxo-propionic acid followed by Pd-catalyzed dehydrogenation (G. Kneen, P. J. Maddocks, *Synth. Comm.* 1986, 16, 1635-1640). Indoles A244-A247 can be obtained from 2-bromo-3-nitrobenzoates by a Stille coupling to the corresponding 1-ethoxystyrene and subsequent Pd-catalyzed cyclization in the presence of CO (R. W. Clawson et al., *Tetrahedron* 2006, 62, 10829-10834).

Benzofurans of type A248-A251 can be synthesized from suitably substituted 2,6-dihydroxy-benzoates by treatment with 2-chloroketones (F. H. Curd, A. Robertson, *J. Chem. Soc.* 1933, 714-720). The corresponding indoles A250/251 might be accessible from 6-hydroxy-3-methyl-2-nitro-benzoic acid in a multi-step reaction sequence consisting of hydrogenation, cyclization, diazotization and hydroxylation (H. D. Hollis Showalter et al., *J. Org. Chem.* 1996, 61, 1155-1158). Benzothiophenes A250/251 could be obtained from 2-(thiophen-3-yl-)acetaldehydes by reaction with propargyl alcohol followed by iodo-cyclization, oxidation and hydroxylation H-IV (J. P. Waldo et al., *J. Org. Chem.* 2008, 73, 6679-6685).

The benzothiophenes of type A252-A255 are accessible from 3-methyl-thiophene-2-carboxylates (J. W. Terpstra, A. M. van Leusen, *J. Org. Chem.* 1986, 51, 230-238). Indoles A252-A255 can be synthesized from methyl 2-methoxy-4-methyl-benzoates by bromination, nitration, reaction with dimethylformamide followed by reductive cyclization (P. L. Beaulieu et al., *Bioorg. Med. Chem. Lett.* 2006, 16, 4987-4993).

Possible precursors of benzofurans A256-A259 and A264-A267 are suitably substituted 2,4-dihydroxy-benzoates that might be alkylated in the 4-position with bromoacetaldehyde dialkyl acetals followed by cyclization (M. Dixit et al., *Synlett* 2006, 10, 1497-1502). Indoles of type A256-A259 and A264-A267 can be obtained from suitably substituted 5-hydroxy-indoles via diethyl carbamates which undergo anionic Fries rearrangement (E. J. Griffen et al., *J. Org. Chem.* 1995, 60, 1484-1485). The benzothiophenes of type A260 and A263 are accessible from 4,6-dibromobenzene-1,3-carbaldehyde by treatment with methoxide and 2-mercaptoacetate followed by cyclization, decarboxylation, demethylation and oxidation of the aldehyde to the acid (A. E. Jakobs et al., *Tetrahedron* 1994, 50, 9315-9324).

Benzofurans of type A268-A271 can be synthesized from the corresponding 4-hydroxy-benzofurans by carboxylation (T. Reichstein, R. Hirt, *Helv. Chim. Acta* 1933, 16, 121-129) or by reacting 5-carbomethoxy-6-hydroxy-salicylaldehydes with bromo-acetates followed by saponification and cyclization (R. T. Foster, A. Robertson, *J. Chem. Soc.* 1948, 115-116). Preparation of the corresponding benzothiophenes A268-A271 can start from a suitably substituted 4-oxo-tetrahydrobenzothiophene which is subjected to acylation and subsequent aromatization (P. P. Yadav et al., *Bioorg. Med. Chem.* 2005, 13, 1497-1505). Similarly indoles A268-A271 can be prepared from 4-oxo-tetrahydroindoles, or alternatively by Claisen rearrangement of the allyl ether of 4-amino-salicylic acid followed by cleavage of the double bond and cyclization (T. Kakigami et al., *Chem. Pharm. Bull.* 1988, 46, 42-52). Benzofurans of type A272-A275 can be synthesized from O-protected 4-hydroxy-salicylaldehydes by reaction with diazoacetate followed by dehydration (M. E. Dudley et al., *Synthesis* 2006, 1711-1714). Benzothiophenes A272-A275 are accessible from 5-bromo-benzothiophene by Friedel-Crafts acylation as key step (S. Mitsumori et al., *J. Med. Chem.* 2003, 46, 2446-2455), and the corresponding indoles A272-A275 by Nenitzescu reaction of para-benzoquinones with substituted 2-aminoacrylates (E. A. Steck et al., *J. Org. Chem.* 1959, 24, 1750-1752). Benzofurans of type A276-A279 can be obtained from 3-acetyl-4-hydroxy-benzoates by bromination and subsequent base-induced cyclization (G. Doria et al., *Farmaco* 1980, 35, 674-680).

Benzothiophenes A276-A279 can be prepared from 4-fluorobenzoates and thioglycolate by intramolecular Friedel-Crafts acylation (D. L. Gernert et al., *Bioorg. Med. Chem. Lett.* 2004, 14, 2759-2764).

Benzofurans and benzothiophenes of type A284-A287 can be synthesized from suitably substituted 3-furaldehydes or 3-formyl-thiophenes by cyclocondensation with succinates (D. Simoni et al., *J. Med. Chem.* 2006, 49, 3143-3152). Indoles of type A284 and A287 are accessible from 3-methoxy-4-aminobenzoates by a reaction sequence consisting of iodination, Sonogashira coupling and cyclization (J. Ezquerra et al., *J. Org. Chem.* 1996, 61, 5804-5812). Benzofurans and benzothiophenes of type A288-A291 can be obtained from suitably substituted 2-furaldehydes (D. Simoni et al., *J. Med. Chem.* 2006, 49, 3143-3152). Indoles A288-A291 are available by cyclocondensation of pyrrole-2-carbaldehydes and diethyl succinate (C. Fuganti, S. Serra, *J. Chem. Res.* (*M*) 1998, 10, 2769-2782). Indoles of type A292-A295 can be prepared from N-protected furo[3,2-b]pyrrole-5-carboxylates by decarboxylation and subsequent Diels-Alder reaction (A. Krutosikova, M. Hanes, *Collect. Czech. Chem. Comm.* 1992, 57, 1487-1494).

Benzofurans of type A296-A299 can be obtained from suitably substituted (p-acetoxyphenoxy)acetyl chlorides by reacting with cyanide followed by $ZnCl_2$-mediated cyclization with 1,3-dihydroxy-benzene (L. Crombie et al., *J. Chem. Soc., Perkin Trans.* 1, 1987, 2783-2786). The corresponding benzothiophenes A296-A299 can be synthesized from suitably substituted 3-bromothiophenols (S. Mitsumori et al., *J. Med. Chem.* 2003, 46, 2446-2455). Indoles A296-A299 are accessible from O-protected 6-hydroxyindoles (M. Fedouloff et al., *Bioorg. Med. Chem.* 2001, 9, 2119-2128).

Benzofurans A300-A303 can be obtained from suitably substituted 3-acetyl-furans via the silylenol ether (A. Benitez et al., *J. Org. Chem.* 1996, 61, 1487-1492).

Benzofurans A304-A307 can be synthesized either from 2-allyl-3-allyloxy-4-methoxy-benzaldehydes by isomerization/metathesis and oxidation (W. A. L. van Otterlo et al.,

*Tetrahedron* 2005, 61, 7746-7755) or from substituted 2-hydroxy-3-methoxy-6-bromobenzaldehydes by reduction of the alcohol, formation of the phosphonium salt, cyclization and subsequent carboxylation (K. Hagihara et al., *Bioorg. Med. Chem. Lett.* 2007, 17, 1616-1621). The corresponding benzothiophenes A304-A307 are accessible from suitably substituted methyl thiophene-2-carboxylates by trans-formation into the 1-(2'-thienyl)-1,4-dioxobutanes followed by $BF_3$-mediated cyclization, Vilsmeier-Haack formylation of the 4-position and subsequent oxidation (S. S. Samanta et al., *J. Chem. Soc., Perkin Trans.* 1, 1997, 3673-3678).

The indoles A304-A307 can be obtained by Diels-Alder reaction of the silylenolate of N-protected 2-acetylpyrrole with propionate followed by air oxidation (M. Ohno et al., *Heterocycles* 1991, 32, 1199-1202).

The mentioned synthetic routes are also feasible for preparing the more highly substituted derivatives A308-A357.

For the related sulfanyl/sulfinyl/sulfonyl and alkenyl/alkyl analogs A666-A671 compare the section about the corresponding phenyl derivatives above.

A358-A372 Pyrrolo[2,3-b]pyridine Derivatives

Pyrrolopyridines A365/366 can be synthesized from 7-azaindoles via pyridine-N-oxides (X. Wang et al., *J. Org. Chem.* 2006, 71, 4021-4023) by a carboxylation reaction of type C-II (A. L'Heureux et al., Tetrahedron Lett. 2004, 45, 2317-2320). Pyrrolopyridines of type A367/368 can be obtained from suitably substituted 4-chloro-3-formyl-pyridines by treatment with azidoacetate and subsequent Hemetsberger-Knittel reaction (P. J. Roy et al., *Synthesis* 2005, 2751-2757).

Pyrrolopyridines of type A369/370 are accessible from the corresponding 5-chloro-pyrrolopyridine by formylation in a Duff reaction, oxidation and hydrolysis (R. H. Bahekar et al., *Bioorg. Med. Chem.* 2007, 15, 6782-6795). The synthesis of pyrrolo-pyridines A371/372 can start from 4-chloro-7-azaindole and proceed via the N-oxide (T. Storz et al., *Synthesis* 2008, 201-214).

A373-A385 Pyrrolo[2,3-c]pyridine Derivatives

Pyrrolopyridines of type A379 can be obtained from suitably substituted 4-iodo-3-nitro-pyridines involving Sonogashira coupling and $TiCl_4$-mediated cyclization as key reactions (T. Sakamoto et al., *Chem. Pharm. Bull.* 1986, 34, 2362-2368). Pyrrolopyridines of type A382/383 can be prepared from 2-methoxy-4-iodo-5-aminopyridines by Sonogashira coupling with TMS-acetylene, CuI-mediated cyclization, formylation and oxidation (D. Mazeas et al., *Heterocycles* 1999, 50, 1065-1080). Pyrrolopyridines of type A384/385 are accessible from suitably substituted 4-methoxy-pyrrole-2-carbaldehydes by reductive amination with 3,3-diethoxy-2-amino-propionate and subsequent cyclization (S. K. Singh et al., *Heterocycles* 1997, 44, 379-392).

A386-A398 Pyrrolo[3,2-c]pyridine Derivatives

Pyrrolopyridines A387/388 are accessible from N-alkylated 2-formyl-pyrroles via 2-pyrrylacryl azides (J. S, New et al., *J. Med. Chem.* 1989, 32, 1147-1156). Pyrrolopyridines of type A389/390 can be obtained from 2-methoxy-3-formyl-pyridines by reaction with azidoacetate and subsequent Hemetsberger-Knittel reaction (P. J. Roy et al., *Synthesis* 2005, 2751-2757).

A399-A413 Pyrrolo[3,2-b]pyridine Derivatives

Pyrrolopyridines of type A406/407 can be obtained from 2-(6-methoxy-3-nitro-2-pyridyl)acetates by Knoevenagel condensation with formaldehyde followed by Pd-catalyzed cyclization in the presence of hydrogen and CO (B. C. G. Soederberg et al., *Synthesis* 2008, 6, 903-912).

Pyrrolopyridines A410 and A413 can be synthesized from suitably substituted 2-chloro-3-nicotinonitriles by Sonogashira coupling with TMS-acetylene and subsequent cyclization as key steps (T. Sakamoto et al., *Chem. Pharm. Bull.* 1986, 34, 2362-2368). Alternatively, their preparation can be achieved by reacting 3-nitro-pyridines with vinylmagnesium bromide (Z. Zhang et al., *J. Org. Chem.* 2002, 67, 2345-2347). Pyrrolopyridines A408 and A412 are available from 2-alkynyl-3-amino-pyridines by CuI-catalyzed cyclization (A. M. Palmer et al., *Bioorg. Med. Chem.* 2008, 16, 1511-1530).

A414-A449 Derivatives of Benzoxazole, Benzothiazole and Benzimidazole

Benzoxazoles A415/416 can be prepared from N-acylated 3-chloro-4-anisidines via benzyne-formation and carboxylation (D. R. Reavill, S. K. Richardson, *Synth. Comm.* 1990, 20, 1423-1436). The corresponding benzimidazoles A415/416 are accessible from 2-amino-3-halo-benzoates by acylation of the amine, nitration and reductive cyclization (K. Kubo et al., *J. Med. Chem.* 1993, 36, 1772-1784).

Benzimidazoles of type A417-A419 can be obtained from the corresponding 4-acetamido-2-methoxy-benzoates by chlorination in 5-position, nitration in 3-position and reductive cyclization (S. Bolgunas et al., *J. Med. Chem.* 2006, 49, 4762-4766).

Benzimidazoles A420-A422 are accessible from the corresponding 5-methoxy-6-methyl-benzimidazoles by oxidations of type C-I (B. D. Palmer et al., *J. Med. Chem.* 1999, 42, 2373-2382). Benzoxazoles of type A423-A425 can be obtained by condensing 4-methylene-2-oxazolin-5-ones and 4-triphenylphosphoranylidene-3-oxobutanoates, followed by aromatization (F. Clerici et al., *Tetrahedron* 1991, 47, 8907-8916). The synthesis of the corresponding benzimidazoles A423-A425 is possible starting from 4-amino-2-hydroxy-5-nitrobenzoates by acylation, reduction of the nitro group and cyclization (A. Tanaka et al., *Chem. Pharm. Bull.* 1994, 42, 560-569). Benzoxazoles of type A426-A428 can be synthesized starting from 2,5-dihydroxybenzoate (D. Diez-Martin et al., *Tetrahedron* 1992, 48, 7899-7939). Benzimidazoles A429-A431 are accessible from O-protected 3,4-diamino-2-hydroxy-benzoates by acylation and subsequent cyclization (Y. Hirokawa et al., *Chem. Pharm. Bull.* 2002, 50, 941-959; A. Viger, P. B. Dervan, *Bioorg. Med. Chem.* 2006, 14, 8539-8549). Benzothiazoles of type A438-A440 can be synthesized by heating suitably substituted 4-amino-3-methoxy-benzoates with thiocyanate in the presence of copper(II)-salts and subsequent 2-desamination (I. A. Ismail et al., *J. Org. Chem.* 1980, 45, 2243-2246). Benzimidazoles A441-A443 can be prepared by a multi-step sequence from 8-aminoquinolines via the corresponding 5,6-dihydro-4H-imidazoquinolines (R. C. Elderfield, F. J. Kreysa, *J. Am. Chem. Soc.* 1948, 70, 44-48). Benzimidazoles A444 and A447 can be obtained by reaction of suitably substituted 3-amino-4-methoxy-benzoates with nitriles followed by NaOCl-induced cyclization (J. Regan et al., *Bioorg. Med. Chem. Lett.* 1998, 8, 2737-2742).

A450-A459 Derivatives of Benzisoxazole, Benzisothiazole and Indazole

Benzisoxazoles A456 and A459 can be synthesized starting from 2,6-dihydroxy-3-formyl-4-methyl-benzoates by reaction with hydroxylamine followed by thermal cyclization (D. H. R. Barton et al., *J. Chem. Soc. C* 1971, 2166-2174); this method also is suitable for benzisoxazoles of types A450-A455 and A457/458.

The preparation of indazoles A457 has been described as reaction between 3-amino-2-methoxy-4-methylbenzoate and isoamylnitrite (S. Bolgunas et al., *J. Med. Chem.* 2006, 49, 4762-4766).

A460-A515 Naphthalene Derivatives

A large number of suitably substituted naphthalene derivatives is commercially available. In addition, naphthalenes A460-A465 and A496-A499 can be obtained from the corresponding 2-hydroxy-naphthalenes via lithiation and carboxylation (cf. C-III) (K. Takahashi et al., *Tetrahedron* 1994, 50, 1327-1340). Higher substituted analogs can be prepared in a multi-step sequence from suitably substituted 2-bromotoluenes via 2-tetralone-1-carboxylates (F. C. Goerth et al., *Eur. J. Org. Chem.* 2000, 2605-2612).

Naphthalenes of type A478-A483 and A508-A511 can be synthesized either by demethylation of 3-methoxynaphthalene-1-carboxylates (R. E. Royer et al., *J. Med. Chem.* 1995, 38, 2427-2432) or by H-II type reaction of 3-aminonaphthalene-1-carboxylates (K. J. Duffy et al., *J. Med. Chem.* 2001, 44, 3730-3745).

The naphthalenes A484-A489 and A504-A507 can easily be built up by condensation of succinic esters with either benzaldehydes (A. M. El-Abbady et al., *J. Org. Chem.* 1961, 26, 4871-4873; M. Kitamura et al., *Angew. Chem. Int. Ed.* 1999, 38, 1229-1232) or with benzophenones (F. G. Baddar et al., *J. Chem. Soc.* 1955, 1714-1718).

Naphthalene derivatives of type A490-A495 and A512-A515 can be obtained from 2-methoxynaphthalenes by bromination in 4-position and C-II type carboxylation (J. A. O'Meara et al., *J. Med. Chem.* 2005, 48, 5580-5588) or from 2-chloro-naphthalene and phthalic anhydride (G. Heller, *Chem. Ber.* 1912, 45, 674-679).

A516-A548 and A672-A674 Quinoline Derivatives

The synthesis of quinolines A516-A518 can be accomplished by reacting suitably substituted isatins with phenacylbromides (H. John, *J. Prakt. Chem.* 1932, 133, 259-272; E. J. Cragoe et al., *J. Org. Chem.* 1953, 18, 552-560).

Quinolines A522-A524 are easily accessible from 2-aminobenzaldehydes via a modified Friedländer synthesis (D. L. Boger, J.-H. Chen, *J. Org. Chem.* 1995, 60, 7369-7371). Similarly, quinoline derivatives A527-A529 can be obtained from 2-aminobenzaldehydes by condensation with malonic acid (J. Troger, C. Cohaus, *J. Prakt. Chem.* 1927, 117, 97-116).

Quinolines A525 can be synthesized from the corresponding 2-cyanoquinoline-1-oxides by rearrangement (C. Kaneko, S. Yamada, *Chem. Pharm. Bull.* 1967, 15, 663-669). Quinolines A526 is accessible from substituted 2-aminoacetophenones by reaction with 3-chloro-3-oxopropionate and subsequent base-induced cyclization (A. Capelli et al., *Bioorg. Med. Chem.* 2002, 10, 779-802).

Quinolines of type A530-A533 can be constructed from 2-anisidines by reacting with 2-oxosuccinic esters followed by thermal cyclization (L. Musajo, M. Minchilli, *Chem. Ber.* 1941, 74, 1839-1843). Syntheses of quinolines A534-A536 and A537-A539 can be achieved via the corresponding halogen substituted analogs followed by carboxylation of type C-II (F. Cottet et al., *Eur. J. Org. Chem.* 2003, 8, 1559-1568).

For the synthesis of quinolines A543-A545 the condensation of isatins with malonic acid is frequently described in the literature (e.g. W. Borsche, W. Jacobs, *Chem. Ber.* 1914, 47, 354-363; J. A. Aeschlimann, *J. Chem. Soc.* 1926, 2902-2911). Derivatives of type A546-A548 can be obtained in a multi-step reaction starting with 3-chloroanilines (A. M. Spivey, F. H. S. Curd, *J. Chem. Soc.* 1949, 2656-2662).

For the related sulfanyl/sulfinyl/sulfonyl quinolines A672 and alkenyl/alkyl quinolines A673/A674 compare the section about the corresponding phenyl derivatives above.

A549-A564 Isoquinoline Derivatives

Isoquinolines of type A549-A553 with a carboxyl in 1-position can be prepared from benzaldehydes in a multistep sequence consisting of transformation into aminoethanes, reaction with oxalic ester, cyclization, and aromatization (M. Keizo et al., *Chem. Pharm. Bull.* 1982, 30, 4170-4174; S, Naoki et al., *Chem. Pharm. Bull.* 1989, 37, 1493-1499).

Isoquinoline-3-carboxylates A554-A556 are accessible from hydroxy-phenylalanines by Bischler-Napieralski reaction and subsequent aromatization, or alternatively from 2-methyl benzaldehydes by reacting with azidoacetate, thermal cyclization and aromatization (Y. Fukuda et al., *J. Med. Chem.* 1999, 42, 1448-1458; T. R. Burke et al., *Heterocycles* 1992, 34, 757-764). Compounds of type A557/558 can be synthesized by reaction of 2-aminobenzoic acids and 5-chloro-3-carboxy-1,2,4-pyrazines in the presence of amylnitrite (A. M. d'A. Rocha Gonsalves, T. M. V. D. Pinho e Melo, *Tetrahedron* 1992, 48, 6821-6826), whereas isoquinolines A559/560 can be prepared from 2-formylbenzoic acids via isothiochromenone (D. J. Dijksman, G. T. Newbold, *J. Chem. Soc.* 1951, 1213-1217).

Access to isoquinolines A561/562 is feasible by transformation of isoquinolines into the corresponding Reissert compounds, nitration in 4-position and hydrolysis (M. Sugiura et al., *Chem. Pharm. Bull.* 1992, 40, 2262-2266).

Isoquinolines of type A563/564 are accessible from (2-methoxycarbonyl-phenyl)acetic acids by reaction with methyl formate followed by cyclization and amination (H. E. Ungnade et al., *J. Org. Chem.* 1945, 10, 533-536).

A565-A577 Quinazoline Derivatives

The most general routes to quinazolines use appropriately substituted phenyl derivatives onto which the pyrimido ring is cyclized, e.g. the cyclocondensation of 2-amino benzamides with oxalates (M. Suesse et al., *Helv. Chim. Acta* 1986, 69, 1017-1024), of ortho-carbonyl substituted phenyl oxalamic acid esters with ammonium formate (S. Ferrini et al., *Org. Lett.* 2007, 9, 69-72), of 2-amino benzonitriles with carbonylformimidate or chloroformamidine (A. McKillop et al., *Tetrahedron Lett.* 1982, 23, 3357-3360; N. Harris et al., *J. Med. Chem.* 1990, 33, 434-444), or of ortho-oxalyl anilides with ammonia (M. T. Bogert, F. P. Nabenhauer, *J. Am. Chem. Soc.* 1924, 46, 1702-1707).

A578-A587 Quinoxaline Derivatives

The synthesis of quinoxalines A578-581 via their 2-carbaldehydes is well-documented (E. Lippmann et al., *Zeitschr. Chem.* 1990, 30, 251-252). Representative structures of type A582-587 are available by cyclocondensation of α,β-dicarbonyl derivatives or β-ketoesters with appropriately substituted orthophenylendiamines (S. Grivas et al., *Acta Chem. Scand.* 1993, 47, 521-528; A. Zychilinski, I. Ugi, *Heterocycles* 1998, 49, 29-32; D. Zhou et al., *Bioorg. Med. Chem.* 2008, 16, 6707-6723). In addition, it is possible to introduce a carboxyl group into the 2-position of the quinoxaline ring by biotransformation with *Arthrobacter nicotianae* (T. Yoshida et al., *Biosci. Biotech. Biochem.* 2002, 66, 2388-2394).

A588-A601 Pyrido[5,4-d]pyrimidine Derivatives

The bicyclic cores A588-A601 can be accessed by annelating suitably substituted pyridines. Feasible starting materials for these cyclocondensation reactions include pyridine-2,3-dicarboxylic acids (A. Tikad et al., *Synlett* 2006, 12, 1938-1942), 3-aminopyridine-2-carboxylates (M. Hayakawa et al., *Bioorg. Med. Chem.* 2006, 14, 6847-6858)

or 3-aminopyridine-2-nitriles (J. B. Smaill et al., *J. Med. Chem.* 2000, 43, 1380-1397).

A602-A608 Pyrimido[5,4-d]pyrimidine Derivatives

Access to the pyrimidopyrimidine group can be achieved via the well-known 4,6-dichloro (G. Rewcastle et al., *J. Med. Chem.* 1997, 40; 12, 1820-1826) or 2,4,6,8-tetrachloro derivatives (J. Northen et al., *J. Chem. Soc., Perkin Trans.* 1, 2002, 108-115) utilizing the general methods described above.

A609-A618 and A675-A683 Tetraline Derivatives

A large number of reaction sequences towards tetralines occur via 1- or 2-tetralones as key intermediates. Their carbonyl groups are elaborated into carboxyl moieties by the action of trimethylsilyl cyanide (TMSCN) or diethyl cyanophosphonate (DECNP) and subsequent hydrolysis (M. Meyer et al., *J. Med. Chem.* 1997, 40, 1049-1062; F. Berardi et al., *J. Med. Chem.* 2004, 47, 2308-2317). These tetralones in turn are synthesized by an intramolecular Friedel-Crafts acylation of cyclization precursors derived from phenylacetonitriles and 2-phenyl malonates (R. S. Natekar, S. D. Samant, *Indian J. Chem., Sect. B: Org. Chem. Incl. Med. Chem.* 2002, 41, 187-190; L. Gong, H. Parnes, *J. Labelled Compd. Radiopharm.* 1996, 38, 425-434). Alternatively, the intramolecular cyclization can be achieved by a Buchner reaction (A. Cheung et al., *Bioorg. Med. Chem. Lett.* 2003, 13, 133-138).

The synthesis of enantiomerically pure analogs is described by D. Obrecht et al., *Helv. Chim. Acta* 1995, 78, 1567-1587. For the related sulfanyl/sulfinyl/sulfonyl and alkenyl/alkyl tetralines A675-A683 compare the section about the corresponding phenyl derivatives above.

A619-A626 Indane Derivatives

Indane derivatives A619-A623 with a carboxyl residue in the 1-position are accessible from easily available 3-cyanoindenes by hydrogenation to the indane followed by hydrolysis to the carboxylic acid moiety (T. McLean et al., *J. Med. Chem.* 2006, 49, 4269-4274). Furthermore, inadan-1-ones can be transferred into indan-1-carboxylic acids, for example via oxiranes (D.-I. Kato et al., *J. Org. Chem.* 2003, 68, 7234-7242), or in a Corey-Seebach-type reaction via 1,3-dithianes (Y.-P. Pang et al., *J. Org. Chem.* 1991, 56, 4499-4508).

Indane derivatives of types A624-A626 with a carboxyl group in 2-position can be obtained from readily accessible indan-1-ones by treatment of the corresponding enolate with dimethyl carbonate, subsequent hydrogenation of the carbonyl group and final hydrolysis (T. Tanaka et al., *Chem. Pharm. Bull.* 1994, 42, 1756-1759; U. Hacksell et al. *J. Med. Chem.* 1981, 24, 429-434). Alternatively the indane ring system can be built up starting from ortho-xylenes by NBS bromination of both methyl groups, followed by alkylative spirocyclization with the enolate of barbituric acid and finally decarboxylative ring cleavage to indan-2-carboxylic acids (G. A. Kraus et al., *J. Org. Chem.* 2002, 67, 5857-5859).

Synthesis of Modulator B Building Blocks

The Modulator B moieties of macrocycle Ia/Ib are derived from appropriately substituted aminoalcohols, wherein the amino and alcohol group, which contribute to the ring connectivity, are separated by 2-4 C-atoms.

If not already present in a commercial building block, the substituent $R^3$ can be introduced by standard nucleophilic addition of organometallic reagents to carbonyl or carboxyl derivatives. For B18-B21, carrying no additional C-substituent on their ring system, such precursors are commercially available. Similarly, in the case of B9, B10, B16 and B17 the diversification of the substitution pattern can be easily achieved by standard transformations of the commercial analogs with free amine functionalities (i.e. $—NH_2→—NR^{11}R^{27}$ in the case of B9 and $—NH→—NR^{11}$ for B10, B16 and B17).

B1 Aziridine Derivatives

Usually, the access to hydroxymethyl aziridines relies on reaction sequences constructing the aziridine ring. The starting materials with the broadest applicability are β-ketoesters: Transformation into the β-hydroxyimino analog, intramolecular cyclization to the aziridine and reduction of the ester group to the alcohol leads to building blocks of type B1 (e.g. T. Sakai et al., *J. Org. Chem.* 2005, 70, 1369-1375). An alternative approach uses α,β-dihaloesters which are elaborated into substances of type B1 via aziridination with ammonia and reduction of the ester group (P. Davoli et al., *Tetrahedron* 2001, 57, 1801-1812).

B2-B3 Azetidine Derivatives

The standard approach to hydroxymethyl azetidines subjects easily accessible O-protected glycidols successively to epoxide-ring opening with azide, transformation of the thus obtained alcohol group into a suitable leaving group (e.g. tosylate or sulfate), and reduction of the azide to amine with concomitant intramolecular cyclization (F. Hosono et al., *Tetrahedron* 1994, 50, 13335-13346; D.-G. Liu, G.-Q. Lin, *Tetrahedron Lett.* 1999, 40, 337-340).

B4-B8 Pyrrolidine Derivatives and B11-B15 Piperidine Derivatives

The synthetic pathways to pyrrolidine and piperidine building blocks B rely on the same strategy, and intramolecular cyclization reactions are the predominant route applicable to diversely substituted substrates. Amines carrying a residue with a leaving group in the ω-position lead directly to the desired saturated ring systems by intramolecular nucleophilic substitution (G. Ceulemans et al., *Tetrahedron* 1997, 53, 14957-14974; S. H. Kang, D. H. Ryu, *Tetrahedron Lett.* 1997, 38, 607-610; J. L. Ruano et al., *Synthesis* 2006, 687-691). Also N-haloamines can be directly transformed into the desired compounds by a Hofmann-Loffler-Freytag reaction (M. E. Wolff, *Chem. Rev.* 1963, 63, 55-64). Alternatively, amines carrying two substituents, each with an alkene or alkyne bond, can be subjected to a ring closing metathesis (RCM) reaction (Y. Coquerel, J. Rodriguez, *Eur. J. Org. Chem.* 2008, 1125-1132) and subsequent reduction of the partially unsaturated ring to the saturated heterocycle.

Another possible access, reduction of aromatic five- or six-membered heterocycles to their saturated analogs, is described in the literature. Due to the large number of commercially available pyridines this approach is especially useful for the synthesis of the piperidine system (J. Bolos et al., *J. Heterocycl. Chem.* 1994, 31, 1493-1496; A. Solladie-Cavallo et al., *Tetrahedron Lett.* 2003, 44, 8501-8504; R. Naef et al., *J. Agric. Food Chem.* 2005, 53, 9161-9164).

General Processes for the Synthesis of Macrocyclic Compounds Ia/Ib

General procedures for the synthesis of libraries of macrocyclic compounds of general structure Ia/Ib are described below. It will be immediately apparent to those skilled in the art how these procedures have to be modified for the synthesis of individual macrocyclic compounds of type Ia/Ib.

The macrocyclic compounds of the invention are obtained by cyclization of suitable linear precursors which are derived from optionally substituted bifunctional phenols or thiophenols A (“Template”), substituted amino alcohols B (“Modulator”), and one to three building blocks forming “Bridge” C.

Phenol or thiophenol building blocks A comprise optionally substituted hydroxyaryl, hydroxyheteroaryl, mercaptoaryl, and mercapto-heteroaryl carboxylic acids, mercaptophenols, hydroxymercapto-heteroaryl compounds, alkenyl phenols or alkenyl thiophenols.

Variable substituents are introduced by pre- or postcyclative derivatization of one or more orthogonally protected attachment points (e.g. amino groups, carboxyl groups, hydroxyl groups) on B, C or A. Variable R-groups may also be introduced as side chain motifs of the subunits of Bridge C.

The macrocyclic products of the invention can be prepared either in solution or on solid support.

The essential ring closure reaction is possible between any of the building blocks; and macrocycles Ia/Ib are obtained by e.g.

- Macrolactamization between C and B;
- Macrolactamization between A and C;
- Macrolactamization between any two subunits of Bridge C;
- Arylether or arylthioether formation between A and B;
- Arylthioether formation between A and C;
- Ring closing metathesis (RCM) reaction between any two subunits of C; or
- Ring closure metathesis reaction between A and C.

SW-1: Synthesis Workflow for the Preparation of Side-Chain Protected Macrocycles Ia/Ib by Macrolactamization in Solution Macrocycles of structure Ia/Ib with orthogonally protected exocyclic functional groups (attachment points for derivatizations) are prepared in solution by the process outlined below. Throughout all steps the orthogonal protection of the side chains stays intact and is not affected by protecting group manipulations of the main chain. Within this workflow SW-1 the generic group M is $NR^4$ or $CHR^6$; and both V and W are $CONR^4$.

a1) Condensation of an appropriately protected hydroxy- or mercapto-aryl/heteroaryl carboxylic acid $PG^1$-A-OH and a suitable C-terminally and side-chain protected C-subunit building block H—$NR^4$-c1-CO—$OPG^2$ to form $PG^1$-A-$NR^4$-c1-CO—$OPG^2$; the related compounds $PG^1$-A-$CHR^6$-c1-CO—$OPG^2$ are obtained if a mercaptophenol or hydroxy-mercapto heteroaryl compound is used as A building block and connected to a C-terminally and side-chain protected compound LG-$CHR^6$-c1-CO—$OPG^2$ by S-alkylation (LG represents a leaving group like halide, alkyl- or aryl-sulfonate).

b1) If required, deprotection of the aryl/heteroaryl hydroxy or mercapto group;

c1) Aryl/heteroaryl ether or thioether formation with a suitably N-protected amino alcohol $PG^3$-B-OH leading to the fully protected linear precursor $PG^3$-B-A-M-c1-CO—$OPG^2$;

d1) Cleavage of the "main chain" protective groups affording the free amino acid H—B-A-M-c1-CO—OH, which is either subjected to (i) immediate macrocyclization (step e1) or (ii) chain elongation by one (steps f1-i1) or (iii) two additional C-subunits followed my macrocyclization (steps j1-o1).

(i) Direct Macrolactamization e1) Intramolecular amide coupling to cyclo(B-A-M-c1-CO—) as macrocyclic product.

(ii) Chain Elongation by One Additional C-Subunit and Subsequent Macrolactamization f1) N-Reprotection of the product of step d1;

g1) Coupling with a second suitably C-protected amino acid to $PG^3$-B-A-M-c1-V-c2-CO—$OPG^2$;

h1) Cleavage of the "main chain" protective groups;

i1) Macrolactamization to the side-chain protected macrocycle cyclo(B-A-M-c1-V-c2-CO—).

(iii) Chain Elongation by Two Additional C-Subunits and Subsequent Macrolactamization j1) N-Protection of the product obtained in step d1;

k1) Coupling with a second suitably C-protected amino acid;

l1) Cleavage of the C-terminal protective group or cleavage of N- and C-terminal protective groups followed by reprotection of the N-terminus;

m1) Coupling with a third suitably C-protected amino acid yielding $PG^3$-B-A-M-c1-V-c2-W-c3-CO—;

n1) Cleavage of the "main chain" protective groups;

o1) Macrolactamization to the side-chain protected macrocycle cyclo(B-A-M-c1-V-c2-W-c3-CO—).

In addition to the steps described above, the free carboxylic acid functionality of the N-reprotected product of step f1, or of a linear precursor (cf. steps a1, g1, k1, m1) after selective deprotection can be further elaborated by chain extensions/homologizations (e.g. Arndt-Eistert reaction) or functional group interconversions like Curtius rearrangement; ultimately affording homologous macrocycles or those where the connection between Modulator B and Bridge C corresponds to a urea moiety.

SW-2: Synthesis Workflow for the Preparation of Side-Chain Protected Macrocycles Ia/Ib by Macrolactamization in Solution As an alternative to SW-1 the protected cyclization precursor $PG^3$-B-A-M-c1-CO—$OPG^2$ (wherein M is $NR^4$) can also be synthesized by an inverted order of reaction steps:

a2) Arylether or arylthioether formation between a hydroxyl or mercapto-aryl/heteroaryl ester H-A-$OPG^4$ and a suitably protected amino alcohol $PG^3$-B-OH to afford $PG^3$-B-A-$OPG^4$;

b2) Deprotection of the carboxylic acid group to $PG^3$-B-A-OH;

c2) Condensation with a C-terminally and side-chain protected building block H-M-c1-CO—$OPG^2$ to $PG^3$-B-A-M-c1-CO—$OPG^2$. Possible subsequent steps are as described in SW-1.

SW-3: Synthesis Workflow for the Preparation of Side-Chain Protected Macrocycles Ia/Ib by Macrolactamization in Solution As an alternative to SW-1 (ii) macrocycles of type cyclo (B-A-M-c1-V-c2-CO—) can be synthesized by interconnecting the C-subunits (i.e. by formation of the V moiety) as last and macrocyclization step:

a3) Synthesis of $PG^1$-A-M-c1-CO—$OPG^2$ as described above (cf. a1);

b3) Deprotection to H-A-M-c1-CO—$OPG^2$ (cf. b1);

c3) N-acylation of aminoalcohol H—B—OH with a suitably N-terminally protected amino acid $PG^5$-$NR^4$-c2-CO—OH to afford amido-alcohol $PG^5$-$NR^4$-c2-CO—B—OH (cf. al);

d3) Arylether or arylthioether bond formation between the products of steps b3 and c3 to $PG^5$-$NR^4$-c2-CO—B-A-M-c1-CO—$OPG^2$ (cf. c1);

e3) Cleavage of the "main chain" protective groups to give the cyclization precursor H—$NR^4$-c2-CO—B-A-M-c1-CO—OH (cf. d1);

f3) Macrolactamization to the side-chain protected macrocycle cyclo(c2-CO—B-A-M-c1-V-) i.e. cyclo(B-A-M-c1-V-c2-CO—) wherein M is $NR^4$ and V is $CONR^4$ (cf. e1 and i1).

Similar to SW-1(iii) a third C-subunit could be introduced by subjecting H—B—OH to two successive N-acylation, N-deprotection sequences affording $PG^5$-$NR^4$-c2-W-c3-CO—B—OH. Subsequent ether or thioether formation and main chain deprotection (cf. d3 and e3) yield H—$NR^4$-c2-W-c3-CO—B-A-M-c1-CO—OH which is finally cyclized to macrolactam cyclo(B-A-M-c1-V-c2-W-c3-CO—) wherein M is $NR^4$ and both V and W are $CONR^4$.

General Procedures for Synthetic Steps Utilized in SW-1 to SW-3

In all general procedures below M represents $NR^4$ or $CHR^6$.

Amidation Reactions (Steps a1, g1, k1, m1, c2)

An appropriately protected (preferably as acetyloxy or acetylmercapto) and optionally substituted aryl/heteroaryl carboxylic acid ($PG^1$-A-OH) is converted into the corresponding acid chloride and then condensed with a suitably protected amino acid ester H—$NR^4$-c1-CO—$OPG^2$ in the presence of an auxiliary base (e.g. i-$Pr_2NEt$, $Et_3N$, pyridine, collidine) in solvents like $CH_2Cl_2$, $CHCl_3$, THF to afford $PG^1$-A-$NR^4$-c1-CO—$OPG^2$. Alternatively this product can be obtained by amide coupling of an acyloxy or acylmercapto aryl/heteroaryl carboxylic acid ($PG^1$-A-OH) with an amino acid ester H—$NR^4$-c1-CO—$OPG^2$ in the presence of a coupling reagent (e.g. benzotriazole derivatives like HBTU, HCTU, PyBOP; their aza analogs like HATU; or carbodiimides like EDC). Hydroxyaryl or heteroaryl carboxylic acids H-A-OH do not necessarily require protection of the phenolic OH-group and can directly be coupled with the H—$NR^4$-c1-CO—$OPG^2$ to the free phenol derivative H-A-$NR^4$-c1-CO—$OPG^2$ in the presence of a coupling reagent.

Deprotection of Aromatic Hydroxy or Mercapto Groups (Step b1)

Deacylation of $PG^1$-A-$NR^4$-c1-CO—$OPG^2$ to the corresponding free hydroxyl or mercapto aryl/heteroaryl amide H-A-$NR^4$-c1-CO—$OPG^2$ is achieved by aminolysis, which is advantageously carried out with a dialkylaminoalkyl amine in solvents like degassed THF at 0-25° C. Acyl amine side products formed in the course of the reaction are easily removed by extraction with acidic aqueous solutions.

Arylether or Arylthioether Formation Between A and B (Steps c1, a2)

Alkylation of the phenol or thiophenol H-A-M-c1-CO—$OPG^2$ with a suitably N-protected amino alcohol $PG^3$-B-OH to the ether or thioether $PG^3$-B-A-M-c1-CO—$OPG^2$ is accomplished with azodicarboxylic acid derivatives such as DEAD, DIAD, TMAD or ADDP in the presence of trialkyl or triaryl phosphines in solvents like benzene, toluene, $CH_2Cl_2$, $CHCl_3$ or THF at 0° to room temperature. As a variation, the reaction is induced with CMBP in toluene at temperatures of 20-110° C.

In an alternative approach, the alcohol $PG^3$-B-OH is converted into the corresponding sulfonate (e.g. mesylate, tosylate or triflate) or halide (e.g. chloride, bromide or iodide) and subsequently treated with the phenol/thiophenol H-A-M-c1-CO—$OPG^2$ in the presence of an auxiliary base such as NaH or $K_2CO_3$ in solvents like DMF, DMSO, NMP, HMPA, or THF, to yield $PG^3$-B-A-M-c1-CO—$OPG^2$.

Cleavage of the Main Chain Protective Groups (Steps d1, h1, l1)

Simultaneous or stepwise cleavage of the main chain protective groups provides the linear amino acids as cyclization precursors. The preferred protecting groups are Alloc as $PG^3$ and/or allylester as $PG^2$, which can be cleaved simultaneously by palladium catalysts (e.g. $Pd(PPh_3)_4$) in the presence of 1,3-dimethyl barbituric acid in solvents like $CH_2Cl_2$ or EtOAc or mixtures thereof.

N-Reprotection (Steps f1, j1, l1)

N-Reprotection is achieved by applying standard amino acid protection protocols with chloroformates or N-hydroxy-succinimidyl carbonates in solvents like dioxane, and if required in the presence of a base such as aqueous $Na_2CO_3$.

Macrolactamization (Steps e1, i1, o1)

Macrolactamization occurs upon treatment of the cyclization precursor with coupling reagents like T3P or FDPP (if required in the presence of an auxiliary base such as i-$Pr_2NEt$) in solvents like $CH_2Cl_2$ or DMF under high dilution conditions and at temperatures ranging from 20 to 100° C.

Due to their synthetic importance macrolactamizations are a well-investigated class of transformations. The favorable application of FDPP as cyclization mediator is described e.g. by J. Dudash et al., *Synth. Commun.* 1993, 23, 349-356; or R. Samy et al., *J. Org. Chem.* 1999, 64, 2711-2728. Many other coupling reagents were successfully utilized in related head to tail cyclizations and might be applied instead; examples include benzotriazole derivatives like HBTU, HCTU, PyBOP; or their aza analogs such as HATU, as well as DPPA, and carbodiimides like EDC or DIC (P. Li, P. P. Roller, *Curr. Top. Med. Chem.* 2002, 2, 325-341; D. L. Boger et al., *J. Am. Chem. Soc.* 1999, 121, 10004-100 µl). Still another route to macrolactams relies on the intramolecular reaction of an active ester with an in situ released amino group (e.g. by carbamate deprotection or azide reduction) as demonstrated in the synthesis of peptide alkaloids and vancomycin model systems (U. Schmidt et al., *J. Org. Chem.* 1982, 47, 3261-3264; K. C. Nicolaou et al., *Chem. Commun.* 1997, 1899-1900).

SW-4: Synthesis Workflow for the Preparation of Side-Chain Protected Macrocycles Ia/Ib by Ring-Closing Metathesis in Solution Ring-closing metathesis (RCM) of olefinic precursors to macrocyclic compounds is well documented (e.g. A. Fürstner et al., *Chem. Eur. J.* 2001, 7, 4811-4820) and supplements the macrocyclization strategies described above. RCM of the examples was accomplished either between subunits of Bridge C or between Template A and Bridge C:

(i)RCM Between Subunits of Bridge C a4) Coupling of an optionally substituted alkenyl amine building block H—$NR^4$-c1-$CR^{12}$═$CH_2$ with the carboxylic acid derivatives $PG^1$-A-OH or H-A-OH to afford PG'-A-$NR^4$-c1-$CR^{12}$═$CH_2$ or H-A-$NR^4$-c1-$CR^{12}$═$CH_2$;

b4) If required release of the aryl/heteroaryl hydroxyl or mercapto group;

c4) N-acylation of the aminoalcohol H—B—OH with an optionally substituted alkenyl carboxylic acid as second C-subunit to afford the amido alcohol $H_2C$═$CR^{13}$-c2-CO—B—OH;

d4) Arylether or arylthioether formation to the cyclization precursor $H_2C$═$CR^{13}$-c2-CO—B-A-$NR^4$-c1-$CR^{12}$═$CH_2$;

e4) Ring-closing metathesis to cyclo($CR^{13}$-c2-CO—B-A-$NR^4$-c1-$CR^{12}$═) i.e. cyclo(B-A-$NR^4$-c1-$CR^{12}$═$CR^{13}$-c2-CO—).

(ii) RCM between Template A and Bridge C a5) Identical to step c4 as described above;

b5) Arylether formation with an alkenyl-substituted phenol H-A=$CH_2$ to the cyclization precursor $H_2C$═$CR^{12}$-c1-CO—B-A=$CH_2$;

c5) Ring-closing metathesis to cyclo(B-A=$CR^{12}$-c1-CO—).

Optionally the olefinic double bonds of the macrocycles obtained in step e4 or step c5 can be hydrogenated to the cyclo(B-A-$NR^4$-c1-$CHR^{12}$—$CHR^{13}$-c2-CO—) or cyclo(B-A-$CHR^{12}$-c1-CO—).

In analogy to SW-1(ii)/(iii) it is also feasible to prepare olefinic macrocycles with extended Bridges C such as cyclo(B-A-$NR^4$-c1-$CR^{12}$═$CR^{13}$-c2-W-c3-CO—), cyclo(B-A═$CR^{12}$-c1-V-c2-CO—) or cyclo(B-A═$CR^{12}$-c1-V-c2-W-c3-CO—) and subsequently the respective hydrogenated analogs.

General Procedures for Synthetic Steps Utilized in SW-4

Apart from the RCM all steps are conducted in analogy to the transformations described for SW-1 to SW-3.

Ring-Closing Metathesis (Steps e4 and c5)

The ring-closing metathesis is conveniently performed in solvents like $CH_2Cl_2$ or toluene at temperatures of 20-100° C. in the presence of indenylidene-ruthenium complexes such as dichloro-(3-phenyl-1H-inden-1-ylidene)bis(tricyclohexyl-phosphine)-ruthenium(II); [1,3-bis(2,4,6-trimethylphenyl)-2-imidazolidinylidene]-dichloro-(3-phenyl-1H-inden-1-ylidene(tricyclohexylphosphine)-ruthenium(II); or [1,3-bis(2,4,6-trimethylphenyl)-2-imidazolidinylidene]-dichloro-(3-phenyl-1H-inden-1-ylidene)(pyridyl)ruthenium (II) (S. Monsaert et al., *Eur. J. Inorg. Chem.* 2008, 432-440 and references cited therein).

SW-5: Synthesis Workflow for Derivatizations of Attachment Points in Solution

The macrocyclic compounds obtained according to SW-1 to SW-4 can be further modified by transformations involving attachment points like, but not limited to, amino, carboxyl or hydroxyl groups. In addition, aromatic halides or sulfonates can be subjected to transition-metal catalyzed C—C or C-hetero-coupling reactions. The orthogonal protection of the attachment points allows stepwise deprotections and derivatizations which are carried out in a parallel fashion to generate substance libraries:

a6) Cleavage of the first protective group;

b6) Derivatization of the unmasked functional group;

c6) Cleavage of the second protective group;

d6) Derivatization of the liberated functional group; etc.

General Procedures for Synthetic Steps Utilized in SW-5

Protecting Group Cleavage (Steps a6 and c6)

The utilized amine protecting groups (e.g. Boc, Cbz, Teoc, Alloc, Fmoc, etc.), carboxylic acid protecting groups (e.g. tert-butyl, benzyl, allyl, methyl, etc.) or alcohol protecting groups (e.g. tert-butyl, benzyl, allyl, acetyl, benzoyl, pivaloyl) are removed under standard conditions (P. G. M. Wuts, T. W. Greene, *Greene's Protective Groups in Organic Synthesis*, John Wiley and Sons, 4th Edition, 2006; P. J. Koncienski, *Protecting Groups,* 3rd ed., Georg Thieme Verlag 2005).

Attachment Point Derivatizations (Steps b6 and d6)

Derivatizations of the liberated functional groups are based on standard synthesis procedures (A. R. Katritzky et al. (eds), *Comprehensive Functional Group Transformations*, Pergamon, 1995; S. Patai, Z. Rappoport (eds), *Chemistry of Functional Groups*, Wiley, 1999; J. March, *Advanced Organic Chemistry,* 4 ed., Wiley, 1992; leading reviews for Mitsunobu reaction: 0. Mitsunobu, Synthesis 1981, 1-28; D. L. Hughes, *Org. Reactions; Wiley,* 1992, *Vol.* 42; leading reviews for reductive amination/alkylation: A. F. Abdel-Magid et al., *J. Org. Chem.* 1996, 61, 3849; E. W. Baxter, A. B. Reitz, *Org. Reactions*, Wiley, 2002, Vol. 59).

Such Prototypical transformations include, but are not limited to:

(i) Amino group derivatizations such as

Amidations with carbonyl chlorides, carboxylic acid anhydrides, active esters; or with carboxylic acids in the presence of coupling reagents (cf. the general procedures);

Formation of sulfonamides with sulfonyl chlorides;

Reductive alkylation with carbonyl compounds; or alkylation with alkyl halides, alkylsulfonates or Michael acceptors;

Formation of ureas by reacting with isocyanates or their equivalents like carbamoyl chlorides or hydroxysuccinimidyl esters;

Transformation into thioureas with isothiocyanates or their equivalents;

Carbamate formation by reacting with chloroformates or their surrogates such as hydroxysuccinimidyl carbonates;

N-arylation to the corresponding N-aryl or N-heteroaryl derivatives with activated aromatic or heteroaromatic halides or sulfonates in the presence of an auxiliary base and/or Pd catalyst (e.g. Buchwald couplings).

(ii) Carboxyl group derivatizations like

Amidation with amines in the presence of a coupling reagent;

Esterification with alcohols.

(iii) Alcoholic hydroxyl group derivatizations as

Alkylation to alkyl ethers with alkyl halides or alkylsulfonates;

Transformation into aryl or heteroaryl ethers by reaction with (a) phenols in the presence of azodicarboxylic acid derivatives and triaryl or trialkyl phosphines (Mitsunobu type reactions); or (b) suitably activated aryl or heteroaryl halides or sulfonates;

Oxidation to carbonyl compounds, which in turn can be further elaborated by e.g. reductive amination, Wittig reaction or related olefination reactions, etc.;

Esterification with carboxylic acids or their activated surrogates.

(iv) Aryl halide or sulfonate derivatizations by e.g. Suzuki, Sonogashira, Buchwald or Negishi coupling reactions etc.

SW-6: Synthesis Workflow for Derivatizations of Attachment Points on Solid Phase As an alternative to SW-5, macrocyclic compounds Ia/Ib with one or more orthogonally protected exocyclic functional groups and one free primary amino group can be converted into fully derivatized products on solid support by:

a7) Attachment of the macrocyclic amine to an appropriately functionalized solid support by reductive amination;

b7) Acylation, carbamoylation, oxycarbonylation or sulfonylation of the secondary amine functionality generated in the previous step a7;

c7) Removal of the protecting group from the second attachment point;

d7) Derivatization of the liberated second functional group whereby e.g. amino groups can be alkylated or converted into amides, ureas, thioureas carbamates, or sulfonamides; and carboxylic acid moieties can be transformed into amides or esters;

e7) Repetitions of steps c7 and d7 if a third, fourth etc. attachment point is available;

f7) Release of the final product from the solid support.

In case of macrocyclic carboxylic acids the attachment to a polymer-supported amine is followed by derivatizations and release in analogy to c7 to f7:

a8) Attachment of an amine to an appropriately functionalized solid support by reductive amination;

b8) Coupling of the macrocyclic carboxylic acid to the polymer-supported amine of step a8;

c8-f8) Derivatizations and release in analogy to steps c7-f7.

General Procedures for Synthetic Steps Utilized in SW-6

The Functionalized Solid Support

The solid support (polymer, resin) is preferably a derivative of polystyrene cross-linked with 1-5% divinylbenzene, of polystyrene coated with polyethyleneglycol (Tentagel®), or of polyacrylamide (D. Obrecht, J.-M. Villalgordo, *Solid-Supported Combinatorial and Parallel Synthesis of Small-Molecular-Weight Compound Libraries*, Tetrahedron Organic Chemistry Series, Vol. 17, Pergamon 1998). It is functionalized by means of a linker, i.e. an α,ω-bifunctional spacer molecule with an anchoring group for the solid support on one end, and on the other end a selectively cleavable functional group that is used for subsequent transformations and finally for release of the product. For the examples of the present invention linkers are used that release an N-acyl (amide, urea, carbamate) or an N-sulfonyl (sulfonamide) derivative under acidic conditions. These kinds of linkers have been applied in the backbone amide linker (BAL) strategy for solid-phase synthesis of linear and cyclic peptides (K. J. Jensen et al., *J. Am. Chem. Soc.* 1998, 120, 5441-5452; J. Alsina et al., *Chem. Eur. J.* 1999, 5, 2787-2795) and heterocyclic compounds as well (T. F. Herpin et al., *J. Comb. Chem.* 2000, 2, 513-521; M. del Fresno et al., *Tetrahedron Lett.* 1998, 39, 2639-2642; N. S. Gray et al., *Tetrahedron Lett.* 1997, 38, 1161-1164).

Examples of such functionalized resins include DFPE polystyrene (2-(3,5-dimethoxy-4-formylphenoxy)ethyl polystyrene), DFPEM polystyrene (2-(3,5-dimethoxy-4-formylphenoxy)ethoxymethyl polystyrene), FMPB resins (4-(4-formyl-3-methoxyphenoxy)butyryl AM-resin), FMPE polystyrene HL (2-(4-formyl-3-methoxyphenoxy)ethyl polystyrene HL), FMPB NovaGel (4-(4-formyl-3-methoxyphenoxy)butyryl NovaGel; a PEG PS resin).

Attachment of the Macrocyclic Amine to the Functionalized Resin (Steps a7 and b7) and Subsequent N-acylation or N-sulfonylation The macrocyclic primary amine is attached to the functionalized solid support by reductive amination preferably with $NaBH(OAc)_3$ as reducing agent in 1,2-dichloroethane and in the presence of trimethyl orthoformate.

The use of reductive aminations for such processes as well as the subsequent N-acylation or N-sulfonylation are well-documented; for example $NaBH_3CN$ in DMF or in methanol, or $NaBH(OAc)_3$ in DMF/acetic acid or in dichloromethane/acetic acid have been used (cf. references cited for the functionalized solid support). The N-acylation is favorably conducted with carboxylic acids in the presence of coupling reagents like PyBOP, PyBroP, or HATU or with carboxylic acid fluorides/chlorides or carboxylic acid anhydrides.

Deprotection (Steps c7)

The second attachment point is an Alloc or Fmoc protected amino group or a carboxyl group protected as allyl ester. Standard methods (cf. SW-5) are applied for their deprotection and derivatization.

Release from the Resin (Step f7)

The final products are detached from the solid support by acids dissolved in organic solvents and/or $H_2O$. The use of TFA in dichloromethane, of TFA in dichloromethane in the presence of a scavenger such as $H_2O$ or dimethyl sulfide, or of TFA/$H_2O$ and TFA/$H_2O$/dimethylsulfide has been described (cf. references cited for the functionalized solid support).

Attachment of the Macrocyclic Carboxylic Acid to the Functionalized Resin (Steps a8 and b8)

A primary amine is attached to the functionalized solid support by reductive amination preferably using $NaBH(OAc)_3$ in 1,2-dichloroethane in the presence of trimethyl orthoformate. Subsequent acylation with the macrocyclic carboxylic acids is favorably conducted in the presence of coupling reagents like HATU, PyBOP, or PyBroP.

It is worth mentioning that the initially attached primary amine corresponds to an attachment point derivatization of the carboxylic acid.

SW-7: Synthesis Workflow for the Preparation of Side-Chain Protected Macrocycles Ia/Ib on Solid Support Macrocyclic compounds of general formula Ia/Ib with highly variable side chain motifs in Bridge C can advantageously be prepared in a parallel array synthesis on solid support with an appropriately protected precursor comprising building blocks A and B as starting material. After its immobilization the precursor is coupled with one to three subunits of Bridge C and macrocyclizd to the product which is finally cleaved from the resin:

a9) Condensation (cf. SW-2) of a suitable hydroxy or mercapto aryl/heteroaryl carboxylic acid ester H-A-OPG$^4$ with an appropriately N-protected amino alcohol PG$^3$-B-OH, which is substituted with an orthogonally protected primary amino group;

b9) Removal of the protective group from the primary amine;

c9) Attachment to the solid support in a reductive alkylation step (cf. SW-6, a7) providing the polymer-supported PG$^3$-B-A-OPG$^4$ carrying a free secondary side chain amino group;

d9) Acylation, carbamoylation, oxycarbonylation or sulfonylation of the secondary amine (cf. SW-6, b7);

e9) Cleavage of the "main chain" amine protecting group to H—B-A-OPG$^4$ which is then condensed with either (i) one C-subunit or (ii) two C-subunits:

(i) Synthesis of a Macrocycle Ia/Ib with a Bridge C Consisting of Two Subunits f9) Coupling of H—B-A-OPG$^4$ with an appropriately protected C-subunit PG$^5$-NR$^4$-c2-CO—OH to PG$^5$-NR$^4$-c2-CO—B-A-OPG$^4$;

g9) Cleavage of the main chain acid protective group PG$^4$ affording PG$^5$-NR$^4$-c2-CO—B-A-OH;

h9) Coupling of PG$^5$-NR$^4$-c2-CO—B-A-OH with a suitably protected C-subunit H—NR$^4$-c1-CO—OPG$^2$ to PG$^5$-NR$^4$-c2-CO—B-A-NR$^4$-c1-CO—OPG$^2$;

i9) Removal of the carboxylic acid protective group PG$^2$;

j9) Removal of the amine protective group PG$^5$;

k9) Macrolactamization of the linear cyclization precursor on solid support to afford cyclo(B-A-M-c1-V-c2-CO—) wherein M is NR$^4$ and V is CONR$^4$;

l9) Detachment of the final product.

(ii) Synthesis of a Macrocycle I with a Bridge C Consisting of Three Subunits f10) Coupling of H—B-A-OPG$^4$ with an appropriately protected C-subunit PG$^5$-NR$^4$-c3-CO—OH to PG$^5$-NR$^4$-c3-CO—B-A-OPG$^4$;

g10) Removal of the amine protective group PG$^5$;

h10) Coupling with the second C-subunit PG$^5$-NR$^4$-c2-CO—OH to PG$^5$-NR$^4$-c2-CO—NR$^4$-c3-CO—B-A-OPG$^4$;

i10) Cleavage of the main chain acid protective group PG$^4$;

j10) Coupling with the suitably protected third C-subunit H—NR$^4$-c1-CO—OPG$^2$ to PG$^5$-NR$^4$-c2-CO—NR$^4$-c3-CO—B-A-NR$^4$-c1-CO—OPG$^2$;

k10) Removal of the carboxylic acid protective group PG$^2$;

l10) Removal of the amine protective group PG$^5$;

m10) Macrolactamization of the linear cyclization precursor on solid support to afford cyclo(B-A-M-c1-V-c2-W-c3-CO—) wherein M is $NR^4$ and both V and W are $CONR^4$;

n10) Detachment of the final product.

Related examples for macrocyclizations (step k9 or m10) on solid support are published by C. Cabrele et al., *J. Org. Chem.* 1999, 64, 4353-4361.

In an alternative approach an equivalent of the product of step d9 can be obtained by reductive alkylation of the product from step b9 with a bifunctional linker such as (4-(4-formyl-3,5-dimethoxy)phenoxy)butyric acid in solution, subsequent derivatization of the resulting secondary amine and coupling to a suitable polymeric support such as aminomethyl polystyrene. In another variation solid phase chemistry and solution chemistry can be combined. In some instances it proved advantageous to synthesize the linear cyclization precursor on solid support (product of steps j9 or l10), then to release it and to conduct the macrolactamization in solution with soluble coupling reagents as described above (cf. SW-1) or with polymer-supported coupling reagents such as N-cyclohexyl-carbodiimide-N'-methylpolystyrene or N-alkyl-2-chloro pyridinium triflate resin (S. Crosignani et al, *Org. Lett.* 2004, 6, 4579-4582).

Further viable alternatives for the synthesis of macrocycles Ia/Ib on solid support could involve

- Macrolactamization in other positions, e.g. between the Modulator B and Bridge C corresponding to an adaptation of SW-1 to solid phase chemistry; or
- Alternative macrocyclizations modes, e.g. similar to the RCM route of SW-4.

Properties and Usefulness

The macrocycles of type Ia/Ib of the present invention interact with specific biological targets. In particular, they show agonistic or antagonistic activity on the motilin receptor (MR receptor), on the serotonin receptor of subtype $5\text{-HT}_{2B}$ ($5\text{-HT}_{2B}$ receptor), on the prostaglandin F2α receptor (FP receptor), on the purinoreceptor $P2Y_1$, on the voltage-gated potassium channel $K_v1.3$, or on the canonical (β-catenin-dependent) Wnt pathway.

Accordingly, these compounds are useful for the treatment of motility disorders of the gastrointestinal tract such as functional dyspepsia, diabetic gastroparesis or constipation type irritable bowl syndrome; of CNS related diseases like migraine, schizophrenia, psychosis, depression or Alzheimer disease; of ocular hypertension such as associated with glaucoma and of preterm labour; of CNS inflammatory disorders like multiple sclerosis; of thromboembolic disorders; of cell proliferation disorders, especially various cancer types; or of bone and cartilage-related disorders.

The macrocycles, as such or after further optimization, may be administered per se or may be applied as an appropriate formulation together with carriers, diluents or excipients well-known in the art.

When used to treat or prevent the diseases mentioned above the macrocycles can be administered singly, as mixtures of several macrocycles, or in combination with other pharmaceutically active agents. The macrocycles can be administered per se or as pharmaceutical compositions.

Pharmaceutical compositions comprising macrocycles of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active macrocycles into preparations which can be used pharmaceutically. Proper formulation depends upon the method of administration chosen.

For topical administration the macrocycles of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the macrocycles of type Ia/Ib may be formulated in adequate solutions, preferably in physiologically compatible buffers such as Hank's solution, Ringer's solution, or physiological saline buffer. The solutions may contain formulatory agents such as suspending, stabilizing and/or dispersing agents. Alternatively, the macrocycles of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated per se or by combining the active macrocycles of the invention with pharmaceutically acceptable carriers well known in the art. Such carriers enable the macrocycles of type Ia/Ib to be formulated as tablets, pills, dragees, capsules, liquids, gels, syrups, slurries, suspensions etc., for oral ingestion by a patient to be treated. For oral formulations such as, for example, powders, capsules and tablets, suitable excipients include fillers such as sugars, (e.g. lactose, sucrose, mannitol or sorbitol) or such as cellulose preparations (e.g. maize starch, wheat starch, rice starch, potato starch, gelatin, gum tragacanth, methyl cellulose, hydroxypropylmethyl cellulose, sodium carboxymethylcellulose); and/or granulating agents; and/or binding agents such as polyvinylpyrrolidone (PVP). If desired, desintegrating agents may be added, such as cross-linked polyvinylpyrrolidones, agar, or alginic acid or a salt thereof, such as sodium alginate. Solid dosage forms may be sugar-coated or enteric-coated using standard techniques. For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the macrocycles of the invention are conveniently delivered in form of an aerosol spray from pressurized packs or a nebulizer, with the use of a suitable propellant, e.g. hydrofluoroalkanes (HFA) such as HFA 134a (1,1,1,2,-tetrafluoroethane); carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the macrocycles of the invention and a suitable powder base such as lactose or starch.

The compounds may also be formulated in rectal or vaginal compositions such as suppositories together with appropriate suppository bases like cocoa butter or other glycerides.

In addition to the formulations described above, the macrocycles of the invention may also be formulated as depot preparations. Such slow release, long acting formulations may be administered by implantation (e.g. subcutaneously or intramuscularly) or by intramuscular injection. For the manufacture of such depot preparations the macrocycles of the invention may be formulated with suitable polymeric or hydrophobic materials (e.g. as an emulsion in an acceptable oil) or with ion exchange resins, or as sparingly soluble salts.

Furthermore, other pharmaceutical delivery systems may be employed such as liposomes and emulsions. Certain organic solvents such as dimethylsulfoxide may also be employed. Additionally, the macrocycles of type Ia/Ib may be delivered using a sustained-release system, such as semipermeable matrices of solid polymers containing the therapeutic agent. Various sustained-release materials have been established and are well-known by those skilled in the art. Sustained-release capsules may, depending on their chemical nature, release the compounds over a period of a few days up to several months. Depending on the chemical nature and the biological stability of the therapeutic agent, additional strategies for stabilization may be employed.

As the macrocycles of the invention may contain charged residues, they may be included in any of the above-described formulations as such or as pharmaceutically acceptable salts. Pharmaceutically acceptable salts tend to be more soluble in aqueous and other protic solvents than the corresponding free base or acid forms.

The macrocycles of the invention, or compositions thereof, will generally be used in an amount effective to achieve the intended purpose. It is understood that the amount used will depend on a particular application.

For example, the therapeutically effective dose for systemic administration can be estimated initially from in vitro assays: A dose can be formulated in animal models to achieve a circulating macrocycle concentration range that includes the $IC_{50}$ or $EC_{50}$ as determined in the cell culture (i.e. the concentration of a test compound that shows half maximal inhibitory concentration in case of antagonists or half maximal effective concentration in case agonists). Such information can be used to more accurately determine useful doses in humans.

Initial dosages can also be determined from in vivo data, e.g. animal models, using techniques that are well known in the art.

Dosage amounts for applications such as gastroparesis or schizophrenia etc. may be adjusted individually to provide plasma levels of the active compound that are sufficient to maintain the therapeutic effect. Therapeutically effective serum levels may be achieved by administering multiple doses each day.

In cases of local administration or selective uptake, the effective local concentration of the macrocycles of the invention may not be related to plasma concentration.

Those having the ordinary skill in the art will be able to optimize therapeutically effective dosages without undue experimentation.

The amount of macrocycle administered will, of course, be dependent on the subject being treated, on the subject's weight, the severity of the affliction, the method of administration and the judgment of the prescribing physician.

Normally, a therapeutically effective dose of the macrocycles described herein will provide therapeutic benefit without causing substantial toxicity.

Toxicity of the macrocycles can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from cell culture assays and animal studies can be used in formulating a dosage range that is not toxic for use in humans. The dosage of the macrocycles of the invention lies preferably within a range of circulating concentrations that include the effective dose with little or no toxicity. The dosage may vary within the range depending upon the dosage form and the route of administration. The exact formulation, route of administration and dose can be chosen by the individual physician in view of the patient's condition (cf. E. Fingl et al. in L. Goodman and A. Gilman (eds), *The Pharmacological Basis of Therapeutics*, $5^{th}$ ed. 1975, Ch. 1, p. 1).

Another embodiment of the present invention may also include compounds, which are identical to the compounds of formula Ia/Ib, except that one or more atoms are replaced by an atom having an atomic mass number or mass different from the atomic mass number or mass usually found in nature, e.g. compounds enriched in $^{2}H$ (D), $^{3}H$, $^{11}C$, $^{14}C$, $^{125}I$ etc. These isotopic analogs and their pharmaceutical salts and formulations are considered useful agents in therapy and/or diagnostics, for example, but not limited to, fine-tuning of in vivo half-life.

EXAMPLES

The following examples illustrate the invention in more detail but are not intended to limit its scope in any way. Before specific examples are described in detail the used abbreviations and applied general methods are listed.

Ac: acetyl
ADDP: azodicarboxylic dipiperidide
All: allyl
Alloc: allyloxycarbonyl
AllocCl: allyl chloroformate
AllocOSu: allyloxycarbonyl-N-hydroxysuccinimide
AM-resin: aminomethyl resin
AM-PS: aminomethyl polystyrene
aq.: aqueous
arom.: aromatic
Bn: benzyl
BnBr: benzyl bromide
Boc: tert-butoxycarbonyl
br.: broad
n-Bu: n-butyl
cat.: catalytic
CEP: N-carboethoxyphthalimide
Cbz: benzyloxycarbonyl
CbzOSu: N-(benzyloxycarbonyloxy)succinimide
Cl-HOBt: 6-chloro-1-hydroxybenzotriazole
CMBP: cyanomethylenetributyl-phosphorane
m-CPBA: 3-chloroperbenzoic acid
d: day(s) or doublet (spectral)
DBU: 1,8-diazabicyclo[5.4.0]undec-7-ene
DCE: 1,2-dichloroethane
DEAD: diethyl azodicarboxylate
DFPE polystyrene: 2-(3,5-dimethoxy-4-formylphenoxy) ethyl polystyrene
DIAD: diisopropyl azodicarboxylate
DIC: N,N'-diisopropylcarbodiimide
DMF: dimethylformamide
DMSO: dimethyl sulfoxide
DPPA: diphenyl phosphoryl azide
DVB: divinylbenzene
EDC: 1-[3-(dimethylamino)propyl-3-ethylcarbodiimide
equiv.: equivalent
Et: ethyl $Et_3N$: triethylamine
$Et_2O$: diethyl ether
EtOAc: ethyl acetate
FC: flash chromatography
FDPP: pentafluorophenyl diphenylphosphinate
Fmoc: 9-fluorenylmethoxycarbonyl
FmocOSu: 9-fluorenylmethoxycarbonyl-N-hydroxysuccinimide
h: hour(s)
HATU: O-(7-azobenzotriazol-1-yl)-N,N,N',N'-tetramethyluronium hexafluorophosphate
HBTU: O-(benortriazol-1-yl)-N,N,N',N'-tetramethyluronium hexafluorophosphate
HCTU: O-(1H-6-chlorobenortriazol-1-yl)-N,N,N',N'-tetramethyluronium hexafluorophosphate
HL: high loading
HOAt: 1-hydroxy-7-azabenzotriazole
$HOBt.H_2O$: 1-hydroxybenzotriazole hydrate
HMPA: hexamethylphosphoramide
i.v.: in vacuo
m: multiplet (spectral)
MeCN: acetonitrile
MeOH: methanol
Me: methyl
NMP: 1-methyl-2-pyrrolidinone
NS: 4-nitrobenzenesulfonyl
$Pd(PPh_3)_4$: tetrakis(triphenylphosphine)palladium(0)
PEG PS resin: polyethyleneglycol coated polystyrene resin
PG: protective group
Ph: phenyl
$PPh_3$: triphenylphosphine
prep.: preparative
i-Pr: isopropyl
$i\text{-}Pr_2NEt$: N-ethyl-N,N-diisopropylamine
PyBOP: (Benzotriazol-1-yloxy)tripyrrolidinophosphonium hexafluorophosphate
PyBroP: Bromotripyrrolidinophosphonium hexafluorophosphate
q: quartet (spectral)
quant.: quantitative
rt: room temperature
sat.: saturated
soln: solution
t: triplet (spectral)
TBAF: tetrabutylammonium fluoride
Teoc: 2-(trimethylsilyl)ethoxycarbonyl
TeocONp: 2-(trimethylsilyl)ethyl 4-nitrophenyl carbonate
TFA: trifluoroacetic acid
THF: tetrahydrofuran
tlc: thin layer chromatography
TMAD: tetramethylazodicarboxamide
T3P: propanphosphonic acid cyclic anhydride
p-TsOH: p-toluenesulfonic acid General Methods TLC: Merck (silica gel 60 F254, 0.25 mm).

Flash chromatography (FC): Fluka silica gel 60 (0.04-0.063 mm) and Interchim Puriflash IR 60 silica gel (0.04-0.063 mm).

I. Analytical HPLC-MS and HPLC Methods:

$R_t$ in min (purity at 220 nm in %), m/z $[M+H]^+$

UV wave length 220 nm, 254 nm

MS: Electrospray Ionization

Volume of injection: 5 μL

Method 1a and 1b

Column: XBridge C18 2.5 μm, 2.1×50 mm (186003085—Waters AG)

Mobile Phases: A: 0.1% TFA in Water; B: 0.085% TFA in MeCN

Column oven temperature: 45° C.

Gradient:

| Time [min.] | Flow [μl/min] | % A | % B |
|---|---|---|---|
| 0 | 500 | 97 | 3 |
| 0.1 | 500 | 97 | 3 |
| 3 | 500 | 3 | 97 |
| 3.6 | 500 | 3 | 97 |
| 3.7 | 500 | 97 | 3 |
| 4.3 | 500 | 97 | 3 |

MS scan range: 100-800 Da; centroid mode (Method 1a) 300-2000 Da; centroid mode (Method 1b)

scan time: 1 sec

Method 2

Column: Gemini NX C18 3 μm, 2.1×50 mm (00B-4453-B0—Phenomenex Inc.)

Mobile Phases: A: 0.1% TFA in Water; B: 0.085% TFA in MeCN

Column oven temperature: 45° C.

Gradient:

| Time [min.] | Flow [μl/min] | % A | % B |
|---|---|---|---|
| 0 | 800 | 97 | 3 |
| 0.1 | 800 | 97 | 3 |
| 2.2 | 800 | 3 | 97 |
| 2.5 | 800 | 3 | 97 |
| 2.55 | 1000 | 97 | 3 |
| 2.75 | 1000 | 97 | 3 |
| 2.8 | 800 | 97 | 3 |

MS scan range: 100-2000 Da; centroid mode scan time: 1 sec

Method 3: cf. Method 2;

Mobile Phases: A: 1 mM ammonium bicarbonate pH 10; B: MeCN

Method 4a-4b

Column: Gemini NX C18 3 μm, 2.1×50 mm (00B-4453-B0—Phenomenex Inc.)

Mobile Phases: A: 0.1% TFA in Water; B: 0.085% TFA in MeCN

Column oven temperature: 45° C.

Gradient:

| Time [min.] | Flow [μl/min] | % A | % B |
|---|---|---|---|
| 0 | 800 | 97 | 3 |
| 0.1 | 800 | 97 | 3 |
| 2.7 | 800 | 3 | 97 |
| 3 | 800 | 3 | 97 |
| 3.05 | 1000 | 97 | 3 |
| 3.25 | 1000 | 97 | 3 |
| 3.3 | 800 | 97 | 3 |

MS scan range: 100-2000 Da; centroid mode (Method 4a) 350-2000 Da; profile mode (Method 4b)

scan time: 1 sec

Method 5a-5b: cf. Method 4a-4b;

Mobile Phases: A: 1 mM ammonium bicarbonate pH 10; B: MeCN

Method 6-7:

Column: Acquity HPLC BEH C18 1.7 μm, 2.1×50 mm (cod. 186002350—Waters AG)

Mobile Phases: A: 0.1% TFA in Water; B: 0.085% TFA in MeCN

Column oven temperature: 55° C.

Gradient:

| Time [min.] | Flow [μl/min] | % A | % B |
|---|---|---|---|
| 0 | 1250 | 97 | 3 |
| 0.05 | 1250 | 97 | 3 |
| 1.65 | 1250 | 3 | 97 |
| 1.95 | 1250 | 3 | 97 |
| 2.00 | 1250 | 97 | 3 |
| 2.30 | 1250 | 97 | 3 |

MS scan range: 100-1650 Da; centroid mode (Method 6)

100-1650 Da; profile mode (Method 7)

scan time: 0.5 sec

Method 8: cf. Method 7;

Mobile Phases: A: 1 mM ammonium bicarbonate pH 10; B: MeCN

Method 9a-9c:

Column: Acquity HPLC BEH C18 1.7 μm, 2.1×100 mm (cod. 186002350—Waters AG)

Mobile Phases: A: 0.1% TFA in Water/MeCN 95/5 (v/v); B: 0.085% TFA in MeCN

Column oven temperature: 55° C.

Gradient:

| Time [min.] | Flow [μl/min] | % A | % B |
|---|---|---|---|
| 0 | 700 | 99 | 1 |
| 0.2 | 700 | 99 | 1 |
| 2.5 | 700 | 3 | 97 |
| 2.85 | 700 | 3 | 97 |
| 2.86 | 700 | 99 | 1 |
| 3.20 | 700 | 99 | 1 |

MS scan range: 100-800 Da; profile mode (Method 9a)

100-1200 Da; profile mode (Method 9b)

200-1400 Da; profile mode (Method 9c)

scan time: 1 sec

Method 10a-10d:

Column: Ascentis Express C18 2.7 μm, 3×50 mm (Supelco Inc.)

Mobile Phases: A: 0.1% TFA in Water; B: 0.085% TFA in MeCN

Gradient:

| Time [min] | Flow [μl/min] | % A | % B |
|---|---|---|---|
| 0 | 1300 | 97 | 3 |
| 0.5 | 1300 | 97 | 3 |
| 2.95 | 1300 | 3 | 97 |
| 3.15 | 1300 | 3 | 97 |
| 3.17 | 1300 | 97 | 3 |
| 3.2 | 1300 | 97 | 3 |

MS scan range:

95-1800 Da; centroid mode; Voltage: 40 V (Method 10a)

95-1800 Da; profile mode; Voltage: 40 V (Method 10b)

95-1800 Da; centroid mode; Voltage: 20 V (Method 10c)

95-1800 Da; centroid mode; Voltage: 80 V (Method 10d)

Methods 11a-11c: cf. Methods 10a-10c;

Mobile Phases: A: 1 mM ammonium bicarbonate pH 10; B: MeCN

Method 12:

Column: AtlantisT3 3 μm, 2×50 mm (Waters AG)

Mobile Phases: A: 0.1% TFA in Water; B: 0.085% TFA in MeCN

Gradient:

| Time [min] | Flow [μl/min] | % A | % B |
|---|---|---|---|
| 0 | 800 | 97 | 3 |
| 0.1 | 800 | 97 | 3 |
| 2.9 | 800 | 3 | 97 |
| 3.2 | 800 | 3 | 97 |
| 3.22 | 800 | 97 | 3 |
| 3.3 | 800 | 97 | 3 |

MS scan range: 90-800 Da; centroid mode; Voltage: 40 V

Method 13:

Column: Ascentis Express C18 2.1 μm, 3×50 mm (Supelco Inc.)

Mobile Phases: A: 0.1% TFA in Water; B: 0.085% TFA in MeCN

Gradient:

| Time [min] | Flow [μl/min] | % A | % B |
|---|---|---|---|
| 0 | 1400 | 97 | 3 |
| 0.5 | 1400 | 97 | 3 |
| 1.95 | 1400 | 3 | 97 |
| 2.15 | 1400 | 3 | 97 |
| 2.18 | 1400 | 97 | 3 |
| 2.3 | 1400 | 97 | 3 |

MS scan range: 100-1650 Da; centroid mode; Voltage: 40 V

General Analytical HPLC (x % $CH_3CN$):

$R_t$ in min (purity at 220 nm in %)

Column: Develosil RPAq 5 4.6×50 mm (Phenomenex Inc.)

Flow rate: 1.5 ml/min 0.0-0.5 min (x % $CH_3CN$, 100-x % $H_2O$ containing 0.1% TFA);

0.5-5.0 min (x % $CH_3CN$, 100-x % $H_2O$ containing 0.1% TFA to 100% $CH_3CN$)

5.0-6.2 min (100% $CH_3CN$)

Details: see individual experiment below.

II. Preparative HPLC Methods:

1. Reverse Phase—Acidic Conditions

Column: XBridge C18 5 μm, 30×150 mm (Waters AG)

Mobile Phases:

A: 0.1% TFA in Water/Acetonitrile 95/5 v/v

B: 0.1% TFA in Water/Acetonitrile 5/95 v/v

2. Reverse Phase—Basic Conditions

Column: XBridge C18 5 μm, 30×150 mm (Waters AG)

Mobile Phases:

A: 10 mM Ammonium Bicarbonate pH 10/Acetonitrile 95/5 v/v

B: Acetonitrile

3. Normal Phase

Column: VP 100/21 NUCLEOSIL 50-10, 21×100 mm (Macherey-Nagel AG)

Mobile phases: A: Hexane

B: Ethylacetate

C: Methanol

NMR Spectroscopy: Bruker Avance 300, $^1H$-NMR (300 MHz) in the indicated solvent at ambient temperature. Chemical shifts δ in ppm, coupling constants J in Hz.

Specific Examples

In the examples below and if no other sources are cited, leading reference for standard conditions of protecting group manipulations (protection and deprotection) are 1) P. G. M. Wuts, T. W. Greene, *Greene's Protective Groups in Organic Synthesis*, John Wiley and Sons, 4th Edition, 2006; 2) P. J. Koncienski, *Protecting Groups,* 3rd ed., Georg Thieme Verlag 2005; and M. Goodman (ed.), *Methods of Organic Chemistry* (*Houben-Weyl*), Vol E22a, Synthesis of Peptides and Peptidomimetics, Georg Thieme Verlag 2004.

Starting Materials

Template A Building Blocks (Scheme 1):

2-Acetoxy-5-fluoro benzoic acid (2) was prepared according to the method of C. M. Suter and A. W. Weston, *J. Am. Chem. Soc.* 1939, 61, 2317-2318.

3-Acetoxybenzoic acid (3) and 4-acetoxybenzoic acid (4) are commercially available.

5-Hydroxy nicotinic acid (5) is commercially available; its conversion into 6 is described below.

8-Acetoxyquinoline-2-carboxylic acid (8) was prepared according to the method of R. W. Hay, C. R. Clark, *J. Chem. Soc. Dalton* 1977, 1993-1998.

(S)-2-tert-Butoxycarbonylamino-8-hydroxy-1,2,3,4-tetrahydronaphthalene-2-carboxylic acid (10) was prepared according to the method of M. M. Altorfer, Dissertation Universität Zürich, 1996.

3-Mercaptobenzoic acid (11) is commercially available; for its conversion into 12 see below.

Ethyl 3-hydroxybenzoate (142) and 3-mercaptophenol (143) are commercially available.

3-Hydroxythiophene-2-carboxylic acid (144) is commercially available; for its conversion into 145 see below.

5-Hydroxy-1,2-dimethyl-1-H-indole-3-carboxylic acid (146) is commercially available; its conversion into 147 is shown below.

3-Methoxybenzyl bromide (148) is commercially available; for conversion into 149 see below.

Methyl 5-bromosalicyclic acid (151) was prepared according to the method of T. Esumi et al. *Bioorg. Med. Chem. Lett.* 2004, 14, 2621-2625.

Modulator B Building Blocks (Scheme 2)

Commercially available are:

tert-Butyl(3S,5S)-5-(hydroxymethyl)pyrrolidin-3-ylcarbamate (13) as well as the corresponding HCl salt (13.HCl);

tert-Butyl(3R,5S)-5-(hydroxymethyl)pyrrolidin-3-ylcarbamate (17) as well as the corresponding HCl salt (17.HCl);

(S)-tert-Butyl 3-(hydroxymethyl)piperazine-1-carboxylate hydrochloride (21.HCl); and (R)-tert-Butyl 3-(hydroxymethyl)piperazine-1-carboxylate hydrochloride (83.HCl) (cf. Scheme 5).

(2S,4S)-Allyl 2-(hydroxymethyl)-4-((2-(trimethylsilyflethoxy)-carbonylamino)pyrrolidine-1-carboxylate (16) was prepared from amino alcohol 13 in three steps by 1) alloc protection of the secondary amino group with allyloxycarbonyl-N-hydroxysuccinimide (AllocOSu) in $CH_2Cl_2$, 2) cleavage of the Boc group with dioxane-HCl, and 3) Teoc protection of the primary amino group with 2-(trimethylsilyl)ethyl 4-nitrophenyl carbonate (Teoc-ONp) in $CH_2Cl_2$ in the presence of $Et_3N$) applying standard conditions.

Data of 16: $C_{15}H_{28}N_2O_5Si$ (344.5): Flow injection MS (APCI): 689 ([2M+H]$^+$), 345 ([M+H]$^+$). $^1H$-NMR (DMSO-d$_6$): 7.28 (d, J=6.1, 1 H), 5.90 (m, 1 H), 5.25 (qd, J=1.7, 17.2, 1 H), 5.16 (qd, J=1.5, 10.5, 1 H), 4.90 (br. t, 1 H), 4.54-4.42 (m, 2 H), 4.04-3.97 (m, 2 H), 3.90 (q, J=6.8, 1 H), 3.80-3.66 (br. m and dd, 2 H), 3.57-3.43 (br. m, 2 H), 2.96 (br. m, 1 H), 2.19 (br. m, 1H), 1.78 (br. m, 1 H), 0.89 (t, J ca. 8.3, 2 H), 0.00 (s, 9 H).

(2S,4R)-Allyl 2-(hydroxymethyl)-4-((2-(trimethylsilyl)ethoxy)-carbonylamino)pyrrolidine-1-carboxylate (20) was prepared from amino alcohol hydrochloride 17.HCl, applying the same trans-formations as described for 16 with the exception of the Alloc protection step which was performed with allyl chloroformate in $CH_2Cl_2$ in the presence of aq. $NaHCO_3$ soln.

Data of 20: $C_{15}H_{28}N_2O_5Si$ (344.5): LC-MS (method 9a): $R_t$=1.98, 345 ([M+H]$^+$); 317; 259. $^1H$-NMR (DMSO-d$_6$): 7.26 (d, J=6.6, 1H), 5.89 (m, 1 H), 5.25 (br. d, J=17.0, 1 H), 5.15 (br. d, J=10.2, 1 H), 4.75 (m, 1H), 4.48 (m, 2 H), 4.16-3.98 (m, 3 H), 3.82 (br. m, 1 H), 3.48-3.30 (m, 3 H), 3.21 (m, 1 H), 2.01 (m, 1 H), 1.80 (m, 1 H), 0.89 (t, J=8.3, 2 H), 0.00 (s, 9 H).

(S)-1-Allyl 4-tert-butyl 2-(hydroxymethyl)piperazine-1,4-dicarboxylate (22) was prepared from amino alcohol hydrochloride 21.HCl, applying allyl chloroformate in $CH_2Cl_2$ in the presence of aq. $NaHCO_3$ soln.

Data of 22: $C_{14}H_{24}N_2O_5$ (300.4): LC-MS (method 9a): $R_t$=1.70, 201 ([M+H]$^+$). $^1H$-NMR (DMSO-d$_6$): 5.90 (m, 1 H), 5.29 (qd, J=1.7, 17.3, 1 H), 5.18 (qd, J=1.5, 10.5, 1 H), 4.81 (t, J=4.9, 1 H), 4.53 (d-like m, J ca. 5.1, 2 H), 4.04-3.75 (br. m, 4 H), 3.39 (m, 2 H), 2.95-2.70 (br. m, 3 H), 1.40 (s, 9 H).

(2S,4R)-2-(Trimethylsilyl)ethyl 4-(tert-butoxycarbonylamino)-2-(hydroxymethyl)pyrrolidine-1-carboxylate (152) 152 was obtained by Teoc protection of the secondary amino group of 17 with 2-(trimethylsilyl)ethyl 4-nitrophenyl carbonate (Teoc-ONp) in $CH_2Cl_2$ in the presence of $Et_3N$ applying standard conditions.

Data of 152: $C_{16}H_{32}N_2O_5Si$ (360.5). $^1H$-NMR (DMSO-d$_6$): 7.03 (br. s, 1 H), 4.71 (m, 1 H), 4.07-4.01 (m, 3 H), 3.76 (m, 1 H), 3.45-3.35 (br. m, 3 H), 3.11 (m, 1 H), 2.00 (m, 1 H), 1.75 (m, 1 H), 1.36 (s, 9 H), 0.91 (t, J=7.8, 2 H), 0.00 (s, 9 H).

(2S,4S)-Allyl 2-(hydroxymethyl)-4-phenoxypyrrolidine-1-carboxylate (156)

$BH_3$—$S(CH_3)_2$ (5.47 mL, 57.7 mmol) was added to a soln of (2S,4S)-1-(tert-butoxycarbonyl)-4-phenoxypyrrolidine-2-carboxylic acid (153, 8.87 g, 28.9 mmol) in THF (170 mL). The mixture was heated to 50° C. for 2 h, cooled to 0° C. and treated with $H_2O$ (100 mL), followed by an aqueous workup ($CH_2Cl_2$, $H_2O$; $Na_2SO_4$). FC (hexane/EtOAc) afforded 154 (8.46 g, quant. yield).

Cleavage of the Boc protective group with HCl-dioxane and introduction of the alloc protective group with allyl chloroformate in $CH_2Cl_2$ in the presence of sat. aq. $NaHCO_3$ soln afforded 156.

Data of 156: $C_{15}H_{19}NO_4$ (277.3). LC-MS (method 4a): $R_t$=1.89 (91), 278 ([M+H]$^+$). $^1H$-NMR (DMSO-d$_6$): 7.30 (t, J=7.9, 2 H), 6.97-6.91 (m, 3 H), 5.93 (m, 1 H), 5.29 (br. d, J=17.5, 1 H), 5.19 (br. d, J=10.5, 1 H), 5.01 (br. m, 1 H), 4.75 (br. m, 1 H), 4.53 (br. m, 2 H), 3.86 (br. m, 1 H), 3.78 (dd, J=5.2, 12.1, 1 H), 3.67 (br. m, 1 H), 3.39-3.30 (br. m, 2 H), 2.24 (br. m, 2 H).

(2S,4S)-Allyl 4-(4-bromobenzyloxy)-2-(hydroxymethyl)pyrrolidine-1-carboxylate (161)

To a suspension of NaH (dispersion, 60% in oil; 3.8 g; 95 mmol) in dry THF (53 mL) was slowly added at 0° C. a soln of (2S,4S)-1-(tert-butoxycarbonyl)-4-hydroxypyrrolidine-2- carboxylic acid (157; 10.0 g, 43 mmol) in THF (83 mL). The mixture was stirred for 15 min, followed by the addition of NaI (7.8 g, 52 mmol). 4-Bromobenzyl bromide (13 g, 52 mmol) in THF (32 mL) was slowly added and the mixture was stirred at rt for 15 h. The mixture was distributed between EtOAc and 0.2 M aq. HCl soln. The organic layer was separated, dried ($Na_2SO_4$), concentrated and purified by FC (hexane/EtOAc/MeOH gradient) to give 158 (17.3 g, 99%). The acid 158 was reduced with $BH_3$—$S(CH_3)_2$ in THF, applying the procedure described for the synthesis of 154.

Cleavage of the Boc protective group with HCl-dioxane and introduction of the alloc protective group with allyl chloroformate in $CH_2Cl_2$ in the presence of sat. aq. $NaHCO_3$ soln applying standard conditions afforded 161.

Data of 161: $C_{16}H_{20}BrNO_4$ (370.2). LC-MS (method 10a): $R_t$=2.05 (94), 370/372 ([M+B]$^+$). $^1$H-NMR (DMSO-$d_6$): 7.55 (d, J=8.4, 2 H), 7.28 (d, J=8.4, 2 H), 5.92 (m, 1 H), 5.28 (br. d, J ca. 17.2, 1 H), 5.18 (br. qd, J ca. 1.5, 10.5, 1 H), 4.73 (q-like m, 1 H), 4.58-4.42 (m, 4 H), 4.12 (br. m, 1 H), 3.78 (br. m, 1 H), 3.61-3.55 (m, 2 H), 3.43-3.29 (m, 2 H), 2.19 (m, 1 H), 2.03 (m, 1 H).

(2S,4S)-Allyl 4-benzyl-2-(hydroxymethyl)pyrrolidine-1-carboxylate (165) was prepared from (2S,4S)-4-benzyl-1-(tert-butoxycarbonyl)pyrrolidine-2-carboxylic acid (162) applying conditions as described for the synthesis of 156.

Data of 165: $C_{16}H_{21}NO_3$ (275.3). LC-MS (method 10a): $R_t$=1.93 (91), 276 ([M+H]$^+$). $^1$H-NMR (DMSO-$d_6$): 7.29 (t, J=7.3, 2 H), 7.21 (d, J=7.4, 3 H), 5.90 (m, 1 H), 5.24 (br. d, J ca. 16.8, 1 H), 5.16 (dd, J=1.2, 10.5, 1 H), 4.69 (br. s, 1 H), 4.47 (br. s, 2 H), 3.71 (br. m, 1 H), 3.59-3.53 (m, 3 H), 2.85 (m, 1 H), 2.65 (d, J=7.2, 2 H); 2.27 (m, 1 H), 2.03 (m, 1 H), 1.57 (m, 1 H).

(2S,4R)-tert-butyl 2-(hydroxymethyl)-4-((2-(trimethylsilyl)-ethoxy)carbonylamino)pyrrolidine-1-carboxylate (167) was obtained from the protected amino alcohol 20 by cleavage of the alloc group ($Pd(PPh_3)_4$, pyrrolidine in $CH_2Cl_2$/EtOAc) and introduction of a Boc group ($Boc_2O$, $CH_2Cl_2$, 1 M aq. NaOH). Data of 167: $C_{16}H_{32}NO_5Si$ (360.5). FI-MS: 361 ([M+H]$^+$). $^1$H-NMR (DMSO-$d_6$): 7.21 (d, J=6.9, 1 H), 4.72 (br. m, 1 H), 4.15-3.98 (m, 3 H), 3.75 (br. m, 1 H), 3.40-3.31 (m, 3 H), 3.06 (dd, J=6.6, 10.6, 1 H), 2.05 (br. m, 1 H), 1.78 (br. m, 1 H), 1.36 (s, 9 H), 0.89 (t, J=8.3, 2 H), 0.00 (s, 9 H).

Building Blocks for Subunits of Bridge C (Scheme 3):

(S)-5-Allyl 1-benzyl 2-(methylamino)pentanedioate hydrochloride (27.HCl)

A mixture of Boc-L-Glu(OAll)-OH (23; 33 g, 115 mmol) and $NaHCO_3$ (27 g, 322 mmol) in DMF (500 mL) was stirred for 1 h at rt followed by slow addition of benzyl bromide (35 mL, 299 mmol) in DMF (15 mL). Stirring was continued for 16 h followed by aqueous workup ($Et_2O$, sat. aq. $NaHCO_3$ soln, sat aq. NaCl soln) and purification by FC ($CH_2Cl_2$/MeOH 100:0 to 98:2) to give the corresponding benzyl ester (34.4 g, 79%), which was dissolved in dioxane (40 mL) and treated with 4M HCl-dioxane (400 mL) for h. The volatiles were evaporated. The residue was crystallized from $Et_2O$ to afford 24.HCl (23.8 g, 83%).

4-Nitrobenzenesulfonyl chloride (39 g, 178 mmol) was added at 0° C. to a soln of 24.HCl (46.5 g, 148 mmol) and pyridine (42 mL, 519 mmol) in $CH_2Cl_2$ (700 mL). The mixture was stirred for 15 h followed by aqueous workup ($CH_2Cl_2$, 1 M aq. HCl soln) and purification of the crude by FC (hexane/EtOAc 80:20 to 75:25) to yield 25 (55.54 g, 81%).

A soln of 25 (41.3 g, 89 mmol) in dry DMF (200 mL) was cooled to 0° C. Methyliodide (5.8 mL, 94 mmol) in DMF (100 mL) was slowly added, followed by a soln of DBU (14 mL, 94 mmol) in DMF (100 mL). The mixture was stirred for 4 h at rt followed by aqueous workup (EtOAc, 1 M aq. HCl soln, $H_2O$, sat. aq. $NaHCO_3$ soln, sat. aq. NaCl soln) to afford 26 (42.8 g, 99%).

A soln of 26 (17.4 g, 37 mmol) in dry, degassed $CH_3CN$ (270 mL) was treated with thiophenol (6.7 mL, 66 mmol) and $Cs_2CO_3$ (39 g, 121 mmol) at rt for 16 h. The mixture was filtered and the residue was washed with $Et_2O$. The filtrate was carefully concentrated (bath temperature 20° C.) and immediately purified by FC (hexane/EtOAc 80:20 to 50:50). The combined product fractions were carefully concentrated, immediately treated with 4M HCl-dioxane (20 mL) for 5 min and concentrated to give 27.HCl (8.62 g, 72%).

Data of 27.HCl: $C_{16}H_{21}NO_4$.HCl (291.3, free base). LC-MS (method 9b): $R_t$=1.44, 292 ([M+H]$^+$). $^1$H-NMR (DMSO-$d_6$): 9.57 (br. s, $NH_2^+$), 7.45-7.34 (m, 5 arom. H), 5.88 (M, 1 H), 5.32-5.19 (m, 4 H), 4.53 (td, J=1.3, 5.4, 1 H), 4.13 (br. t, J ca. 6.0, 1 H), 2.69-2.40 (m, 2 H), 2.56 (s, 3 H), 2.30-2.05 (m, 2 H).

(R)-5-Allyl 1-benzyl 2-(methylamino)pentanedioate hydrochloride (29.HCl) was prepared from Boc-D-Glu (OAll)OH (28) applying the methods described above for the synthesis of the enantiomer (27.HCl).

Data of 29.HCl: $C_{16}H_{2l}NO_4$.HCl (291.3, free base). LC-MS (method 9b): $R_t$=1.44, 292 ([M+H]$^+$). $^1$H-NMR (DMSO-$d_6$): 9.92 (br. s, $NH^+$), 9.54 (br. s, NH+), 7.45-7.34 (m, 5 arom. H), 5.88 (M, 1 H), 5.32-5.19 (m, 4 H), 4.53 (td, J=1.3, 5.4, 1 H), 4.13 (br. t, J ca. 6.0, 1 H), 2.69-2.40 (m, 2 H), 2.56 (s, 3 H), 2.30-2.05 (m, 2 H).

(S)-Allyl 2-(benzyloxycarbonylamino)-3-(methylamino) propanoate hydrochloride (32.HCl)

Cbz-L-Ser-OH (30) was converted into amino acid 31 by β-lactone formation and opening with $HNCH_3Si(CH_3)_3$ (J. Kim et al., *Inorg. Chem.* 1998, 37, 3835-3841), following literature procedures (J. K. Kretsinger, J. P. Schneider, *J. Am. Chem. Soc.* 2003, 125, 7907-7913; E. S. Ratemi, J. C. Vederas, *Tetrahedron Lett.* 1994, 35, 7605-7608).

A soln of 31.HCl (2.2 g, 7.6 mmol) in allyl alcohol (55 mL) was treated with thionyl chloride (1.7 mL, 23 mmol) for 15 min at rt and for 1.5 h at 70° C. The volatiles were evaporated. The crude product was dissolved in $CH_2Cl_2$ and washed with aq. $NaHCO_3$ soln. The aqueous layer was extracted with $CH_2Cl_2$ and with EtOAc. The combined organic phase was dried ($Na_2SO_4$), filtered, and concentrated. The resulting oil (2.18 g) was dissolved in $CH_2Cl_2$ (80 mL), treated with 4M HCl-dioxane (20 mL), stirred for 5 min and concentrated to afford 32.HCl (2.5 g, quant.).

Data of 32.HCl: $C_{15}H_{20}N_2O_4$.HCl (292.3, free base). LC-MS (method 9a): $R_t$=1.26, 293 ([M+H]$^+$). $^1$H-NMR (DMSO-$d_6$): 9.20 (br. s, $NH^+$), 9.03 (br. s, $NH^+$), 8.02 (d, J=8.2, NH), 7.38-7.30 (m, 5 arom. H), 5.89 (m, 1 H), 5.33 (d, J=17.3, 1 H), 5.23 (d, J=10.5, 1 H), 5.08 (s, 2 H), 4.63 (d, J=5.3, 2 H), 4.56 (m, 1 H), 3.35 (br. m, 1 H), 3.25 (br. m, 1 H), 2.56 (br. s, 3 H).

As an alternative, 32.HCl was prepared from Cbz-L-Dap-OH applying the method described below for the synthesis of the enantiomer 36.HCl.

(R)-Allyl 2-(benzyloxycarbonylamino)-3-(methylamino) propanoate hydrochloride (36.HCl)

Cbz-D-DapOH was converted into the allylester-pTsOH salt 33.pTsOH according to the procedure of T. M. Kamenecka, S. J. Danishefsky, *Chem. Eur. J.* 2001, 7, 41-63.

The amino ester 33.pTsOH was converted into the free base by extraction ($CH_2Cl_2$, sat. aq. $NaHCO_3$ soln) and treated with 4-nitrobenzenesulfonyl chloride (1.05 equiv.) in $CH_2Cl_2$ in the presence of pyridine (3.0 equiv.) to give the p-nitrophenyl sulfonamide 34.

At 0° C., a soln of methyl iodide (2.3 mL, 37 mmol) in DMF (80 mL) was added to a soln of 34 (16.4 g, 35 mmol) in DMF (80 mL). A soln of DBU (5.6 mL, 37 mmol) in DMF (80 mL) was slowly added over 2 h. The mixture was stirred at rt for 1.5 h, followed by an aqueous workup (EtOAc, 1 M HCl soln, $H_2O$, sat. aq. $NaHCO_3$ soln, sat. aq. NaCl soln) to afford 35 (17.07 g, quant.).

At 0° C., thiophenol (3.02 mL, 29.6 mmol) was added (dropwise, rapidly) to a mixture of 35 (7.85 g, 16.5 mmol) and $K_2CO_3$ (7.95 g, 57.5 mmol) in DMF (78 mL). The mixture was stirred for 2.5 h at 0-10° C. The mixture was diluted with EtOAc and washed with $H_2O$ and sat. aq. NaCl soln. The organic layer was extracted with ice-cold 1 M aq. HCl soln. The aqueous phase (base extract) was poured onto aq. $Na_2CO_3$ soln to reach pH ca. 7; 2 M aq. NaOH soln was added to reach pH ca. 10, followed by extraction with EtOAc. The organic phase was dried ($Na_2SO_4$) and concentrated. The remaining oil (2.72 g) was dissolved in $CH_2Cl_2$ (30 mL) and treated with 4M HCl-dioxane (10 mL) to afford after evaporation of the volatiles 36.HCl (3.34 g, 62%). Data of 36.HCl: $C_{15}H_{20}N_2O_4$.HCl (292.3, free base). LC-MS (method 7): $R_t$=0.88, 293 ([M+H]$^+$). $^1$H-NMR (DMSO-$d_6$): 9.06 (br. s, NH$^+$), 8.94 (br. s, NH'), 8.00 (d, J=8.3, NH), 7.38-7.30 (m, 5 arom. H), 5.88 (m, 1 H), 5.33 (d, J=17.3, 1 H), 5.23 (d, J=10.5, 1 H), 5.08 (s, 2 H), 4.63 (d, J=5.3, 2 H), 4.56 (m, 1 H), 3.35 (br. m, 1 H), 3.20 (br. m, 1 H), 2.57 (br. s, 3 H).

(S)-Allyl 2-(benzyloxycarbonylamino)-4-(methylamino)butanoate hydrochloride (40.HCl)

Cbz-L-Dab-OH (37) was converted into the allylester-pTsOH salt 38.pTsOH (T. M. Kamenecka, S. J. Danishefsky, l.c.)

A mixture of 38.pTsOH (45 g, 97 mmol) in $CH_2Cl_2$ (600 mL) was cooled to 0° C. MeOH (60 mL) was added, followed by ethyl trifluoroacetate (23 mL, 194 mmol). $Et_3N$ (53 mL, 387 mmol) was added dropwise. The mixture was stirred at 0° C. for 15 min, then at rt for 4 h. The volatiles were evaporated. The residue was dissolved in EtOAc, washed (1 M aq. HCl soln, sat. aq. $Na_2CO_3$ soln), dried ($Na_2SO_4$), filtered and concentrated to afford the corresponding trifluoroacetamide (32 g, 84%). N-Methylation of the acetamide (21.78 g, 56 mmol; applying $CH_3I$ and $K_2CO_3$ in DMF) following the procedure described by Chu-Biao Xue et al. *J. Med. Chem.* 2001, 44, 2636-2660—with the exception that the transformation was performed at rt for 4 h—afforded 39 (25 g, ca. 90%).

Treatment of 39 (8.0 g, ca. 18 mmol) in THF (80 mL) with $Pd(PPh_3)_4$ (0.2 g) and morpholine (8.5 mL, 98 mmol) at rt for 3 h afforded after aqueous workup (EtOAc, 1 M aq HCl soln) the corresponding trifluoroacetamido acid (7.3 g) which was treated with $NH_3$ (25% in $H_2O$; 50 mL) for 2 h and concentrated to give the corresponding amino acid (8 g). This material was dissolved in allyl alcohol (150 mL) and treated at 0° C. with thionyl chloride (6.6 mL, 91 mmol). The mixture was stirred at 0° C. for 15 min and at rt for 3 h and concentrated to give 40.HCl (7.6 g, used in the next step without further purification)

Data of 40.HCl: $C_{26}H_{22}N_2O_4$.HCl (306.3, free base). Flow injection

MS (ESI, positive modus): 307 ([M+H]$^+$). $^1$H-NMR (DMSO-$d_6$): 8.97 (br. s, $NH_2$'), 7.92 (d, J=7.8, NH), 7.40-7.25 (m, 5 arom. H), 5.88 (m, 1 H), 5.32 (d, J=17.2, 1 H), 5.22 (d, J=10.5, 1 H), 5.05 (s, 2 H), 4.60 (d, J=5.2, 2 H), 4.22 (m, 1 H), 2.94 (m, 2 H), 2.50 (s, 3 H, superimposed by DMSO-d signal), 2.10 (m, 1 H), 2.00 (m, 1 H).

(S)-Allyl 2-(benzyloxycarbonylamino)-5-(methylamino)pentanoate hydrochloride (44.HCl)

Cbz-L-Orn-OH (41) was converted into the allylester-pTsOH salt 42.pTsOH (T. M. Kamenecka and S. J. Danishefsky, l.c.).

The ester 42.pTsOH (5.5 g, 11 mmol) was converted into 43 (3.97 g, 83%) applying the conditions described for the synthesis of 39, with the exception that the N-methylation was continued at rt for 8 h.

The allyl ester group was then cleaved applying the conditions described for the treatment of 39. The saponification of the resulting trifluoroacetamido acid was performed according to the procedure of Chu-Biao Xue et al. *J. Med. Chem.* 2001, 44, 2636-2660, with the exception that 2 equiv. of LiOH were used. The resulting amino acid (3.80 g, containing LiCl ca. 9 mmol) was treated at rt with allyl alcohol (100 mL) and thionyl chloride (3.0 mL, 41 mmol). The mixture was heated for 2 h at 70° C. Stirring was continued at rt for 17 h. The volatiles were evaporated; and the resulting solid was washed with $CH_2Cl_2$ to afford 44.HCl (3.62 g, ca. 75% w/w; yield 83%, used without further purification).

Data of 44.HCl: $C_{17}H_{24}N_2O_4$.HCl (320.4, free base). LC-MS (method 9b): $R_t$=1.48, 321 ([M+H]$^+$). $^1$H-NMR (DMSO-$d_6$): 9.26 (br. s, $NH_2$'), 7.86 (d, J=7.7, NH), 7.39-7.13 (m, 5 arom. H), 5.89 (m, 1 H), 5.31 (br. d, J=17.3, 1 H), 5.20 (br. d, J=10.4, 1 H), 5.04 (s, 2 H), 4.58 (d, J=5.2, 2 H), 4.05 (br. m, 1 H), 2.81 (br. m, 2 H), 2.44 (s, 3 H), 1.80-1.60 (br. m, 4 H), Sarcosine allyl ester (46) was prepared as p-TsOH salt (T. M. Kamenecka and S. J. Danishefsky, l.c.).

2-((Allyloxycarbonyl)(methyl)amino)acetic acid (47) and 3-((Allyloxycarbonyl)(methyl)amino)propanoic acid (49) were prepared according to the method of M. Mori et al., *Chem. Pharm. Bull.* 2000, 48, 716-728.

(S)-2-(Benzyloxycarbonylamino)pent-4-enoic acid (51) was prepared from (S)-allylglycine by N-protection (CBzOSu, dioxane, aq. $Na_2CO_3$) in analogy to the procedure of D. R. Ijzendoorn et al., *Org. Lett* 2006, 8, 239-242.

Methyl 1-aminocyclopentanecarboxylate hydrochloride (169.HCl) was obtained by treatment of 1-aminocyclopentanecarboxylic acid (168) with MeOH and $SOCl_2$ as described by L. V. Adriaenssens et al., *J. Org. Chem.* 2007, 72, 10287-10290, for the synthesis β-aminoacid methylesters hydrochlorides.

(S)-Methyl 3-amino-4-(naphthalen-2-yl)butanoate hydrochloride (171.HCl) was obtained by treatment of (S)-3-amino-4-(naphthalen-2-yl)butanoic acid hydrochloride (170.HCl) with MeOH and $SOCl_2$ (L. V. Adriaenssens et al., l.c.).

(S)-Benzyl 3-(2-(allyloxy)-2-oxoethoxy)-2-(methylamino)propanoate hydrochloride (178.HCl)

Boc-Ser-OH (172; 4.0 g, 19.5 mmol) was converted into the allyl ether 173 according to the procedure of M. P. Glenn et al. *J. Med. Chem.* 2002, 45 (2), 371-381. The crude product 173 was converted into the benzyl ester 174 (4.95 g, 76% over the two steps) applying the procedure described for the synthesis of 24 with the exception that 1.7 equivalents of benzyl bromide were used and the volatiles were evaporated prior to aqueous workup. $Ag_2O$ (9.64 g, 41.6 mmol), acetic acid (0.79 mL, 13.9 mmol) and methyliodide (17.3 mL, 277 mmol) were successively added to a soln of 174 (4.65 g, 13.9 mmol) in DMF (60 mL). The suspension was stirred for 24 h, filtered through a pad of celite and distributed between $Et_2O$ and sat. aq. $NaHCO_3$ soln. The organic layer was separated, washed ($H_2O$, sat. aq. NaCl soln), dried ($Na_2SO_4$), filtered and concentrated. FC (hexane/acetone 100:0 to 90:10) yielded 175 (4.37 g used without further purification).

At rt, N-methylmorpholine-N-oxide (0.84 g, 7.2 mmol) and osmium tetroxide (2.5% w/w in tert butanol; 3.47 mL, 0.27 mmol) were added to a soln of 175 (1.93 g, ca. 4 mmol) in acetone (60 mL) and $H_2O$ (15 mL). The mixture was stirred for 18 h. Celite (20 g) and $Na_2S_2O_3$ (5 g) were added and stirring was continued for 45 min. The mixture was filtered through celite. The residue was washed with acetone. The filtrate was concentrated and evaporated with toluene. FC (hexane/EtOAc 50:50 to 100:0) afforded 176 (1.3 g, 60%).

A soln of 176 (2.63 g, 6.86 mmol) in THF (50 mL) and $H_2O$ (50 mL) was treated with $NaIO_4$ (2.93 g, 13.7 mmol) and stirred at rt for 1.5 h. The mixture was diluted with $H_2O$ and extracted with $CH_2Cl_2$. The organic layer was dried ($Na_2SO_4$), filtered and concentrated. The product (2.45 g) thus obtained was dissolved in $CH_2Cl_2$ (25 mL). $CH_3CN$ (25 mL) and $H_2O$ (40 mL) were added. $NaIO_4$ (2.93 g, 13.7 mmol) and ruthenium(III)-chloride hydrate (77 mg, 0.34 mmol) were added. The mixture was vigorously stirred for 2 h and distributed between $CH_2Cl_2$ and $H_2O$. The organic layer was separated, washed (sat. aq. NaCl soln), dried ($Na_2SO_4$), filtered and concentrated. A soln of the product (2.29 g) in dry DMF (33 mL) was treated with $NaHCO_3$ (1.05 g, 12.5 mmol) and allyl bromide (1.05 mL, 12.5 mmol). The mixture was stirred for 3 d followed by an aqueous workup ($Et_2O$, $H_2O$, sat. aq. NaCl soln; $Na_2SO_4$) to afford 177 (2.37 g, 85%). At −10° C., TFA (24 mL) was added to a soln of 177 (2.4 g, 5.9 mmol) in $CH_2Cl_2$ (24 mL). The soln was stirred for 1.5 h at this temperature, poured onto sat. aq. $NaHCO_3$ soln and extracted with $CH_2Cl_2$. The organic layer was separated, dried ($Na_2SO_4$), filtered and concentrated (bath temperature 30° C.) to give 1.7 g of a light brown oil, which was dissolved in $CH_2Cl_2$ (20 mL) and treated with 4M HCl-dioxane (7.3 mL). The volatiles were evaporated to afford 178.HCl (2.13 g, quant.).

Data of 178.HCl: $C_{16}H_{21}NO_5$.HCl (307.3, free base). LC-MS (method 5a): $R_t$=1.99 (86), 308 ([M+H]$^+$). $^1$H-NMR (DMSO-d$_6$): 9.58 (br. s, $NH_2^+$), 7.46-7.33 (m, 5 H), 5.92 (m, 1 H), 5.32 (qd, J=1.6, 17.2, 1 H), 5.28 (s, 2 H), 5.23 (qd, J=1.4, 10.5, 1 H), 4.62 (d, J=5.5, 2 H), 4.45 (t-like s, 1 H), 4.26 (s, 2 H), 4.18-4.04 (m, 2H), 2.63 (s, 3 H).

(S)-Allyl 2-(benzyloxycarbonylamino)-6-(methylamino) hexanoate hydrochloride (182.HCl)

The amino ester 182.HCl was prepared from Cbz-L-Lys-OH (179) applying the methods described for the synthesis of 44.HCl.

An analytical sample of 182.HCl was purified by prep. HPLC (method 1).

Data of 182.HCl: $C_{18}H_{26}N_2O_4$.HCl (334.4, free base). LC-MS (method 10a): $R_t$=1.39 (98), 335 ([M+H]$^+$). $^1$H-NMR (DMSO-d$_6$): 8.34 (br. s, $NH_2^+$), 7.77 (d, J=7.8, 1 H), 7.29 (m, 5 H), 5.90 (m, 1 H), 5.31 (dd, J=1.6, 17.2, 1 H), 5.22 (dd, J=1.4, 10.5, 1 H), 5.07 (d, J=12.5, 1 H), 5.01 (d, J=12.5, 1 H), 4.59 (d, J=5.3, 2H), 4.05 (m, 1 H), 2.94-2.73 (m, 2 H), 2.54 (s, 3 H), 1.75-1.30 (several m, 6 H).

(S)-Allyl 6-bromo-2-(tert-butoxycarbonylamino)hexanoate (185)

At 0° C., allyl bromide (3.9 mL, 45 mmol) was slowly added to a soln of Boc-L-6-hydroxynorleucine (183; 8.55 g, 34.6 mmol) and $NaHCO_3$ (7.26 g, 86.4 mmol) in DMF (120 mL). The mixture was stirred for 4 h at 0° C. to rt, followed by the addition of more $NaHCO_3$ (7.26 g, 86.4 mmol) and allyl bromide (3.9 mL, 45 mmol). Stirring was continued for 18 h. The mixture was distributed between EtOAc and aq. NaCl soln. The organic phase was separated, washed (diluted aq. NaCl soln, $H_2O$, sat. aq. NaCl soln), dried ($Na_2SO_4$), filtered and concentrated. FC (hexane/EtOAc 2:1 to 1:2) afforded 184 (9.17 g, 92%). The alcohol 184 was converted into the bromide 185 following the procedure described for the synthesis of (2S)-2[(benzyloxycarbonyl)amino]-6-bromohexanoic acid methyl ester (R. Bambal and R. P. Hanzlik, *J. Org. Chem.* 1994, 59, 729-732). Data of 185: $C_{14}H_{24}BrNO_4$ (350.2). LC-MS (method 10c): $R_t$=2.30 (91), 352/350 ([M+H]$^+$). $^1$H-NMR (DMSO-d$_6$): 7.29 (d, J=7.8, 1 H), 5.89 (m, 1 H), 5.32 (dd, J=1.6, 17.2, 1 H), 5.21 (dd, J=1.3, 10.5, 1 H), 4.59-4.55 (m, 2 H), 3.94 (m, 1 H), 3.51 (t, J=6.6, 2 H), 1.83-1.57 (2 m, 4 H), 1.47-1.33 (m, 2 H), 1.38 (s, 9 H).

Synthesis of (S)-allyl 5-amino-2-hydroxypentanoate (190)

(2S)-2-amino-5-phthalimidopentanoic acid hydrochloride (187.HCl; 17.3 g, 65%) was obtained from L-ornithine hydrochloride (186.HCl; 15 g, 89 mmol) and N-carbethoxyphthalimide (CEP; 19.5 g, 89 mmol; M. J. Bunegar et al., *Org. Process Res. Dev.* 1998, 2, 334-336); 187.HCl was isolated by diluting the mixture with $H_2O$ and 3 M aq. HCl soln until all precipitate was dissolved. The aq. soln was washed twice with EtOAc and concentrated to ca. 20% of its volume. A precipitate was formed which was collected, washed with cold $H_2O$ and $Et_2O$ and dried i.v.

$H_2SO_4$ (95% w/w; 3.4 mL, 60 mmol) was added at 0° C. to a soln of 187.HCl (4.5 g, 15 mmol) in $H_2O$ (40 mL). The mixture was carefully warmed until all starting material was dissolved. $NaNO_2$ (4.2 g, 60 mmol) in $H_2O$ (20 mL) was added at rt over 2 h. The mixture was stirred for 16 h. The precipitate formed was collected, washed with cold $H_2O$ (10 mL) and dried i.v. to give 188 (3.37 g) which was used without further purification. KOH (6.21 g, 111 mmol) was added to a soln of 188 (7.28 g, 28 mmol) in $H_2O$ (100 mL). The mixture was stirred for 3 h at rt, acidified with 1 M aq. HCl soln to pH ca. 1 and heated to reflux for 1 h. The mixture was extracted with EtOAc. The aqueous phase was concentrated and dried i.v. to give crude 189 (11.5 g) which was dissolved in allyl alcohol (122 mL). $SOCl_2$ (8.07 mL, 111 mmol) was added at 0° C. The mixture was heated to 70° C. for 2.5 h. The mixture was concentrated to afford 190.HCl (13.17 g, ca. 80%; containing ca. 50% w/w KCl)

Data of 190.HCl: $C_8H_{15}NO_3$.HCl (173.2, free base). FIA-MS: 174 ([M+H]$^+$). $^1$H-NMR ($D_2O$): 5.89 (m, 1 H), 5.36-5.10 (m, 2 H), ca. 4.6 (m, 2 H, partially superimposed by HDO signal), 4.30 (m, 1 H), 2.94 (t-like m, 2 H), 1.88-1.63 (m, 4 H).

Synthesis of the A-C fragment H-A-M-c1-CO—OPG$^2$

Procedure A

A.1: Acid Chloride Formation

Oxalyl chloride (3.5-5.0 equiv.) was added to a mixture of the acetoxyaryl carboxylic acid (Ac-A-OH) and dry $Et_2O$ or $CH_2Cl_2$. The resulting mixture was stirred at rt for 15 min followed by the addition of a few drops (ca 50-100 μL) of dry DMF. Stirring was continued for 16 h. The mixture was filtered. The filtrate was concentrated and the residue dried i.v. to afford the crude acetoxyaryl carboxylic acid chloride (Ac-A-Cl), which was immediately used in the next step.

A.2: Amide Coupling

A mixture of the amino ester salt (H—NR$^4$-c1-CO—OAll.HX), the crude acetoxyaryl carboxylic acid chloride (Ac-A-Cl, 1.1-1.5 equiv.) and dry $CH_2Cl_2$ or THF was cooled to 0° C. An auxiliary base (sym-collidine or i-$Pr_2$NEt; 3.0 equiv.) was added dropwise. The mixture was stirred at rt for 16 h. The mixture was distributed between EtOAc and 1 M aq. HCl soln. The organic phase was washed (1 M aq. HCl soln, then sat. aq. $NaHCO_3$ soln or sat aq. NaCl soln), dried ($Na_2SO_4$), filtered and concentrated. FC (hexane/EtOAc gradients) gave the acetoxyaryl amide (Ac-A-$NR^4$-c1-CO—OAll).

A.3: Deacetylation

A soln of acetoxyarylamide (Ac-A-$NR^4$-c1-CO—OAll) in dry THF was treated at 0° C. with 3-dimethylaminopropylamine (3.0-4.5 equiv.). The soln was stirred at rt for 1-5 h. The mixture was distributed between EtOAc and ice-cold 0.1 M or 1 M aq. HCl soln. The organic phase was washed (0.1 or 1 M aq. HCl soln, sat. aq. NaCl soln), dried ($Na_2SO_4$), filtered and concentrated to afford the hydroxyaryl amide (H-A-$NR^4$-c1-CO—OAll).

Synthesis of the Linear Cyclization Precursor H—B-A-M-c1-CO—OH

Procedure B

B.1.1: Mitsunobu Aryl Ether Synthesis Using $PPh_3$/DEAD

A mixture of the hydroxyaryl amide (H-A-M-c1-CO—OAll; M=$NR^4$, $CHR^6$) and $PPh_3$ (1.5 equiv.) was dried i.v. for 15 min. Under argon a soln of alcohol (HO—B-Alloc, 1.2 equiv.) in dry benzene was added and the resulting soln was cooled to 0° C. A soln of DEAD (40% in toluene, 1.2 equiv.) in benzene was slowly added (by syringe pump). The mixture was stirred at rt for 18 h and concentrated. FC (hexane/EtOAc gradients) gave the protected amino acid Alloc-B-A-M-c1-CO—OAll used in the next step without further purification.

B.1.2: Mitsunobu Aryl Ether Synthesis Using CMBP

A soln of the hydroxyaryl amide (H-A-M-c1-CO—OAll; M=$CHR^6$), the alcohol (HO—B-Alloc, 1.2-1.3 equiv.) and CMBP (2 equiv.) was heated in dry toluene at reflux for 1-4 h. The soln was concentrated. FC (hexane/EtOAc gradients) afforded the protected amino acid (Alloc-B-A-M-c1-CO—OAll).

B.2: Cleavage of the Allyl/Alloc Protective Groups $Pd(PPh_3)_4$ (0.05-0.1 equiv.) was added to a mixture of the protected amino acid (Alloc-B-A-M-c1-CO—OAll) and 1,3-dimethylbarbituric acid (2.5 equiv.) in degassed EtOAc/$CH_2Cl_2$ (ca. 1:1). The resulting soln was stirred at rt for 1-3 h and concentrated. FC (EtOAc, $CH_2Cl_2$/EtOH, or $CH_2Cl_2$/MeOH gradients) afforded the free amino acid (H—B-A-M-c1-CO—OH).

Synthesis of the Cyclization Precursor H—B-A-M-c1-V-c2-CO—OH

Procedure C

C.1: Allyl Carbamate Formation

At 0° C. allylchloroformate (1.1 equiv.) was slowly added to a mixture of amino acid (H—B-A-M-c1-CO—OH) and $Na_2CO_3$ (1.5-3 equiv.) in dioxane/$H_2O$ 1:1. The mixture was stirred at rt for 15 h. The mixture was diluted with EtOAc and treated with 1 M aq. HCl soln until pH ca. 2 was reached. The organic phase was separated, washed (sat. aq. NaCl soln), dried ($Na_2SO_4$), filtered, concentrated and dried i.v. to afford the alloc protected amino acid (Alloc-B-A-M-c1-CO—OH).

C.2: Amide Coupling i-$Pr_2$NEt (5.0 equiv.) was slowly added to a mixture of the alloc protected amino acid (Alloc-B-A-M-c1-CO—OH), the amino acid ester salt (H—$NR^4$-c2-CO—OAll.p-TsOH, 1.2 equiv.), HOAt (1.5 equiv.) and HATU (1.5 equiv.) in DMF. The mixture was stirred at rt for 20 h followed by distribution between EtOAc and ice-cold 0.5 M aq. HCl soln. The organic phase was washed (0.5 M aq. HCl soln, $H_2O$, sat. aq. $NaHCO_3$ soln, sat. aq. NaCl soln), dried ($Na_2SO_4$), filtered and concentrated. FC (hexane/EtOAc gradients) afforded the protected amino acid (Alloc-B-A-M-c1-V-c2-CO—OAll; V=$CONR^4$).

C.3: Cleavage of the Allyl/Alloc Protective Groups $Pd(PPh_3)_4$ (0.1 equiv.) was added to a mixture of the protected amino acid (Alloc-B-A-M-c1-V-c2-CO—OAll) and 1,3-dimethylbarbituric acid (2.5 equiv.) in degassed EtOAc/$CH_2Cl_2$ 1:1. The resulting soln was stirred at rt for 1-2 h and concentrated. FC (EtOAc, $CH_2Cl_2$/EtOH, or $CH_2Cl_2$/MeOH gradients) afforded the free amino acid (H—B-A-M-c1-V-c2-CO—OH).

Synthesis of the C—B Fragment $PG^5$-$NR^4$-c2-CO—B—OH

Procedure D

Synthesis in Two Steps, Via Amidoester and Subsequent Saponification i-$Pr_2$NEt (5.0 equiv.) was slowly added to a mixture of the N-protected amino acid (Alloc-$NR^4$-c2-CO—OH, 2.2 equiv.), the aminoalcohol hydrochloride HO—B—H.HCl, Cl-HOBt (0.25 equiv.) and HCTU (2.5 equiv.) in DMF. The resulting soln was stirred at rt for 17 h, followed by distribution between EtOAc and sat. aq. $Na_2CO_3$ soln. The organic phase was washed (1 M aq. HCl soln, sat. aq. NaCl soln), dried ($Na_2SO_4$), filtered and concentrated. FC (hexane/EtOAc or $CH_2Cl_2$/MeOH gradients) afforded the corresponding amidoester, which was dissolved in THF/$H_2O$ 4:1 and treated with lithium hydroxide monohydrate (3.0 equiv.) for 2 h at rt. The mixture was concentrated to about 50% of the original volume, diluted with EtOAc and extracted with 1 M aq. NaOH soln. The organic phase was washed ($H_2O$, sat. aq. NaCl soln), dried ($Na_2SO_4$), filtered and concentrated to afford the amidoalcohol (HO—B—CO-c2-$NR^4$-Alloc).

Synthesis of Cyclization Precursor H—$NR^4$-c2-CO—B-A-M-c1-CO—OH

Procedure E

E.1.1: Mitsunobu Aryl Ether Synthesis Using $PPh_3$/DEAD

A mixture of the hydroxyaryl amide (H-A-M-c1-CO—OAll) and $PPh_3$ (1.5-4.5 equiv.) was dissolved in benzene. The soln was concentrated and the residue was dried i.v. for 15-30 min. Under argon, a soln of alcohol HO—B—CO-c2-$NR^4$-Alloc (1.2-2.3 equiv.) in dry and degassed benzene was added and the resulting mixture was cooled to 0° C. A soln of DEAD (40% in toluene, 1.2-4.5 equiv.) was slowly added. The mixture was stirred at rt for h. In case of incomplete consumption of the hydroxyaryl amide as indicated by tlc control, additional triphenylphosphine (1.0-1.3 equiv.) and DEAD (40% in toluene, 1.0 equiv.) and alcohol (1.0 equiv.) were added and stirring was continued for 18 h. The mixture was concentrated. FC (hexane/EtOAc, $CH_2Cl_2$/EtOH, or $CH_2Cl_2$/MeOH gradients) afforded Alloc-$NR^4$-c2-CO—B-A-M-c1-CO—OAll used in the next step without further purification.

E.1.2: Mitsunobu Aryl Ether Synthesis Using CMBP

CMBP (2-3 equiv.) was added to a mixture of the hydroxyaryl amide (H-A-M-c1-CO—OAll) and the alcohol (HO—B—CO-c2-$NR^4$-Alloc, 1.2-2.2 equiv.) in dry toluene. The mixture was heated at reflux for 16 h and concentrated.

FC (hexane/EtOAc gradients) afforded the protected amino acid (Alloc-$NR^4$-c2-CO—B-A-M-c1-CO—OAll).

E.2: Cleavage of the Allyl/Alloc Protective Groups $Pd(PPh_3)_4$ (0.05-0.1 equiv.) was added to a mixture of the protected amino acid (Alloc-$NR^4$-c2-CO—B-A-M-c1-CO—OAll) and 1,3-dimethylbarbituric acid (2.4 equiv.) in degassed EtOAc/$CH_2Cl_2$ 1:1. The resulting soln was stirred at rt for 1-3 h and concentrated. FC (EtOAc, $CH_2Cl_2$/EtOH, or $CH_2Cl_2$/MeOH gradients) afforded the free amino acid (H—$NR^4$-c2-CO—B-A-M-c1-CO—OH).

Synthesis of Macrocyclic Compounds cyclo(B-A-M-c1-CO—) and cyclo(B-A-M-c1-V-c2-CO—)

Procedure F

The macrolactamization was typically performed at final concentrations ranging from 0.01 M to 0.001 M.

F.1.1: T3P Mediated Lactam Formation

A soln of the precursor (H—B-A-M-c1-CO—OH, H—B-A-M-c1-V-c2-CO—OH or H—$NR^4$-c2-CO—B-A-M-c1-CO—OH) in dry $CH_2Cl_2$ was added within 2 h by syringe pump to a soln of T3P (50% in EtOAc, 2 equiv.) and i-$Pr_2NEt$ (4 equiv.) in dry $CH_2Cl_2$. The soln was stirred at rt for 20 h, extracted with sat. aq. $Na_2CO_3$ soln and with $H_2O$, dried ($Na_2SO_4$), filtered and then concentrated. FC (hexane/EtOAc/MeOH or $CH_2Cl_2$/MeOH gradients) afforded macrocycle cyclo(B-A-M-c1-CO—) or cyclo(B-A-M-c1-V-c2-CO—) wherein V is $NR^4$.

F.1.2: FDPP Mediated Lactam Formation

A soln of the precursor (H—B-A-M-c1-CO—OH, H—B-A-M-c1-V-c2-CO—OH or H—$NR^4$-c2-CO—B-A-M-c1-CO—OH) in dry DMF was added within 2 h to a soln of FDPP (2.0 equiv.) in dry DMF. The soln was stirred at rt for 20 h. The volatiles were evaporated and the residue taken up in EtOAc and washed (sat. aq. $NaHCO_3$ soln, $H_2O$, sat. aq. NaCl soln). The organic phase was dried ($Na_2SO_4$), filtered and concentrated. FC (hexane/EtOAc/MeOH or $CH_2Cl_2$/MeOH gradients) afforded the macrocycle cyclo(B-A-M-c1-CO—) or cyclo(B-A-M-c1-V-c2-CO— wherein V is $NR^4$.

Attachment of Substituents to the Macrocyclic Core Structures: Synthesis of the Final Products Deprotection Reactions Procedure H A soln of a macrocyclic benzyl ester or benzyl ether in MeOH or MeOH/THF (ca 100 mL per g of starting material) was hydrogenolyzed for 2 h at rt and at normal pressure in the presence of palladium hydroxide on activated charcoal (moistened with 50% $H_2O$; 0.5 g per g of starting material). The mixture was filtered through a pad of celite. The residue was washed (MeOH, MeOH/$CH_2Cl_2$ 1:1, THF). The combined filtrate and washings were concentrated to obtain a macrocyclic acid or alcohol.

Procedure I 1.1: Teoc Deprotection with dioxane-HCl

A soln of a macrocyclic Teoc-amine (1.5 mmol) in dioxane (18 mL) was treated with 4M HCl in dioxane (18 mL) and stirred at rt for 4-16 h. The mixture was treated with $Et_2O$ and filtered. The solid was washed with $Et_2O$ and dried i.v. to give the macrocyclic amine hydrochloride.

1.2: Teoc Deprotection with TBAF in THF

A soln of TBAF (1 M in THF, 3 equiv.) was added at 0° C. to a soln of a macrocyclic Teoc-amine (1.3 mmol) in THF (34 mL). Stirring at 0° C. to rt was continued for 3 h. The soln was distributed between $CH_2Cl_2$ and $H_2O$. The organic phase was washed ($H_2O$), dried ($Na_2SO_4$), filtered and concentrated to provide after FC the macrocyclic amine.

Procedure J

A soln of a macrocyclic Boc-amine in dioxane (10 mL per g of starting material) was treated with 4M HCl in dioxane (20 mL per g of starting material) and stirred at rt for 2 h. The mixture was filtered. The solid was washed with $Et_2O$ and dried i.v. to give the macrocyclic amine hydrochloride.

Procedure K

K.1: A soln of a macrocyclic benzylcarbamate (0.9 mmol) in MeOH (52 mL) was hydrogenolyzed for 4 h at rt and at normal pressure in the presence of palladium hydroxide on activated charcoal (moistened with 50% $H_2O$; 0.3 g). The mixture was filtered through a pad of celite. The residue was washed (MeOH). The combined filtrate and washings were concentrated to obtain the macrocyclic amine.

K.2: A soln of a macrocyclic benzylcarbamate (0.16 mmol) in MeOH (2 mL) was treated with $NH_3$ soln (7 M in MeOH; 4 equiv.) and hydrogenolyzed for 3 h at rt and at normal pressure in the presence of 5% palladium on activated charcoal (moistened with 50% $H_2O$; 32 mg). The mixture was filtered through a pad of celite. The residue was washed (MeOH). The combined filtrate and washings were concentrated to give the macrocyclic amine.

K.3: A soln of the macrocyclic benzylamine (0.7 mmol) in acetic acid (11 mL) was hydrogenolyzed for 15 h at rt and at normal pressure in the presence of palladium hydroxide on activated charcoal (moistened with 50% $H_2O$; 0.14 g). The mixture was filtered through a pad of celite. The residue was washed (MeOH). The combined filtrate and washings were concentrated to obtain the macrocyclic amine.

Acylation, Carbamoylation, Sulfonylation, and Alkylation Reactions

Procedure L

L.1: Amide Coupling of a Macrocyclic Amine with

L.1.1: Carboxylic Acid Anhydrides or Acylchlorides

At 0° C. a soln of an amino macrocycle (free amine or hydrochloride; 0.09 mmol) in $CH_2Cl_2$ (1 mL) was successively treated with pyridine (10 equiv.) and the carboxylic acid anhydride (1.05-5 equiv.) or a carboxylic acid chloride (1.05-2.0 equiv.). The soln was stirred at rt for 15 h. After the addition of MeOH (0.1 mL) the soln was stirred for 10 min and concentrated. The resulting crude product was co-evaporated with toluene and purified by chromatography (FC, normal phase or reverse phase prep. HPLC) to give an N-acylamino macrocycle.

L.1.2: Carboxylic Acid and Polymer-Supported Carbodiimide

A soln of an amino macrocycle (free amine or hydrochloride; 0.09 mmol), a carboxylic acid (1.2 equiv.), HOBt.$H_2O$ (1.2 equiv.) in $CH_2Cl_2$ (1 mL) was treated with N-cyclohexylcarbodiimide-N'-methylpolystyrene (1.9 mmol/g; 1.5 equiv.) and i-$Pr_2NEt$ (3.0 equiv.). The mixture was stirred for 15 h at rt. (Polystyrylmethyl)trimethylammonium bicarbonate (3.5 mmol/g; 3 equiv.) was added and stirring was continued for 1 h. The mixture was diluted with $CH_2Cl_2$/MeOH 9:1 (2 mL) and filtered. The polymer was washed twice with $CH_2Cl_2$/MeOH 8:2 (5 mL). The combined filtrate and washings were concentrated. Purification of the crude product by chromatography (FC, normal phase or reverse phase prep. HPLC) afforded an N-acylamino macrocycle.

L.1.3: Carboxylic Acid and HATU

A soln of an amino macrocycle (free amine or hydrochloride; 0.145 mmol), a carboxylic acid (2.0 equiv.), HATU (2.0 equiv.), HOAt (2.0 equiv.) in DMF (2 mL) was treated with i-$Pr_2NEt$ (4.0 equiv.). The mixture was stirred for 15 h at rt. The solvent was removed. The residue was distributed between $CHCl_3$ and sat. aq. $NaHCO_3$ soln. The organic phase was washed ($H_2O$), dried ($Na_2SO_4$), filtered and concentrated. Purification of the crude product by chromatography (FC, normal phase or reverse phase prep. HPLC) afforded an N-acylamino macrocycle.

L.2: Amide Coupling of a Macrocyclic Carboxylic Acid with an Amine and HATU

A soln of a macrocyclic carboxylic acid (0.78 mmol), an amine (2.0 equiv.), HATU (2.0 equiv.), HOAt (2.0 equiv.) in DMF (6 mL) was treated with i-$Pr_2NEt$ (4.0 equiv.). The mixture was stirred for 15 h at rt. The solvent was removed. The residue was distributed between $CHCl_3$ and sat. aq. $NaHCO_3$ soln. The organic phase was washed ($H_2O$), dried ($Na_2SO_4$), filtered and concentrated. Purification of the crude product by chromatography (FC, normal phase or reverse phase prep. HPLC) afforded a macrocyclic amide.

L.3: Sulfonamide Formation with Sulfonyl Chlorides

At 0° C. a soln of an amino macrocycle (0.24 mmol) in $CH_2Cl_2$ (1 mL) was successively treated with triethylamine (2.0 equiv.) and the sulfonyl chloride (1.0 equiv.). The mixture was stirred at 0° C. to rt for 0.5-16 h, followed by an aqueous workup ($CHCl_3$, sat. aq. $Na_2CO_3$ soln; $Na_2SO_4$). The crude product was purified by chromatography (FC, normal phase or reverse phase prep. HPLC) to afford the macrocyclic sulfonamide.

L.4: Urea Formation with Isocyanates or Equivalents of Isocyanates

A soln of an amino macrocycle (0.1 mmol) in $CH_2Cl_2$ was treated at rt with an isocyanate (1.1 equiv.) or with a succinimidyl carbamate (1.1 equiv.) and i-$Pr_2$NEt (3 equiv.). Aqueous workup ($CH_2Cl_2$, sat. aq. $Na_2CO_3$ soln; $Na_2SO_4$) and purification by chromatography (FC, normal phase or reverse phase prep. HPLC) afforded the targeted urea.

N-Alkylation by Reductive Amination

Procedure M

M.1: N,N-Diethylamino Macrocycles by Reductive Amination

At 0° C. $NaBH(OAc)_3$ (5 equiv.) and acetaldehyde (1 mL) were added to a soln of the amino macrocycle (free amine or hydrochloride; 0.09 mmol) in THF (1 mL). The mixture was stirred at 0° C. to rt for 15 h. The mixture was diluted with $CHCl_3$ and washed with sat. aq. $NaHCO_3$ soln. The organic phase was dried ($Na_2SO_4$), filtered and concentrated. Purification of the crude product by chromatography (FC, normal phase or reverse phase prep. HPLC) afforded the diethylamino macrocycle.

M.2: Synthesis of Secondary Amines by Reductive Amination

Activated molecular sieve powder (3 Å; 1 mg per mg of starting material) was added at rt to a soln of an amino macrocycle (0.8 mmol) and an aldehyde (1.1 equiv.) in THF (3.5 mL). The suspension was stirred for 4 h at rt, followed by the addition of acetic acid (1.1 equiv.) and $NaBH(OAc)_3$ (2.0 equiv.). The mixture was stirred for 18 h and filtered. Aqueous workup of the filtrate ($CH_2Cl_2$, sat. aq. $Na_2CO_3$ soln; $Na_2SO_4$) and purification of the crude product by chromatography (FC, normal phase or reverse phase prep. HPLC) afforded the alkylamino macrocycle.

M.3: Synthesis of Tertiary Amines by N-Methylation of Secondary Amines

At 0° C. formaldehyde soln (36.5% in $H_2O$; 5 equiv.) and $NaBH(OAc)_3$ (2.5 equiv.) were added to a soln of the macrocyclic amine (0.16 mmol) in THF (3 mL). The mixture was stirred at rt for 3 h followed by aqueous workup ($CH_2Cl_2$, sat. aq. $Na_2CO_3$ soln; $Na_2SO_4$). Purification of the crude product by chromatography (FC, normal phase or reverse phase prep. HPLC) afforded the desired N-methyl-N-alkylamino macrocycle.

If the HCl salt of the macrocyclic amine was used, the transformation was carried out in the presence of 2 equiv. of i-$Pr_2$NEt.

M.4: Synthesis of Tertiary Amines by Debenzylation/N-methyllation

A soln of a tert. benzylamine (0.1 mmol) in MeOH (2.0 mL)/acetic acid (0.5 mL) was hydrogenolyzed for 2 h at rt and normal pressure in the presence of palladium hydroxide on activated charcoal (moistened with 50% $H_2O$; 20 mg). Aq. formaldehyde soln (36.5% in $H_2O$; 10 equiv.) was added and hydrogenation was continued for 1 h.

The mixture was filtered through a pad of celite. The residue was washed (MeOH). The combined filtrate and washings were concentrated followed by aqueous workup ($CHCl_3$, sat. aq. $Na_2CO_3$ soln; $Na_2SO_4$). The crude product was purified by chromatography (FC, normal phase or reverse phase prep. HPLC) to afford a tertiary methylamino macrocycle.

M.5: Synthesis of Tertiary Amines by Reductive Amination of Secondary Amines i-$Pr_2$NEt (2 equiv.) was added at 0° C. to a mixture of the macrocyclic amine (0.15 mmol) and DCE (1.0 mL). The aldehyde (1.2 equiv.) was added. The mixture was stirred for 0.5 h, followed by the addition of $NaBH(OAc)_3$ (3 equiv.). Stirring was continued at rt for 15 h. After aqueous workup ($CHCl_3$, 1 M aq. $Na_2CO_3$ soln; $Na_2SO_4$) the crude product was purified by chromatography (FC, normal phase or reverse phase prep. HPLC) to afford the macrocyclic tertiary amine.

Miscellaneous Transformations

Procedure N: Methylester Cleavage

A soln of the methylester (57 μMol) in THF (1.5 mL) and MeOH (0.5 mL) was treated with $H_2O$ (0.5 mL) and lithium hydroxide monohydrate (3 equiv.) for 2 h at rt. The mixture was acidified by addition of aq. 1 M HCl and concentrated. The crude product was purified by chromatography (FC, normal phase or reverse phase prep. HPLC).

Procedure O: Conversion of Macrocyclic Primary Amines into Piperazines by N-Alkylation A mixture of the amino macrocycle (1.4 mmol) and N-benzyl-2-chloro-N-(2-chloroethyl)ethanamine (1.5 equiv.) in ethanol (15 mL) was treated with $NaHCO_3$ (4 equiv.) and heated to reflux for 3 h. Aqueous workup (EtOAc, half-sat. aq. $NaHCO_3$ soln; $Na_2SO_4$) and chromatography (FC, normal phase or reverse phase prep. HPLC) afforded the N-benzylpiperazino macrocycle.

Procedure P: Suzuki Couplings

A soln of $Na_2CO_3$ (3.0 equiv.) in $H_2O$ (1.6 mL) was added to a mixture of the macrocyclic arylbromide (0.25 mmol), the boronic acid (2.0 equiv.) and $Pd(PPh_3)_4$ (0.1 equiv.) in DME (5.2 mL). The mixture was heated to reflux for 1 h, followed by aqueous workup (EtOAc, sat. aq. $Na_2CO_3$ soln; $Na_2SO_4$). Purification of the crude product by chromatography (FC, normal phase or reverse phase prep. HPLC) afforded the biaryl-substituted macrocyclic product.

Procedure Q: O-Alkylation of Macrocyclic Alcohols

At 0° C. NaH (60% in oil, 2 equiv.) was added portionwise to a soln of the macrocyclic alcohol (0.38 mmol) and the alkylhalide (1.1 equiv.) in THF (3.7 mL)/DMF (1.3 mL). The mixture was stirred at rt for 2 h, treated with 1 M aq. HCl soln and extracted with EtOAc. The organic phase was dried ($Na_2SO_4$), filtered and concentrated. Purification of the crude product by chromatography (FC, normal phase or reverse phase prep. HPLC) afforded the macrocyclic alkyl ether.

Procedures R and S: Vide Infra "Transformations on Solid Support"

Synthesis of the A-B Fragments $PG^3$-B-A-OH and $PG^3$-B-A=$CH_2$

1. Synthesis of 3-(H2S,4S)-1-(allyloxycarbonyl)-4-(tert-butoxycarbonylamino)pyrrolidin-2-yl)methoxy)benzoic acid (192) (Scheme 4)

A soln of ethyl 3-hydroxybenzoate (142; 3.1 g, 18.6 mmol), alcohol 14 (5.66 g, 18.8 mmol) and CMBP (9.0 g, 37.3 mmol) in toluene (60 mL) was heated to reflux for 2 h. Evaporation of the volatiles and FC (hexane/EtOAc) gave 191 (7.3 g, 87%). A soln of ester 191 (4.3 g, 9.5 mmol) in THF/MeOH/$H_2O$ (3:1:1; 55 mL) was cooled to 0° C., treated with $LiOH.H_2O$ (801 mg, 19.1 mmol) and stirred at 0° C. to rt for 16 h. The mixture was treated with 1 M aq.

$NaH_2PO_4$ soln (100 mL) and repeatedly extracted with $CH_2Cl_2$. The combined organic layer was dried ($Na_2SO_4$), filtered and concentrated to yield 192 (3.86 g, 96%). Data of 192: $C_{21}H_{28}N_2O_7$ (420.5). LC-MS (method 10c): $R_t$=1.97 (97), 421 ($[M+H]^+$).

2. Synthesis of (2S,4S)-4-(4-bromobenzyloxy)-2-(3-(but-3-enyl)phenoxy)methyl)pyrrolidine (194)

2.1 Synthesis of 3-(But-3-enyl)phenol (149) (Scheme 1)

3-Methoxybenzyl bromide (148; 3.3 g, 16.3 mmol) was converted into 1-(but-3-enyl)-3-methoxybenzene (2.3 g, 86%) according to the procedure of A. B. Smith et al., *Org. Lett.* 2005, 7, 315-318, describing the synthesis of (3-but-enyl-phenoxy)-tert-butyl dimethylsilane.

At 0° C., $BBr_3$ (0.775 mL, 7.9 mmol) was slowly added to a soln of 1-(but-3-enyl)-3-methoxybenzene (1.36 g, 8.4 mmol) in dry $CH_2Cl_2$ (48 mL). Stirring at 0° C. was continued for 3 h, then 1 M aq. $NaHCO_3$ soln (20 mL) was added and stirring continued for 30 min. The mixture was diluted with $CH_2Cl_2$ (100 mL) and 1 M aq. $NaHCO_3$ soln (100 mL). The organic layer was separated. The aqueous layer was extracted with $CH_2Cl_2$. The combined organic layer was dried ($Na_2SO_4$), filtered and concentrated. FC (hexane/EtOAc 98:2 to 80:20) afforded 149 (896 mg, 72%).

Data of 149: $C_{10}H_{12}O$ (148.2). $^1$H-NMR (DMSO-$d_6$): 9.21 (s, OH), 7.04 (t, J=7.5, 1 H), 6.76-6.55 (m, 3 H), 5.82 (m, 1 H), 5.06-4.93 (m, 2 H), 2.59 (t, J=7.7, 2 H), 2.30 (q-like m, 1H).

2.2 Synthesis of Amine 194 (Scheme 4)

A mixture of phenol 149 (1.095 g, 7.3 mmol), alcohol 161 (2.28 g, 6.16 mmol) and $PPh_3$ (2.42 g, 9.24 mmol) was dissolved in $CHCl_3$ (46 mL) and degassed. ADDP (2.33 g, 9.24 mmol) was added and the mixture was stirred for 20 h at rt. The mixture was diluted with $CH_2Cl_2$, washed with sat. aq. $NaHCO_3$ soln, dried ($Na_2SO_4$), filtered and concentrated. FC (hexane/EtOAc gradient) afforded 193 (2.94 g, 95%).

To a degassed soln of 193 (200 mg, 0.4 mmol) in $CH_2Cl_2$/EtOAc (1:1, 5.2 mL) were added $Pd(PPh_3)_4$ (2.5 mg) and 1,3-dimethylbarbituric acid (125 mg, 0.8 mmol). The mixture was stirred for 45 min at rt followed by an aqueous workup ($CH_2Cl_2$, sat. aq. $Na_2CO_2$ soln; $Na_2SO_4$) and FC (EtOAc/MeOH gradient) to yield 194 (160 mg, 96%).

Data of 194: $C_{22}H_{26}BrNO_2$ (416.3). LC-MS (method 10a): $R_t$=2.00 (82), 416/418 ($[M+H]^+$). $^1$H-NMR (DMSO-$d_6$): 7.51 (d, J=8.3, 2 H), 7.28 (d, J=8.4, 2 H), 7.17 (t, J=7.8, 1 H), 6.79-6.70 (m, 3 H), 5.83 (m, 1 H), 5.03 (qd, J=1.7, 17.2, 1 H), 4.96 (d-like m, J ca. 10.2, 1 H), 4.42 (s, 2 H), 4.11 (m, 1 H), 3.91 (d, J=6.3, 2 H), 3.45 (m, 1 H), 2.97 (d, J=4.3, 2 H), 2.63 (t, J ca. 7.7, 2 H), 2.31 (q-like m, 2 H), 2.15 (m, 1 H), 1.66 (m, 1 H).

3. Synthesis of 5-bromo-2-(((2S,4R)-4-(tert-butoxycarbonylamino)-1-((2-(trimethylsilylflethoxy)carbonyl)pyrrolidin-2-yl)-methoxy)benzoic acid (196) (Scheme 4)

At 0° C. DEAD (40% in toluene; 3.5 mL, 7.6 mmol) was slowly added to a mixture of phenol 151 (1.76 g, 7.6 mmol), alcohol 152 (1.83 g, 5.1 mmol) and $PPh_3$ (2.0 g, 7.6 mmol) in benzene (50 mL). The mixture was stirred at rt for 16 h, followed by evaporation of the volatiles and FC (hexane/EtOAc 2:1) to yield 195 (2.78 g, 95%).

A soln of ester 195 (2.6 g, 4.5 mmol) in THF (20 mL) was treated with 2M aq. LiOH soln (22.5 mL, 45 mmol). The mixture was heated to 50° C. for 15 h. The organic solvent was evaporated. The remaining aqueous phase was acidified with 3 M aq. HCl soln and extracted with EtOAc. The organic phase was dried ($Na_2SO_4$), filtered and concentrated to give 196 (2.44 g, 96%).

Data of 196: $C_{23}H_{35}BrN_2O_7Si$ (559.5). LC-MS (method 10a): $R_t$=2.49 (98), 559/561 ($[M+H]^+$).

4. Synthesis of 3-(((2S,4S)-1-(allyloxycarbonyl)-4-(4-bromobenzyloxy)pyrrolidin-2-yl)methoxy)benzoic acid (198) (Scheme 4)

TMAD (5.0 g, 28 mmol) in degassed benzene (100 mL) was slowly added at 0° C. to a soln of ethyl 3-hydroxybenzoate (142; 4.7 g, 28 mmol), alcohol 161 (6.92 g, 19 mmol) and $PPh_3$ (7.4 g, 28 mmol) in benzene (300 mL). The resulting suspension was diluted with benzene (100 mL) and stirred at rt for 20 h. $Et_2O$ was added and the mixture was filtered. The filtrate was concentrated and purified by FC (hexane/EtOAc 75:25 to 70:30) to afford 197 (6.24 g, 64%).

A soln of 197 (883 mg, 1.7 mmol) in THF (5 mL) was treated with 2 M aq. LiOH soln (3 mL, 6 mmol) and MeOH (2.5 mL) for 2 h at rt. The volatiles were partially evaporated. The remaining soln was acidified with 1 M aq. HCl soln and extracted with EtOAc. The organic phase was dried ($Na_2SO_4$), filtered and concentrated to yield 198 (770 mg, 92%).

Data of 198: $C_{23}H_{24}BrNO_6$ (490.3). LC-MS (method 10a): $R_t$=2.30 (98), 492/490 ($[M+H]^+$).

Synthesis of the A-C Fragments H-A-M-c1-CO—OPG$^2$ and H-A-M-c1-CR$^{12}$=$CH_2$ 1. Synthesis of (S)-5-allyl 1-benzyl 2-(5-fluoro-2-hydroxy-N-methylbenzamido)pentanedioate (54) (Scheme 4)

Following procedure A (steps A.1-A.3), the reaction of 2-acetoxy-5-fluoro benzoic acid (2, 11.78 g, 59 mmol) and oxalylchloride (18 mL, 206 mmol) in dry $CH_2Cl_2$ (516 mL) in the presence of DMF (50 μL) afforded 2-acetoxy-5-fluoro benzoyl chloride (52).

Reaction of acid chloride 52 with (S)-5-allyl 1-benzyl 2-(methylamino)pentanedioate hydrochloride (27.HCl, 15.0 g, 46 mmol) in THF (260 mL) in the presence of i-$Pr_2NEt$ (23 mL, 137 mmol) yielded acetate 53 (19.35 g, 90%), which was treated with 3-dimethylamino-1-propylamine (23 mL, 185 mmol) in THF (200 mL) to afford after aqueous workup (EtOAc, 0.1 M aq. HCl soln, sat. aq. NaCl soln) and after FC (hexane/EtOAc 8:2 to 7:3) the phenol 54 (14.4 g, 81%).

Data of 54: $C_{23}H_{24}FNO_6$ (429.4). HPLC (30% $CH_3CN$): $R_t$=3.79 (87%). LC-MS (method 9a): $R_t$=2.09, 430 ($[M+H]^+$).

2. Synthesis of (R)-5-allyl 1-benzyl 2-(5-fluoro-2-hydroxy-N-methylbenzamido)pentanedioate (56) (Scheme 4)

Following procedure A (steps A.1-A.3), the reaction of 2-acetoxy-5-fluoro benzoic acid (2, 13.0 g, 67 mmol) and oxalylchloride (20 mL, 233 mmol) in dry $CH_2Cl_2$ (585 mL) in the presence of DMF (50 μL) afforded 2-acetoxy-5-fluoro benzoyl chloride (52).

Reaction of acid chloride 52 with (R)-5-allyl 1-benzyl 2-(methylamino)pentanedioate hydrochloride (29.HCl, 17.0 g, 52 mmol) in THF (280 mL) in the presence of i-$Pr_2NEt$ (27 mL, 156 mmol) yielded 55 (21.5 g, 88%), which was treated with 3-dimethylamino-1-propylamine (26 mL, 205 mmol) in THF (200 mL) to afford after aqueous workup (EtOAc, 0.1 M aq. HCl soln, sat. aq. NaCl soln) and after FC (hexane/EtOAc 8:2 to 7:3) phenol 56 (14.8 g, 75%).

Data of 56: $C_{23}H_{24}FNO_6$ (429.4). HPLC (30% $CH_3CN$): $R_t$=3.79 (89). LC-MS (method 9c): $R_t$=2.11, 430 ($[M+H]^+$).

3. Synthesis of (S)-allyl 2-(benzyloxycarbonylamino)-3-(3-hydroxy-N-methylbenzamido)propanoate (59) (Scheme 4)

Following procedure A (steps A.1-A.3), the reaction of 3-acetoxybenzoic acid (3, 6.0 g, 33 mmol) and oxalylchloride (14 mL, 164 mmol) in dry $Et_2O$ (216 mL) in the presence of DMF (50 μL) afforded 3-acetoxybenzoyl chloride (57, 7.0 g, quant.).

Reaction of 57 (7.0 g, 35 mmol) with (S)-allyl 2-(benzyloxycarbonylamino)-3-(methylamino)propanoate hydrochloride (32.HCl, 10.5 g, 32 mmol) in $CH_2Cl_2$ (285 mL) in the presence of 2,4,6-collidine (12.8 mL, 96 mmol) yielded 58 (12.34 g, 82%).

The acetate 58 (12.82 g, 28.2 mmol) was treated with 3-dimethylamino-1-propylamine (10.6 mL, 84.6 mmol) in THF (114 mL) to afford phenol 59 (10.45 g, 90%).

Data of 59: $C_{22}H_{24}N_2O_6$ (412.4). HPLC (10% $CH_3CN$): $R_t$=3.91 (96). LC-MS (method 9a): $R_t$=1.77, 413 ($[M+H]^+$).

4. Synthesis of (R)-allyl 2-(benzyloxycarbonylamino)-3-(3-hydroxy-N-methylbenzamido)propanoate (61) (Scheme 4)

Following procedure A (steps A.1-A.3), the reaction of 3-acetoxybenzoic acid (3, 5.82 g, 32.3 mmol) and oxalylchloride (11.1 mL, 129 mmol) in dry $Et_2O$ (210 mL) in the presence of DMF (50 μL) afforded 3-acetoxybenzoyl chloride (57, 6.5 g, 100%). Reaction of 57 (6.5 g, 32.3 mmol) with (R)-allyl 2-(benzyloxycarbonylamino)-3-(methylamino)propanoate hydrochloride (36.HCl, 8.5 g, 26 mmol) in $CH_2Cl_2$ (220 mL) in the presence of 2,4,6-collidine (10.3 mL, 77.6 mmol) yielded 60 (10.73 g, 92%).

Acetate 60 (15.46 g, 34 mmol) was treated with 3-dimethylamino-1-propylamine (12.8 mL, 102 mmol) in THF (140 mL) to afford phenol 61 (12.92 g, 92%).

Data of 61: $C_{22}H_{24}N_2O_6$ (412.4). LC-MS (method 2): $R_t$=1.77 (98), 413 ($[M+H]^+$).

5. Synthesis of (S)-allyl 2-(benzyloxycarbonylamino)-4-(3-hydroxy-N-methylbenzamido)butanoate (63) (Scheme 4)

Following procedure A (steps A.1-A.3), the reaction of 3-acetoxybenzoic acid (3, 7.65 g, 43 mmol) and oxalylchloride (18.2 mL, 213 mmol) in dry $CH_2Cl_2$ (140 mL) in the presence of DMF (300 μL) afforded after 3 h at rt 3-acetoxybenzoyl chloride (57).

Reaction of 57 with (S)-allyl 2-(benzyloxycarbonylamino)-5-(methylamino)butanoate hydrochloride (40.HCl, 8.7 g, 28 mmol) in THF (140 mL) in the presence of i-$Pr_2$NEt (15 mL, 85 mmol) yielded 62 (8.1 g, 61%).

Acetate 62 (4.85 g, 10 mmol) was treated with 3-dimethylamino-1-propylamine (3.8 mL, 31 mmol) in THF (90 mL) to afford phenol 63 (4.23 g, 95%).

Data of 63: $C_{23}H_{26}N_2O_6$ (426.5). LC-MS: (method 6): $R_t$=1.06 (99), 427 ($[M+H]^+$).

6. Synthesis of (S)-allyl 2-(benzyloxycarbonylamino)-5-(3-hydroxy-N-methylbenzamido)pentanoate (65) (Scheme 4)

Following procedure A (steps A.1-A.3), the reaction of 3-acetoxybenzoic acid (3, 10 g, 58 mmol) and oxalylchloride (19 mL, 218 mmol) in dry $CH_2Cl_2$ (450 mL) in the presence of DMF (500 μL) afforded 3-acetoxybenzoyl chloride (57).

Reaction of 57 with (S)-allyl 2-(benzyloxycarbonylamino)-5-(methylamino)pentanoate hydrochloride (44.HCl, 17.3 g, 48 mmol) in THF (200 mL) in the presence of i-$Pr_2$NEt (25 mL, 145 mmol) yielded 64 (12.08 g, 51%), which was treated with 3-dimethylamino-1-propylamine (9.3 mL, 75 mmol) in THF (240 mL) to afford after aqueous workup (EtOAc, 1 M aq. HCl soln, sat. aq. $NaHCO_3$ soln, sat. aq. NaCl soln) phenol 65 (10.84 g, 98%). Data of 65: $C_{24}H_{28}N_2O_6$ (440.5). LC-MS (method 6): $R_t$=1.15 (91), 441 ($[M+H]^+$).

7. Synthesis of (S)-5-allyl 1-benzyl 2-(4-hydroxy-N-methylbenzamido)pentanedioate (68) (Scheme 4)

Following procedure A (steps A.1-A.3), the reaction of 4-acetoxybenzoic acid (4, 10.7 g, 59.5 mmol) and oxalylchloride (17.7 mL, 206 mmol) in dry $CH_2Cl_2$ (350 mL) in the presence of DMF (50 μL) afforded 4-acetoxybenzoyl chloride (66). Reaction of 66 with (S)-5-allyl 1-benzyl 2-(methylamino)pentanedioate hydrochloride (27.HCl, 15.0 g, 46 mmol) in THF (250 mL) in the presence of i-$Pr_2$NEt (23.3 mL, 137 mmol) yielded 67 (16.24 g, 78%).

Treatment of 67 (15.2 g, 33.5 mmol) with 3-dimethylamino-1-propylamine (12.6 mL, 101 mmol) in THF (140 mL) afforded phenol 68 (14.86 g, quant.).

Data of 68: $C_{23}H_{28}NO_6$ (411.4). LC-MS (method 9b): $R_t$=1.96, 412 ($[M+H]^+$).

8. Synthesis of (S)-allyl 2-(benzyloxycarbonylamino)-3-(5-hydroxy-N-methylnicotinamido)propanoate (71) (Scheme 4)

A mixture of 5-hydroxy nicotinic acid (5, 3.5 g, 25.1 mmol) and acetic anhydride (23 mL, 243 mmol) was heated at 95° C. for 45 min and cooled to rt. The mixture was filtered. The solid was washed ($H_2O$, $Et_2O$) and dried i.v. to give 5-acetoxynicotinic acid (6; 3.76 g, 82%) (cf. Scheme 1)

5-Acetoxynicotinic acid (6; 5.7 g, 31.5 mmol) was suspended in $CHCl_3$ (stabilized with amylene, 230 mL). Oxalylchloride (9.0 mL, 105 mmol) was added followed by DMF (ca. 50 μL). The mixture was stirred at rt for 15 h, then concentrated, coevaporated with dry $CH_2Cl_2$ and dried i.v. to afford 5-acetoxynicotinoyl chloride (69). (S)-allyl 2-(benzyloxycarbonylamino)-3-(methylamino)propanoate hydrochloride (32.HCl, 8.6 g, 26.2 mmol) and THF (225 mL) were added. The mixture was cooled to 0° C. $Et_3N$ (13 mL, 92 mmol) was slowly added. The mixture was stirred at 0° C. to rt for 18 h. 3-dimethylamino-1-propylamine (9.9 mL, 78.6 mmol) was added and stirring at rt was continued for 2 h. The mixture was distributed between EtOAc and 1 M aq. $NaH_2PO_4$ soln. The organic layer was separated, washed (sat. aq. NaCl soln), dried ($Na_2SO_4$), filtered and concentrated. FC ($CH_2Cl_2$/MeOH 19:1) afforded phenol 71 (8.81 g, 81%).

Data of 71: $C_{21}H_{23}N_3O_6$ (413.4). LC-MS (method 6): $R_t$=0.94 (92), 414 ($[M+H]^+$).

9. Synthesis of allyl (2S)-2-[(benzyloxy)carbonyl]amino-3-[((2S)-2-[(tert-butoxycarbonyl)amino]-8-hydroxy-1,2,3,4-tetrahydro-2-naphthalenylcarbonyl)(methyl)amino]propanoate (72) (Scheme 4)

A mixture of 10 (3.0 g, 9.76 mmol), HATU (5.57 g, 14.6 mmol), HOAt (1.99 g, 14.6 mmol) and 32.HCl (6.4 g, 19.5 mmol) was dissolved in DMF (113 mL). i-$Pr_2$NEt (8.36 mL, 48.8 mmol) was added. The mixture was stirred at rt for 3 d, then distributed between $H_2O$ and EtOAc. The organic phase was dried ($Na_2SO_4$), filtered, and concentrated. FC (hexane/EtOAc 75:25 to 50:50) afforded 72 (2.58 g, 45%).

Data of 72: $C_{31}H_{39}N_3O_8$ (581.3). LC-MS (method 7): $R_t$=1.27 (97), 582 ($[M+H]^+$).

10. Synthesis of 5-allyl 1-benzyl (2S)-2-[[(8-hydroxy-2-quinolinyl)carbonyl](methyl)amino]pentanedioate(75) (Scheme 4) Following procedure A (steps A.1-A.3), the reaction of 8-acetoxyquinoline-2-carboxylic acid (8, 2.22 g 9.6 mmol) and oxalylchloride (2.1 mL, 24 mmol) in dry $CH_2Cl_2$ (90 mL) (no addition of DMF) afforded after 2 h at rt acetoxyquinoline-2-carboxylic acid chloride (73).

Reaction of 73 with (S)-5-allyl 1-benzyl 2-(methylamino)-pentanedioate hydrochloride (27HCl, 2.3 g, 8.0 mmol) in $CH_2Cl_2$ (200 mL) in the presence of i-$Pr_2$NEt (5.5 mL, 32 mmol) yielded after 2.5 h at rt and purification by FC (hexane/EtOAc gradient) 74 (3.03 g, 74%), which was treated with 3-dimethylamino-1-propylamine (2.3 mL, 18 mmol) in THF (54 mL) to afford after aqueous workup (EtOAc, 1 M aq. HCl soln, sat. aq. $NaHCO_3$ soln, sat. aq. NaCl soln) the phenol 75 (2.79 g, 99%). Data of 75: $C_{26}H_{26}N_2O_6$ (462.5). LC-MS (method 7): $R_t$=1.29 (94), 463 ($[M+H]^+$).

11. Synthesis of N-allyl-3-hydroxy-N-methylbenzamide (77) (Scheme 4)

Following procedure A (steps A.1-A.3), the reaction of 3-acetoxybenzoic acid (3, 23.7 g, 132 mmol) and oxalyl-chloride (45.3 mL, 527 mmol) in dry $Et_2O$ (800 mL) in the presence of DMF (100 μl) afforded 3-acetoxybenzoyl chloride (57).

Reaction of 57 with N-allylmethylamine (10.1 ml, 105 mmol) in $CH_2Cl_2$ (500 mL) in the presence of 2,4,6-collidine (42 mL, 316 mmol) yielded 76 (24 g, 98%).

The acetate 76 (10.9 g, 46.7 mmol) was treated with 3-dimethylamino-1-propylamine (17.5 mL, 140 mmol) in THF (90 mL) to afford after aqueous workup (EtOAc, 1 M aq. HCl soln, sat. aq. NaCl soln) the phenol 77 (9.0 g, 100%).

Data of 77: $C_{11}H_{13}NO_2$ (191.2). LC-MS (method 2): $R_t$=1.52 (99), 192 ($[M+H]^+$).

12. Synthesis of (S)-5-allyl-1-benzyl 2-(3-mercapto-N-methylbenzamido)pentanedioate (80) (Scheme 4)

Acetic anhydride (0.46 mL, 4.86 mmol) was added at 0° C. to a soln of 3-mercaptobenzoic acid (11, 250 mg, 1.62 mmol) in 1 M aq. NaOH soln (5.0 mL, 5.0 mmol). The mixture was stirred at 0° C. for 1 h. A precipitate formed; and the mixture was acidified by the addition of 1 M aq. HCl soln and filtered. The solid was dried i.v. to afford 3-(acetylthio)benzoic acid (12; 280 mg, 88%) (cf. Scheme 1).

Oxalyl chloride (0.34 mL, 3.97 mmol) was added to a mixture of (260 mg, 1.33 mmol) and $CHCl_3$ (stabilized with amylene; 16 mL). DMF (7 μL) was added. The mixture was stirred at rt for 2 h. The volatiles were evaporated to afford 3-(acetylthio)benzoyl chloride (78).

(S)-5-allyl 1-benzyl 2-(methylamino)pentanedioate hydrochloride (27.HCl, 434 mg, 1.33 mmol) and dry THF (5 mL) were added. The mixture was cooled to 0° C., followed by the addition of i-$Pr_2$NEt (0.79 mL, 4.6 mmol). The mixture was stirred at rt for 16 h and distributed between EtOAc and 1 M aq. HCl soln. The organic phase was separated, dried ($Na_2SO_4$), filtered and concentrated. FC (hexane/EtOAc 2:1) afforded the acetate 79 (420 mg, 67%).

At rt, a soln of 79 (246 mg, 0.52 mmol) in degassed THF (3.6 mL) was treated with 3-dimethylamino-1-propylamine (0.13 mL, 1.05 mmol) for 1 h. The mixture was distributed between EtOAc and 1 M aq. HCl soln. The organic phase was separated, dried ($Na_2SO_4$), filtered and concentrated. FC (hexane/EtOAc 2:1) afforded 80 (153 mg, 68%).

Data of 80: $C_{23}H_{25}NO_5S$ (427.5). LC-MS (method 7): $R_t$=1.39 (84), 428 ($[M+H]^+$).

13. Synthesis of (S)-allyl 2-(benzyloxycarbonylamino)-4-(5-fluoro-2-hydroxybenzamido) butanoate (199) (Scheme 4)

Following procedure A (step A.1), the reaction of 2-acetoxy-5-fluoro benzoic acid (2; 10.5 g, 53.1 mmol) and oxalyl chloride (15.8 mL, 184 mmol) in dry $CH_2Cl_2$ (460 mL) in the presence of DMF (0.2 mL) afforded 2-acetoxy-5-fluoro benzoyl chloride (52). (S)-Allyl-4-amino-2-(benzyloxycarbonylamino)butanoate toluene-4-sulfonate (38.pTsOH, 19.0 g, 40.9 mmol) and THF (230 mL) were added. The mixture was cooled to 0° C. and i-$Pr_2$NEt (21 mL, 123 mmol) was added dropwise. The mixture was stirred at rt for 2 h. 3-Dimethylaminopropylamine (15.5 mL, 123 mmol) was added. The mixture was stirred at rt for 2 h followed by aqueous workup ($CH_2Cl_2$, 1 M aq. $NaH_2PO_4$ soln). The organic layer was separated, dried ($Na_2SO_4$), filtered and concentrated. FC (hexane/EtOAc) afforded 199 (15.5 g, 88%).

Data of 199: $C_{22}H_{23}FN_2O_6$ (430.4). LC-MS (method 10a): $R_t$=2.14 (90), 431 ($[M+H]^+$).

14. Synthesis of (S)-allyl 2-(benzyloxycarbonylamino)-5-(3-hydroxybenzamido)pentanoate (200) (Scheme 4)

Following procedure A (step A.1), the reaction of 3-acetoxy benzoic acid (3, 4.2 g, 23.3 mmol) and oxalyl chloride (7.5 mL, 87.6 mmol) in dry $CH_2Cl_2$ (160 mL) in the presence of DMF (0.1 mL) afforded after 2 h at rt 3-acetoxybenzoyl chloride (57). (S)-Allyl-5-amino-2-(benzyloxycarbonylamino)pentanoate toluene-4-sulfonate (42.pTsOH; 9.3 g, 19.5 mmol) and THF (70 mL) were added. The mixture was cooled to 0° C. and i-$Pr_2$NEt (10.0 mL, 58.4 mmol) was added within 5 min. The mixture was stirred at rt for 2 h followed by the addition of 3-dimethylaminopropylamine (7.4 mL, 58.4 mmol). Stirring was continued for 2 h. The mixture was distributed between EtOAc and 1 M aq. HCl soln. The organic layer was separated, washed ($H_2O$, sat. aq. $NaHCO_3$ soln, sat. aq. NaCl soln), dried ($Na_2SO_4$), filtered and concentrated. FC (EtOAc/hexane) afforded 200 (5.83 g, 70%). Data of 200: $C_{23}H_{26}N_2O_6$ (426.5). LC-MS (method 4b): $R_t$=1.96 (97), 427 ($[M+H]^+$).

15. Synthesis of (S)-allyl 2-(benzyloxycarbonylamino)-5-(5-fluoro-2-hydroxy-N-methylbenzamido)pentanoate (202) (Scheme 4)

Following procedure A (steps A.1-A.3) the reaction of 2-acetoxy-5-fluoro benzoic acid (2; 5.6 g, 28.6 mmol) and oxalyl chloride (9.2 mL, 107 mmol) in dry $CH_2Cl_2$ (220 mL) in the presence of DMF (0.05 mL) afforded after 6 h at rt 2-acetoxy-5-fluoro benzoyl chloride (52).

Reaction of the acid chloride 52 with (S)-allyl-2-(benzyloxycarbonylamino)-5-(methylamino)pentanoate hydrochloride (44.HCl; 8.5 g, 23.8 mmol) in THF (130 mL) in the presence of i-$Pr_2$NEt (12.2 mL, 71.5 mmol) yielded 201 (4.86 g, 41%).

Acetate 201 was treated with 3-dimethylaminopropylamine (3.64 mL, 29.1 mmol) in THF (45 mL) to afford after aqueous workup (EtOAc, 1 M aq. HCl soln, sat. aq. NaCl soln) the phenol 202 (4.08 g, 92%).

Data of 202: $C_{24}H_{27}FN_2O_6$ (458.5). LC-MS (method 4b): $R_t$=2.08 (83), 459 ($[M+H]^+$).

16. Synthesis of 5-allyl 1-benzyl (2S)-2-[[(3-hydroxy-2-thienyl)carbonyl](methyl)amino]pentanedioate (205) (Scheme 4)

At 0° C. acetic anhydride (6.5 mL, 69.4 mmol) was added to a soln of 3-hydroxythiophene-2-carboxylic acid (144; 2.0 g, 13.9 mmol) in 2 M aq. NaOH (34.7 mL, 69.4 mmol). The mixture was stirred for 5 h, acidified with 1 M aq. HCl soln and extracted with EtOAc. The organic layer was separated, dried ($Na_2SO_4$), filtered and concentrated to give 3-acetoxythiophene-2-carboxylic acid (145; 1.74 g, 67%) (cf. Scheme 1).

Following procedure A (steps A.1-A.3) the reaction of 145 (1.74 g, 9.3 mmol) and oxalyl chloride (8.0 mL, 93 mmol) in dry $CH_2Cl_2$ (130 mL) in the presence of DMF (0.05 mL) afforded after 2.5 h at rt 2-(chlorocarbonyl)thiophen-3-yl acetate (203). Reaction of the acid chloride 203 with (S)-5-allyl-1-benzyl-2-(methylamino)pentanedioate hydrochloride (27.HCl; 2.80 g, 8.5 mmol) in THF (95 mL) in the presence of i-$Pr_2$NEt (4.4 mL, 25.6 mmol) yielded after aqueous workup (EtOAc, 1 M aq. HCl soln, $H_2O$, sat. aq. NaCl soln) the crude acetate 204 (3.56 g), which was treated with 3-dimethylaminopropylamine (1.95 mL, 15.5 mmol) in THF (87 mL) to afford after aqueous workup (EtOAc, 1 M aq. HCl soln, sat. aq. NaCl soln) and after FC ($CH_2Cl_2$) phenol 205 (1.65 g, 42%).

Data of 205: $C_{21}H_{23}NO_6S$ (417.5). LC-MS (method 7): $R_t$=1.43 (93), 418 ($[M+H]^+$).

17. Synthesis of (S)-allyl 2-(benzyloxycarbonylamino)-6-(5-hydroxy-N-methylnicotinamido)hexanoate (207) (Scheme 4)

Following procedure A (step A.1), the reaction of 5-acetoxynicotinic acid (6, 41 g, 226 mmol, synthesized as described above, cf. phenol 71) and oxalyl chloride (71.8 mL, 849 mmol) in $CHCl_3$ (1660 mL) in the presence of DMF (0.26 mL) afforded after 1.5 h at rt 5-acetoxy-nicotinoyl chloride (69). At 0° C. a suspension of the acid chloride 69 in $CH_2Cl_2$ (100 mL) was added over 10 min to a mixture of (S)-allyl-2-(benzyloxycarbonylamino)-6-(methylamino) hexanoate hydrochloride (182.HCl; 70.0 g, 189 mmol) in $CH_2Cl_2$ (260 mL) and 1 M aq. $Na_2CO_3$ soln (360 mL). The mixture was stirred at rt for 2 h. The organic layer was separated; the aqueous layer was extracted twice with $CH_2Cl_2$ (250 mL). The combined organic layer was dried ($Na_2SO_4$), filtered and concentrated. FC (hexane/EtOAc/MeOH gradient) afforded 206 (33.5 g, 36%).

Following procedure A (step A.3), acetate 206 was treated with 3-dimethylaminopropylamine (25.4 mL, 202 mmol) in THF (330 mL) to afford after 2 h at rt and aqueous workup (EtOAc, 1 M aq. $NaH_2PO_4$ soln) 207 (29.1 g, 95%).

Data of 207: $C_{24}H_{29}N_3O_6$ (455.5). LC-MS (method 4a): $R_t$=1.77 (96), 456 ([M+H]$^+$).

18. Synthesis of 5-allyl 1-benzyl (2S)-2-[[(5-hydroxy-1,2-dimethyl-1H-indol-3-yl)carbonyl](methyl)amino]pentanedioate (210) (Scheme 4)

Pyridine (6.3 mL, 78 mmol) was added to a suspension of 5-hydroxy-1,2-dimethyl-1H-indole-3-carboxylic acid (146; 4.0 g, 19 mmol) in EtOAc (40 mL). Acetic anhydride (3.7 mL, 39 mmol) was added. The mixture was stirred at rt for 3 h followed by distribution between $CH_2Cl_2$ and 1 M aq. HCl soln. The organic layer was separated, dried ($Na_2SO_4$), filtered and concentrated. FC ($CH_2Cl_2$/MeOH 100:0 to 97:3). The product was suspended in $Et_2O$, filtered and dried i.v. to afford 5-acetoxy-1,2-dimethyl-1H-indole-3-carboxylic acid (147; 3.62 g, 75%) (cf. Scheme 1). Following procedure A (step A.1), the reaction of 147 (3.6 g, 15 mmol) and oxalyl chloride (3.1 mL, 37 mmol) in dry $CH_2Cl_2$ (90 mL) afforded after 2 h at rt 3-(chlorocarbonyl)-1,2-dimethyl-1H-indol-5-yl acetate (208).

At 0° C. (S)-5-allyl-1-benzyl-2-(methylamino)pentanedioate hydrochloride (27.HCl; 4.0 g 12 mmol) was added portionwise to a mixture of the acid chloride 208 and i-$Pr_2$NEt (8.4 mL, 49 mmol) in $CH_2Cl_2$ (43 mL). The mixture was stirred for 2 h at rt followed by distribution between EtOAc and 1 M aq. HCl soln. The organic layer was separated, washed (sat. aq. $NaHCO_3$ soln, sat. aq. NaCl soln), dried ($Na_2SO_4$), filtered and concentrated.

FC ($CH_2Cl_2$/MeOH 100:0 to 97:3) afforded 209 (6.34 g, 99%). Treatment of 209 with 3-dimethylaminopropylamine (6.8 mL, 54 mmol) in THF (70 mL) at rt for 16 h afforded after aqueous workup (EtOAc, 1 M aq. HCl soln, sat. aq. $NaHCO_3$ soln, sat. aq. NaCl soln) 210 (5.40 g, 93%).

Data of 210: $C_{27}H_{30}N_2O_6$ (478.5). LC-MS (method 4b): $R_t$=2.20 (95), 479 ([M+H]$^+$).

19. Synthesis of (S)-allyl 2-(tert.-butoxycarbonylamino)-5-(3-mercapto-N-methylbenzamido)pentanoate (212) (Scheme 4)

Following procedure A (steps A.1-A.3) the reaction of 3-(acetylthio)benzoic acid (12, 10.0 g, 51 mmol; synthesized as described above, cf. thiophenol 80) and oxalyl chloride (16.0 mL, 192 mmol) in dry $CH_2Cl_2$ (380 mL) in the presence of DMF (0.1 mL) afforded after 3.5 h at rt 3-(acetylthio)benzoyl chloride (78).

Reaction of the acid chloride 78 with (S)-allyl-2-(benzyloxycarbonylamino)-5-(methylamino)pentanoate hydrochloride (44.HCl; 15.2 g, 43 mmol) in THF (175 mL) in the presence of i-$Pr_2$NEt (22 mL, 128 mmol) yielded after aqueous workup (EtOAc, 1 M aq. HCl soln) and FC (hexane/EtOAc) 211 (12.31 g, 57%). Treatment of 211 (8.0 g, 16 mmol) with 3-dimethylaminopropylamine (6.1 mL, 48 mmol) in THF (135 mL) afforded after 1 h and aqueous workup (EtOAc, 1 M aq. HCl soln) 212 (7.49 g, quant. yield; used without further purification).

Data of 212: $C_{24}H_{28}N_2O_5S$ (456.5). LC-MS (method 10a): $R_t$=2.12 (83), 457 ([M+H]$^+$). $^1$H-NMR (DMSO-$d_6$): 7.83-7.74 (m, 1 H), 7.39-7.28 (m, 8 H), 7.08 (m, 1 H), 5.89 (m, 1 H), 5.61 (s, 1 H), 5.31 (d, J=17.0, 1 H), 5.21 (td, J=1.4, 10.5, 1 H), 5.05 (s, 2 H), 4.58 (br. s, 2 H), 4.12, 4.04 (2 br. m, 1 H), 3.49, 3.38 (2 br. m, 1 H), 3.18 (br. m, 1 H), 2.89, 2.81 (2 br. s, 3H), 1.80-1.40 (br. m, 4 H).

20. Synthesis of (S)-allyl 2-(benzyloxycarbonylamino)-6-(3-hydroxyphenylthio)hexanoate (213) (Scheme 4)

A mixture of 185 (4.97 g, 14.2 mmol) and $NaHCO_3$ (3.57 g, 42.6 mmol) was suspended in degassed anhydrous DMF (85 mL). At 0° C. a soln of 3-mercaptophenol (143; 2.17 mL, 21.3 mmol) in DMF (5 mL) was added dropwise. The mixture was stirred for 6 h at rt. The mixture was distributed between EtOAc and aq. NaCl soln. The organic phase was separated, washed ($H_2O$, NaCl soln), dried ($Na_2SO_4$), filtered and concentrated to yield after FC (hexane/EtOAc 3:1) 213 (5.6 g, quant. yield).

Data of 213: $C_{20}H_{29}NO_5S$ (395.5). LC-MS (method 10c): $R_t$=2.24 (95), 396 ([M+H]$^+$).

Synthesis of the C—B Fragments $PG^5$-$NR^4$-c2-CO—B—OH and $H_2C$=$CR^{12}$-c2-CO—B—OH 1. Synthesis of allyl N-2-[(2S,4S)-4-[(tert-butoxycarbonyl)-amino]-2-(hydroxymethyl)tetrahydro-1H-pyrrol-1-yl]-2-oxoethyl-N-methylcarbamate (81) (Scheme 5)

A soln of (2-((allyloxycarbonyl)(methyl)amino)acetic acid (47, 8.0 g, 46 mmol) and aminoalcohol 13 (11.0 g, 51 mmol) in DMF (120 mL) was cooled to 0° C. 2,4,6-Collidine (11 mL, 82 mmol) was added followed by HATU (22 g, 58 mmol). The mixture was stirred for 1 h at 0° C. then for 16 h at rt followed by distribution between EtOAc and sat. aq. $Na_2CO_3$ soln. The organic phase was washed (1 M aq. HCl soln, sat. aq. NaCl soln), dried ($Na_2SO_4$), filtered and concentrated. FC (EtOAc/MeOH 100:0 to 95:5) afforded amidoalcohol 81 (14.7 g, 86%).

Data of 81: $C_{17}H_{29}N_3O_6$ (371.4). HPLC (20% $CH_3CN$): $R_t$=2.94 (97). LC-MS (method 9c): $R_t$=1.55, 743 ([2M+H]$^+$), 372 ([M+H]$^+$).

2. Synthesis of allyl N-2-[(2S,4R)-4-[(tert-butoxycarbonyl)-amino]-2-(hydroxymethyl)tetrahydro-1H-pyrrol-1-yl]-2-oxoethyl-N-methylcarbamate (82) (Scheme 5)

Following procedure D, the reaction of the aminoalcohol 17.HCl (10.0 g, 39.6 mmol) and 2-((allyloxycarbonyl)(methyl)amino)acetic acid (47, 15.1 g, 87 mmol) in DMF (100 mL) in the presence of HCTU (40.9 g, 98.9 mmol), Cl-HOBt (1.68 g, 9.89 mmol) and i-$Pr_2$NEt (33.6 mL, 198 mmol) afforded after FC (hexane/EtOAc 20:80 to 0:100) the corresponding amido ester intermediate (13.7 g) which was saponified with lithium hydroxide monohydrate (3.28 g, 78.1 mmol) in THF (350 mL) and $H_2O$ (90 mL) to yield amidoalcohol 82 (8.89 g, 61%).

Data of 82: $C_{17}H_{29}N_3O_6$ (371.4). LC-MS (method 9b): $R_t$=1.57; 372 ([M+H]$^+$), 316, 272 ([M+H-Boc]$^+$), 156.

3. Synthesis of tert-butyl (3R)-4-{2-[[(allyloxy)carbonyl]-(methyl)amino]acetyl}-3-(hydroxymethyl)tetrahydro-1(2H)-pyrazinecarboxylate (84) (Scheme 5)

Following procedure D, the reaction of (R)-tert-butyl 3-(hydroxymethyl)piperazine-1-carboxylate hydrochloride (83.HCl, 19.7 g, 78 mmol) and 3-((allyloxycarbonyl)(methyl)amino)acetic acid (47, 30 g, 172 mmol) in DMF (188 mL) in the presence of HCTU (81.0 g, 195 mmol), Cl-HOBt (3.3 g, 19 mmol) and i-$Pr_2$NEt (67 mL, 390 mmol)

afforded after FC (EtOAc) the corresponding amido ester intermediate (40 g) which was saponified with lithium hydroxide monohydrate (9.5 g, 228 mmol) in THF (1020 mL) and $H_2O$ (245 mL) to yield after FC (EtOAc) amido-alcohol 84; 22.8 g, 79%).

Data of 84: $C_{17}H_{29}H_3O_6$ (371.4). LC-MS (method 7): $R_t$=0.99 (93), 372 ([M+H]$^+$).

4. Synthesis of benzyl N-((1S)-1-[(2S,4S)-4-[(tert-butoxy-carbonyl)amino]-2-(hydroxymethyl)tetrahydro-1H-pyrrol-1-yl]-carbonyl-3-butenyl)carbamate (85) (Scheme 5)

Aminoalcohol-hydrochloride 13.HCl (3.7 g, 14.7 mmol) was added to a soln of acid 51 (5.22 g, 14.7 mmol) in DMF (80 ml). The mixture was cooled to 0° C. HATU (7.0 g, 18.4 mmol) and 2,4,6-collidine (3.51 ml, 26.4 mmol) were added. The soln was stirred at 0° C. to rt for 17 h, followed by distribution between EtOAc and sat. aq. $Na_2CO_3$ soln. The organic phase was washed (1 M aq. HCl soln, sat. aq. $NaHCO_3$ soln, sat. aq. NaCl soln), dried ($Na_2SO_4$), filtered and concentrated. FC (hexane/EtOAc 30:70 to 20:80) afforded the amidoalcohol (85, 5.78 g, 88%)

Data of 85: $C_{23}H_{33}N_3O_6$ (447.5). LC=MS (method 2): $R_t$=1.92 (92), 448 ([M+H]$^+$).

5. Synthesis of allyl N-3-[(2S,4R)-4-[(tert-butoxycarbonyl)-amino]-2-(hydroxymethyl)tetrahydro-1H-pyrrol-1-yl]-3-oxopropyl-N-methylcarbamate (86) (Scheme 5)

Following procedure D, the reaction of aminoalcohol 17.HCl (7.5 g, 30 mmol) and 3-((allyloxycarbonyl)(methyl) amino)propanoic acid (49, 12.3 g, 66 mmol) in DMF (77 mL) in the presence of HCTU (31.0 g, 75.0 mmol), $C_1$—HOBt (1.27 g, 7.5 mmol) and i-$Pr_2$NEt (25.6 mL, 150 mmol) afforded after FC ($CH_2Cl_2$/MeOH 100:0 to 97:3) the corresponding amido ester intermediate (17.1 g) which was saponified with lithium hydroxide monohydrate (3.8 g, 90 mmol) in THF (388 mL) and $H_2O$ (105 mL) to yield amido-alcohol 86 (10.48 g, 86%).

Data of 86: $C_{18}H_{31}N_3O_6$ (385.4). HPLC (10% $CH_3CN$): $R_t$=3.49 (88). LC-MS (method 9a): $R_t$=1.62; 386 ([M+H]$^+$), 330 ([M+H-tBu]$^+$), 286 ([M+H-Boc]$^+$).

Core 01: Synthesis of Ex. 1 (Scheme 6)

Synthesis of Mitsunobu Product 87

To a soln of 54 (350 mg, 0.82 mmol), 16 (590 mg, 1.7 mmol) and $PPh_3$ (1069 mg, 4.08 mmol) in dry degassed $CHCl_3$ (11 mL) was added ADDP (1028 mg, 4.08 mmol) in one portion at 0° C., under an $N_2$ atmosphere. The resulting mixture was stirred for 16 h at rt. The mixture was filtered and the slurry washed further with $Et_2O$. The combined filtrates were concentrated in vacuo. The crude residue was purified by FC ($CH_2Cl_2$/EtOH 100:0 to 99:1) to afford 87 (1.05 g containing residual triphenylphosphine oxide), which was used in the next step without further purification.

Synthesis of Amino Acid 88

Following procedure B.2, the reaction of 87 (441 mg, contaminated with triphenylphosphine oxide, ca. 0.5 mmol), 1,3-dimethylbarbituric acid (219 mg, 1.4 mmol) and $Pd(PPh_3)_4$ (34 mg) in EtOAc/$CH_2Cl_2$ (55:45, 10 mL) yielded after 1.5 h and subsequent FC ($CH_2Cl_2$/MeOH 100:0 to 80:20) amino acid 88 (267 mg, 72%).

Data of 88: $C_{31}H_{42}FN_3O_sSi$ (631.7). LC-MS (method 9a): $R_t$=2.02, 632 ([M+H]$^+$). HPLC (30% $CH_3CN$): $R_t$=3.41 (96).

Synthesis of Macrolactam Ex. 1

According to procedure F.1.1 amino acid 88 (75 mg, 0.12 mmol) in dry $CH_2Cl_2$ (6 mL) was added within 4 h to T3P (50% in EtOAc, 0.21 mL, 0.36 mmol) and i-$Pr_2$NEt (0.1 mL, 0.59 mmol) in dry $CH_2Cl_2$ (6 mL) to give after FC ($CH_2Cl_2$/MeOH 100:0 to 96:4) macrolactam Ex. 1 (45 mg, 61%).

Data of Ex. 1: $C_{31}H_{40}FN_3O_7Si$ (613.7). LC-MS (method 7):

$R_t$=1.45 (41), 614 ([M+H]$^+$); 1.47 (44), 614 ([M+H]$^+$).

$^1$H-NMR (DMSO-$d_6$): complex spectrum, several isomers; 7.45-7.01 (m, 8 H), 6.78-6.58 (2 m, 1 H), 5.42-5.06 (m, 3 H), 4.50-3.50 (several m, 7 H), 3.30-1.40 (several m, 7 H), 2.84, 2.70, 2.66 (s, 3 H), 0.97-0.82 (m, 2 H), 0.03, 0.02, 0.00 (s, 9 H).

Core $O_2$: Synthesis of Ex. 2 (Scheme 11)

Synthesis of the Protected Macrolactam Ex. 2

A soln of T3P (50% in EtOAc, 0.75 mL, 1.27 mmol) and i-$Pr_2$NEt (0.36 mL, 2.2 mmol) in dry $CH_2Cl_2$ (20 mL) was added within 2 h to a soln of amino acid 98 (250 mg, 0.43 mmol) in dry $CH_2Cl_2$ (730 mL). The soln was stirred at rt for 20 h, followed by extraction with sat. aq. $Na_2CO_3$ soln. The organic phase was dried ($Na_2SO_4$), filtered and concentrated. FC ($CH_2Cl_2$/MeOH 100:0 to 95:5) afforded Ex. 2 (187 mg, 77%).

Data of Ex. 2: $C_{30}H_{36}FN_3O_7$ (569.6) LC-MS (method 7): $R_t$=1.35 (62), 570 ([M+H]$^+$); 1.39 (15), 570 ([M+H]$^+$).

$^1$H-NMR (DMSO-$d_6$): complex spectrum, several isomers; 7.46-7.30 (m, 5 H), 7.27-7.06 (m, 2 H), 6.98-6.67 (4 dd, 1 H), 5.54-5.06 (m, 3 H), 4.68-3.48 (m, 6 H), 3.05-1.98 (m 10 H; s at 2.82, 2.69, 2.64), 1.44-1.41 (3 s, 9 H).

Core 03: Synthesis of Ex. 3, Ex. 4, and Ex. 5 (Scheme 7)

Synthesis of Mitsunobu Product 89

Following procedure E.1.1, the reaction of phenol 54 (7.8 g, 18 mmol), alcohol 81 (16 g, 43 mmol), DEAD (40% in toluene, 37 mL, 82 mmol), and $PPh_3$ (21 g, 80 mmol) in dry benzene (250 mL) afforded after FC ($CH_2Cl_2$/EtOH 100:0 to 95:5) the protected amino acid 89 (15.9 g, contaminated with ca. 30% triphenylphosphine oxide, used in the next step without further purification).

Synthesis of Amino Acid 90

Following procedure E.2, the reaction of 89 (9.6 g, contaminated with triphenylphosphine oxide, ca. 9 mmol), 1,3-dimethylbarbituric acid (5.0 g, 32.0 mmol) and $Pd(PPh_3)_4$ (0.4 g) in EtOAc/$CH_2C17$ (55:45, 266 mL) yielded after 1.5 h and after FC ($CH_2Cl_2$/MeOH 90:10 to 50:50) amino acid 90 (4.34 g, 76%).

Data of 90: $C_{33}H_{43}FN_4O_9$ (658.7). HPLC (10% $CH_3CN$): $R_t$=3.87 (99). LC-MS (method 9a): $R_t$=1.77, 659 ([M+H]$^+$).

Synthesis of the Protected Macrolactam Ex. 3

According to procedure F.1.2, amino acid 90 (2.5 g, 3.80 mmol) in dry DMF (50 mL) was treated with FDPP (2.51 g, 6.53 mmol) in DMF (400 mL) to afford after FC (EtOAc/MeOH 100:0 to 95:5) macrolactam Ex. 3 (2.29 g, 94%).

Data of Ex. 3: $C_{33}H_{41}FN_4O_8$ (640.7). HPLC (30% $CH_3CN$): $R_t$=3.20 (96). LC-MS (method 9c): $R_t$=2.06, 641 ([M+H]$^+$). $^1$H-NMR ($CDCl_3$): 7.45-7.32 (m, 5 H), 7.06 (m, 1 H), 6.94-6.88 (m, 2 H), 5.57 (dd, J=2.8, 12.6, 1 H), 5.42 (br. m, 1 H), 5.26 (d, J=12.2, 1 H), 5.15 (d, J=12.2, 1 H), 4.90 (dd, J=2.5, 11.0, 1 H), 4.34 (d, J=17.2, 1 H), 4.35-4.11 (m, 3 H), 3.82 (br. t, J ca. 8.5, 1 H), 3.65 (d, J=17.3, 1 H), 3.29 (t, J ca. 8.8, 1 H), 3.14 (s, 3 H), 2.65 (s, 3 H), 2.51-1.98 (several m, 5 H), 1.76 (td, J=8.2, 12.7, 1 H), 1.36 (s, 9 H).

Synthesis of Acid Ex. 4

According to procedure H, ester Ex. 3 (2.0 g, 3.1 mmol) was hydrogenolyzed in MeOH (120 mL)/THF (40 mL) in the presence of catalyst (1 g) for 2 h to afford Ex. 4 (1.68 g, 97%).

Data of Ex. 4: $C_{76}H_{35}FN_4O_8$ (550.6). HPLC (5% $CH_3CN$): $R_t$=3.60 (86). LC-MS: (method 9c): $R_t$=1.53; 551 ([M+H]$^+$), 451 ([M+H-Boc]$^+$).

Synthesis of Amine Ex. 5:

According to procedure J, ester Ex. 3 (100 mg, 0.16 mmol) in dioxane (3 mL) was treated with 4M HCl-dioxane (3 mL) to afford Ex. 5.HCl (100 mg, quant.).

Data of Ex. 5.HCl: $C_{28}H_{33}FN_4O_6$.HCl (540.6, free base). LC-MS: (method 9c): $R_t$=1.44, 541 ([M+H]$^+$).

Core 04: Synthesis of Ex. 56 and Ex. 57 (Scheme 8)

Synthesis of Mitsunobu Product 91

Following procedure E.1.1 the reaction of phenol 54 (8.0 g, 19 mmol), alcohol 82 (16.0 g, 43 mmol), DEAD (40% in toluene, 38 mL, 84 mmol), and $PPh_3$ (22 g, 84 mmol) in dry benzene (260 mL) afforded after FC the protected amino acid 91 (33.5 g, contaminated with triphenylphosphine oxide) which was used in the next step without further purification).

Synthesis of Amino Acid 92

Following procedure E.2, the reaction of 91 (33.5 g, contaminated with triphenylphosphine oxide), 1,3-dimethylbarbituric acid (16 g, 102 mmol) and $Pd(PPh_3)_4$ (0.2 g) in EtOAc/$CH_2Cl_2$ (45:55, 340 mL) yielded after 3 h and after FC ($CH_2Cl_2$/EtOH 100:0 to 70:30 then $CH_2Cl_2$/MeOH 90:10 to 70:30) amino acid 92 (4.8 g, 39% over two steps based on phenol 54).

Data of 92: $C_{33}H_{43}FN_4O_9$ (658.7). HPLC (10% $CH_3CN$): $R_t$=3.80 (95). LC-MS (method 9c): $R_t$=1.81, 659 ([M+H]$^+$).

Synthesis of the Protected Macrolactam Ex. 56

According to procedure F.1.1, amino acid 92 (3.8 g, 5.80 mmol) in dry $CH_2Cl_2$ (40 mL) was treated with T3P (50% in EtOAc, 6.8 mL, 12 mmol) and i-$Pr_2$NEt (4.0 mL, 23 mmol) in dry $CH_2Cl_2$ (510 mL) to afford after FC (EtOAc/MeOH 100:0 to 95:5) macrolactam Ex. 56 (3.23 g, 87%).

Data of Ex. 56: $C_{33}H_{41}FN_4O_8$ (640.7). HPLC (30% $CH_3CN$): $R_t$=3.49 (88). LC-MS (method 9c): $R_t$=2.02, 641 ([M+H]$^+$). $^1$H-NMR ($CDCl_3$): 7.41-7.32 (m, 5 H), 7.04 (m, 1 H), 6.94-6.83 (m, 2 H), 5.54 (dd, J=3.0, 12.7, 1 H), 5.25 (d, J=12.2, 1 H), 5.14 (d, J=12.2, 1 H), 4.89 (dd, J=2.1, 11.0, 1 H), 4.63 (br. m, 1 H), 4.39-4.10 (m, 4 H), 3.79-3.64 (m, 2 H), 3.49 (br. m, 1 H), 3.12 (s, 3 H), 2.64 (s, 3 H), 2.51-2.36 (m, 2 H), 2.23-1.98 (m, 4 H), 1.44 (s, 9 H).

Synthesis of Acid Ex. 57

According to procedure H, ester Ex. 56 (2.25 g, 3.5 mmol) was hydrogenolyzed in MeOH (120 mL)/THF (40 mL) in the presence of catalyst (1.1 g) for 2 h to afford, after washing of the filtration residue with warm (50° C.) MeOH/THF 3:1, acid Ex. 57 (1.9 g, 98%).

Data of Ex. 57: $C_{26}H_{35}FN_4O_8$ (550.6). HPLC LC-MS: (method 2): $R_t$=1.54 (82), 551 ([M+H]$^+$).

Core 05: Synthesis of Ex. 85 and Ex. 86 (Scheme 9)

Synthesis of Mitsunobu Product 93

Following procedure E.1.1, the reaction of phenol 56 (6.6 g, 15 mmol), alcohol 81 (13 g, 35 mmol), DEAD (40% in toluene, 32 mL, 69 mmol), and $PPh_3$ (18 g, 69 mmol) in dry benzene (220 mL) afforded after FC ($CH_2Cl_2$/MeOH 100:0 to 94:6) the protected amino acid 93 (34.5 g, crude product used in the next step without further purification).

Synthesis of Amino Acid 94

Following procedure E.2, the reaction of 93 (34.5 g, crude material), 1,3-dimethylbarbituric acid (17 g, 106 mmol) and $Pd(PPh_3)_4$ (0.1 g) in EtOAc/$CH_2Cl_2$ (55:45, 350 mL) yielded after 3 h and after FC ($CH_2Cl_2$/EtOH 100:0 to 70:30 then $CH_2Cl_2$/MeOH 90:10 to 70:30) amino acid 94 (5.6 g, 55% over two steps based on phenol 56).

Data of 94: $C_{33}H_{43}FN_4O_9$ (658.7). HPLC (10% $CH_3CN$): $R_t$=3.79 (96).

LC-MS (method 9c): $R_t$=1.77, 659 ([M+H]$^+$).

Synthesis of the Protected Macrolactam Ex. 85

According to procedure F.1.1, amino acid 94 (2.75 g, 4.2 mmol) in dry $CH_2Cl_2$ (35 mL) was treated with T3P (50% in EtOAc, 4.9 mL, 8.3 mmol) and i-$Pr_2$NEt (2.9 mL, 17 mmol) in dry $CH_2Cl_2$ (355 mL) to yield after FC (EtOAc/MeOH 100:0 to 95:5) macrolactam Ex. 85 (2.47 g, 92%).

Data of Ex. 85: $C_{33}H_{41}FN_4O_8$ (640.7). HPLC (30% $CH_3CN$): $R_t$=3.52 (96). LC-MS (method 9c): $R_t$=2.06; 641 ([M+H]$^+$), 541 ([M+H-Boc]$^+$). $^1$H-NMR ($CDCl_3$): two isomers, ratio 85:15, 7.42-7.31 (m, 5 H), 7.08-6.77 (m, 3 H), 5.33 (d, J=8.3, 1 H), 5.23 (d, J=12.2, 1 H), 5.17 (d, J=12.1, 1 H), 4.84 (dd, J=2.9, 8.9, 1 H), 4.37-4.25 (m, 3 H), 4.11 (dd, J=4.2, 12.0, 1 H), 3.89 (t, J=8.3, 1 H), 3.80 (d, J=8.9, 1 H), 3.61 (d, J=17.1, 1 H), 3.16 (t, J=9.1, 1 H), 3.13 (s, 2.55 H, $NCH_3$ of major isomer), 3.03 (s, 0.45H, $NCH_3$ of minor isomer), 2.98 (s, 2.55 H, $NCH_3$ of major isomer), 2.87 (0.45 H, $NCH_3$ of minor isomer), 2.64-2.41 (m, 2 H), 2.27-2.09 (m, 1 H), 1.98-1.83 (m, 2 H), 1.79-1.66 (m, 2 H), 1.45 (s, 7.65 H, Boc, major isomer), 1.35 (s, 1.35H, Boc, minor isomer).

Synthesis of Acid Ex. 86

According to procedure H, ester Ex. 85 (2.0 g, 3.1 mmol) was hydrogenolyzed in MeOH (120 mL)/THF (40 mL) in the presence of the catalyst (1 g) for 2 h to afford, after washing of the filtration residue with warm (50° C.) MeOH/TFH 3:1, acid Ex. 86 (1.67 g, 97%).

Data of Ex. 86: $C_{26}H_{35}FN_4O_8$ (550.6). LC-MS: (method 3): $R_t$=1.10 (83), 551 ([M+H]$^+$); 1.17 (15), 551 ([M+H]$^+$).

Core 06: Synthesis of Ex. 104 and Ex. 105 (Scheme 10)

Synthesis of Mitsunobu Product 95

Following procedure E.1.2, the reaction of phenol 56 (13.1 g, 30.5 mmol), alcohol 82 (13.6 g, 36.6 mmol), and CMBP (14.7 g, mmol) in dry toluene (500 mL) afforded after FC (hexane/EtOAc 50:50 to 30:70) the protected amino acid 95 (16 g, 67%).

Synthesis of Amino Acid 96

Following procedure E.2, the reaction of 95 (16.0 g, 20 mmol), 1,3-dimethylbarbituric acid (8 g, 49 mmol) and $Pd(PPh_3)_4$ (0.1 g) in EtOAc/$CH_2Cl_2$ (55:45, 220 mL) yielded after 3 h and after FC ($CH_2Cl_2$/EtOH 100:0 to 70:30 then $CH_2Cl_2$/MeOH 90:10 to 70:30) amino acid 96 (11 g, 81%).

Data of 96: $C_{33}H_{43}FN_4O_9$ (658.7). LC-MS (method 2): $R_t$=1.63 (97), 659 ([M+H]$^+$).

Synthesis of the Protected Macrolactam Ex. 104

According to procedure F.1.1, amino acid 96 (4.0 g, 6.1 mmol) in dry $CH_2Cl_2$ (40 mL) was treated with T3P (50% in EtOAc, 7.2 mL, 12.1 mmol) and i-$Pr_2$NEt (4.2 mL, 24.3 mmol) in dry $CH_2Cl_2$ (1160 mL) to give after FC ($CH_2Cl_2$/MeOH 100:0 to 95:5) macrolactam Ex. 104 (2.32 g, 60%).

Data of Ex. 104: $C_{33}H_{41}FN_4O_8$ (640.7). LC-MS (method 7): $R_t$=1.21 (47), 641 ([M+H]$^+$); 1.24 (53), 641 ([M+H]). $^1$H-NMR (DMSO-$d_6$): complex spectrum, mixture of isomers, 7.44-6.65 (m, 9 H), 5.32-5.05 (m, 2 H), 4.70-3.30 (several m, 9 H), 2.92 (s, $NCH_3$ of major isomer), 2.84 (s, $NCH_3$ of major isomer), 2.30-1.70 (several m, 6 H), 1.40, 1.38 (2 s, 9 H).

Synthesis of Acid Ex. 105

According to procedure H, ester Ex. 104 (2.15 g, 3.3 mmol) was hydrogenolyzed in MeOH (215 mL) in the presence of catalyst (1.07 g) for 4 h to afford acid Ex. 105 (1.72 g, 93%).

Data of Ex. 105: $C_{26}H_{35}FN_4O_8$ (550.6). LC-MS: (method 7): $R_t$=0.91 (45), 551 ([M+H]$^+$); 0.95 (38), 551 ([M+H]$^+$).

Core 07: Synthesis of Ex. 115 and Ex. 116 (Scheme 11)

Synthesis of Mitsunobu Product 97

A mixture of the phenol 54 (6.42 g, 14.9 mmol), alcohol 22 (4.04 g, 13.5 mmol), and $PPh_3$ (9.73 g, 37.1 mmol) was dried i.v. for 15 min. and dissolved in dry, degassed chloroform (130 mL). The soln was cooled to 0° C. A soln of ADDP (9.36 g, 37.1 mmol) in chloroform (20 mL) was slowly added. The mixture was stirred at rt for 3 h followed by the addition of more 22 (4.04 g, 13.5 mmol) and $PPh_3$ (5.97 g, 22.8 mmol) in chloroform (20 mL). Again, the mixture was cooled to 0° C.; and a soln of ADDP (5.74 g, 22.7 mmol) in chloroform (20 mL) was slowly added. The soln was stirred at rt for 16 h and concentrated. The residue was suspended in $Et_2O$ and filtered. The solid was washed with $Et_2O$. The combined filtrate and washings were concentrated. FC ($CH_2Cl_2$/EtOAc 10:1) gave 97 (7.73 g, 73%).

Synthesis of Amino Acid 98

Following procedure B.2, the reaction of 97 (7.72 g, 11 mmol), 1,3-dimethylbarbituric acid (4.1 g, 26.0 mmol) and $Pd(PPh_3)_4$ (0.63 g) in EtOAc/$CH_2Cl_2$ (53:47, 190 mL) yielded after 2 h and after FC (EtOAc, then $CH_2Cl_2$/MeOH 95:5 to 90:10) amino acid 98 (4.31 g, 67%).

Data of 98: $C_{30}H_{38}FN_3O_8$ (587.6). HPLC (10% $CH_3CN$): $R_t$=3.86 (84). LC-MS (method 9a): $R_t$=1.76; 588 ([M+H]$^+$), 488 ([M+H-Boc]$^+$).

Synthesis of the Alloc Protected Amino Acid 99

Following procedure C.1, the reaction of amino acid 98 (4.3 g, 7.3 mmol), allyl chloroformate (0.86 mL, 8.0 mmol) and $Na_2CO_3$ (1.2 g, 11 mmol) in dioxane (62 mL) and $H_2O$ (60 mL) gave acid 99 (5.07 g, 100%).

Synthesis of the Protected Diamide 100

Following procedure C.2, acid 99 (4.9 g, 7.3 mmol) was reacted with sarcosine allylester p-toluenesulfonate (46.p-TsOH, 2.6 g, 8.8 mmol), HOAt (1.5 g, 11 mmol), HATU (4.2 g, 11 mmol) and i-$Pr_2$NEt (6.2 mL, 36 mmol) in DMF (75 mL) to afford the protected amino acid 100 (4.37 g, 76%).

Data of 100: $C_{40}H_{51}FN_4O_{11}$ (782.8). HPLC (50% $CH_3CN$): $R_t$=3.56 (99). LC-MS (method 9a): $R_t$=2.45; 783 ([M+H]$^+$), 683 ([M+H-Boc]$^+$).

Synthesis of the Deprotected Amino Acid 101

Following procedure C.3, the reaction of the protected amino acid 100 (4.36 g, 5.6 mmol), 1,3-dimethylbarbituric acid (2.1 g, 13 mmol) and $Pd(PPh_3)_4$ (0.32 g) in EtOAc/$CH_2Cl_2$ (45:55, 106 mL) yielded amino acid 101 (3.46 g, 93%).

Data of 101: $C_{33}H_{43}FN_4O_9$ (658.7). LC-MS (method 9b): $R_t$=1.74; 659 ([M+H]$^+$), 559 ([M+H-Boc]$^+$).

Synthesis of the Protected Macrolactam Ex. 115

According to procedure F.1.1, amino acid 101 (3.44 g, 5.2 mmol) in dry $CH_2Cl_2$ (50 mL) was treated with T3P (50% in EtOAc, 6.2 mL, 10 mmol) and i-$Pr_2$NEt (3.6 mL, 21 mmol) in dry $CH_2Cl_2$ (470 mL) to give after FC ($CH_2Cl_2$/MeOH 95:5) macrolactam Ex. 115 (2.95 g, 90%).

Data of Ex. 115: $C_{33}H_{41}FN_4O_8$ (640.7). HPLC (20% $CH_3CN$): $R_t$=4.05 (93). LC-MS (method 9c): $R_t$=2.08; 641 ([M+H]$^+$). $^1$H-NMR (DMSO-$d_6$): complex spectrum, mixture of isomers, 7.38 (s, 5 H), 7.35-6.95 (several m, 2 H), 6.81-6.72 (several m, 0.4 H), 6.64 (dd, J=3.1, 8.2, 0.25 H), 6.39 (dd, J=3.2, 7.7, 0.25 H), 6.30 (dd, J=3.3, 8.2, 0.1 H), 5.37-4.99 (m, 3 H), 4.60-3.60 (several m, 9 H), 3.20-2.60 (several m and s, 8 H), 2.40-1.70 (several m, 4 H), 1.45, 1.43, 1.42, 1.38 (4 s, Boc).

Synthesis of Acid Ex. 116

According to procedure H, ester Ex. 115 (1.2 g, 1.9 mmol) was hydrogenolyzed in MeOH (120 mL) in the presence of catalyst (0.6 g) for 2 h to afford acid Ex. 116 (1.02 g, 99%).

Data of Ex. 116: $C_{26}H_{35}FN_4O_8$ (550.6). HPLC (10% $CH_3CN$): $R_t$=3.47 (20), 3.55 (75). LC-MS: (method 9c): $R_t$=1.53, 1.58; 551 ([M+H]$^+$).

Core 08: Synthesis of Ex. 132 and Ex. 133 (Scheme 12)

Synthesis of Mitsunobu Product 102

Following procedure E.1.2, the reaction of phenol 56 (2.0 g, 4.7 mmol), alcohol 84 (2.08 g, 5.6 mmol), and CMBP (2.25 g, 9.3 mmol) in dry toluene (80 mL) afforded after 3 h and after FC (hexane/EtOAc 1:1 to 1:2) the protected amino acid 102 (2.06 g, 56%).

Synthesis of Amino Acid 103

Following procedure E.2, the reaction of 102 (2.05 g, 2.6 mmol), 1,3-dimethylbarbituric acid (1.0 g, 6.3 mmol) and $Pd(PPh_3)_4$ (0.15 g) in EtOAc/$CH_2Cl_2$ (55:45; 45 mL) yielded after 2 h and after FC (EtOAc, then $CH_2Cl_2$/MeOH 95:5 to 70:30) amino acid 103 (1.45 g, 85%).

Data of 103: $C_{33}H_{43}FN_4O_9$ (658.7). HPLC (5% $CH_3CN$): $R_t$=4.04 (97). LC-MS (method 9c): $R_t$=1.87, 659 ([M+H]$^+$).

Synthesis of the Protected Macrolactam Ex. 132

According to procedure F.1.1, the amino acid 103 (1.44 g, 2.19 mmol) in dry $CH_2Cl_2$ (40 mL) was treated with T3P (50% in EtOAc, 2.6 mL, 4.37 mmol) and i-$Pr_2$NEt (1.5 mL, 8.74 mmol) in dry $CH_2Cl_2$ (170 mL) to give after FC ($CH_2Cl_2$/MeOH 95:5) macrolactam Ex. 132 (1.36 g, 96%).

Data of Ex. 132: $C_{33}H_{41}FN_4O_8$ (640.7). LC-MS (method 2): $R_t$=1.93 (100), 641 ([M+H]$^+$); LC-MS (method 9c): $R_t$=2.12, 641 ([M+H]$^+$).

$^1$H-NMR (DMSO-$d_6$): complex spectrum, mixture of isomers, 7.38 (s, 5 H), 7.35-6.99 (several m, 2 H), 6.85-6.73 (several m, 0.4H), 6.65 (dd, J=3.1, 8.2, 0.25 H), 6.39 (dd, J=3.1, 7.9, 0.25 H), 6.30 (dd, J=3.3, 8.1, 0.1 H), 5.37-4.99 (m, 3 H), 4.6-3.6 (several m, 9 H), 3.2-2.6 (several m and s, 8 H), 2.4-1.7 (several m, 4 H), 1.45, 1.43, 1.41, 1.38 (4 s, Boc).

Synthesis of Acid Ex. 133

According to procedure H, ester Ex. 132 (1.13 g, 1.7 mmol) was hydrogenolyzed in MeOH (110 mL) in the presence of catalyst (0.56 g) for 4 h to afford acid Ex. 133 (0.92 g, 94%).

Data of Ex. 133: $C_{26}H_{35}FN_4O_8$ (550.6). HPLC (5% $CH_3CN$): $R_t$=3.65 (27), 3.72 (71). LC-MS: (method 9c): $R_t$=1.53, 551 ([M+H]$^+$); 1.57, 551 ([M+H]$^+$).

Core 09: Synthesis of Ex. 142 and Ex. 143 (Scheme 13)

Synthesis of Mitsunobu Product 104

Following procedure E.1.2, the reaction of phenol 54 (3.1 g, 7.2 mmol), alcohol 86 (3.34 g, 8.7 mmol), and CMBP (3.49 g, 14.4 mmol) in dry toluene (123 mL) afforded after 3 h and after FC (hexane/EtOAc 1:1 to 1:2) the protected amino acid 104 (4.11 g, 71%).

Synthesis of Amino Acid 105

Following procedure E.2, the reaction of 104 (4.07 g, 5.1 mmol), 1,3-dimethylbarbituric acid (1.9 g, 12 mmol) and $Pd(PPh_3)_4$ (0.3 g) in EtOAc/$CH_2Cl_2$ (45:55, 90 mL) yielded after 2 h and after FC (EtOAc, then $CH_2Cl_2$/MeOH 95:5 to 70:30) amino acid 105 (3.19 g, 93%).

Data of 105: $C_{34}H_{45}FN_4O_9$ (672.7). HPLC (5% $CH_3CN$): $R_t$=3.96 (88). LC-MS (method 9c): $R_t$=1.83, 673 ([M+H]$^+$).

Synthesis of the Protected Macrolactam Ex. 142

According to procedure F.1.1, amino acid 105 (2.4 g, 3.6 mmol) in dry $CH_2Cl_2$ (40 mL) was treated with T3P (50% in EtOAc, 4.2 mL, 7.1 mmol) and i-$Pr_2$NEt (2.4 mL, 14.2 mmol) in dry $CH_2Cl_2$ (300 mL) to give after FC ($CH_2Cl_2$/MeOH 95:5) macrolactam Ex. 142 (1.92 g, 82%).

Data of Ex. 142: $C_{34}H_{43}FN_4O_8$ (654.7). HPLC (30% $CH_3CN$): $R_t$=3.50 (89). LC-MS (method 9b): $R_t$=2.01; 655 ([M+H]$^+$), 599 ([M+H-tBu]$^+$), 555 ([M+H-Boc]$^+$). $^1$H-NMR (DMSO-$d_6$): complex spectrum, mixture of isomers, 7.41-7.38 (m, 5 H), 7.37-7.14 (m, 3 H), 6.80-6.67 (m, 1 H), 5.45-5.13 (m, 3 H), 4.60-3.30 (several m, 8 H), 3.10-2.50 (several m and s, 8 H), 2.50-1.80 (several m, 6 H), 1.39, 1.38, 1.36 (3 s, Boc).

Synthesis of Acid Ex. 143

According to procedure H, ester Ex. 142 (1.07 g, 1.6 mmol) was hydrogenolyzed in NeOH (100 mL) in the presence of catalyst (0.53 g) for 4 h to afford acid Ex. 143 (0.92 g, 99%).

Data of Ex. 143: $C_{27}H_{37}FN_4O_8$ (564.6). LC-MS: (method 2): $R_t$=1.54 (91), 565 ($[M+H]^+$).

Core 10: Synthesis of Ex. 164 and Ex. 165 (Scheme 14)

Synthesis of Mitsunobu Product 106

Following procedure B.1.2, the reaction of phenol 63 (4.2 g, 9.8 mmol), alcohol 16 (4.4 g, 13 mmol), and CMBP (4.8 g, 20 mmol) in dry toluene (120 mL) afforded after 4 h and FC (hexane/EtOAc 50:50) the protected amino acid 106 (6.37 g, 86%).

Synthesis of Amino Acid 107

Following procedure B.2, the reaction of 106 (1.18 g, 1.6 mmol), 1,3-dimethylbarbituric acid (0.6 g, 3.8 mmol) and $Pd(PPh_3)_4$ (90 mg) in $EtOAc/CH_2Cl_2$ (60:40, 15 mL) yielded after 3 h and after FC ($CH_2Cl_2$/EtOH 100:0 to 80:20) the amino acid 107 (0.86 g, 87%).

Data of 107: $C_{31}H_{44}N_4O_8Si$ (628.8). LC-MS: (method 6): $R_t$=1.08 (88), 629 ($[M+H]^+$).

Synthesis of the Protected Macrolactam Ex. 164

According to procedure F.1.2, amino acid 107 (310 mg, 0.49 mmol) in dry DMF (5 mL) was treated with FDPP (379 mg, 0.99 mmol) in dry DMF (500 mL) to afford after FC (hexane/EtOAc/MeOH 50:50:0 to 0:95:5) macrolactam Ex. 164 (131 mg, 43%).

Data of Ex. 164: $C_{31}H_{42}N_4O_7Si$ (610.8). LC-MS: (method 7): $R_t$=1.34 (98), 611 ($[M+H]^+$). $^1$H-NMR (DMSO-$d_6$): 7.42-7.27 (m, 8 H), 6.98 (dd, J=1.4, 8.2, 1 H), 6.91 (d, J=7.5, 1 H), 6.84 (s, 1 H), 4.98 (s, 2 H), 4.50 (d, J=11.9, 1 H), 4.35-4.15 (m, 3 H), 4.0.6-3.96 (m, 4 H), 3.21 (m, 1 H), 3.10-2.95 (m, 2 H), 2.87 (s, 3 H), 2.30-1.80 (m, 4 H), 0.91 (t, J=8.3, 2 H), 0.00 (s, 9 H).

Synthesis of Amine Ex. 165

At 0° C. a soln of TBAF in THF (1 M, 3.9 mL, 3.9 mmol) was added to a soln of Ex. 164 (1.2 g, 1.96 mmol) in THF (42 mL). The soln was stirred at 0° C. to rt for 15 h, followed by the addition of TBAF in THF (1 M, 1.18 mL, 1.18 mmol). Stirring was continued for 2 h. The soln was distributed between $CH_2Cl_2$ and $H_2O$. The aqueous phase was repeatedly extracted with CH2C19. The combined organic phase was dried ($Na_2SO_4$), filtered and concentrated. FC ($CH_2Cl_2$/MeOH 100:0 to 90:10) afforded Ex. 165 (0.76 g, 83%).

Data of Ex. 165: $C_{25}H_{30}N_4O_5$ (466.52). LC-MS: (method 4a): $R_t$=1.49 (99), 467 ($[M+H]^+$).

Core 11a: Synthesis of Ex. 181 and Ex. 182 (Scheme 15)

Synthesis of Mitsunobu Product 108

Following procedure B.1.2, the reaction of phenol 65 (10.7 g, 24 mmol), alcohol 16 (10.0 g, 29 mmol), and CMBP (12.0 g, 49 mmol) in dry toluene (362 mL) afforded after FC (hexane/EtOAc 50:50 to 70:30) the protected amino acid 108 (14.55 g, 78%).

Synthesis of Amino Acid 109

Following procedure B.2, the reaction of 108 (14.50 g, 19 mmol), 1,3-dimethylbarbituric acid (7.0 g, 47.0 mmol) and $Pd(PPh_3)_4$ (0.1 g) in $EtOAc/CH_2Cl_2$ (55:45, 203 mL) yielded after 3 h and after FC ($CH_2Cl_2$/MeOH 99:1 to 90:10) amino acid 109 (11.26 g, 92%).

Data of 109: $C_{32}H_{46}N_4O_8Si$ (642.8). LC-MS: (method 6): $R_t$=1.13 (94), 643 ($[M+H]^+$).

Synthesis of the Protected Macrolactam Ex. 181

According to procedure F.1.1, amino acid 109 (4.0 g, 6.2 mmol) in dry $CH_2Cl_2$ (100 mL) was treated with T3P (50% in EtOAc, 7.4 mL, 12.4 mmol) and i-$Pr_2$NEt (4.3 mL, 24.8 mmol) in dry $CH_2Cl_2$ (560 mL). Prior to aqueous workup, the $CH_2Cl_2$ was replaced by EtOAc. FC (hexane/EtOAc 50:50 to 0:100) afforded the macrolactam Ex. 181 (2.11 g, 54%).

Data of Ex. 181: $C_{32}H_{44}N_4O_7Si$ (624.8). LC-MS (method 7): $R_t$=1.37 (99), 625 ($[M+H]^+$). $^1$H-NMR (DMSO-$d_6$): 7.46 (d, J=8.0, 1 H), 7.42 (d, J=7.2, 1 H), 7.34-7.23 (m, 6 H), 7.06 (d, J=8.2, 1H), 6.82 (d, J=7.4, 1 H), 6.78 (s, 1 H), 5.02-4.86 (m, 3 H), 4.13 (t, J=8.5, 1 H), 4.06-3.67 (m, 7 H), 3.05 (br. m, 1 H), 2.88 (br. m, 1 H), 2.88 (s, 3 H), 2.15 (m, 2 H), 1.51 (br. m, 2 H), 1.33 (br. m, 1 H), 1.12 (br. m, 1 H), 0.91 (t-like m, J ca. 8.4, 2 H), 0.00 (s, 9 H).

Synthesis of Amine Ex. 182

According to procedure I.2, carbamate Ex. 181 (844 mg, 1.3 mmol) in THF (34 mL) was treated with TBAF soln (4.1 mL) to afford after FC ($CH_2Cl_2$/MeOH 90:10) amine Ex. 182 (620 mg, 95%)

Data of Ex. 182: $C_{26}H_{32}N_4O_5$ (480.5). LC-MS: (method 2): $R_t$=1.35 (99), 481 ($[M+H]^+$).

Core 11b: Synthesis of Ex. 560 and Ex. 561 (Scheme 15)

Synthesis of Mitsunobu Product 214

Following procedure B.1.2, the reaction of phenol 65 (2.60 g, 5.9 mmol), alcohol 156 (1.96 g, 7.08 mmol) and CMBP (2.85 g, 11.8 mmol) in toluene (84 mL) afforded after 3 h and after FC (hexane/EtOAc gradient) 214 (3.85 g, 93%).

Synthesis of Amino Acid 215

Following procedure B.2, the reaction of 214 (3.8 g, 5.4 mmol), 1,3-dimethylbarbituric acid (2.12 g, 13.6 mmol) and $Pd(PPh_3)_4$ (31 mg) in $EtOAc/CH_2Cl_2$ (1:1, 50 mL) afforded after 20 h at rt, evaporation of the volatiles and repeated washing (EtOAc) the solid 215 (3.04 g, 97%).

Data of 215: $C_{32}H_{37}N_3O_7$ (575.6). LC-MS: (method 4a): $R_t$=1.81 (84), 576 ($[M+H]^+$).

Synthesis of Macrolactam Ex. 560

FDPP (1.73 g, 4.5 mmol) was added to a suspension of amino acid 215 (1.51 g, 2.62 mmol) in dry DMF (460 mL). The mixture was stirred at rt for 20 h and concentrated. FC (hexane/EtOAc gradient) afforded Ex. 560 (0.92 g, 63%).

Data of Ex. 560: $C_{32}H_{35}N_3O_6$ (557.6). LC-MS: (method 4b): $R_t$=2.29 (95), 558 ($[M+H]^+$). $^1$H-NMR (DMSO-$d_6$): 7.48 (d, J=7.8, 1 H), 7.37-7.26 (m, 8 H), 7.06-6.94 (m, 4 H), 6.85-6.76 (m, 2 H), 5.01 (s, 2 H), 4.94-4.82 (m, 2 H), 4.39 (t-like m, 1 H), 4.14-4.04 (m, 2 H), 3.95 (q-like m, 1 H), 3.10 (m, 1 H), 3.00-2.82 (m, 2 H), 2.91 (s, 3 H), 2.58 (m, 1 H), 2.19 (td, J=6.4, 13.3, 1 H), 1.65-1.50 (m, 2 H), 1.38 (m, 1 H), 1.17 (m, 1 H).

Synthesis of Amine Ex. 561

A soln of the benzyl carbamate Ex. 560 (0.87 g, 1.55 mmol) in MeOH (25 mL) was hydrogenolyzed in the presence of 10% palladium on activated charcoal (185 mg) at rt and normal pressure for 4 h. The mixture was filtered through a pad of celite. The filtrate was concentrated. FC ($CH_2Cl_2$/MeOH 80:20) afforded Ex. 561 (0.65 g, 99%).

Data of Ex. 561: $C_{24}H_{29}N_3O_4$ (423.5). LC-MS: (method 4a): $R_t$=1.56 (98), 424 ($[M+H]^+$).

Core 11c: Synthesis of Ex. 567 and Ex. 568 (Scheme 15)

Synthesis of Mitsunobu Product 216

Following procedure B.1.2, the reaction of phenol 65 (3.0 g, 6.8 mmol), alcohol 161 (3.0 g, 8.2 mmol) and CMBP (3.8 g, 16 mmol) in toluene (76 mL) afforded after 1.5 h and after FC (hexane/EtOAc/MeOH gradient) 216 (3.88 g, 71%).

Synthesis of Amino Acid 217

Following procedure B.2, the reaction of 216 (25.4 g, 32 mmol), 1,3-dimethylbarbituric acid (13 g, 80 mmol) and $Pd(PPh_3)_4$ (1.9 g) in $EtOAc/CH_2Cl_2$ (50:50, 410 mL) afforded after 20 h at rt, filtration and washing ($CH_2Cl_2$) the solid 217 (18.05 g, 84%).

Data of 217: $C_{33}H_{38}BrN_3O_7$ (668.6). LC-MS: (method 10a): $R_t$=1.75 (88), 668/670 ([M+H]$^+$).

Synthesis of Macrolactam Ex. 567

According to procedure F.1.1, a mixture of 217 (1.95 g, 2.9 mmol) and i-$Pr_2$NEt (2 mL, 12 mmol) in $CH_2Cl_2$ (85 mL) was treated with T3P (50% in EtOAc, 4.3 mL, 7.3 mmol) in $CH_2Cl_2$ (440 mL). After stirring at rt for 20 h, evaporation of the volatiles, aqueous workup ($CH_2Cl_2$, sat. aq. $NaHCO_3$ soln; $Na_2SO_4$) and FC (hexane/EtOAc 25:75) Ex. 567 (1.1 g, 57%) was obtained.

Data of Ex. 567: $C_{33}H_{36}BrN_3O_6$ (650.5). LC-MS: (method 10b): $R_t$=2.33 (96), 652/650 ([M+H]$^+$). $^1$H-NMR (DMSO-$d_6$): 7.56 (d, J=8.4, 2 H), 7.42 (d, J=7.8, 1 H), 7.34-7.27 (m, 8 H), 6.90 (dd, J=1.9, 10.1, 1 H), 6.84 (d, J=7.5, 1 H), 6.78 (s, 1 H), 5.00 (s, 2 H), 4.81 (d, J=12.7, 1 H), 4.48 (d, J=12.2, 1 H), 4.43 (d, J=12.2, 1 H), 4.27 (t-like m, 1 H), 4.07-3.89 (m, 4 H), 3.07 (m, 1 H), 2.93 (m, 1 H), 2.93 (s, 3 H), 2.70 (dd, J=7.3, 10.3, 1 H), 2.30 (m, 1 H), 2.10 (m, 1 H), 1.65-1.50 (m, 2 H), 1.36 (m, 1 H), 1.17 (m, 1 H).

Synthesis of Amine Ex. 568

A soln of Ex. 567 (1.5 g, 2.3 mmol) in MeOH (31 mL) was treated with $NH_3$ (7 M in MeOH; 1 mL, 7 mmol) and hydrogenolyzed at rt and normal pressure in the presence of 5% palladium on activated charcoal (moistened with 50% $H_2O$; 400 mg) for 15 h. The mixture was filtered through a pad of celite. The filtrate was concentrated, dissolved in $CH_2Cl_2$, washed (sat. aq. $NaHCO_3$ soln), filtered and concentrated to afford Ex. 568 (0.98 g, 97%).

Data of Ex. 568: $C_{26}H_{31}N_3O_4$ (437.5). LC-MS: (method 10a): $R_t$=1.41 (96), 438 ([M+H]$^+$).

Core 11d: Synthesis of Ex. 586 and Ex. 587 (Scheme 15)

Synthesis of Mitsunobu Product 218

Following procedure B.1.2, the reaction of the phenol 65 (0.94 g, 2.1 mmol), alcohol 165 (0.705 g, 2.5 mmol) and CMBP (1.03 g, 4.27 mmol) in toluene (22 mL) afforded after 1.5 h and after FC (hexane/EtOAc 1:1) 218 (1.2 g, 80%).

Synthesis of Amino Acid 219

Following procedure B.2, the reaction of 218 (1.19 g, 1.17 mmol), 1,3-dimethylbarbituric acid (0.64 g, 4.1 mmol) and $Pd(PPh_3)_4$ (0.1 g) in EtOAc/$CH_2Cl_2$ (55:45, 29 mL) afforded after 2 h and after FC (EtOAc, then $CH_2Cl_2$/MeOH 100:0 to 80:20) 219 (0.88 g, 89%).

Data of 219: $C_{33}H_{39}N_3O_6$ (573.7). LC-MS: (method 10a): $R_t$=1.67 (87), 574 ([M+H]$^+$).

Synthesis of Macrolactam Ex. 586

According to procedure F.1.1, a mixture of 219 (0.87 g, 1.5 mmol) in $CH_2Cl_2$ (30 mL) was treated with T3P (50% in EtOAc, 2.7 mL, 4.5 mmol) and i-$Pr_2$NEt (1.0 mL, 6 mmol) in $CH_2Cl_2$ (300 mL). After stirring at rt for 0.5 h, aqueous workup ($CH_2Cl_2$, sat. aq. $Na_2CO_3$ soln; $Na_2SO_4$) and FC (hexane/EtOAc 25:75), Ex. 586 (0.313 g, 37%) was obtained.

Data of Ex. 586: $C_{33}H_{37}N_3O_5$ (555.6). LC-MS: (method 10b): $R_t$=2.22 (96), 556 ([M+H]$^+$). $^1$H-NMR (DMSO-$d_6$): 7.43 (d, J=8.1, 1 H), 7.39-7.18 (m, 11 H), 6.86-6.79 (m, 3 H), 4.95-4.85 (m, 3 H), 4.14 (br. t, J=8.4, 1 H), 3.91 (d, J=11.3, 1 H), 3.76 (br. q, J=7.2, 1 H), 3.55 (t-like m, 1 H), 3.08 (m, 1 H), 2.93 (m, 1 H), 2.91 (s, 3 H), 2.67 (d, J=6.5, 2 H), 2.37 (t, J=10.4, 1 H), 2.25 (m, 1 H), 2.01-1.93 (m, 2 H), 1.65-1.50 (m, 2 H), 1.32 (m, 1 H), 1.15 (m, 1 H).

Synthesis of Amine Ex. 587

According to procedure K, the benzyl carbamate Ex. 586 (279 mg, 0.5 mmol) was hydrogenolyzed in MeOH (17 mL) in the presence of the catalyst (56 mg) for 3 h to afford Ex. 587 (203 mg, 96%).

Data of Ex. 587: $C_{25}H_{31}N_3O_3$ (421.5). LC-MS (method 10a): $R_t$=1.47 (99), 422 ([M+H]$^+$).

Core 12: Linear Synthesis of Ex. 196 and Ex. 197 (Scheme 16)

Synthesis of Mitsunobu Product 110

Following procedure B.1.1, the reaction of phenol 59 (5.22 g, 12.6 mmol), alcohol 16 (5.2 g, 15.2 mmol), $PPh_3$ (5.0 g, 19 mmol) in dry benzene (124 mL) and DEAD (40% in toluene, 7.0 mL, 15.2 mmol) in dry benzene (36 mL) afforded after FC (hexane/EtOAc 60:40 to 40:60) the protected amino acid 110 (8.3 g, 88%, contaminated with triphenylphosphine oxide, used in the next stop without further purification).

Synthesis of Amino Acid 111

Following procedure B.2, the reaction of 110 (4.15 g, 5.62 mmol), 1,3-dimethylbarbituric acid (2.19 g, 14.0 mmol) and $Pd(PPh_3)_4$ (0.71 g) in EtOAc/$CH_2Cl_2$ 1:1 (60 mL) yielded after 1 h and after FC ($CH_2Cl_2$/EtOH 95:5 to 90:10 then $CH_2Cl_2$/MeOH 90:10 to 70:30) amino acid 111 (2.75 g, 80%).

Data of 111: $C_{30}H_{42}N_4O_8Si$ (614.8). HPLC (10% $CH_3CN$): $R_t$=3.82 (99). LC-MS (method 9a): $R_t$=1.81, 615 ([M+H]$^+$).

Synthesis of the Alloc Protected Amino Acid 112

Following procedure C.1, the reaction of amino acid 111 (1.5 g, 2.4 mmol), allyl chloroformate (0.29 mL, 2.68 mmol) and $Na_2CO_3$ (0.72 g, 6.83 mmol) in dioxane (40 mL) and $H_2O$ (40 mL) gave acid 112 (1.7 g, 100%).

Synthesis of the Protected Amino Acid 113

Following procedure C.2, the acid 112 (1.7 g, 2.4 mmol) was reacted with sarcosine allylester p-toluenesulfonate (46.p-TsOH, 0.88 g, 2.9 mmol), HOAt (0.5 g, 3.6 mmol), HATU (1.4 g, 3.6 mmol) and i-$Pr_2$NEt (2.1 mL, 12 mmol) in DMF (25 mL) to afford the protected amino acid 113 (1.51 g, 75%).

Data of 113: $C_{40}H_{55}N_5O_{11}Si$ (809.9). HPLC (40% $CH_3CN$): $R_t$=4.43 (91). LC-MS (method 9c): $R_t$=2.51, 810 ([M+H]$^+$).

Deprotection to Amino Acid 114

Following procedure C.3, the reaction of the protected amino acid 113 (1.5 g, 1.85 mmol), 1,3-dimethylbarbituric acid (0.72 g, 4.6 mmol) and $Pd(Pn_3)_4$ (0.23 g) in EtOAc/$CH_2Cl_2$ (1:1, 25 mL) yielded amino acid 114 (1.05 g, 83%).

Data of 114: $C_{33}H_{47}N_5O_9Si$ (685.8). HPLC (10% $CH_3CN$): $R_t$=3.85 (95). LC-MS (method 9c): $R_t$=1.78, 686 ([M+H]$^+$).

Synthesis of the Protected Macrolactam Ex. 196

According to procedure F.1.2, amino acid 114 (1.0 g, 1.46 mmol) in dry DMF (20 mL) was treated with FDPP (1.12 g, 2.92 mmol) in dry DMF (130 mL) to yield after FC (EtOAc) the macrolactam Ex. 196 (0.61 g, 63%).

Data of Ex. 196: $C_{33}H_{45}N_5O_8Si$ (667.8). LC-MS (method 1a): $R_t$=2.66 (100), 668 ([M+H]$^+$). LC-MS (method 9c): $R_t$=2.12, 668 ([M+H]$^+$), 640. $^1$H-NMR ($CDCl_3$): 7.34-7.26 (m, 6 H), 7.17 (d, J=7.6, 1 H), 7.02 (s, 1 H), 6.91 (d, J=9.5, 1 H), 5.49 (d, J=9.5, 2 H), 5.10 (m, 1 H), 5.06 (s, 2 H), 4.39-4.13 (m, 5 H), 4.00-3.95 (m, 2 H), 3.65 (m, 1 H), 3.36 (br. s, 2 H), 3.14 (m, 2 H), 3.09 (s, 3 H), 2.74 (s, 3 H), 2.45 (m, 1 H), 2.08 (m, 1 H), 0.98 (m, 2 H), 0.00 (s, 9H). $^1$H-NMR (DMSO-$d_6$): 7.98 (d, J=9.9, 1 H), 7.52 (d, J=7.9, 1 H), 7.36-7.27 (m, 6 H), 7.18 (s, 1 H), 7.06 (dd, J=1.8, 8.1, 1 H), 6.83 (d, J=7.5, 1 H), 5.12 (d, J=12.5, 1 H), 5.04 (d, J=12.5, 1 H), 4.87 (d, J=8.8, 1 H), 4.25-3.89 (m, 8 H), 3.71-3.66 (m, 2 H), 3.20 (m, 1 H), 3.02 (m, 1 H), 2.97 (s, 3 H), 2.65 (s, 3 H), 2.20 (m, 1 H), 2.09 (m, 1 H), 0.92 (t, J=8.2, 2H), 0.00 (s, 9H).

Synthesis of Amine Ex. 197

According to procedure 1.1, carbamate Ex. 196 (120 mg, 0.18 mmol) in dioxane (3 mL) was treated with 4M HCl-dioxane (3 mL) to afford Ex. 197.HCl (59 mg, 58%).

Data of Ex. 197.HCl: $C_{27}H_{33}N_5O_6$.HCl (523.5, free base). HPLC (5% $CH_3CN$): $R_t$=3.05 (83). LC-MS (method 9c): $R_t$=1.12, 524 ([M+H]$^+$). $^1$H-NMR (DMSO-$d_6$): 8.53 (br. s, $NH_3^+$), 8.03 (d, J=9.9, 1 H), 7.41-7.31 (m, 7 H), 7.15 (m, 1 H), 6.85 (d, J=7.5, 1 H), 5.14 (d, J=12.5, 1 H), 5.04 (d, J=12.5, 1 H), 4.86 (dd, J ca. 2.2, 11.0, 1 H), 4.42-4.13 (m, 2 H), 4.05 (t, J=8.5, 1 H), 3.96 (d, J=17.8, 1 H), 3.85-3.75 (m, 2 H), 3.65 (br. m, 1 H), ca. 3.3-3.1 (m, 3 H, partially superimposed by the $H_2O$ signal), 2.97 (s, 3 H), 2.67 (s, 3 H), 2.42 (m, 1 H), 2.18 (br. q, J ca. 11.1, 1 H).

Core 12: Convergent Synthesis of Ex. 197 and Ex. 198 (Scheme 17)

Synthesis of Mitsunobu Product 115

Following procedure E.1.1, phenol 59 (4.6 g, 11 mmol) was treated for 40 h with alcohol 81 (5.0 g, 13 mmol), DEAD (40% in toluene, 6.1 mL, 13 mmol) and $PPh_3$ (4.4 g, 17 mmol) in dry benzene (150 mL). After 2 h and after 18 h, additional $PPh_3$ (1.82 g, 6.9 mmol), alcohol 81 (2.04 g, 5.5 mmol) in benzene (50 mL), and DEAD (40% in toluene, 2.55 mL, 5.6 mmol) in benzene (13 mL) were added. FC (hexane/EtOAc 50:50 to 90:10) afforded the protected amino acid 115.1 (2.5 g, 29%).

Following procedure E.1.2, the reaction of phenol 59 (2.9 g, 7.0 mmol), alcohol 81, (5.7 g, 15 mmol) and CMBP (5.1 g, 21 mmol) in dry toluene (121 mL) afforded after FC (hexane/EtOAc 20:80 to 90:10) the protected amino acid 115.2 (2.92 g, 54%).

Synthesis of Amino Acid 116

Following procedure E.2, the reaction of 115.1 (3.17 g, 4.14 mmol), 1,3-dimethylbarbituric acid (1.62 g, 10.3 mmol) and $Pd(PPh_3)_4$ (0.53 g) in EtOAc/$CH_2Cl_2$ (1:1, 46 mL) yielded after 1 h and after FC ($CH_2Cl_2$/MeOH 90:10 to 70:30) the amino acid 116.1 (1.86 g, 70%).

Data of 116.1: $C_{32}H_{43}N_5O_9$ (641.7). HPLC (5% $CH_3CN$): $R_t$=3.65 (100). LC-MS (method 9c): $R_t$=1.60, 642 ([M+H]$^+$).

Following procedure E.2, the reaction of 115.2 (2.9 g, 3.8 mmol), 1,3-dimethylbarbituric acid (1.5 g, 9.5 mmol) and $Pd(PPh_3)_4$ (0.48 g) in EtOAc/$CH_2Cl_2$ (1:1, 46 mL) yielded after 1 h and after FC ($CH_2Cl_2$/MeOH 90:10 to 70:30) the amino acid 116.2 (2.0 g, 83%).

Data of 116.2: $C_{32}H_{43}N_5O_9$ (641.7). HPLC (5% $CH_3CN$): $R_t$=3.73 (98). LC-MS (method 9c): $R_t$=1.61, 642 ([M+H]$^+$).

Synthesis of the Protected Macrolactam Ex. 198

According to procedure F.1.1, the amino acid 116.1 (1.0 g, 1.6 mmol) in dry $CH_2Cl_2$ (200 mL) was treated with T3P (50% in EtOAc, 1.8 mL, 3.1 mmol) and i-$Pr_2$NEt (1.1 mL, 6.2 mmol) in dry $CH_2Cl_2$ (1400 mL) to afford after FC (EtOAc/MeOH 95:5 to 80:20) the macrolactam Ex. 198 (containing 15% of the epimer Ex. 231; 0.38 g, 39%).

Data of Ex. 198: $C_{32}H_{41}N_5O_8$ (623.7). LC-MS: (method 2): $R_t$=1.78 (84), 624 ([M+H]$^+$); 1.82 (15). LC-MS (method 9c): $R_t$=1.87, 624 ([M+H]$^+$).

$^1$H-NMR ($CDCl_3$): 7.42-7.25 (m, 7 H), 7.07 (s, 1 H), 7.00 (d, J=8.2, 1 H), 5.59 (d, J=9.5, 1 H), 5.38 (br. d, J ca. 7.9, 1 H), 5.18 (dd, J=2.5, 12.2, 1 H), 5.13 (s, 2 H), 4.43-4.01 (m, 5 H), 3.73 (m, 1 H), 3.47 (d, J=17.7, 1 H), 3.33 (d, J=17.7, 1 H), 3.20-3.11 (m, 2 H), 3.17 (s, 3 H), 2.81 (s, 3 H), 2.50 (m, 1 H), 2.15 (m, 1 H), 1.51 (s, Boc, major isomer), 1.45 (s, Boc, minor isomer); $^1$H-NMR (DMSO-$d_6$): 7.97 (d, J=10.3, 1 H), 7.41-7.30 (m, 7 H), 7.18 (s, 1 H), 7.09 (d, J=8.2, 1 H), 6.85 (J=7.6, 1 H), 5.12 (d, J=12.5, 1 H), 5.05 (d, J=12.6, 1 H), 4.89 (J=9.6, 1 H), 4.30-3.55 (m, 6 H), 3.40 (2 H, superimposed by $H_2O$ signal), 3.25-3.00 (m, 2 H), 2.99 (s, 3 H), 2.65 (s, 3 H), 2.22 (m, 1 H), 2.05 (br. q, 1 H), 1.41, (s, 9 H).

According to procedure F.1.1, amino acid 116.2 (0.85 g, 1.3 mmol) in dry $CH_2Cl_2$ (170 mL) was treated with T3P (50% in EtOAc, 1.56 mL, 2.6 mmol) and i-$Pr_2$NEt (0.91 mL, 5.3 mmol) in dry $CH_2Cl_2$ (1190 mL) to afford after FC (EtOAc/MeOH 95:5 to 80:20) the macrolactam Ex. 198 and its epimer Ex. 231 (ca 1:1 mixture; 0.61 g, 73%).

Data of the mixture Ex. 198/Ex. 231: $C_{32}H_{41}N_5O_8$ (623.7). LC-MS: (method 2): $R_t$=1.78 (44), 624 ([M+H]$^+$); 1.82 (56), 624 ([M+H]$^+$). $^1$H-NMR ($CDCl_3$): complex spectrum, mixture of epimers, 7.41-7.20 (m, 6 H), 7.07-6.92 (m, 3 H) 5.8-4.8 (several m, 5 H), 4.3-3.0 (several m, 10 H), 3.16 (s, $NCH_3$), 2.81 (s, $NCH_3$), 2.58-2.45 (m, 1 H), 2.19-2.03 (m, 1 H), 1.51, 1.41 (2 s, 9 H)

Synthesis of Amine Ex. 197

According to procedure J, carbamate Ex. 198/Ex. 231 (ca. 85:15, 749 mg, 1.2 mmol) in dioxane (7.5 mL) was treated with 4M HCl-dioxane (15 mL) to afford. Ex. 197.HCl/Ex. 232.HCl (607 mg, 90%). Data of Ex. 197.HCl/Ex. 232.HCl: $C_{27}H_{33}N_5O_6$.HCl (523.5, free base). LC-MS (method 2): $R_t$=1.26 (75), 1.33 (14); 524 ([M+H]$^+$).

$^1$H-NMR (DMSO-$d_6$), major component Ex. 197.HCl: spectrum identical with the one described above for compound Ex. 197.HCl (cf. Scheme 16).

According to procedure J, carbamate Ex. 198/Ex. 231 (ca. 1:1, 1.32 g, 2.12 mmol) in dioxane (13 mL) was treated with 4M HCl-dioxane (26 mL) to afford after separation of the isomers by preparative RP-HPLC (method 1) Ex. 197.TFA (460 mg, 34%) and Ex. 232.TFA (470 mg, 35%).

Data of Ex. 197.TFA: $C_{27}H_{33}N_5O_6$.$C_2HF_3O_2$ (523.5, free base). LC-MS (method 2): $R_t$=1.25 (99), 524 ([M+H]$^+$). LC-MS (method 7): $R_t$=0.74 (97), 524 ([M+H]$^+$). $^1$H-NMR (DMSO-$d_6$): 8.34 (br. s, $NH_3$1, 8.07 (d, J=9.9, 1 H), 7.43-7.33 (m, 6 H), 7.20 (s, 1 H), 7.10 (dd, J=1.5, 8.2, 1 H), 6.87 (d, J=7.4, 1 H), 5.17 (d, J=12.5, 1 H), 5.05 (d, J=12.5, 1 H), 4.87 (br. dd, 1 H), 4.27-4.16 (m, 2 H), 4.06 (t, J=8.6, 1 H), 4.01-3.91 (m, 2 H), 3.82 (t-like dd, J ca. 8.1, 1 H), 3.70 (br. m, 1 H), 3.35-3.20 (m, 3 H), 2.98 (s, 3 H), 2.70 (s, 3 H), 2.49 (m, 1 H), 2.18 (br. q, J ca. 11.0, 1 H).

Data of Ex. 232.TFA: See below; Core 14.

Core 13: Synthesis of Ex. 215 and Ex. 216 (Scheme 18)

Synthesis of Mitsunobu Product 117

Following procedure B.1.1, the reaction of phenol 59 (2.1 g, 5.1 mmol), alcohol 20 (2.1 g, 6.1 mmol), $PPh_3$ (2.0 g, 7.6 mmol) in dry benzene (50 mL) and DEAD (40% in toluene, 2.8 mL, 6.1 mmol) in dry benzene (14 mL) afforded, after further addition of $PPh_3$ (0.84 g, 3.2 mmol), alcohol 20 (0.88 g, 2.6 mmol) in benzene (21 mL) and DEAD (40% in toluene, 1.2 mL, 2.6 mmol) in benzene (6 mL) and after FC (hexane/EtOAc 50:50) the protected amino acid 117 (3.8 g, 100%).

Synthesis of Amino Acid 118

Following procedure B.2, the reaction of 117 (7.63 g, 10.3 mmol), 1,3-dimethylbarbituric acid (4.03 g, 25.8 mmol) and $Pd(PPh_3)_4$ (1.31 g) in EtOAc/$CH_2Cl_2$ (1:1, 110 mL) yielded after 1 h and after FC ($CH_2Cl_2$/MeOH 95:5 to 70:30) amino acid 118 (3.48 g, 60%).

Data of 118: $C_{30}H_{42}N_4O_8Si$ (614.8). HPLC (10% $CH_3CN$): $R_t$=3.88 (100). LC-MS (method 9a): $R_t$=1.80, 615 ([M+H]$^+$).

Synthesis of the Alloc Protected Amino Acid 119

Following procedure C.1, the reaction of amino acid 118 (3.36 g, 5.5 mmol), allyl chloroformate (0.64 mL, 6.0 mmol) and $Na_2CO_3$ (0.87 g, 8.2 mmol) in dioxane (51 mL) and $H_2O$ (51 mL) gave acid 119 (3.51 g, 92%).

Synthesis of the Protected Amino Acid 120

Following procedure C.2, acid 119 (3.47 g, 5.0 mmol) was reacted with sarcosine allylester p-toluenesulfonate (46.p-TsOH, 1.8 g, 6.0 mmol), HOAt (1.0 g, 7.4 mmol), HATU (2.8 g, 7.4 mmol) and i-$Pr_2NEt$ (4.2 mL, 25 mmol) in DMF (108 mL) to afford the protected amino acid 120 (3.52 g, 88%).

Data of 120: $C_{40}H_{55}N_5O_{11}Si$ (809.9). LC-MS: (method 4b): $R_t$=2.51 (95), 810 ([M+H]$^+$)

Deprotection to Amino Acid 121

Following procedure C.3, the reaction of the protected amino acid 120 (3.49 g, 4.31 mmol), 1,3-dimethylbarbituric acid (1.68 g, 10.8 mmol) and $Pd(PPh_3)_4$ (0.55 g) in EtOAc/$CH_2Cl_2$ (1:1; 50 mL) yielded amino acid 121 (2.72 g, 92%).

Data of 121: $C_{33}H_{47}N_5O_9Si$ (685.8). LC-MS: (method 4b): $R_t$=1.84 (94), 686 ([M+H]$^+$)

Synthesis of the Protected Macrolactam Ex. 215

According to procedure F.1.2, amino acid 121 (1.33 g, 1.94 mmol) in dry DMF (27 mL) was treated with FDPP (1.49 g, 3.88 mmol) in dry DMF (164 mL) to yield after FC (EtOAc/MeOH 95:5) macrolactam Ex. 215 (0.89 g, 68%).

Data of Ex. 215: $C_{33}H_{45}N_5O_8Si$ (667.8). LC-MS: (method 1b): $R_t$=2.60 (99), 668 ([M+H]$^+$). LC-MS: (method 9c): $R_t$=2.14, 668 ([M+H]$^+$). $^1$H-NMR (DMSO-$d_6$): 7.94 (d, J=9.8, 1 H), 7.39-7.27 (m, 7 H), 7.11 (s, 1 H), 6.97 (dd, J=1.5, 8.2, 1 H), 6.82 (d, J=7.5, 1 H), 5.05 (s, 2 H), 4.83 (br. d, 1 H), 4.25 (br. m, 1 H), 4.17-3.96 (m, 5 H), 3.73 (br. q, J ca. 16.8, 2 H), 3.47 (m, 1 H), 3.33 (m, 1 H), 3.19 (m, 2 H), 2.96 (s, 3 H), 2.67 (s, 3 H), 2.20 (m, 1 H), 2.00 (m, 1 H), 0.91 (t, J=8.4, 2 H), 0.00 (s, 9 H).

Synthesis of Amine Ex. 216

According to procedure 1.1, carbamate Ex. 215 (881 mg, 1.3 mmol) in dioxane (16 mL) was treated with 4M HCl-dioxane (16 mL) to afford Ex. 216.HCl (666 mg, 90%).

Data of Ex. 216.HCl: $C_{27}H_{33}N_5O_6$.HCl (523.5, free base). HPLC (5% $CH_3CN$): $R_t$=3.11 (91). LC-MS (method 9c): $R_t$=1.19, 524 ([M+H]$^+$).

Core 14: Synthesis of Ex. 231 and Ex. 232 (Scheme 19)

Synthesis of Mitsunobu Product 122

A mixture of phenol 61 (4.6 g, 11.2 mmol) and $PPh_3$ (5.27 g, 20.1 mmol) was dissolved in benzene. The soln was concentrated and the residue was dried i.v. for 20 min. A soln of the alcohol 81, (7.46 g, 20.1 mmol) in dry, degassed benzene (120 mL) was added. The resulting mixture was cooled to 0° C. DEAD (40% in toluene, 11.5 mL, 25.1 mmol)

in benzene (10 mL) was slowly added. The soln was stirred at rt for 16 h. More $PPh_3$ (1.46 g, 5.6 mmol), alcohol 81 (1.04 g, 2.8 mmol) and at 0° C., a soln of DEAD (40% in toluene, 2.6 mL, 5.7 mmol) in benzene (2 mL) were added and stirring at rt was continued for 7 h. More $PPh_3$ (1.46 g, 5.6 mmol), alcohol 81 (1.04 g, 2.8 mmol), and at 0° C., a soln of DEAD (40% in toluene, 2.6 mL, 5.7 mmol) in benzene (2 mL) were added. Stirring at rt was continued for 16 h. The mixture was concentrated. FC (hexane/EtOAc 30:70 to 0:100) afforded 122 (12.8 g, contaminated with ca. 40% triphenylphosphine oxide, yield ca. 90%), which was used in the next step without further purification.

Synthesis of Amino Acid 123

Following procedure E.2, the reaction of the protected amino acid 122 (contaminated with ca. 40% of triphenylphosphine oxide, 12.8 g, ca. 10 mmol), 1,3-dimethylbarbituric acid (3.91 g, 25.1 mmol) and $Pd(PPh_3)_4$ (1.27 g) in EtOAc/$CH_2Cl_2$ (1:1, 120 mL) yielded after 1 h and after FC ($CH_2Cl_2$/MeOH 100:0 to 70:30 then $CHCl_3$/MeOH 70:30) the amino acid 123 (2.80 g, 44%).

Data of 123: $C_{32}H_{43}N_5O_9$ (641.7). LC-MS: (method 2): $R_t$=1.56 (94), 642 ([M+H]$^+$).

Synthesis of the Protected Macrolactam Ex. 231

According to procedure F.1.2, amino acid 123 (3.29 g, 5.13 mmol) in dry DMF (150 mL) was added within 4 h at 60° C. to FDPP (3.94 g, 10.3 mmol) in dry DMF (4980 mL) to afford after 16 h at 60° C. and after FC (EtOAc/MeOH 100:0 to 95:5) macrolactam Ex. 231 (containing ca. 15% of its epimer Ex. 198; 2.5 g, 78%).

Data of Ex. 231: $C_{32}H_{41}N_5O_8$ (623.7). LC-MS: (method 2): $R_t$=1.78 (12), 1.82 (83), 624 ([M+H]$^+$). LC-MS: (method 7): $R_t$=1.16 (18), 624 ([M+H]$^+$); 1.18 (80), 624 ([M+H]$^+$). $^1$H-NMR ($CDCl_3$): complex spectrum, two epimers; 7.38-7.22 (m, 6 H), 7.06-6.90 (m, 3 H), 5.80-4.80 (several m, 4 H), 5.08, 5.12 (2 s, 2 H), 4.43-2.80 (several br. m, 15 H), 2.51 (m, 1 H), 2.19-2.03 (m, 1 H), 1.50, 1.42 (2 s, 9 H).

Synthesis of Amine Ex. 232

According to procedure J, carbamate Ex. 231 (containing 15% of the epimer Ex. 198; 1.42 g, 2.3 mmol) in dioxane (30 mL) was treated with 4M HCl-dioxane (45 mL) to afford after preparative RP-HPLC (method 1) Ex. 232.TFA (1.10 g, 71%) and Ex. 197.TFA (0.27 g, 17%).

Data of Ex. 232.TFA: $C_{27}H_{33}N_5O_6.C_2HF_3O_2$ (523.5, free base). LC-MS (method 2): $R_t$=1.32 (99), 524 ([M+H]$^+$). $^1$H-NMR (DMSO-$d_6$): complex spectrum, mixture of isomers; 8.40 (br. s), 8.20 (br. s), 7.84 (d, J=7.1), 7.50-6.80 (several m), 5.25-3.40 (several m, partially superimposed by the $H_2O$ signal), 3.30-2.80 (m), 3.04 (s, $NCH_3$), 2.98 (s, $NCH_3$), 2.67 (s, $NCH_3$), 2.64 (s, $NCH_3$), 2.6-1.9 (several m).

Data of Ex. 197.TFA: See above; Core 12.

Core 15 and Core 16:

Synthesis of Ex. 238 and Ex. 239 (Scheme 20)

Synthesis of Mitsunobu Product 124

Following procedure E.1.1, phenol 77 (1.63 g, 8.5 mmol), alcohol 85 (5.72 g, 12.8 mmol) and $PPh_3$ (4.02 g, 15.3 mmol) in dry benzene (80 mL) were treated with DEAD (40% in toluene, 8.79 mL, 19.2 mmol) for 20 h. Purification by FC (hexane/EtOAc 20:80 to 100:0) then (hexane/EtOAc 50:50 to 20:80) afforded the protected amino acid 124 (1.96 g, 37%).

Synthesis of the Macrocycle Ex. 238

Dichloro-[1,3-bis(mesityl)-2-imidazoldinylidene]-(3-phenyl-1H-inden-1-ylidene)(tricyclohexylphosphine)ruthenium (II)

(Umicore M2 catalyst; 88 mg) was added to a soln of 124 (1160 mg, 1.29 mmol) in dry, degassed $CH_2Cl_2$ (170 mL). The soln was stirred in a sealed tube at 40° C. for 68 h, followed by 45 h at rt. During this period further equal portions of catalyst (in total 350 mg) were added after 20 h, 28 h, 44 h, and 52 h. The soln was concentrated. FC (hexane/EtOAc 70:30 to 0:100) gave Ex. 238 (350 mg, 46%, mixture of two isomers, ratio>9:1, acceptable for the use in the next step). An analytical sample (69 mg) was further purified by preparative RP-HPLC (method 2) to afford pure Ex. 238 (major isomer; 45 mg).

Data of Ex. 238 (major isomer): $C_{32}H_{40}N_4O_7$ (592.6). LC-MS: (method 4a): $R_t$=2.23 (92), 593 ([M+H]$^+$). $^1$H-NMR ($CDCl_3$): 7.62-7.31 (m, 6 H), 7.07 (d, J=7.6, 1 H), 6.99 (dd, J=2.0, 7.9, 1 H), 6.85 (s, 1 H), 5.69-5.61 (m, 2 H), 5.48 (d, J=8.2, 1 H), 5.21 (m, 1 H), 5.10 (s, 2 H), 4.76 (d, J=10.1, 1 H), 4.54 (dt, J=3.5, 7.9, 1 H), 4.41-4.25 (m, 2 H), 4.13 (d, J=10.7, 1 H), 3.97 (m, 1 H), 3.62 (m, 2 H), 3.48 (m, 1 H), 3.10 (s, 3 H), 2.73 (m, 1 H), 2.60-2.45 (m, 2 H), 2.02 (m, 1 H), 1.46 (s, 9 H).

Synthesis of Amine Ex. 239

A soln of Ex. 238 (430 mg, 0.73 mmol) in MeOH/THF 1:3, 36 mL) was hydrogenated for 3.5 h at rt under normal pressure in the presence of palladium hydroxide on activated charcoal (moistened with 50% $H_2O$; 215 mg). The mixture was filtered through a pad of celite. The filtrate was concentrated to give Ex. 239 (355 mg, quant.; used in the next step without further purification).

An analytical sample (68 mg) was purified by preparative RP-HPLC (method 2) to afford pure Ex. 239 (37 mg).

Data of Ex. 239: $C_{24}H_{36}N_4O_5$ (460.6): LC-MS (method 7): $R_t$=0.88 (97), 461 ([M+H]$^+$). $^1$H-NMR (DMSO-$d_6$): 7.36 (t, J=7.8, 1 H), 7.25 (d, J=6.1, 1 H), 7.03 (dd, J=1.6, 8.2, 1 H), 6.88-6.65 (m, 2 H), 4.51 (d, J=8.3, 1 H), 4.18 (t, J=10.3, 2 H), 4.09 (br. s, 1 H), 3.96 (br. m, 2 H), 3.19-2.72 (m, 3 H), 2.92 (s, 3 H), 2.34 (m, 2 H), 2.05 (br. q, 1 H), 1.82 (m, 1 H), 1.60-0.85 (m, 5 H), 1.40 (s, 9 H), 0.82 (m, 1 H).

Core 17: Synthesis of Ex. 248 and Ex. 249 (Scheme 21)

Synthesis of Mitsunobu Product 125

Following procedure E.1.1, phenol 68 (6.0 g, 14.6 mmol), alcohol 82 (9.75 g, 26.2 mmol), and $PPh_3$ (6.88 g, 26.2 mmol) were treated in dry benzene (160 mL) with DEAD (40% in toluene, 15 mL, 32.8 mmol) for 40 h. After 18 h and after 25 h, more $PPh_3$ (1.27 g, 4.8 mmol) and DEAD (40% in toluene, 2.23 mL, 4.9 mmol) in benzene (2 mL) were added. FC (hexane/EtOAc 30:70 to 20:80) afforded the protected amino acid 125 (16.85 g, contaminated with ca. 40% triphenylphosphine oxide, yield ca. 85%), which was used in the next step without further purification.

Synthesis of Amino Acid 126

Following procedure E.2, the reaction of 125 (16.8 g, contaminated with ca. 40% of triphenylphosphine oxide, ca. 12 mmol), 1,3-dimethylbarbituric acid (4.80 g, 30.8 mmol) and $Pd(PPh_3)_4$ (1.56 g) in EtOAc/$CH_2Cl_2$ (1:1, 170 mL) yielded after 1 h and after FC ($CH_2Cl_2$/MeOH 0:100 to 70:30, then $CHCl_3$/MeOH 70:30) amino acid 126 (4.15 g, ca. 52%).

Data of 126: $C_{33}H_{44}N_4O_9$ (640.7). HPLC (10% $CH_3CN$): $R_t$=3.67 (69). LC-MS (method 9c): $R_t$=1.75, 641 ([M+H]$^+$).

Synthesis of the Protected Macrolactam Ex. 248

According to procedure F.1.1, amino acid 126 (4.55 g, 7.1 mmol) in dry $CH_2Cl_2$ (120 mL) was added within 3 h to T3P (50% in EtOAc, 8.37 ml, 14.2 mmol) and i-$Pr_2$NEt (4.83 ml, 28.4 mmol) in dry $CH_2Cl_2$ (6660 mL). Prior to aqueous workup, $CH_2Cl_2$ was replaced with EtOAc. FC ($CH_2Cl_2$/MeOH 100:0 to 95:5) yielded macrolactam Ex. 248 (2.38 g, 54%).

Data of Ex. 248: $C_{33}H_{42}N_4O_8$ (622.7). LC-MS: (method 2): $R_t$=1.83 (100), 623 ([M+H]$^+$). LC-MS: (method 9c): $R_t$=1.97, 623 ([M+H]$^+$). $^1$H-NMR (DMSO-$d_6$): 7.45-7.34 (m, 5 H), 7.15-6.78 (m, 5 H), 5.25 (s, 2 H), 5.08 (d, J=12.8, 1 H), 4.62 (d, J=13.5, 2 H), 4.29 (m, 1 H), 4.09 (d, J=7.3, 1 H), 3.89 (d, J=12.4, 1 H), 3.54 (br. t, 1 H), 3.27 (m, 1 H), 3.07 (s, 3 H), 2.80 (m, 1 H), 2.71 (s, 3 H), 2.28-2.06 (m, 4 H), 1.94 (m, 1 H), 1.71 (m, 1 H), 1.39 (s, 9 H).

Synthesis of Acid Ex. 249

According to procedure H, the ester Ex. 248 (2.16 g, 3.5 mmol) was hydrogenolyzed in MeOH (130 mL)/THF (40 mL) in the presence of the catalyst (1.09 g) for 2.5 h to afford the acid Ex. 249 (1.83 g, 99%).

Data of Ex. 249: $C_{26}H_{36}N_4O_8$ (532.6). LC-MS: (method 2): $R_t$=1.42 (95), 533 ([M+H]$^+$).

Core 18: Synthesis of Ex. 272, Ex. 273, and Ex. 274 (Scheme 22)

Synthesis of Mitsunobu Product 127

Following procedure E.1.1, the reaction of phenol 71 (6.47 g, 15.7 mmol), alcohol 81 (10.5 g, 28.2 mmol), DEAD (40% in toluene, 26 mL, 56.3 mmol), and $PPh_3$ (14.8 g, 56.3 mmol) in dry benzene (380 mL) afforded after 2 h at rt and after aqueous workup (EtOAc, sat. aq. $Na_2CO_3$ soln, sat. aq. NaCl soln), drying ($Na_2SO_4$), concentration of the organic layer and FC (hexane/EtOAc 30:70, 0:100, then $CH_2Cl_2$/MeOH 90:10) the protected amino acid 127 (12.0 g, 99%).

Synthesis of Amino Acid 128

Following procedure E.2, the reaction of 127 (12.0 g, 16 mmol), 1,3-dimethylbarbituric acid (5.9 g, 38.0 mmol) and $Pd(PPh_3)_4$ (0.9 g) in EtOAc/$CH_2Cl_2$ (55:45, 275 mL) yielded after 2 h and after FC (EtOAc, then $CH_9Cl_2$/MeOH 90:10 to 60:40) amino acid 128 (9.05 g, 90%).

Data of 128: $C_{31}H_{42}N_6O_9$ (642.7). LC-MS: (method 7): $R_t$=0.90 (94), 643 ([M+H]$^+$).

Synthesis of the Protected Macrolactam Ex. 272

According to procedure F.1.1, amino acid 128 (5.04 g, 7.8 mmol) in dry $CH_2Cl_2$ (100 mL) was treated with T3P (50% in EtOAc, 9.2 mL, 16 mmol) and i-$Pr_2$NEt (5.4 mL, 31 mmol) in dry $CH_2Cl_2$ (700 mL) to afford after FC ($CH_2Cl_2$/MeOH 39:1 to 19:1) the epimeric macrolactams Ex. 272 (1.90 g, 38%).

Data of Ex. 272: $C_{31}H_{40}N_6O_8$ (624.7). LC-MS: (method 2): $R_t$=1.61 (99), 625 ([M+H]$^+$). LC-MS: (method 7): $R_t$=1.01 (99), 625 ([M+H]$^+$). $^1$H-NMR (DMSO-$d_6$): 8.47 (d, J=2.6, 1 H), 8.12 (s, 1 H), 7.95 (d, J=9.6, 1 H), 7.61 (s, 1 H), 7.40-7.29 (m, 6 H), 5.10 (d, J=12.6, 1 H), 5.04 (d, J=12.6, 1 H), 4.98 (br. d, J=10.7, 1 H), 4.16 (br. d, J=11.8, 1 H), 4.10-3.90 (m, 4 H), 3.71 (br. t, J ca. 8.4, 1 H), 3.65-3.40 (m, 2 H), 3.23 (br. dd, J=11.1, 15.2, 1 H), 3.04 (s, 3 H), 2.92 (t, J=9.6, 1 H), 2.66 (s, 3 H), 2.12 (m, 1 H), 2.09 (br. q, 1 H), 1.42 (s, 9 H).

Synthesis of Amine Ex. 273

According to procedure J, carbamate Ex. 272 (3.12 g, 5 mmol) in dioxane (31 mL) was treated with 4M HCl-dioxane (62 mL) to afford Ex. 273.2HCl (2.9 g, 97%)

Data of Ex. 273.2HCl: $C_{26}H_{32}N_6O_6$.2HCl (524.5, free base). LC-MS (method 2): $R_t$=1.31 (92), 525 ([M+H]$^+$).

Synthesis of Amine Ex. 274

According to procedure K, carbamate Ex. 272 (200 mg, 0.32 mmol) was hydrogenolyzed in MeOH (20 mL) in the presence of the catalyst (100 mg) to afford Ex. 274 (154 mg, 97%).

Data of Ex. 274: $C_{23}H_{34}N_6O_6$. (490.5). LC-MS (method 2): $R_t$=1.26 (98), (491 ([M+H]$^+$).

Core 19: Synthesis of Ex. 297 and Ex. 298 (Scheme 23)

Synthesis of Mitsunobu Product 129

Following procedure E.1.2, the reaction of phenol 75 (4.58 g, 9.9 mmol), alcohol 81 (5.5 g, 15 mmol), and CMBP (4.8 g, 20 mmol) in dry toluene (24 mL) afforded after FC (hexane/EtOAc 1:3) the protected amino acid 129 (5.54 g, 68%).

Synthesis of Amino Acid 130

Following procedure E.2, the reaction of 129 (5.53 g, 6.8 mmol), 1,3-dimethylbarbituric acid (2.5 g, 16 mmol) and $Pd(PPh_3)_4$ (0.39 g) in EtOAc/$CH_2Cl_2$ 55:45 (118 mL) yielded after 2 h and after FC ($CH_2Cl_2$/MeOH 95:5 to 70:30) amino acid 130 (1.45 g, 85%).

Data of 130: $C_{36}H_{45}N_5O_9$ (691.7). LC-MS (method 7): $R_t$=1.09 (96), 692 ([M+H]$^+$).

Synthesis of the Protected Macrolactam Ex. 297

According to procedure F.1.1, amino acid 130 (2.57 g, 3.7 mmol) in dry $CH_2Cl_2$ (40 mL) was treated with T3P (50% in EtOAc, 4.4 mL, 7.4 mmol) and i-$Pr_2$NEt (2.5 mL, 14.9 mmol) in dry $CH_2Cl_2$ (330 mL) to give after FC ($CH_2Cl_2$/MeOH 99:1 to 90:10) macrolactam Ex. 297 (2.5 g, contaminated with ca. 20% i-$Pr_2$NEt; yield 80%).

Data of Ex. 297: $C_{36}H_{43}N_5O_8$ (673.7). LC-MS: (method 7): $R_t$=1.18 (93), 674 ([M+H]$^+$).

Aqueous workup (EtOAc, 1 M aq. $NaH_2PO_4$ soln) of an analytical sample (100 mg) afforded pure Ex. 297 (81 mg).

LC-MS: (method 2): $R_t$=2.20 (93), 674 ([M+H]$^+$). $^1$H-NMR (DMSO-d$_6$): complex spectrum, several isomers, 8.51 (d, J=8.5, 0.2 H), 8.47 (d, J=8.7, 0.1 H), 8.40 (d, J=8.5, 0.55 H), 8.32 (d, J=8.5, 0.15 H), 7.68-7.10 (several m, 10 H), 5.96 (br. s, 0.3 H), 5.90 (br. s, 0.3 H), 5.4-5.0 (m, 2.4 H), 4.8-3.8 (several m, 8 H), 3.3-2.5 (several m and s, 8 H), 2.5-1.6 (several m, 4 H), 1.42, 1.41, 1.36, 1.26 (4 s, Boc).

Synthesis of Acid Ex. 298

According to procedure H, the ester Ex. 297 (2.0 g, contaminated with ca. 20% i-$Pr_2NEt$ 2.4 mmol) was hydrogenolyzed in MeOH (200 mL) in the presence of catalyst (1 g) for 3 h.

The crude product was suspended in $Et_2O$ (20 mL) stirred for 20 min, filtered, washed ($Et_2O$) and dried to afford Ex. 298 (1.63 g, contaminated with 15% i-$Pr_2NEt$, quant. yield).

Aqueous workup ($CH_2Cl_2$, 1 M aq. $NaH_2PO_4$ soln) of an analytical sample (200 mg) afforded pure Ex. 298 (135 mg).

Data of Ex. 298: $C_{29}H_{37}N_5O_8$ (583.6). LC-MS: (method 4a): $R_t$=1.78 (86), 584 ([M+H]$^+$).

Core 20: Synthesis of Ex. 311 (Scheme 24)

Synthesis of Mitsunobu Product 131

A soln of phenol 72 (200 mg, 0.34 mmol), alcohol 16 (178 mg, 0.52 mmol) and $PPh_3$ (180 mg, 0.69 mmol) in benzene (5 mL) was degassed. At 0° C., DEAD (40% in toluene, 0.32 mL, 0.69 mmol) was added. The mixture was stirred at rt for 15 h. Additional alcohol 16 (178 mg, 0.52 mmol) and $PPh_3$ (180 mg, 0.69 mmol) were added. DEAD (40% in toluene, 0.32 mL, 0.69 mmol) was added at 0° C. The mixture was stirred for 20 h and concentrated. FC ($CH_2Cl_2$/EtOAc 100:0 to 80:20) afforded 131 (containing ca. 20% of diethyl hydrazine-1,2-dicarboxylate; used without further purification).

Synthesis of Amino Acid 132

Following procedure B.2, the reaction of 131 (250 mg, ca. 80%, 0.22 mmol), 1.3-dimethylbarbituric acid (107 mg, 0.69 mmol) and $Pd(PPh_3)_4$ (16 mg) in EtOAc/$CH_2Cl_2$ (55:45, 4.8 mL) yielded after 3 h and after FC (EtOAc/MeOH 100:0 to 90:10, then $CH_2Cl_2$/MeOH 90:10 to 80:20) 132 (177 mg, yield over the two steps: 73%).

Data of 132: $C_{39}H_{57}N_5O_{10}Si$ (784.0): LC-MS: (method 7): $R_t$=1.31, 784.2 ([M+H]).

Synthesis of the Alloc Protected Amino Acid 133

Following procedure C.1, the reaction of 132 (150 mg, 0.19 mmol), allyl chloroformate (23 µL, 0.21 mmol) and $Na_2CO_3$ (61 mg, 0.57 mmol) in dioxane (1.5 mL) and $H_2O$ (1.5 mL) gave, after 2 h at 0° C., acid 133 (154 mg, 92%).

Synthesis of the Protected Amino Acid 134

Following procedure C.2, acid 133 (140 mg, 0.16 mmol) was reacted with sarcosine allylester p-toluenesulfonate (46.pTsOH, 58 mg, 0.194 mmol), HOAt (33 mg, 0.24 mmol), HATU (92 mg, 0.24 mmol) and i-$Pr_2NEt$ (0.138 mL, 0.81 mmol) in DMF (2.4 mL) to afford the protected amino acid 134 (106 mg, 67%).

Data of 134: $C_{49}H_{70}N_6O_{13}Si$ (979.2). LC-MS: (method 7): $R_t$=1.68, 979.3 ([M+H]$^+$).

Synthesis of Amino Acid 135

Following procedure C.3, the reaction of the protected amino acid 134 (100 mg, 0.10 mmol), 1.3-dimethylbarbituric acid (38 mg, 0.25 mmol) and $Pd(PPh_3)_4$ (6 mg) in EtOAc/$CH_2Cl_2$ (45:55, 1.9 mL) yielded after 16 h and after FC (EtOAc, then $CH_2Cl_2$/MeOH 90:10) 135 (70 mg, 80%).

Data of 135: $C_{42}H_{62}N_6O_{11}Si$ (855.1). LC-MS: (method 7): $R_t$=1.30, 855.5 ([M+H]$^+$).

Synthesis of the Protected Macrolactam Ex. 311

According to procedure F.1.1, a soln of the amino acid 135 (60 mg, 0.07 mmol) in dry $CH_2Cl_2$ (2 mL), was added within 2 h to T3P (50% in EtOAc; 84 µL, 0.14 mmol) and i-$Pr_2NEt$ (48 µL, 0.28 mmol) in $CH_2Cl_2$ (5 mL). Then sat. aq. $NaHCO_3$ soln was added and the mixture was extracted with $CH_2Cl_2$. The organic phase was dried ($Na_2SO_4$), filtered and concentrated. FC (EtOAc) afforded Ex. 311 (26 mg, 44%).

Data of Ex. 311: ($C_{42}H_{60}N_6O_{10}Si$ (837.0). LC-MS: (method 7): $R_t$=1.51 (90), 837.4 ([M+H]$^+$). $^1$H-NMR ($CDCl_3$): 7.26 (s, 5 H), 7.09 (t, J=8.4, 1 H), 6.78 (d-like m, 1 H), 6.61 (d, J=7.4, 1 H), 5.50-4.90 (several br. m, 5 H), 4.90-3.80 (several br. m, 8 H), 3.69 (br. t, J ca. 8.5, 1 H), 3.6-2.3 (several br. m, 14 H), 2.12 (m, 1 H), 1.61 (m, 1 H), 1.38 (s, 9 H), 1.24 (s, 2 H), 0.93 (br. t, J ca. 8.0, 2 H), 0.00, −0.03 (2 s, 9 H).

Core 21: Synthesis of Ex. 312-Ex. 315 (Scheme 25)

Synthesis of Mitsunobu Product 136

Alcohol 82 (217 mg, 0.58 mmol) and CMBP (212 mg, 0.88 mmol) were dissolved in dry degassed toluene (7 mL) and heated at 100° C. for 30 min. A soln of 80 (250 mg, 0.58 mmol) in toluene (2 mL) was added dropwise. Stirring at 100° C. was continued for 1 h. The volatiles were evaporated. FC (hexane/EtOAc 2:1 to 1:1) yielded 136 (290 mg, 63%).

Synthesis of Amino Acid 137

Following procedure E.2 the reaction of 136 (250 mg, 0.32 mmol), 1,3-dimethylbarbituric acid (120 mg, 0.77 mmol) and $Pd(PPh_3)_4$ (18 mg) in EtOAc/$CH_2Cl_2$ (45:55, 5.5 mL) yielded after 0.5 h and after FC ($CH_2Cl_2$/MeOH 95:5 to 70:30) amino acid 137 (164 mg, 78%).

Data of 137: $C_{33}H_{44}N_4O_8S$ (656.8). LC-MS (method 7): $R_t$=1.15 (95), 657 ([M+H]$^+$).

Synthesis of the Protected Macrolactam Ex. 312

According to procedure F.1.1, a soln of the amino acid 137 (100 mg, 0.15 mmol) in dry $CH_2Cl_2$ (2 mL) was added over 2 h to T3P (50% in EtOAc, 0.18 mL, 0.31 mmol) and i-$Pr_2NEt$ (0.1 mL, 0.61 mmol) in dry $CH_2Cl_2$ (13 mL). Stirring at rt was continued for 1 h, followed by aqueous workup (EtOAc, sat. aq. $NaHCO_3$ soln, $Na_2SO_4$) and FC (EtOAc) to afford Ex. 312 (56 mg, 57%).

Data of Ex. 312: $C_{33}H_{42}N_4O_7S$ (638.7). LC-MS (method 7): $R_t$=1.33 (95), 639 ([M+H]$^+$). $^1$H-NMR ($CDCl_3$): 7.37-7.23 (m, 8 H), 6.92 (br. s, 1 H), 5.25 (m, 2 H), 5.17 (s, 1 H), 4.88 (d, J=16.2, 1 H), 4.62 (br. m, 1 H), 4.46 (br. t-like m, 1 H), 4.31 (br. m, 1 H), 4.17 (dd, J=4.1, 14.2, 1 H), 3.72 (dd, J=4.8, 10.7, 1 H), 3.50 (m, 1 H), 3.30-2.80 (several m, 2 H), 3.14 (s, 3 H), 3.01 (s, 3 H), 2.60-1.90 (several m, 6 H), 1.46 (s, 9 H).

Synthesis of Sulfone Ex. 313 m-CPBA (70% w/w; 10 mg, 41 µmol) was added at 0° C. to a soln of Ex. 312 (20 mg, 31 µmol) in $CH_2Cl_2$ (0.5 mL). The mixture was stirred for 15 min followed by the addition of m-CPBA (9 mg, 37 µmol). The mixture was allowed to warm to rt over 1 h, diluted with $CH_2Cl_2$ and washed with aq. $Na_2S_2O_3$ soln and with aq. $NaHCO_3$ soln. The organic phase was dried ($Na_2SO_4$), filtered and concentrated. FC (EtOAc/MeOH 100:0 to 90:10) afforded Ex. 313 (8 mg, 38%).

Data of Ex. 313: $C_{33}H_{42}N_4O_9S$ (670.7). LC-MS (method 6): $R_t$=1.24 (95), 671 ([M+H]$^+$). $^1$H-NMR ($CDCl_3$): 7.89 (td, J=1.7, 7.3, 1 H), 7.71 (s, 1 H), 7.43-7.28 (m, 7 H), 5.17 (d, J=12.0, 1 H), 5.10 (d, J=12.0, 1 H), 5.01 (dd, J=5.9, 9.1, 1 H), 4.96-4.85 (m, 2 H), 4.71 (d, J=15.4, 1 H), 4.57 (br. m, 1 H), 4.33 (br. m, 2 H), 3.85 (dd, J=7.8, 12.3, 1 H), 3.25 (s, 3 H), 3.20 (m, 1 H), 3.10 (m, 1 H), 2.97 (s, 3 H), 2.73-2.54 (m, 2 H), 2.45-2.23 (m, 2 H), 2.17 (m, 1 H), 1.99 (m, 1 H), 1.46 (s, 9 H).

A soln of the benzyl ester Ex. 312 (1.69 g, 2.6 mmol) in THF/MeOH (3:1; 36 mL) was treated with $H_2O$ (9 mL) and at 0° C. $LiOH.H_2O$ (0.22 g, 5.2 mmol) was added. The mixture was stirred for 1 h at 0° C., acidified to pH 5 with 1 M aq. $NaH_2PO_4$ soln and extracted with $CHCl_3$. The organic layer was dried ($Na_2SO_4$), filtered and concentrated. The resulting solid was suspended in $Et_2O$ and filtered to give Ex. 314 (1.4 g, 96%).

Data of Ex. 314: $C_{26}H_{36}N_4O_7S$ (548.6). LC-MS (method 7): $R_t$=1.29 (97), 549 ([M+H]$^+$).

Synthesis of Acid Ex. 315

According to procedure H, a soln of the benzyl ester Ex. 313 (1.69 g, 2.5 mmol) was hydrogenolyzed in MeOH (65 mL) in the presence the catalyst (1.69 g) for 4 h, filtered through a pad of celite and concentrated to afford Ex. 315 (1.35 g, 92%). Data of Ex. 315: $C_{26}H_{36}N_4O_9S$ (580.6). LC-MS (method 4b): $R_t$=1.62 (99), 581 ([M+H]$^+$).

Core 22: Synthesis of Ex. 342 and Ex. 343 (Scheme 26)

Synthesis of Mitsunobu Product 220

At 0° C. DEAD (40% in toluene, 33 mL, 71.6 mmol) was slowly added to a soln of phenol 199 (15.42 g, 35.8 mmol), alcohol 14 (12.9 g, 43 mmol) and $PPh_3$ (18.8 g, 71.6 mmol) in dry benzene (306 mL). The mixture was stirred for 3.5 h at 0° C. to rt. $H_2O$ (0.64 mL, 35.8 mmol) was added and stirring continued for 5 min. The mixture was concentrated. The residue was suspended in $Et_2O$ (150 mL) and filtered. The filtrate was concentrated. This washing procedure was repeated twice to afford after concentration of the filtrate and FC (hexane/EtOAc) the protected amino acid 220 (20.3 g, 80%; contaminated with diethyl hydrazine-1,2-dicarboxylate, used without further purification).

Synthesis of Amino Acid 221

Following procedure B.2, the reaction of 220 (19.86 g, 27.8 mmol), 1,3-dimethylbarbituric acid (10.87 g, 69.6 mmol) and $Pd(PPh_3)_4$ (0.32 g) in $EtOAc/CH_2Cl_2$ (55:45, 300 mL) yielded after 2 h and evaporation of the volatiles a solid which was filtered and washed with EtOAc to give 221 (13.95 g, 85%).

Data of 221: $C_{29}H_{37}FN_4O_8$ (588.6). LC-MS (method 10a): $R_t$=1.58 (95), 589 ([M+H]$^+$).

Synthesis of the Protected Macrolactam Ex. 342

Amino acid 221 (12.58 g, 21.4 mmol) was added in portions to a soln of T3P (50% in EtOAc, 37.8 mL, 64.1 mmol) and $i\text{-}Pr_2NEt$ (18.3 mL, 106.9 mmol) in dry $CH_2Cl_2$ (4280 mL). Stirring at rt was continued for 2 h, followed by evaporation of the volatiles. FC (hexane/EtOAc/MeOH gradient) afforded the macrolactam Ex. 342 (9.4 g, contaminated with 10% of the cyclic dimer). Further purification of this material (1.0 g) by FC (hexane/EtOAc/MeOH gradient) afforded pure Ex. 342 (0.81 g).

Data of Ex. 342: $C_{29}H_{35}FN_4O_7$ (570.6). LC-MS (method 10b): $R_t$=2.05 (97), 571 ([M+H]$^+$), 471. $^1$H-NMR (DMSO-$d_6$): 8.21 (br. t, 1 H), 7.57 (d, J=6.7, 1 H), 7.50 (d, J=8.8, 1 H), 7.40-7.31 (m, 7 H), 7.22 (d, J=6.6, 1 H), 5.06 (d, J=12.4, 1 H), 4.99 (d, J=12.6, 1 H), 4.45-4.40 (m, 2 H), 4.35-4.25 (m, 2 H), 4.13 (m, 1 H), 4.03 (m, 1 H), 3.64 (m, 1 H), 3.30 (m, 2 H, superimposed by $H_2O$ signal), 2.27 (m, 1 H), 1.99-1.86 (m, 3 H), 1.39 (s, 9 H).

Synthesis of Amine Ex. 343

According to procedure K, benzyl carbamate Ex. 342 (5.0 g, 8.7 mmol) was hydrogenolyzed in MeOH (100 mL) in the presence of catalyst (656 mg) for 2 h to afford after filtration, evaporation of the volatiles and FC ($CH_2Cl_2$/MeOH 95:5 to 80:20) amine Ex. 343 (3.2 g, 84%).

Data of Ex. 343: $C_{21}H_{29}FN_4O_5$ (436.5). LC-MS (method 10b): $R_t$=1.37 (100), 437 ([M+H]$^+$), 381, 337.

Core 23: Synthesis of Ex. 363 and Ex. 364 (Scheme 27)

Synthesis of the Amide 222

T3P (50% in EtOAc, 6.8 mL, 11.5 mmol) was added to a soln of acid 192 (2.4 g, 5.8 mmol) and amine hydrochloride 178.HCl (1.8 g, 5.8 mmol) in dry $CH_2Cl_2$ (65 mL). $i\text{-}Pr_2NEt$ (4.1 mL, 23.9 mmol) was slowly added; and the mixture was stirred for 5 h at rt. The mixture was distributed between 1 M aq. $NaH_2PO_4$ soln and $CH_2Cl_2$. The organic phase was dried ($Na_2SO_4$), filtered and concentrated. FC (hexane/EtOAc gradient) afforded amide 222 (3.49 g, 93%).

Data of 222: $C_{37}H_{47}N_3O_{11}$ (709.8). LC-MS (method 10a): $R_t$=2.50 (96), 710 ([M+H]$^+$).

Synthesis of Amino Acid 223

Following procedure B.2, the reaction of 222 (3.45 g, 4.86 mmol), 1,3-dimethylbarbituric acid (1.9 g, 12.1 mmol) and $Pd(PPh_3)_4$ (28 mg) in $EtOAc/CH_2Cl_2$ (1:1, 60 mL) yielded after 4 h and after FC ($CH_2Cl_2$/MeOH 90:10 to 70:30) amino acid 223 (2.32 g, 81%).

Data of 223: $C_{30}H_{39}N_3O_9$ (585.6). LC-MS (method 10a): $R_t$=1.62 (97), 586 ([M+H]$^+$).

Synthesis of the Protected Macrolactam Ex. 363

According to procedure F.1.2, the amino acid 223 (2.3 g, 3.9 mmol) in dry DMF (50 mL) was treated with FDPP (3.15 g, 8.2 mmol) in DMF (700 mL). After completion of the addition, the mixture was concentrated. FC (hexane/EtOAc/MeOH gradient) afforded macrolactam Ex. 363 (1.78 g, 80%).

Data of Ex. 363: $C_{30}H_{37}N_3O_8$ (567.6). LC-MS (method 10b): $R_t$=2.00 (98), 568 ([M+H]$^+$). $^1$H-NMR (DMSO-$d_6$): 7.43-7.34 (m, 5 H), 7.27 (t, J=7.8, 1 H), 7.20 (d, J=7.2, 1 H), 7.01 (m, 1 H), 6.85 (br. s, 1 H), 6.79 (d, J=7.4, 1 H), 5.22 (s, 2 H), 5.05 (d, J=12.5, 1 H), 4.76 (dd, J=3.7, 9.8, 1 H), 4.08 (t, J=8.7, 1 H), 3.94-3.80 (m, 4 H), 3.59 (dd, J=3.7, 12.3, 1 H), 3.26 (br. t, J ca. 8.5, 1 H), 3.15 (d, J=14.1, 1 H), 2.78 (s, 3 H), 2.22-2.03 (m, 3 H), 1.37 (s, 9 H).

Synthesis of Acid Ex. 364

Ester Ex. 363 (1.5 g, 2.6 mmol) was hydrogenolyzed in MeOH (30 mL) in the presence of 10% palladium on charcoal (moistened with 50% $H_2O$; 0.34 g) for 4 h, filtered through a pad of celite and concentrated to afford Ex. 364 (1.26 g, 97%).

Data of Ex. 364: $C_{23}H_{31}N_3O_8$ (477.5). LC-MS (method 10c): $R_t$=1.42 (98), 478 ([M+H]$^+$).

Core 24a: Synthesis of Ex. 379 and Ex. 380 (Scheme 28)

Synthesis of Mitsunobu Product Ex. 379

Following procedure B.1.2, the reaction of phenol 200 (4.31 g, 10.1 mmol), alcohol 14 (3.64 g, 12.1 mmol) and CMBP (4.88 g, 20.2 mmol) in dry toluene (180 mL) afforded after 2 h and after FC (hexane/EtOAc/MeOH gradient) the protected amino acid 224 (8.8 g, contaminated with ca. 20% of tributylphosphine oxide; used without any further purification).

Synthesis of Amino Acid 225

Following procedure B.2, the reaction of 224 (8.8 g), 1,3-dimethylbarbituric acid (3.86 g, 24.7 mmol) and $Pd(PPh_3)_4$ (57 mg) in $EtOAc/CH_2Cl_2$ (1:1, 88 mL) yielded after 3 h, dilution with EtOAc and centrifugation an orange solid, which was washed (EtOAc) to give 225 (6.02 g, ca. 80% over the two steps).

Data of 225: $C_{30}H_{40}N_4O_8$ (584.6). LC-MS (method 4a): $R_t$=1.70 (90), 585 ([M+H]$^+$). Purity based on $^1$H-NMR ca. 80%; used without further purification.

Synthesis of Macrolactam Ex. 379

According to procedure F.1.1, the amino acid 225 (2.0 g, 3.06 mmol) and $i\text{-}Pr_2NEt$ (1.0 mL, 5.9 mmol) in dry DMF (20 mL) was treated with T3P (50% in EtOAc; 3.6 mL, 6.1 mmol) and $i\text{-}Pr_2NEt$ (1.2 mL, 7 mmol) in $CH_2Cl_2$ (550 mL)

to afford after evaporation of the volatiles and FC (hexane/EtOAc/MeOH gradient) Ex. 379 (1.23 g, 71%).

Data of Ex. 379: $C_{30}H_{38}N_4O_7$ (566.6). LC-MS (method 10c): $R_t$=1.94 (98), 567 ([M+H]$^+$). $^1$H-NMR (DMSO-$d_6$): 7.98 (d, J=6.8, 0.5 H), 7.63 (br. t, 0.5 H), 7.56 (d, J=7.5, 0.5 H), 7.37-7.11 (several m, 8.5 H), 7.00 (d, J=7.4, 1 H), 6.87 (d, J=7.4, 0.5 H), 6.82 (s, 0.5 H), 5.03-4.87 (s and m, 3 H), 4.41 (m, 0.5 H), 4.28 (t-like m, 0.5 H), 4.13 (m, 1 H), 3.97-3.65 (m, 3 H), 3.04 (br. d, J ca. 11.1, 1 H), 2.81 (m, 1 H), 2.30 (t, J=9.5, 1 H), 2.14 (m, 1 H), 1.90 (m, 1 H), 1.66 (m, 2 H), 1.40, 1.34 (2 s, 9 H), 1.40-1.15 (m, 2 H).

Synthesis of Amine Ex. 380

According to procedure K, benzyl carbamate Ex. 379 (700 mg, 1.23 mmol) was hydrogenolyzed in MeOH (7.0 mL) in the presence of catalyst (139 mg) for 2 h. After filtration and evaporation of the volatiles, Ex. 380 (550 mg, 100%) was obtained.

Data of Ex. 380: $C_{22}H_{32}N_4O_5$ (432.5). LC-MS (method 10a): $R_t$=1.34 (100), 433 ([M+H]$^+$).

Core 24b: Synthesis of Ex. 392 and Ex. 393 (Scheme 28)

Synthesis of Mitsunobu Product 226

Following procedure B.1.2, the reaction of phenol 200 (2.74 g, 6.4 mmol), alcohol 156 (2.14 g, 7.7 mmol) and CMBP (3.1 g, 12.8 mmol) in dry toluene (96 mL) afforded after 2 h and after FC (hexane/EtOAc gradient) the protected amino acid 226 (3.16 g, 72%).

Synthesis of Amino Acid 227

Following procedure B.2, the reaction of 226 (2.98 g, 4.35 mmol), 1,3-dimethylbarbituric acid (1.7 g, 10.9 mmol) and $Pd(PPh_3)_4$ (25 mg) in EtOAc/$CH_2Cl_2$ (1:1, 58 mL) yielded after 4 h, evaporation of the volatiles and repeated washing (EtOAc) of the residue the amino acid 227 (2.42 g, 97%).

Data of 227: $C_{31}H_{35}N_3O_7$ (561.6). LC-MS (method 10a): $R_t$=1.59 (97), 562 ([M+H]$^+$).

Synthesis of Macrolactam Ex. 392

To a soln of HATU (1.24 g, 3.3 mmol), HOAt (0.44 g, 3.2 mmol) and i-$Pr_2$NEt (1.2 mL, 6.5 mmol) in DMF (1600 mL) was added within 2 h via syringe pump a soln of 227 (0.916 g, 1.6 mmol) in DMF (40 mL). The mixture was stirred for 20 h at rt, followed by evaporation of the volatiles. FC (hexane/EtOAc/MeOH gradient) afforded Ex. 392 (0.78 g, 88%).

Data of Ex. 392: $C_{31}H_{33}N_3O_6$ (543.6). LC-MS (method 10b): $R_t$=2.04 (96), 544 ([M+H]$^+$).

Synthesis of Amine Ex. 393

According to procedure K, benzyl carbamate Ex. 392 (66 mg, 0.12 mmol) was hydrogenolyzed in MeOH (1.5 mL) in the presence of catalyst (25 mg) for 1 h. After filtration, evaporation of the volatiles and FC ($CH_2Cl_2$/MeOH 95:5 to 80:20) Ex. 393 (40 mg, 80%) was obtained.

Data of Ex. 393: $C_{23}H_{27}N_3O_4$ (409.5). LC-MS (method 10a): $R_t$=1.34 (99), 410 ([M+H]$^+$). $^1$H-NMR (DMSO-$d_6$): 7.93 (d, J=6.2, 0.67 H), 7.75 (br. s, 0.33 H), 7.37-6.81 (m, 8 H), 6.74 (d, J=8.0, 1 H), 4.94 (d, J=13.8, 1 H), 4.86 (m, 1 H), 4.47-4.30 (m, 1 H), 4.25-4.04 (m, 2 H), 3.74 (br. s, 1 H), 3.12 (t-like m, 1 H), 2.80 (m, 1 H), 2.66 (dd, J=5.7, 11.1, 1 H), 2.50-2.00 (several m, 2 H), 1.80-1.50 (br. m, 3 H), 1.31 (m, 1 H).

Core 24c: Synthesis of Ex. 398 (Scheme 28)

Synthesis of the Amide 228

A soln of 198 (750 mg, 1.53 mmol) in $CH_2Cl_2$ (14 mL) was treated with $SOCl_2$ (0.34 mL, 4.59 mmol) and heated to 45° C. for 1 h. The volatiles were evaporated. 190.HCl (ca. 50% w/w; 1.01 g, 2.4 mmol) and $CH_2Cl_2$ (14 mL) were added. The mixture was cooled to 0° C. i-$Pr_2$NEt (0.785 mL, 4.5 mmol) was slowly added and stirring was continued for 1 h. The volatiles were evaporated.

Aqueous workup (EtOAc, 0.2 M aq. HCl soln) and FC (hexane/EtOAc 1:1) afforded 228 (693 mg, 70%).

Data of 228: $C_{31}H_{37}BrN_2O_8$ (645.5). LC-MS (method 10a): $R_t$=2.32 (95), 647/645 ([M+H]$^+$).

Synthesis of Amino Acid 229

Following procedure B.2, the reaction of 228 (680 mg, 1.05 mmol), 1,3-dimethylbarbituric acid (395 mg, 2.5 mmol) and $Pd(PPh_3)_4$ (61 mg) in EtOAc/$CH_2Cl_2$ (9:8, 17 mL) yielded after 2 h, evaporation of the volatiles and washing (EtOAc) 229 (571 mg, quant. yield).

Data of 229: $C_{24}H_{29}BrN_2O_6$ (521.4). LC-MS (method 10a): $R_t$=1.39 (94), 521/523 ([M+H]$^+$).

Synthesis of Macrolactam Ex. 398

A suspension of amino acid 229 (550 mg, 1.06 mmol) in dry $CH_2Cl_2$ (100 mL) was added over 2 h to a soln of T3P (50% in EtOAc; 1.5 mL, 2.6 mmol) and i-$Pr_2$NEt (0.72 mL, 4.2 mmol) in $CH_2Cl_2$ (930 mL). The mixture was stirred for 2 h. More T3P 50% in EtOAc; 1.5 mL, 2.6 mmol) and i-$Pr_2$NEt (0.72 mL, 4.2 mmol) in $CH_2Cl_2$ (30 mL) were added and stirring was continued until completion of the transformation. Evaporation of the solvent, aqueous workup (EtOAc, 0.1 M aq. HCl soln, sat. aq. $NaHCO_3$ soln; $Na_2SO_4$) and FC ($CH_2Cl_2$/MeOH 100:0 to 95:5) afforded Ex. 398 (254 mg, 47%).

Data of Ex. 398: $C_{24}H_{27}BrN_2O_5$ (503.3). LC-MS (method 10a): $R_t$=1.81 (97), 505/503 ([M+H]$^+$). $^1$H-NMR (DMSO-$d_6$): 8.16-6.77 (several m, 9 H), 4.96-4.81 (m, 1 H), 4.71 (d, J=6.9, exchanged upon addition of $D_2O$, OH), 4.54-3.97 (several m, 6H), 3.65-3.30 (several m, 2 H), 3.11 (d-like m, 1 H), 2.90-2.60 (several m, 1 H), 2.40-1.50 (several br. m, 6 H).

Core 25: Synthesis of Ex. 403 and Ex. 404 (Scheme 29)

Synthesis of Mitsunobu Product 230

At rt CMBP (2.44 g, 9.6 mmol) was added to a soln of alcohol 167 (2.31 g, 6.41 mmol) in toluene (100 mL). The mixture was heated to 100° C. for 30 min, followed by the addition of a soln of phenol 202 (2.82 g, 6.15 mmol) in toluene (25 mL). The mixture was stirred for 3 h at 100° C. and concentrated. FC (hexane/acetone) afforded 230 (3.17 g, 62%).

Data of 230: $C_{40}H_{57}FN_4O_{10}Si$ (800.9). LC-MS (method 4b): $R_t$=2.67 (93), 801 ([M+H]$^+$).

Synthesis of Amino Ester 231

At 0° C. TBAF (1 M in THF; 15.7 mL, 15.7 mmol) was added to a soln of 230 (3.15 g, 3.96 mmol) in THF (50 mL). The mixture was stirred at 0° C. to rt for 3 h. More TBAF soln (15.7 mL) was added and stirring continued for 4 h. The mixture was concentrated and the residue dissolved in $CH_2Cl_2$, washed (sat. aq. $NaHCO_3$ soln, sat. aq. NaCl soln), dried ($Na_7SO_4$), filtered and concentrated. FC ($CH_2Cl_2$/MeOH/conc. aq. $NH_3$ soln 95:5:0.5 to 90:10:0.5) afforded 231 (2.06 g, 87%).

Synthesis of Amino Acid 232

A soln of 231 (2.0 g, 3.05 mmol), 1,3-dimethylbarbituric acid (0.59 g, 3.81 mmol) and $Pd(PPh_3)_4$ (0.35 g) in EtOAc/$CH_2Cl_2$ (50:50, 35 mL) was stirred at rt for 2 h, concentrated and purified by FC ($CH_2Cl_2$/MeOH 100:0 to 90:10, then 70:30) to yield 232 (1.36 g, 72%).

Data of 232: $C_{31}H_{41}FN_4O_8$ (616.6). LC-MS (method 7): $R_t$=1.09 (98), 617 ([M+H]$^+$).

Synthesis of the Macrolactam Ex. 403

According to procedure F.1.2, a soln of 232 (1.34 g, 2.17 mmol) in dry DMF (100 mL) was treated with FDPP (1.67 g, 4.35 mmol) in DMF (2070 mL). Purification by FC (hexane/EtOAc/MeOH 60:40:0 to 0:90:10) afforded Ex. 403 (0.934 g, 73%).

Data of Ex. 403: $C_{31}H_{39}FN_4O_7$ (598.6). LC-MS (method 4b): $R_t$=2.16 (100), 599 ([M+H]$^+$). $^1$H-NMR (DMSO-$d_6$): 8.69, 8.51 (2 br. s, 1 H), 7.51 (d, J=7.5, 1 H), 7.40-7.28 (m, 5 H), 7.19-7.04 (m, 3 H), 5.01 (s, 2 H), 4.82, 4.55 (2 br. s, 1 H), 4.20-3.80 (m, 4 H), 3.75-3.26 (m, 4 H, partially superimposed by the $H_2O$ signal), 2.70 (s, 3 H), 2.66 (m, 1 H), 2.22 (m, 1 H), ca. 1.8-1.2 (br. m, 4 H), 1.42, 1.35 (2 s, 9 H).

Synthesis of Amine Ex. 404

According to procedure K, benzyl carbamate Ex. 403 (180 mg, 0.30 mmol) was hydrogenolyzed in MeOH (2.0 mL) in the presence of catalyst (34 mg) for 2 h. After filtration and evaporation of the volatiles, Ex. 404 (139 mg, 99%) was obtained.

Data of Ex. 404: $C_{23}H_{33}FN_4O_5$ (464.5). LC-MS (method 4a): $R_t$=1.61 (98), 465 ([M+H]$^+$).

Core 26: Synthesis of Ex. 415 and Ex. 416 (Scheme 30)

Synthesis of Mitsunobu Product 233

According to procedure E.1.1, a mixture of phenol 205 (1.65 g, 3.95 mmol), alcohol 82 (1.75 g, 4.7 mmol) and $PPh_3$ (3.08 g, 11.7 mmol) in dry benzene (42 mL) was treated at 0° C. with DEAD (40% in toluene, 5.4 mL, 11.7 mmol) in benzene (28 mL). After 16 h at rt, additional $PPh_3$ (1.36 g, 5.2 mmol) and alcohol 82 (0.35 g, 0.94 mmol) in benzene (8.4 mL) were added, followed by DEAD (40% in toluene, 2.4 mL, 5.2 mmol) in benzene (11 mL). Stirring was continued for 7 h. Evaporation of the volatiles and repeated FC ($CH_2Cl_2$/MeOH and hexane/EtOAc) afforded 233 (2.27 g, 75%, contaminated with triphenylphosphine oxide; used without further purification).

Synthesis of Amino Acid 234

Following procedure E.2, the reaction of 233 (2.26 g, 2.93 mmol), 1,3-dimethylbarbituric acid (1.14 g, 7.33 mmol) and $Pd(PPh_3)_4$ (0.37 g) in EtOAc/$CH_2Cl_2$ (50:50, 32 mL) yielded after 30 min and after FC (EtOAc, then $CH_2Cl_2$/MeOH 90:10 to 60:40) 234 (1.40 g, 74%).

Data of 234: $C_{31}H_{42}N_4O_9S$ (646.7). LC-MS (method 4b): $R_t$=1.76 (95), 647 ([M+H]$^+$).

Synthesis of the Protected Macrolactam Ex. 415

According to procedure F.1.1, amino acid 234 (500 mg, 0.77 mmol) in dry $CH_2Cl_2$ (11 mL) was treated with T3P (50% in EtOAc, 0.92 mL, 1.5 mmol) and i-$Pr_2$NEt (0.53 mL, 3.1 mmol) in $CH_2Cl_2$ (66 mL). After stirring at rt for 1 h, aqueous workup (EtOAc, sat. aq. $NaHCO_3$ soln) and FC (EtOAc), Ex. 415 (0.34 g, 69%) was obtained.

Data of Ex. 415: $C_{31}H_{40}N_4O_8S$ (628.7). LC-MS (method 4b): $R_t$=2.05 96), 629 ([M+H]$^+$). $^1$H-NMR ($CDCl_3$): 7.39-7.29 (m, 6 H), 6.74 (d, J=5.5, 1 H), 5.21 (J=12.3, 1 H), 5.15 (d, J=12.3, 1 H), 5.15 (m, 1 H), 5.00 (br. dd, J=2.7, 10.6, 1 H), 4.40 (br. t, J=7.4, 1 H), 4.23-4.18 (m, 2 H), 3.98 (br. d, J=10.2, 1 H), 3.75-3.61 (m, 2 H), 3.45 (br. d, 1 H), 3.06 (s, 3 H), 2.91 (s, 3 H), 2.58-2.06 (m, 7 H), 1.45 (s, 9 H).

Synthesis of Acid Ex. 416

According to procedure H, ester Ex. 415 (530 mg, 0.84 mmol) was hydrogenolyzed in MeOH (9 mL)/THF (9 mL) in the presence of catalyst (0.55 g) for 6 h to afford after filtration and washing of the residue with $CHCl_3$ Ex. 416 (494 mg, quant. yield).

Data of Ex. 416: $C_{24}H_{34}N_4O_8S$ (538.6). LC-MS (method 4b): $R_t$=1.61 (92), 539 ([M+H]$^+$).

Core 27: Synthesis of Ex. 424 and Ex. 425 (Scheme 31)

Synthesis of Mitsunobu Product 235

Following procedure B.1.2, the reaction of phenol 207 (12.1 g, 26.5 mmol), alcohol 14 (9.57 g, 31.8 mmol) and CMBP (12.8 g, 53.1 mmol) in dry toluene (354 mL) afforded after FC (hexane/EtOAc 50:50 to 0:100) the protected amino acid 235 (19.2 g, 98%).

Synthesis of Amino Acid 236

Following procedure B.2, the reaction of 235 (19.1 g, 25.8 mmol), 1,3-dimethylbarbituric acid (10.1 g, 64.7 mmol) and $Pd(PPh_3)_4$ (0.3 g) in EtOAc/$CH_2Cl_2$ (55:45, 278 mL) yielded after 2 h and after FC ($CH_2Cl_2$/MeOH 98:2 to 90:10, then 70:30) 236 (14.38 g, 91%).

Data of 236: $C_{31}H_{43}N_5O_8$ (613.7). LC-MS (method 4a): $R_t$=1.65 (95), 614 ([M+H]$^+$).

Synthesis of the Protected Macrolactam Ex. 424

According to procedure F.1.1, the amino acid 236 (3.37 g, 5.5 mmol) in dry $CH_2Cl_2$ (50 mL) was treated with T3P (50% in EtOAc; 9.7 mL, 16.5 mmol) and i-$Pr_2$NEt (4.7 mL, 27.6 mmol) in $CH_2Cl_2$ (1100 mL). Aqueous workup ($CH_2Cl_2$, 1 M aq. $Na_2CO_3$ soln) and FC ($CH_2Cl_2$/MeOH 100:0 to 95:5) yielded Ex. 424 (2.58 g, 79%).

Data of Ex. 424: $C_{31}H_{41}N_5O_7$ (595.6). LC-MS (method 11a): $R_t$=1.87 (95), 596 ([M+H]$^+$). $^1$H-NMR (DMSO-$d_6$): 8.39 (d, J=2.7, 1 H), 8.15 (d, J=1.5, 1 H), 7.37-7.26 (m, 7 H), 7.20 (d, J=6.3, 1 H), 4.99 (s, 2 H), 4.65 (d, J=9.8, 1 H), 4.23-3.93 (m, 5 H), 3.16-2.94 (m, 2 H), 3.14 (t, J ca. 9.0, 1 H), 2.94 (s, 3 H), 2.30 (m, 1 H), 2.04 (br. q, 1 H), 1.67 (m, 1 H), 1.41 (s, 9 H), 1.30-0.93 (m, 5 H).

Synthesis of Amine Ex. 425

According to procedure K, benzyl carbamate Ex. 424 (600 mg, 1.0 mmol) was hydrogenolyzed in MeOH (12 mL) in the presence of catalyst (113 mg) for 2 h to afford Ex. 425 (482 mg, quant. yield).

Data of Ex. 425: $C_{23}H_{35}N_5O_5$ (461.5). LC-MS (method 4a): $R_t$=1.32 (99), 462 ([M+H]$^+$).

Core 28: Synthesis of Ex. 435, Ex. 436 and Ex. 437 (Scheme 32)

Synthesis of Mitsunobu Product 237

Tributylphosphine (7.0 mL, 28.2 mmol) was added to a soln of phenol 210 (4.5 g, 9.4 mmol) and alcohol 82 (5.2 g, 14.1 mmol) in dry, degassed benzene (235 mL). The mixture was cooled to 0° C., followed by the slow addition of TMAD (4.85 g, 28.1 mmol) in benzene (40 mL). The soln was stirred for 30 min at 0° C. and for 15 h at rt and filtered. The filtrate was concentrated and purified by FC (hexane/EtOAc 40:60 to 25:75) to yield 237 (7.2 g, 92%).

Synthesis of Amino Acid 238

Following procedure B.2, the reaction of 237 (7.15 g, 8.6 mmol), 1,3-dimethylbarbituric acid (3.35 g, 21.5 mmol) and $Pd(PPh_3)_4$ (0.5 g) in EtOAc/$CH_2Cl_2$ (45:55, 145 mL) yielded after 16 h and after FC ($CH_2Cl_2$/MeOH 100:0 to 70:30) 238 (4.80 g, 79%).

Data of 238: $C_{37}H_{49}N_5O_9$ (707.8). LC-MS (method 10a): $R_t$=1.76 (98), 708 ([M+H]$^+$).

Synthesis of the Protected Macrolactam Ex. 435

According to procedure F.1.1, the amino acid 238 (4.7 g, 6.6 mmol) in dry $CH_2Cl_2$ (100 mL) was treated with T3P (50% in EtOAc; 9.9 mL, 16.7 mmol) and i-$Pr_2$NEt (4.6 mL, 26.8 mmol) in $CH_2Cl_2$ (570 mL). Aqueous workup ($CH_2Cl_2$, sat. aq. $NaHCO_3$ soln) after completion of the addition and FC (EtOAc/$CH_3$CN 95:5) yielded Ex. 435(2.7 g, 58%).

Data of Ex. 435: $C_{37}H_{47}N_5O_8$ (689.8). LC-MS (method 10a): $R_t$=2.06 (100), 690 ([M+H]$^+$). $^1$H-NMR ($C_6D_6$): 7.34-7.09 (m, 8 H), 6.87 (d, J=9.0, 1 H), 5.59 (br. d, J ca. 12.7, 1 H), 5.20 (br. d, J ca. 12.7, 1 H), 5.15 (br. d, J ca. 12.6, 1 H), 4.75-4.60 (m, 3 H), 4.20 (br. d, J ca. 7.6, 1 H), 3.88 (br. d, J ca. 9.4, 1 H), 3.73-3.62 (m, 2 H), ca. 3.2 (m, 1 H), 3.08 (s, 3 H), 2.97 (s, 3 H), 2.75 (s, 3 H), 2.72-2.57 (m, 2 H), 2.27 (s, 3 H), 2.27-2.04 (m, 2 H), 1.58 (s, 9 H), 1.54-1.41 (m, 2 H).

Synthesis of Acid Ex. 436

According to procedure H, a soln of Ex. 435 (300 mg, 0.43 mmol) in MeOH (18 mL)/THF (6 mL) was hydrogenolyzed in the presence of catalyst (163 mg) to yield Ex. 436 (250 mg, 91%).

Data of Ex. 436: $C_{30}H_{41}N_5O_8$ (599.6). LC-MS (method 10a): $R_t$=1.62 (98), 600 ([M+H]$^+$).

Synthesis of Amine Ex. 437

TFA (1 mL) was added at 0° C. to a soln of Ex. 435 (320 mg, 0.46 mmol) in $CH_2C17$ (3 mL). The soln was allowed to warm to rt over 2 h. The volatiles were evaporated. Residual solvent was removed by co-evaporation (twice) with $CHCl_3$ to afford Ex. 437.$CF_3CO_2H$ (322 mg, 98%). Data of Ex. 437.$CF_3CO_2H$: $C_{32}H_{39}H_5O_6.C_2HF_3O_2$ (589.7, free base). LC-MS (method 10a): $R_t$=1.48 (97), 590([M+H]$^+$).

Core 29: Synthesis of Ex. 447 and Ex. 448 (Scheme 33)

Synthesis of bis-olefine 240

A mixture of 194 (1.515 g, 3.64 mmol), 51 (2.72 g, 5.46 mmol), HATU (2.075 g, 5.46 mmol) and HOAt (743 mg, 5.46 mmol) in DMF (36 mL) was cooled to 0° C. i-$Pr_2NEt$ (2.0 mL, 11.7 mmol) was slowly added and the soln was stirred for 2 h. Aqueous workup (EtOAc, 1 M aq. $Na_2CO_3$ soln; $Na_2SO_4$) and FC (hexane/EtOAc afforded 240 (1.96 g, 84%).

Data of 240: $C_{35}H_{39}BrN_2O_5$ (647.6). LC-MS (method 10a): $R_t$=2.99 (93), 649/647 ([M+H]$^+$).

Synthesis of Macrocycle Ex. 447

[1,3-Bis(2,4,6-trimethylphenyl)-2-imidazolidinylidene] dichloro-(3-phenyl-1H-inden-1-ylidene)pyridyl)ruthenium (II) (Umicore M31 catalyst; 10 mg) was added to a degassed soln of 240 (80 mg, 0.124 mmol) in $CH_2Cl_2$ (15 mL). The soln was stirred at 40° C. for 24 h. Evaporation of the solvent and purification by prep. HPLC method 1 afforded Ex. 447 (24 mg, 31%).

Data of Ex. 447: $C_{33}H_{35}BrN_2O_5$ (619.5). LC-MS (method 10b): $R_t$=2.79 (95), 621/619([M+H]$^+$).

Synthesis of Amino Alcohol Ex. 448

A soln of Ex. 447 (79 mg, 0.128 mmol) in MeOH (1.5 mL) and THF (0.5 mL) was hydrogenated for 5 h under normal pressure at rt in the presence of palladium hydroxide on activated charcoal (moistened with 50% $H_2O$; 30 mg). The mixture was filtered through a pad of celite. The filtrate was concentrated, suspended in $CH_2Cl_2$ and filtered. The solid was then further purified by prep HPLC method 1 to afford Ex. 448.$CF_3CO_2H$ (24 mg, 50%).

Data of Ex. 448.$CF_3CO_2H$: $C_{18}H_{26}N_2O_3.C_2HF_3O_2$ (318.4, free base). LC-MS (method 10a): 1.22 (91), 319 ([M+H]$^+$). $^1$H-NMR (DMSO-$d_6$): 7.96 (br. s, 3 H), 7.16 (t, J=7.7, 1 H), 6.78-6.72 (m, 3 H), 5.34 (br. s, 1 H), 4.76 (d, J=11.1, 1 H), 4.18-4.10 (m, 4 H), 3.84 (dd, J=6.7, 10.0, 1 H), 2.83 (t-like m, J ca. 9.4, 1 H), 2.70 (m, 1 H), 2.45 (m, 1 H), 2.25 (m, 1 H), 2.07 (m, 1 H), 1.80-0.80 (several br. m, 8 H).

Core 30: Synthesis of Ex. 451, Ex. 452 and Ex. 453 (Scheme 34)

Synthesis of Mitsunobu Product 241

Following procedure B.1.2, the reaction of thiophenol 212 (2.0 g, 4.4 mmol), alcohol 161 (1.9 g, 5.3 mmol) and CMBP (1.6 g, 6.6 mmol) in dry toluene (87 mL) afforded after 1 h and after FC (hexane/$Et_2O$ 30:70 to 0:100, then hexane/EtOAc 50:50 to 30:70) the protected amino acid 241 (2.43 g, crude, used without further purification).

Synthesis of Amino Acid 242

Following procedure B.2, the reaction of 241 (2.38 g) 1,3-dimethylbarbituric acid (1.1 g, 7.1 mmol) and $Pd(PPh_3)_4$ (0.17 g) in EtOAc/$CH_2Cl_2$ (55:45, 52 mL) yielded after 2 h and after FC (EtOAc, then $CH_2Cl_2$/MeOH 100:0 to 80:20) 242 (1.89 g, 64% over the two steps).

Data of 242: $C_{33}H_{38}BrN_3O_6S$ (684.6). LC-MS (method 10a): $R_t$=1.83 (94), 686/684 ([M+H]$^+$).

Synthesis of the Protected Macrolactam Ex. 451

According to procedure F.1.1, amino acid 242 (1.5 g, 2.2 mmol) in dry $CH_2Cl_2$ (45 mL) was treated with T3P (50% in EtOAc; 4.5 mL, 7.7 mmol) and i-$Pr_2NEt$ (2.6 mL, 15 mmol) in $CH_2Cl_2$ (1080 mL). After 3 h at rt, aqueous workup ($CH_2Cl_2$, sat. aq. $Na_9CO_3$ soln) and FC (hexane/EtOAc/MeOH) yielded Ex. 451 (1.15 g, 79%).

Data of Ex. 451: $C_{33}H_{36}BrN_3O_5S$ (666.6). LC-MS (method 10b): $R_t$=2.33 (96), 668/666 ([M+H]$^+$). $^1$H-NMR (DMSO-$d_6$): 7.85 (s, 0.5 H), 7.69 (d, J=8.0, 0.5 H), 7.57 (d, J=7.6, 2 H), 7.50 (d, J=7.9, 0.5 H), 7.39-7.18 (m, 10.5 H), 5.08 (d, J=12.6, 0.5 H), 4.99 (s, 1 H), 4.96 (d, J=12.8, 0.5 H), 4.49-4.38 (4 d, 2 H), 4.16 (t-like m, 0.5 H), 4.00-3.65 (m, 3 H), 3.60-3.45 (m, 1 H), 3.12-2.98 (m, 3 H), 2.91, 2.89 (2 s, 3 H), 2.55-2.44 (m, 1 H, superimposed by DMSO-d signal), 2.35-2.15 (br. m, 2 H), 1.70-1.20 (several br. m, 4 H).

Synthesis of the Sulfone Ex. 452 m-CPBA (70%; 462 mg, 1.88 mmol) was added at 0° C. to a soln of Ex. 451 (500 mg, 0.75 mmol) in $CH_2Cl_2$ (12 mL). The mixture was stirred for 15 min at 0° C. and for 2 h at rt. The mixture was diluted with $CH_2Cl_2$, washed (sat. aq. $NaHCO_3$ soln, 10% aq. $Na_2S_2O_3$ soln, sat. aq. $NaHCO_3$ soln), dried ($Na_2SO_4$), filtered and concentrated to yield Ex. 452 (471 mg, 89%).

Data of Ex. 452: $C_{33}H_{36}BrN_3O_7S$ (698.6). LC-MS (method 10a): $R_t$=2.13 (95), 700/698 ([M+H]$^+$). $^1$H-NMR (DMSO-$d_6$): 8.16 (s, 0.75 H), 8.05-7.26 (several m, 13.25 H), 5.01 (d, J=12.6, 0.75 H), 4.97 (s, 0.5 H), 4.89 (d, J=12.6, 0.75 H), 4.53 (s, 1.5 H), 4.53-4.10 (m, 2.5 H), 4.10-3.65 (m, 2 H), 3.45 (s, 2 H), 3.25-2.75 (br. m, 3 H), 2.97 (s, 3 H), ca. 2.6 (m, 1 H), 2.35-2.20 (m, 1 H), 1.80-1.30 (m, 4 H).

Synthesis of Amine Ex. 453

$NH_3$ soln (7 M in MeOH, 0.49 mL, 3.43 mmol) was added to a soln of Ex. 452 (600 mg, 0.86 mmol) in MeOH (13 mL). The soln was hydrogenolyzed at rt under normal pressure for 17 h in the presence of 5% palladium on activated charcoal (moistened with 50% $H_2O$; 165 mg). The mixture was filtered through a pad of celite and $Na_2CO_3$. The filtrate was concentrated, dissolved in 1 M aq. HCl soln (15 mL) and washed with EtOAc. Sat. aq. $Na_2CO_3$ soln was added. The aqueous layer was treated with sat. aq. $Na_2CO_3$ soln and repeatedly extracted with $CHCl_3$. The combined organic phase was dried ($Na_2SO_4$), filtered and concentrated to give Ex. 453 (369 mg, 88%).

Data of Ex. 453: $C_{25}H_{31}H_3O_5S$ (485.6). LC-MS (method 10a): $R_t$=1.29 (98), 486 ([M+H]$^+$).

Core 31: Synthesis of Ex. 460, Ex. 461, Ex. 462 and Ex. 466 (Scheme 35)

Synthesis of Mitsunobu Product 243

A soln of phenol 213 (770 mg, 1.9 mmol) in dry benzene (10 mL) was added to a soln of $PPh_3$ (776 mg, 2.9 mmol) and alcohol 161 (865 mg, 2.3 mmol) in benzene (25 mL). The soln was cooled to 0° C. DEAD (40% in toluene, 1.33 mL, 2.9 mmol) was added slowly. The mixture was stirred at rt for 40 h followed by addition of more alcohol 161 (360 mg, 0.97 mmol) in benzene (3 mL), $PPh_3$ (510 mg, 1.9 mmol) and DEAD (40% in toluene, 0.9 mL, 2 mmol). Stirring was continued for 19 h. The mixture was treated with MeOH (1 mL), pre-adsorbed on silica gel and purified by FC (hexane/EtOAc 80:20 to 75:25) to give 243 (810 mg, 56%).

Synthesis of Amino Acid 244

Following procedure B.2, the reaction of 243 (949 mg, 1.27 mmol) 1,3-dimethylbarbituric acid (476 mg, 3.0 mmol) and $Pd(PPh_3)_4$ (73 mg) in EtOAc/$CH_2Cl_2$ (55:45, 22 mL)

yielded after 3 h and after FC (EtOAc; $CH_2Cl_2$/MeOH 95:5 to 75:25) 244 (492 mg, 62%).

Data of 244: $C_{29}H_{39}BrN_2O_6S$ (623.6). LC-MS (method 10a): $R_t$=1.93 (99), 625/623 ([M+H]$^+$).

Synthesis of the Protected Macrolactam Ex. 460

According to procedure F.1.1, amino acid 244 (491 mg, 0.79 mmol) in dry $CH_2Cl_2$ (10 mL) was treated with T3P (50% in EtOAc; 0.93 mL, 1.57 mmol) and i-$Pr_2$NEt (0.54 mL, 3.1 mmol) in $CH_2Cl_2$ (385 mL). After 4 h at rt, aqueous workup ($CH_2Cl_2$, sat. aq. $NaHCO_3$ soln) and FC (hexane/EtOAc 1:2) yielded Ex. 460 (471 mg, 99%).

Data of Ex. 460: $C_{29}H_{37}BrN_2O_5S$ (605.6). LC-MS (method 10a): $R_t$=2.84 (99), 607/605 ([M+H]$^+$). $^1$H-NMR (DMSO-$d_6$): 7.58 (d, J=8.4, 2 H), 7.46 (d, J=8.5, 1 H), 7.34 (d, J=8.4, 2 H), 7.21-7.15 (m, 2 H), 6.82 (d, J=7.6, 1 H), 6.72 (d, J=8.2, 1 H), 4.96 (d, J=9.5, 1 H), 4.53 (s, 2 H), 4.41 (t-like m, 1 H), 4.30-4.10 (m, 3 H), 3.54 (s, 2 H), 3.12 (br. t, J=12.5, 1 H), 2.78 (t-like m, 1 H), 2.35 (d, J=13.9, 1 H), 2.11 (m, 1 H), 1.77 (m, 1 H), 1.61-1.32 (m, 5 H), 1.40 (s, 9 H).

Synthesis of Sulfone Ex. 461 m-CPBA (70%; 440 mg, 1.78 mmol) was added at 0° C. to a soln of Ex. 460 (432 mg, 0.71 mmol) in $CH_2Cl_2$ (10 mL). The mixture was stirred for 15 min at 0° C. and for 2 h at rt. The mixture was diluted with $CH_2Cl_2$, washed (sat. aq. $NaHCO_3$ soln, 10% aq. $Na_2S_2O_9$ soln, sat. aq. $NaHCO_3$ soln), dried ($Na_2SO_4$), filtered and concentrated to yield Ex. 461 (443 mg, 97%).

Data of Ex. 461: $C_{29}H_{37}BrN_2O_7S$ (637.6). LC-MS (method 10a): $R_t$=2.41 (93), 639/637 ([M+H]$^+$). $^1$H-NMR ($CDCl_3$): 7.54-7.42 (m, 4 H), 7.28-7.24 (m, 3 H), 7.20 (td, J=2.6, 6.8, 1 H), 5.16 (d, J=8.4, 1 H), 4.91 (dd, J=1.7, 12.8, 1 H), 4.55 (s, 2 H), 4.40 (t-like m, 1 H), 4.31-4.24 (m, 2 H), 4.15-4.04 (m, 2 H), 3.26-3.16 (m, 3 H), 2.35-2.26 (m, 2 H), 1.76-1.65 (m, 2 H) 1.42 (s, 9 H), 1.25-1.13 (m, 2 H), 1.05-0.80 (m, 2 H).

Synthesis of Amine Ex. 462

A soln of Ex. 461 (414 mg, 0.649 mmol) in dioxane (2.0 mL) was treated at rt with 4M HCl-dioxane (4.0 mL) for 2 h. The mixture was concentrated. The remaining solid was washed with $Et_2O$ and dried i.v. to afford Ex. 462.HCl (325 mg, 87%).

Data of Ex. 462.HCl: cf. Table 47b

Synthesis of Amine Ex. 466

A soln of Ex. 460 (650 mg, 1.073 mmol) in dioxane (3.5 mL) was treated at rt with 4M HCl-dioxane (6.5 mL) for 4 h. The mixture was concentrated. The remaining solid was washed with $Et_2O$ and dried i.v. to afford Ex. 466.HCl (523 mg, 90%).

Data of Ex. 466.HCl: cf. Table 47b

Core 32: Synthesis of Ex. 470-Ex. 475 (Scheme 36)

Synthesis of Acid 246 i-$Pr_2$NEt (2.2 mL, 12.8 mmol) was added to a mixture of acid 196 (2.4 g, 4.3 mmol), aminoester hydrochloride 169.HCl (0.925 g, 5.15 mmol), HATU (2.44 g, 6.4 mmol) and HOAt (0.876 g, 6.4 mmol) in DMF (50 mL). The mixture was stirred at rt for 12 h, treated with 1 M aq. HCl soln and extracted with EtOAc. The organic phase was dried ($Na_2SO_4$), filtered and concentrated. FC (hexane/EtOAc 1:1) afforded 245 (2.42 g, 82%) which was dissolved in THF (34 mL) and treated with 2 M aq. LiOH soln (26.2 mL, 52.4 mmol). The mixture was heated to 60° C. for 5 h. The mixture was acidified with 1 M aq. HCl soln and extracted with EtOAc. The organic phase was dried ($Na_2SO_4$), filtered and concentrated to give 246 (2.3 g 97%).

Data of 246: $C_{29}H_{44}BrN_3O_8Si$ (670.6). LC-MS (method 10a): $R_t$=2.50 (100), 670/672 ([M+H]$^+$).

Synthesis of Amino Acid 249 i-$Pr_2$NEt (1.59 mL, 9.3 mmol) was added to a mixture of acid 246 (2.1 g, 3.1 mmol), aminoester hydrochloride 171.HCl (1.04 g, 3.7 mmol), HATU (1.41 g, 3.7 mmol) and HOAt (0.50 g, 3.7 mmol) in DMF (53 mL). The mixture was stirred at rt for 48 h, diluted with $H_2O$ (170 mL), acidified with 1 M aq. HCl soln (30 mL) and extracted with EtOAc. The organic phase was dried ($Na_2SO_4$), filtered and concentrated. FC (hexane/EtOAc 2:1 to 1:1) afforded 247 (2.58 g, 83%)

At 0° C., TBAF (1 M in THF; 8.4 mL, 8.4 mmol) was added to a soln of 247 (2.52 g, 2.8 mmol) in THF (58 mL). The mixture was stirred at 0° C. to rt for 15 h, treated with sat. aq. $NaHCO_3$ soln and extracted with EtOAc.

The organic phase was dried ($Na_2SO_4$), filtered and concentrated. FC ($CH_2Cl_2$/MeOH 100:0 to 98:2) yielded 248 (1.75 g, 82%), which was dissolved in THF (13 mL) and treated with 2 M aq. LiOH soln (3.45 mL, 6.9 mmol). The mixture was heated to 60° C. for 2 h and concentrated. The residue was dissolved in $H_2O$, acidified with 3 M aq. HCl soln to pH ca. 1 and extracted with EtOAc. The organic phase was dried ($Na_2SO_4$), filtered and concentrated to give a colorless solid (2.2 g), which was suspended in $Et_2O$ and filtered to afford 249.HCl (1.69 g, 94%).

Data of 249.HCl: $C_{37}H_{45}BrN_4O_7$ (737.6, internal salt). LC-MS (method 10d): $R_t$=1.92 (97), 737/739 ([M+H]$^+$).

Synthesis of Macrolactam Ex. 470

According to procedure F.1.1, amino acid 249 (120 mg, 0.16 mmol) in dry $CH_2Cl_2$ (20 mL) was treated with T3P (50% in EtOAc; 0.24 mL, 0.41 mmol) and i-$Pr_2$NEt (0.11 mL, 0.65 mmol) in $CH_2Cl_2$ (140 mL). After 2 h at rt, aqueous workup ($CH_2Cl_2$, sat. aq. $NaHCO_3$ soln) and FC (hexane/EtOAc 10:90 then $CH_2Cl_2$/MeOH 90:10) Ex. 470 (80 mg, 68%) was obtained.

Data of Ex. 470: $C_{37}H_{43}BrN_4O_6$ (719.6). LC-MS (method 10a): $R_t$=2.41 (97), 719/721 ([M+H]$^+$). $^1$H-NMR (DMSO-$d_6$): 7.89-7.79 (m, 4 H), 7.64 (s, 1 H), 7.57-7.36 (m, 6 H), 7.10-7.06 (m, 2 H), 4.31 (br. d, J ca. 8.9, 1 H), 4.24 (br. t, 1 H), 4.12 (m, 1 H), 4.03 (d, J ca. 7.6, 1 H), 3.95 (m, 1 H), 3.71 (t-like m, 1 H), 3.44-3.30 (m, 3 H), 3.15 (br. t, J ca. 12.7, 1 H), 2.98 (dd, J=6.7, 13.2, 1 H), 2.37 (m, 1 H), 2.31 (d, J=13.1, 1 H), 2.05-1.90 (m, 3 H), 1.65-1.37 (m, 5 H), 1.37 (s, 9 H).

Synthesis of the Suzuki Product Ex. 471

A soln of $Na_2CO_3$ (13 mg, 0.125 mmol) in $H_2O$ (0.225 mL) was added to a suspension of Ex. 470 (30 mg, 0.042 mmol), 2-naphthaleneboronic acid (14 mg, 0.083 mmol) and $Pd(PPh_3)_4$ (5 mg) in DME (1.75 mL). The mixture was heated to reflux for 2 h, diluted with $H_2O$ and extracted with EtOAc. The organic layer was dried ($Na_2SO_4$), filtered and concentrated. FC ($CH_2Cl_2$/MeOH) yielded Ex. 471 (20 mg, 62%).

Data of Ex. 471: cf. Table 48b

Synthesis of Amine Ex. 474

A soln of Ex. 471 (15 mg, 0.02 mmol) in dioxane (0.91 mL) was treated with 4M HCl-dioxane (0.66 mL) at rt for 15 h. The volatiles were evaporated to afford Ex. 474.HCl (14 mg, quant. yield).

Data of Ex. 474.HCl: cf. Table 48b

Synthesis of the Suzuki Product Ex. 472

Ex. 472 (20 mg, 62%) was obtained from Ex. 470 (30 mg, 0.042 mmol) and 1H-indol-4-ylboronic acid (6.7 mg, 0.42 mmol) by following the conditions described for the synthesis of Ex. 471.

Data of Ex. 472: cf. Table 48b

Synthesis of Amine Ex. 475

A soln of Ex. 472 (14 mg, 0.02 mmol) in $CH_3CN$ (1.0 mL) and $H_2O$ (0.05 mL) was treated with bismuth(III)-trifluoromethane-sulphonate (12.1 mg, 0.018 mmol) and heated to 75° C. for 5 h. The mixture was diluted with EtOAc, washed (sat. aq. $Na_2CO_3$ soln), dried ($Na_2SO_4$), filtered and concentrated. FC ($CH_2Cl_2$/MeOH 95:5 to 90:10) afforded Ex. 475 (10 mg, 83%).

Data of Ex. 475: cf. Table 48b

Synthesis of Amine Ex. 473

A soln of Ex. 470 (15 mg, 0.02 mmol) in dioxane (0.8 mL) was treated with 4M HCl-dioxane (0.7 mL) at rt for 15 h. The volatiles were evaporated to afford Ex. 473.HCl (13 mg, 92%).

Data of Ex. 473.HCl: cf. Table 48b

Transformations on Solid Support

Core 33: Synthesis of Ex. 476 (Scheme 37)

Synthesis of N-methyl-L-alanine Allyl Ester Hydrochloride (257.HCl)

4M HCl-dioxane (3.0 mL) was added to a suspension of N-methyl L-alanine (256, 1.05 g, 10.1 mmol) in $CH_2Cl_2$ (16 mL). $PCl_5$ (2.54 g, 12.2 mmol) was added portionwise at 0° C. The mixture was allowed to warm to rt over 15 h. The volatiles were evaporated. The residue was dissolved in $CH_2Cl_2$ (10 mL) and allyl alcohol (0.83 mL, 12.2 mmol) was added dropwise. The mixture was stirred for 2 h and concentrated to give 257.HCl (1.80 g, 98%). Data of 257.HCl: $C_7H_{13}NO_2$.HCl (143.2, free base). $^1$H-NMR (DMSO-$d_6$): 9.79 (br. s, 1 H), 9.40 (br. s, 1 H), 5.94 (m, 1 H), 5.38 (qd, J=1.6, 17.3, 1 H), 5.28 (qd, J=1.4, 10.5, 1 H), 4.85 (m, 2 H), 4.41 (q, J ca. 6.8, 1 H), 2.55 (s, 3 H), 1.48 (d, J=7.2, 3 H).

Synthesis of 9 H-fluoren-9-ylmethyl (2S,4R)-4-[(tert-butoxycarbonyl)amino]-2-(hydroxymethyl)tetrahydro-1 H-pyrrole-1-carboxylate (252)

252 was obtained by Fmoc protection of the secondary amino group of 17.HCl with (9 H-fluoren-9-yl)methyl 2,5-dioxopyrrolidin-1-yl carbonate (FmocOSu) in dioxane in the presence of aq. $NaHCO_2$ soln under standard conditions.

Data of 252: $C_{25}H_{30}N_2O_5$ (438.5). LC-MS (method 6): $R_t$=1.26 (99), 439([M+H]$^+$).

Synthesis of 9H-fluoren-9-ylmethyl (2S,4R)-2-(3-[(allyloxy)-carbonyl]phenoxymethyl)-4-aminotetrahydro-1H-pyrrole-1-carboxylate hydrochloride (254.HCl)

Oxalyl chloride (64 mL, 749 mmol) was added to a soln of 3-acetoxybenzoic acid (30 g, 167 mmol) in $CH_2Cl_2$ (300 mL). Few drops of DMF were added. The soln was stirred for 4 h at rt. The volatiles were evaporated. The residue was dissolved in $CH_2Cl_2$ (300 mL) and at 0° C. allyl alcohol (34 mL, 500 mmol) was added. Triethylamine (23 mL, 167 mmol) was slowly added. The mixture was stirred for 1 h at rt followed by an aqueous workup ($CH_2Cl_2$, 1 M aq. HCl soln; $Na_2SO_4$). FC (hexane/EtOAc 17:3) yielded 250 (24.3 g, 65%).

The material was dissolved in THF (485 mL) and treated for 3 h at 0° C. to rt with 3-dimethylaminopropylamine (25 mL, 1.8 mmol). The soln was diluted with EtOAc and washed with 0.1 M aq. HCl soln, then with sat. aq. NaCl soln, dried ($Na_2SO_4$) and concentrated to afford 251 (17.13 g, 85%).

A soln of phenol 251 (3.6 g, 20 mmol), alcohol 252 (11 g, 24 mmol) and $PPh_3$ (6.4 g, 24 mmol) in benzene (140 mL) was cooled to 0° C. DEAD (40% in toluene, 11 mL, 24 mmol) was slowly added.

The mixture was stirred at rt for 16 h. The volatiles were evaporated. FC ($CH_2Cl_2$/EtOAc) afforded 253 (7.35 g, 61%).

Data of 253: $C_{35}H_{30}N_2O_7$ (598.7). LC-MS (method 4b): $R_t$=2.72 (96), 599 ([M+H]$^+$), 243.

A soln of 253 (4.0 g, 6.68 mmol) in dioxane (11 mL) was treated with 4M HCl-dioxane (65 mL) for 3 h at rt.

The volatiles were evaporated to yield 254.HCl (3.75 g, containing ca. 5% of dioxane, quant. yield).

Data of 254.HCl: $C_{30}H_{30}N_2O_5$ (498.6, free base). LC-MS (method 4b): $R_t$=2.00 (97), 499([M+H]$^+$).

Synthesis of 4-(4-((N-((3R,5S)-1-(((9H-fluoren-9-yl)methoxy)-carbonyl)-5-((3-(allyloxycarbonyl)phenoxy)methyl)pyrrolidin-3-yl)benzamido)methyl)-3,5-dimethoxyphenoxy)butanoic acid (255)

$NaBH_3CN$ (117 mg, 1.86 mmol) was added to a mixture of 254.HCl (1.0 g, 1.87 mmol) and 4-(4-formyl-3,5-dimethoxyphenoxy)-butanoic acid (501 mg, 1.86 mmol) in MeOH (33 mL). The mixture was stirred for 1 h at rt. More 4-(4-formyl-3,5-dimethoxyphenoxy)butanoic acid (76 mg, 0.28 mmol) and $NaBH_3CN$ (18 mg, 0.28 mmol) were added and stirring was continued for 15 min, followed by evaporation of the volatiles. The residue was dissolved in EtOAc, washed with 1 M aq. HCl soln and concentrated. The residue was dissolved in $H_2O$ (13 mL). Dioxane (20 mL) and $NaHCO_3$ (471 mg, 5.6 mmol) were added. The mixture was cooled to 0° C. followed by the addition of benzoyl chloride (0.20 mL, 1.68 mmol). The mixture was stirred for 75 min at 0° C. Aqueous workup (EtOAc, 1 M aq HCl soln; $Na_2SO_4$) and FC ($CH_2Cl_2$/MeOH 100:0 to 95:5) gave 255 (930 mg, 58%).

Data of 255: $C_{50}H_{50}N_2O_{11}$ (854.9). LC-MS (method 4b): $R_t$=2.64 (91), 855([M+H]$^+$).

Synthesis of Resin 259

Aminomethyl-PS (0.90 mmol/g; 8.5 g, 7.65 mmol) was swollen in DMF (170 mL) for 30 min and filtered. DMF (85 mL), 255 (6.5 g, 6.89 mmol), i-$Pr_2$NEt (2.6 mL, 15.3 mmol) and HATU (2.91 g, 7.65 mmol) were successively added to the resin and the mixture was shaken for 15 h. The resin was filtered, washed three times with DMF, capped by treatment with acetic anhydride for 30 min (1.4 mL, 15.3 mmol) and i-$Pr_2$NEt (2.6 mL, 15.3 mmol) in DMF (85 mL). The mixture was filtered. The resin was washed three times with DMF, and $CH_2Cl_2$, twice with MeOH and three times with DMF. The resin was twice treated with 2% (v/v) DBU in DMF (85 mL) for 10 min and filtered. The resin was washed three times with DMF and $CH_2Cl_2$, twice with MeOH and dried i.v. to afford resin 259 (12.95 g, loading 0.56 mmol/g).

Synthesis of Resin 260 a) First Coupling Step

Resin 259 (120 mg, 0.067 mmol) was swollen in DMF (1 mL) for 1 h and filtered. DMF (1 mL), Fmoc-3-aminopropanoic acid (Fmoc-Apa-OH; 42 mg, 0.134 mmol), i-$Pr_2$NEt (0.046 mL, 0.269 mmol) and HATU (51 mg, 0.134 mmol) were added. The mixture was shaken for 1 h and filtered. The resin was washed with DMF. The coupling step was repeated. The mixture was filtered and the resin washed three times each with DMF and $CH_2Cl_2$.

b) First Allyl Ester Cleavage $CH_2Cl_2$ (1 mL), phenylsilane (0.08 mL, 0.612 mmol) and $Pd(PPh_3)_4$ (8 mg, 0.007 mmol) were added to the resin. The suspension was shaken for 15 min. The resin was filtered and washed with $CH_2Cl_2$. The deprotection step was repeated. The resin was filtered and washed three times with $CH_2Cl_2$ and DMF, twice with MeOH and then three times with DMF.

c) Second Coupling Step

DMF (1 mL), N-methylalanine allylester hydrochloride (257.HCl; 18 mg, 0.10 mmol), i-$Pr_2$NEt (0.046 mL, 0.269 mmol) and HATU (51 mg, 0.134 mmol) were added. The mixture was shaken for 3 h and filtered. The mixture was filtered and the resin washed three times each with DMF and $CH_2Cl_2$.

d) Second allyl ester cleavage was performed applying the conditions described above for the first allyl ester cleavage step.

e) Fmoc Cleavage

The resin was twice treated with 2% (v/v) DBU in DMF (1 mL) for 10 min and filtered. The resin was washed five times with DMF, then twice with MeOH and $CH_2Cl_2$ to afford resin 260.

Synthesis of the Macrocycle Ex. 476

1. Cyclization on Solid Support

The resin 260 was treated with DMF (1 mL) and FDPP (52 mg, 0.134 mmol) for 15 h. The mixture was washed five times with DMF. DMF (1 mL) and i-$Pr_2NEt$ (0.012 mL, 0.067 mmol) were added to the resin and the mixture was shaken for 15 h. The resin was filtered and washed three times each with DMF and $CH_2Cl_2$, twice with MeOH and three times with $CH_2Cl_2$.

A soln of 20% (v/v) TFA in $CH_2Cl_2$ (1 mL) was added to the resin. The mixture was shaken for 10 min and filtered. The resin was washed with $CH_2Cl_2$. The cleavage step was repeated. The combined filtrates and washings were concentrated and dried i.v. Purification by prep. HPLC method 1 afforded Ex. 476 (5 mg, 16%). Data of Ex. 476: $C_{26}H_{30}N_4O_5$ (478.5). LC-MS (method 10a): $R_t$=1.33 (86), 479 ($[M+H]^+$).

$^1$H-NMR (DMSO-$d_6$): 8.53 (d, J=6.4, 1 H), 7.85-7.78 (m, 3 H), 7.56-7.44 (m, 3 H), 7.38 (t, J=7.8, 1 H), 7.06 (d, J ca. 7.4, 1 H), 6.92 (d, J ca. 7.3, 1 H), 6.48 (br. s, 1 H), 4.61 (m, 1 H), 4.41 (m, 1 H), 4.27 (m, 2 H), ca. 3.8 (m, 2 H, superimposed by $H_2O$ signal), 3.49 (br. d, 1 H), 3.28 (m, 1 H), 3.05 (m, 1 H), 2.99 (s, 3 H), 2.85 (m, 1 H), 2.35-2.26 (m, 3 H), 1.26 (d, J=6.9, 3 H).

2. Cyclization in Solution

The resin 260 was treated with 20% (v/v) TFA in $CH_2Cl_2$ (1 mL) for 10 min and filtered. The resin was washed ($CH_2Cl_2$) and this cleavage step was repeated.

The combined filtrates and washings were concentrated, dissolved in $CH_3CN$, again concentrated and dried i.v. Purification by prep. HPLC method 1 afforded 261.$CF_3CO_2H$ (27 mg, 66%).

Data of 261.$CF_3CO_2H$: $C_{26}H_{32}N_4O_6$.$CF_3CO_2H$ (496.5, free base). LC-MS (method 13): $R_t$=0.80 (97), 497 ($[M+H]^+$).

FDPP (13 mg, 0.033 mmol) was added to a soln of 261.$CF_3CO_2H$ (10 mg, 0.016 mmol) in DMF (16 mL). i-$Pr_2NEt$ (0.003 mL, 0.016 mmol) was added. The soln was stirred at rt for 15 h and concentrated. Purification of the residue by prep. HPLC method 1 afforded Ex. 476 (7 mg, 88%).

LC-MS (method 10a): $R_t$=1.33 (96), 479 ($[M+H]^+$).

General Procedures for the Synthesis of Final Products on Solid Support

Procedure R, exemplified below for Core 03, is generally applicable to macrocyclic core structures with an exocyclic carboxyl and amino group.

Procedure S, exemplified below for Core 11a and Core 27, is generally applicable to macrocyclic core structures with two exocyclic amino groups.

Procedure R: Derivatization of a Carboxyl Group and an Amino Group

Core 03 (Scheme 38)

Synthesis of the N-Protected Amino Acid Ex. 591

A soln of Ex. 4 (5.59 g, 10.2 mmol) in dioxane (23 mL) was treated with 4M HCl-dioxane (45 mL) for 3 h. $Et_2O$ was added. The mixture was filtered. The solid was washed ($Et_2O$) and dried i.v. to afford Ex. 590.HCl (5.46 g; crude, used without further purification).

A soln of Ex. 590.HCl (5.46 g) in dioxane (130 mL) and $H_2O$ (110 mL) was treated with sat. aq. $Na_2CO_3$ soln (14.8 mL). Allyl chloroformate (1.18 mL, 11.1 mmol) was added. The mixture was stirred for 1 h, concentrated to ca. 70% of the original volume and acidified with cold 0.5 M HCl soln (200 mL). The mixture was extracted with EtOAc. The organic layer was dried ($Na_2SO_4$), filtered and concentrated to afford Ex. 591 (5.72 g, quant. yield, contains ca. 5% of dioxane).

Data of Ex. 591: $C_{25}H_{31}FN_4O_8$ (534.5). LC-MS (method 4b): $R_t$=1.58 (91), 535 ($[M+H]^+$).

General Procedure for the Synthesis of the Resins 262

DFPE polystyrene (1% DVB, 100-200 mesh, loading 0.89 mmol/g; 10 g, 8.9 mmol) was swollen in DCE (100 mL) for 1 h. The resin was filtered. DCE (60 mL), a soln of the amine (5-10 equiv.) in DCE (40 mL) and finally trimethyl orthoformate (50 mL) were added. The resin was shaken for 0.5 h at rt, followed by the addition of sodium triacetoxyborohydride (5-10 equiv.). The mixture was shaken for 18 h and the resin was filtered. The resin was successively washed with MeOH, three times each with DCE, DMF, 10% i-$Pr_2NEt$ in DMF, DMF, $CH_2Cl_2$, MeOH and dried i.v. to afford resin 262:

262a (10.8 g, 0.7 mmol/g) was obtained from DFPE polystyrene (1% DVB, 100-200 mesh, loading 0.87 mmol/g; 10 g, 8.7 mmol), N,N-dimethylethylenediamine (3.8 g, 43.5 mmol) and $NaBH(OAc)_3$ (9.2 g, 43.5 mmol).

262b (10.94 g, 0.61 mmol/g) was obtained from DFPE polystyrene (1% DVB, 100-200 mesh, loading 0.87 mmol/g; 10 g, 8.7 mmol), 3-pyridinemethylamine (9.4 g, 87 mmol) and $NaBH(OAc)_3$ (18 g, 87 mmol).

262c (21.1 g, 0.83 mmol/g) was obtained from DFPE polystyrene (1% DVB, 100-200 mesh, loading 0.87 mmol/g; 20 g, 17 mmol), isobutylamine (6.4 g, 87 mmol) and $NaBH(OAc)_3$ (18 g, 87 mmol).

262d (11.74 g, 0.77 mmol/g) was obtained from DFPE polystyrene (1% DVB, 100-200 mesh, loading 0.87 mmol/g; 10 g, 8.7 mmol), 2-naphthylmethylamine (6.8 g, 43.5 mmol) and $NaBH(OAc)_3$ (9.2 g, 43.5 mmol). 262e (2.25 g, 0.60 mmol/g) was obtained from DFPE polystyrene (1% DVB, 100-200 mesh, loading 0.89 mmol/g; 2.0 g, 1.78 mmol), 1-naphthylmethylamine (1.4 g, 8.9 mmol) and $NaBH(OAc)_3$ (1.9 g, 8.9 mmol).

Synthesis of Resins 265

1) Immobilization of Acid Ex. 591

A soln of i-$Pr_2NEt$ (6 equiv.) in $CH_2Cl_2$ (0.15 mL) was added to resin 262 (loading 0.82 mmol/g; 100 mg, 0.082 mmol). A soln of carboxylic acid Ex. 591 (0.67 equiv.) in $CH_2Cl_2$/DMF (1:1; 0.45 mL) and a soln of HATU (3 equiv.) and HOAt (3 equiv.) in DMF (0.4 mL) were added. The mixture was shaken for 16 h and filtered. The resin was washed three times with DMF and $CH_2Cl_2$.

2) Capping

A soln of i-$Pr_2NEt$ (6 equiv.) in $CH_2Cl_2$ (0.15 mL) was added. Acetic anhydride (6 equiv.) in $CH_2Cl_2$/DMF (1:1; 0.75 mL) was added. The mixture was shaken for 0.5 h and filtered. The capping step was repeated. The resin was washed three times with DMF and $CH_2Cl_2$ to give resin 263.

3) Cleavage of the Alloc Group

The conditions described for the synthesis of resin 141 (see below) were applied.

4) Derivatization

The conditions described for the second derivatization step of resin 141 were applied (see below). In case of an isocyanate/isocyanate equivalent or a sulfonyl chloride the derivatization step was repeated once.

5) Release of the Final Products:

The final products of general structure 266 were cleaved from solid support and purified as described for the products of Core 11a (see below).

Exception: Resins 265a-b were treated with 20% TFA in $CH_2Cl_2$ for 3×30 min.

Procedure S: Derivatization of Two Amino Groups

Core 11a (Scheme 39)

Synthesis of Amine Ex. 594

A soln of Ex. 181 (2.0 g, 3.2 mmol) in MeOH (200 mL) was hydrogenolyzed for 3 h at rt under normal pressure in the presence of palladium hydroxide on activated charcoal (15-20% Pd, moistened with 50% $H_2O$; 400 mg). The mixture was filtered through a pad of celite. The residue was washed (MeOH). The combined filtrate and washings were concentrated and dried i.v. to give the corresponding amine (1.57 g), which was dissolved in $CH_2Cl_2$ (8 mL) and treated with sat. aq. $NaHCO_3$ soln (2.9 mL) and allyl chloroformate (0.36 mL, 3.43 mmol). The mixture was stirred at rt for 2 h. The organic phase was separated and concentrated. Purification of the residue by FC (EtOAc) afforded allyl carbamate 138(1.65 g, 92%).

TBAF soln (1 M in THF, 7 mL, 7 mmol) was added at 0° C. to a soln of 138 (1.29 g, 2.24 mmol) in THF (53 mL). The soln was stirred at 0° C. to rt for 3 h and concentrated. The residue was distributed between $CH_2Cl_2$ and sat. aq. $NaHCO_3$ soln. The aqueous phase was separated and extracted with $CH_2Cl_2$. The combined organic phase was dried ($Na_2SO_4$), filtered and concentrated. The residue was dissolved in $CH_2Cl_2$ (10 mL) and treated for 20 min with 25% aq. HCl soln (0.29 mL). The volatiles were evaporated and the residue was dried i.v. to afford Ex. 594HCl (1.14 g; contaminated with ca. 15% tetrabutylammonium salt and used without further purification; yield ca. 90%).

Data of Ex. 594.HCl: $C_{22}H_{30}N_4O_5$.HCl (430.5, free base). LC-MS (method 4a): $R_t$=1.22 (92), 431.3 $[M+H]^+$.

Synthesis of Resin 140

DFPE polystyrene (1% DVB, 100-200 mesh, loading 0.89 mmol/g; 200 mg, 0.178 mmol) was swollen in DCE (2 mL) for 1 h. The resin was filtered. A soln of amine hydrochloride Ex. 594.HCl (ca 85% w/w, 166 mg, 0.303 mmol) in DCE (1.33 mL) and trimethyl orthoformate (0.66 mL, 6.02 mmol) were added. The resin was shaken for 1 h at rt, followed by addition of sodium triacetoxyborohydride (75 mg, 0.356 mmol). The mixture was shaken for 15 h and the resin was filtered. The resin was successively washed three times each with DMF, 10% i-$Pr_2$NEt in DMF, DMF, $CH_2Cl_2$ and dried i.v. to afford resin 140 (293 mg).

Synthesis of Resin 141

1) First Derivatization Step

Resin 140 (loading 0.58 mmol/g; 120 mg, 0.07 mmol) was swollen in DMF (1 mL) for 30 min and filtered. The pre-swelling step was repeated. A soln of i-$Pr_2$NEt (8 equiv.) in $CH_2Cl_2$ (0.15 mL) was added to the resin. A soln of a) the carboxylic acid $R^{III}CO_2H$ (4 equiv.) in $CH_2Cl_2$/DMF (1:1; 0.45 mL) and a soln of HATU (4 equiv.) in DMF (0.4 mL), or b) the carboxylic acid chloride $R^{III}COCl$ (4 equiv.) in $CH_2Cl_2$ (0.45 mL) and $CH_2Cl_2$/DMF (1:1; 0.4 mL), or c) the isocyanate $R^{III}NCO$ or succinimidyl carbamate $R^{III}NHCO_2Su$ (4 equiv.) in $CH_2Cl_2$/DMF (1:1; 0.85 mL), or d) the sulfonyl chloride $R^{III}SO_2Cl$ (4 equiv.) in $CH_2Cl_2$/DMF (1:1; 0.85 mL), or e) the chloroformate $R^{III}OCOCl$ (4 equiv.) in $CH_2Cl_2$ (0.45 mL) and $CH_2Cl_2$/DMF (1:1; 0.45 mL) were added. The mixture was shaken for 1 h and filtered. The resin was washed with DMF. The coupling step was repeated. The resin was washed three times with DMF and $CH_2Cl_2$.

2) Cleavage of the Alloc Group

Phenylsilane (10 equiv.) in $CH_2Cl_2$ (0.5 mL), and $Pd(PPh_3)_4$ (0.2 equiv.) in $CH_2Cl_2$ (0.5 mL), were added to the resin. The mixture was shaken for 15 min and filtered. The resin was washed with $CH_2Cl_2$ and the deprotection step was repeated. The resin was filtered, washed three times each with $CH_7Cl_2$, DMF and twice with MeOH and three times with $CH_2Cl_2$.

3) Second Derivatization Step

The carboxylic acids $R^{IV}CO_2H$, the isocyanates $R^{IV}NCO$ or isocyanate equivalents $R^{IV}NCO_2Su$ and the sulfonyl chlorides $R^{14}SO_2Cl$ were coupled analogously to the first derivatization step, however with two exceptions: a) For couplings of carboxylic PyBOP was used as coupling reagent and b) all couplings were conducted only once.

The resin was filtered, washed three times each with DMF, twice with MeOH and three times with $CH_2Cl_2$ to afford resin 141.

Release of the Final Products

The resin 141 was treated twice with 20% TFA in $CH_2Cl_2$ (1 mL) for 10 min, filtered and washed three times with $CH_2Cl_2$. The combined filtrates and washings were concentrated. The residue was treated with $CH_3CN$, evaporated and dried i.v. Purification of the crude product by normal phase or reversed phase prep. HPLC afforded products of general structure 267.

Core 27 (Scheme 40)

Synthesis of Amine Ex. 593

A soln of Ex. 424 (19.2 g, 32 mmol) in MeOH (385 mL) was hydrogenolyzed for 2 h at rt under normal pressure in the presence of palladium hydroxide on activated charcoal (15-20% Pd, moistened with 50% $H_2O$; 4.0 g). The mixture was filtered through a pad of celite. The residue was washed (MeOH). The combined filtrate and washings were concentrated and dried i.v. to give the corresponding amine (15.5 g), which was dissolved in $CH_2Cl_2$ (90 mL) and treated with sat. aq. $NaHCO_3$ soln (32 mL) and allyl chloroformate (4.40 mL, 41.5 mmol). The mixture was stirred at rt for 2 h. Additional allyl chloroformate (0.9 mL, 8.5 mmol) was added and stirring was continued for 1 h. The mixture was diluted with sat. aq. $NaHCO_3$ soln and extracted with $CH_2Cl_2$. The organic phase was separated and concentrated. Purification of the residue by FC ($CH_2Cl_2$/MeOH 95:5) afforded the allyl carbamate Ex. 592 (15.48 g, 85%).

The material was dissolved in $CH_2Cl_2$ (73 mL) and treated at 0° C. with TFA (73 mL) for 30 min. Stirring was continued at rt for 1 h. The volatiles were evaporated. The residue was treated with sat. aq. $Na_2CO_3$ soln and repeatedly extracted with $CHCl_3$. The organic phase was dried ($Na_2SO_4$), filtered and concentrated. The resulting free amine was dissolved in dioxane (147 mL) and treated with 4M HCl-dioxane (29.5 mL). A precipitate was formed. The volatiles were evaporated. The residue was suspended in $CH_2Cl_2$ and the volatiles were evaporated to afford Ex. 593.2HCl (14.49 g, 87%).

Data of Ex. 593.2HCl: $C_{22}H_{31}H_5O_5$.2HCl (445.5, free base). LC-MS (method 10a): $R_t$=0.98 (96), 446 ($[M+H]^+$).

Synthesis of Resins 269

Resins 269 was prepared from Ex. 593 by applying the conditions described as for the synthesis of resin 141 from Ex. 594. The second derivatization step was repeated once if an isocyanate or isocyanate equivalent or sulfonyl chloride was used.

Release of the Final Products

The final products of general structure 270 were cleaved from solid support and purified as described for the products of Core 11a (see above).

Synthesis of Final Products

Advanced macrocyclic intermediates and final products depicted in Tables 21a-49a (Scheme 26) were prepared starting from the suitable precursor macrocyclic acid or macrocyclic amine applying the general procedures (H-Q, R, S) described above. Deviations from general procedures are indicated in Tables 21a-49a.

Analytical data of these intermediates and final products are depicted in Tables 21b-49b.

IUPAC names of all examples are listed in Tables 20 and 21c-49c.

The generic macrocyclic ring structures (Cores) related to Tables 20-49 are depicted in Scheme 41 in the order of their core numbers.

Reagents used in the derivatizations are commercially available with the exception of few N-succinimidyl carbamates which were synthesized from amines, anilines or heteroaryl amines according to the procedure of K. Takeda et al. *Tetrahedron Lett.* 1983, 24, 4569-4572.

Detailed Description of Selected Examples

Core 03: Synthesis of Selected Advanced Intermediates and Final Products (Scheme 42)

Synthesis of Amide Ex. 27

A mixture of Ex. 4 (432 mg, 0.79 mmol), HATU (597 mg, 1.57 mmol) and HOAt (214 mg, 1.57 mmol) was dissolved in DMF (6 mL). N,N-Dimethylethylenediamine (173 μL, 1.57 mmol) and i-$Pr_2NEt$ (537 μL, 3.14 mmol) were added. The soln was stirred at rt for 15 h and concentrated. The residue was dissolved in $CHCl_3$ and washed with sat. aq. $NaHCO_3$ soln and with $H_2O$. The organic phase was dried ($Na_2SO_4$), filtered and concentrated. FC ($CH_2Cl_2$/MeOH/conc. aq. $NH_3$ soln 100:0:0 to 90:10:0.5) afforded Ex. 27 (405 mg, 83%).

Data of Ex. 27: cf. Table 21b

Synthesis of Amine Ex. 28

A soln of Ex. 27 (400 mg, 0.64 mmol) in dioxane (4 mL) was treated at rt with 4M HCl-dioxane (8 mL) for 2 h. The volatiles were evaporated. The residue was dissolved in $CH_2Cl_2$/MeOH, concentrated and dried i.v. to afford Ex. 28.HCl (343 mg, 90%). Data of Ex. 28: cf. Table 21b Synthesis of Amide Ex. 11

A mixture of Ex. 28.HCl (75 mg, 0.126 mmol), 1H-indole-3-acetic acid (44 mg, 0.253 mmol), HATU (96 mg, 0.253 mmol) and HOAt (34 mg, 0.253 mmol) was dissolved in DMF (2 mL). i-$Pr_2NEt$ (87 μL, 0.505 mmol) was added. The soln was stirred at rt for 15 h and concentrated. The residue was dissolved in $CHCl_3$ and washed with sat. aq. $NaHCO_3$ soln and with $H_2O$. The organic phase was dried ($Na_2SO_4$), filtered and concentrated. FC ($CH_2Cl_2$/MeOH/conc. aq. $NH_3$ soln 100:0:0 to 90:10:1) afforded Ex. 11 (50 mg, 58%). Data of Ex. 11: cf. Table 21b $^1$H-NMR (DMSO-$d_6$): 10.81 (s, 1 H), 8.26 (d, J=7.4, 1 H), 7.62 (t, J=5.5, 1 H), 7.46 (d, J=7.9, 1 H), 7.37-7.15 (m, 4 H), 7.09 (d, J=2.2, 1 H), 7.04 (t, J=7.5, 1 H), 6.92 (t, J ca. 7.4, 1 H), 5.08 (d, J ca. 12.5, 1 H), 4.74 (d, J=8.9, 1 H), 4.37 (d, J=11.0, 1 H), 4.25 (d, J=17.7, 1 H), 4.22-4.13 (m, 2 H), 3.97 (d, J=17.6, 1 H), 3.78 (t, J=8.3, 1 H), 3.41 (s, 2 H), 3.24 (m, 1 H), 3.15 (m, 1 H), 2.98 (t, J=9.2, 1 H), 2.88 (s, 3 H), 2.53 (s, 3 H), 2.41-2.27 (m, 4 H), 2.17 (s, 6 H), 2.04 (m, 1 H), 1.83 (t-like m, 2 H), 1.69 (q-like m, 1 H).

Synthesis of Amide Ex. 48

Ex. 48 (58 mg, 83%) was obtained from Ex. 28.HCl (60 mg, 0.101 mmol) and 2-naphthylacetic acid (23 mg, 0.121 mmol) following the procedure described for the synthesis of Ex. 49 (see below). After purification by FC, the material was submitted to an aqueous extraction ($CHCl_3$, aq. $NaHCO_3$ soln).

Data of Ex. 48: cf. Table 21b

Synthesis of Amide Ex. 49

A mixture of Ex. 28.HCl (60 mg, 0.101 mmol), 1-naphthylacetic acid (23 mg, 0.121 mmol), and HOBt.$H_2O$ (19 mg, 0.121 mmol) was dissolved in $CH_2Cl_2$ (1 mL). N-Cyclohexyl-carbodiimide-N'-methylpolystyrene (1.9 mmol/g; 80 mg, 0.152 mmol) and i-$Pr_2NEt$ (52 μL, 0.303 mmol) were added. The mixture was stirred for 15 h at rt. (Polystyrylmethyl)-trimethylammonium bicarbonate (3.5 mmol/g; 87 mg, 0.303 mmol) was added and stirring was continued for 1 h. The mixture was diluted with $CH_2Cl_2$/MeOH 9:1 (2 mL) and filtered. The polymer was washed with twice with $CH_2Cl_2$/MeOH 8:2 (5 mL). The combined filtrate and washings were concentrated. Purification of the crude product by FC ($CH_2Cl_2$/MeOH/conc. aq. $NH_3$ soln 100:0:0 to 90:10:1) afforded Ex. 49 (58 mg, 83%).

Data of Ex. 49: cf. Table 21b $^1$H-NMR (DMSO-$d_6$): 8.45 (d, J=7.3, 1 H), 8.00-7.87 (m, 2 H), 7.79 (d, J=8.0, 1 H), 7.62 (t, J=5.5, 1 H), 7.53-7.25 (m, 6 H), 7.19 (dd, J=3.0, 8.4, 1 H), 5.10 (d, J=12.3, 1 H), 4.75 (d, J=8.9, 1 H), 4.39 (d, J=10.8, 1 H), 4.27 (d, J=17.8, 1 H), 4.28-4.08 (m, 2 H), 3.95 (d, J=17.9, 1 H), 3.83 (m, 1 H), 3.81 (s, 2 H), 3.24 (m, 1 H), 3.16 (m, 1 H), 3.03 (t, J=9.2, 1 H), 2.87 (s, 3 H), 2.54 (s, 3 H), 2.42-2.27 (m, 4 H), 2.16 (s, 6 H), 2.02 (m, 1 H), 1.84 (t-like m, 2 H), 1.71 (q, J ca. 9.4, 1 H).

Synthesis of Amine Ex. 486

A mixture of activated molecular sieves (powder, 4 Å; 120 mg) and Ex. 28 (free base obtained from acid Ex. 591 (Scheme 38) by coupling of N,N-dimethylethylenediamine according to Procedure L.2 and subsequent cleavage of the Alloc group with $Pd(PPh_3)_4$ and morpholine in THF; 60 mg, 0.115 mmol) was suspended in THF (1 mL). 2-(Naphthalen-1-yl)acetaldehyde (20 mg, 0.115 mmol) in THF (0.25 mL) was added. The mixture was stirred at rt for 4 h. A soln of acetic acid (0.0073 mL, 0.127 mmol) in THF (0.25 mL) was added, followed by $NaBH(OAc)_3$ (49 mg, 0.231 mmol) and stirring was continued for 15 h. Aqueous workup ($CHCl_3$, sat. aq. $NaHCO_3$ soln; $Na_2SO_4$) and purification by FC ($CH_2Cl_2$/MeOH/conc. aq. $NH_3$ soln 98:2:2 to 90:10:2) and by prep. HPLC method 1 afforded Ex. 486.$CF_3CO_2H$ (6 mg; 6%).

Data of Ex. 486.$CF_3CO_2H$: cf. Table 21b

Synthesis of Amide Ex. 30

A mixture of Ex. 4 (400 mg, 0.73 mmol), HATU (552 mg, 1.45 mmol), HOAt (198 mg, 1.45 mmol) and tryptamine (233 mg, 1.45 mmol) was dissolved in DMF (6 mL). i-$Pr_2NEt$ (497 μL, 2.91 mmol) was added. The soln was stirred at rt for 15 h followed by aqueous workup ($CHCl_3$, sat. aq. $NaHCO_3$ soln, $H_2O$). The organic phase was dried ($Na_2SO_4$), filtered and concentrated. FC ($CH_2Cl_2$/MeOH 100:0 to 95:5) afforded Ex. 30 (410 mg, 81%).

Data of Ex. 30: cf. Table 21b $^1$H-NMR (DMSO-$d_6$): 10.80 (s, 1 H), 7.91 (t, J=5.6, 1 H), 7.56 (d, J=7.7, 1 H), 7.32 (d, J=8.0, 1 H), 7.27-7.12 (m, 5 H), 7.06 (t, J=7.5, 1 H), 6.97 (t, J=7.4, 1 H), 5.08 (d, J=12.4, 1 H), 4.75 (d, J=9.3, 1 H), 4.34 (d, J=10.9, 1 H), 4.24 (d, J=17.8, 1 H), 4.10 (t-like m, 1 H), 3.97 (d, J=17.7, 1 H), 3.86 (m, 1 H), 3.77 (m, 1 H), 3.42-3.30 (m, 2 H), 2.96-2.83 (m, 3 H), 2.89 (s, 3 H), 2.50 (s, 3 H, superimposed by DMSO-d signal), 2.27 (m, 2 H), 2.08 (m, 1 H), 1.84 (t-like m, 2 H), 1.65 (q, J=10.8, 1 H), 1.34 (s, 9H).

Synthesis of Amine Ex. 55

A soln of Ex. 30 (380 mg, 0.55 mmol) in dioxane (4 mL) was treated at rt with 4M HCl-dioxane (8 mL) for 4 h. The volatiles were evaporated. The residue was dissolved in dioxane (4 mL) and treated again for 2 h with 4M HCl-dioxane (8 mL). The volatiles were evaporated. The residue was washed with $Et_2O$ and purified by FC ($CH_2Cl_2$/MeOH/conc. aq. $NH_3$ soln 90:10:0 to 90:10:1) to afford Ex. 55 (136 mg, 42%).

Data of Ex. 55: cf. Table 21b

Synthesis of Amide Ex. 498

A mixture of Ex. 5.HCl (874 mg, 1.52 mmol), 1-naphthylacetic acid (564 mg, 3.03 mmol), HATU (1.15 g, 3.03 mmol) and HOAt (412 mg, 3.03 mmol) was dissolved in DMF (9 mL). i-$Pr_2NEt$ (0.778 mL, 4.54 mmol) was added. The soln was stirred at rt for 2 h and concentrated. The residue was dissolved in $CH_2Cl_2$ and washed with sat. aq. $NaHCO_3$ soln and with $H_2O$. The organic phase was dried ($Na_2SO_4$), filtered and concentrated. Purification by FC (EtOAc/MeOH gradient) afforded Ex. 498 contaminated with some i-$Pr_2NEt$ which was removed by extraction ($CH_2Cl_2$, 1 M aq. HCl, sat. aq. $NaHCO_3$ soln) to give Ex. 498 (940 mg, 87%).

Data of Ex. 498: cf. Table 21b

Synthesis of Acid Ex. 499

A soln of Ex. 498 (871 mg, 1.23 mmol) in MeOH (9 mL) was hydrogenolyzed under normal pressure at rt in the presence of palladium hydroxide on activated charcoal (moistened with 50% $H_2O$; 0.14 g) for 2 h. The mixture was filtered through a pad of celite. The filtrate was concentrated to afford Ex. 499 (732 mg; 96%).

Data of Ex. 499: cf. Table 21b

Synthesis of Amide Ex. 488

A mixture of Ex. 499 (70 mg, 0.11 mmol), HATU (86 mg, 0.23 mmol) and HOAt (31 mg, 0.23 mmol) was suspended in DMF (1 mL). 3-Dimethylaminopropylamine (0.028 mL, 0.23 mol) and i-$Pr_2NEt$ (0.039 mL, 0.23 mmol) were added. The mixture was stirred for 3 h and concentrated. Aqueous workup ($CHCl_3$, sat. aq. $NaHCO_3$ soln, $H_2O$; $Na_2SO_4$) and purification by prep. HPLC method 2 afforded Ex. 488 (53 mg, 66%).

Data of Ex. 488: cf. Table 21b

Synthesis of Amide Ex. 485

A mixture of Ex. 499 (70 mg, 0.11 mmol), HATU (86 mg, 0.23 mmol) and HOAt (31 mg, 0.23 mmol) was suspended in DMF (1 mL). N-(2-Aminoethyl)pyridine-2-amine (31 mg, 0.23 mol) and i-$Pr_2NEt$ (0.039 mL, 0.23 mmol) were added. The mixture was stirred for 3 h and concentrated. Aqueous workup ($CHCl_3$, sat. aq. $NaHCO_3$ soln, $H_2O$; $Na_2SO_4$) and purification by prep. HPLC method 2 afforded Ex. 485 (50 mg, 60%).

Data of Ex. 485: cf. Table 21b

Synthesis of Amide Ex. 500

A mixture of Ex. 499 (250 mg, 0.40 mmol), HATU (307 mg, 0.81 mmol) and HOAt (110 mg, 0.81 mmol) was suspended in DMF (2.5 mL). tert. Butyl-2-aminoethylcarbamate (129 mg, 0.81 mmol) and i-$Pr_2NEt$ (0.138 mL, 0.81 mmol) were added. The mixture was stirred for 3 h and concentrated. Aqueous workup ($CHCl_3$, sat. aq. $NaHCO_3$ soln, $H_2O$; $Na_2SO_4$) and purification by prep. HPLC method 2 afforded Ex. 500 (227 mg, 74%).

Data of Ex. 500: cf. Table 21b

Synthesis of Amine Ex. 483

4M HCl-dioxane (2 mL) was added to a soln of Ex. 500 (201 mg, 0.26 mmol) in dioxane (2 mL). The mixture was stirred for 2 h at rt and concentrated to afford Ex. 483.HCl (200 mg, 97%).

Data of Ex. 483.HCl: cf. Table 21b $^1H$-NMR (DMSO-$d_6$): 8.46 (d, J=7.1, 1 H), 8.00-7.78 (several m and br. s, 7 H), 7.52-7.21 (several m, 7 H), 5.15 (d, J=12.3, 1 H), 4.76 (d, J=8.8, 1 H), 4.40 (d, J=10.8, 1 H), 4.28 (d, J=17.7, 1 H), 4.25-4.12 (m, 3 H), 4.03-3.94 (m, 2 H), 3.81 (m, 1 H), 3.81 (s, 2 H), 3.35 (m, 1 H, superimposed by $H_2O$ signal), 3.01 (m, 1 H), 2.90 (m, 1 H), 2.88 (s, 3 H), 2.56 (s, 3 H), 2.42-2.33 (m, 2 H), 2.10 (m, 1 H), 1.91-1.82 (m, 2 H), 1.70 (m, 1 H).

Synthesis of Guanidine Ex. 484

Triethylamine (0.066 mL) was added to a suspension of Ex. 483.HCl (110 mg, 0.158 mmol) in $CHCl_3$ (1 mL). 1,3-Di-Boc-(trifluoromethylsulfonyl)-guanidine (65 mg, 0.17 mmol) was added. The mixture was stirred for 22 h at rt, followed by aqueous workup ($CHCl_3$, sat. aq. $Na_2CO_3$ soln, sat. aq. NaCl soln; $Na_2SO_4$) and purification by FC (EtOAc/MeOH 100:0 to 80:20) to afford a colorless solid (74 mg) which was dissolved in dioxane (1 mL) and treated with 4M HCl-dioxane (1 mL) for 2 h. More 4M HCl-dioxane (1 mL) was added and stirring was continued for 15 h. The volatiles were evaporated and the residue purified by prep. HPLC (method 1) to afford Ex. 484.$CF_3CO_2H$. Data of Ex. 484.$CF_3CO_2H$: cf. Table 21b Synthesis of Amide Ex. 487

At 0° C., pyridine (0.081 mL, 1.0 mmol) and acetic anhydride (0.047 mL, 0.5 mmol) were added to a mixture of Ex. 483.HCl (70 mg, 0.10 mmol) in $CH_2Cl_2$ (1 mL). The mixture was stirred for 2 h and concentrated. Purification by prep. HPLC (method 1) afforded Ex. 487 (53 mg, 75%).

Data of Ex. 487: cf. Table 21b

Synthesis of Urea Ex. 482

Ex. 482.$CF_3CO_2H$ (11 mg, 25%) was obtained from resin 263a (0.7 mmol/g; 118 mg, 0.082 mmol) and 1-naphthyl isocyanate (84 mg, 0.498 mmol) according to procedure R.

The product was purified by prep. HPLC (method 1). Data of Ex. 482.$CF_3CO_2H$: cf. Table 21b Synthesis of Amide Ex. 495

Ex. 495.$CF_3CO_2H$ (11 mg, 24%) was obtained from resin 263a (0.7 mmol/g; 118 mg, 0.083 mmol) and 3-(trifluoromethyl)phenylacetic acid (102 mg, 0.498 mmol) according to procedure R.

The product was purified by prep. HPLC (method 1).

Data of Ex. 495.$CF_3CO_2H$: cf. Table 21b

Synthesis of Amide Ex. 496

Ex. 496.$CF_3CO_2H$ (10 mg, 23%) was obtained from resin 263a (0.7 mmol/g; 118 mg, 0.083 mmol) and 3-methoxyphenylacetic acid (83 mg, 0.489 mmol) according to procedure R.

The product was purified by prep. HPLC (method 1).

Data of Ex. 496.$CF_3CO_2H$: cf. Table 21b

Synthesis of Amide Ex. 497

Ex. 497.$CF_3CO_2H$ (8 mg, 18%) was obtained from the resin 263b (0.61 mmol/g; 130 mg, 0.079 mmol) and 1-naphthylacetic acid (93 mg, 0.498 mmol) according to procedure R.

The product was purified by prep. HPLC (method 1).

Data of Ex. 497.$CF_3CO_2H$: cf. Table 21b

Synthesis of Amide Ex. 501

Ex. 501 (18 mg, 44%) was obtained from resin 263e (0.602 mmol/g; 130 mg, 0.078 mmol) and 2-naphthylacetic acid (86 mg, 0.498 mmol) according to procedure R.

The product was purified by prep. HPLC (method 3).

Data of Ex. 501: cf. Table 21b

Synthesis of Amide Ex. 502

Ex. 502 (19 mg, 48%) was obtained from resin 263e (0.602 mmol/g; 130 mg, 0.078 mmol/g) and 3-chlorobenzoic acid (95 mg, 0.498 mmol) according to procedure R.

The product was purified by prep. HPLC (method 3).

Data of Ex. 502: cf. Table 21b $^1H$-NMR (DMSO-$d_6$): 8.71 (d, J=7.1, 1 H), 8.39 (t-like m, 1 H), 8.10 (m, 1 H), 7.95 (m, 1 H), 7.87-7.82 (m, 2 H), 7.75 (d, J ca. 7.8, 1 H), 7.59-7.42 (m, 6 H), 7.29-7.22 (m, 2 H), 6.91 (dd, J=3.0, 8.4, 1 H), 5.15 (d, J ca. 12.1, 1 H), 4.85-4.70

(m, 2 H), 4.50-4.10 (m, 4 H), 4.03 (d, J=18.1, 1 H), 3.88 (t, J ca. 8.2, 1 H), 3.08 (t-like m, 1 H), 2.90 (m, 1 H), 2.89 (s, 3 H), 2.57 (s, 3 H), 2.50-2.25 (m, 2 H), 2.10-1.80 (m, 4 H).

Synthesis of Amide Ex. 503

Ex. 503 (17 mg, 43%) was obtained from resin 263d (0.77 mmol/g; 108 mg, 0.083 mmol) and 1-naphthoic acid (85.8 mg, 0.498 mmol) according to procedure R.

The product was purified by prep. HPLC (method 3).

Data of Ex. 503: cf. Table 21b

Synthesis of Amide Ex. 12

A mixture of Ex. 55 (68 mg, 0.092 mmol), 1H-indole-3-acetic acid (32 mg, 0.184 mmol), HATU (70 mg, 0.184 mmol) and HOAt (25 mg, 0.184 mmol) was dissolved in DMF (2 mL). i-$Pr_2NEt$ (63 μL, 0.367 mmol) was added. The soln was stirred at rt for 15 h and concentrated. The residue was dissolved in $CHCl_3$ and washed with sat. aq. $NaHCO_3$ soln and with $H_2O$. The organic phase was dried ($Na_2SO_4$), filtered and concentrated. Purification by prep. HPLC, method 1, afforded Ex. 12 (38 mg, 55%).

Data of Ex. 12: cf. Table 21b $^1$H-NMR (DMSO-$d_6$): 10.81 (s, 2 H), 8.26 (d, J=7.2, 1 H), 7.93 (t, J=5.7, 1 H), 7.57 (d, J=7.8, 1 H), 7.46 (d, J=7.7, 1 H), 7.38-6.90 (m, 11 H), 5.10 (d, J=12.1, 1 H), 4.76 (d, J=9.3, 1 H), 4.38 (d, J=10.8, 1 H), 4.26 (d, J=17.8, 1 H), 4.23-4.11 (m, 2 H), 3.96 (d, J=18.0, 1 H), 3.78 (t, J=8.3, 1 H), 3.7-3.25 (m, 3 H), 3.60 (s, 2 H), 3.01-2.81 (m, 2 H), 2.88 (s, 3 H), ca. 2.5 (s, 3 H, superimposed by DMSO-d signal), 2.33 (m, 2 H), 2.06 (m, 1 H), 1.85 (t-like m, 2 H), 1.63 (q, J ca. 10.7, 1 H).

Synthesis of Amide Ex. 16

A mixture of Ex. 55 (68 mg, 0.092 mmol), N,N-dimethyl glycine (19 mg, 0.184 mmol), HATU (70 mg, 0.184 mmol) and HOAt (25 mg, 0.184 mmol) was dissolved in DMF (2 mL). i-$Pr_2NEt$ (63 μL, 0.367 mmol) was added. The soln was stirred at rt for 15 h and concentrated. The residue was dissolved in $CHCl_3$ and washed with sat. aq. $NaHCO_3$ soln and with $H_2O$. The organic phase was dried ($Na_2SO_4$), filtered and concentrated. Purification by prep. HPLC, method 1, afforded Ex. 16.TFA (40 mg, 55%).

Data of Ex. 16.TFA: cf. Table 21b $^1$H-NMR (DMSO-$d_6$): 10.81 (s, 1 H), 9.66 (br. s, $NH^+$), 8.75 (d, J=6.9, 1 H), 7.90 (t, J=5.6, 1 H), 7.56 (d, J=7.8, 1 H), 7.34-7.14 (m, 5 H), 7.06 (t, J ca. 7.5, 1 H), 6.97 (t, J=7.4, 1 H), 5.08 (d, J=12.3, 1 H), 4.78 (d, J=9.2, 1 H), 4.39 (d, J=10.7, 1 H), 4.24 (d, J=17.8, 1 H), 4.24-4.14 (m, 2 H), 4.00 (d, J=17.8, 1 H), 3.96-3.75 (m, 3 H), 3.45-3.35 (m, 2 H), 3.0-2.67 (m, 3 H), 2.90 (s, 3 H), 2.75 (s, 6 H), 2.50 (s, 3 H, superimposed by DMSO-d signal), 2.5-2.27 (m, 2 H); 2.08 (m, 1 H), 1.85 (t-like m, 2 H), 1.64 (q, J=10.8, 1 H).

Synthesis of Amide Ex. 53

Pyridine (2 mL) and acetic anhydride (0.14 mL, 1.48 mmol) were added to a soln of Ex. 5.HCl (95 mg, 0.15 mmol) in dry $CH_2Cl_2$ (2 mL). The soln was stirred at rt for 20 h. The soln was diluted with EtOAc and washed with 1 M aq. HCl soln, sat. aq. NaCl soln, sat. aq. $NaHCO_3$ soln, and sat. aq. NaCl soln. The organic phase was dried ($Na_2SO_4$), filtered and concentrated. FC of the crude product afforded Ex. 53 (60 mg, 70%).

Data of Ex. 53: cf. Table 21b

Synthesis of Acid Ex. 54

A soln of Ex. 53 (58 mg, 0.01 mmol) in MeOH (5 mL) was hydrogenolyzed at rt and normal pressure for 2 h in the presence of palladium hydroxide on activated charcoal (moistened with 50% $H_2O$; 50 mg). The mixture was filtered through a pad of celite. The residue was washed (MeOH). The combined filtrate and washings were concentrated and dried i.v. to yield Ex. 54 (45 mg, 92%).

Data of Ex. 54: cf. Table 21b

Synthesis of Amide Ex. 9

A mixture of Ex. 54 (45 mg, 0.091 mmol), HATU (52 mg, 0.137 mmol) HOAt (19 mg, 0.137 mmol) and tryptamine (22 mg, 0.137 mmol) was dissolved in DMF (1 mL). i-$Pr_2NEt$ (47 μL, 0.274 mmol) was added. The soln was stirred at rt for 20 h followed by aqueous workup ($CHCl_3$, sat. aq. $NaHCO_3$ soln, $H_2O$). The organic phase was dried ($Na_2SO_4$), filtered and concentrated. FC ($CH_2Cl_2$/MeOH 100:0 to 86:14) afforded Ex. 9 (36 mg, 62%).

Data of Ex. 9: cf. Table 21b $^1$H-NMR (DMSO-$d_6$): 10.81 (s, 1 H), 8.06 (d, J=7.0, 1 H), 7.93 (t, J=5.6, 1 H), 7.56 (d, J=7.8, 1 H), 7.34-7.14 (m, 5 H), 7.05 (t, J ca. 7.5, 1 H), 6.97 (t, J ca. 7.4, 1 H), 5.09 (d, J=12.4, 1 H), 4.75 (d, J=9.1, 1 H), 4.38 (d, J=10.8, 1 H), 4.26 (d, J=17.7, 1 H), 4.19-4.10 (m, 2 H), 3.97 (d, J=17.9, 1 H), 3.78 (t, J=8.3, 1 H), 3.43-3.30 (m, 2 H), 2.96-2.83 (m, 3 H), 2.89 (s, 3 H), 2.50 (s, 3 H, superimposed by DMSO-d signal), 2.40-2.27 (m, 2 H), 2.08 (m, 1 H), 1.85 (m, 2 H), 1.71 (s, 3 H), 1.62 (q, J ca. 10.6, 1 H).

Core 10: Synthesis of Selected Advanced Intermediates and Final Products (Scheme 43)

Synthesis of Amide Ex. 166

Pyridine (0.48 mL, 5.9 mmol) and valeroyl chloride (0.141 mL, 1.83 mmol) were added to a mixture of Ex. 165 (345 mg, 0.59 mmol) and $CH_2Cl_2$ (6.0 mL). The mixture was stirred at 0° C. for 1 h followed by the addition of MeOH (0.1 mL). Stirring was continued for 10 min. The volatiles were evaporated. Purification by FC (EtOAc/MeOH 100:0 to 95:5) afforded Ex. 166 (220 mg, 67%).

Data of Ex. 166: cf. Table 28b

Synthesis of Amine Ex. 167

A soln of Ex. 166 (190 mg, 0.345 mmol) in MeOH/THF (3:1; 16 mL) was hydrogenolyzed under normal pressure at rt for 2 h in the presence of palladium hydroxide on activated charcoal (moistened with 50% $H_2O$; 95 mg). The mixture was filtered through a pad of celite. The filtrate was concentrated to afford Ex. 167 (152 mg, quant. yield).

Data of Ex. 167: cf. Table 28b

Synthesis of Amide Ex. 168

A mixture of Ex. 165 (438 mg, 0.94 mmol), 2-naphthylacetic acid (350 mg, 1.88 mmol), HATU (714 mg, 1.88 mmol) and HOAt (256 mg, 1.88 mmol) was dissolved in DMF (5 mL). i-$Pr_2NEt$ (0.65 mL, 3.7 mmol) was added. The soln was stirred at rt for 20 h and concentrated. The residue was dissolved in $CHCl_3$ and washed with sat. aq. $NaHCO_2$ soln. The organic phase was dried ($Na_2SO_4$), filtered and concentrated. FC (EtOAc) afforded Ex. 168 (404 mg, 68%).

Data of Ex. 168: cf. Table 28b $^1$H-NMR (DMSO-$d_6$): 8.45 (d, J=6.4, 1 H), 7.95-7.83 (m, 3 H), 7.74 (s, 1 H), 7.51-7.41 (m, 4 H), 7.36-7.26 (m, 6 H), 7.03 (dd, J=1.3, 8.2, 1 H), 6.96 (d, J=7.5, 1 H), 6.86 (s, 1 H), 4.99 (s, 2 H), 4.55 (d, J=12.1, 1 H), 4.32 (t-like m, 1 H), 4.24-4.04 (m, 4 H), 3.61 (s, 2 H), ca. 3.2 (m, 1 H), 3.15-2.95 (m, 2 H), 2.89 (s, 3 H), 2.35-2.18 (m, 2 H), 2.06 (m, 1 H), 1.90 (m, 1 H).

Synthesis of Amide Ex. 169

A mixture of Ex. 165 (293 mg, 0.63 mmol), 1-pyrrolidineacetic acid (162 mg, 1.25 mmol), HATU (478 mg, 1.25 mmol) and HOAt (171 mg, 1.25 mmol) was dissolved in DMF (5 mL). i-$Pr_2NEt$ (0.43 mL, 2.5 mmol) was added. The soln was stirred at rt for 20 h and concentrated. The residue was dissolved in $CHCl_3$ and washed with sat. aq. $NaHCO_3$ soln. The organic phase was dried ($Na_2SO_4$), filtered and concentrated. FC (EtOAc, then EtOAc/MeOH 9:1) afforded Ex. 169 (277 mg, 76%).

Data of Ex. 169: cf. Table 28b

Synthesis of Amide Ex. 170

A soln of Ex. 167 (62 mg, 0.15 mmol), 3-(pyridine-4-yl) propanoic acid (27 mg, 0.179 mmol) and $HOBt.H_2O$ (27 mg, 0.179 mmol) in $CH_2Cl_2$ (1 mL) was treated with N-cyclohexyl-carbodiimide-N'-methylpolystyrene (1.9 mmol/g; 118 mg, 0.223 mmol) and i-$Pr_2$NEt (0.076 mL, 0.447 mmol). The mixture was stirred for 15 h at rt. (Polystyrylmethyl)trimethylammonium bicarbonate (3.5 mmol/g; 128 mg, 0.447 mmol) was added and stirring was continued for 1 h. The mixture was diluted with $CH_2Cl_2$/MeOH 9:1 (2 mL) and filtered. The polymer was washed twice with $CH_2Cl_2$/MeOH 8:2 (5 mL). The combined filtrate and washings were concentrated. Purification by FC ($CH_2Cl_2$/MeOH 100:0 to 95:5) afforded Ex. 170 (64 mg, 78%).

Data of Ex. 170: cf. Table 28b

Synthesis of Amide Ex. 171

Pyridine (0.12 mL, 1.5 mmol) and 2-naphthoyl chloride (74 mg, 0.38 mmol) were added to a mixture of Ex. 167 (62 mg, 0.15 mmol) and $CH_2Cl_2$ (1.0 mL). The mixture was stirred at 0° C. for 15 h. More 2-naphthoyl chloride (42 mg, 0.22 mmol) was added. Stirring was continued for 1 h followed by addition of MeOH (0.1 mL). Stirring was continued for 10 min. Aqueous workup ($CHCl_3$, sat. aq. $NaHCO_3$ soln; $Na_2SO_4$) and purification by prep. HPLC (method 3) afforded Ex. 171 (36 mg, 42%).

Data of Ex. 171: cf. Table 28b

Synthesis of Amine Ex. 172

A soln of Ex. 168 (380 mg, 0.60 mmol) in MeOH/THF (3:1; 32 mL) was hydrogenolyzed under normal pressure at rt for 2 h in the presence of palladium hydroxide on activated charcoal (moistened with 50% $H_2O$; 190 mg). The mixture was filtered through a pad of celite. The filtrate was concentrated to afford Ex. 172 (292 mg, 97%).

Data of Ex. 172: cf. Table 28b

Synthesis of Amine Ex. 173

A soln of Ex. 169 (257 mg, 0.445 mmol) in MeOH/THF (3:1; 16 mL) was hydrogenolyzed under normal pressure at rt for 2 h in the presence of palladium hydroxide on activated charcoal (moistened with 50% $H_2O$; 190 mg). The mixture was filtered through a pad of celite. The filtrate was concentrated to afford Ex. 173 (190 mg, 96%).

Data of Ex. 173: cf. Table 28b

Synthesis of Amide Ex. 177

A soln of Ex. 172 (65 mg 0.13 mmol), 1-naphthylacetic acid (29 mg, 0.16 mmol) and $HOBt.H_2O$ (24 mg, 0.16 mmol) in $CH_2Cl_2$ (1 mL) was treated with N-cyclohexyl-carbodiimide-N'-methylpolystyrene (1.9 mmol/g; 103 mg, 0.19 mmol) and i-$Pr_2$NEt (0.067 mL, 0.39 mmol). The mixture was stirred for 15 h at rt and filtered. The filtrate was submitted to aqueous workup ($CHCl_3$, sat. aq. $NaHCO_3$ soln; $Na_9SO_4$). Purification by prep. HPLC (method 3) afforded Ex. 177 (59 mg, 68%).

Data of Ex. 177: cf. Table 28b $^1$H-NMR (DMSO-$d_6$): 8.41 (d, J=6.4, 1 H), 8.34 (d, J=7.1, 1 H), 8.03 (d, J=8.2, 1 H), 7.87-7.72 (m, 6 H), 7.49-7.38 (m, 7 H), 7.31 (t, J=7.8, 1 H), 7.00 (dd, J=1.5, 8.2, 1 H), 6.94 (d, J=7.5, 1 H), 6.85 (s, 1 H), 4.53 (t, J=7.3, 1 H), 4.44 (d, J=12.8, 1 H), 4.27-3.96 (m, 5 H), 3.96 (d, J=13.8, 1 H), 3.87 (d, J=14.9, 1 H), 3.57 (s, 2 H), 3.11 (m, 1 H), 2.94 (m, 1 H), 2.85 (s, 3 H), 2.35-2.20 (m, 2 H), 2.05-1.80 (m, 2 H).

Synthesis of Amide Ex. 179

A soln of Ex. 173 (55 mg 0.12 mmol), 1-naphthylacetic acid (28 mg, 0.15 mmol) and $HOBt.H_2O$ (23 mg, 0.15 mmol) in $CH_2Cl_2$ (1 mL) was treated with N-cyclohexyl-carbodiimide-N'-methylpolystyrene (1.9 mmol/g; 98 mg, 0.19 mmol) and i-$Pr_2$NEt (0.064 mL, 0.372 mmol). The mixture was stirred for 15 h at rt. The mixture was filtered. The filtrate was submitted to aqueous workup ($CHCl_3$, sat. aq. $NaHCO_3$ soln; $Na_2SO_4$). Purification by prep. HPLC (method 3) afforded Ex. 179 (64 mg, 84%).

Data of Ex. 179: cf. Table 28b

Core 11a: Synthesis of Selected Advanced Intermediates and Final Products (Scheme 44)

Synthesis of Amide Ex. 184

A mixture of Ex. 182 (500 mg, 1.04 mmol), 2-naphthylacetic acid (232 mg, 1.25 mmol), HATU (791 mg, 2.08 mmol) and HOAt (283 mg, 2.08 mmol) was dissolved in DMF (15 mL). i-$Pr_2$NEt (712 4.16 mmol) was added. The soln was stirred at rt for 20 h and concentrated. The residue was dissolved in $CHCl_3$ and washed with sat. aq. $NaHCO_3$ soln and with $H_2O$. The organic phase was dried ($Na_2SO_4$), filtered and concentrated. FC (EtOAc, then $CH_2Cl_2$/MeOH 95:5) afforded Ex. 184 (637 mg, 94%).

Data of Ex. 184: cf. Table 29.1.b $^1$H-NMR (DMSO-$d_6$): 8.41 (d, J=7.0, 1 H), 7.90-7.83 (m, 3 H), 7.77 (s, 1 H), 7.53-7.44 (m, 4 H), 7.32-7.22 (m, 6 H), 7.04 (d, J=8.4, 1 H), 6.86 (d, J=7.4, 1 H), 6.81 (s, 1 H), 5.02-4.90 (m, 3 H), 4.19 (t, J ca. 8.6, 1 H), 4.14-3.96 (m, 2 H), 3.83 (t-like m, 2 H), 3.63 (s, 2 H), ca. 3.3 (m, 1 H, superimposed by $H_2O$ signal), 3.05 (m, 1 H), 2.95 (m, 1 H), 2.91 (s, 3 H), 2.27 (m, 1 H), 2.16 (br. q, J ca. 11.3, 1 H), 1.54 (m, 2 H), 1.31 (m, 1 H), 1.15 (m, 1 H).

Synthesis of Amine Ex. 194

A soln of Ex. 181 (600 mg, 0.96 mmol) in MeOH (52 mL) was hydrogenolyzed for 4 h at normal pressure and rt in the presence of palladium hydroxide on activated charcoal (moistened with 50% $H_2O$; 300 mg). The mixture was filtered through a pad of celite. The filtrate was concentrated to afford Ex. 194 (471 mg, 100%).

Data of Ex. 194: cf. Table 29.1.b

Synthesis of Amide Ex. 532

At 0° C. tert.-butylacetyl chloride (0.195 mL, 1.39 mmol) was slowly added to a mixture of Ex. 194 (620 mg, 1.26 mmol) and pyridine (0.51 mL, 6.32 mmol) in $CH_2Cl_2$ (6 mL). The mixture was stirred at rt for 2 h, then tert.-butylacetyl chloride (0.04 mL, 0.32 mmol) was added and stirring was continued for 1 h. Aqueous workup ($CH_2Cl_2$, sat. aq. $Na_2CO_3$ soln; $Na_2SO_4$) and FC (hexane/EtOAc/MeOH gradient) afforded Ex. 532 (679 mg, 91%).

Data of Ex. 532: cf. Table 29.1.b

Synthesis of Amine Ex. 533

At 0° C. TFA (3.2 mL) was added to a soln of Ex. 532 (656 mg, 1.11 mmol) in $CH_2Cl_2$ (3.2 mL). The soln was stirred at 0° C. to rt for 1 h. Aqueous workup ($CH_3C1$/1-PrOH 9:1, aq. $Na_2CO_3$ soln; $Na_2SO_4$) afforded Ex. 533 (395 mg, 80%).

Data of Ex. 533: cf. Table 29.1.b

Synthesis of Urea Ex. 552

A soln of Ex. 533 (90 mg, 0.20 mmol) in THF (1 mL) was treated with 2,5-dioxopyrrolidin-1-yl-3-(dimethylamino) phenylcarbamate (62 mg, 0.22 mmol) and i-$Pr_2$NEt (0.069 mL, 0.41 mmol) for 18 h at rt. Aqueous workup ($CHCl_3$, aq. $Na_2CO_3$ soln; $Na_2SO_4$) and prep. HPLC (method 3) afforded Ex. 552 (102 mg, 83%).

Data of Ex. 552: cf. Table 29.1.b

Synthesis of Urea Ex. 553

2,5-Dioxopyrrolidin-1-yl-3-(dimethylamino)phenylcarbamate (177 mg, 0.64 mmol) and i-$Pr_2$NEt (0.2 mL, 1.16 mmol) were added to a soln of Ex. 594 (obtained from Ex. 594.HCl by aqueous extraction ($CH_2Cl_2$, sat. aq. $Na_2CO_3$ soln; 250 mg, 0.58 mmol) in THF (2 mL). The mixture was stirred at rt for 18 h. Aqueous workup ($CHCl_3$, sat. aq. $Na_2CO_3$ soln; $Na_2SO_4$) and FC (hexane/EtOAc/MeOH gradient) afforded Ex. 553 (313 mg, 91%).

Data of Ex. 553: $C_{31}H_{40}N_6O_6$ (592.7). LC-MS (method 4a): $R_t$=1.47 (99), 593 ($[M+H]^+$).

Synthesis of Amine Ex. 554

$Pd(PPh_3)_4$ (5.6 mg) and 1,3-dimethylbarbituric acid (188 mg, 1.2 mmol) were added to a soln of Ex. 553 (285 mg, 0.48 mmol) in degassed $CH_2Cl_2$/EtOAc (45:55; 5.1 mL). The mixture was stirred at rt for 2 h. More $Pd(PPh_3)_4$ (5.6 mg) was added and stirring continued for 1 h. The volatiles were evaporated. FC ($CH_2Cl_2$/MeOH 90:10 to 50:50) afforded Ex. 554 (234 mg, 93%). Data of Ex. 554: $C_{27}H_{36}N_6O_4$ (508.6): LC-MS (method 4a): $R_t$=1.20 (96), 509 ($[M+H]^+$).

Synthesis of Amide Ex. 508

A mixture of Ex. 554 (120 mg, 0.236 mmol), 2-naphthylacetic acid (88 mg, 0.47 mmol), HATU (179 mg, 0.47 mmol) and HOAt (64 mg, 0.472 mmol) in DMF (1.8 mL) was treated with i-$Pr_2$NEt (0.162 mmol, 0.94 mmol) and stirred at rt for 16 h. The mixture was concentrated. Aqueous workup (EtOAc, sat. aq. $NaHCO_3$ soln; $Na_2SO_4$) and FC (hexane/EtOAc/MeOH gradient) gave the product contaminated with a salt of i-$Pr_2$NEt. The material was again extracted ($CH_2Cl_2$, sat. aq. $Na_2CO_3$ soln; $Na_7SO_4$) and purified by FC ($CH_2Cl_2$/MeOH 100:0 to 95:5) to afford Ex. 508 (89 mg, 57%).

Data of Ex. 508: cf. Table 29.1.b $^1$H-NMR (DMSO-$d_6$): 8.48 (d, J=8.1, 1 H), 8.29 (s, 1 H), 7.83-7.73 (m, 3 H), 7.69 (s, 1 H), 7.45-7.29 (m, 4 H), 7.07-7.01 (m, 2 H), 6.90-6.84 (m, 3 H), 6.69 (d, J ca. 8.5, 1 H), 6.39 (d, J=7.5, 1 H), 6.34 (dd, J=2.2, 8.2, 1 H), 4.96 (d, J=12.8, 1 H), 4.23 (t, J=8.0, 1 H), 4.10-3.96 (m, 3 H), 3.71 (t-like m, 1 H), 3.61 (s, 2 H), 3.10 (m, 1 H), 2.90 (m, 1 H), 2.90 (s, 3 H), 2.86 (s, 6 H), 2.42-2.27 (m, 2 H), 2.03 (m, 1 H), 1.67-1.46 (m, 2H), 1.37 (m, 1 H), 1.17 (m, 1 H).

Synthesis of Amide Ex. 186

Ex. 186 (11 mg, 41%) was obtained by treatment of resin 140 (0.77 mmol/g; 50 mg, 0.038 mmol) with 2-naphthylacetic acid (65 mg, 0.35 mmol; first coupling step) and with 2-naphthylacetic acid (70 mg, 0.375 mmol; second coupling step) according to procedure S.

Data of Ex. 186: cf. Table 29.1.b $^1$H-NMR (DMSO-$d_6$): 8.38 (d, J=7.0, 2 H), 7.91-7.69 (m, 8 H), 7.54-7.27 (m, 7 H), 7.03 (dd, J=1.5, 8.2, 1 H), 6.86-6.82 (m, 2 H), 4.94 (d, J=12.7, 1 H), 4.19 (t, J=8.6, 1 H), 4.11-3.94 (m, 3 H), 3.71 (dd, J=9.2, 16.5, 1 H), 3.62 (s, 2 H), 3.58 (s, 2 H), 3.08 (m, 1 H), 2.89 (m, 1 H), 2.89 (s, 3 H), 2.5 (m, 1 H, superimposed by DMSO-d signal), 2.30 (m, 1 H), 2.14 (q-like m, 1 H), 1.64-1.49 (m, 2 H), 1.34 (m, 1 H), 1.14 (m, 1H).

The $^1$H-NMR spectrum is identical with the spectrum of the sample prepared in soln, cf. Table 29.1.

Synthesis of Amide Ex. 504

Ex. 504 (10 mg, 26%) was obtained by treatment of resin 140 (0.48 mmol/g; 120 mg, 0.058 mmol) with 2-naphthylacetic acid (108 mg, 0.576 mmol; first coupling step) and with decanoic acid (50 mg, 0.288 mmol; second coupling step) according to procedure S.

The product was purified by prep. HPLC (method 1).

Data of Ex. 504: cf. Table 29.1.b

Synthesis of Amide Ex. 505

Ex. 505 (7 mg, 33%) was obtained by treatment of resin 140 (0.61 mmol/g; 50 mg, 0.031 mmol) with 2-naphthylacetic acid (114 mg, 0.61 mmol; first coupling step) and with 1-naphthylacetic acid (28 mg, 0.15 mmol; second coupling step) according to procedure S.

The product was purified by prep. HPLC (method 3).

Data of Ex. 505: cf. Table 29.1.b

Synthesis of Amide Ex. 506

Ex. 506 (10 mg, 45%) was obtained by treatment of resin 140 (0.67 mmol/g; 50 mg, 0.034 mmol) with 2-naphthylacetic acid (63 mg, 0.34 mmol; first coupling step) and with 1-isocyanato-3-methylbenzene (14 mg, 0.10 mmol; second coupling step; THF/DMF 1:1 was used instead of $CH_2Cl_2$/DMF) according to procedure S.

The product was purified by prep. HPLC (method 3).

Data of Ex. 506: cf. Table 29.1.b

Synthesis of Amide Ex. 507

Ex. 507 (11 mg, 48%) was obtained by treatment of resin 140 (0.67 mmol/g; 50 mg, 0.034 mmol) with 2-naphthylacetic acid (63 mg, 0.34 mmol; first coupling step) and with 2,5-dioxopyrrolidin-1-yl-3-(dimethylamino)phenylcarbamate (28 mg, 0.10 mmol; second coupling step; THF/DMF 1:1 was used instead of $CH_2Cl_2$/DMF) according to procedure S.

The product was purified by prep. HPLC (method 3).

Data of Ex. 507: cf. Table 29.1.b

Synthesis of Amide Ex. 509

Ex. 509 (20 mg, 48%) was obtained by treatment of resin 140 (0.66 mmol/g; 100 mg, 0.066 mmol) with 3-phenylpropanoic acid (80 mg, 0.53 mmol; first coupling step) and with decanoic acid (46 mg, 0.26 mmol; second coupling step) according to procedure S.

The product was purified by prep. HPLC (method 3).

Data of Ex. 509: cf. Table 29.1.b

Synthesis of Amide Ex. 510

Ex. 510 (11 mg, 20%) was obtained by treatment of resin 140 (0.66 mmol/g; 100 mg, 0.066 mmol) with 3-morpholinobenzoic acid (110 mg, 0.528 mmol; first coupling step) and with decanoic acid (46 mg, 0.26 mmol; second coupling step) according to procedure S.

The product was purified by prep. HPLC (method 3).

Data of Ex. 510: cf. Table 29.1.b

Synthesis of Amide Ex. 511

Ex. 511.$CF_3CO_2H$ (26 mg, 55%) was obtained by treatment of resin 140 (0.61 mmol/g; 100 mg, 0.061 mmol) with 2,5-dioxopyrrolidin-1-yl-3-(dimethylamino)phenylcarbamate (135 mg, 0.49 mmol; first coupling step) and with decanoic acid (42 mg, 0.24 mmol; second coupling step) according to procedure S.

The product was purified by prep. HPLC (method 1).

Data of Ex. 511.$CF_3CO_2H$: cf. Table 29.1.b $^1$H-NMR (DMSO-$d_6$): 8.37 (br. s, 1 H), 8.10 (d, J=8.3, 1 H), 7.34 (t, J ca. 7.8, 1 H), 7.12-7.03 (m, 3 H), 6.89-6.79 (m, 3 H), 6.55-6.47 (m, 2 H), 4.97 (d, J=12.5, 1 H), 4.22 (t, J=8.3, 1 H), 4.08-3.91 (m, 3 H), 3.70 (dd, J=7.5, 9.7, 1 H), 3.16 (m, 1 H), 2.96 (m, 1 H), 2.92 (s, 9 H), 2.45-2.31 (m, 3 H), 2.04 (t-like m, 3 H), 1.64-1.41 (m, 5 H), 1.19 (br. s, 12 H), 0.83 (t, J=6.7, 3 H).

Synthesis of Amide Ex. 512

Ex. 512.$CF_3CO_2H$ (27 mg, 56%) was obtained by treatment of resin 140 (0.61 mmol/g; 100 mg, 0.061 mmol) with 2,5-dioxopyrrolidin-1-yl-3-(dimethylamino)phenylcarbamate (135 mg, 0.49 mmol; first coupling step) and with 1-naphthylacetic acid (45 mg, 0.24 mmol; second coupling step) according to procedure S.

The product was purified by prep. HPLC (method 1).

Data of Ex. 512.$CF_3CO_2H$: cf. Table 29.1.b

Synthesis of Amide Ex. 513

Ex. 513 (10 mg, 25%) was obtained by treatment of resin 140 (0.61 mmol/g; 100 mg, 0.061 mmol) with 1-isocyanato-3-methoxybenzene (73 mg, 0.49 mmol; first coupling step) and with 2-naphthylacetic acid (45 mg, 0.24 mmol; second coupling step) according to procedure S.

The product was purified by prep. HPLC (method 3).

Data of Ex. 513: cf. Table 29.1.b

Synthesis of Amide Ex. 514

Ex. 514 (22 mg, 54%) was obtained by treatment of resin 140 (0.61 mmol/g; 100 mg, 0.061 mmol) with 2-(3-methoxyphenyl)-acetic acid (81 mg, 0.49 mmol; first coupling step) and with 2-naphthylacetic acid (45 mg, 0.24 mmol; second coupling step) according to procedure S.

The product was purified by prep. HPLC (method 3).

Data of Ex. 514: cf. Table 29.1.b

Synthesis of Amide Ex. 515

Ex. 515 (21 mg, 48%) was obtained by treatment of resin 140 (0.61 mmol/g; 100 mg, 0.061 mmol) with 2-(3-phenoxyphenyl)-acetic acid (111 mg, 0.49 mmol; first coupling step) and with decanoic acid (42 mg, 0.24 mmol; second coupling step) according to procedure S.

The product was purified by prep. HPLC (method 3).

Data of Ex. 515: cf. Table 29.1.b

Synthesis of Amide Ex. 516

Ex. 516 (27 mg, 64%) was obtained by treatment of resin 140 (0.61 mmol/g; 100 mg, 0.061 mmol) with 2-naphthylacetic acid (91 mg, 0.49 mmol; first coupling step) and with 6-phenylhexanoic acid (46 mg, 0.24 mmol; second coupling step) according to procedure S.

The product was purified by prep. HPLC (method 3).

Data of Ex. 516: cf. Table 29.1.b

Synthesis of Amide Ex. 517

Ex. 517 (24 mg, 57%) was obtained by treatment of resin 140 (0.61 mmol/g; 100 mg, 0.061 mmol) with 2-naphthylacetic acid (91 mg, 0.49 mmol; first coupling step) and with 5-phenoxypentanoic acid (48 mg, 0.24 mmol; second coupling step) according to procedure S.

The product was purified by prep. HPLC (method 3).

Data of Ex. 517: cf. Table 29.1.b

Synthesis of Amide Ex. 518

Ex. 518 (21 mg, 52%) was obtained by treatment of resin 140 (0.61 mmol/g; 100 mg, 0.061 mmol) with 2-naphthylacetic acid (91 mg, 0.48 mmol; first coupling step) and with (E)-dec-3-enoic acid (42 mg, 0.24 mmol; second coupling step) according to procedure S.

The product was purified by prep. HPLC (method 3).

Data of Ex. 518: cf. Table 29.1.b

Synthesis of Amide Ex. 519

Ex. 519 (24 mg, 59%) was obtained by treatment of resin 140 (0.61 mmol/g; 100 mg, 0.061 mmol) with 1-naphthylacetic acid (91 mg, 0.49 mmol; first coupling step) and with decanoic acid (42 mg, 0.24 mmol; second coupling step) according to procedure S.

The product was purified by prep. HPLC (method 3).

Data of Ex. 519: cf. Table 29.1.b

Synthesis of Amide Ex. 520

Ex. 520 (22 mg, 59%) was obtained by treatment of resin 140 (0.61 mmol/g; 100 mg, 0.061 mmol) with (Z)-hex-3-enoic acid (56 mg, 0.49 mmol; first coupling step) and with 1-naphthylacetic acid (45 mg, 0.24 mmol; second coupling step) according to procedure S.

The product was purified by prep. HPLC (method 3).

Data of Ex. 520: cf. Table 29.1.b

Synthesis of Amide Ex. 521

Ex. 521 (30 mg, 68%) was obtained by treatment of resin 140 (0.61 mmol/g; 100 mg, 0.061 mmol) with 2-naphthylacetic acid (91 mg, 0.49 mmol; first coupling step) and with 6-(benzyloxy)hexanoic acid (54 mg, 0.24 mmol; second coupling step) according to procedure S.

The product was purified by prep. HPLC (method 3).

Data of Ex. 521: cf. Table 29.1.b

Synthesis of Amide Ex. 522

Ex. 522 (27 mg, 62%) was obtained by treatment of resin 140 (0.61 mmol/g; 100 mg, 0.061 mmol) with 2-naphthylacetic acid (91 mg, 0.49 mmol; first coupling step) and with 2-(biphenyl-4-yl)acetic acid (52 mg, 0.24 mmol; second coupling step) according to procedure S.

The product was purified by prep. HPLC (method 3).

Data of Ex. 522: cf. Table 29.1.b

Synthesis of Amide Ex. 523

Ex. 523 (28 mg, 63%) was obtained by treatment of resin 140 (0.61 mmol/g; 100 mg, 0.061 mmol) with 2-naphthylacetic acid (91 mg, 0.49 mmol; first coupling step) and with 3,3-diphenylpropanoic acid (55 mg, 0.24 mmol; second coupling step) according to procedure S.

The product was purified by prep. HPLC (method 3).

Data of Ex. 523: cf. Table 29.1.b

Synthesis of Amide Ex. 524

Ex. 524 (17 mg, 38%) was obtained by treatment of resin 140 (0.61 mmol/g; 100 mg, 0.061 mmol) with 6-(benzyloxy) hexanoic acid (108 mg, 0.49 mmol; first coupling step) and with 6-phenylhexanoic acid (94 mg, 0.48 mmol; second coupling step repeated twice) according to procedure S.

The product was purified by prep. HPLC (method 3).

Data of Ex. 524: cf. Table 29.1.b

Synthesis of Amide Ex. 525

Ex. 525 (27 mg, 54%) was obtained by treatment of resin 140 (0.61 mmol/g; 100 mg, 0.061 mmol) with 2,5-dioxopyrrolidin-1-yl-3-(dimethylamino)phenylcarbamate (135 mg, 0.49 mmol; first coupling step) and with 2-(biphenyl-3-yl) acetic acid (52 mg, 0.24 mmol; second coupling step) according to procedure S.

The product was purified by prep. HPLC (method 3).

Data of Ex. 525: cf. Table 29.1.b $^{1}$H-NMR (DMSO-$d_6$): 8.39 (d, J=7.9, 1 H), 8.25 (br. s, 1 H), 7.61 (d, J=7.0, 2 H), 7.53 (s, 1 H), 7.48-7.42 (m, 3 H), 7.38-7.30 (m, 3 H), 7.22 (d, J=7.6, 1 H), 7.06-7.02 (m, 2 H), 6.93 (br. s, 1 H), 6.87-6.83 (m, 2 H), 6.70 (d, J=7.7, 1 H), 6.39-6.37 (m, 2 H), 4.96 (d, J=12.7, 1 H), 4.23 (t, J=8.4, 1 H), 4.09-3.96 (m, 3 H), 3.73 (t-like m, 1 H), 3.52 (s, 2 H), 3.07 (m, 1 H), 2.93 (m, 1 H), 2.89 (s, 3 H), 2.86 (s, 6 H), 2.50-2.27 (m, 2 H), 2.01 (m, 1 H), 1.64-1.52 (m, 2 H), 1.35 (m, 1 H), 1.14 (m, 1 H).

Synthesis of Amide Ex. 526

Ex. 526 (27 mg, 54%) was obtained by treatment of resin 140 (0.61 mmol/g; 100 mg, 0.061 mmol) with 2,5-dioxopyrrolidin-1-yl-3-(dimethylamino)phenylcarbamate (135 mg, 0.49 mmol; first coupling step) and with 2-(biphenyl-4-yl) acetic acid (52 mg, 0.24 mmol; second coupling step) according to procedure S.

The product was purified by prep. HPLC (method 3).

Data of Ex. 526: cf. Table 29.1.b

Synthesis of Amide Ex. 527

Ex. 527 (27 mg, 61%) was obtained by treatment of resin 140 (0.61 mmol/g; 100 mg, 0.061 mmol) with 2-naphthylacetic acid (91 mg, 0.48 mmol; first coupling step) and with biphenyl-4-sulfonyl chloride (62 mg, 0.24 mmol; second coupling step) according to procedure S.

The product was purified by prep. HPLC (method 3).

Data of Ex. 527: cf. Table 29.1.b

Synthesis of Amide Ex. 537

Ex. 537 (25 mg, 63%) was obtained by treatment of resin 140 (0.61 mmol/g; 100 mg, 0.061 mmol) with 1-fluoro-3-isocyanatobenzene (67 mg, 0.49 mmol; first coupling step)

and with 2-naphthylacetic acid (45 mg, 0.24 mmol; second coupling step) according to procedure S.

The product was purified by prep. HPLC (method 3).

Data of Ex. 537: cf. Table 29.1.b

Synthesis of Amide Ex. 538

Ex. 538.$CF_3CO_2H$ (30 mg, 62%) was obtained by treatment of resin 140 (0.61 mmol/g; 100 mg, 0.061 mmol) with 2,5-dioxopyrrolidin-1-yl 4-(dimethylamino)phenylcarbamate (79 mg, 0.49 mmol; first coupling step) and with 2-naphthylacetic acid (45 mg, 0.24 mmol; second coupling step) according to procedure S.

The product was purified by prep. HPLC (method 1).

Data of Ex. 538.$CF_3CO_2H$: cf. Table 29.1.b

Synthesis of Amide Ex. 539

Ex. 539 (18 mg, 46%) was obtained by treatment of resin 140 (0.61 mmol/g; 100 mg, 0.061 mmol) with phenylchloroformate (76 mg, 0.49 mmol; first coupling step) and with 2-naphthylacetic acid (45 mg, 0.24 mmol; second coupling step) according to procedure S.

The product was purified by prep. HPLC (method 3).

Data of Ex. 539: cf. Table 29.1.b

Synthesis of Amide Ex. 540

Ex. 540 (26 mg, 53%) was obtained by treatment of resin 140 (0.61 mmol/g; 100 mg, 0.061 mmol) with 2-(quinolin-7-yl)acetic acid (92 mg, 0.49 mmol; first coupling step) and with 2-naphthylacetic acid (45 mg, 0.24 mmol; second coupling step) according to procedure S.

The product was purified by prep. HPLC (method 3).

Data of Ex. 540: cf. Table 29.1.b

Synthesis of Amide Ex. 541

Ex. 541 (30 mg, 68%) was obtained by treatment of resin 140 (0.61 mmol/g; 100 mg, 0.061 mmol) with 2-(3-phenoxyphenyl)acetic acid (111 mg, 0.49 mmol; first coupling step) and with 2-naphthylacetic acid (45 mg, 0.24 mmol; second coupling step) according to procedure S.

The product was purified by prep. HPLC (method 3).

Data of Ex. 541: cf. Table 29.1.b

Synthesis of Amide Ex. 542

Ex. 542 (23 mg, 56%) was obtained by treatment of resin 140 (0.61 mmol/g; 100 mg, 0.061 mmol) with decanoic acid (84 mg, 0.49 mmol; first coupling step) and with 2-naphthylacetic acid (45 mg, 0.24 mmol; second coupling step) according to procedure S.

The product was purified by prep. HPLC (method 3).

Data of Ex. 542: cf. Table 29.1.b

Synthesis of Amide Ex. 543

Ex. 543 (25 mg, 61%) was obtained by treatment of resin 140 (0.61 mmol/g; 100 mg, 0.061 mmol) with decanoic acid (84 mg, 0.49 mmol; first coupling step) and with 1-naphthylacetic acid (45 mg, 0.24 mmol; second coupling step) according to procedure S.

The product was purified by prep. HPLC (method 3).

Data of Ex. 543: cf. Table 29.1.b

Synthesis of Amide Ex. 544

Ex. 544 (20 mg, 54%) was obtained by treatment of resin 140 (0.61 mmol/g; 100 mg, 0.061 mmol) with hexanoic acid (57 mg, 0.49 mmol; first coupling step) and with 1-naphthylacetic acid (45 mg, 0.24 mmol; second coupling step) according to procedure S.

The product was purified by prep. HPLC (method 3).

Data of Ex. 544: cf. Table 29.1.b

Synthesis of Amide Ex. 545

Ex. 545 (28 mg, 65%) was obtained by treatment of resin 140 (0.61 mmol/g; 100 mg, 0.061 mmol) with 2-(biphenyl-4-yl)acetic acid (104 mg, 0.49 mmol; first coupling step) and with 1-naphthylacetic acid (45 mg, 0.24 mmol; second coupling step) according to procedure S.

The product was purified by prep. HPLC (method 3).

Data of Ex. 545: cf. Table 29.1.b

Synthesis of Amides Ex. 546 and Ex. 551

Ex. 546 (9 mg, 20%) and Ex. 551 (8 mg, 18%) were obtained by treatment of resin 140 (0.61 mmol/g; 100 mg, 0.061 mmol) with 2,2-diphenylacetic acid (104 mg, 0.49 mmol; first coupling step) and with 2-(biphenyl-4-yl)acetic acid (52 mg, 0.24 mmol; second coupling step) according to procedure S.

The products were purified by prep. HPLC (method 1).

Data of Ex. 546: cf. Table 29.1.b

Data of Ex. 551: cf. Table 29.1.b

Synthesis of Amide Ex. 547

Ex. 547 (29 mg, 65%) was obtained by treatment of resin 140 (0.61 mmol/g; 100 mg, 0.061 mmol) with 2-(biphenyl-4-yl)acetic acid (104 mg, 0.49 mmol; first coupling step) and with 2,2-diphenylacetic acid (52 mg, 0.24 mmol; second coupling step) according to procedure S.

The product was purified by prep. HPLC (method 3).

Data of Ex. 547: cf. Table 29.1.b

Synthesis of Amide Ex. 548

Ex. 548 (12 mg, 28%) was obtained by treatment of resin 140 (0.61 mmol/g; 100 mg, 0.061 mmol) with 2,2-diphenylacetic acid (104 mg, 0.49 mmol; first coupling step) and with decanoic acid (42 mg, 0.24 mmol; second coupling step) according to procedure S.

The product was purified by prep. HPLC (method 1).

Data of Ex. 548: cf. Table 29.1.b

Synthesis of Amide Ex. 549

Ex. 549 (10 mg, 23%) was obtained by treatment of resin 140 (0.61 mmol/g; 100 mg, 0.061 mmol) with 2,2-diphenylacetic acid (104 mg, 0.49 mmol; first coupling step) and with 1-naphthylacetic acid (45 mg, 0.24 mmol; second coupling step) according to procedure S.

The product was purified by prep. HPLC (method 1).

Data of Ex. 549: cf. Table 29.1.b

Synthesis of Amide Ex. 550

Ex. 550 (21 mg, 49%) was obtained by treatment of resin 140 (0.61 mmol/g; 100 mg, 0.061 mmol) with 3,3-diphenylpropanoic acid (110 mg, 0.49 mmol; first coupling step) and with decanoic acid (42 mg, 0.24 mmol; second coupling step) according to procedure S.

The product was purified by prep. HPLC (method 3).

Data of Ex. 550: cf. Table 29.1.b

Core 12: Synthesis of Selected Advanced Intermediates and Final Products (Scheme 45)

Synthesis of Amide Ex. 200

A mixture of Ex. 197.TFA (60 mg, 0.094 mmol), 1H-indole-3-acetic acid (25 mg, 0.14 mmol), HATU (54 mg, 0.14 mmol) and HOAt (19 mg, 0.14 mmol) was dissolved in DMF (1.5 mL). i-$Pr_2NEt$ (81 μL, 0.471 mmol) was added. The soln was stirred for 18 h at rt and concentrated. The residue was dissolved in $CHCl_3$ and washed (sat. aq. $NaHCO_3$ soln, $H_2O$). The organic phase was dried ($Na_7SO_4$), filtered and concentrated, followed by FC (EtOAc, then $CH_2Cl_2$/MeOH 95:5) to afford Ex. 200 (50 mg, 78%).

Data of Ex. 200: cf. Table 30b $^1$H-NMR (DMSO-$d_6$): 10.86 (s, 1 H), 8.42 (d, J=7.8, 1 H), 8.01 (d, J=10.0, 1 H), 7.58 (d, J=7.8, 1 H), 7.36-7.19 (m, 9 H), 7.07-7.02 (m, 2 H), 6.97 (t, J=7.1, 1 H), 6.86 (d, J=7.6, 1 H), 5.08 (s, 2 H), 4.88 (d, J=8.7, 1 H), 4.30-4.10 (m, 2H), 4.13 (d, J=10.9, 1 H), 4.01 (t-like m, 1 H), 3.95 (d, J=18.0, 1 H), 3.75-3.70 (m, 2 H), 3.56 (s, 2 H), 3.4-3.2 (m, 2 H, partially superimposed by $H_2O$ signal), 3.04 (t, J=9.9, 1 H), 2.98 (s, 3 H), 2.65 (s, 3 H), 2.27 (m, 1 H), 2.09 (q, J=11.7, 1 H).

Synthesis of Amine Ex. 202

A soln of Ex. 200 (320 mg, 0.47 mmol) in MeOH (28 mL) was hydrogenolyzed under normal pressure at rt for 4 h in the presence of palladium hydroxide on activated charcoal (moistened with 50% $H_2O$; 158 mg). The mixture was filtered through a pad of celite. The residue was washed (MeOH). The combined filtrate and washings were concentrated and dried i.v. to yield Ex. 202 (250 mg, 97%).

Data of Ex. 202: cf. Table 30b

Synthesis of Amide Ex. 213

A soln of Ex. 202 (60 mg, 0.11 mmol) in dry $CH_2Cl_2$ (1 mL) was treated with pyridine (89 μL, 1.1 mmol). Decanoyl chloride (46 μL, 0.22 mmol) was slowly added at 0° C. The mixture was stirred at 0° C. to rt for 18 h followed by the addition of MeOH (0.1 mL). Stirring was continued for 10 min. The volatiles were evaporated. The residue was treated three times with toluene and evaporated. Purification by prep. HPLC (method 1) and subsequent FC (EtOAc/MeOH 90:10 to 80:20) afforded Ex. 213 (27 mg, 35%).

Data of Ex. 213: cf. Table 30b $^1$H-NMR (DMSO-$d_6$): 10.86 (s, 1 H), 8.53 (d, J=9.8, 1 H), 8.44 (d, J=7.7, 1 H), 7.57 (d, J=7.7, 1 H), 7.35-7.30 (m, 3 H), 7.27 (s, 1 H), 7.19-6.95 (m, 3 H), 6.84 (d, J=7.5, 1 H), 4.86 (dd, J=2.4, 11.2, 1 H), 4.60 (q, J=8.4, 1 H), 4.25 (q-like m, 1 H), 4.14 (d, J=10.7, 1 H), 4.04-3.82 (m, 3 H), 3.73 (t, J ca. 8.5, 1 H), 3.55 (s, 2 H), 3.24 (d, J=7.8, 2 H), 3.09 (t, J=9.5, 1 H), 2.99 (s, 3 H), 2.67 (s, 3 H), 2.26 (m, 1 H), 2.15 (t, J=7.2, 2 H), 2.09 (m, 1 H), 1.51 (t-like m, 2 H), 1.24 (s, 12 H), 0.85 (t, J=6.6, 3 H).

Core 21: Synthesis of Selected Advanced Intermediates and Final Products (Scheme 46)

Synthesis of Amide Ex. 316

A mixture of Ex. 314 (500 mg, 0.91 mmol), HATU (693 mg, 1.82 mmol) and HOAt (248 mg, 1.82 mmol) in DMF (7 mL) was treated with 2-naphthylmethylamine (287 mg, 1.82 mmol) and i-$Pr_2$NEt (0.6 mL, 3.65 mmol) for 15 h. The volatiles were evaporated. Aqueous workup ($CHCl_3$, sat. aq. $NaHCO_3$ soln, $H_2O$; $Na_2SO_4$) and FC ($CH_2Cl_2$/MeOH 97:3 to 95:5) afforded Ex. 316 (542 mg, 86%).

Data of Ex. 316: cf. Table 37.2.b

Synthesis of Amide Ex. 317

A mixture of Ex. 314 (500 mg, 0.91 mmol), HATU (693 mg, 1.82 mmol) and HOAt (248 mg, 1.82 mmol) in DMF (7 mL) was treated with N,N-dimethylethylenediamine (0.2 mL, 1.82 mmol) and i-$Pr_2$NEt (0.6 mL, 3.65 mmol) for 15 h. The volatiles were evaporated. Aqueous workup ($CHCl_3$, sat. aq. $NaHCO_3$ soln, $H_2O$; $Na_2SO_4$) and FC ($CH_2Cl_2$/MeOH 90:10 to 80:20) afforded 317 (406 mg, 72%).

Data of Ex. 317: cf. Table 37.2.b

Synthesis of Amine Ex. 318

A soln of Ex. 316 (500 mg, 0.727 mmol) in dioxane (4.5 mL) was treated with 4M HCl-dioxane (9 mL) at rt for 3 h. The volatiles were evaporated to give Ex. 318.HCl (479 mg, quantitative yield).

Data of Ex. 318.HCl: cf. Table 37.2.b

Synthesis of Amine Ex. 319

A soln of Ex. 317 (360 mg, 0.582 mmol) in dioxane (3.6 mL) was treated with 4M HCl-dioxane (7.3 mL) at rt for 3 h. The volatiles were evaporated to give Ex. 319.HCl (391 mg, quant. yield).

Data of Ex. 319.HCl: cf. Table 37.2.b

Synthesis of Amide Ex. 320

A suspension of Ex. 318 (80 mg, 0.128 mmol) in $CH_2Cl_2$ (1.5 mL) was treated at rt with pyridine (0.10 mL, 1.28 mmol) and acetic anhydride (0.06 mL, 0.64 mmol) for 15 h. MeOH (0.15 mL) was added and stirring was continued for 15 min. The volatiles were evaporated and the residue purified by prep. HPLC (method 1) to afford Ex. 320 (35 mg, 43%).

Data of Ex. 320: cf. Table 37.2.b

Synthesis of Amide Ex. 321

A mixture of Ex. 318 (80 mg, 0.13 mmol), 3-(pyridine-4-yl)propanoic acid (21 mg, 0.14 mmol), HATU (73 mg, 0.19 mmol) and HOAt (26 mg, 0.19 mmol) in DMF (2.2 mL) was treated with i-$Pr_2$NEt (0.11 mL, 0.64 mmol) for 15 h. The volatiles were evaporated. Aqueous workup ($CHCl_3$, sat. aq. $NaHCO_3$ soln, $H_2O$; $Na_2SO_4$) and prep. HPLC (method 1) afforded Ex. 321.$CF_3CO_2H$ (42 mg, 39%).

Data of Ex. 321.$CF_3CO_2H$: cf. Table 372.2.b

Synthesis of Amide Ex. 322

Pyridine (0.10 mL, 1.28 mmol) and valeroyl chloride (0.031 mL, 0.256 mmol) were added to a mixture of Ex. 318 (80 mg, 0.13 mmol) and $CH_2Cl_2$ (1.5 mL). The mixture was stirred at rt for 15 h followed by the addition of MeOH (0.15 mL). Stirring was continued for 10 min. The volatiles were evaporated. Purification by prep. HPLC (method 1) afforded Ex. 322 (43 mg, 49%).

Data of Ex. 322: cf. Table 37.2.b

Synthesis of Amide Ex. 326

A mixture of Ex. 319 (65 mg, 0.11 mmol), 3-(pyridine-4-yl)propanoic acid (33 mg, 0.22 mmol), HATU (84 mg, 0.22 mmol) and HOAt (30 mg, 0.22 mmol) in DMF (1.5 mL) was treated with i-$Pr_2$NEt (0.075 mL, 0.44 mmol) for 15 h. Aqueous workup ($CHCl_3$, sat. aq. $NaHCO_3$ soln, $H_2O$; $Na_2SO_4$) and prep. HPLC (method 2) afforded Ex. 326 (42 mg, 39%).

Data of Ex. 326: cf. Table 37.2.b

Core 24a: Synthesis of Selected Advanced Intermediates and Final Products (Scheme 47)

Synthesis of Amide Ex. 382 i-$Pr_2$NEt (0.079 mL, 0.462 mmol) was added to a mixture of Ex. 380 (100 mg, 0.231 mmol), 2-naphthylacetic acid (86 mg, 0.462 mmol), HATU (176 mg, 0.462 mmol) and HOAt (63 mg, 0.462 mmol) in DMF (1 mL). The mixture was stirred at rt for 16 h and concentrated. Aqueous workup ($CH_2Cl_2$, sat. aq. $NaHCO_3$ soln, $Na_2SO_4$) and FC (hexane/EtOAc/MeOH gradient) and FC ($CH_2Cl_2$/MeOH) gave Ex. 382 (101 mg, 72%).

Data of Ex. 382: cf. Table 40.1.b

Synthesis of Amine Ex. 384

A soln of Ex. 382 (82 mg, 0.137 mmol) in dioxane (1 mL) was treated with 4M HCl-dioxane (1.0 mL) for 2 h at rt. The volatiles were evaporated. The residue was washed with $Et_2O$ to give Ex. 384.HCl (70 mg, 96%)

Data of Ex. 384.HCl: cf. Table 40.1.b

Synthesis of Amide Ex. 386

2,5-Dioxopyrrolidin-1-yl-3-(dimethylamino)phenylcarbamate (36 mg, 0.129 mmol) and i-$Pr_2$NEt (0.06 mL, 0.352 mmol) were added to a suspension of Ex. 384.HCl (63 mg, 0.117 mmol) in THF (1.0 mL). Stirring of the mixture at rt for 16 h followed by aqueous workup ($CH_2Cl_2$, sat. aq. $Na_2CO_3$ soln, $Na_2SO_4$) and FC (hexane/EtOAc/MeOH gradient) gave Ex. 386 (43 mg, 55%).

Data of Ex. 386: cf. Table 40.1.b

Synthesis of Amide Ex. 388

At rt Ex. 379 (93 mg, 0.164 mmol) was treated with 4M HCl-dioxane (3 mL) for 4 h. The volatiles were evaporated to afford Ex. 387.HCl (86 mg).

i-$Pr_2$NEt (0.084 mL, 0.49 mmol) was added to a mixture of crude Ex. 387.HCl (82 mg), 2-naphthylacetic acid (36 mg, 0.196 mmol), HATU (93 mg, 0.245 mmol) and HOAt (33 mg, 0.245 mmol) in DMF (2.4 mL). The mixture was stirred at rt for 20 h and concentrated. Aqueous workup ($CH_2Cl_2$, 1 M aq. $Na_2CO_3$ soln, $Na_2SO_4$) and FC (hexane/EtOAc/MeOH gradient) gave Ex. 388 (64 mg, 61%).

Data of Ex. 388: cf. Table 40.1.b

Synthesis of Amide Ex. 389 i-$Pr_2$NEt (0.079 mL, 0.462 mmol) was added to a mixture of Ex. 380 (100 mg, 0.231 mmol), decanoic acid (80 mg, 0.462 mmol), HATU (176 mg, 0.462 mmol) and HOAt (63 mg, 0.462 mmol) in DMF (1 mL). The mixture was stirred at rt for 16 h and concentrated. Aqueous workup ($CH_2Cl_2$, sat. aq. $NaHCO_3$ soln, $Na_2SO_4$) and FC (hexane/EtOAc/MeOH gradient) gave Ex. 389 (97 mg, 71%).

Data of Ex. 389: cf. Table 40.1.b

Synthesis of Amine Ex. 390

A soln of Ex. 389 (81 mg, 0.138 mmol) in dioxane (1 mL) was treated with 4M HCl-dioxane (1.0 mL) for 2 h at rt. The volatiles were evaporated. The residue was washed with $Et_2O$ to give Ex. 390.HCl (76 mg, 91%).

Data of Ex. 390.HCl: cf. Table 40.1.b

Synthesis of Amide Ex. 391 i-$Pr_2$NEt (0.062 mL, 0.12 mmol) was added to a mixture of Ex. 390.HCl (63 mg 0.12 mmol), 2-naphthylacetic acid (45 mg, 0.241 mmol), HATU (92 mg, 0.241 mmol) and HOAt (33 mg, 0.241 mmol) in DMF (1 mL). The mixture was stirred at rt for 2 h and concentrated. Aqueous workup ($CH_2Cl_2$, sat. aq. $NaHCO_3$ soln, $Na_2SO_4$) and FC (hexane/EtOAc/MeOH gradient) afforded Ex. 391 (56 mg, 70%).

Data of Ex. 391: cf. Table 40.1.b

The generic macrocyclic ring structures (Cores) related to Tables 20-49 are depicted in Scheme 41 in the order of their core numbers.

TABLE 20

Examples of Core 01 and Core 02 (Ex.1-Ex.2)

| No | | | IUPAC name |
|---|---|---|---|
| Core 01 | $R^2$ | $R^{54}$ | |
| Ex.1 | 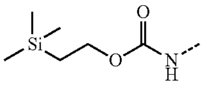 | $OCH_2Ph$ | 8-benzyl 2-[2-(trimethylsilyl) ethyl] (2S,8S,16aS)-12-fluoro-9-methyl-5,10-dioxo-2,3,5,6,7,8,9,10,16,16a-decahydro-1H-pyrrolo[2,1-c] [1,4,9] benzoxadiazacyclo-dodecine-2,8-dicarboxylate |
| Core 02 | $R^{11}$ | $R^{54}$ | |
| Ex.2 | 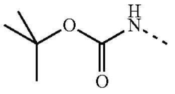 | $OCH_2Ph$ | 9-benzyl 2-(tert-butyl) (9S,17aS)-13-fluoro-10-methyl-6,11-dioxo-3,4,6,7,8,9,10,11,17,17a-decahydropyrazino [2,1-c] [1,4,9] benzoxadiazacyclo-dodecine-2,9(1H)-dicarboxylate |

TABLE 21a

Examples of Core 03

(Ex.3-Ex.55, Ex.482-Ex.503 and Ex.590-Ex.591; continued on the following pages)

Ex.3-Ex.5: cf. experimental description

| No | $R^{54}$ | $R^2$ | Starting material | General Procedure | Purification Reagent | Yield Method | (isolated salt) |
|---|---|---|---|---|---|---|---|
| Ex.6 | OH | 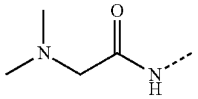 | Ex.52 | H | H2, Pd(OH)2-C*) | Crude product | 70% |
| Ex.7 | 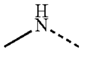 | 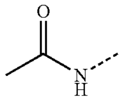 | Ex.25 | L.1.1 | acetic anhydride (5 equiv.) | prep. HPLC, method 1 | 56% |
| Ex.8 | 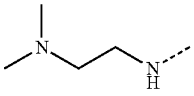 | 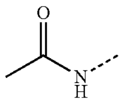 | Ex.28 | L.1.1 | acetic anhydride (10 equiv.) | prep. HPLC, method 1 | 26% (TFA salt) |
| Ex.9 | 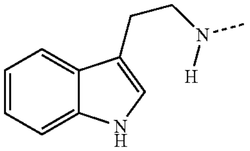 | 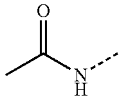 | Ex.53 | L.2 | tryptamine (1.5 equiv.) HATU (1.5 equiv.) HOAt (1.5 equiv.) i-$Pr_2$NEt (3 equiv. ) | FC ($CH_2Cl_2$/MeOH) | 62% |
| Ex.10 | 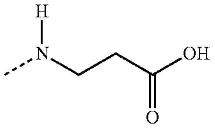 | 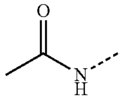 | Ex.31 | N | LiOH•$H_2O$ | prep. HPLC, method 1 | 57% |

TABLE 21a-continued

Examples of Core 03
(Ex.3-Ex.55, Ex.482-Ex.503 and Ex.590-Ex.591; continued on the following pages)
Ex.3-Ex.5: cf. experimental description

| No | $R^{54}$ | $R^2$ | Starting material | General Procedure | Purification Reagent | Yield Method | (isolated salt) |
|---|---|---|---|---|---|---|---|
| Ex.11 | 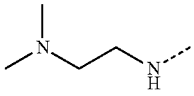 | 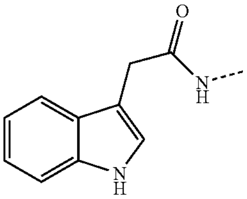 | Ex.28 | L.1.3 | 3-indoleacetic acid | FC ($CH_2Cl_2$/ MeOH/ aq. $NH_3$) | 58% |
| Ex.12 | 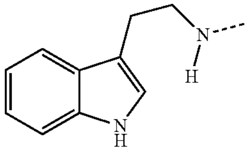 | 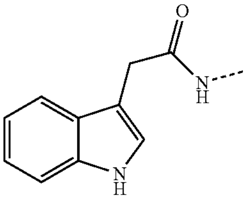 | Ex.55 | L.1.3 | 3-indoleacetic acid | prep. HPLC, method 1 | 55% |
| Ex.13 | 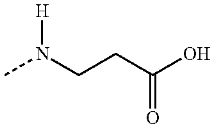 | 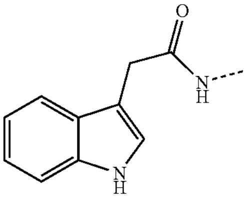 | Ex.34 | N | LiOH•$H_2O$ | prep. HPLC, method 1 | 60% |
| Ex.14 | 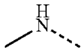 | 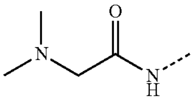 | Ex.25 | **) | N,N-dimethyl glycine | prep. HPLC, method 1 | 22% (TFA salt) |
| Ex.15 | 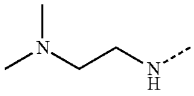 | 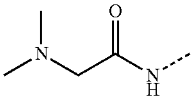 | Ex.28 | L.1.3 | N,N-dimethyl glycine | prep. HPLC, method 1 | 42% (TFA salt) |
| Ex.16 | 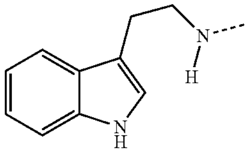 | 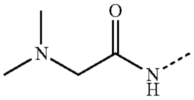 | Ex.55 | L.1.3 | N,N-dimethyl glycine | prep. HPLC, method 1 | 56% (TFA salt) |
| Ex.17 | 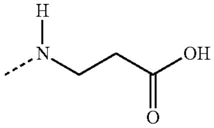 | 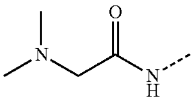 | Ex.33 | N | LiOH•$H_2O$ | prep. HPLC, method 1 | 77% (TFA salt) |
| Ex.18 | 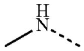 | 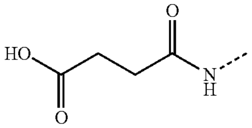 | Ex.25 | L.1.1 | succinic anhydride (1.05 equiv) | prep. HPLC, method 1 | 62% |
| Ex.19 | 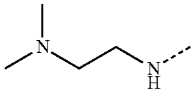 | 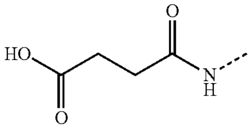 | Ex.28 | L.1.1 | succinic anhydride (1.05 equiv) pyridine (49 equiv.) | prep. HPLC, method 1 | 67% (TFA salt) |

TABLE 21a-continued

Examples of Core 03
(Ex.3-Ex.55, Ex.482-Ex.503 and Ex.590-Ex.591; continued on the following pages)
Ex.3-Ex.5: cf. experimental description

| No | $R^{54}$ | $R^2$ | Starting material | General Procedure | Purification Reagent | Yield Method | (isolated salt) |
|---|---|---|---|---|---|---|---|
| Ex.20 | 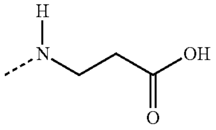 | 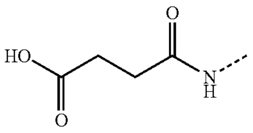 | Ex.32 | N | LiOH•$H_2O$ | prep. HPLC, method 1 | 75% |
| Ex.21 | 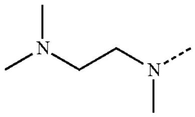 | 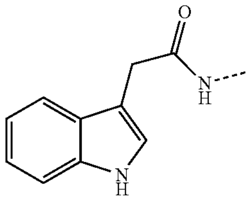 | Ex.23 | L.1.3 | 3-indoleacetic acid | prep. HPLC, method 1 | 32% |
| Ex.22 | 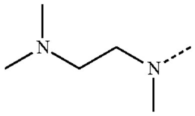 | 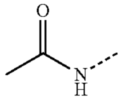 | Ex.23 | L.1.1 | acetic anhydride (10 equiv) pyridine (120 equiv.) | prep. HPLC, method 1 | 53% (TFA salt) |
| Ex.23 | 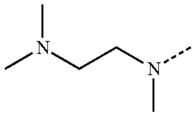 | $NH_2$ | Ex.29 | J | HCl-dioxane | prep. HPLC, method 1 | 52% (TFA salt) |
| Ex.24 | 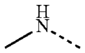 | 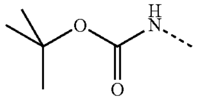 | Ex.4 | L.2 | methylamine-HCl (10 equiv.), HATU (1.5 equiv.) HOAt (1.5 equiv.) i-$Pr_2$NEt (13 equiv.) | FC ($CH_2Cl_2$/MeOH) | 89% |
| Ex.25 | 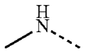 | $NH_2$ | Ex.24 | J | HCl-dioxane | crude product | 84% (HCl salt) |
| Ex.26 | 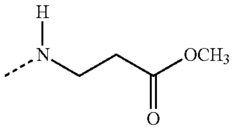 | 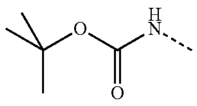 | Ex.4 | L.2 | β-alanine-methylester hydrochloride | FC ($CH_2Cl_2$/MeOH) | 97% |
| Ex.27 | 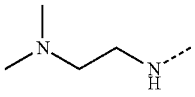 | 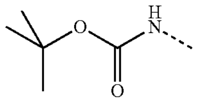 | Ex.4 | L.2 | N,N-dimethyl-ethylenedi-amine | FC ($CH_2Cl_2$/MeOH/aq. $NH_3$) | 83% |
| Ex.28 | 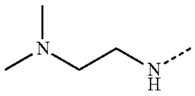 | $NH_2$ | Ex.27 | J | HCl-dioxane | (crude product) | 90% (HCl salt) |
| Ex.29 | 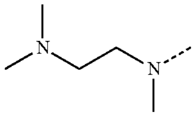 | 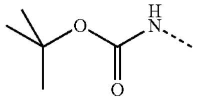 | Ex.4 | L.2 | N,N,N'-trimethyl-ethylenedi-amine | FC ($CH_2Cl_2$/MeOH/aq. $NH_3$) | 74% |

TABLE 21a-continued

Examples of Core 03
(Ex.3-Ex.55, Ex.482-Ex.503 and Ex.590-Ex.591; continued on the following pages)
Ex.3-Ex.5: cf. experimental description

| No | $R^{54}$ | $R^2$ | Starting material | General Procedure | Purification Reagent | Yield Method | (isolated salt) |
|---|---|---|---|---|---|---|---|
| Ex.30 | 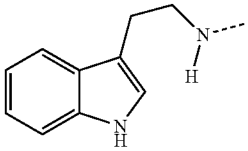 | 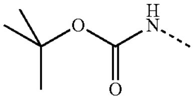 | Ex.4 | L.2 | tryptamine | FC ($CH_2Cl_2$/ MeOH) | 81% |
| Ex.31 | 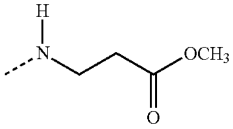 | 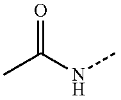 | Ex.51 | L.1.1 | acetic anhydride (5 equiv) | prep. HPLC, method 1 | 72% |
| Ex.32 | 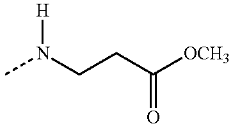 | 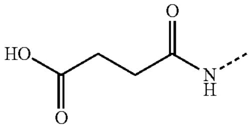 | Ex.51 | L.1.1 | succinic anhydride (1.05 equiv) | prep. HPLC, method 1 | 68% |
| Ex.33 | 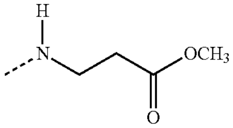 | 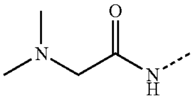 | Ex.51 | L.1.3 | N,N-dimethyl glycine | prep. HPLC, method 1 | 64% (TFA salt) |
| Ex.34 | 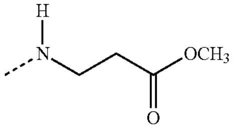 | 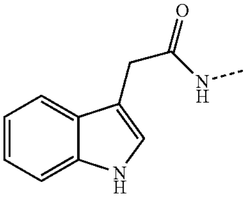 | Ex.51 | L.1.3 | 3-indoleacetic acid | prep. HPLC, method 1 | 24% |
| Ex.35 | 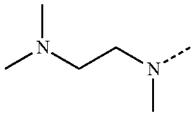 | 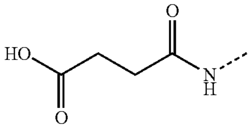 | Ex.23 | L.1.1 | succinic anhydride (1.05 equiv) | prep. HPLC, method 1 | 63% (TFA salt) |
| Ex.36 | 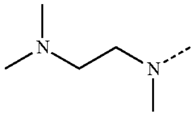 | 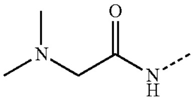 | Ex.23 | L.1.3 | N,N-dimethyl glycine | prep. HPLC, method 1 | 40% (TFA salt) |
| Ex.37 | 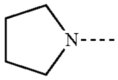 | 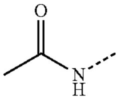 | Ex.42 | L.1.1 | acetic anhydride (5 equiv) | prep. HPLC, method 1 | 61% |
| Ex.38 | 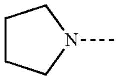 | 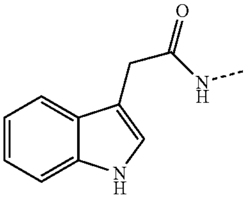 | Ex.42 | L.1.3 | 3-indoleacetic acid | prep. HPLC, method 1 | 43% |
| Ex.39 | 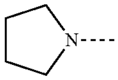 | 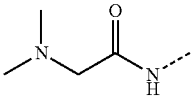 | Ex.42 | L.1.3 | N,N-dimethyl glycine | prep. HPLC, method 1 | 56% (TFA salt) |

TABLE 21a-continued

Examples of Core 03
(Ex.3-Ex.55, Ex.482-Ex.503 and Ex.590-Ex.591; continued on the following pages)
Ex.3-Ex.5: cf. experimental description

| No | $R^{54}$ | $R^2$ | Starting material | General Procedure | Purification Reagent | Yield Method | (isolated salt) |
|---|---|---|---|---|---|---|---|
| Ex.40 | 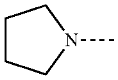 | 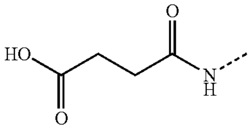 | Ex.42 | L.1.1 | succinic anhydride (1.05 equiv) | prep. HPLC, method 1 | 37% |
| Ex.41 | 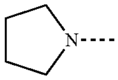 | 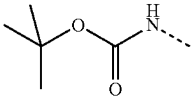 | Ex.4 | L.2 | pyrrolidine | FC ($CH_2Cl_2$/ MeOH) | 76% |
| Ex.42 | 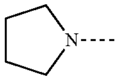 | $NH_2$ | Ex.41 | J | HCl-dioxane | (crude product) | 90% (HCl salt) |
| Ex.43 | 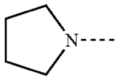 | 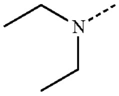 | Ex.42 | M.1 | acetaldehyde | prep. HPLC, method 1 | 67% (TFA salt) |
| Ex.44 | 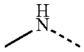 | 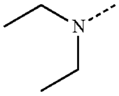 | Ex.25 | M.1 | acetaldehyde | prep. HPLC, method 1 | 33% (TFA salt) |
| Ex.45 | 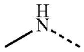 | 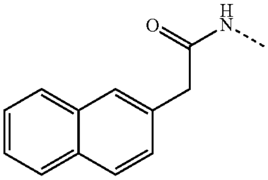 | Ex.25 | L.1.3 | 2-naphthyl-acetic acid | prep. HPLC, method 1 | 46% |
| Ex.46 | 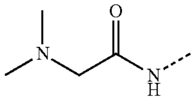 | 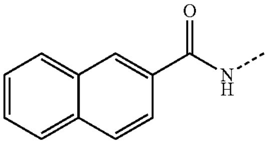 | Ex.28 | L.1.1 | 2-naphthoyl chloride (3.6 equiv.) | FC ($CH_2Cl_2$/ MeOH/ aq. $NH_3$) | 85% |
| Ex.47 | 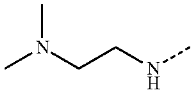 | 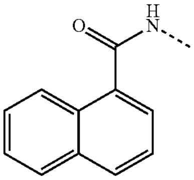 | Ex.28 | L.1.2 | 1-naphthoic acid | FC ($CH_2Cl_2$/ MeOH/ aq. $NH_3$) | 85% |
| Ex.48 | 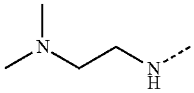 | 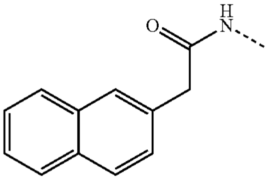 | Ex.28 | L.1.2 | 2-naphthyl-acetic acid | FC ($CH_2Cl_2$/ MeOH/ aq. $NH_3$) | 83% |

TABLE 21a-continued

Examples of Core 03
(Ex.3-Ex.55, Ex.482-Ex.503 and Ex.590-Ex.591; continued on the following pages)
Ex.3-Ex.5: cf. experimental description

| No | $R^{54}$ | $R^2$ | Starting material | General Procedure | Purification Reagent | Yield Method | (isolated salt) |
|---|---|---|---|---|---|---|---|
| Ex.49 | 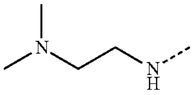 | 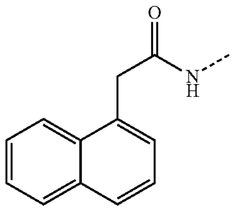 | Ex.28 | L.1.2 | 1-naphthyl-acetic acid | FC ($CH_2Cl_2$/MeOH/aq. $NH_3$) | 83% |
| Ex.50 | 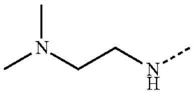 | 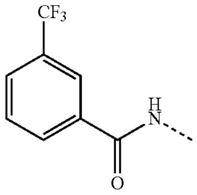 | Ex.28 | L.1.1 | 3- (trifluoro-methyl)-benzoyl chloride (4 equiv.) | FC ($CH_2Cl_2$/MeOH/aq. $NH_3$) | 24% |
| Ex.51 | 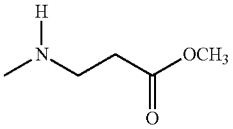 | $NH_2$ | Ex.26 | J | HCl-dioxane | crude product | 93% (HCl salt) |
| Ex.52 | $OCH_2Ph$ | 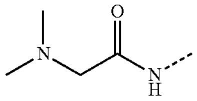 | Ex.5 | L.1.3 | N,N-dimethyl-glycine (1.7 equiv.) HATU (1.0 equiv.) HOAt (2.0 equiv.) i-$Pr_2$NEt (4.0 equiv.) | prep. HPLC, method 1 | 88% (TFA salt) |
| Ex.53 | $OCH_2Ph$ | 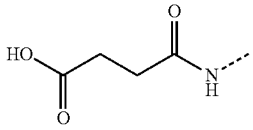 | Ex.5 | L.1.1 | Acetic anhydride (10 equiv.) pyridine/$CH_2Cl_2$ 1:1 | FC | 70% |
| Ex.54 | OH | 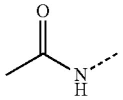 | Ex.54 | H | $H_2$, $Pd(OH)_2$-C | crude product | 92% |
| Ex.55 | 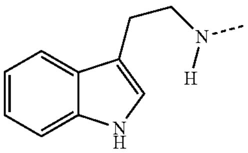 | $NH_2$ | Ex.30 | J | HCl-dioxane | FC ($CH_2Cl_2$/MeOH/aq. $NH_3$) | 42% |
| Ex.482 | 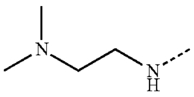 | 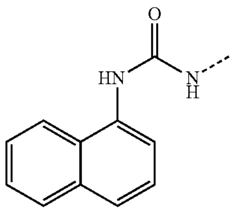 | 262a | R | 1-naphthyl isocyanate | prep. HPLC, method 1 | 25% (TFA salt) |

TABLE 21a-continued

Examples of Core 03
(Ex.3-Ex.55, Ex.482-Ex.503 and Ex.590-Ex.591; continued on the following pages)
Ex.3-Ex.5: cf. experimental description

| No | $R^{54}$ | $R^2$ | Starting material | General Procedure | Purification Reagent | Yield Method | (isolated salt) |
|---|---|---|---|---|---|---|---|
| Ex.483 | 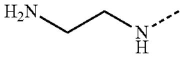 | 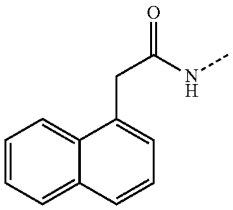 | Ex.500 | J | HCl-dioxane | crude product | 97% (HCl salt) |
| Ex.484 | 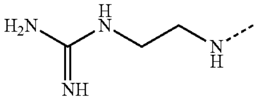 | 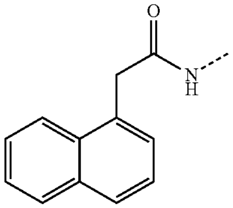 | Ex.483 | — | cf. detailed description of examples | prep. HPLC, method 1 | 18% (TFA salt) |
| Ex.485 | 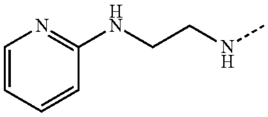 | 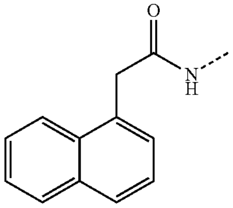 | Ex.499 | L.2 | N-(2-amino-ethyl)pyridine-2-amine (2 equiv.) i-$Pr_2$NEt (2 equiv.) | prep. HPLC, method 2 | 60% |
| Ex.486 | 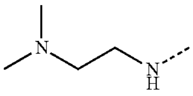 | 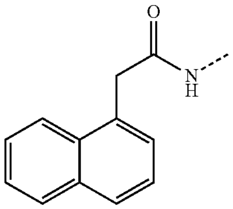 | Ex.28 | M.2 | 2-(naphthalene-1-yl) acetaldehyde | FC($CH_2Cl_2$/ MeOH/ aq. $NH_3$), then prep. HPLC, method 1 | 6% (TFA salt) |
| Ex.487 | 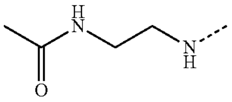 | 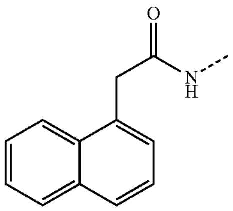 | Esx.483 | L.1.1 | acetic anhydride (5 equiv.) pyridine (10 equiv) | prep. HPLC, method 1 | 75% |
| Ex.488 | 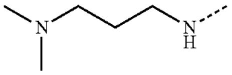 | 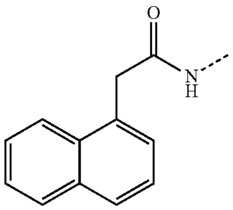 | Ex.499 | L.2 | N,N-dimethyl-propylene-diamine (2 equiv.) i-$Pr_2$NEt (2 equiv.) | prep. HPLC, method 2 | 66% |
| Ex.489 | 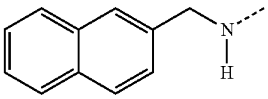 | 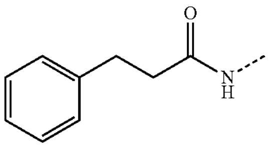 | 262d | R | 3-(pyridin-4-yl)propanoic acid | FC ($CH_2Cl_2$/ EtOAc/ MeOH) | 37% |

TABLE 21a-continued

Examples of Core 03
(Ex.3-Ex.55, Ex.482-Ex.503 and Ex.590-Ex.591; continued on the following pages)
Ex.3-Ex.5: cf. experimental description

| No | $R^{54}$ | $R^2$ | Starting material | General Procedure | Purification Reagent | Yield Method | (isolated salt) |
|---|---|---|---|---|---|---|---|
| Ex.490 | 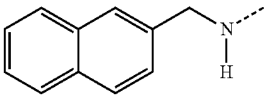 | 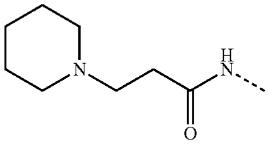 | 262d | R | 3-morpholino-propanoic acid hydrochloride | prep. HPLC, method 1 | 52% (TFA salt) |
| Ex.491 | 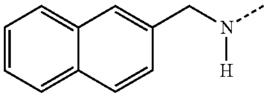 | 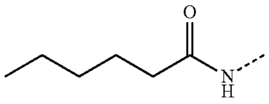 | 262d | R | hexanoic acid | prep. HPLC, method 3 | 43% |
| Ex.492 | 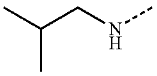 | 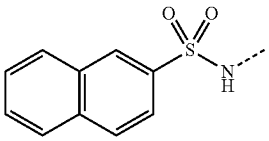 | 262c | R | naphthalene-2-sulfonyl chloride | prep. HPLC, method 3 | 24% |
| Ex.493 | 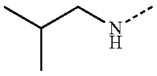 | 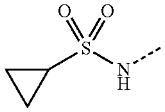 | 262c | R | cyclopropane-sulfonyl chloride | prep. HPLC, method 1 | 35% |
| Ex.494 | 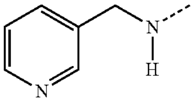 | 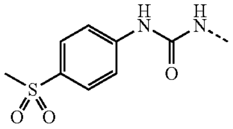 | 262b | R | 2,5-dioxo-pyrrolidin-1-yl-4-(methyl-sulfonyl)-phenyl-carbamate | prep. HPLC, method 1 | 34% (TFA salt) |
| Ex.495 | 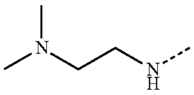 | 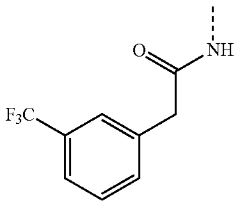 | 262a | R | 3-(trifluoro-methyl) phenylacetic acid | prep. HPLC, method 1 | 24% (TFA salt) |
| Ex.496 | 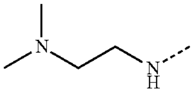 | 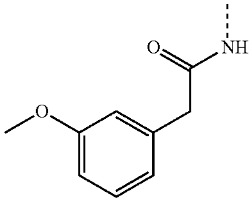 | 262a | R | 3-methoxy phenylacetic acid | prep. HPLC, method 1 | 24% (TFA salt) |
| Ex.497 | 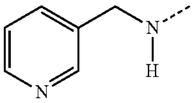 | 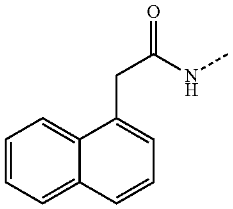 | 262b | R | 1-naphthyl-acetic acid | prep. HPLC, method 1 | 18% (TFA salt) |

TABLE 21a-continued

Examples of Core 03
(Ex.3-Ex.55, Ex.482-Ex.503 and Ex.590-Ex.591; continued on the following pages)
Ex.3-Ex.5: cf. experimental description

| No | $R^{54}$ | $R^2$ | Starting material | General Procedure | Purification Reagent | Yield Method | (isolated salt) |
|---|---|---|---|---|---|---|---|
| Ex.498 | $OCH_2Ph$ | 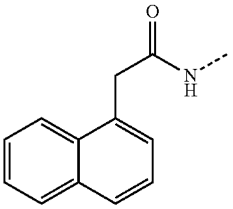 | Ex.5 | L.1.3 | 1-naphthyl-acetic acid (2 equiv.) i-$Pr_2$NEt (3 equiv.) | FC (EtOAc/ MeOH) | 87% |
| Ex.499 | OH | 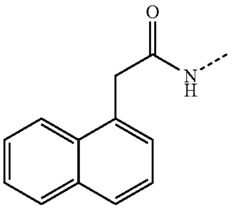 | Ex.498 | H | $H_2$, $Pd(OH)_2$-C | crude product | 96% |
| Ex.500 | 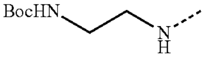 | 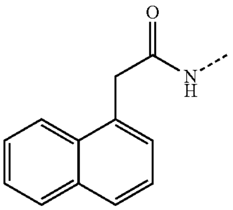 | Ex.499 | L.2 | tert. butyl 2-aminoethyl-carbamate (2 equiv.) i-$Pr_2$NEt (2 equiv. ) | FC ($CH_2Cl_2$/ MeOH/ aq. $NH_3$) | 74% |
| Ex.501 | 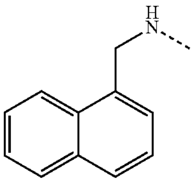 | 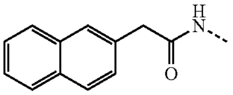 | 262e | R | 2-naphthyl-acetic acid | prep. HPLC, method 3 | 44% |
| Ex.502 | 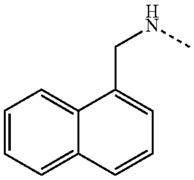 | 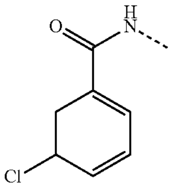 | 262e | R | 3-chloro-benzoic acid | prep. HPLC, method 3 | 48% |
| Ex.503 | 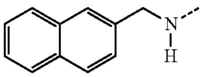 | 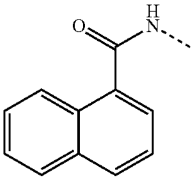 | 262d | R | 1-naphthoic acid | prep. HPLC, method 3 | 43% |
| Ex.590 | OH | $NH_2$ | Ex.4 | ***) | HCl-dioxane | crude product | quant. (HCl salt) |
| Ex.591 | OH | 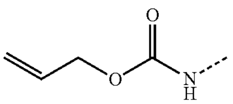 | Ex.590 | ***) | AllocCl | crude product | 95% |

* Prior to debenzylation starting material Ex.52 · TFA was converted into the free base ($CHCl_3$, aq. $Na_2CO_3$ soln)

** The amide coupling was performed at room temperature with N,N-dimethyl glycine (2.2 equiv.) in $CH_2Cl_2$, in the presence of T3P (50% in EtOAc; 2.2 equiv.) and i-$Pr_2$NEt (3 equiv.).

*** cf. detailed description

TABLE 21b
Examples of Core 03 (Ex.3-Ex.55, Ex.482-Ex.503 and Ex.590-Ex.591; continued on the following pages)
Ex.3-Ex.5: cf. experimental description
| No | $R^{54}$ | $R^2$ | FORMULA | MONO-ISOTOPIC MASS | Rt (purity at 220 nm) | $[M+H]^+$ found | LC-MS-Method |
|---|---|---|---|---|---|---|---|
| Ex.6 | OH | 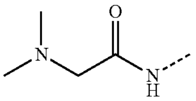 | C25H34FN5O7 | 535.2 | 1.05 (99) | 536.3 | Method 2 |
| Ex.7 | 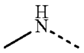 | 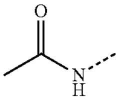 | C24H32FN5O6 | 505.2 | 1.21 (87) | 506.3 | Method 2 |
| Ex.9 | 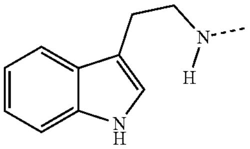 | 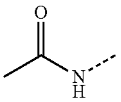 | C33H39FN6O6 | 634.3 | 2.12 (99) | 635.4 | Method 1a |
| Ex.10 | 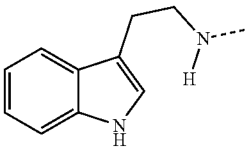 | 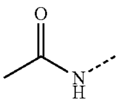 | C26H34FN5O8 | 563.2 | 1.20 (91) | 564.2 | Method 2 |
| Ex.11 | 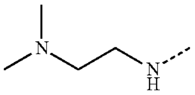 | 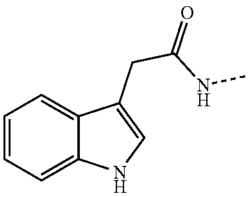 | C35H44FN7O6 | 677.3 | 1.34 (93) | 678.4 | Method 2 |
| Ex.12 | 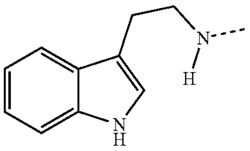 | 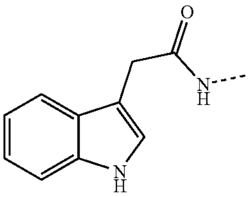 | C41H44FN7O6 | 749.3 | 1.73 (92) | 750.4 | Method 2 |
| Ex.13 | 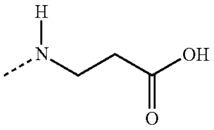 | 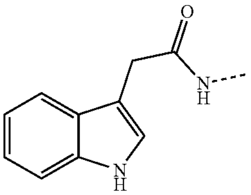 | C34H39FN6O8 | 678.3 | 1.45 (87) | 679.3 | Method 2 |
| Ex.14 | 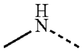 | 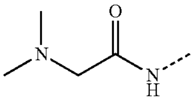 | C26H37FN6O6 | 548.3 | 1.08 (88) | 549.3 | Method 2 |
| Ex.15 | 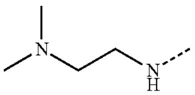 | 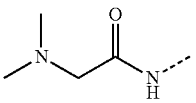 | C29H44FN7O6 | 605.3 | 0.99 (96) | 606.4 | Method 2 |

TABLE 21b-continued

Examples of Core 03 (Ex.3-Ex.55, Ex.482-Ex.503 and Ex.590-Ex.591; continued on the following pages)
Ex.3-Ex.5: cf. experimental description

| No | $R^{54}$ | $R^2$ | FORMULA | MONO-ISOTOPIC MASS | Rt (purity at 220 nm) | $[M+H]^+$ found | LC-MS-Method |
|---|---|---|---|---|---|---|---|
| Ex.16 | 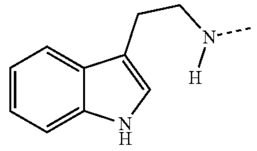 | 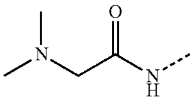 | C35H44FN7O6 | 677.3 | 1.41 (97) | 678.4 | Method 2 |
| Ex.17 | 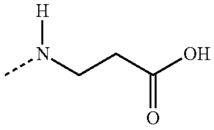 | 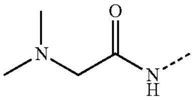 | C28H39FN6O8 | 606.3 | 1.09 (94) | 607.3 | Method 2 |
| Ex.18 | 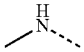 | 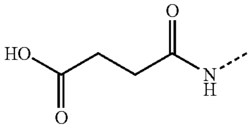 | C26H34FN5O8 | 563.2 | 1.20 (88) | 564.3 | Method 2 |
| Ex.19 | 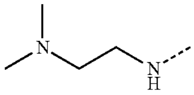 | 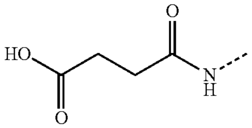 | C29H41FN6O8 | 620.3 | 1.08 (100) | 621.3 | Method 2 |
| Ex.20 | 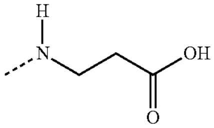 | 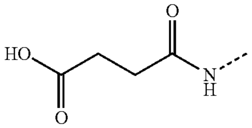 | C28H36FN5O10 | 621.2 | 1.18 (91) | 622.2 | Method 2 |
| Ex.21 | 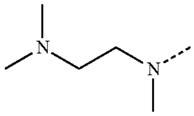 | 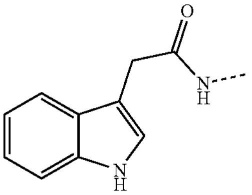 | C36H46FN7O6 | 691.4 | 1.36 (88) | 692.4 | Method 2 |
| Ex.22 | 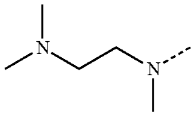 | 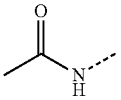 | C28H41FN6O6 | 576.3 | 1.12 (96) | 577.4 | Method 2 |
| Ex.23 | 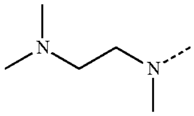 | $NH_2$ | C26H39FN6O5 | 534.3 | 0.96 (88) | 535.4 | Method 2 |
| Ex.24 | 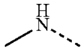 | 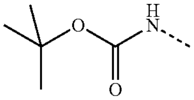 | C27H38FN5O7 | 563.3 | 1.54 (93) | 564.3 | Method 2 |
| Ex.25 | 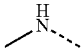 | $NH_2$ | C22H30FN5O5 | 463.2 | 1.06 (91) | 464.2 | Method 2 |

TABLE 21b-continued

Examples of Core 03 (Ex.3-Ex.55, Ex.482-Ex.503 and Ex.590-Ex.591; continued on the following pages)
Ex.3-Ex.5: cf. experimental description

| No | $R^{54}$ | $R^2$ | FORMULA | MONO-ISOTOPIC MASS | Rt (purity at 220 nm) | [M + H]+ found | LC-MS-Method |
|---|---|---|---|---|---|---|---|
| Ex.26 | 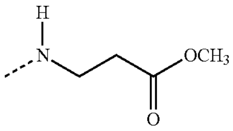 | 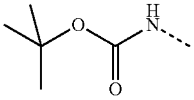 | C30H42FN5O9 | 635.3 | 1.61 (87) | 636.4 | Method 2 |
| Ex.27 | 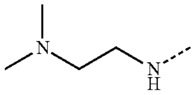 | 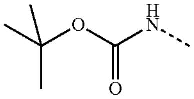 | C30H45FN6O7 | 620.3 | 1.53 (92) | 621.3 | Method 4a |
| Ex.28 | 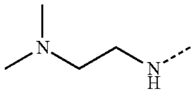 | $NH_2$ | C25H37FN6O5 | 520.3 | 0.93 (94) | 521.3 | Method 2 |
| Ex.29 | 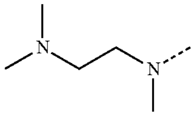 | 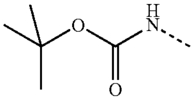 | C31H47FN6O7 | 634.4 | 1.41 (96) | 635.4 | Method 2 |
| Ex.30 | 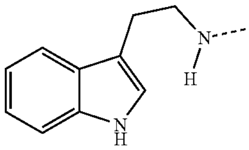 | 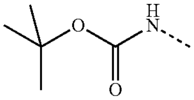 | C36H45FN6O7 | 692.3 | 1.79 (99) | 693.4 | Method 2 |
| Ex.31 | 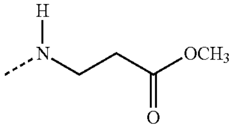 | 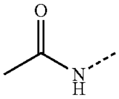 | C27H36FN5O8 | 577.3 | 1.32 (90) | 578.3 | Method 2 |
| Ex.32 | 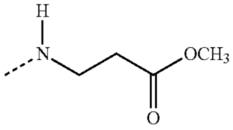 | 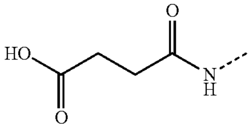 | C29H38FN5O10 | 635.3 | 1030 (83) | 636.2 | Method 2 |
| Ex.33 | 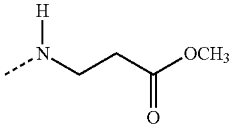 | 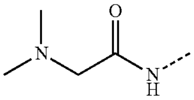 | C29H41FN6O8 | 620.3 | 1.18 (100) | 621.3 | Method 2 |
| Ex.34 | 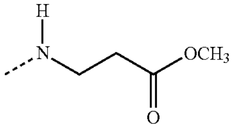 | 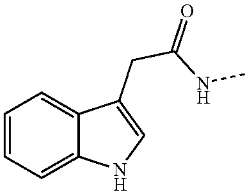 | C35H41FN6O8 | 692.3 | 1.56 (90) | 693.3 | Method 2 |
| Ex.35 | 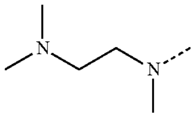 | 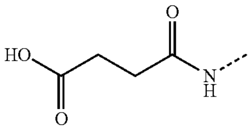 | C30H43FN6O8 | 634.3 | 1.10 (94) | 635.3 | Method 2 |

TABLE 21b-continued

Examples of Core 03 (Ex.3-Ex.55, Ex.482-Ex.503 and Ex.590-Ex.591; continued on the following pages)
Ex.3-Ex.5: cf. experimental description

| No | $R^{54}$ | $R^2$ | FORMULA | MONO-ISOTOPIC MASS | Rt (purity at 220 nm) | [M + H]$^+$ found | LC-MS-Method |
|---|---|---|---|---|---|---|---|
| Ex.36 | 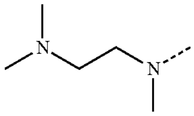 | 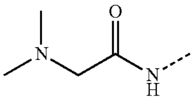 | C30H46FN7O6 | 619.4 | 1.00 (91) | 620.3 | Method 2 |
| Ex.37 | 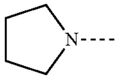 | 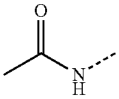 | C27H36FN5O6 | 545.3 | 1.36 (93) | 546.3 | Method 2 |
| Ex.38 | 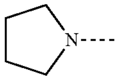 | 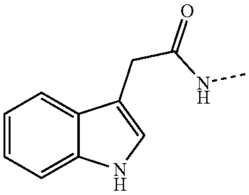 | C35H41FN6O6 | 660.3 | 1.60 (94) | 661.3 | Method 2 |
| Ex.39 | 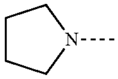 | 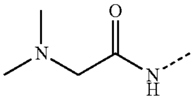 | C29H41FN6O6 | 588.3 | 1.19 (94) | 589.3 | Method 2 |
| Ex.40 | 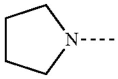 | 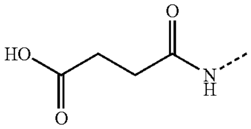 | C29H38FN5O8 | 603.3 | 1.33 (94) | 604.3 | Method 2 |
| Ex.41 | 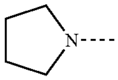 | 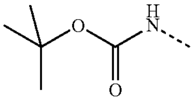 | C30H42FN5O7 | 603.3 | 1.67 (90) | 604.3 | Method 2 |
| Ex.42 | 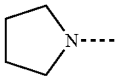 | $NH_2$ | C25H34FN5O5 | 503.3 | 1.17 (92) | 504.2 | Method 2 |
| Ex.43 | 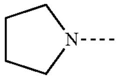 | 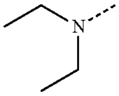 | C29H42FN5O5 | 559.3 | 1.26 (96) | 560.3 | Method 2 |
| Ex.44 | 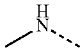 | 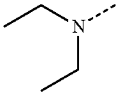 | C26H38FN5O5 | 519.3 | 1.13 (97) | 520.3 | Method 2 |
| Ex.45 | 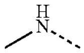 | 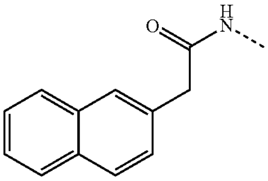 | C34H38FN5O6 | 631.3 | 1.65 (97) | 632.2 | Method 2 |
| Ex.46 | 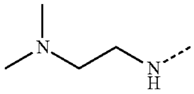 | 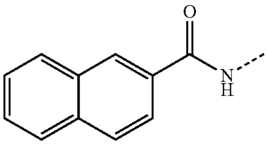 | C36H43FN6O6 | 674.3 | 1.49 (97) | 675.5 | Method 2 |

TABLE 21b-continued

Examples of Core 03 (Ex.3-Ex.55, Ex.482-Ex.503 and Ex.590-Ex.591; continued on the following pages)
Ex.3-Ex.5: cf. experimental description

| No | $R^{54}$ | $R^2$ | FORMULA | MONO-ISOTOPIC MASS | Rt (purity at 220 nm) | $[M + H]^+$ found | LC-MS-Method |
|---|---|---|---|---|---|---|---|
| Ex.47 | 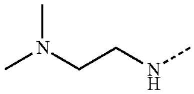 | 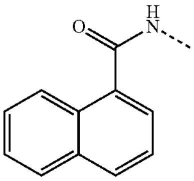 | C36H43FN6O6 | 674.3 | 1.43 (96) | 675.5 | Method 2 |
| Ex.48 | 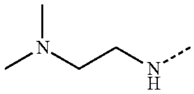 | 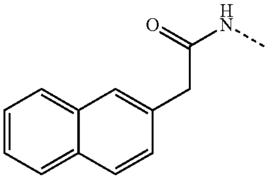 | C37H45FN6O6 | 688.3 | 1.50 (95) | 689.5 | Method 2 |
| Ex.49 | 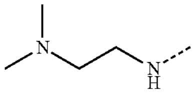 | 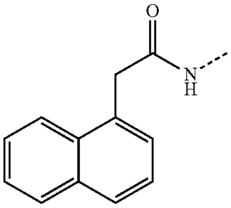 | C37H45FN6O6 | 688.3 | 1.48 (95) | 689.5 | Method 2 |
| Ex.50 | 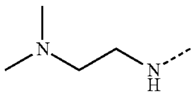 | 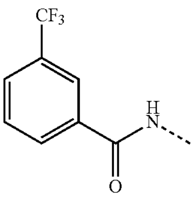 | C33H40F4N6O6 | 692.3 | 1.49 (97) | 693.5 | Method 2 |
| Ex.51 | 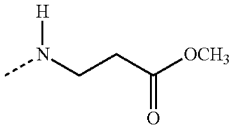 | $NH_2$ | C25H34FN5O7 | 535.2 | 1.08 | 536.3 | Method 9c |
| Ex.52 | $OCH_2Ph$ | 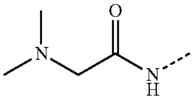 | C32H40FN5O7 | 625.3 | 1.47 | 626.3 | Method 9c |
| Ex.53 | $OCH_2Ph$ | 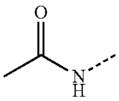 | C30H35FN4O7 | 582.3 | 1.65 | 582.9 | Method 9c |
| Ex.54 | OH | 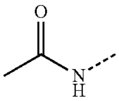 | C23H29FN4O7 | 492.2 | 1.04 | 493.1 | Method 9c |
| Ex.55 | 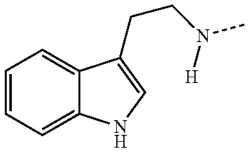 | $NH_2$ | C31H37FN6O5 | 592.3 | 1.38 | 593.0 | Method 9c |

TABLE 21b-continued
Examples of Core 03 (Ex.3-Ex.55, Ex.482-Ex.503 and Ex.590-Ex.591; continued on the following pages)
Ex.3-Ex.5: cf. experimental description
| No | $R^{54}$ | $R^2$ | FORMULA | MONO-ISOTOPIC MASS | Rt (purity at 220 nm) | [M + H]+ found | LC-MS-Method |
|---|---|---|---|---|---|---|---|
| Ex.482 | 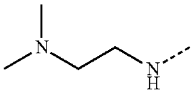 | 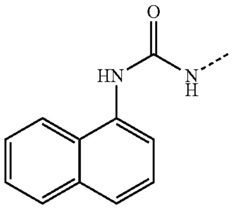 | C36H44FN7O6 | 689.3 | 1.43 (91) | 690.4 | Method 10a |
| Ex.483 | 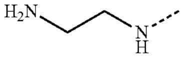 | 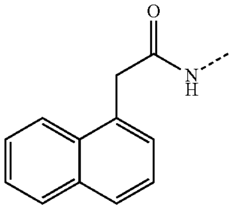 | C35H41FN6O6 | 660.3 | 1.42 (85) | 661.4 | Method 10a |
| Ex.484 | 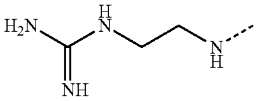 | 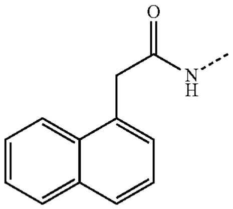 | C36H43FN8O6 | 702.3 | 1.46 (90) | 703.3 | Method 10a |
| Ex.485 | 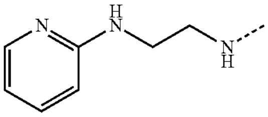 | 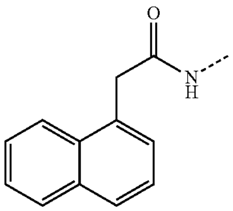 | C40H44FN7O6 | 737.3 | 1.79 (93) | 738.4 | Method 11a |
| Ex.486 | 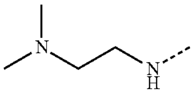 | 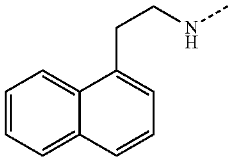 | C37H47FN6O5 | 674.4 | 1.34 (80) | 675.3 | Method 10a |
| Ex.487 | 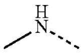 | 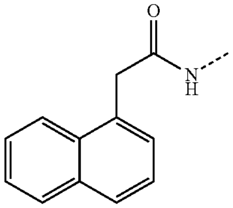 | C37H43FN6O7 | 702.3 | 1.56 (78) | 703.4 | Method 10a |
| Ex.488 | 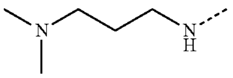 | 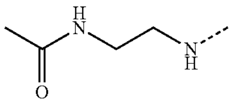 | C38H47FN6O6 | 702.4 | 1.79 (91) | 703.5 | Method 11a |

TABLE 21b-continued
Examples of Core 03 (Ex.3-Ex.55, Ex.482-Ex.503 and Ex.590-Ex.591; continued on the following pages)
Ex.3-Ex.5: cf. experimental description
| No | $R^{54}$ | $R^2$ | FORMULA | MONO-ISOTOPIC MASS | Rt (purity at 220 nm) | $[M + H]^+$ found | LC-MS-Method |
|---|---|---|---|---|---|---|---|
| Ex.489 | 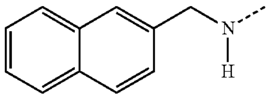 | 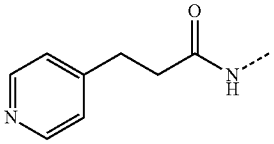 | C40H43FN6O6 | 722.3 | 1.52 (97) | 723.4 | Method 10a |
| Ex.490 | 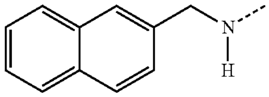 | 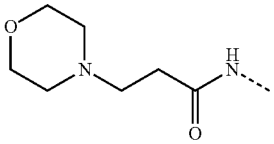 | C39H47FN6O7 | 730.4 | 1.68 (97) | 731.4 | Method 4a |
| Ex.491 | 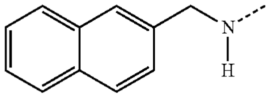 | 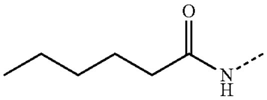 | C38H46FN5O6 | 687.3 | 2.14 (96) | 688.4 | Method 4a |
| Ex.492 | 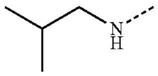 | 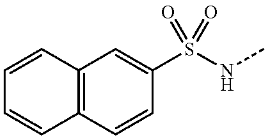 | C35H42FN5O7S | 695.3 | 1.94 (93) | 696.4 | Method 10a |
| Ex.493 | 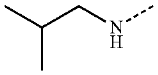 | 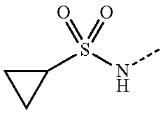 | C28H40FN5O7S | 609.3 | 1.58 (87) | 610.3 | Method 10a |
| Ex.494 | 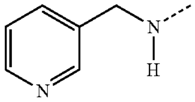 | 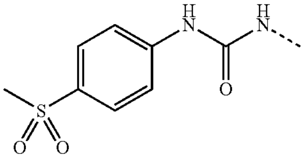 | C35H40FN7O8S | 737.3 | 1.21 (95) | 738.3 | Method 10a |
| Ex.495 | 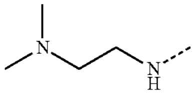 | 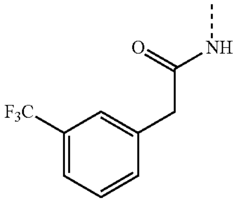 | C34H42F4N6O0 | 706.3 | 1.50 (91) | 707.4 | Method 10a |
| Ex.496 | 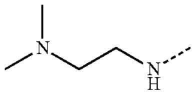 | 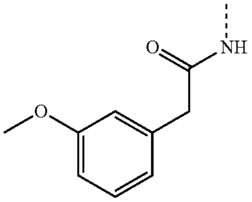 | C34H45FN6O7 | 668.3 | 1.31 (93) | 669.4 | Method 10a |

TABLE 21b-continued
Examples of Core 03 (Ex.3-Ex.55, Ex.482-Ex.503 and Ex.590-Ex.591; continued on the following pages)
Ex.3-Ex.5: cf. experimental description
| No | $R^{54}$ | $R^2$ | FORMULA | MONO-ISOTOPIC MASS | Rt (purity at 220 nm) | [M + H]+ found | LC-MS-Method |
|---|---|---|---|---|---|---|---|
| Ex.497 | 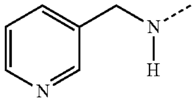 | 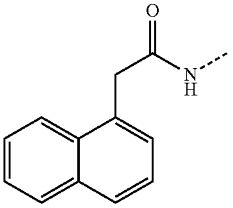 | C39H41FN6O6 | 708.3 | 1.47 (87) | 709.4 | Method 10a |
| Ex.498 | $OCH_2Ph$ | 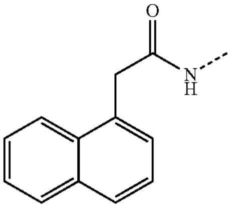 | C40H41FN4O7 | 708.3 | 2.13 (90) | 709.4 | Method 10a |
| Ex.499 | OH | 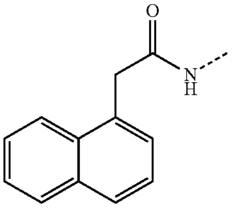 | C33H35FN4O7 | 618.3 | 1.63 (90) | 619.2 | Method 10a |
| Ex.500 | 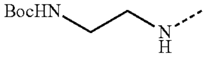 | 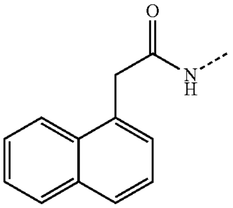 | C40H49FN6O8 | 760.4 | 1.90 (95) | 761.5 | Method 10a |
| Ex.501 | 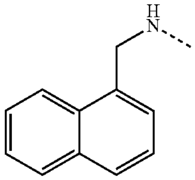 | 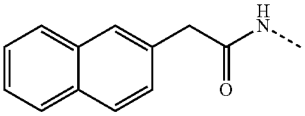 | C44H44FN5O6 | 757.3 | 2.27 (93) | 758.4 | Method 4a |
| Ex.502 | 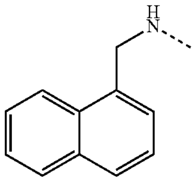 | 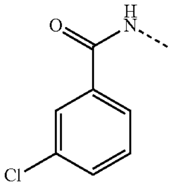 | C39H39ClFN5O6 | 727.3 | 2.22 (95) | 728.3 | Method 4a |
| Ex.503 | 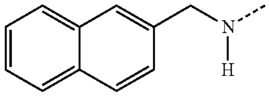 | 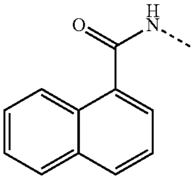 | C43H42FN5O6 | 743.3 | 2.17 (97) | 744.4 | Method 4a |
| Ex.590 | OH | $NH_2$ | C21H27FN4O6 | 450.2 | 1.08 (93) | 451.0 | Method 4b |

TABLE 21b-continued

Examples of Core 03 (Ex.3-Ex.55, Ex.482-Ex.503 and Ex.590-Ex.591; continued on the following pages)
Ex.3-Ex.5: cf. experimental description

| No | $R^{54}$ | $R^2$ | FORMULA | MONO-ISOTOPIC MASS | Rt (purity at 220 nm) | [M + H]$^+$ found | LC-MS-Method |
|---|---|---|---|---|---|---|---|
| Ex.591 | OH | 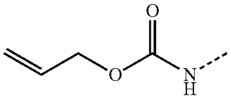 | C25H31FN4O8 | 534.2 | 1.58 (91) | 535.2 | Method 4b |

TABLE 21c

Examples of Core 03 (Ex.3-Ex.55, Ex.482-Ex.503 and Ex.590-Ex.591; continued on the following pages)

| No | $R^{54}$ | $R^2$ | IUPAC name |
|---|---|---|---|
| Ex.3 | $OCH_2PH$ | 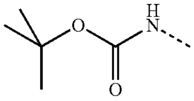 | benzyl (2S,11S,19aS)-2-[(tert-butoxycarbonyl)amino)-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylate |
| Ex.4 | OH | 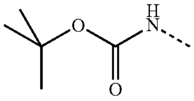 | (2S,11S,19aS)-2-[(tert-butoxycarbonyl)amino)-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylic acid |
| Ex.5 | $OCH_2Ph$ | $NH_2$ | benzyl (2S,11S,19aS)-2-amino-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylate |
| Ex.6 | OH | 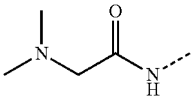 | (2S,11S,19aS)-2-{[2-(dimethylamino)acetyl]amino}-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylic acid |
| Ex.7 | 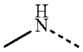 | 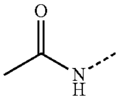 | (2S,11S,19aS)-2-(acetylamino)-15-fluoro-N,7,12-trimethyl-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxamide |
| Ex.8 | 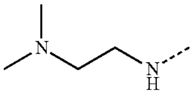 | 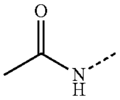 | (2S,11S,19aS)-2-(acetylamino)-N-[2-(dimethylamino)ethyl]-15-fluoro-7,12-dimethyl-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxamide |
| Ex.9 | 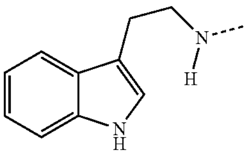 | 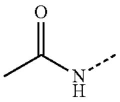 | (2S,11S,19aS)-2-(acetylamino)-15-fluoro-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxamide |
| Ex.10 | 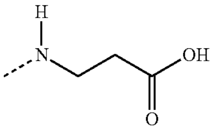 | 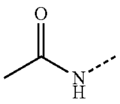 | 3-({[(2S,11S,19aS)-2-(acetylamino)-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-11-yl]carbonyl}amino)propanoic acid |
| Ex.11 | 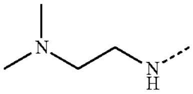 | 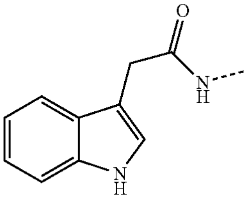 | (2S,11S,19aS)-N-[2-(dimethylamino)ethyl]-15-fluoro-2-{[2-(1H-indol-3-yl)acetyl]amino}-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |

TABLE 21c-continued

Examples of Core 03 (Ex.3-Ex.55, Ex.482-Ex.503 and Ex.590-Ex.591; continued on the following pages)

| No | $R^{54}$ | $R^2$ | IUPAC name |
|---|---|---|---|
| Ex.12 | 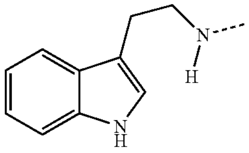 | 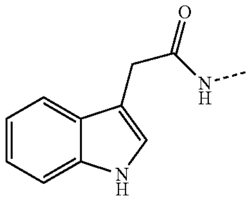 | (2S,11S,19aS)-15-fluoro-2-{[2-(1H-indol-3-yl) acetyl]amino}-N-[2-(1H-indol-3-yl)ethyl]-7,12-dimethyl-5,8,13-trioxo-2,3,6,7,8,9,10,11,12,13, 19,19a-dodecahydro-1H,5H-pyrrolo[2,1-c] [1,4, 7,12]benzoxatriazacyclopentadecine-11-carboxamide |
| Ex.13 | 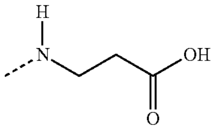 | 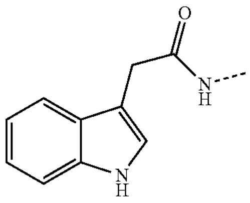 | 3-{[((2S,11S,19aS)-15-fluoro-2-{[2-(1H-indol-3-yl)acetyl]amino}-7,12-dimethyl-5,8,13-trioxo-2,3,6,7,8,9,10,11,12,13,19,19a-dodecahydro-1H,5H-pyrrolo[2,1-c][1,4,7,12]benzoxatriaza-cyclopentadecin-11-yl)carbonyl]amino}propanoic acid |
| Ex.14 | 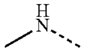 | 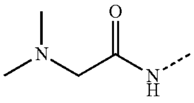 | (2S,11S,19aS)-2-{[2-(dimethylamino)acetyl] amino}-15-fluoro-N,7,12-trimethyl-5,8,13-trioxo-2,3,6,7,8,9,10,11,12,13,19,19a-dodecahydro-1H, 5H-pyrrolo(2,1-c] [1,4,7,12]benzoxatriazacyclo-pentadecine-11-carboxamide |
| Ex.15 | 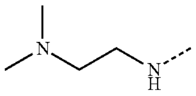 | 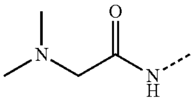 | (2S,11S,19aS)-2-{[2-(dimethylamino)acetyl] amino}-N-[2-(dimethylamino)ethyl]-15-fluoro-7,12-dimethyl-5,8,13-trioxo-2,3,6,7,8,9,10,11, 12,13,19,19a-dodecahydro-1H,5H-pyrrolo [2,1-c] [1,4,7,12]benzoxatriazacyclopentadecine-11-carboxamide |
| Ex.16 | 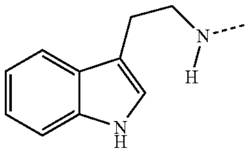 | 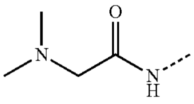 | (2S,11S,19aS)-2-{[2-(dimethylamino)acetyl] amino}-15-fluoro-N-[2-(1H-indol-3-yl)ethyl]-7,12-dimethyl-5,8,13-trioxo-2,3,6,7,8,9,10,11, 12,13,19,19a-dodecahydro-1H,5H-pyrrolo [2,1-c] [1,4,7,12]benzoxatriazacyclopentadecine-11-carboxamide |
| Ex.17 | 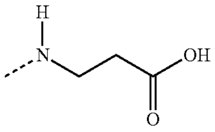 | 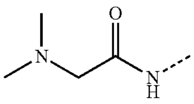 | 3-{[((2S,11S,19aS)-2-{[2-(dimethylamino) acetyl]amino}-15-fluoro-7,12-dimethyl-5,8,13-trioxo-2,3,6,7,8,9,10,11,12,13,19, 19a-dodecahydro-1H,5H-pyrrolo[2,1-c] [1,4,7,12]benzoxatriazacyclopentadecin-11-yl)carbonyl]amino}propanoic acid |
| Ex.18 | 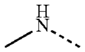 | 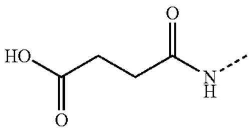 | 4-({(2S,11S,19aS)-15-fluoro-7,12-dimethyl-11-[(methylamino)carbonyl]-5,8,13-trioxo-2,3,6,7,8,9,10,11,12,13,19,19a-dodecahydro-1H,5H-pyrrolo[2,1-c] [1,4,7,12]benzoxatri-azacyclopentadecin-2-yl}amino)-4-oxobutanoic acid |
| Ex.19 | 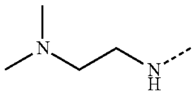 | 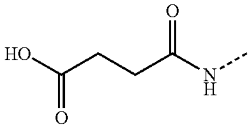 | 4-{[(2S,11S,19aS)-11-({[2-(dimethylamino) ethyl]amino}carbonyl)-15-fluoro-7,12-dimethyl-5,8,13-trioxo-2,3,6,7,8,9,10,11, 12,13,19,19a-dodecahydro-1H,5H-pyrrolo[2,1-c] [1,4,7,12]benzoxatriazacyclo-pentadecin-2-yl]amino}-4-oxobutanoic acid |
| Ex.20 | 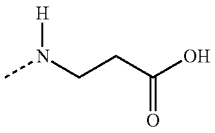 | 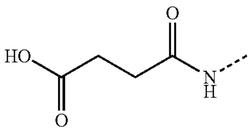 | 4-[({2S,11S,19aS)-15-fluoro-11-{[(3-hydroxy-3-oxopropyl)amino]carbonyl}-7,12-dimethyl-5,8,13-trioxo-2,3,6,7,8,9, 10,11,12,13,19,19a-dodecahydro-1H,5H-pyrrolo[2,1-c] [1,4,7,12]benzoxatriazacyclo-pentadecin-2-yl)amino]-4-oxobutanoic acid |

TABLE 21c-continued

Examples of Core 03 (Ex.3-Ex.55, Ex.482-Ex.503 and Ex.590-Ex.591; continued on the following pages)

| No | $R^{54}$ | $R^2$ | IUPAC name |
|---|---|---|---|
| Ex.21 | 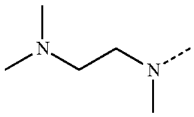 | 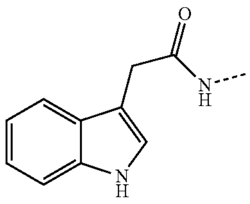 | (2S,11S,19aS)-N-[2-(dimethylaraino)ethyl]-15-fluoro-2-{[2-(1H-indol-3-yl)acetyl]amino}-N,7,12-trimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex.22 | 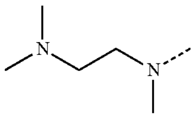 | 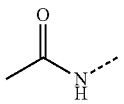 | (2S,11S,19aS)-2-(acetylamino)-N-[2-(dimethylamino)ethyl]-15-fluoro-N,7,12-trimethyl-5,8,13-trioxo-2,3,6,7,8,9,10,11,12,13,19,19a-dodecahydro-1H,5H-pyrrolo[2,1-c] [1,4,7,12]benzoxatriazacyclo-pentadecine-11-carboxamide |
| Ex.23 | 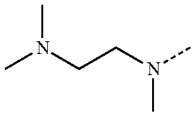 | $NH_2$ | (2S,11S,19aS)-2-amino-N-[2-(dimethylamino)ethyl]-15-fluoro-N,7,12-trimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex.24 | 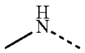 | 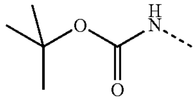 | tert-butyl N-{(2S,11S,19aS)-15-fluoro-7,12-diraethyl-11-[(methylamino)carbonyl]-5,8,13-trioxo-2,3,6,7,8,9,10,11,12,13,19,19a-dodecahydro-1H,5H-pyrrolo(2,1-c][1,4,7,12]benzoxatriazacyclopentadecin-2-yl}carbamate |
| Ex.25 | 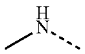 | $NH_2$ | (2S,11S,19aS)-2-amino-15-fluoro-N,7,12-trimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex.26 | 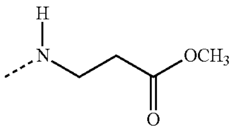 | 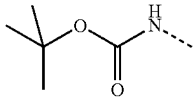 | methyl 3-[({(2S,11S,19aS)-2-[(tert-butoxycarbonyl)amino]-15-fluoro-7,12-dimethyl-5,8,13-trioxo-2,3,6,7,8,9,10,11,12,13,19,19a-dodecahydro-1H,5H-pyrrolo[2,1-c] [1,4,7,12]benzoxatriazacyclopentadecin-11-yl}carbonyl)amino]propanoate |
| Ex.27 | 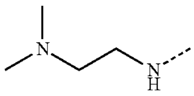 | 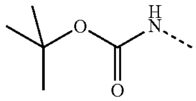 | tert-butyl N-[(2S,11S,19aS)-11-({[2-(dimethylamino)ethyl]amino}carbonyl)-15-fluoro-7,12-dimethyl-5,8,13-trioxo-2,3,6,7,8,9,10,11,12,13,19,19a-dodecahydro-1H,5H-pyrrolo[2,1-c] [1,4,7,12]benzoxatriazacyclo-pentadecin-2-yl]carbamate |
| Ex.28 | 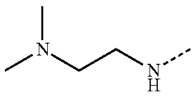 | $NH_2$ | [2S,11S,19aS)-2-amino-N-[2-(dimethylamino)ethyl]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex.29 | 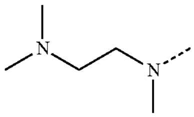 | 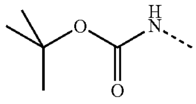 | tert-butyl N-((2S,11S,19aS)-11-{[[2-(dimethylamino)ethyl](methyl)amino]carbonyl}-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl)carbamate |
| Ex.30 | 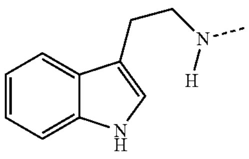 | 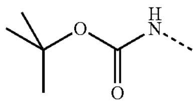 | tert-butyl N-[(2S,11S,19aS)-15-fluoro-11-({[2-(1H-indol-3-yl)ethyl]amino}carbonyl)-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl]carbamate |
| Ex.31 | 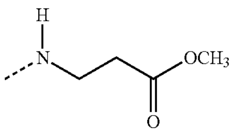 | 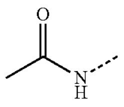 | methyl 3-({[(2S,11S,19aS)-2-(acetylamino)-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-11-yl]carbonyl}amino)propanoate |

TABLE 21c-continued

Examples of Core 03 (Ex.3-Ex.55, Ex.482-Ex.503 and Ex.590-Ex.591; continued on the following pages)

| No | $R^{54}$ | $R^2$ | IUPAC name |
|---|---|---|---|
| Ex.32 | 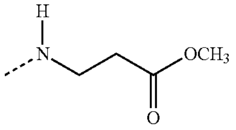 | 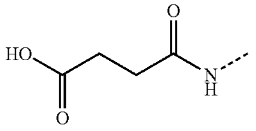 | 4-[((2S,11S,19aS)-15-fluoro-11-{[(3-methoxy-3-oxopropyl)amino]carbonyl}-7,12-dimethyl-5,8,13-trioxo-2,3,6,7,8,9,10,11,12,13,19,19a-dodecahydro-1H,5H-pyrrolo[2,1-c] [1,4,7,12] benzoxatriazacyclopentadecin-2-yl)amino]-4-oxobutanoic acid |
| Ex.33 | 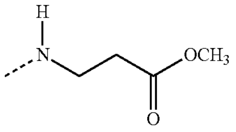 | 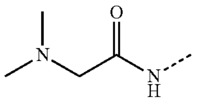 | methyl 3-{[((2S,11S,19aS)-2-{[2-(dimethylamino) acetyl]amino}-15-fluoro-7,12-dimethyl-5,8,13-trioxo-2,3,6,7,8,9,10,11,12,13,19,19a-dodecahydro-1H,5H-pyrrolo[2,1-c] [1,4,7,12]benzoxatriazacyclopentadecin-11-yl)carbonyl]amino}propanoate |
| Ex.34 | 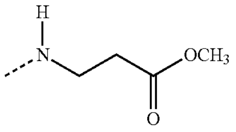 | 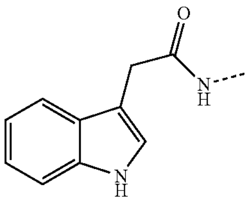 | methyl 3-{[((2S,11S,19aS)-15-fluoro-2-{[2-(1H-indol-3-yl)acetyl]amino}-7,12-dimethyl-5,8,13-trioxo-2,3,6,7,8,9,10,11,12,13,19,19a-dodecahydro-2H,5H-pyrrolo[2,1-c] [1,4,7,12]benzoxatriazacyclo-pentadecin-11-yl)carbonyl]amino}propanoate |
| Ex.35 | 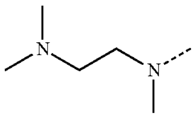 | 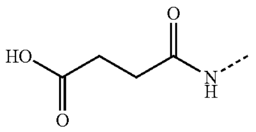 | 4-[((2S,11S,19aS)-11-{[[2-(dimethylamino) ethyl](methyl)amino]carbonyl}-15-fluoro-7,12-dimethyl-5,8,13-trioxo-2,3,6,7,8,9,10,11,12,13,19,19a-dodecahydro-1H,5H-pyrrolo[2,1-c] [1,4,7,12]benzoxatriaza-cyclopentadecin-2-yl)amino]-4-oxobutanoic acid |
| Ex.36 | 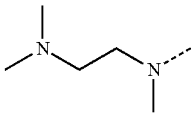 | 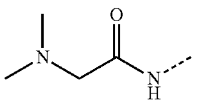 | (2S,11S,19aS)-2-{[2-(dimethylamino)acetyl] amino}-N-[2-(dimethylamino)ethyl}-15-fluoro-N,7,12-trimethyl-5,8,13-trioxo-2,3,6,7,8,9,10,11,12,13,19,19a-dodecahydro-1H,5H-pyrrolo[2,1-c] [1,4,7,12]benzoxatriaza-cyclopentadecine-11-carboxamide |
| Ex.37 | 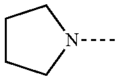 | 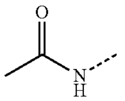 | N-[(2S,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c] [1,4,7,12]benzoxatriazacyclo-pentadecin-2-yl]acetamide |
| Ex.38 | 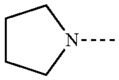 | 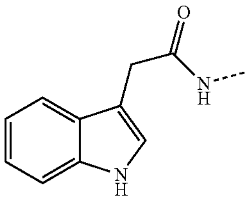 | N-[(2S,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c] [1,4,7,12]benzoxatriazacyclopentadecin-2-yl]-2-(1H-indol-3-yl)acetamide |
| Ex.39 | 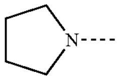 | 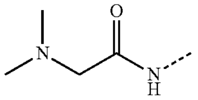 | N-[(2S,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c] [1,4,7,12]benzoxatriazacyclopentadecin-2-yl]-2-(dimethylamino)acetamide |
| Ex.40 | 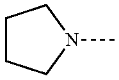 | 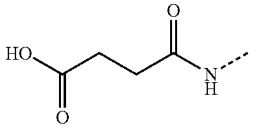 | 4-{[(2S,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c] [1,4,7,12]benzoxalriazacyclo-pentadecin-2-yl]amino}-4-oxobutanoic acid |
| Ex.41 | 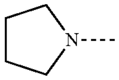 | 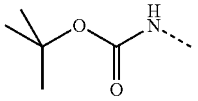 | tert-butyl N-[(2S,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c] [1,4,7,12]benzoxatriazacyclopentadecin-2-yl]carbamate |

TABLE 21c-continued

| Examples of Core 03 (Ex.3-Ex.55, Ex.482-Ex.503 and Ex.590-Ex.591; continued on the following pages) | | | |
|---|---|---|---|
| No | $R^{54}$ | $R^2$ | IUPAC name |
| Ex.42 | 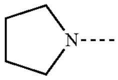 | $NH_2$ | (2S,11S,19aS)-2-amino-15-fluoro-7,12-dimethyl-11-(1-pyrrolidinylcarbonyl)-2,3,6,7,9,10,11,12,19,19a-decahydro-1H,5H-pyrrolo[2,1-c][1,4,7,12]benzoxatriazacyclopentadecine-5,8,13-trione |
| Ex.43 | 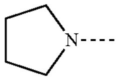 | 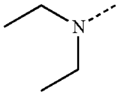 | (2S,11S,19aS)-2-(diethylamino)-15-fluoro-7,12-dimethyl-11-(1-pyrrolidinylcarbonyl)-2,3,6,7,9,10,11,12,19,19a-decahydro-1H,5H-pyrrolo[2,1-c] [1,4,7,12]benzoxatriazacyclopentadecine-5,8,13-trione |
| Ex.44 | 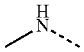 | 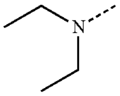 | (2S,11S,19aS)-2-(diethylamino)-15-fluoro-N,7,12-trimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex.45 | 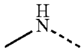 | 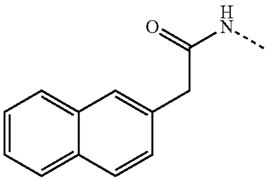 | (2S,11S,19aS)-15-fluoro-N,7,12-trimethyl-2-{[2-(2-naphthyl)acetyl]amino)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex.46 | 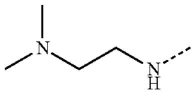 | 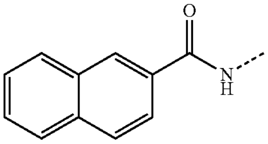 | (2S,11S,19aS)-N-[2-(dimethylamino)ethyl]-15-fluoro-7,12-dimethyl-2-(2-naphthoylamino)-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxamide |
| Ex.47 | 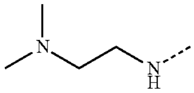 | 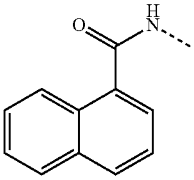 | (2S,11S,19aS)-N-[2-(dimethylamino)ethyl]-15-fluoro-7,12-dimethyl-2-(1-naphthoylamino)-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxamide |
| Ex.48 | 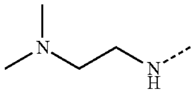 | 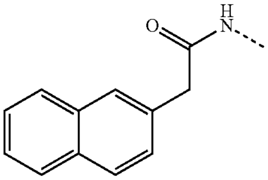 | (2S,11S,19aS)-N-[2-(dimethylamino)ethyl]-15-fluoro-7,12-dimethyl-2-{[2-(2-naphthyl)acetyl]amino}-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxamide |
| Ex.49 | 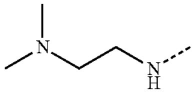 | 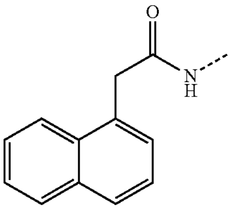 | (2S,11S,19aS}-N-[2-(dimethylamino)ethyl]-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxamide |
| Ex.50 | 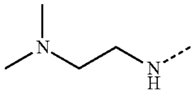 | 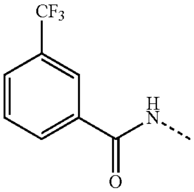 | (2S,11S,19aS)-N-[2-(dimethylamino)ethyl]-15-fluoro-7,12-dimethyl-5,8,13-trioxo-2-{[3-(trifluoromethyl)benzoyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |

TABLE 21c-continued

Examples of Core 03 (Ex.3-Ex.55, Ex.482-Ex.503 and Ex.590-Ex.591; continued on the following pages)

| No | $R^{54}$ | $R^2$ | IUPAC name |
| --- | --- | --- | --- |
| Ex.51 | 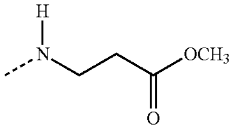 | $NH_2$ | methyl 3-({[(2S,11S,19aS)-2-amino-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-11-yl]carbonyl}amino)propanoate |
| Ex.52 | $OCH_2Ph$ | 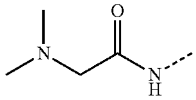 | benzyl {2S,11S,19aS)-2-{[2-(dimethylamino)acetyl]amino)-15-fluoro-7,12-dimethyl-5,13-trioxo-2,3,6,7,8,9,10,11,12,13,19,19a-dodecahydro-1H,5H-pyrrolo[2,1-c][1,4,7,12]benzoxatriazacyclopentadecine-11-carboxylate |
| Ex.53 | $OCH_2Ph$ | 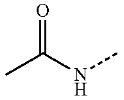 | benzyl (2S,11S,19aS)-2-(acetylamino)-15-fluoro-7,12-dimethyl-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxylate |
| Ex.54 | OH | 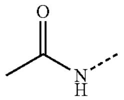 | (2S,11S,19aS)-2-(acetylamino)-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylic acid |
| Ex.55 | 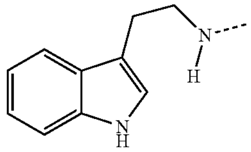 | $NH_2$ | (2S,11S,19aS)-2-amino-15-fluoro-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex.482 | 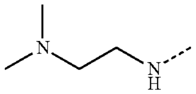 | 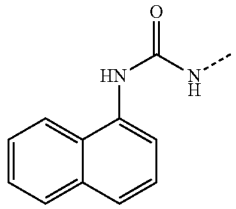 | (2S,11S,19aS)-N-[2-(dimethylamino)ethyl]-15-fluoro-7,12-dimethyl-2-{[(1-naphthylamino)carbonyl]amino}-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxamide |
| Ex.483 | 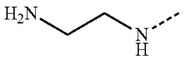 | 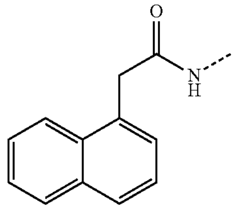 | (2S,11S,19aS)-N-(2-aminoethyl)-15-fluoro-7,12-dimethyl-2-{[2-(1-naphthyl)acetyl]amino)-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxamide |
| Ex.484 | 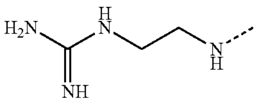 | 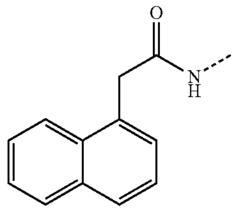 | (2S,11S,19aS)-N-(2-{[amino(imino)methyl]amino}ethyl)-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxamide |
| Ex.485 | 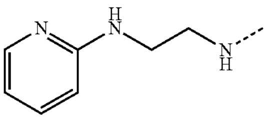 | 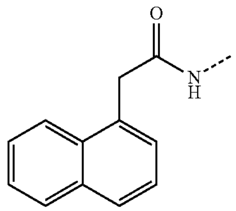 | [2S,11S,19aS)-15-fluoro-7,12-dimethyl-2-{[2-(1-naphthyl)acetyl]amino}-5,8,13-trioxo-N-[2-(2-pyridinylamino)ethyl]-2,3,6,7,8,9,10,11,12,13,19,19a-dodecahydro-1H,5H-pyrrolo[2,1-c] [1,4,7,12]benzoxatriaza-cyclopentadecine-11-carboxamide |

TABLE 21c-continued

| Examples of Core 03 (Ex.3-Ex.55, Ex.482-Ex.503 and Ex.590-Ex.591; continued on the following pages) | | | |
|---|---|---|---|
| No | $R^{54}$ | $R^2$ | IUPAC name |
| Ex.486 | 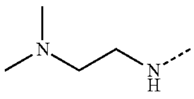 | 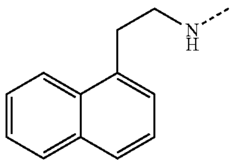 | (2S,11S,19aS)-N-[2-(dimethylamino) ethyl]-15-fluoro-7,12-dimethyl-2-{[2-(1-naphthyl)ethyl]amino}-5,8,13-trioxo-2,3,6,7,8,9,10,11,12,13,19,19a-dodecahydro-1H,5H-pyrrolo[2,1-c] [1,4,7,12]benzoxatri-azacyclopentadecine-11-carboxamide |
| Ex.487 | 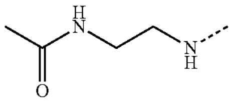 | 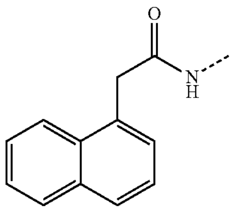 | (2S,11S,19aS)-N-[2-(acetylamino)ethyl]-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c] [1,4,7,12]benzoxatri-azacyclopentadecine-11-carboxamide |
| Ex.488 | 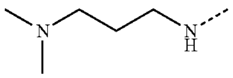 | 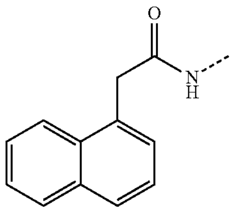 | (2S,11S,19aS)-N-[3-(dimethylamino)propyl]-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c] [1,4,7,12] benzoxatriazacyclopentadecine-11-carboxamide |
| Ex.489 | 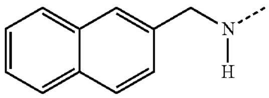 | 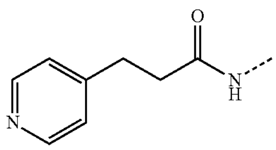 | (2S,11S,19aS)-15-fluoro-7,12-dimethyl-N-(2-naphthylmethyl)-5,8,13-trioxo-2-{[3-(4-pyridinyl)propanoyl]amino}-2,3,6,7,8,9,10,11,12,13,19,19a-dodecahydro-1H,5H-pyrrolo[2,1-c] [1,4,7,12]benzoxatriazacyclo-pentadecine-11-carboxamide |
| Ex.490 | 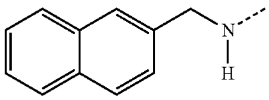 | 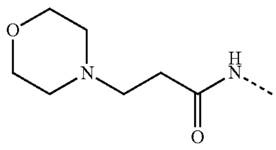 | (2S,11S,19aS)-15-fluoro-7,12-dimethyl-2-[(3-morpholinopropanoyl)amino]-N-(2-naphthylmethyl)-5,8,13-trioxo-2,3,6,7,8,9,10,11,12,13,19,19a-dodecahydro-1H,5H-pyrrolo[2,1-c] [1,4,7,12]benzoxatriazacyclo-pentadecine-11-carboxamide |
| Ex.491 | 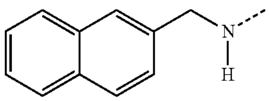 | 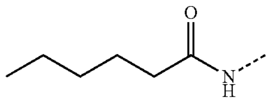 | (2S,11S,19aS)-15-fluoro-2-(hexanoylamino)-7,12-dimethyl-N-(2-naphthylmethyl)-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxamide |
| Ex.492 | 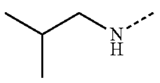 | 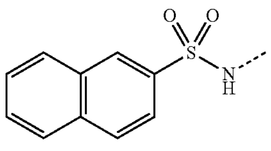 | (2S,11S,19aS)-15-fluoro-N-isobutyl-7,12-dimethyl-2-[(2-naphthylsulfonyl)amino]-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxamide |
| Ex.493 | 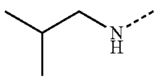 | 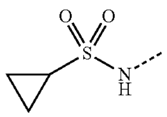 | (2S,11S,19aS)-2-[(cyclopropylsulfonyl) amino]-15-fluoro-N-isobutyl-7,12-dimethyl-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxamide |
| Ex.494 | 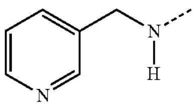 | 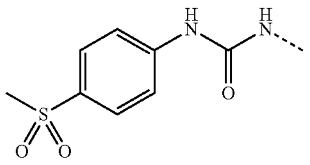 | (2S,11S,19aS)-15-fluoro-7,12-dimethyl-2-({[4-(methylsulfonyl)anilino]carbonyl}amino)-5,8,13-trioxo-N-(3-pyridinylmethyl)-2,3,6,7,8,9,10,11,12,13,19,19a-dodecahydro-1H,5H-pyrrolo[2,1-c] [1,4,7,12]benzoxatriazacyclopentadecine-11-carboxamide |

TABLE 21c-continued

| Examples of Core 03 (Ex.3-Ex.55, Ex.482-Ex.503 and Ex.590-Ex.591; continued on the following pages) | | | |
|---|---|---|---|
| No | $R^{54}$ | $R^2$ | IUPAC name |
| Ex.495 | 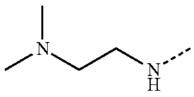 | 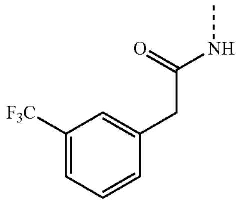 | (2S,11S,19aS)-N-[2-(dimethylamino)ethyl]-15-fluoro-7,12-dimethyl-5,8,13-trioxo-2-({2-[3-(trifluoromethyl)phenyl]acetyl}amino)-2,3,6,7,8,9,10,11,12,13,19,19a-dodecahydro-1H,5H-pyrrolo[2,1-c] [1,4,7,12] benzoxatriazacyclopentadecine-11-carboxamide |
| Ex.496 | 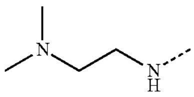 | 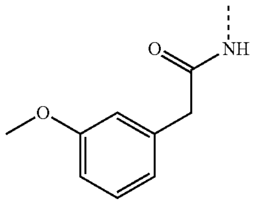 | (2S,11S,19aS)-N-[2-(dimethylamino) ethyl]-15-fluoro-2-{[2-{3-methoxyphenyl) acetyl]amino}-7,12-dimethyl-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxamide |
| Ex.497 | 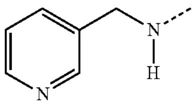 | 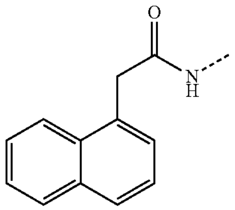 | (2S,11S,19aS)-15-fluoro-7,12-dimethyl-2-{[2-(1-naphthyl)acetyl]amino}-5,8,13-trioxo-N-(3-pyridinylmethyl)-2,3,6,7,8,9,10,11,12,13,19,19a-dodecahydro-1H,5H-pyrrolo[2,1-c][1,4,7,12]benzoxatriazacyclo-pentadecine-11-carboxamide |
| Ex.498 | $OCH_2Ph$ | 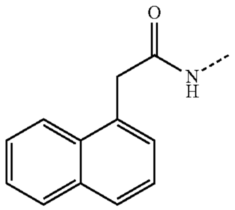 | benzyl (2S,11S,19aS)-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxylate |
| Ex.499 | OH | 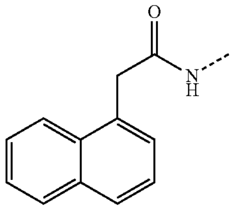 | (2S,11S,19aS)-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxylic acid |
| Ex.500 | 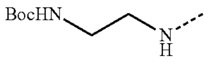 | 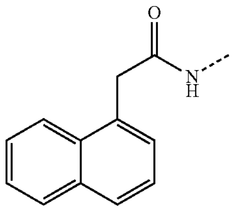 | tert-butyl N-(2-{[((2S,11S,19aS)-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c] [1,4,7,12] benzoxatriazacyclopentadecin-11-yl)carbonyl]amino}ethyl)carbamate |
| Ex.501 | 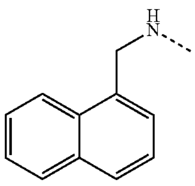 | 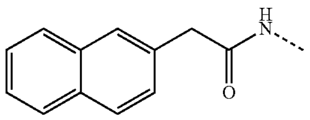 | (2S,11S,19aS)-15-fluoro-7,12-dimethyl-2-{[2-(2-naphthyl)acetyl]amino}-N-(1-naphthylmethyl)-5,8,13-trioxo-2,3,6,7,8,9,10,11,12,13,19,19a-dodecahydro-1H,5H-pyrrolo[2,1-c] [1,4,7,12]benzoxatriazacyclo-pentadecine-11-carboxamide |

TABLE 21c-continued

| Examples of Core 03 (Ex.3-Ex.55, Ex.482-Ex.503 and Ex.590-Ex.591; continued on the following pages) | | | |
|---|---|---|---|
| No | $R^{54}$ | $R^2$ | IUPAC name |
| Ex.502 | 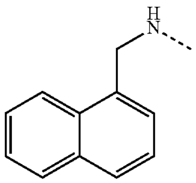 | 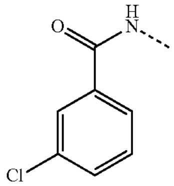 | (2S,11S,19aS)-2-[(3-chlorobenzoyl)amino]-15-fluoro-7,12-dimethyl-N-(1-naphthylmethyl)-5,8,13-trioxo-2,3,6,7,8,9,10,11,12,13,19,19a-dodecahydro-1H,5H-pyrrolo[2,1-c] [1,4,7,12] benzoxatriazacyclopentadecine-11-carboxamide |
| Ex.503 | 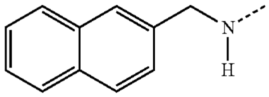 | 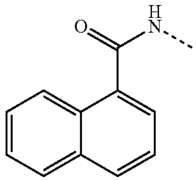 | (2S,11S,19aS)-15-fluoro-7,12-dimethyl-2-(1-naphthoylamino)-N-(2-naphthylmethyl)-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxamide |
| Ex.590 | OH | $NH_2$ | (2S,11S,19aS)-2-amino-15-fluoro-7,12-dimethyl-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxylic acid |
| Ex.591 | OH | 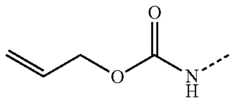 | [2S,11S,19aS)-2-{[(allyloxy)carbonyl] amino}-15-fluoro-7,12-dimethyl-5,8,13-trioxo-2,3,6,7,8,9,10,11,12,13,19,19a-dodecahydro-1H,5H-pyrrolo[2,1-c] [1,4,7,12]benzoxatriazacyclopentadecine-11-carboxylic acid |

TABLE 22a

| Examples of Core 04 (Ex. 56-Ex. 84, continued on the following pages) | | | | | | | |
|---|---|---|---|---|---|---|---|
| No | $R^{54}$ | $R^2$ | Starting material | General Procedure | Reagent | Purification Method | Yield (isolated salt) |
| Ex. 56-Ex. 57: cf. experimental description | | | | | | | |
| Ex. 58 | 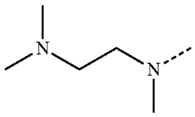 | 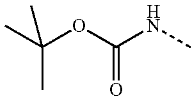 | Ex. 57 | L.2 | N,N,N'-trimetylethylene-diamine | FC ($CH_2Cl_2$/ MeOH/aq. $NH_3$) | 86% |
| Ex. 59 | 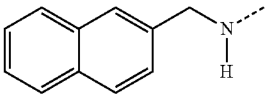 | 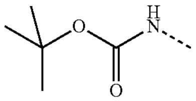 | Ex. 57 | L.2 | 2-naphthyl-methylamine | FC ($CH_2Cl_2$/ MeOH) | 91% |
| Ex. 60 | 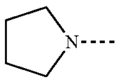 | 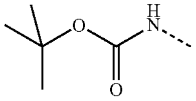 | Ex. 57 | L.2 | pyrrolidine | FC ($CH_2Cl_2$/ MeOH) | 79% |
| Ex. 61 | 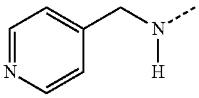 | 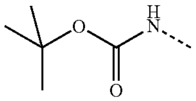 | Ex. 57 | L.2 | 4-(aminomethyl)-pyridine | FC ($CH_2Cl_2$/ MeOH) | 81% |
| Ex. 62 | 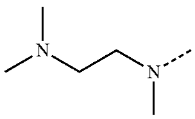 | $NH_2$ | Ex. 58 | J | HCl-dioxane | crude product | 98% (HCl salt) |

TABLE 22a-continued

Examples of Core 04 (Ex. 56-Ex. 84, continued on the following pages)

| No | $R^{54}$ | $R^2$ | Starting material | General Procedure | Reagent | Purification Method | Yield (isolated salt) |
|---|---|---|---|---|---|---|---|
| Ex. 63 | 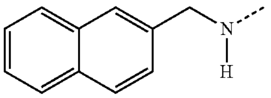 | $NH_2$ | Ex. 59 | J | HCl-dioxane | crude product | 76% (HCl salt) |
| Ex. 64 | 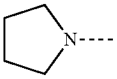 | $NH_2$ | Ex. 60 | J | HCl-dioxane | crude product | 94% (HCl salt) |
| Ex. 65 | 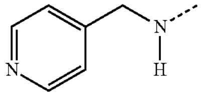 | $NH_2$ | Ex. 61 | J | HCl-dioxane | crude product | 91% (HCl salt) |
| Ex. 66 | 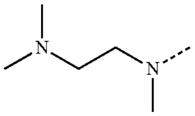 | 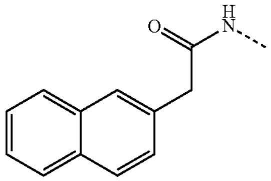 | Ex. 62 | L.1.3 | 2-naphthylacetic acid | prep. HPLC, method 1 | 67% (TFA salt) |
| Ex. 67 | 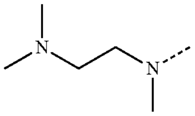 | 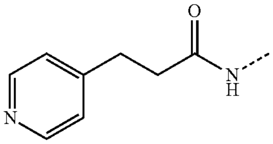 | Ex. 62 | L.1.2 | 3-(pyridine-4-yl)propanoic acid | prep. HPLC, method 2 | 56% |
| Ex. 68 | 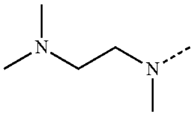 | 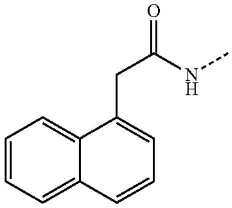 | Ex. 62 | L.1.2 | 1-naphthylacetic acid (1.5 equiv.) | prep. HPLC, method 1 | 24% (TFA salt) |
| Ex. 69 | 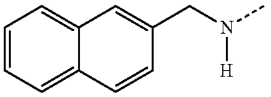 | 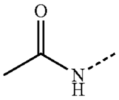 | Ex. 63 | L.1.1 | acetic anhydride (5 equiv.) | prep. HPLC, method 1 | 75% |
| Ex. 70 | 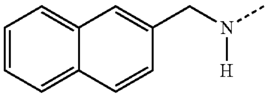 | 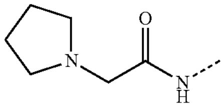 | Ex. 63 | L.1.3 | 1-pyrrolidinacetic acid | prep. HPLC, method 1 | 62% (TFA salt) |
| Ex. 71 | 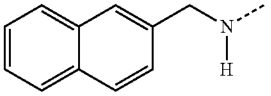 | 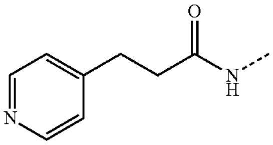 | Ex. 63 | L.1.2 | 3-(pyridine-4-yl)propanoic acid | prep. HPLC, method 1 | 22% (TFA salt) |
| Ex. 72 | 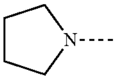 | 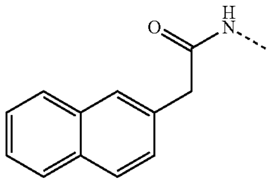 | Ex. 64 | L.1.3 | 2-naphthylacetic acid | prep. HPLC, method 2 | 51% |

TABLE 22a-continued

Examples of Core 04 (Ex. 56-Ex. 84, continued on the following pages)

| No | $R^{54}$ | $R^2$ | Starting material | General Procedure | Reagent | Purification Method | Yield (isolated salt) |
|---|---|---|---|---|---|---|---|
| Ex. 73 | 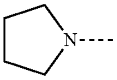 | 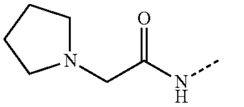 | Ex. 64 | L.1.2 | 1-pyrrolidinacetic acid (1.7 equiv.) | prep. HPLC, method 1 | 39% (TFA salt) |
| Ex. 74 | 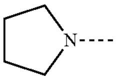 | 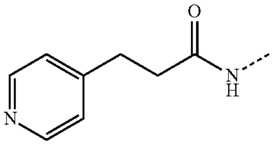 | Ex. 64 | L.1.2 | 3-(pyridine-4-yl)propanoic acid | prep. HPLC, method 2 | 29% |
| Ex. 75 | 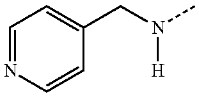 | 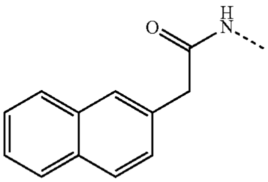 | Ex. 65 | L.1.3 | 2-naphthylacetic acid | prep. HPLC, method 1 | 37% (TFA salt) |
| Ex. 76 | 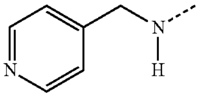 | 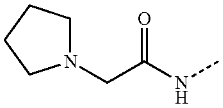 | Ex. 65 | L.1.2 | 1-pyrrolidinacetic acid (1.7 equiv.) | prep. HPLC, method 2 | 45% |
| Ex. 77 | 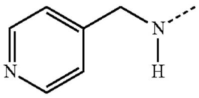 | 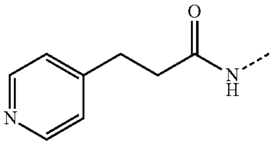 | Ex. 65 | L.1.2 | 3-(pyridine-4-yl)propanoic acid | prep. HPLC, method 2 | 45% |
| Ex. 78 | 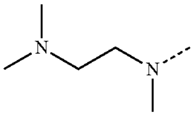 | 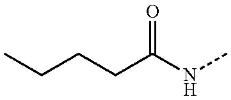 | Ex. 62 | L.1.1 | valeroyl chloride (1.6 equiv.) | prep. HPLC, method 1 | 56% |
| Ex. 79 | 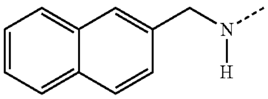 | 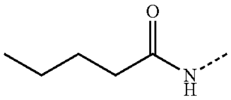 | Ex. 63 | L.1.1 | valeroyl chloride (1.6 equiv.) | prep. HPLC, method 1 | 77% |
| Ex. 80 | 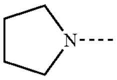 | 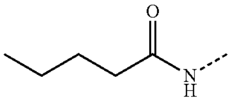 | Ex. 64 | L.1.1 | valeroyl chloride (1.3 equiv.) | prep. HPLC, method 1 | 46% |
| Ex. 81 | 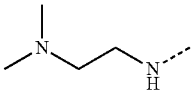 | $NH_2$ | Ex. 84 | J | HCl-dioxane | crude product | 99% (HCl salt) |
| Ex. 82 | 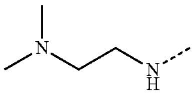 | 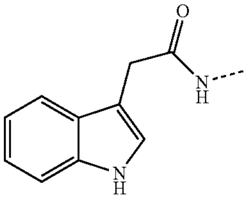 | Ex. 81 | L.1.3 | 3-indoleacetic acid (1.5 equiv.) HATU (1.5 equiv.) HOAt (1.5 equiv.) i-$Pr_2NEt$ (5 equiv.) | prep. HPLC, method 1, then FC ($CH_2Cl_2$/MeOH/aq. $NH_3$) | 15% |

TABLE 22a-continued

| Examples of Core 04 (Ex. 56-Ex. 84, continued on the following pages) | | | | | | | |
|---|---|---|---|---|---|---|---|
| No | $R^{54}$ | $R^2$ | Starting material | General Procedure | Reagent | Purification Method | Yield (isolated salt) |
| Ex. 83 | 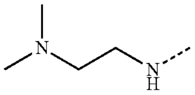 | 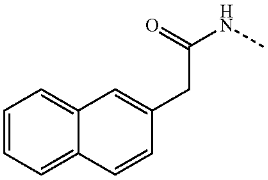 | Ex. 81 | L.1.3 | 2-naphthylacetic acid (1.2 equiv.) | (FC $CH_2Cl_2$/ MeOH/aq. $NH_3$), t hen prep. HPLC, method 1 | 58% |
| Ex. 84 | 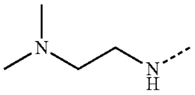 | 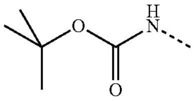 | Ex. 57 | L.2 | 2-dimethyl-aminoethyl-amine | FC ($CH_2Cl_2$/ MeOH) | 89% |

TABLE 22b

| Examples of Core 04 (Ex. 56-Ex. 84; continued on the following pages) | | | | | | | |
|---|---|---|---|---|---|---|---|
| No | $R^{54}$ | $R^2$ | FORMULA | MONOISO-TOPIC MASS | Rt (purity at 220 nm) | $[M + H]^+$ found | LC-MS-Method |
| Ex. 56-Ex. 57: cf. experimental description | | | | | | | |
| Ex. 58 | 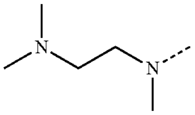 | 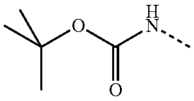 | C31H47FN6O7 | 634.4 | 1.44 (91) | 635.5 | Method 2 |
| Ex. 59 | 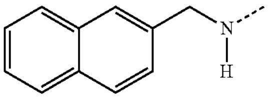 | 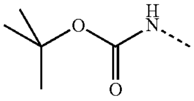 | C37H44FN5O7 | 689.3 | 1.89 (87) | 690.5 | Method 2 |
| Ex. 60 | 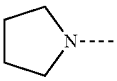 | 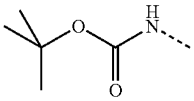 | C30H42FN5O7 | 603.3 | 1.67 (84) | 604.4 | Method 2 |
| Ex. 61 | 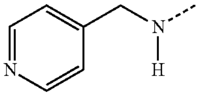 | 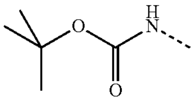 | C32H41FN6O7 | 640.3 | 1.42 (92) | 641.4 | Method 2 |
| Ex. 62 | 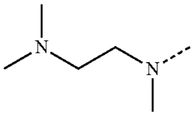 | $NH_2$ | C26H39FN6O5 | 534.3 | 0.97 (91) | 535.4 | Method 2 |
| Ex. 63 | 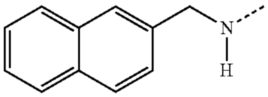 | $NH_2$ | C32H36FN5O5 | 589.3 | 1.53 (95) | 590.4 | Method 2 |
| Ex. 64 | 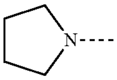 | $NH_2$ | C25H34FN5O5 | 503.3 | 1.23 (82) | 504.3 | Method 2 |
| Ex. 65 | 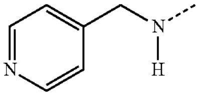 | $NH_2$ | C27H33FN6O5 | 540.3 | 0.97 (97) | 541.4 | Method 2 |

TABLE 22b-continued
Examples of Core 04 (Ex. 56-Ex. 84; continued on the following pages)
| No | $R^{54}$ | $R^2$ | FORMULA | MONOISO-TOPIC MASS | Rt (purity at 220 nm) | [M + H]$^+$ found | LC-MS-Method |
|---|---|---|---|---|---|---|---|
| Ex. 66 | 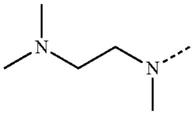 | 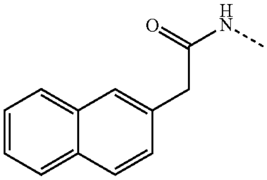 | C38H47FN606 | 702.4 | 1.51 (97) | 703.5 | Method 2 |
| Ex. 67 | 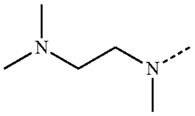 | 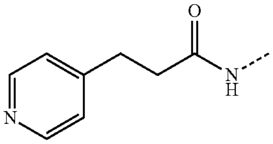 | C34H46FN706 | 667.4 | 1.08 (94) | 668.5 | Method 2 |
| Ex. 68 | 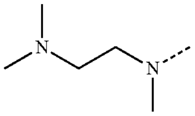 | 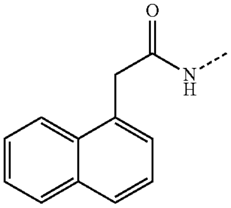 | C38H47FN606 | 702.4 | 1.51 (88) | 703.5 | Method 2 |
| Ex. 69 | 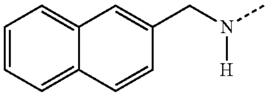 | 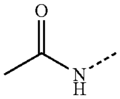 | C34H38FN506 | 631.3 | 1.66 (90) | 632.3 | Method 2 |
| Ex. 70 | 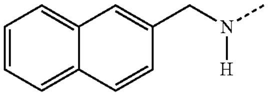 | 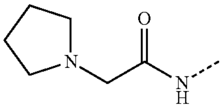 | C38H45FN606 | 700.3 | 1.56 (95) | 701.5 | Method 2 |
| Ex. 71 | 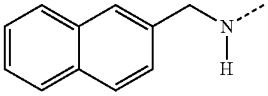 | 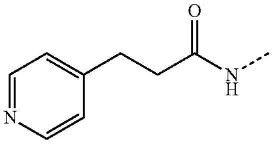 | C40H43FN606 | 722.3 | 1.55 (93) | 723.5 | Method 2 |
| Ex. 72 | 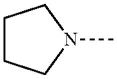 | 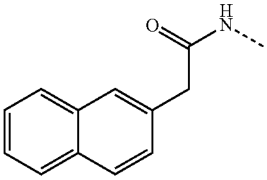 | C37H42FN506 | 671.3 | 1.73 (87) | 672.4 | Method 2 |
| Ex. 73 | 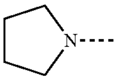 | 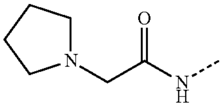 | C31H43FN606 | 614.3 | 1.28 (90) | 615.4 | Method 2 |
| Ex. 74 | 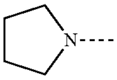 | 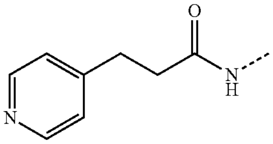 | C33H41FN606 | 636.3 | 1.29 (91) | 637.4 | Method 2 |

TABLE 22b-continued
| No | R[54] | R[2] | FORMULA | MONOISO-TOPIC MASS | Rt (purity at 220 nm) | [M + H]+ found | LC-MS-Method |
|---|---|---|---|---|---|---|---|
| Examples of Core 04 (Ex. 56-Ex. 84; continued on the following pages) | | | | | | | |
| Ex. 75 | 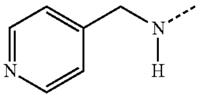 | 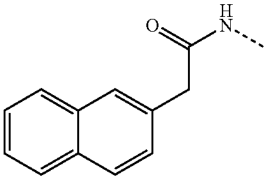 | C39H41FN6O6 | 708.3 | 1.50 (92) | 709.4 | Method 2 |
| Ex. 76 | 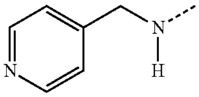 | 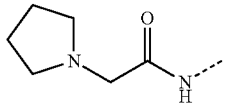 | C33H42FN7O6 | 651.3 | 1.07 (91) | 652.4 | Method 2 |
| Ex. 77 | 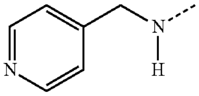 | 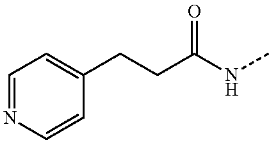 | C35H40FN7O6 | 673.3 | 1.07 (90) | 674.5 | Method 2 |
| Ex. 78 | 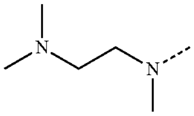 | 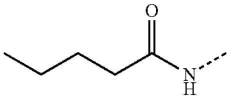 | C31H47FN6O6 | 618.4 | 1.33(98) | 619.4 | Method 2 |
| Ex. 79 | 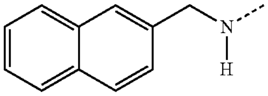 | 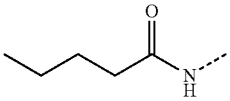 | C37H44FN5O6 | 673.3 | 1.81 (91) | 674.4 | Method 2 |
| Ex. 80 | 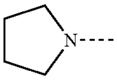 | 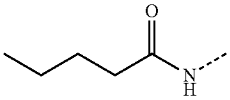 | C30H42FN5O6 | 587.3 | 1.56 (93) | 588.4 | Method 2 |
| Ex. 81 | 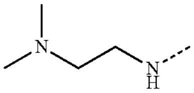 | $NH_2$ | C25H37FN6O5 | 520.3 | 1.10 (88) | 521.4 | Method 2 |
| Ex. 82 | 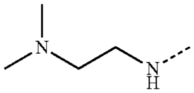 | 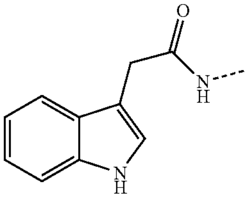 | C35H44FN7O6 | 677.3 | 1.36 (93) | 678.5 | Method 2 |
| Ex. 83 | 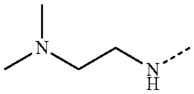 | 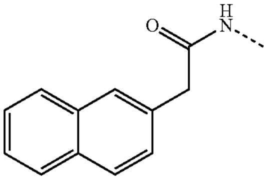 | C37H45FN6O6 | 688.3 | 1.49 (93) | 689.5 | Method 2 |
| Ex. 84 | 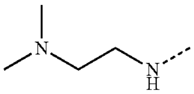 | 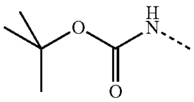 | C30H45FN6O7 | 620.3 | 1.38 (87) | 621.5 | Method 2 |

TABLE 22c

Examples of Core 04 (Ex. 56-Ex. 84; continued on the following pages)

| No | $R^{54}$ | $R^2$ | IUPAC name |
|---|---|---|---|
| Ex. 56 | $OCH_2Ph$ | 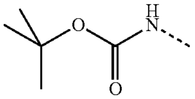 | benzyl (2R,11S,19aS)-2-[(tert-butoxycarbonyl)amino]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylate |
| Ex. 57 | OH | 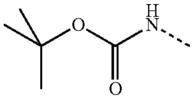 | (2R,11S,19aS)-2-[(tert-butoxycarbonyl)amino]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylic acid |
| Ex. 58 | 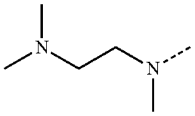 | 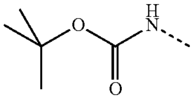 | tert-butyl N-H2R,11S,19aS)-11-{[[2-(dimethylamino)ethyl](methyl)amino]carbonyl}-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl)-carbamate |
| Ex. 59 | 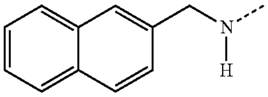 | 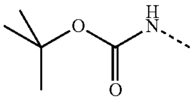 | tert-butyl N-((2R, 11S,19aS)-15-fluoro-7,12-dimethyl-11-{[(2-naphthylmethyl)amino]carbonyl}-5,8,13-trioxo-2,3,6,7,8,9,10,11,12,13,19,19a-dodecahydro-1H,5H-pyrrolo[2,1-c][1,4,7,12] benzoxatriazacyclopentadecin-2-yl)carbamate |
| Ex. 60 | 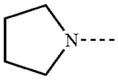 | 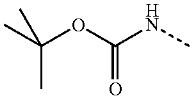 | tert-butyl N-[(2R,11S,19aS)-15-fluoro-7,12-dimethyl-5,8, 13 -trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]carbamate |
| Ex. 61 | 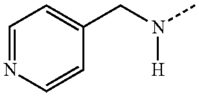 | 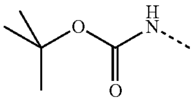 | tert-butyl N-((2R,11S,19aS)-15-fluoro-7,12-dimethyl-5,8, 13-trioxo-11-{[(4-pyridinylmethyl)amino]carbonyl}-2,3,6,7,8,9,10,11,12,13, 19,19a-dodecahydro-1H,5H-pyrrolo[2,1-c][1,4,7,12] benzoxatriazacyclopentadecin-2-yl)-carbamate |
| Ex. 62 | 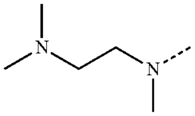 | $NH_2$ | (2R,11S,19aS)-2-amino-N-[2-(dimethylamino)ethyl}-15-fluoro-N,7,12-trimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 63 | 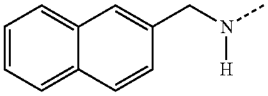 | $NH_2$ | (2R,11S,19aS)-2-amino-15-fluoro-7,12-dimethyl-N-(2-naphthylmethyl)-5,8,13-trioxo-2,3,6,7,8,9,10,11,12,13,19,19a-dodecahydro-1H, 5H-pyrrolo[2,1-c][1,4,7,12]benzoxatriazacyclopentadecine-11-carboxamide |
| Ex. 64 | 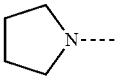 | $NH_2$ | (2R,11S,19aS)-2-amino-15-fluoro-7,12-dimethyl-11-(1-pyrrolidinylcarbonyl)-2,3,6,7,9,10,11,12,19,19a-decahydro-1H,5H-pyrrolo[2,1-c][1,4,7,12]benzoxatriazacyclopentadecine-5,8,13-trione |
| Ex. 65 | 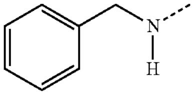 | $NH_2$ | (2R,11S,19aS)-2-amino-15-fluoro-7,12-dimethyl-5,8,13-trioxo-N-(4-pyridinylmethyl)-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 66 | 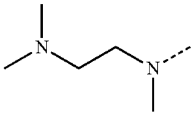 | 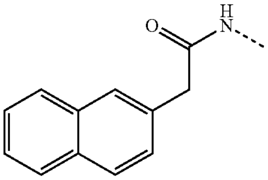 | (2R,11S,19aS)-N-{2-(dimethylamino)ethyl}-15-fluoro-N,7,12-trimethyl-2-{(2-(2-naphthyl)acetyl]amino}-5,8,13-trioxo-2,3,6,7,8,9,10,11, 12,13,19,19a-dodecahydro-1H,5H-pyrrolo[2,1-c][1,4,7,12] benzoxatriazacyclopentadecine-11-carboxamide |

TABLE 22c-continued

Examples of Core 04 (Ex. 56-Ex. 84; continued on the following pages)

| No | $R^{54}$ | $R^2$ | IUPAC name |
|---|---|---|---|
| Ex. 67 | 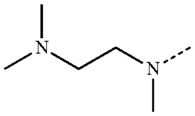 | 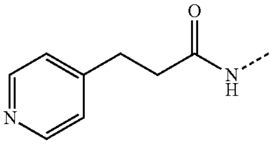 | (2R,11S,19aS)-N-[2-(dimethylamino)ethyl]-15-fluoro-N,7,12-trimethyl-5,8,13-trioxo-2-{[3-(4-pyridinyl)propanoyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 68 | 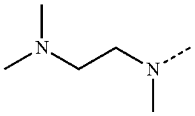 | 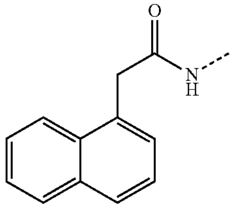 | (2R,11S,19aS)-N-[2-(dimethylamino)ethyl]-15-fluoro-N,7,12-trimethyl-2-{2[2-(1-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 69 | 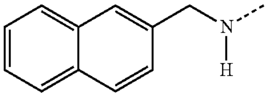 | 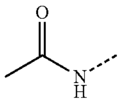 | (2R,11S,19aS)-2-(acetylamino)-15-fluoro-7,12-dimethyl-N-(2-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 70 | 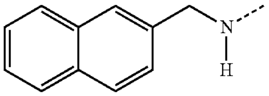 | 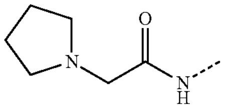 | (2R,11S,19aS)-15-fluoro-7,12-dimethyl-N-(2-naphthylmethyl)-5,8,13-trioxo-2-{[2-(1-pyrrolidinyl)acetyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 71 | 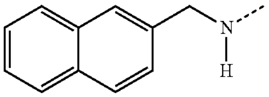 | 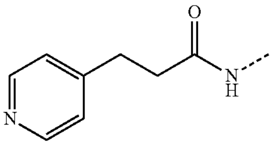 | (2R,11S,19aS)-15-fluoro-7,12-dimethyl-N-(2-naphthylmethyl)-5,8,13-trioxo-2-{[3-(4-pyridinyl)propanoyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 72 | 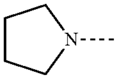 | 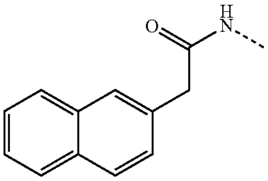 | N-[(2R,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]-2-(2-naphthyl)acetamide |
| Ex. 73 | 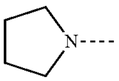 | 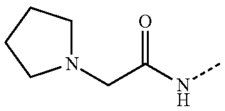 | N-[(2R,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo]2,1-c][1,4,7,12]benzoxatriazacyclopentadecin-2-yl]-2-(1-pyrrolidinyl)acetamide |
| Ex. 74 | 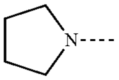 | 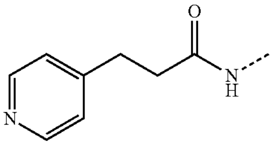 | N-[(2R,11,5,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]-3-(4-pyridinyl)propanamide |
| Ex. 75 | 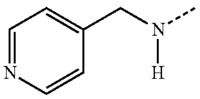 | 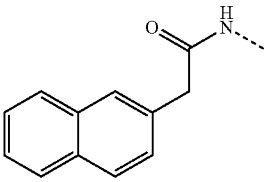 | (2R,11S,19aS)-15-fluoro-7,12-dimethyl-2-{[2-(2-naphthyl)acetyl]amino}-5,8,13-trioxo-N-(4-pyridinylmethyl)-2,3,6,7,8,9,10,11,12,13,19,19a-dodecahydro-1H,5H-pyrrolo[2,1-c][1,4,7,12]benzoxatriazacyclopentadecine-11-carboxamide |

TABLE 22c-continued

Examples of Core 04 (Ex. 56-Ex. 84; continued on the following pages)

| No | $R^{54}$ | $R^2$ | IUPAC name |
| --- | --- | --- | --- |
| Ex. 76 | 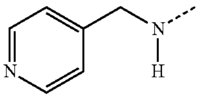 | 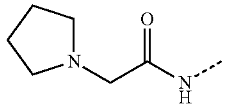 | (2R,11S,19aS)-15-fluoro-7,12-dimethyl-5,8,13-trioxo-N-(4-pyridinylmethyl)-2-{[2-(1-pyrrolidinyl)acetyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 77 | 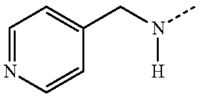 | 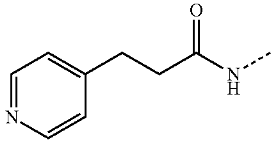 | (2R,11S,19aS)-15-fluoro-7,12-dimethyl-5,8,13-trioxo-N-(4-pyridinylmethyl)-2-{[3-(4-pyridinyl)propanoyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 78 | 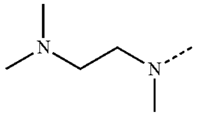 | 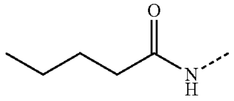 | (2R,11S,19aS)-N-[2-(dimethylamino)ethyl]-15-fluoro-N,7,12-trimethyl-5,8,13-trioxo-2-(pentanoylamino)-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 79 | 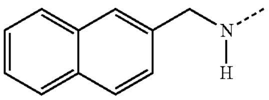 | 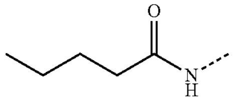 | (2R,11S,19aS)-15-fluoro-7,12-dimethyl-N-(2-naphthylmethyl)-5,8,13-trioxo-2-(pentanoylamino)-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 80 | 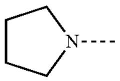 | 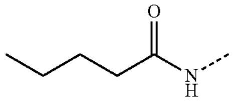 | N-[(2R,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]pentanamide |
| Ex. 81 | 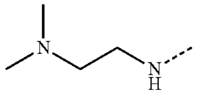 | $NH_2$ | (2R,115,19aS)-2-amino-N-[2-(dimethylamino)ethyl]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 82 | 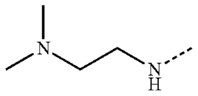 | 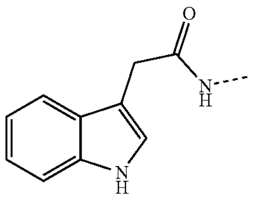 | (2R,11S,19aS)-N-[2-(dimethylamino)ethyl]-15-fluoro-2-{[2-(1H-indol-3-yl)acetyl]amino}-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 83 | 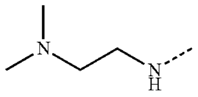 | 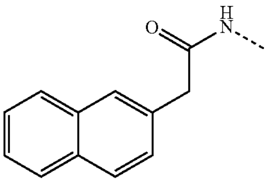 | (2R,11S,19aS)-N-[2-(dimethylamino)ethyl]-15-fluoro-7,12-dimethyl-2-{[2-(2-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 84 | 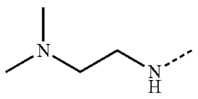 | 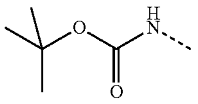 | tert-butyl N-[(2R,11S,19aS)-11-{[2-(dimethylamino)ethyl]amino}carbonyl)-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl]-carboxamide |

TABLE 23a

Examples of Core 05 (Ex. 85-Ex. 103; continued on the following pages)

| No | $R^2$ | $R^{54}$ | Starting material | General Procedure | Reagent | Purification Method | Yield (isolated salt) |
|---|---|---|---|---|---|---|---|
| Ex. 85-Ex. 86: cf. experimental description | | | | | | | |
| Ex. 87 | 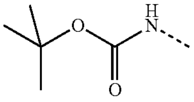 | 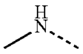 | Ex. 86 | L.2 | methylamine-hydrochloride (10 equiv.) HATU (1.5 equiv.) HOAt (1.5 equiv.) i-Pr2NEt (13 equiv.) | FC ($CH_2Cl_2$/MeOH) | 76% |
| Ex. 88 | 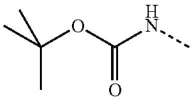 | 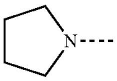 | Ex. 86 | L.2 | pyrrolidine | FC ($CH_2Cl_2$/MeOH) then prep. HPLC, method 2 | 64% |
| Ex. 89 | 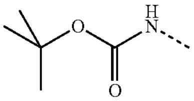 | 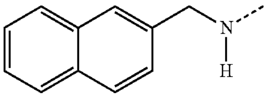 | Ex. 86 | L.2 | 2-naphthyl-methylamine | FC (EtOAc/MeOH) | 93% |
| Ex. 90 | $NH_2$ | 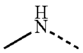 | Ex. 87 | J | HCl-dioxane | crude product | 86% (HCl salt) |
| Ex. 91 | $NH_2$ | 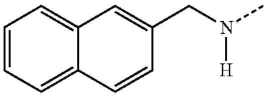 | Ex. 89 | J | HCl-dioxane | crude product | 98% (HCl salt) |
| Ex. 92 | $NH_2$ | 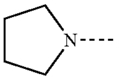 | Ex. 88 | J | HCl-dioxane | crude product | 94% (HCl salt) |
| Ex. 93 | 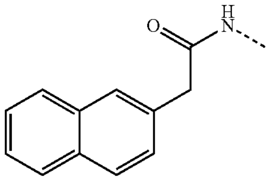 | 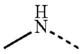 | Ex. 90 | L.1.2 | 2-naphthylacetic acid | prep. HPLC, method 3 | 66% |
| Ex. 94 | 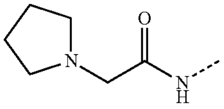 | 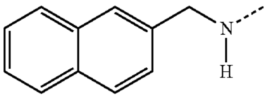 | Ex. 91 | L.1.2 | 1-pyrrolidineacetic acid (1.7 equiv.) | prep. HPLC, method 1 | 46% (TFA salt) |
| Ex. 95 | 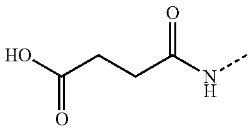 | 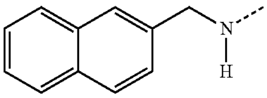 | Ex. 91 | L.1.1 | succinic anhydride (1.05 equiv.) | prep. HPLC, method 2 | 47% ($NH4^+$ salt) |
| Ex. 96 | 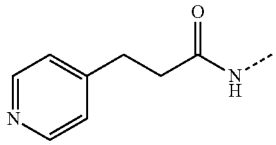 | 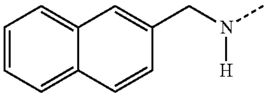 | Ex. 91 | L.1.2 | 3-(pyridine-4-yl)propanoic acid (3.7 equiv.) | FC ($CH_2Cl_2$/MeOH) | 74% |

TABLE 23a-continued

Examples of Core 05 (Ex. 85-Ex. 103; continued on the following pages)

| No | $R^2$ | $R^{54}$ | Starting material | General Procedure | Reagent | Purification Method | Yield (isolated salt) |
|---|---|---|---|---|---|---|---|
| Ex. 97 | 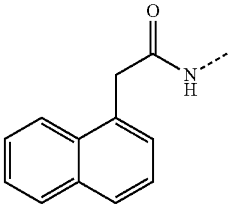 | 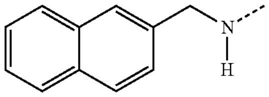 | Ex. 91 | L.1.2 | 1-naphthylacetic acid (1.4 equiv.) | prep. HPLC, method 3 | 72% |
| Ex. 98 | 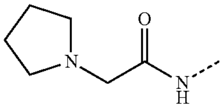 | 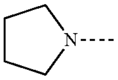 | Ex. 92 | L.1.2 | 1-pyrrolidineacetic acid | prep. HPLC, method 1 | 68% (TFA salt) |
| Ex. 99 | 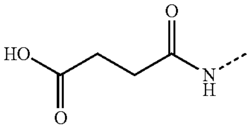 | 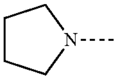 | Ex. 92 | L.1.1 | succinic anhydride (1.05 equiv.) | prep. HPLC, method 2 | 40% ($NH4^+$ salt) |
| Ex. 100 | 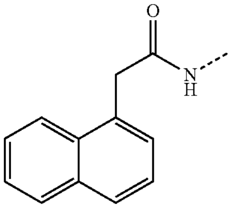 | 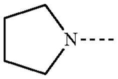 | Ex. 92 | L.1.2 | 1-naphthylacetic acid | FC (EtOAc/ MeOH) | 83% |
| Ex. 101 | 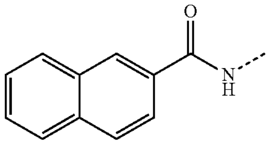 | 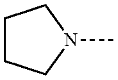 | Ex. 92 | L.1.1 | 2-naphthoyl chloride (1.6 equiv.) | FC (EtOAc/ MeOH) | 84% |
| Ex. 102 | 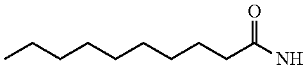 | 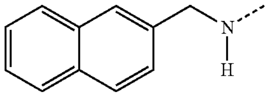 | Ex. 91 | L.1.1 | decanoyl chloride (4.1 equiv.) pyridine (15 equiv.) | prep. HPLC, method 3 | 64% |
| Ex. 103 | 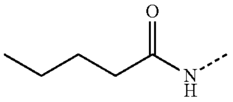 | 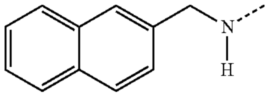 | Ex. 91 | L.1.1 | valeroyl chloride (2.0 equiv.) | prep. HPLC, method 3 | 87% |

TABLE 23b

Examples of Core 05 (Ex. 85-Ex. 103; continued on the following pages)

| No | $R^2$ | $R^{54}$ | FORMULA | MONO-ISO-TOPIC MASS | Rt (purity at 220 nm) | $[M + H]^+$ found | LC-MS-Method |
|---|---|---|---|---|---|---|---|
| Ex. 85-Ex. 86: cf. experimental description | | | | | | | |
| Ex. 87 | 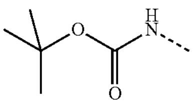 | 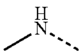 | C27H38FN5O7 | 563.3 | 1.52 (78) | 564.4 | Method 2 |

TABLE 23b-continued
Examples of Core 05 (Ex. 85-Ex. 103; continued on the following pages)
| No | $R^2$ | $R^{54}$ | FORMULA | MONO-ISO-TOPIC MASS | Rt (purity at 220 nm) | $[M + H]^+$ found | LC-MS-Method |
|---|---|---|---|---|---|---|---|
| Ex. 88 | 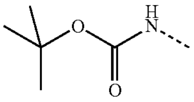 | 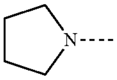 | C30H42FN5O7 | 603.3 | 1.59 (64) 1.63 (27) | 604.4/604.4 | Method 2 |
| Ex. 89 | 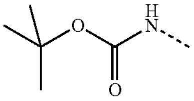 | 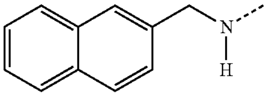 | C37H44FN5O7 | 689.3 | 1.89 (97) | 690.5 | Method 2 |
| Ex. 90 | $NH_2$ | 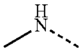 | C22H30FN5O5 | 463.2 | 1.02 (95) | 464.3 | Method 2 |
| Ex. 91 | $NH_2$ | 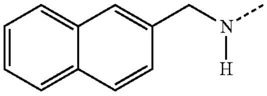 | C32H36FN5O5 | 589.3 | 1.51 (98) | 590.4 | Method 2 |
| Ex. 92 | $NH_2$ | 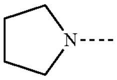 | C25H34FN5O5 | 503.3 | 1.20 (97) | 504.3 | Method 2 |
| Ex. 93 | 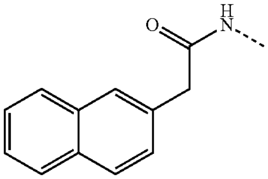 | 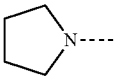 | C34H38FN5O6 | 631.3 | 1.65 (98) | 632.3 | Method 2 |
| Ex. 94 | 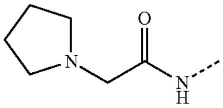 | 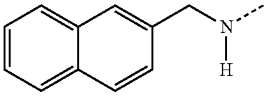 | C38H45FN6O6 | 700.3 | 1.55 (100) | 701.5 | Method 2 |
| Ex. 95 | 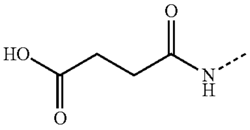 | 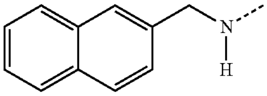 | C36H40FN5O8 | 689.3 | 1.65 (98) | 690.5 | Method 2 |
| Ex. 96 | 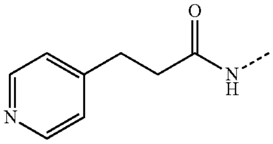 | 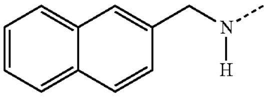 | C40H43FN6O6 | 722.3 | 1.51 (96) | 723.5 | Method 2 |
| Ex. 97 | 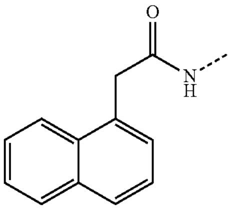 | 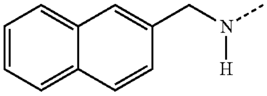 | C44H44FN5O6 | 757.3 | 1.96 (92) | 758.5 | Method 2 |
| Ex. 98 | 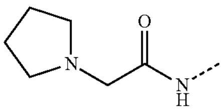 | 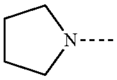 | C31H43FN6O6 | 614.3 | 1.25 (98) | 615.3 | Method 2 |

TABLE 23b-continued

Examples of Core 05 (Ex. 85-Ex. 103; continued on the following pages)

| No | $R^2$ | $R^{54}$ | FORMULA | MONO-ISO-TOPIC MASS | Rt (purity at 220 nm) | $[M + H]^+$ found | LC-MS-Method |
|---|---|---|---|---|---|---|---|
| Ex. 99 | 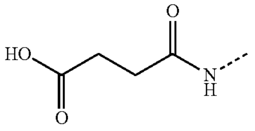 | 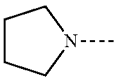 | C29H38FN5O8 | 603.3 | 1.34 (100) | 604.4 | Method 2 |
| Ex. 100 | 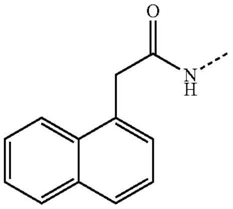 | 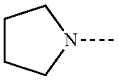 | C37H42FN5O6 | 671.3 | 1.73 (85) | 672.4 | Method 3 |
| Ex. 101 | 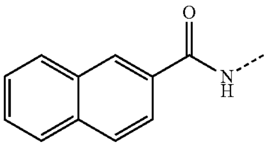 | 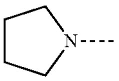 | C36H40FN5O6 | 657.3 | 1.73 (98) | 658.4 | Method 2 |
| Ex. 102 | 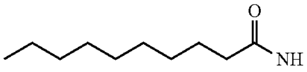 | 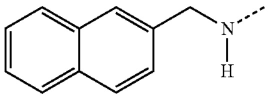 | C42H54FN5O6 | 743.4 | 2.16 (95) | 744.6 | Method 3 |
| Ex. 103 | 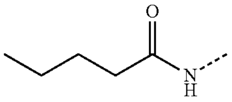 | 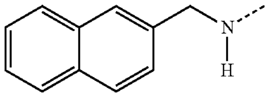 | C37H44FN5O6 | 673.3 | 1.83 (96) | 674.5 | Method 2 |

TABLE 23c

Examples of Core 05 (Ex. 85-Ex. 103; continued on the following pages)

| No | $R^2$ | $R^{54}$ | IUPAC name |
|---|---|---|---|
| Ex. 85 | 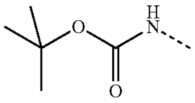 | $OCH_2Ph$ | benzyl (2S,11R,19aS)-2-[(tert-butoxycarbonyl) amino]-15-fluoro-7,12-dimethyl-5,8,13-trioxo-2,3,6,7,8,9,10,11,12,13,19,19a-dodecahydro-1H,5H-pyrrol[2,1-c][1,4,7,12] benzoxatriazacyclopentadecine-11-carboxylate |
| Ex. 86 | 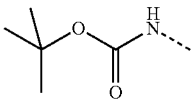 | OH | (2S,11R,19aS)-2-[(tert-butoxycarbonyl)amino]-15-fluoro-7,12-dimethyl-5,8,13-trioxo-2,3,6,7,8,9,10,11,12,13,19,19a-dodecahydro-1H,5H-pyrrolo[2,1-c][1,4,7,12] benzoxatriazacyclopentadecine-11-carboxylic acid |

TABLE 23c-continued

| Examples of Core 05 (Ex. 85-Ex. 103; continued on the following pages) | | | |
|---|---|---|---|
| No | $R^2$ | $R^{54}$ | IUPAC name |
| Ex. 87 | 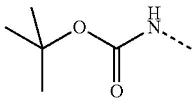 | 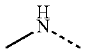 | tert-butyl N-{(2S,11R, 19aS)-15-fluoro-7,12-dimethyl-11-[(methylamino) carbonyl]-5,8,13-trioxo-2,3,6,7,8,9,10,11,12,13,19,19a-dodecahydro-1H,5H-pyrrolo[2,1-c][1,4,7,12]benzoxatriazacyclopentadecin-2 yl}carbamate |
| Ex. 88 | 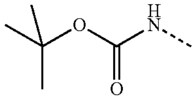 | 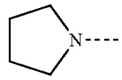 | tert-butyl N-[(2S,11R,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12] benzoxatriazacyclopentadecin-2-yl]carbamate |
| Ex. 89 | 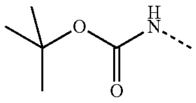 | 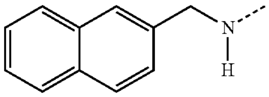 | tert-butyl N-((2S,11R,19aS)-15-fluoro-7,12-dimethyl-11-{[(2-naphthylmethyl)amino]carbonyl}-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl]carbamate |
| Ex. 90 | $NH_2$ | 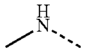 | (2S,11R,19aS)-2-amino-15-fluoro-N,7,12-trimethyl-5,8,13-trioxo-2,3,6,7,8,9,10,11,12,13,19,19a-dodecahydro-1H,5H-pyrrolo[2,1-c][1,4,7,12] benzoxatriazacyclopentadecine-11-carboxamide |
| Ex. 91 | $NH_2$ | 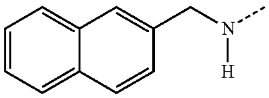 | (2S,11R,19aS)-2-amino-15-fluoro-7,12-dimethyl-N-(2-naphthylmethyl)-5,8,13-trioxo-2,3,6,7,8,9,10,11,12,13,19,19a-dodecahydro-1H,5H-pyrrolo[2,1-c][1,4,7,12] benzoxatriazacyclopentadecine-11-carboxamide |
| Ex. 92 | $NH_2$ | 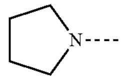 | (2S,11R,19aS)-2-amino-15-fluoro-7,12-dimethyl-11-(1-pyrrolidinylcarbonyl)-2,3,6,7,9,10,11,12,19,19a-decahydro-1H,5H-pyrrolo[2,1-c][1,4,7,12] benzoxatriazacyclopentadecine-5,8,13-trione |
| Ex. 93 | 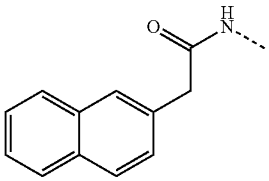 | 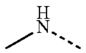 | (2S,11R,19aS)-15-fluoro-N,7,12-trimethyl-2-{[2-(2-naphthyl) acetyl]amino}-5,8,13-trioxo-2,3,6,7,8,9,10,11,12,13,19,19a-dodecahydro-1H,5H-pyrrolo[2,1-c][1,4,7,12] benzoxatriazacyclopentadecine-11-carboxamide |
| Ex. 94 | 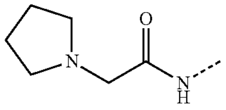 | 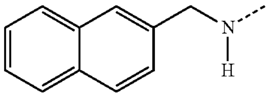 | (2S,11R,19aS)-15-fluoro-7,12-dimethyl-N-(2-naphthylmethyl)-5,8,13-trioxo-2-{[2-(1-pyrrolidinyl)acetyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |

TABLE 23c-continued

| Examples of Core 05 (Ex. 85-Ex. 103; continued on the following pages) | | | |
|---|---|---|---|
| No | $R^2$ | $R^{54}$ | IUPAC name |
| Ex. 95 | 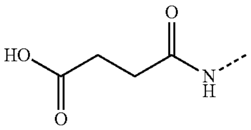 | 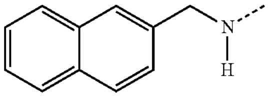 | 4-[((2S,11R,19aS)-15-fluoro-7,12-dimethyl-11-{[2-naphthylmethyl)amino]carbonyl}-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl)amino]-4-oxobutanoic acid |
| Ex. 96 | 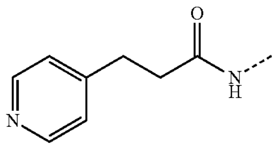 | 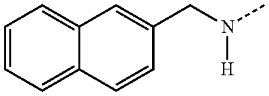 | (2S,11R,19aS)-15-fluoro-7,12-dimethyl-N-(2-naphthylmethyl)-5,8,13-trioxo-2-{[3-(4-pyridinyl)propanoyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 97 | 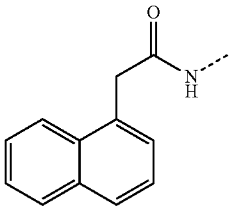 | 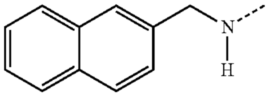 | (2S,11R,19aS) -15-fluoro-7,12-dimethyl-2-{[2-(1-naphthyl)acetyl)amino}-N-(2-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 98 | 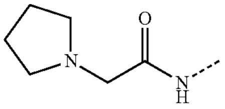 | 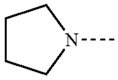 | N-[(2S,11R,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]-2-(1-pyrrolidinyl)acetamide |
| Ex. 99 | 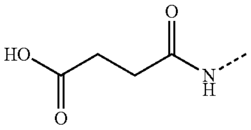 | 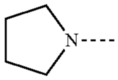 | 4-{[(2S,11R,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]amino}-4-oxobutanoic acid |
| Ex. 100 | 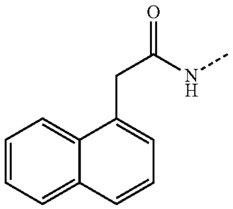 | 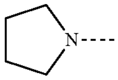 | N-[(2S,11R,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]-2-(1-naphthyl)acetamide |
| Ex. 101 | 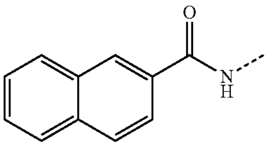 | 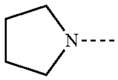 | N-[(2S,11R,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]-2-naphthamide |
| Ex. 102 | 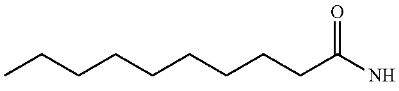 | 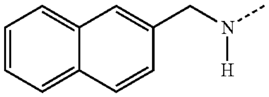 | (2S,11R,19aS)-2-(decanoylamino)-15-fluoro-7,12-dimethyl-N-(2-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |

TABLE 23c-continued

| Examples of Core 05 (Ex. 85-Ex. 103; continued on the following pages) | | | |
|---|---|---|---|
| No | $R^2$ | $R^{54}$ | IUPAC name |
| Ex. 103 | 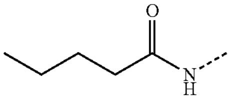 | 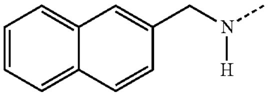 | (2S,11R,19aS)-15-fluoro-7,12-dimethyl-N-(2-naphthylmethyl)-5,8,13-trioxo-2-(pentanoylamino)-2,3,6,7,8,9,10,11,12,13,19,19a-dodecahydro-1H,5H-pyrrolo[2,1-c][1,4,7,12]benzoxatriazacyclopentadecine-11-carboxamide |

TABLE 24a

| Examples of Core 06 (Ex. 104-Ex. 114; continued on the following page) | | | | | | | |
|---|---|---|---|---|---|---|---|
| No | $R^2$ | $R^{54}$ | Starting material | General Procedure | Reagent | Purification Method | Yield (isolated salt) |
| Ex. 104-Ex. 105: cf. experimental description | | | | | | | |
| Ex. 106 | 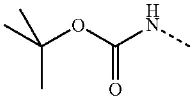 | 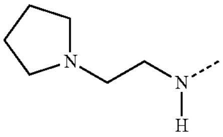 | Ex. 105 | L.2 | N-(2-aminoethyl) pyrolidine | FC ($CH_2Cl_2$/MeOH/aq.$NH_3$) | 78% |
| Ex. 107 | 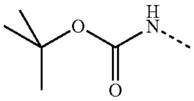 | 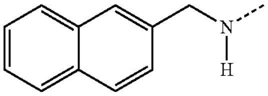 | Ex. 105 | L.2 | 2-naphthyl-methylamine | FC ($CH_2Cl_2$/MeOH) | 96% |
| Ex. 108 | NH2 | 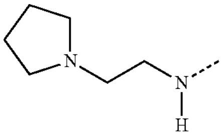 | Ex. 106 | J | HCl-dioxane | crude product | 99% |
| Ex. 109 | NH2 | 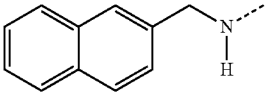 | Ex. 107 | J | HCl-dioxane | crude product | 95% |
| Ex. 110 | 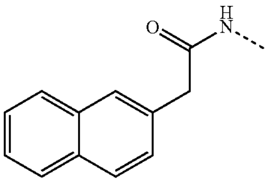 | 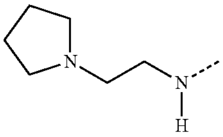 | Ex. 108 | L.1.2 | 2-naphthylacetic acid | prep. HPLC, method 1 and workup ($CHCl_3$/aq. $NaHCO_3$ soln) | 51% |
| Ex. 111 | 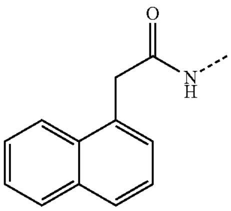 | 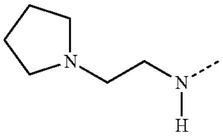 | Ex. 108 | L.1.2 | 1-naphthylacetic acid | prep. HPLC, method 1 | 55% |
| Ex. 112 | 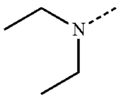 | 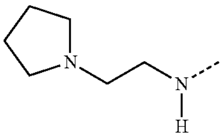 | Ex. 108 | M.1 | acetaldehyde | FC ($CH_2Cl_2$/MeOH/aq.$NH_3$) | 48% |

TABLE 24a-continued

Examples of Core 06 (Ex. 104-Ex. 114; continued on the following page)

| No | $R^2$ | $R^{54}$ | Starting material | General Procedure | Reagent | Purification Method | Yield (isolated salt) |
|---|---|---|---|---|---|---|---|
| Ex. 113 | 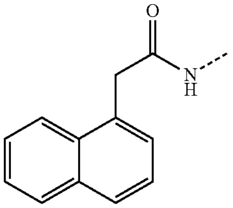 | 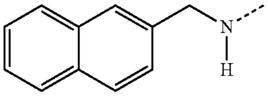 | Ex. 109 | L.1.2 | 1-naphthylacetic acid (3.7 equiv.) | prep. HPLC, method 3 | 77% |
| Ex. 114 | 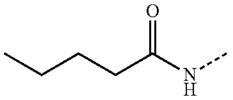 | 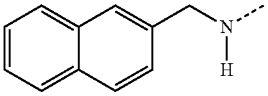 | Ex. 109 | L.1.1 | valeroyl chloride (2 equiv.) | prep. HPLC, method 3 | 84% |

TABLE 24b

Examples of Core 06 (Ex. 104-Ex. 114; continued on the following page)

| No | $R^2$ | $R^{54}$ | FORMULA | MONO-ISO-TOPIC MASS | Rt (purity at 220 nm) | $[M + H]^+$ found | LC-MS-Method |
|---|---|---|---|---|---|---|---|
| Ex. 104-Ex. 105: cf. experimental description | | | | | | | |
| Ex. 106 | 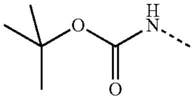 | 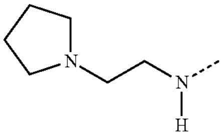 | C32H47FN607 | 646.4 | 1.36 (43), 1.42(27), 1.44 (27) | 647.5/647.5 647.5 | Method 2 |
| Ex. 107 | 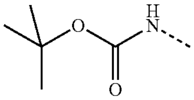 | 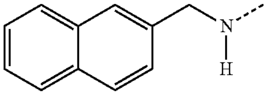 | C37H44FN507 | 689.3 | 1.94 (42)/ 1.98 (50) | 690.5/690.5 | Method 2 |
| Ex. 108 | $NH_2$ | 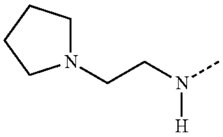 | C27H39FN605 | 546.3 | 1.37 (50), 1.44 (38) | 547.5/547.5 | Method 3 |
| Ex. 109 | $NH_2$ | 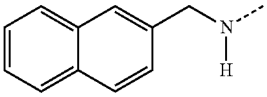 | C32H36FN505 | 589.3 | 1.55 (96) | 590.3 | Method 2 |
| Ex. 110 | 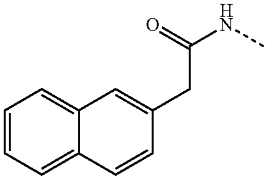 | 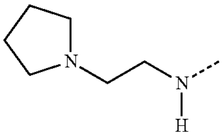 | C39H47FN606 | 714.4 | 1.62 (44), 1.66 (52) | 715.4/715.4 | Method 2 |

TABLE 24b-continued

Examples of Core 06 (Ex. 104-Ex. 114; continued on the following page)

| No | $R^2$ | $R^{54}$ | FORMULA | MONO-ISO-TOPIC MASS | Rt (purity at 220 nm) | [M + H]+ found | LC-MS-Method |
|---|---|---|---|---|---|---|---|
| Ex. 111 | 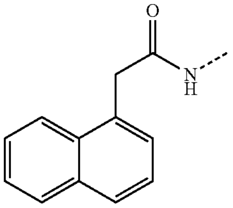 | 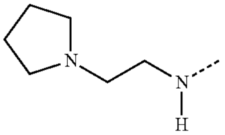 | C39H47FN6O6 | 714.4 | 1.51 (46), 1.56 (54) | 715.5/715.5 | Method 2 |
| Ex. 112 | 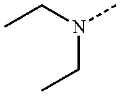 | 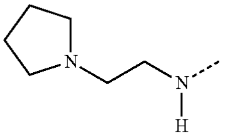 | C31H47FN6O5 | 602.4 | 1.14 (57), 1.18 (39) | 603.4/603.5 | Method 2 |
| Ex. 113 | 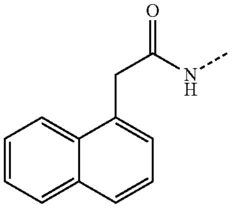 | 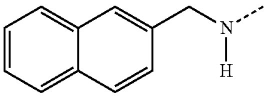 | C44H44FN5O6 | 757.3 | 2.15 (52), 2.19 (41) | 758.4/758.4 | Method 4a |
| Ex. 114 | 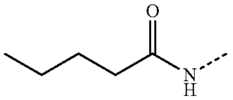 | 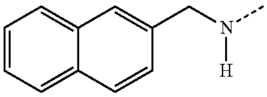 | C37H44FN5O6 | 673.3 | 2.00 (58), | 674.4/674.4 | Method 4a |

TABLE 24c

Examples of Core 06 (Ex.104-Ex.114; continued on the following page)

| No | $R^2$ | $R^{54}$ | IUPAC name |
|---|---|---|---|
| Ex.104 | 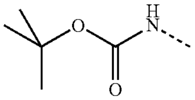 | $OCH_2Ph$ | benzyl(2R,11R,19aS)-2-[(tert-butoxycarbonyl)amino]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylate |
| Ex.105 | 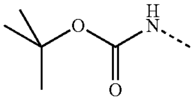 | OH | (2R,11R,19aS)-2-[(tert-butoxycarbonyl)amino]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylic acid |
| Ex.106 | 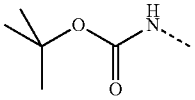 | 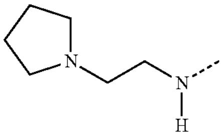 | tert-butyl N-[(2R,11R,19aS)-15-fluoro-7,12-dimethyl-5,8,13-trioxo-11-({[2-(1-pyrrolidinyl)ethyl]amino}carbonyl)-2,3,6,7,8,9,10,11,12,13,19,19a-dodecahydro-1H,5H-pyrrolo[2,1-c][1,4,7,12]benzoxatriazacyclopentadecin-2-yl]carbamate |
| Ex.107 | $NH_2$ | 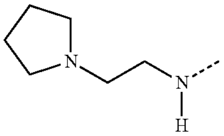 | tert-butyl N-((2R,11R,19aS)-15-fluoro-7,12-dimethyl-11-{[(2-naphthylmethyl)amino]carbonyl}-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl)carbamate |

TABLE 24c-continued

| No | $R^2$ | $R^{54}$ | IUPAC name |
|---|---|---|---|
| | | Examples of Core 06 (Ex.104-Ex.114; continued on the following page) | |
| Ex.108 | $NH_2$ | 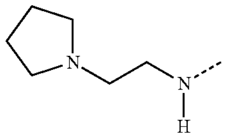 | (2R,11R,19aS)-2-amino-15-fluoro-7,12-dimethyl-5,8,13-trioxo-N-[2-(1-pyrrolidinyl)ethyl]-2,3,6,7,8,9,10,11,12,13,19,19a-dodecahydro-1H,5H-pyrrolo[2,1-c][1,4,7,12]benzoxatriazacyclopentadecine-11-carboxamide |
| Ex.109 | $NH_2$ | 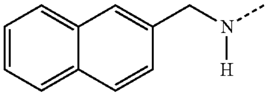 | (2R,11R,19aS)-2-amino-15-fluoro-7,12-dimethyl-N-(2-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex.110 | 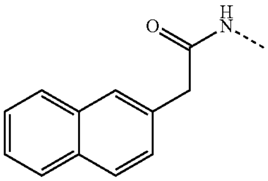 | 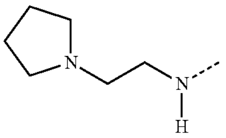 | (2R,11R,19aS)-15-fluoro-7,12-dimethy1-2-{[2-(2-naphthyl)acetyl]amino}-5,8,13-trioxo-N-[2-(1-pyrrolidinyl)ethyl]-2,3,6,7,8,9,10,11,12,13,19,19a-dodecahydro-1H,5H-pyrrolo[2,1-c][1,4,7,12]benzoxatriazacyclopentadecine-11-carboxamide |
| Ex.111 | 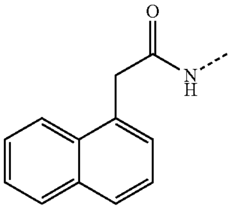 | 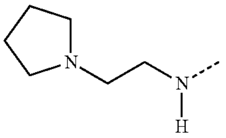 | (2R,11R,19aS)-15-fluoro-7,12-dimethyl-2-{[2-(1-naphthyl)acetyl]amino}-5,8,13-trioxo-N-[2-(1-pyrrolidinyl)ethyl]-2,3,6,7,8,9,10,11,12,13,19,19a-dodecahydro-1H,5H-pyrrolo[2,1-c][1,4,7,12]benzoxatriazacyclopentadecine-11-carboxamide |
| Ex.112 | 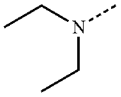 | 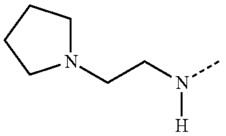 | (2R,11R,19aS)-2-(diethylamino)-15-fluoro-7,12-dimethyl-5,8,13-trioxo-N-[2-(1-pyrrolidinyl)ethyl]-2,3,6,7,8,9,10,11,12,13,19,19a-dodecahydro-1H,5H-pyrrolo[2,1-c][1,4,7,12]benzoxatriazacyclopentadecine-11-carboxamide |
| Ex.113 | 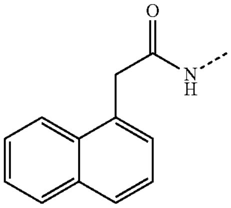 | 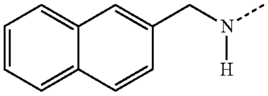 | (2R,11R,19aS)-15-fluoro-7,12-dimethyl-2-{[2-(1-naphthyl)acetyl]amino}-N-(2-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex.114 | 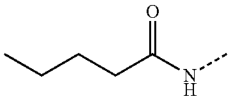 | 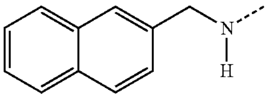 | (2R,11R,19aS)-15-fluoro-7,12-dimethyl-N-(2-naphthylmethyl)-5,8,13-trioxo-2-(pentanoylamino)-2,3,6,7,8,9,10,11,12,13,19,19a-dodecahydro-1H,5H-pyrrolo[2,1-c][1,4,7,12]benzoxatriazacyclopentadecine-11-carboxamide |

TABLE 25a

| No | $R^{11}$ | $R^{54}$ | Starting material | General Procedure | Reagent | Purification Method | Yield, (isolated salt) |
|---|---|---|---|---|---|---|---|
| | | | Examples of Core 07 (Ex.115-Ex.131; continued on the following pages) | | | | |
| | | | Ex. 115-Ex. 116: cf. experimental description | | | | |
| Ex.117 | 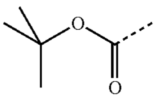 | 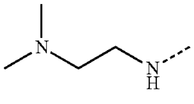 | Ex.116 | L.2 | N,N-dimethyl-ethylenediamine | FC ($CH_2Cl_2$/MeOH/aq. $NH_3$ | 73% |

TABLE 25a-continued

Examples of Core 07 (Ex.115-Ex.131; continued on the following pages)

| No | $R^{11}$ | $R^{54}$ | Starting material | General Procedure | Reagent | Purification Method | Yield, (isolated salt) |
|---|---|---|---|---|---|---|---|
| Ex.118 | 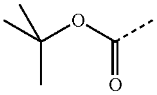 | 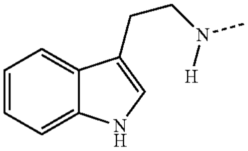 | Ex.116 | L.2 | tryptamine | FC ($CH_2Cl_2$/MeOH) | 98% |
| Ex.119 | 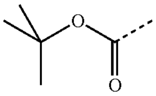 | 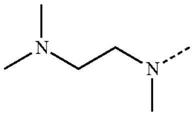 | Ex.116 | L.2 | N,N,N'-trimethyl-ethylenediamine | FC ($CH_2Cl_2$/MeOH) | 79% |
| Ex.120 | 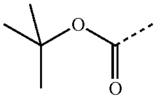 | 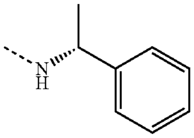 | Ex.116 | L.2 | D-(+)-α-methylbenzylamine | prep. HPLC, method 1 | 70% |
| Ex.121 | H | 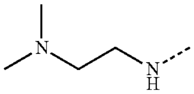 | Ex.117 | J | HCl-dioxane | crude product | 98% (HCl salt) |
| Ex.122 | H | 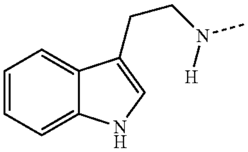 | Ex.118 | J | HCl-dioxane | crude product | 98% (HCl salt) |
| Ex.123 | H | 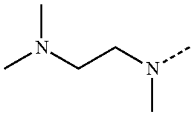 | Ex.119 | J | HCl-dioxane THF/$CH_2Cl_2$ as cosolvent | crude product | quant. (HCl salt) |
| Ex.124 | H | 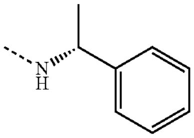 | Ex.120 | J | HCl-dioxane | crude product | 95% (HCl salt) |
| Ex.125 | 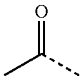 | 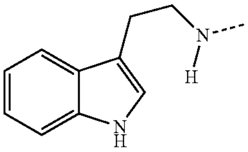 | Ex.122 | L.1.1 | acetic anhydride (1.1 equiv.) pyridine/$CH_2Cl_2$ 1:1 (3 mL) | prep. HPLC, method 1 | 62% |
| Ex.126 | 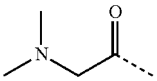 | 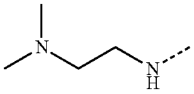 | Ex.121 | L.1.3 | N,N-dimethylglycine | prep. HPLC, method 1 | 39% (TFA salt) |
| Ex.127 | 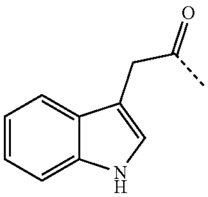 | 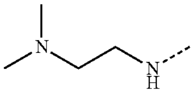 | Ex.121 | L.1.3 | 3-indoleacetic acid | prep. HPLC, method 1 | 20% (TFA salt) |

TABLE 25a-continued

Examples of Core 07 (Ex.115-Ex.131; continued on the following pages)

| No | $R^{11}$ | $R^{54}$ | Starting material | General Procedure | Reagent | Purification Method | Yield, (isolated salt) |
|---|---|---|---|---|---|---|---|
| Ex.128 | 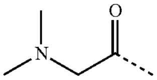 | 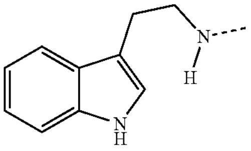 | Ex.122 | L.1.3 | N,N-dimethylglycine | prep. HPLC, method 1 | 21% (TFA salt) |
| Ex.129 | 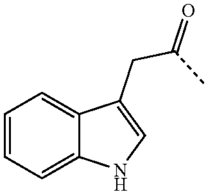 | 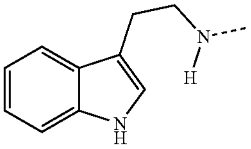 | Ex.122 | L.1.3 | 3-indoleacetic acid | prep. HPLC, method 1 | 45% |
| Ex.130 | 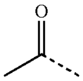 | 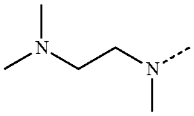 | Ex.123 | L.1.1 | acetic anhydride (5 equiv.) | prep. HPLC, method 1 | 14% (TFA salt) |
| Ex.131 | 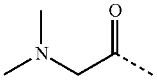 | 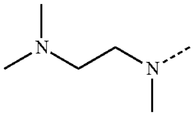 | Ex.123 | L.1.3 | N,N-dimethylglycine | prep. HPLC, method 1 | 44% (TFA salt) |

TABLE 25b

Examples of Core 07 (Ex.115-Ex.131; continued on the following pages)

| No | $R^{11}$ | $R^{54}$ | FORMULA | MONOISOTOPIC MASS | Rt (purity at 220 nm) | $[M+H]^+$ found | LC-MS-Method |
|---|---|---|---|---|---|---|---|
| Ex.115-Ex.116: cf. experimental description | | | | | | | |
| Ex.117 | 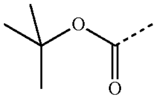 | 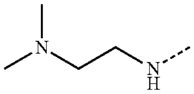 | C30H45FN6O7 | 620.3 | 1.45 | 621.2 | Method 9c |
| Ex.118 | 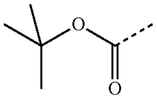 | 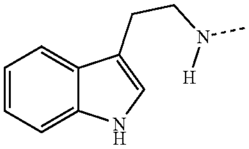 | C36H45FN6O7 | 692.3 | 1.94 | 693.1 | Method 9c |
| Ex.119 | 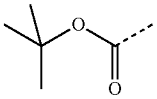 | 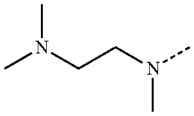 | C31H47FN6O7 | 634.4 | 1.48 | 635.4 | Method 9c |
| Ex.120 | 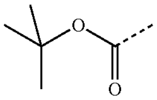 | 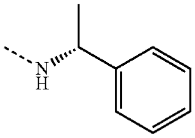 | C34H44FN5O7 | 653.3 | 1.99 | 653.9 | Method 9c |
| Ex.121 | H | 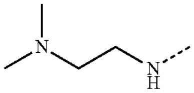 | C25H37FN6O5 | 520.3 | 1.23 (17), 1.29 (80) | 521.3/ 521.3 | Method 3 |

TABLE 25b-continued
Examples of Core 07 (Ex.115-Ex.131; continued on the following pages)
| No | $R^{11}$ | $R^{54}$ | FORMULA | MONOISOTOPIC MASS | Rt (purity at 220 nm) | $[M+H]^+$ found | LC-MS-Method |
|---|---|---|---|---|---|---|---|
| Ex.122 | H | 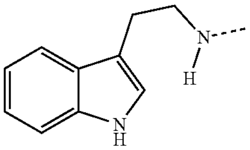 | C31H37FN6O5 | 592.3 | 1.40 (89) | 593.3 | Method 2 |
| Ex.123 | H | 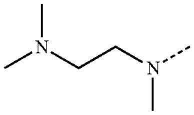 | C26H39FN6O5 | 534.3 | 1.32 (96) | 535.3 | Method 3 |
| Ex.124 | H | 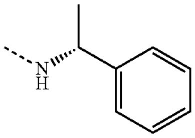 | C29H36FN5O5 | 553.3 | 1.41 (98) | 554.3 | Method 2 |
| Ex.125 | 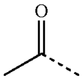 | 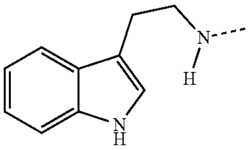 | C33H39FN6O6 | 634.3 | 1.54 (100) | 635.3 | Method 2 |
| Ex.126 | 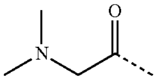 | 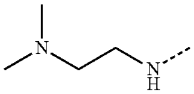 | C29H44FN7O6 | 605.3 | 1.37 (83) | 606.4 | Method 3 |
| Ex.127 | 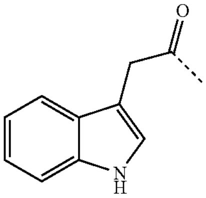 | 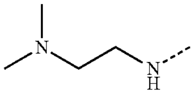 | C35H44FN7O6 | 677.3 | 1.32 (12),<br>1.38 (84) | 678.3/<br>678.3 | Method 2 |
| Ex.128 | 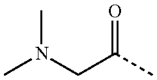 | 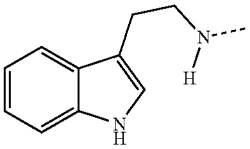 | C35H44FN7O6 | 677.3 | 1.40 (98) | 678.4 | Method 2 |
| Ex.129 | 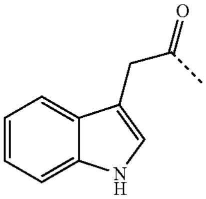 | 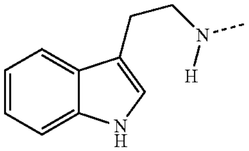 | C41H44FN7O6 | 749.3 | 1.73 (85) | 750.4 | Method 2 |
| Ex.130 | 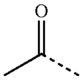 | 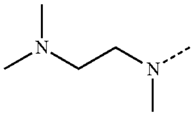 | C28H41FN6O6 | 576.3 | 1.10 (98) | 577.3 | Method 2 |
| Ex.131 | 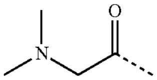 | 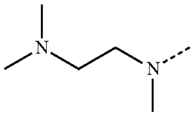 | C30H46FN7O6 | 619.4 | 1.41 (96) | 620.4 | Method 3 |

TABLE 25c

Examples of Core 07 (Ex.115-Ex.131; continued on the following pages)

| No | $R^{11}$ | $R^{54}$ | IUPAC name |
|---|---|---|---|
| Ex.115 | 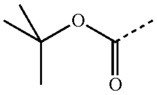 | $OCH_2Ph$ | 12-benzyl 2-(tert-butyl) (12S,20aS)-16-fluoro-8,13-dimethyl-6,9,14-trioxo-3,4,7,8,9,10,11,12,13,14,20,20a-dodecahydro-6H-pyrazino[2,1-c][1,4,7,12]benzoxatriazacyclopentadecine-2,12(1H)-dicarboxylate |
| Ex.116 | 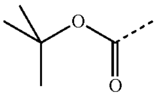 | OH | (12S,20aS)-2-(tert-butoxycarbonyl)-16-fluoro-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxylic acid |
| Ex.117 | 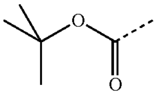 | 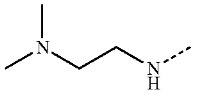 | tert-butyl (12S,20aS)-12-({[2-(dimethylamino)ethyl]amino}carbonyl)-16-fluoro-8,13-dimethyl-6,9,14-trioxo-3,4,7,8,9,10,11,12,13,14,20,20a-dodecahydro-6H-pyrazino[2,1-c][1,4,7,12]benzoxatriazacyclopentadecine-2(1H)-carboxylate |
| Ex.118 | 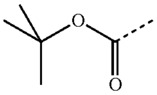 | 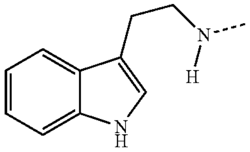 | tert-butyl (12S,20aS)-16-fluoro-12-({[2-(1H-indol-3-yl)ethyl]amino}carbonyl)-8,13-dimethyl-6,9,14-trioxo-3,4,7,8,9,10,11,12,13,14,20,20a-dodecahydro-6H-pyrazino[2,1-c][1,4,7,12]benzoxatriazacyclopentadecine-2(1H)-carboxylate |
| Ex.119 | 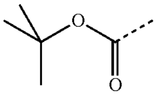 | 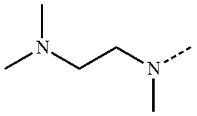 | tert-butyl (12S,20aS)-12-{[[2-(dimethylamino)ethyl](methyl)amino]carbonyl}-16-fluoro-8,13-dimethyl-6,9,14-trioxo-3,4,7,8,9,10,11,12,13,14,20,20a-dodecahydro-6H-pyrazino[2,1-c][1,4,7,12]benzoxatriazacyclopentadecine-2(1H)-carboxylate |
| Ex.120 | 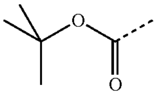 | 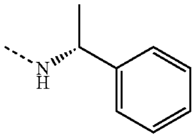 | tert-butyl (12S,20aS)-16-fluoro-8,13-dimethyl-6,9,14-trioxo-12-({[(1R)-1-phenylethyl]amino}carbonyl)-3,4,7,8,9,10,11,12,13,14,20,20a-dodecahydro-6H-pyrazino[2,1-c][1,4,7,12]benzoxatriazacyclopentadecine-2(1H)-carboxylate |
| Ex.121 | H | 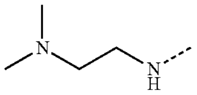 | (12S,20aS)-N-[2-(dimethylamino)ethyl]-16-fluoro-8,13-dimethyl-6,9,14-trioxo-1,2,3,4,7,8,9,10,11,12,13,14,20,20a-tetradecahydro-6H-pyrazino [2,1-c][1,4,7,12]benzoxatriazacyclopentadecine-12-carboxamide |
| Ex.122 | H | 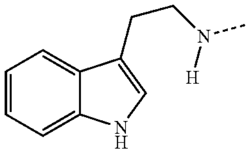 | (12S,20aS)-16-fluoro-N-[2-(1H-indol-3-yl)ethyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex.123 | H | 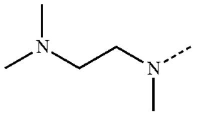 | (12S,20aS)-N-[2-(dimethylamino)ethyl]-16-fluoro-N,8,13-trimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex.124 | H | 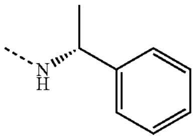 | (12S,20aS)-16-fluoro-8,13-dimethyl-6,9,14-trioxo-N-[(1R)-1-phenylethyl]-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex.125 | 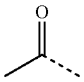 | 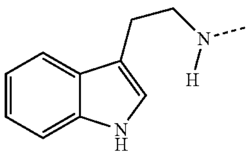 | (12S, 20aS)-2-acetyl-16-fluoro-N-[2-(1H-indol-3-yl)ethyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |

TABLE 25c-continued

| No | $R^{11}$ | $R^{54}$ | IUPAC name |
|---|---|---|---|
| Examples of Core 07 (Ex.115-Ex.131; continued on the following pages) | | | |
| Ex.126 | 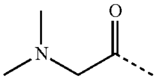 | 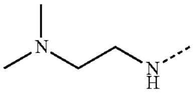 | (12S, 20aS)-2-[2-(dimethylamino)acetyl]-N-[2-(dimethylamino)ethyl]-16-fluoro-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex.127 | 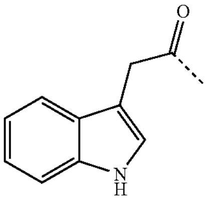 | 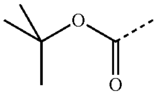 | (12S, 20aS)-N-[2-(dimethylamino)ethyl]-16-fluoro-2-[2-(1H-indol-3-yl)acetyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex.128 | 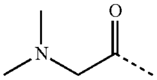 | 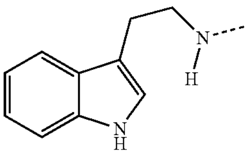 | (12S, 20aS)-2-[2-(dimethylamino)acetyl]-16-fluoro-N-[2-(1H-indol-3-yl)ethyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex.129 | 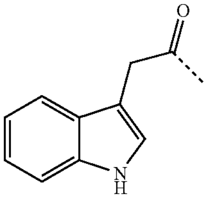 | 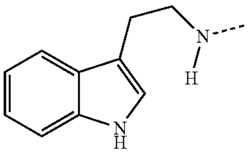 | (12S,20aS)-16-fluoro-2-[2-(1H-indol-3-yl)acetyl]-N-[2-(1H-indol-3-yl)ethyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex.130 | 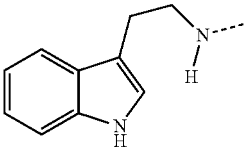 | 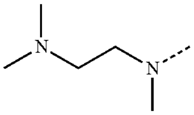 | (12S, 20aS)-2-acetyl-N-[2-(dimethylamino)ethyl]-16-fluoro-N,8,13-trimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex.131 | 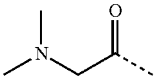 | 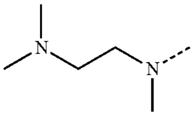 | (12S, 20aS)-2-[2-(dimethylamino)acetyl]-N-[2-(dimethylamino)ethyl]-16-fluoro-N,8,13-trimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |

TABLE 26a

| No | $R^{11}$ | $R^{54}$ | Starting material | General Procedure | Reagent | Purification Method | Yield (isolated salt) |
|---|---|---|---|---|---|---|---|
| Examples of Core 08 (Ex.132-Ex.141; continued on the following page) | | | | | | | |
| Ex.132-Ex.133: cf. experimental description | | | | | | | |
| Ex.134 | 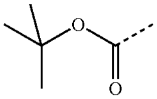 | 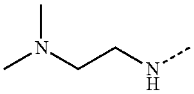 | Ex. 133 | L.2 | N,N-dimethylethylenediamine | FC ($CH_2Cl_2$/MeOH/aq. $NH_3$) | 80% |
| Ex.135 | H | 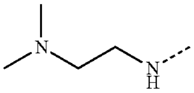 | Ex.134 | J | HCl-dioxane | crude product | 100% (HCl salt) |

TABLE 26a-continued

Examples of Core 08 (Ex.132-Ex.141; continued on the following page)

| No | $R^{11}$ | $R^{54}$ | Starting material | General Procedure | Reagent | Purification Method | Yield (isolated salt) |
|---|---|---|---|---|---|---|---|
| Ex.136 | 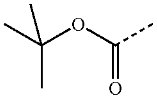 | 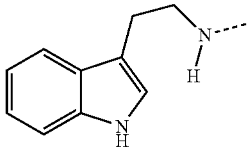 | Ex.133 | L.2 | tryptamine | FC ($CH_2Cl_2$/ MeOH/ aq. $NH_3$) | 89% |
| Ex.137 | H | 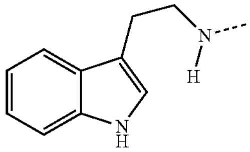 | Ex.136 | J | HCl-dioxane | crude product | 100% (HCl salt) |
| Ex.138 | 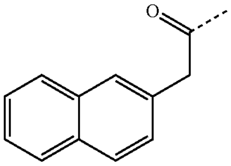 | 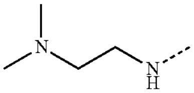 | Ex.135 | L.1.2 | 2-naphthylacetic acid | prep. HPLC, method 1 | 71% (TFA salt) |
| Ex.139 | 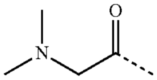 | 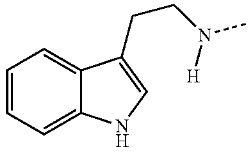 | Ex.137 | L.1.2 | N,N-dimethyl glycine | prep. HPLC, method 1 | 40% (TFA salt) |
| Ex.140 | 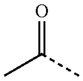 | 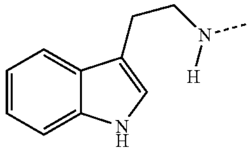 | Ex.137 | L.1.1 | acetic anhydride (5 equiv.) | prep. HPLC, method 1 | 50% |
| Ex.141 | 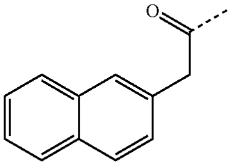 | 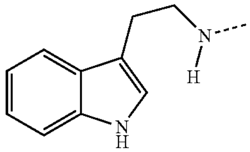 | Ex.137 | L.1.2 | 2-naphthylacetic acid | prep. HPLC, method 3, then FC (EtOAc/ MeOH) | 39% |

TABLE 26b

Examples of Core 08 (Ex.132-Ex.141; continued on the following page)

| No | $R^{11}$ | $R^{54}$ | FORMULA | MONOISOTOPIC MASS | Rt (purity at 220 nm) | $[M+H]^+$ found | LC-MS-Method |
|---|---|---|---|---|---|---|---|
| Ex.132-Ex.133: cf. experimental description | | | | | | | |
| Ex.134 | 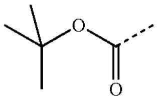 | 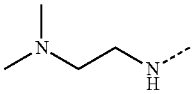 | C30H45FN6O7 | 620.3 | 1.40 (20), 1.45 (77) | 621.5/ 621.5 | Method 2 |
| Ex.135 | H | 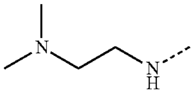 | C25H37FN6O5 | 520.3 | 0.94 (85) | 521.4 | Method 2 |

TABLE 26b-continued

Examples of Core 08 (Ex.132-Ex.141; continued on the following page)

| No | $R^{11}$ | $R^{54}$ | FORMULA | MONOISOTOPIC MASS | Rt (purity at 220 nm) | $[M+H]^+$ found | LC-MS-Method |
|---|---|---|---|---|---|---|---|
| Ex.136 | 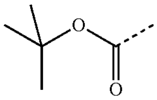 | 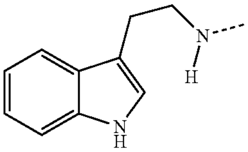 | C36H45FN6O7 | 692.3 | 1.83 (91) | 693.5 | Method 2 |
| Ex.137 | H | 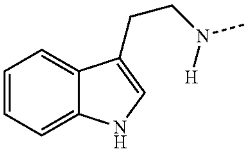 | C31H37FN6O5 | 592.3 | 1.41 (80) | 593.4 | Method 2 |
| Ex.138 | 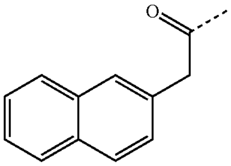 | 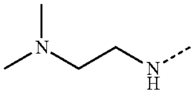 | C37H45FN6O6 | 688.3 | 1.46 (15), 1.51 (84) | 689.5/ 689.5 | Method 2 |
| Ex.139 | 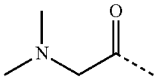 | 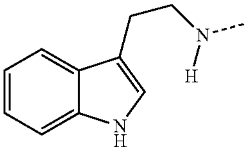 | C35H44FN7O6 | 677.3 | 1.43 (92) | 678.5 | Method 2 |
| Ex.140 | 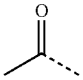 | 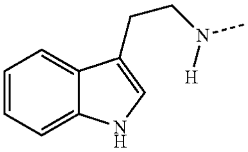 | C33H39FN6O6 | 634.3 | 1.57 (97) | 635.5 | Method 2 |
| Ex.141 | 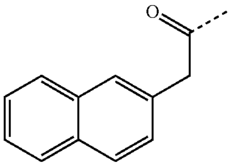 | 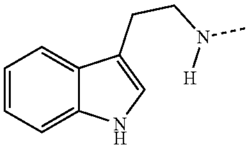 | C43H45FN6O6 | 760.3 | 1.86 (95) | 761.5 | Method 2 |

TABLE 26c

Examples of Core 08 (Ex.132-Ex.141; continued on the following page)

| No | $R^{11}$ | $R^{54}$ | IUPAC name |
|---|---|---|---|
| Ex.132 | 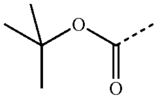 | $OCH_2Ph$ | 12-benzyl 2-(tert-butyl) (12R,20aR)-16-fluoro-8,13-dimethyl-6,9,14-trioxo-3,4,7,8,9,10,11,12,13,14,20,20a-dodecahydro-6H-pyrazino[2,1-c][1,4,7,12]benzoxatriazacyclopentadecine-2,12(1H)-dicarboxylate |
| Ex.133 | 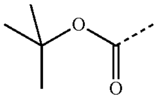 | OH | (12R,20aR)-2-(tert-butoxycarbonyl)-16-fluoro-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxylic acid |

TABLE 26c-continued

Examples of Core 08 (Ex.132-Ex.141; continued on the following page)

| No | $R^{11}$ | $R^{54}$ | IUPAC name |
|---|---|---|---|
| Ex.134 | 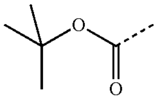 | 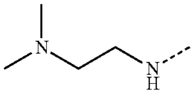 | tert-butyl(12R,20aR)-12-({[2-(dimethylamino)ethyl]amino}carbonyl)-16-fluoro-8,13-dimethyl-6,9,14-trioxo-3,4,7,8,9,10,11,12,13,14,20,20a-dodecahydro-6H-pyrazino[2,1-c][1,4,7,12]benzoxatriazacyclopentadecine-2(1H)-carboxylate |
| Ex.135 | H | 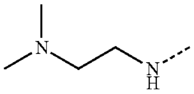 | (12R,20aR)-N-[2-(dimethylamino)ethyl]-16-fluoro-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex.136 | 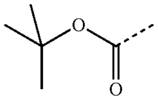 | 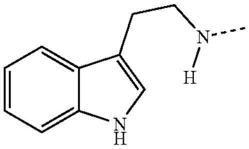 | tert-butyl(12R,20aR)-16-fluoro-12-({[2-(1H-indol-3-yl)ethyl]amino}carbonyl)-8,13-dimethyl-6,9,14-trioxo-3,4,7,8,9,10,11,12,13,14,20,20a-dodecahydro-6H-pyrazino[2,1-c][1,4,7,12]benzoxatriazacyclopentadecine-2(1H)-carboxylate |
| Ex.137 | H | 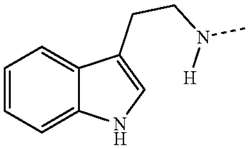 | (12R,20aR)-16-fluoro-N-[2-(1H-indol-3-yl)ethyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex.138 | 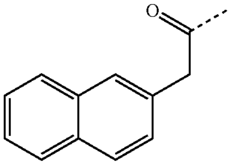 | 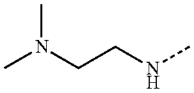 | (12R,20aR)-N-[2-(dimethylamino)ethyl]-16-fluoro-8,13-dimethyl-2-[2-(2-naphthyl)acetyl]-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex.139 | 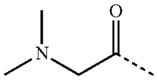 | 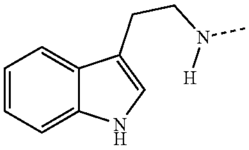 | (12R,20aR)-2-[2-(dimethylamino)acetyl]-16-fluoro-N-[2-(1H-indol-3-yl)ethyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex.140 | 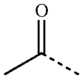 | 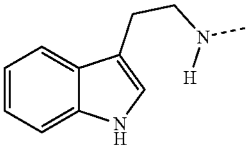 | (12R,20aR)-2-acetyl-16-fluoro-N-[2-(1H-indol-3-yl)ethyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex.141 | 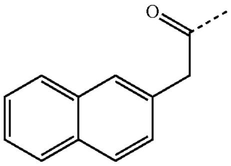 | 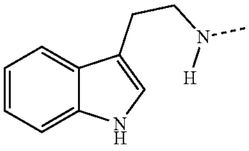 | (12R,20aR)-16-fluoro-N-[2-(1H-indol-3-yl)ethyl]-8,13-dimethyl-2-[2-(2-naphthyl)acetyl]-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |

TABLE 27a

Examples of Core 09 (Ex.142-Ex.163; continued on the following pages)

| No | $R^2$ | $R^{54}$ | Starting material | General Procedure | Reagent | Purification Method | Yield (isolated salt) |
|---|---|---|---|---|---|---|---|
| Ex.142-Ex.143: cf. experimental description | | | | | | | |
| Ex.144 | 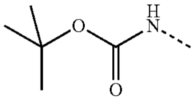 | 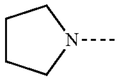 | Ex.143 | L.2 | pyrrolidine | FC ($CH_2Cl_2$/ MeOH) | 91% |
| Ex.145 | 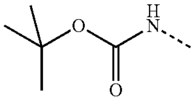 | 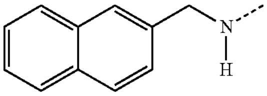 | Ex.143 | L.2 | 2-naphthylmethylamine | FC ($CH_2Cl_2$/ MeOH) | 72% |
| Ex.146 | 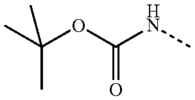 | 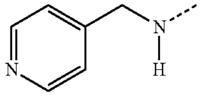 | Ex.143 | L.2 | 4-(aminomethyl)pyridine | FC ($CH_2Cl_2$/ MeOH) | 87% |
| Ex.147 | $NH_2$ | 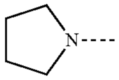 | Ex.144 | J | HCl-dioxane | crude product | 100% (HCl salt) |
| Ex.148 | $NH_2$ | 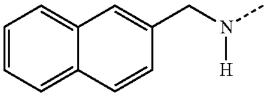 | Ex.145 | J | HCl-dioxane | crude product | 97% (HCl salt) |
| Ex.149 | $NH_2$ | 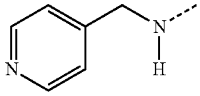 | Ex.146 | J | HCl-dioxane | crude product | 87% (HCl salt) |
| Ex.150 | 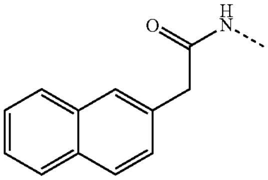 | 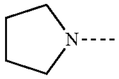 | Ex.147 | L.1.2 | 2-naphthylacetic acid | Prep. HPLC, method 3 | 72% |
| Ex.151 | 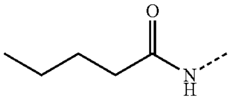 | 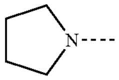 | Ex.147 | L.1.1 | valeroyl chloride (2.0 equiv.) | Prep. HPLC, method 3 | 73% |
| Ex.152 | 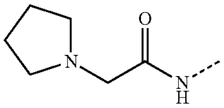 | 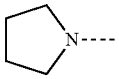 | Ex.147 | L.1.2 | 1-pyrriolidinacetic acid | Prep. HPLC, method 2 | 26% |
| Ex.153 | 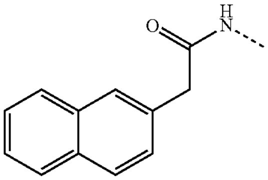 | 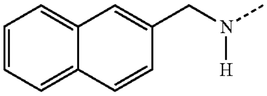 | Ex.148 | L.1.2 | 2-naphthylacetic acid | Prep. HPLC, method 3 | 68% |
| Ex.154 | 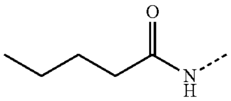 | 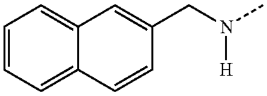 | Ex.148 | L.1.1 | valeroyl chloride (2.0 equiv.) | Prep. HPLC, method 3 | 76% |

TABLE 27a-continued

Examples of Core 09 (Ex.142-Ex.163; continued on the following pages)

| No | $R^2$ | $R^{54}$ | Starting material | General Procedure | Reagent | Purification Method | Yield (isolated salt) |
|---|---|---|---|---|---|---|---|
| Ex.155 | 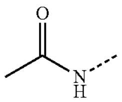 | 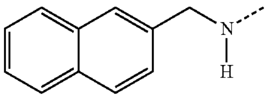 | Ex.148 | L.1.1 | acetic anhydride (5.0 equiv.) | Prep. HPLC, method 3 | 72% |
| Ex.156 | 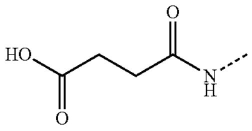 | 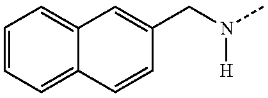 | Ex.148 | L.1.1 | succinic anhydride (1.05 equiv.) | Prep. HPLC, method 2 | 69% ($NH_4^+$ salt) |
| Ex.157 | 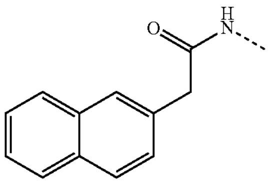 | 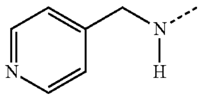 | Ex.149 | L.1.2 | 2-naphthylacetic acid (1.7 equiv.) | Prep. HPLC, method 2 | 24% |
| Ex.158 | 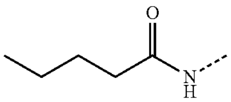 | 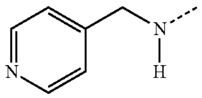 | Ex.149 | L.1.1 | valeroyl chloride (2.0 equiv.) | Prep. HPLC, method 2 | 42% |
| Ex.159 | 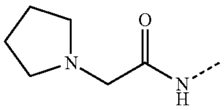 | 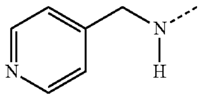 | Ex.149 | L.1.2 | 1-pyrriolidinacetic acid (2.5 equiv.) | Prep. HPLC, method 2 | 55% |
| Ex.160 | 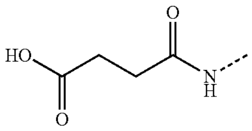 | 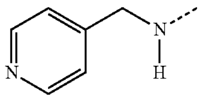 | Ex.149 | L.1.1 | succinic anhydride (1.05 equiv.) | Prep. HPLC, method 2 | 69% ($NH_4^+$ salt) |
| Ex.161 | 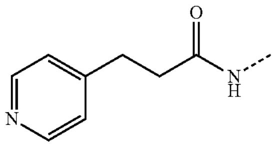 | 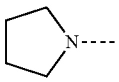 | Ex.147 | L.1.2 | 3-(pyridine-4-yl)propanoic acid | Prep. HPLC, method 2 | 53% |
| Ex.162 | 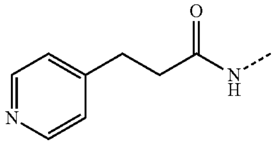 | 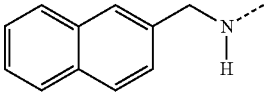 | Ex.148 | L.1.2 | 3-(pyridine-4-yl)propanoic acid | Prep. HPLC, method 2 | 48% |
| Ex.163 | 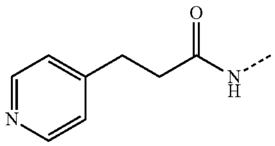 | 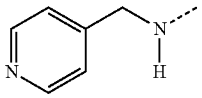 | Ex.149 | L.1.2 | 3-(pyridine-4-yl)propanoic acid (1.7 equiv.) | Prep. HPLC, method 2 | 63% |

TABLE 27b

| No | $R^2$ | $R^{54}$ | FORMULA | MONOISOTOPIC MASS | Rt (purity at 220 nm) | $[M+H]^+$ found | LC-MS-Method |
|---|---|---|---|---|---|---|---|
| Examples of Core 09 (Ex.142-Ex.163; continued on the following pages) | | | | | | | |
| Ex.142-Ex.143: cf. experimental description | | | | | | | |
| Ex.144 | 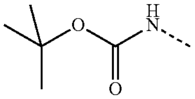 | 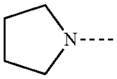 | C31H44FN5O7 | 617.3 | 1.66 (90) | 618.4 | Method 2 |
| Ex.145 | 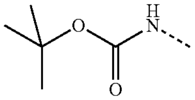 | 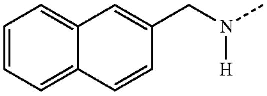 | C38H46FN5O7 | 703.3 | 1.90 (90) | 704.5 | Method 2 |
| Ex.146 | 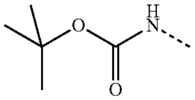 | 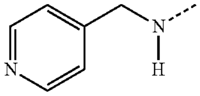 | C33H43FN6O7 | 654.3 | 1.39 (92) | 655.5 | Method 2 |
| Ex.147 | $NH_2$ | 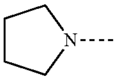 | C26H36FN5O5 | 517.3 | 1.36 (79) | 518.4 | Method 3 |
| Ex.148 | $NH_2$ | 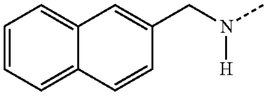 | C33H38FN5O5 | 603.3 | 1.53 (98) | 604.4 | Method 2 |
| Ex.149 | $NH_2$ | 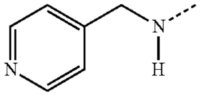 | C28H35FN6O5 | 554.3 | 1.25 (8), 1.31 (85) | 555.4 | Method 3 |
| Ex.150 | 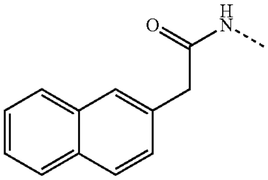 | 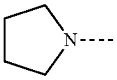 | C38H44FN5O6 | 685.3 | 1.72 (98) | 686.5 | Method 2 |
| Ex.151 | 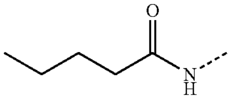 | 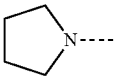 | C31H44FN5O6 | 601.3 | 1.55 (98) | 602.5 | Method 2 |
| Ex.152 | 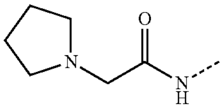 | 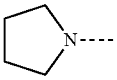 | C32H45FN6O6 | 628.3 | 1.52 (94) | 629.5 | Method 3 |
| Ex.153 | 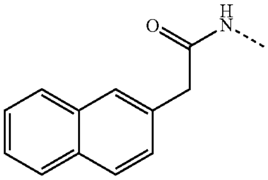 | 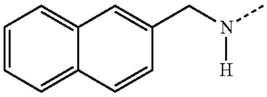 | C45H46FN5O6 | 771.3 | 1.94 (96) | 772.5 | Method 2 |
| Ex.154 | 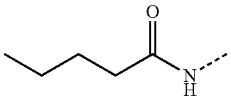 | 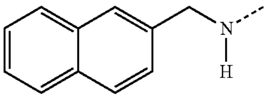 | C38H46FN5O6 | 687.3 | 1.82 (97) | 688.5 | Method 2 |

TABLE 27b-continued
Examples of Core 09 (Ex.142-Ex.163; continued on the following pages)
| No | $R^2$ | $R^{54}$ | FORMULA | MONOISOTOPIC MASS | Rt (purity at 220 nm) | $[M+H]^+$ found | LC-MS-Method |
|---|---|---|---|---|---|---|---|
| Ex.155 | 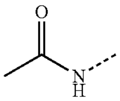 | 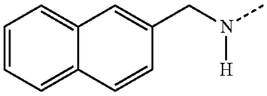 | C35H40FN5O6 | 645.3 | 1.67 (99) | 646.4 | Method 2 |
| Ex.156 | 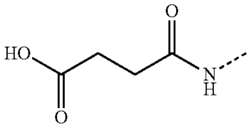 | 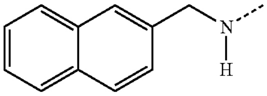 | C37H42FN5O8 | 703.3 | 1.65 (99) | 704.5 | Method 2 |
| Ex.157 | 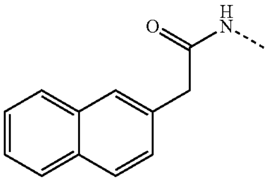 | 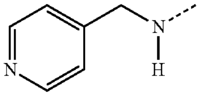 | C40H43FN6O6 | 722.3 | 1.48 (94) | 723.8 | Method 2 |
| Ex.158 | 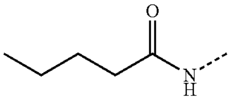 | 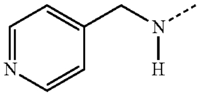 | C33H43FN6O6 | 638.3 | 1.50 (95) | 639.5 | Method 3 |
| Ex.159 | 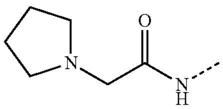 | 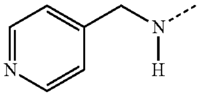 | C34H44FN7O6 | 665.3 | 1.47 (96) | 666.5 | Method 3 |
| Ex.160 | 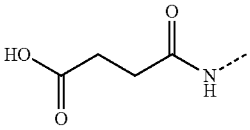 | 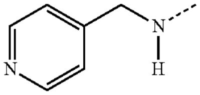 | C32H39FN6O8 | 654.3 | 1.04 (96) | 655.4 | Method 3 |
| Ex.161 | 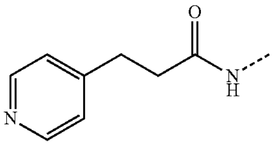 | 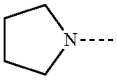 | C34H43FN6O6 | 650.3 | 1.47 (91) | 651.5 | Method 3 |
| Ex.162 | 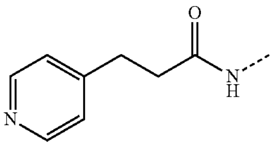 | 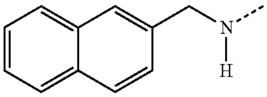 | C41H45FN6O6 | 736.3 | 1.55 (96) | 737.6 | Method 2 |
| Ex.163 | 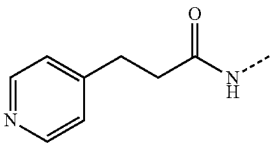 | 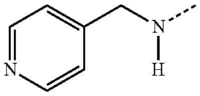 | C36H42FN7O6 | 687.3 | 1.42 (99) | 688.5 | Method 3 |

TABLE 27c

Examples of Core 09 (Ex.142-Ex.163; continued on the following pages)

| No | $R^2$ | $R^{54}$ | IUPAC name |
|---|---|---|---|
| Ex.142 | 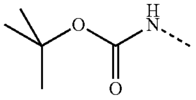 | $OCH_2Ph$ | benzyl (2R,12S,20aS)-2-[(tert-butoxycarbonyl)amino]-16-fluoro-8,13-dimethyl-5,9,14-trioxo-2,3,5,6,7,8,9,10,11,12,13,14,20,20a-tetradecahydro-1H-pyrrolo[2,1-c][1,4,8,13]benzoxatriazacyclohexadecine-12-carboxylate |
| Ex.143 | 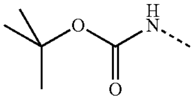 | OH | (2R,12S,20aS)-2-[(tert-butoxycarbonyl)amino]-16-fluoro-8,13-dimethyl-5,9,14-trioxo-2,3,5,6,7,8,9,10,11,12,13,14,20,20a-tetradecahydro-1H-pyrrolo[2,1-c][1,4,8,13]benzoxatriazacyclohexadecine-12-carboxylic acid |
| Ex.144 | 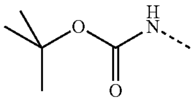 | 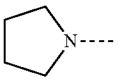 | tert-butyl N-[(2R,12S,20aS)-16-fluoro-8,13-dimethyl-5,9,14-trioxo-12-(1-pyrrolidinylcarbonyl)-2,3,5,6,7,8,9,10,11,12,13,14,20,20a-tetradecahydro-1H-pyrrolo[2,1-c][1,4,8,13]benzoxatriazacyclohexadecin-2-yl]carbamate |
| Ex.145 | 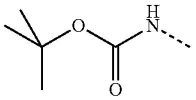 | 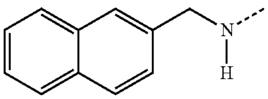 | tert-butyl N-((2R,12S,20aS)-16-fluoro-8,13-dimethyl-12-{[(2-naphthylmethyl)amino]carbonyl}-5,9,14-trioxo-2,3,5,6,7,8,9,10,11,12,13,14,20,20a-tetradecahydro-1H-pyrrolo[2,1-c][1,4,8,13]benzoxatriazacyclohexadecin-2-yl)carbamate |
| Ex.146 | 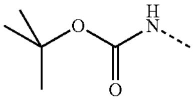 | 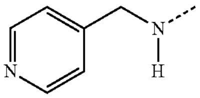 | tert-butyl N-((2R,12S,20aS)-16-fluoro-8,13-dimethyl-5,9,14-trioxo-12-{[(4-pyridinylmethyl)amino]carbonyl}-2,3,5,6,7,8,9,10,11,12,13,14,20,20a-tetradecahydro-1H-pyrrolo[2,1-c][1,4,8,13]benzoxatriazacyclohexadecin-2-yl)carbamate |
| Ex.147 | $NH_2$ | 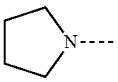 | (2R,12S,20aS)-2-amino-16-fluoro-8,13-dimethyl-12-(1-pyrrolidinylcarbonyl)-2,3,7,8,10,11,12,13,20,20a-decahydro-1H-pyrrolo[2,1-c][1,4,8,13]benzoxatriazacyclohexadecine-5,9,14(6H)-trione |
| Ex.148 | $NH_2$ | 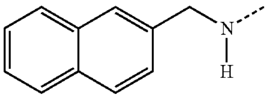 | (2R,12S,20aS)-2-amino-16-fluoro-8,13-dimethyl-N-(2-naphthylmethyl)-5,9,14-trioxo-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex.149 | $NH_2$ | 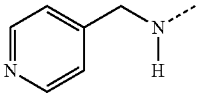 | (2R,12S,20aS)-2-amino-16-fluoro-8,13-dimethyl-5,9,14-trioxo-N-(4-pyridinylmethyl)-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex.150 | 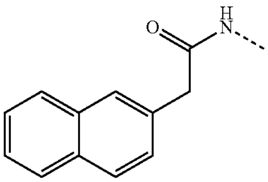 | 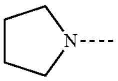 | N-[(2R,12S,20aS)-16-fluoro-8,13-dimethyl-5,9,14-trioxo-12-(1-pyrrolidinylcarbonyl)-2,3,5,6,7,8,9,10,11,12,13,14,20,20a-tetradecahydro-1H-pyrrolo[2,1-c][1,4,8,13]benzoxatriazacyclohexadecin-2-yl]-2-(2-naphthyl)acetamide |
| Ex.151 | 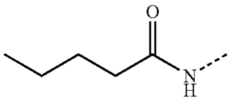 | 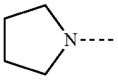 | N-[(2R,12S,20aS)-16-fluoro-8,13-dimethyl-5,9,14-trioxo-12-(1-pyrrolidinylcarbonyl)-2,3,5,6,7,8,9,10,11,12,13,14,20,20a-tetradecahydro-1H-pyrrolo[2,1-c][1,4,8,13]benzoxatriazacyclohexadecin-2-yl]pentanamide |
| Ex.152 | 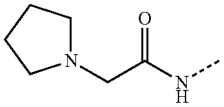 | 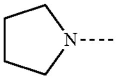 | N-[(2R,12S,20aS)-16-fluoro-8,13-dimethyl-5,9,14-trioxo-12-(1-pyrrolidinylcarbonyl)-2,3,5,6,7,8,9,10,11,12,13,14,20,20a-tetradecahydro-1H-pyrrolo[2,1-c][1,4,8,13]benzoxatriazacyclohexadecin-2-yl]-2-(1-pyrrolidinyl) acetamide |

TABLE 27c-continued

Examples of Core 09 (Ex.142-Ex.163; continued on the following pages)

| No | $R^2$ | $R^{54}$ | IUPAC name |
|---|---|---|---|
| Ex.153 | 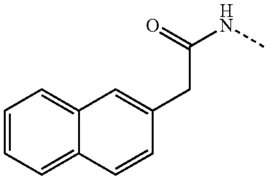 | 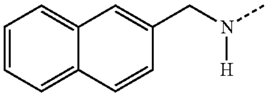 | (2R,12S,20aS)-16-fluoro-8,13-dimethyl-2-{[2-(2-naphthyl)acetyl]amino}-N-(2-naphthylmethyl)-5,9,14-trioxo-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex.154 | 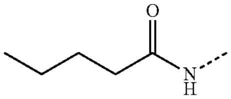 | 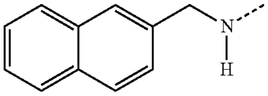 | (2R,12S,20aS)-16-fluoro-8,13-dimethyl-N-(2-naphthylmethyl)-5,9,14-trioxo-2-(pentanoylamino)-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex.155 | 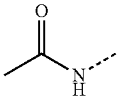 | 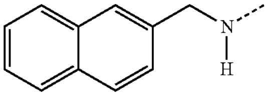 | (2R,12S,20aS)-2-(acetylamino)-16-fluoro-8,13-dimethyl-N-(2-naphthylmethyl)-5,9,14-trioxo-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex.156 | 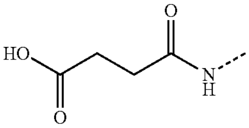 | 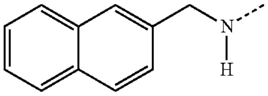 | 4-[((2R,12S,20aS)-16-fluoro-8,13-dimethyl-12-{[(2-naphthylmethyl)amino]carbonyl}-5,9,14-trioxo-2,3,5,6,7,8,9,10,11,12,13,14,20,20a-tetradecahydro-1H-pyrrolo[2,1-c][1,4,8,13]benzoxatriazacyclohexadecin-2-yl)amino]-4-oxobutanoic acid |
| Ex.157 | 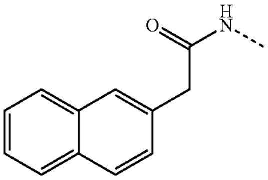 | 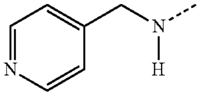 | (2R,12S,20aS)-16-fluoro-8,13-dimethyl-2-{[2-(2-naphthyl)acetyl]amino}-5,9,14-trioxo-N-(4-pyridinylmethyl)-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex.158 | 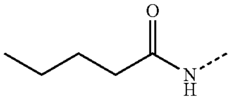 | 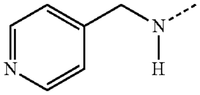 | (2R,12S,20aS)-16-fluoro-8,13-dimethyl-5,9,14-trioxo-2-(pentanoylamino)-N-(4-pyridinylmethyl)-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex.159 | 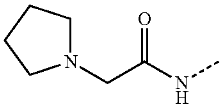 | 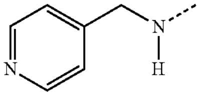 | (2R,12S,20aS)-16-fluoro-8,13-dimethyl-5,9,14-trioxo-N-(4-pyridinylmethyl)-2-{[2-(1-pyrrolidinyl)acetyl]amino}-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex.160 | 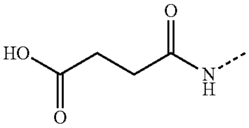 | 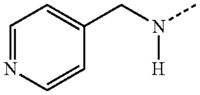 | 4-[((2R,12S,20aS)-16-fluoro-8,13-dimethyl-5,9,14-trioxo-12-{[(4-pyridinylmethyl)amino]carbonyl}-2,3,5,6,7,8,9,10,11,12,13,14,20,20a-tetradecahydro-1H-pyrrolo[2,1-c][1,4,8,13]benzoxatriazacyclohexadecin-2-yl)amino]-4-oxobutanoic acid |
| Ex.161 | 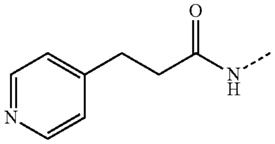 | 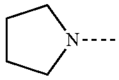 | N-[(2R,12S,20aS)-16-fluoro-8,13-dimethyl-5,9,14-trioxo-12-(1-pyrrolidinylcarbonyl)-2,3,5,6,7,8,9,10,11,12,13,14,20,20a-tetradecahydro-1H-pyrrolo[2,1-c][1,4,8,13]benzoxatriazacyclohexadecin-2-yl]-3-(4-pyridinyl)propanamide |
| Ex.162 | 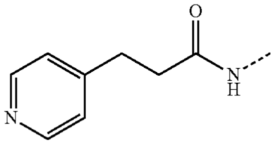 | 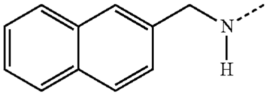 | (2R,12S,20aS)-16-fluoro-8,13-dimethyl-N-(2-naphthylmethyl)-5,9,14-trioxo-2-{[3-(4-pyridinyl)propanoyl]amino}-2,3,5,6,7,8,9,10,11,12,13,14,20,20a-tetradecahydro-1H-pyrrolo[2,1-c][1,4,8,13]benzoxatriazacyclohexadecine-12-carboxamide |

TABLE 27c-continued

| Examples of Core 09 (Ex.142-Ex.163; continued on the following pages) | | | |
|---|---|---|---|
| No | $R^2$ | $R^{54}$ | IUPAC name |
| Ex.163 | 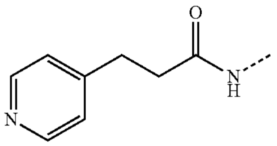 | 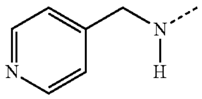 | (2R,12S,20aS)-16-fluoro-8,13-dimethyl-5,9,14-trioxo-N-(4-pyridinylmethyl)-2-{[3-(4-pyridinyl)propanoyl]amino}-2,3,5,6,7,8,9,10,11,12,13,14,20,20a-tetradecahydro-1H-pyrrolo[2,1-c][1,4,8,13]benzoxatriazacyclohexadecine-12-carboxamide |

TABLE 28a

| Examples of Core 10 (Ex. 164-Ex. 180; continued on the following pages) | | | | | | | |
|---|---|---|---|---|---|---|---|
| No | $R^2$ | $R^5$ | Starting material | General Procedure | Reagent | Purification Method | Yield (isolated salt) |
| Ex. 164-Ex. 165: cf. experimental description | | | | | | | |
| Ex. 166 | 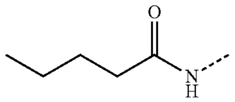 | 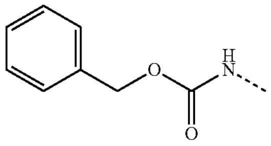 | Ex. 165 | L.1.1 | valeroyl chloride (2.0 equiv.) | FC (EtOAc/MeOH) | ca.70% |
| Ex. 167 | 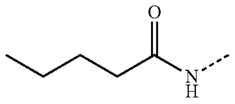 | $NH_2$ | Ex. 166 | K.1 | H2, $Pd(OH)_2$—C | crude product | quant. |
| Ex. 168 | 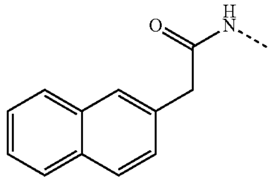 | 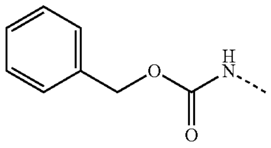 | Ex. 165 | L.1.3 | 2-naphthylacetic acid | FC (EtOAc) | 68% |
| Ex. 169 | 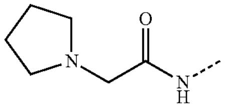 | 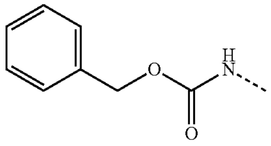 | Ex. 165 | L.1.3 | 1-pyrrolidinacetic acid | FC (EtOAc/MeOH) | 76% |
| Ex. 170 | 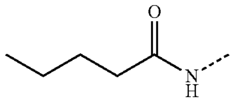 | 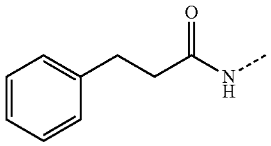 | Ex. 167 | L.1.2 | 3-(pyridine-4-yl)propanoic acid | FC ($CH_2Cl_2$/MeOH) | 78% |
| Ex. 171 | 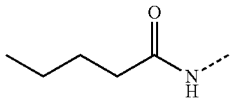 | 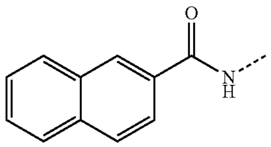 | Ex. 167 | L.1.1 | 2-naphthoyl chloride (2.6 equiv.) | Prep. HPLC, method 3 | 42% |
| Ex. 172 | 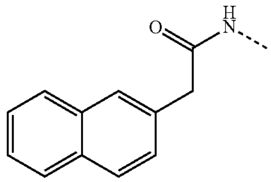 | $NH_2$ | Ex. 168 | K.1 | $H_2$, $Pd(OH)_2$—C | crude product | 97% |

TABLE 28a-continued

Examples of Core 10 (Ex. 164-Ex. 180; continued on the following pages)

| No | $R^2$ | $R^5$ | Starting material | General Procedure | Reagent | Purification Method | Yield (isolated salt) |
|---|---|---|---|---|---|---|---|
| Ex. 173 | 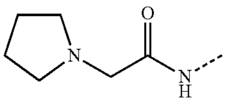 | $NH_2$ | Ex. 169 | K.1 | $H_2$, $Pd(OH)_2$—C | crude product | 96% |
| Ex. 174 | 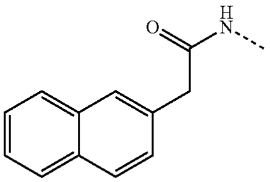 | 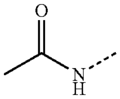 | Ex. 172 | L.1.1 | acetic anhydride (5 equiv.) | Prep. HPLC, method 3 | 97% |
| Ex. 175 | 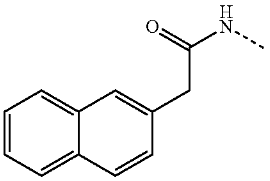 | 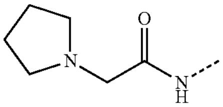 | Ex. 172 | L.1.2 | 1-pyrrolidinacetic acid (2.2 equiv.) | Prep. HPLC, method 3 | 58% |
| Ex. 176 | 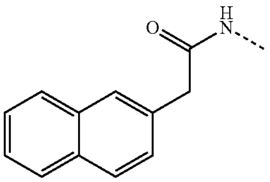 | 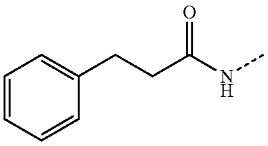 | Ex. 172 | L.1.2 | 3-(pyridine-4-yl)propanoic acid | Prep. HPLC, method 3 | 71% |
| Ex. 177 | 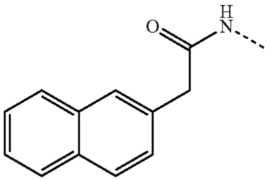 | 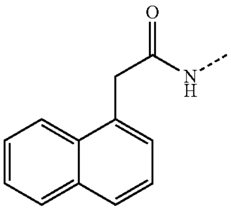 | Ex. 172 | L.1.2*) | 1-naphthylacetic acid | Prep. HPLC, method 3 | 68% |
| Ex. 178 | 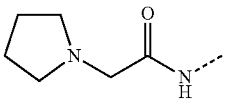 | 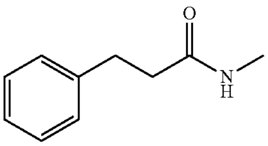 | Ex. 173 | L.1.2 | 3-(pyridine-4-yl)propanoic acid | Prep. HPLC, method 2 | 48% |
| Ex. 179 | 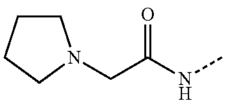 | 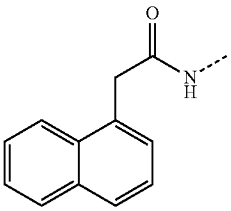 | Ex. 173 | L.1.2*) | 1-naphthylacetic acid | Prep. HPLC, method 3 | 84% |
| Ex. 180 | 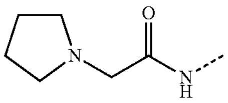 | 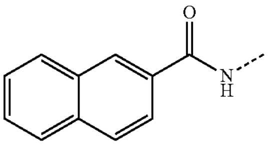 | Ex. 173 | L.1.1*) | 2-naphthoyl chloride (1.5 equiv.) | Prep. HPLC, method 3 | 78% |

*) The treatment with (polystyrylmethyl)trimethylammonium bicarbonate was replaced by an aqueous workup ($CHCl_3$, sat. aq. $NaHCO_3$ soln)

TABLE 28b
Examples of Core 10 (Ex. 164-Ex. 180; continued on the following pages)
| No | $R^2$ | $R^5$ | FORMULA | MONO-ISOTOPIC MASS | Rt (purity at 220 nm) | $[M + H]^+$ found | LC-MS-Method |
|---|---|---|---|---|---|---|---|
| Ex. 164-Ex. 165: cf. experimental description | | | | | | | |
| Ex. 166 | 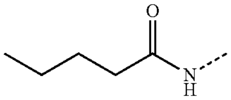 | 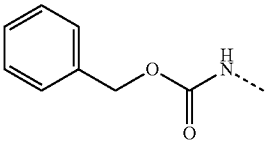 | C30H38N4O6 | 550.3 | 1.96 (99) | 551.3 | Method 4a |
| Ex. 167 | 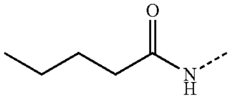 | $NH_2$ | C22H32N4O4 | 416.2 | 1.4 (99) | 417.3 | Method 4a |
| Ex. 168 | 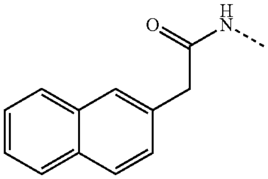 | 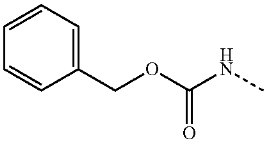 | C37H38N4O6 | 634.3 | 2.2 (98) | 635.3 | Method 4a |
| Ex. 169 | 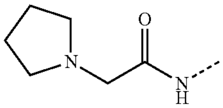 | 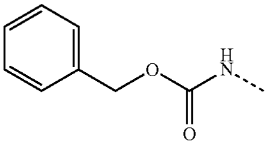 | C31H39N5O6 | 577.3 | 1.57 (99) | 578.4 | Method 4a |
| Ex. 170 | 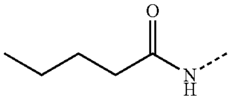 | 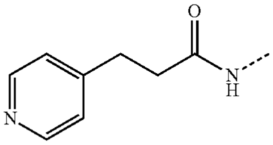 | C30H39N5O5 | 549.3 | 1.47 (97) | 550.4 | Method 4a |
| Ex. 171 | 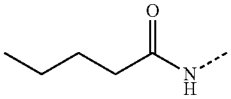 | 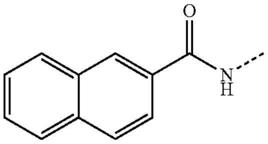 | C33H38N4O5 | 570.3 | 2.1 (100) | 571.3 | Method 4a |
| Ex. 172 | 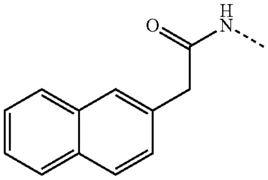 | $NH_2$ | C29H32N4O4 | 500.2 | 1.60 (91) | 501.3 | Method 4a |
| Ex. 173 | 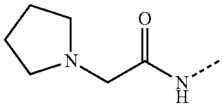 | $NH_2$ | C23H33N5O4 | 443.3 | 1.48 (99) | 444.2 | Method 5a |
| Ex. 174 | 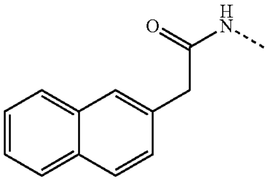 | 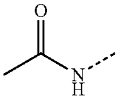 | C31H34N4O5 | 542.3 | 1.82 (99) | 543.2 | Method 4a |

TABLE 28b-continued

Examples of Core 10 (Ex. 164-Ex. 180; continued on the following pages)

| No | $R^2$ | $R^5$ | FORMULA | MONO-ISOTOPIC MASS | Rt (purity at 220 nm) | $[M + H]^+$ found | LC-MS-Method |
|---|---|---|---|---|---|---|---|
| Ex. 175 | 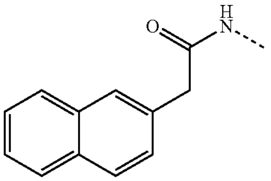 | 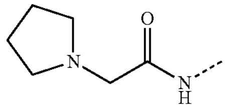 | C35H41N5O5 | 611.3 | 1.69 (96) | 612.2 | Method 4a |
| Ex. 176 | 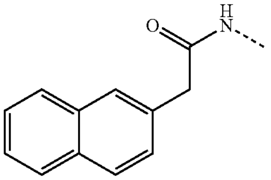 | 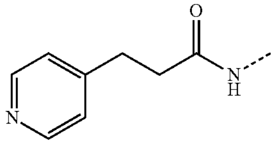 | C37H39N5O5 | 633.3 | 1.68 (99) | 634.3 | Method 4a |
| Ex. 177 | 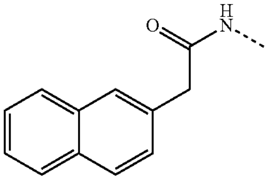 | 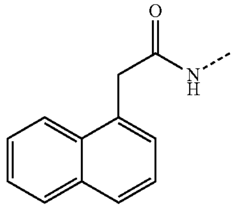 | C41H40N4O5 | 668.3 | 2.24 (92) | 669.3 | Method 4a |
| Ex. 178 | 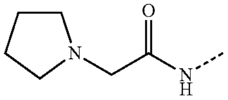 | 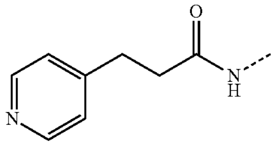 | C31H40N6O5 | 576.3 | 1.07 (98) | 577.3 | Method 4a |
| Ex. 179 | 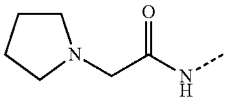 | 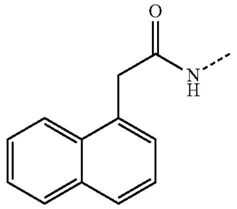 | C35H41N5O5 | 611.3 | 1.69 (93) | 612.3 | Method 4a |
| Ex. 180 | 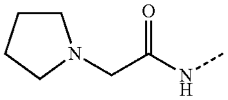 | 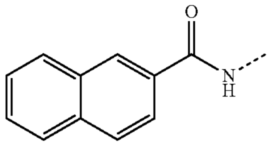 | C34H39N5O5 | 597.3 | 1.69 (97) | 597.8 | Method 4a |

TABLE 28c

Examples of Core 10 (Ex. 164-Ex. 180; continued on the following pages)

| No | $R^2$ | $R^5$ | IUPAC name |
|---|---|---|---|
| Ex. 164 | 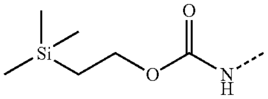 | 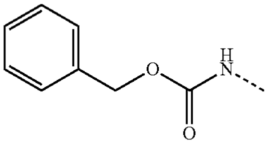 | benzyl N-[(4S,6S,10S)-13-methyl-9,14-dioxo-6-({[2-(trimethylsilyl)ethoxy]carbonyl}amino)-2-oxa-8,13-diazatricyclo[$13.3.1.0^{4,8}$]nonadeca-1(19),15,17-trien-10-yl] carbamate |

TABLE 28c-continued

| Examples of Core 10 (Ex. 164-Ex. 180; continued on the following pages) | | | |
|---|---|---|---|
| No | $R^2$ | $R^5$ | IUPAC name |
| Ex. 165 | $NH_2$ | 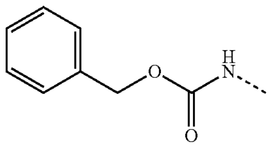 | benzyl N-[(4S,6S,10S)-6-amino-13-methyl-9,14-dioxo-2-oxa-8,13-diazatricyclo[13.3.1.$0^{4,8}$]nonadeca-1(19),15,17-trien-10-yl]carbamate |
| Ex. 166 | 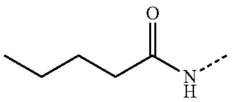 | 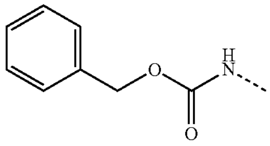 | benzyl N-[(4S,6S,10S)-13-methyl-9,14-dioxo-6-(pentanoylamino)-2-oxa-8,13-diazatricyclo[13.3.1.$0^{4,8}$] nonadeca-1(19),15,17-trien-10-yl]carbamate |
| Ex. 167 | 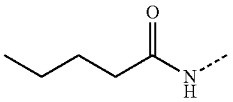 | $NH_2$ | N-[(4S,6S,10S)-10-amino-13-methyl-9,14-dioxo-2-oxa-8,13-diazatricyclo[13.3.1.$0^{4,8}$]nonadeca-1(19),15,17-trien-6-yl] pentanamide |
| Ex. 168 | 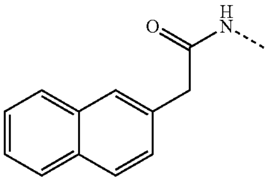 | 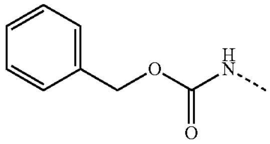 | benzyl N-[(4S,6S,10S)-13-methyl-6-{[2-(2-naphthyl) acetyl]amino}-9,14-dioxo-2-oxa-8,13-diazatricyclo [13.3.1.$0^{4,8}$]nonadeca-1(19),15,17-trien-10-yl]carbamate |
| Ex. 169 | 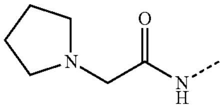 | 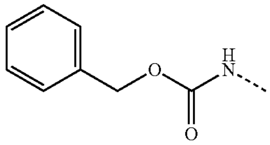 | benzyl N-[(4S,6S,10S)-13-methyl-9,14-dioxo-6-{[2-(1-pyrrolidinyl) acetyl] amino}-2-oxa-8,13-diazatricyclo [13.3.1.$0^{4,8}$ ] nonadeca-1(19),15,17-trien-10-yl]carbamate |
| Ex. 170 | 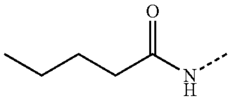 | 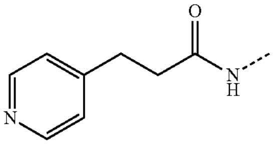 | N-[(4S,6S,10S)-13-methyl-9,14-dioxo-10-{[3-(4-pyridinyl) propanoyl]aminol-2-oxa-8,13-diazatricyclo[13.3.1.$0^{4,8}$] nonadeca-1(19),15,17-trien-6-yl]pentanamide |
| Ex. 171 | 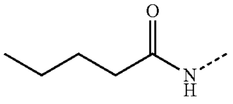 | 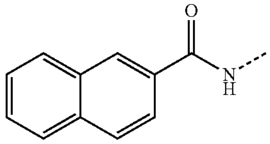 | N-[(4S,6S,10S)-13-methyl-9,14-dioxo-6-(pentanoylamino)-2-oxa-8,13-diazatricyclo[13.3.1.$0^{4,8}$]nonadeca-1(19),15,17-trien-10-yl]-2-naphthamide |
| Ex. 172 | 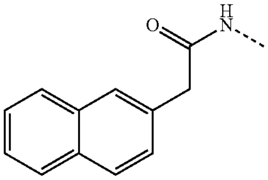 | $NH_2$ | N-[(4S,6S,10S)-10-amino-13-methyl-9,14-dioxo-2-oxa-8,13-diazatricyclo[13.3.1.$0^{4,8}$]nonadeca-1(19),15,17-trien-6-yl]-2-(2-naphthyl)acetamide |
| Ex. 173 | 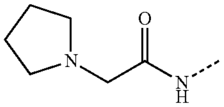 | $NH_2$ | N-[(4S,6S,10S)-10-amino-13-methyl-9,14-dioxo-2-oxa-8,13-diazatricyclo[13.3.1.$0^{4,8}$]nonadeca-1(19),15,17-trien-6-yl]-2-(1-pyrrolidinyl) acetamide |

TABLE 28c-continued

| No | $R^2$ | $R^5$ | IUPAC name |
|---|---|---|---|
| Examples of Core 10 (Ex. 164-Ex. 180; continued on the following pages) | | | |
| Ex. 174 | 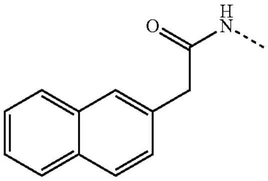 | 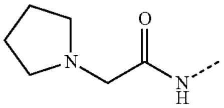 | N-[(4S,6S,10S)-10-(acetylamino)-13-methyl-9,14-dioxo-2-oxa-8,13-diazatricyclo [13.3.1.$0^{4,8}$] nonadeca-1 (19),15,17-trien-6-yl]-2-(2-naphthyl) acetamide |
| Ex. 175 | 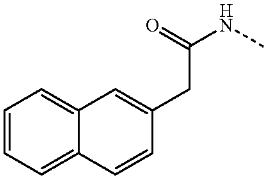 | 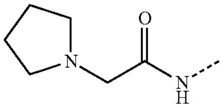 | N-[(4S,6S,10S)-13-methyl-9,14-dioxo-10-{[2-(1-pyrrolidinyl)acetyl]amino}-2-oxa-8,13-diazatricyclo [13.3.1.$0^{4,8}$]nonadeca-1(19),15,17-trien-6-yl]-2-(2-naphthyl)acetamide |
| Ex. 176 | 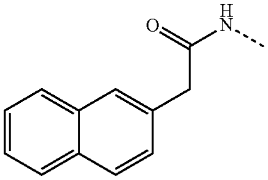 | 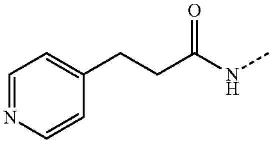 | N-[(4S,6S,10S)-13-methyl-6-{[2-(2-naphthyl)acetyl] amino1-9,14-dioxo-2-oxa-8,13-diazatricyclo[13.3.1.$0^{4,8}$] nonadeca-1(19),15,17-trien-10-yl]-3-(4-pyridinyl)propanamide |
| Ex. 177 | 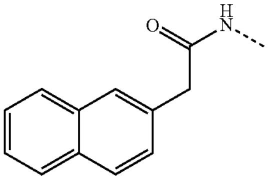 | 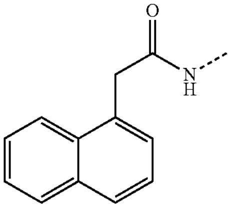 | N-[(4S,6S,10S)-13-methyl-6-{[2-(2-naphthyl)acetyl] amino}-9,14-dioxo-2-oxa-8,13-diazatricyclo[13.3.1.$0^{4,8}$] nonadeca-1(19),15,17-trien-10-yl]-2-(1-naphthyl)acetamide |
| Ex. 178 | 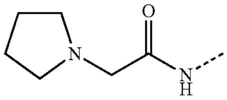 | 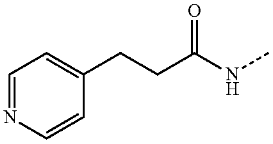 | N-[(4S,6S,10S)-13-methy1-9,14-dioxo-6-{[2-(1-pyrrolidinyl)acetyl]amino}-2-oxa-8,13-diazatricyclo [13.3.1.$0^{4,8}$]nonadeca-1(19),15,17-trien-10-yl]-3-(4-pyridinyl)propanamide |
| Ex. 179 | 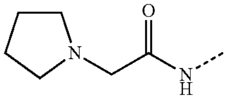 | 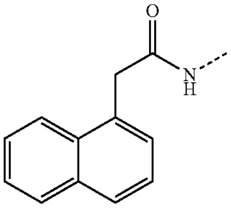 | N-[(4S,6S,10S)-13-methyl-9,14-dioxo-6-{[2-(1-pyrrolidinyl)acetyl]amino}-2-oxa-8,13-diazatricyclo [13.3.1.$0^{4,8}$]nonadeca-1(19),15,17-trien-10-yl]-2-(1-naphthyl)acetamide |
| Ex. 180 | 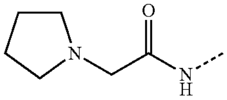 | 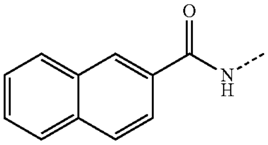 | N-[(4S,6S,10S)-13-methyl-9,14-dioxo-6-{[2-(1-pyrrolidinyl)acetyl]amino}-2-oxa-8,13-diazatricyclo[13.3.1.$0^{4,8}$]nonadeca-1(19),15,17-trien-10-yl]-2-naphthamide |

TABLE 29.1.a

Examples of Core 11a (Ex. 181-Ex. 195, Ex. 504-Ex. 559 and Ex. 594; continued on the following pages)

| No | $R^2$ | $R^5$ | Starting material | General Procedure | Reagent | Purification Method | Yield (isolated salt) |
|---|---|---|---|---|---|---|---|
| Ex. 181-Ex. 182: cf. experimental description | | | | | | | |
| Ex. 183 | 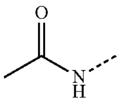 | 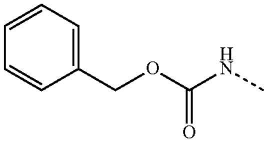 | Ex. 182 | L.1.1 | acetic anhydride (5 equiv.) | FC ($CH_2Cl_2$/MeOH) | 75% |
| Ex. 184 | 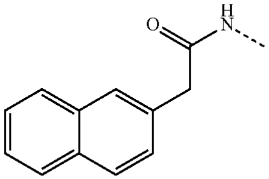 | 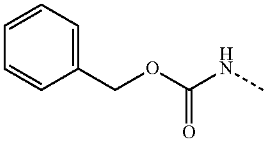 | Ex. 182 | L.1.3 | 2-naphthyl-acetic acid (1.2 equiv.) | FC (EtOAc, then $CH_2Cl_2$/MeOH) | 94% |
| Ex. 185 | 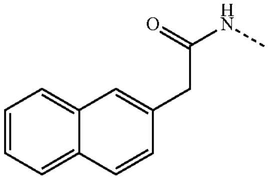 | $NH_2$ | Ex. 184 | K.1 | $H_2$, $Pd(OH)_2$—C | crude product | 99% |
| Ex. 186 | 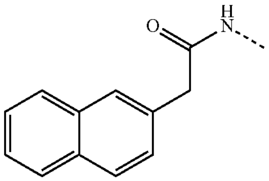 | 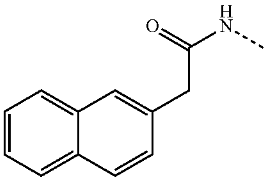 | Ex. 185 | L.1.3 | 2-naphthyl-acetic acid (1.2 equiv.) | prep. HPLC, method 3 | 60% |
| Ex. 186 | 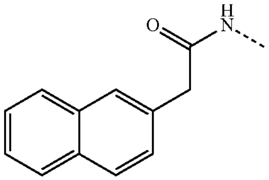 | 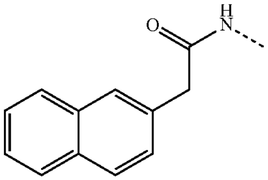 | Ex. 594 | S | 2-naphthyl-acetic acid | prep. HPLC, method 3 | 32% |

TABLE 29.1.a-continued

Examples of Core 11a (Ex. 181-Ex. 195, Ex. 504-Ex. 559 and Ex. 594; continued on the following pages)

| No | $R^2$ | $R^5$ | Starting material | General Procedure | Reagent | Purification Method | Yield (isolated salt) |
|---|---|---|---|---|---|---|---|
| Ex. 187 | 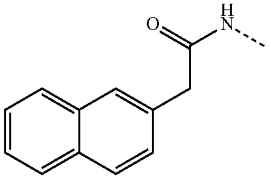 | 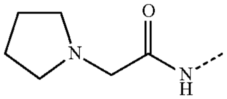 | Ex. 185 | L.1.3 | pyrrolidin-l-acetic acid (1.2 equiv.) | prep. HPLC, method 3 then prep. HPLC, method 1 | 38% (TFA salt) |
| Ex. 188 | 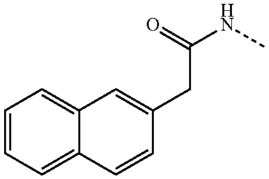 | 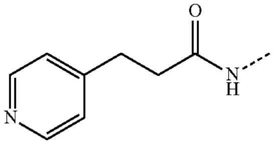 | Ex. 185 | L.1.3 | 3-(pyridine-4-yl)propanoic acid (1.2 equiv.) | prep. HPLC, method 3 then prep. HPLC, method 1 | 32% (TFA salt) |
| Ex. 189 | 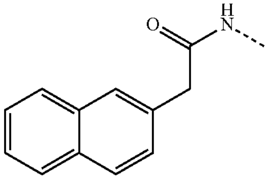 | 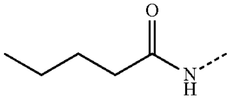 | Ex. 185 | L.1.1 | valeroyl chloride (2 equiv.) | prep. HPLC, method 3 | 52% |
| Ex. 190 | $NH_2$ | 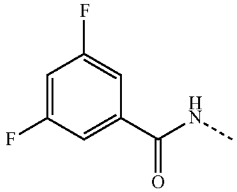 | Ex. 193 | I.2 | TBAF (4 equiv.) in THF | crude product, contaminated with TBAF | ca 70% |
| Ex. 191 | 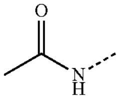 | 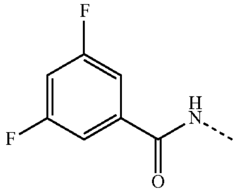 | Ex. 190 | L.1.1 | Acetic anhydride (10 equiv.) Pyridine/$CH_2Cl_2$ 1:1 (3 mL) | prep. HPLC, method 3 | 62% |

TABLE 29.1.a-continued

Examples of Core 11a (Ex. 181-Ex. 195, Ex. 504-Ex. 559 and Ex. 594; continued on the following pages)

| No | $R^2$ | $R^5$ | Starting material | General Procedure | Reagent | Purification Method | Yield (isolated salt) |
|---|---|---|---|---|---|---|---|
| Ex. 192 | 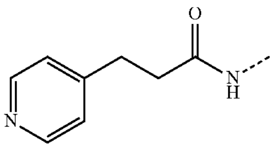 | 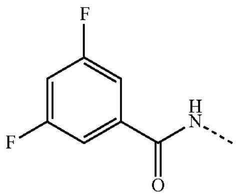 | Ex. 190 | L.1.3 | 3-(pyridine-4-yl)propanoic acid (1.2 equiv.) | prep. HPLC, method 3 | 63% |
| Ex. 193 | 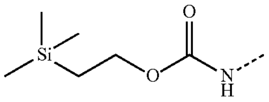 | 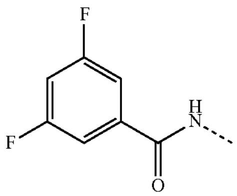 | Ex. 194 | L.1.1 | 3,5-difluoro-benzoyl chloride (2 equiv.) | FC (EtOAc) | 85% |
| Ex. 194 | 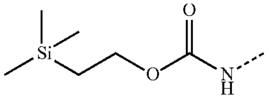 | $NH_2$ | Ex. 181 | K.1 | H2, $Pd(OH)_2$—C | crude product | quant. |
| Ex. 195 | 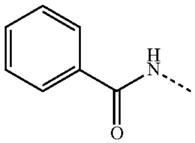 | 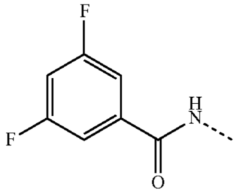 | Ex. 190 | L.1.1 | benzoyl chloride (2 equiv.) | prep. HPLC, method 3 | 78% |
| Ex. 504 | 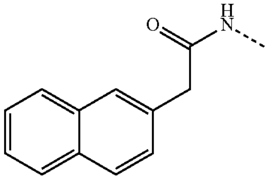 | $CH_3(CH_2)_8CONH$ | 140 | S | cf. detailed description | prep. HPLC method 1 | 26% |

TABLE 29.1.a-continued

Examples of Core 11a (Ex. 181-Ex. 195, Ex. 504-Ex. 559 and Ex. 594; continued on the following pages)

| No | $R^2$ | $R^5$ | Starting material | General Procedure | Reagent | Purification Method | Yield (isolated salt) |
|---|---|---|---|---|---|---|---|
| Ex. 505 | 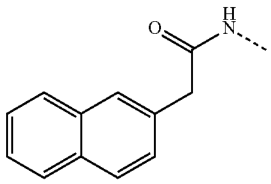 | 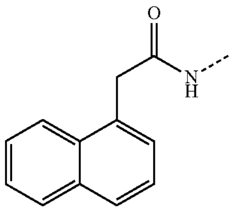 | 140 | S | cf. detailed description | prep. HPLC method 3 | 33% |
| Ex. 506 | 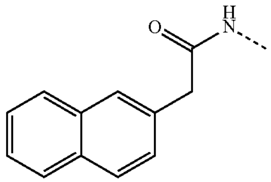 | 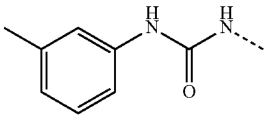 | 140 | S | cf. detailed description | prep. HPLC method 3 | 45% |
| Ex. 507 | 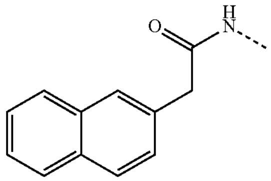 | 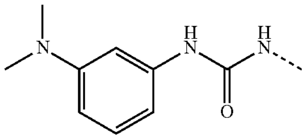 | 140 | S | cf. detailed description | prep. HPLC method 3 | 48% |
| Ex. 508 | 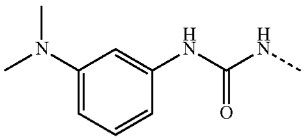 | 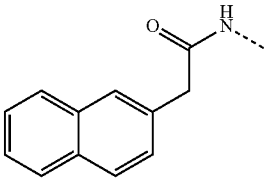 | Ex. 554 | L.1.3 | cf. detailed description | prep. HPLC method 3 | 57% |
| Ex. 509 | 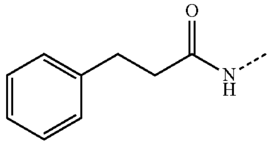 | $CH_3(CH_2)_8CONH$ | 140 | S | cf. detailed description | prep. HPLC method 3 | 48% |

TABLE 29.1.a-continued

Examples of Core 11a (Ex. 181-Ex. 195, Ex. 504-Ex. 559 and Ex. 594; continued on the following pages)

| No | $R^2$ | $R^5$ | Starting material | General Procedure | Reagent | Purification Method | Yield (isolated salt) |
|---|---|---|---|---|---|---|---|
| Ex. 510 | 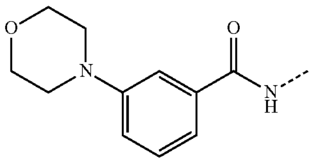 | $CH_3(CH_2)_8CONH$ | 140 | S | cf. detailed description | prep. HPLC method 3 | 20% |
| Ex. 511 | 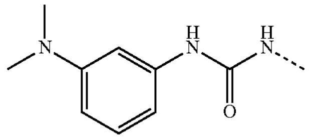 | $CH_3(CH_2)_8CONH$ | 140 | S | cf. detailed description | prep. HPLC method 1 | 55% (TFA salt) |
| Ex. 512 | 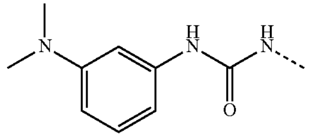 | 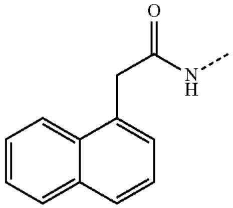 | 140 | S | cf. detailed description | prep. HPLC method 1 | 56% (TFA salt) |
| Ex. 513 | 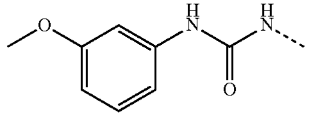 | 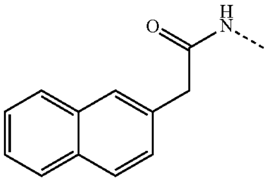 | 140 | S | cf. detailed description | prep. HPLC method 3 | 25% |
| Ex. 514 | 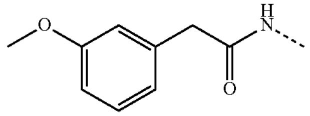 | 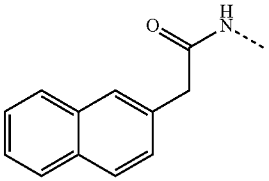 | 140 | S | cf. detailed description | prep. HPLC method 3 | 54% |

TABLE 29.1.a-continued

| Examples of Core 11a (Ex. 181-Ex. 195, Ex. 504-Ex. 559 and Ex. 594; continued on the following pages) | | | | | | | |
|---|---|---|---|---|---|---|---|
| No | $R^2$ | $R^5$ | Starting material | General Procedure | Reagent | Purification Method | Yield (isolated salt) |
| Ex. 515 | 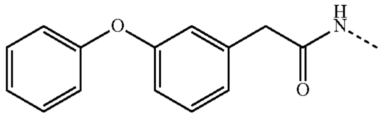 | $CH_3(CH_2)_8CONH$ | 140 | S | cf. detailed description | prep. HPLC method 3 | 48% |
| Ex. 516 | 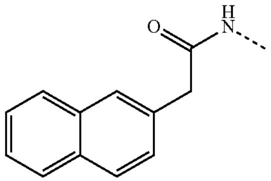 | 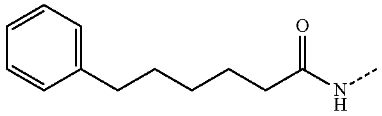 | 140 | S | cf. detailed description | prep. HPLC method 3 | 64% |
| Ex. 517 | 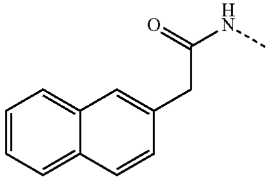 | 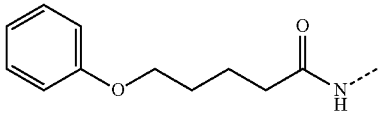 | 140 | S | cf. detailed description | prep. HPLC method 3 | 57% |
| Ex. 518 | 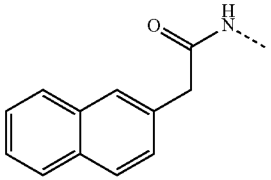 | 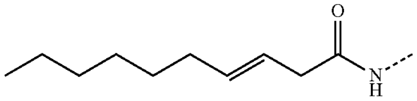 | 140 | S | cf. detailed description | prep. HPLC method 3 | 52% |
| Ex. 519 | 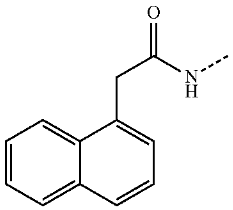 | $CH_3(CH_2)_8CONH$ | 140 | S | cf. detailed description | prep. HPLC method 3 | 59% |

TABLE 29.1.a-continued

Examples of Core 11a (Ex. 181-Ex. 195, Ex. 504-Ex. 559 and Ex. 594; continued on the following pages)

| No | $R^2$ | $R^5$ | Starting material | General Procedure | Reagent | Purification Method | Yield (isolated salt) |
|---|---|---|---|---|---|---|---|
| Ex. 520 | 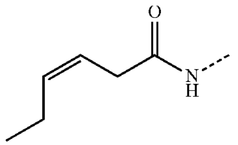 | 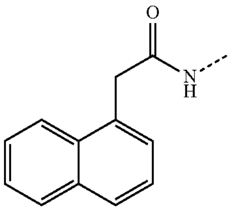 | 140 | S | cf. detailed description | prep. HPLC method 3 | 59% |
| Ex. 521 | 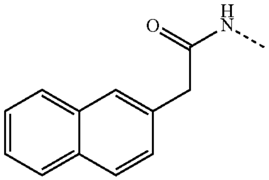 | 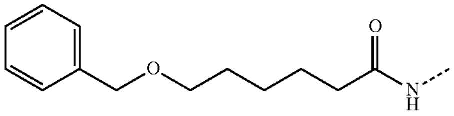 | 140 | S | cf. detailed description | prep. HPLC method 3 | 68% |
| Ex. 522 | 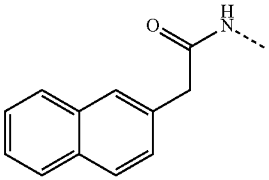 | 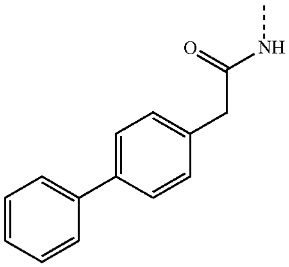 | 140 | S | cf. detailed description | prep. HPLC method 3 | 62% |
| Ex. 523 | 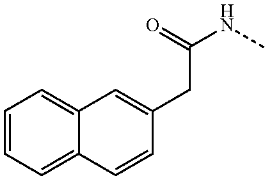 | 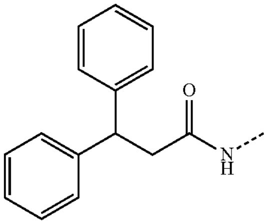 | 140 | S | cf. detailed description | prep. HPLC method 3 | 63% |

TABLE 29.1.a-continued

| Examples of Core 11a (Ex. 181-Ex. 195, Ex. 504-Ex. 559 and Ex. 594; continued on the following pages) | | | | | | | |
|---|---|---|---|---|---|---|---|
| No | $R^2$ | $R^5$ | Starting material | General Procedure | Reagent | Purification Method | Yield (isolated salt) |
| Ex. 524 | 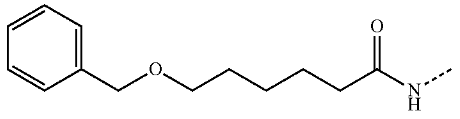 | 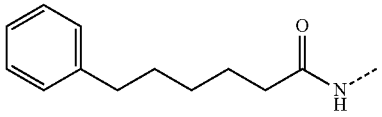 | 140 | S | cf. detailed description | prep. HPLC method 3 | 38% |
| E x. 525 | 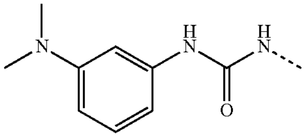 | 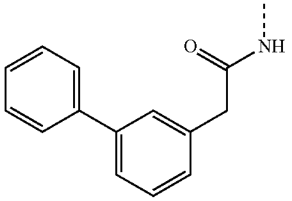 | 140 | S | cf. detailed description | prep. HPLC method 3 | 54% |
| Ex. 526 | 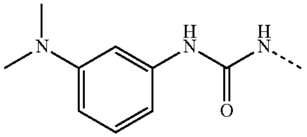 | 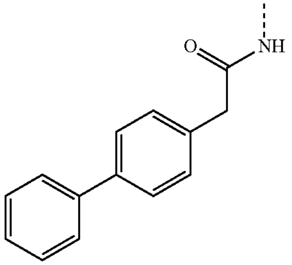 | 140 | S | cf. detailed description | prep. HPLC method 3 | 54% |
| Ex. 527 | 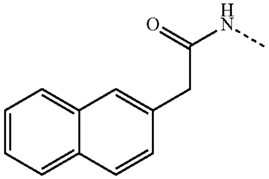 | 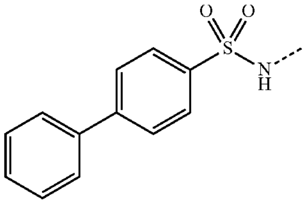 | 140 | S | cf. detailed description | prep. HPLC method 3 | 61% |

TABLE 29.1.a-continued

Examples of Core 11a (Ex. 181-Ex. 195, Ex. 504-Ex. 559 and Ex. 594; continued on the following pages)

| No | $R^2$ | $R^5$ | Starting material | General Procedure | Reagent | Purification Method | Yield (isolated salt) |
|---|---|---|---|---|---|---|---|
| Ex. 528 | 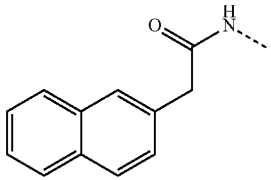 | 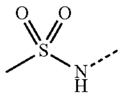 | 140 | S | 1. 2-naphthyl-acetic acid 2. methane-sulfonyl chloride | prep. HPLC method 3 | 45% |
| Ex. 529 | 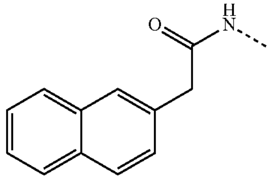 | 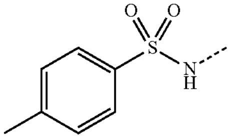 | 140 | S | 1. 2-naphthyl-acetic acid 2. toluene-4-sulfonyl chloride | prep. HPLC method 3 | 61% |
| Ex. 530 | 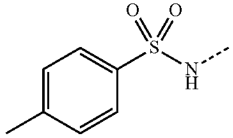 | 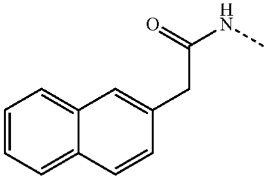 | 140 | S | 1. toluene-4-sulfonyl chloride 2. 2-naphthyl-acetic acid | prep. HPLC method 3 | 19% |
| Ex. 531 | 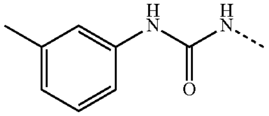 | 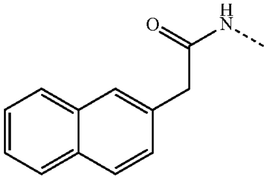 | 140 | S | 1. 3-methyl-phenyl isocyanate 2. 2-naphthyl-acetic acid | prep. HPLC method 3 | 44% |
| Ex. 532 | 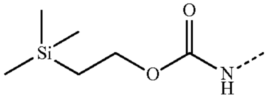 | 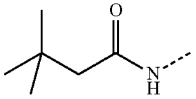 | Ex. 194 | L.1.1 | cf. detailed description | FC (hexane/ EtOAc/MeOH) | 91% |
| Ex. 533 | $NH_2$ | 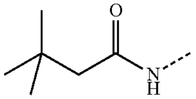 | Ex. 532 | — | cf. detailed description | crude product | 80% |

TABLE 29.1.a-continued

Examples of Core 11a (Ex. 181-Ex. 195, Ex. 504-Ex. 559 and Ex. 594; continued on the following pages)

| No | $R^2$ | $R^5$ | Starting material | General Procedure | Reagent | Purification Method | Yield (isolated salt) |
|---|---|---|---|---|---|---|---|
| Ex. 534 | 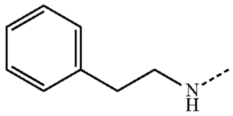 | 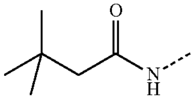 | Ex. 533 | M.2 | 2-phenyl-acetaldehyde | prep. HPLC method 3 | 59% |
| Ex. 535 | 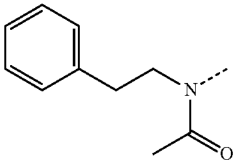 | 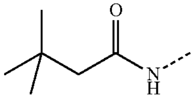 | Ex. 558 | L.1.1 | 3,3-dimethyl-butanoyl chloride (1.1 equiv.) pyridine (5 equiv.) | FC (hexane/ EtOAc/MeOH) | 91% |
| Ex. 536 | 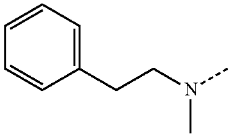 | 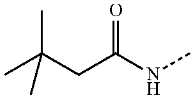 | Ex. 559 | L.1.1 | 3,3-dimethyl-butanoyl chloride (1.1 equiv.) pyridine (5 equiv.) | FC (hexane/ EtOAc/MeOH) | 74% |
| Ex. 537 | 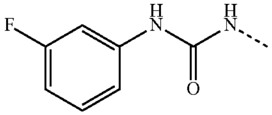 | 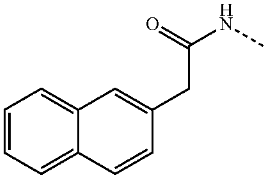 | 140 | S | cf. detailed description | prep. HPLC method 3 | 63% |
| Ex. 538 | 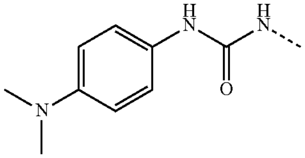 | 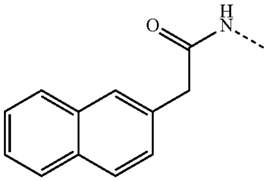 | 140 | S | cf. detailed description | prep. HPLC method 1 | 62% (TFA salt) |

TABLE 29.1.a-continued

Examples of Core 11a (Ex. 181-Ex. 195, Ex. 504-Ex. 559 and Ex. 594; continued on the following pages)

| No | $R^2$ | $R^5$ | Starting material | General Procedure | Reagent | Purification Method | Yield (isolated salt) |
|---|---|---|---|---|---|---|---|
| Ex. 539 | 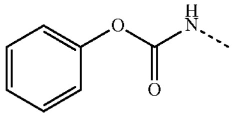 | 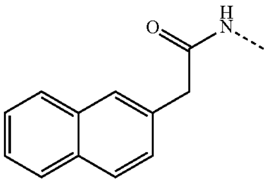 | 140 | S | cf. detailed description | prep. HPLC method 3 | 46% |
| Ex. 540 | 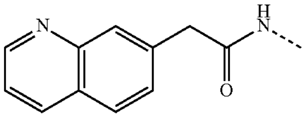 | 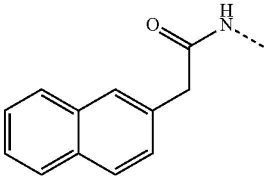 | 140 | S | cf. detailed description | prep. HPLC method 3 | 53% |
| Ex. 541 | 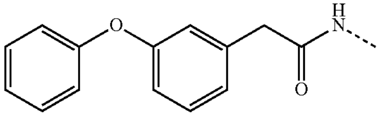 | 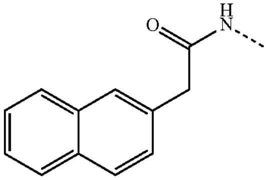 | 140 | S | cf. detailed description | prep. HPLC method 3 | 68% |
| Ex. 542 | $CH_3(CH_2)_8CONH$ | 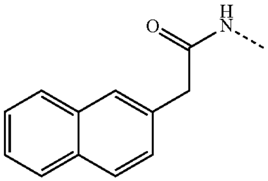 | 140 | S | cf. detailed description | prep. HPLC method 3 | 56% |
| Ex. 543 | $CH_3(CH_2)_8CONH$ | 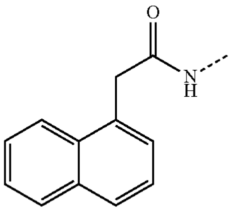 | 140 | S | cf. detailed description | prep. HPLC method 3 | 61% |

TABLE 29.1.a-continued
| Examples of Core 11a (Ex. 181-Ex. 195, Ex. 504-Ex. 559 and Ex. 594; continued on the following pages) | | | | | | | |
|---|---|---|---|---|---|---|---|
| No | $R^2$ | $R^5$ | Starting material | General Procedure | Reagent | Purification Method | Yield (isolated salt) |
| Ex. 544 | $CH_3(CH_2)_4CONH$ | 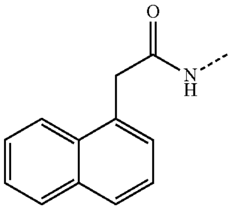 | 140 | S | cf. detailed description | prep. HPLC method 3 | 54% |
| Ex. 545 | 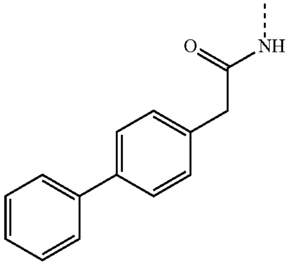 | 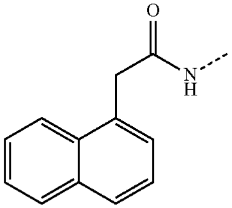 | 140 | S | cf. detailed description | prep. HPLC method 3 | 65% |
| Ex. 546 | 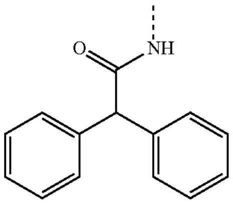 | 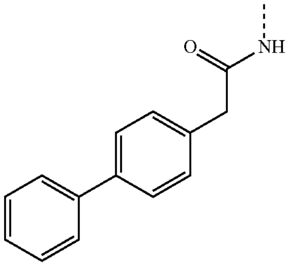 | 140 | S | cf. detailed description | prep. HPLC method 1 | 20% |

TABLE 29.1.a-continued

Examples of Core 11a (Ex. 181-Ex. 195, Ex. 504-Ex. 559 and Ex. 594; continued on the following pages)

| No | $R^2$ | $R^5$ | Starting material | General Procedure | Reagent | Purification Method | Yield (isolated salt) |
|---|---|---|---|---|---|---|---|
| Ex. 547 | 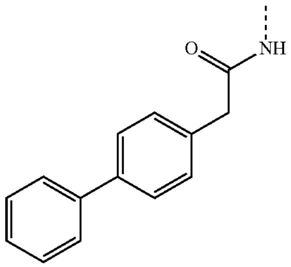 | 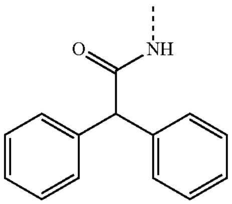 | 140 | S | cf. detailed description | prep. HPLC method 3 | 65% |
| Ex. 548 | 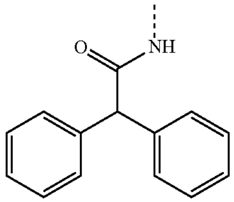 | $CH_3(CH_2)_8CONH$ | 140 | S | cf. detailed description | prep. HPLC method 1 | 28% |
| Ex. 549 | 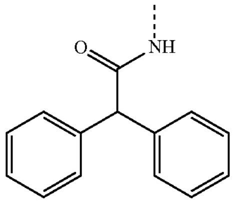 | 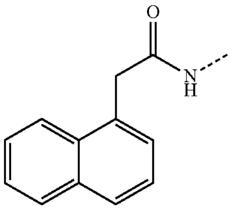 | 140 | S | cf. detailed description | prep. HPLC method 1 | 23% |
| Ex. 550 | 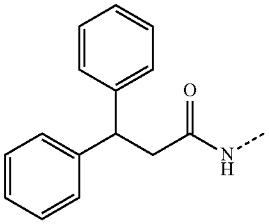 | $CH_3(CH_2)_8CONH$ | 140 | S | cf. detailed description | prep. HPLC method 3 | 49% |

TABLE 29.1.a-continued

Examples of Core 11a (Ex. 181-Ex. 195, Ex. 504-Ex. 559 and Ex. 594; continued on the following pages)

| No | $R^2$ | $R^5$ | Starting material | General Procedure | Reagent | Purification Method | Yield (isolated salt) |
|---|---|---|---|---|---|---|---|
| E x. 551 | 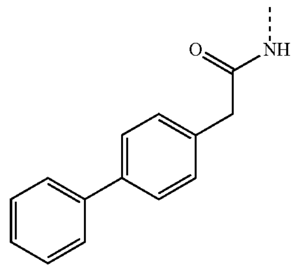 | 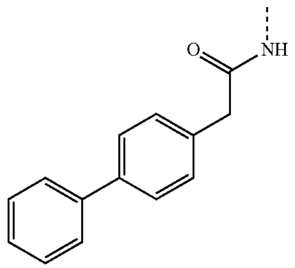 | 140 | S | cf. detailed description | prep. HPLC method 1 | 18% |
| Ex. 552 | 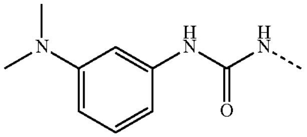 | 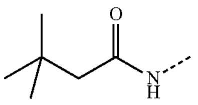 | Ex. 533 | L.4 | cf. detailed description | prep. HPLC method 3 | 83% |
| Ex. 553 | 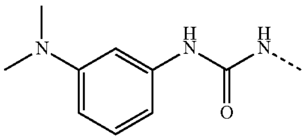 | 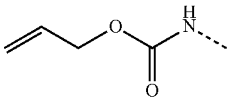 | Ex. 594 | L.4 | cf. detailed description | FC (hexane/EtOAc/ MeOH) | 91% |
| Ex. 554 | 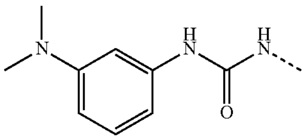 | $NH_2$ | Ex. 534 | B .2 | cf. detailed description | FC ($CH_2Cl_2$/MeOH) | 93% |
| Ex. 555 | 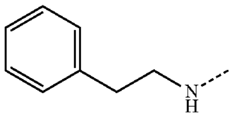 | 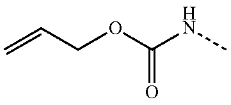 | Ex. 594 | M.2 | 2-phenyl-acetaldehyde | prep. HPLC method 3 | 73% |

TABLE 29.1.a-continued

Examples of Core 11a (Ex. 181-Ex. 195, Ex. 504-Ex. 559 and Ex. 594; continued on the following pages)

| No | $R^2$ | $R^5$ | Starting material | General Procedure | Reagent | Purification Method | Yield (isolated salt) |
|---|---|---|---|---|---|---|---|
| Ex. 556 | 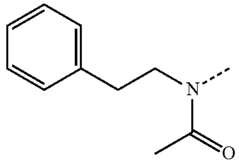 | 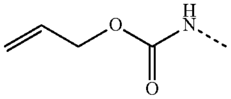 | Ex. 555 | L.1.1 | acetic anhydride (5 equiv.) pyridine (10 equiv.) | FC (hexane/ EtOAc/MeOH) | 67% |
| Ex. 557 | 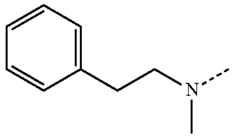 | 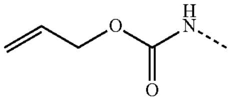 | Ex. 555 | M.3 | aq. formaldehyde soln | FC (hexane/ EtOAc/MeOH) | 86% |
| Ex. 558 | 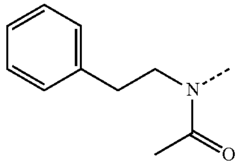 | $NH_2$ | Ex. 556 | B.2 | Pd(PPh3) 4, 1,3-dimethyl-barbituric acid | FC ($CH_2Cl_2$/MeOH/ aq. $NH_3$) | 96% |
| Ex. 559 | 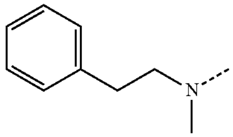 | $NH_2$ | Ex. 556 | B.2 | $Pd(PPh_3)_4$, 1,3-dimethyl-barbituric acid | FC ($CH_2Cl_2$/MeOH/ aq. $NH_3$) | 86% |
| Ex. 594 | $NH_2$ | 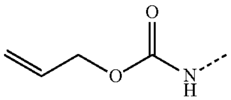 | Ex. 181 | *) | 1. $H_2$,$Pd(OH)_2$—C *) 2. AllocCl 3. TBAF in THF | | ca 80% (HCl salt) |

*) cf. detailed description

TABLE 29.1.b
Examples of Core 11a (Ex. 181-Ex. 195, Ex. 504-Ex. 559 and Ex. 594; continued on the following pages)
| No | $R^2$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 181-Ex. 182: cf. experimental description | | | | | | | |
| Ex. 183 | 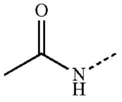 | 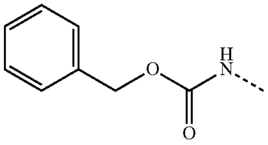 | C28H34N4O6 | 522.3 | 1.56 (99) | 523.3 | Method 2 |
| Ex. 184 | 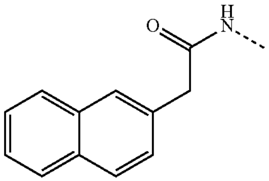 | 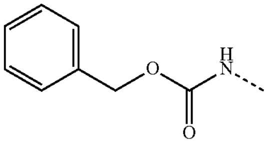 | C38H40N4O6 | 648.3 | 1.92 (96) | 649.5 | Method 2 |
| Ex. 185 | 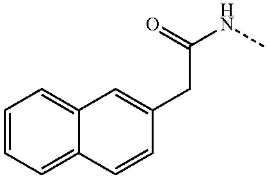 | $NH_2$ | C30H34N4O4 | 514.3 | 1.48 (98) | 515.4 | Method 2 |
| Ex. 186 | 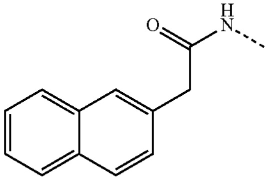 | 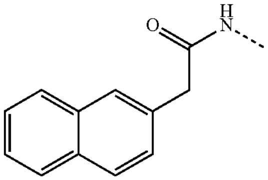 | C42H42N4O5 | 682.3 | 2.00 (91) | 683.5 | Method 2 |

TABLE 29.1.b-continued
Examples of Core 11a (Ex. 181-Ex. 195, Ex. 504-Ex. 559 and Ex. 594; continued on the following pages)
| No | $R^2$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 186 | 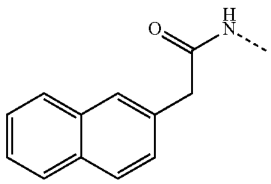 | 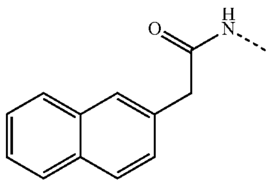 | C42H42N4O5 | 682.3 | 2.26 (98) | 683.3 | Method 4a |
| Ex. 187 | 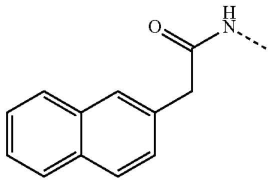 | 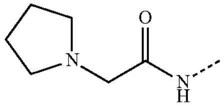 | C36H43N5O5 | 625.3 | 1.62 (100) | 626.4 | Method 2 |
| Ex. 188 | 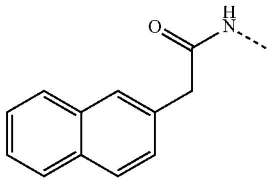 | 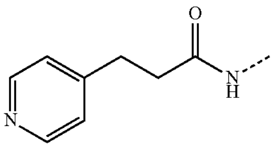 | C38H41N5O5 | 647.3 | 1.60 (99) | 648.3 | Method 2 |
| Ex. 189 | 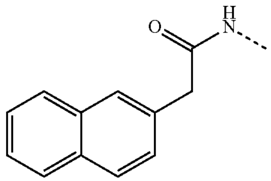 | 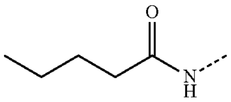 | C35H42N4O5 | 598.3 | 1.88 (85), 1.93 (8) | 599.5 | Method 2 |
| Ex. 190 | $NH_2$ | 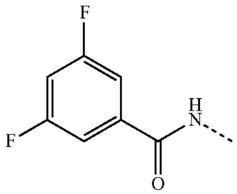 | C25H28F2N4O4 | 486.2 | 1.42 (98) | 487.3 | Method 4a |

TABLE 29.1.b-continued
Examples of Core 11a (Ex. 181-Ex. 195, Ex. 504-Ex. 559 and Ex. 594; continued on the following pages)
| No | $R^2$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 191 | 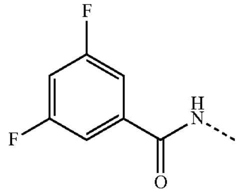 | 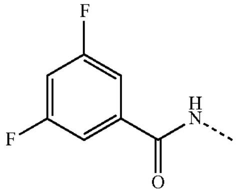 | C27H30F2N4O5 | 528.2 | 1.69 (99) | 529.3 | Method 4a |
| Ex. 192 | 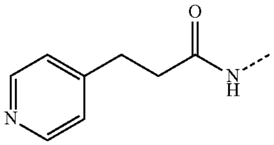 | 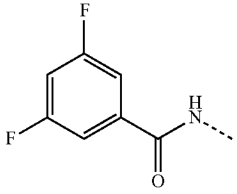 | C33H35F2N5O5 | 619.3 | 1.50 (99) | 620.3 | Method 4a |
| Ex. 193 | 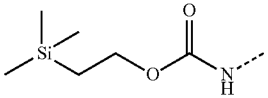 | 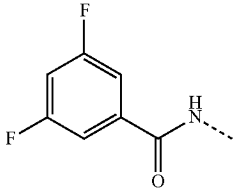 | C31H40F2N4O6Si | 630.3 | 2.13 (97) | 631.4 | Method 2 |
| Ex. 194 | 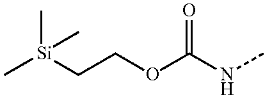 | $NH_2$ | C24H38N4O5Si | 490.3 | 1.62 (99) | 491.3 | Method 2 |
| Ex. 195 | 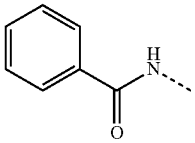 | 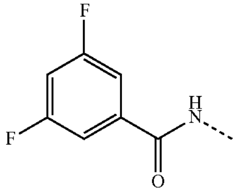 | C32H32F2N4O5 | 590.2 | 1.99 (98) | 591.3 | Method 4a |

TABLE 29.1.b-continued
Examples of Core 11a (Ex. 181-Ex. 195, Ex. 504-Ex. 559 and Ex. 594; continued on the following pages)
| No | $R^2$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 504 | 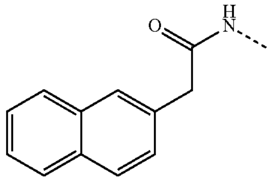 | $CH_3(CH_2)_8CONH$ | C40H52N4O5 | 668.4 | 2.54 (99) | 669.3 | Method 4b |
| Ex. 505 | 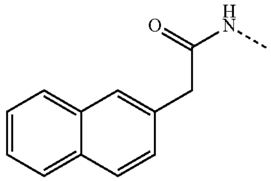 | 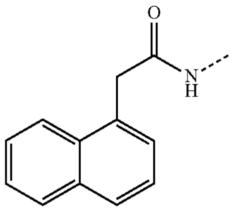 | C42H42N4O5 | 682.3 | 2.23 (95) | 683.3 | Method 4b |
| Ex. 506 | 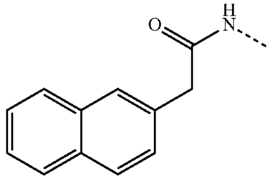 | 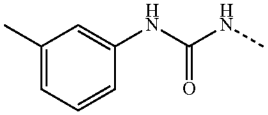 | C38H41N5O5 | 647.3 | 2.19 (99) | 648.3 | Method 4a |
| Ex. 507 | 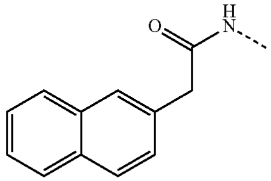 | 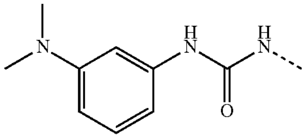 | C39H44N6O5 | 676.3 | 1.75 (94) | 677.3 | Method 4a |
| Ex. 508 | 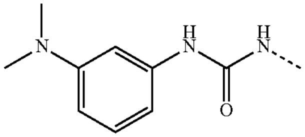 | 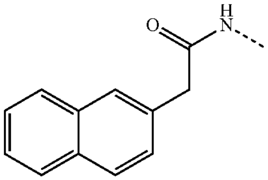 | C39H44N6O5 | 676.3 | 1.72 (94) | 677.3 | Method 4b |

TABLE 29.1.b-continued
Examples of Core 11a (Ex. 181-Ex. 195, Ex. 504-Ex. 559 and Ex. 594; continued on the following pages)
| No | $R^2$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 509 | 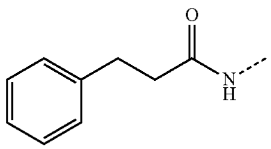 | $CH_3(CH_2)_8CONH$ | C37H52N4O5 | 632.4 | 2.43 (98) | 633.3 | Method 4b |
| Ex. 510 | 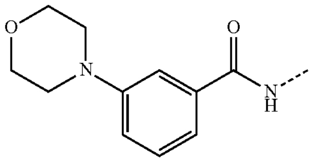 | $CH_3(CH_2)_8CONH$ | C39H55N5O6 | 689.4 | 2.31 (99) | 690.3 | Method 4b |
| Ex. 511 | 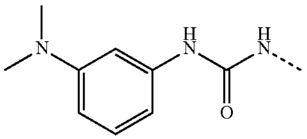 | $CH_3(CH_2)_8CONH$ | C37H54N6O5 | 662.4 | 1.96 (99) | 663.4 | Method 4a |
| Ex. 512 | 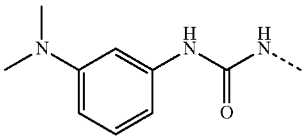 | 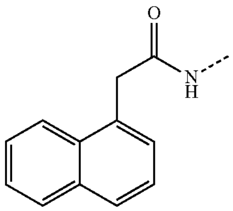 | C39H44N6O5 | 676.3 | 1.72 (98) | 677.3 | Method 4a |
| Ex. 513 | 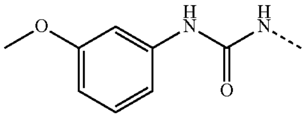 | 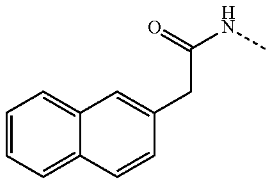 | C38H41N5O6 | 663.3 | 2.13 (95) | 664.3 | Method 4a |

TABLE 29.1.b-continued
| Examples of Core 11a (Ex. 181-Ex. 195, Ex. 504-Ex. 559 and Ex. 594; continued on the following pages) | | | | | | | |
|---|---|---|---|---|---|---|---|
| No | $R^2$ | $R^5$ | FORMULA | MONOISOTOPIC MASS | Rt (purity at 220 nm) | $[M + H]^+$ found | LC-MS-Method |
| Ex. 514 | 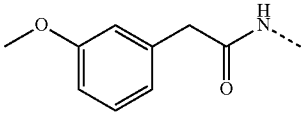 | 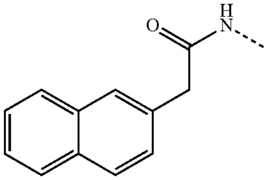 | C39H42N4O6 | 662.3 | 2.12 (98) | 663.3 | Method 4a |
| Ex. 515 | 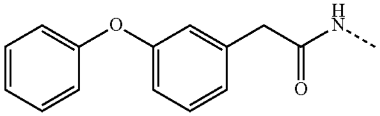 | $CH_3(CH_2)_8CONH$ | C42H54N4O6 | 710.4 | 2.60 (97) | 711.4 | Method 4a |
| Ex. 516 | 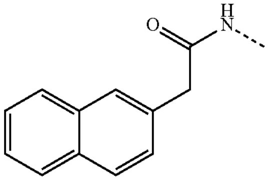 | 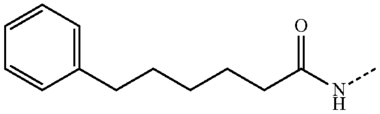 | C42H48N4O5 | 688.4 | 2.36 (97) | 689.4 | Method 4a |
| Ex. 517 | 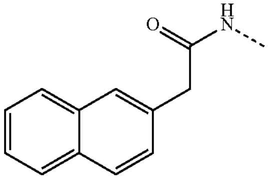 | 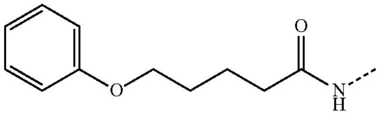 | C41H46N4O6 | 690.3 | 2.26 (98) | 691.4 | Method 4a |
| Ex. 518 | 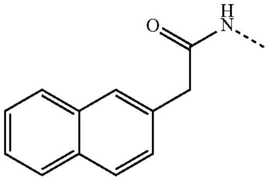 | 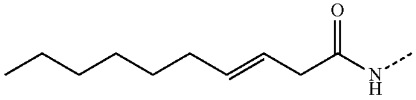 | C40H50N4O5 | 666.4 | 2.36 (92) | 667.5 | Method 10a |

TABLE 29.1.b-continued
Examples of Core 11a (Ex. 181-Ex. 195, Ex. 504-Ex. 559 and Ex. 594; continued on the following pages)
| No | $R^2$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 519 | 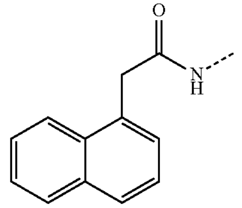 | $CH_3(CH_2)_8CONH$ | C40H52N4O5 | 668.4 | 2.53 (94) | 669.4 | Method 4a |
| Ex. 520 | 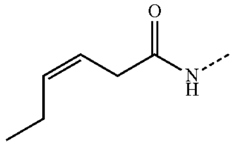 | 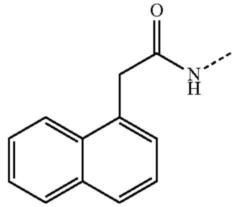 | C36H42N4O5 | 610.3 | 2.15 (98) | 611.3 | Method 4a |
| Ex. 521 | 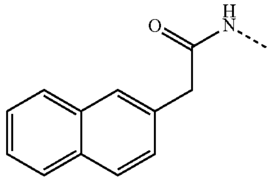 | 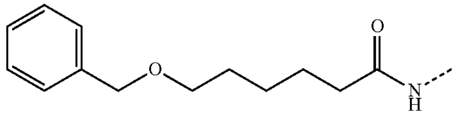 | C43H50N4O6 | 718.4 | 2.14 (92) | 719.5 | Method 10a |
| Ex. 522 | 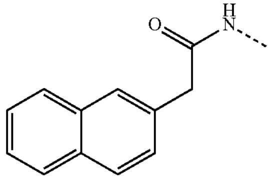 | 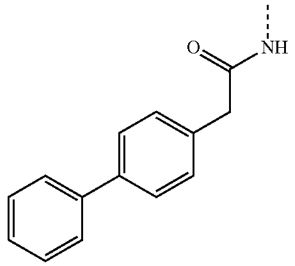 | C44H44N4O5 | 708.3 | 2.35 (98) | 709.4 | Method 4a |

TABLE 29.1.b-continued
Examples of Core 11a (Ex. 181-Ex. 195, Ex. 504-Ex. 559 and Ex. 594; continued on the following pages)
| No | $R^2$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 523 | 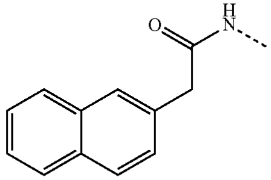 | 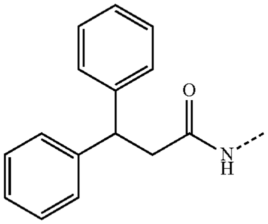 | C45H46N4O5 | 722.4 | 2.33 (97) | 723.4 | Method 4a |
| Ex. 524 | 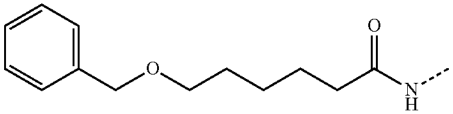 | 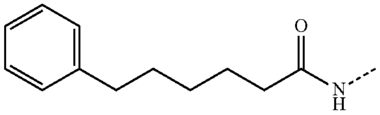 | C43H56N4O6 | 724.4 | 2.28 (95) | 725.5 | Method 10a |
| Ex. 525 | 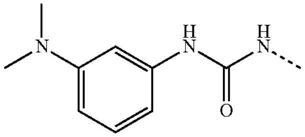 | 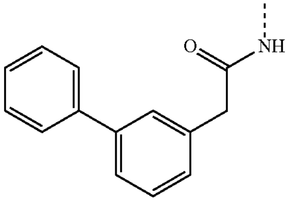 | C41H46N6O5 | 702.4 | 1.63 (97) | 703.4 | Method 10a |
| Ex. 526 | 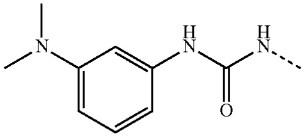 | 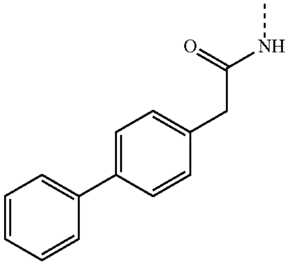 | C41H46N6O5 | 702.4 | 1.63 (97) | 703.4 | Method 10a |

TABLE 29.1.b-continued
Examples of Core 11a (Ex. 181-Ex. 195, Ex. 504-Ex. 559 and Ex. 594; continued on the following pages)
| No | $R^2$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 527 | 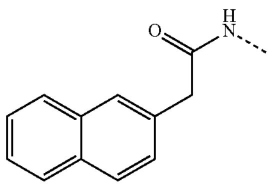 | 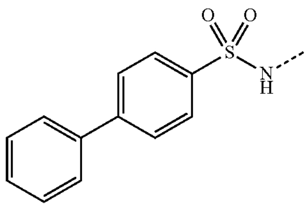 | C42H42N4O6S | 730.3 | 2.37 (95) | 731.3 | Method 4a |
| Ex. 528 | 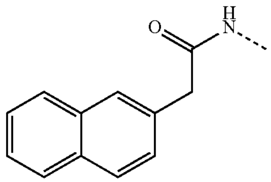 | 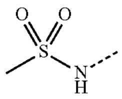 | C31H36N4O6S | 592.2 | 1.92 (95) | 593.2 | Method 4a |
| Ex . 529 | 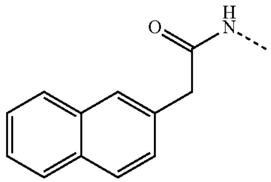 | 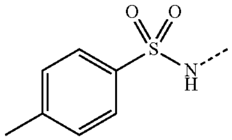 | C37H40N406S | 668.3 | 2.18 (96) | 669.3 | Method 4a |
| Ex. 530 | 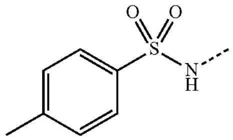 | 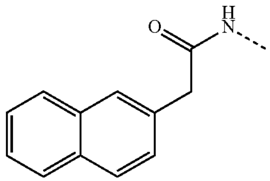 | C37H40N4O6S | 668.3 | 2.20 (91) | 669.3 | Method 4b |
| Ex. 531 | 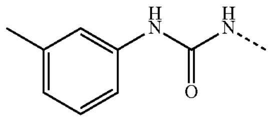 | 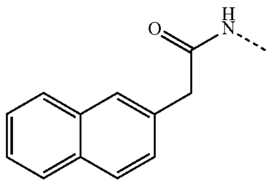 | C38H41N5O5 | 647.3 | 2.19 (98) | 648.3 | Method 4b |

TABLE 29.1.b-continued
| Examples of Core 11a (Ex. 181-Ex. 195, Ex. 504-Ex. 559 and Ex. 594; continued on the following pages) | | | | | | | |
|---|---|---|---|---|---|---|---|
| No | $R^2$ | $R^5$ | FORMULA | MONOISOTOPIC MASS | Rt (purity at 220 nm) | $[M + H]^+$ found | LC-MS-Method |
| Ex. 532 | 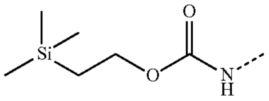 | 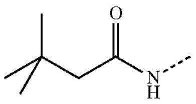 | C30H48N4O6Si | 588.3 | 2.27 (99) | 589.2 | Method 4b |
| Ex. 533 | $NH_2$ | 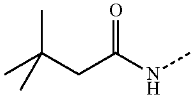 | C24H36N4O4 | 444.3 | 1.36 (99) | 445.3 | Method 4b |
| Ex. 534 | 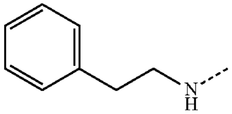 | 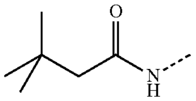 | C32H44N4O4 | 548.3 | 1.70 (86) | 549.4 | Method 4a |
| Ex. 535 | 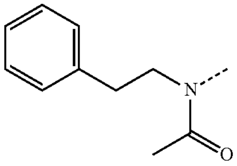 | 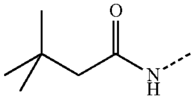 | C34H46N4O5 | 590.4 | 2.06 (95) | 591.4 | Method 4a |
| Ex. 536 | 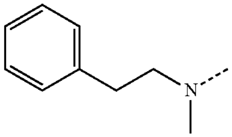 | 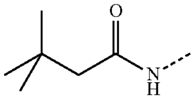 | C33H46N4O4 | 562.4 | 1.78 (97) | 563.4 | Method 4a |
| Ex. 537 | 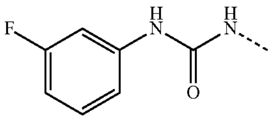 | 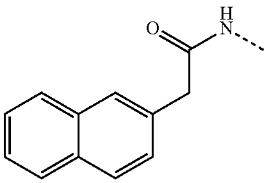 | C37H38FN5O5 | 651.3 | 2.18 (92) | 652.1 | Method 4a |

TABLE 29.1.b-continued
Examples of Core 11a (Ex. 181-Ex. 195, Ex. 504-Ex. 559 and Ex. 594; continued on the following pages)
| No | $R^2$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 538 | 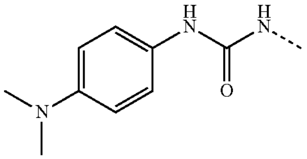 | 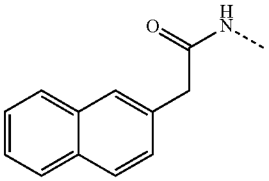 | C39H44N6O5 | 676.3 | 1.70 (98) | 677.3 | Method 4a |
| Ex. 539 | 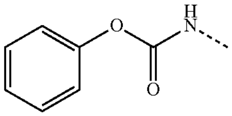 | 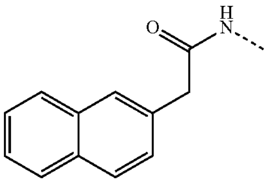 | C37H38N4O6 | 634.3 | 2.20 (97) | 635.3 | Method 4a |
| Ex. 540 | 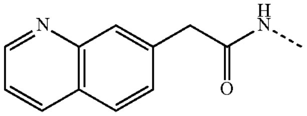 | 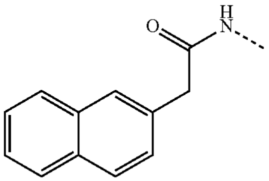 | C41H41N5O5 | 683.3 | 1.49 (98) | 684.1 | Method 10a |
| Ex . 541 | 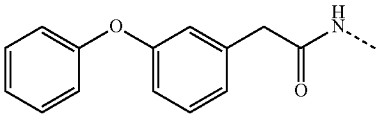 | 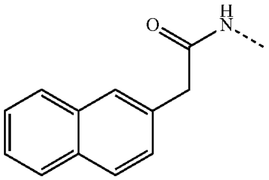 | C44H44N4O6 | 724.3 | 2.34 (96) | 725.4 | Method 4a |
| Ex. 542 | $CH_3(CH_2)_8CONH$ | 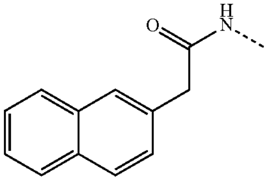 | C40H52N4O5 | 668.4 | 2.54 (99) | 669.4 | Method 4a |

TABLE 29.1.b-continued
Examples of Core 11a (Ex. 181-Ex. 195, Ex. 504-Ex. 559 and Ex. 594; continued on the following pages)
| No | $R^2$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 543 | $CH_3(CH_2)_8CONH$ | 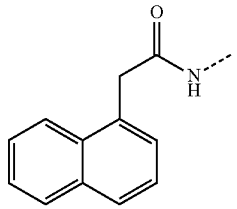 | C40H52N4O5 | 668.4 | 2.54 (95) | 669.4 | Method 4a |
| Ex . 544 | $CH_3(CH_2)_4CONH$ | 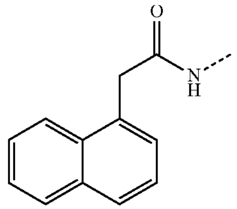 | C36H44N4O5 | 612.3 | 2.18 (98) | 613.3 | Method 4a |
| Ex. 545 | 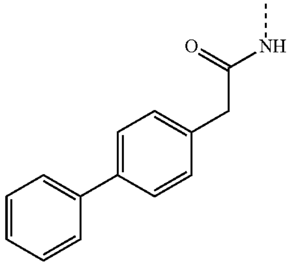 | 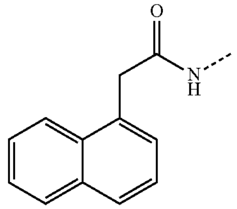 | C44H44N4O5 | 708.3 | 2.33 (97) | 709.4 | Method 4a |
| Ex. 546 | 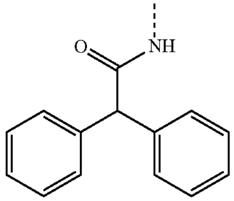 | 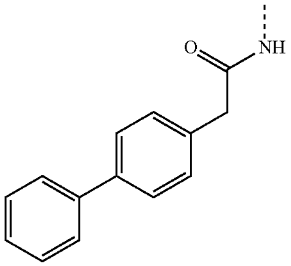 | C46H46N4O5 | 734.4 | 2.30 (99) | 735.4 | Method 10a |

TABLE 29.1.b-continued
Examples of Core 11a (Ex. 181-Ex. 195, Ex. 504-Ex. 559 and Ex. 594; continued on the following pages)
| No | $R^2$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 547 | 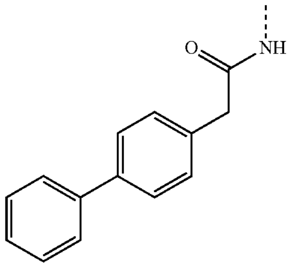 | 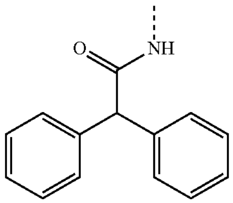 | C46H46N4O5 | 734.4 | 2.42 (99) | 735.4 | Method 4a |
| Ex. 548 | 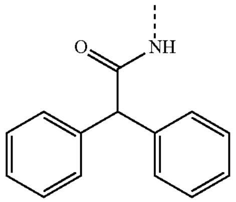 | $CH_3(CH_2)_8CONH$ | C42H54N405 | 694.4 | 2.61 (98) | 695.4 | Method 4a |
| Ex. 549 | 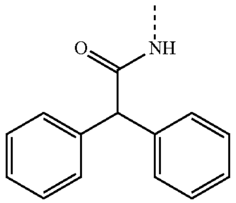 | 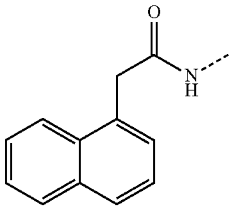 | C44H44N4O5 | 708.3 | 2.34 (97) | 709.4 | Method 4a |
| Ex. 550 | 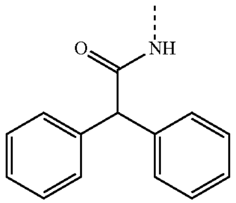 | $CH_3(CH_2)_8CONH$ | C43H56N4O5 | 708.4 | 2.58 (98) | 709.5 | Method 4a |

TABLE 29.1.b-continued
Examples of Core 11a (Ex. 181-Ex. 195, Ex. 504-Ex. 559 and Ex. 594; continued on the following pages)
| No | $R^2$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 551 | 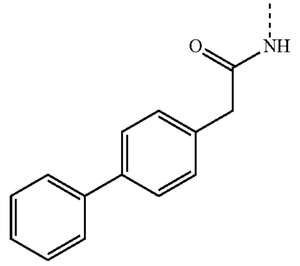 | 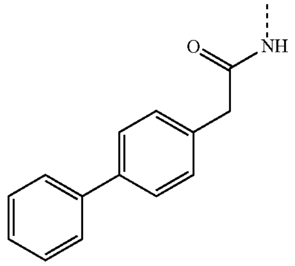 | C46H46N4O5 | 734.4 | 2.29 (95) | 735.4 | Method 10a |
| Ex. 552 | 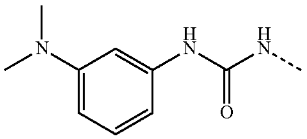 | 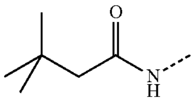 | C33H46N6O5 | 606.4 | 1.54 (99) | 607.3 | Method 4b |
| Ex. 553 | 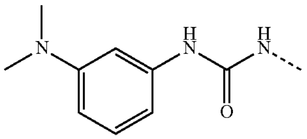 | 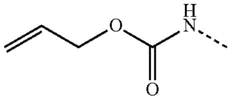 | C31H40N6O6 | 592.3 | 1.47 (99) | 593.3 | Method 4a |
| Ex. 554 | 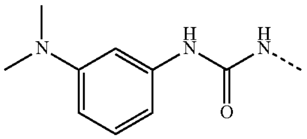 | $NH_2$ | C27H36N6O4 | 508.3 | 1.20 (95) | 509.2 | Method 4a |
| Ex . 555 | 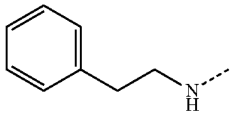 | 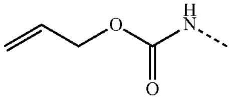 | C30H38N4O5 | 534.3 | 1.64 (93) | 535.3 | Method 4a |

TABLE 29.1.b-continued
Examples of Core 11a (Ex. 181-Ex. 195, Ex. 504-Ex. 559 and Ex. 594; continued on the following pages)
| No | $R^2$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 556 | 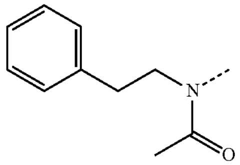 | 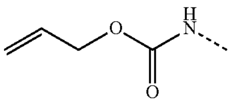 | C32H40N4O6 | 576.3 | 2.00 (93) | 577.3 | Method 4a |
| Ex. 557 | 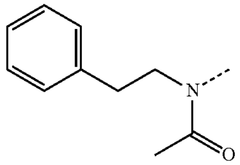 | 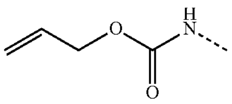 | C31H40N4O5 | 548.3 | 1.65 (92) | 549.4 | Method 4a |
| Ex. 558 | 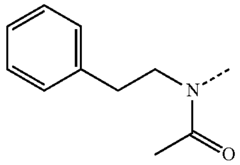 | $NH_2$ | C28H36N4O4 | 492.3 | 1.58 (94) | 493.2 | Method 4a |
| Ex. 559 | 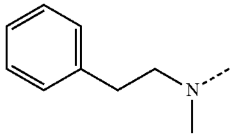 | $NH_2$ | C27H36N4O3 | 464.3 | 1.32 (86) | 465.3 | Method 4a |
| Ex. 594 | $NH_2$ | 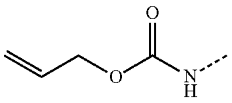 | C22H30N4O5 | 430.2 | 1.22 (92) | 431.3 | Method 4a |

TABLE 29.1.c
| Examples of Core 11a (Ex. 181-Ex. 195, Ex. 504-Ex. 559 and Ex. 594) | | |
|---|---|---|
| No | $R^2$ | $R^5$ |
| Ex. 181 | 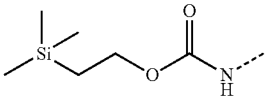 | 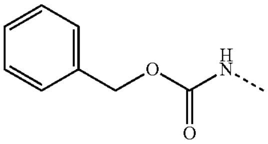 |
| Ex. 182 | $NH_2$ | 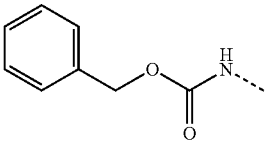 |
| Ex. 183 | 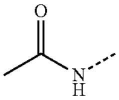 | 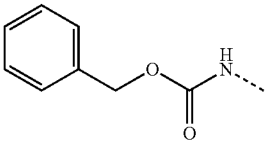 |
| Ex. 184 | 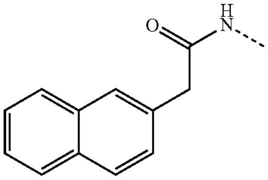 | 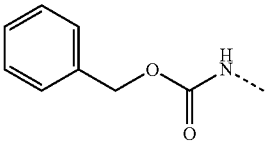 |
| Ex. 185 | 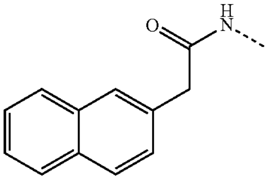 | $NH_2$ |
| Ex. 186 | 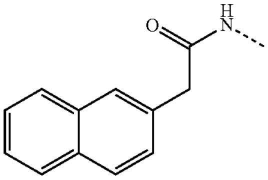 | 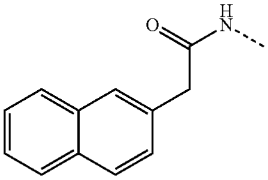 |
| Ex. 187 | 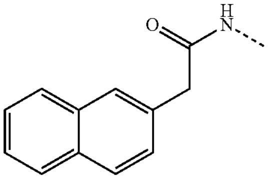 | 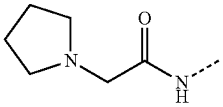 |
| Ex. 188 | 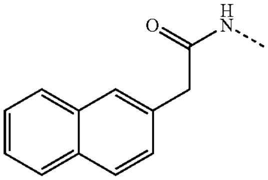 | 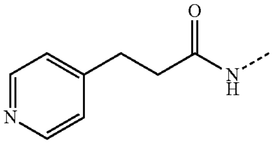 |

TABLE 29.1.c-continued
| Examples of Core 11a (Ex. 181-Ex. 195, Ex. 504-Ex. 559 and Ex. 594) | | |
|---|---|---|
| Ex. 189 | 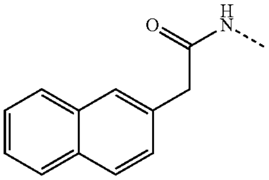 | 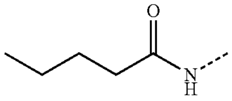 |
| Ex. 190 | $NH_2$ | 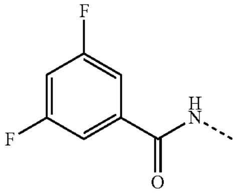 |
| Ex. 191 | 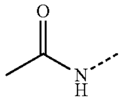 | 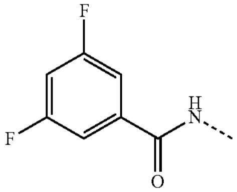 |
| Ex. 192 | 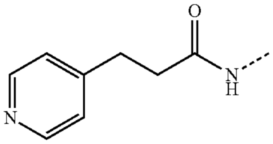 | 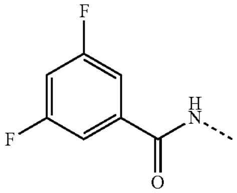 |
| Ex. 193 | 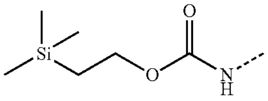 | 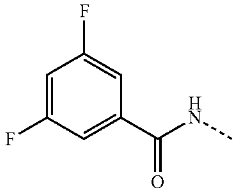 |
| Ex. 194 | 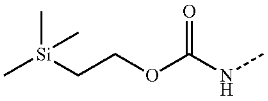 | $NH_2$ |
| Ex. 195 | 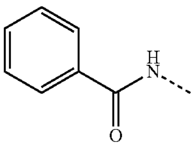 | 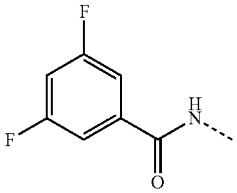 |
| Ex. 504 | 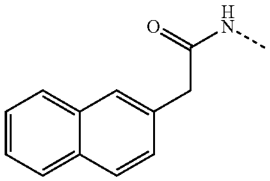 | $CH_3(CH_2)_8CONH$ |

TABLE 29.1.c-continued
| Examples of Core 11a (Ex. 181-Ex. 195, Ex. 504-Ex. 559 and Ex. 594) | | |
|---|---|---|
| Ex. 505 | 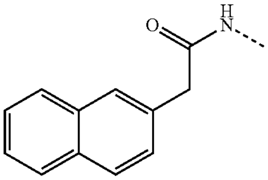 | 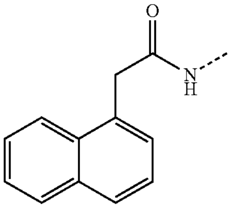 |
| Ex. 506 | 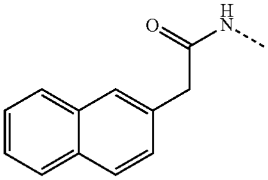 | 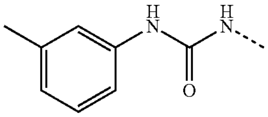 |
| Ex. 507 | 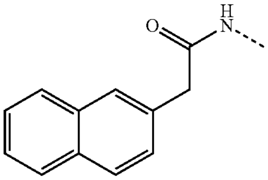 | 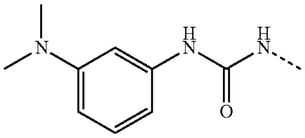 |
| Ex. 508 | 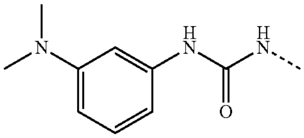 | 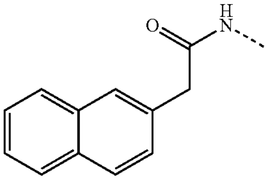 |
| Ex. 509 | 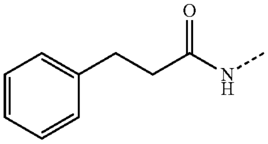 | $CH_3(CH_2)_8CONH$ |
| Ex. 510 | 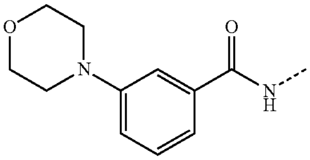 | $CH_3(CH_2)_8CONH$ |
| Ex. 511 | 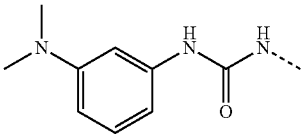 | $CH_3(CH_2)_8CONH$ |
| Ex. 512 | 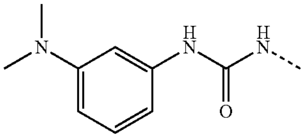 | 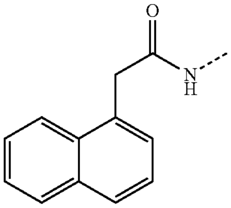 |

TABLE 29.1.c-continued
| Examples of Core 11a (Ex. 181-Ex. 195, Ex. 504-Ex. 559 and Ex. 594) | | |
|---|---|---|
| Ex. 513 | 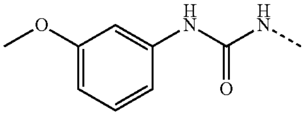 | 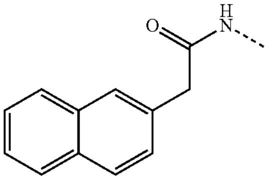 |
| Ex. 514 | 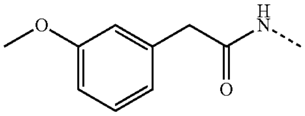 | 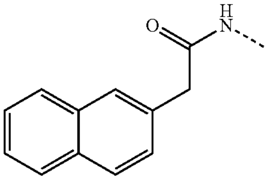 |
| Ex. 515 | 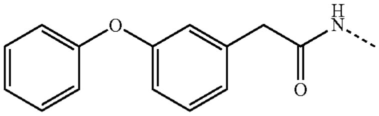 | $CH_3(CH_2)_8CONH$ |
| Ex. 516 | 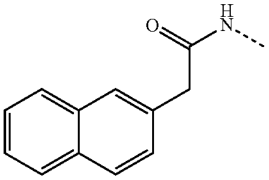 | 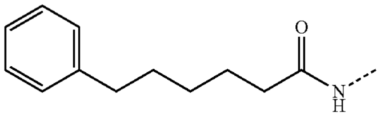 |
| Ex. 517 | 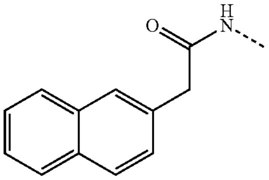 | 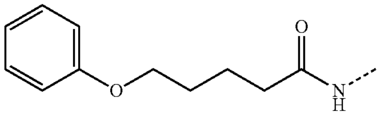 |
| Ex. 518 | 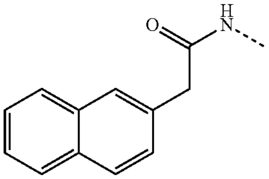 | 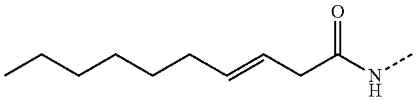 |
| Ex. 519 | 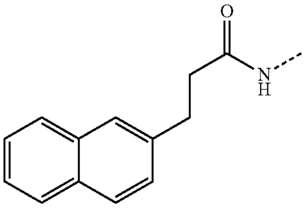 | $CH_3(CH_2)_8CONH$ |
| Ex. 520 | 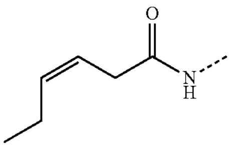 | 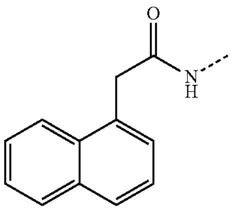 |

TABLE 29.1.c-continued
| Examples of Core 11a (Ex. 181-Ex. 195, Ex. 504-Ex. 559 and Ex. 594) | | |
|---|---|---|
| Ex. 521 | 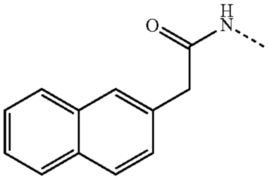 | 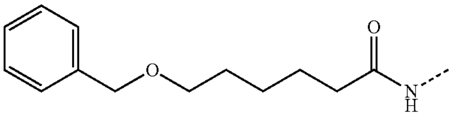 |
| Ex. 522 | 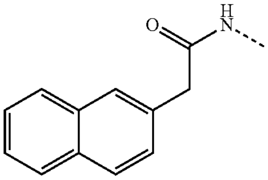 | 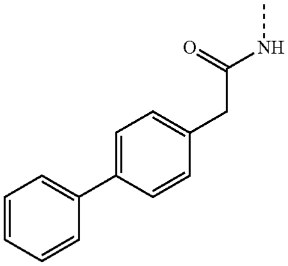 |
| Ex. 523 | 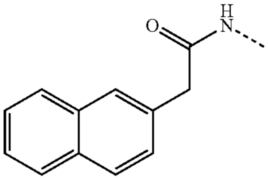 | 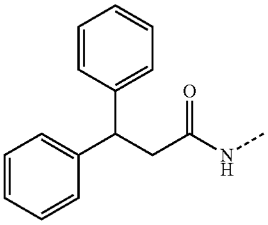 |
| Ex. 524 | 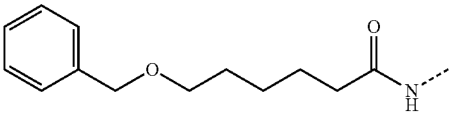 | 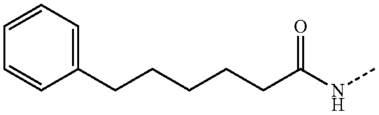 |
| Ex. 525 | 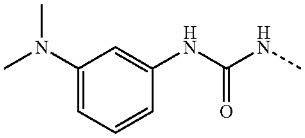 | 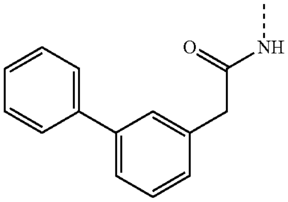 |
| Ex. 526 | 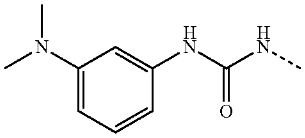 | 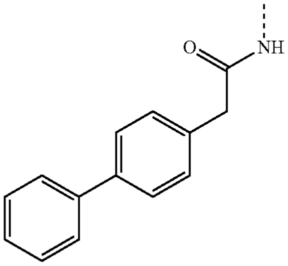 |
| Ex. 527 | 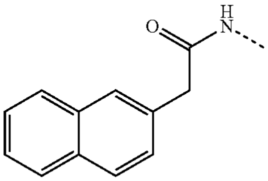 | 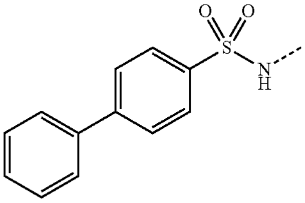 |

TABLE 29.1.c-continued
Examples of Core 11a (Ex. 181-Ex. 195, Ex. 504-Ex. 559 and Ex. 594)
| | | |
|---|---|---|
| Ex. 528 | 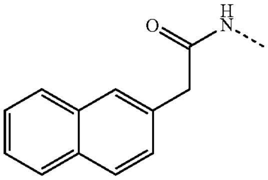 | 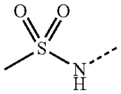 |
| Ex. 529 | 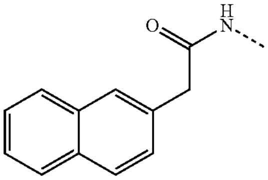 | 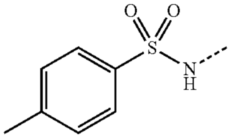 |
| Ex. 530 | 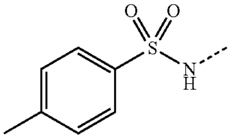 | 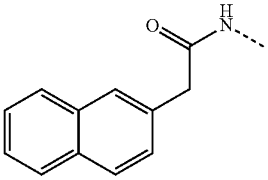 |
| Ex. 531 | 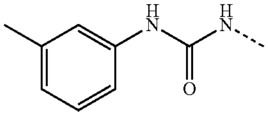 | 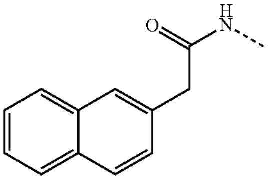 |
| Ex. 532 | 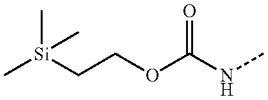 | 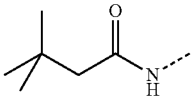 |
| Ex. 533 | $NH_2$ | 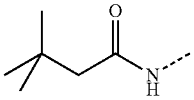 |
| Ex. 534 | 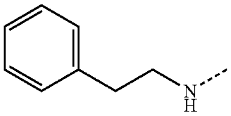 | 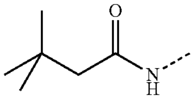 |
| Ex. 535 | 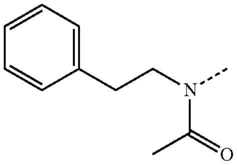 | 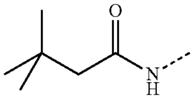 |
| Ex. 536 | 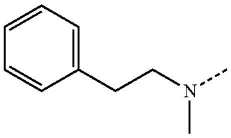 | 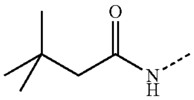 |

TABLE 29.1.c-continued
| Examples of Core 11a (Ex. 181-Ex. 195, Ex. 504-Ex. 559 and Ex. 594) | | |
|---|---|---|
| Ex. 537 | 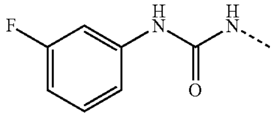 | 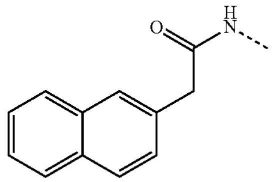 |
| Ex. 538 | 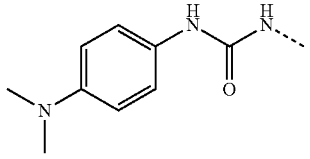 | 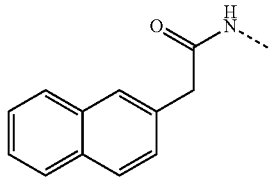 |
| Ex. 539 | 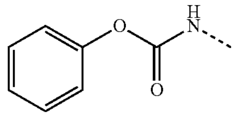 | 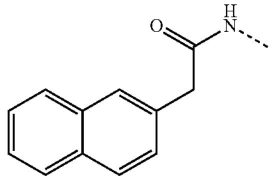 |
| Ex. 540 | 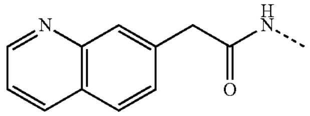 | 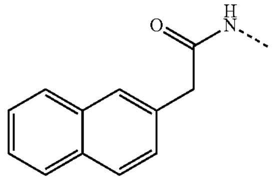 |
| Ex. 541 | 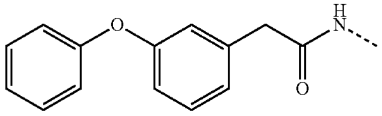 | 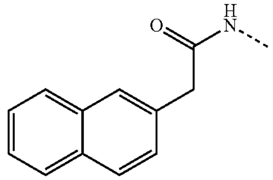 |
| Ex. 542 | $CH_3(CH_2)_8CONH$ | 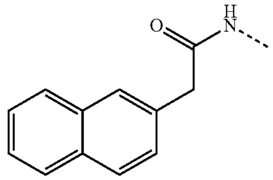 |
| Ex. 543 | $CH_3(CH_2)_8CONH$ | 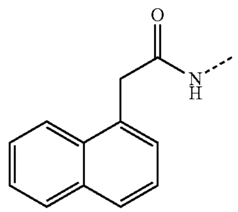 |
| Ex. 544 | $CH_3(CH_2)_4CONH$ | 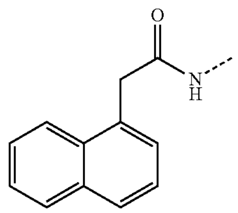 |

TABLE 29.1.c-continued
Examples of Core 11a (Ex. 181-Ex. 195, Ex. 504-Ex. 559 and Ex. 594)
| | | |
|---|---|---|
| Ex. 545 | 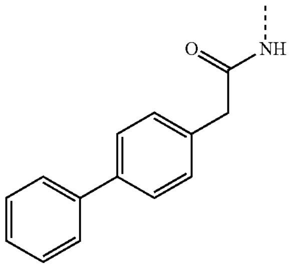 | 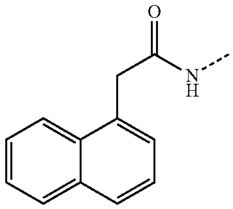 |
| Ex. 546 | 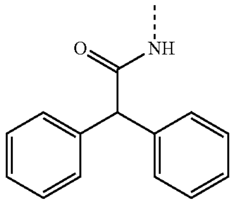 | 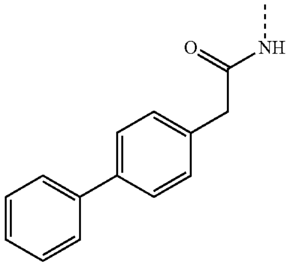 |
| Ex. 547 | 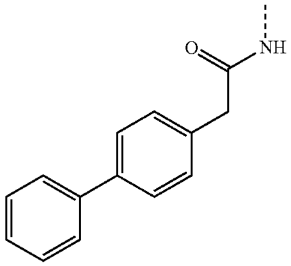 | 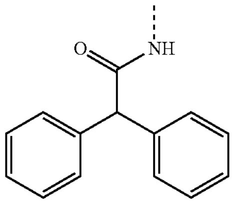 |
| Ex. 548 | 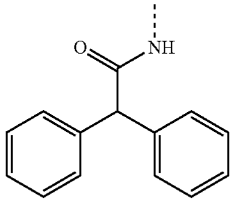 | $CH_3(CH_2)_8CONH$ |
| Ex. 549 | 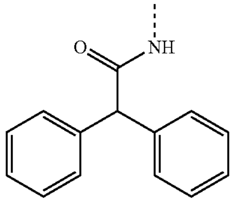 | 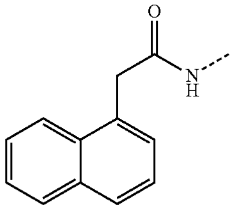 |
| Ex. 550 | 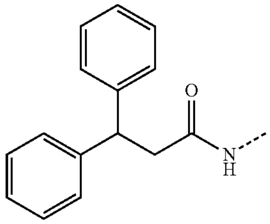 | $CH_3(CH_2)_8CONH$ |

TABLE 29.1.c-continued
Examples of Core 11a (Ex. 181-Ex. 195, Ex. 504-Ex. 559 and Ex. 594)
| | | |
|---|---|---|
| Ex. 551 | 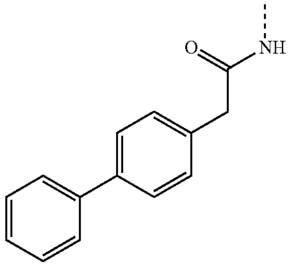 | 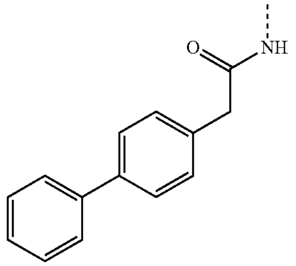 |
| Ex. 552 | 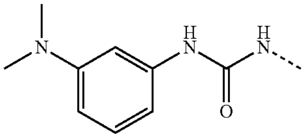 | 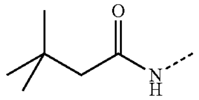 |
| Ex. 553 | 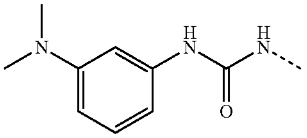 | 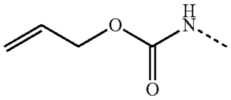 |
| Ex. 554 | 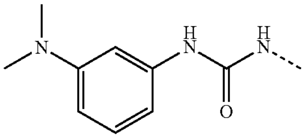 | $NH_2$ |
| Ex. 555 | 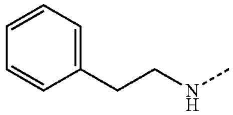 | 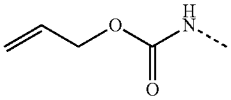 |
| Ex. 556 | 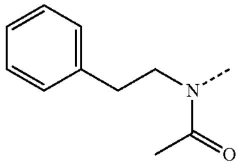 | 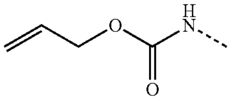 |
| Ex. 557 | 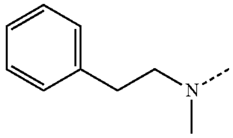 | 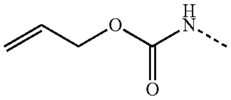 |
| Ex. 558 | 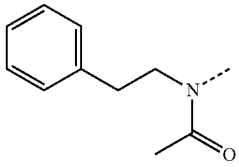 | $NH_2$ |
| Ex. 559 | 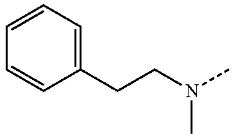 | $NH_2$ |

TABLE 29.1.c-continued

| Examples of Core 11a (Ex. 181-Ex. 195, Ex. 504-Ex. 559 and Ex. 594) | | |
|---|---|---|
| Ex. 594 | $NH_2$ | 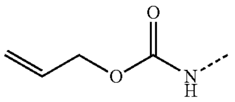 |

| No | IUPAC name |
|---|---|
| Ex. 181 | benzyl N-[(4S,6S,10S)-14-methyl-9,15-dioxo-6-({[2- (trimethylsilyl)ethoxy]carbonyl}amino)-2-oxa-8,14-diazatricyclo[14.3.1.0$^{4,8}$]icosa-1(20),16,18-trien-10-yl]carbamate |
| Ex. 182 | benzyl N-[(4S,6S,10S)-6-amino-14-methyl-9,15-dioxo-2-oxa-8,14- diazatricyclo[14.3.1.0$^{4,8}$]icosa-1(20),16,18-trien-10-yl]carbamate |
| Ex. 183 | benzyl N-[(4S,6S,10S)-6-(acetylamino)-14-methyl-9,15-dioxo-2-oxa- 8,14-diazatricyclo[14.3.1.0$^{4,8}$]icosa-1(20),16,18-trien-<br>10-yl]carbamate |
| Ex. 184 | benzyl N-[(4S,6S,10S)-14-methyl-6-{[2-(2-naphthyl)acetyl]amino}- 9,15-dioxo-2-oxa-8,14-diazatricyclo[14.3.1.0$^{4,8}$]icosa-1(20),16,18-trien-10-yl]carbamate |
| Ex. 185 | N-[(4S,6S,10S)-10-amino-14-methyl-9,15-dioxo-2-oxa-8,14- diazatricyclo[14.3.1.0$^{4,8}$]icosa-1(20),16,18-trien-6-yl]-2-(2-naphthyl)acetamide |
| Ex. 186 | N-[(4S,6S,10S)-14-methyl-10-{[2-(2-naphthyl)acetyl]amino}-9,15- dioxo-2-oxa-8,14-diazatricyclo[14.3.1.0$^{4,8}$]icosa-1(20),16,18-trien-6-yl]-2-(2-naphthyl)acetamide |
| Ex. 187 | N-[(4S,6S,10S)-14-methyl-9,15-dioxo-10-{[2-(1-pyrrolidinyl)- acetyl]amino}-2-oxa-8,14-diazatricyclo[14.3.1.0$^{4,8}$]icosa-1(20),16,18-trien-6-yl]-2-(2-naphthyl)acetamide |
| Ex. 188 | N-[(4S,6S,10S)-14-methyl-6-{[2-(2-naphthyl)acetyl]amino}-9,15-dioxo- 2-oxa-8,14-diazatricyclo[14.3.1.0$^{4,8}$]icosa-1(20),16,18-trien-10-yl]-3-(4-pyridinyl)propanamide |
| Ex. 189 | N-[(4S,6S,10S)-14-methyl-6-{[2-(2-naphthyl)acetyl]amino}-9,15-dioxo- 2-oxa-8,14-diazatricyclo[14.3.1.0$^{4,8}$]icosa-1(20),16,18-trien-10-yl]pentanamide |
| Ex. 190 | N-[(4S,6S,10S)-6-amino-14-methyl-9,15-dioxo-2-oxa-8,14- diazatricyclo[14.3.1.0$^{4,8}$]icosa-1(20),16,18-trien-10-yl]-3,5-difluorobenzamide |
| Ex. 191 | N-[(4S,6S,10S)-6-(acetylamino)-14-methyl-9,15-dioxo-2-oxa-8,14- diazatricyclo[14.3.1.0$^{4,8}$]icosa-1(20),16,18-trien-10-yl]-3,5-difluorobenzamide |
| Ex. 192 | 3,5-difluoro-N-[(4S,6S,10S)-14-methyl-9,15-dioxo-6-{[3-(4- pyridinyl)propanoyl]amino}-2-oxa-8,14-diazatricyclo[14.3.1.0$^{4,8}$]icosa-1(20),16,18-trien-10-yl]benzamide |
| Ex. 193 | 2-(trimethylsilyl)ethyl N-[(4S,6S,10S)-10-[(3,5- difluorobenzoyl)amino]-14-methyl-9,15-dioxo-2-oxa-8,14-diazatricyclo[14.3.1.0$^{4,8}$]icosa-1(20),16,18-trien-6-yl]carbamate |
| Ex. 194 | 2-(trimethylsilyl)ethyl N-[(4S,6S,10S)-10-amino-14-methyl-9,15- dioxo-2-oxa-8,14-diazatricyclo[14.3.1.0$^{4,8}$]icosa-1(20),16,18-trien-6-yl]carbamate |
| Ex. 195 | N-[(4S,6S,10S)-6-(benzoylamino)-14-methyl-9,15-dioxo-2-oxa-8,14- diazatricyclo[14.3.1.0$^{4,8}$]icosa-1(20),16,18-trien-10-yl]-3,5-difluorobenzamide |
| Ex. 504 | N-[(4S,6S,10S)-14-methyl-6-{[2-(2-naphthyl)acetyl]amino}-9,15-dioxo- 2-oxa-8,14-diazatricyclo[14.3.1.0$^{4,8}$]icosa-1(20),16,18-trien-10-yl]decanamide |
| Ex. 505 | N-[(4S,6S,10S)-14-methyl-6-{[2-(2-naphthyl)acetyl]amino}-9,15-dioxo- 2-oxa-8,14-diazatricyclo[14.3.1.0$^{4,8}$]icosa-1(20),16,18-trien-10-yl]-2-(1-naphthyl)acetamide |
| Ex. 506 | N-[(4S,6S,10S)-14-methyl-9,15-dioxo-10-[(3-toluidinocarbonyl)amino]- 2-oxa-8,14-diazatricyclo[14.3.1.0$^{4,8}$]icosa-1(20),16,18-trien-6-yl]-2-(2-naphthyl)acetamide |
| Ex. 507 | N-[(4S,6S,10S)-10-({[3-(dimethylamino)anilino]carbonyl}amino)-14- methyl-9,15-dioxo-2-oxa-8,14-diazatricyclo[14.3.1.0$^{4,8}$]icosa-1(20),16,18-trien-6-yl]-2-(2-naphthyl)acetamide |
| Ex. 508 | N-[(4S,6S,10S)-6-({[3-(dimethylamino)anilino]carbonyl}amino)-14- methyl-9,15-dioxo-2-oxa-8,14-diazatricyclo[14.3.1.0$^{4,8}$]icosa-1(20),16,18-trien-10-yl]-2-(2-naphthyl)acetamide |
| Ex. 509 | N-[(4S,6S,10S)-14-methyl-9,15-dioxo-6-[(3-phenylpropanoyl)amino]-2- oxa-8,14-diazatricyclo[14.3.1.0$^{4,8}$]icosa-1(20),16,18-trien-10-yl]decanamide |
| Ex. 510 | N-[(4S,6S,10S)-14-methyl-6-[(3-morpholinobenzoyl)amino]-9,15-dioxo- 2-oxa-8,14-diazatricyclo[14.3.1.0$^{4,8}$]icosa-1(20),16,18-trien-10-yl]decanamide |
| Ex. 511 | N-[(4S,6S,10S)-6-({[3-(dimethylamino)anilino]carbonyl}amino)-14- methyl-9,15-dioxo-2-oxa-8,14-diazatricyclo[14.3.1.0$^{4,8}$]icosa-1(20),16,18-trien-10-yl]decanamide |
| Ex. 512 | N-[(4S,6S,10S)-6-({[3-(dimethylamino)anilino]carbonyl}amino)-14- methyl-9,15-dioxo-2-oxa-8,14-diazatricyclo[14.3.1.0$^{4,8}$]icosa-1(20),16,18-trien-10-yl]-2-(1-naphthyl)acetamide |
| Ex. 513 | N-[(4S,6S,10S)-6-{[(3-methoxyanilino)carbonyl]amino}-14-methyl-9,15- dioxo-2-oxa-8,14-diazatricyclo[14.3.1.0$^{4,8}$]icosa-1(20),16,18-trien-10-yl]-2-(2-naphthyl)acetamide |
| Ex. 514 | 2-(3-methoxyphenyl)-N-[(4S,6S,10S)-14-methyl-10-{[2-(2- naphthyl)acetyl]amino}-9,15-dioxo-2-oxa-8,14-diazatricyclo[14.3.1.0$^{4,8}$]icosa-1(20),16,18-trien-6-yl]acetamide |
| Ex. 515 | N-[(4S,6S,10S)-14-methyl-9,15-dioxo-6-{[2-(3- phenoxyphenyl)acetyl]amino}-2-oxa-8,14-diazatricyclo[14.3.1.0$^{4,8}$]icosa-1(20),16,18-trien-10-yl]decanamide |
| Ex. 516 | N-[(4S,6S,10S)-14-methyl-6-([2-(2-naphthyl)acetyl]amino}-9,15-dioxo- 2-oxa-8,14-diazatricyclo[14.3.1.0$^{4,8}$]icosa-1(20),16,18-trien-10-yl]-6-phenylhexanamide |
| Ex. 517 | N-[(4S,6S,10S)-14-methyl-6-{[2-(2-naphthyl)acetyl]amino}-9,15-dioxo- 2-oxa-8,14-diazatricyclo[14.3.1.0$^{4,8}$]icosa-1(20),16,18-trien-10-yl]-5-phenoxypentanamide |
| Ex. 518 | (E)-N-[(4S,6S,10S)-14-methyl-6-{[2-(2-naphthyl)acetyl]amino}-9,15- dioxo-2-oxa-8,14-diazatricyclo[14.3.1.0$^{4,8}$]icosa-1(20),16,18-trien-10-yl]-3-decenamide |
| Ex. 519 | N-[(4S,6S,10S)-14-methyl-6-{[2-(1-naphthyl)acetyl]amino}-9,15-dioxo- 2-oxa-8,14-diazatricyclo[14.3.1.0$^{4,8}$]icosa-1(20),16,18-trien-10-yl]decanamide |
| Ex. 520 | (Z)-N-[(4S,6S,10S)-14-methyl-10-{[2-(1-naphthyl)acetyl]amino}-9,15- dioxo-2-oxa-8,14-diazatricyclo[14.3.1.0$^{4,8}$]icosa-1(20),16,18-trien-6-yl]-3-hexenamide |
| Ex. 521 | 6-(benzyloxy)-N-[(4S,6S,10S)-14-methyl-6-{[2-(2- naphthyl)acetyl]amino}-9,15-dioxo-2-oxa-8,14-diazatricyclo[14.3.1.0$^{4,8}$]icosa-1(20),16,18-trien-10-yl]hexanamide |
| Ex. 522 | 2-[1,1'-biphenyl]-4-yl-N-[(4S,6S,10S)-14-methyl-6-{[2-(2- naphthyl)acetyl]amino}-9,15-dioxo-2-oxa-8,14-diazatricyclo[14.3.1.0$^{4,8}$]icosa-1(20),16,18-trien-10-yl]acetamide |

TABLE 29.1.c-continued

| Examples of Core 11a (Ex. 181-Ex. 195, Ex. 504-Ex. 559 and Ex. 594) | |
|---|---|
| Ex. 523 | N-[(4S,6S,10S)-14-methyl-6-{[2-(2-naphthyl)acetyl]amino}-9,15-dioxo- 2-oxa-8,14-diazatricyclo[14.3.1.0$^{4,8}$]icosa-1(20),16,18-trien-10-yl]-3,3-diphenylpropanamide |
| Ex. 524 | 6-(benzyloxy)-N-[(4S,6S,10S)-14-methyl-9,15-dioxo-10-[(6- phenylhexanoyl)amino]-2-oxa-8,14-diazatricyclo[14.3.1.0$^{4,8}$]icosa-1(20),16,18-trien-6-yl]hexanamide |
| Ex. 525 | 2-[1,1'-biphenyl]-3-yl-N-[(4S,6S,10S)-6-({[3- (dimethylamino)anilino]carbonyl}amino)-14-methyl-9,15-dioxo-2-oxa-8,14-diazatricyclo[14.3.1.0$^{4,8}$]icosa-1(20),16,18-trien-10-yl]acetamide |
| Ex. 526 | 2-[1,1'-biphenyl]-4-yl-N-[(4S,6S,10S)-6-({[3- (dimethylamino)anilino]carbonyl}amino)-14-methyl-9,15-dioxo-2-oxa-8,14-diazatricyclo[14.3.1.0$^{4,8}$]icosa-1(20),16,18-trien-10-yl]acetamide |
| Ex. 527 | N-[(4S,6S,10S)-10-[([1,1'-biphenyl]-4-ylsulfonyl)amino]-14-methyl- 9,15-dioxo-2-oxa-8,14-diazatricyclo[14.3.1.0$^{4,8}$]icosa-1(20),16,18-trien-6-yl]-2-(2-naphthyl)acetamide |
| Ex. 528 | N-[(4S,6S,10S)-14-methyl-10-[(methylsulfonyl)amino]-9,15-dioxo-2- oxa-8,14-diazatricyclo[14.3.1.0$^{4,8}$]icosa-1(20),16,18-trien-6-yl]-2-(2-naphthyl)acetamide |
| Ex. 529 | N-[(4S,6S,10S)-14-methyl-10-{[(4-methylphenyl)sulfonyl]amino}-9,15- dioxo-2-oxa-8,14-diazatricyclo[14.3.1.0$^{4,8}$]icosa-1(20),16,18-trien-6-yl]-2-(2-naphthyl)acetamide |
| Ex. 530 | N-[(4S,6S,10S)-14-methyl-6-{[(4-methylphenyl)sulfonyl]amino}-9,15- dioxo-2-oxa-8,14-diazatricyclo[14.3.1.0$^{4,8}$]icosa-1(20),16,18-trien-10-yl]-2-(2-naphthyl)acetamide |
| Ex. 531 | N-[(4S,6S,10S)-14-methyl-9,15-dioxo-6-[(3-toluidinocarbonyl)amino]- 2-oxa-8,14-diazatricyclo[14.3.1.0$^{4,8}$]icosa-1(20),16,18-trien-10-yl]-2-(2-naphthyl)acetamide |
| Ex. 532 | 2-(trimethylsilyl)ethyl N-[(4S,6S,10S)-10-[(3,3- dimethylbutanoyl)amino]-14-methyl-9,15-dioxo-2-oxa-8,14-diazatricyclo[14.3.1.0$^{4,8}$]icosa-1(20),16,18-trien-6-yl]carbamate |
| Ex. 533 | N-[(4S,6S,10S)-6-amino-14-methyl-9,15-dioxo-2-oxa-8,14- diazatricyclo[14.3.1.0$^{4,8}$]icosa-1(20),16,18-trien-10-yl]-3,3-dimethylbutanamide |
| Ex. 534 | 3,3-dimethyl-N-[(4S,6S,10S)-14-methyl-9,15-dioxo-6-(phenethylamino)- 2-oxa-8,14-diazatricyclo[14.3.1.0$^{4,8}$]icosa-1(20),16,18-trien-10-yl]butanamide |
| Ex. 535 | N-[(4S,6S,10S)-6-[acetyl(phenethyl)amino]-14-methyl-9,15-dioxo-2- oxa-8,14-diazatricyclo[14.3.1.0$^{4,8}$]icosa-1(20),16,18-trien-10-yl]-3,3-dimethylbutanamide |
| Ex. 536 | 3,3-dimethyl-N-[(4S,6S,10S)-14-methyl-6-[methyl(phenethyl)amino]- 9,15-dioxo-2-oxa-8,14-diazatricyclo[14.3.1.0$^{4,8}$]icosa-1(20),16,18-trien-10-yl]butanamide |
| Ex. 537 | N-[(4S,6S,10S)-6-{[(3-fluoroanilino)carbonyl]amino}-14-methyl-9,15- dioxo-2-oxa-8,14-diazatricyclo[14.3.1.0$^{4,8}$]icosa-1(20),16,18-trien-10-yl]-2-(2-naphthyl)acetamide |
| Ex. 538 | N-[(4S,6S,10S)-6-({[4-(dimethylamino)anilino]carbonyl}amino)-14- methyl-9,15-dioxo-2-oxa-8,14-diazatricyclo[14.3.1.0$^{4,8}$]icosa-1(20),16,18-trien-10-yl]-2-(2-naphthyl)acetamide |
| Ex. 539 | phenyl N-[(4S,6S,10S)-14-methyl-10-{[2-(2-naphthyl)acetyl]amino}- 9,15-dioxo-2-oxa-8,14-diazatricyclo[14.3.1.0$^{4,8}$]icosa-1(20),16,18-trien-6-yl]carbamate |
| Ex. 540 | N-[(4S,6S,10S)-14-methyl-9,15-dioxo-6-{[2-(7- quinolinyl)acetyl]amino}-2-oxa-8,14-diazatricyclo[14.3.1.0$^{4,8}$]icosa-1(20),16,18-trien-10-yl]-2-(2-naphthyl)acetamide |
| Ex. 541 | N-[(4S,6S,10S)-14-methyl-9,15-dioxo-6-{[2-(3- phenoxyphenyl)acetyl]amino}-2-oxa-8,14-diazatricyclo[14.3.1.0$^{4,8}$]icosa-1(20),16,18-trien-10-yl]-2-(2-naphthyl)acetamide |
| Ex. 542 | N-[(4S,6S,10S)-14-methyl-10-{[2-(2-naphthyl)acetyl]amino}-9,15- dioxo-2-oxa-8,14-diazatricyclo[14.3.1.0$^{4,8}$]icosa-1(20),16,18-trien-6-yl]decanamide |
| Ex. 543 | N-[(4S,6S,10S)-14-methyl-10-{[2-(1-naphthyl)acetyl]amino}-9,15- dioxo-2-oxa-8,14-diazatricyclo[14.3.1.0$^{4,8}$]icosa-1(20),16,18-trien-6-yl]decanamide |
| Ex. 544 | N-[(4S,6S,10S)-14-methyl-10-{[2-(1-naphthyl)acetyl]amino}-9,15- dioxo-2-oxa-8,14-diazatricyclo[14.3.1.0$^{4,8}$]icosa-1(20),16,18-trien-6-yl]hexanamide |
| Ex. 545 | 2-[1,1'-biphenyl]-4-yl-N-[(4S,6S,10S)-14-methyl-10-{[2-(1- naphthyl)acetyl]amino}-9,15-dioxo-2-oxa-8,14-diazatricyclo[14.3.1.0$^{4,8}$]icosa-1(20),16,18-trien-6-yl]acetamide |
| Ex. 546 | N-[(4S,6S,10S)-10-[(2-[1,1'-biphenyl]-4-ylacetyl)amino]-14-methyl- 9,15-dioxo-2-oxa-8,14-diazatricyclo[14.3.1.0$^{4,8}$]icosa-1(20),16,18-trien-6-yl]-2,2-diphenylacetamide |
| Ex. 547 | N-[(4S,6S,10S)-6-[(2-[1,1'-biphenyl]-4-ylacetyl)amino]-14-methyl- 9,15-dioxo-2-oxa-8,14-diazatricyclo[14.3.1.0$^{4,8}$]icosa-1(20),16,18-trien-10-yl]-2,2-diphenylacetamide |
| Ex. 548 | N-[(4S,6S,10S)-6-[(2,2-diphenylacetyl)amino]-14-methyl-9,15-dioxo-2- oxa-8,14-diazatricyclo[14.3.1.0$^{4,8}$]icosa-1(20),16,18-trien-10-yl]decanamide |
| Ex. 549 | N-[(4S,6S,10S)-14-methyl-10-{[2-(1-naphthyl)acetyl]amino}-9,15- dioxo-2-oxa-8,14-diazatricyclo[14.3.1.0$^{4,8}$]icosa-1(20),16,18-trien-6-yl]-2,2-diphenylacetamide |
| Ex. 550 | N-[(4S,6S,10S)-6-[(3,3-diphenylpropanoyl)amino]-14-methyl-9,15- dioxo-2-oxa-8,14-diazatricyclo[14.3.1.0$^{4,8}$]icosa-1(20),16,18-trien-10-yl]decanamide |
| Ex. 551 | 2-[1,1'-biphenyl]-4-yl-N-[(4S,6S,10S)-10-[(2-[1,1'-biphenyl]-4- ylacetyl)amino]-14-methyl-9,15-dioxo-2-oxa-8,14-diazatricyclo[14.3.1.0$^{4,8}$]icosa-1(20),16,18-trien-6-yl]acetamide |
| Ex. 552 | N-[(4S,6S,10S)-6-({[3-(dimethylamino)anilino]carbonyl}amino)-14- methyl-9,15-dioxo-2-oxa-8,14-diazatricyclo[14.3.1.0$^{4,8}$]icosa-1(20),16,18-trien-10-yl]-3,3-dimethylbutanamide |
| Ex. 553 | allyl N-[(4S,6S,10S)-6-({[3-(dimethylamino)anilino]carbonyl}amino)- 14-methyl-9,15-dioxo-2-oxa-8,14-diazatricyclo[14.3.1.0$^{4,8}$]icosa-1(20),16,18-trien-10-yl]carbamate |
| Ex. 554 | N-[(4S,6S,10S)-10-amino-14-methyl-9,15-dioxo-2-oxa-8,14- diazatricyclo[14.3.1.0$^{4,8}$]icosa-1(20),16,18-trien-6-yl]-N'-[3-(dimethylamino)phenyl]urea |
| Ex. 555 | allyl N-[(4S,6S,10S)-14-methyl-9,15-dioxo-6-(phenethylamino)-2-oxa- 8,14-diazatricyclo[14.3.1.0$^{4,8}$]icosa-1(20),16,18-trien-10-yl]carbamate |
| Ex. 556 | allyl N-[(4S,6S,10S)-6-[acetyl(phenethyl)amino]-14-methyl-9,15- dioxo-2-oxa-8,14-diazatricyclo[14.3.1.0$^{4,8}$]icosa-1(20),16,18-trien-10-yl]carbamate |
| Ex. 557 | allyl N-[(4S,6S,10S)-14-methyl-6-[methyl(phenethyl)amino]-9,15- dioxo-2-oxa-8,14-diazatricyclo[14.3.1.0$^{4,8}$]icosa-1(20),16,18-trien-10-yl]carbamate |
| Ex. 558 | N-[(4S,6S,10S)-10-amino-14-methyl-9,15-dioxo-2-oxa-8,14- diazatricyclo[14.3.1.0$^{4,8}$]icosa-1(20),16,18-trien-6-yl]-N-phenethylacetamide |
| Ex. 559 | (4S,6S,10S)-10-amino-14-methyl-6-[methyl(phenethyl)amino]-2-oxa- 8,14-diazatricyclo[14.3.1.0$^{4,8}$]icosa-1(20),16,18-triene-9,15-dione |
| Ex. 594 | allyl N-[(4S,6S,10S)-6-amino-14-methyl-9,15-dioxo-2-oxa-8,14- diazatricyclo[14.3.1.0$^{4,8}$]icosa-1(20),16,18-trien-10-yl]carbamate |

TABLE 29.2.a

Examples of Core 11b (Ex. 560-Ex. 566)

| No | $R^2$ | $R^5$ | Starting material | General Procedure | Reagent | Purification Method | Yield (isolated salt) |
|---|---|---|---|---|---|---|---|
| Ex. 560-Ex. 561: cf. experimental description | | | | | | | |
| Ex. 562 | 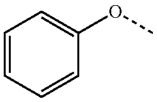 | 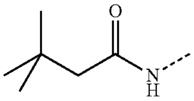 | Ex. 561 | L.1.1 | 3,3-dimethylbutanoyl chloride (1.5 equiv.) pyridine (5 equiv.) | FC ($CH_2Cl_2$/MeOH) | 85% |
| Ex. 563 | 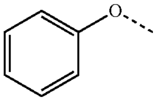 | 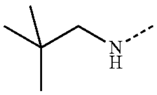 | Ex. 561 | M.2 | Pivalaldehyde (1.0 equiv.) | FC ($CH_2Cl_2$/MeOH) | 30% |
| Ex. 564 | 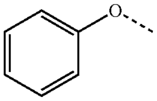 | 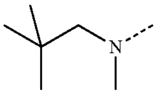 | Ex. 563 | M.3 | aq. formaldehyde soln | FC ($CH_2Cl_2$/MeOH) | 93% |
| Ex. 565 | 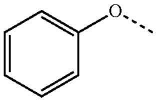 | 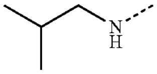 | Ex. 561 | M.2 | isobutyraldehyde | FC ($CH_2Cl_2$/MeOH) | 63% |
| Ex. 566 | 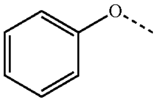 | 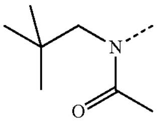 | Ex. 563 | L.1.1 | acetic anhydride (1.2 mL), pyridine (1.1 mL), $CH_2Cl_2$ (1.2 mL) | crude product | 95% |

TABLE 29.2.b

Examples of Core 11b (Ex. 560-Ex. 566)

| No | $R^2$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 560-Ex. 561: cf. experimental description | | | | | | | |
| Ex. 562 | 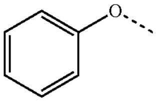 | 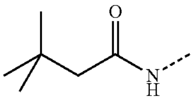 | C30H39N3O5 | 521.3 | 2.21 (97) | 522.4 | Method 4a |
| Ex. 563 | 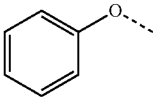 | 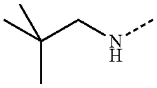 | C29H39N3O4 | 493.3 | 1.80 (98) | 494.3 | Method 4a |
| Ex. 564 | 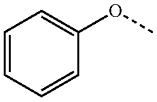 | 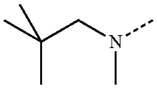 | C30H41N3O4 | 507.3 | 1.61 (96) | 508.2 | Method 10b |
| Ex. 565 | 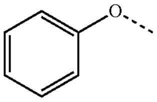 | 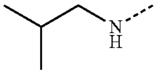 | C28H37N3O4 | 479.3 | 1.57 (99) | 480.3 | Method 10b |
| Ex. 566 | 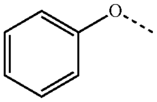 | 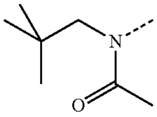 | C31H41N3O5 | 535.3 | 2.07 (94) | 536.3 | Method 10a |

TABLE 29.2.c

| Examples of Core 11b (Ex. 560-Ex. 566) | | | |
|---|---|---|---|
| No | $R^2$ | $R^5$ | IUPAC name |
| Ex. 560 | 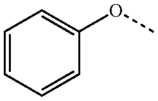 | 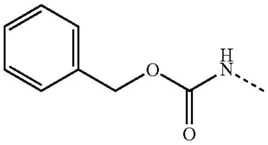 | benzyl N-[(4S,6S,10S)-14-methyl-9,15-dioxo-6-phenoxy-2-oxa-8,14-diazatricyclo[14.3.1.0$^{4,8}$]icosa-1(20),16,18-trien-10-yl]carbamate |
| Ex. 561 | 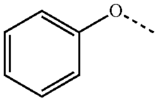 | $NH_2$ | (4S,6S,10S)-10-amino-14-methyl-6-phenoxy-2-oxa-8,14-diazatricyclo[14.3.1.0$^{4,8}$]icosa-1(20),16,18-triene-9,15-dione |
| Ex. 562 | 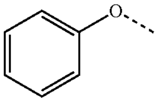 | 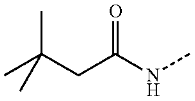 | 3,3-dimethyl-N-[(4S,6S,10S)-14-methyl-9,15-dioxo-6-phenoxy-2-oxa-8,14-diazatricyclo[14.3.1.0$^{4,8}$]icosa-1(20),16,18-trien-10-yl]butanamide |
| Ex. 563 | 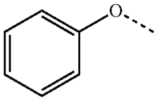 | 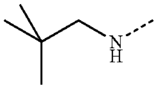 | (4S,6S,10S)-14-methyl-10-(neopentylamino)-6-phenoxy-2-oxa-8,14-diazatricyclo[14.3.1.0$^{4,8}$]icosa-1(20),16,18-triene-9,15-dione |
| Ex. 564 | 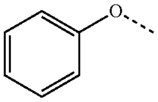 | 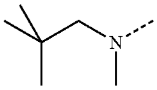 | (4S,6S,10S)-14-methyl-10-[methyl(neopentyl)amino]-6-phenoxy-2-oxa-8,14-diazatricyclo[14.3.1.0$^{4,8}$]icosa-1(20),16,18-triene-9,15-dione |
| Ex. 565 | 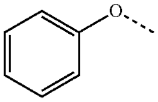 | 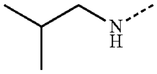 | (4S,6S,10S)-10-(isobutylamino)-14-methyl-6-phenoxy-2-oxa-8,14-diazatricyclo[14.3.1.0$^{4,8}$]icosa-1(20),16,18-triene-9,15-dione |
| Ex. 566 | 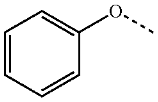 | 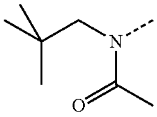 | N-[(4S,6S,10S)-14-methyl-9,15-dioxo-6-phenoxy-2-oxa-8,14-diazatricyclo[14.3.1.0$^{4,8}$]icosa-1(20),16,18-trien-10-yl]-N-neopentylacetamide |

TABLE 29.3.a

| Examples of Core 11c (Ex. 567-Ex. 585) | | | | | | | |
|---|---|---|---|---|---|---|---|
| No | $R^2$ | $R^5$ | Starting material | General Procedure | Reagent | Purification Method | Yield (isolated salt) |
| Ex. 567-Ex. 568: cf. experimental description | | | | | | | |
| Ex. 569 | 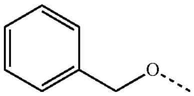 | 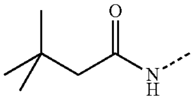 | Ex. 568 | L.1.1 | 3,3-dimethyl-butanoyl chloride (1.1 equiv.) i-$Pr_2NEt$ (5 equiv.) | FC (hexane/ EtOAc) | 76% |
| Ex. 570 | 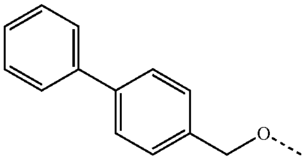 | $NH_2$ | Ex. 584 | K.2 | $H_2$, 5% Pd—C, $NH_3$—MeOH | crude product | 81% (HCl salt)*) |

TABLE 29.3.a-continued

Examples of Core 11c (Ex. 567-Ex. 585)

| No | $R^2$ | $R^5$ | Starting material | General Procedure | Reagent | Purification Method | Yield (isolated salt) |
|---|---|---|---|---|---|---|---|
| Ex. 571 | OH | 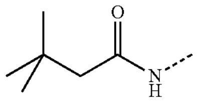 | Ex. 569 | H | $H_2$, $Pd(OH)_2$—C, MeOH/ AcOH 2:1 | crude product | 93% |
| Ex. 572 | $OCH_3$ | 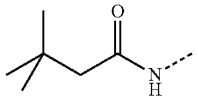 | Ex. 571 | **) | **) | FC (EtOAc) | 38% |
| Ex. 573 | 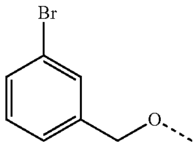 | 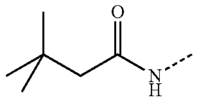 | Ex. 571 | Q | 3-bromobenzyl bromide | FC (hexane/ EtOAc) | 60% |
| Ex. 574 | OH | 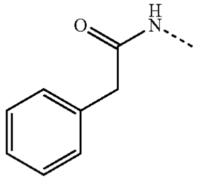 | Ex. 585 | H | $H_2$, $Pd(OH)_2$—C, MeOH/ AcOH 4:1 | crude product | 100% |
| Ex. 575 | 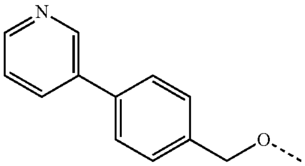 | 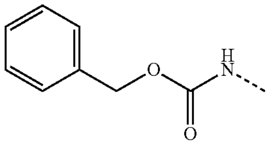 | Ex. 567 | P | pyridine-3-boronic acid | prep. HPLC method 3 | 91% |
| Ex. 576 | 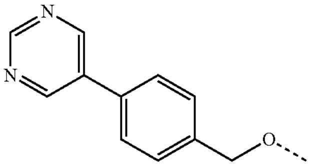 | 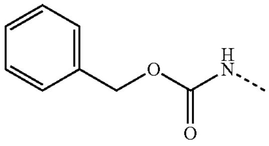 | Ex. 567 | P | pyrimidine-5-boronic acid | prep. HPLC method 3 | 86% |
| Ex. 577 | 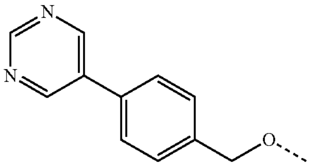 | $NH_2$ | Ex. 576 | K.2 | $H_2$, 5% Pd—C, $NH_3$—MeOH | crude product | 93% |
| Ex. 578 | 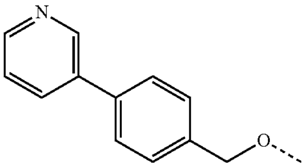 | $NH_2$ | Ex. 575 | K.2 | $H_2$, 5% Pd—C, $NH_3$—MeOH | crude product | 91% |
| Ex. 579 | 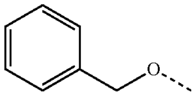 | 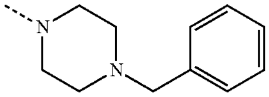 | Ex. 568 | O | N-benzyl-2-chloro-N-(2-chloroethyl) ethanamine | FC (hexane/ EtOAc/ MeOH) | 61% |
| Ex. 580 | OH | 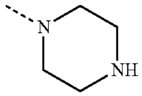 | Ex 579 | K.3 | $H_2$, $Pd(OH)_2$—C, AcOH | FC ($CH_2Cl_2$/ MeOH/ aq. $NH_3$) | 94% |

TABLE 29.3.a-continued

Examples of Core 11c (Ex. 567-Ex. 585)

| No | $R^2$ | $R^5$ | Starting material | General Procedure | Reagent | Purification Method | Yield (isolated salt) |
|---|---|---|---|---|---|---|---|
| Ex. 581 | OH | 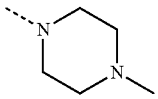 | Ex. 580 | M.3 | aq. formaldehyde soln | FC ($CH_2Cl_2$/ MeOH/ aq. $NH_3$) | 70% |
| Ex. 582 | OH | 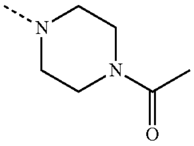 | Ex. 580 | L.1.1 | acetyl chloride (1.0 equiv.) triethylamine (2 equiv.) 0° C., 30 min | FC ($CH_2Cl_2$/ MeOH) | 75% |
| Ex. 583 | OH | 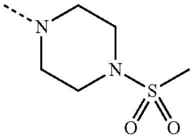 | Ex. 580 | L.3 | methanesulfonyl chloride 0° C., 30 min | FC (hexane/ EtOAc/ MeOH) | 63% |
| Ex. 584 | 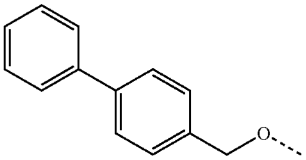 | 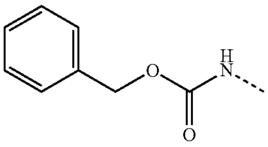 | Ex. 567 | P | phenylboronic acid (2 equiv.) | FC (EtOAc/ hexane) | 75% |
| Ex. 585 | 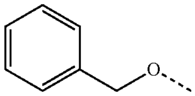 | 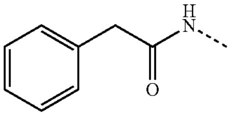 | Ex. 568 | L.1.1 | phenylacetyl chloride (1 equiv.) DIPEA (3 equiv.) | FC (EtOAc) | 70% |

*)the crude product was converted into the HCl salt

**) dimethyl sulfate, benzyltriethylammonium chloride, toluene, 2M aq. NaOH

TABLE 29.3.b

Examples of Core 11c (Ex. 567-Ex. 585)

| No | $R^2$ | $R^5$ | FORMULA | MONO-ISO-TOPIC MASS | Rt (purity at 220 nm) | $[M + H]^+$ found | LC-MS-Method |
|---|---|---|---|---|---|---|---|
| Ex. 567-Ex. 568: cf. experimental description | | | | | | | |
| Ex. 569 | 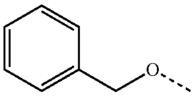 | 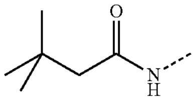 | C31H41N3O5 | 535.3 | 2.22 (92) | 536.4 | Method 4a |
| Ex. 570 | 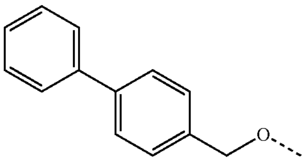 | $NH_2$ | C31H35N3O4 | 513.3 | 1.88 (97) | 514.3 | Method 4a |
| Ex. 571 | OH | 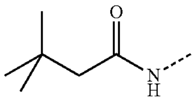 | C24H35N3O5 | 445.3 | 1.59 (95) | 446.3 | Method 4a |

TABLE 29.3.b-continued
Examples of Core 11c (Ex. 567-Ex. 585)
| No | $R^2$ | $R^5$ | FORMULA | MONO-ISO-TOPIC MASS | Rt (purity at 220 nm) | $[M + H]^+$ found | LC-MS-Method |
|---|---|---|---|---|---|---|---|
| Ex. 572 | $OCH_3$ | 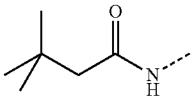 | C25H37N3O5 | 459.3 | 1.62 (96) | 460.2 | Method 10a |
| Ex. 573 | 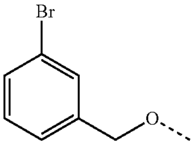 | 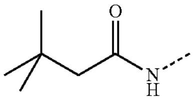 | C31H40BrN3O5 | 613.2 | 2.33 (93) | 616.2 | Method 4a |
| Ex. 574 | OH | 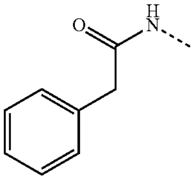 | C26H31N3O5 | 465.2 | 1.35 (87) | 466.3 | Method 10a |
| Ex. 575 | 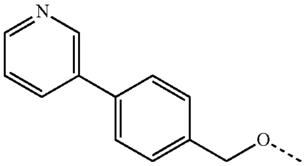 | 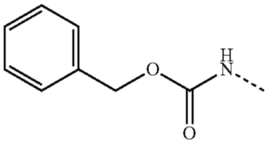 | C38H40N4O6 | 648.3 | 1.57 (94) | 649.1 | Method 10a |
| Ex. 576 | 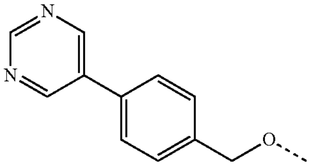 | 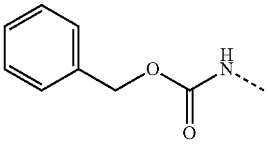 | C37H39N5O6 | 649.3 | 1.90 (98) | 650.3 | Method 10a |
| Ex. 577 | 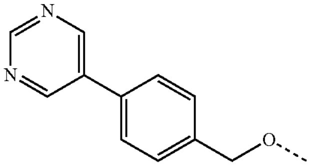 | $NH_2$ | C29H33N5O4 | 515.3 | 1.30 (95) | 516.3 | Method 10a |
| Ex. 578 | 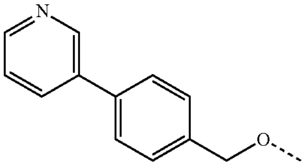 | $NH_2$ | C30H34N4O4 | 514.3 | 1.08 (95) | 515.3 | Method 10a |
| Ex. 579 | 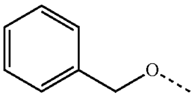 | 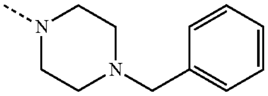 | C36H44N4O4 | 596.3 | 1.61 (97) | 597.3 | Method 10a |
| Ex. 580 | OH | 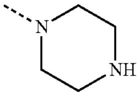 | C22H32N4O4 | 416.2 | 0.80 (98) | 417.2 | Method 10a |
| Ex. 581 | OH | 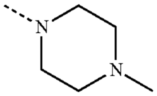 | C23H34N4O4 | 430.3 | 0.83 (99) | 431.2 | Method 10a |

TABLE 29.3.b-continued

| Examples of Core 11c (Ex. 567-Ex. 585) | | | | | | | |
|---|---|---|---|---|---|---|---|
| No | $R^2$ | $R^5$ | FORMULA | MONO-ISO-TOPIC MASS | Rt (purity at 220 nm) | $[M + H]^+$ found | LC-MS-Method |
| Ex. 582 | OH | 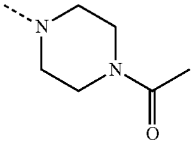 | C24H34N4O5 | 458.3 | 0.82 (97) | 459.2 | Method 10a |
| Ex. 583 | OH | 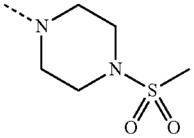 | C23H34N4O6S | 494.2 | 0.84 (94) | 495.2 | Method 10a |
| Ex. 584 | 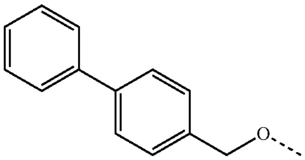 | 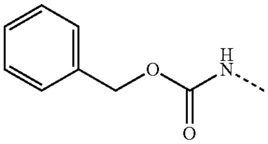 | C39H41N3O6 | 647.3 | 2.46 (65%) | 648.3 | Method 12 |
| Ex. 585 | 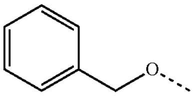 | 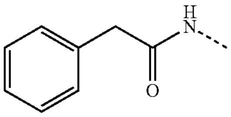 | C33H37N3O5 | 555.3 | 1.99 (88%) | 557.3 | Method 10a |

TABLE 29.3.c

| Examples of Core 11c (Ex. 567-Ex. 585; continued on the following pages) | | | |
|---|---|---|---|
| No | $R^2$ | $R^5$ | IUPAC name |
| Ex. 567 | 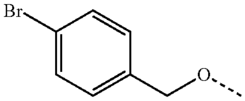 | 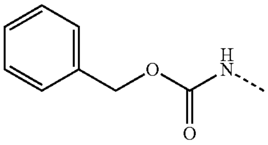 | benzyl N-[(4S,6S,10S)-6-[(4-bromobenzyl)oxy]-14-methyl-9,15-dioxo-2-oxa-8,14-diazatricyclo[14.3.1.0$^{4,8}$]icosa-1(20),16,18-trien-10-yl]carbamate |
| Ex. 568 | 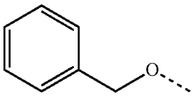 | $NH_2$ | (4S,6S,10S)-10-amino-6-(benzyloxy)-14-methyl-2-oxa-8,14-diazatricyclo[14.3.1.0$^{4,8}$]icosa-1(20),16,18-triene-9,15-dione |
| Ex. 569 | 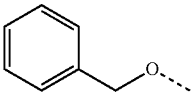 | 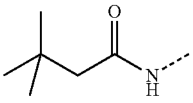 | N-[(4S,6S,10S)-6-(benzyloxy)-14-methyl-9,15-dioxo-2-oxa-8,14-diazatricyclo[14.3.1.0$^{4,8}$]icosa-1(20),16,18-trien-10-yl]-3,3-dimethylbutanamide |
| Ex. 570 | 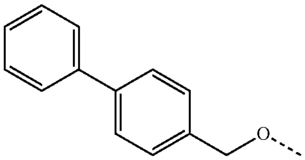 | $NH_2$ | (4S,65,10S)-10-amino-6-([1,1'-biphenyl]-4-ylmethoxy)-14-methyl-2-oxa-8,14-diazatricyclo[14.3.1.0$^{4,8}$]icosa-1(20),16,18-triene-9,15-dione |
| Ex. 571 | OH | 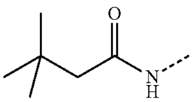 | N-[(4S,6S,10S)-6-hydroxy-14-methyl-9,15-dioxo-2-oxa-8,14-diazatricyclo[14.3.1.0$^{4,8}$]icosa-1(20),16,18-trien-10-yl]-3,3-dimethylbutanamide |

TABLE 29.3.c-continued

Examples of Core 11c (Ex. 567-Ex. 585; continued on the following pages)

| No | $R^2$ | $R^5$ | IUPAC name |
|---|---|---|---|
| Ex. 572 | $OCH_3$ | 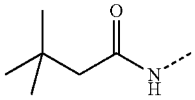 | N-[(4S,6S,10S)-6-methoxy-14-methyl-9,15-dioxo-2-oxa-8,14-diazatricyclo[14.3.1.0$^{4,8}$]icosa-1(20),16,18-trien-10-yl]-3,3-dimethylbutanamide |
| Ex. 573 | 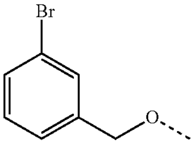 | 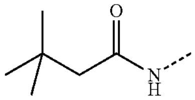 | N-[(4S,6S,10S)-6-[(3-bromobenzyl)oxy]-14-methyl-9,15-dioxo-2-oxa-8,14-diazatricyclo[14.3.1.0$^{4,8}$]icosa-1(20),16,18-trien-10-yl]-3,3-dimethylbutanamide |
| Ex. 574 | OH | 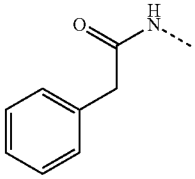 | N-[(4S,6S,10S)-6-hydroxy-14-methyl-9,15-dioxo-2-oxa-8,14-diazatricyclo[14.3.1.0$^{4,8}$]icosa-1(20),16,18-trien-10-yl]-2-phenylacetamide |
| Ex. 575 | 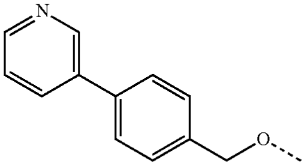 | 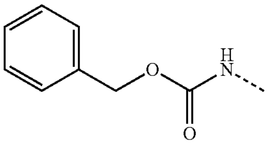 | benzyl N-[(4S,6S,10S)-14-methyl-9,15-dioxo-6-{[4-(3-pyridinyl)benzyl]oxy}-2-oxa-8,14-diazatricyclo[14.3.1.0$^{4,8}$]icosa-1(20),16,18-trien-10-yl]carbamate |
| Ex. 576 | 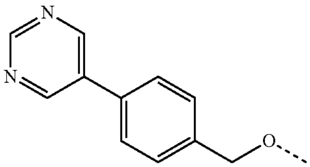 | 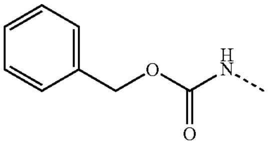 | benzyl N-[(4S,6S,10S)-14-methyl-9,15-dioxo-6-{[4-(5-pyrimidinyl)benzyl]oxy}-2-oxa-8,14-diazatricyclo[14.3.1.0$^{4,8}$]icosa-1(20),16,18-trien-10-yl]carbamate |
| Ex. 577 | 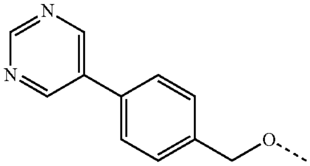 | $NH_2$ | (4S,6S,10S)-10-amino-14-methyl-6-{[4-(5-pyrimidinyl)benzyl]oxy}-2-oxa-8,14-diazatricyclo[14.3.1.0$^{4,8}$]icosa-1(20),16,18-triene-9,15-dione |
| Ex. 578 | 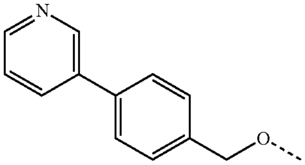 | $NH_2$ | (4S,6S,10S)-10-amino-14-methyl-6-{[4-(3-pyridinyl)benzyl]oxy}-2-oxa-8,14-diazatricyclo[14.3.1.0$^{4,8}$]icosa-1(20),16,18-triene-9,15-dione |
| Ex. 579 | 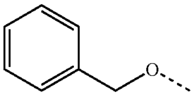 | 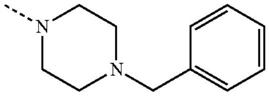 | (4S,6S,10S)-6-(benzyloxy)-10-(4-benzylpiperazino)-14-methyl-2-oxa-8,14-diazatricyclo[14.3.1.0$^{4,8}$]icosa-1(20),16,18-triene-9,15-dione |
| Ex. 580 | OH | 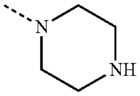 | (4S,6S,10S)-6-hydroxy-14-methyl-10-piperazino-2-oxa-8,14-diazatricyclo[14.3.1.0$^{4,8}$]icosa-1(20),16,18-triene-9,15-dione |
| Ex. 581 | OH | 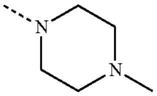 | (4S,6S,10S)-6-hydroxy-14-methyl-10-(4-methylpiperazino)-2-oxa-8,14-diazatricyclo[14.3.1.0$^{4,8}$]icosa-1(20),16,18-triene-9,15-dione |

TABLE 29.3.c-continued

Examples of Core 11c (Ex. 567-Ex. 585; continued on the following pages)

| No | $R^2$ | $R^5$ | IUPAC name |
|---|---|---|---|
| Ex. 582 | OH | 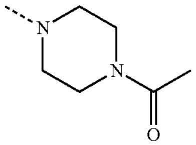 | (4S,6S,10S)-10-(4-acetylpiperazino)-6-hydroxy-14-methyl-2-oxa-8,14-diazatricyclo[14.3.1.$0^{4,8}$]icosa-1(20),16,18-triene-9,15-dione |
| Ex. 583 | OH | 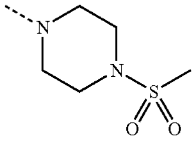 | (4S,6S,10S)-6-hydroxy-14-methyl-10-[4-(methylsulfonyl)piperazino]-2-oxa-8,14-diazatricyclo[14.3.1.$0^{4,8}$]icosa-1(20),16,18-triene-9,15-dione |
| Ex. 584 | 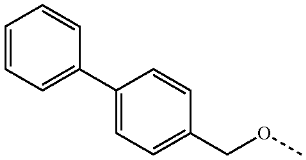 | 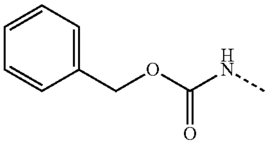 | benzyl N-[(4S,6S,10S)-6-([1,1'-biphenyl]-4-ylmethoxy)-14-methyl-9,15-dioxo-2-oxa-8,14-diazatricyclo[14.3.1.$0^{4,8}$]icosa-1(20),16,18-trien-10-yl]carbamate |
| Ex. 585 | 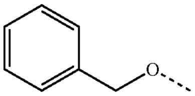 | 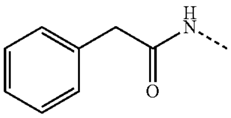 | N-[(4S,6S,10S)-6-(benzyloxy)-14-methyl-9,15-dioxo-2-oxa-8,14-diazatricyclo[14.3.1.$0^{4,8}$]icosa-1(20),16,18-trien-10-yl]-2-phenylacetamide |

TABLE 29.4.a

Examples of Core 11d (Ex. 586-Ex. 589; continued on the following page)

| No | $R^2$ | $R^5$ | Starting material | General Procedure | Reagent | Purification Method | Yield (isolated salt) |
|---|---|---|---|---|---|---|---|
| Ex. 586-Ex. 587: cf. experimental description | | | | | | | |
| Ex. 588 | $CH_2Ph$ | 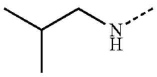 | Ex. 587 | M.2 | isobutyraldehyde | prep. HPLC, method 3 | 61% |
| Ex. 589 | $CH_2Ph$ | 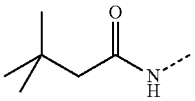 | Ex. 587 | L.1.1 | 3,3-dimethylbutanoyl chloride (1.2 equiv.) pyridine (5 equiv.) | prep. HPLC, method 3 | 70% |

TABLE 29.4.b

Examples of Core 11d (Ex. 586-Ex. 589)

| No | $R^2$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 586-Ex. 587: cf. experimental description | | | | | | | |
| Ex. 588 | $CH_2Ph$ | 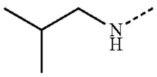 | C29H39N3O3 | 477.3 | 1.67 (98) | 478.3 | Method 10a |
| Ex. 589 | $CH_2Ph$ | 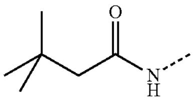 | C31H41N3O4 | 519.3 | 2.13 (98) | 520.3 | Method 10a |

TABLE 29.4.c

| Examples of Core 11d (Ex. 586-Ex. 589) | | | |
|---|---|---|---|
| No | $R^2$ | $R^5$ | IUPAC name |
| Ex. 586 | $CH_2Ph$ | 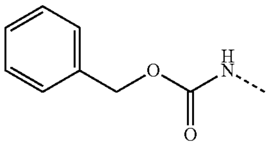 | benzyl N-[(4S,6S,10S)-6-benzyl-14-methyl-9,15-dioxo-2-oxa-8,14-diazatricyclo[14.3.1.0$^{4,8}$]icosa-1(20),16,18-trien-10-yl]carbamate |
| Ex. 587 | $CH_2Ph$ | $NH_2$ | (4S,6S,10S)-10-amino-6-benzyl-14-methyl-2-oxa-8,14-diazatricyclo[14.3.1.0$^{4,8}$]icosa-1(20),16,18-triene-9,15-dione |
| Ex. 588 | $CH_2Ph$ | 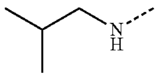 | (4S,6S,10S)-6-benzyl-10-(isobutylamino)-14-methyl-2-oxa-8,14-diazatricyclo[14.3.1.0$^{4,8}$]icosa-1(20),16,18-triene-9,15-dione |
| Ex. 589 | $CH_2Ph$ | 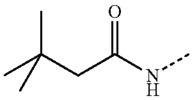 | N-[(4S,6S,10S)-6-benzyl-14-methyl-9,15-dioxo-2-oxa-8,14-diazatricyclo[14.3.1.0$^{4,8}$]icosa-1(20),16,18-trien-10-yl]-3,3-dimethylbutanamide |

TABLE 30a

| Examples of Core 12 (Ex. 196-Ex. 214; continued on the following pages) | | | | | | | |
|---|---|---|---|---|---|---|---|
| No | $R^2$ | $R^5$ | Starting material | General Procedure | Reagent | Purification Method | Yield (isolated salt) |
| Ex. 196-Ex. 198: cf. experimental description | | | | | | | |
| Ex. 199 | 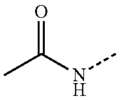 | 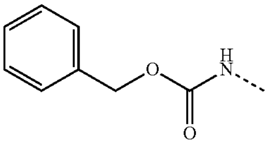 | Ex. 197 •HCl | L.1.1 | acetic anhydride (10 equiv.) pyridine (2 mL) | FC ($CH_2Cl_2$/MeOH) then prep HPLC, method 1 | 36% |
| Ex. 200 | 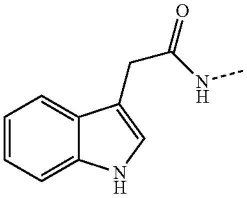 | 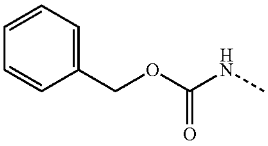 | Ex. 197 •HCl | L.1.3 | 3-indoleacetic acid (1.5 equiv.), HATU (1.5 equiv.), HOAt (1.5 equiv), i-$Pr_2$NEt (5 equiv.) | FC ($CH_2Cl_2$/MeOH) then prep HPLC, method 1 | 22% |
| Ex. 200 | 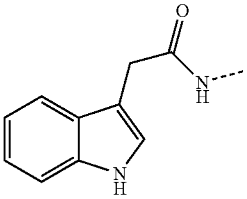 | 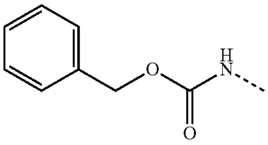 | Ex. 197 •TFA | L.1.3 | 3-indoleacetic acid (1.5 equiv.), HATU (1.5 equiv.), HOAt (1.5 equiv), i-$Pr_2$NEt (5 equiv.) | FC (EtOAc, then $CH_2Cl_2$/MeOH) | 78% |
| Ex. 201 | 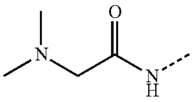 | 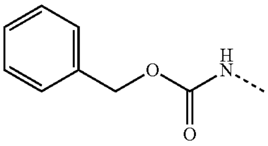 | Ex. 197 •HCl | L.1.3 | N,N-dimethyl glycine (1.7 equiv.) | FC ($CH_2Cl_2$/MeOH) and prep HPLC, method 1 | 91%*⁾ (TFA salt) |

TABLE 30a-continued

Examples of Core 12 (Ex. 196-Ex. 214; continued on the following pages)

| No | $R^2$ | $R^5$ | Starting material | General Procedure | Reagent | Purification Method | Yield (isolated salt) |
|---|---|---|---|---|---|---|---|
| Ex. 202 | 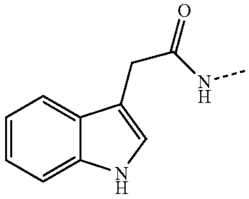 | $NH_2$ | Ex. 200 | K.1 | $H_2$, $Pd(OH)_2$—C | crude product | 97% |
| Ex. 203 | 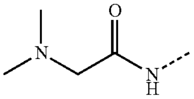 | $NH_2$ | Ex. 201 | K.1 | $H_2$, $Pd(OH)_2$—C | crude product | 99% |
| Ex. 204 | 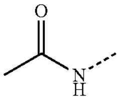 | 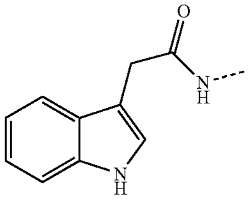 | Ex. 214 | L.1.3 | 3-indoleacetic acid (1.2 equiv.), HATU (1.5 equiv.), HOAt (1.5 equiv), i-$Pr_2$NEt (3 equiv.) | FC ($CH_2Cl_2$/MeOH) | 64% |
| Ex. 205 | 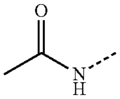 | 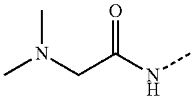 | Ex. 214 | L.1.3 | N,N-dimethyl glycine (1.7 equiv.) | prep HPLC, method 1 | 47% (TFA salt) |
| Ex. 206 | 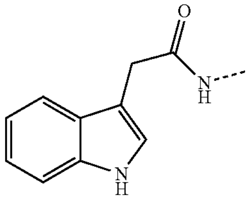 | 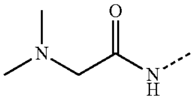 | Ex. 202 | L.1.3 | N,N-dimethyl glycine (1.7 equiv.) | prep HPLC, method 1 | 39% (TFA salt) |
| Ex. 207 | 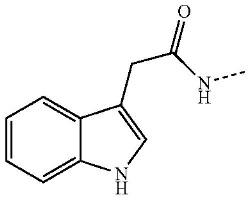 | 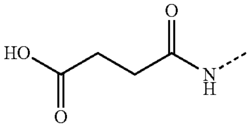 | Ex. 202 | L.1.1 | succinic anhydride (1.05 equiv.) pyridine (49 equiv.) | prep HPLC, method 2 | 48% |
| Ex. 208 | 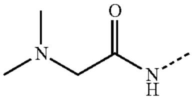 | 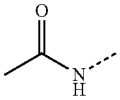 | Ex. 203 | L.1.1 | acetic anhydride (10 equiv.) pyridine/$CH_2Cl_2$ 1.1 (3 mL) | prep HPLC, method 2 | 59% |
| Ex. 209 | 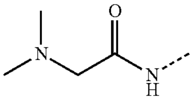 | 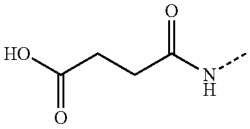 | Ex. 203 | L.1.1 | succinic anhydride (1.05 equiv.) pyridine (49 equiv.) | prep HPLC, method 2 | 35% |

TABLE 30a-continued

Examples of Core 12 (Ex. 196-Ex. 214; continued on the following pages)

| No | $R^2$ | $R^5$ | Starting material | General Procedure | Reagent | Purification Method | Yield (isolated salt) |
|---|---|---|---|---|---|---|---|
| Ex. 210 | 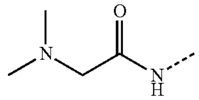 | 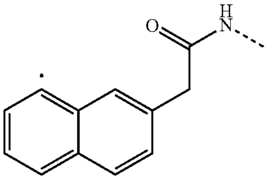 | Ex. 203 | L.1.3 | 2-naphthylacetic acid (1.2 equiv.) | prep HPLC, method 1 | 38% (TFA salt) |
| Ex. 211 | 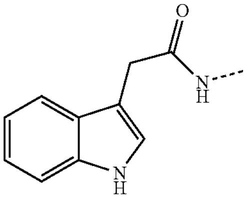 | 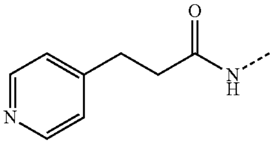 | Ex. 202 | L.1.2 | 3-(pyridine-4-yl)propanoic acid | prep HPLC, method 1 | 44% (TFA salt) |
| Ex. 212 | 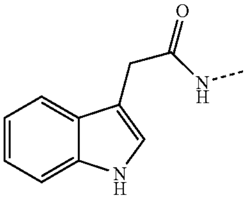 | 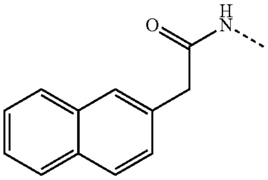 | Ex. 202 | L.1.3 | 2-naphthylacetic acid (1.2 equiv.) | prep HPLC, method 1 then FC (EtOAc/MeOH) | 53% |
| Ex. 213 | 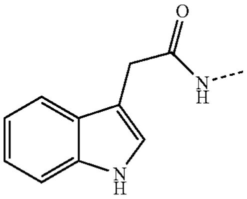 | $CH_3(CH_2)_8CONH$ | Ex. 202 | L.1.1 | decanoyl chloride (2 equiv.) | prep HPLC, method 1 then FC (EtOAc/MeOH) | 35% |
| Ex. 214 | 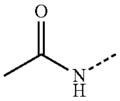 | $NH_2$ | Ex. 199 | K.1 | $H_2$, $Pd(OH)_2$—C | crude product | 98% |

*)An analytical sample was further purified by prep. HPLC (method 1), to afford the TFA salt of the corresponding product TABLE 30b Examples of Core 12 (Ex. 196-Ex. 214; continued on the following page)

| No | $R^2$ | $R^5$ | FORMULA | MONO-ISOTOPIC MASS | Rt (purity at 220 nm) | $[M + H]^+$ found | LC-MS-Method |
|---|---|---|---|---|---|---|---|
| Ex. 196-Ex. 198: cf. experimental description | | | | | | | |
| Ex. 199 | 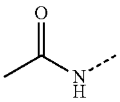 | 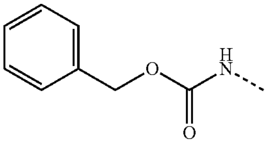 | C29H35N5O7 | 565.3 | 1.92 (100) | 566.4 | Method 1a |

TABLE 30b-continued
Examples of Core 12 (Ex. 196-Ex. 214; continued on the following page)
| No | $R^2$ | $R^5$ | FORMULA | MONO-ISOTOPIC MASS | Rt (purity at 220 nm) | $[M + H]^+$ found | LC-MS-Method |
|---|---|---|---|---|---|---|---|
| Ex. 200 | 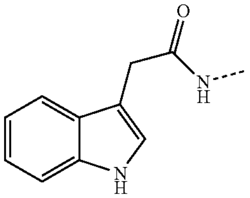 | 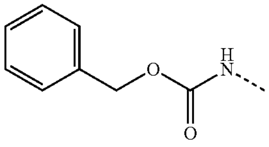 | C37H40N6O7 | 680.3 | 2.23 (98) | 681.4 | Method 1a |
| Ex. 200 | 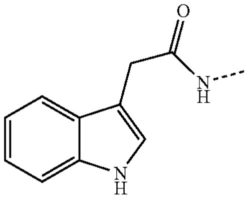 | 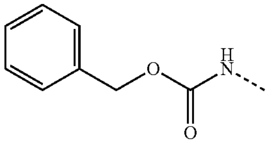 | C37H40N6O7 | 680.3 | 1.68 (93) | 681.5 | Method 2 |
| Ex. 201 | 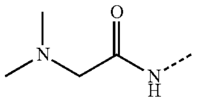 | 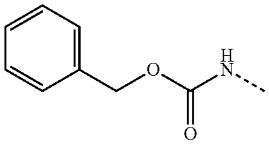 | C31H40N6O7 | 608.3 | 1.28 (99) | 609.4 | Method 2 |
| Ex. 202 | 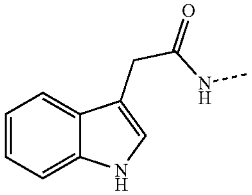 | $NH_2$ | C29H34N6O5 | 546.3 | 1.32 (76) | 547.4 | Method 2 |
| Ex. 203 | 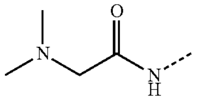 | $NH_2$ | C23H34N6O5 | 474.3 | 0.77 | 475.5 | Method 9c |
| Ex. 204 | 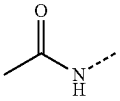 | 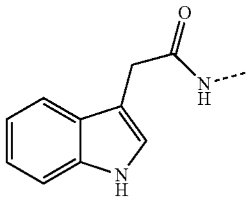 | C31H36N6O6 | 588.3 | 1.49 (87) | 589.2 | Method 4a |
| Ex. 205 | 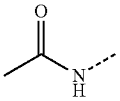 | 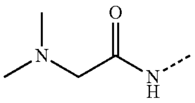 | C25H36N6O6 | 516.3 | 1.42 (100) | 517.3 | Method 1a |
| Ex. 206 | 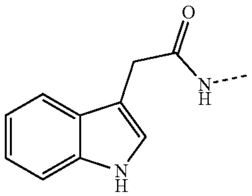 | 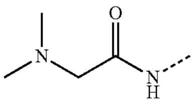 | C33H41N7O6 | 631.3 | 1.84 (97) | 632.4 | Method 1a |

TABLE 30b-continued
Examples of Core 12 (Ex. 196-Ex. 214; continued on the following page)
| No | $R^2$ | $R^5$ | FORMULA | MONO-ISOTOPIC MASS | Rt (purity at 220 nm) | $[M + H]^+$ found | LC-MS-Method |
|---|---|---|---|---|---|---|---|
| Ex. 207 | 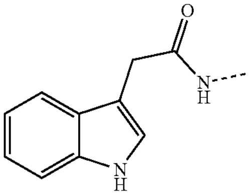 | 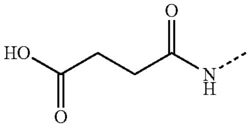 | C33H38N6O8 | 646.3 | 1.42 (100) | 647.4 | Method 2 |
| Ex. 208 | 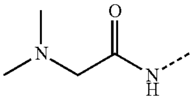 | 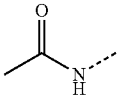 | C25H36N6O6 | 516.3 | 0.95 (100) | 517.4 | Method 2 |
| Ex. 209 | 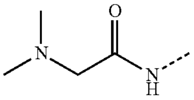 | 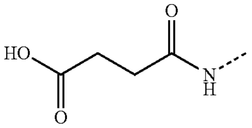 | C27H38N6O8 | 574.3 | 1.02 (92) | 575.4 | Method 3 |
| Ex. 210 | 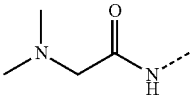 | 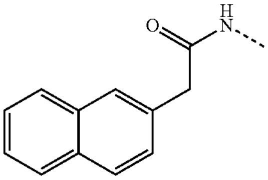 | C35H42N6O6 | 642.3 | 1.37 (100) | 643.4 | Method 2 |
| Ex. 211 | 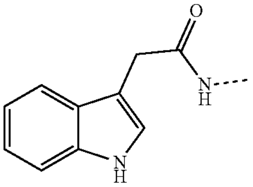 | 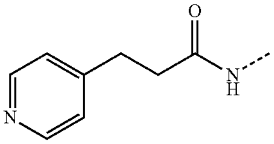 | C37H41N7O6 | 679.3 | 1.34 (92) | 680.5 | Method 2 |
| Ex. 212 | 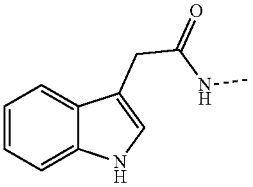 | 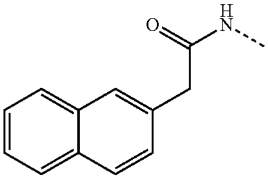 | C41H42N6O6 | 714.3 | 1.75 (86) | 715.5 | Method 2 |
| Ex. 213 | 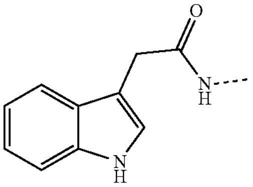 | $CH_3(CH_2)_8CONH$ | C39H52N6O6 | 700.4 | 1.96 (99) | 701.6 | Method 2 |
| Ex. 214 | 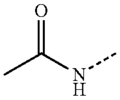 | $NH_2$ | C21H29N5O5 | 431.2 | 0.81*) | 432.2 | Method 9c |
*)Analytical HPLC (5% $CH_3CN$): 2.52 (93)

TABLE 30c

Examples of Core 12 (Ex. 196-Ex. 214; continued on the following pages)

| No | $R^2$ | $R^5$ | IUPAC name |
|---|---|---|---|
| Ex. 196 | 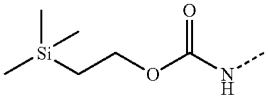 | 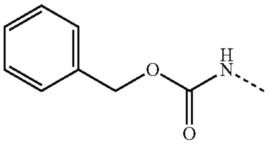 | benzyl N-[(4S,6S,13S)-11,15-dimethyl-9,12,16-trioxo-6-({[2-(trimethylsilyl)ethoxy]carbonyl}amino)-2-oxa-8,11,15-triazatricyclo[15.3.1.$0^{4,8}$]henicosa-1(21),17,19-trien-13-yl]carbamate |
| Ex. 197 | $NH_2$ | 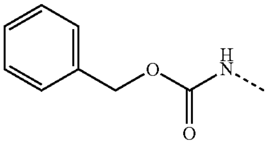 | benzyl N-[(4S,6S,13S)-6-amino-11,15-dimethyl-9,12,16-trioxo-2-oxa-8,11,15-triazatricyclo[15.3.1.$0^{4,8}$]henicosa-1(21),17,19-trien-13-yl]carbamate |
| Ex. 198 | 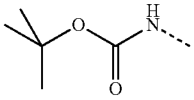 | 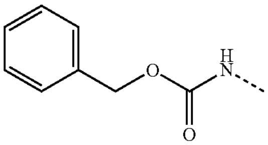 | benzyl N-[(4S,6S,13S)-6-[(tert-butoxycarbonyl)amino]-11,15-dimethyl-9,12,16-trioxo-2-oxa-8,11,15-triazatricyclo[15.3.1.$0^{4,8}$]henicosa-1(21),17,19-trien-13-yl]carbamate |
| Ex. 199 | 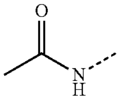 | 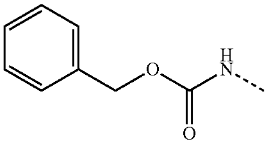 | benzyl N-[(4S,6S,13S)-6-(acetylamino)-11,15-dimethyl-9,12,16-trioxo-2-oxa-8,11,15-triazatricyclo[15.3.1.$0^{4,8}$]henicosa-1(21),17,19-trien-13-yl]carbamate |
| Ex. 200 | 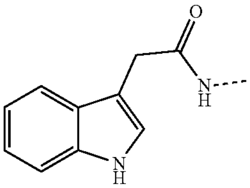 | 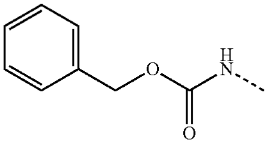 | benzyl N-[(4S,6S,13S)-6-{[2-(1H-indol-3-yl)acetyl]amino}-11,15-dimethyl-9,12,16-trioxo-2-oxa-8,11,15-triazatricyclo[15.3.1.$0^{4,8}$]henicosa-1(21),17,19-trien-13-yl]carbamate |
| Ex. 201 | 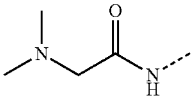 | 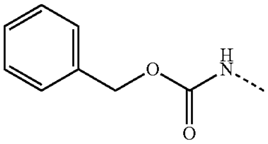 | benzyl N-[(4S,6S,13S)-6-{[2-(dimethylamino)acetyl]amino}-11,15-dimethyl-9,12,16-trioxo-2-oxa-8,11,15-triazatricyclo[15.3.1.$0^{4,8}$]henicosa-1(21),17,19-trien-13-yl]carbamate |
| Ex. 202 | 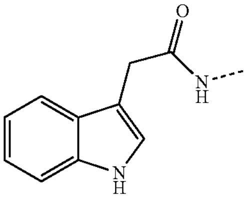 | $NH_2$ | N-[(4S,6S,13S)-13-amino-11,15-dimethyl-9,12,16-trioxo-2-oxa-8,11,15-triazatricyclo[15.3.1.$0^{4,8}$]henicosa-1(21),17,19-trien-6-yl]-2-(1H-indol-3-yl)acetamide |
| Ex. 203 | 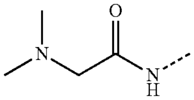 | $NH_2$ | N-[(4S,6S,13S)-13-amino-11,15-dimethyl-9,12,16-trioxo-2-oxa-8,11,15-triazatricyclo[15.3.1.$0^{4,8}$]henicosa-1(21),17,19-trien-6-yl]-2-(dimethylamino)acetamide |
| Ex. 204 | 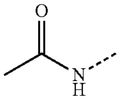 | 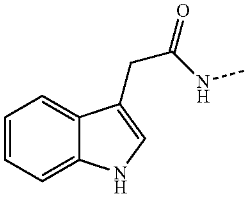 | N-[(4S,6S,13S)-6-(acetylamino)-11,15-dimethyl-9,12,16-trioxo-2-oxa-8,11,15-triazatricyclo[15.3.1.$0^{4,8}$]henicosa-1(21),17,19-trien-13-yl]-2-(1H-indol-3-yl)acetamide |

TABLE 30c-continued

Examples of Core 12 (Ex. 196-Ex. 214; continued on the following pages)

| No | $R^2$ | $R^5$ | IUPAC name |
|---|---|---|---|
| Ex. 205 | 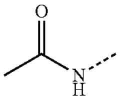 | 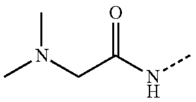 | N-[(4S,6S,13S)-6-(acetylamino)-11,15-dimethyl-9,12,16-trioxo-2-oxa-8,11,15-triazatricyclo[15.3.1.$0^{4,8}$]henicosa-1(21),17,19-trien-13-yl]-2-(dimethylamino)acetamide |
| Ex. 206 | 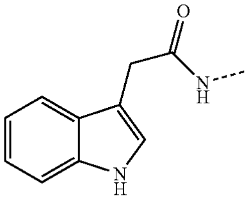 | 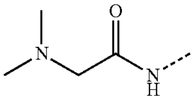 | 2-(dimethylamino)-N-[(4S,6S,13S)-6-{[2-(1H-indol-3-yl)acetyl]amino}-11,15-dimethyl-9,12,16-trioxo-2-oxa-8,11,15-triazatricyclo[15.3.1.$0^{4,8}$]henicosa-1(21),17,19-trien-13-yl]acetamide |
| Ex. 207 | 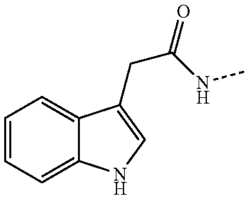 | 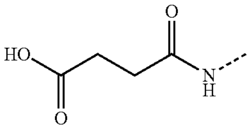 | 4-{[(4S,6S,13S)-6-{[2-(1H-indol-3-yl)acetyl]amino}-11,15-dimethyl-9,12,16-trioxo-2-oxa-8,11,15-triazatricyclo[15.3.1.$0^{4,8}$]henicosa-1(21),17,19-trien-13-yl]amino}-4-oxobutanoic acid |
| Ex. 208 | 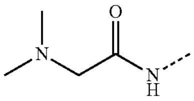 | 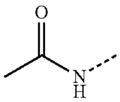 | N-[(4S,6S,13S)-13-(acetylamino)-11,15-dimethyl-9,12,16-trioxo-2-oxa-8,11,15-triazatricyclo[15.3.1.$0^{4,8}$]henicosa-1(21),17,19-trien-6-yl]-2-(dimethylamino)acetamide |
| Ex. 209 | 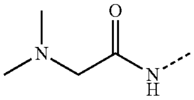 | 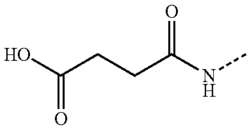 | 4-{[(4S,6S,13S)-6-{[2-(dimethylamino)acetyl]amino}-11,15-dimethyl-9,12,16-trioxo-2-oxa-8,11,15-triazatricyclo[15.3.1.$0^{4,8}$]henicosa-1(21),17,19-trien-13-yl]amino}-4-oxobutanoic acid |
| Ex. 210 | 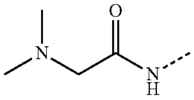 | 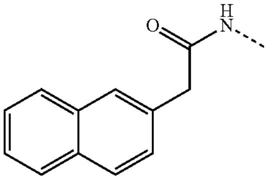 | 2-(dimethylamino)-N-[(4S,6S,13S)-11,15-dimethyl-13-{[2-(2-naphthyl)acetyl]amino}-9,12,16-trioxo-2-oxa-8,11,15-triazatricyclo[15.3.1.$0^{4,8}$]henicosa-1(21),17,19-trien-6-yl]acetamide |
| Ex. 211 | 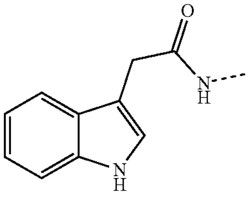 | 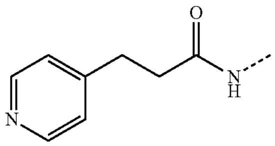 | N-[(4S,6S,13S)-6-{[2-(1H-indol-3-yl)acetyl]amino}-11,15-dimethyl-9,12,16-trioxo-2-oxa-8,11,15-triazatricyclo[15.3.1.$0^{4,8}$]henicosa-1(21),17,19-trien-13-yl]-3-(4-pyridinyl)propanamide |
| Ex. 212 | 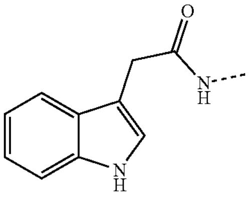 | 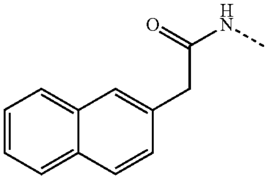 | N-[(4S,6S,13S)-11,15-dimethyl-13-{[2-(2-naphthyl)acetyl]amino}-9,12,16-trioxo-2-oxa-8,11,15-triazatricyclo[15.3.1.$0^{4,8}$]henicosa-1(21),17,19-trien-6-yl]-2-(1H-indol-3-yl)acetamide |

TABLE 30c-continued

| Examples of Core 12 (Ex. 196-Ex. 214; continued on the following pages) | | | |
|---|---|---|---|
| No | $R^2$ | $R^5$ | IUPAC name |
| Ex. 213 | 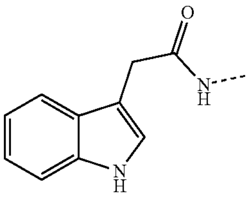 | $CH_3(CH_2)_8CONH$ | N-[(4S,6S,13S)-6-{[2-(1H-indol-3-yl)acetyl]amino}-11,15-dimethyl-9,12,16-trioxo-2-oxa-8,11,15-triazatricyclo[15.3.1.0$^{4,8}$]henicosa-1(21),17,19-trien-13-yl]decanamide |
| Ex. 214 | 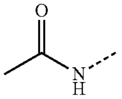 | $NH_2$ | N-[(4S,6S,13S)-13-amino-11,15-dimethyl-9,12,16-trioxo-2-oxa-8,11,15-triazatricyclo[15.3.1.0$^{4,8}$]henicosa-1(21),17,19-trien-6-yl]acetamide |

TABLE 31a

| Examples of Core 13 (Ex. 215-Ex. 230; continued on the following pages) | | | | | | | |
|---|---|---|---|---|---|---|---|
| No | $R^2$ | $R^5$ | Starting material | General Pro-cedure | Reagent | Purification Method | Yield (isolated salt) |
| Ex. 215-Ex. 216: cf. experimental description | | | | | | | |
| Ex. 217 | 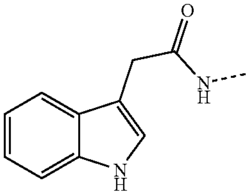 | 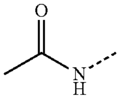 | Ex. 221 | L.1.1 | acetic anhydride (10 equiv.) pyridine/$CH_2Cl_2$ 1:1 (2 mL) | prep. HPLC, method 1 | 41% |
| Ex. 218 | 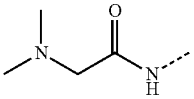 | 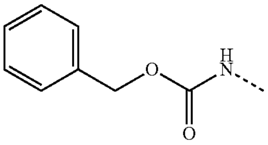 | Ex. 216 •HCl | L.1.3 | N,N-dimetyl glycine (1.7 equiv.) | FC ($CH_2Cl_2$/MeOH) | 85%*) |
| Ex. 219 | 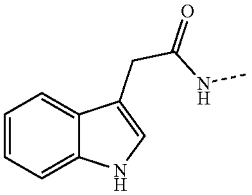 | 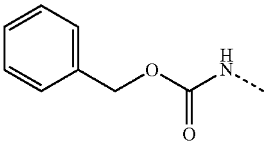 | Ex. 216 •HCl | L.1.3 | 3-indoleacetic acid (1.1 equiv.) HATU (1.5 equiv.) HOAt (1.5 equiv.) i-$Pr_2$NEt (5 equiv.) | FC ($CH_2Cl_2$/MeOH) | 63% |
| Ex. 220 | 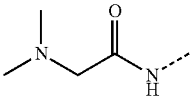 | $NH_2$ | Ex. 218 | K.1 | $H_2$, $Pd(OH)_2$—C | crude product | 93%*) |
| Ex. 221 | 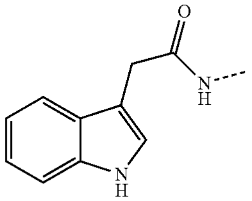 | $NH_2$ | Ex. 219 | K.1 | $H_2$, $Pd(OH)_2$—C | crude product | 94%*) |

TABLE 31a-continued

Examples of Core 13 (Ex. 215-Ex. 230; continued on the following pages)

| No | $R^2$ | $R^5$ | Starting material | General Procedure | Reagent | Purification Method | Yield (isolated salt) |
|---|---|---|---|---|---|---|---|
| Ex. 222 | 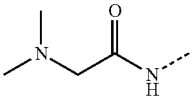 | 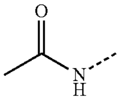 | Ex. 220 | L.1.1 | acetic anhydride (5 equiv.) | prep. HPLC, method 1 | 25% (TFA salt) |
| Ex. 223 | 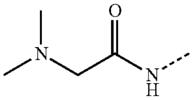 | 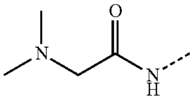 | Ex. 220 | L.1.3 | N,N-dimetyl glycine (1.7 equiv.) | prep. HPLC, method 1 | 24% (TFA salt) |
| Ex. 224 | 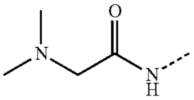 | 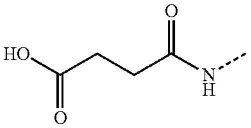 | Ex. 220 | L.1.1 | succinic anhydride (1.05 equiv.) | prep. HPLC, method 1 | 37% (TFA salt) |
| Ex. 225 | 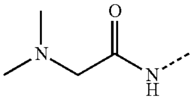 | 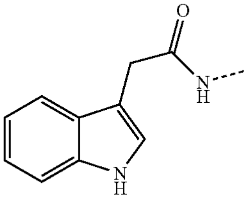 | Ex. 220 | L.1.3 | 3-indoleacetic acid (1.2 equiv.) HATU (1.5 equiv.) HOAt (1.5 equiv.) i-$Pr_2NEt$ (3 equiv.) | prep. HPLC, method 1 | 28% (TFA salt) |
| Ex. 226 | 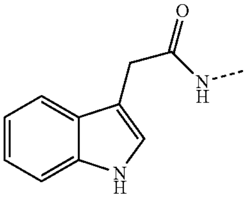 | 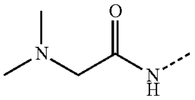 | Ex. 221 | L.1.3 | N,N-dimetyl glycine (1.7 equiv.) | prep. HPLC, method 1 | 45% (TFA salt) |
| Ex. 227 | 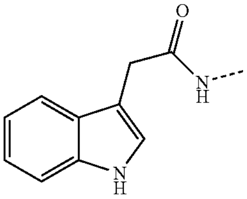 | 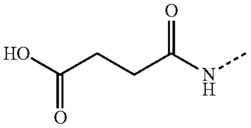 | Ex. 221 | L.1.1 | succinic anhydride (1.05 equiv.) pyridine (49 equiv.) | prep. HPLC, method 1 | 49% |
| Ex. 228 | 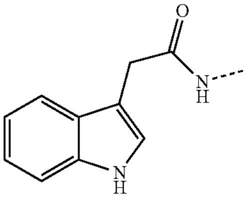 | 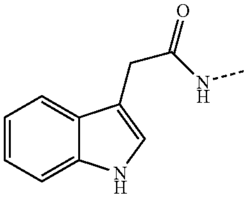 | Ex. 221 | L.1.3 | 3-indoleacetic acid (1.2 equiv.) HATU (1.5 equiv.) HOAt (1.5 equiv.) i-$Pr_2NEt$ (3 equiv.) | prep. HPLC, method 1 | 33% |
| Ex. 229 | 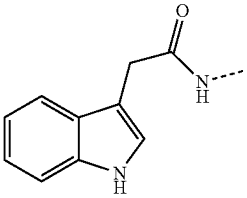 | 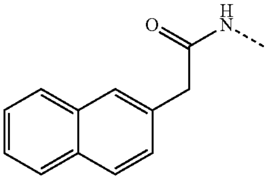 | Ex. 221 | L.1.3 | 2-naphthylacetic acid (1.2 equiv.) | prep. HPLC, method 1 | 56% |

TABLE 31a-continued

| Examples of Core 13 (Ex. 215-Ex. 230; continued on the following pages) | | | | | | | |
|---|---|---|---|---|---|---|---|
| No | $R^2$ | $R^5$ | Starting material | General Pro-cedure | Reagent | Purification Method | Yield (isolated salt) |
| Ex. 230 | 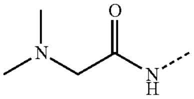 | 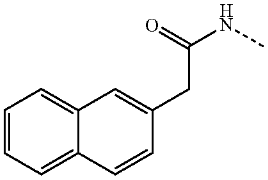 | Ex. 220 | L.1.3 | 2-naphthylacetic acid (1.2 equiv.) | prep. HPLC, method 1 | 52% (TFA salt) |

*⁾Analytical sample further purified by prep. HPLC, method 1 to afford the TFA salt of the product TABLE 31b

| Examples of Core 13 (Ex. 215-Ex. 230; continued on the following pages) | | | | | | | |
|---|---|---|---|---|---|---|---|
| No | $R^2$ | $R^5$ | FORMULA | MONO-ISOTOPIC MASS | Rt (purity at 220 nm) | $[M + H]^+$ found | LC-MS-Method |
| Ex. 215-Ex. 216: cf. experimental description | | | | | | | |
| Ex. 217 | 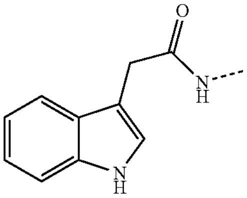 | 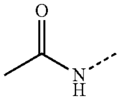 | C31H36N6O6 | 588.3 | 1.82 (94) | 589.2 | Method 1b |
| Ex. 218 | 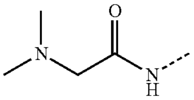 | 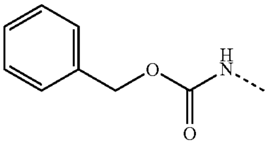 | C31H40N6O7 | 608.3 | 1.36 (100) | 609.2 | Method 4b |
| Ex. 219 | 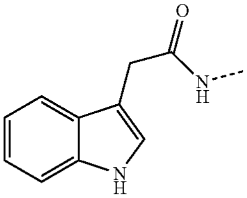 | 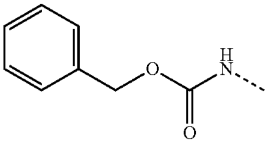 | C37H40N6O7 | 680.3 | 1.64 (96) | 681.3 | Method 2 |
| Ex. 220 | 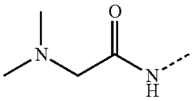 | $NH_2$ | C23H34N6O5 | 474.3 | 1.19 (92) | 475.2 | Method 5b |
| Ex. 221 | 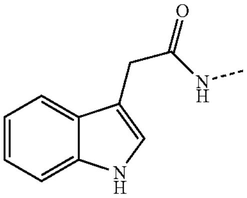 | $NH_2$ | C29H34N6O5 | 546.3 | 1.38 (96) | 547.2 | Method 4b |
| Ex. 222 | 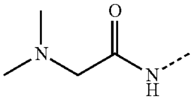 | 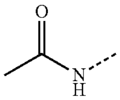 | C25H36N6O6 | 516.3 | 1.23 (97) | 517.2 | Method 5b |

TABLE 31b-continued
Examples of Core 13 (Ex. 215-Ex. 230; continued on the following pages)
| No | $R^2$ | $R^5$ | FORMULA | MONO-ISOTOPIC MASS | Rt (purity at 220 nm) | $[M + H]^+$ found | LC-MS-Method |
|---|---|---|---|---|---|---|---|
| Ex. 223 | 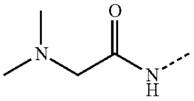 | 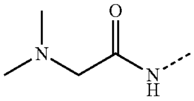 | C27H41N7O6 | 559.3 | 1.33 (94) | 560.3 | Method 5b |
| Ex. 224 | 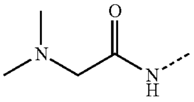 | 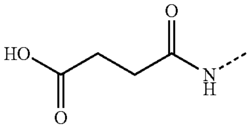 | C27H38N6O8 | 574.3 | 1.04 (100) | 575.2 | Method 5b |
| Ex. 225 | 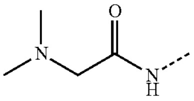 | 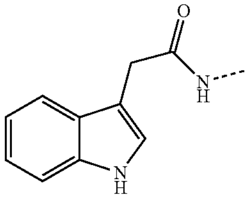 | C33H41N7O6 | 631.3 | 1.30 (97) | 632.3 | Method 4b |
| Ex. 226 | 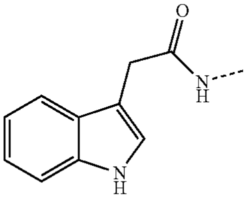 | 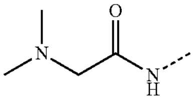 | C33H41N7O6 | 631.3 | 1.39 (92) | 632.2 | Method 4b |
| Ex. 227 | 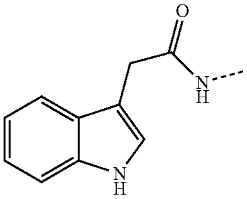 | 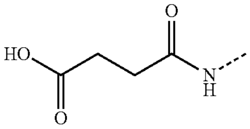 | C33H38N6O8 | 646.3 | 1.49 (94) | 647.2 | Method 4b |
| Ex. 228 | 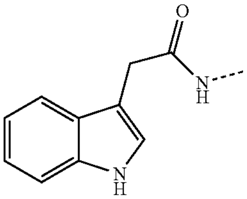 | 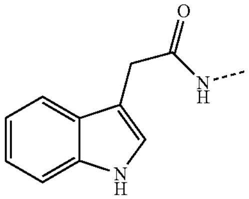 | C39H41N7O6 | 703.3 | 1.75 (91) | 704.3 | Method 4b |
| Ex. 229 | 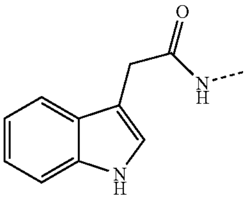 | 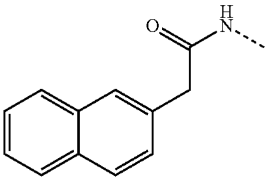 | C41H42N6O6 | 714.3 | 1.91 (92) | 715.3 | Method 4b |
| Ex. 230 | 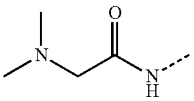 | 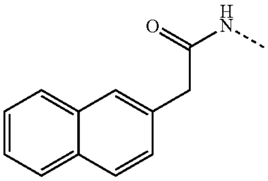 | C35H42N6O6 | 642.3 | 1.50 (100) | 643.2 | Method 4b |

TABLE 31c

| Examples of Core 13 (Ex. 215-Ex. 230; continued on the following pages) | | | |
|---|---|---|---|
| No | $R^2$ | $R^5$ | IUPAC name |
| Ex. 215 | 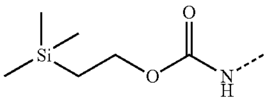 | 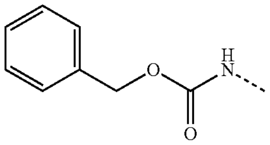 | benzyl N-[(4S,6R,13S)-11,15-dimethyl-9,12,16-trioxo-6-({[2-(trimethylsilyl)ethoxy]carbonyl}amino)-2-oxa-8,11,15-triazatricyclo[15.3.1.0$^{4,8}$]henicosa-1(21),17,19-trien-13-yl]carbamate |
| Ex. 216 | $NH_2$ | 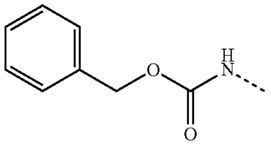 | benzyl N-[(4S,6R,13S)-6-amino-11,15-dimethyl-9,12,16-trioxo-2-oxa-8,11,15-triazatricyclo[15.3.1.0$^{4,8}$]henicosa-1(21),17,19-trien-13-yl]carbamate |
| Ex. 217 | 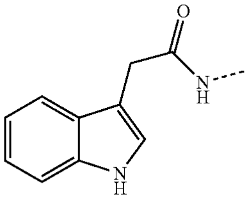 | 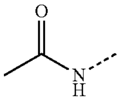 | N-[(4S,6R,13S)-13-(acetylamino)-11,15-dimethyl-9,12,16-trioxo-2-oxa-8,11,15-triazatricyclo[15.3.1.0$^{4,8}$]henicosa-1(21),17,19-trien-6-yl]-2-(1H-indol-3-yl)acetamide |
| Ex. 218 | 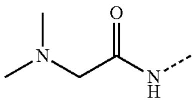 | 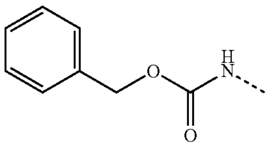 | benzyl N-[(4S,6R,13S)-6-{[2-(dimethylamino)acetyl]amino}-11,15-dimethyl-9,12,16-trioxo-2-oxa-8,11,15-triazatricyclo[15.3.1.0$^{4,8}$]henicosa-1(21),17,19-trien-13-yl]carbamate |
| Ex. 219 | 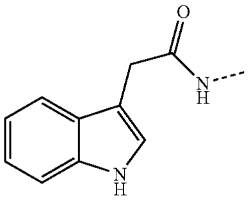 | 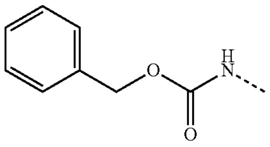 | benzyl N-[(4S,6R,13S)-6-{[2-(1H-indol-3-yl)acetyl]amino}-11,15-dimethyl-9,12,16-trioxo-2-oxa-8,11,15-triazatricyclo[15.3.1.0$^{4,8}$]henicosa-1(21),17,19-trien-13-yl]carbamate |
| Ex. 220 | 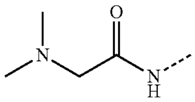 | $NH_2$ | N-[(4S,6R,13S)-13-amino-11,15-dimethyl-9,12,16-trioxo-2-oxa-8,11,15-triazatricyclo[15.3.1.0$^{4,8}$]henicosa-1(21),17,19-trien-6-yl]-2-(dimethylamino)acetamide |
| Ex. 221 | 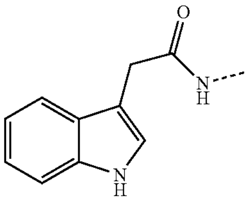 | $NH_2$ | N-[(4S,6R,13S)-13-amino-11,15-dimethyl-9,12,16-trioxo-2-oxa-8,11,15-triazatricyclo[15.3.1.0$^{4,8}$]henicosa-1(21),17,19-trien-6-yl]-2-(1H-indol-3-yl)acetamide |
| Ex. 222 | 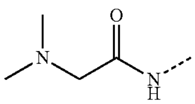 | 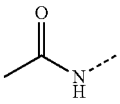 | N-[(4S,6R,13S)-13-(acetylamino)-11,15-dimethyl-9,12,16-trioxo-2-oxa-8,11,15-triazatricyclo[15.3.1.0$^{4,8}$]henicosa-1(21),17,19-trien-6-yl]-2-(dimethylamino)acetamide |
| Ex. 223 | 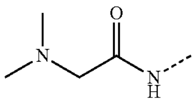 | 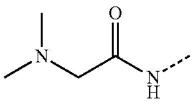 | 2-(dimethylamino)-N-[(4S,6R,13S)-13-{[2-(dimethylamino)acetyl]amino}-11,15-dimethyl-9,12,16-trioxo-2-oxa-8,11,15-triazatricyclo[15.3.1.0$^{4,8}$]henicosa-1(21),17,19-trien-6-yl]acetamide |

TABLE 31c-continued

| Examples of Core 13 (Ex. 215-Ex. 230; continued on the following pages) | | | |
|---|---|---|---|
| No | $R^2$ | $R^5$ | IUPAC name |
| Ex. 224 | 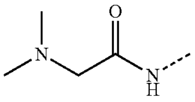 | 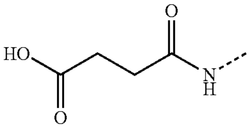 | 4-{[(4S,6R,13S)-6-{[2-(dimethylamino)acetyl]amino}-11,15-dimethyl-9,12,16-trioxo-2-oxa-8,11,15-triazatricyclo[15.3.1.0$^{4,8}$]henicosa-1(21),17,19-trien-13-yl]amino}-4-oxobutanoic acid |
| Ex. 225 | 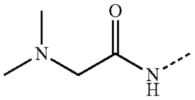 | 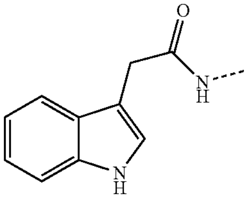 | 2-(dimethylamino)-N-[(4S,6R,13S)-13-{[2-(1H-indol-3-yl)acetyl]amino}-11,15-dimethyl-9,12,16-trioxo-2-oxa-8,11,15-triazatricyclo[15.3.1.0$^{4,8}$]henicosa-1(21),17,19-trien-6-yl]acetamide |
| Ex. 226 | 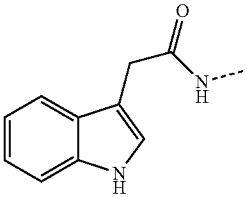 | 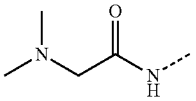 | 2-(dimethylamino)-N-[(4S,6R,13S)-6-{[2-(1H-indol-3-yl)acetyl]amino}-11,15-dimethyl-9,12,16-trioxo-2-oxa-8,11,15-triazatricyclo[15.3.1.0$^{4,8}$]henicosa-1(21),17,19-trien-13-yl]acetamide |
| Ex. 227 | 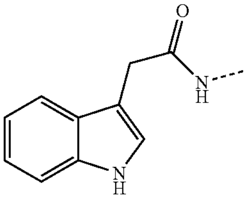 | 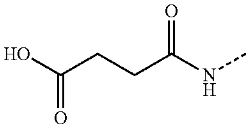 | 4-{[(4S,6R,13S)-6-{[2-(1H-indol-3-yl)acetyl]amino}-11,15-dimethyl-9,12,16-trioxo-2-oxa-8,11,15-triazatricyclo[15.3.1.0$^{4,8}$]henicosa-1(21),17,19-trien-13-yl]amino}-4-oxobutanoic acid |
| Ex. 228 | 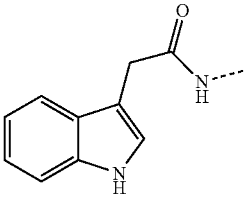 | 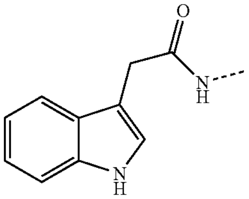 | 2-(1H-indol-3-yl)-N-[(4S,6R,13S)-13-{[2-(1H-indol-3-yl)acetyl]amino}-11,15-dimethyl-9,12,16-trioxo-2-oxa-8,11,15-triazatricyclo[15.3.1.0$^{4,8}$]henicosa-1(21),17,19-trien-6-yl]acetamide |
| Ex. 229 | 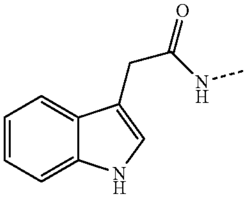 | 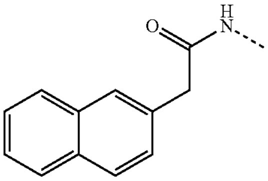 | N-[(4S,6R,13S)-11,15-dimethyl-13-{[2-(2-naphthyl)acetyl] amino}-9,12,16-trioxo-2-oxa-8,11,15-triazatricyclo[15.3.1.0$^{4,8}$]henicosa-1(21),17,19-trien-6-yl]-2-(1H-indol-3-yl)acetamide |
| Ex. 230 | 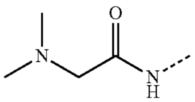 | 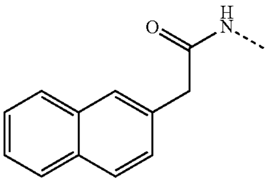 | 2-(dimethylamino)-N-[(4S,6R,13S)-11,15-dimethyl-13-{[2-(2-naphthyl)acetyl]amino}-9,12,16-trioxo-2-oxa-8,11,15-triazatricyclo[15.3.1.0$^{4,8}$]henicosa-1(21),17,19-trien-6-yl]acetamide |

TABLE 32a

Examples of Core 14 (Ex. 231-Ex. 237)

| No | $R^2$ | $R^5$ | Starting material | General Procedure | Reagent | Purification Method | Yield (isolated salt) |
|---|---|---|---|---|---|---|---|
| Ex. 231-Ex. 232: cf. experimental description | | | | | | | |
| Ex. 233 | 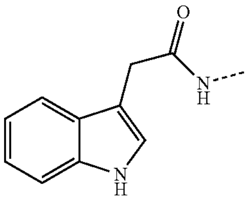 | 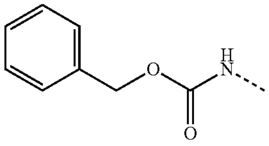 | Ex. 232 •TFA | L.1.3 | 3-indoleacetic acid (1.5 equiv.) HATU (1.5 equiv.) HOAt (1.5 equiv.) i-$Pr_2NEt$ (5 equiv) | FC (EtOAc, then $CH_2Cl_2$/MeOH) | 68% |
| Ex. 234 | 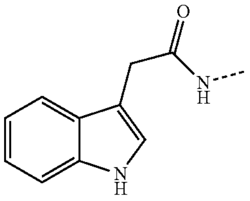 | $NH_2$ | Ex. 233 | K.1 | $H_2$, $Pd(OH)_2$—C | crude product | 99% |
| Ex. 235 | 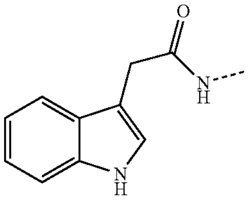 | 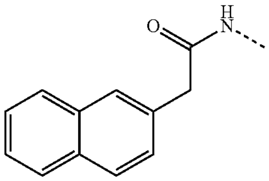 | Ex. 234 | L.1.3 | 2-naphthylacetic acid (1.2 equiv.) | prep. HPLC, method 3 | 68% |
| Ex. 236 | 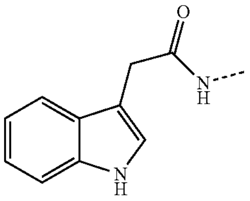 | 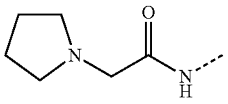 | Ex. 234 | L.1.3 | pyrrolidin-1-acetic acid (1, 2 equiv.) | prep. HPLC method 3 | 28% |
| Ex. 237 | 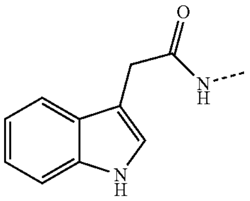 | 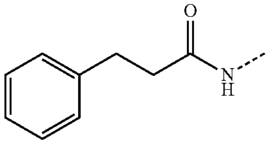 | Ex. 234 | L.1.3 | 3-phenyl-propionic acid | prep. HPLC, method 3 | 66% |

TABLE 32b

| Examples of Core 14 (Ex. 231-Ex. 237) | | | | | | | |
|---|---|---|---|---|---|---|---|
| No | $R^2$ | $R^5$ | FORMULA | MONO-ISOTOPIC MASS | Rt (purity at 220 nm) | $[M + H]^+$ found | LC-MS-Method |
| Ex. 231-Ex. 232: cf. experimental description | | | | | | | |
| Ex. 233 | 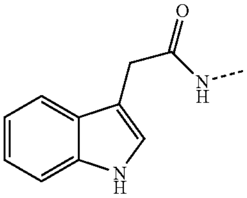 | 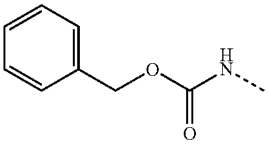 | C37H40N6O7 | 680.3 | 1.80 (96) | 681.4 | Method 2 |
| Ex. 234 | 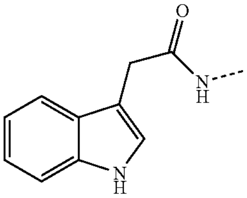 | $NH_2$ | C29H34N6O5 | 546.3 | 1.47 (93) | 547.3 | Method 2 |
| Ex. 235 | 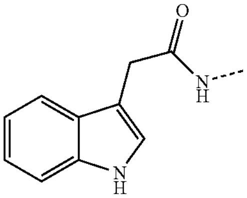 | 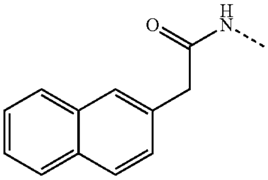 | C41H42N6O6 | 714.3 | 1.80 (90) | 715.4 | Method 2 |
| Ex. 236 | 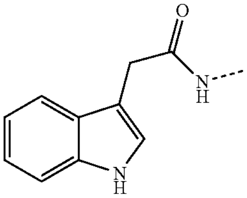 | 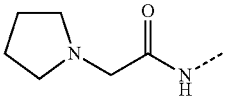 | C35H43N7O6 | 657.3 | 1.45 (94) | 658.4 | Method 2 |
| Ex. 237 | 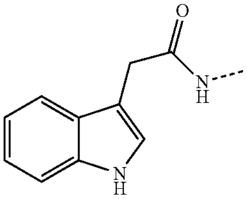 | 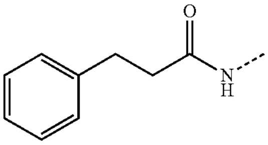 | C38H42N6O6 | 678.3 | 1.81 (96) | 679.4 | Method 2 |

TABLE 32c

| Examples of Core 14 (Ex. 231-Ex. 237) | | | |
|---|---|---|---|
| No | $R^2$ | $R^5$ | IUPAC name |
| Ex. 231 | 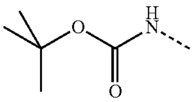 | 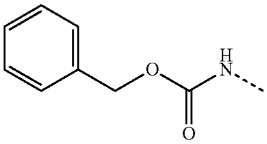 | benzyl N-[(4S,6S,13R)-6-[(tert-butoxycarbonyl)amino]-11,15-dimethyl-9,12,16-trioxo-2-oxa-8,11,15-triazatricyclo[15.3.1.0$^{4,8}$]henicosa-1(21),17,19-trien-13-yl]carbamate |

TABLE 32c-continued

| Examples of Core 14 (Ex. 231-Ex. 237) | | | |
|---|---|---|---|
| No | $R^2$ | $R^5$ | IUPAC name |
| Ex. 232 | $NH_2$ | 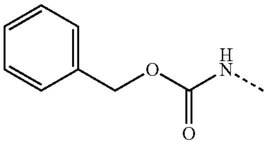 | benzyl N-{(4S,6S,13R)-6-amino-11,15-dimethyl-9,12,16-trioxo-2-oxa-8,11,15-triazatricyclo[15.3.1.0$^{4,8}$]henicosa-1(21),17,19-trien-13-yl]carbamate |
| Ex. 233 | 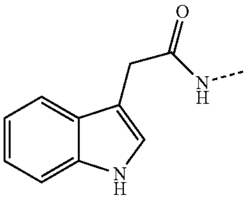 | 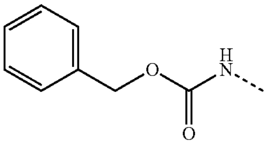 | benzyl N-[(4S,6S,13R)-6-{[2-(1H-indol-3-yl)acetyl]amino}-11,15-dimethyl-9,12,16-trioxo-2-oxa-8,11,15-triazatricyclo[15.3.1.0$^{4,8}$]henicosa-1(21),17,19-trien-13-yl]carbamate |
| Ex. 234 | 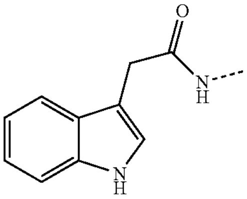 | $NH_2$ | N-[(4S,6S,13R)-13-amino-11,15-dimethyl-9,12,16-trioxo-2-oxa-8,11,15-triazatricyclo[15.3.1.0$^{4,8}$]henicosa-1(21),17,19-trien-6-yl]-2-(1H-indol-3-yl)acetamide |
| Ex. 235 | 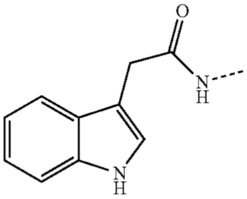 | 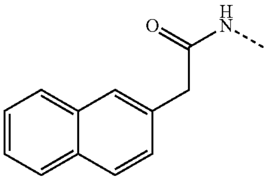 | N-[(4S,6S,13R)-11,15-dimethyl-13-{[2-(2-naphthyl)acetyl] amino}-9,12,16-trioxo-2-oxa-8,11,15-triazatricyclo[15.3.1.0$^{4,8}$]henicosa-1(21),17,19-trien-6-yl]-2-(1H-indol-3-yl)acetamide |
| Ex. 236 | 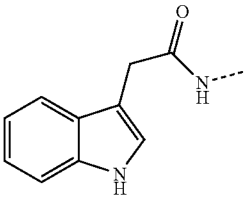 | 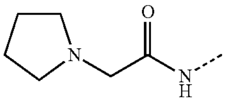 | N-[(4S,6S,13R)-11,15-dimethyl-9,12,16-trioxo-13-{[2-(1-pyrrolidinyl)acetyl]amino}-2-oxa-8,11,15-triazatricyclo[15.3.1.0$^{4,8}$]henicosa-1(21),17,19-trien-6-yl]-2-(1H-indol-3-yl)acetamide |
| Ex. 237 | 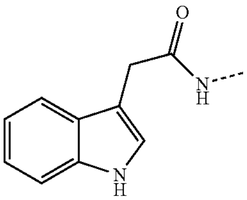 | 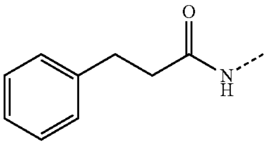 | N-[(4S,6S,13R)-6-{[2-(1H-indol-3-yl)acetyl]amino}-11,15-dimethyl-9,12,16-trioxo-2-oxa-8,11,15-triazatricyclo[15.3.1.0$^{4,8}$]henicosa-1(21),17,19-trien-13-yl]-3-phenylpropanamide |

TABLE 33a

Examples of Core 15 and Core 16 (Ex. 238-Ex. 247; continued on the following page)

| No | $R^2$ | $R^5$ | Starting material | General Pro-cedure | Reagent | Purification Method | Yield (isolated salt) |
|---|---|---|---|---|---|---|---|
| Ex. 238-Ex. 239: cf. experimental description | | | | | | | |
| Ex. 240 | 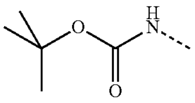 | 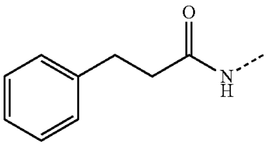 | Ex. 239 | L.1.3 | 3-phenyl-poanoic acid | FC (EtOAc/MeOH)*) | 47% |
| Ex. 241 | 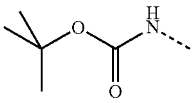 | 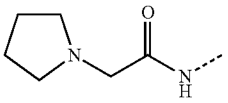 | Ex. 239 | L.1.3 | pyrrolidin-1-acetic acid | FC ($CH_2Cl_2$/MeOH/aq. $NH_3$) | 56% |
| Ex. 242 | $NH_2$ | 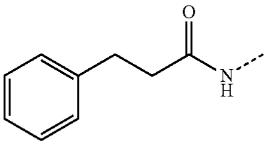 | Ex. 240 | J | HCl-dioxane | crude product | quant. (HCl salt) |
| Ex. 243 | $NH_2$ | 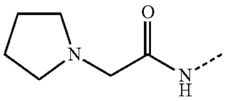 | Ex. 241 | J | HCl-dioxane | crude product | quant. (HCl salt) |
| Ex. 244 | 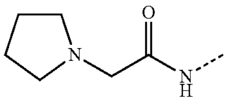 | 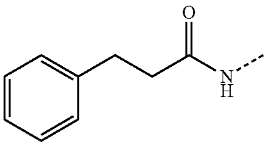 | Ex. 242 | L.1.3 | pyrrolidin-1-acetic acid | FC ($CH_2Cl_2$/MeOH/aq. $NH_3$) | 81% |
| Ex. 245 | 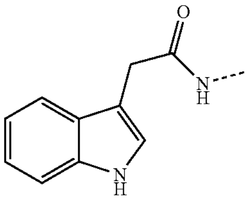 | 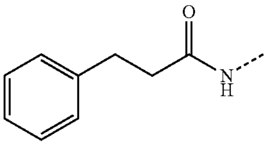 | Ex. 242 | L.1.3 | 3-indoleacetic acid | FC ($CH_2Cl_2$/MeOH/aq. $NH_3$) | 59% |
| Ex. 246 | 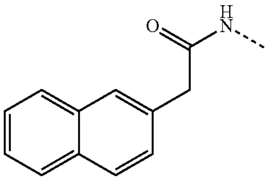 | 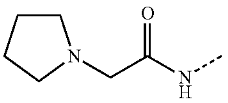 | Ex. 243 | L.1.3 | 2-naphthyl-acetic acid | FC ($CH_2Cl_2$/MeOH/aq. $NH_3$) | 51% |
| Ex. 247 | 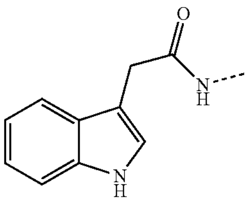 | 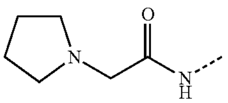 | Ex. 243 | L.1.3 | 3-indoleacetic acid | FC ($CH_2Cl_2$/MeOH/aq. $NH_3$) | 58% |

*)An analytical sample was further purified by prep. HPLC, method 2

TABLE 33b
Examples of Core 15 and Core 16 (Ex. 238-Ex. 247; continued on the following page)
| No | $R^2$ | $R^5$ | FORMULA | MONO-ISOTOPIC MASS | Rt (purity at 220 nm) | $[M + H]^+$ found | LC-MS-Method |
|---|---|---|---|---|---|---|---|
| Ex. 238-Ex. 239: cf. experimental description | | | | | | | |
| Ex. 240 | 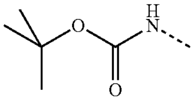 | 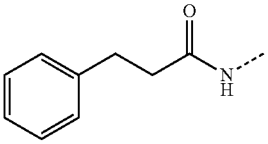 | C33H44N4O6 | 592.3 | 2.12 (90) | 593.3 | Method 4a |
| Ex. 241 | 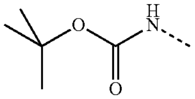 | 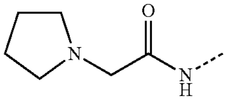 | C30H45N5O6 | 571.3 | 1.58 (91') | 572.3 | Method 4a |
| Ex. 242 | $NH_2$ | 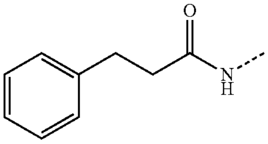 | C28H36N4O4 | 492.3 | 1.53 (88), 1.59 (6) | 493.2 | Method 4a |
| Ex. 243 | $NH_2$ | 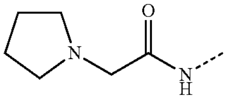 | C25H37N5O4 | 471.3 | 1.08 (91) | 472.4 | Method 4a |
| Ex. 244 | 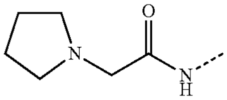 | 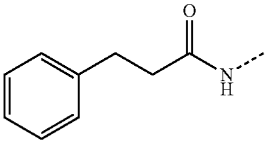 | C34H45N5O5 | 603.3 | 1.63 (93) | 604.4 | Method 4a |
| Ex. 245 | 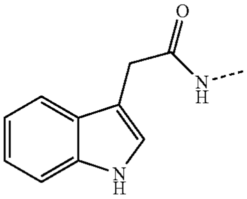 | 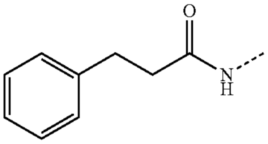 | C38H43N5O5 | 649.3 | 2.01 (91) | 650.3 | Method 4a |
| Ex. 246 | 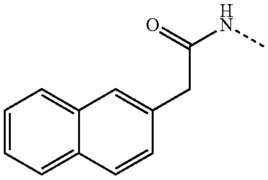 | 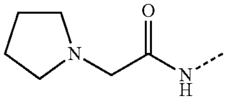 | C37H45N5O5 | 639.3 | 1.69 (90) | 640.3 | Method 4a |
| Ex. 247 | 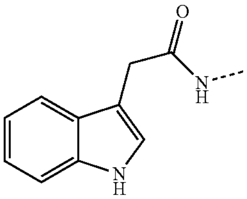 | 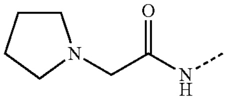 | C35H44N6O5 | 628.3 | 1.52 (94) | 629.3 | Method 4a |

TABLE 33c

Examples of Core 15 and Core 16 (Ex. 238-Ex. 247; continued on the following page)

| No | $R^2$ | $R^5$ | IUPAC name |
|---|---|---|---|
| | | Core 15 | |
| Ex. 238 | 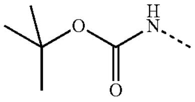 | 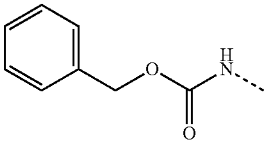 | benzyl N-[(4S,6S,10S)-6-[(tert-butoxycarbonyl)amino]-15-methyl-9,16-dioxo-2-oxa-8,15-diazatricyclo[15.3.1.0$^{4,8}$]henicosa-1(21),12,17,19-tetraen-10-yl]carbamate |
| | | Core 16 | |
| Ex. 239 | 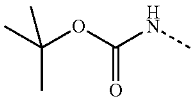 | $NH_2$ | tert-butyl N-[(4S,6S,10S)-10-amino-15-methyl-9,16-dioxo-2-oxa-8,15-diazatricyclo[15.3.1.0$^{4,8}$]henicosa-1(21),17,19-trien-6-yl]carbamate |
| Ex. 240 | 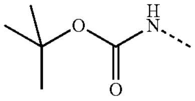 | 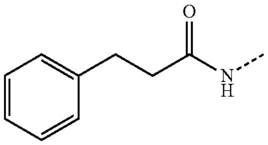 | tert-butyl N-[(4S,6S,10S)-15-methyl-9,16-dioxo-10-[(3-phenylpropanoyl)amino]-2-oxa-8,15-diazatricyclo[15.3.1.0$^{4,8}$]henicosa-1(21),17,19-trien-6-yl]carbamate |
| Ex. 241 | 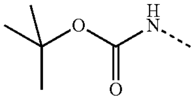 | 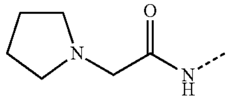 | tert-butyl N-[(4S,6S,10S)-15-methyl-9,16-dioxo-10-{[2-(1-pyrrolidinyl)acetyl]amino}-2-oxa-8,15-diazatricyclo[15.3.1.0$^{4,8}$]henicosa-1(21),17,19-trien-6-yl]carbamate |
| Ex. 242 | $NH_2$ | 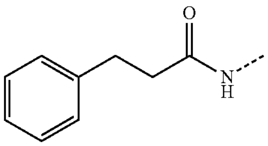 | N-[(4S,6S,10S)-6-amino-15-methyl-9,16-dioxo-2-oxa-8,15-diazatricyclo[15.3.1.0$^{4,8}$]henicosa-1(21),17,19-trien-10-yl]-3-phenylpropanamide |
| Ex. 243 | $NH_2$ | 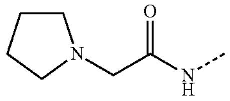 | N-[(4S,6S,10S)-6-amino-15-methyl-9,16-dioxo-2-oxa-8,15-diazatricyclo[15.3.1.0$^{4,8}$]henicosa-1(21),17,19-trien-10-yl]-2-(1-pyrrolidinyl)acetamide |
| Ex. 244 | 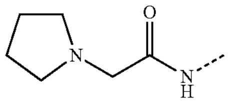 | 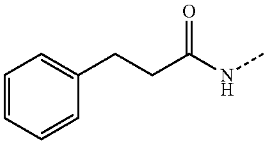 | N-[(4S,6S,10S)-15-methyl-9,16-dioxo-6-{[2-(1-pyrrolidinyl)acetyl]amino}-2-oxa-8,15-diazatricyclo[15.3.1.0$^{4,8}$]henicosa-1(21),17,19-trien-10-yl]-3-phenylpropanamide |
| Ex. 245 | 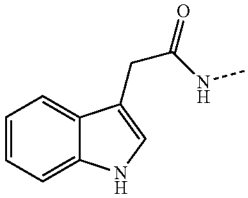 | 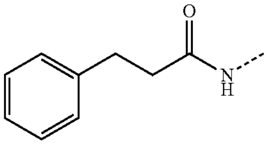 | N-[(4S,6S,10S)-6-{[2-(1H-indol-3-yl)acetyl]amino}-15-methyl-9,16-dioxo-2-oxa-8,15-diazatricyclo[15.3.1.0$^{4,8}$]henicosa-1(21),17,19-trien-10-yl]-3-phenylpropanamide |
| Ex. 246 | 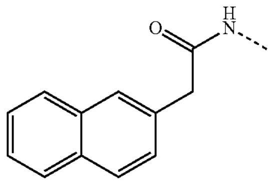 | 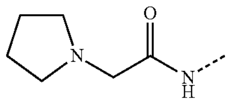 | N-[(4S,6S,10S)-15-methyl-9,16-dioxo-10-{[2-(1-pyrrolidinyl)acetyl]amino}-2-oxa-8,15-diazatricyclo[15.3.1.0$^{4,8}$]henicosa-1(21),17,19-trien-6-yl]-2-(2-naphthyl)acetamide |

TABLE 33c-continued

| Examples of Core 15 and Core 16 (Ex. 238-Ex. 247; continued on the following page) | | | |
|---|---|---|---|
| No | $R^2$ | $R^5$ | IUPAC name |
| Ex. 247 | 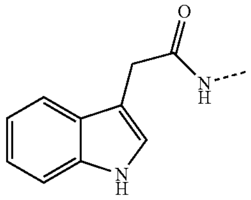 | 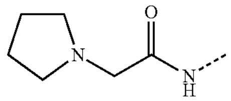 | 2-(1H-indol-3-yl)-N-[(4S,6S,10S)-15-methyl-9,16-dioxo-10-{[2-(1-pyrrolidinyl)acetyl]amino}-2-oxa-8,15-diazatricyclo[15.3.1.0$^{4,8}$]henicosa-1(21),17,19-trien-6-yl]acetamide |

TABLE 34a

| Examples of Core 17 (Ex. 248-Ex. 271; continued on the following pages) | | | | | | | |
|---|---|---|---|---|---|---|---|
| No | $R^2$ | $R^{54}$ | Starting material | General Procedure | Reagent | Purification Method | Yield (isolated salt) |
| Ex. 248-Ex. 249: cf. experimental description | | | | | | | |
| Ex. 250 | 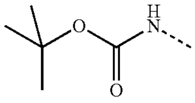 | 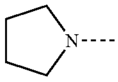 | Ex. 249 | L.2 | pyrrolidine | FC ($CH_2Cl_2$/MeOH) | 81% |
| Ex. 251 | 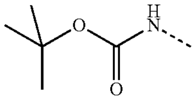 | 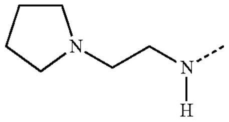 | Ex. 249 | L.2 | N-(2-aminoethyl) pyrrolidine | FC ($CH_2Cl_2$/MeOH/aq. $NH_3$ soln) | 88% |
| Ex. 252 | 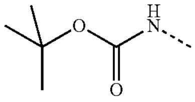 | 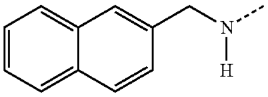 | Ex. 249 | L.2 | 2-naphthylmethyl-amine (1.5 equiv.) HATU (1.5 equiv.) HOAt (1.5 equiv.) i-$Pr_2$NEt (3 equiv.) | FC ($CH_2Cl_2$/MeOH) | 91% |
| Ex. 253 | 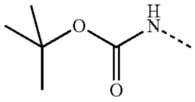 | 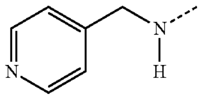 | Ex. 249 | L.2 | 4-(aminomethyl)-pyridine (1.5 equiv.) HATU (1.5 equiv.) HOAt (1.5 equiv.) i-$Pr_2$NEt (3 equiv.) | FC ($CH_2Cl_2$/MeOH)*) | 97% |
| Ex. 254 | $NH_2$ | 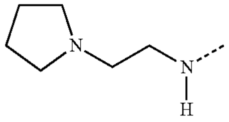 | Ex. 251 | J | HCl-dioxane | crude product | 96% (HCl salt) |
| Ex. 255 | $NH_2$ | 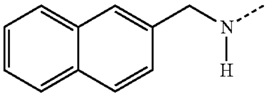 | Ex. 252 | J | HCl-dioxane | crude product | 100% (HCl salt) |
| Ex. 256 | $NH_2$ | 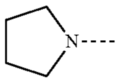 | Ex. 250 | J | HCl-dioxane | crude product | 93% (HCl salt) |
| Ex. 257 | $NH_2$ | 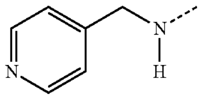 | Ex. 253 | J | HCl-dioxane | crude product | 91% (HCl salt) |

TABLE 34a-continued

Examples of Core 17 (Ex. 248-Ex. 271; continued on the following pages)

| No | $R^2$ | $R^{54}$ | Starting material | General Procedure | Reagent | Purification Method | Yield (isolated salt) |
|---|---|---|---|---|---|---|---|
| Ex. 258 | 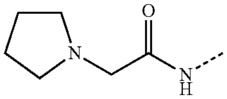 | 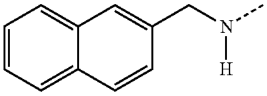 | Ex. 255 | L.1.2 | 1-pyrrolidinacetic acid (2.7 equiv.) i-$Pr_2NEt$ v(4 equiv.) | FC ($CH_2Cl_2$/MeOH) | 61% |
| Ex. 259 | 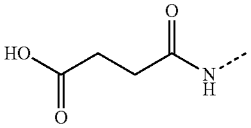 | 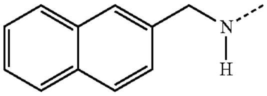 | Ex. 255 | L.1.1 | succininc anhydride (1.05 equiv.) pyridine (49 equiv.) | prep. HPLC, method 1 | 15% |
| Ex. 260 | 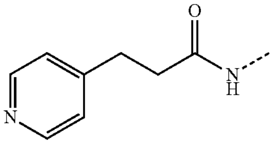 | 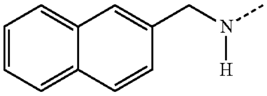 | Ex. 255 | L.1.2 | 3-(pyridine-4-yl)propanoic acid | prep. HPLC, method 1 | 55% (TFA salt) |
| Ex. 261 | 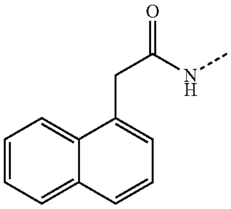 | 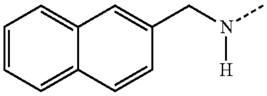 | Ex. 255 | L.1.3 | 1-naphthylacetic acid (1.2 equiv.) | prep. HPLC, method 1 | 69% |
| Ex. 262 | 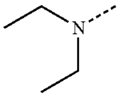 | 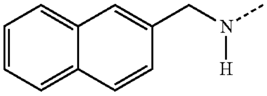 | Ex. 255 | M.1 | acetaldehyde | prep. HPLC, method 1 | 76% (TFA salt) |
| Ex. 263 | 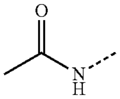 | 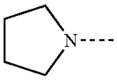 | Ex. 256 | L.1.1 | acetic anhydride (10 equiv.) Pyridine/$CH_2Cl_2$ 1:1 (3 mL) | prep. HPLC, method 1 | 82% |
| Ex. 264 | 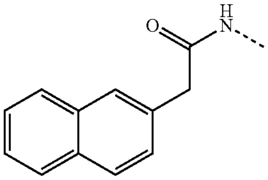 | 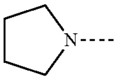 | Ex. 256 | L.1.3 | 2-naphthylacetic acid (1.2 equiv.) | prep. HPLC, method 1 | 61% |
| Ex. 265 | 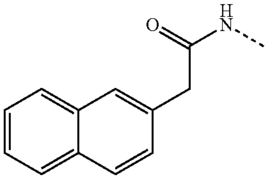 | 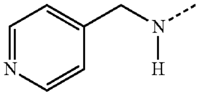 | Ex. 257 | L.1.3 | 2-naphthylacetic acid (1.2 equiv.) | prep. HPLC, method 1 | 59% (TFA salt) |
| Ex. 266 | 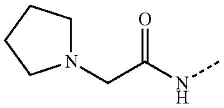 | 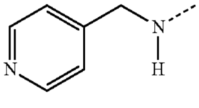 | Ex. 257 | L.1.2 | 1-pyrrolidinacetic acid | prep. HPLC, method 2 | 71% |
| Ex. 267 | 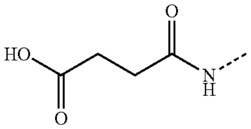 | 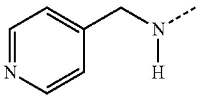 | Ex. 257 | L.1.1 | succininc anhydride (1.5 equiv.) pyridine (49 equiv.) | prep. HPLC, method 1 | 89% |

TABLE 34a-continued

Examples of Core 17 (Ex. 248-Ex. 271; continued on the following pages)

| No | $R^2$ | $R^{54}$ | Starting material | General Procedure | Reagent | Purification Method | Yield (isolated salt) |
|---|---|---|---|---|---|---|---|
| Ex. 268 | 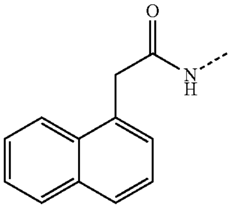 | 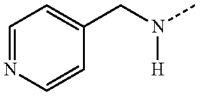 | Ex. 257 | L.1.3 | 1-naphthylacetic acid (1.2 equiv.) | prep. HPLC, method 2 | 45% |
| Ex. 269 | 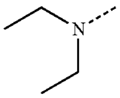 | 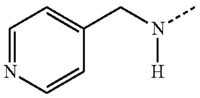 | Ex. 257 | M.1 | acetaldehyde (0.75 mL) | prep. HPLC, method 2 | 70% |
| Ex. 270 | 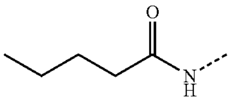 | 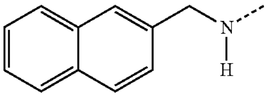 | Ex. 255 | L.1.1 | valeroyl chloride (2 equiv.) | prep. HPLC, method 1 | 77% |
| Ex. 271 | 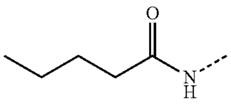 | 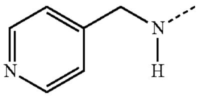 | Ex. 257 | L.1.1 | valeroyl chloride (2 equiv.) | prep. HPLC, method 1 | 58% (TFA salt) |

*)An analytical sample was further purified by prep HPLC, method 1

TABLE 34b

Examples of Core 17 (Ex. 248-Ex. 271; continued on the following pages)

| No | $R^2$ | $R^{54}$ | FORMULA | MONO-ISOTOPIC MASS | Rt (purity at 220 nm) | $[M + H]^+$ found | LC-MS-Method |
|---|---|---|---|---|---|---|---|
| Ex. 248-Ex. 249: cf. experimental description | | | | | | | |
| Ex. 250 | 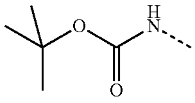 | 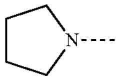 | C30H43N5O7 | 585.4 | 1.58 (96) | 586.4 | Method 2 |
| Ex. 251 | 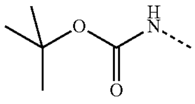 | 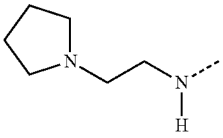 | C32H48N6O7 | 628.4 | 1.35 (98) | 629.5 | Method 2 |
| Ex. 252 | 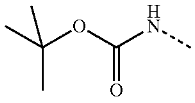 | 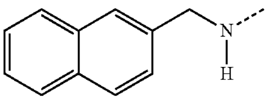 | C37H45N5O7 | 671.3 | 1.86 (88) | 672.4 | Method 2 |
| Ex. 253 | 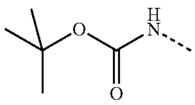 | 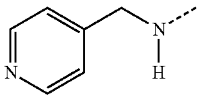 | C32H42N6O7 | 622.3 | 1.29 (92) | 623.4 | Method 2 |

TABLE 34b-continued
Examples of Core 17 (Ex. 248-Ex. 271; continued on the following pages)
| No | $R^2$ | $R^{54}$ | FORMULA | MONO-ISOTOPIC MASS | Rt (purity at 220 nm) | $[M + H]^+$ found | LC-MS-Method |
|---|---|---|---|---|---|---|---|
| Ex. 254 | $NH_2$ | 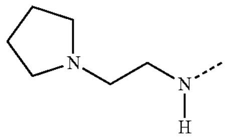 | C27H40N6O5 | 528.3 | 1.31 (97) | 529.5 | Method 3 |
| Ex. 255 | $NH_2$ | 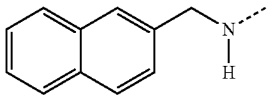 | C32H37N5O5 | 571.3 | 1.45 (94) | 572.4 | Method 2 |
| Ex. 256 | $NH_2$ | 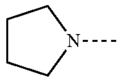 | C25H35N5O5 | 485.3 | 1.06 (96) | 486.4 | Method 2 |
| Ex. 257 | $NH_2$ | 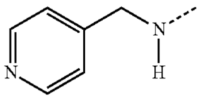 | C27H34N6O5 | 522.3 | 0.85 (96) | 523.3 | Method 2 |
| Ex. 258 | 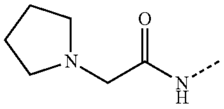 | 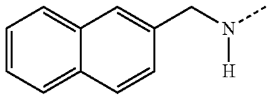 | C38H46N6O6 | 682.4 | 1.47 (95) | 683.5 | Method 2 |
| Ex. 259 | 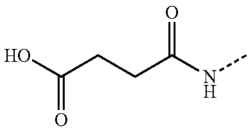 | 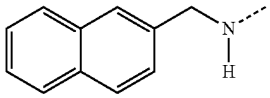 | C36H41N5O8 | 671.3 | 1.59 (87) | 672.4 | Method 2 |
| Ex. 260 | 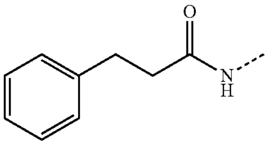 | 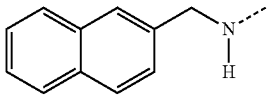 | C40H44N6O6 | 704.3 | 1.47 (100) | 705.5 | Method 2 |
| Ex. 261 | 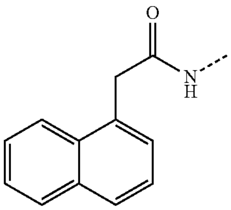 | 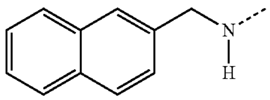 | C44H45N5O6 | 739.3 | 1.93 (99) | 740.5 | Method 2 |
| Ex. 262 | 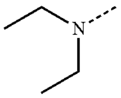 | 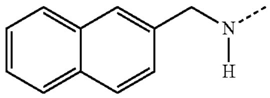 | C36H45N5O5 | 627.3 | 1.50 (100) | 628.5 | Method 2 |
| Ex. 263 | 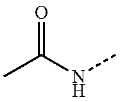 | 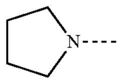 | C27H37N5O6 | 527.3 | 1.23 (99) | 528.3 | Method 2 |
| Ex. 264 | 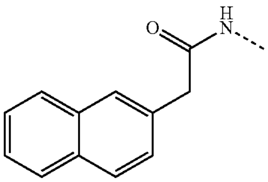 | 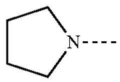 | C37H43N5O6 | 653.3 | 1.68 (100) | 654.4 | Method 2 |

TABLE 34b-continued

Examples of Core 17 (Ex. 248-Ex. 271; continued on the following pages)

| No | $R^2$ | $R^{54}$ | FORMULA | MONO-ISOTOPIC MASS | Rt (purity at 220 nm) | [M + H]$^+$ found | LC-MS-Method |
|---|---|---|---|---|---|---|---|
| Ex. 265 | 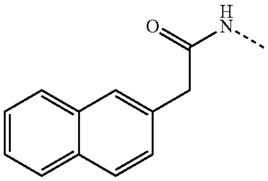 | 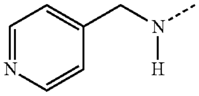 | C39H42N6O6 | 690.3 | 1.44 (99) | 691.5 | Method 2 |
| Ex. 266 | 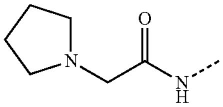 | 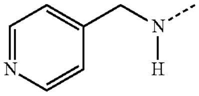 | C33H43N7O6 | 633.3 | 0.99 (94) | 634.5 | Method 2 |
| Ex. 267 | 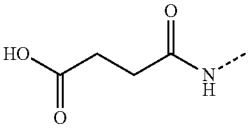 | 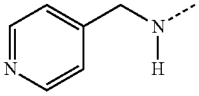 | C31H38N6O8 | 622.3 | 1.05 (94) | 623.3 | Method 2 |
| Ex. 268 | 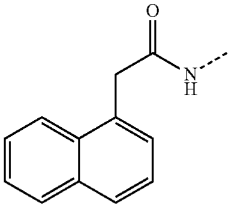 | 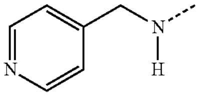 | C39H42N6O6 | 690.3 | 1.68 (93) | 691.5 | Method 3 |
| Ex. 269 | 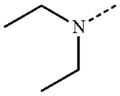 | 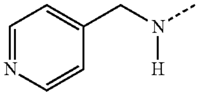 | C31H42N6O5 | 578.3 | 0.96 (96) | 579.5 | Method 2 |
| Ex. 270 | 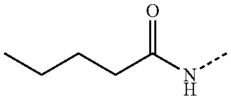 | 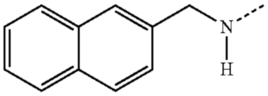 | C37H45N5O6 | 655.3 | 1.81 (100) | 656.4 | Method 2 |
| Ex. 271 | 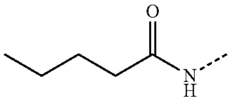 | 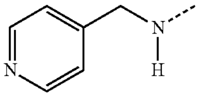 | C32H42N6O6 | 606.3 | 1.25 (100) | 607.4 | Method 2 |

TABLE 34c

Examples of Core 17 (Ex. 248-Ex. 271; continued on the following pages)

| No | $R^2$ | $R^{54}$ | IUPAC name |
|---|---|---|---|
| Ex. 248 | 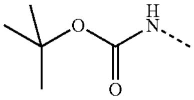 | $OCH_2Ph$ | benzyl (4S,6R,15S)-6-[(tert-butoxycarbonyl)amino]-11,16-dimethyl-9,12,17-trioxo-2-oxa-8,11,16-triazatricyclo[16.2.2.0$^{4,8}$]docosa-1(20),18,21-triene-15-carboxylate |
| Ex. 249 | 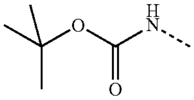 | OH | (4S,6R,15S)-6-[(tert-butoxycarbonyl)amino]-11,16-dimethyl-9,12,17-trioxo-2-oxa-8,11,16-triazatricyclo[16.2.2.0$^{4,8}$]docosa-1(20),18,21-triene-15-carboxylic acid |

TABLE 34c-continued

Examples of Core 17 (Ex. 248-Ex. 271; continued on the following pages)

| No | $R^2$ | $R^{54}$ | IUPAC name |
|---|---|---|---|
| Ex. 250 | 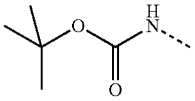 | 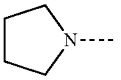 | tert-butyl N-[(4S,6R,15S)-11,16-dimethyl-9,12,17-trioxo-15-(1-pyrrolidinylcarbonyl)-2-oxa-8,11,16-triazatricyclo[16.2.2.$0^{4,8}$]docosa-1(20),18,21-trien-6-yl]carbamate |
| Ex. 251 | 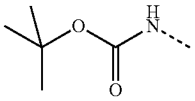 | 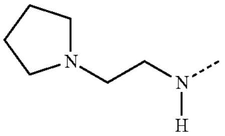 | tert-butyl N-[(4S,6R,15S)-11,16-dimethyl-9,12,17-trioxo-15-({[2-(1-pyrrolidinyl)ethyl]amino}carbonyl)-2-oxa-8,11,16-triazatricyclo[16.2.2.$0^{4,8}$]docosa-1(20),18,21-trien-6-yl]carbamate |
| Ex. 252 | 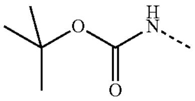 | 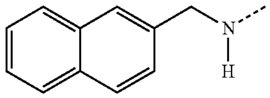 | tert-butyl N-[(4S,6R,15S)-11,16-dimethyl-15-{[(2-naphthylmethyl)amino]carbonyl}-9,12,17-trioxo-2-oxa-8,11,16-triazatricyclo[16.2.2.$0^{4,8}$]docosa-1(20),18,21-trien-6-yl]carbamate |
| Ex. 253 | 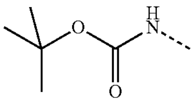 | 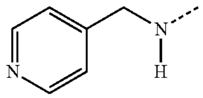 | tert-butyl N-[(4S,6R,15S)-11,16-dimethyl-9,12,17-trioxo-15-{[(4-pyridinylmethyl)amino]carbonyl}-2-oxa-8,11,16-triazatricyclo[16.2.2.$0^{4,8}$]docosa-1(20),18,21-trien-6-yl]carbamate |
| Ex. 254 | $NH_2$ | 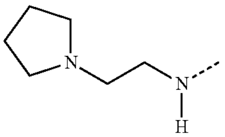 | (4S,6R,15S)-6-amino-11,16-dimethyl-9,12,17-trioxo-N-[2-(1-pyrrolidinyl)ethyl]-2-oxa-8,11,16-triazatricyclo[16.2.2.$0^{4,8}$]docosa-1(20),18,21-triene-15-carboxamide |
| Ex. 255 | $NH_2$ | 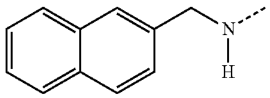 | (4S,6R,15S)-6-amino-11,16-dimethyl-N-(2-naphthylmethyl)-9,12,17-trioxo-2-oxa-8,11,16-triazatricyclo[16.2.2.$0^{4,8}$]docosa-1(20),18,21-triene-15-carboxamide |
| Ex. 256 | $NH_2$ | 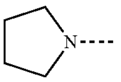 | (4S,6R,15S)-6-amino-11,16-dimethyl-15-(1-pyrrolidinyl-carbonyl)-2-oxa-8,11,16-triazatricyclo[16.2.2.$0^{4,8}$]docosa-1(20),18,21-triene-9,12,17-trione |
| Ex. 257 | $NH_2$ | 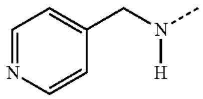 | (4S,6R,15S)-6-amino-11,16-dimethyl-9,12,17-trioxo-N-(4-pyridinylmethyl)-2-oxa-8,11,16-triazatricyclo[16.2.2.$0^{4,8}$]docosa-1(20),18,21-triene-15-carboxamide |
| Ex. 258 | 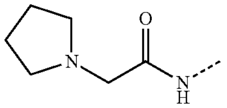 | 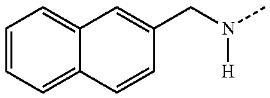 | (4S,6R,15S)-11,16-dimethyl-N-(2-naphthylmethyl)-9,12,17-trioxo-6-{[2-(1-pyrrolidinyl)acetyl]amino}-2-oxa-8,11,16-triazatricyclo[16.2.2.$0^{4,8}$]docosa-1(20),18,21-triene-15-carboxamide |
| Ex. 259 | 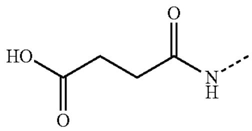 | 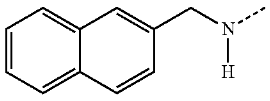 | 4-{[(4S,6R,15S)-11,16-dimethyl-15-{[(2-naphthylmethyl)amino]carbonyl}-9,12,17-trioxo-2-oxa-8,11,16-triazatricyclo[16.2.2.$0^{4,8}$]docosa-1(20),18,21-trien-6-yl]amino}-4-oxobutanoic acid |
| Ex. 260 | 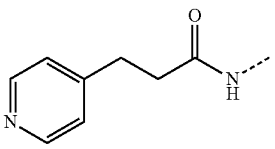 | 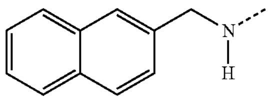 | (4S,6R,15S)-11,16-dimethyl-N-(2-naphthylmethyl)-9,12,17-trioxo-6-{[3-(4-pyridinyl)propanoyl]amino}-2-oxa-8,11,16-triazatricyclo[16.2.2.$0^{4,8}$]docosa-1(20),18,21-triene-15-carboxamide |

TABLE 34c-continued

Examples of Core 17 (Ex. 248-Ex. 271; continued on the following pages)

| No | $R^2$ | $R^{54}$ | IUPAC name |
|---|---|---|---|
| Ex. 261 | 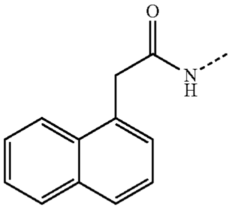 | 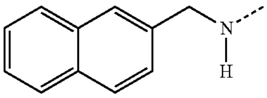 | (4S,6R,15S)-11,16-dimethyl-6-{[2-(1-naphthyl)acetyl]amino}-N-(2-naphthylmethyl)-9,12,17-trioxo-2-oxa-8,11,16-triazatricyclo[16.2.2.$0^{4,8}$]docosa-1(20),18,21-triene-15-carboxamide |
| Ex. 262 | 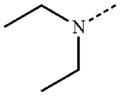 | 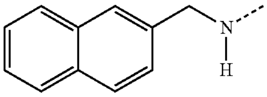 | (4S,6R,15S)-6-(diethylamino)-11,16-dimethyl-N-(2-naphthylmethyl)-9,12,17-trioxo-2-oxa-8,11,16-triazatricyclo[16.2.2.$0^{4,8}$]docosa-1(20),18,21-triene-15-carboxamide |
| Ex. 263 | 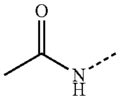 | 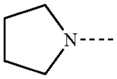 | N-[(4S,6R,15S)-11,16-dimethyl-9,12,17-trioxo-15-(1-pyrrolidinylcarbonyl)-2-oxa-8,11,16-triazatricyclo[16.2.2.$0^{4,8}$]docosa-1(20),18,21-trien-6-yl]acetamide |
| Ex. 264 | 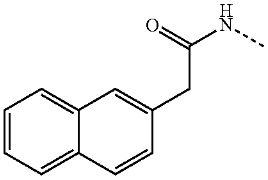 | 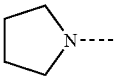 | N-[(4S,6R,15S)-11,16-dimethyl-9,12,17-trioxo-15-(1-pyrrolidinylcarbonyl)-2-oxa-8,11,16-triazatricyclo[16.2.2.$0^{4,8}$]docosa-1(20),18,21-trien-6-yl]-2-(2-naphthyl)acetamide |
| Ex. 265 | 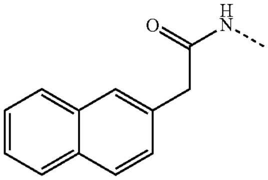 | 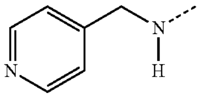 | (4S,6R,15S)-11,16-dimethyl-6-{[2-(2-naphthyl)acetyl]amino}-9,12,17-trioxo-N-(4-pyridinylmethyl)-2-oxa-8,11,16-triazatricyclo[16.2.2.$0^{4,8}$]docosa-1(20),18,21-triene-15-carboxamide |
| Ex. 266 | 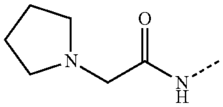 | 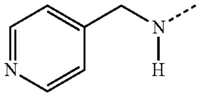 | (4S,6R,15S)-11,16-dimethyl-9,12,17-trioxo-N-(4-pyridinylmethyl)-6-{[2-(1-pyrrolidinyl)acetyl]amino}-2-oxa-8,11,16-triazatricyclo[16.2.2.$0^{4,8}$]docosa-1(20),18,21-triene-15-carboxamide |
| Ex. 267 | 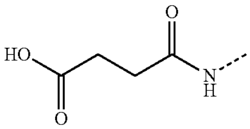 | 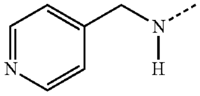 | 4-{[(4S,6R,15S)-11,16-dimethyl-9,12,17-trioxo-15-{[(4-pyridinylmethyl)amino]carbonyl}-2-oxa-8,11,16-triazatricyclo[16.2.2.$0^{4,8}$]docosa-1(20),18,21-trien-6-yl]amino}-4-oxobutanoic acid |
| Ex. 268 | 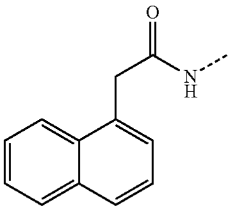 | 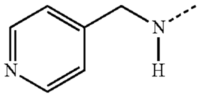 | (4S,6R,15S)-11,16-dimethyl-6-{[2-(1-naphthyl)acetyl]amino}9,12,17-trioxo-N-(4-pyridinylmethyl)-2-oxa-8,11,16-triazatricyclo[16.2.2.$0^{4,8}$]docosa-1(20),18,21-triene-15-carboxamide |
| Ex. 269 | 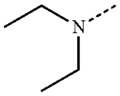 | 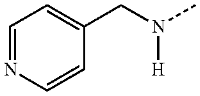 | (4S,6R,15S)-6-(diethylamino)-11,16-dimethyl-9,12,17-trioxo-N-(4-pyridinylmethyl)-2-oxa-8,11,16-triazatricyclo[16.2.2.$0^{4,8}$]docosa-1(20),18,21-triene-15-carboxamide |
| Ex. 270 | 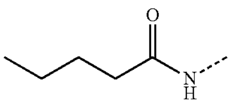 | 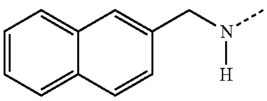 | (4S,6R,15S)-11,16-dimethyl-N-(2-naphthylmethyl)-9,12,17-trioxo-6-(pentanoylamino)-2-oxa-8,11,16-triazatricyclo[16.2.2.$0^{4,8}$]docosa-1(20),18,21-triene-15-carboxamide |

TABLE 34c-continued

| Examples of Core 17 (Ex. 248-Ex. 271; continued on the following pages) | | | |
|---|---|---|---|
| No | $R^2$ | $R^{54}$ | IUPAC name |
| Ex. 271 | 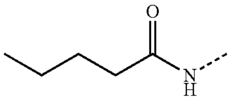 | 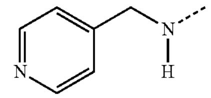 | (4S,6R,15S)-11,16-dimethyl-9,12,17-trioxo-6-(pentanoylamino)-N-(4-pyridinylmethyl)-2-oxa-8,11,16-triazatricyclo[16.2.2.0$^{4,8}$]docosa-1(20),18,21-triene-15-carboxamide |

TABLE 35a

| Examples of Core 18 (Ex. 272-Ex. 296; continued on the following pages) | | | | | | | |
|---|---|---|---|---|---|---|---|
| No | $R^2$ | $R^5$ | Starting material | General Procedure | Reagent | Purification Method | Yield (isolated salt) |
| Ex. 272-Ex. 274: cf. experimental description | | | | | | | |
| Ex. 275 | 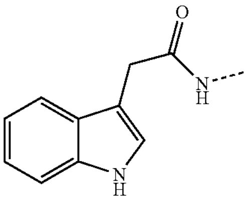 | 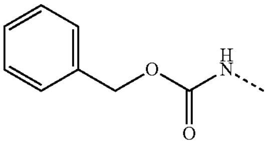 | Ex. 273 (HCl salt) | L.1.3 | 3-indoleacetic acid (1.1 equiv.) HATU (1.5 equiv.) HOAt (1.5 equiv.) i-$Pr_2NEt$ (5 equiv.) | FC ($CH_2Cl_2$/MeOH) | 53% |
| Ex. 276 | 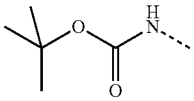 | 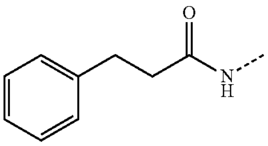 | Ex. 274 | L.1.3 | 3-phenylpropanoic acid (1.2 equiv.) HATU (1.5 equiv.) HOAt (1.5 equiv.) i-$Pr_2NEt$ (3 equiv.) | FC ($CH_2Cl_2$/MeOH) | 72% |
| Ex. 277 | $NH_2$ | 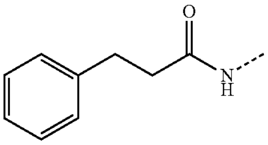 | Ex. 276 | J | HCl-dioxane | crude product | quant. (HCl salt) |
| Ex. 278 | 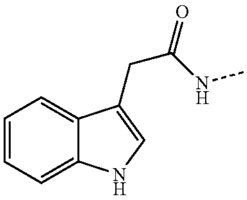 | 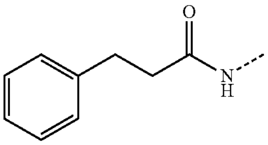 | Ex. 277 | L.1.3 | 3-indoleacetic acid (1.1 equiv.) HATU (1.5 equiv.) HOAt (1.5 equiv.) i-$Pr_2NEt$ (5 equiv.) | FC ($CH_2Cl_2$/MeOH) | 75% |
| Ex. 279 | 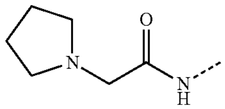 | 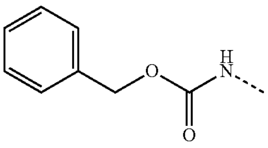 | Ex. 273 (HCl salt) | L.1.3 | pyrrolidine-1-acetic acid (1.2 equiv.) | FC (EtOAc/MeOH) | 67% |
| Ex. 280 | 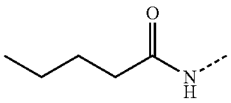 | 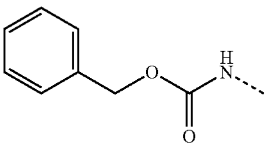 | Ex. 273 (HCl salt) | L.1.1 | valeroyl chloride (2 equiv.) | FC (EtOAc/MeOH) | 71% |

TABLE 35a-continued

Examples of Core 18 (Ex. 272-Ex. 296; continued on the following pages)

| No | $R^2$ | $R^5$ | Starting material | General Procedure | Reagent | Purification Method | Yield (isolated salt) |
|---|---|---|---|---|---|---|---|
| Ex. 281 | 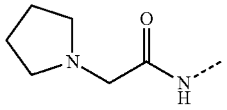 | $NH_2$ | Ex. 279 | K.1 | $H_2$, $Pd(OH)_2$—C | crude product | quant. |
| Ex. 282 | 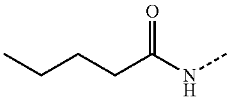 | $NH_2$ | Ex. 280 | K.1 | $H_2$, $Pd(OH)_2$—C | crude product | quant. |
| Ex. 283 | 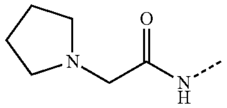 | 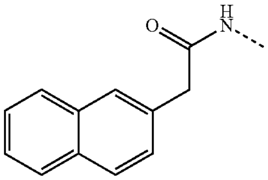 | Ex. 281 | L.1.3 | 2-naphthylacetic acid (1.2 equiv.) | Prep. HPLC, method 3 | 27% |
| Ex. 284 | 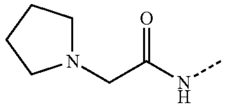 | 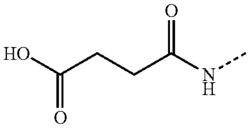 | Ex. 281 | L.1.1 | succinic anhydride (1.5 equiv.) Pyridine (49 equiv.) | Prep. HPLC, method 2 | 51% |
| Ex. 285 | 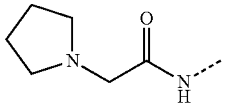 | 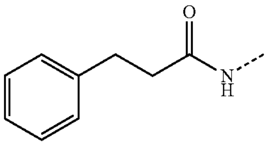 | Ex. 281 | L.1.3 | 3-(pyridine-4-yl)propanoic acid (1.2 equiv.) | Prep. HPLC, method 2 | 12% |
| Ex. 286 | 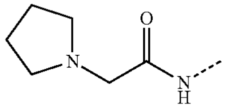 | 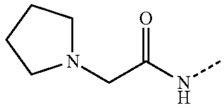 | Ex. 281 | L.1.3 | pyrrolidine-1-acetic acid (1.2 equiv.) | Prep. HPLC, method 2 | 16% |
| Ex. 287 | 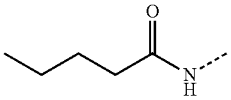 | 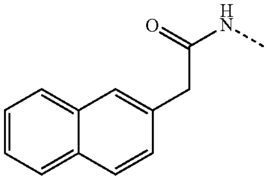 | Ex. 282 | L.1.3 | 2-naphthylacetic acid (1.2 equiv.) | FC ($CH_2Cl_2$/MeOH/aq. $NH_3$) | 79% |
| Ex. 288 | 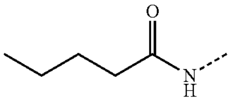 | 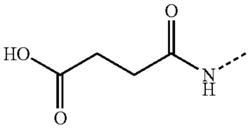 | Ex. 282 | L.1.1 | succinic anhydride (1.5 equiv.) Pyridine (49 equiv.) | Prep. HPLC, method 2 | 57% |
| Ex. 289 | 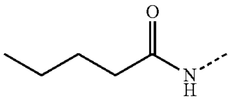 | 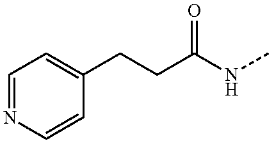 | Ex. 282 | L.1.3 | 3-(pyridine-4-yl)propanoic acid (1.2 equiv.) | Prep. HPLC, method 3 | 17% |

TABLE 35a-continued

Examples of Core 18 (Ex. 272-Ex. 296; continued on the following pages)

| No | $R^2$ | $R^5$ | Starting material | General Procedure | Reagent | Purification Method | Yield (isolated salt) |
|---|---|---|---|---|---|---|---|
| Ex. 290 | 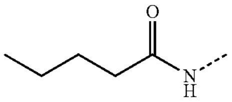 | 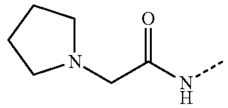 | Ex. 282 | L.1.3 | pyrrolidine-1-acetic acid (1.2 equiv.) | FC ($CH_2Cl_2$/MeOH/aq. $NH_3$) | 65% |
| Ex. 291 | 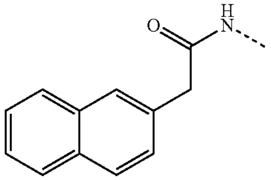 | 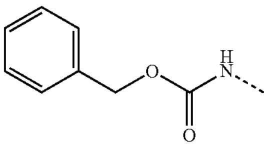 | Ex. 273 (HCl salt) | L.1.3 | 2-naphthylacetic acid (1.2 equiv.) | FC (EtOAc/MeOH)*⁾ | 79% |
| Ex. 292 | 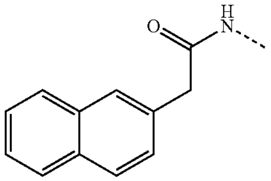 | $NH_2$ | Ex. 291 | K.1 | $H_2$, $Pd(OH)_2$—C | FC (EtOAc/MeOH) | 69% |
| Ex. 293 | 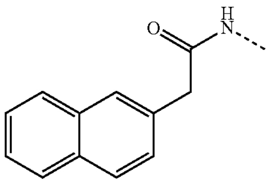 | 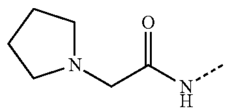 | Ex. 292 | L.1.3 | pyrrolidine-1-acetic acid (1.2 equiv.) | Prep. HPLC, method 3 | 64% |
| Ex. 294 | 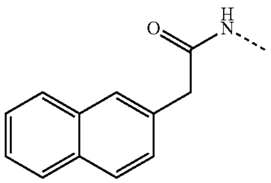 | 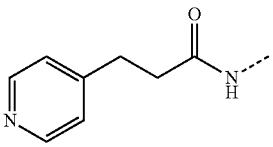 | Ex. 292 | L.1.3 | 3-(pyridine-4-yl)propanoic acid (1.2 equiv.) | Prep. HPLC, method 3 | 70% |
| Ex. 295 | 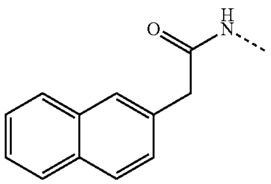 | 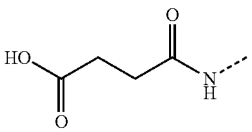 | Ex. 292 | L.1.1 | succinic anhydride (1.5 equiv.) Pyridine (49 equiv.) | Prep. HPLC, method 2 | 73% |
| Ex. 296 | 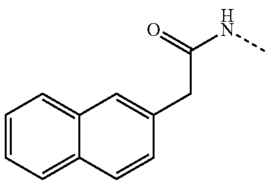 | $CH_3(CH_2)_8$ CONH | Ex. 292 | L.1.1 | decanoyl chloride (2 equiv.) | Prep. HPLC, method 3 | 40% |

*⁾An analytical sample was further purified by prep. HPLC, method 3

TABLE 35b
Examples of Core 18 (Ex. 272-Ex. 296; continued on the following pages)
| No | $R^2$ | $R^5$ | FORMULA | MONO-ISOTOPIC MASS | Rt (purity at 220 nm) | $[M + H]^+$ found | LC-MS-Method |
|---|---|---|---|---|---|---|---|
| Ex. 272-Ex. 274: cf. experimental description | | | | | | | |
| Ex. 275 | 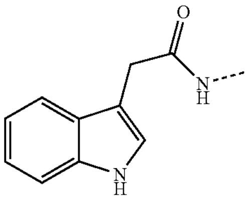 | 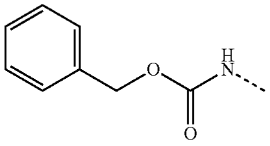 | C36H39N7O7 | 681.3 | 1.53 (97) | 682.5 | Method 2 |
| Ex. 276 | 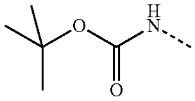 | 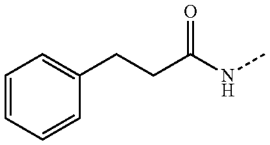 | C32H42N6O7 | 622.3 | 1.57 (95) | 623.4 | Method 2 |
| Ex. 277 | $NH_2$ | 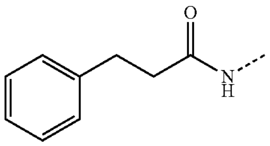 | C27H34N6O5 | 522.3 | 1.10 (98) | 523.4 | Method 2 |
| Ex. 278 | 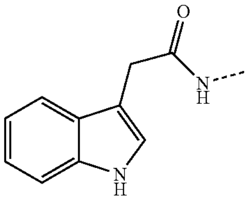 | 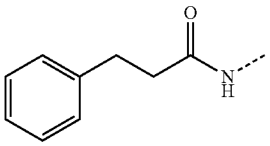 | C37H41N7O6 | 679.3 | 1.50 (98) | 680.5 | Method 2 |
| Ex. 279 | 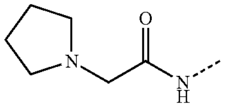 | 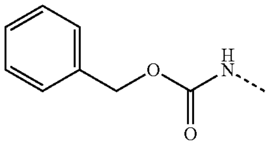 | C32H41N7O7 | 635.3 | 1.32 (98) | 636.3 | Method 2 |
| Ex. 280 | 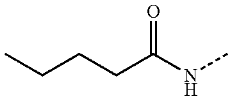 | 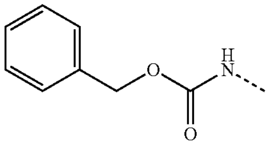 | C31H40N6O7 | 608.3 | 1.54 (98) | 609.3 | Method 2 |
| Ex. 281 | 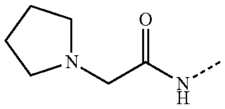 | $NH_2$ | C24H35N7O5 | 501.3 | 1.32 (98) | 502.3 | Method 5a |
| Ex. 282 | 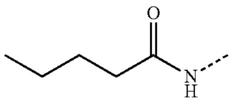 | $NH_2$ | C23H34N6O5 | 474.3 | 1.24 (94) | 475.1 | Method 4a |
| Ex. 283 | 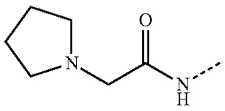 | 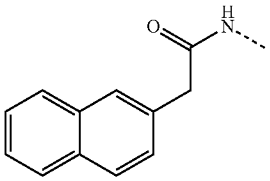 | C36H43N7O6 | 669.3 | 1.42 (95) | 670.3 | Method 4a |

TABLE 35b-continued
| Examples of Core 18 (Ex. 272-Ex. 296; continued on the following pages) | | | | | | | |
|---|---|---|---|---|---|---|---|
| No | $R^2$ | $R^5$ | FORMULA | MONO-ISOTOPIC MASS | Rt (purity at 220 nm) | $[M + H]^+$ found | LC-MS-Method |
| Ex. 284 | 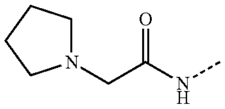 | 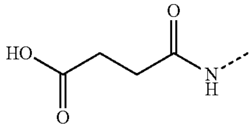 | C28H39N7O8 | 601.3 | 0.99 (100) | 602.2 | Method 5a |
| Ex. 285 | 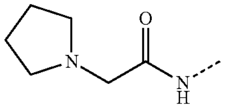 | 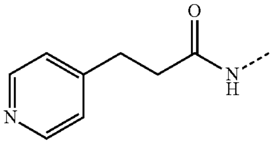 | C32H42N8O6 | 634.3 | 1.47 (98) | 635.2 | Method 5a |
| Ex. 286 | 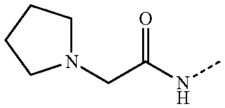 | 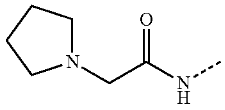 | C30H44N8O6 | 612.3 | 1.55 (99) | 613.3 | Method 5a |
| Ex. 287 | 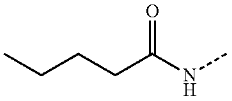 | 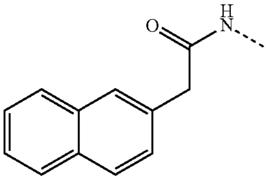 | C35H42N6O6 | 642.3 | 1.77 (98) | 643.3 | Method 4a |
| Ex. 288 | 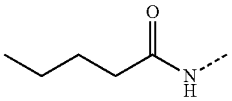 | 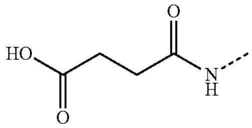 | C27H38N6O8 | 574.3 | 1.32 (100) | 575.2 | Method 4a |
| Ex. 289 | 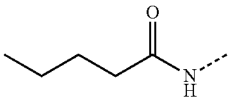 | 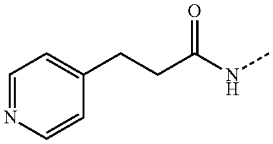 | C31H41N7O6 | 607.3 | 1.25 (95) | 608.3 | Method 4a |
| Ex. 290 | 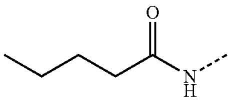 | 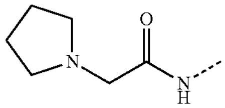 | C29H43N7O6 | 585.3 | 1.30 (95) | 586.4 | Method 4a |
| Ex. 291 | 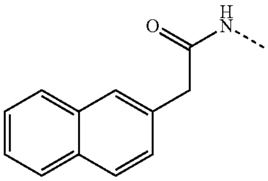 | 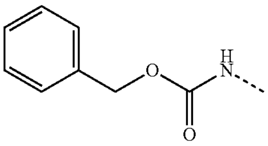 | C38H40N6O7 | 692.3 | 1.91 (97) | 693.3 | Method 4a |
| Ex. 292 | 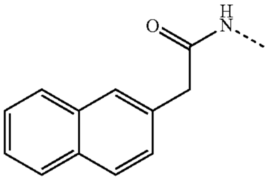 | $NH_2$ | C30H34N6O5 | 558.3 | 1.55 (99) | 559.3 | Method 4a |

TABLE 35b-continued

Examples of Core 18 (Ex. 272-Ex. 296; continued on the following pages)

| No | $R^2$ | $R^5$ | FORMULA | MONO-ISOTOPIC MASS | Rt (purity at 220 nm) | $[M + H]^+$ found | LC-MS-Method |
|---|---|---|---|---|---|---|---|
| Ex. 293 | 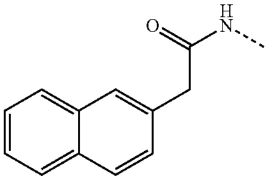 | 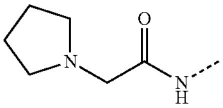 | C36H43N7O6 | 669.3 | 1.52 (96) | 670.3 | Method 4a |
| Ex. 294 | 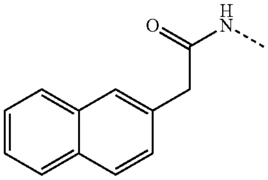 | 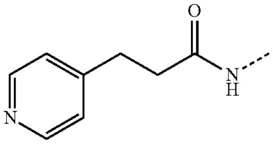 | C38H41N7O6 | 691.3 | 1.46 (97) | 692.3 | Method 4a |
| Ex. 295 | 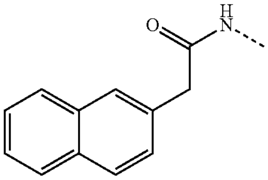 | 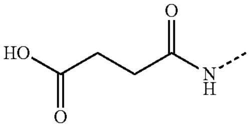 | C34H38N6O8 | 658.3 | 1.58 (99) | 659.2 | Method 4a |
| Ex. 296 | 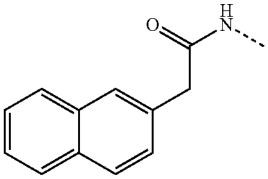 | $CH_3(CH_2)_8CONH$ | C40H52N6O6 | 712.4 | 2.22 (99) | 713.4 | Method 4a |

TABLE 35c

Examples of Core 18 (Ex. 272-Ex. 296; continued on the following pages)

| No | $R^2$ | $R^5$ | IUPAC name |
|---|---|---|---|
| Ex. 272 | 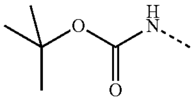 | 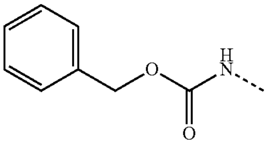 | benzyl N-[(4S,6S,13S)-6-[(tert-butoxycarbonyl)amino]-11,15-dimethyl-9,12,16-trioxo-2-oxa-8,11,15,19-tetraazatricyclo[15.3.1.$0^{4,8}$]henicosa-1(21),17,19-trien-13-yl]carbamate |
| Ex. 273 | $NH_2$ | 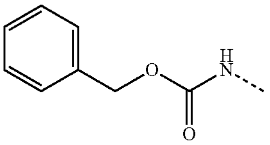 | benzyl N-[(4S,6S,13S)-6-amino-11,15-dimethyl-9,12,16-trioxo-2-oxa-8,11,15,19-tetraazatricyclo[15.3.1.$0^{4,8}$]henicosa-1(21),17,19-trien-13-yl]carbamate |
| Ex. 274 | 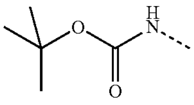 | $NH_2$ | tert-butyl N-[(4S,6S,13S)-13-amino-11,15-dimethyl-9,12,16-trioxo-2-oxa-8,11,15,19-tetraazatricyclo[15.3.1.$0^{4,8}$]henicosa-1(21),17,19-trien-6-yl]carbamate |

TABLE 35c-continued

Examples of Core 18 (Ex. 272-Ex. 296; continued on the following pages)

| No | $R^2$ | $R^5$ | IUPAC name |
|---|---|---|---|
| Ex. 275 | 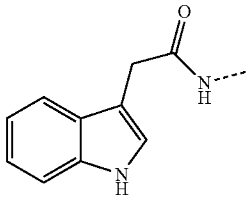 | 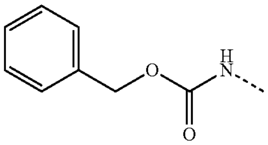 | benzyl N-[(4S,6S,13S)-6-{[2-(1H-indol-3-yl)acetyl]amino}-11,15-dimethyl-9,12,16-trioxo-2-oxa-8,11,15,19-tetraazatricyclo[15.3.1.0$^{4,8}$]henicosa-1(21),17,19-trien-13-yl]carbamate |
| Ex. 276 | 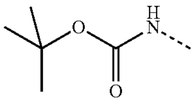 | 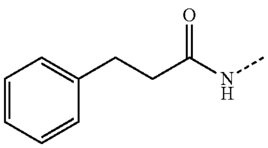 | tert-butyl N-[(4S,6S,13S)-11,15-dimethyl-9,12,16-trioxo-13-[(3-phenylpropanoyl)amino]-2-oxa-8,11,15,19-tetraazatricyclo[15.3.1.0$^{4,8}$]henicosa-1(21),17,19-trien-6-yl]carbamate |
| Ex. 277 | $NH_2$ | 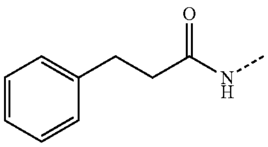 | N-[(4S,6S,13S)-6-amino-11,15-dimethyl-9,12,16-trioxo-2-oxa-8,11,15,19-tetraazatricyclo[15.3.1.0$^{4,8}$]henicosa-1(21),17,19-trien-13-yl]-3-phenylpropanamide |
| Ex. 278 | 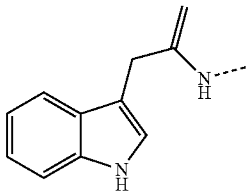 | 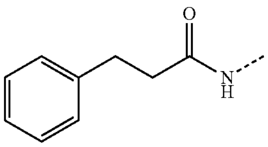 | N-[(4S,6S,13S)-6-{[2-(1H-indol-3-yl)acetyl]amino}-11,15-dimethyl-9,12,16-trioxo-2-oxa-8,11,15,19-tetraazatricyclo[15.3.1.0$^{4,8}$]henicosa-1(21),17,19-trien-13-yl]-3-phenylpropanamide |
| Ex. 279 | 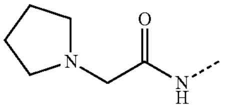 | 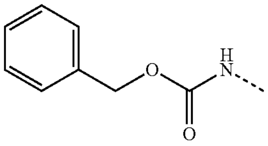 | benzyl N-[(4S,6S,13S)-11,15-dimethyl-9,12,16-trioxo-6-{[2-(1-pyrrolidinyl)acetyl]amino}-2-oxa-8,11,15,19-tetraazatricyclo[15.3.1.0$^{4,8}$]henicosa-1(21),17,19-trien-13-yl]carbamate |
| Ex. 280 | 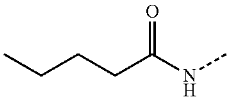 | 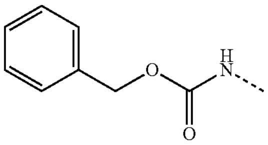 | benzyl N-[(4S,6S,13S)-11,15-dimethyl-9,12,16-trioxo-6-(pentanoylamino)-2-oxa-8,11,15,19-tetraazatricyclo[15.3.1.0$^{4,8}$]henicosa-1(21),17,19-trien-13-yl]carbamate |
| Ex. 281 | 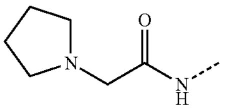 | $NH_2$ | N- [(4S,6S,13S)-13-amino-11,15-dimethyl-9,12,16-trioxo-2-oxa-8,11,15,19-tetraazatricyclo[15.3.1.0$^{4,8}$]henicosa-1(21),17,19-trien-6-yl]-2-(1-pyrrolidinyl)acetamide |
| Ex. 282 | 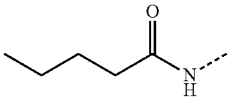 | $NH_2$ | N-[(4S,6S,13S)-13-amino-11,15-dimethyl-9,12,16-trioxo-2-oxa-8,11,15,19-tetraazatricyclo[15.3.1.0$^{4,8}$]henicosa-1(21),17,19-trien-6-yl]pentanamide |
| Ex. 283 | 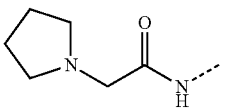 | 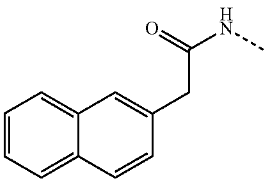 | N-[(4S,6S,13S)-11,15-dimethyl-9,12,16-trioxo-6-{[2-(1-pyrrolidinyl)acetyl]amino}-2-oxa-8,11,15,19-tetraazatricyclo[15.3.1.0$^{4,8}$]henicosa-1(21),17,19-trien-13-yl]-2-(2-naphthyl)acetamide |

TABLE 35c-continued

Examples of Core 18 (Ex. 272-Ex. 296; continued on the following pages)

| No | $R^2$ | $R^5$ | IUPAC name |
|---|---|---|---|
| Ex. 284 | 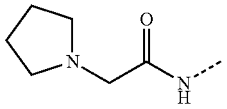 | 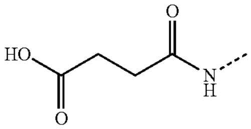 | 4-{[(4S,6S,13S)-11,15-dimethyl-9,12,16-trioxo-6-{[2-(1-pyrrolidinyl)acetyl]amino}-2-oxa-8,11,15,19-tetraazatricyclo[15.3.1.0$^{4,8}$]henicosa-1(21),17,19-trien-13-yl]amino}-4-oxobutanoic acid |
| Ex. 285 | 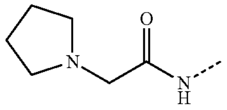 | 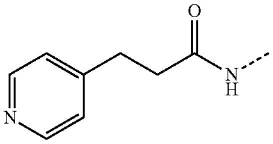 | N-[(4S,6S,13S)-11,15-dimethyl-9,12,16-trioxo-6-{[2-(1-pyrrolidinyl)acetyl]amino}-2-oxa-8,11,15,19-tetraazatricyclo[15.3.1.0$^{4,8}$]henicosa-1(21),17,19-trien-13-yl]-3-(4-pyridinyl)propanamide |
| Ex. 286 | 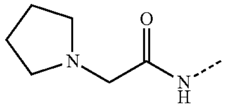 | 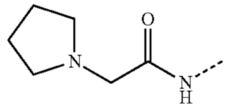 | N-[(4S,6S,13S)-11,15-dimethyl-9,12,16-trioxo-13-{[2-(1-pyrrolidinyl)acetyl]amino}-2-oxa-8,11,15,19-tetraazatricyclo[15.3.1.0$^{4,8}$]henicosa-1(21),17,19-trien-6-yl]-2-(1-pyrrolidinyl)acetamide |
| Ex. 287 | 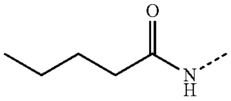 | 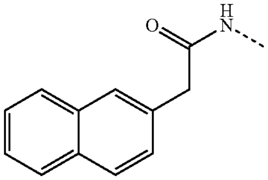 | N-[(4S,6S,13S)-11,15-dimethyl-13-{[2-(2-naphthyl)acetyl]amino}-9,12,16-trioxo-2-oxa-8,11,15,19-tetraazatricyclo[15.3.1.0$^{4,8}$]henicosa-1(21),17,19-trien-6-yl]pentanamide |
| Ex. 288 | 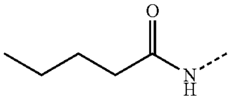 | 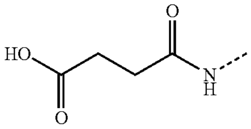 | 4-{[(4S,6S,13S)-11,15-dimethyl-9,12,16-trioxo-6-(pentanoylamino)-2-oxa-8,11,15,19-tetraazatricyclo[15.3.1.0$^{4,8}$]henicosa-1(21),17,19-trien-13-yl]amino}-4-oxobutanoic acid |
| Ex. 289 | 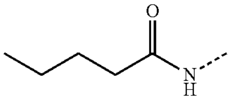 | 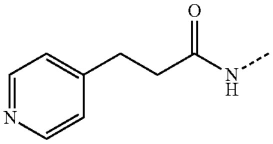 | N-[(4S,6S,13S)-11,15-dimethyl-9,12,16-trioxo-13-{[3-(4-pyridinyl)propanoyl]amino}-2-oxa-8,11,15,19-tetraazatricyclo[15.3.1.0$^{4,8}$]henicosa-1(21),17,19-trien-6-yl]pentanamide |
| Ex. 290 | 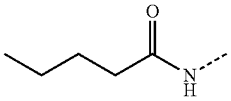 | 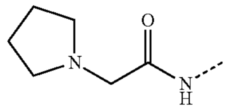 | N-[(4S,6S,13S)-11,15-dimethyl-9,12,16-trioxo-13-{[2-(1-pyrrolidinyl)acetyl]amino}-2-oxa-8,11,15,19-tetraazatricyclo[15.3.1.0$^{4,8}$]henicosa-1(21),17,19-trien-6-yl]pentanamide |
| Ex. 291 | 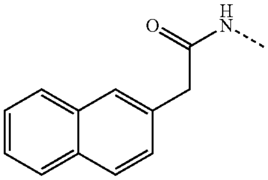 | 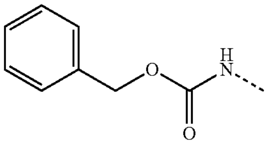 | benzyl N-[(4S,6S,13S)-11,15-dimethyl-6-{[2-(2-naphthyl)acetyl]amino}-9,12,16-trioxo-2-oxa-8,11,15,19-tetraazatricyclo[15.3.1.0$^{4,8}$]henicosa-1(21),17,19-trien-13-yl]carbamate |
| Ex. 292 | 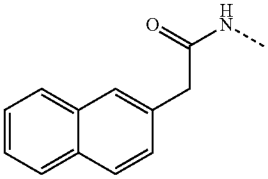 | $NH_2$ | N-[(4S,6S,13S)-13-amino-11,15-dimethyl-9,12,16-trioxo-2-oxa-8,11,15,19-tetraazatricyclo[15.3.1.0$^{4,8}$]henicosa-1(21),17,19-trien-6-yl]-2-(2-naphthyl)acetamide |

TABLE 35c-continued

| Examples of Core 18 (Ex. 272-Ex. 296; continued on the following pages) | | | |
|---|---|---|---|
| No | $R^2$ | $R^5$ | IUPAC name |
| Ex. 293 | 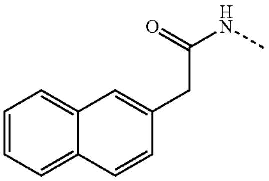 | 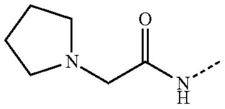 | N-[(4S,6S,13S)-11,15-dimethyl-9,12,16-trioxo-13-{[2-(1-pyrrolidinyl)acetyl]amino}-2-oxa-8,11,15,19-tetraazatricyclo[15.3.1.0$^{4,8}$]henicosa-1(21),17,19-trien-6-yl]-2-(2-naphthyl)acetamide |
| Ex. 294 | 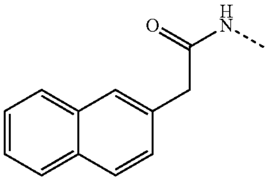 | 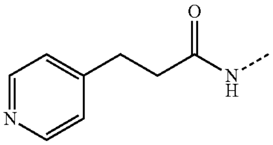 | N-[(4S,6S,13S)-11,15-dimethyl-6-{[2-(2-naphthyl)acetyl]amino}-9,12,16-trioxo-2-oxa-8,11,15,19-tetraazatricyclo[15.3.1.0$^{4,8}$]henicosa-1(21),17,19-trien-13-yl]-3-(4-pyridinyl)propanamide |
| Ex. 295 | 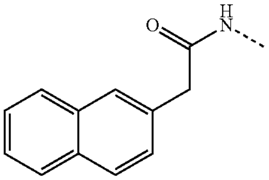 | 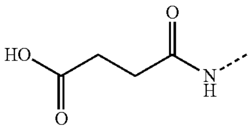 | 4-{[(4S,6S,13S)-11,15-dimethyl-6-{[2-(2-naphthyl)acetyl]amino}-9,12,16-trioxo-2-oxa-8,11,15,19-tetraazatricyclo[15.3.1.0$^{4,8}$]henicosa-1(21),17,19-trien-13-yl]amino}-4-oxobutanoic acid |
| Ex. 296 | 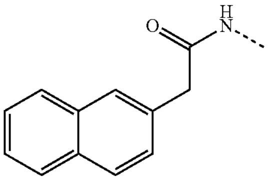 | $CH_3(CH_2)_8CONH$ | N-[(4S,6S,13S)-11,15-dimethyl-6-{[2-(2-naphthyl)acetyl]amino}-9,12,16-trioxo-2-oxa-8,11,15,19-tetraazatricyclo[15.3.1.0$^{4,8}$]henicosa-1(21),17,19-trien-13-yl]decanamide |

TABLE 36a

| Examples of Core 19 (Ex. 297-Ex. 310) | | | | | | | |
|---|---|---|---|---|---|---|---|
| No | $R^2$ | $R^{54}$ | Starting material | General Procedure | Reagent | Purification Method | Yield (isolated salt) |
| Ex. 297-Ex. 298: cf. experimental description | | | | | | | |
| Ex. 299 | 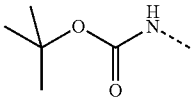 | 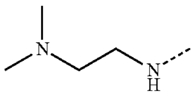 | Ex. 298 | L.2 | N,N-dimethyl-ethylene-diamine | Flash Chromatography | 80% |
| Ex. 300 | $NH_2$ | 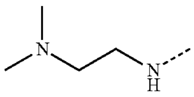 | Ex. 299 | J | HCl-dioxane | No purification | quant. (HCl salt) |
| Ex. 301 | 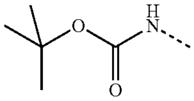 | 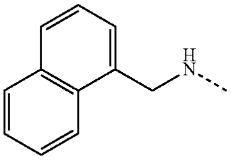 | Ex. 298 | L.2 | 1-naphthyl-methylamine | FC ($CH_2Cl_2$/MeOH) | 75% |

TABLE 36a-continued

Examples of Core 19 (Ex. 297-Ex. 310)

| No | $R^2$ | $R^{54}$ | Starting material | General Procedure | Reagent | Purification Method | Yield (isolated salt) |
|---|---|---|---|---|---|---|---|
| Ex. 302 | $NH_2$ | 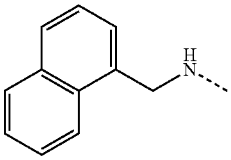 | Ex. 301 | J | HCl-dioxane | Crude product | quant. (HCl salt) |
| Ex. 303 | 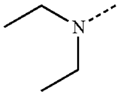 | 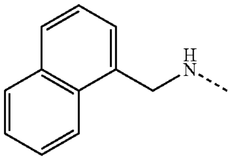 | Ex. 302 | M.1 | acetaldehyde | Prep. HPLC, method 2 | 45% |
| Ex. 304 | 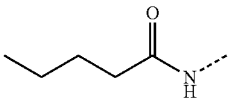 | 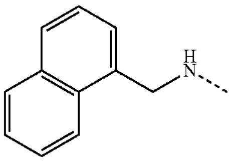 | Ex. 302 | L.1.1 | valeroyl chloride (5 equiv.) | Prep. HPLC, method 2 | 22% |
| Ex. 305 | 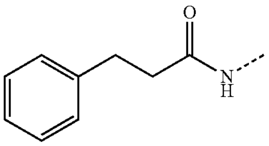 | 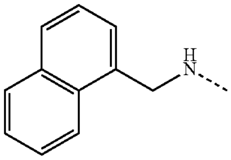 | Ex. 302 | L.1.2 | 3-(pyridine-4-yl)propanoic acid (3.7 equiv.) i-$Pr_2$NEt (4 equiv.) bicarbonate resin (4 equiv.) | FC ($CH_2Cl_2$/MeOH/ aq. $NH_3$) then Prep. HPLC, method 3 | 55% |
| Ex. 306 | 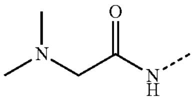 | 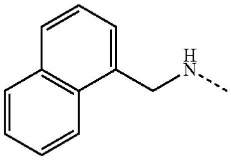 | Ex. 302 | L.1.2 | N,N-dimethyl glycine (6.2 equiv.) carbodiimide resin (2.5 equiv.) i-$Pr_2$NEt (5 equiv.) bicarbonate resin (5 equiv.) | FC ($CH_2Cl_2$/MeOH) | 43% |
| Ex. 307 | 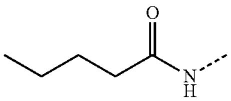 | 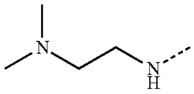 | Ex. 300 | L.1.1 | valeroyl chloride (2 equiv.) | Prep. HPLC, method 2 | 36% |
| Ex. 308 | 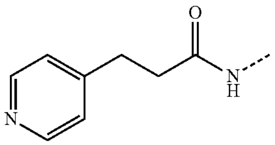 | 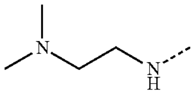 | Ex. 300 | L.1.2 | 3-(pyridine-4-yl)propanoic acid (1.2 equiv.) i-$Pr_2$NEt (4 equiv.), bicarbonate resin (4 equiv.) | FC ($CH_2Cl_2$/MeOH) | 77% |
| Ex. 309 | 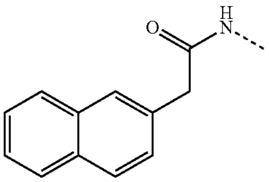 | 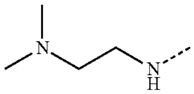 | Ex. 300 | L.1.2*⁾ | 2-naphthylacetic acid i-$Pr_2$NEt (4 equiv.) | Prep. HPLC, method 2 | 58% |

TABLE 36a-continued

| Examples of Core 19 (Ex. 297-Ex. 310) | | | | | | | |
|---|---|---|---|---|---|---|---|
| No | $R^2$ | $R^{54}$ | Starting material | General Procedure | Reagent | Purification Method | Yield (isolated salt) |
| Ex. 310 | 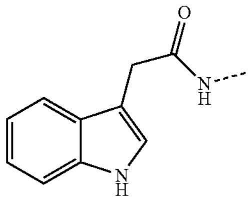 | 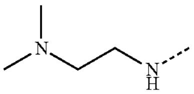 | Ex. 300 | L.1.2 | 3-indoleacetic acid (3.7 equiv.) i-$Pr_2NEt$ (4 equiv.) DMF (0.2 mL) bicarbonate resin (4 equiv.) | Prep. HPLC, method 2 | 28% |

*)The treatment with (polystyrylmethyl)trimethylammonium bicarbonate was replaced by an aqueous workup ($CHCl_3$, sat. aq. $NaHCO_3$ soln)

TABLE 36b

| Examples of Core 19 (Ex. 297-Ex. 310) | | | | | | | |
|---|---|---|---|---|---|---|---|
| No | $R^2$ | $R^{54}$ | FORMULA | MONO-ISOTOPIC MASS | Rt (purity at 220 nm) | $[M + H]^+$ found | LC-MS-Method |
| Ex. 297-Ex. 298: cf. experimental description | | | | | | | |
| Ex. 299 | 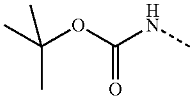 | 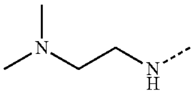 | C33H47N7O7 | 653.4 | 1.62 (97) | 654.4 | Method 4a |
| Ex. 300 | $NH_2$ | 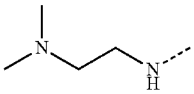 | C28H39N7O5 | 553.3 | 1.11 (64), 1.08 (35) | 554.3 | Method 4a |
| Ex. 301 | 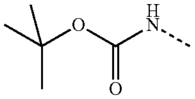 | 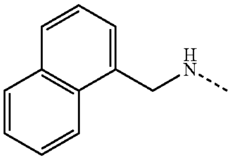 | C40H46N6O7 | 722.3 | 2.19 (89) | 723.4 | Method 4a |
| Ex. 302 | $NH_2$ | 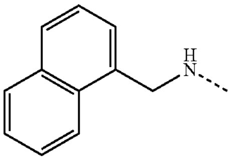 | C35H38N6O5 | 622.3 | 1.70 (79) | 623.3 | Method 4a |
| Ex. 303 | 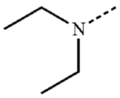 | 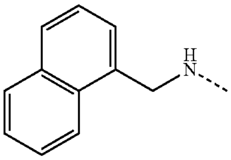 | C39H46N6O5 | 678.4 | 1.75 (100) | 679.4 | Method 4a |
| Ex. 304 | 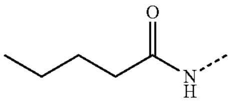 | 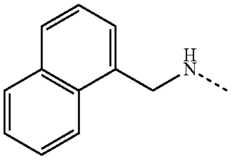 | C40H46N6O6 | 706.4 | 2.09 (100) | 707.4 | Method 4a |

TABLE 36b-continued

| Examples of Core 19 (Ex. 297-Ex. 310) | | | | | | | |
|---|---|---|---|---|---|---|---|
| No | $R^2$ | $R^{54}$ | FORMULA | MONO-ISOTOPIC MASS | Rt (purity at 220 nm) | $[M + H]^+$ found | LC-MS-Method |
| Ex. 305 | 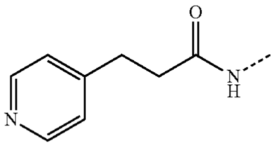 | 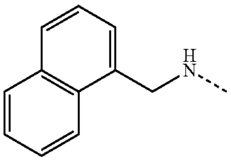 | C43H45N7O6 | 755.3 | 1.67 (57), 1.70 (38) | 756.4 | Method 4a |
| Ex. 306 | 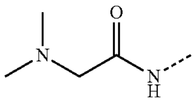 | 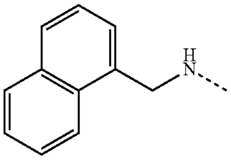 | C39H45N7O6 | 707.3 | 1.71 (86) | 708.3 | Method 4a |
| Ex. 307 | 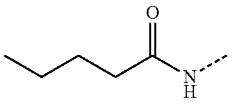 | 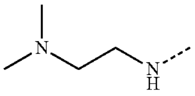 | C33H47N7O6 | 637.4 | 1.50 (638.3) | 638.3 | Method 4a |
| Ex. 308 | 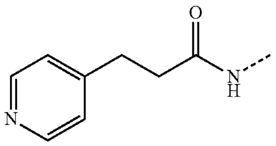 | 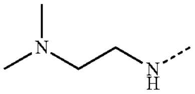 | C36H46N8O6 | 686.4 | 1.57 (92) | 687.4 | Method 5a |
| Ex . 309 | 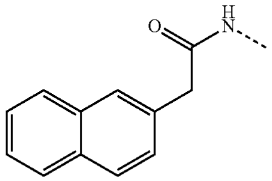 | 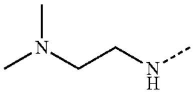 | C40H47N7O6 | 721.4 | 1.68 (98) | 722.4 | Method 4a |
| Ex. 310 | 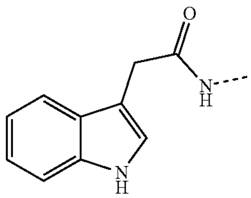 | 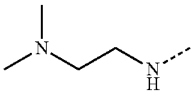 | C38H46N8O6 | 710.4 | 1.52 (97) | 711.4 | Method 4a |

TABLE 36c

| Examples of Core 19 (Ex. 297-Ex. 310) | | | |
|---|---|---|---|
| No | $R^2$ | $R^{54}$ | IUPAC name |
| Ex. 297 | 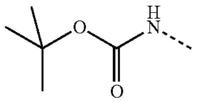 | $OCH_2Ph$ | benzyl (4S,6S,15S)-6-[(tert-butoxycarbonyl)amino]-11,16-dimethyl-9,12,17-trioxo-2-oxa-8,11,16,26-tetra-azatetracyclo[16.6.2.$0^{4,8}$.$0^{21,25}$]hexacosa-1(24),18,20,22,25-pentaene-15-carboxylate |
| Ex. 298 | 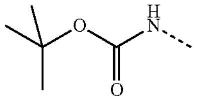 | OH | (4S,6S,15S)-6-[(tert-butoxycarbonyl)amino]-11,16-dimethyl-9,12,17-trioxo-2-oxa-8,11,16,26-tetra-azatetracyclo[16.6.2.$0^{4,8}$.$0^{21,25}$]hexacosa-1(24),18,20,22,25-pentaene-15-carboxylic acid |

TABLE 36c-continued

Examples of Core 19 (Ex. 297-Ex. 310)

| No | $R^2$ | $R^{54}$ | IUPAC name |
|---|---|---|---|
| Ex. 299 | 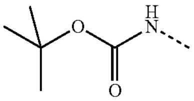 | 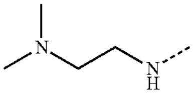 | tert-butyl N-[(4S,6S,15S)-15-({[2-(dimethylamino)-ethyl]amino}carbonyl)-11,16-dimethyl-9,12,17-trioxo-2-oxa-8,11,16,26-tetraazatetracyclo[16.6.2.0$^{4,8}$.0$^{21,25}$]-hexacosa-1(24),18,20,22,25-pentaen-6-yl]carbamate |
| Ex. 300 | $NH_2$ | 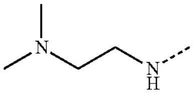 | (4S,6S,15S)-6-amino-N-[2-(dimethylamino)ethyl]-11,16-dimethyl-9,12,17-trioxo-2-oxa-8,11,16,26-tetra-azatetracyclo[16.6.2.0$^{4,8}$.0$^{21,25}$]hexacosa-1(24),18,20,22,25-pentaene-15-carboxamide |
| Ex. 301 | 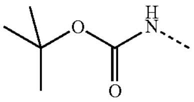 | 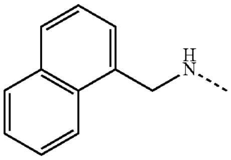 | tert-butyl N-[(4S,6S,15S)-11,16-dimethyl-15-{[(1-naphthylmethyl)amino]carbonyl}-9,12,17-trioxo-2-oxa-8,11,16,26-tetraazatetracyclo[16.6.2.0$^{4,8}$.0$^{21,25}$]-hexacosa-1(25),18(26),19,21,23-pentaen-6-yl]carbamate |
| Ex. 302 | $NH_2$ | 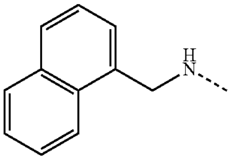 | (4S,6S,15S)-6-amino-11,16-dimethyl-N-(1-naphthylmethyl)-9,12,17-trioxo-2-oxa-8,11,16,26-tetraazatetracyclo-[16.6.2.0$^{4,8}$.0$^{21,25}$]hexacosa-1(25),18(26),19,21,23-pentaene-15-carboxamide |
| Ex . 303 | 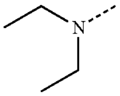 | 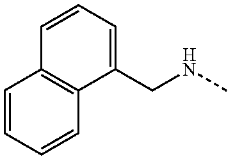 | (4S,6S,15S)-6-(diethylamino)-11,16-dimethyl-N-(1-naphthylmethyl)-9,12,17-trioxo-2-oxa-8,11,16,26-tetraazatetracyclo[16.6.2.0$^{4,8}$.0$^{21,25}$]hexacosa-1(25),18(26),19,21,23-pentaene-15-carboxamide |
| Ex. 304 | 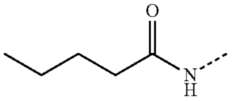 | 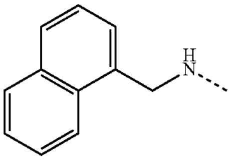 | (4S,6S,15S)-11,16-dimethyl-N-(1-naphthylmethyl)-9,12,17-trioxo-6-(pentanoylamino)-2-oxa-8,11,16,26-tetra-azatetracyclo[16. 6.2.0$^{4,8}$.0$^{21,25}$]hexacosa-1(25),18(26),19,21,23-pentaene-15-carboxamide |
| Ex. 305 | 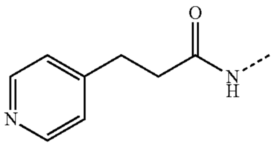 | 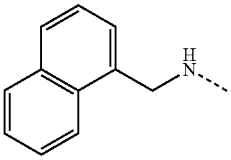 | (4S,6S,15S)-11,16-dimethyl-N-(1-naphthylmethyl)-9,12,17-trioxo-6-{[3-(4-pyridinyl)propanoyl]amino}-2-oxa-8,11,16,26-tetraazatetracyclo[16.6.2.0$^{4,8}$.0$^{21,25}$]hexacosa-1(25),18(26),19,21,23-pentaene-15-carboxamide |
| Ex . 306 | 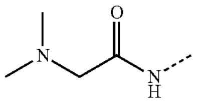 | 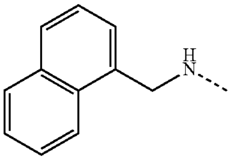 | (4S,6S,15S)-6-{[2-(dimethylamino)acetyl]amino}-11,16-dimethyl-N-(1-naphthylmethyl)-9,12,17-trioxo-2-oxa-8,11,16,26-tetraazatetracyclo-[16.6.2.0$^{4,8}$.0$^{21,25}$]hexacosa-1(25),18(26),19,21,23-pentaene-15-carboxamide |
| Ex. 307 | 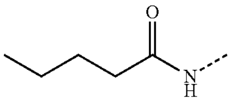 | 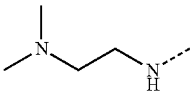 | (4S,6S,15S)-N-[2-(dimethylamino)ethyl]-11,16-dimethyl-9,12,17-trioxo-6-(pentanoylamino)-2-oxa-8,11,16,26-tetraazatetracyclo[16.6.2.0$^{4,8}$.0$^{21,25}$]hexacosa-1(25),18(26),19,21,23-pentaene-15-carboxamide |
| Ex. 308 | 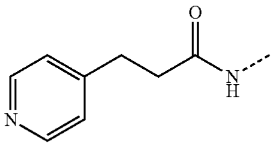 | 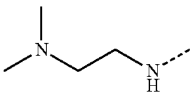 | (4S,6S,15S)-N-[2-(dimethylamino)ethyl]-11,16-dimethyl-9,12,17-trioxo-6-{[3-(4-pyridinyl)propanoyl]-amino}-2-oxa-8,11,16,26-tetraazatetracyclo-[16.6.2.0$^{4,8}$.0$^{21,25}$]hexacosa-1(25),18(26),19,21,23-pentaene-15-carboxamide |

TABLE 36c-continued

| Examples of Core 19 (Ex. 297-Ex. 310) | | | |
|---|---|---|---|
| No | $R^2$ | $R^{54}$ | IUPAC name |
| Ex. 309 | 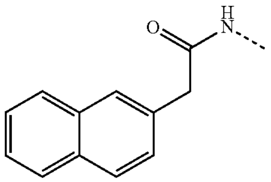 | 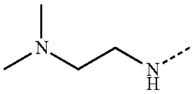 | (4S,6S,15S)-N-[2-(dimethylamino)ethyl]-11,16-dimethyl-6-{[2-(2-naphthyl)acetyl]amino}-9,12,17-trioxo-2-oxa-8,11,16,26-tetraazatetracyclo-[16.6.2.$0^{4,8}$.$0^{21,25}$]hexacosa-1(25),18(26),19,21,23-pentaene-15-carboxamide |
| Ex. 310 | 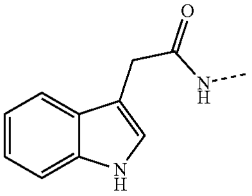 | 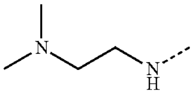 | (4S,6S,15S)-N-[2-(dimethylamino)ethyl]-6-{[2-(1H-indol-3-yl)acetyl]amino}-11,16-dimethyl-9,12,17-trioxo-2-oxa-8,11,16,26-tetraazatetracyclo-[16.6.2.$0^{4,8}$.$0^{21,25}$]-hexacosa-1(25),18(26),19,21,23-pentaene-15-carboxamide |

TABLE 37.1.a

| Example of Core 20 (Ex.311) | | | | | | | | |
|---|---|---|---|---|---|---|---|---|
| No | $R^2$ | $R^5$ | $R^{38}$ | Starting material | General Procedure | Reagent | Purification Method | Yield (isolated salt) |
| Ex.311: cf. experimental description | | | | | | | | |

TABLE 37.1.b

| Example of Core 20 (Ex.311) | | | | | | | | |
|---|---|---|---|---|---|---|---|---|
| No | $R^2$ | $R^5$ | $R^{38}$ | FORMULA | MONOISOTOPIC MASS | Rt (purity at 220 nm) | $[M + H]^+$ found | LC-MS-Method |
| Ex.311: cf. experimental description | | | | | | | | |

TABLE 37.1.c

| Example of Core 20 (Ex. 311) | | | | |
|---|---|---|---|---|
| No | $R^2$ | $R^5$ | $R^{38}$ | IUPAC name |
| Ex. 311 | 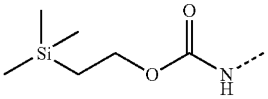 | 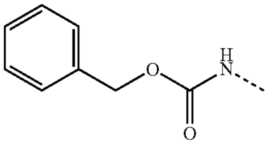 | 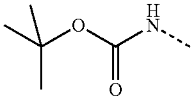 | benzyl N-[(4S,6S,13S,17S)-17-[(tert-butoxycarbonyl)amino]-11,15-dimethyl-9,12,16-trioxo-6-({[2-(trimethylsilyl)ethoxy]carbonyl}amino)-2-oxa-8,11,15-triazatetracyclo-[15.6.2.$0^{4,8}$.$0^{20,24}$]pentacosa-1(24),20,22-trien-13-yl]carbamate |

TABLE 37.2.a

Examples of Core 21 (Ex. 312-Ex. 341)

| No | X | $R^2$ | $R^{54}$ | Starting material | General Pro-cedure | Reagent | Puri-fication Method | Yield (isolated salt) |
|---|---|---|---|---|---|---|---|---|
| Ex. 312-Ex. 315: cf. experimental description | | | | | | | | |
| Ex. 316 | S | 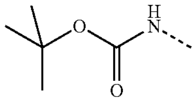 | 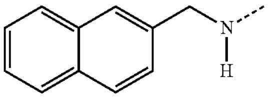 | Ex. 314 | L.2 | 2-naphthyl-methyl amine (2 equiv.) | FC ($CH_2Cl_2$/ MeOH) | 86% |
| Ex. 317 | S | 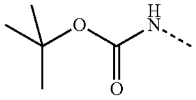 | 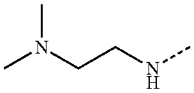 | Ex. 314 | L.2 | N,N-dimethyl-ethyl amine (2 equiv.) | FC ($CH_2Cl_2$/ MeOH) | 72% |
| Ex. 318 | S | $NH_2$ | 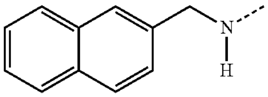 | Ex. 316 | J | HCl (4M dioxane) | crude product | quant. (HCl salt) |
| Ex. 319 | S | $NH_2$ | 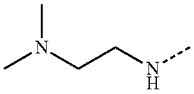 | Ex. 317 | J | HCl (4M dioxane) | crude product | quant. (HCl salt) |
| Ex. 320 | S | 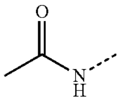 | 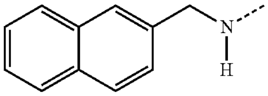 | Ex. 318 | L.1.1 | acetic anhydride (5 equiv.) | prep. HPLC, method 1 | 43% |
| Ex. 321 | S | 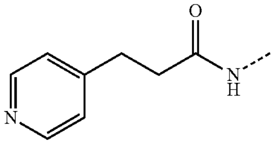 | 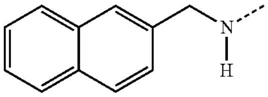 | Ex. 318 | L.1.3 | HATU (1.5 equiv.), HOAt (1.5 equiv.), DIPEA (5 equiv), 3-pyridyl-propanoic acide (1.1 equiv.) | prep. HPLC, method 1 | 39% (TFA salt) |
| Ex. 322 | S | 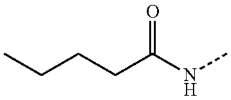 | 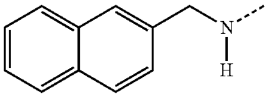 | Ex. 318 | L.1.1 | pentanoic acid chloride (2 equiv.) | prep. HPLC, method 1 | 49% |
| Ex. 323 | S | 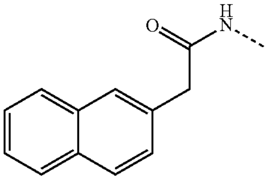 | 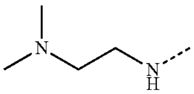 | Ex. 319 | L.1.3 | 2-naphthyl-acetic acid (2 equiv.) | prep. HPLC, method 2 | 40% |
| Ex. 324 | S | 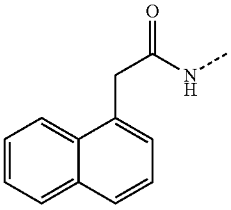 | 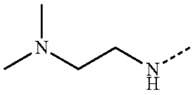 | Ex. 319 | L.1.3 | 1-naphthyl-acetic acid (2 equiv.) | prep. HPLC, method 2 | 43% |
| Ex. 325 | S | 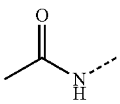 | 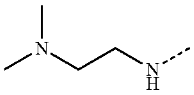 | Ex. 319 | L.1.1 | acetic anhydride (5 equiv.) | prep. HPLC, method 2 | 73% |

TABLE 37.2.a-continued

| Examples of Core 21 (Ex. 312-Ex. 341) | | | | | | | | |
|---|---|---|---|---|---|---|---|---|
| No | X | $R^2$ | $R^{54}$ | Starting material | General Pro-cedure | Reagent | Puri-fication Method | Yield (isolated salt) |
| Ex. 326 | S | 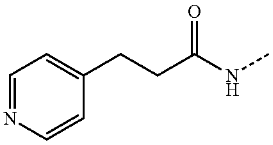 | 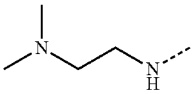 | Ex. 319 | L.1.3 | 3-pyridinyl-propanoic acid (2 equiv.) | prep. HPLC, method 2 | 43% |
| Ex. 327 | S | 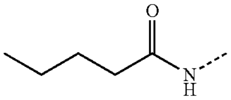 | 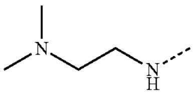 | Ex. 319 | L.1.1 | pentanoyl chloride (4 equiv.) | prep. HPLC, method 2 | 55% |
| Ex. 328 | $SO_2$ | 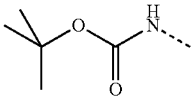 | 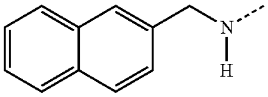 | Ex. 315 | L.2 | 2-naphthyl-methylamine (2 equiv.) | prep. HPLC, method 2 | 75% |
| Ex. 329 | $SO_2$ | 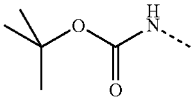 | 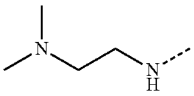 | Ex. 315 | L.2 | N,N-dimethylene-diamine (2 equiv.) | FC ($CH_2Cl_2$/ MeOH/ aq. NH3) | 97% |
| Ex. 330 | $SO_2$ | $NH_2$ | 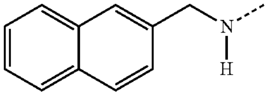 | Ex. 328 | J | HCl (4M dioxane) | crude product | 88% (HCl salt) |
| Ex. 331 | $SO_2$ | $NH_2$ | 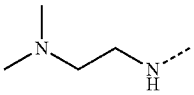 | Ex. 329 | J | HCl (4M dioxane) | crude product | 75% (HCl salt) |
| Ex. 332 | $SO_2$ | 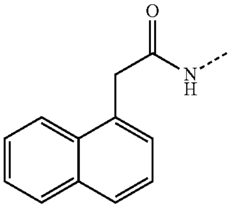 | 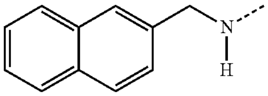 | Ex. 330 | L.1.2 | 1-naphthyl-acetic acid (1.2 equiv.) | prep. HPLC, method 1 then method 3 | 60% |
| Ex. 333 | $SO_2$ | 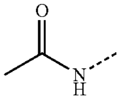 | 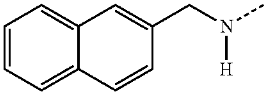 | Ex. 330 | L.1.1 | acetic anhydride (5 equiv). | prep. HPLC, method 2 then method 3 | 65% |
| Ex. 334 | $SO_2$ | 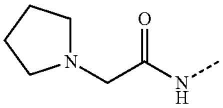 | 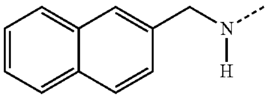 | Ex. 330 | L.1.2 | 1-pyrrolidine-acetic acid (1.8 equiv.) HOBt•$H_2O$ (1.8 equiv.) | prep. HPLC, method 2 | 60% |
| Ex. 335 | $SO_2$ | 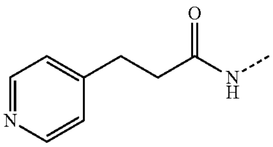 | 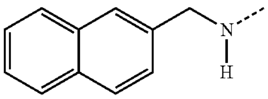 | Ex. 330 | L.1.2 | 4-pyridinyl-propanoic acid (2.5 equiv.) HOBt•$H_2O$ (1.8 equiv.) | prep. HPLC, method 2 | 67% |
| Ex. 336 | $SO_2$ | 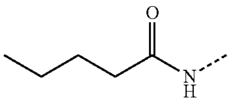 | 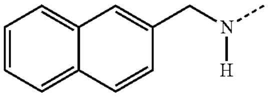 | Ex. 330 | L.1.1 | pentanoyl chloride (6 equiv.) pyridine (10 equiv.), $Et_3N$ (5 equiv.) | prep. HPLC, method 1 then method 3 | 49% |

TABLE 37.2.a-continued

Examples of Core 21 (Ex. 312-Ex. 341)

| No | X | $R^2$ | $R^{54}$ | Starting material | General Procedure | Reagent | Purification Method | Yield (isolated salt) |
|---|---|---|---|---|---|---|---|---|
| Ex. 337 | $SO_2$ | 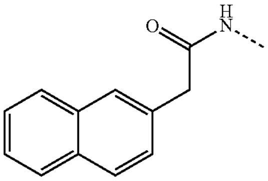 | 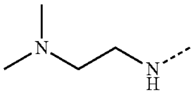 | Ex. 331 | L.1.3 | 2-naphthyl-acetic acid (2 equiv.) | prep. HPLC, method 2 | 41% |
| Ex. 338 | $SO_2$ | 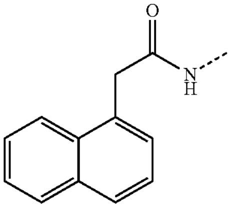 | 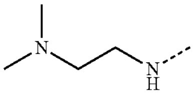 | Ex. 331 | L.1.3 | 1-naphthyl-acetic acid (2 equiv.) | prep HPLC, method 2 | 45% |
| Ex. 339 | $SO_2$ | 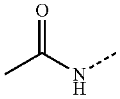 | 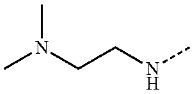 | Ex. 331 | L.1.1 | acetic anhydride (5 equiv.) | prep. HPLC, method 2 | 30% |
| Ex. 340 | $SO_2$ | 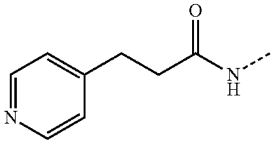 | 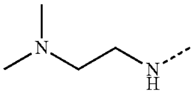 | Ex. 331 | L.1.3 | 3-pyridinyl-propanoic acid (2 equiv.) | prep. HPLC, method 2 | 23% |
| Ex. 341 | $SO_2$ | 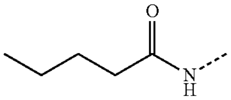 | 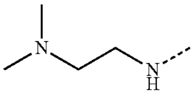 | Ex. 331 | L.1.1 | pentanoyl chloride (4 equiv.) | prep. HPLC, method 2 | 48% |

TABLE 37.2.b

Examples of Core 21 (Ex. 312-Ex. 341)

| No | X | $R^2$ | $R^{54}$ | FORMULA | MONO-ISO-TOPIC MASS | Rt (purity at 220 nm) | $[M + H]^+$ found | LC-MS-Method |
|---|---|---|---|---|---|---|---|---|
| Ex. 312-Ex. 315: cf. experimental description | | | | | | | | |
| Ex. 316 | S | 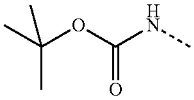 | 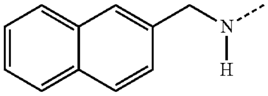 | C37H45N5O6S | 687.3 | 2.20 (95) | 688.2 | Method 4b |
| Ex. 317 | S | 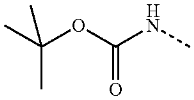 | 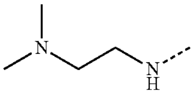 | C30H46N6O6S | 618.3 | 1.57 (95) | 619.2 | Method 4b |
| Ex. 318 | S | $NH_2$ | 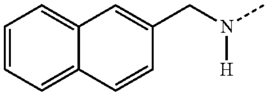 | C32H37N5O4S | 587.3 | 1.66 (91) | 588.0 | Method 4b |
| Ex. 319 | S | $NH_2$ | 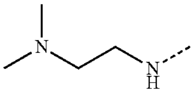 | C25H38N6O4S | 518.3 | 1.44 (87) | 519.2 | Method 5b |

TABLE 37.2.b-continued
Examples of Core 21 (Ex. 312-Ex. 341)
| No | X | $R^2$ | $R^{54}$ | FORMULA | MONO-ISO-TOPIC MASS | Rt (purity at 220 nm) | $[M + H]^+$ found | LC-MS-Method |
|---|---|---|---|---|---|---|---|---|
| Ex. 320 | S | 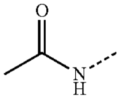 | 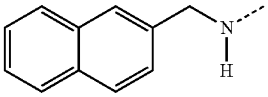 | C34H39N5O5S | 629.3 | 1.88 (92) | 630.2 | Method 4b |
| Ex. 321 | S | 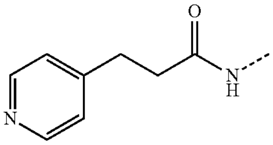 | 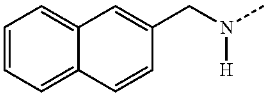 | C40H44N6O5S | 720.3 | 1.56 (93) | 721.3 | Method 2 |
| Ex. 322 | S | 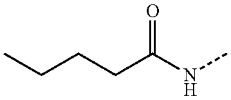 | 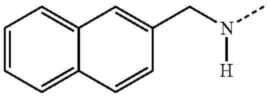 | C37H45N5O5S | 671.3 | 2.08 (91) | 672.3 | Method 4b |
| Ex. 323 | S | 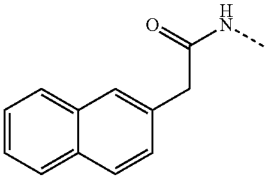 | 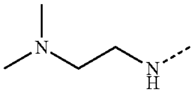 | C37H46N6O5S | 686.3 | 1.67 (96) | 687.2 | Method 4b |
| Ex. 324 | S | 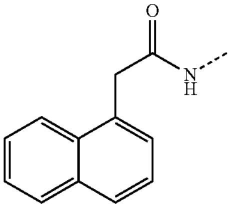 | 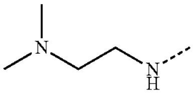 | C37H46N6O5S | 686.3 | 1.66 (96) | 687.2 | Method 4b |
| Ex. 325 | S | 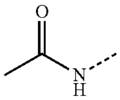 | 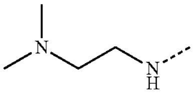 | C27H40N6O5S | 560.3 | 1.19 (98) | 561.2 | Method 4b |
| Ex. 326 | S | 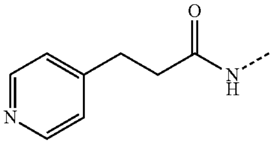 | 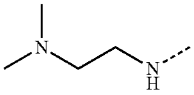 | C33H45N7O5S | 651.3 | 1.12 (89) | 652.2 | Method 4b |
| Ex. 327 | S | 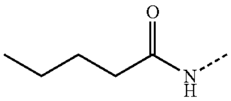 | 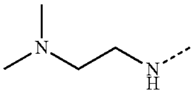 | C30H46N6O5S | 602.3 | 1.46 (97) | 603.0 | Method 4b |
| Ex. 328 | $SO_2$ | 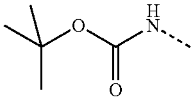 | 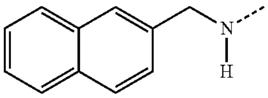 | C37H45N5O8S | 719.3 | 2.08 (98) | 720.2 | Method 4b |
| Ex. 329 | $SO_2$ | 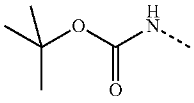 | 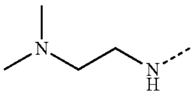 | C30H46N6O8S | 650.3 | 1.45 (94) | 651.2 | Method 4b |

TABLE 37.2.b-continued
Examples of Core 21 (Ex. 312-Ex. 341)
| No | X | $R^2$ | $R^{54}$ | FORMULA | MONO-ISO-TOPIC MASS | Rt (purity at 220 nm) | $[M + H]^+$ found | LC-MS-Method |
|---|---|---|---|---|---|---|---|---|
| Ex. 330 | $SO_2$ | $NH_2$ | 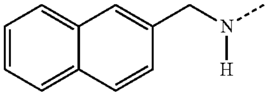 | C32H37N5O6S | 619.3 | 1.58 (94) | 620.0 | Method 4b |
| Ex. 331 | $SO_2$ | $NH_2$ | 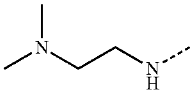 | C25H38N6O6S | 550.3 | 1.28 (80) | 551.2 | Method 5a |
| Ex. 332 | $SO_2$ | 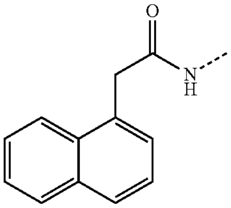 | 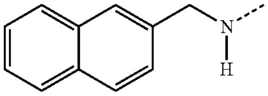 | C44H45N5O7S | 787.3 | 2.14 (96) | 788.2 | Method 4b |
| Ex. 333 | $SO_2$ | 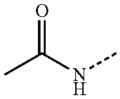 | 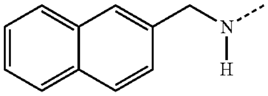 | C34H39N5O7S | 661.3 | 1.78 (95) | 661.8 | Method 4b |
| Ex. 334 | $SO_2$ | 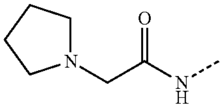 | 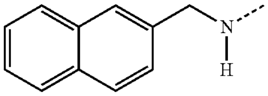 | C38H46N6O7S | 730.3 | 1.64 (95) | 731.2 | Method 4b |
| Ex. 335 | $SO_2$ | 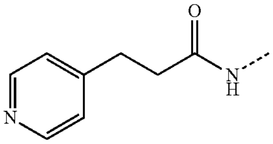 | 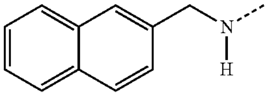 | C40H44N6O7S | 752.3 | 1.63 (98) | 753.2 | Method 4b |
| Ex. 336 | $SO_2$ | 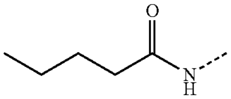 | 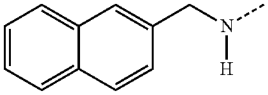 | C37H45N5O7S | 703.3 | 1.98 (96) | 704.2 | Method 4b |
| Ex. 337 | $SO_2$ | 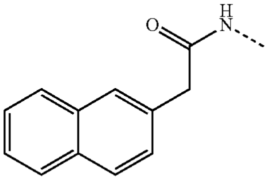 | 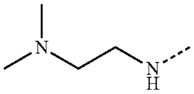 | C37H46N6O7S | 718.3 | 1.61 (96) | 719.3 | Method 4a |
| Ex. 338 | $SO_2$ | 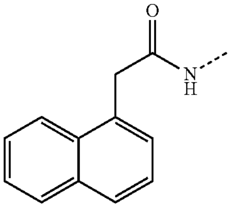 | 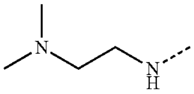 | C37H46N6O7S | 718.3 | 1.59 (96) | 719.3 | Method 4a |
| Ex. 339 | $SO_2$ | 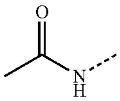 | 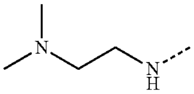 | C27H40N6O7S | 592.3 | 1.33 (95) | 593.3 | Method 5a |

TABLE 37.2.b-continued

| Examples of Core 21 (Ex. 312-Ex. 341) | | | | | | | | |
|---|---|---|---|---|---|---|---|---|
| No | X | $R^2$ | $R^{54}$ | FORMULA | MONO-ISO-TOPIC MASS | Rt (purity at 220 nm) | $[M + H]^+$ found | LC-MS-Method |
| Ex. 340 | $SO_2$ | 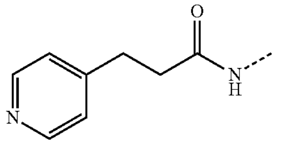 | 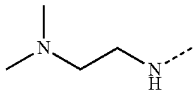 | C33H45N7O7S | 683.3 | 1.49 (100) | 684.1 | Method 5a |
| Ex. 341 | $SO_2$ | 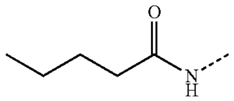 | 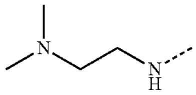 | C30H46N6O7S | 634.3 | 1.61 (91) | 635.3 | Method 5a |

TABLE 37.2.c

| Examples Core 21 (Ex . 312-Ex . 341) | | | | |
|---|---|---|---|---|
| No | $R^2$ | $R^{54}$ | X | IUPAC name |
| Ex. 312 | 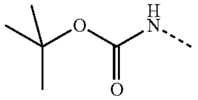 | $OCH_2Ph$ | S | benzyl (4S,6R,15S)-6-[(tert-butoxycarbonyl)amino]-11,16-dimethyl-9,12,17-trioxo-2-thia-8,11,16-triazatricyclo[16.3.1.$0^{4,8}$]docosa-1(22),18,20-triene-15-carboxylate |
| Ex. 313 | 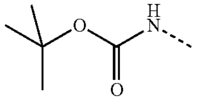 | $OCH_2Ph$ | $SO_2$ | benzyl (4S,6R,15S)-6-[tert-butoxycarbonyl)amino]-11,16-dimethyl-2,2,9,12,17-pentaoxo-2$\lambda^6$-thia-8,11,16-triazatricyclo[16.3.1.$0^{4,8}$]docosa-1(22),18,20-triene-15-carboxylate |
| Ex. 314 | 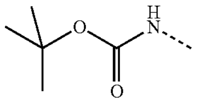 | OH | S | (4S,6R,15S)-6-[(tert-butoxycarbonyl)amino]-11,16-dimethyl-9,12,17-trioxo-2-thia-8,11,16-triazatricyclo-[16.3.1.$0^{4,8}$]docosa-1(22),18,20-triene-15-carboxylic acid |
| Ex. 315 | 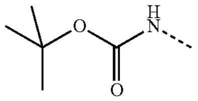 | OH | $SO_2$ | (4S,6R,15S)-6-[(tert-butoxycarbonyl)amino]-11,16-dimethyl-2,2,9,12,17-pentaoxo-2$\lambda^6$-thia-8,11,16-triazatricyclo[16.3.1.$0^{4,8}$]docosa-1(22),18,20-triene-15-carboxylic acid |
| Ex. 316 | 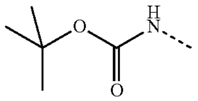 | 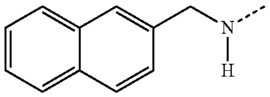 | S | tert-butyl N-[(4S,6R,15S)-11,16-dimethyl-15-{[(2-naphthylmethyl)amino]carbonyl}-9,12,17-trioxo-2-thia-8,11,16-triazatricyclo[16.3.1.$0^{4,8}$]docosa-1(22),18,20-trien-6-yl]carbamate |
| Ex. 317 | 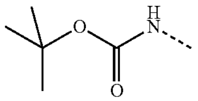 | 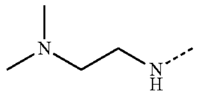 | S | tert-butyl N-[(4S,6R,15S)-15-({[2-(dimethylamino)ethyl]amino}carbonyl)-11,16-dimethyl-9,12,17-trioxo-2-thia-8,11,16-triazatricyclo-[16.3.1.$0^{4,8}$]docosa-1(22),18,20-trien-6-yl]carbamate |
| Ex. 318 | $NH_2$ | 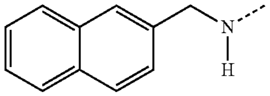 | S | (4S,6R,15S)-6-amino-11,16-dimethyl-N-(2-naphthyl-methyl)-9,12,17-trioxo-2-thia-8,11,16-triazatricyclo-[16.3.1.$0^{4,8}$]docosa-1(22),18,20-triene-15-carboxamide |
| Ex. 319 | $NH_2$ | 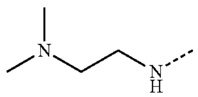 | S | (4S,6R,15S)-6-amino-N-[2-(dimethylamino)ethyl]-11,16-dimethyl-9,12,17-trioxo-2-thia-8,11,16-triazatricyclo-[16.3.1.$0^{4,8}$]docosa-1(22),18,20-triene-15-carboxamide |
| Ex. 320 | 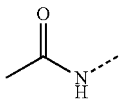 | 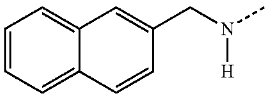 | S | (4S,6R,15S)-6-(acetylamino)-11,16-dimethyl-N-(2-naphthylmethyl)-9,12,17-trioxo-2-thia-8,11,16-triazatricyclo[16.3.1.$0^{4,8}$]docosa-1(22),18,20-triene-15-carboxamide |

TABLE 37.2.c-continued

| No | $R^2$ | $R^{54}$ | X | IUPAC name |
|---|---|---|---|---|
| | | Examples Core 21 (Ex . 312-Ex . 341) | | |
| Ex. 321 | 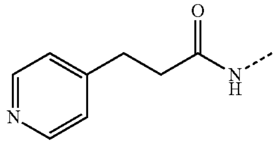 | 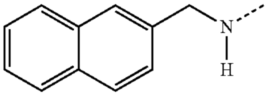 | S | (4S,6R,15S)-11,16-dimethyl-N-(2-naphthylmethyl)-9,12,17-trioxo-6-{[3-(4-pyridinyl)propanoyl]amino}-2-thia-8,11,16-triazatricyclo[16.3.1.0$^{4,8}$]docosa-1(22),18,20-triene-15-carboxamide |
| Ex. 322 | 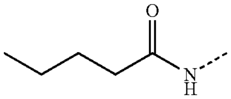 | 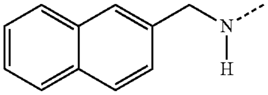 | S | (4S,6R,15S)-11,16-dimethyl-N-(2-naphthylmethyl)-9,12,17-trioxo-6-(pentanoylamino)-2-thia-8,11,16-triazatricyclo[16.3.1.0$^{4,8}$]docosa-1(22),18,20-triene-15-carboxamide |
| Ex. 323 | 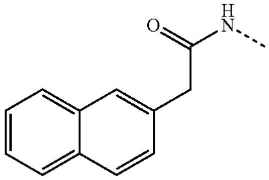 | 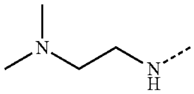 | S | (4S,6R,15S)-N-[2-(dimethylamino)ethyl]-11,16-dimethyl-6-{[2-(2-naphthyl)acetyl]amino}-9,12,17-trioxo-2-thia-8,11,16-triazatricyclo[16.3.1.0$^{4,8}$]-docosa-1(22),18,20-triene-15-carboxamide |
| Ex. 324 | 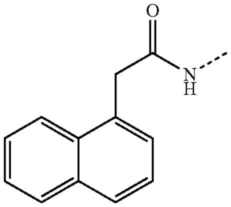 | 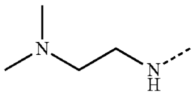 | S | (4S,6R,15S)-N-[2-(dimethylamino)ethyl]-11,16-dimethyl-6-{[2-(1-naphthyl)acetyl]amino}-9,12,17-trioxo-2-thia-8,11,16-tiazatricyclo[16.3.1.0$^{4,8}$]-docosa-1(22),18,20-triene-15-carboxamide |
| Ex. 325 | 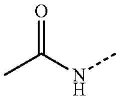 | 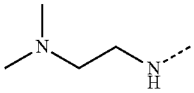 | S | (4S,6R,15S)-6-(acetylamino)-N-[2-(dimethylamino)-ethyl]-11,16-dimethyl-9,12,17-trioxo-2-thia-8,11,16-triazatricyclo[16.3.1.0$^{4,8}$]docosa-1(22),18,20-triene-15-carboxamide |
| Ex. 326 | 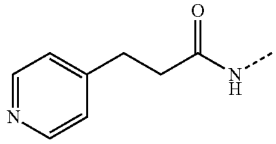 | 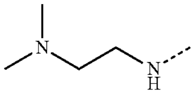 | S | (4S,6R,15S)-N-[2-(dimethylamino)ethyl]-11,16-dimethyl-9,12,17-trioxo-6-{[3-(4-pyridinyl)-propanoyl]amino}-2-thia-8,11,16-triazatricyclo[16.3.1.0$^{4,8}$]docosa-1(22),18,20-triene-15-carboxamide |
| Ex. 327 | 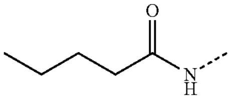 | 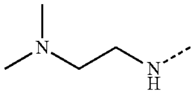 | S | (4S,6R,15S)-N-[2-(dimethylamino)ethyl]-11,16-dimethyl-9,12,17-trioxo-6-(pentanoylamino)-2-thia-8,11,16-triazatricyclo[16.3.1.0$^{4,8}$]docosa-1(22),18,20-triene-15-carboxamide |
| Ex. 328 | 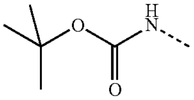 | 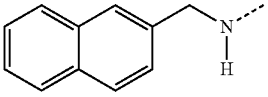 | $SO_2$ | tert-butyl N-[(4S,6R,15S)-11,16-dimethyl-15-{[(2-naphthylmethyl)amino]carbonyl}-2,2,9,12,17-pentaoxo-2λ$^6$-thia-8,11,16-triazatricyclo-[16.3.1.0$^{4,8}$]docosa-1(22),18,20-trien-6-yl]carbamate |
| Ex. 329 | 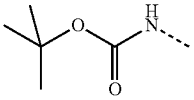 | 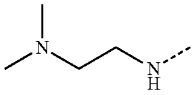 | $SO_2$ | tert-butyl N-[(4S,6R,15S)-15-({[2-(dimethylamino)ethyl]amino}carbonyl)-11,16-dimethyl-2,2,9,12,17-pentaoxo-2λ$^6$-thia-8,11,16-triazatricyclo-[16.3.1.0$^{4,8}$]docosa-1(22),18,20-trien-6-yl]carbamate |
| Ex. 330 | $NH_2$ | 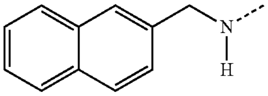 | $SO_2$ | (4S,6R,15S)-6-amino-11,16-dimethyl-N-(2-naphthylmethyl)-2,2,9,12,17-pentaoxo-2λ$^6$-thia-8,11,16-triazatricyclo[16.3.1.0$^{4,8}$]docosa-1(22),18,20-triene-15-carboxamide |
| Ex. 331 | $NH_2$ | 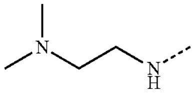 | $SO_2$ | (4S,6R,15S)-6-amino-N-[2-(dimethylamino)ethyl]-11,16-dimethyl-2,2,9,12,17-pentaoxo-2λ$^6$-thia-8,11,16-triazatricyclo[16.3.1.0$^{4,8}$]docosa-1(22),18,20-triene-15-carboxamide |

TABLE 37.2.c-continued

| Examples Core 21 (Ex . 312-Ex . 341) | | | | |
|---|---|---|---|---|
| No | $R^2$ | $R^{54}$ | X | IUPAC name |
| Ex. 332 | 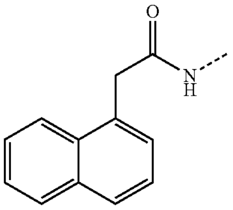 | 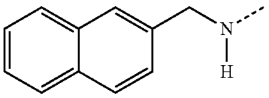 | $SO_2$ | (4S,6R,15S)-11,16-dimethyl-6-{[2-(1-naphthyl)-acetyl]amino}-N-(2-naphthylmethyl)-2,2,9,12,17-pentaoxo-2λ$^6$-thia-8,11,16-triazatricyclo[16.3.1.0$^{4,8}$]-docosa-1(22),18,20-triene-15-carboxamide |
| Ex. 333 | 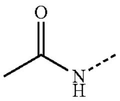 | 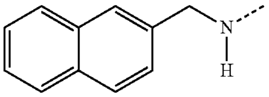 | $SO_2$ | (4S,6R,15S)-6-(acetylamino)-11,16-dimethyl-N-(2-naphthylmethyl)-2,2,9,12,17-pentaoxo-2λ$^6$-thia-8,11,16-triazatricyclo[16.3.1.0$^{4,8}$]docosa-1(22),18,20-triene-15-carboxamide |
| Ex. 334 | 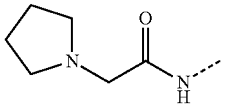 | 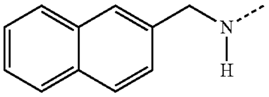 | $SO_2$ | (4S,6R,15S)-11,16-dimethyl-N-(2-naphthylmethyl)-2,2,9,12,17-pentaoxo-6-{[2-(1-pyrrolidinyl)acetyl]-amino}-2λ$^6$-thia-8,11,16-triazatricyclo[16.3.1.0$^{4,8}$]-docosa-1(22),18,20-triene-15-carboxamide |
| Ex. 335 | 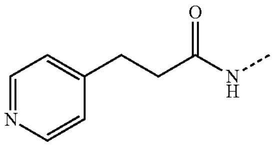 | 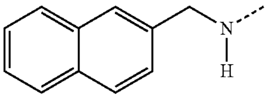 | $SO_2$ | (4S,6R,15S)-11,16-dimethyl-N-(2-naphthylmethyl)-2,2,9,12,17-pentaoxo-6-{[3-(4-pyridinyl)propanoyl]-amino}-2λ$^6$-thia-8,11,16-triazatricyclo[16.3.1.0$^{4,8}$]-docosa-1(22),18,20-triene-15-carboxamide |
| Ex. 336 | 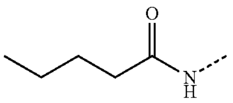 | 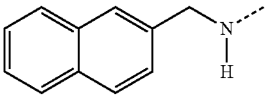 | $SO_2$ | (4S,6R,15S)-11,16-dimethyl-N-(2-naphthylmethyl)-2,2,9,12,17-pentaoxo-6-(pentanoylamino)-2λ$^6$-thia-8,11,16-triazatricyclo[16.3.1.0$^{4,8}$]docosa-1(22),18,20-triene-15-carboxamide |
| Ex. 337 | 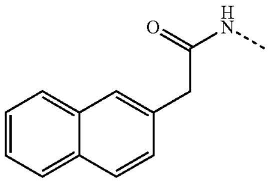 | 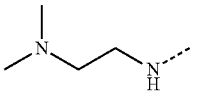 | $SO_2$ | (4S,6R,15S)-N-[2-(dimethylamino)ethyl]-11,16-dimethyl-6-{[2-(2-naphthyl)acetyl]amino}-2,2,9,12,17-pentaoxo-2λ$^6$-thia-8,11,16-triazatricyclo[16.3.1.0$^{4,8}$]docosa-1(22),18,20-triene-15-carboxamide |
| Ex. 338 | 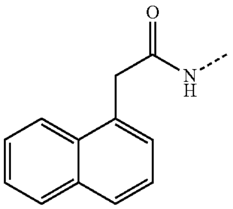 | 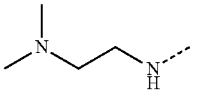 | $SO_2$ | (4S,6R,15S)-N-[2-(dimethylamino)ethyl]-11,16-dimethyl-6-{[2-(1-naphthyl)acetyl]amino}-2,2,9,12,17-pentaoxo-2λ$^6$-thia-8,11,16-triazatricyclo[16.3.1.0$^{4,8}$]docosa-1(22),18,20-triene-15-carboxamide |
| Ex. 339 | 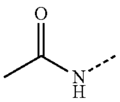 | 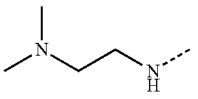 | $SO_2$ | (4S,6R,15S)-6-(acetylamino)-N-[2-(dimethyl-amino)ethyl]-11,16-dimethyl-2,2,9,12,17-pentaoxo-2λ$^6$-thia-8,11,16-triazatricyclo-[16.3.1.0$^{4,8}$]docosa-1(22),18,20-triene-15-carboxamide |
| Ex. 340 | 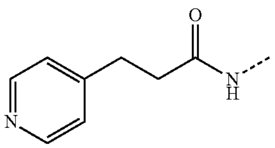 | 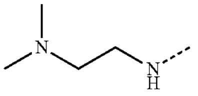 | $SO_2$ | (4S,6R,15S)-N-[2-(dimethylamino)ethyl]-11,16-dimethyl-2,2,9,12,17-pentaoxo-6-{[3-(4-pyridinyl)propanoyl]amino}-2λ$^6$-thia-8,11,16-triazatricyclo[16.3.1.0$^{4,8}$]docosa-1(22),18,20-triene-15-carboxamide |
| Ex. 341 | 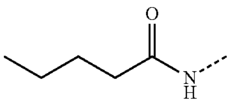 | 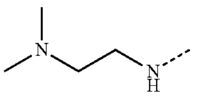 | $SO_2$ | (4S,6R,15S)-N-[2-(dimethylamino)ethyl]-11,16-dimethyl-2,2,9,12,17-pentaoxo-6-(pentanoylamino)-2λ$^6$-thia-8,11,16-triazatricyclo[16.3.1.0$^{4,8}$]docosa-1(22),18,20-triene-15-carboxamide |

TABLE 38a

Examples of Core 22 (Ex. 342-Ex. 362)

| No | $R^2$ | $R^5$ | Starting material | General Pro-cedure | Reagent | Purification Method | Yield (isolated salt) |
|---|---|---|---|---|---|---|---|
| Ex. 342-Ex. 343: cf. experimental description | | | | | | | |
| Ex. 344 | 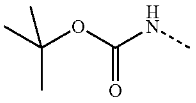 | 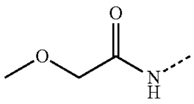 | Ex. 343 | L.1.1 | 2-methoxy-acetyl chloride (1.5 equiv.) pyridine (5 equiv.) | FC (hexane/ EtOAc/ MeOH) | 97% |
| Ex. 345 | $NH_2$ | 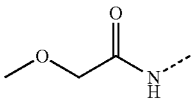 | Ex. 344 | J | HCl-dioxane | crude product | 76% (HCl salt) |
| Ex. 346 | 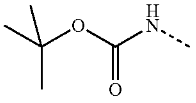 | 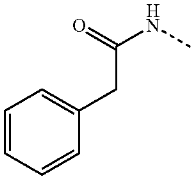 | Ex. 343 | L.1.1 | phenylacetyl chloride (1.5 equiv.) pyridine (5 equiv.) | FC (hexane/ EtOAc/ MeOH) | 84% |
| Ex. 347 | $NH_2$ | 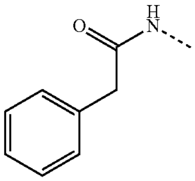 | Ex. 346 | J | HCl-dioxane | crude product | 94% (HCl salt) |
| Ex. 348 | 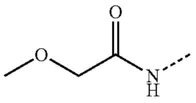 | 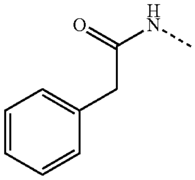 | Ex. 347 | L.1.1 | 2-methoxy-acetyl chloride (1.5 equiv.) pyridine (5 equiv.) | FC (hexane/ EtOAc/ MeOH) | 97% |
| Ex. 349 | 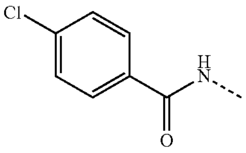 | 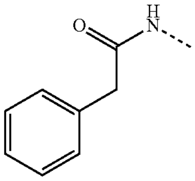 | Ex. 347 | L.1.1 | 4-chlorobenzoyl chloride (1.5 equiv.) pyridine (5 equiv.) | FC (hexane/ EtOAc/ MeOH) | 77% |
| Ex. 350 | 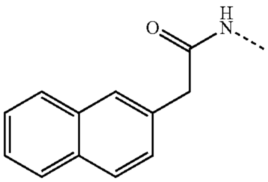 | 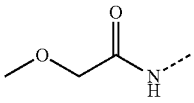 | Ex. 345 | L.1.3 | 2-naphthylacetic acid (1.0 equiv.), HATU (1.0 equiv.) HOAt (1.0 equiv.) pyridine (5 equiv.) | FC (hexane/ EtOAc/ MeOH) | 77% |
| Ex. 351 | 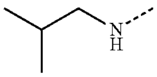 | 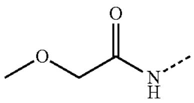 | Ex. 345*) | M.2 | isobutyraldehyde (1.0 equiv.) | FC (hexane/ EtOAc/ MeOH) | 65% |
| Ex. 352 | 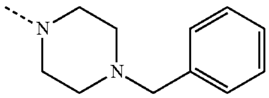 | 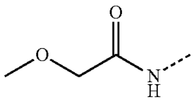 | Ex. 345 | O | N-benzyl-2-chloro-N-(2-chloroethyl)-ethanamine | FC (hexane/ EtOAc/ MeOH) | 52% |

TABLE 38a-continued

| Examples of Core 22 (Ex. 342-Ex. 362) | | | | | | | |
|---|---|---|---|---|---|---|---|
| No | $R^2$ | $R^5$ | Starting material | General Procedure | Reagent | Purification Method | Yield (isolated salt) |
| Ex. 353 | 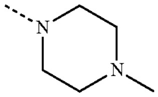 | 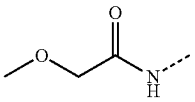 | Ex. 352 | M.4 | $H_2$, $Pd(OH)_2$—C aq. formaldehyde soln | FC ($CH_2Cl_2$/ MeOH/ aq. $NH_3$) | 75% |
| Ex. 354 | $NH_2$ | 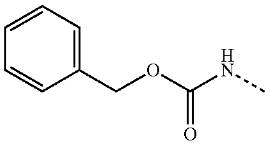 | Ex. 342 | J | HCl-dioxane | crude product | 93% (HCl salt) |
| Ex. 355 | 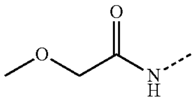 | 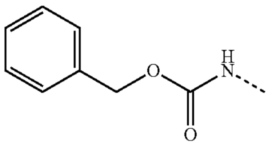 | Ex. 354 | L.1.1 | 2-methoxyacetyl chloride (1.5 equiv.) pyridine (5 equiv.) | FC (hexane/ EtOAc/ MeOH) | 86% |
| Ex. 356 | 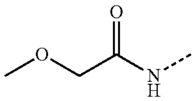 | $NH_2$ | Ex. 355 | K.1 | $H_2$, $Pd(OH)_2$—C | crude product | 94% |
| Ex. 357 | 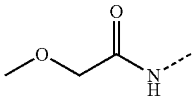 | 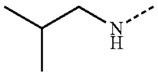 | Ex. 356 | M.2 | isobutyraldehyde (1.0 equiv.) | FC (hexane/ EtOAc/ MeOH) | 73% |
| Ex. 358 | 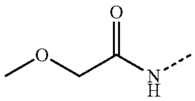 | 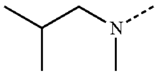 | Ex. 357 | M.3 | aq. formaldehyde soln (2.5 equiv.) $NaBH(OAc)_3$ (3 equiv.) | FC (hexane/ EtOAc/ MeOH) | 78% |
| Ex. 359 | 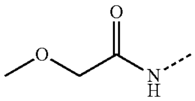 | 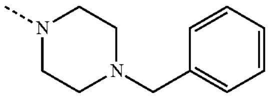 | Ex. 356 | O | N-benzyl-2-chloro-N-(2-chloroethyl)-ethanamine | FC (EtOAc/ MeOH) | 52% |
| Ex. 360 | 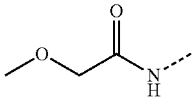 | 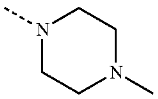 | Ex. 359 | M.4 | $H_2$, $Pd(OH)_2$—C aq. formaldehyde soln | FC ($CH_2Cl_2$/ MeOH/ aq. $NH_3$) | 66% |
| Ex. 361 | 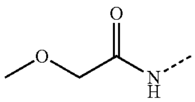 | 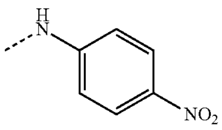 | Ex. 356 | **) | **) | FC (hexane/ EtOAc/ MeOH) | 59% |
| Ex. 362 | 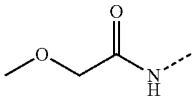 | 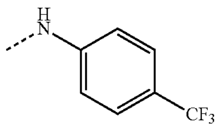 | Ex. 356 | ***) | ***) | prep. HPLC method 1 | 9% |

*)Used as free base

**) A soln of Ex. 356 (60 mg, 0.15 mmol) in DMSO (0.3 mL) was treated with 1-fluoro-4-nitrobenzene (0.031 mL, 0.3 mmol) and i-$Pr_2NEt$ (0.084 mL, 0.6 mmol) at 50° C. for 15 h. Aq. workup (EtOAc, $H_2O$, 1M aq. HCl soln; $Na_2SO_4$) and FC (hexane/EtOAc/MeOH) afforded Ex. 361 (46 mg, 59%).

***) Dioxane (2.0 mL) was added to a mixture of 4-bromobenzotrifluoride (0.05 mL, 0.35 mmol), bis(dibenzylideneacetone)dipalladium(0)-chloroform adduct (30 mg), 9,9-dimethyl-4,5-bis(diphenylphosphino)xanthene (18 mg), Ex. 356 (60 mg, 0.15 mmol) and $Cs_2CO_3$ (115 mg, 0.35 mmol). The mixture was heated to 90° C. for 36 h, followed by aq. workup ($CH_2Cl_2$, aq. $Na_2CO_3$ soln; $Na_2SO_4$) and prep. HPLC method 3 afforded Ex. 362 (7 mg, 9%).

TABLE 38b
Examples of Core 22 (Ex. 342-Ex. 362; continued on the following page)
| No | $R^2$ | $R^5$ | FORMULA | MONO-ISO-TOPIC MASS | Rt (purity at 220 nm) | [M + H]$^+$ found | LC-MS-Method |
|---|---|---|---|---|---|---|---|
| Ex. 342-Ex. 343: cf. experimental description | | | | | | | |
| Ex. 344 | 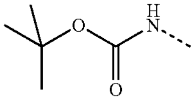 | 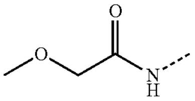 | C24H33FN4O7 | 508.2 | 1.66 (99) | 509.1 | Method 10a |
| Ex. 345 | $NH_2$ | 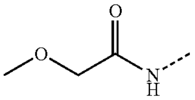 | C19H25FN4O5 | 408.2 | 0.91 (100) | 409.2 | Method 10a |
| Ex. 346 | 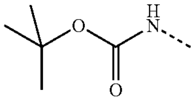 | 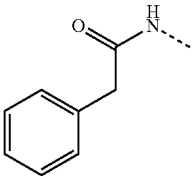 | C29H35FN4O6 | 554.3 | 1.92 (99) | 555.3 | Method 10a |
| Ex. 347 | $NH_2$ | 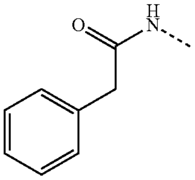 | C24H27FN4O4 | 454.2 | 1.20 (98) | 455.2 | Method 10a |
| Ex. 348 | 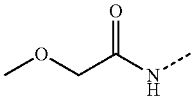 | 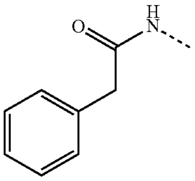 | C27H31FN4O6 | 526.2 | 1.50 (97) | 527.2 | Method 10a |
| Ex. 349 | 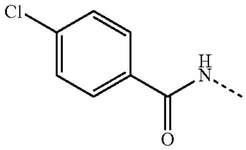 | 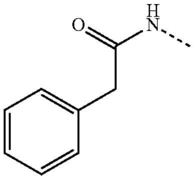 | C31H30ClFN4O5 | 592.2 | 1.93 (97) | 593.2 | Method 10a |
| Ex. 350 | 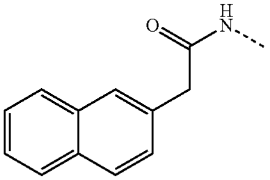 | 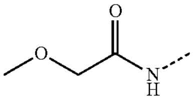 | C31H33FN4O6 | 576.2 | 1.72 (97) | 577.2 | Method 10a |
| Ex. 351 | 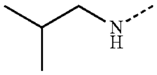 | 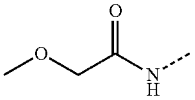 | C23H33FN4O5 | 464.2 | 1.16 (93) | 465.2 | Method 10a |
| Ex. 352 | 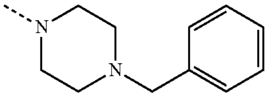 | 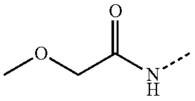 | C30H38FN5O5 | 567.3 | 1.24 (84) | 568.3 | Method 10a |

TABLE 38b-continued
Examples of Core 22 (Ex. 342-Ex. 362; continued on the following page)
| No | $R^2$ | $R^5$ | FORMULA | MONO-ISO-TOPIC MASS | Rt (purity at 220 nm) | $[M + H]^+$ found | LC-MS-Method |
|---|---|---|---|---|---|---|---|
| Ex. 353 | 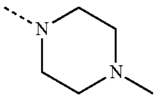 | 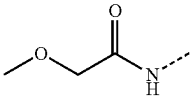 | C24H34FN5O5 | 491.2 | 1.01 (88) | 492.1 | Method 10a |
| Ex. 354 | $NH_2$ | 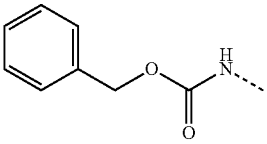 | C24H27FN4O5 | 470.2 | 1.29 (93) | 471.2 | Method 10a |
| Ex. 355 | 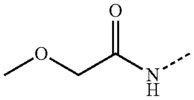 | 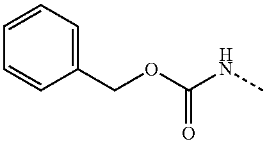 | C27H31FN4O7 | 542.2 | 1.60 (95) | 543.2 | Method 10a |
| Ex. 356 | 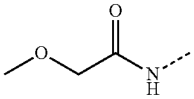 | $NH_2$ | C19H25FN4O5 | 408.2 | 1.02 (99) | 409.2 | Method 10a |
| Ex. 357 | 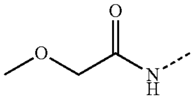 | 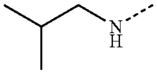 | C23H33FN4O5 | 464.2 | 1.15 (96) | 465.2 | Method 10a |
| Ex. 358 | 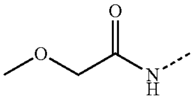 | 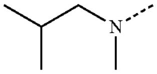 | C24H35FN4O5 | 478.2 | 1.19 (100) | 479.3 | Method 10a |
| Ex. 359 | 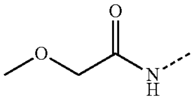 | 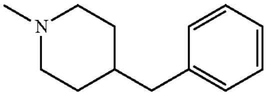 | C30H38FN5O5 | 567.3 | 1.22 (96) | 568.3 | Method 10a |
| Ex. 360 | 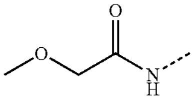 | 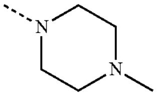 | C24H34FN5O5 | 491.3 | 1.04 (96) | 492.1 | Method 10a |
| Ex. 361 | 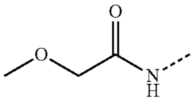 | 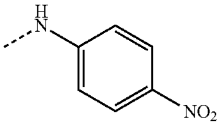 | C25H28FN5O7 | 529.2 | 1.61 (98) | 530.2 | Method 10a |
| Ex. 362 | 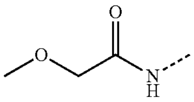 | 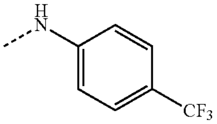 | C26H28F4N4O5 | 552.2 | 1.90 (97) | 553.2 | Method 10a |

TABLE 38c

Examples of Core 22 (Ex. 342-Ex. 362; continued on the following pages)

| No | $R^2$ | $R^5$ | IUPAC name |
|---|---|---|---|
| Ex. 342 | 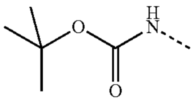 | 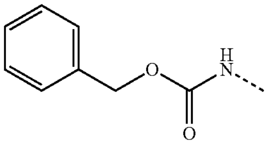 | tert-butyl N-((2S,6S,16aS)-6-{[(benzyloxy)carbonyl]amino}-12-fluoro-5,10-dioxo-2,3,5,6,7,8,9,10,16,16a-decahydro-1H-pyrrolo[2,1-c][1,4,9]benzoxadiazacyclododecin-2-yl)carbamate |
| Ex. 343 | 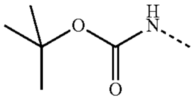 | $NH_2$ | tert-butyl N-[(2S,6S,16aS)-6-amino-12-fluoro-5,10-dioxo-2,3,5,6,7,8,9,10,16,16a-decahydro-1H-pyrrolo[2,1-c][1,4,9]benzoxadiazacyclododecin-2-yl]carbamate |
| Ex. 344 | 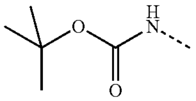 | 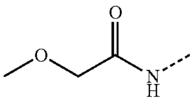 | tert-butyl N-{(2S,6S,16aS)-12-fluoro-6-[(2-methoxyacetyl)amino]-5,10-dioxo-2,3,5,6,7,8,9,10,16,16a-decahydro-1H-pyrrolo[2,1-c][1,4,9]benzoxadiazacyclododecin-2-yl}carbamate |
| Ex. 345 | $NH_2$ | 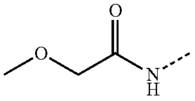 | N-[(2S,6S,16aS)-2-amino-12-fluoro-5,10-dioxo-2,3,5,6,7,8,9,10,16,16a-decahydro-1H-pyrrolo[2,1-c][1,4,9]benzoxadiazacyclododecin-6-yl]-2-methoxyacetamide |
| Ex. 346 | 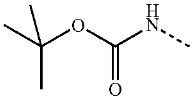 | 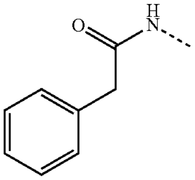 | tert-butyl N-{(2S,6S,16aS)-12-fluoro-5,10-dioxo-6-[(2-phenylacetyl)amino]-2,3,5,6,7,8,9,10,16,16a-decahydro-1H-pyrrolo[2,1-c][1,4,9]benzoxadiazacyclododecin-2-yl}carbamate |
| Ex. 347 | $NH_2$ | 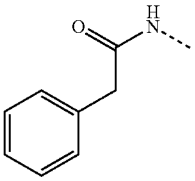 | N-[(2S,6S,16aS)-2-amino-12-fluoro-5,10-dioxo-2,3,5,6,7,8,9,10,16,16a-decahydro-1H-pyrrolo[2,1-c][1,4,9]benzoxadiazacyclododecin-6-yl]-2-phenylacetamide |
| Ex. 348 | 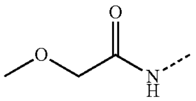 | 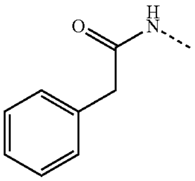 | N-{(2S,6S,16aS)-12-fluoro-5,10-dioxo-6-[(2-phenylacetyl)amino]-2,3,5,6,7,8,9,10,16,16a-decahydro-1H-pyrrolo[2,1-c][1,4,9]benzoxadiazacyclododecin-2-yl}-2-methoxyacetamide |
| Ex. 349 | 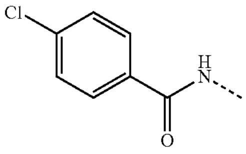 | 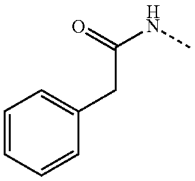 | N-{(2S,6S,16aS)-12-fluoro-5,10-dioxo-6-[(2-phenylacetyl)amino]-2,3,5,6,7,8,9,10,16,16a-decahydro-1H-pyrrolo[2,1-c][1,4,9]benzoxadiazacyclododecin-2-yl}-4-chlorobenzamide |
| Ex. 350 | 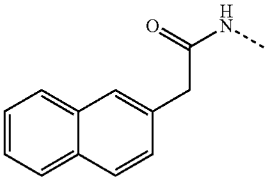 | 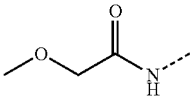 | N-((2S,6S,16aS)-12-fluoro-2-{[2-(2-naphthyl)acetyl]amino}-5,10-dioxo-2,3,5,6,7,8,9,10,16,16a-decahydro-1H-pyrrolo[2,1-c][1,4,9]benzoxadiazacyclododecin-6-yl)-2-methoxyacetamide |
| Ex. 351 | 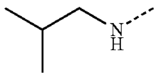 | 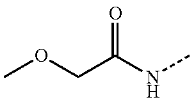 | N-[(2S,6S,16aS)-12-fluoro-2-(isobutylamino)-5,10-dioxo-2,3,5,6,7,8,9,10,16,16a-decahydro-1H-pyrrolo[2,1-c][1,4,9]benzoxadiazacyclododecin-6-yl]-2-methoxyacetamide |

TABLE 38c-continued

Examples of Core 22 (Ex. 342-Ex. 362; continued on the following pages)

| No | $R^2$ | $R^5$ | IUPAC name |
| --- | --- | --- | --- |
| Ex. 352 | 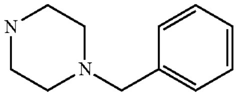 | 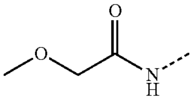 | N-[(2S,6S,16aS)-2-(4-benzylpiperazino)-12-fluoro-5,10-dioxo-2,3,5,6,7,8,9,10,16,16a-decahydro-1H-pyrrolo[2,1-c][1,4,9]benzoxadiazacyclododecin-6-yl]-2-methoxyacetamide |
| Ex. 353 | 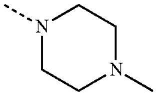 | 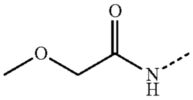 | N-[(2S,6S,16aS)-12-fluoro-2-(4-methylpiperazino)-5,10-dioxo-2,3,5,6,7,8,9,10,16,16a-decahydro-1H-pyrrolo[2,1-c][1,4,9]benzoxadiazacyclododecin-6-yl]-2-methoxyacetamide |
| Ex. 354 | $NH_2$ | 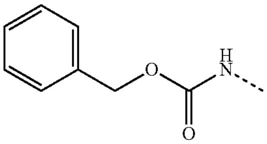 | benzyl N-[(2S,6S,16aS)-2-amino-12-fluoro-5,10-dioxo-2,3,5,6,7,8,9,10,16,16a-decahydro-1H-pyrrolo[2,1-c][1,4,9]benzoxadiazacyclododecin-6-yl]carbamate |
| Ex. 355 | 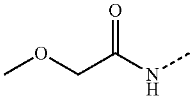 | 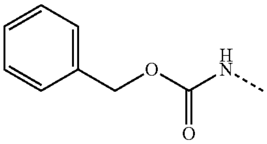 | benzyl N-{(2S,6S,16aS)-12-fluoro-2-[(2-methoxyacetyl)amino]-5,10-dioxo-2,3,5,6,7,8,9,10,16,16a-decahydro-1H-pyrrolo[2,1-c][1,4,9]benzoxadiazacyclododecin-6-yl}carbamate |
| Ex. 356 | 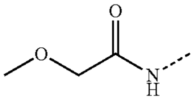 | $NH_2$ | N-[(2S,6S,16aS)-6-amino-12-fluoro-5,10-dioxo-2,3,5,6,7,8,9,10,16,16a-decahydro-1H-pyrrolo[2,1-c][1,4,9]benzoxadiazacyclododecin-2-yl]-2-methoxyacetamide |
| Ex. 357 | 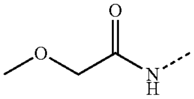 | 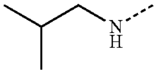 | N-[(2S,6S,16aS)-12-fluoro-6-(isobutylamino)-5,10-dioxo-2,3,5,6,7,8,9,10,16,16a-decahydro-1H-pyrrolo[2,1-c][1,4,9]benzoxadiazacyclododecin-2-yl]-2-methoxyacetamide |
| Ex. 358 | 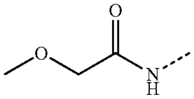 | 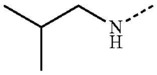 | N-{(2S,6S,16aS)-12-fluoro-6-[isobutyl(methyl)amino]-5,10-dioxo-2,3,5,6,7,8,9,10,16,16a-decahydro-1H-pyrrolo[2,1-c][1,4,9]benzoxadiazacyclododecin-2-yl}-2-methoxyacetamide |
| Ex. 359 | 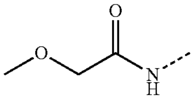 | 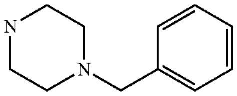 | N-[(2S,6S,16aS)-6-(4-benzylpiperazino)-12-fluoro-5,10-dioxo-2,3,5,6,7,8,9,10,16,16a-decahydro-1H-pyrrolo[2,1-c][1,4,9]benzoxadiazacyclododecin-2-yl]-2-methoxyacetamide |
| Ex. 360 | 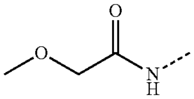 | 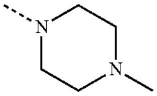 | N-[(2S,6S,16aS)-12-fluoro-6-(4-methylpiperazino)-5,10-dioxo-2,3,5,6,7,8,9,10,16,16a-decahydro-1H-pyrrolo[2,1-c][1,4,9]benzoxadiazacyclododecin-2-yl]-2-methoxyacetamide |
| Ex. 361 | 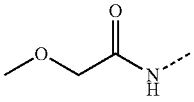 | 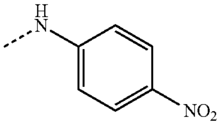 | N-[(2S,6S,16aS)-12-fluoro-6-(4-nitroanilino)-5,10-dioxo-2,3,5,6,7,8,9,10,16,16a-decahydro-1H-pyrrolo[2,1-c][1,4,9]benzoxadiazacyclododecin-2-yl]-2-methoxyacetamide |
| Ex. 362 | 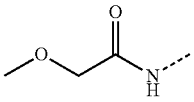 | 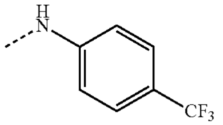 | N-{(2S,6S,16aS)-12-fluoro-5,10-dioxo-6-[4-(trifluoromethyl)anilino]-2,3,5,6,7,8,9,10,16,16a-decahydro-1H-pyrrolo[2,1-c][1,4,9]benzoxadiazacyclododecin-2-yl}-2-methoxyacetamide |

TABLE 39a

Examples of Core 23 (Ex. 363-Ex . 378; continued on the following pages)

| No | $R^2$ | $R^{54}$ | Starting material | General Procedure | Reagent | Purification Method | Yield (isolated salt) |
|---|---|---|---|---|---|---|---|
| Ex. 363-Ex. 364: cf. experimental description | | | | | | | |
| Ex. 365 | 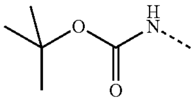 | 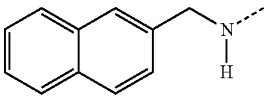 | Ex. 364 | L.2 | 2-naphthyl-methylmaine | FC (EtOAc/MeOH) | 97% |
| Ex. 366 | 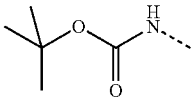 | 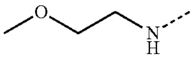 | Ex. 364 | L.2 | 2-methoxy-ethylamine | FC (EtOAc/MeOH) | 100% |
| Ex. 367 | 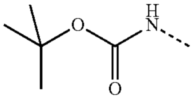 | 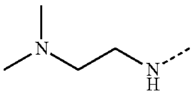 | Ex. 364 | L.2 | N,N-dimethyl-ethylenediamine | FC ($CH_2Cl_2$/MeOH/aq. $NH_3$) | 94% |
| Ex. 368 | $NH_2$ | 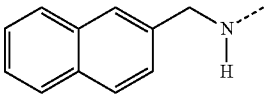 | Ex. 365 | J | HCl-dioxane | FC ($CH_2Cl_2$/MeOH/aq. $NH_3$) | 83% |
| Ex. 369 | $NH_2$ | 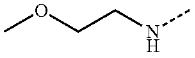 | Ex. 366 | J | HCl-dioxane | FC ($CH_2Cl_2$/MeOH/aq. $NH_3$) | 94% |
| Ex. 370 | $NH_2$ | 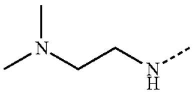 | Ex. 367 | J | HCl-dioxane | FC ($CH_2Cl_2$/MeOH/aq. $NH_3$) | 83% |
| Ex. 371 | 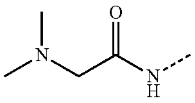 | 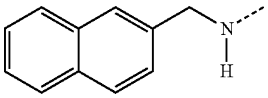 | Ex. 368 | L.1.3 | N,N-dimethyl glycine (1.2 equiv.) HATU (1.5 equiv.) HOAt (1.5 equiv.) i-$Pr_2$NEt (3 equiv.) | FC ($CH_2Cl_2$/MeOH) | 57% |
| Ex. 372 | 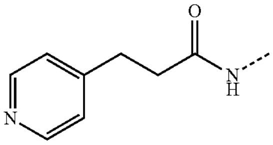 | 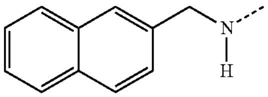 | Ex. 368 | L.1.3 | 3-(pyridin-4-yl)propanoic acid (1.2 equiv.) HATU (1.5 equiv.) HOAt (1.5 equiv.) i-$Pr_2$NEt (3 equiv.) | FC ($CH_2Cl_2$/MeOH) | 44% |
| Ex. 373 | 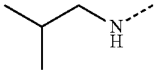 | 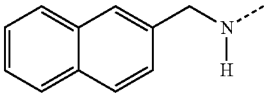 | Ex. 368 | M.2 | isobutyraldehyde | FC ($CH_2Cl_2$/MeOH) | 70% |
| Ex. 374 | 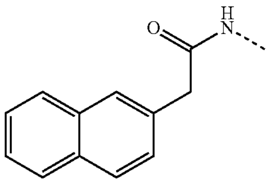 | 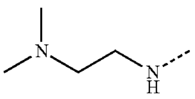 | Ex. 370 | L.1.3 | 2-naphthylacetic acid (1.2 equiv.) HATU (1.5 equiv.) HOAt (1.5 equiv.) i-$Pr_2$NEt (3 equiv.) | FC ($CH_2Cl_2$/MeOH/aq. $NH_3$) | 85% |

TABLE 39a-continued

| Examples of Core 23 (Ex. 363-Ex . 378; continued on the following pages) | | | | | | | |
|---|---|---|---|---|---|---|---|
| No | $R^2$ | $R^{54}$ | Starting material | General Procedure | Reagent | Purification Method | Yield (isolated salt) |
| Ex. 375 | 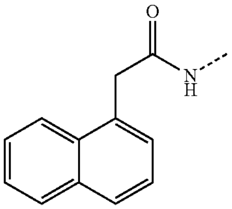 | 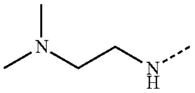 | Ex. 370 | L.1.3 | 1-naphthylacetic acid (1.2 equiv.) HATU (1.5 equiv.) HOAt (1.5 equiv.) i-$Pr_2NEt$ (3 equiv.) | FC ($CH_2Cl_2$/MeOH/aq. $NH_3$) | 40% |
| Ex. 376 | 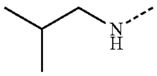 | 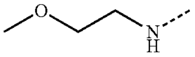 | Ex. 369 | M.2 | isobutyraldehyde | FC ($CH_2Cl_2$/MeOH) | 48% |
| Ex. 377 | 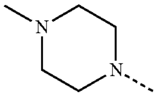 | 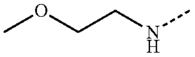 | Ex. 378 | M.4 | $H_2$, $Pd(OH)_2$; $CH_2O$ | crude product | 75% |
| Ex. 378 | 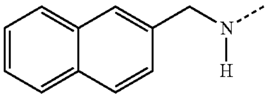 | 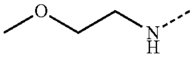 | Ex. 369 | O | N-benzyl-2-chloro-N-(2-chloroethyl)-ethanamine | FC ($CH_2Cl_2$/MeOH) and prep. HPLC Method 3 | 43% |

TABLE 39b

| Examples of Core 23 (Ex. 363-Ex. 378; continued on the following pages) | | | | | | | |
|---|---|---|---|---|---|---|---|
| No | $R^2$ | $R^{54}$ | FORMULA | MONO-ISOTOPIC MASS | Rt (purity at 220 nm) | $[M + H]^+$ found | LC-MS-Method |
| Ex. 363-Ex. 364: cf. experimental description | | | | | | | |
| Ex. 365 | 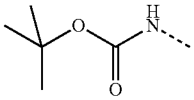 | 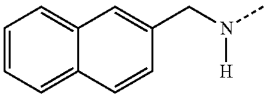 | C34H40N4O7 | 616.3 | 2.04 (91) | 617.2 | Method 10a |
| Ex. 366 | 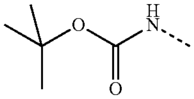 | 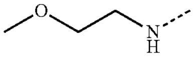 | C26H38N4O8 | 534.3 | 1.53 (100) | 535.2 | Method 10a |
| Ex. 367 | 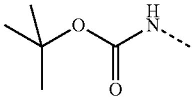 | 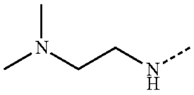 | C27H41N5O7 | 547.3 | 1.25 (98) | 548.3 | Method 10a |
| Ex. 368 | $NH_2$ | 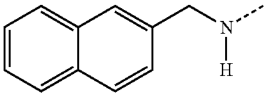 | C29H32N4O5 | 516.2 | 1.38 (96) | 517.2 | Method 10a |
| Ex. 369 | $NH_2$ | 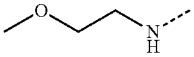 | C21H30N4O6 | 434.2 | 0.71 (99) | 435.2 | Method 10a |
| Ex. 370 | $NH_2$ | 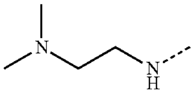 | C22H33N5O5 | 447.3 | 1.02 (99) | 448.2 | Method 11a |

TABLE 39b-continued

Examples of Core 23 (Ex. 363-Ex. 378; continued on the following pages)

| No | $R^2$ | $R^{54}$ | FORMULA | MONO-ISOTOPIC MASS | Rt (purity at 220 nm) | $[M + H]^+$ found | LC-MS-Method |
|---|---|---|---|---|---|---|---|
| Ex. 371 | 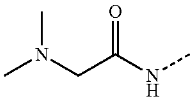 | 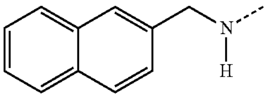 | C33H39N5O6 | 601.2 | 1.39 (95) | 602.3 | Method 10a |
| Ex. 372 | 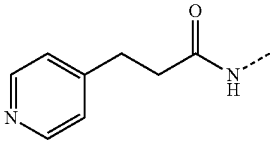 | 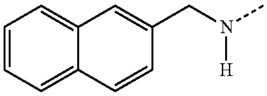 | C37H39N5O6 | 649.3 | 1.41 (96) | 650.3 | Method 10a |
| Ex. 373 | 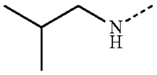 | 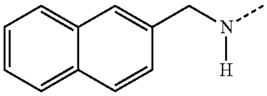 | C33H40N4O5 | 572.3 | 1.54 (94) | 573.2 | Method 10a |
| Ex. 374 | 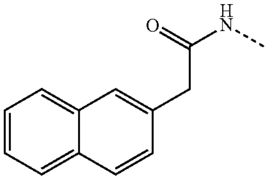 | 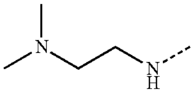 | C34H41N5O6 | 615.3 | 1.38 (98) | 616.3 | Method 10a |
| Ex. 375 | 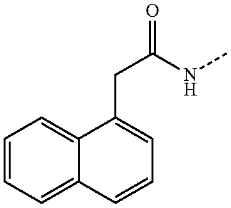 | 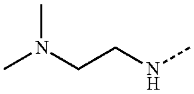 | C34H41N5O6 | 615.3 | 1.36 (90) | 616.3 | Method 10a |
| Ex. 376 | 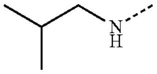 | 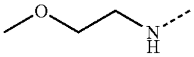 | C25H38N4O6 | 490.3 | 0.99 (97) | 491.3 | Method 10a |
| Ex. 377 | 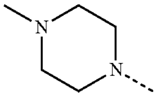 | 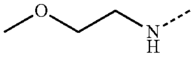 | C26H39N5O6 | 517.3 | 0.83 (97) | 518.3 | Method 10a |
| Ex. 378 | 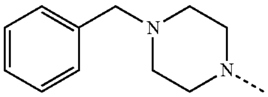 | 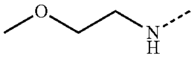 | C32H43N5O6 | 593.3 | 1.14 (97) | 594.3 | Method 10a |

TABLE 39c

Examples of Core 23 (Ex. 363-Ex. 378; continued on the following pages)

| No | $R^2$ | $R^{54}$ | IUPAC name |
|---|---|---|---|
| Ex. 363 | 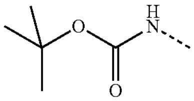 | 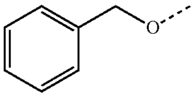 | benzyl (4S,6S,13S)-6-[(tert-butoxycarbonyl)amino]-14-methyl-9,15-dioxo-2,11-dioxa-8,14-diazatricyclo[14.3.1.$0^{4,8}$]icosa-1(20),16,18-triene-13-carboxylate |

TABLE 39c-continued

Examples of Core 23 (Ex. 363-Ex. 378; continued on the following pages)

| No | $R^2$ | $R^{54}$ | IUPAC name |
|---|---|---|---|
| Ex. 364 | 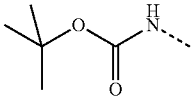 | OH | (4S,6S,13S)-6-[(tert-butoxycarbonyl)amino]-14-methyl-9,15-dioxo-2,11-dioxa-8,14-diazatricyclo[14.3.1.0$^{4,8}$]icosa-1(20),16,18-triene-13-carboxylic acid |
| Ex. 365 | 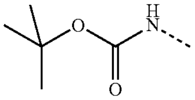 | 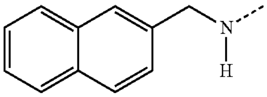 | tert-butyl N-[(4S,6S,13S)-14-methyl-13-{[(2-naphthylmethyl)amino]carbonyl}-9,15-dioxo-2,11-dioxa-8,14-diazatricyclo[14.3.1.0$^{4,8}$]icosa-1(20),16,18-trien-6-yl]carbamate |
| Ex. 366 | 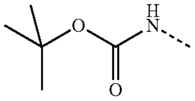 | 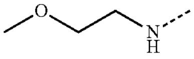 | tert-butyl N-[(4S,6S,13S)-13-{[(2-methoxyethyl)amino]carbonyl}-14-methyl-9,15-dioxo-2,11-dioxa-8,14-diazatricyclo[14.3.1.0$^{4,8}$]icosa-1(20),16,18-trien-6-yl]carbamate |
| Ex. 367 | 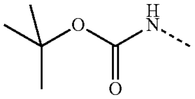 | 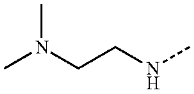 | tert-butyl N-[(4S,6S,13S)-13-({[2-(dimethylamino)ethyl]amino}carbonyl)-14-methyl-9,15-dioxo-2,11-dioxa-8,14-diazatricyclo[14.3.1.0$^{4,8}$]icosa-1(20),16,18-trien-6-yl]carbamate |
| Ex. 368 | $NH_2$ | 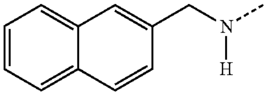 | (4S,6S,13S)-6-amino-14-methyl-N-(2-naphthylmethyl)-9,15-dioxo-2,11-dioxa-8,14-diazatricyclo[14.3.1.0$^{4,8}$]icosa-1(20),16,18-triene-13-carboxamide |
| Ex. 369 | $NH_2$ | 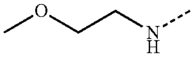 | (4S,6S,13S)-6-amino-N-(2-methoxyethyl)-14-methyl-9,15-dioxo-2,11-dioxa-8,14-diazatricyclo[14.3.1.0$^{4,8}$]icosa-1(20),16,18-triene-13-carboxamide |
| Ex. 370 | $NH_2$ | 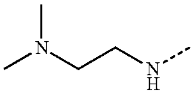 | (4S,6S,13S)-6-amino-N-[2-(dimethylamino)ethyl]-14-methyl-9,15-dioxo-2,11-dioxa-8,14-diazatricyclo[14.3.1.0$^{4,8}$]icosa-1(20),16,18-triene-13-carboxamide |
| Ex. 371 | 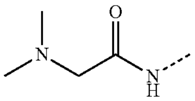 | 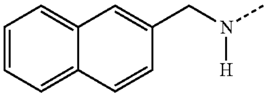 | (4S,6S,13S)-6-{[2-(dimethylamino)acetyl]amino)-14-methyl-N-(2-naphthylmethyl)-9,15-dioxo-2,11-dioxa-8,14-diazatricyclo[14.3.1.0$^{4,8}$]icosa-1(20),16,18-triene-13-carboxamide |
| Ex. 372 | 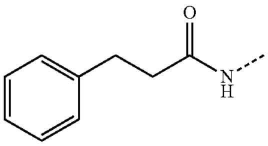 | 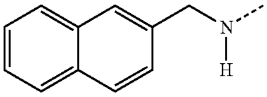 | (4S,6S,13S)-14-methyl-N-(2-naphthylmethyl)-9,15-dioxo-6-{[3-(4-pyridinyl)propanoyl]amino}-2,11-dioxa-8,14-diazatricyclo[14.3.1.0$^{4,8}$]icosa-1(20),16,18-triene-13-carboxamide |
| Ex. 373 | 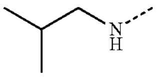 | 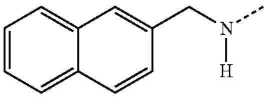 | (4S,6S,13S)-6-(isobutylamino)-14-methyl-N-(2-naphthylmethyl)-9,15-dioxo-2,11-dioxa-8,14-diazatricyclo[14.3.1.0$^{4,8}$]icosa-1(20),16,18-triene-13-carboxamide |
| Ex. 374 | 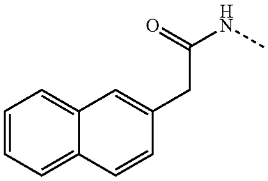 | 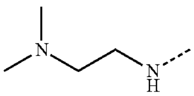 | (4S,6S,13S)-N-[2-(dimethylamino)ethyl]-14-methyl-6-{[2-(2-naphthyl)acetyl]amino}-9,15-dioxo-2,11-dioxa-8,14-diazatricyclo[14.3.1.0$^{4,8}$]icosa-1(20),16,18-triene-13-carboxamide |

TABLE 39c-continued

| Examples of Core 23 (Ex. 363-Ex. 378; continued on the following pages) | | | |
|---|---|---|---|
| No | $R^2$ | $R^{54}$ | IUPAC name |
| Ex. 375 | 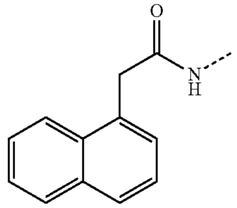 | 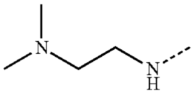 | (4S,6S,13S)-N-[2-(dimethylamino)ethyl]-14-methyl-6-{[2-(1-naphthyl)acetyl]amino}-9,15-dioxo-2,11-dioxa-8,14-diazatricyclo[14.3.1.0$^{4,8}$]icosa-1(20),16,18-triene-13-carboxamide |
| Ex. 376 | 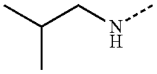 | 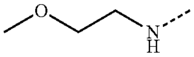 | (4S,6S,13S)-6-(isobutylamino)-N-(2-methoxyethyl)-14-methyl-9,15-dioxo-2,11-dioxa-8,14-diazatricyclo[14.3.1.0$^{4,8}$]icosa-1(20),16,18-triene-13-carboxamide |
| Ex. 377 | 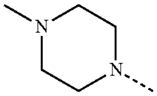 | 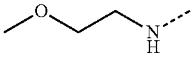 | (4S,6S,13S)-N-(2-methoxyethyl)-14-methyl-6-(4-methylpiperazino)-9,15-dioxo-2,11-dioxa-8,14-diazatricyclo[14.3.1.0$^{4,8}$]icosa-1(20),16,18-triene-13-carboxamide |
| Ex. 378 | 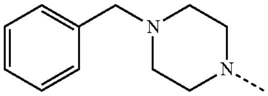 | 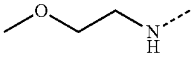 | (4S,6S,13S)-6-(4-benzylpiperazino)-N-(2-methoxyethyl)-14-methyl-9,15-dioxo-2,11-dioxa-8,14-diazatricyclo[14.3.1.0$^{4,8}$]icosa-1(20),16,18-triene-13-carboxamide |

TABLE 40.1.a

| Examples of Core 24a (Ex. 379-Ex. 391; continued on the following page) | | | | | | | |
|---|---|---|---|---|---|---|---|
| No | $R^2$ | $R^5$ | Starting material | General Procedure | Reagent | Purification Method | Yield (isolated salt) |
| Ex. 379-Ex. 380: cf. experimental description | | | | | | | |
| Ex. 381 | 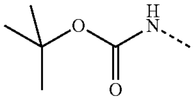 | 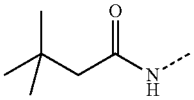 | Ex. 380 | L.1.1 | 3,3-dimethylbutanoyl chloride (1.5 equiv.) Pyridine (5 equiv.) | FC (hexane/EtOAc/MeOH) | 60% |
| Ex. 382 | 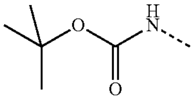 | 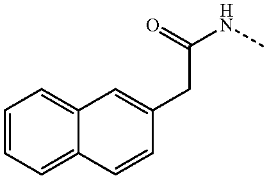 | Ex. 380 | L.1.3 | 2-naphthylacetic acid i-$Pr_2NEt$ (2 equiv.) | FC (hexane/EtOAc/MeoH), FC (CH2Cl2/MeOH) | 72% |
| Ex. 383 | $NH_2$ | 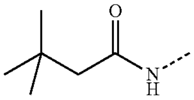 | Ex. 381 | J | HCl-dioxane | crude product | quant. (HCl salt) |
| Ex. 384 | $NH_2$ | 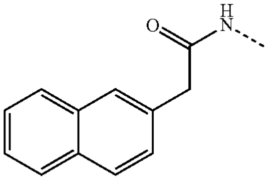 | Ex. 382 | J | HCl-dioxane | crude product | 96% (HCl salt) |

TABLE 40.1.a-continued

Examples of Core 24a (Ex. 379-Ex. 391; continued on the following page)

| No | $R^2$ | $R^5$ | Starting material | General Procedure | Reagent | Purification Method | Yield (isolated salt) |
|---|---|---|---|---|---|---|---|
| Ex. 385 | 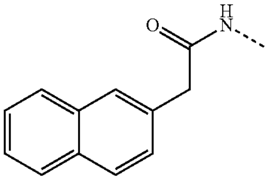 | 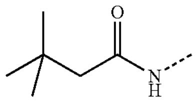 | Ex. 383 | L.1.3 | 2-naphthyl-acetic acid<br>i-$Pr_2$NEt<br>(3 equiv.) | FC (hexane/EtOAc/MeOH) | 79% |
| Ex. 386 | 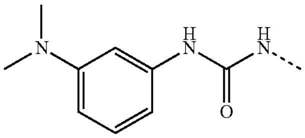 | 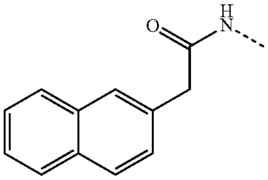 | Ex. 384 | L.4 | 2,5-dioxo-pyrrolidin-1-yl-3-(dimethyl-amino) phenyl-carbamate | FC (hexane/EtOAc/MeOH) | 55% |
| Ex. 387 | $NH_2$ | 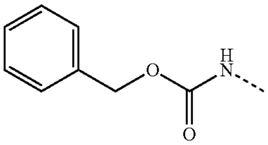 | Ex. 379 | J | HCl-dioxane | crude product | quant. (HCl salt) |
| Ex. 388 | 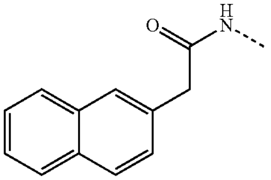 | 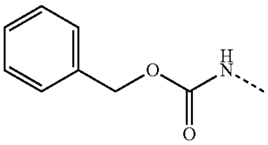 | Ex. 387 | L.1.3 | 2-naphthyl-acetic acid<br>(1.2 equiv.)<br>HATU<br>(1.5 equiv.)<br>HOAt<br>(1.5 equiv.)<br>i-$Pr_2$NEt<br>(3 equiv.) | FC (hexane/EtOAc/MeOH) | 63% |
| Ex. 389 | 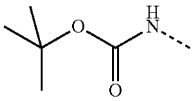 | $CH_3(CH_2)_8$CONH | Ex. 380 | L.1.3 | decanoic acid<br>i-$Pr_2$NEt<br>(2 equiv.) | FC (hexane/EtOAc/MeOH) | 71% |
| Ex. 390 | $NH_2$ | $CH_3(CH_2)_8$CONH | Ex. 389 | J | HCl-dioxane | crude product | quant. (HCl salt) |
| Ex. 391 | 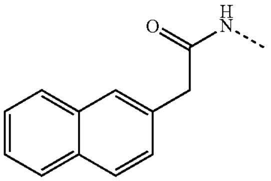 | $CH_3(CH_2)_8$CONH | Ex. 390 | L.1.3 | 2-naphthyl-acetic acid<br>i-$Pr_2$NEt<br>(3 equiv.) | FC (hexane/EtOAc/MeOH) | 70% |

TABLE 40.1.b
Examples of Core 24a (Ex. 379-Ex. 391; continued on the following page)
| No | $R^2$ | $R^5$ | FORMULA | MONO-ISO-TOPIC MASS | Rt (purity at 220 nm) | $[M + H]^+$ found | LC-MS-Method |
|---|---|---|---|---|---|---|---|
| Ex. 379-Ex. 380: cf. experimental description | | | | | | | |
| Ex. 381 | 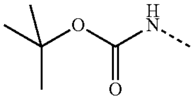 | 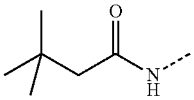 | C28H42N4O6 | 530.3 | 1.84 (99) | 531.3 | Method 10c |
| Ex. 382 | 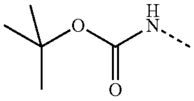 | 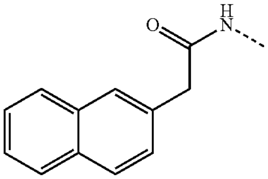 | C34H40N4O6 | 600.3 | 2.01 (99) | 601.3 | Method 10a |
| Ex. 383 | $NH_2$ | 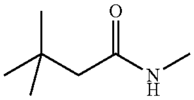 | C23H34N4O4 | 430.3 | 1.15 (98) | 431.3 | Method 10a |
| Ex. 384 | $NH_2$ | 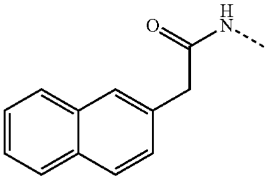 | C29H32N4O4 | 500.2 | 1.39 (93) | 501.3 | Method 10a |
| Ex. 385 | 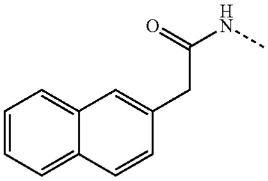 | 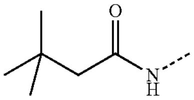 | C35H42N4O5 | 598.3 | 1.91 (90) | 599.2 | Method 10a |
| Ex. 386 | 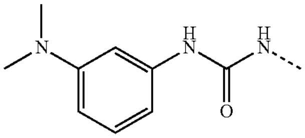 | 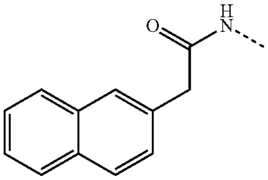 | C38H42N6O5 | 662.3 | 1.52 (98) | 663.3 | Method 10a |
| Ex. 387 | $NH_2$ | 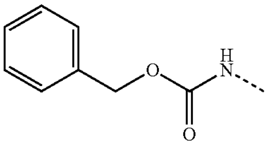 | C25H30N4O5 | 466.2 | 1.22 (56) | 467.3 | Method 10a |
| Ex. 388 | 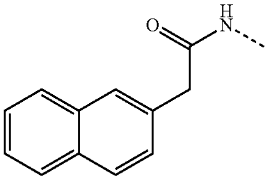 | 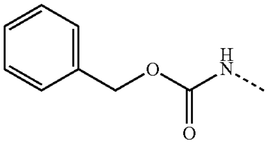 | C37H38N4O6 | 634.3 | 1.99 (97) | 635.3 | Method 10a |
| Ex. 389 | 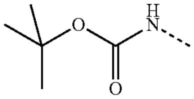 | $CH_3(CH_2)_8CONH$ | C32H50N4O6 | 586.4 | 2.38 (87) | 587.4 | Method 10a |

TABLE 40.1.b-continued

Examples of Core 24a (Ex. 379-Ex. 391; continued on the following page)

| No | $R^2$ | $R^5$ | FORMULA | MONO-ISO-TOPIC MASS | Rt (purity at 220 nm) | $[M + H]^+$ found | LC-MS-Method |
|---|---|---|---|---|---|---|---|
| Ex. 390 | $NH_2$ | $CH_3(CH_2)_8CONH$ | C27H42N4O4 | 486.3 | 1.69 (91) | 487.3 | Method 10a |
| Ex. 391 | 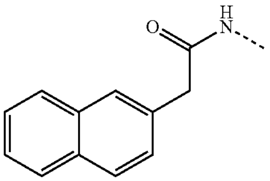 | $CH_3(CH_2)_8CONH$ | C39H50N4O5 | 654.4 | 2.38 (90) | 655.4 | Method 10a |

TABLE 40.1.c

Examples of Core 24a (Ex. 379-Ex. 391; continued on the following pages)

| No | $R^2$ | $R^5$ | IUPAC name |
|---|---|---|---|
| Ex. 379 | 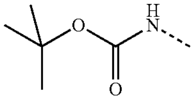 | 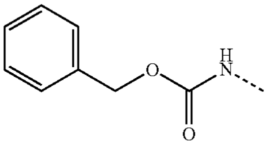 | benzyl N-[(4S,6S,10S)-6-[(tert-butoxycarbonyl)amino]-9,15-dioxo-2-oxa-8,14-diazatricyclo[14.3.1.$0^{4,8}$]icosa-1(20),16,18-trien-10-yl]carbamate |
| Ex. 380 | 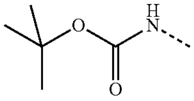 | $NH_2$ | tert-butyl N-[(4S,6S,10S)-10-amino-9,15-dioxo-2-oxa-8,14-diazatricyclo[14.3.1.$0^{4,8}$]icosa-1(20),16,18-trien-6-yl]carbamate |
| Ex. 381 | 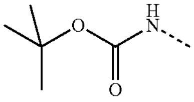 | 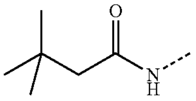 | tert-butyl N-[(4S,6S,10S)-10-[(3,3-dimethylbutanoyl)amino]-9,15-dioxo-2-oxa-8,14-diazatricyclo[14.3.1.$0^{4,8}$]icosa-1(20),16,18-trien-6-yl]carbamate |
| Ex. 382 | 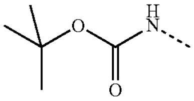 | 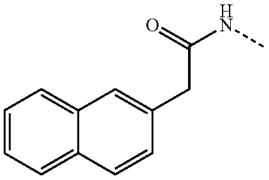 | tert-butyl N-[(4S,6S,10S)-10-{[2-(2-naphthyl)acetyl]amino}-9,15-dioxo-2-oxa-8,14-diazatricyclo[14.3.1.$0^{4,8}$]icosa-1(20),16,18-trien-6-yl]carbamate |
| Ex. 383 | $NH_2$ | 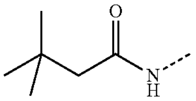 | N-[(4S,6S,10S)-6-amino-9,15-dioxo-2-oxa-8,14-diazatricyclo[14.3.1.$0^{4,8}$]icosa-1(20),16,18-trien-10-yl]-3,3-dimethylbutanamide |
| Ex. 384 | $NH_2$ | 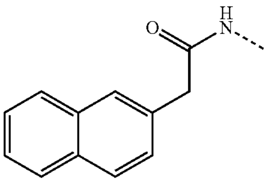 | N-[(4S,6S,10S)-6-amino-9,15-dioxo-2-oxa-8,14-diazatricyclo[14.3.1.$0^{4,8}$]icosa-1(20),16,18-trien-10-yl]-2-(2-naphthyl)acetamide |

TABLE 40.1.c-continued

Examples of Core 24a (Ex. 379-Ex. 391; continued on the following pages)

| No | $R^2$ | $R^5$ | IUPAC name |
|---|---|---|---|
| Ex. 385 | 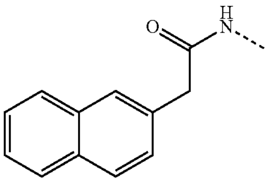 | 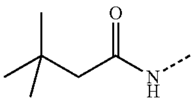 | 3,3-dimethyl-N-[(4S,6S,10S)-6-{[2-(2-naphthyl)acetyl]amino}-9,15-dioxo-2-oxa-8,14-diazatricyclo[14.3.1.0$^{4,8}$]icosa-1(20),16,18-trien-10-yl]butanamide |
| Ex. 386 | 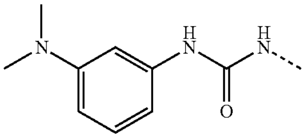 | 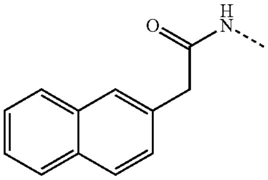 | N-[(4S,6S,10S)-6-({[3-(dimethylamino)anilino]carbonyl}amino)-9,15-dioxo-2-oxa-8,14-diazatricyclo[14.3.1.0$^{4,8}$]icosa-1(20),16,18-trien-10-yl]-2-(2-naphthyl)acetamide |
| Ex. 387 | $NH_2$ | 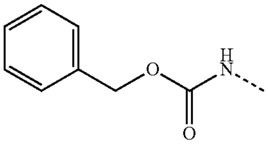 | benzyl N-[(4S,6S,10S)-6-amino-9,15-dioxo-2-oxa-8,14-diazatricyclo[14.3.1.0$^{4,8}$]icosa-1(20),16,18-trien-10-yl]carbamate |
| Ex. 388 | 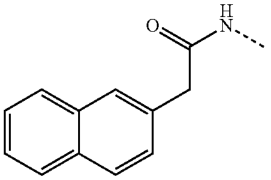 | 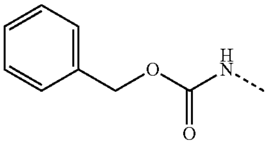 | benzyl N-[(4S,6S,10S)-6-{[2-(2-naphthyl)acetyl]amino}-9,15-dioxo-2-oxa-8,14-diazatricyclo[14.3.1.0$^{4,8}$]icosa-1(20),16,18-trien-10-yl]carbamate |
| Ex. 389 | 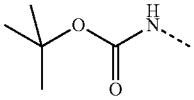 | $CH_3(CH_2)_8CONH$ | tert-butyl N-[(4S,6S,10S)-10-(decanoylamino)-9,15-dioxo-2-oxa-8,14-diazatricyclo[14.3.1.0$^{4,8}$]icosa-1(20),16,18-trien-6-yl]carbamate |
| Ex. 390 | $NH_2$ | $CH_3(CH_2)_8CONH$ | N-[(4S,6S,10S)-6-amino-9,15-dioxo-2-oxa-8,14-diazatricyclo[14.3.1.0$^{4,8}$]icosa-1(20),16,18-trien-10-yl]decanamide |
| Ex. 391 | 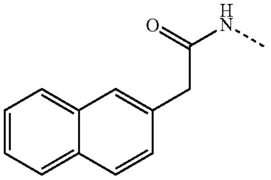 | $CH_3(CH_2)_8CONH$ | N-[(4S,6S,10S)-6-{[2-(2-naphthyl)acetyl]amino}-9,15-dioxo-2-oxa-8,14-diazatricyclo[14.3.1.0$^{4,8}$]icosa-1(20),16,18-trien-10-yl]decanamide |

TABLE 40.2.a

Examples of Core 24b (Ex. 392-Ex. 396)

| No | $R^2$ | $R^5$ | Starting material | General Procedure | Reagent | Purification Method | Yield (isolated salt) |
|---|---|---|---|---|---|---|---|
| Ex. 392-Ex. 393: cf. experimental description | | | | | | | |
| Ex. 394 | 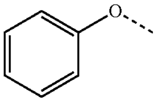 | 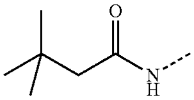 | Ex. 353 | L.1.1 | 3,3-dimezhylbutanoyl chloride (1.5 equiv.) Pyridine (5 equiv.) | FC (hexane/EtOAc/MeOH) | 68% |

TABLE 40.2.a-continued

| Examples of Core 24b (Ex. 392-Ex. 396) | | | | | | | |
|---|---|---|---|---|---|---|---|
| No | $R^2$ | $R^5$ | Starting material | General Procedure | Reagent | Purification Method | Yield (isolated salt) |
| Ex. 395 | 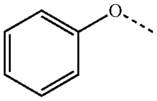 | 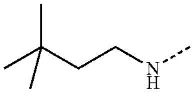 | Ex. 353 | M.2 | pivalaldehyde | FC (hexane/EtOAc/MeOH) | 40% |
| Ex. 396 | 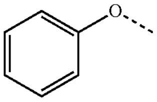 | 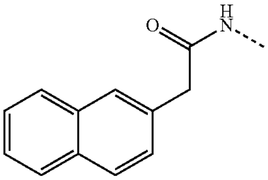 | Ex. 353 | L.1.3 | 2-naphthylacetic acid $i\text{-}Pr_2NEt$ (2 equiv.) | FC (hexane/EtOAc/MeOH) | 37% |

TABLE 40.2.b

| Examples of Core 24b (Ex. 392-Ex. 396; continued on the following page) | | | | | | | |
|---|---|---|---|---|---|---|---|
| No | $R^2$ | $R^5$ | FORMULA | MONOISOTOPIC MASS | Rt (purity at 220 nm) | $[M + H]^+$ found | LC-MS-Method |
| Ex. 392-Ex. 393: cf. experimental description | | | | | | | |
| Ex. 394 | 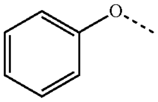 | 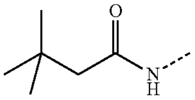 | C29H37N3O5 | 507.3 | 1.97 (95) | 508.2 | Method 10a |
| Ex. 395 | 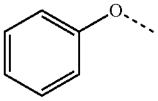 | 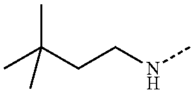 | C28H37N3O4 | 479.3 | 1.62 (99) | 480.2 | Method 10a |
| Ex. 396 | 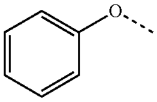 | 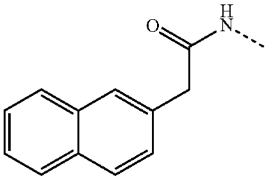 | C35H35N3O5 | 577.3 | 2.12 (97) | 578.0 | Method 10a |

TABLE 40.2.c

| Examples of Core 24b (Ex. 392-Ex. 396) | | | |
|---|---|---|---|
| No | $R^2$ | $R^5$ | IUPAC name |
| Ex. 392 | 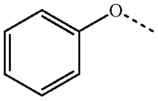 | 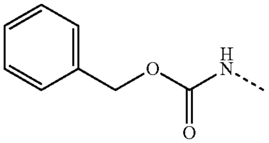 | benzyl N-[(4S,6S,10S)-9,15-dioxo-6-phenoxy-2-oxa-8,14-diazatricyclo[14.3.1.0$^{4,8}$]icosa-1(20),16,18-trien-10-yl]carbamate |
| Ex. 393 | 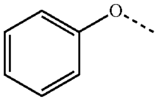 | $NH_2$ | (4S,6S,10S)-10-amino-6-phenoxy-2-oxa-8,14-diazatricyclo[14.3.1.0$^{4,8}$]icosa-1(20),16,18-triene-9,15-dione |

TABLE 40.2.c-continued

| Examples of Core 24b (Ex. 392-Ex. 396) | | | |
|---|---|---|---|
| No | $R^2$ | $R^5$ | IUPAC name |
| Ex. 394 | 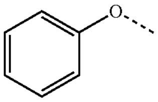 | 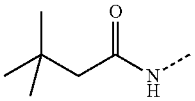 | N-[(4S,6S,10S)-9,15-dioxo-6-phenoxy-2-oxa-8,14-diazatricyclo[14.3.1.0$^{4,8}$]icosa-1(20),16,18-trien-10-yl]-3,3-dimethylbutanamide |
| Ex. 395 | 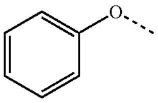 | 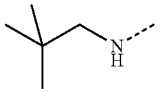 | (4S,6S,10S)-10-(neopentylamino)-6-phenoxy-2-oxa-8,14-diazatricyclo[14.3.1.0$^{4,8}$]icosa-1(20),16,18-triene-9,15-dione |
| Ex. 396 | 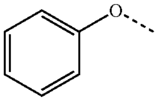 | 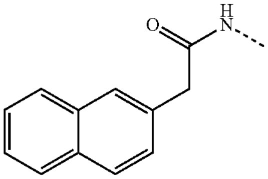 | N-[(4S,6S,10S)-9,15-dioxo-6-phenoxy-2-oxa-8,14-diazatricyclo[14.3.1.0$^{4,8}$]icosa-1(20),16,18-trien-10-yl]-2-(2-naphthyl)acetamide |

TABLE 40.3.a

| Examples of Core 24c (Ex. 398-Ex. 402) | | | | | | | |
|---|---|---|---|---|---|---|---|
| No | $R^2$ | $R^5$ | Starting material | General Procedure | Reagent | Purification Method | Yield (isolated salt) |
| Ex. 398: cf. experimental description | | | | | | | |
| Ex. 399 | OH | OH | Ex. 397 | K.1 | $H_2$, $Pd(OH)_2$—C, $CH_2Cl_2$/MeOH 1:1 | FC ($CH_2Cl_2$/MeOH) | 97% |
| Ex. 400 | 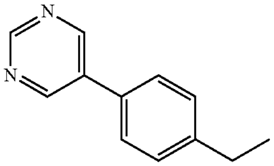 | OH | Ex. 397 | P | 5-pyrimidineboronic acid (1.3 equiv.) | prep. HPLC, method 1 | 61% |
| Ex. 401 | 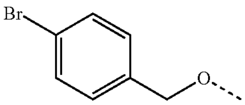 | 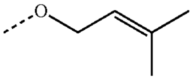 | Ex. 397 | Q | 4-bromo-2-methyl-2-butene (2 equiv.) | FC ($CH_2Cl_2$/MeOH) | 52% |
| Ex. 402 | OH | 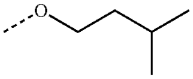 | Ex. 401 | K.1 | $H_2$, $Pd(OH)_2$—C, MeOH | FC ($CH_2Cl_2$/MeOH) | 51% |

TABLE 40.3.b

| Examples of Core 24c (Ex. 398-Ex. 402; continued on the following page) | | | | | | | |
|---|---|---|---|---|---|---|---|
| No | $R^2$ | $R^5$ | FORMULA | MONO-ISOTOPIC MASS | Rt (purity at 220 nm) | $[M + H]^+$ found | LC-MS-Method |
| Ex. 398: cf. experimental description | | | | | | | |
| Ex. 399 | OH | OH | C17H22N2O5 | 334.2 | 0.79 (98) | 335.1 | Method 10a |
| Ex. 400 | 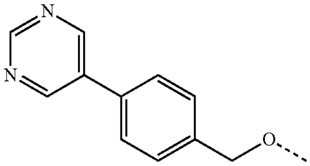 | OH | C28H30N4O5 | 502.2 | 1.40 (98) | 503.2 | Method 10a |

TABLE 40.3.b-continued

Examples of Core 24c (Ex. 398-Ex. 402; continued on the following page)

| No | $R^2$ | $R^5$ | FORMULA | MONO-ISOTOPIC MASS | Rt (purity at 220 nm) | $[H + H]^+$ found | LC-MS-Method |
|---|---|---|---|---|---|---|---|
| Ex. 401 | 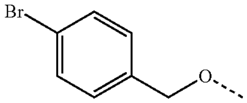 | 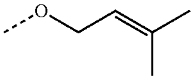 | C29H35BrN2O5 | 570.2 | 2.27 (96) | 573.0/571.0 | Method 10a |
| Ex. 402 | OH | 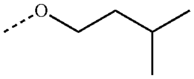 | C22H32N2O5 | 404.2 | 1.49 (93) | 405.2 | Method 10a |

TABLE 40.3.c

Examples of Core 24c (Ex. 398-Ex. 402)

| No | R2 | R5 | IUPAC name |
|---|---|---|---|
| Ex. 398 | 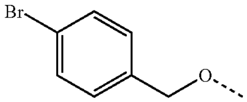 | OH | (4S,6S,10S)-6-[(4-bromobenzyl)oxy]-10-hydroxy-2-oxa-8,14-diazatricyclo$[14.3.1.0^{4,8}]$icosa-1(20),16,18-triene-9,15-dione |
| Ex. 399 | OH | OH | (4S,6S,10S)-6,10-dihydroxy-2-oxa-8,14-diazatricyclo$[14.3.1.0^{4,8}]$icosa-1(20),16,18-triene-9,15-dione |
| Ex. 400 | 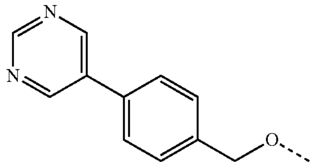 | OH | (4S,6S,10S)-10-hydroxy-6-{[4-(5-pyrimidinyl)benzyl]oxy}-2-oxa-8,14-diazatricyclo$[14.3.1.0^{4,8}]$icosa-1(20),16,18-triene-9,15-dione |
| Ex. 401 | 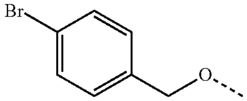 | 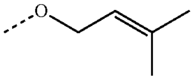 | (4S,6S,10S)-6-[(4-bromobenzyl)oxy]-10-[(3-methyl-2-butenyl)oxy]-2-oxa-8,14-diazatricyclo$[14.3.1.0^{4,8}]$icosa-1(20),16,18-triene-9,15-dione |
| Ex. 402 | OH | 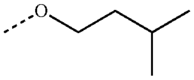 | (4S,6S,10S)-6-hydroxy-10-(isopentyloxy)-2-oxa-8,14-diazatricyclo$[14.3.1.0^{4,8}]$icosa-1(20),16,18-triene-9,15-dione |

TABLE 41a

Examples of Core 25 (Ex. 403-Ex. 414; continued on the following pages)

| No | $R^{11}$ | $R^5$ | Starting Reagent | General material | Procedure | Purification Method | Yield (isolated salt) |
|---|---|---|---|---|---|---|---|
| Ex. 403-Ex. 404: cf. experimental description | | | | | | | |
| Ex. 405 | 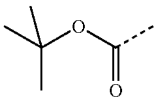 | 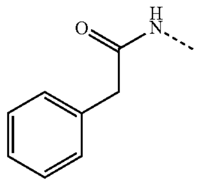 | Ex. 404 | L.1.3 | phenylacetic acid $i\text{-}Pr_2NEt$ (2 equiv.) | FC (hexane/EtOAc) | 75% |

TABLE 41a-continued

Examples of Core 25 (Ex. 403-Ex. 414; continued on the following pages)

| No | $R^{11}$ | $R^5$ | Starting Reagent | General material | Procedure | Purification Method | Yield (isolated salt) |
|---|---|---|---|---|---|---|---|
| Ex. 406 | H | 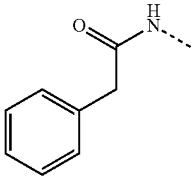 | Ex. 405 | J | HCl-dioxane | crude product | 88%*) |
| Ex. 407 | 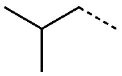 | 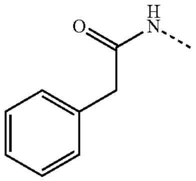 | Ex. 406 | **) | isobutyraldehyde**) | prep. HPLC, method 3 | 72% |
| Ex. 408 | 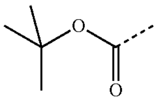 | 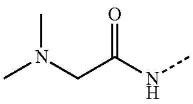 | Ex. 404 | L.1.3 | N,N-dimethylglycine<br>i-$Pr_2$NEt (3 equiv.) | FC (hexane/EtOAc/MeOH) | 81% |
| Ex. 409 | H | 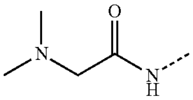 | Ex. 408 | J | HCl-dioxane | crude product | 94% (HCl salt) |
| Ex. 410 | 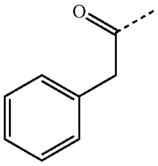 | 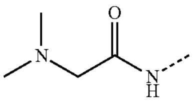 | Ex. 409 | L.1.3 | phenylacetic acid (1.0 equiv)<br>HATU (1.0 equiv.)<br>HOAt (1.0 equiv.)<br>i-$Pr_2$NEt (2.0 equiv) | FC (EtOAc, then $CH_2Cl_2$/MeOH) | 46% |
| Ex. 411 | 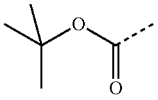 | 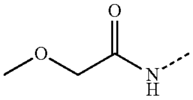 | Ex. 404 | L.1.1 | 2-methoxyacetyl chloride (1.5 equiv.)<br>pyridine (5 equiv.) | FC (hexane/EtOAc/MeOH) | 84% |
| Ex. 412 | H | 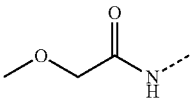 | Ex. 411 | J | HCl-dioxane | crude product | 97% (HCl salt) |
| Ex. 413 | $CH_3$ | 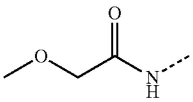 | Ex. 412 | M.5 | aq. formaldehyde soln<br>(2.5 equiv.) | FC (EtOAc/MeOH) | 82% |
| Ex. 414 | 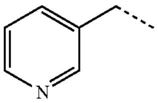 | 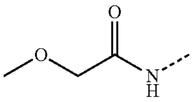 | Ex. 412 | M.5 | nicotin aldehyde | FC (EtOAc/MeOH) | 77% |

*)workup ($CHCl_2$. aq. $Na_2CO_3$ soln) to yield the free base

**) in analogy to procedure M.3; isobutyraldehyde (1.2 equiv.), acetic acid (1.2 equiv.), $NaBH(OAc)_3$ (2.5 equiv.) in THF TABLE 41b
Examples of Core 25 (Ex. 403-Ex. 414; continued on the following page)
| No | $R^{11}$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 403-Ex. 404: cf. experimental description | | | | | | | |
| Ex. 405 | 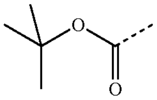 | 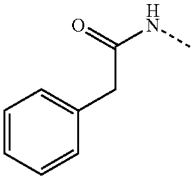 | C31H39FN4O6 | 582.3 | 2.06 (93) | 583.3 | Method 4a |
| Ex. 406 | H | 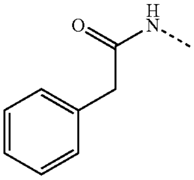 | C26H31FN4O4 | 482.2 | 1.48 (94) | 483.3 | Method 4a |
| Ex. 407 | 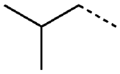 | 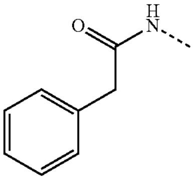 | C30H39FN4O4 | 538.3 | 1.45 (97) | 539.4 | Method 10a |
| Ex. 408 | 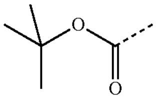 | 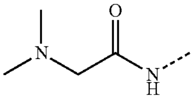 | C27H40FN5O6 | 549.3 | 1.44 (98) | 550.3 | Method 10a |
| Ex. 409 | H | 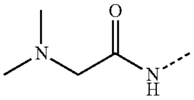 | C22H32FN5O4 | 449.2 | 1.27 (98) | 450.2 | Method 12 |
| Ex. 410 | 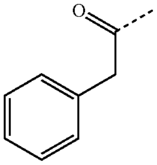 | 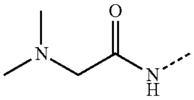 | C30H38FN5O5 | 567.3 | 1.36 (93) | 568.3 | Method 10a |
| Ex. 411 | 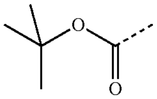 | 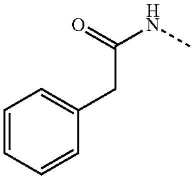 | C26H37FN4O7 | 536.3 | 1.66 (97) | 537.3 | Method 10c |
| Ex. 412 | H | 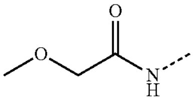 | C21H29FN4O5 | 436.2 | 1.02 (97) | 437.2 | Method 10a |
| Ex. 413 | $CH_3$ | 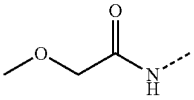 | C22H31FN4O5 | 450.2 | 1.02 (94) | 451.2 | Method 10a |

TABLE 41b-continued

Examples of Core 25 (Ex. 403-Ex. 414; continued on the following page)

| No | $R^{11}$ | $R^5$ | FORMULA | MONOISOTOPIC MASS | Rt (purity at 220 nm) | $[M + H]^+$ found | LC-MS-Method |
|---|---|---|---|---|---|---|---|
| Ex. 414 | 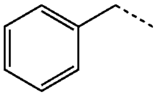 | 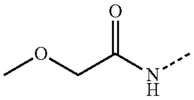 | C27H34FN5O5 | 527.3 | 1.03 (95) | 528.2 | Method 10a |

TABLE 41c

Examples of Core 25 (Ex. 403-Ex. 414, continued on the following page)

| No | $R^{11}$ | $R^5$ | IUPAC name |
|---|---|---|---|
| Ex. 403 | 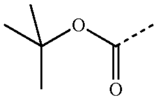 | 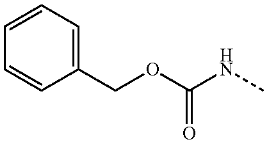 | tert-butyl (1S,15S,18R)-15-{[(benzyloxy)carbonyl]amino}-7-fluoro-11-methyl-10,16-dioxo-3-oxa-11,17,20-triazatricyclo[16.2.1.$0^{4,9}$]henicosa-4,6,8-triene-20-carboxylate |
| Ex. 404 | 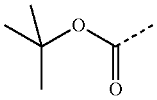 | $NH_2$ | tert-butyl (1S,15S,18R)-15-amino-7-fluoro-11-methyl-10,16-dioxo-3-oxa-11,17,20-triazatricyclo[16.2.1.$0^{4,9}$]henicosa-4,6,8-triene-20-carboxylate |
| Ex. 405 | 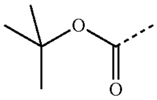 | 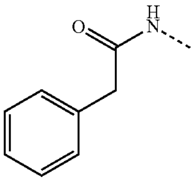 | tert-butyl (1S,15S,18R)-7-fluoro-11-methyl-10,16-dioxo-15-[(2-phenylacetyl)amino]-3-oxa-11,17,20-triazatricyclo[16.2.1.$0^{4,9}$]henicosa-4,6,8-triene-20-carboxylate |
| Ex. 406 | H | 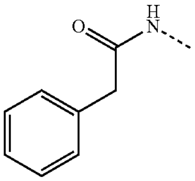 | N-[(1S,15S,18R)-7-fluoro-11-methyl-10,16-dioxo-3-oxa-11,17,20-triazatricyclo[16.2.1.$0^{4,9}$]henicosa-4,6,8-trien-15-yl]-2-phenylacetamide |
| Ex. 407 | 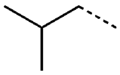 | 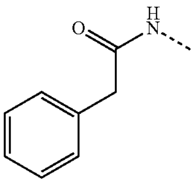 | N-[(1S,15S,18R)-7-fluoro-20-isobutyl-11-methyl-10,16-dioxo-3-oxa-11,17,20-triazatricyclo[16.2.1.$0^{4,9}$]henicosa-4,6,8-trien-15-yl]-2-phenylacetamide |
| Ex. 408 | 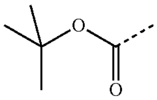 | 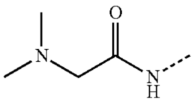 | tert-butyl (1S,15S,18R)-15-{[2-(dimethylamino)acetyl]amino}-7-fluoro-11-methyl-10,16-dioxo-3-oxa-11,17,20-triazatricyclo[16.2.1.$0^{4,9}$]henicosa-4,6,8-triene-20-carboxylate |
| Ex. 409 | H | 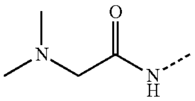 | 2-(dimethylamino)-N-[(1S,15S,18R)-7-fluoro-11-methyl-10,16-dioxo-3-oxa-11,17,20-triazatricyclo[16.2.1.$0^{4,9}$]henicosa-4,6,8-trien-15-yl]acetamide |

TABLE 41c-continued

Examples of Core 25 (Ex. 403-Ex. 414, continued on the following page)

| No | $R^{11}$ | $R^5$ | IUPAC name |
|---|---|---|---|
| Ex. 410 | 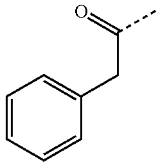 | 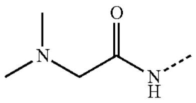 | 2-(dimethylamino)-N-[(1S,15S,18R)-7-fluoro-11-methyl-10,16-dioxo-20-(2-phenylacetyl)-3-oxa-11,17,20-triazatricyclo[16.2.1.0$^{4,9}$]henicosa-4,6,8-trien-15-yl]acetamide |
| Ex. 411 | 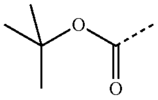 | 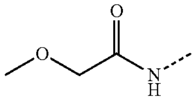 | tert-butyl (1S,15S,18R)-7-fluoro-15-[(2-methoxyacetyl)amino]-11-methyl-10,16-dioxo-3-oxa-11,17,20-triazatricyclo[16.2.1.0$^{4,9}$]henicosa-4,6,8-triene-20-carboxylate |
| Ex. 412 | H | 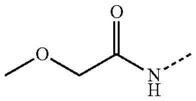 | N-[(1S,15S,18R)-7-fluoro-11-methyl-10,16-dioxo-3-oxa-11,17,20-triazatricyclo[16.2.1.0$^{4,9}$]henicosa-4,6,8-trien-15-yl]-2-methoxyacetamide |
| Ex. 413 | $CH_3$ | 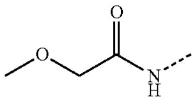 | N-[(1S,15S,18R)-7-fluoro-11,20-dimethyl-10,16-dioxo-3-oxa-11,17,20-triazatricyclo[16.2.1.0$^{4,9}$]henicosa-4,6,8-trien-15-yl]-2-methoxyacetamide |
| Ex. 414 | 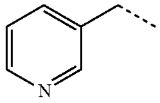 | 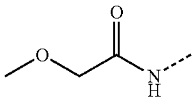 | N-[(1S,15S,18R)-7-fluoro-11-methyl-10,16-dioxo-20-(3-pyridinylmethyl)-3-oxa-11,17,20-triazatricyclo[16.2.1.0$^{4,9}$]henicosa-4,6,8-trien-15-yl]-2-methoxyacetamide |

TABLE 42a

Examples of Core 26 (Ex. 415-Ex. 423; continued on the following page)

| No | $R^2$ | $R^{54}$ | Starting material | General Procedure | Reagent | Purification Method | Yield (isolated salt) |
|---|---|---|---|---|---|---|---|
| Ex. 415-Ex. 416: cf. experimental description | | | | | | | |
| Ex. 417 | 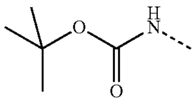 | 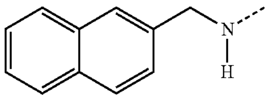 | Ex. 416 | L.2 | 2-naphthyl-methylamine (2 equiv.) | FC (hexane/EtOAc/MeOH) | 96% |
| Ex. 418 | 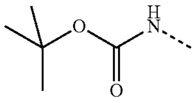 | 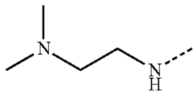 | Ex. 416 | L.2 | 2-dimethyl-aminoetyl-amine (2 equiv.) | FC ($CH_2Cl_2$/MeOH/aq. $NH_3$) | 81% |
| Ex. 419 | $NH_2$ | 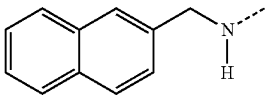 | Ex. 417 | J | HCl (4M dioxane) | crude product | 89% (HCl salt) |
| Ex. 420 | $NH_2$ | 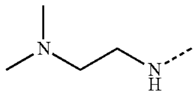 | Ex. 418 | J | HCl (4M dioxane) | crude product | 88% (HCl salt) |
| Ex. 421 | 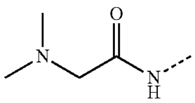 | 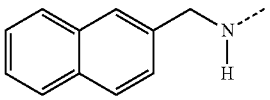 | Ex. 419 | L.1.2 | N,N-dimethyl-glycine (1.8 equiv.) | prep. HPLC, method 11 | 38% (TFA salt) |

TABLE 42a-continued

| Examples of Core 26 (Ex. 415-Ex. 423; continued on the following page) | | | | | | | |
|---|---|---|---|---|---|---|---|
| No | $R^2$ | $R^{54}$ | Starting material | General Procedure | Reagent | Purification Method | Yield (isolated salt) |
| Ex. 422 | 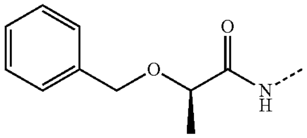 | 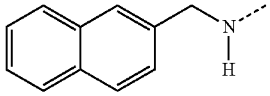 | Ex. 419 | L.1.3 | (R)(+)-2-benzyloxy-proppionic acide (2 equiv.) | prep. HPLC, method 1 | 73% |
| Ex. 423 | 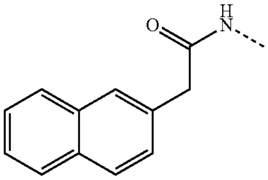 | 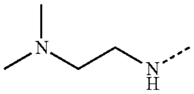 | Ex. 420 | L.1.2 | 2-naphthyl-acetic acide ((1.2 equiv.) | prep. HPLC, method 1 | 36% (TFA salt) |

TABLE 42b

| Examples of Core 26 (Ex. 415-Ex. 423; continued on the following page) | | | | | | | |
|---|---|---|---|---|---|---|---|
| No | $R^2$ | $R^{54}$ | FORMULA | MONO-ISOTOPIC MASS | Rt (purity at 220 nm) | $[M + H]^+$ found | LC-MS-Method |
| Ex. 415-Ex. 416: cf. experimental description | | | | | | | |
| Ex. 417 | 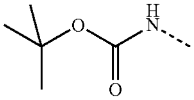 | 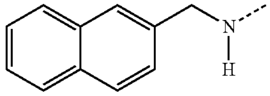 | C35H43N5O7S | 677.3 | 2.08 (89) | 678.2 | Method 4b |
| Ex. 418 | 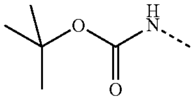 | 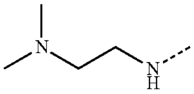 | C28H44N6O7S | 608.3 | 1.42 (96) | 609.2 | Method 4b |
| Ex. 419 | $NH_2$ | 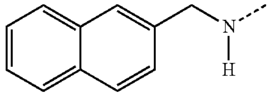 | C30H35N5O5S | 577.2 | 1.61 (84) | 578.0 | Method 4b |
| Ex. 420 | $NH_2$ | 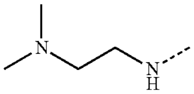 | C23H36N6O5S | 508.3 | 1.29 (95) | 509.2 | Method 5b |
| Ex. 421 | 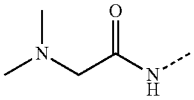 | 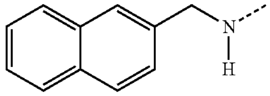 | C34H42N6O6S | 662.3 | 1.86 (91) | 663.2 | Method 5b |
| Ex. 422 | 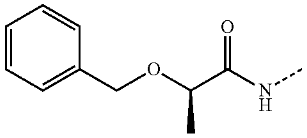 | 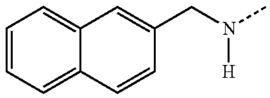 | C40H45N5O7S | 739.3 | 2.10 (97) | 740.2 | Method 5b |

TABLE 42b-continued

| No | $R^2$ | $R^{54}$ | FORMULA | MONO-ISOTOPIC MASS | Rt (purity at 220 nm) | $[M + H]^+$ found | LC-MS-Method |
|---|---|---|---|---|---|---|---|
| Examples of Core 26 (Ex. 415-Ex. 423; continued on the following page) | | | | | | | |
| Ex. 423 | 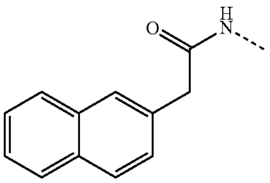 | 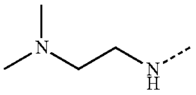 | C35H44N6O6S | 676.3 | 1.85 (97) | 677.2 | Method 5b |

TABLE 42c

| No | $R^2$ | $R^{54}$ | IUPAC name |
|---|---|---|---|
| Examples of Core 26 (15-007-01) (Ex. 415-Ex. 423, continued on the following pages) | | | |
| Ex. 415 | 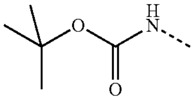 | 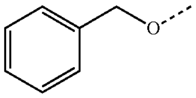 | benzyl (6S,15R,16aS)-15-[(tert-butoxycarbonyl)amino]-5,10-dimethyl-4,9,12-trioxo-5,6,7,8,9,10,11,12,15,16,16a,17-dodecahydro-4H,14H-pyrrolo[2,1-c]thieno[2,3-n][1,4,7,12]oxatriazacyclopentadecine-6-carboxylate |
| Ex. 416 | 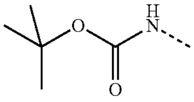 | OH | (6S,15R,16aS)-15-[(tert-butoxycarbonyl)amino]-5,10-dimethyl-4,9,12-trioxo-5,6,7,8,9,10,11,12,15,16,16a,17-dodecahydro-4H,14H-pyrrolo[2,1-c]thieno[2,3-n][1,4,7,12]oxatriazacyclopentadecine-6-carboxylic acid |
| Ex. 417 | 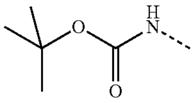 | 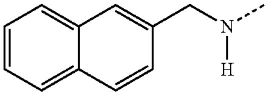 | tert-butyl N-((6S,15R,16aS)-5,10-dimethyl-6-{[(2-naphthylmethyl)amino]carbonyl}-4,9,12-trioxo-5,6,7,8,9,10,11,12,15,16,16a,17-dodecahydro-4H,14H-pyrrolo[2,1-c]thieno[2,3-n][1,4,7,12]oxatriazacyclopentadecin-15-yl)carbamate |
| Ex. 418 | 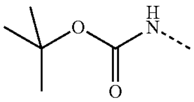 | 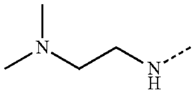 | tert-butyl N-[(6S,15R,16aS)-6-({[2-(dimethylamino)ethyl]amino}carbonyl)-5,10-dimethyl-4,9,12-trioxo-5,6,7,8,9,10,11,12,15,16,16a,17-dodecahydro-4H,14H-pyrrolo[2,1-c]thieno[2,3-n][1,4,7,12]oxatriazacyclopentadecin-15-yl]carbamate |
| Ex. 419 | $NH_2$ | 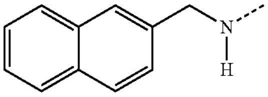 | (6S,15R,16aS)-15-amino-5,10-dimethyl-N-(2-naphthylmethyl)-4,9,12-trioxo-5,6,7,8,9,10,11,12,15,16,16a,17-dodecahydro-4H,14H-pyrrolo[2,1-c]thieno[2,3-n][1,4,7,12]oxatriazacyclopentadecine-6-carboxamide |
| Ex. 420 | $NH_2$ | 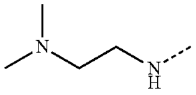 | (6S,15R,16aS)-15-amino-N-[2-(dimethylamino)ethyl]-5,10-dimethyl-4,9,12-trioxo-5,6,7,8,9,10,11,12,15,16,16a,17-dodecahydro-4H,14H-pyrrolo[2,1-c]thieno[2,3-n][1,4,7,12]oxatriazacyclopentadecine-6-carboxamide |
| Ex. 421 | 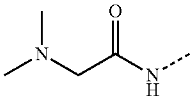 | 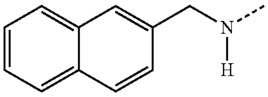 | (6S,15R,16aS)-15-{[2-(dimethylamino)acetyl]amino}-5,10-dimethyl-N-(2-naphthylmethyl)-4,9,12-trioxo-5,6,7,8,9,10,11,12,15,16,16a,17-dodecahydro-4H,14H-pyrrolo[2,1-c]thieno[2,3-n][1,4,7,12]oxatriazacyclopentadecine-6-carboxamide |
| Ex. 422 | 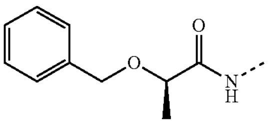 | 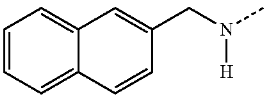 | (6S,15R,16aS)-15-{[(2R)-2-(benzyloxy)propanoyl]amino}-5,10-dimethyl-N-(2-naphthylmethyl)-4,9,12-trioxo-5,6,7,8,9,10,11,12,15,16,16a,17-dodecahydro-4H,14H-pyrrolo[2,1-c]thieno[2,3-n][1,4,7,12]oxatriazacyclopentadecine-6-carboxamide |
| Ex. 423 | 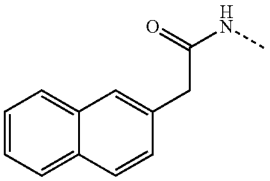 | 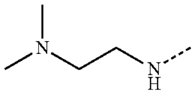 | (6S,15R,16aS)-N-[2-(dimethylamino)ethyl]-5,10-dimethyl-15-{[2-(2-naphthyl)acetyl]amino}-4,9,12-trioxo-5,6,7,8,9,10,11,12,15,16,16a,17-dodecahydro-4H,14H-pyrrolo[2,1-c]thieno[2,3-n][1,4,7,12]oxatriazacyclopentadecine-6-carboxamide |

TABLE 43a

Examples of Core 27 (Ex. 424-Ex. 434 and Ex. 592-Ex. 593; continued on the following pages)

| No | $R^2$ | $R^5$ | Starting material | General Procedure | Reagent | Purification Method | Yield (isolated salt) |
|---|---|---|---|---|---|---|---|
| Ex. 424-Ex. 425: cf. experimental description | | | | | | | |
| Ex. 426 | 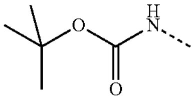 | 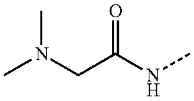 | Ex. 425 | L.1.3 | 2-dimethylamino carboxylic acid (2 equiv.) i-$Pr_2$EtN (2 equiv.) | prep. HPLC, Methode 3 | 75% |
| Ex. 427 | $NH_2$ | 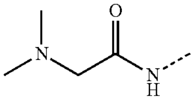 | Ex. 426 | J | HCl (4M dioxane) | crude product | 90% (HCl salt) |
| Ex. 428 | 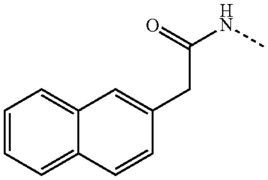 | 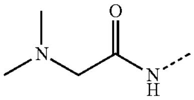 | Ex. 427 | | T3P (50% in EtOAc; 1.2 quiv.) 2-naphthylacetic acid (1.2 equiv.) i-$Pr_2$EtN (4 equiv.), $CH_2Cl_2$, rt, 15 h | prep. HPLC, methode 1 | 35% (TFA salt) |
| Ex. 429 | 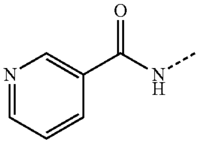 | 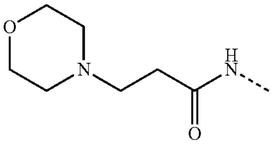 | 268 | S | i) nicotinic acid (2 × 5 equiv.) ii) 3-morpholino-propanoic acid•HCl (1 × 5 equiv.) | prep. HPLC, methode 1 | 25% (TFA salt) |
| Ex. 430 | 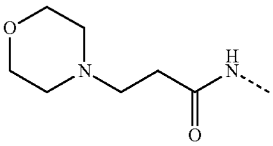 | 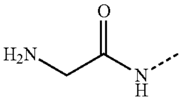 | 268 | S | i) 3-morpholino propanoic acid•HCl (2 × 5 equiv.) ii) BOC-glycine (1 × 5 equiv.) | prep. HPLC, methode 1 | 23% (TFA salt) |
| Ex. 431 | 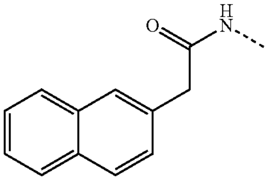 | 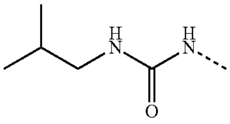 | 268 | S | i) naphthylacetic acid (2 × 5 equiv.) ii) N-succinimidyl-N-isobutyl-carbamate (1 equiv.) | prep. HPLC, methode 1 | 37% (TFA salt) |
| Ex. 432 | 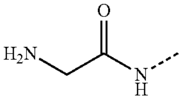 | 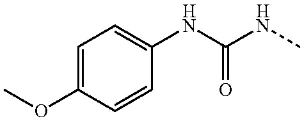 | 268 | S | i) BOC-glycine (2 × 5 equiv.) ii) 4-methoxy-phenylisocyanate (2 × 5 equiv.) | prep. HPLC, methode 1 | 53% (TFA salt) |
| Ex. 433 | 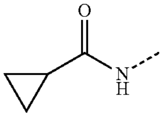 | 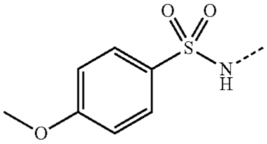 | 268 | S | i) cyclopropane carboxylic acid (2 × 5 equiv.) ii) 4-methoxy-benzylsulfonyl chloride (2 × 5 equiv.) | Prep. HPLC, methode 3 | 42% (TFA salt) |
| Ex. 434 | 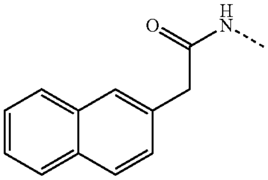 | 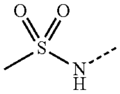 | 268 | S | i) 2-naphthylaceti acid (2 × 5 equiv.) ii) methanesulfonyl chloride (2 × 5 equiv.) | Prep. HPLC, Methode 3 | 48% (TFA salt) |

TABLE 43a-continued

Examples of Core 27 (Ex. 424-Ex. 434 and Ex. 592-Ex. 593; continued on the following pages)

| No | $R^2$ | $R^5$ | Starting material | General Procedure | Reagent | Purification Method | Yield (isolated salt) |
|---|---|---|---|---|---|---|---|
| Ex. 592 | 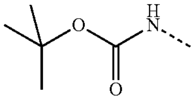 | 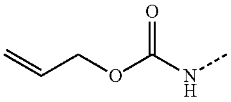 | Ex. 424 | *) | 1. H2, $Pd(OH)_2$—C<br>2. AllocCl | FC ($CH_2Cl_2$/MeOH 95:5) | 85% |
| Ex. 593 | $NH_2$ | 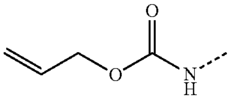 | Ex. 592 | *) | 1. TFA, $CH_2Cl_2$<br>2. HCl-dioxane | crude product | 87% (HCl salt) |

*) cf. detailed description

TABLE 43b

Examples of Core 27 (Ex. 424-Ex. 434 and Ex. 592-Ex. 593; continued on the following page)

| No | $R^2$ | $R^5$ | FORMULA | MONO-ISOTOPIC MASS | Rt (purity at 220 nm) | $[M+H]^+$ found | LC-MS-Method |
|---|---|---|---|---|---|---|---|
| Ex. 424-Ex. 425: cf. experimental description | | | | | | | |
| Ex. 426 | 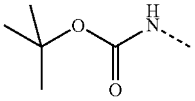 | 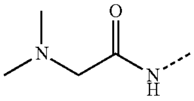 | C27H42N6O6 | 546.3 | 1.35 | 547.4 | Method 4a |
| Ex. 427 | $NH_2$ | 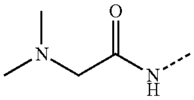 | C22H34N6O4 | 446.3 | 1.23 | 447.3 | Method 5a |
| Ex. 428 | 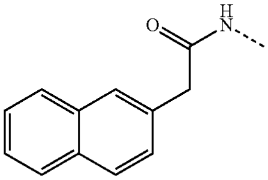 | 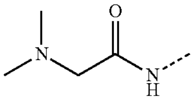 | C34H42N6O5 | 614.3 | 1.32 (95) | 615.3 | Method 10a |
| Ex. 429 | 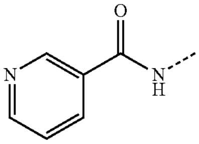 | 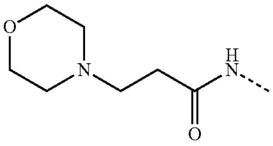 | C31H41N7O6 | 607.3 | 0.78 (96) | 608.3 | Method 10a |
| Ex. 430 | 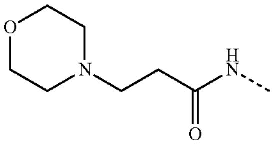 | 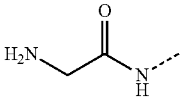 | C27H41N7O6 | 559.3 | 0.61 (91) | 560.2 | Method 10a |
| Ex. 431 | 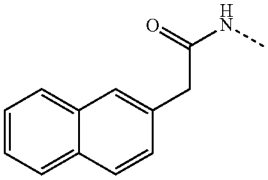 | 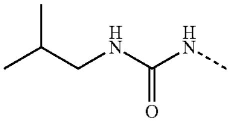 | C35H44N6O5 | 628.3 | 1.63 (95) | 629.3 | Method 10a |

TABLE 43b-continued

Examples of Core 27 (Ex. 424-Ex. 434 and Ex. 592-Ex. 593; continued on the following page)

| No | $R^2$ | $R^5$ | FORMULA | MONO-ISOTOPIC MASS | Rt (purity at 220 nm) | [M + H]$^+$ found | LC-MS-Method |
|---|---|---|---|---|---|---|---|
| Ex. 432 | 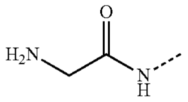 | 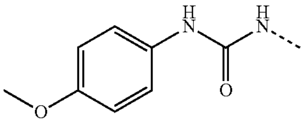 | C28H37N7O6 | 567.3 | 1.09 (98) | 568.2 | Method 10a |
| Ex. 433 | 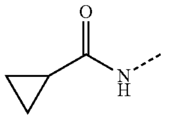 | 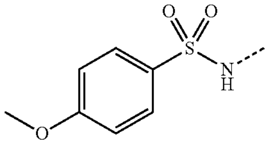 | C29H37N5O7S | 599.2 | 1.38 (96) | 600.2 | Method 10a |
| Ex. 434 | 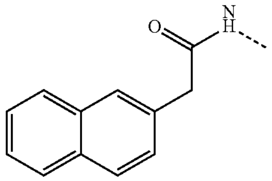 | 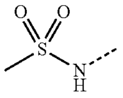 | C31H37N5O6S | 607.3 | 1.49 (90) | 608.2 | Method 10a |
| Ex. 592 | 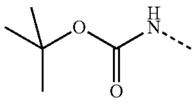 | 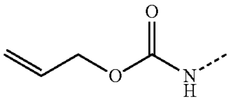 | C27H39N5O7 | 545.2 | 1.56 (96) | 546.2 | Method 10a |
| Ex. 593 | $NH_2$ | 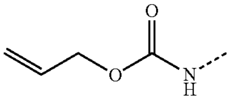 | C22H31N5O5 | 445.2 | 0.98 (96) | 446.1 | Method 10a |

TABLE 43c

Examples of Core 27 (Ex. 424-Ex. 434 and Ex. 592-Ex. 593; continued on the following page)

| No | $R^2$ | $R^5$ | IUPAC name |
|---|---|---|---|
| Ex. 424 | 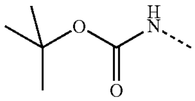 | 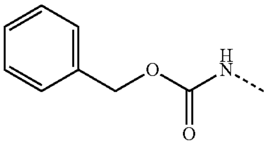 | benzyl N-[(4S,6S,10S)-6-[(tert-butoxycarbonyl)amino]-15-methyl-9,16-dioxo-2-oxa-8,15,19-triazatricyclo[15.3.1.0$^{4,8}$]henicosa-1(21),17,19-trien-10-yl]carbamate |
| Ex. 425 | 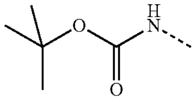 | $NH_2$ | tert-butyl N-[(4S,6S,10S)-10-amino-15-methyl-9,16-dioxo-2-oxa-8,15,19-triazatricyclo[15.3.1.0$^{4,8}$]henicosa-1(21),17,19-trien-6-yl]carbamate |
| Ex. 426 | 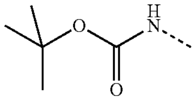 | 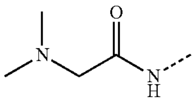 | tert-butyl N-[(4S,6S,10S)-10-{[2-(dimethylamino)acetyl]amino}-15-methyl-9,16-dioxo-2-oxa-8,15,19-triazatricyclo[15.3.1.0$^{4,8}$]henicosa-1(21),17,19-trien-6-yl]carbamate |
| Ex. 427 | $NH_2$ | 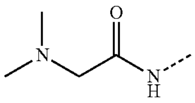 | N-[(4S,6S,10S)-6-amino-15-methyl-9,16-dioxo-2-oxa-8,15,19-triazatricyclo[15.3.1.0$^{4,8}$]henicosa-1(21),17,19-trien-10-yl]-2-(dimethylamino)acetamide |

TABLE 43c-continued

Examples of Core 27 (Ex. 424-Ex. 434 and Ex. 592-Ex. 593; continued on the following page)

| No | $R^2$ | $R^5$ | IUPAC name |
|---|---|---|---|
| Ex. 428 | 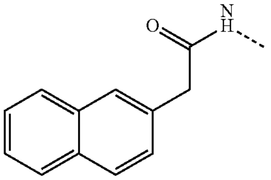 | 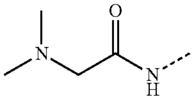 | 2-(dimethylamino)-N-[(4S,6S,10S)-15-methyl-6-{[2-(2-naphthyl)acetyl]amino}-9,16-dioxo-2-oxa-8,15,19-triazatricyclo[15.3.1.0$^{4,8}$]henicosa-1(21),17,19-trien-10-yl]acetamide |
| Ex. 429 | 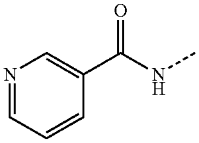 | 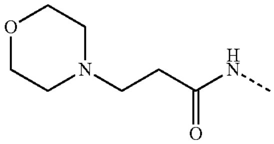 | N-[(4S,6S,10S)-15-methyl-10-[(3-morpholinopropanoyl)amino]-9,16-dioxo-2-oxa-8,15,19-triazatricyclo[15.3.1.0$^{4,8}$]henicosa-1(21),17,19-trien-6-yl]nicotinamide |
| Ex. 430 | 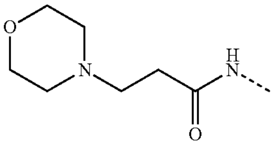 | 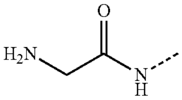 | N-[(4S,6S,10S)-10-[(2-aminoacetyl)amino]-15-methyl-9,16-dioxo-2-oxa-8,15,19-triazatricyclo[15.3.1.0$^{4,8}$]henicosa-1(21),17,19-trien-6-yl]-3-morpholinopropanamide |
| Ex. 431 | 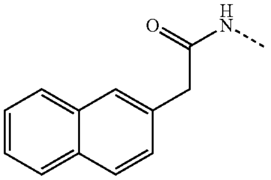 | 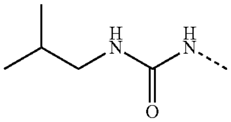 | N-[(4S,6S,10S)-10-{[(isobutylamino)carbonyl]amino}-15-methyl-9,16-dioxo-2-oxa-8,15,19-triazatricyclo[15.3.1.0$^{4,8}$]henicosa-1(21),17,19-trien-6-yl]-2-(2-naphthyl) acetamide |
| Ex. 432 | 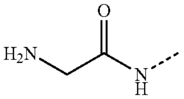 | 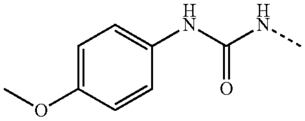 | 2-amino-N-[(4S,6S,10S)-10-{[(4-methoxyanilino)carbonyl]amino}-15-methyl-9,16-dioxo-2-oxa-8,15,19-triazatricyclo[15.3.1.0$^{4,8}$]henicosa-1(21),17,19-trien-6-yl]acetamide |
| Ex. 433 | 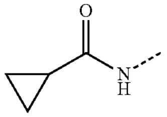 | 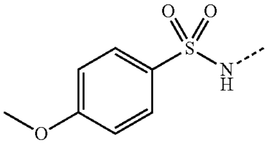 | N-[(4S,6S,10S)-10-{[(4-methoxyphenyl)sulfonyl]amino}-15-methyl-9,16-dioxo-2-oxa-8,15,19-triazatricyclo[15.3.1.0$^{4,8}$]henicosa-1(21),17,19-trien-6-yl]cyclopropanecarboxamide |
| Ex. 434 | 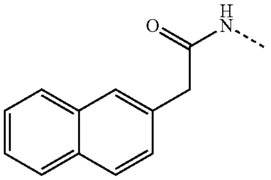 | 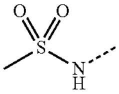 | N-[(4S,6S,10S)-15-methyl-10-[(methylsulfonyl)amino]-9,16-dioxo-2-oxa-8,15,19-triazatricyclo[15.3.1.0$^{4,8}$]henicosa-1(21),17,19-trien-6-yl]-2-(2-naphthyl)acetamide |
| Ex. 592 | 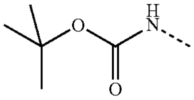 | 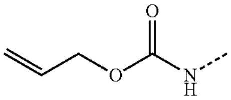 | allyl N-[(4S,6S,10S)-6-[(tert-butoxycarbonyl)amino]-15-methyl-9,16-dioxo-2-oxa-8,15,19-triazatricyclo[15.3.1.0$^{4,8}$]henicosa-1(21),17,19-trien-10-yl]carbamate |
| Ex. 593 | $NH_2$ | 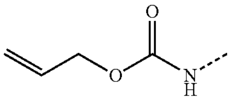 | allyl N-[(4S,6S,10S)-6-amino-15-methyl-9,16-dioxo-2-oxa-8,15,19-triazatricyclo[15.3.1.0$^{4,8}$]henicosa-1(21),17,19-trien-10-yl]carbamate |

TABLE 44a

Examples of Core 28 (Ex. 435-Ex. 446; continued on the following page)

| No | $R^2$ | $R^{54}$ | Starting material | General Procedure | Reagent | Purification Method | Yield (isolated salt) |
|---|---|---|---|---|---|---|---|
| Ex. 435-Ex. 437: cf. experimental description | | | | | | | |
| Ex. 438 | 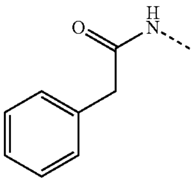 | 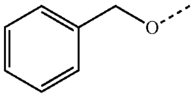 | Ex. 437 | L.1.1 | Phenylacetylchloride (1.1 equiv.), i-$Pr_2$NEt (3 equiv.) | FC (EtOAc/MeOH) | 75% |
| Ex. 439 | 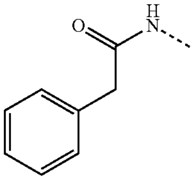 | OH | Ex. 438 | H | $H_2$, $Pd(OH)_2$—C | crude product | 99% |
| Ex. 440 | 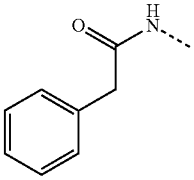 | 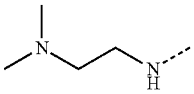 | Ex. 439 | L.2 | 2-dimethylaminoethylamine | FC ($CH_2Cl_2$/MeOH/$NH_4OH$)) | 90% |
| Ex. 441 | 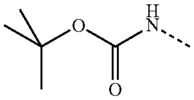 | 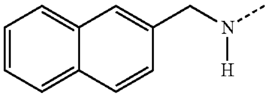 | Ex. 436 | L.2 | HATU (2.6 equiv.) HOAt (2.6 equiv.) i-$Pr_2$NEt (5 equiv.) 2-naphthylmethylamine (2.6 equiv.) | Prep. HPLC, method 3 + size exclusion chromatography | 64% |
| Ex. 442 | $NH_2$ | 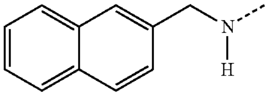 | Ex. 441 | *) | TFA, triisopropylsilane *) | crude product | 72% |
| Ex. 443 | 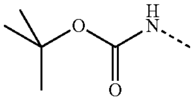 | 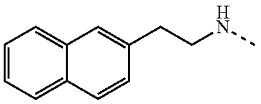 | Ex. 436 | L.2 | HATU (2.6 equiv.) HOAt (2.6 equiv.) i-$Pr_2$NEt (8 equiv.) 2-Naphthylethylamine hydrochloride | Prep. HPLC, method 3 + size exclusion chromatography | 86% |
| Ex. 444 | $NH_2$ | 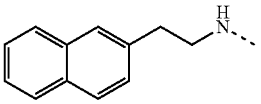 | Ex. 443 | *) | TFA, triisopropylsilane *) | prep. HPLC, method 1 | 43% (TFA salt) |
| Ex. 445 | 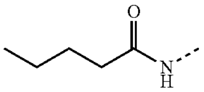 | 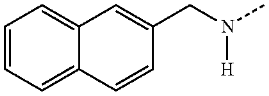 | Ex. 442 | L.1.1 | Valeroylchloride (4 equiv.) | prep. HPLC, method 3 | 72% |
| Ex. 446 | 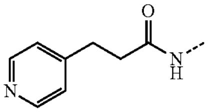 | 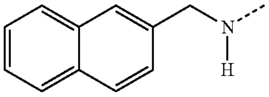 | Ex. 442 | L.1.2 | 3-(pyridin-4-yl)propanoic acid (1.8 equiv.) | prep. HPLC, method 3 | 90% |

*) A soln of the Boc amine (0.04 mmol) in $CH_2Cl_2$ (1 mL) was treated at 0° C. with triisopropylsilane (3 equiv.) and TFA (0.2 mL). The mixture was stirred for 2.5 h, treated with sat. aq. $Na_2CO_3$ soln and extracted with $CH_2Cl_2$. The organic phase was dried ($Na_2SO_4$), filtered and concentrated to afford the corresponding amine.

TABLE 44b
Examples of Core 28 (Ex. 435-Ex. 446; continued on the following page)
| No | $R^2$ | $R^{54}$ | FORMULA | MONO-ISOTOPIC MASS | Rt (purity at 220 nm) | $[M + H]^+$ found | LC-MS-Method |
|---|---|---|---|---|---|---|---|
| Ex. 435-Ex. 437: cf. experimental description | | | | | | | |
| Ex. 438 | 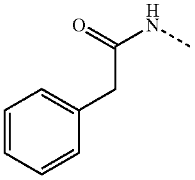 | 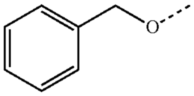 | C40H45N5O7 | 707.3 | 1.93 (97) | 708.4 | Method 10a |
| Ex. 439 | 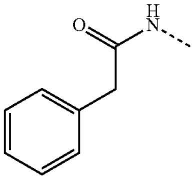 | OH | C33H39N5O7 | 617.3 | 1.50 (97) | 618.3 | Method 10a |
| Ex. 440 | 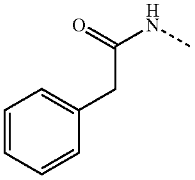 | 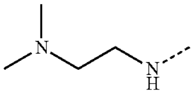 | C37H49N7O6 | 687.4 | 1.38 (98) | 688.4 | Method 10a |
| Ex. 441 | 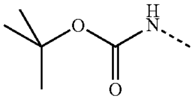 | 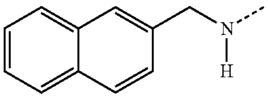 | C41H50N6O7 | 738.4 | 2.08 (98) | 739.1 | Method 10a |
| Ex. 442 | $NH_2$ | 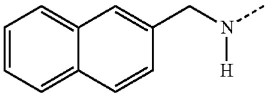 | C36H42N6O5 | 638.3 | 1.50 (94) | 639.2 | Method 10a |
| Ex. 443 | 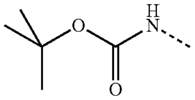 | 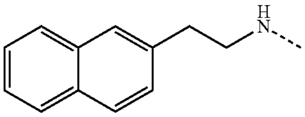 | C42H52N6O7 | 752.4 | 2.12 (96) | 753.1 | Method 10a |
| Ex. 444 | $NH_2$ | 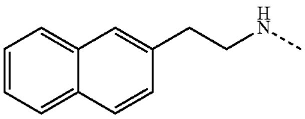 | C37H44N6O5 | 652.3 | 1.57 (86) | 653.3 | Methode 10a |
| Ex. 445 | 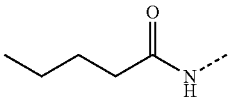 | 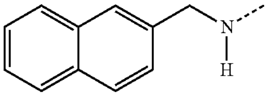 | C41H50N6O6 | 722.4 | 2.11 (99) | 723.3 | Method 4b |
| Ex. 446 | 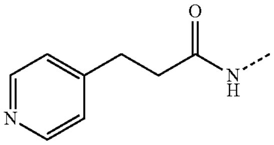 | 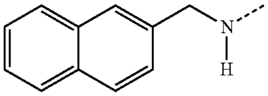 | C44H49N7O6 | 771.4 | 1.73 (99) | 772.3 | Method 4b |

TABLE 44c

Examples of Core 28 (Ex. 435-Ex. 446; continued on the following pages)

| No | $R^2$ | $R^{54}$ | IUPAC name |
|---|---|---|---|
| Ex. 435 | 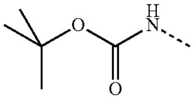 | 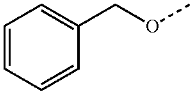 | benzyl (4S,6R,15S)-6-[(tert-butoxycarbonyl)amino]-11,16,19,20-tetramethyl-9,12,17-trioxo-2-oxa-8,11,16,20-tetraazatetracyclo[16.5.2.$0^{4,8}$.$0^{21,25}$]pentacosa-1(23),18,21,24-tetraene-15-carboxylate |
| Ex. 436 | 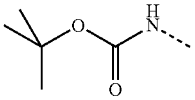 | OH | (4S,6R,15S)-6-[(tert-butoxycarbonyl)amino]-11,16,19,20-tetramethyl-9,12,17-trioxo-2-oxa-8,11,16,20-tetraazatetracyclo[16.5.2.$0^{4,8}$.$0^{21,25}$]pentacosa-1(23),18,21,24-tetraene-15-carboxylic acid |
| Ex. 437 | $NH_2$ | 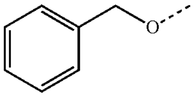 | benzyl (4S,6R,15S)-6-amino-11,16,19,20-tetramethyl-9,12,17-trioxo-2-oxa-8,11,16,20-tetraazatetracyclo[16.5.2.$09^{4,8}$.$0^{21,25}$]pentacosa-1(23),18,21,24-tetraene-15-carboxylate |
| Ex. 438 | 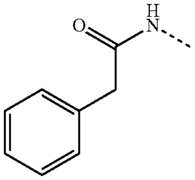 | 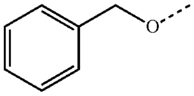 | benzy (4S,6R,15S)-11,16,19,20-tetramethyl-9,12,17-trioxo-6-[(2-phenylacetyl)amino]-2-oxa-8,11,16,20-tetraazetetracyclo[16.5.2.$0^{4,8}$.$0^{21,25}$]pentacosa-1(23),18,21,24-tetraene-15-carboxylate |
| Ex. 439 | 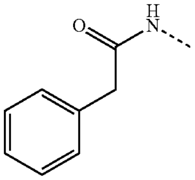 | OH | (4S,6R,15S)-11,16,19,20-tetramethyl-9,12,17-trioxo-6-[(2-phenylacetyl)amino]-2-oxa-8,11,16,20-tetraazatetracyclo[16.5.2.$0^{4,8}$.$0^{21,25}$]pentacosa-1(23),18,21,24-tetraene-15-carboxylic acid |
| Ex. 440 | 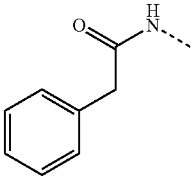 | 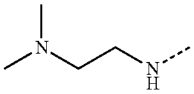 | (4S,6R,15S)-N-[2-(dimethylamino)ethyl]-11,16,19,20-tetramethyl-9,12,17-trioxo-6-[(2-phenylacetyl)amino]-2-oxa-8,11,16,20-tetraazatetracyclo[16.5.2.$0^{4,8}$.$0^{21,25}$]pentacosa-1(23),18,21,24-tetraene-15-carboxamide |
| Ex. 441 | 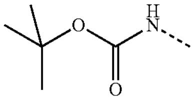 | 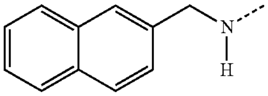 | tert-butyl N-[(4S,6R,15S)-11,16,19,20-tetramethyl-15-{[(2-naphthylmethyl)amino]carbonyl}-9,12,17-trioxo-2-oxa-8,11,16,20-tetraazatetracyclo[16.5.2.$0^{4,8}$.$0^{21,25}$]pentacosa-1(23),18,21,24-tetraen-6-yl]carbamate |
| Ex. 442 | $NH_2$ | 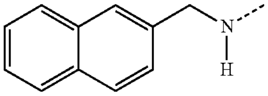 | (4S,6R,15S)-6-amino-11,16,19,20-tetramethyl-N-(2-naphthylmethyl)-9,12,17-trioxo-2-oxa-8,11,16,20-tetraazatetracyclo[16.5.2.$0^{4,8}$. $0^{21,25}$]pentacosa-1(23),18,21,24-tetraene-15-carboxamide |
| Ex. 443 | 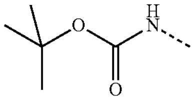 | 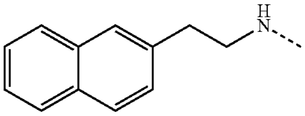 | tert-butyl N-[(4S,6R,15S)-11,16,19,20-tetramethyl-15-({[2-(2-naphthyl)ethyl]amino}carbonyl)-9,12,17-trioxo-2-oxa-8,11,16,20-tetraazatetracyclo[16.5.2.$0^{4,8}$.$0^{21,25}$]pentacosa-1(23),18,21,24-tetraen-6-yl]carbamate |
| Ex. 444 | $NH_2$ | 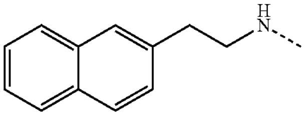 | (4S,6R,15S)-6-amino-11,16,19,20-tetramethyl-N-[2-(2-naphthyl)ethyl]-9,12,17-trioxo-2-oxa-8,11,16,20-tetraazatetracyclo[16.5.2.$0^{4,8}$.$0^{21,25}$]pentacosa-1(23),18,21,24-tetraene-15-carboxamide |
| Ex. 445 | 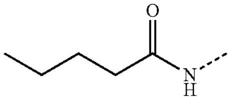 | 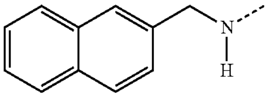 | (4S,6R,15S)-11,16,19,20-tetramethyl-N-(2-naphthylmethyl)-9,12,17-trioxo-6-(pentanoylamino)-2-oxa-8,11,16,20-tetraazatetracyclo[16.5.2.$0^{4,8}$.$0^{21,25}$]pentacosa-1(23),18,21,24-tetraene-15-carboxamide |

TABLE 44c-continued

| Examples of Core 28 (Ex. 435-Ex. 446; continued on the following pages) | | | |
|---|---|---|---|
| No | $R^2$ | $R^{54}$ | IUPAC name |
| Ex. 446 | 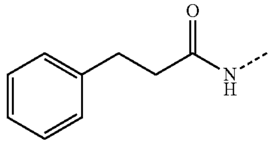 | 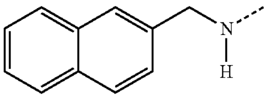 | (4S,6R,15S)-11,16,19,20-tetramethyl-N-(2-naphthylmethyl)-9,12,17-trioxo-6-{[3-(4-pyridinyl)propanoyl]amino}-2-oxa-8,11,16,20-tetraazatetracyclo[16.5.2.0$^{4,8}$.0$^{21,25}$]pentacosa-1(23),18,21,24-tetraene-15-carboxamide |

TABLE 45a

| Examples of Core 29 (Ex. 447-Ex. 450) | | | | | | | |
|---|---|---|---|---|---|---|---|
| No | $R^2$ | $R^5$ | Starting material | General Procedure | Reagent | Purification Method | Yield (isolated salt) |
| Ex. 447-Ex. 448: cf. experimental description | | | | | | | |
| Ex. 449 | OH | 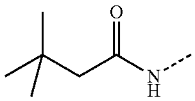 | Ex. 448 | L.1.1 | 3,3-dimethylbutanoyl chloride (4.1 equiv.) pyridine (19 equiv.) | FC ($CH_2Cl_2$/MeOH) | 72% |
| Ex. 450 | OH | 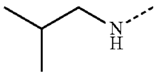 | Ex. 448 | M.2 | isobutyraldehyde (1.1 equiv.) $NaBH(OAc)_3$ (2.5 equiv.) | prep. HPLC method 1 | 9% (TFA salt) |

TABLE 45b

| Examples of Core 29 (Ex. 447-Ex. 450) | | | | | | | |
|---|---|---|---|---|---|---|---|
| No | $R^2$ | $R^5$ | FORMULA | MONOISOTOPIC MASS | Rt (purity at 220 nm) | $[M + H]^+$ found | LC-MS-Method |
| Ex. 447-Ex. 448: cf. experimental description | | | | | | | |
| Ex. 449 | OH | 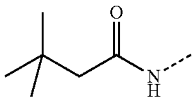 | C24H36N2O4 | 416.3 | 2.01 (91) | 417.3 | Method 10a |
| Ex. 450 | OH | 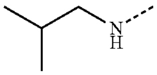 | C22H34N2O3 | 374.3 | 1.41 (98) | 375.2 | Method 10a |

TABLE 45c

| Examples of Core 29 (Ex. 447-Ex. 450) | | | |
|---|---|---|---|
| No | $R^2$ | $R^5$ | IUPAC name |
| Ex. 447 | 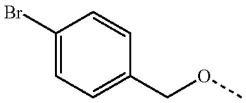 | 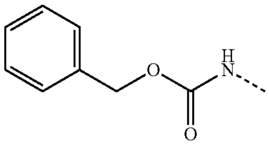 | 1:1 mixture of the 12-(E)- and 12-(Z)-stereoisomer of benzyl N-[(4S,6S,10S)-6-[(4-bromobenzyl)oxy]-9-oxo-2-oxa-8-azatricyclo[14.3.1.0$^{4,8}$]icosa-1(20),12,16,18-tetraen-10-yl]carbamate |
| Ex. 448 | OH | $NH_2$ | (4S,6S,10S)-10-amino-6-hydroxy-2-oxa-8-azatricyclo[14.3.1.0$^{4,8}$]icosa-1(20),16,18-trien-9-one |

TABLE 45c-continued

| Examples of Core 29 (Ex. 447-Ex. 450) | | | |
|---|---|---|---|
| No | $R^2$ | $R^5$ | IUPAC name |
| Ex. 449 | OH | 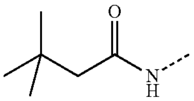 | N-[(4S,6S,10S)-6-hydroxy-9-oxo-2-oxa-8-azatricyclo[14.3.1.$0^{4,8}$]icosa-1(20),16,18-trien-10-yl]-3,3-dimethylbutanamide |
| Ex. 450 | OH | 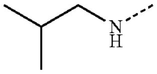 | (4S,6S,10S)-6-hydroxy-10-(isobutylamino)-2-oxa-8-azatricyclo[14.3.1.$0^{4,8}$]icosa-1(20),16,18-trien-9-one |

TABLE 46a

| Examples of Core 30 (Ex. 451-Ex. 459) | | | | | | | | |
|---|---|---|---|---|---|---|---|---|
| No | X | $R^2$ | $R^5$ | Starting material | General Procedure | Reagent | Purification Method | Yield (isolated salt) |
| Ex. 451-Ex. 452 cf. experimental description | | | | | | | | |
| Ex. 453 | $SO_2$ | 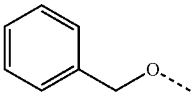 | $NH_2$ | Ex. 452 | K.2 | $H_2$, 5% Pd—C $NH_3$—MeOH cf. detailed description | crude product | 88% |
| Ex. 454 | $SO_2$ | HO | $NH_2$ | Ex. 452 | K.1 | $H_2$, $Pd(OH)_2$—C MeOH/AcOH 1:1 | FC ($CH_2Cl_2$/ MeOH/ aq. $NH_3$) | 78% |
| Ex. 455 | $SO_2$ | 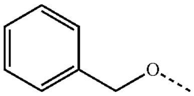 | 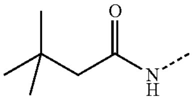 | Ex. 453 | L.1.1 | 3,3-dimethyl-butanoyl chloride (1.2 equiv.) pyridine (5 equiv.) | prep. HPLC method 3 | 83% |
| Ex. 456 | $SO_2$ | 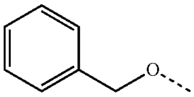 | 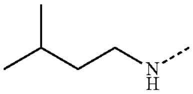 | Ex. 453 | M.2 | isovaleraldehyde | prep. HPLC method 3 | 77% |
| Ex. 457 | $SO_2$ | HO | 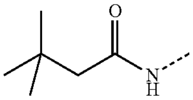 | Ex. 455 | H | $H_2$, $Pd(OH)_2$—C MeOH/AcOH 4:1 | crude product | 86% |
| Ex. 458 | $SO_2$ | HO | 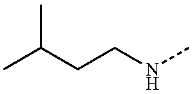 | Ex. 456 | H | $H_2$, $Pd(OH)_2$—C MeOH/AcOH 4:1 | prep. HPLC method 3 | 19% |
| Ex. 459*⁾ | $SO_2$ | HO | 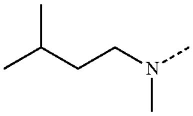 | Ex. 456 | H | $H_2$, $Pd(OH)_2$—C MeOH/AcOH 4:1 | prep. HPLC method 3 | 17%*⁾ |

*⁾obtained as a side product

TABLE 46b

Examples of Core 30 (Ex. 451-Ex. 459)

| No | X | $R^2$ | $R^5$ | FORMULA | MONO-ISOTOPIC MASS | Rt (purity at 220 nm) | $[M + H]^+$ found | LC-MS-Method |
|---|---|---|---|---|---|---|---|---|
| Ex. 451-Ex. 452: cf. experimental description | | | | | | | | |
| Ex. 453 | $SO_2$ | 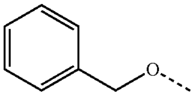 | $NH_2$ | C25H31N3O5S | 485.2 | 1.29 (98) | 486.2 | Method 10a |
| Ex. 454 | $SO_2$ | HO | $NH_2$ | C18H25N3O5S | 395.2 | 0.70 (100) | 396.1 | Method 11a |
| Ex. 455 | $SO_2$ | 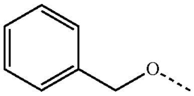 | 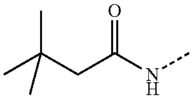 | C31H41N3O6S | 583.3 | 1.90 (95) | 584.3 | Method 10a |
| Ex. 456 | $SO_2$ | 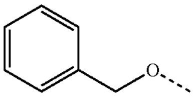 | 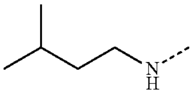 | C30H41N3O5S | 555.3 | 1.57 (99) | 556.2 | Method 10a |
| Ex. 457 | $SO_2$ | HO | 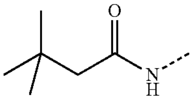 | C24H35N3O6S | 493.2 | 1.27 (95) | 494.2 | Method 10a |
| Ex. 458 | $SO_2$ | HO | 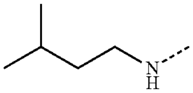 | C23H35N3O5S | 465.2 | 1.03 (95) | 466.2 | Method 10a |
| Ex. 459 | $SO_2$ | HO | 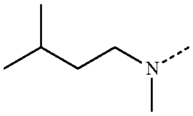 | C24H37N3O5S | 479.2 | 1.03 (94) | 480.2 | Method 10a |

TABLE 46c

Examples of Core 30 (Ex. 451-Ex. 459)

| No | X | $R^2$ | $R^5$ | IUPAC name |
|---|---|---|---|---|
| Ex. 451 | S | 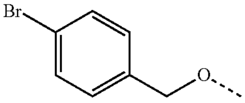 | 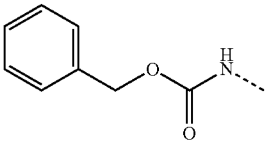 | benzyl N-[(4S,6S,10S)-6-[(4-bromobenzyl)oxy]-14-methyl-9,15-dioxo-2-thia-8,14-diazatricyclo[14.3.1.$0^{4,8}$]icosa-1(20),16,18-trien-10-yl]carbamate |
| Ex. 452 | $SO_2$ | 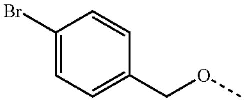 | 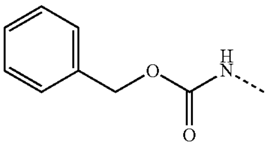 | benzyl N-[(4S,6S,10S)-6-[(4-bromobenzyl)oxy]-14-methyl-2,2,9,15-tetraoxo-2$\lambda^6$-thia-8,14-diazatricyclo[14.3.1.$0^{4,8}$]icosa-1(20),16,18-trien-10-yl]carbamate |
| Ex. 453 | $SO_2$ | 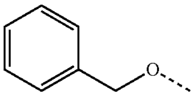 | $NH_2$ | (4S,6S,10S)-10-amino-6-(benzyloxy)-14-methyl-2$\lambda^6$-thia-8,14-diazatricyclo[14.3.1.$0^{4,8}$]icosa-1(20),16,18-triene-2,2,9,15-tetrone |
| Ex. 454 | $SO_2$ | HO | $NH_2$ | (4S,6S,10S)-10-amino-6-hydroxy-14-methyl-2$\lambda^6$-thia-8,14-diazatricyclo[14.3.1.$0^{4,8}$]icosa-1(20),16,18-triene-2,2,9,15-tetrone |

TABLE 46c-continued

| Examples of Core 30 (Ex. 451-Ex. 459) | | | | |
|---|---|---|---|---|
| No | X | $R^2$ | $R^5$ | IUPAC name |
| Ex. 455 | $SO_2$ | 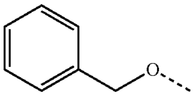 | 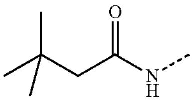 | N-[(4S,6S,10S)-6-(benzyloxy)-14-methyl-2,2,9,15-tetraoxo-2λ$^6$-thia-8,14-diazatricyclo[14.3.1.0$^{4,8}$]icosa-1(20),16,18-trien-10-yl]-3,3-dimethylbutanamide |
| Ex. 456 | $SO_2$ | 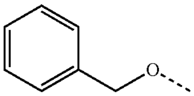 | 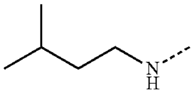 | (4S,6S,10S)-6-(benzyloxy)-10-(isopentylamino)-14-methyl-2λ$^6$-thia-8,14-diazatricyclo[14.3.1.0$^{4,8}$]icosa-1(20),16,18-triene-2,2,9,15-tetrone |
| Ex. 457 | $SO_2$ | HO | 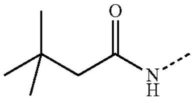 | N-[(4S,6S,10S)-6-hydroxy-14-methyl-2,2,9,15-tetraoxo-2λ$^6$-thia-8,14-diazatricyclo[14.3.1.0$^{4,8}$]icosa-1(20),16,18-trien-10-yl]-3,3-dimethylbutanamide |
| Ex. 458 | $SO_2$ | HO | 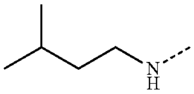 | (4S,6S,10S)-6-hydroxy-10-(isopentylamino)-14-methyl-2λ$^6$-thia-8,14-diazatricyclo[14.3.1.0$^{4,8}$]icosa-1(20),16,18-triene-2,2,9,15-tetrone |
| Ex. 459 | $SO_2$ | HO | 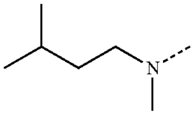 | (4S,6S,10S)-6-hydroxy-10-[isopentyl(methyl)amino]-14-methyl-2λ$^6$-thia-8,14-diazatricyclo[14.3.1.0$^{4,8}$]icosa-1(20),16,18-triene-2,2,9,15-tetrone |

TABLE 47a

| Examples of Core 31 (Ex. 460-Ex. 469) | | | | | | | | |
|---|---|---|---|---|---|---|---|---|
| No | L | $R^2$ | $R^5$ | Starting material | General Procedure | Reagent | Purification Method | Yield (isolated salt) |
| Ex. 460-Ex. 461: cf. experimental description | | | | | | | | |
| Ex. 462 | $SO_2$ | 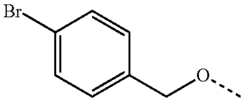 | $NH_2$ | Ex. 461 | J | HCl-dioxane | crude product | 87% (HCl salt) |
| Ex. 463 | $SO_2$ | 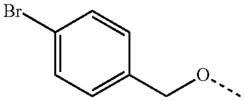 | 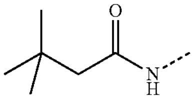 | Ex. 462 | L.1.1 | 3,3-dimethyl-butanoyl chloride (1.5 equiv.) pyridine (5 equiv.) | FC (hexane/EtOAc) | 76% |
| Ex. 464 | $SO_2$ | 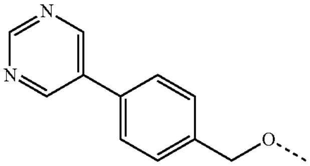 | 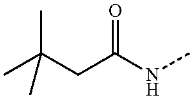 | Ex. 463 | P | pyrimidin-5-yl boronic acid | FC (hexane/EtOAc/MeOH) and FC ($CH_2Cl_2$/MeOH) | 67% |
| Ex. 465 | $SO_2$ | OH | 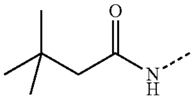 | Ex. 463 | H | $H_2$, $Pd(OH)_2$—C | FC ($CH_2Cl_2$/MeOH/aq. $NH_3$) | 98% |
| Ex. 466 | S | 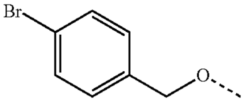 | $NH_2$ | Ex. 460 | J | HCl-dioxane | crude product | 90% (HCl salt) |

TABLE 47a-continued

Examples of Core 31 (Ex. 460-Ex. 469)

| No | L | $R^2$ | $R^5$ | Starting material | General Procedure | Reagent | Purification Method | Yield (isolated salt) |
|---|---|---|---|---|---|---|---|---|
| Ex. 467 | S | 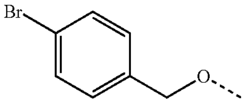 | 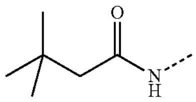 | Ex. 466 | L.1.1 | 3,3-dimethyl-butanoyl chloride (1.5 equiv.) pyridine (5 equiv.) | FC (hexane/ EtOAc) | 83% |
| Ex. 468 | S | 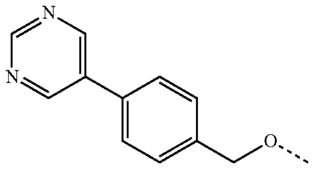 | 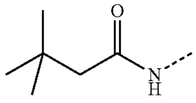 | Ex. 467 | P | pyrimidin-5-yl boronic acid | FC (hexane/ EtOAc/ MeOH) | 72% |
| Ex. 469 | S | 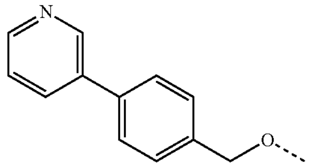 | 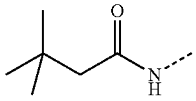 | Ex. 467 | P | pyridin-3-yl boronic acid | FC (hexane/ EtOAc/ MeOH) | 66% |

TABLE 47b

Examples of Core 31 (Ex. 460-Ex. 469)

| No | L | $R^2$ | $R^5$ | FORMULA | MONO-ISOTOPIC MASS | Rt (purity at 220 nm) | $[M + H]^+$ found | LC-MS-Method |
|---|---|---|---|---|---|---|---|---|
| Ex. 460-Ex. 461: cf. experimental description | | | | | | | | |
| Ex. 462 | $SO_2$ | 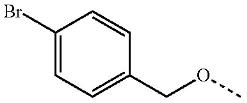 | $NH_2$ | C24H29BrN2O5S | 536.1 | 1.63 (96) | 539.1/537.1 | Method 10a |
| Ex. 463 | $SO_2$ | 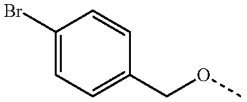 | 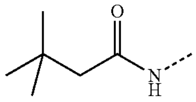 | C30H39BrN2O6S | 634.1 | 2.33 (99) | 635.1/637.1 | Method 10a |
| Ex. 464 | $SO_2$ | 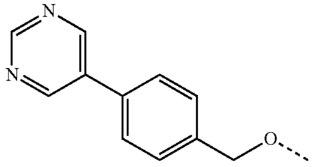 | 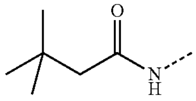 | C34H42N4O6S | 634.3 | 1.89 (93) | 635.2 | Method 10a |
| Ex. 465 | $SO_2$ | OH | 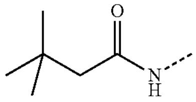 | C23H34N2O6S | 466.2 | 1.47 (97) | 467.2 | Method 10a |
| Ex. 466 | S | 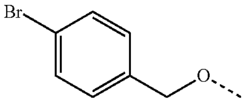 | $NH_2$ | C24H29BrN2O3S | 504.1 | 1.89 (93) | 507.1/505.1 | Method 10a |
| Ex. 467 | S | 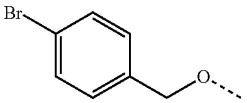 | 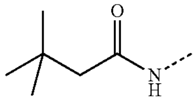 | C30H39BrN2O4S | 602.2 | 2.75 (96) | 605.1/603.1 | Method 10a |

TABLE 47b-continued

| Examples of Core 31 (Ex. 460-Ex. 469) | | | | | | | | |
|---|---|---|---|---|---|---|---|---|
| No | L | $R^2$ | $R^5$ | FORMULA | MONO-ISOTOPIC MASS | Rt (purity at 220 nm) | $[M + H]^+$ found | LC-MS-Method |
| Ex. 468 | S | 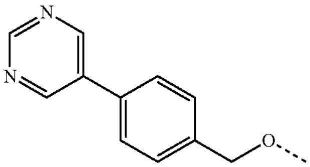 | 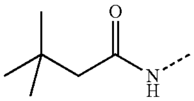 | C34H42N4O4S | 602.3 | 2.33 (90) | 603.3 | Method 10a |
| Ex. 469 | S | 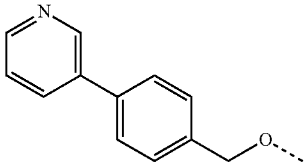 | 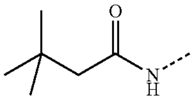 | C35H43N3O4S | 601.3 | 1.92 (98) | 602.3 | Method 10a |

TABLE 47c

| Examples of Core 31 (Ex. 460-Ex. 469) | | | | |
|---|---|---|---|---|
| No | L | $R^2$ | $R^5$ | IUPAC name |
| Ex. 460 | S | 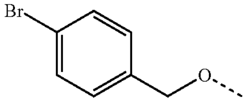 | 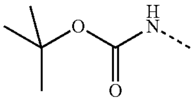 | tert-butyl N-[(4S,6S,10S)-6-[(4-bromobenzyl)oxy]-9-oxo-2-oxa-15-thia-8-azatricyclo[14.3.1.$0^{4,8}$]icosa-1(20),16,18-trien-10-yl]carbamate |
| Ex. 461 | $SO_2$ | 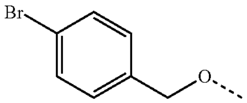 | 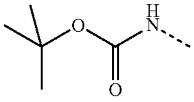 | tert-butyl N-[(4S,6S,10S)-6-[(4-bromobenzyl)oxy]-9,15,15-trioxo-2-oxa-15$\lambda^6$-thia-8-azatricyclo[14.3.1.$0^{4,8}$]icosa-1(20),16,18-trien-10-yl]carbamate |
| Ex. 462 | $SO_2$ | 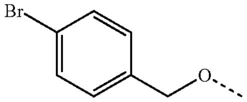 | $NH_2$ | (4S,6S,10S)-10-amino-6-[(4-bromobenzyl)oxy]-2-oxa-15$\lambda^6$-thia-8-azatricyclo[14.3.1.$0^{4,8}$]icosa-1(20),16,18-triene-9,15,15-trione |
| Ex. 463 | $SO_2$ | 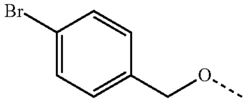 | 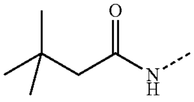 | N-[(4S,6S,10S)-6-[(4-bromobenzyl)oxy]-9,15,15-trioxo-2-oxa-15$\lambda^6$-thia-8-azatricyclo[14.3.1.$0^{4,8}$]icosa-1(20),16,18-trien-10-yl]-3,3-dimethylbutanamide |
| Ex. 464 | $SO_2$ | 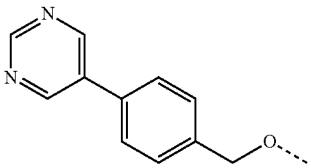 | 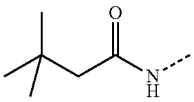 | 3,3-dimethyl-N-[(4S,6S,10S)-9,15,15-trioxo-6-{[4-(5-pyrimidinyl)benzyl]oxy}-2-oxa-15$\lambda^6$-thia-8-azatricyclo[14.3.1.$0^{4,8}$]icosa-1(20),16,18-trien-10-yl]butanamide |
| Ex. 465 | $SO_2$ | OH | 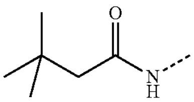 | N-[(4S,6S,10S)-6-hydroxy-9,15,15-trioxo-2-oxa-15$\lambda^6$-thia-8-azatricyclo[14.3.1.$0^{4,8}$]icosa-1(20),16,18-trien-10-yl]-3,3-dimethylbutanamide |
| Ex. 466 | S | 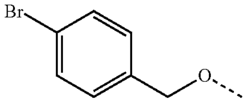 | $NH_2$ | (4S,6S,10S)-10-amino-6-[(4-bromobenzyl)oxy]-2-oxa-15-thia-8-azatricyclo[14.3.1.$0^{4,8}$]icosa-1(20),16,18-trien-9-one |

TABLE 47c-continued

| Examples of Core 31 (Ex. 460-Ex. 469) | | | | |
|---|---|---|---|---|
| No | L | $R^2$ | $R^5$ | IUPAC name |
| Ex. 467 | S | 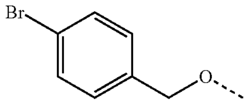 | 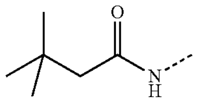 | N-[(4S,6S,10S)-6-[(4-bromobenzyl)oxy]-9-oxo-2-oxa-15-thia-8-azatricyclo[14.3.1.0$^{4,8}$]icosa-1(20),16,18-trien-10-yl]-3,3-dimethylbutanamide |
| Ex. 468 | S | 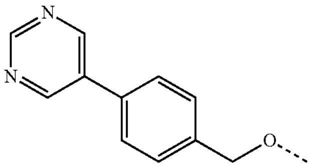 | 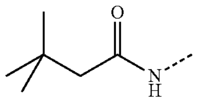 | 3,3-dimethyl-N-[(4S,6S,10S)-9-oxo-6-{[4-(5-pyrimidinyl)-benzyl]oxy}-2-oxa-15-thia-8-azatricyclo[14.3.1.0$^{4,8}$]icosa-1(20),16,18-trien-10-yl]butanamide |
| Ex. 469 | S | 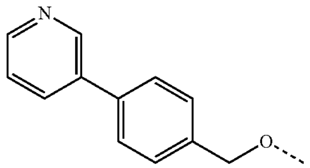 | 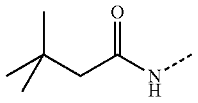 | 3,3-dimethyl-N-[(4S,6S,10S)-9-oxo-6-{[4-(3-pyridinyl)-benzyl]oxy}-2-oxa-15-thia-8-azatricyclo[14.3.1.0$^{4,8}$]icosa-1(20),16,18-trien-10-yl]butanamide |

TABLE 48a

| Examples of Core 32 (Ex. 470-Ex. 475) | | | | | | | |
|---|---|---|---|---|---|---|---|
| No | $R^2$ | $R^1$ | Starting material | General Procedure | Reagent | Purification Method | Yield (isolated salt) |
| Ex. 470: cf. experimental description | | | | | | | |
| Ex. 471 | 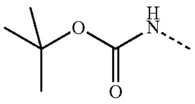 | 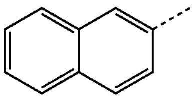 | Ex. 470 | P | cf. experimental description | FC ($CH_2Cl_2$/MeOH) | 62% |
| Ex. 472 | 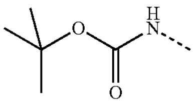 | 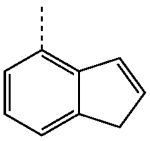 | Ex. 470 | P | cf. experimental description | FC ($CH_2Cl_2$/MeOH) | 62% |
| Ex. 473 | $NH_2$ | (Br) | Ex. 470 | J | cf. experimental description | crude product | 92% (HCl salt) |
| Ex. 474 | $NH_2$ | 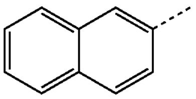 | Ex. 471 | J | cf. experimental description | crude product | 100% (HCl salt) |
| Ex. 475 | $NH_2$ | 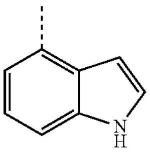 | Ex. 474 | — | cf. experimental description | FC ($CH_2Cl_2$/MeOH) | 83% |

TABLE 48b

| Examples of Core 32 (Ex. 470-Ex. 475) | | | | | | | |
|---|---|---|---|---|---|---|---|
| No | $R^2$ | $R^1$ | FORMULA | MONO-ISOTOPIC MASS | Rt (purity at 220 nm) | $[M + H]^+$ found | LC-MS-Method |
| Ex. 470: cf. experimental description | | | | | | | |
| Ex. 471 | 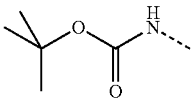 | 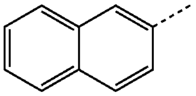 | C47H50N4O6 | 766.9 | 2.68 (95) | 767.4 | Method 10a |
| Ex. 472 | 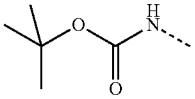 | 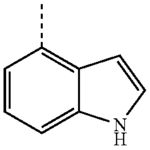 | C45H49N5O6 | 755.4 | 2.37 (92) | 756.4 | Method 10a |
| Ex. 473 | $NH_2$ | (Br) | C32H35BrN4O4 | 618.2 | 1.75 (98) | 621.1/ 619.1 | Method 10a |
| Ex. 474 | $NH_2$ | 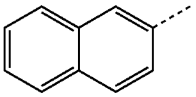 | C42H42N4O4 | 666.3 | 2.02 (96) | 667.3 | Method 10a |
| Ex. 475 | $NH_2$ | 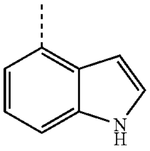 | C40H41N5O4 | 655.3 | 1.76 (90) | 656.3 | Method 10a |

TABLE 48c

| Examples of Core 32 (Ex. 470-Ex. 475) | | | |
|---|---|---|---|
| No | $R^2$ | $R^1$ | IUPAC name |
| Ex. 470 | 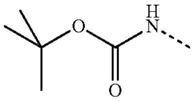 | (Br) | tert-butyl (2R,7S,18aS)-14-bromo-7-(naphthalen-2-ylmethyl)-5,9,12-trioxo-1,2,3,5,6,7,8,9,11,12,18,18a-dodecahydrospiro[benzo[m]pyrrolo[2,1-c][1,4,8,11]oxatriazacyclotetradecine-10,1'-cyclopentane]-2-ylcarbamate |
| Ex . 471 | 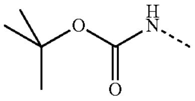 | 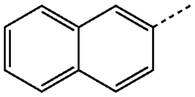 | tert-butyl (2R,7S,18aS)-14-(naphthalen-2-yl)-7-(naphthalen-2-ylmethyl)-5,9,12-trioxo-1,2,3,5,6,7,8,9,11,12,18,18a-dodecahydrospiro[benzo[m]pyrrolo[2,1-c][1,4,8,11]oxatriazacyclotetradecine-10,1'-cyclopentane]-2-ylcarbamate |
| Ex. 472 | 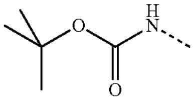 | 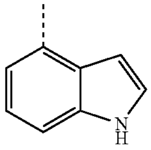 | tert-butyl (2R,7S,18aS)-14-(1H-indol-4-yl)-7-(naphthalen-2-ylmethyl)-5,9,12-trioxo-1,2,3,5,6,7,8,9,11,12,18,18a-dodecahydrospiro[benzo[m]pyrrolo[2,1-c][1,4,8,11]oxatriazacyclotetradecine-10,1'-cyclopentane]-2-ylcarbamate |
| Ex. 473 | $NH_2$ | (Br) | (2R,7S,18aS)-2-amino-14-bromo-7-(naphthalen-2-ylmethyl)-2,3,7,8,18,18a-hexahydrospiro[benzo[m]pyrrolo[2,1-c][1,4,8,11]oxatriazacyclotetradecine-10,1'-cyclopentane]-5,9,12(1H,6H,11H)-trione |
| Ex. 474 | $NH_2$ | 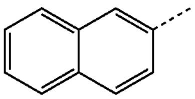 | (2R,7S,18aS)-2-amino-14-(naphthalen-2-yl)-7-(naphthalen-2-ylmethyl)-2,3,7,8,18,18a-hexahydrospiro[benzo[m]pyrrolo[2,1-c][1,4,8,11]oxatriazacyclotetradecine-10,1'-cyclopentane]-5,9,12(1H,6H,11H)-trione |

TABLE 48c-continued

| Examples of Core 32 (Ex. 470-Ex. 475) | | | |
|---|---|---|---|
| No | $R^2$ | $R^1$ | IUPAC name |
| Ex. 475 | $NH_2$ | 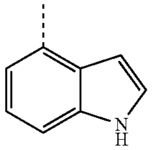 | (2R,7S,18aS)-2-amino-14-(1H-indol-4-yl)-7-(naphthalen-2-ylmethyl)-2,3,7,8,18,18a-hexahydrospiro[benzo[m]pyrrolo[2,1-c][1,4,8,11]oxatriazacyclotetradecine-10,1'-cyclopentane]-5,9,12(1H,6H,11H)-trione |

TABLE 49a

| Examples of Core 33*) (Ex. 476-Ex. 481) | | | | | | | | |
|---|---|---|---|---|---|---|---|---|
| No | $R^4$ | $R^5$ | $R^7$ | Starting material | General Procedure | Reagent | Purification Method | Yield (isolated salt) |
| Ex. 476 cf. experimental description | | | | | | | | |
| Ex. 477 | $CH_3$ | $CH_2Ph$ (S) | H | 259 | **) | 1. Fmoc-Apa-OH<br>2. H—MePhe—OAll•pTsOH | Method 2 | 28% |
| Ex. 478 | H | H | H | 259 | **) | 1. Fmoc-Apa-OH<br>i-$Pr_2$NEt (6 equiv.)<br>2. H-Gly-OAll•pTsOH<br>(2 equiv.),<br>i-$Pr_2$NEt (6 equiv.)<br>***) | Method 2 | 25% |
| Ex. 479 | H | H | 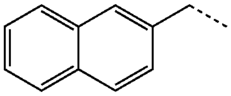<br>(S) | 259 | **) | 1. Fmoc-$\beta^3$-H2Nal-OH<br>i-$Pr_2$NEt (6 equiv.)<br>2. H-Gly-OAll•pTsOH<br>(2 equiv.),<br>i-$Pr_2$NEt (6 equiv.)<br>***) | Method 2 | 8% |
| Ex. 480 | $CH_3$ | $CH_3$ (S) | $CH_3$ | 259 | **) | 1. Fmoc-$\beta^3$-HAla-OH<br>i-$Pr_2$NEt (6 equiv.)<br>2. H—MeAla—OAll•HCl<br>(2 equiv.),<br>i-$Pr_2$NEt (6 equiv.) | Method 2 | 40% |
| Ex. 481 | $CH_3$ | $CH_3$ (S) | 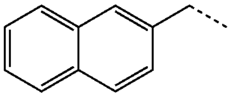<br>(S) | 259 | **) | 1. Fmoc-$\beta^3$-H2Nal-OH<br>i-$Pr_2$NEt (6 equiv.)<br>2. H—MeAla—OAll•HCl<br>(2 equiv.),<br>i-$Pr_2$NEt (6 equiv.) | Method 2 | 16% |

*)$R^2$ = benzamido (Ph—CO—NH—)
**) See details in experimental description of Ex. 476
***) Second coupling was repeated once.

TABLE 49b

| Examples of Core 33*) (Ex. 476-Ex. 481) | | | | | | | | |
|---|---|---|---|---|---|---|---|---|
| No | $R^4$ | $R^5$ | $R^7$ | FORMULA | MONOISOTOPIC MASS | Rt (purity at 220 nm) | $[M + H]^+$ found | LC-MS-Method |
| Ex. 476: cf. experimental description | | | | | | | | |
| Ex. 477 | $CH_3$ | $CH_2Ph$ (S) | H | C32H34N4O5 | 554.2 | 1.68 (90) | 555.2 | Method 10b |
| Ex. 478 | H | H | H | C24H26N4O5 | 450.2 | 1.29 (95) | 451.2 | Method 10b |
| Ex. 479 | H | H | 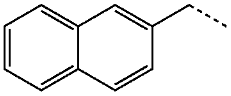<br>(S) | C35H34N4O5 | 590.3 | 1.88 (94) | 591.2 | Method 10b |
| Ex. 480 | $CH_3$ | $CH_3$ | $CH_3$ | C27H32N4O5 | 492.2 | 1.42 (99) | 493.0 | Method 10b |

TABLE 49b-continued

| Examples of Core 33*) (Ex. 476-Ex. 481) | | | | | | | | |
|---|---|---|---|---|---|---|---|---|
| No | $R^4$ | $R^5$ | $R^7$ | FORMULA | MONOISOTOPIC MASS | Rt (purity at 220 nm) | $[M + H]^+$ found | LC-MS-Method |
| Ex. 481 | $CH_3$ | (S) $CH_3$ (S) | (S) 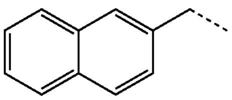 (S) | C37H38N4O5 | 618.3 | 1.94 (94) | 619.2 | Method 10b |

*)$R^2$ = benzamide (Ph—CO—NH—)

TABLE 49c

| Examples of Core 33*) (Ex. 476-Ex. 481) | | | | |
|---|---|---|---|---|
| No | $R^4$ | $R^5$ | $R^7$ | IUPAC name |
| Ex. 476 | $CH_3$ | $CH_3$ (S) | H | N-[(4S,6R,14S)-14,15-dimethyl-9,13,16-trioxo-2-oxa-8,12,15-triazatricyclo[15.3.1.$0^{4,8}$]henicosa-1(21),17,19-trien-6-yl]benzamide |
| Ex. 477 | $CH_3$ | $CH_2Ph$ (S) | H | N-[(4S,6R,14S)-14-benzyl-15-methyl-9,13,16-trioxo-2-oxa-8,12,15-triazatricyclo[15.3.1.$0^{4,8}$]henicosa-1(21),17,19-trien-6-yl]benzamide |
| Ex. 478 | H | H | H | N-[(4S,6R)-9,13,16-trioxo-2-oxa-8,12,15-triazatricyclo[15.3.1.$0^{4,8}$]henicosa-1(21),17,19-trien-6-yl]benzamide |
| Ex. 479 | H | H | 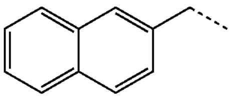 (S) | N-[(4S,6R,11S)-11-(2-naphthylmethyl)-9,13,16-trioxo-2-oxa-8,12,15-triazatricyclo[15.3.1.$0^{4,8}$]henicosa-1(21),17,19-trien-6-yl]benzamide |
| Ex. 480 | $CH_3$ | $CH_3$ (S) | $CH_3$ (S) | N-[(4S,6R,11S,14S)-11,14,15-trimethyl-9,13,16-trioxo-2-oxa-8,12,15-triazatricyclo[15.3.1.$0^{4,8}$]henicosa-1(21),17,19-trien-6-yl]benzamide |
| Ex. 481 | $CH_3$ | $CH_3$ (S) | 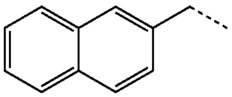 (S) | N-[(4S,6R,11S,14S)-14,15-dimethyl-11-(2-naphthylmethyl)-9,13,16-trioxo-2-oxa-8,12,15-triazatricyclo[15.3.1.$0^{4,8}$]henicosa-1(21),17,19-trien-6-yl]benzamide |

*)$R^2$ = benzamido (Ph—CO—NH—)

Scheme 1

Builiding Blocks Type A

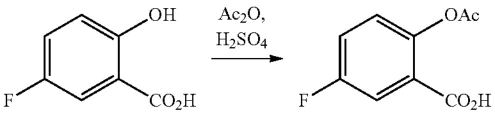

1 2

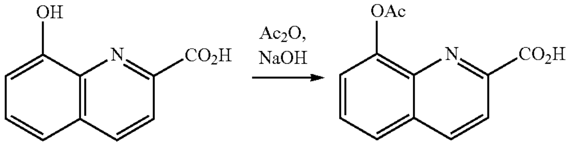

7 8

-continued

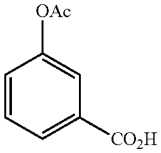

3
commercially available

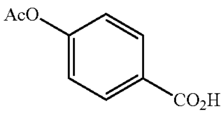

4
commercially available

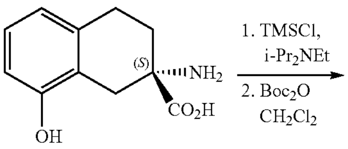

9

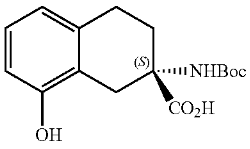

10

-continued
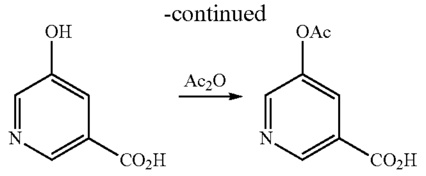
5 6
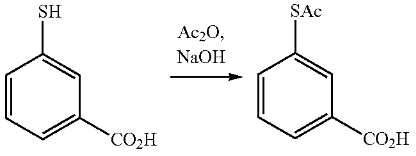
11 12
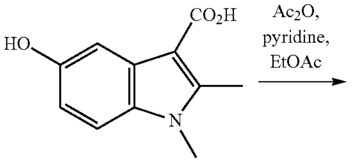
146
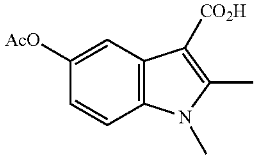
147
-continued
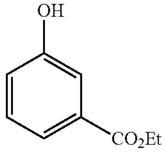
142
commercially available
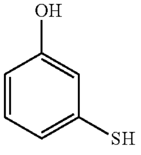
143
commercially available
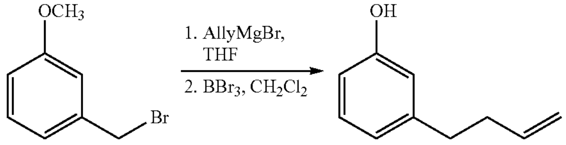
148 149
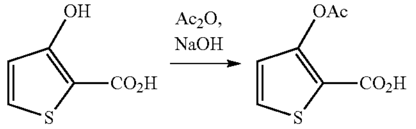
144 145
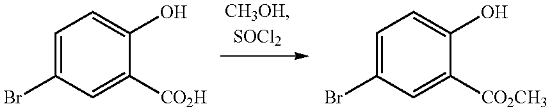
150 151
Scheme 2
Building Blocks of Type B
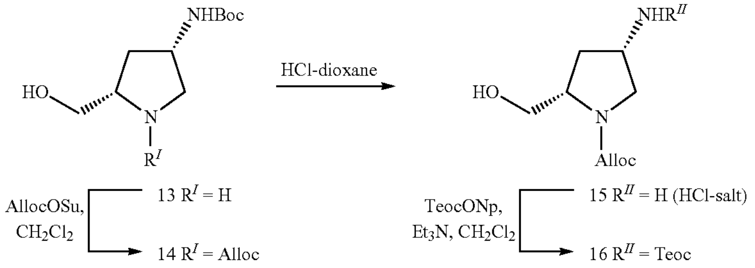
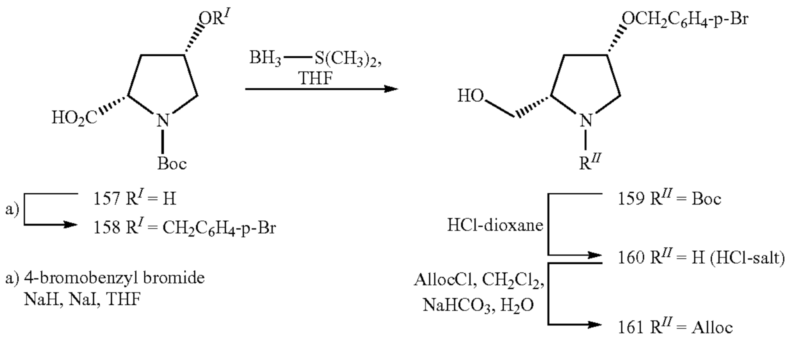
a) 4-bromobenzyl bromide
NaH, NaI, THF -continued
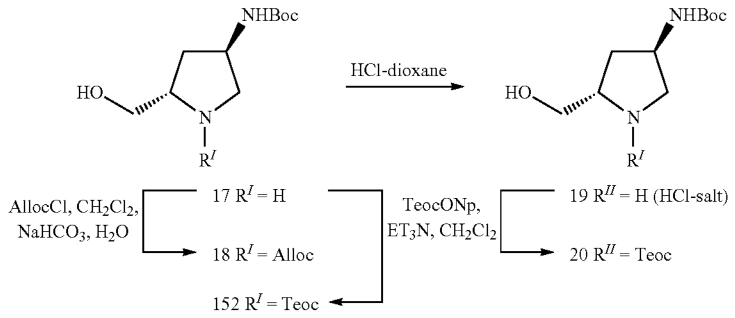
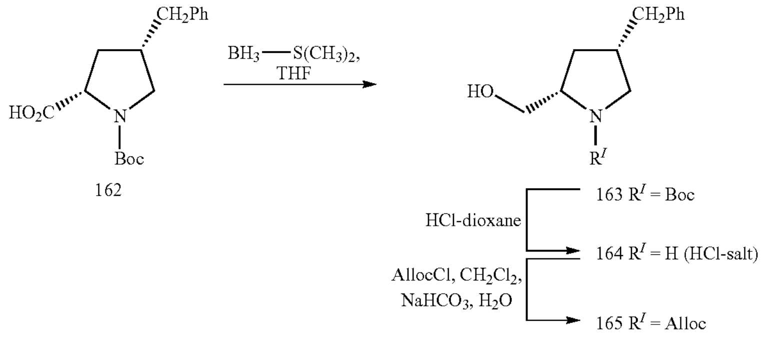
162
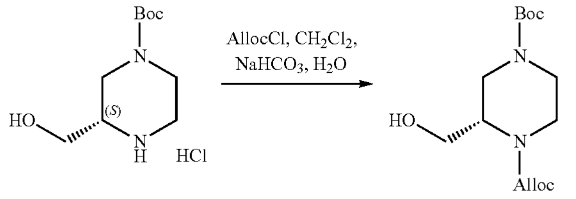
21•HCl 22
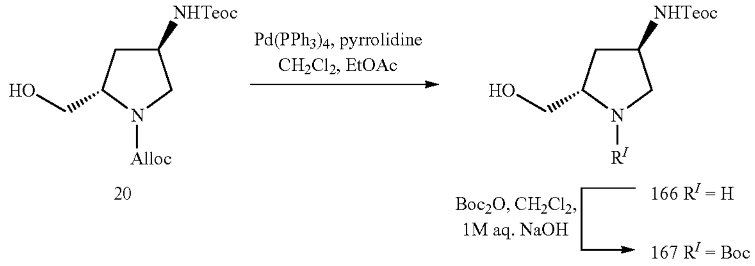
20
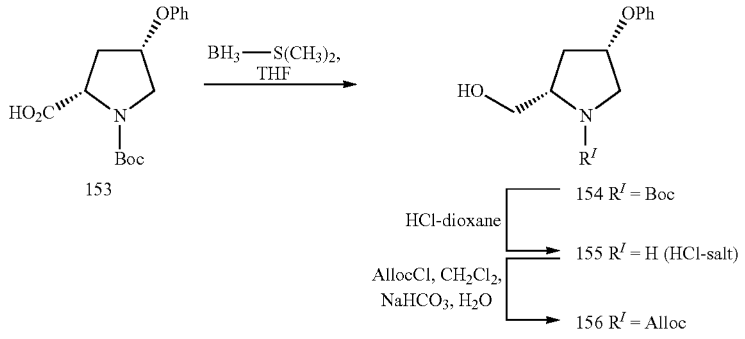
153

Scheme 3
Building Blocks of C-subunits:
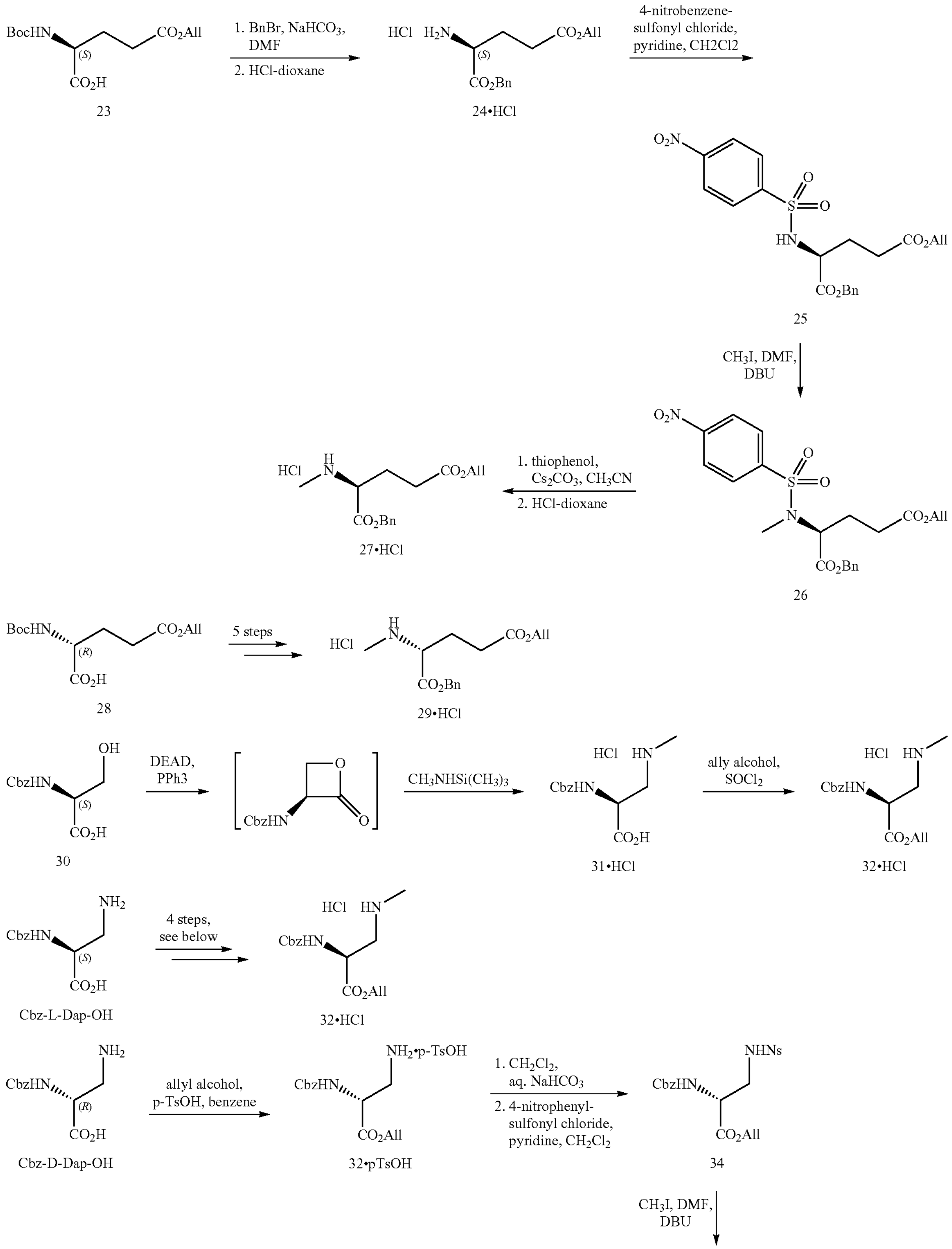
23
24•HCl
25
26
27•HCl
28
29•HCl
30
31•HCl
32•HCl
Cbz-L-Dap-OH
32•HCl
Cbz-D-Dap-OH
32•pTsOH
34

-continued
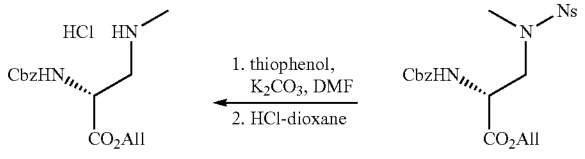
36•HCl 35
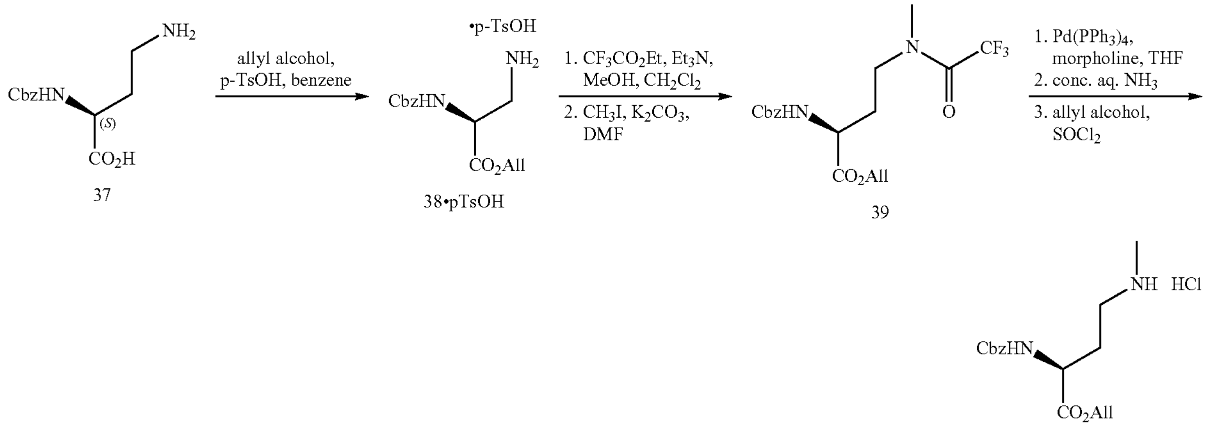
37 38•pTsOH 39
40•HCl
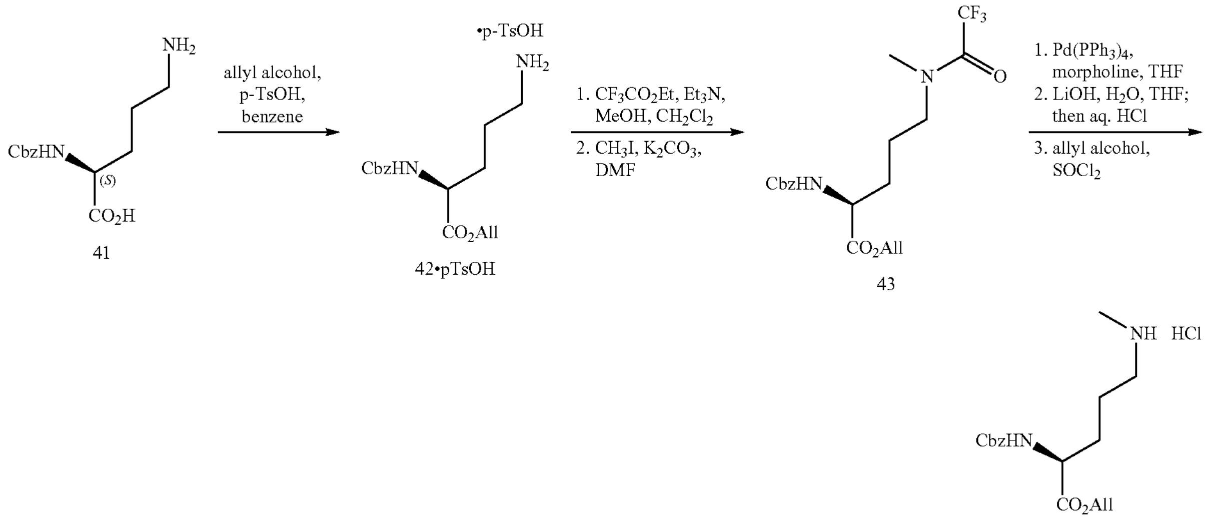
41 42•pTsOH 43
44•HCl
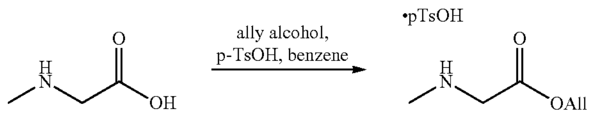
45 46•pTsOH
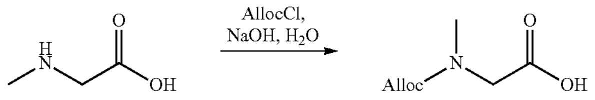
45 47
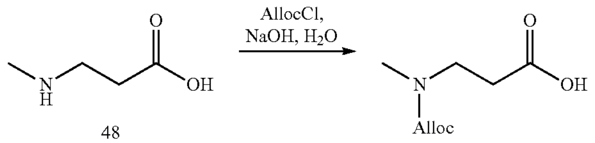
48 49

-continued
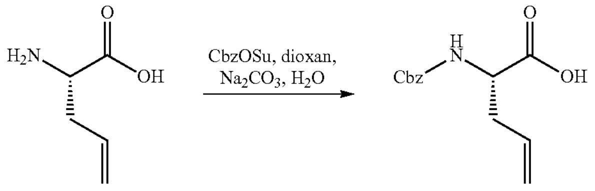
50 51
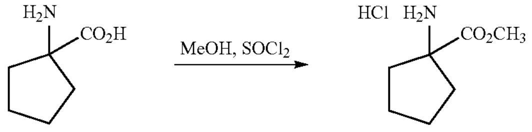
168 169•HCl
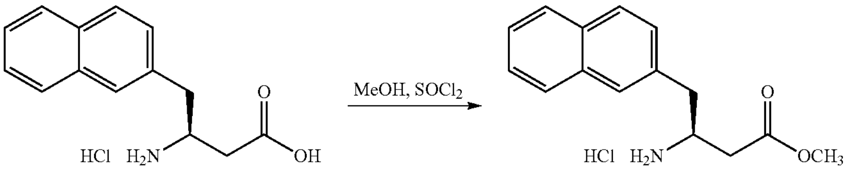
170•HCl 171•HCl
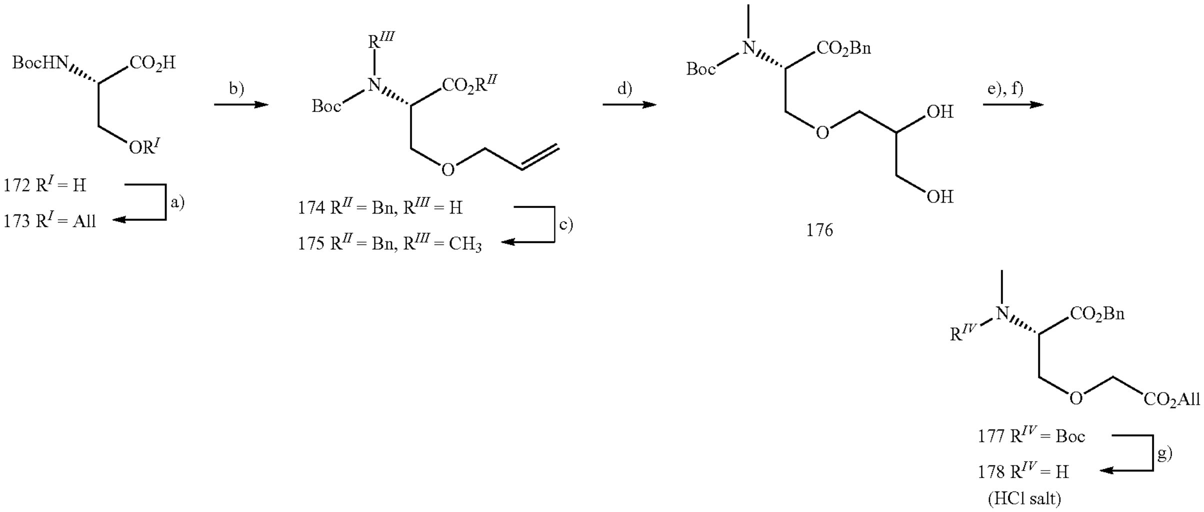
172 $R^I$ = H
173 $R^I$ = All
174 $R^{II}$ = Bn, $R^{III}$ = H
175 $R^{II}$ = Bn, $R^{III}$ = $CH_3$
176
177 $R^{IV}$ = Boc
178 $R^{IV}$ = H (HCl salt)
a) NaH, DMF, allyl bromide; b) BnBr, $NaHCO_3$, DMF; c) $CH_3I$, $Ag_2O$, DMF, AcOH; d) NMO, $OsO_4$, acetone. $H_2O$; e) 1. $NaIO_4$, THF, $H_2O$; 2. $NaIO_4$, $RuCl_3$, $CH_2Cl_2$, $CH_3CN$, $H_2O$; f) allyl bromide, $NaHCO_3$, DMF; g) TFA-$CH_2Cl_2$, then HCl-dioxane
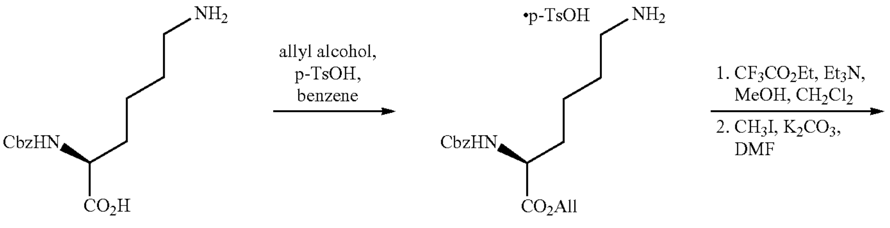
179 180•pTsOH
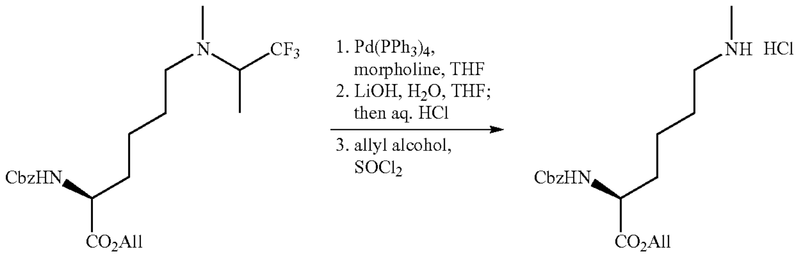
181 182•HCl -continued
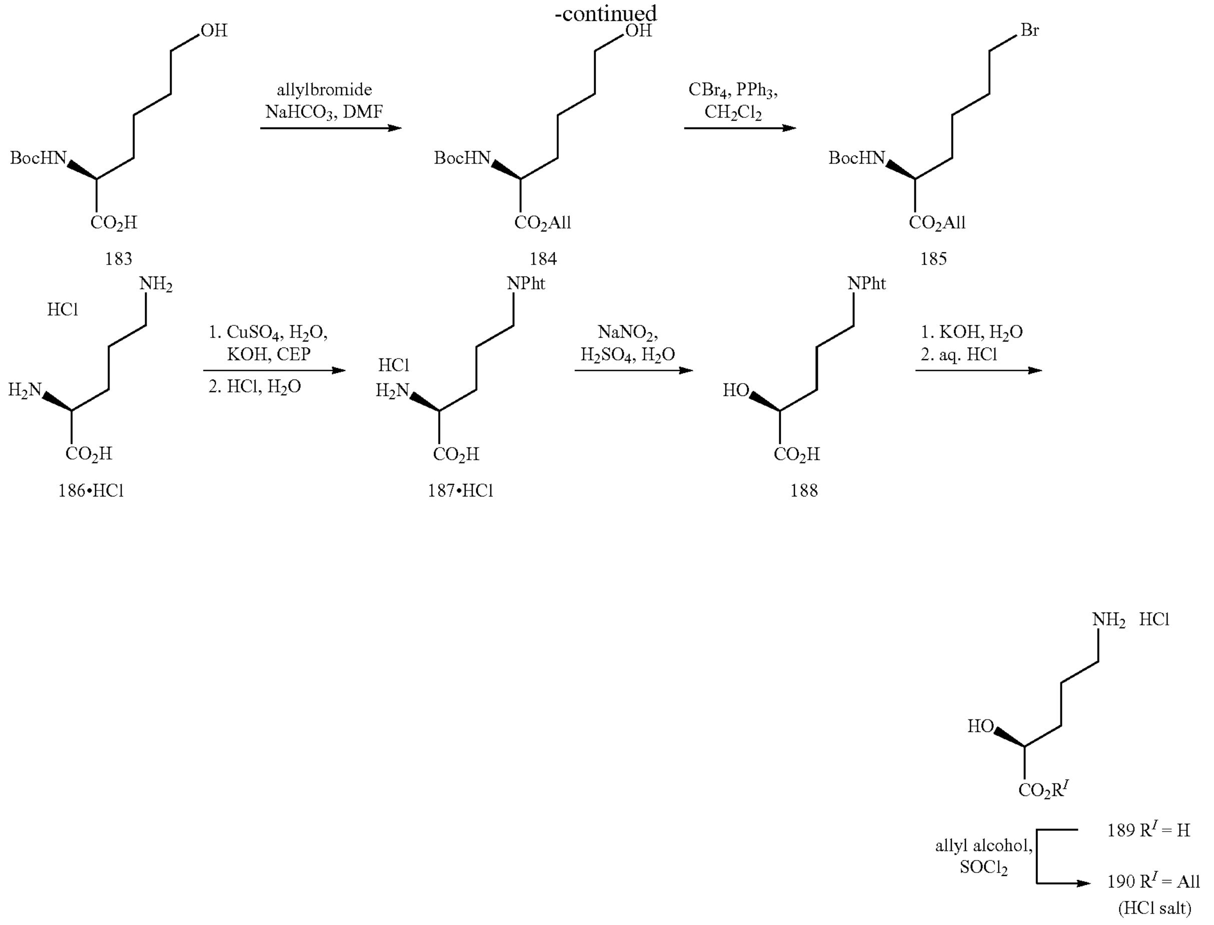
183
184
185
186•HCl
187•HCl
188
189 $R^I$ = H
190 $R^I$ = All (HCl salt)
NPht =
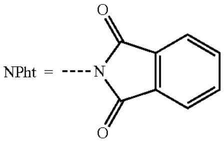
Scheme 4
A-B Fragments
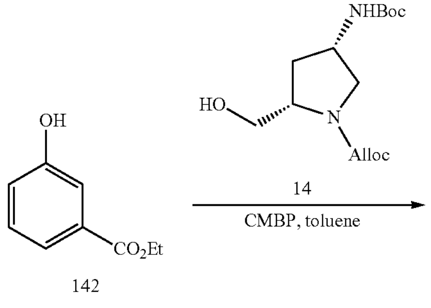
142
14
-continued
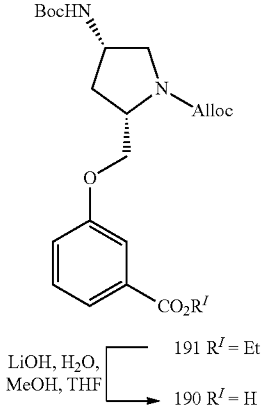
191 $R^I$ = Et
190 $R^I$ = H -continued
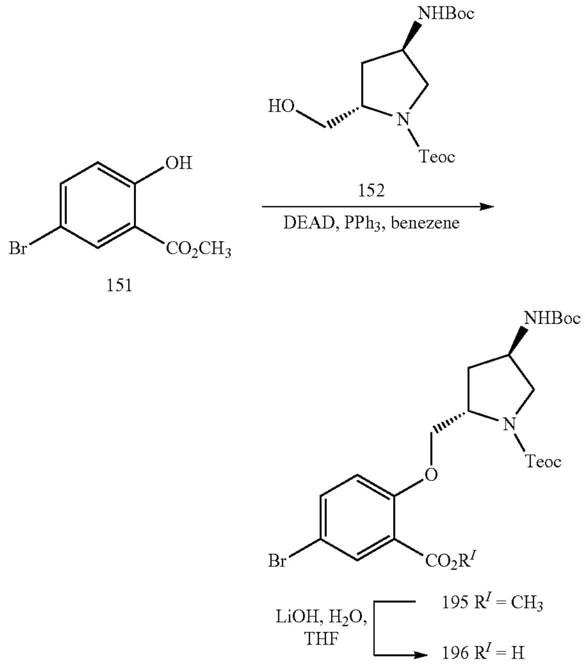
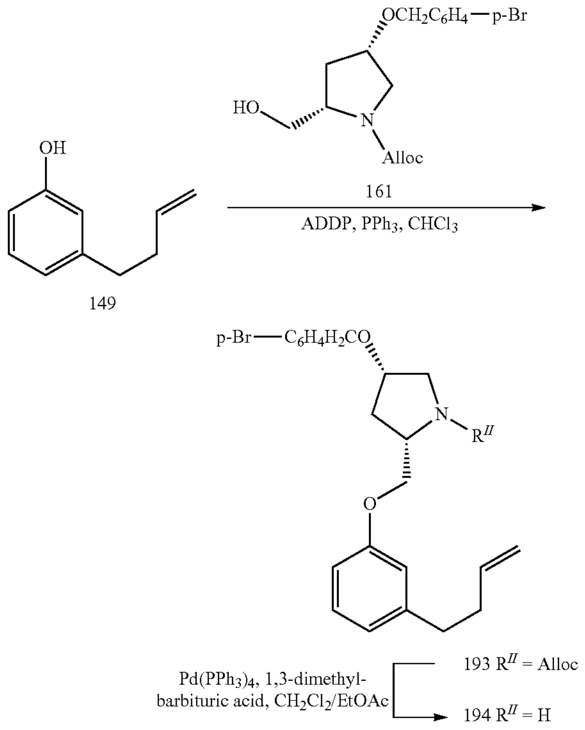
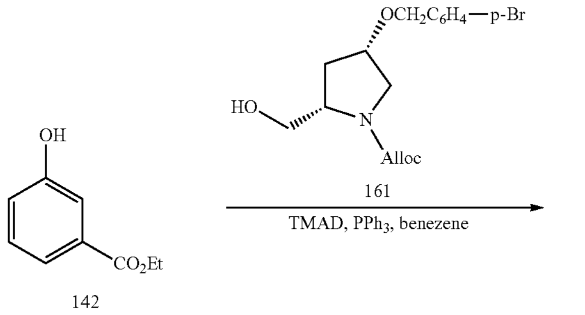
-continued
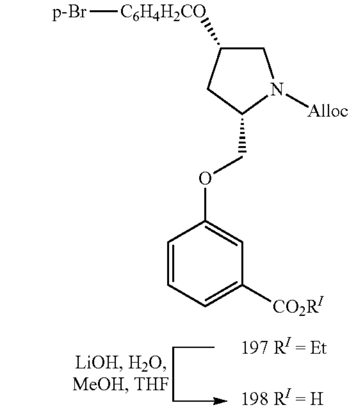
A-C Fragments
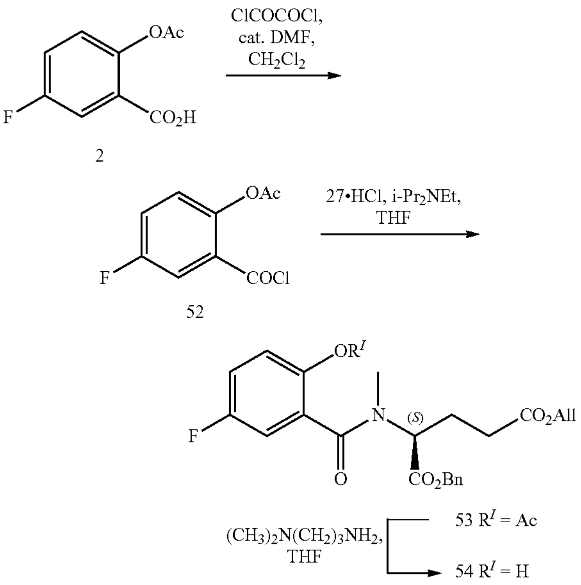
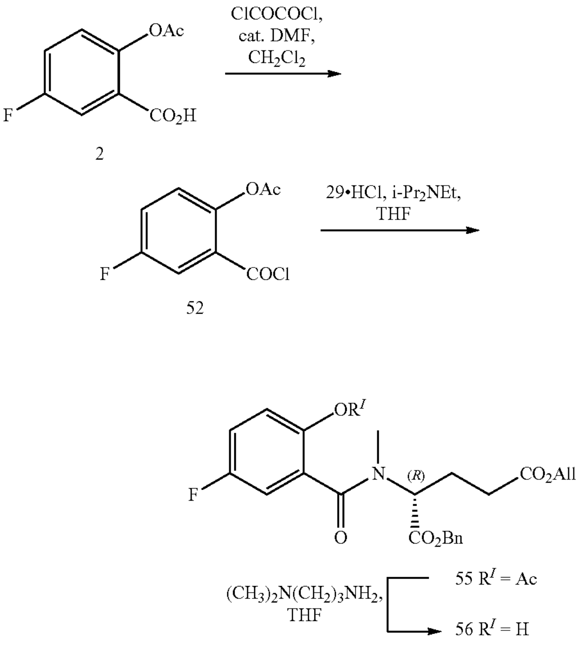

-continued
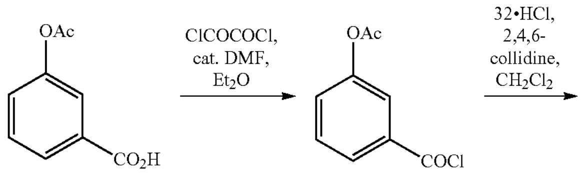
3
57
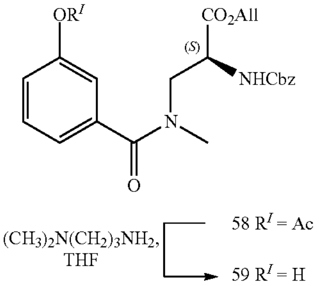
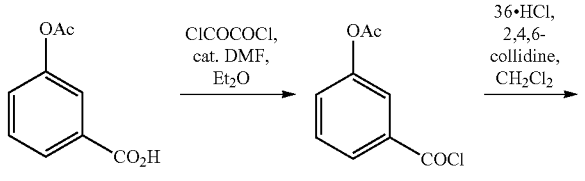
3
57
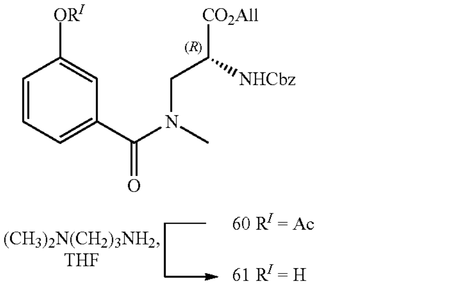
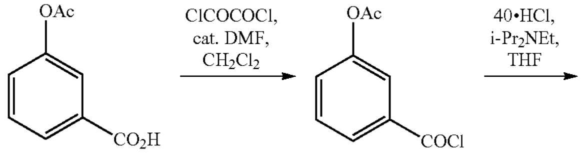
3
57
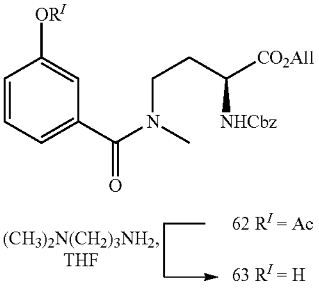
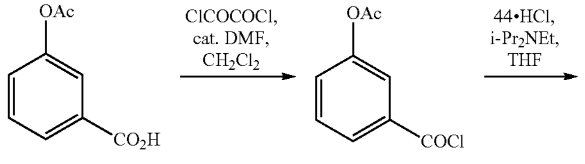
3
57
-continued
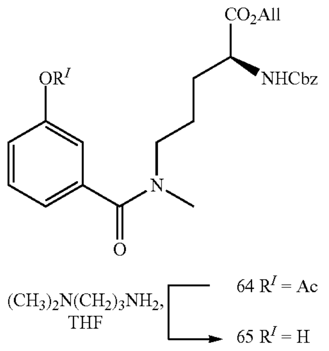
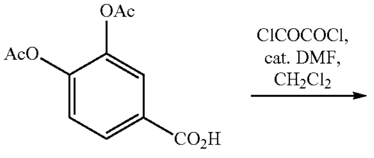
4
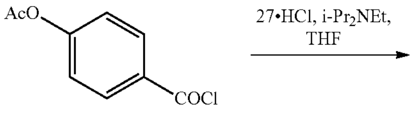
66
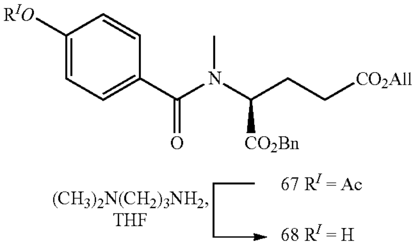
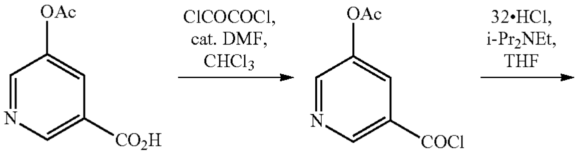
6
69
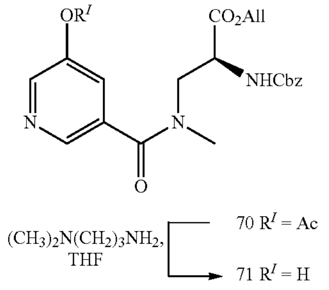
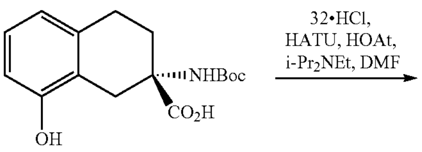
10

-continued
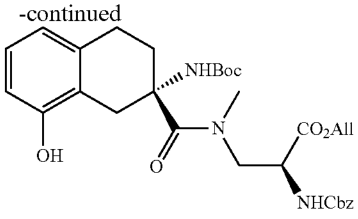
72
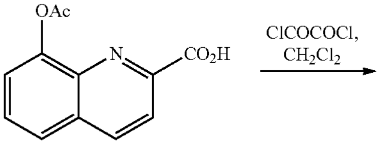
8
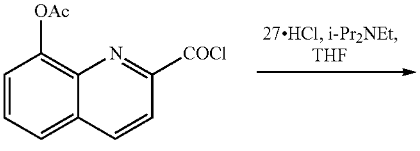
73
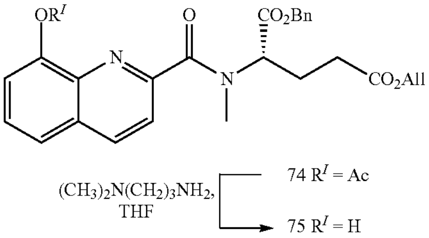
74 $R^I$ = Ac
75 $R^I$ = H
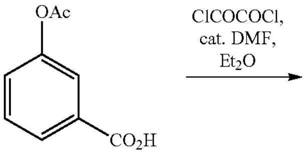
3
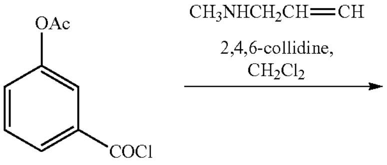
57
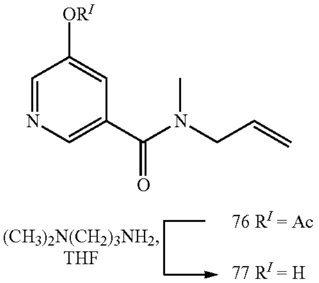
76 $R^I$ = Ac
77 $R^I$ = H
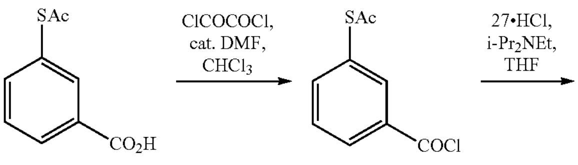
12 78
-continued
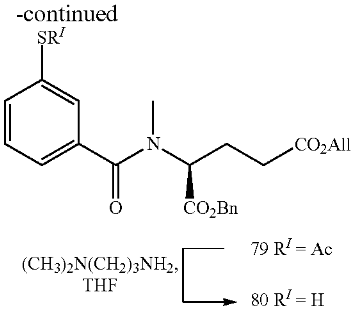
79 $R^I$ = Ac
80 $R^I$ = H
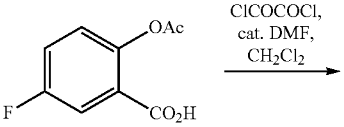
2
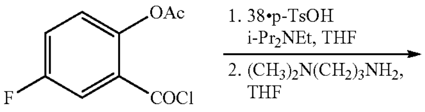
52
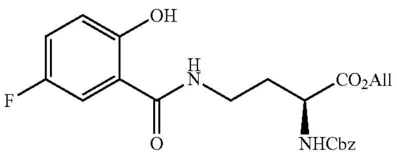
199
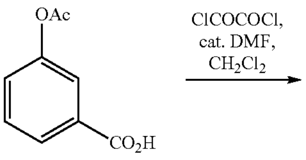
3
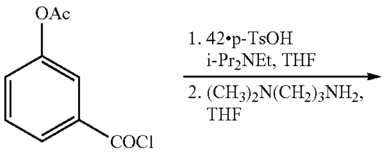
57
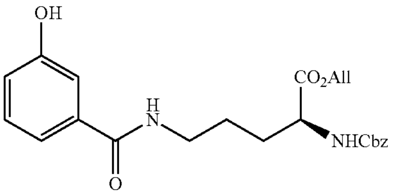
200
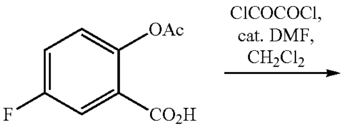
2
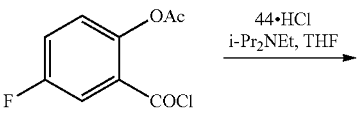
52

-continued
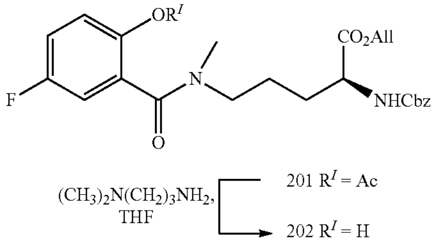
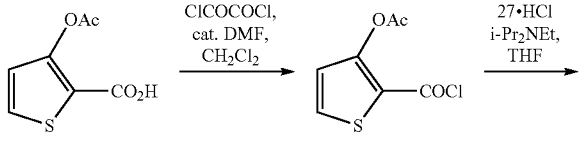
145 203
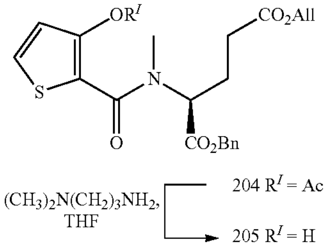
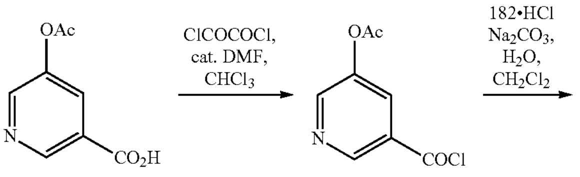
6 69
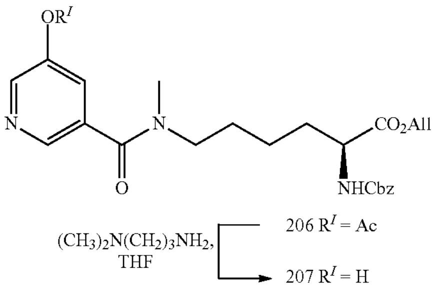
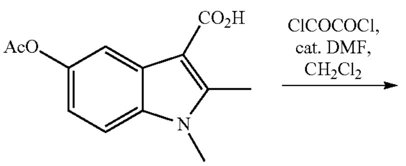
147
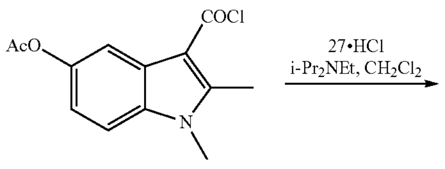
208
-continued
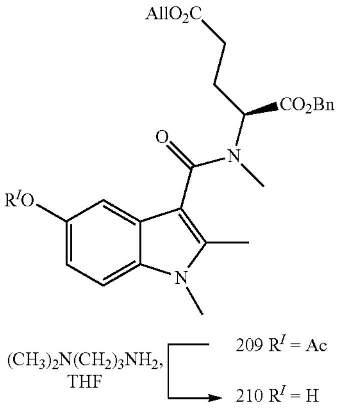
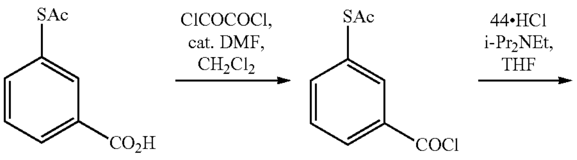
12 78
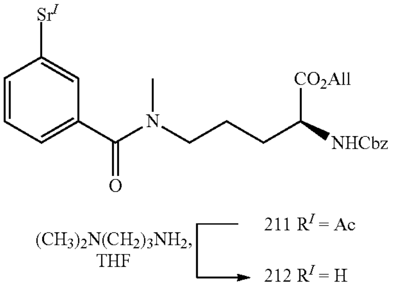
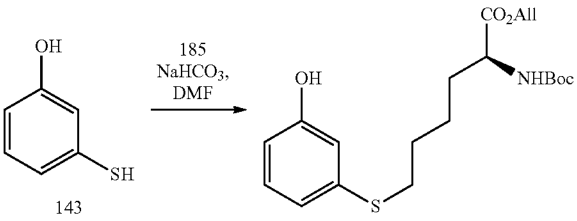
143 213
Scheme 5
C-B Fragments
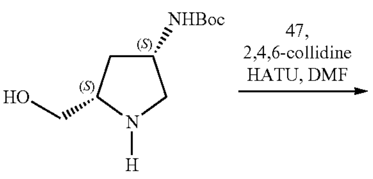
13

-continued
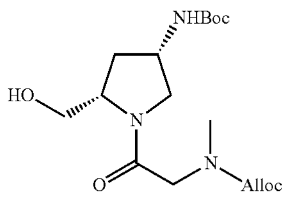
81
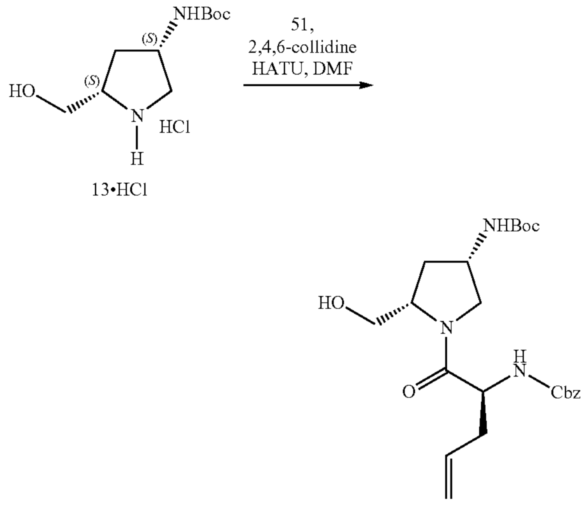
13•HCl
85
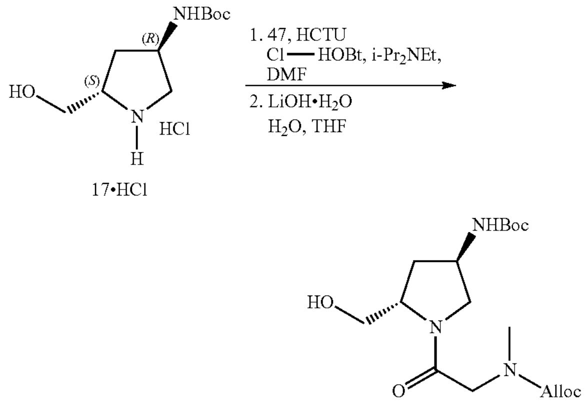
17•HCl
82
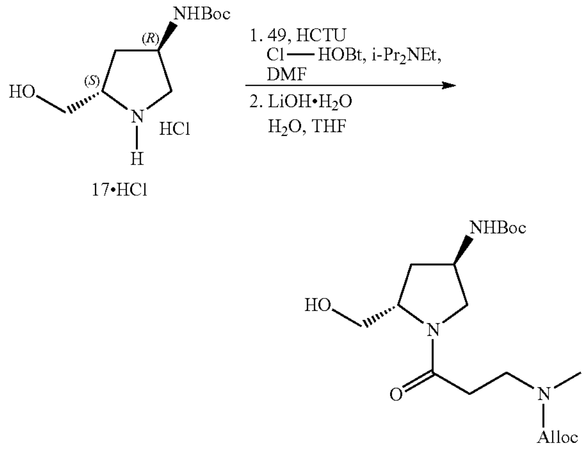
17•HCl
86
-continued
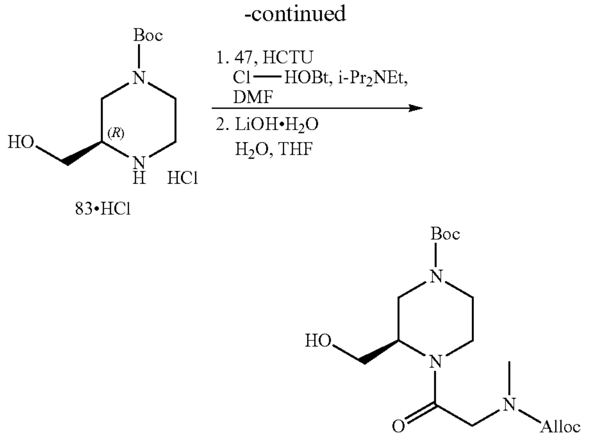
83•HCl
84
Scheme 6
Core 01
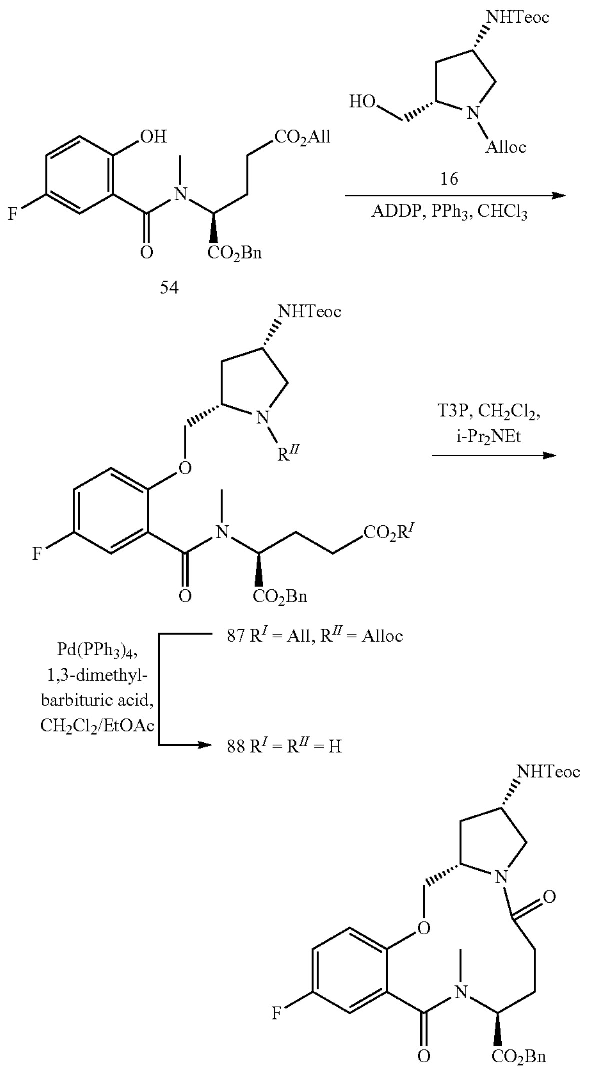
54
87 $R^I$ = All, $R^{II}$ = Alloc
88 $R^I$ = $R^{II}$ = H
Ex.1
Core 02: cf. Scheme 11

Scheme 7
Core 03
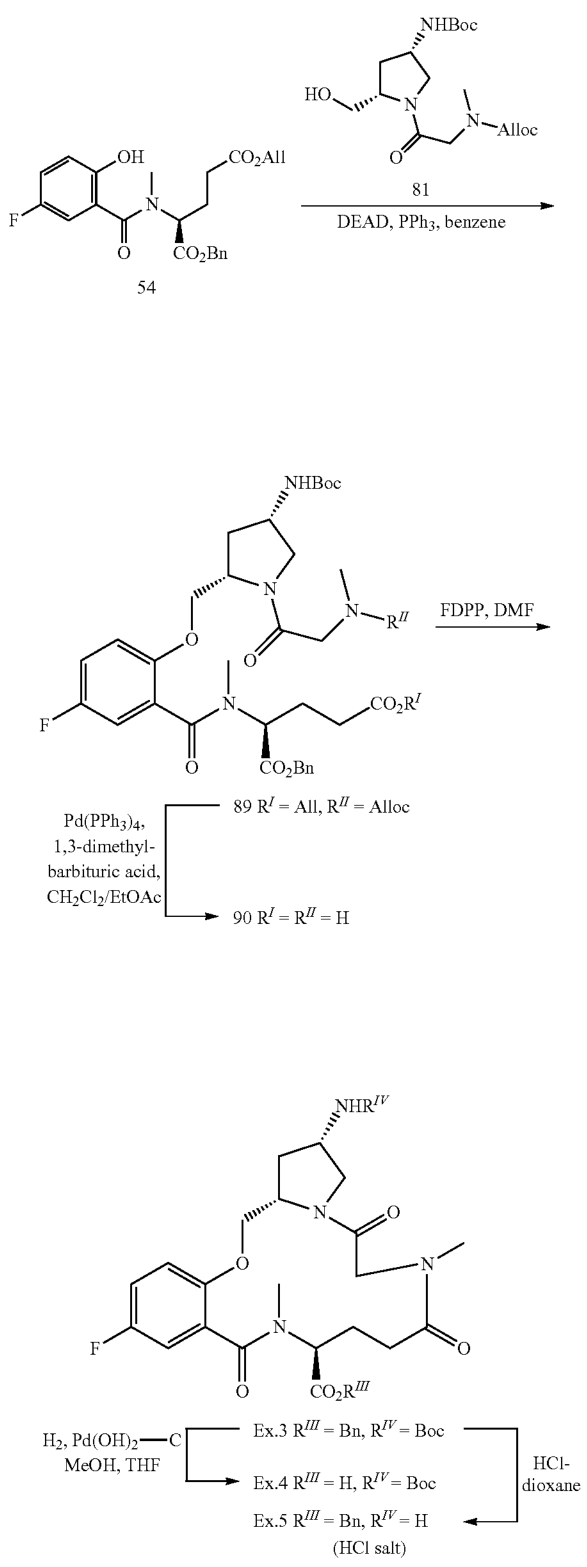
Scheme 8
Core 04
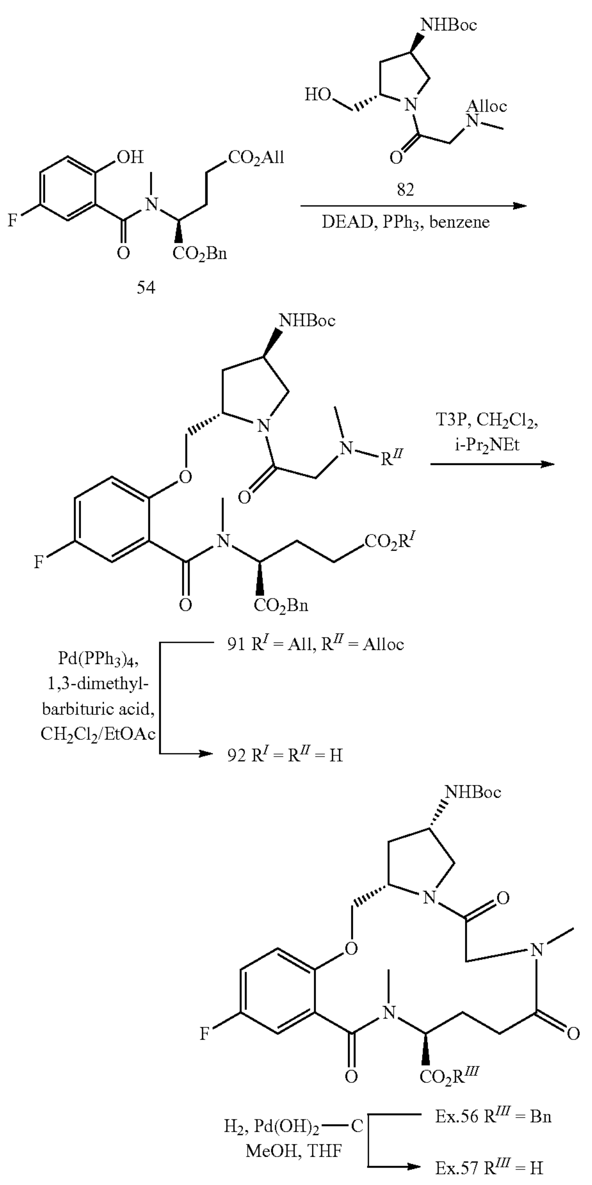
Scheme 9
Core 05
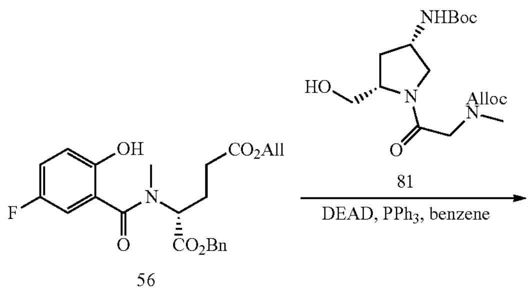

-continued
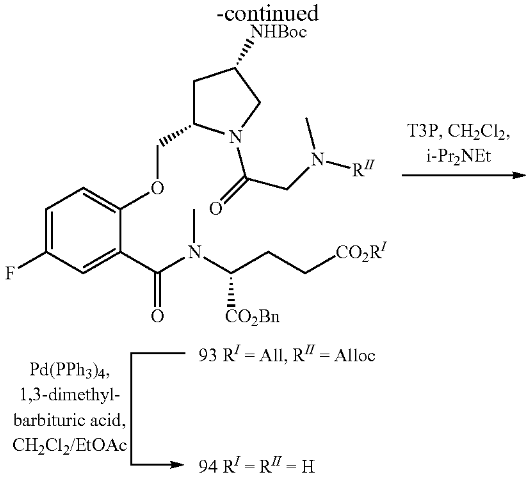
93 $R^I$ = All, $R^{II}$ = Alloc
94 $R^I$ = $R^{II}$ = H
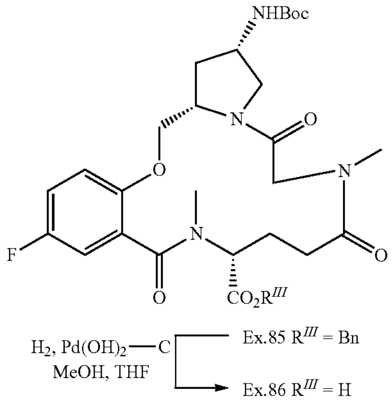
Ex.85 $R^{III}$ = Bn
Ex.86 $R^{III}$ = H
Scheme 10
Core 06
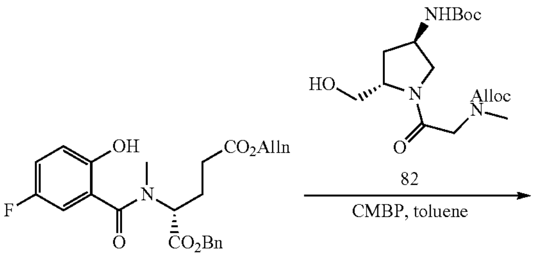
56
82
-continued
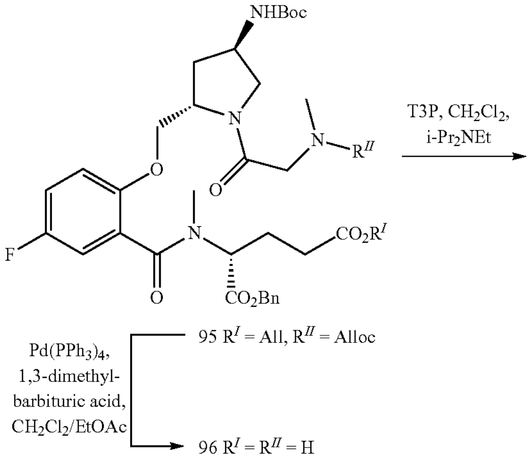
95 $R^I$ = All, $R^{II}$ = Alloc
96 $R^I$ = $R^{II}$ = H
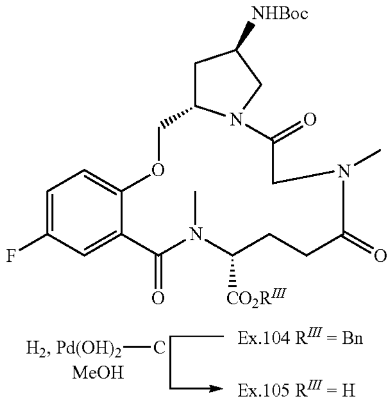
Ex.104 $R^{III}$ = Bn
Ex.105 $R^{III}$ = H Core 02 and 07
Scheme 11
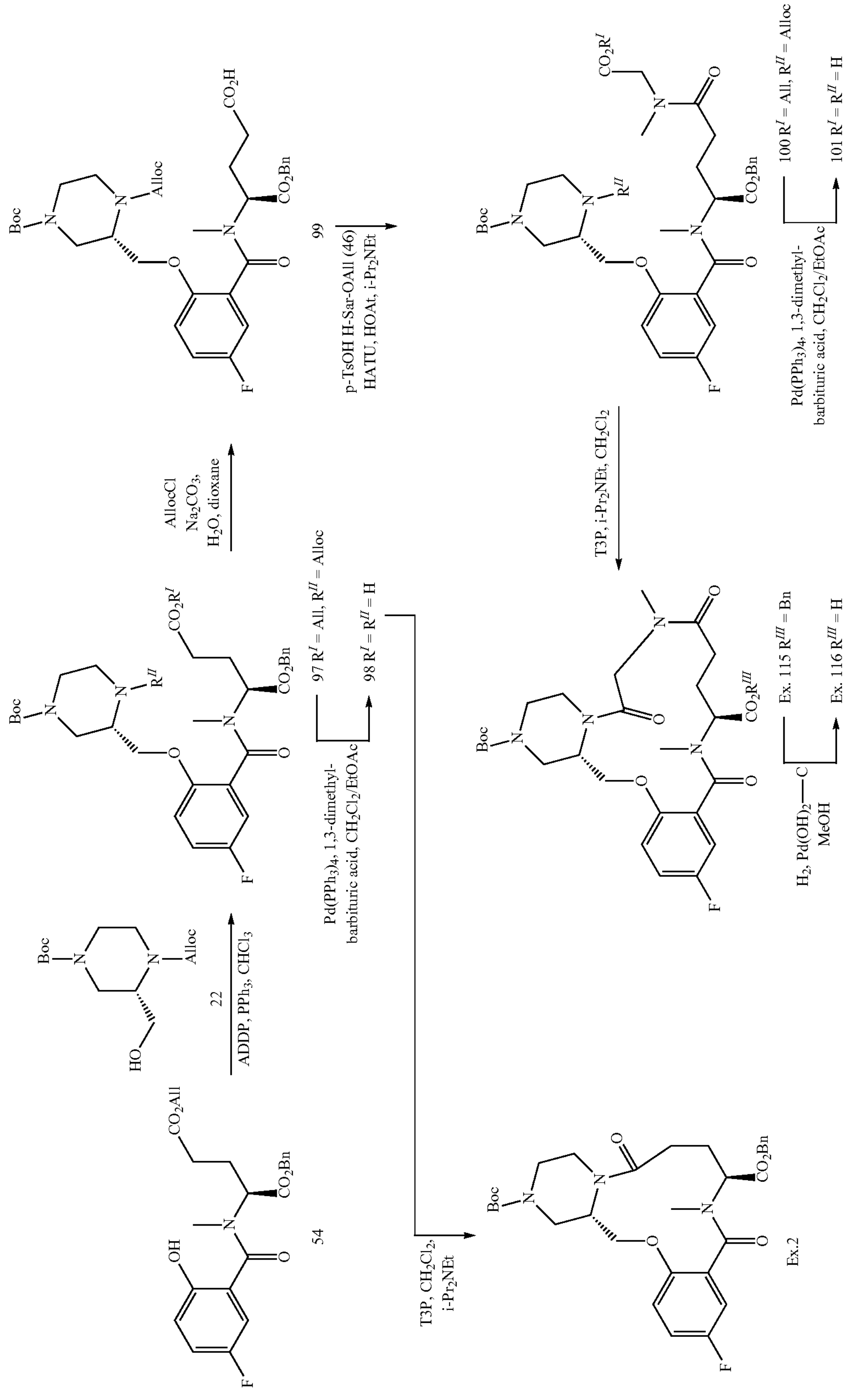
54
97 $R^I$ = All, $R^{II}$ = Alloc
98 $R^I$ = $R^{II}$ = H
99
100 $R^I$ = All, $R^{II}$ = Alloc
101 $R^I$ = $R^{II}$ = H
Ex. 115 $R^{III}$ = Bn
Ex. 116 $R^{III}$ = H
Ex.2

Scheme 12

Core 08

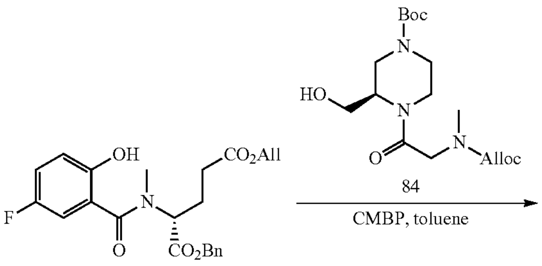

56

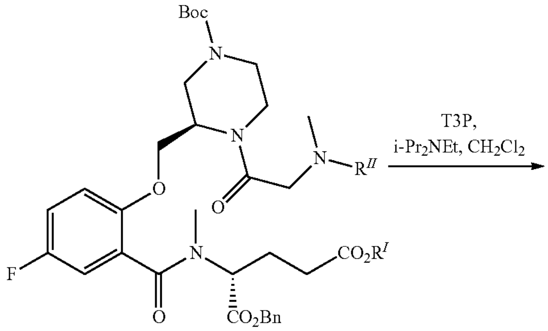

$Pd(PPh_3)_4$, 1,3-dimethyl-barbituric acid, $CH_2Cl_2$/EtOAc

102 $R^I$ = All, $R^{II}$ = Alloc

103 $R^I$ = $R^{II}$ = H

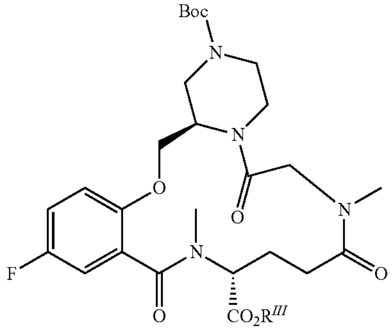

$H_2$, $Pd(OH)_2$—C MeOH

Ex.132 $R^{III}$ = Bn

Ex.133 $R^{III}$ = H

Scheme 13

Core 09

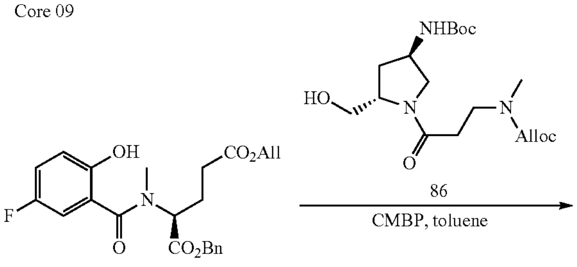

54

-continued

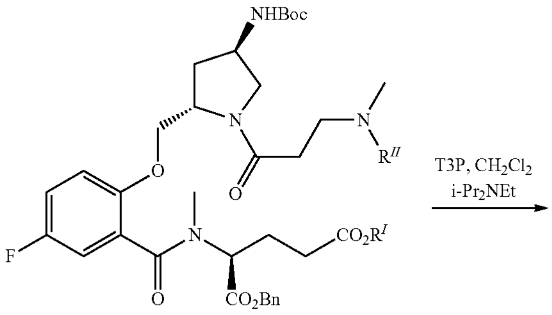

$Pd(PPh_3)_4$, 1,3-dimethyl-barbituric acid, $CH_2Cl_2$/EtOAc

104 $R^I$ = All, $R^{II}$ = Alloc

105 $R^I$ = $R^{II}$ = H

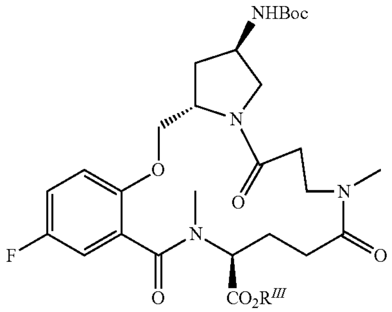

$H_2$, $Pd(OH)_2$—C MeOH

Ex. 142 $R^{III}$ = Bn

Ex. 143 $R^{III}$ = H

Scheme 14

Core 10

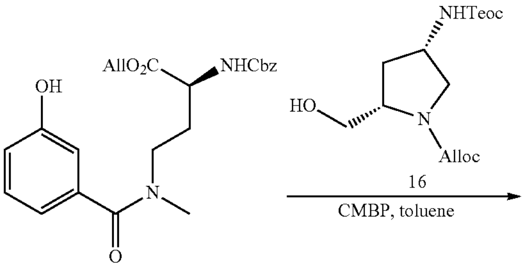

63

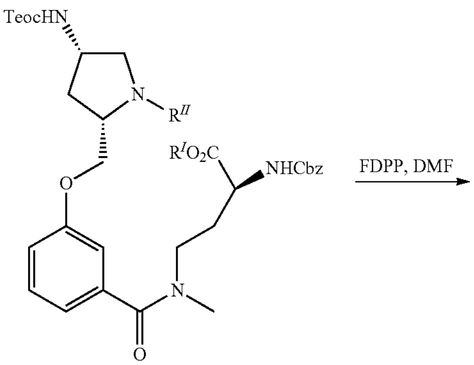

1,3-dimethylbarbituric acid, $Pd(PPh_3)_4$, $CH_2Cl_2$/EtOAc

106 $R^I$ = All, $R^{II}$ = Alloc

107 $R^I$ = $R^{II}$ = H

-continued
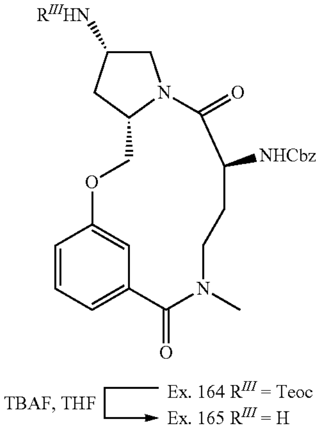
-continued
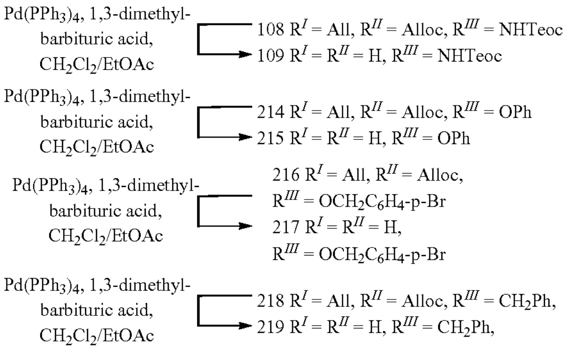
Scheme 15
Cores 11a-11d
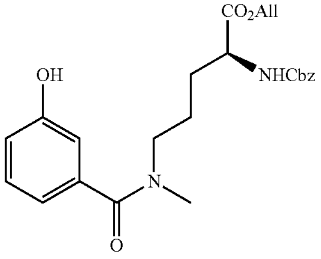
65
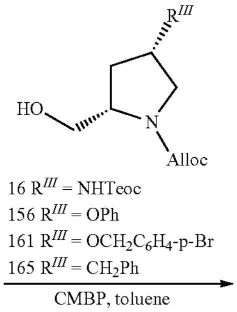
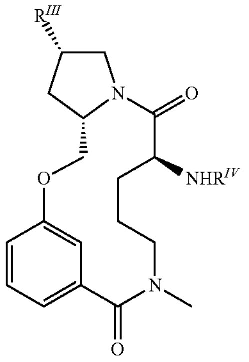
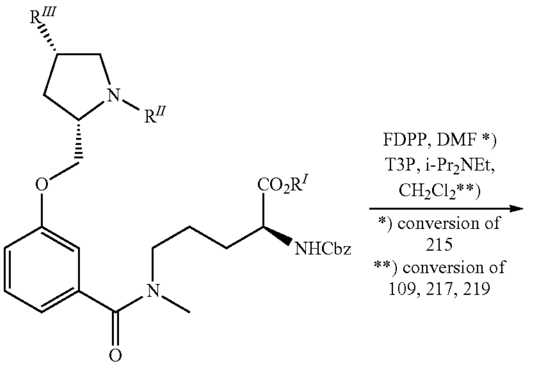
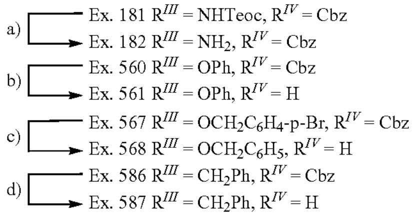
a) TBAF, THF
b) $H_2$, 10% Pd—C, MeOH
c) $H_2$, 5% Pd—C, $NH_3$, MeOH
d) $H_2$, $Pd(OH)_2$—C, MeOH Scheme 16
Core 12 (linear synthesis)
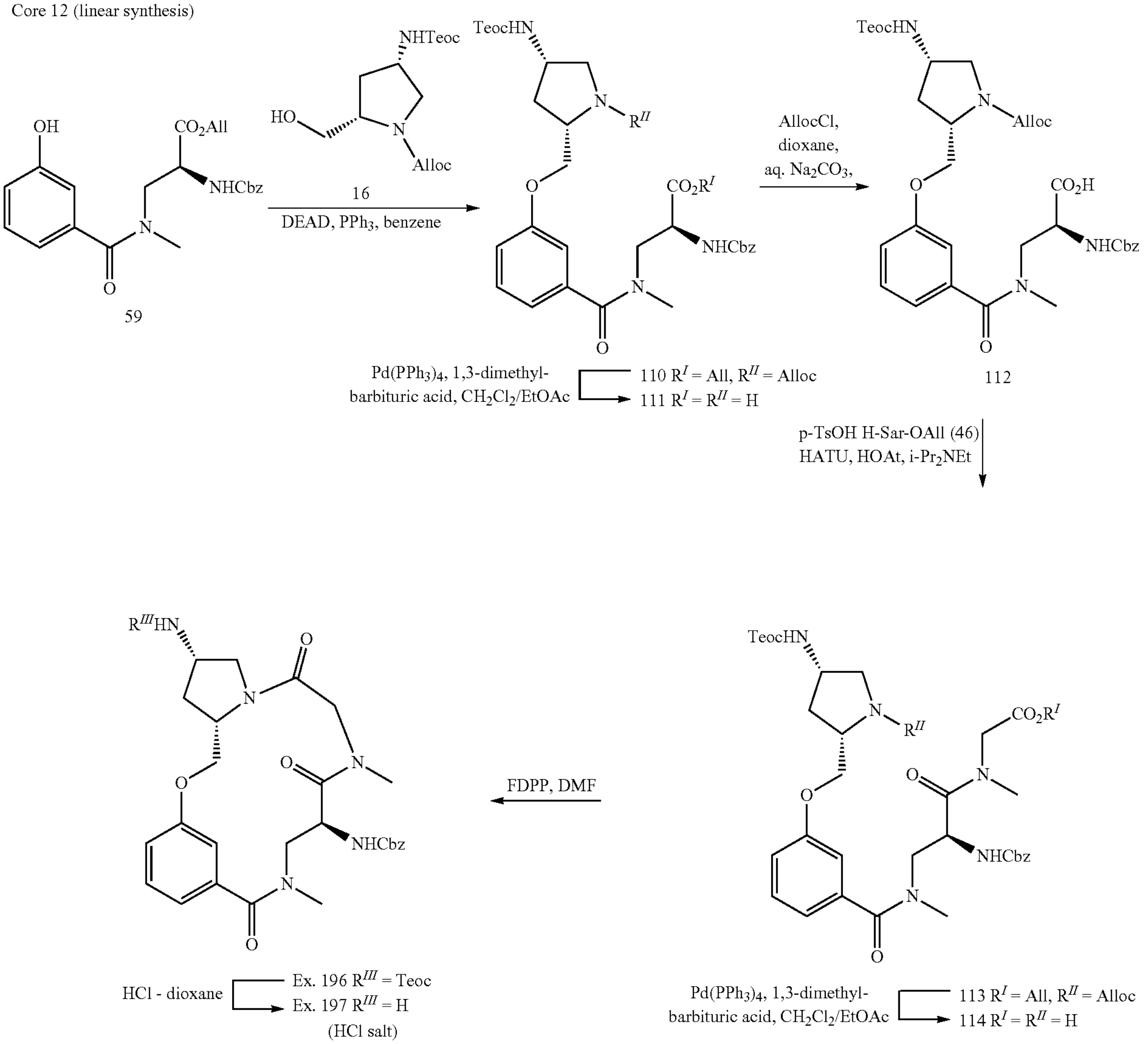
Scheme 17
Core 12 (convergent synthesis)
-continued
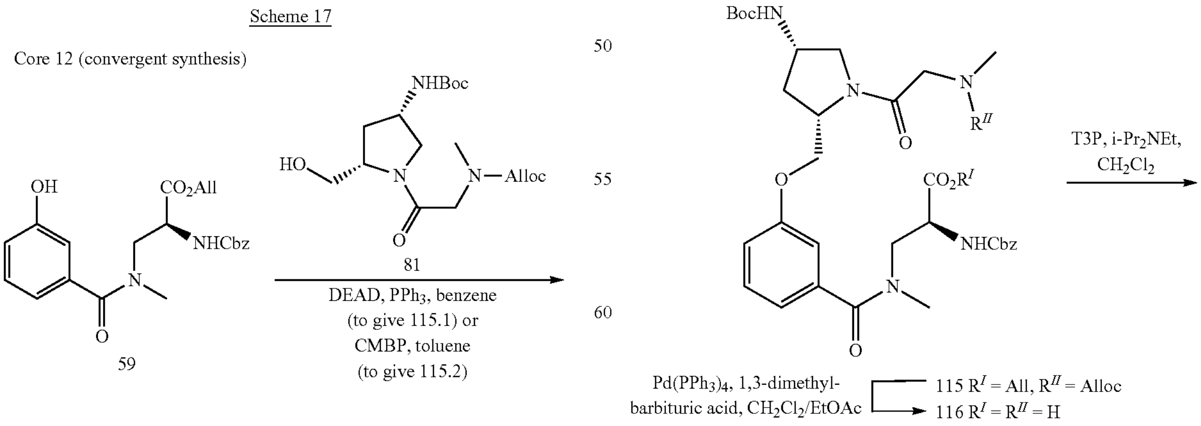

-continued
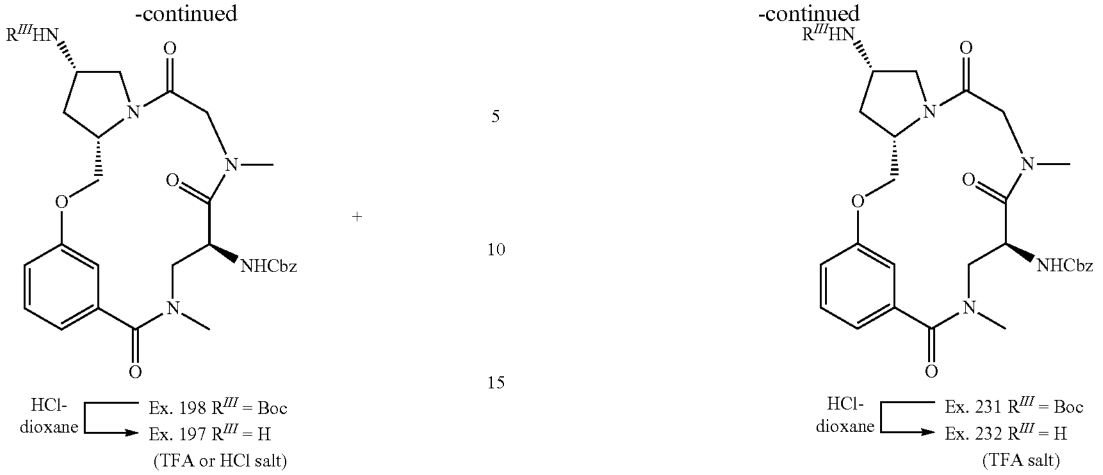
Scheme 18
Core 13
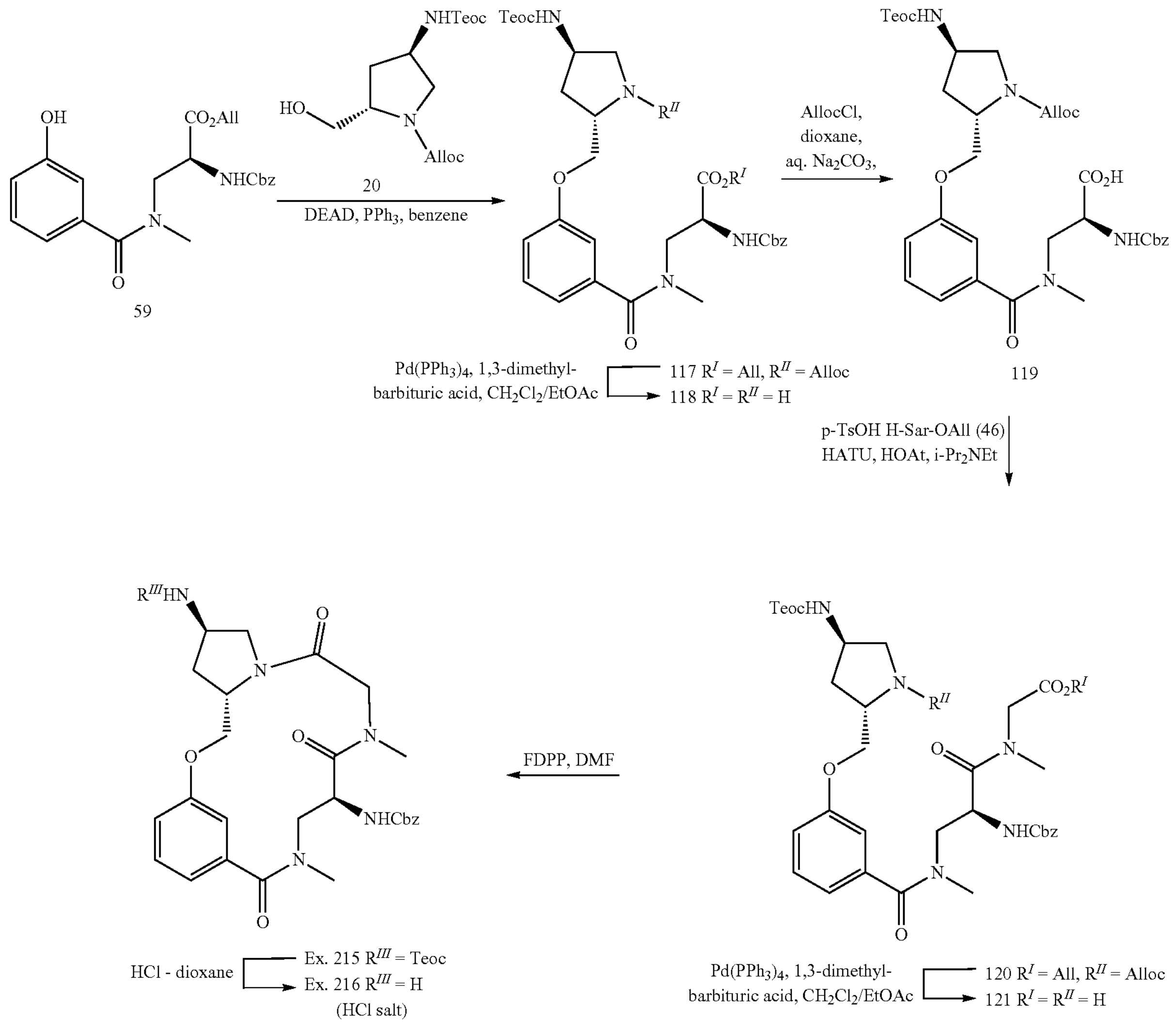

Scheme 19
Core 14
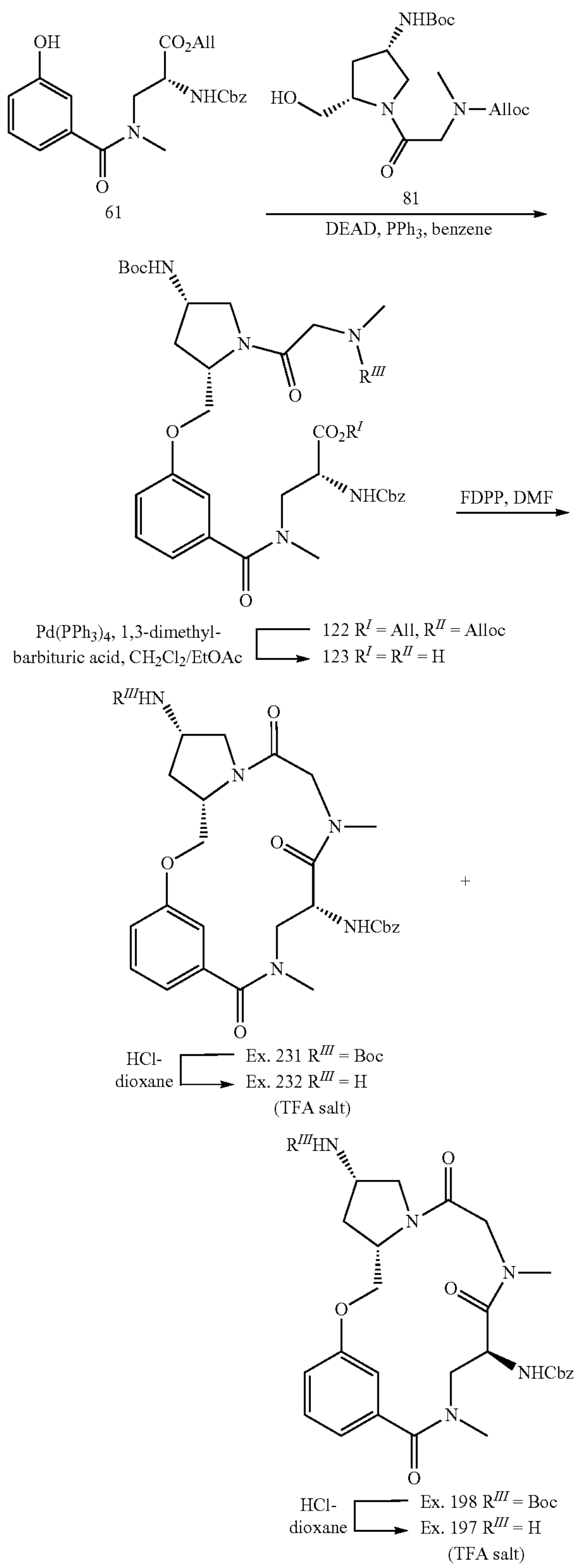
Scheme 20
Core 15 and Core 16
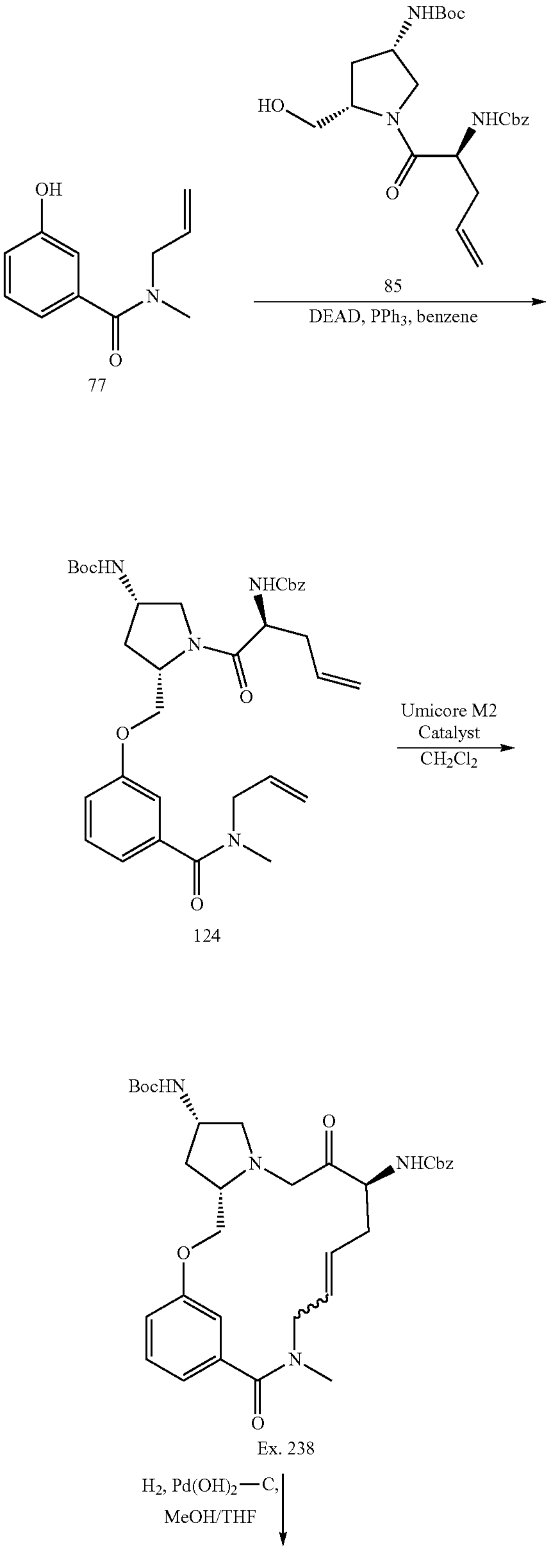

-continued
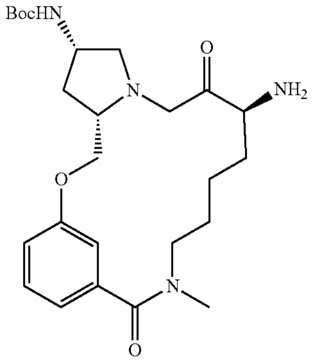
Ex. 239
Scheme 21
Core 17
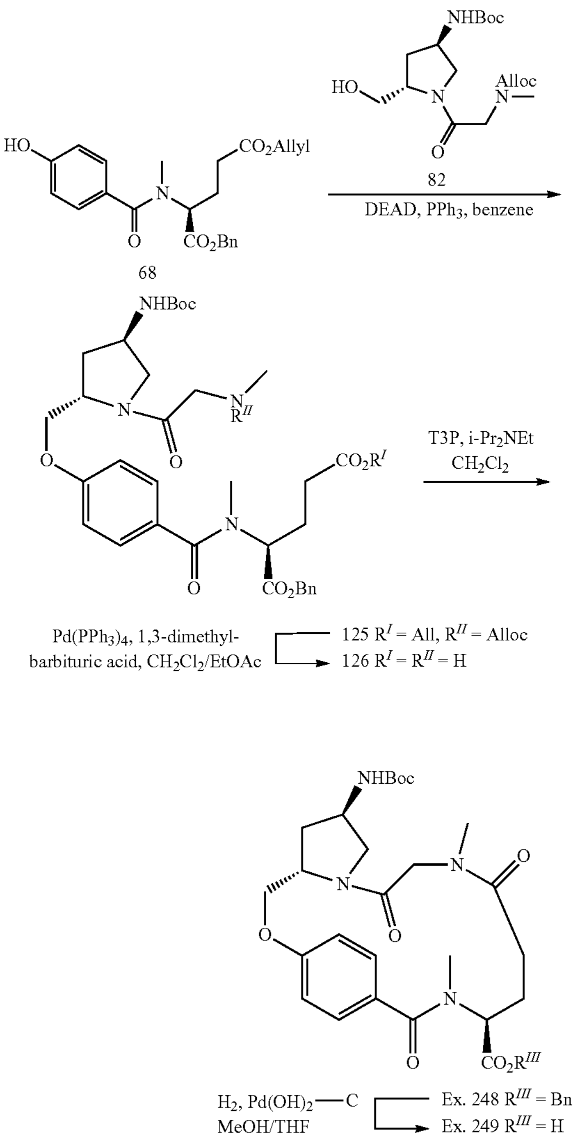
Scheme 22
Core 18
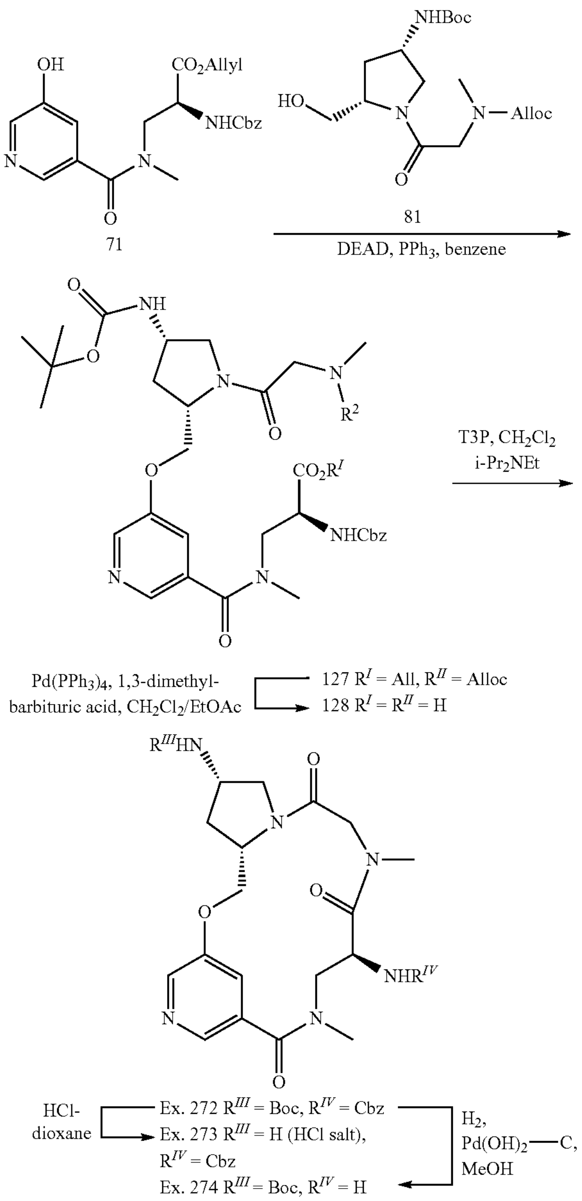
Scheme 23
Core 19
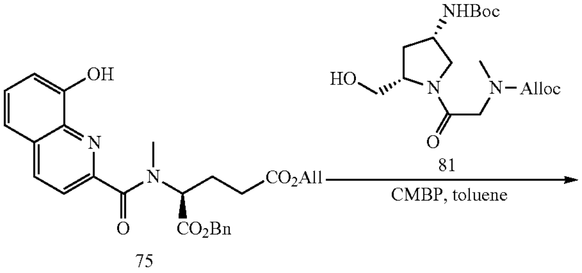

-continued
-continued
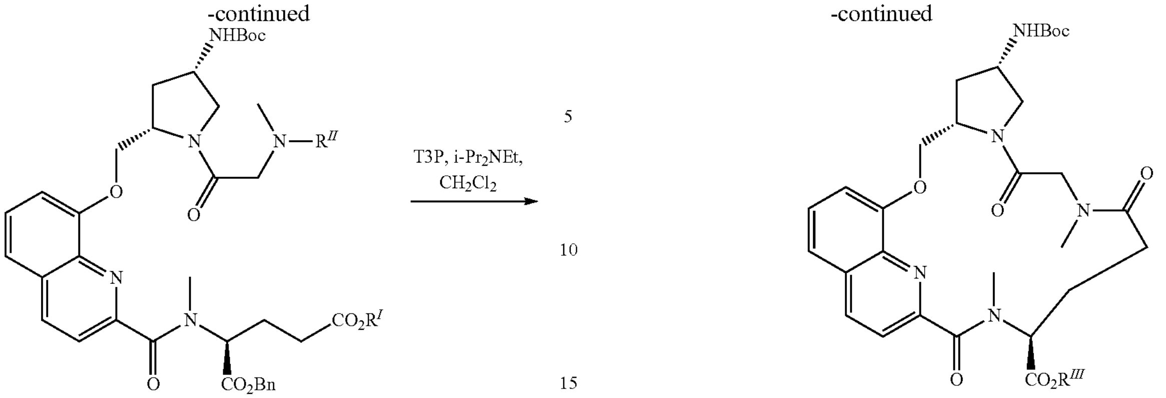
1,3-dimethylbarbituric acid, $Pd(PPh_3)_4$, $CH_2Cl_2$/EtOAc — 129 $R^I$ = All, $R^{II}$ = Alloc → 130 $R^I$ = $R^{II}$ = H
$H_2$, $Pd(OH)_2$—C MeOH/THF — Ex. 297 $R^{III}$ = Bn → Ex. 298 $R^{III}$ = H
Scheme 24
Core 20
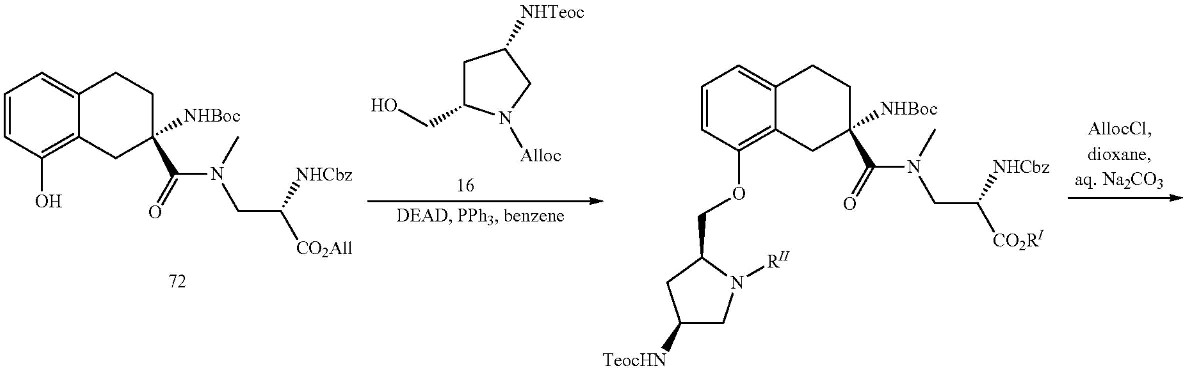
72
$Pd(PPh_3)_4$, 1,3-dimethyl-barbituric acid, $CH_2Cl_2$/EtOAc — 131 $R^I$ = All, $R^{II}$ = Alloc → 132 $R^I$ = $R^{II}$ = H
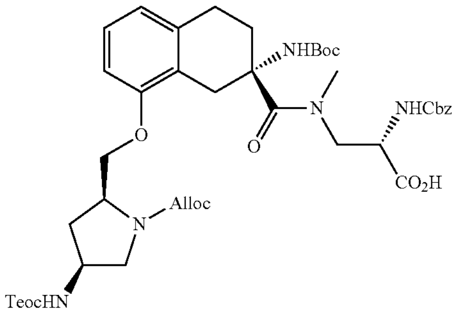
133
p-TsOH•H-SarOAll (46)
HATU, HOAt, i-$Pr_2NEt$ -continued

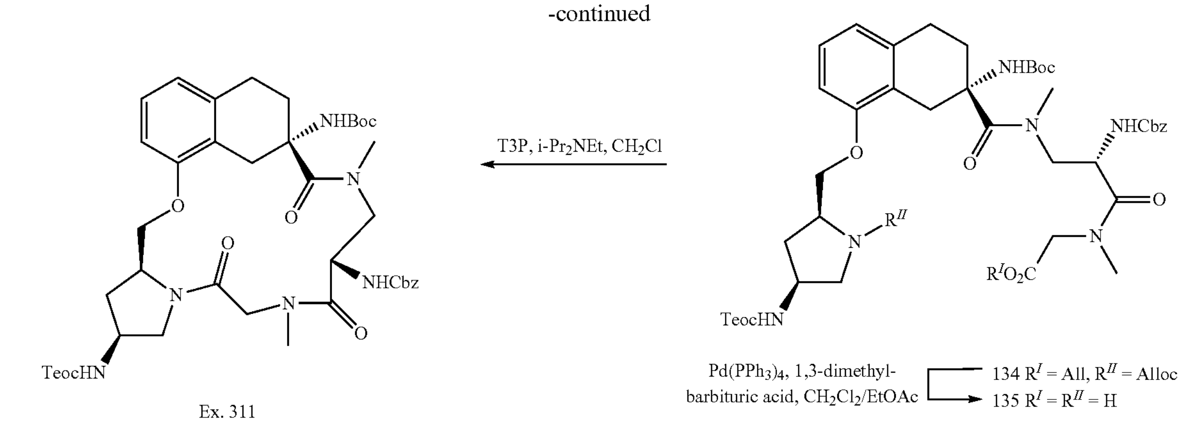

Ex. 311

Pd$(PPh_3)_4$, 1,3-dimethyl-barbituric acid, $CH_2Cl_2$/EtOAc
134 $R^I$ = All, $R^{II}$ = Alloc
135 $R^I$ = $R^{II}$ = H Scheme 25

Core 21

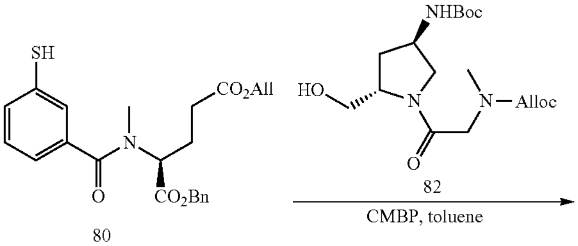

80

82

-continued

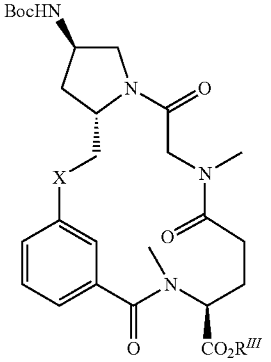

m-CPBA, $CH_2Cl_2$
Ex. 312 X = S, $R^{III}$ = Bn
Ex. 313 X = $SO_2$, $R^{III}$ = Bn

LiOH, $H_2O$, MeOH, THF
Ex. 312 X = S, $R^{III}$ = Bn
Ex. 314 X = S, $R^{III}$ = H $H_2$, Pd$(OH)_2$—C MeOH
Ex. 313 X = $SO_2$, $R^{III}$ = Bn
Ex. 315 X = $SO_2$, $R^{III}$ = H

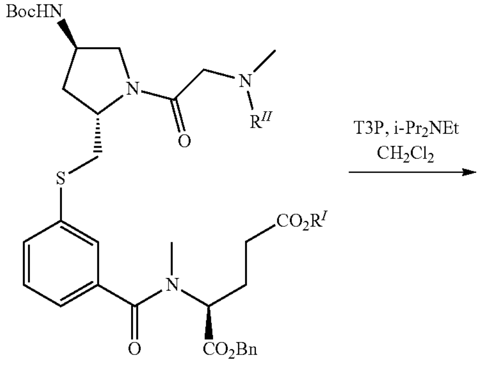

Pd$(PPh_3)_4$, 1,3-dimethyl-barbituric acid, $CH_2Cl_2$/EtOAc
136 $R^I$ = All, $R^{II}$ = Alloc
137 $R^I$ = $R^{II}$ = H Scheme 26

Core 22

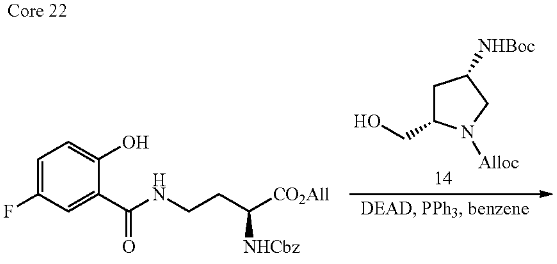

199

14

-continued
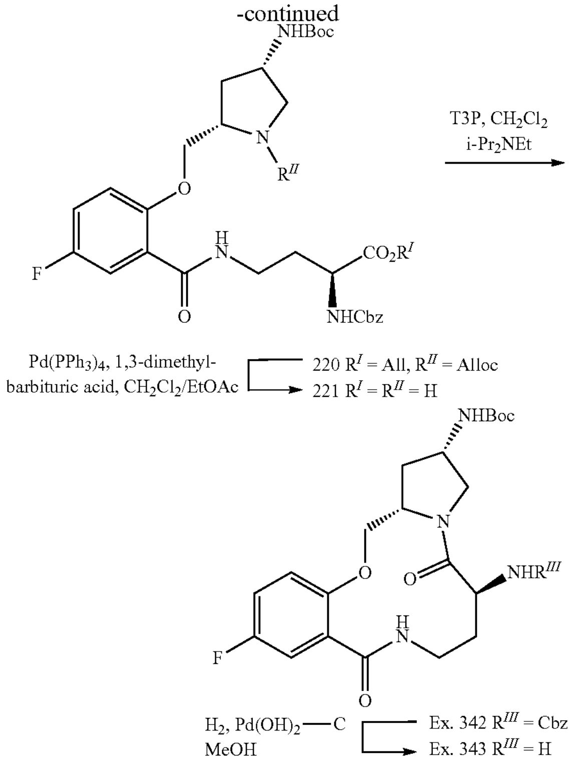
Scheme 27
Core 23
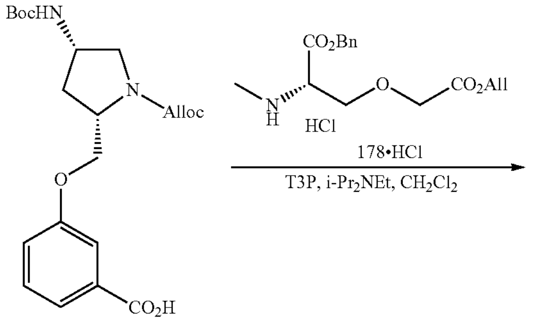
192
-continued
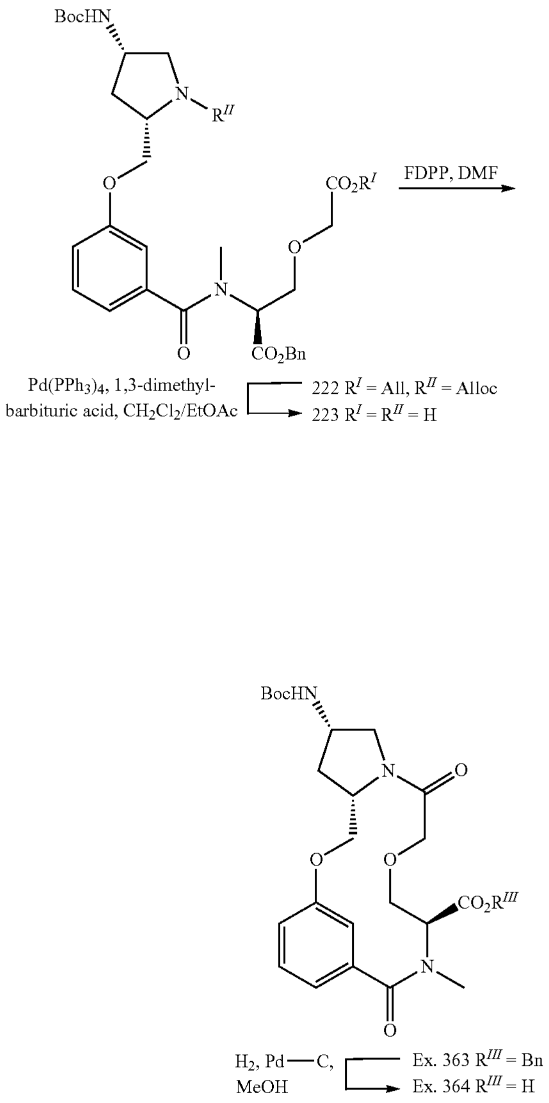
Scheme 28
Core 24a/24b
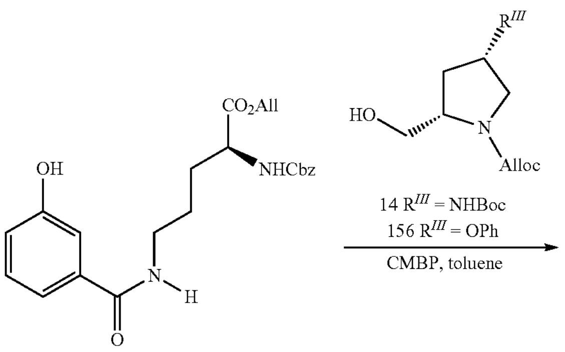
200

-continued
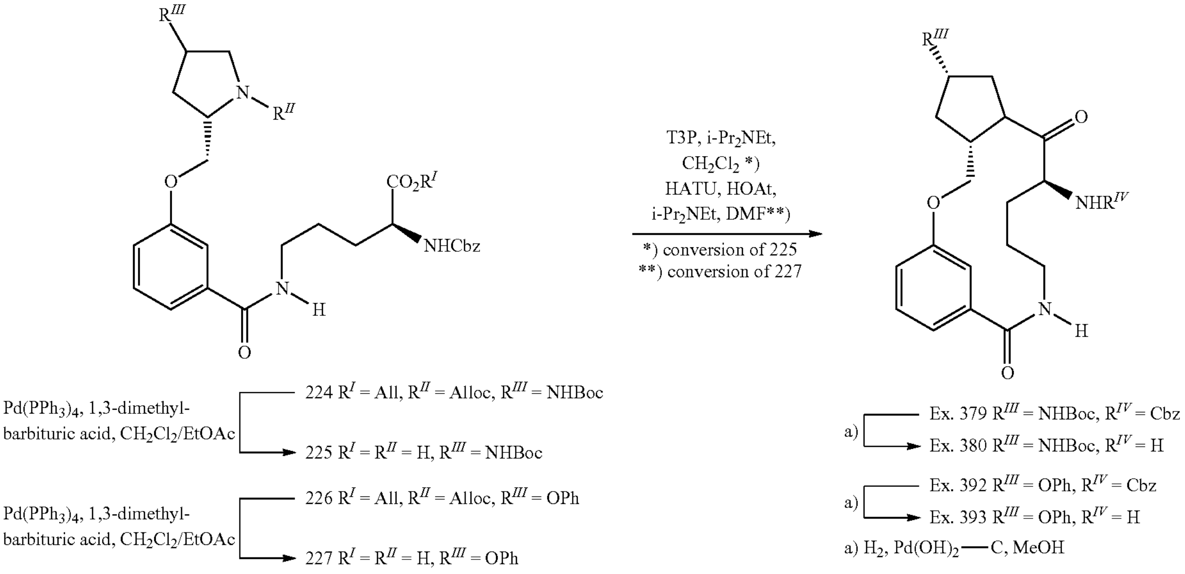
Core 24c
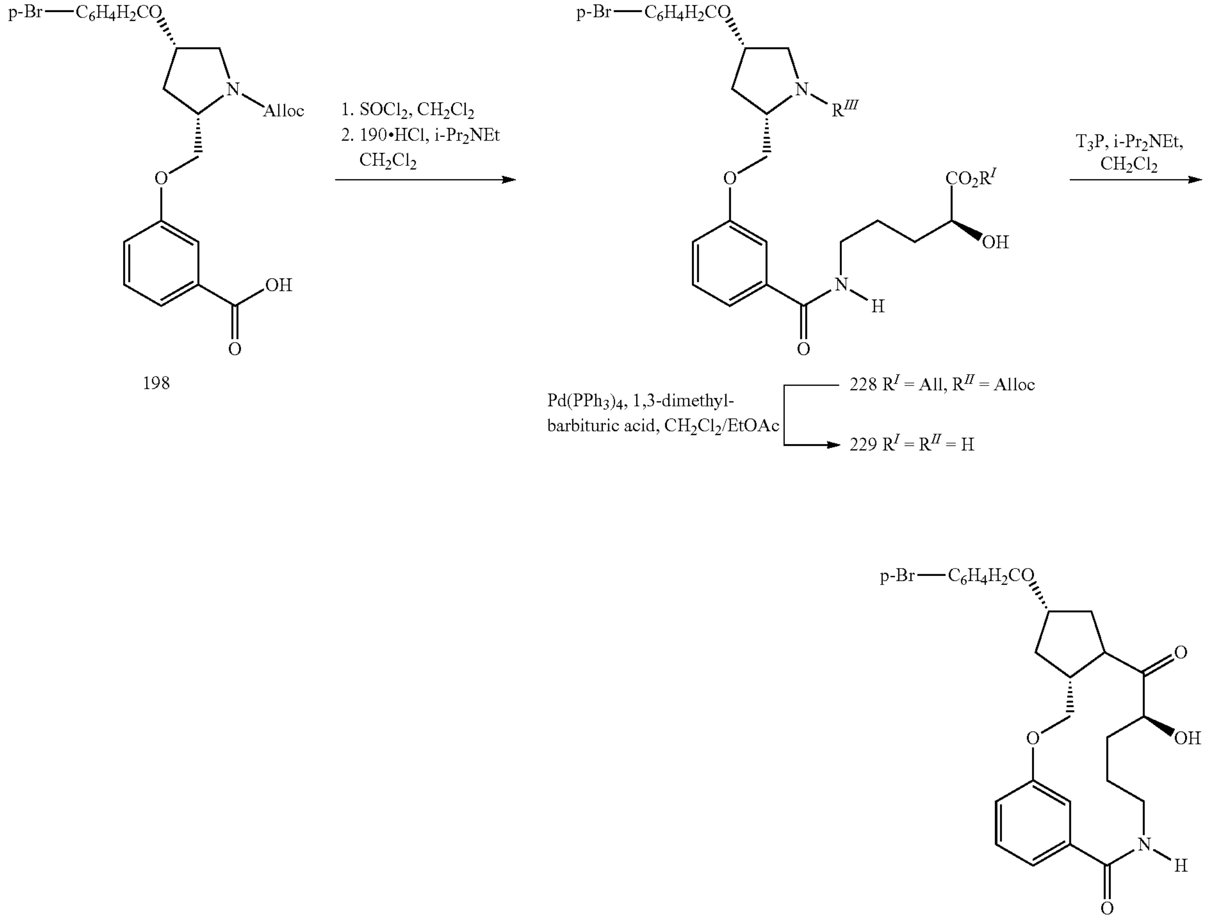
198
Ex. 398

Scheme 29
Core 25
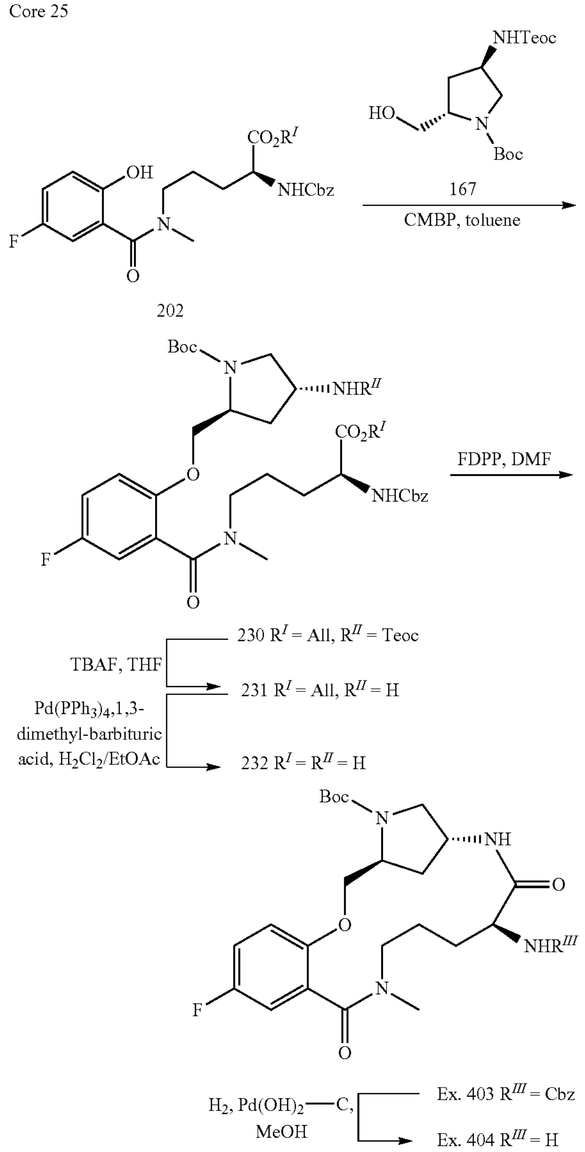
Scheme 30
Core 26
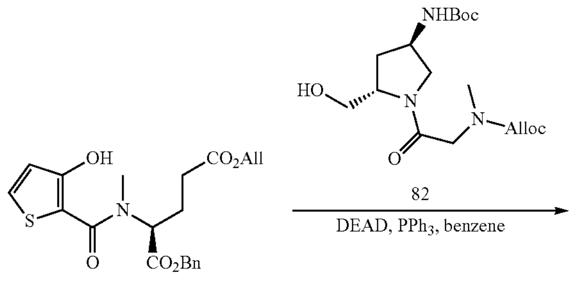
205
-continued
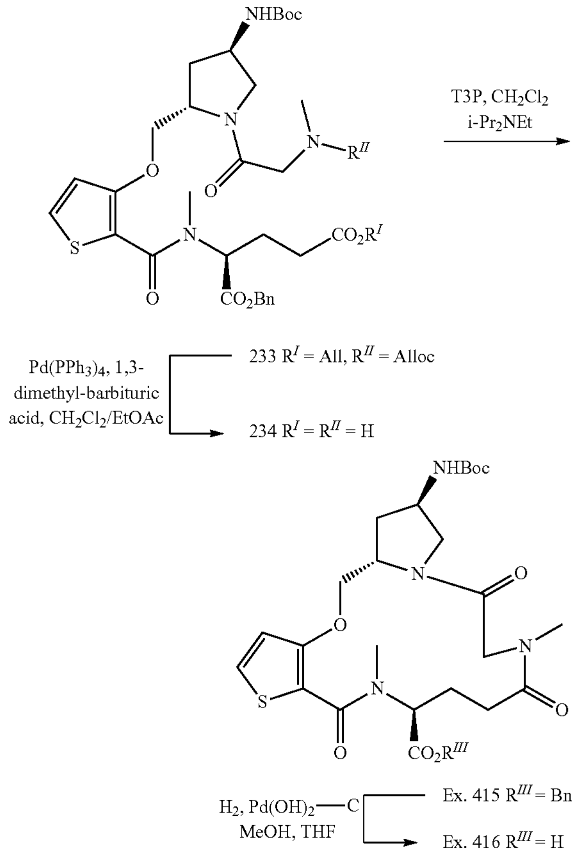
Scheme 31
Core 27
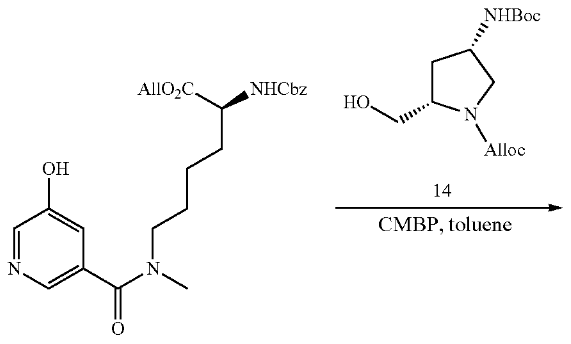
207

-continued
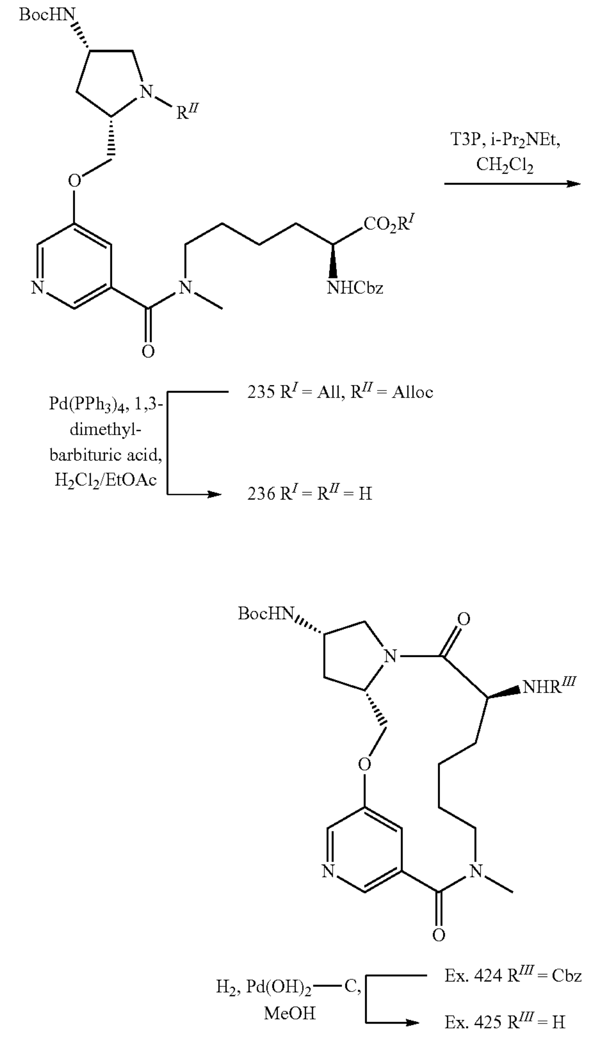
-continued
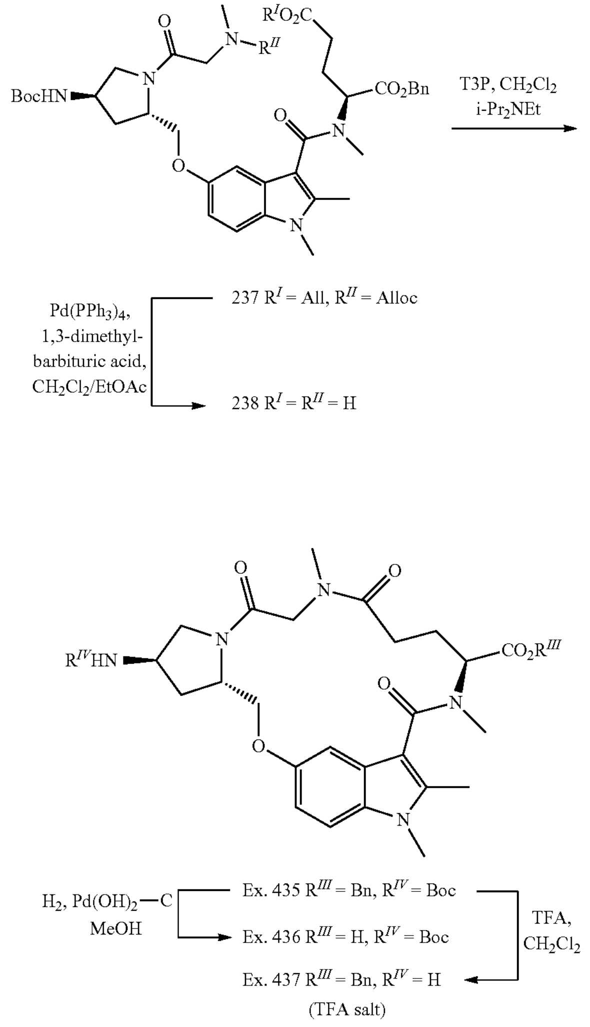
Scheme 32
Core 28
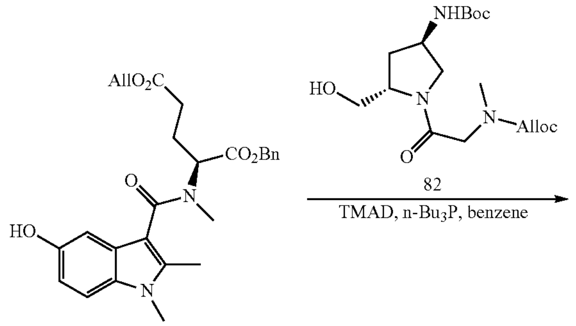
210
Scheme 33
Core 29
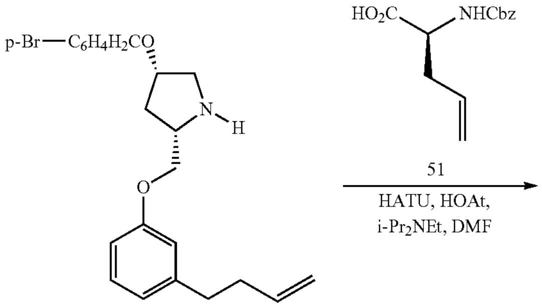
194

-continued
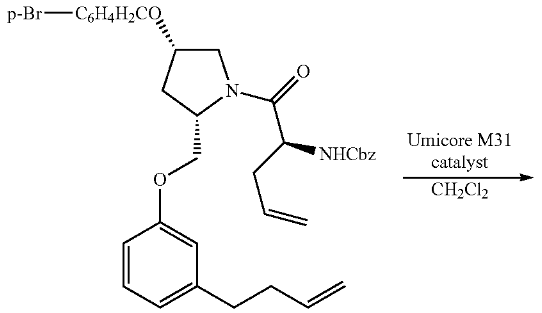
240
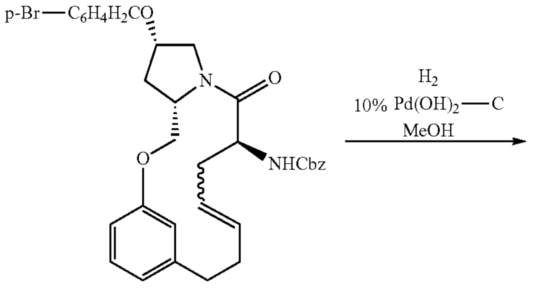
Ex. 447
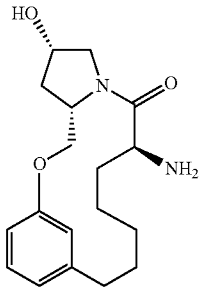
Ex. 448
Scheme 34
Core 30
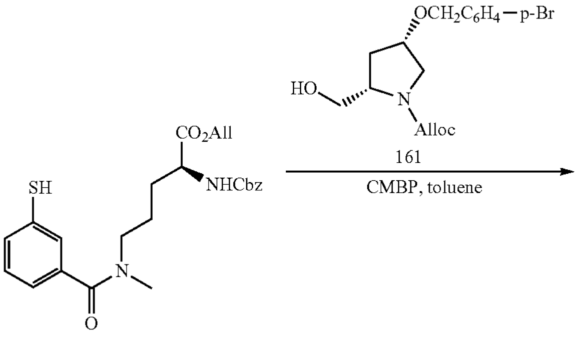
212
-continued
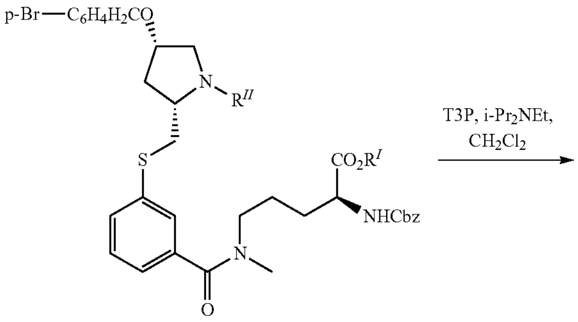
$Pd(PPh_3)_4$,
1,3-dimethyl-
barbituric acid,
$CH_2Cl_2$/EtOAc
241 $R^I$ = All, $R^{II}$ = Alloc
242 $R^I$ = $R^{II}$ = H
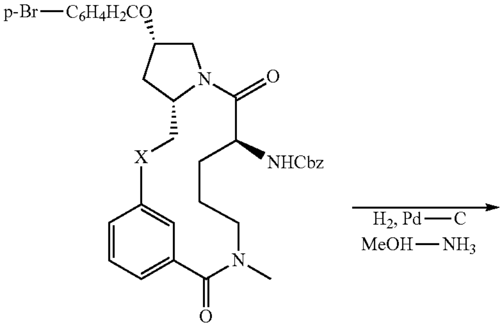
m-CPBA,
$CH_2Cl_2$
Ex. 451 X = S
Ex. 452 X = $SO_2$
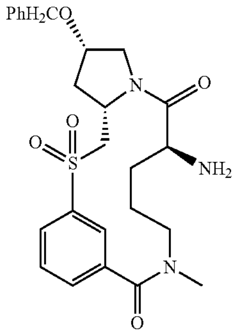
Ex. 453
Scheme 35
Core 31
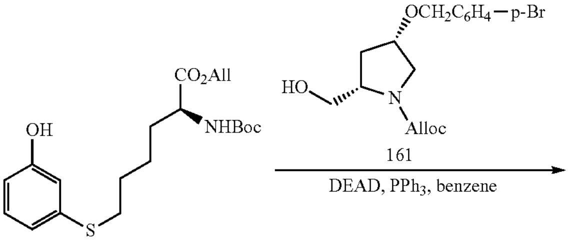
213

-continued
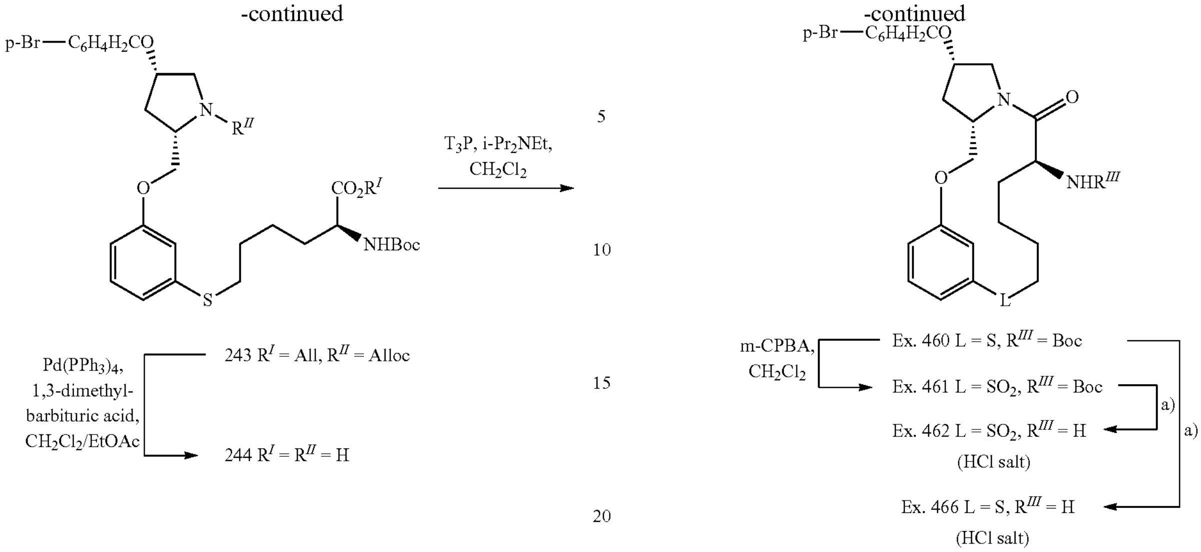
a) HCl-dioxane
Scheme 36
Core 32
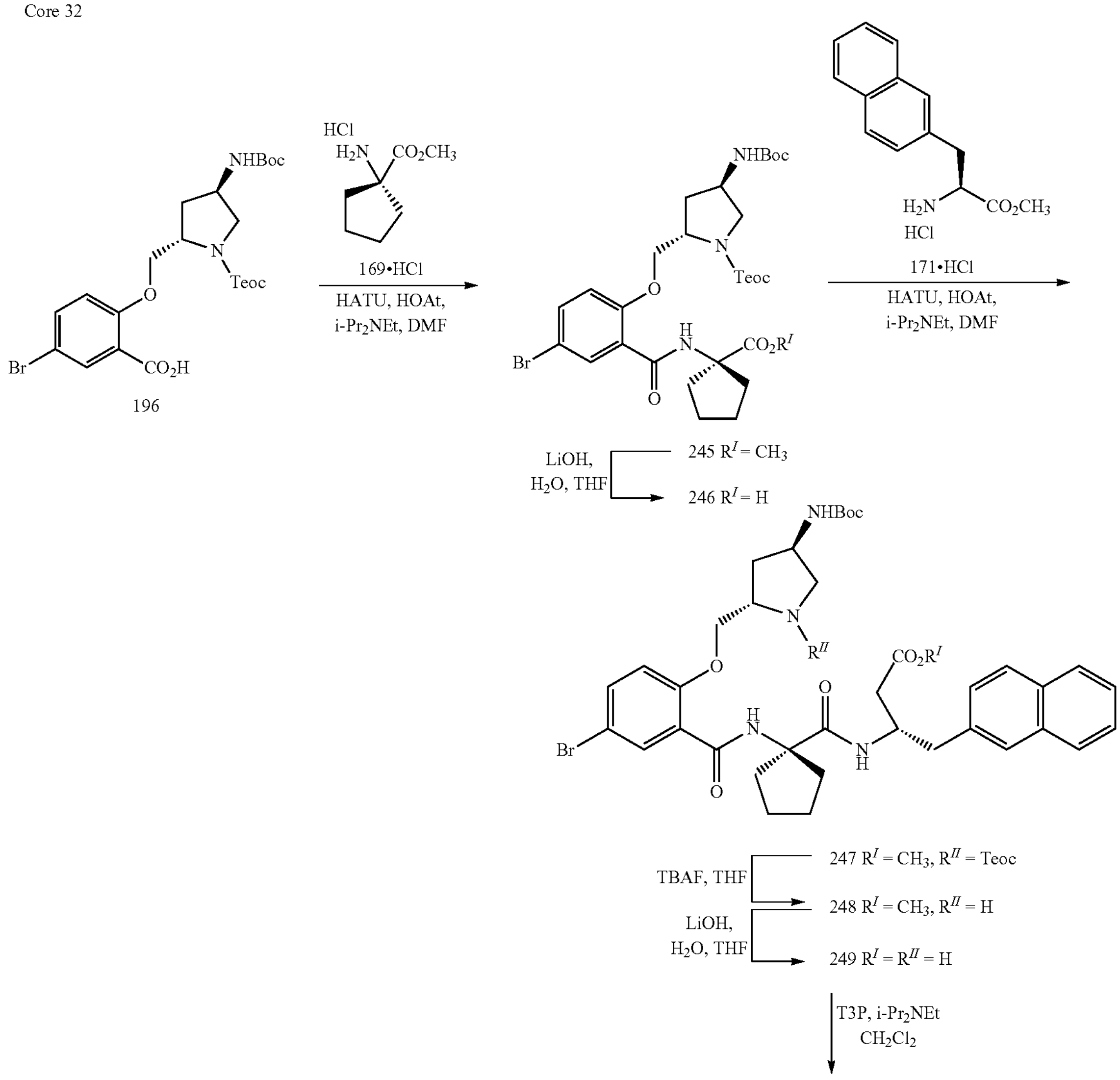
196

-continued
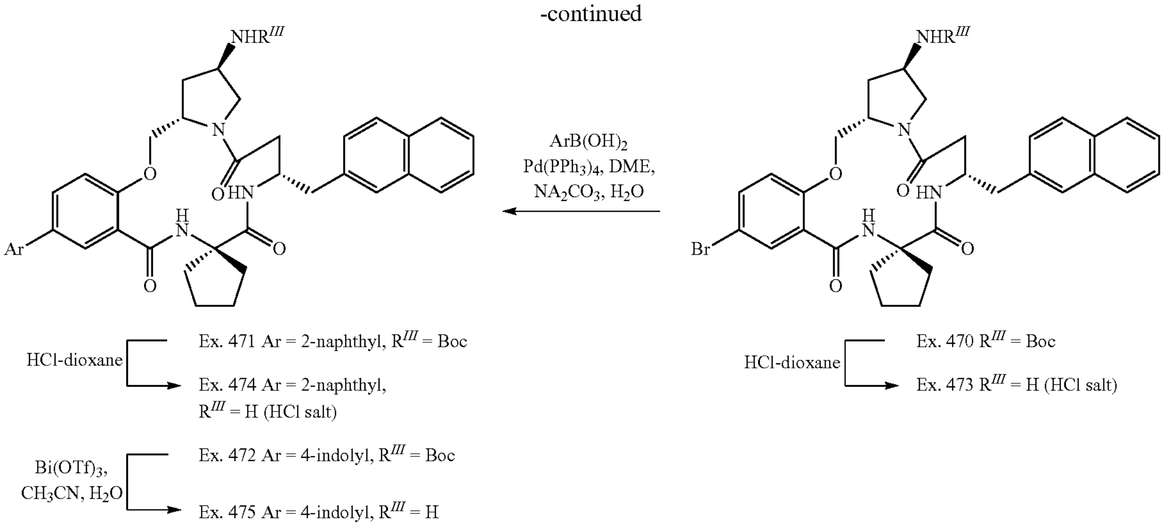
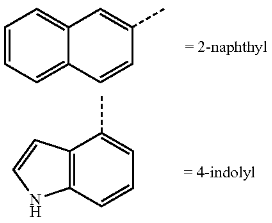
Scheme 37
Core 33
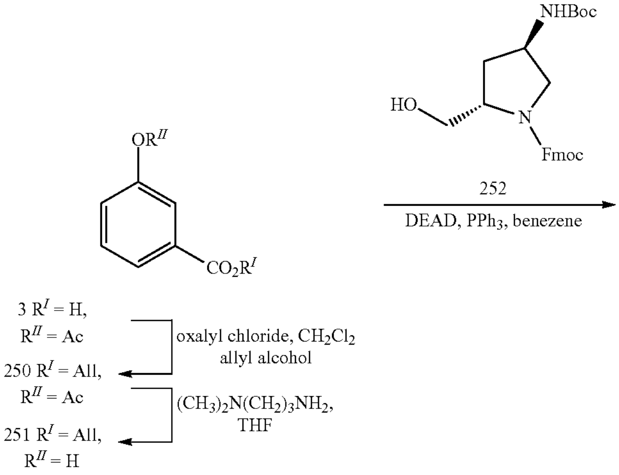

-continued
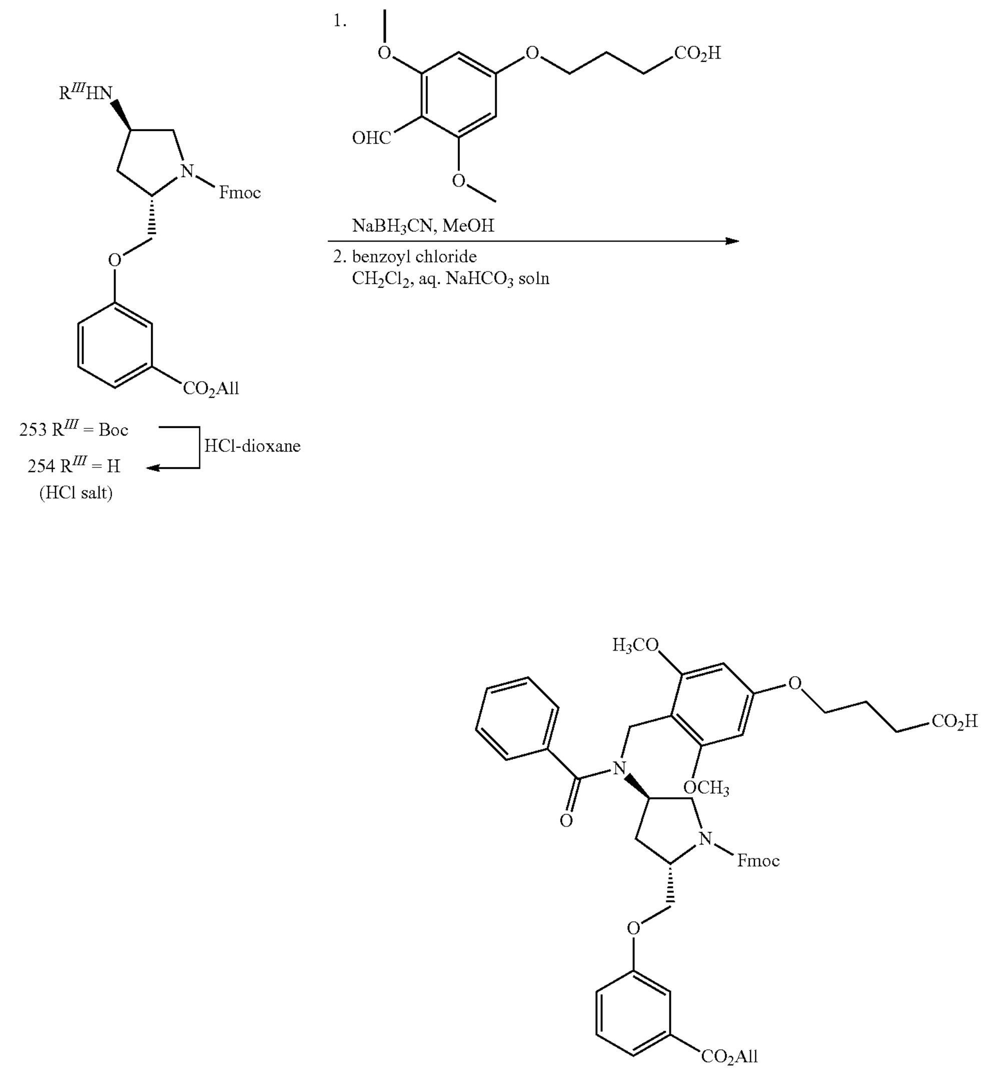
253 $R^{III}$ = Boc
254 $R^{III}$ = H
(HCl salt)
255
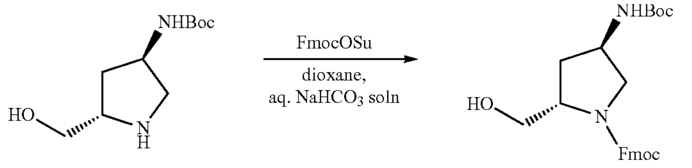
17
252
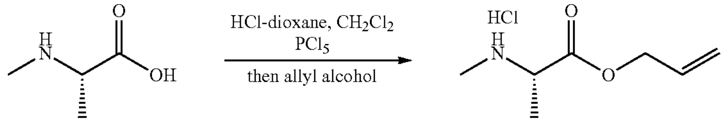
256
257•HCl -continued
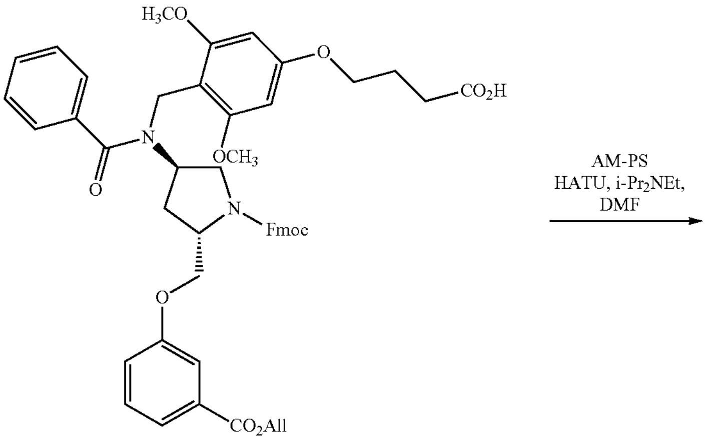
255
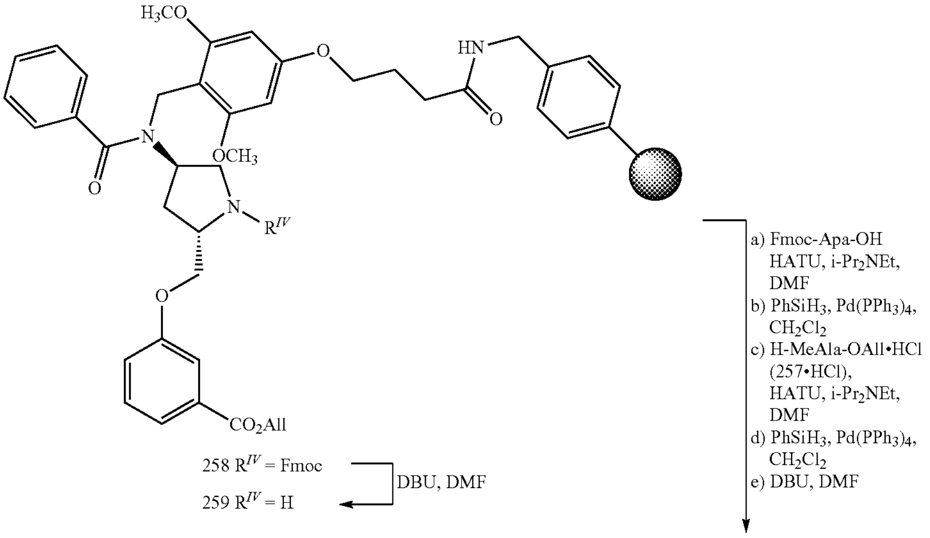
258 $R^{IV}$ = Fmoc
259 $R^{IV}$ = H
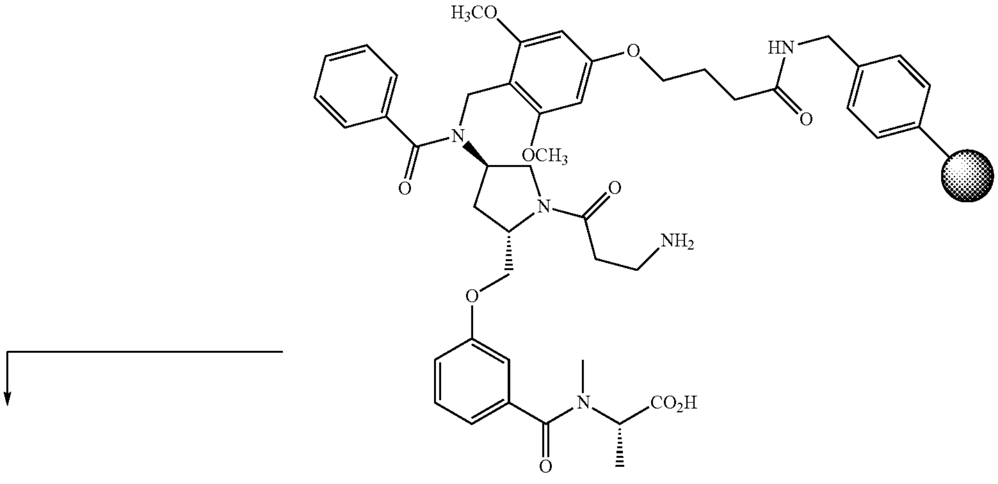
260

-continued
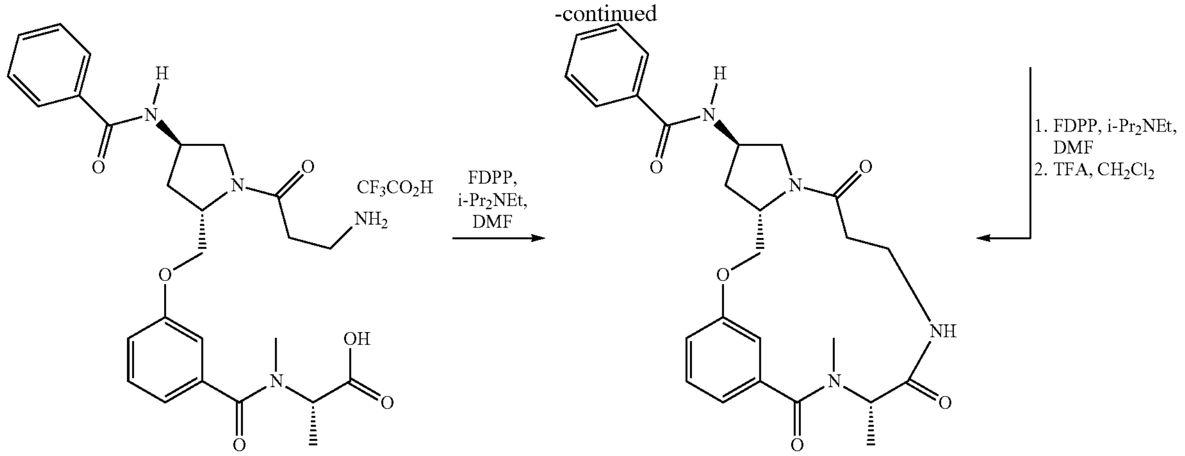
261•TFA
Ex. 476

Scheme 38
Core 03
Derivatization on Solid Support
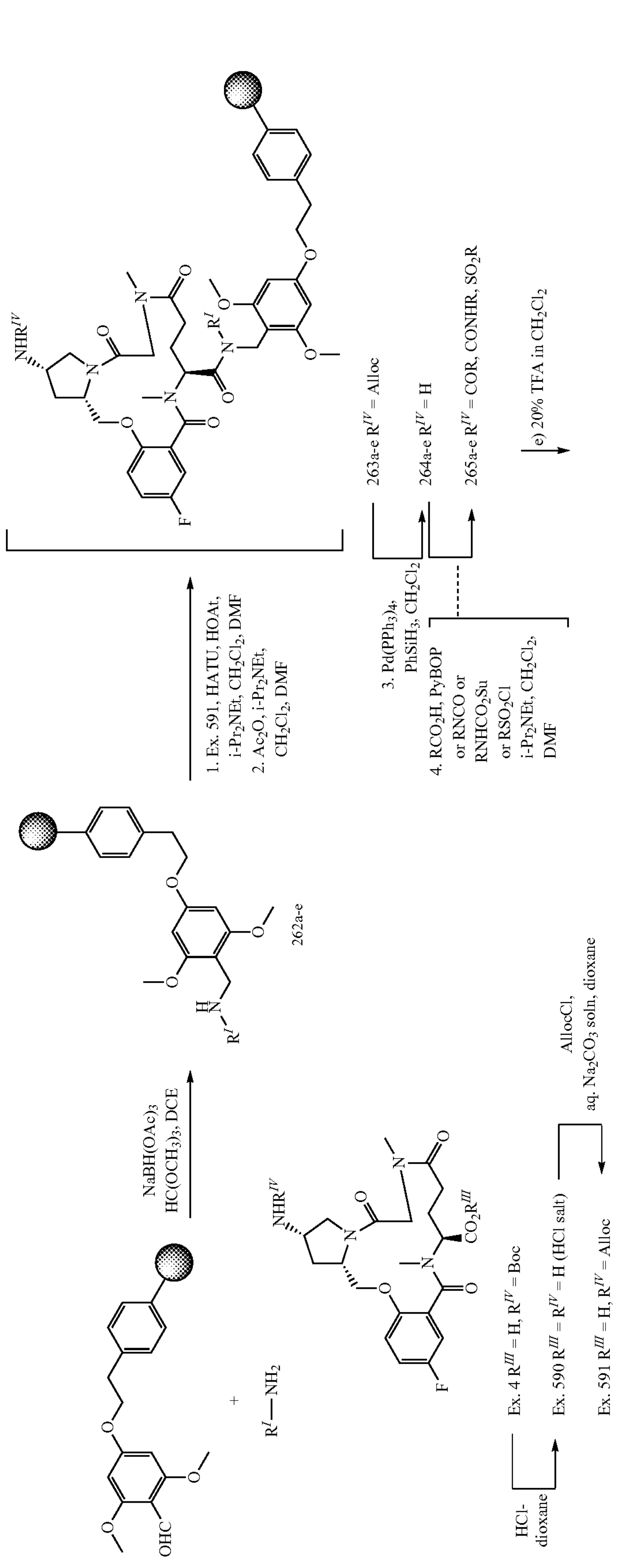

-continued
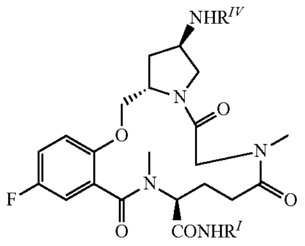
266
a $R^I$ = 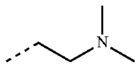 c $R^I$ = 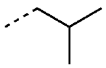 e $R^I$ = 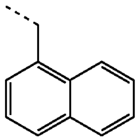
b $R^I$ = 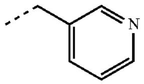 d $R^I$ = 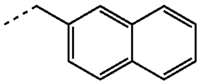

Scheme 39
Core 11a;
Derivatization on Solid Support
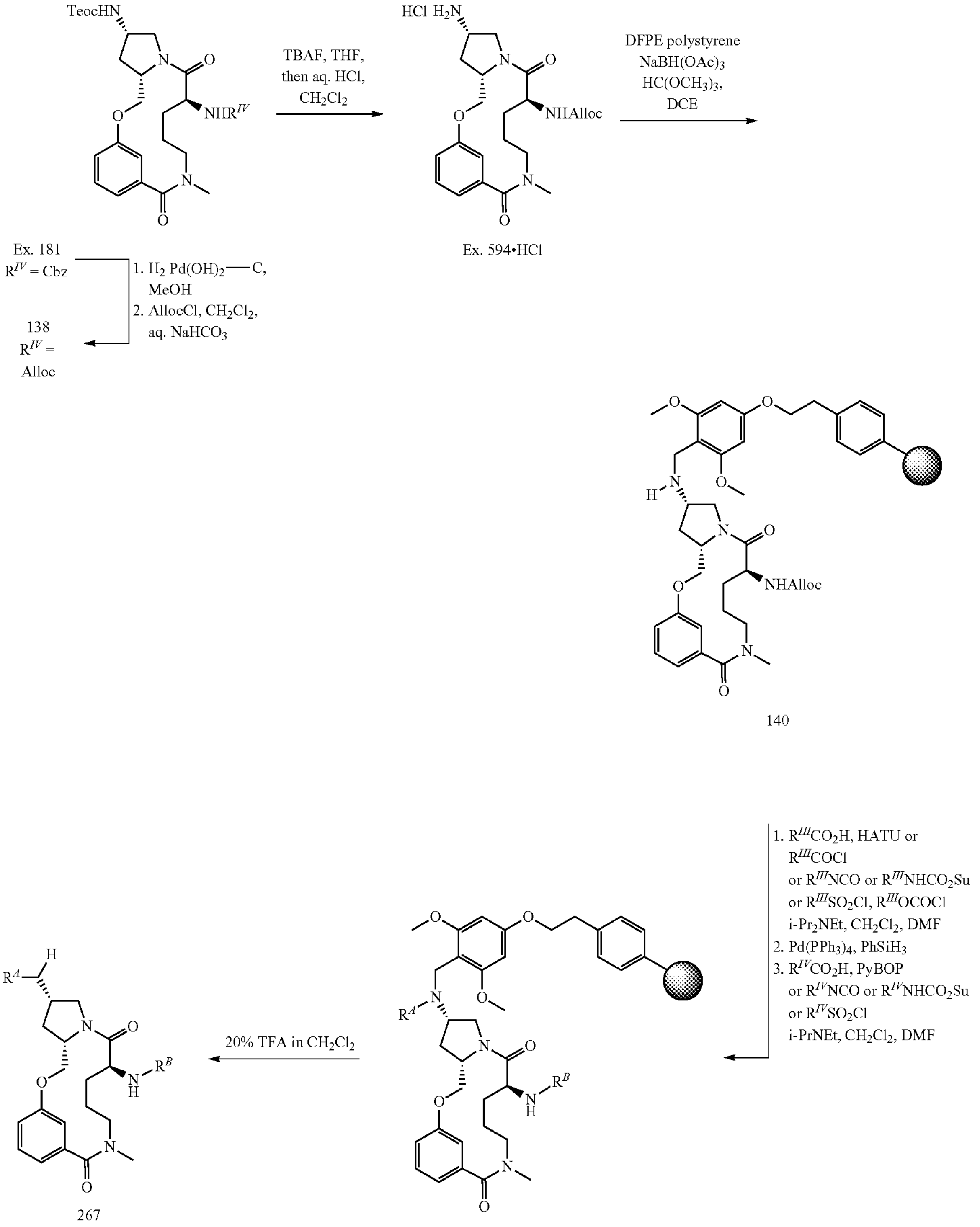
Ex. 181
$R^{IV}$ = Cbz
138
$R^{IV}$ =
Alloc
Ex. 594•HCl
140
141
267
$R^A$ = $R^{III}CO$, $^{III}NHCO$, $R^{III}SO_2$, $R^{III}OCO$
$R^B$ = $R^{IV}CO$, $R^{IV}NHCO$, $R^{IV}SO_2$ Scheme 40
Core 27
Derivatization on Solid Support
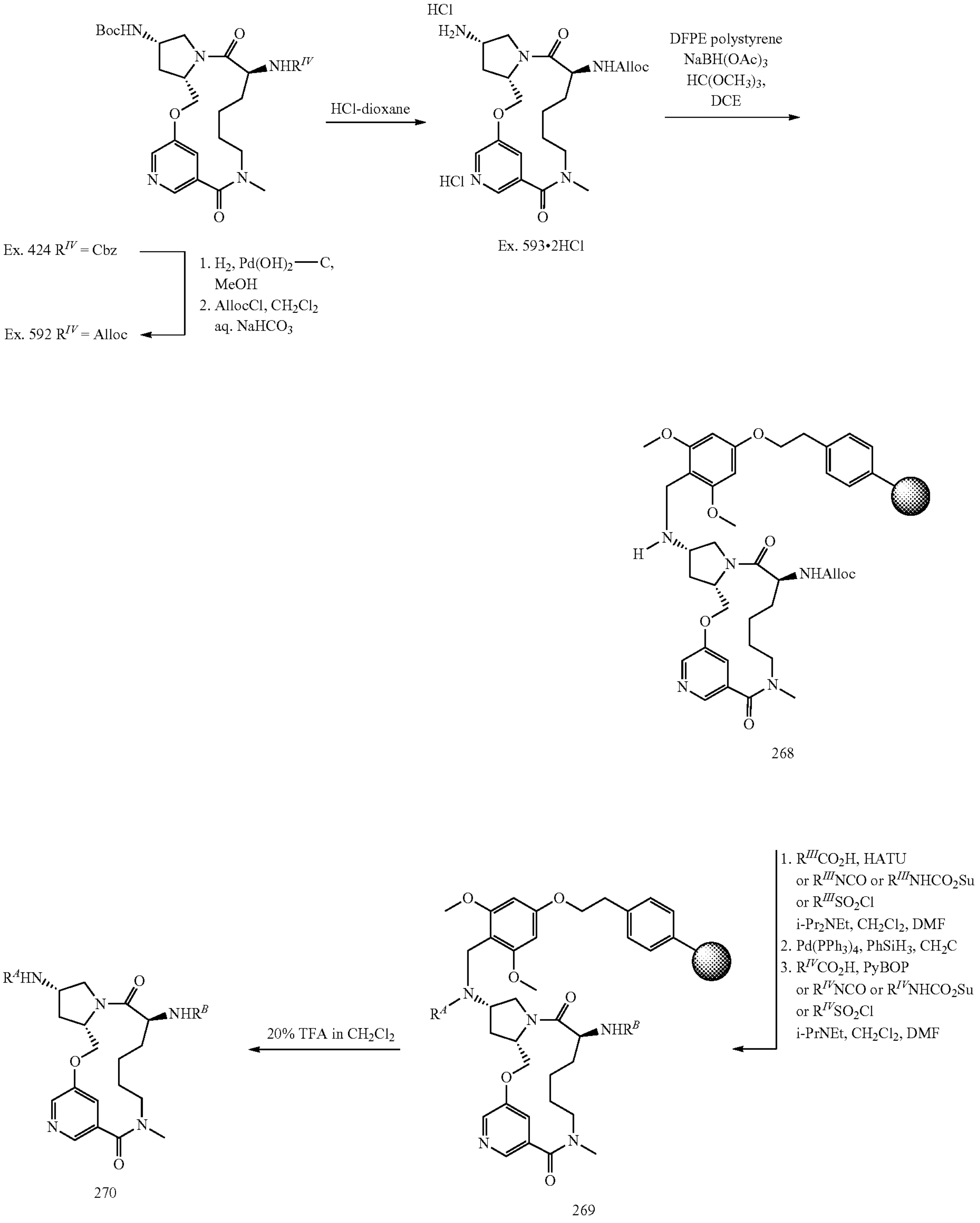
Ex. 424 $R^{IV}$ = Cbz
Ex. 592 $R^{IV}$ = Alloc
Ex. 593•2HCl
268
269
270
$R^A = R^{III}CO, R^{III}NHCO, R^{III}SO_2$
$R^B = R^{IV}CO, R^{IV}NHCO, R^{IV}SO_2$ Scheme 41
Structures of Examples
Core 01
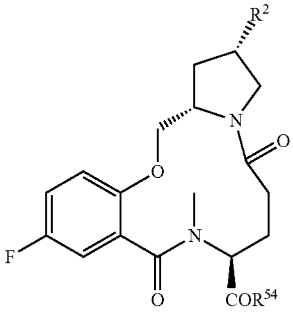
Ex. 1
definition of R-groups
cf. Table 20
Core 02
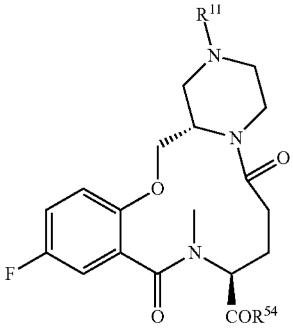
Ex. 2
definition of R-groups
cf. Table 20
Core 03
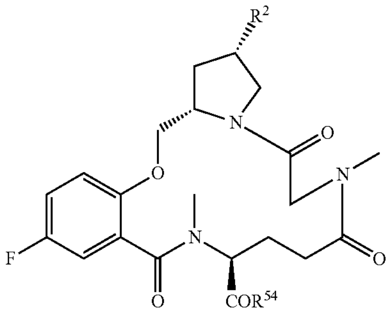
Ex. 3-Ex. 55
Ex. 482-Ex. 503;
Ex. 590, Ex. 591
definition of R-groups
cf. Table 21
-continued
Core 04
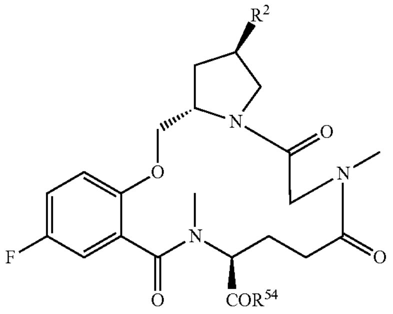
Ex. 56-Ex. 84
definition of R-groups
cf. Table 22
Core 05
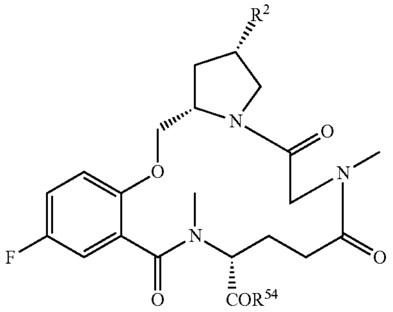
Ex. 85-Ex. 103
definition of R-groups
cf. Table 23
Core 06
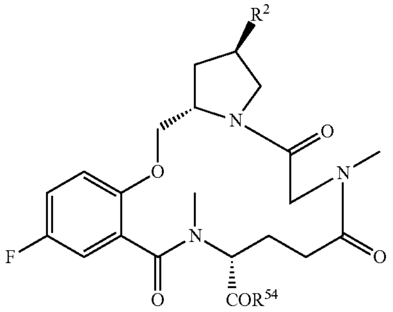
Ex. 104-Ex. 114
definition of R-groups
cf. Table 24
Core 07
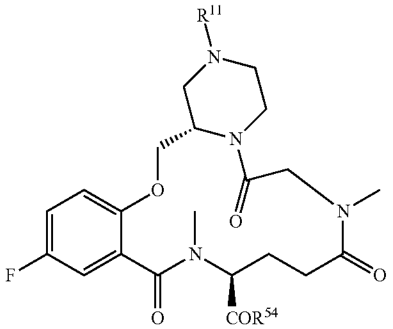
Ex. 115-Ex. 131
definition of R-groups
cf. Table 25

-continued
Core 08
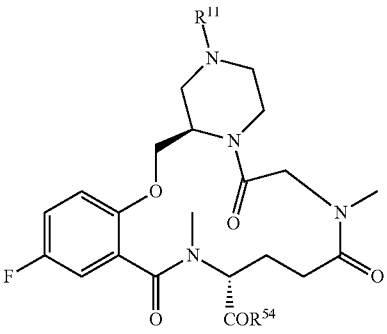
Ex. 132-Ex. 141
definition of R-groups
cf. Table 6
Core 09
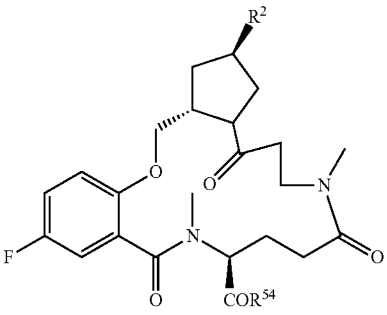
Ex. 142-Ex. 163
definition of R-groups
cf. Table 27
Core 10
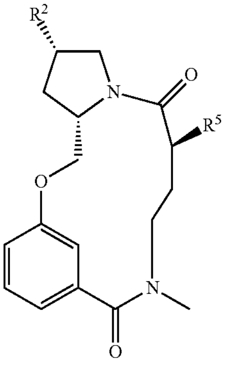
Ex. 164-Ex. 180
definition of R-groups
cf. Table 28
-continued
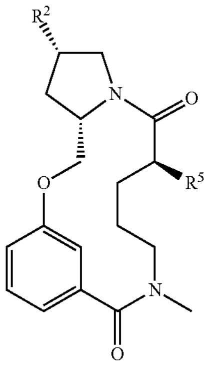
Core 11a
Ex. 181-Ex.195
Ex. 504-Ex. 559, Ex. 594
Core 11b
Ex. 560-Ex.566
Core 11c
Ex. 567-Ex. 585
Core 11d
Ex. 586-Ex.589
definition of R-groups
cf. Tables 29.1 to 29.4
Core 12
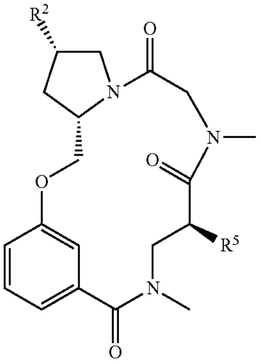
Ex. 196-Ex. 214
definition of R-groups
cf. Table 30
Core 13
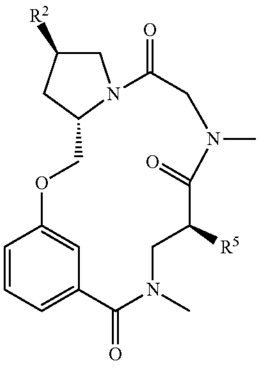
Ex. 215-Ex. 230
definition of R-groups
cf. Table 31

-continued
Core 14
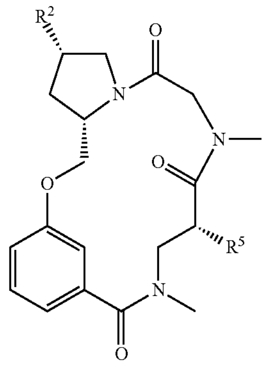
Ex. 231-Ex. 237
definition of R-groups
cf. Table 32
Core 15
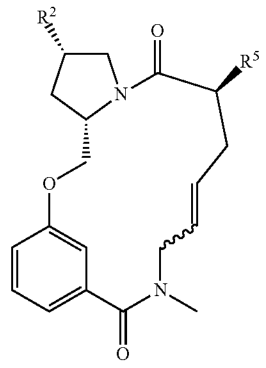
Ex. 238
definition of R-groups
cf. Table 33
Core 16
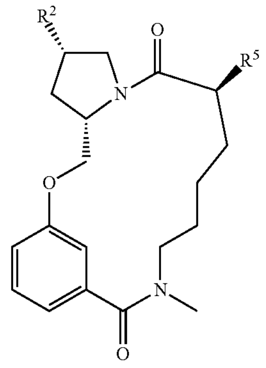
Ex. 239-Ex. 247
definition of R-groups
cf. Table 33
-continued
Core 17
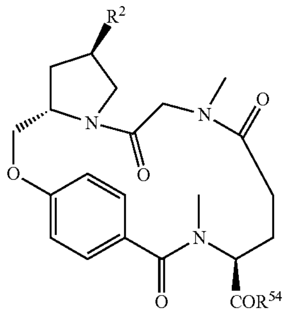
Ex. 248-Ex. 271
definition of R-groups
cf. Table 34
Core 18
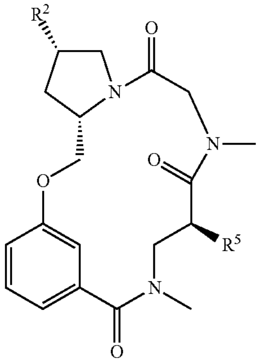
Ex. 272-Ex. 296
definition of R-groups
cf. Table 35
Core 19
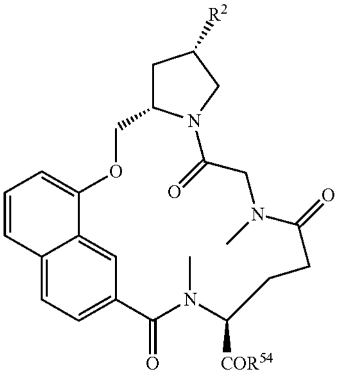
Ex. 297-Ex. 310
definition of R-groups
cf. Table 36

Core 20
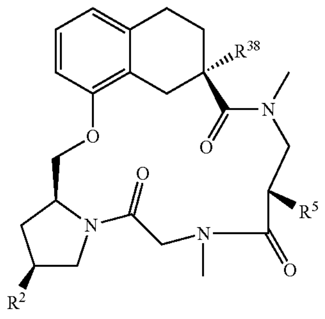
Ex. 311
definitions of R-groups
cf. Table 37.1
Core 21
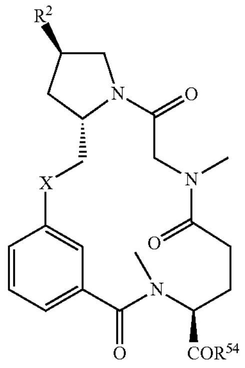
(X = S, $SO_2$)
Ex. 312-Ex. 341
definitions of R-groups
cf. Table 37.2
Core 22
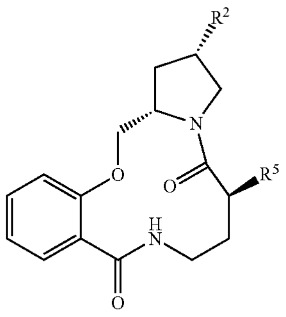
Ex. 342-Ex. 362
definitions of R-groups
cf. Table 38
Core 23
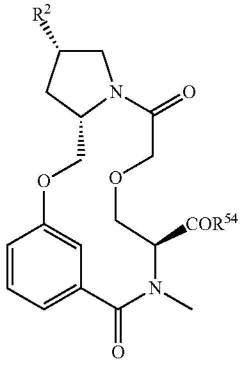
Ex. 363-Ex. 378
definitions of R-groups
cf. Table 39
Core 24a
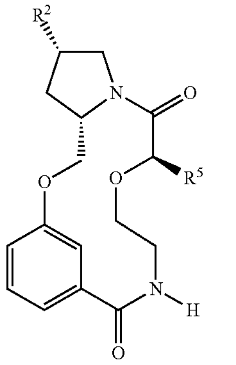
Ex. 379-Ex. 391
Core 24b
Ex. 392-Ex. 396
Core 24c
Ex. 398-Ex. 402
definitions of R-groups
cf. Table 40.1 to 40.3
Core 25
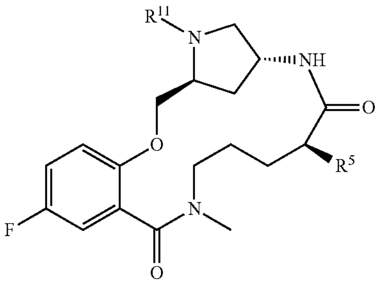
Ex. 403-Ex. 414
definitions of R-groups
cf. Table 41

-continued
Core 26
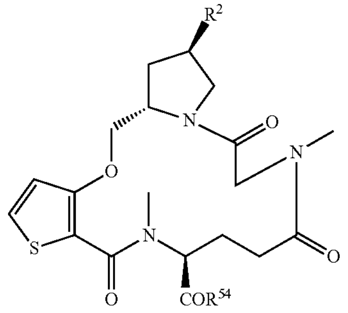
Ex. 415-Ex. 423
definitions of R-groups
cf. Table 42
Core 27
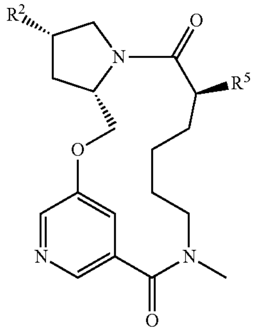
Ex. 424-Ex. 434,
Ex. 592, Ex. 593
definitions of R-groups
cf. Table 43
Core 28
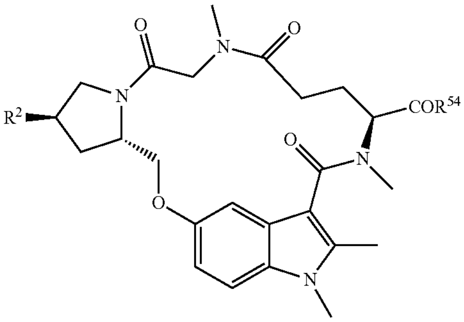
Ex. 435-Ex. 446
definitions of R-groups
cf. Table 44
Core 29
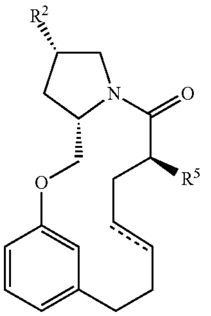
Ex. 447-Ex. 450
definitions of R-groups
cf. Table 45
-continued
Core 30
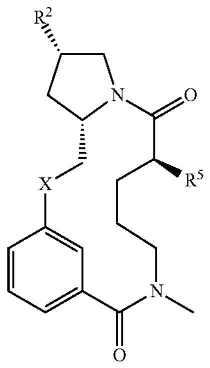
(X = S, SO2)
Ex. 451-Ex. 459
definitions of R-groups
cf. Table 46
Core 31
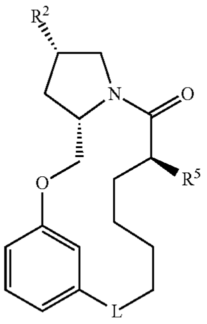
(L = S, SO2)
Ex. 460-Ex. 469
definitions of R-groups
cf. Table 47
Core 32
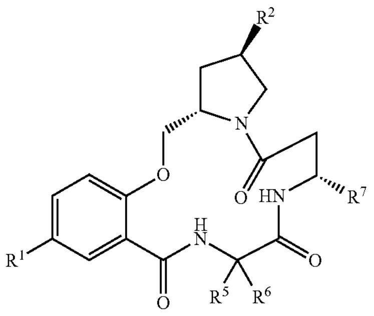
Ex. 470-Ex. 475
definitions of R-groups
cf. Table 48

-continued
Core 33
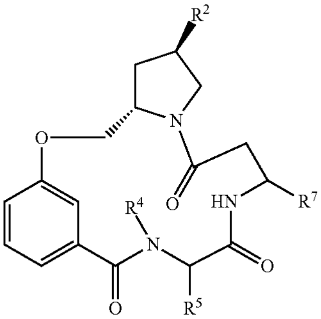
Ex. 476-Ex. 481
definitions of R-groups
cf. Table 49
Scheme 42
Core 03; selected Final Products
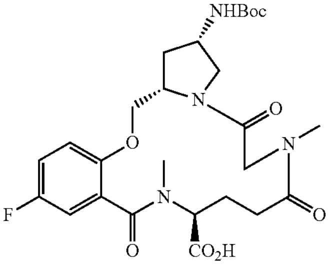
Ex. 4
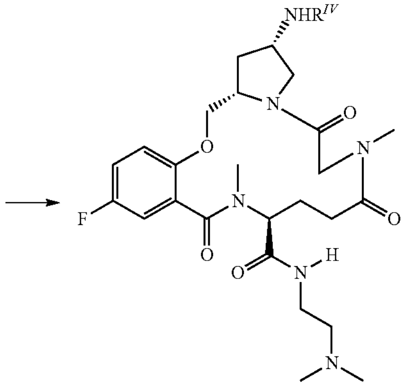
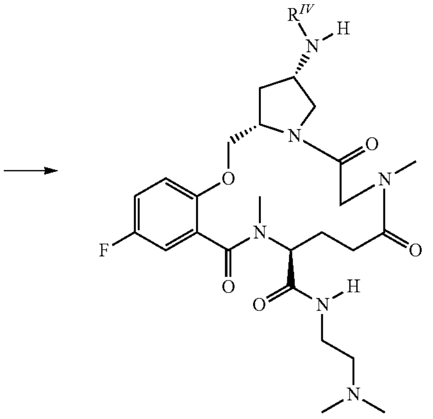
Ex. 27 $R^{IV}$ = Boc
Ex. 27 $R^{IV}$ = H
(HCl salt)
$R^{IV}$ =
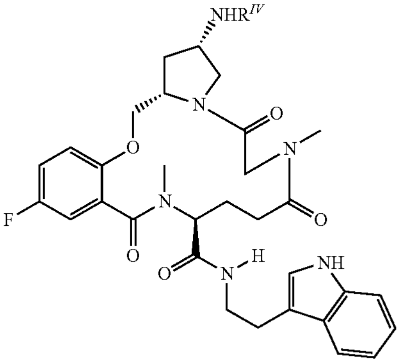
Ex. 30 $R^{IV}$ = Boc
Ex. 30 $R^{IV}$ = H
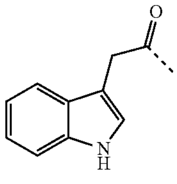
Ex. 11
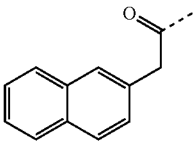
Ex. 48
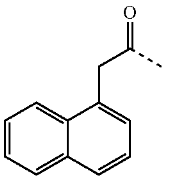
Ex. 49
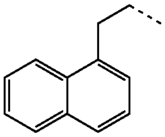
Ex. 486 (TFA salt)

-continued
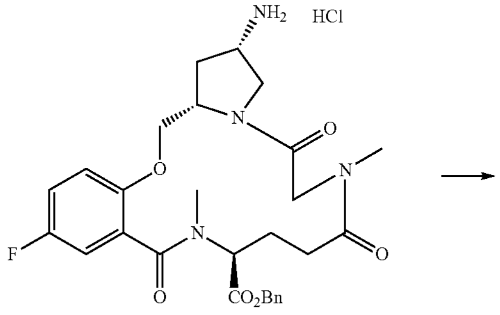
Ex. 5 (HCl salt)
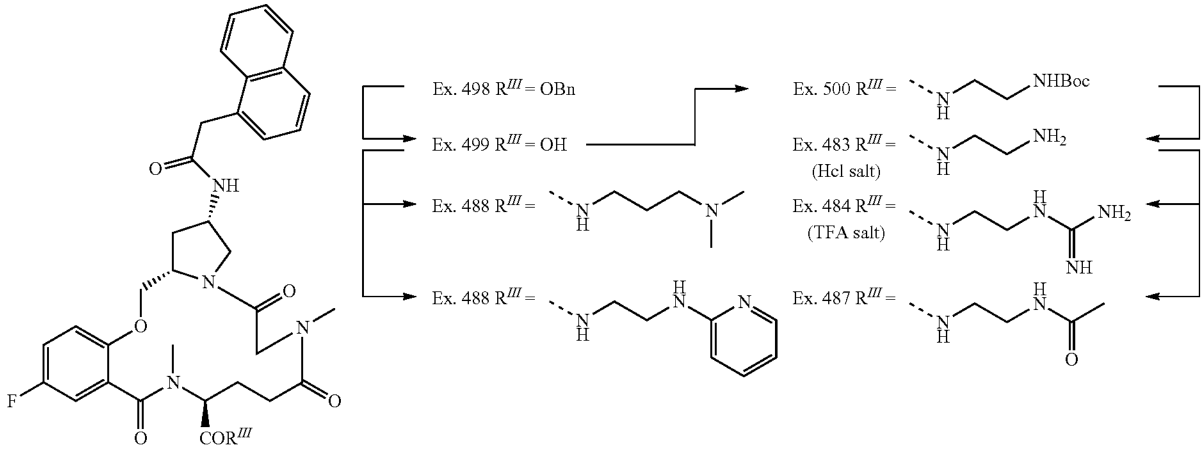
262a
or
262b
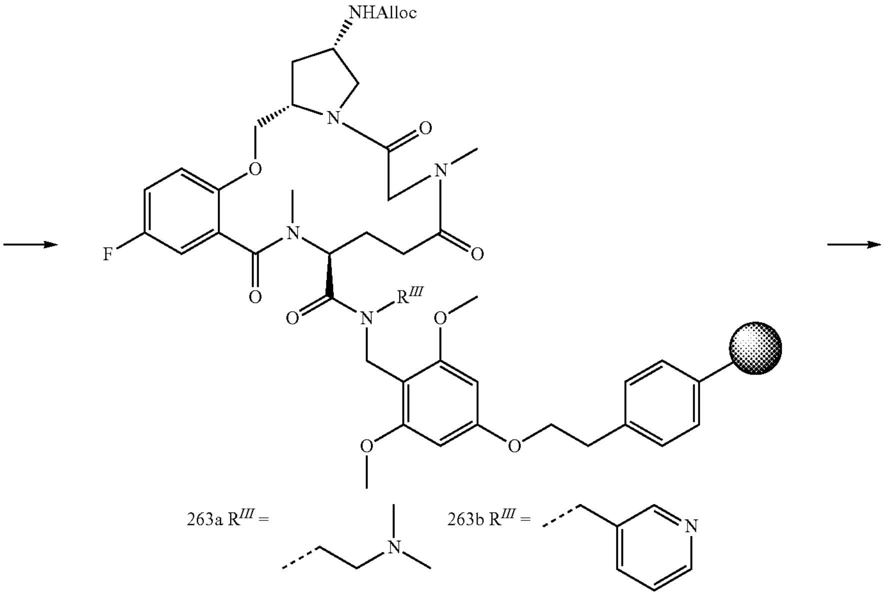

-continued
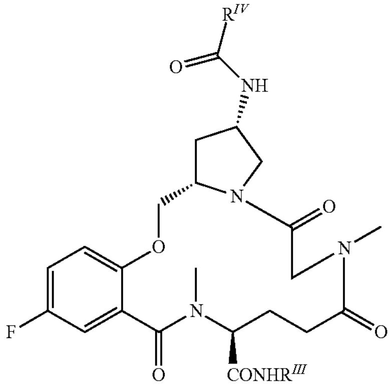
Ex. 482 $R^{III}$ =
(TFA salt)
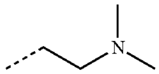
$R^{IV}CO$ =
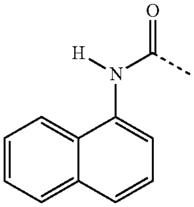
Ex. 495 $R^{III}$ =
(TFA salt)
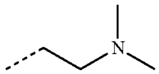
$R^{IV}CO$ =
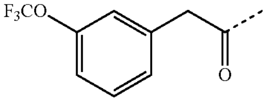
Ex. 496 $R^{III}$ =
(TFA salt)
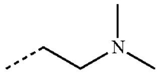
$R^{IV}CO$ =
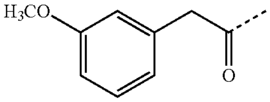
Ex. 496 $R^{III}$ =
(TFA salt)
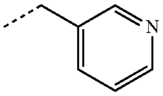
$R^{IV}CO$ =
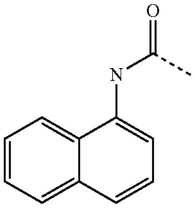
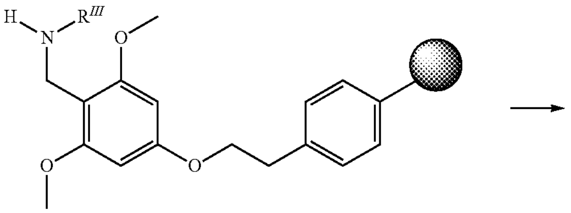
262d $R^{III}$ =
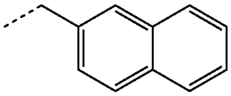
262d $R^{III}$ =
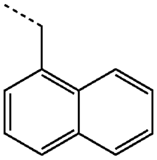

-continued
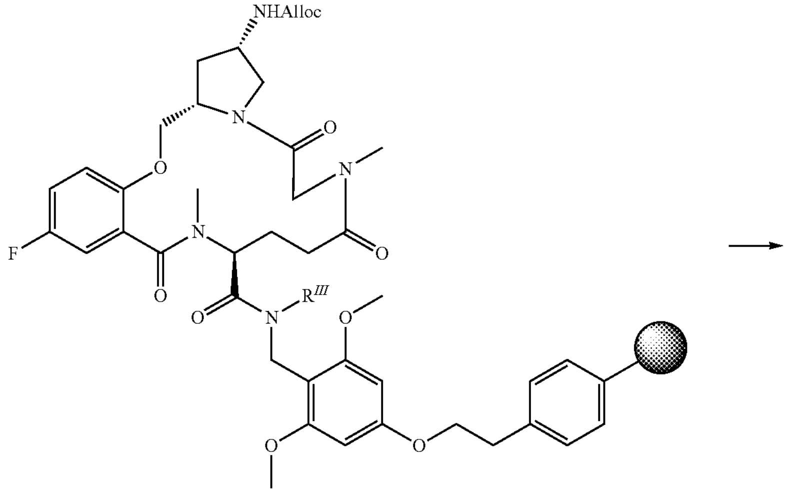
263d
263e
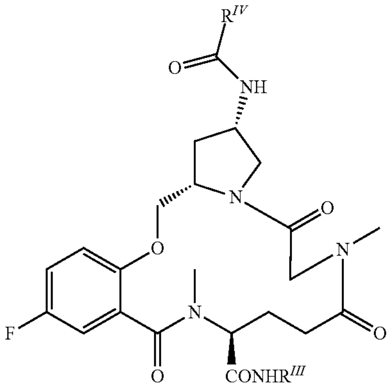
Ex. 501 $R^{III}$ = 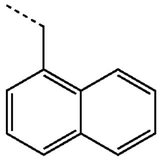 $R^{IV}CO$ = 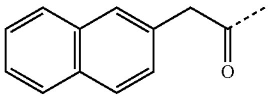
Ex. 501 $R^{III}$ = 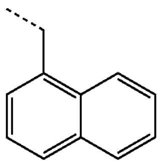 $R^{IV}CO$ = 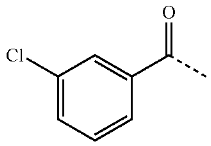
Ex. 503 $R^{III}$ = 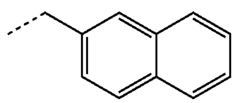 $R^{IV}CO$ = 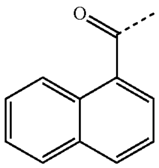

-continued
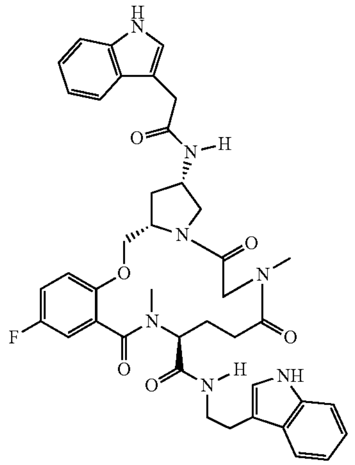
Ex. 12
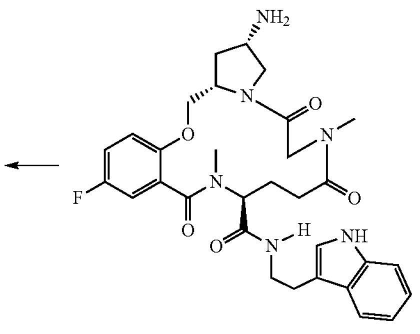
Ex. 55
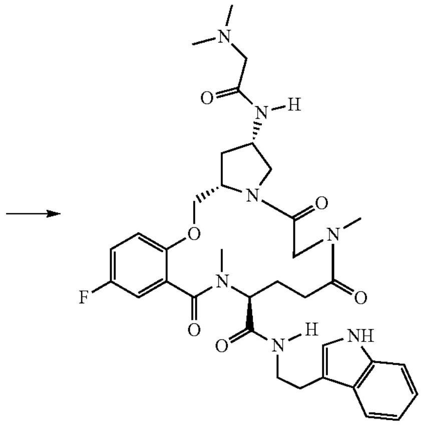
Ex. 16 (TFA salt)
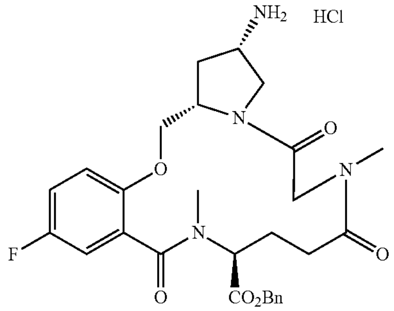
Ex. 5 (HCl salt)
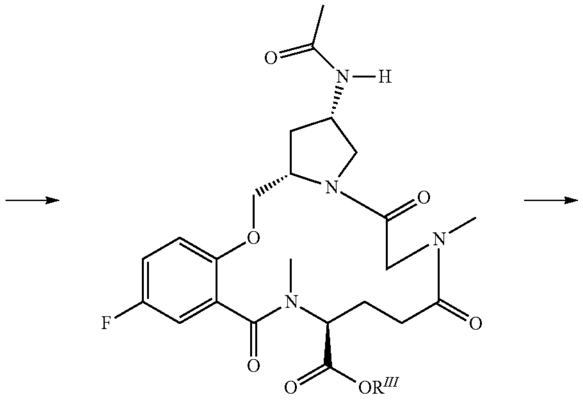
Ex. 53 $R^{III}$ = Bn
Ex. 54 $R^{III}$ = H
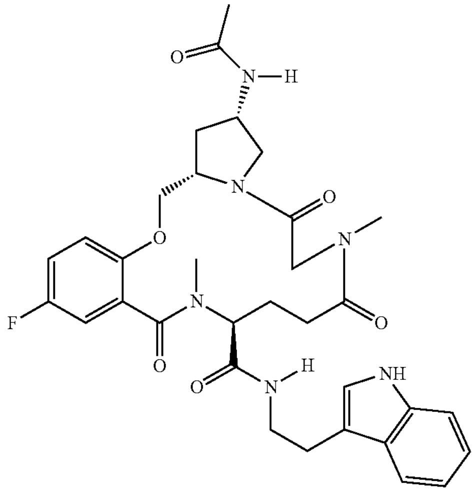
Ex. 9

Scheme 43
Core 10;
examples
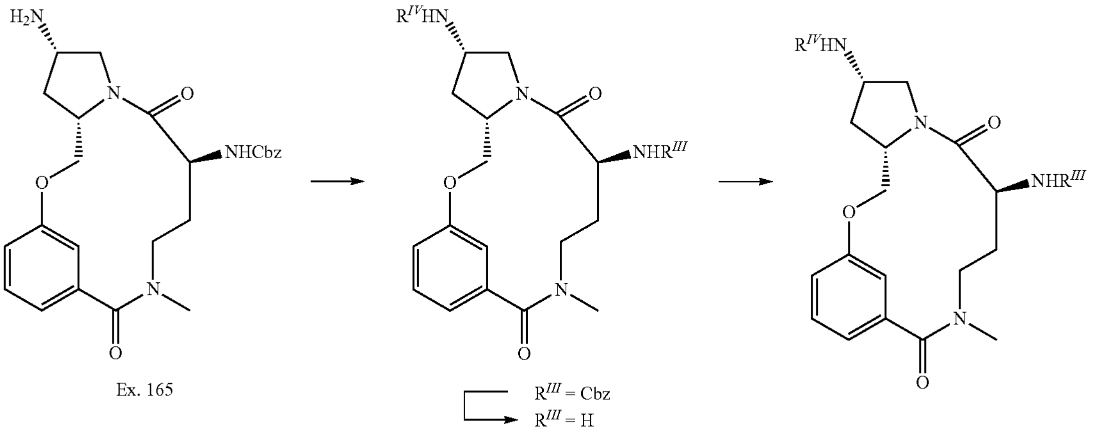
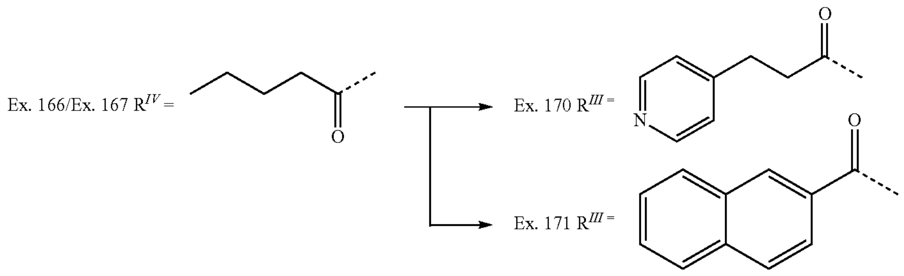
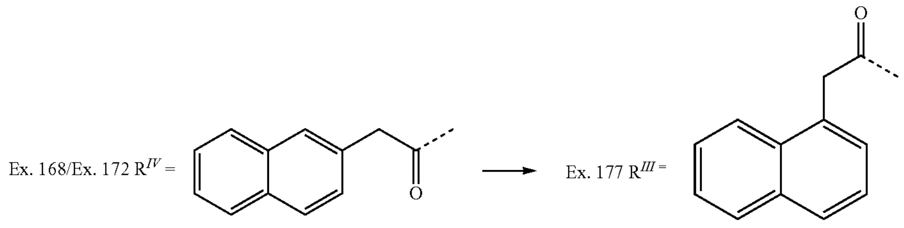
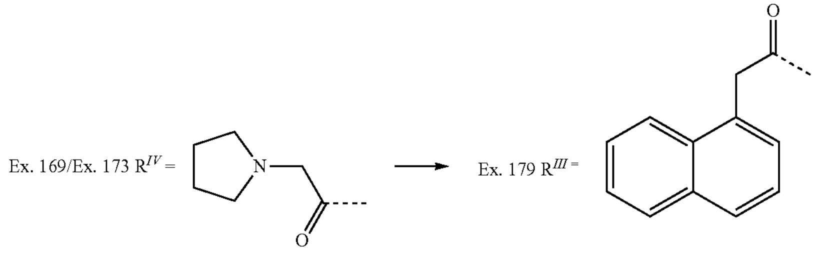

Scheme 44
Core 11a;
Selected Examples prepared in solution
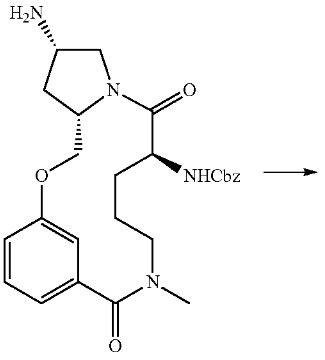
Ex. 182
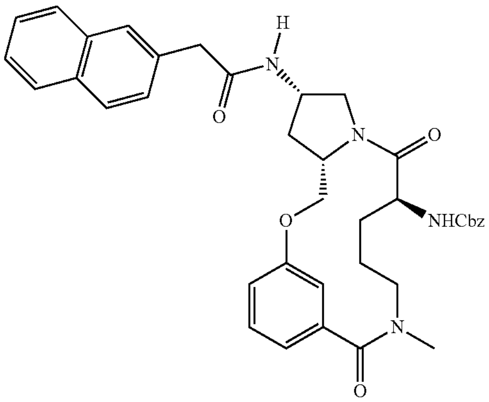
Ex. 184
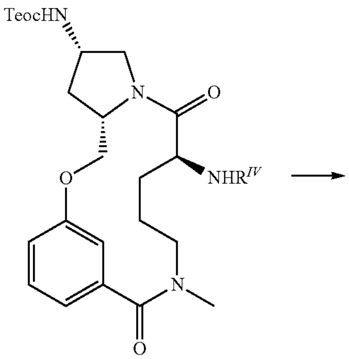
Ex. 181 $R^{IV}$ = Cbz
Ex. 194 $R^{IV}$ = H
-continued
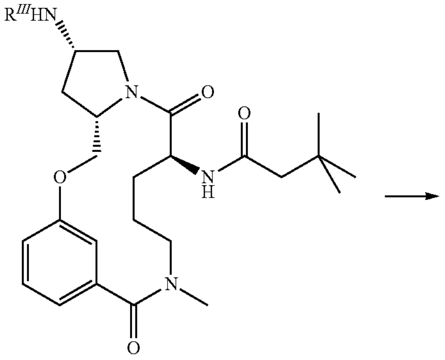
Ex. 532 $R^{III}$ = Teoc
Ex. 533 $R^{III}$ = H
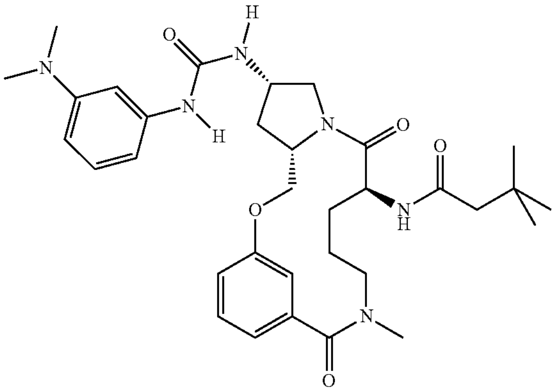
Ex. 552
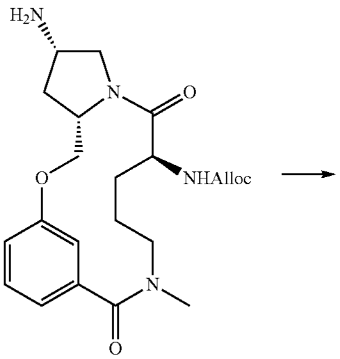
Ex. 594

-continued
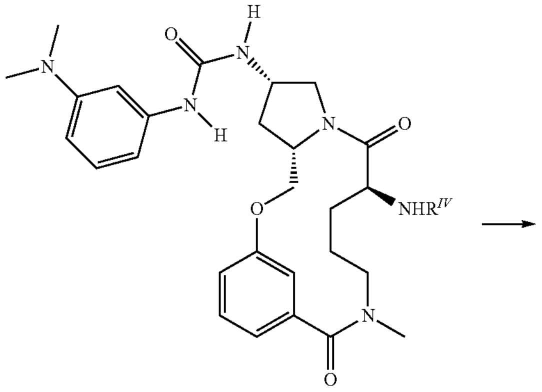
Ex. 553 $R^{IV}$ = Alloc
Ex. 534 $R^{IV}$ = H
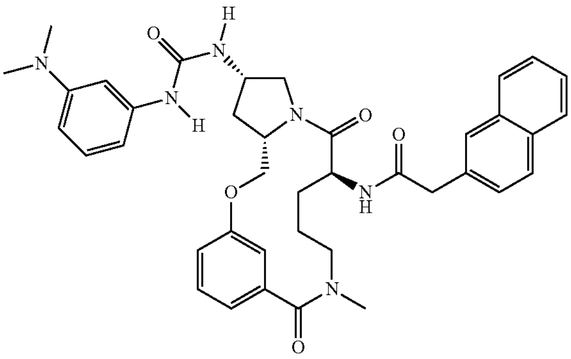
Ex. 508
Core 11a;
Selected Examples prepared on solid support
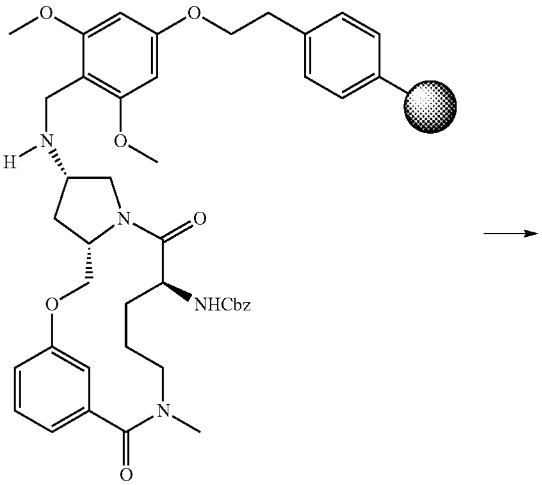
140
-continued
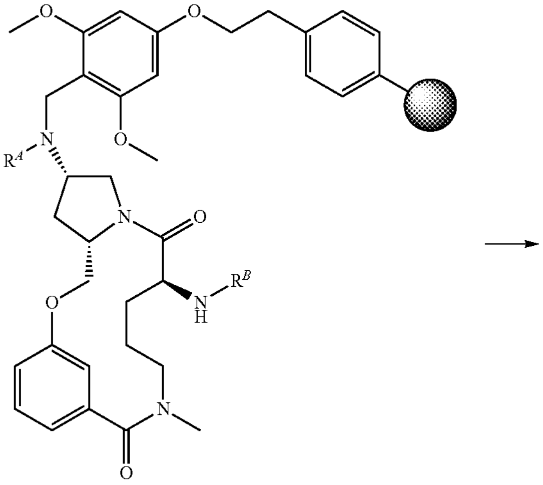
141
definitions of $R^2$ and $R^5$ cf. Tab. 29.1
$R^ANH = R^2$; $R^BNH = R^5$
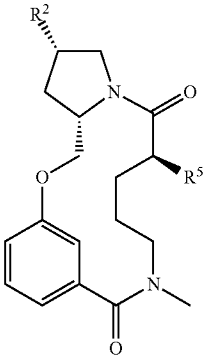
Ex. 186,
Ex. 504 - Ex. 507
Ex. 509 - Ex. 527
Ex. 537 - Ex. 551
Scheme 45
Core 12;
Selected Examples
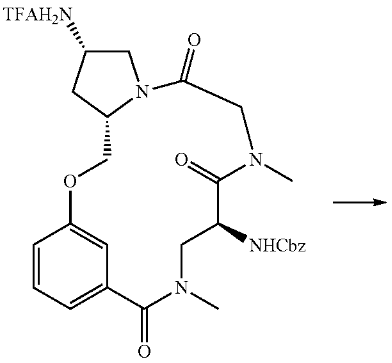
Ex. 197 (TFA salt)

-continued
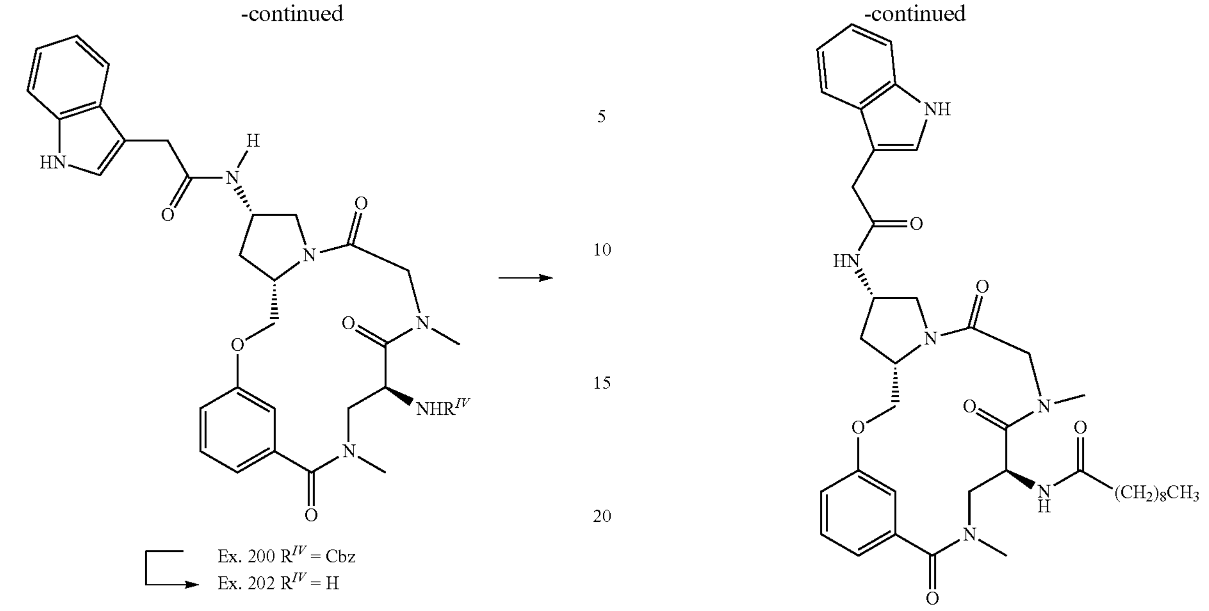
Ex. 200 $R^{IV}$ = Cbz
Ex. 202 $R^{IV}$ = H
Ex. 213
Scheme 46
Core 21;
Examples
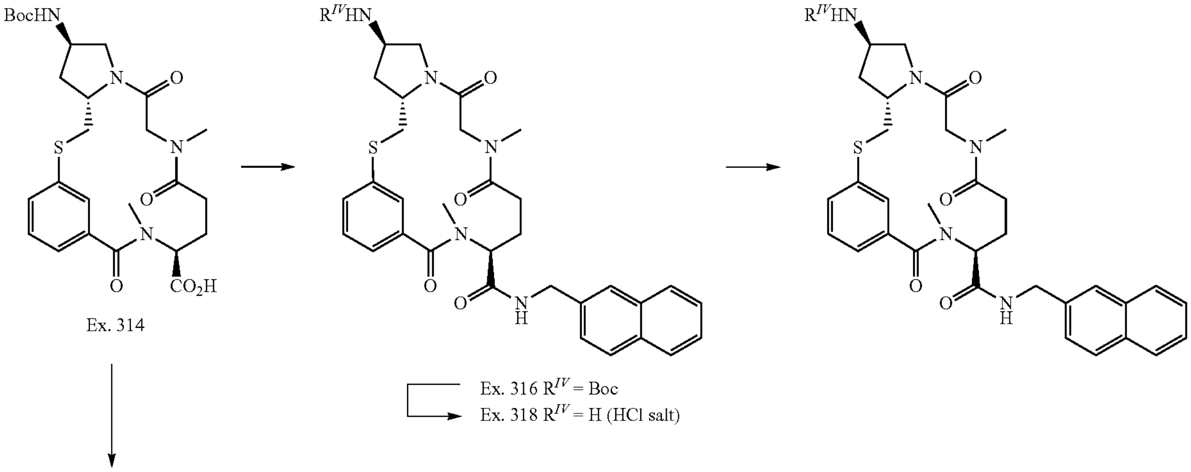
Ex. 314
Ex. 316 $R^{IV}$ = Boc
Ex. 318 $R^{IV}$ = H (HCl salt)

-continued
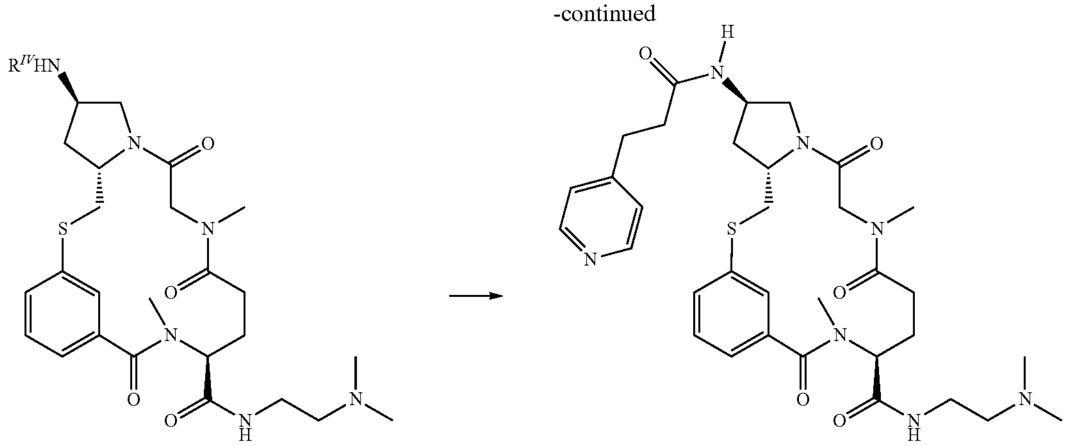
Ex. 317 $R^{IV}$ = Boc
Ex. 319 $R^{IV}$ = H (HCl salt)
Ex.326
Ex. 320 $R^{IV}$ =
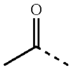
Ex. 321 $R^{IV}$ =
(TFA salt)
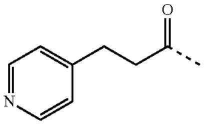
Ex. 322 $R^{IV}$ =
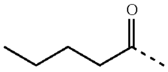
Scheme 47
Core 24a;
Selected Examples
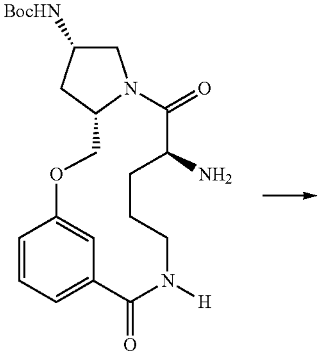
Ex. 380
-continued
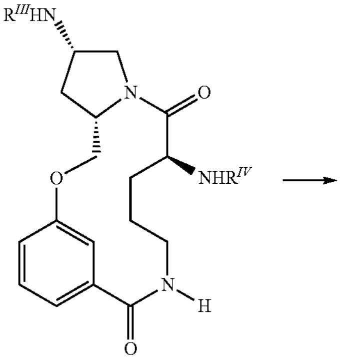
$R^{III}$ = Boc
$R^{III}$ = H
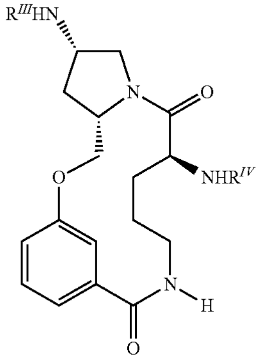

-continued

Ex. 382/
Ex. 384 $R^{IV}$ =
(HCl salt)

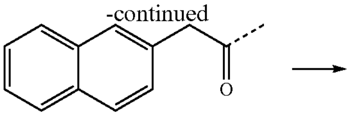

Ex. 386 $R^{III}$ =

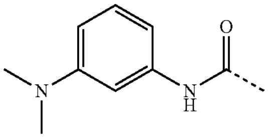

Ex. 389/Ex. 390 $R^{IV}$ =
(HCl salt)

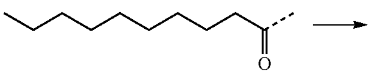

Ex. 391 $R^{III}$ =

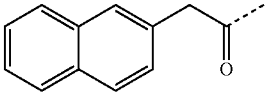

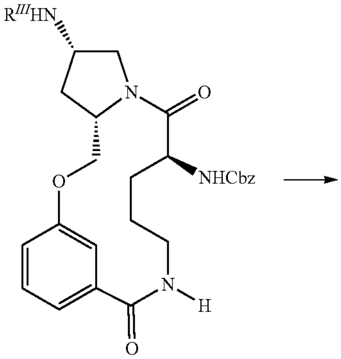

Ex. 379 $R^{III}$ = Boc

Ex. 387 $R^{III}$ = H
(HCl salt)

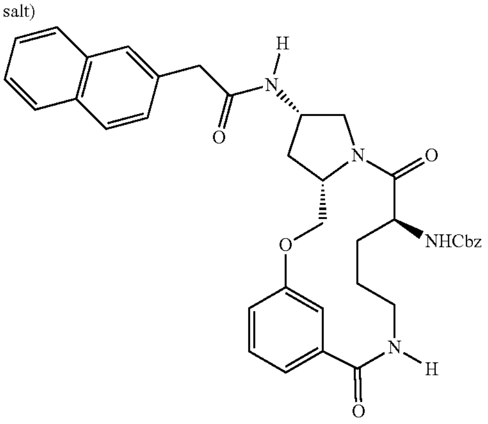

Ex. 388

Biological and Pharmacological Methods

1. $Ca^{2+}$ Assays for the GPCRs Motilin Receptor, Prostaglandin F (FP) Receptor, 5-hydroxytryptamine 2B (5-$HT_{2B}$) Receptor, and Purinoreceptor $P2Y_1$ Assays were performed using on a FLIPR$^{TETRA}$ fluorometric imaging plate reader (Molecular Devices) with ScreenWorks Version 2 (Molecular Devices) as device operating and data analysis software.

Dose dependent agonist and antagonist activities were determined. Percentage activation and percentage inhibition values were determined.

Percentage activation was determined upon initial addition of the sample compounds followed by 10 minutes incubation at 25° C. Following compound incubation, reference agonists were added at $EC_{80}$ to determine percentage inhibition.

Reference agonists were purchased from reputable commercial vendors and prepared according to each ligand's specifications. All handling of ligands were done to ensure proper control throughout the experiments.

Example compounds were weighed on a Microbalance (Mettler MX5) and dissolved in 100% DMSO to a final concentration of 2.5 mM and subsequently diluted into the assay buffer.

The Assay buffer was a supplemented HBSS (Hank's Balanced Salt Solution). HBSS was supplemented with 20 mM HEPES (4-(2-hydroxyethyl)-piperazin-1-ethansulfonic acid) and 2.5 mM Probenecid (Sigma P8761).

Assay Plate Seeding:

GPCR assays were performed using $Ca^{2+}$ optimized hematopoietic cell lines (rat) with cultures never exceeding 90% confluency. Cells were harvested and seeded (from cultures at less than 90% confluency) at 50000 cells/well for a 96-well plate (12500 cells/well for 384). After seeding, the assay plates were incubated for forty-five (45) minutes at room temperature. After room temperature incubation, the assay plates were incubated at 37° C. 5% $CO_2$ for 24 hours prior to assaying.

Calcium Dye Loading:

All GPCR assays were performed using Fluo-8 $Ca^{2+}$ dye. $Ca^{2+}$ dye was prepared at 1× dye concentration in GPCR assay buffer. After 24 hours of incubation, cells were washed with GPCR assay buffer, and then $Ca^{2+}$-dye (100 μL/well) was added.

The plates were incubated for 90 minutes at 30° C. 5% $CO_2$ prior to FLIPR assay.

Agonist Assay:

Compound plates were prepared to add 50 μL/well during the agonist assay mode. During the FLIPR assay, 50 μL/well from the compound plate was diluted 3-fold into the existing 100 μL/well from the dye loading step. Therefore all compounds were prepared as 3× the final concentration desired in the assay.

Antagonist Assay:

After completion of the first single addition assay run, assay plate was removed from the FLIPR Tetra and placed at 25° C. for seven (7) minutes before antagonist assay.

Using the $EC_{80}$ values determined during the agonist assay, all pre-incubated sample compound and reference antagonist (if applicable) wells were stimulated at the $EC_{80}$ of the reference agonist. As reference ligands for the first three assays their obvious natural ligands motilin, prostaglandin F2α, and serotonin (5-HT, 5-Hydroxytryptamine) were used; and for the $P2Y_1$ assay 2MeSATP (2-methylthio-adeno-sine 5'-triphosphate, i.e. (2R,3S,4R)-5-(6-amino-2-methylsulfanyl-purin-9-yl)-3,4-dihydroxy-tetrahydrofuran-2-yl]methyl (hydroxy-phosphonooxy-phosphoryl) hydrogen phosphate) was applied.

After the addition of the reference agonist fluorescence was monitored for 180 sec using FLIPR Tetra.

Data Analysis and Results:

From the FLIPR data, with negative control correction enabled, the maximum statistic for each well was exported and percentage activation relative to $E_{max}$ control was calculated.

The results of the GPCR assay are summarized in Table 50.1 to Table 50.4.

2. Assay for the Voltage Gated Ion Channel $K_v1.3$

Assays were performed and analyzed with a FLIPR$^{TETRA}$ device as specified above.

Compounds for inhibition of ion channel $K_v1.3$ were assayed in Jurkat cells recombinantly expressing human $K_v1.3$. For high throughput screening a thallium-sensitive, fluorescence-based assay was used. Cells were incubated with the $Tl^+$ sensitive dye according to the protocol suggested by the manufacturer (FluxOR potassium ion channel assay, Invitrogen AG). Channel activation was carried out as suggested by the supplier by depolarization, accomplished by increasing the extracellular potassium concentration (thallium sulfate containing buffer at concentrations between 10-15 mM $Tl^+$ and 30 mM $K_2SO_4$, FluxOR potassium ion channel assay, Invitrogen AG). To identify blockers of this ion channel the cells were incubated with different concentrations of compounds 5 min before increasing the potassium and thallium concentration. The fluorescence signals by increasing potassium were then compared in the absence and presence of compounds. Dose response curves were established by adding different concentrations of compounds and analyzing the signal. As reference $K_v$1.3 blockers margatoxin and quinidine in Cl-free buffer were used as described in the literature.

The results of the $K_v$1.3 assay are depicted in Table 51 below.

3. Assays for the Wnt-Pathway

For determining the activity of the test compounds on the Wnt-pathway each substances war subjected to two distinct assays: The first (Wnt/Beta-Catenin) assay screened for inhibitors of the Wnt-pathway while the second (MAPK/MEK/B-raf) was conducted in order to confirm that the test compounds modulate the β-catenin-dependent, canonical Wnt pathway and are not acting via a possibly competing β-catenin-independent, noncanonical Wnt messaging system. All examples were inactive in this negative control.

Both assays were performed and analyzed with a Tecan Safire$^2$ fluorescence plate reader.

The results are shown in Table 52 below.

Wnt/Beta-Catenin (APC−/−)—LEF-TCF-bla SW480—Inhibitor Screen, Constitutively Activated LEF-TCF-bla SW480 cells are thawed and resuspended in Assay Media (OPTI-MEM, 0.5% dialyzed FBS, 0.1 mM NEAA, 1 mM Sodium Pyruvate, 100 U/mL/100 μg/mL Pen/Strep) to a concentration of 312,500 cells/mL. 4 μL of a 10× serial dilution of ICG-001 (control inhibitor starting concentration, 10,000 nM) or compounds are added to appropriate wells of a TC-Treated assay plate. 32 μL of cell suspension (10,000 cells) is added to the wells. 4 μL of Assay Media is added to all wells to bring the final assay volume to 40 μL. The plate is incubated for 16-24 hours at 37° C./5% $CO_2$ in a humidified incubator. 8 μL of 1 μM Substrate Loading Solution is added to each well and the plate is incubated for 2 hours at room temperature.

MAPK/MEK/B-raf—APl-bla A375—Inhibitor Screen, Constitutively Activated

AP1-bla A375 cells are thawed and resuspended in Assay Media (OPTI-MEM, 0.5% dialyzed FBS, 0.1 mM NEAA, 1 mM Sodium Pyruvate, 100 U/mL/100 μg/mL Pen/Strep) to a concentration of 312,500 cells/mL. 4 μL of a 10× serial dilution of Raf1 Kinase Inhibitor (control inhibitor starting concentration, 10,000 nM) or compounds are added to appropriate wells of a TC-Treated assay plate. 32 μL of cell suspension (10,000 cells) is added to the wells. 4 μL of Assay Media is added to all wells to bring the final assay volume to 40 μL. The plate is incubated for 16-24 hours at 37° C./5% $CO_2$ in a humidified incubator. 8 μL of 1 μM Substrate Loading Solution is added to each well and the plate is incubated for 2 hours at room temperature.

4. Plasma and Metabolic Stability Assays

Example compounds were dissolved in DMSO/$H_2O$ 90:10 to a final concentration of 10 mM for plasma stability determination and metabolic stability determination.

The assays were conducted according to literature precedents (F. P. Guengerich, *Analysis and Characterization of Enzymes*; in: Principles and Methods of Toxicology; A. W. Hayes (Ed.) Raven Press: New York, 1989, 777-813; R. Singh et al., *In vitro metabolism of a potent HIV-protease inhibitor* (141*W*94) *using rat, monkey and human liver S9, Rapid Commun. Mass Spectrom.* 1996, 10, 1019-1026).

Results of the stability assays are listed in Table 53 below.

Plasma Stability Assay

Human plasma (3-5 donors, Blutspendedienst SRK, Basel) and CD-1 mouse plasma (mixed gender pool >50 animals, Innovative Research, CA, USA) are both sodium citrate stabilized. The assay is performed in triplicates at 10 μM compound concentration and 37° C. Samples are taken at 0, 15, 60, and 240 minutes and stopped by precipitation with 2 volumes of acetonitrile. The supernatant is collected, evaporated and reconstituted in a 5% acetonitrile solution to be analyzed by HPLC/MS/MS. The resulting peak area counts are expressed in percent of the 0 value and used to determine the endpoint stability in % and the half life in minutes. In order to monitor assay integrity the degradation of propantheline is assayed with every experimental set.

Metabolic Stability Assay

Microsomes from a human 50 donor mixed gender pool and 1:1 mixtures of microsomes from CD-1 mouse single-gender pools are purchased from Celsis (Belgium). The enzymatic reaction is performed in a buffer containing an NADPH regeneration system and microsomes with the following end concentrations: 100 mM potassium phosphate buffer (all from Sigma), 1 mg/mL glucose-6-phosphate, 1 mg/mL β-nicotinamide adenine dinucleotide phosphate (NADP), 0.65 mg/mL magnesium chloride, 0.8 units/mL of glucose-6-phosphate dehydrogenase (prediluted with 5 mM citrate buffer), 10 μM compound and 1 mg/ml microsomal protein. Compounds are incubated at 37° C. in duplicates and samples are taken after 0, 20 and 60 minutes. After acetonitrile precipitation (2 volumes) and HPLC/MS/MS analysis metabolic turnover is expressed in % of the initial 0 minutes value and half life T½ (min) is calculated. Verapamil for human and propranolol for mouse are used as reference and are assayed with every experimental set.

5. Pharmacokinetic Study (PK) Analysis

Pharmacokinetic analyses after single intravenous (i.v.) and two different peroral (p.o.) administrations were performed for the test compounds. 240 grams (±10 gram) male SD rats were catheterized and used in the study. The vehicle, Solutol HS-15/0.9% saline (5:95), was added to give a final concentration of 0.33 mg/ml of the compounds for i.v. application, and 0.5 or 2.0 mg/ml for p.o. applications. The volumes used for applications were 3 ml/kg i.v. and 10 ml/kg p.o. resulting in a final dose of 1 mg/kg for the intravenous dose and 5 or 20 mg/kg for the peroral doses.

Blood samples were withdrawn via the catheter at 1) predose, 5, 15, 30, 60, 120, 240, and 480 minutes for the i.v. application and 2) predose, 15, 30, 60, 120, 240, 480 and 720 minutes for the p.o. applications. Plasma was prepared by centrifugation of heparinized whole blood. Plasma samples (~120 μl each time point, Li-Heparin, 20 IE/ml) were stored at −80° C. until HPLC-MSMS analysis.

Preparation of the Plasma Calibration Samples:

"Blank" rat plasma from untreated animals was used. Aliquots of plasma of 50 μL each were spiked with Internal Standard (ISTD) and with known amounts test compounds in order to obtain 11 plasma calibration samples in the range 0.25-4000 ng/mL.

Preparation of Plasma Samples:

To 50 μL of sample from treated animals 20 μL of internal standard were added. After mixing with 200 μL of acetonitrile, 2% HCOOH were added and each sample was vortexed for several seconds. Precipitated material was removed by centrifugation for 10 min (13200 rpm), the supernatant removed and dried under a constant flow of N2 (Porvair, MiniVap). To reconstitute the dried samples, 200 μL of [DMSO/acetonitrile/$H_2O$, 4/4/2 (v/v/v)+2% HCOOH] were added and the sample was shaken for at least 5 minutes.

LC-MSMS Analysis of Samples:

Reconstituted samples were analysed by HPLC/MSMS on a reverse phase analytical column (BEH C18, 100×2.1 mm, 1.7 μm, Waters). Mobile phase A: $H_2O$/acetonitrile (95:5, v:v) 0.1% formic acid, mobile phase B: Acetonitrile/$H_2O$ (95:5, v:v) 0.1% formic acid. Compounds were eluted from the column by using a gradient from 1% B to 60% B in 2.5 min.).

Pharmacokinetic Evaluation:

PK analysis was performed on mean values (generally n=3) using WinNonLin software (Version 5.3, Pharsight Corporation). The area under the curve AUC was calculated by the linear trapezoidal rule (linear interpolation, uniform weighting). $AUC_{(t-\infty)}$ was estimated as Ct/b (b: elimination rate constant). $AUC_{(t-\infty)}$ is the sum of $AUC_{(0-t)}$ and $AUC_{(t-\infty)}$. Elimination half-life was calculated by the linear regression on at least three data points during the elimination phase. The time intervals selected for the half-life determinations were evaluated by the correlation coefficient ($r^2$), which should be at least above 0.85 and ideally above 0.96.

In case of i.v. administration the initial concentration at $t_{zero}$ was determined by extrapolation of the curve through the first two time points. Finally bioavailability after p.o. administration was calculated from the dose normalized $AUC_{(0-\infty)}$ ration after p.o. versus i.v. administration.

The results are shown in Table 54 below.

TABLE 50.1

Motilin Receptor Assay

| No | Antagonist activity [% Inhibition at 10 μM] | Antagonist activity $IC_{50}$ [μM]] |
|---|---|---|
| Ex. 11 | 79 | 0.78 |
| Ex. 12 | 95 | 2.7 |
| Ex. 48 | 29 | n.d. |
| Ex. 49 | 98 | 0.16 |
| Ex. 482 | 62 | 1.1 |
| Ex. 483 | 100 | 0.023 |
| Ex. 484 | 99 | 0.20 |
| Ex. 485 | 93 | 0.28 |
| Ex. 486 | 93 | 0.18 |
| Ex. 487 | 47 | n.d. |
| Ex. 488 | 23 | n.d. |
| Ex. 495 | 26 | n.d. |
| Ex. 496 | 31 | n.d. |
| Ex. 497 | 24 | n.d. |

TABLE 50.2

FP Receptor Assay (continued on the following pages)

| No | Antagonist activity [% Inhibition at 10 μM] | Antagonist activity $IC_{50}$ [μM] |
|---|---|---|
| Ex. 12 | 44 | n.d. |
| Ex. 184 | 74 | 0.52 |

TABLE 50.2-continued

FP Receptor Assay (continued on the following pages)

| No | Antagonist activity [% Inhibition at 10 μM] | Antagonist activity $IC_{50}$ [μM] |
|---|---|---|
| Ex. 186 | 53 | 1.2 |
| Ex. 200 | 38 | 28 |
| Ex. 213 | 78 | 1.7 |
| Ex. 386 | 85 | 2.7 |
| Ex. 388 | 99 | 0.32 |
| Ex. 391 | 93 | 0.25 |
| Ex. 504 | 62 | 0.441 |
| Ex. 505 | 47 | 0.64 |
| Ex. 506 | 55 | 2.2 |
| Ex. 507 | 51 | 1.1 |
| Ex. 508 | 93 | 0.43 |
| Ex. 509 | 54 | 2.1 |
| Ex. 510 | 42 | 1.5 |
| Ex. 511 | 99 | 0.059 |
| Ex. 512 | 97 | 0.120 |
| Ex. 513 | 95 | 0.65 |
| Ex. 515 | 32 | 5.1 |
| Ex. 516 | 97 | 0.59 |
| Ex. 517 | 98 | 0.65 |
| Ex. 518 | 80 | 0.49 |
| Ex. 519 | n.d. | 3.0 |
| Ex. 521 | 81 | 1.0 |
| Ex. 522 | 95 | 0.35 |
| Ex. 523 | 92 | 0.86 |
| Ex. 524 | 85 | 1.7 |
| Ex. 525 | 99 | 0.094 |
| Ex. 526 | 99 | 0.180 |
| Ex. 527 | 73 | 0.204 |
| Ex. 537 | 75 | n.d. |
| Ex. 538 | 80 | n.d. |
| Ex. 539 | 59 | n.d. |
| Ex. 540 | 43 | n.d. |
| Ex. 541 | 65 | n.d. |
| Ex. 542 | 74 | n.d. |
| Ex. 543 | 82 | n.d. |
| Ex. 544 | 81 | n.d. |
| Ex. 545 | 80 | n.d. |
| Ex. 546 | 37 | n.d. |
| Ex. 547 | 47 | n.d. |
| Ex. 548 | 69 | n.d. |
| Ex. 549 | 62 | n.d. |
| Ex. 550 | 73 | n.d. |
| Ex. 551 | 72 | n.d. |
| Ex. 552 | 71 | n.d. |

TABLE 50.3

$5-HT_{2B}$ Receptor Assay

| No | Agonist activity [% activation at 12.5 μM] | Agonist activity $EC_{50}$ [μM] |
|---|---|---|
| Ex. 9 | 48 | 12 |
| Ex. 12 | 36 | 3.3 |
| Ex. 16 | 45 | 6.6 |
| Ex. 30 | 48 | 3.3 |

TABLE 50.4

$P2Y_1$ Receptor Assay

| No | Antagonist [% Inhibition at 10 μM] | Antagonist activity $IC_{50}$ [μM] |
|---|---|---|
| Ex. 316 | 57 | n.d. |
| Ex. 321 | 45 | 7.5 |

TABLE 50.4-continued

| P2Y$_1$ Receptor Assay | | |
|---|---|---|
| No | Antagonist [% Inhibition at 10 μM] | Antagonist activity $IC_{50}$ [μM] |
| Ex. 320 | 19 | n.d. |
| Ex. 322 | 60 | n.d. |

TABLE 51

| $K_{V1,3}$ Ionchannel Assay | | |
|---|---|---|
| No | $K_{V1,3}$ antagonist activity [% Inhibition at 10 μM] | $K_{V1,3}$ antagonist activity IC50 [μM]] |
| Ex. 166 | 20 | n.d. |
| Ex. 168 | 44 | 1.69 |
| Ex. 170 | 10 | n.d. |

TABLE 51-continued

| $K_{V1,3}$ Ionchannel Assay | | |
|---|---|---|
| No | $K_{V1,3}$ antagonist activity [% Inhibition at 10 μM] | $K_{V1,3}$ antagonist activity IC50 [μM]] |
| Ex. 171 | 12 | n.d. |
| Ex. 177 | 54 | 3.5 |

TABLE 52

| Wnt-Pathway Assays | | | |
|---|---|---|---|
| No | TCF/LEF receptor gene activity [% inhibition at 10 μM] | TCF/LEF receptor gene activity $IC_{50}$ [μM] | AP receptor gene activity $IC_{50}$ [μM] |
| Ex. 501 | 100 | 1.1 | >50 |
| Ex. 502 | 82 | 5.5 | >50 |
| Ex. 503 | 68 | 5.8 | >50 |

TABLE 53

Plasma Stability and Metabolic Stability Assays of Selected Examples

| | Plasma Stability | | | | Metabolic Stability | | | |
|---|---|---|---|---|---|---|---|---|
| No | T½ [min] hum | 240 min hum [% remain.] | T½ [min] mouse/ (rat) | 240 min mouse/ (rat) [% remain.] | T½ [min] hum | 60 min hum [% remain.] | T½ [min] mouse/ (rat) | 60 min mouse/ (rat) [% remain.] |
| Ex. 9 | 240 | 99 | 240 | 93 | 32 | 20 | 60 | 80 |
| Ex. 11 | 240 | 100 | 240 | 100 | 60 | 74 | 60 | 77 |
| Ex. 12 | 240 | 99 | 240 | 100 | 17 | 7 | 35 | 33 |
| Ex. 16 | 240 | 95 | 240 | 97 | 38 | 31 | 60 | 79 |
| Ex. 30 | 240 | 85 | 240 | 100 | 22 | 2 | 60 | 55 |
| Ex. 37 | 240 | 77 | 240 | 100 | 60 | 100 | 60 | 100 |
| Ex. 43 | 240 | 82 | 240 | 89 | 60 | 100 | 60 | 98 |
| Ex. 49 | 240 | 83 | 240 | 96 | 24 | 10 | 60 | 83 |
| Ex. 78 | 240 | 65 | 240 | 100 | 60 | 78 | 60 | 100 |
| Ex. 91 | 240 | 96 | 240 | 88 | 60 | 91 | 60 | 95 |
| Ex. 93 | 240 | 100 | 240 | 100 | 24 | 1 | 29 | 15 |
| Ex. 95 | 240 | 100 | 240 | 93 | 60 | 76 | 60 | 94 |
| Ex. 98 | 240 | 100 | 240 | 78 | 60 | 97 | 60 | 100 |
| Ex. 102 | 240 | 65 | 240 | 75 | 23 | 4 | 42 | 39 |
| Ex. 103 | 240 | 97 | 240 | 75 | 35 | 22 | 36 | 25 |
| Ex. 138 | 240 | 89 | 240 | 78 | 60 | 62 | 60 | 99 |
| Ex. 184 | 240 | 66 | 240 | 58 | 15 | 0 | 22 | 0 |
| Ex. 200 | 240 | 91 | 240 | 100 | 27 | 12 | 30 | 26 |
| Ex. 208 | 240 | 98 | 240 | 90 | 60 | 84 | 60 | 100 |
| Ex. 213 | n.d. | n.d. | n.d. | n.d. | 16 | 0 | 17 | 4 |
| Ex. 230 | 240 | 100 | 240 | 95 | 60 | 61 | 60 | 90 |
| Ex. 260 | 240 | 100 | 240 | 100 | 37 | 19 | 60 | 69 |
| Ex. 262 | 240 | 100 | 240 | 93 | 21 | 0 | 23 | 4 |
| Ex. 264 | 240 | 94 | 240 | 88 | n.d. | n.d. | 42 | 32 |
| Ex. 266 | 240 | 92 | 240 | 74 | 60 | 100 | 60 | 98 |
| Ex. 267 | 240 | 75 | 240 | 79 | 60 | 99 | 60 | 100 |
| Ex. 272 | 240 | 95 | 240 | 92 | 60 | 65 | 60 | 81 |
| Ex. 482 | 240 | 100 | 240 | 100 | 22 | 11 | 60 | 84 |
| Ex. 483 | 240 | 100 | 240 | 100 | 60 | 55 | 60 | 85 |
| Ex. 484 | 240 | 100 | 240 | 90 | 21 | 11 | 60 | 100 |
| Ex. 485 | 240 | 100 | 240 | 99 | 14 | 8 | 17 | 11 |
| Ex. 486 | 240 | 100 | 240 | 98 | 23 | 13 | 60 | 100 |
| Ex. 168 | 240 | 85 | 240 | 99 | 25 | 17 | 26 | 21 |
| Ex. 170 | 240 | 92 | 240 | 100 | 60 | 60 | 60 | 86 |
| Ex. 167 | n.d | n.d. | 35 | 17 | 60 | 58 | 60 | 65 |
| Ex. 505 | 240 | 100 | 240 | 98 | 21 | 9 | 13 | 3 |
| Ex. 511 | 240 | 100 | n.d. | n.d. | 2 | 1 | 14 | 14 |
| Ex. 512 | 240 | 86 | n.d. | n.d. | 17 | 8 | 12 | 10 |
| Ex. 525 | 240 | 100 | n.d. | n.d. | 16 | 13 | 25 | 29 |
| Ex. 527 | 109 | 26 | n.d. | n.d. | 22 | 23 | 20 | 24 |
| Ex. 533 | 240 | 95 | 240 | 100 | 60 | 59 | 60 | 93 |

TABLE 53-continued

Plasma Stability and Metabolic Stability Assays of Selected Examples

| No | Plasma Stability T½ [min] hum | 240 min hum [% remain.] | T½ [min] mouse/ (rat) | 240 min mouse/ (rat) [% remain.] | Metabolic Stability T½ [min] hum | 60 min hum [% remain.] | T½ [min] mouse/ (rat) | 60 min mouse/ (rat) [% remain.] |
|---|---|---|---|---|---|---|---|---|
| Ex. 561 | 240 | 99 | 240 | 100 | 39 | 42 | 60 (56) | 79 (53) |
| Ex. 568 | 240 | 97 | 240 | 89 | 60 | 53 | 60 (60) | 60 (57) |
| Ex. 563 | 240 | 88 | 240 | 81 | 8 | 1 | 12 (31) | 4 (32) |
| Ex. 570 | 240 | 92 | 240 | 100 | 13 | 20 | 60 (60) | 69 (76) |
| Ex. 571 | 240 | 86 | 240 | 89 | 60 | 90 | 60 (60) | 74 (88) |
| Ex. 572 | 240 | 85 | 240 | 100 | 54 | 49 | 60 (60) | 54 (92) |
| Ex. 574 | 240 | 91 | 240 | 95 | 60 | 94 | 60 (60) | 93 (92) |
| Ex. 577 | 240 | 87 | 240 | 101 | 47 | 41 | 27 | 25 |
| Ex. 578 | 240 | 100 | 240 | 86 | 52 | 46 | 60 | 55 |
| Ex. 580 | 240 | 70 | (240) | (79) | 60 | 100 | n.d. | n.d. |
| Ex. 581 | 240 | 70 | (210) | (77) | 60 | 98 | 60 | 100 |
| Ex. 582 | 240 | 100 | 240 | 96 | 60 | 100 | 60 | 98 |
| Ex. 583 | 240 | 91 | 240 | 83 | 60 | 100 | 60 | 95 |
| Ex. 368 | 240 | 72 | (240) | (100) | 60 | 83 | 60 (60) | 82 (98) |
| Ex. 369 | 240 | 85 | (240) | (79) | 60 | 100 | 60 (60) | 80 (100) |
| Ex. 372 | 240 | 68 | (240) | (100) | 46 | 43 | 60 (60) | 73 (72) |
| Ex. 373 | 240 | 55 | (240) | (100) | 12 | 12 | 36 (7) | 39 (0) |
| Ex. 374 | 240 | 57 | (240) | (82) | 60 | 61 | 60 (60) | 94 (90) |
| Ex. 376 | 240 | 90 | (240) | (89) | 60 | 79 | 60 (60) | 91 (78) |
| Ex. 377 | 240 | 95 | (240) | (100) | 60 | 72 | 60 (60) | 86 (97) |
| Ex. 378 | 240 | 48 | (240) | (100) | 60 | 65 | 60 (60) | 87 (72) |
| Ex. 403 | 240 | 100 | 240 | 65 | 36 | 37 | 57 | 55 |
| Ex. 406 | 240 | 75 | 240 | 89 | 60 | 77 | 60 (60) | 94 (96) |
| Ex. 407 | 240 | 80 | 240 | 98 | 51 | 47 | 60 | 84 |

TABLE 54

PK-Data of Selected Examples

| | | Ex. 561 | | | Ex. 568 Route | | | Ex. 571 | | |
|---|---|---|---|---|---|---|---|---|---|---|
| Parameter | mg/kg | iv 1 | po 5 | po 20 | iv 1 | po 5 | po 20 | iv 1 | po 5 | po 20 |
| $R^2$ | | 0.997 | 1.000 | 0.968 | 0.979 | 0.999 | 0.992 | 1.000 | 0.990 | 0.991 |
| $T_{1/2}$ (terminal) | hr | 2.11 | 3.00 | 2.71 | 1.67 | 1.92 | 2.07 | 1.70 | 2.18 | 2.30 |
| Tmax | hr | 0.08 | 0.50 | 0.25 | 0.08 | 0.25 | 0.25 | 0.08 | 0.25 | 0.25 |
| Cmax | ng/mL | 183.67 | 67.00 | 248.00 | 194.67 | 64.33 | 379.67 | 643.67 | 340.33 | 1516.67 |
| Cmax dose normalized | kg*ng/mL/mg | 183.67 | 13.40 | 12.40 | 194.67 | 12.87 | 18.98 | 643.67 | 68.07 | 75.83 |
| $C_0$ | ng/mL | 240.24 | | | 284.59 | | | 932.47 | | |
| V (terminal) | mL/kg | 13831.40 | | | 14320.56 | | | 7618.59 | | |
| $AUC_{(t-\infty)}$ dose normalized | hr*kg*ng/mL/mg | 219.89 | 24.00 | 36.88 | 167.93 | 29.83 | 36.22 | 321.32 | 93.34 | 87.49 |
| Bioavailability | % | | 10.9 | 16.8 | | 17.8 | 21.6 | | 29.0 | 27.2 |

The invention claimed is:

1. Compounds consisting of a cyclic arrangement of the building blocks A, B and C and represented by the general formula Ia Ia

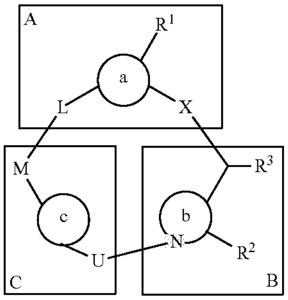

wherein building block A ("Template") is represented by

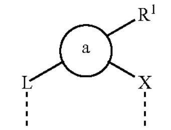

building block B ("Modulator") is represented by

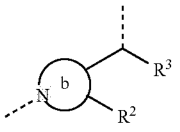

building block C ("Bridge") is represented by

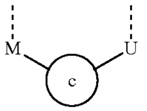

wherein

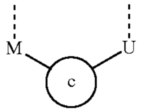

is further represented by respectively

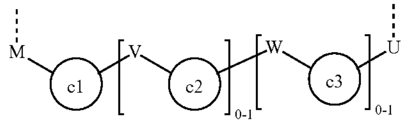

and wherein

M represents a divalent or trivalent radical selected from the group of

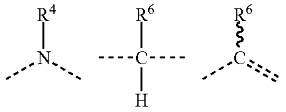

forming an integral part of the

M-L connectivity which in turn represents a divalent radical selected from the group of

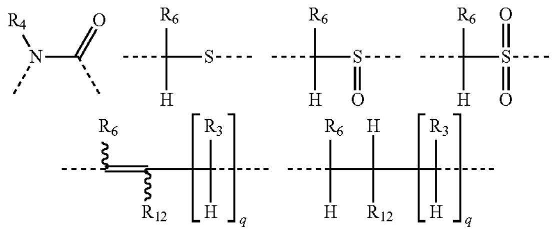

U represents a divalent radical selected from the group of

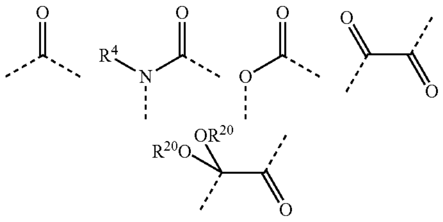

X represents a divalent radical selected from the group of

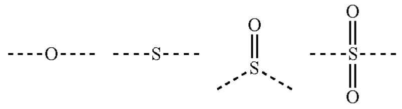

V and W are independently representing a divalent radical selected from the group of

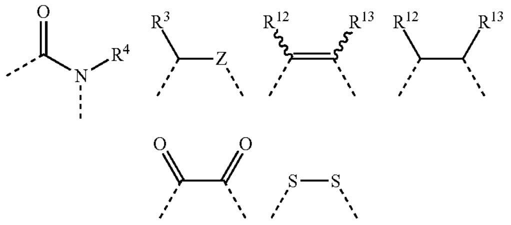

and wherein said building block A is a bivalent radical selected from the group consisting of

A1

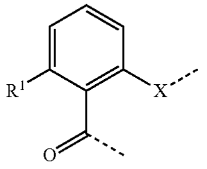

(a1)

A2

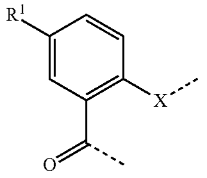

(a1)

A3

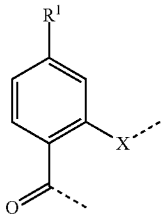

(a1)

A4

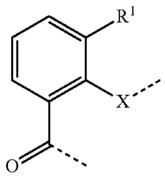

(a1)

-continued
A5
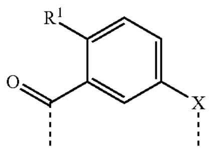
(a1)
A6
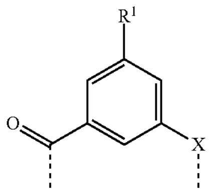
(a1)
A7
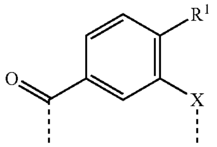
(a1)
A8
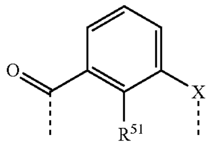
(a1)
A9
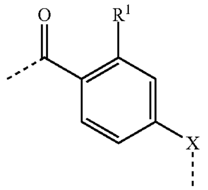
(a1)
A10
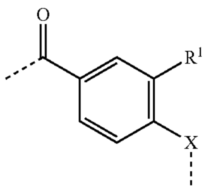
(a1)
A11
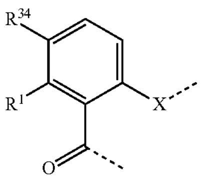
(a1)
-continued
A12
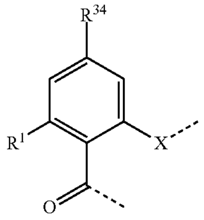
(a1)
A13
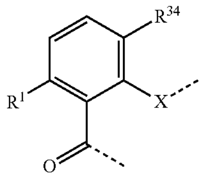
(a1)
A14
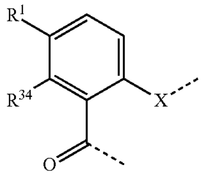
(a1)
A15
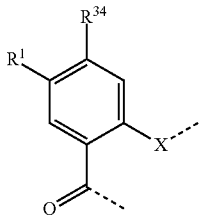
(a1)
A16
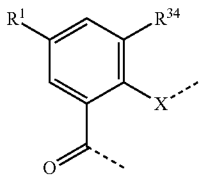
(a1)
A17
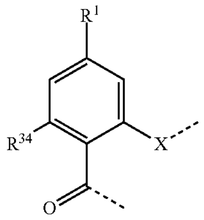
(a1)

-continued
A18
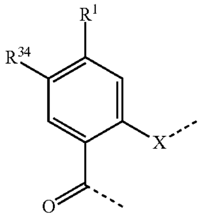
(a1)
A19
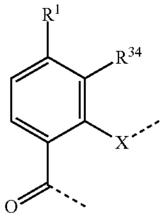
(a1)
A20
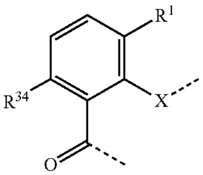
(a1)
A21
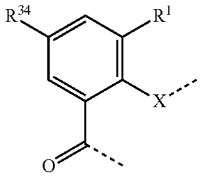
(a1)
A22
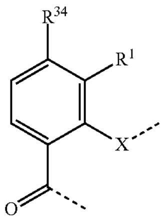
(a1)
A23
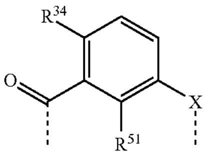
(a1)
-continued
A24
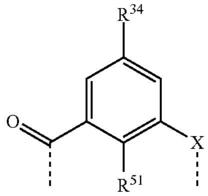
(a1)
A25
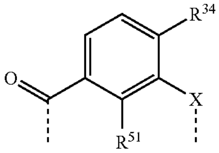
(a1)
A26
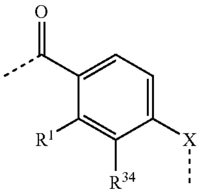
(a1)
A27
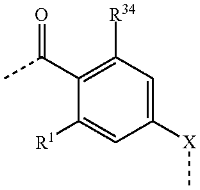
(a1)
A28
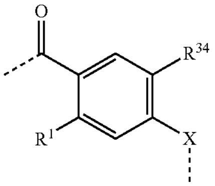
(a1)
A29
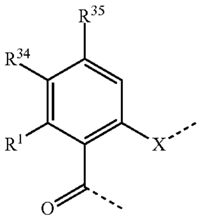
(a1)

-continued
A30
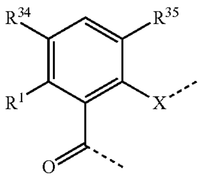
(a1)
A31
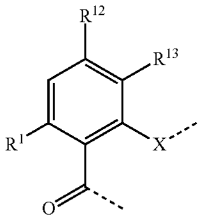
(a1)
A32
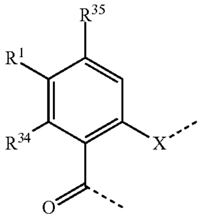
(a1)
A33
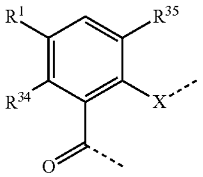
(a1)
A34
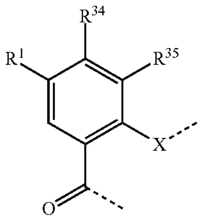
(a1)
A35
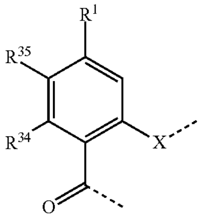
(a1)
-continued
A36
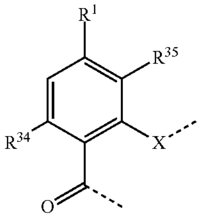
(a1)
A37
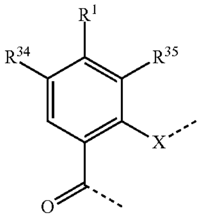
(a1)
A38
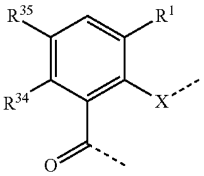
(a1)
A39
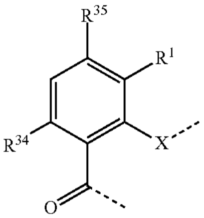
(a1)
A40
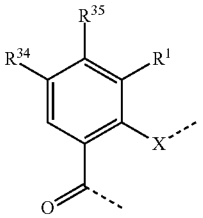
(a1)
A41
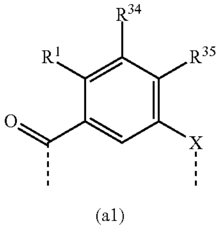
(a1)

-continued
A42
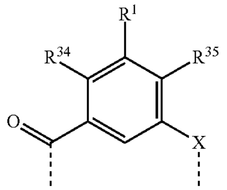
(a1)
A43
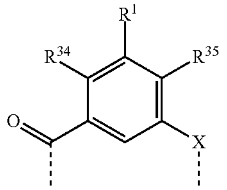
(a1)
A44
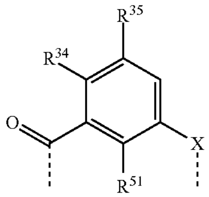
(a1)
A45
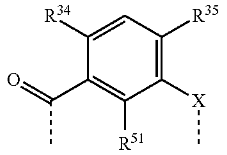
(a1)
A46
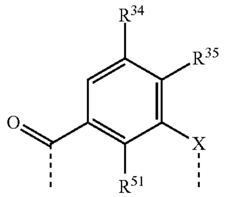
(a1)
A47
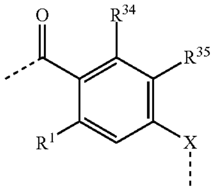
(a1)
A48
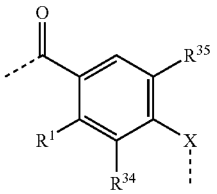
(a1)
-continued
A49
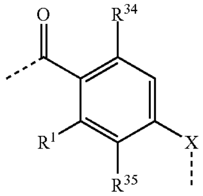
(a1)
A50
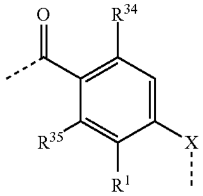
(a1)
A51
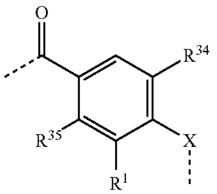
(a1)
A52
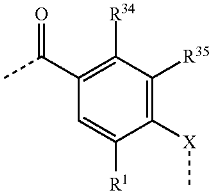
(a1)
A53
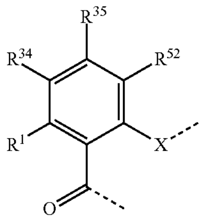
(a1)
A54
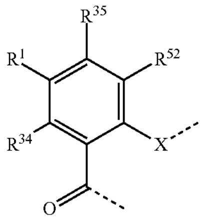
(a1)

-continued
A55
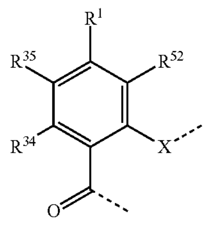
(a1)
A56
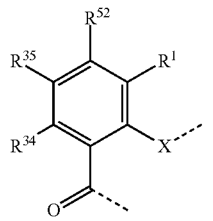
(a1)
A57
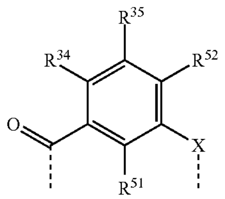
(a1)
A58
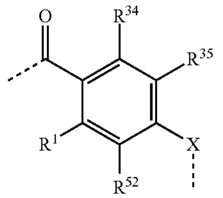
(a1)
A59
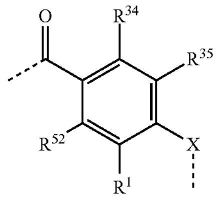
(a1)
A60
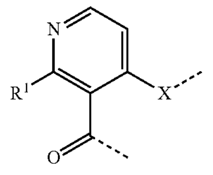
(a2)
-continued
A61
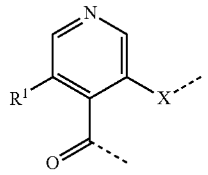
(a2)
A62
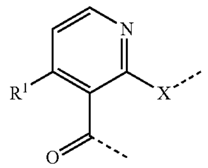
(a2)
A63
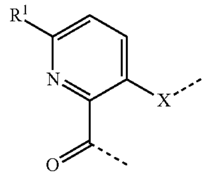
(a2)
A64
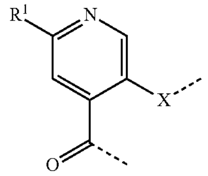
(a2)
A65
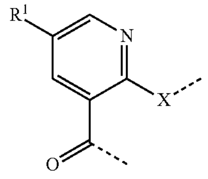
(a2)
A66
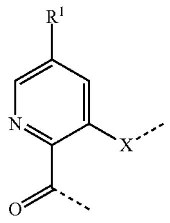
(a2)
A67
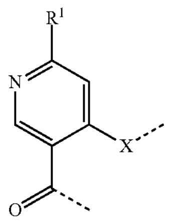
(a2)

-continued
A68
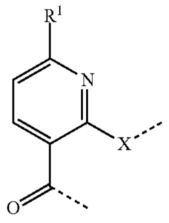
(a2)
A69
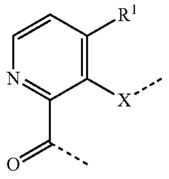
(a2)
A70
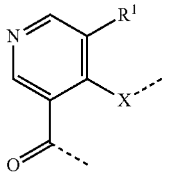
(a2)
A71
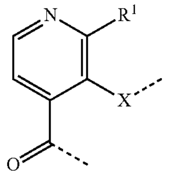
(a2)
A72
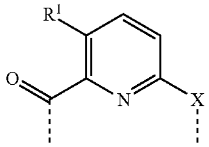
(a2)
A73
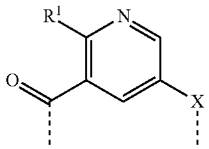
(a2)
A74
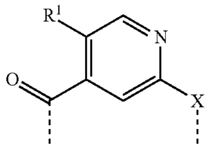
(a2)
-continued
A75
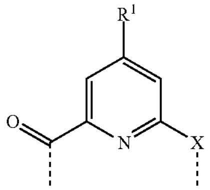
(a2)
A76
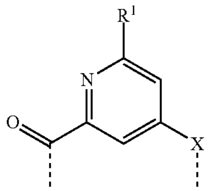
(a2)
A77
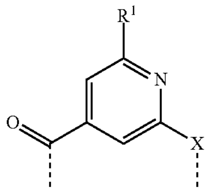
(a2)
A78
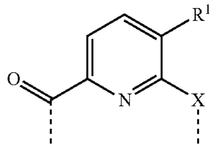
(a2)
A79
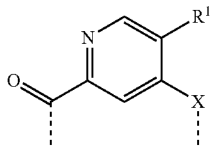
(a2)
A80
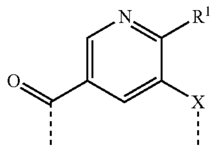
(a2)
A81
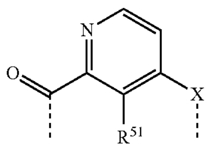
(a2)

A82
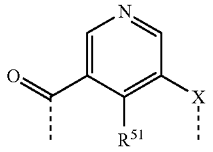
(a2)
A83
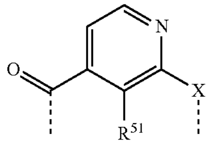
(a2)
A84
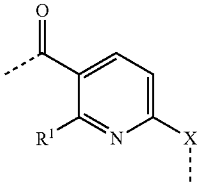
(a2)
A85
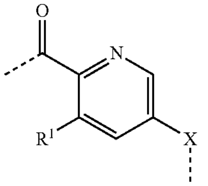
(a2)
A86
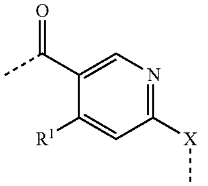
(a2)
A87
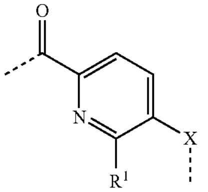
(a2)
A88
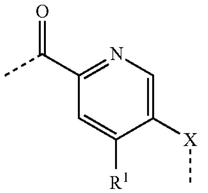
(a2)
A89
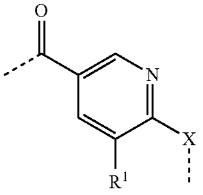
(a2)
A90
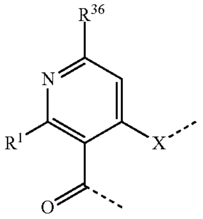
(a2)
A91
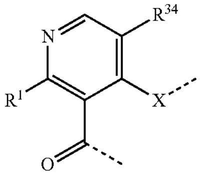
(a2)
A92
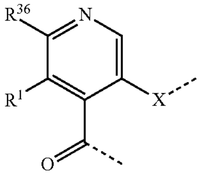
(a2)
A93
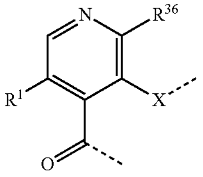
(a2)
A94
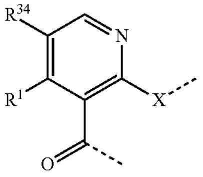
(a2)

-continued
A95
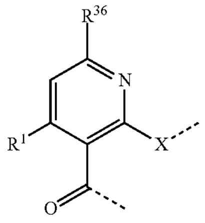
(a2)
A96
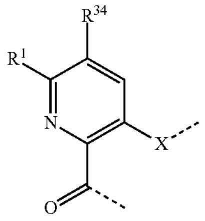
(a2)
A97
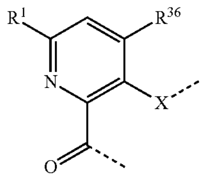
(a2)
A98
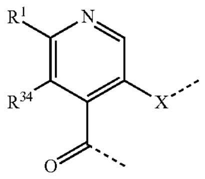
(a2)
A99
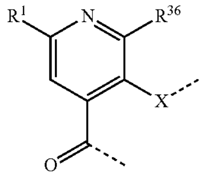
(a2)
A100
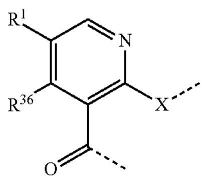
(a2)
-continued
A101
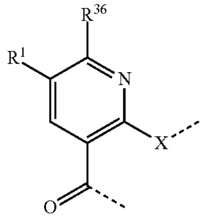
(a2)
A102
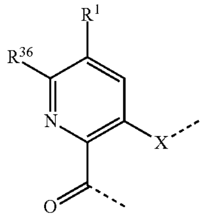
(a2)
A103
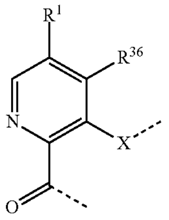
(a2)
A104
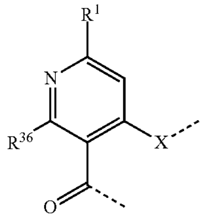
(a2)
A105
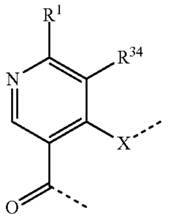
(a2)
A106
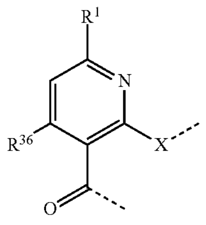
(a2)

-continued
A107
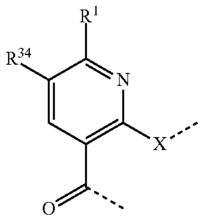
(a2)
A108
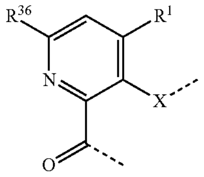
(a2)
A109
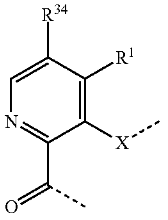
(a2)
A110
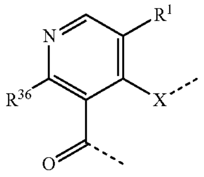
(a2)
A111
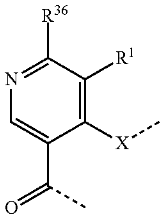
(a2)
A112
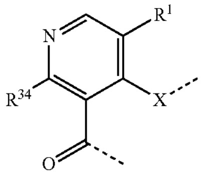
(a2)
-continued
A113
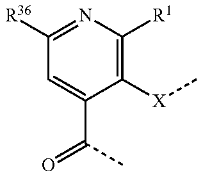
(a2)
A114
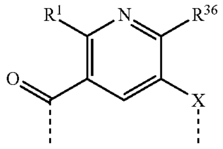
(a2)
A115
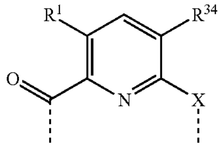
(a2)
A116
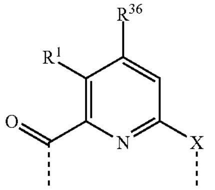
(a2)
A117
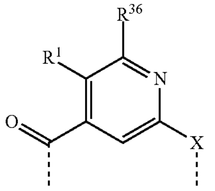
(a2)
A118
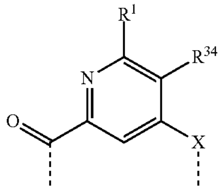
(a2)
A119
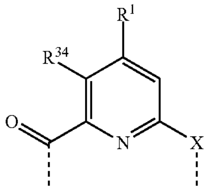
(a2)

-continued
A120
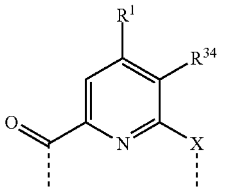
(a2)
A121
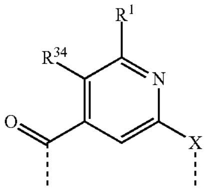
(a2)
A122
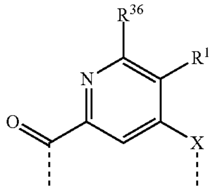
(a2)
A123
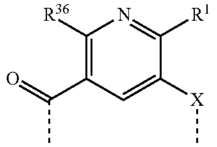
(a2)
A124
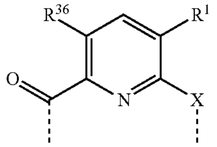
(a2)
A125
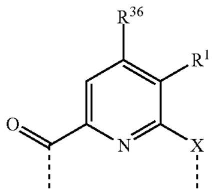
(a2)
A126
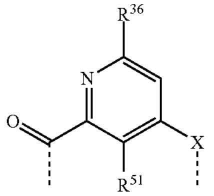
(a2)
-continued
A127
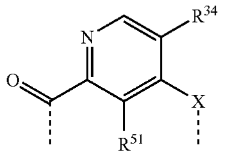
(a2)
A128
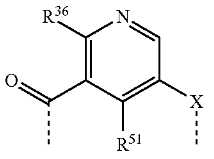
(a2)
A129
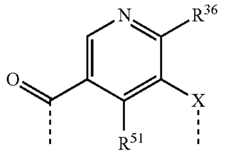
(a2)
A130
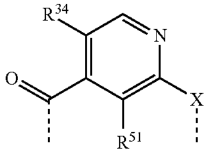
(a2)
A131
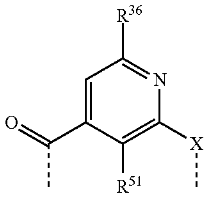
(a2)
A132
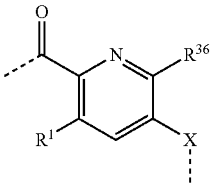
(a2)
A133
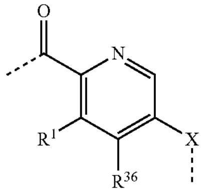
(a2)

-continued
A134
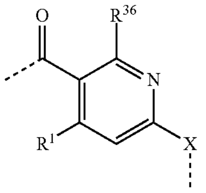
(a2)
A135
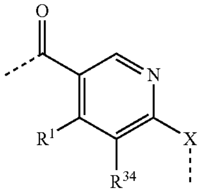
(a2)
A136
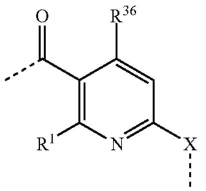
(a2)
A137
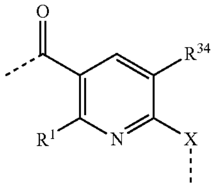
(a2)
A138
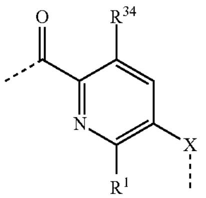
(a2)
A139
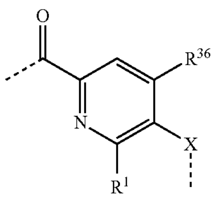
139
(a2)
-continued
A140
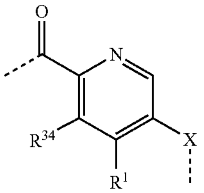
(a2)
A141
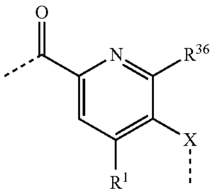
(a2)
A142
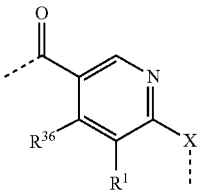
(a2)
A143
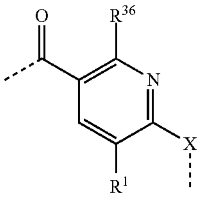
(a2)
building block B is a bivalent radical selected from the group of
B4
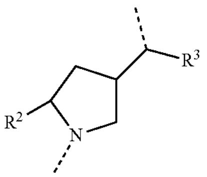
(b3)
B5
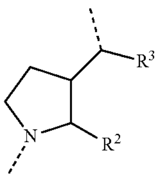
(b3)

-continued

B6

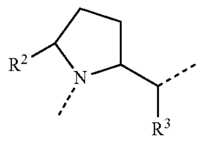

(b3)

B7

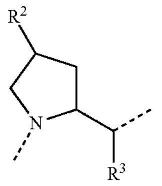

(b3)

B8

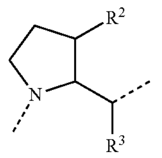

(b3)

B9

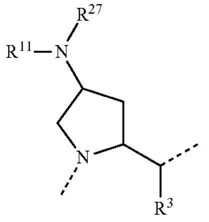

(b3)

building block C is a bivalent radical selected from the group of

C9

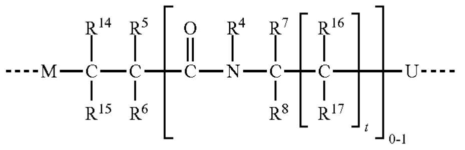

C19

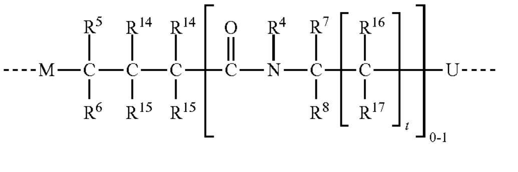

C25

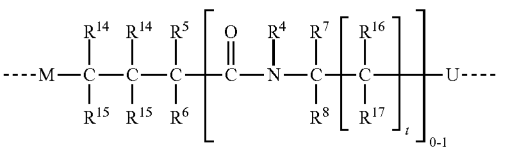

-continued

C47

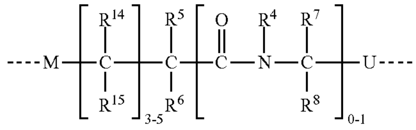

and wherein further $R^1$ is H; F; Cl; Br; $CH_3$; $OCH_3$; OH; or aryl;

$R^2$ is H; $CH_3$; heterocycloalkyl; aryl; benzyl; heteroaryl; —$OR^{20}$; —$NR^4R^{11}$; —$NR^4COOR^{21}$; —$NR^4COR^{22}$; —$NR^4CONR^4R^{11}$; or —$NR^4SO_2R^{23}$;

$R^3$ is H;

$R^4$ is H; acetyl; lower alkyl; lower alkenyl; or a suitable N-protecting group;

$R^5$, $R^7$ and $R^9$ are independently defined as H; $CF_3$; lower alkyl; lower alkenyl; lower cycloalkyl; lower heteroarylalkyl; aryl; heteroaryl; lower arylalkyl; lower heteroarylalkyl; —$OR^{20}$; —$NR^4R^{11}$; —$NR^4COR^{22}$; —$NR^4CONR^4R^{11}$; —$NR^4SO_2R^{23}$; —$COOR^{21}$; —$COOR^{21}$; —$CONR^4R^{11}$; or —$COR^{22}$;

$R^6$, $R^8$ and $R^{10}$ are defined as H;

$R^{11}$ is H; alkyl; aryl; heteroaryl; lower arylalkyl; lower heteroarylalkyl; —$(CR^{18}R^{19})_rOR^{20}$; —$(CR^{18}R^{19})_rNR^4R^{27}$; —$(CR^{18}R^{19})_qCOOR^{21}$; —$COR^{22}$; —$(CR^{18}R^{19})_qR^{24}$; or —$(CR^{18}R^{19})_qR^{31}$;

$R^{12}$ and $R^{13}$ are defined as H;

$R^{14}$ and $R^{16}$ are independently defined as H; lower alkyl; or lower arylalkyl;

$R^{15}$ and $R^{17}$ are defined as H;

$R^{18}$ and $R^{19}$ are defined as H;

$R^{20}$ is H; aryl; heteroaryl; lower arylalkyl; lower heteroarylalkyl; or —$(CR^{29}R^{30})_qR^{24}$;

$R^{21}$ is H; lower alkyl; lower arylalkyl; or a suitable O-protecting group;

$R^{22}$ is lower alykyl; lower alkenyl; aryl; heteroaryl; lower arylalkyl; lower heteroarylalkyl; —$(CR^{29}R^{30})_sOR^{31}$; —$(CR^{29}R^{30})_sNR^{28}R^{31}$; —$(CR^{29}R^{30})_sCOOR^{21}$; —$(CR^{29}R^{30})_rR^{24}$; or —$(CR^{29}R^{30})_rR^{31}$;

$R^{23}$ is H; lower alkyl; aryl; heteroaryl; or —$R^{24}$;

$R^{24}$ is aryl; heteroaryl; or —$C_6H_2R^{34}R^{35}R^{31}$;

$R^{27}$ is H; acetyl; $CH_3$; or —$(CH_2)_qR^{24}$;

$R^{28}$ is H; —$(CR^{23}R^{33})_sOR^{21}$; or —$(CR^{32}R^{33})_sNR^{43}R^{42}$;

$R^{29}$ is H; lower alkyl; aryl; or heteroaryl;

$R^{30}$, $R^{32}$ and $R^{33}$ are independently defined as H; $CF_3$; or $CH_3$;

$R^{31}$ is H; alkyl; cycloalkyl; heterocycloalkyl; aryl; heteroaryl; arylalkyl; or heteroarylalkyl;

$R^{34}$ and $R^{35}$ are independently defined as H; heterocycloalkyl; —$OR^{31}$; or —$NR^{28}R^{31}$;

$R^{36}$ is H; alkyl; alkenyl; alkynyl; cycloalkyl; heterocycloalkyl; aryl; heteroaryl; arylalkyl; heteroarylalkyl; or —$NR^{28}R^{31}$;

$R^{38}$ is H; —$NR^{28}R^{31}$; —$NR^{28}COR^{31}$; or —$NR^{28}COOR^{31}$;

$R^{42}$ and $R^{43}$ are independently defined as H; $CH_3$; or benzyl;

$R^{51}$ is H; F; Cl; $CF_3$; $OCF_3$; or lower alkyl;

$R^{52}$ is H; F; Cl; $CF_3$; $OCF_3$; $OCHF_3$; $NO_2$; CN; lower alkyl; lower alkenyl; lower alkynyl; lower cycloalkyl; lower heterocycloalkyl; aryl; heteroaryl; lower arylalkyl; or lower heteroarylalkyl;

Z is O; S; S(=O); $S(=O)_2$; or $NR^{28}$;

Y is O; S; or $NR^4$;

Q is O; S; or $NR^{28}$;

q is an integer of 0-4;

r is an integer of 2-4;

s is an integer of 1-4;

t is an integer of 0-2;

and all possible stereoisomers of such compounds; or salts, solvates, clathrates, N-oxides, isotopically enriched or enantiomerically enriched versions thereof.

2. Compounds according to claim 1 wherein

M is —N($R^4$)—;

and all possible stereoisomers of such compounds;

or pharmaceutical acceptable salts thereof.

3. Compounds according to claim 1 or 2 wherein the building block of type A is selected from the group consisting of A1(a1); A2(a1); A3(a1); A4(a1); A5(a1); A6(a1); A7(a1); A9(a1); A10(a1); and A73(a2);

and wherein

Z is O; S; S(═O); or S(═O)$_2$;

U is —C(═O)—; —NR$^4$—C(═O)—; —C(═O)—; or —C(—OR$^{20}$)$_2$—C(═O)—.

4. Compounds according to claim 1 or 2 wherein the building block of type A is selected from the group consisting of A1(a1); A2(a1); A3(a1); A4(a1); A5(a1); A6(a1); A7(a1); A9(a1); A10(a1); and A73(a2);

the building block of type B is selected from the group consisting of

B7(b3); B8(b3); and B9(b3);

and wherein

Z is O; S or S(═O)$_2$;

U is —C(═O)—; —NR$^4$—C(═O)—; or —C(═O)—C(═O)—.

5. Compounds according to claim 1 or 2 wherein the building block of type A is selected from the croup consisting of A2(a1); A5(a1); A9(a1); and A73(a2);

the building block of type B is selected from the group consisting of

B7 and B9;

and wherein

X is O; S; S(═O); or S(═O)$_2$;

Y is O; S; or NR$^4$;

Z is O; S or S(═O)$_2$;

U is —C(═O)—; —NR$^4$—C(═O)—; or —C(═O)—C(═O)—;

or pharmaceutically acceptable salts, solvates, clathrates, isotopically enriched or enantiomerically enriched versions thereof.

6. Compounds according to claim 4 wherein the building block of type C is represented by $$--[-C_{AA}-]_{1\text{-}3}-$$

and wherein $C_{AA}$ is an amino acid or its complementary enantiomer selected from the list of Ala L-Alanirte;

Arg L-Arginine;

Asn L-Asparagine;

Asp L-Aspartic acid;

Cys L-Cysteine;

Glu L-Glutamic acid;

Gln L-Glutamine;

Gly Glycine;

His L-Histidine;

Ile L-Isoleucine;

Leu L-Leucine;

Lys L-Lysine;

Met L-Methionine;

Phe L-Phenylalanine;

Pro L-Proline;

Ser L-Serine;

Thr L-Threonine;

Trp L-Tryptophan;

Tyr L-Tyrosine;

Val L-Valine;

Apa 3-Amino-propanoic acid;

H-β$^3$-HAla-OH (3S)-3-Amino-butyric acid;

H-β$^3$-HVal-OH (3R)-3-Amino-4-methyl-valeric acid;

H-β$^3$-HIle-OH (3R, 4S)-3-Amino-4-methyl-hexanoic acid;

H-β$^3$-HLeu-OH (3S)-3-Amino-5-methyl-hexanoic acid;

H-β$^3$-HMet-OH (3S)-3-Amino-5-methylthio pentanoic acid;

H-β$^3$-HTyr-OH (3S)-3-Amino-4-(4'-hydroxyphenyl)-butyric acid;

H-β$^3$-HHis-OH (3S)-3-Amino-4-(imidazole-4'-yl)-butyric acid;

H-β$^3$-HPhe-OH (3S)-3-Amino-4-phenyl butyric acid;

H-β$^3$-HTrp-OH (3S)-3-Amino-4-(indol-3'-yl)-butyric acid;

H-β$^3$-HSer-OH (3R)-3-Amino-4-hydroxy-butyric acid;

H-β$^3$-HAsp-OH 3-Amino-pentanedioic acid;

H-β$^3$-HGlu-OH (3S)-3-Amino-hexanedioic acid;

H-β$^3$-HLys-OH (3S)-3,7-Diamino-heptanoic acid;

H-β$^3$-HArg-OH (3S)-3-Amino-6-guanidino-hexanoic-acid;

H-β$^3$-HCys-OH (3R)-3-Amino-4-mercapto-butyric acid;

H-β$^3$-HAsn-OH (3S)-3-Amino-4-carbanioyl-butyric acid;

H-β$^3$-HGln-OH (3S)-3-Amino-5-carbarnoyl-pentanoic acid;

H-β$^3$-HThr-OH (3R,4R)-3-Amino-4-hydroxy-peruanoic acid;

Gaba 4-Amino-butyric acid;

H-γ$^4$-DiHAla-OH (4S)-4-Amino-pentanoic acid;

H-γ$^4$-DiHVal-OH (4R)-4-Amino-5-methyl-hexanoic acid;

H-γ$^4$-DiHIle-OH (4R, 5S)-4-Amino-5-methyl-heptanoic acid;

H-γ$^4$-DiHLeu-OH (4R)-4-Amino-6-methyl-heptanoic acid;

H-γ$^4$-DiHMet-OH (4R)-4-Amino-6-methylthio-hexanoic acid;

H-γ$^4$-DiHTyr-OH (4R)-4-Amino-5-(4'-hydroxyphenyl)-pentanoic acid;

H-γ$^4$-DiHHis-OH (4R)-4-Amino-5-(imidazole-4'-yl)-pentanoic acid;

H-γ$^4$-DiHPhe-OH (4R)-4-Amino-5-phenyl-pentanoic acid;

H-γ$^4$-DiHTrp-OH (4R)-4-Amino-5-(indol-3'-yl)-pentanoic acid;

H-γ$^4$-DiHSer-OH (4R)-4-Amino-5-hydroxy-pentanoic acid;

H-γ$^4$-DiHAsp-OH (4R)-4-Amino-hexanedioic acid;

H-γ$^4$-DiHGlu-OH 4-Amino-heptanedioic acid;

H-γ$^4$-DiHLys-OH (4S)-4,8-Diamino-octanoic acid;

H-γ$^4$-DiHArg-OH (4S)-4-Amino-7-guanidino-heptanoic-acid;

H-γ$^4$-DiHCys-OH (4R)-4-Amino-5-mercapto-pentanoic acid;

H-γ$^4$-DiHAsn-OH (4R)-4-Amino-5-carbatnoyl-pentanoic acid;

H-$\gamma^4$-DiHGln-OH (3S)-3-Amino-5-carbamoyl-hexanoic acid;

H-$\gamma^4$-DiHThr-OH (4R,5R)-4-Amino-5-hydroxy-hexanoic acid;

Cit L-Citrulline;

Orn L-Ornithine;

tBuA L-t-Butylalanine;

Sar Sarcosine;

Pen L-Penicillamine;

tBuG L-tert.-Butylglycine;

4AmPhe L-para-Aminophenylalanine;

3AmPhe L-Meta-Aminophenylalanine;

2AmPhe L-ortho-Aminophenylalanine;

Phe(mC($NH_2$)═NH) L-meta-Amidinophenylalanine;

Phe(pC($NH_2$)═NH) L-para-Amidinophenylalanine;

Phe(mNHC($NH_2$)═NH) L-meta-Guanidinophenylalanine;

Phe(pNHC($NH_2$)═NH) L-para-Guanidinophenylalanine;

2Pal (2S)-2-Amino-3-(pyridine-2'-yl)-propionic acid;

4Pal (2S)-2-Amino-3-(pyridine-4'-yl)-propionic acid;

Phg L-Phenylglycine;

Cha L-Cyclohexylalanine;

$C_4$al L-3-Cyclobutylalanine;

$C_5$al L-3-Cyclopentylalanine;

Nle L-Norleucine;

2-Nal L-2-Naphthylalanine;

1-Nal L-1-Naphthylalanine;

4ClPhe L-4-Chlorophenylalanine;

3ClPhe L-3-Chlorophenylalanine;

2ClPhe L-2-Chlorophenylalanine;

3,4$Cl_2$Phe L-3,4-Dichlorophenylalanine;

4FPhe L-4-Fluorophenylalanine;

3FPhe L-3-Fluorophenylalanine;

2FPhe L-2-Fluorophenylalanine;

Thi L-β-2-Thienylalanine;

Tza L-2-Thiazolylalanine;

Mso L-Methionine sulfoxide;

AcLys N-Acetyllysine;

Dap 2,3-Diaminopropionic acid;

Dab 2,4-Diaminobutyric acid;

Dbu (2S)-2,3-Diamino-butyric acid;

Abu γ-Aminobutyric acid (GABA);

Aha ϵ-Aminohexanoic acid;

Aib α-Aminoisobutyric acid;

ACC 1-Amino cyclopropane carboxylic acid;

ACBC 1-Amino cyclobutane carboxylic acid;

ACPC 1-Amino cyclopentane carboxylic acid;

ACHC 1-Amino cyclohexane carboxylic acid;

Y(Bzl) L-O-Benzyltyrosine;

H(Bzl) (3S)-2-Amino-3-(1'-benzylimidazole-4'-yl)-propionic acid;

Bip L-(4-phenyl)phenylalanine;

S(Bzl) L-O-Benzylserine;

T(Bzl) L-O-Berizyltbreonine;

alloT (2S,3S)-2-Amino-3-hydroxy-butyric acid;

Leu3OH (2S,3R)-2-Amino-3-hydroxy-4-methyl-pentanoic acid;

hAla L-Homo-alanine;

hArg L-Homo-arginine;

hCys L-Homo-cysteine;

hGlu L-Homo-glutamic acid;

hGln L-Homo-glutamine;

hHis L-Homo-histidine;

hIle L-Homo-isolcucine;

hLeu L-Homo-leucine;

hNle L-homo-norlencine;

hLys L-Homo-lysine;

hMet L-Homo-methionine;

hPhe L-Homo-phenylaianine;

hSer L-Homo-serine;

hThr L-Homo-threonine;

hTrp L-Homo-tryptophan;

hTyr L-Homo-tyrosine;

hVal L-Homo-valine;

hCha L-Homo-cyclohexylalanine;

Bpa L-4-Benzoylphenylalanine;

OctG L-Octylgycine;

Tic (3S)-1,2,3,4-Tetrahydroisoquinoline-3-carboxylic acid;

Tiq (1S)-1,2,3,4-Tetrahydroisoquinoline-1-carboxylic acid;

Oic (2S,3aS,7aS)-1-Octahydro-1H-indole-2-carboxylic acid;

4AmPyrr1 (2S,4S)-4-Amino-pyrrolidine-2-carboxylic acid;

4AmPyrr2 (2S,4R)-4-Amino-pyrrolidine-2-carboxylic acid;

4PhePyrr1 (2S,4R)-4-Phenyl-pyrrolidine-2-carboxylic acid;

4PhePyrr2 (2S,4S)-4-Phenyl-pyrrolidine-2-carboxylic acid;

5PhePyrr1 (2S,5R)-5-Phenyl-pyrrolidine-2-carboxylic acid;

5PhePyrr2 (2S,5S)-5-Phenyl-pyrrolidine-2-carboxylic acid;

4Hyp1 (4S)-L-Hydroxyproline;

4Hyp2 (4R)-L-Hydroxyproline;

4Mp1 (4S)-L-Mercaptoproline;

4Mp2 (4R)-L-Mercaptoproline;

Pip L-Pipecolic acid;

H-$\beta^3$-HCit-OH (3S)-3-Amino-6-carbamidyl-hexanoic acid;

H-$\beta^3$-HOrn-OH (3S)-3,6-Diamino-hexanoic acid;

H-$\beta^3$-HtBuA-OH (3S)-3-Amino-5,5-dimethyl-hexanoic acid;

H-$\beta^3$-HSar-OH N-Methyl-3-amino-propionic acid;

H-$\beta^3$-HPen-OH (3R)-3-Amino-4-methyl-4-mercapto-peritanoic acid;

H-$\beta^3$-HtBuG-OH (3R)-3-Amino-4,4-dimethyl-pentanoic acid;

H-$\beta^3$-H4AmPhe-OH (3S)-3-Amino-4-(4'-aminophenyl)-butyric acid;

H-$\beta^3$-H3AmPhe-OH (3S)-3-Amino-4-(3'-aminophenyl)-butyric acid;

H-$\beta^3$-H2AmPhe-OH (3S)-3-Amino-4-(2'-aminophenyl)-butyric acid;

H-$\beta^3$-HPhe(mC($NH_2$)═NH)—OH (3S)-3-Amino-4-(3'-amidinophenyl)-butyric acid;

H-$\beta^3$-HPhe(pC($NH_2$)═NH)—OH (3S)-3-Amino-4-(4'-amidinophenyl)-butyric acid;

H-$\beta^3$-HPhe(mNHC($NH_2$)═NH)—OH (3S)-3-Amino-4-(3'-guanidinophenyl)-butyric acid;

H-$\beta^3$-HPhe(pNHC($NH_2$)═NH)—OH (3S)-3-Amino-4-(4'-guanidino-phenyl)-butyric acid;

H-$\beta^3$-H2Pal-OH (3S)-3-Amino-4-(pyridine-2'-yl)-butyric acid;

H-$\beta^3$-H4Pal-OH (3S)-3-Amino-4-(pyridine-4'-yl)-butyric acid;

H-$\beta^3$-HPhg-OH (3R)-3-Amino-3-phenyl-propionic acid;

H-$\beta^3$-HCha-OH (3S)-3-Amino-4-cyclohexyl-butyric acid;

H-$\beta^3$-H$C_4$al-OH (3S)-3-Amino-4-cyclobutyl-butyric acid;

H-$\beta^3$-HC$_5$al-OH (3S)-3-Amino-4-cyclopentyl-butyric acid;
H-$\beta^3$-HNle-OH (3S)-3-Amino-heptanoic acid;
H-$\beta^3$-H2Nal-OH (3S)-3-Amino-4-(2'-naphthyl)-butyric acid;
H-$\beta^3$-H1Nal-OH (3S)-3-Amino-4-(1'-naphthyl)-butyric acid;
H-$\beta^3$-H4ClPhe-OH (3S)-3-Amino-4-(4'-chlorophenyl)-butpic acid;
H-$\beta^3$-H3ClPhe-OH (3S)-3-Amino-4-(3'-chlorophenyl)-butyric acid;
H-$\beta^3$-H2ClPhe-OH (3S)-3-Amino-4-(2'-chlorophenyl)-butyric acid;
H-$\beta^3$-H3,4Cl$_2$,Phe-OH (3S)-3-Amino-4-(3',4'-dichloro-phenyl)-butyric acid;
H-$\beta^3$-H4FPhe-OH (3S)-3-Amino-4-(4'-fluorophenyl)-butyric acid;
H-$\beta^3$-H3FPhe-OH (3S)-3-Amino-4-(3'-fluorophenyl)-butyric add;
H-$\beta^3$-H2FPhe-OH (3S)-3-Amino-4-(2'-fluorophenyl)-butyric acid;
H-$\beta^3$-HThi-OH (3R)-3-Amino-4-(2'-thienyl)-butyric acid;
H-$\beta^3$-HTza-OH (3R)-3-Amino-4-(2'-thiazolyl)-butyric acid;
H-$\beta^3$-HMso-OH (3R)-3-Amino-4-methylsulfoxyl-butyric acid;
H-$\beta^3$-HAcLys-OH (3S)-7-Acetylamino-3-amino-heptanoic acid;
H-$\beta^3$-HDpr-OH (3R)-3,4-diamino-butyric acid;
H-$\beta^3$-HA$_2$Bu-OH (3S)-3,5-Diamino-pentanoic acid;
H-$\beta^3$-HDbu-OH (3R)-3,4-Diamino-pentanoic acid;
H-$\beta^3$-HAib-OH Amino-dimethyl acetic acid;
H-$\beta^3$-HCyp-OH 1-Amino-cyclopentane-1-yl-acetic acid;
H-$\beta^3$-HY(Bzl)-OH (3S)-3-Amino-4-(4-benzyloxyphenyl)-butyric acid;
H-$\beta^3$-HH(Bzl)-OH (3S)-3-Amino-4-(1'-benzylimidazole-4'-yl)-butyric acid;
H-$\beta^3$-HBip-OH (3S)-3-Amino-4-biphenylyl-butyric acid;
H-$\beta^3$-HS(Bzl)-OH (3S)-3-Amino-4-(benzyloxy)-butyric acid;
H-$\beta^3$-HT(Bzl)-OH (3R,4R)-3-Amino-4-benzyloxy-pentanoic acid;
H-$\beta^3$-HalloT-OH (3R,4S)-3-Amino-4-hydxoxy-pentanoic acid;
H-$\beta^3$-HLeu3OH—OH (3R,4R)-3-Amino-4-hydroxy-5-methyl-hexaioic acid;
H-$\beta^3$-HhAla-OH (3S)-3-Amino-pentanoic acid;
H-$\beta^3$-HhArg-OH (3S)-3-Amino-7-guanidino-heptanoic acid;
H-$\beta^3$-HhCys-OH (3R)-Amino-5-mercapto-pentanoic acid;
H-$\beta^3$-HhGlu-OH (3S)-3-Amino-heptanedioic acid;
H-$\beta^3$-HhGln-OH (3S)-3-Amino-6-carbamoyl hexanoic acid;
H-$\beta^3$-HhHis-OH (3S)-3-Amino-5-(imidazole-4'-yl)-pentanoic acid;
H-$\beta^3$-HhIle-OH (3S,5S)-3-Amino-5-methyl-heptancic acid;
H-$\beta^3$-HhLeu-OH (3S)-3-Amino-6-methyl-heptanoic acid;
H-$\beta^3$-HhNle-OH (3S)-3-Amino-octanoic acid;
H-$\beta^3$-DiAoc-OH (3S)-3,8-Diamino-octanoic acid;
H-$\beta^3$-HhMet-OH (3S)-3-Amino-6-metlayithio-hexanoic acid;
H-$\beta^3$-HhPe-OH (3S)-3-Amino-5-phenyl-pentanoic acid;
H-$\beta^3$-HhSer-OH (3S)-3-Amino-5-hydroxy-pentanoic acid;
H-$\beta^3$-HhThr-OH (3S,5R)-3-Amino-5-hydroxy-hexanoic acid;
H-$\beta^3$-HhTrp-OH (3S)-3-Amino-5-(indol-3'-yl)-pentanoic acid;
H-$\beta^3$-HhThr-OH (3S)-3-Amino-5-(4'-hydroxyphenyl)-pentanoic acid;
H-$\beta^3$-HhCha-OH (3S)-3-Amino-5-cyclothexyl-pentanoic acid;
H-$\beta^3$-HBpa-OH (3S)-3-Amino-4-(4'-benzoylphenyl)-butyric acid;
H-$\beta^3$-HOctG-OH (3S)-3-Amino-undecanoic acid;
H-$\beta^3$-HNle-OH (3S)-3-Amino-heptanoic acid;
H-$\beta^3$-HTic-OH (3S)-1,2,3,4-Tetrahydroisoquinoline-3-yl-acetic acid;
H-$\beta^3$-HTiq-OH (1S)-1,2,3,4-Tetrahydroiscquinoline-1-acetic acid;
H-$\beta^3$-HOic-OH (2S,3aS,7aS)-1-Octahydro-1H-indole-2-yl-acetic acid;
H-$\beta^3$-H4AmPyrr1-OH (2S,4S)-4-Amino-pyrrolidine-2-acetic acid;
H-$\beta^3$-H4AmPyrr2-OH (2S,4R)-4-Amino-pyrrolidine-2-acetic acid;
H-$\beta^3$-H4PhePyrr1-OH (2S,4R)-4-Phenyl-pyrrolidine-2-acetic acid;
H-$\beta^3$-H4PhePyrr2-OH (2S,4S)-4-Phenyl-pyrrolidine-2-acetic acid;
H-$\beta^3$-H5PhePyrr1-OH (2S,5R)-5-Phenyl-pyrrolidine-2-acetic acid;
H-$\beta^3$-H5PhePyrr2-OH (2S,5S)-5-Phenyl-pyrrolidine-2-acetic acid;
H-$\beta^3$-H4Hyp1-OH (2S,4S)-4-Hydroxy-pyrrolidine-2-acetic acid;
H-$\beta^3$-H4Hyp2-OH (2S,4R)-4-Hydroxy-pyrrolidine-2-acetic acid;
H-$\beta^3$-H4Mp1-OH (2R,4S)-4-Mercapto-pyrrolidine-2-acetic acid;
H-$\beta^3$-H4Mp2-OH (2R,4R)-4-Mercapto-pyrrolidine-2-acetic acid;
H-$\beta^3$-HPip-OH (2S)-Piperidine-2-acetic acid;
H-$\beta^3$-HPro-OH (2S)-Pyrrolidine-2-acetic acid;
Ahb 4-Amino-2-hydroxy butyric, acid;
H-$\gamma^4$-DiHCit-OH (4S)-4-Amino-7-carbamidyl-heptanoic acid;
H-$\gamma^4$-DiHOrn-OH (4S)-4,7-Diamino-heptanoic acid;
H-$\gamma^4$-DiHtBuA-OH (4R)-4-Amino-6,6-dimethyl-heptanoic acid;
H-$\gamma^4$-DiHSar-OH N-Methyl-4-amino-butyric acid;
H-$\gamma^4$-DiHPen-OH (4R)-4-amino-5-methyl-5-mercapto-hexanoic acid;
H-$\gamma^4$-DiHtBuG-OH (4R)-4-Amino-5,5-dimethyl-heximoic acid;
H-$\gamma^4$-DiH4AmPhe-OH (4R)-4-Amino-5-(4'-aminophenyl)-pentanoic acid;
H-$\gamma^4$-DiH3AmPhe-OH (4R)-4-Amino-5-(3'-aminophenyl)-pentanoic acid;
H-$\gamma^4$-DiH2AmPhe-OH (4R)-4-Amino-5-(2'-aminophenyl)-pentanoic acid;
H-$\gamma^4$-DiHPhe(mC(NH$_2$)=NH)—OH (4R)-4-Amino-5-(3'-amidinophenyl)-pentanoic acid;
H-$\gamma^4$-DiHPhe(pC(NH$_2$)=NH)—OH (4R)-4-Amino-5-(4'-amidinophenyl)-pentanoic acid;
H-$\gamma^4$-DiHPhe(mNHC(NH$_2$)=NH)—OH (4R)-4-Amino-5-(3'-guanidino-phenyl)-pentanoic acid;
H-$\gamma^4$-DiHPhe(pNHC(NH$_2$)=NH)—OH(4R)-4-Amino-5-(4'-guanidino-phenyl)-pentanoic acid;

H-$\gamma^4$-DiH2Pal-OH (4R)-4-Amino-5-(pyridine-4'-yl)-pentanoic acid;
H-$\gamma^4$-DiH4Pal-OH (4R)-4-Amino-5-(pyridine-4'-yl)-pentanoic acid;
H-$\gamma^4$-DiHPhg-OH (4R)-4-Amino-4-phenyl-butyric acid;
H-$\gamma^4$-DiHCha-OH (4R)-4-Amino-5-cyclohexyl-pentanoic acid;
H-$\gamma^4$-DiH$C_4$al-OH (4R)-4-Amino-5-cyclobutyl-pontanoic acid;
H-$\gamma^4$-DiH$C_5$al-OH (4R)-4-Amino-5-cyclopentyl-pentanoic acid;
H-$\gamma^4$-DiHNle-OH (4S)-4-Amino-octanoic acid;
H-$\gamma^4$-DiH2Nal-OH (4S)-4-Amino-5-(2'-naphthyl)-pentanoic acid;
H-$\gamma^4$-DiH1Nal-OH (4S)-4-Amino-5-(1'-naphthyl)-pentanoic acid;
H-$\gamma^4$-DiH4ClPhe-OH (4R)-4-Amino-5-(4'-chlorophenyl)-pentanoic acid;
H-$\gamma^4$-DiH3ClPhe-OH (4R)-4-Amino-5-(3'-chlorophenyl)-pentanoic acid;
H-$\gamma^4$-DiH2ClPhe-OH (4R)-4-Amino-5-(2'-chlorophenyl)-pentanoic acid;
H-$\gamma^4$-DiH3,4$Cl_2$Phe-OH (4R)-4-Amino-5-(3',4'-dlichloro-phenyl)-pentanoic acid
H-$\gamma^4$-DiH4FPhe-OH (4R)-4-Amino-5-(4'-fluorophenyl)-pentanoic acid;
H-$\gamma^4$-DiH3FPhe-OH (4R)-4-Amino-5-(3'-fluorophenyl)-pcntanoic acid;
H-$\gamma^4$-DiH2FPhe-OH (4R)-4-Amino-5-(2'-fluorophenyl)-pentanoic acid;
H-$\gamma^4$-DiHThi-OH (4R)-4-Amino-5-(2'-thienyl)-pentanoic acid;
H-$\gamma^4$-DiHTza-OH (4R)-4-Amino-5-(2'-thiazolyl)-pentanoic acid;
H-$\gamma^4$-DiHMso-OH (4R)-4-Amino-5-methylsulfoxyl-pentanoic acid;
H-$\gamma^4$-DiHAcLys-OH (4S)-8-Acetylamino-4-amino-ocatanoic acid;
H-$\gamma^4$-DiHDpr-OH (4R)-4,5-diamino-pentanoic acid;
H-$\gamma^4$-DiH$A_2$Bu-OH (4R)-4,5-Diamino-hexanoic acid;
H-$\gamma^4$-DiHDbu-OH (4R)-4,5-Diamion-hexanoic acid;
H-$\gamma^4$-DiHAib-OH 3-Amino-3,3-dimethyl propionic acid;
H-$\gamma^4$-DiHCyp-OH (1'-Amino-cyclopentane-1'-yl)-3-propionic acid;
H-$\gamma^4$-DiHY(Bzl)-OH (4R)-4-Amino-5-(4'-benzyloxyphenyl)-pentanoic acid;
H-$\gamma^4$-DiHH(Bzl)-OH (4R)-4-Amino-5-(1'-benzylimidazole-4'-yl)-pentanoic acid;
H-$\gamma^4$-DiHBip-OH (4R)-4-Amino-5-biphenylyl-pentanoic acid;
H-$\gamma^4$-DiHS(Bzl)-OH (4S)-4-Amino-5-(benzyloxy)-pentanoic acid;
H-$\gamma^4$-DiHT(Bzl)-OH (4R,5R)-4-Amino-5-benzyloxy-hexanoic acid;
H-$\gamma^4$-DiHalloT-OH (4R,5S)-4-Amino-5-hydroxy-hexanoic acid;
H-$\gamma^4$-DiHLeu3OH—OH (4R,5R)-4-Amino-5-hydroxy-6-methyl-heptanoic acid;
H-$\gamma^4$-DiHhAla-OH (4S)-4-Amino-hexanoic acid;
H-$\gamma^4$-DiHhArg-OH (4S)-4-Amino-8-guanidino-octanoic acid;
H-$\gamma^4$-DiHhCys-OH (4R)-Amino-6-mercapto-hexanoic acid;
H-$\gamma^4$-DiHhGlu-OH (4S)-4-Amino-ocatanedioic acid;
H-$\gamma^4$-DiHhGln-OH (4S)-4-Amino-7-carbamoyl-heptanoic acid;
H-$\gamma^4$-DiHhHis-OH (4S)-4-Amino-6-(imidazole-4'-yl)-hexanoic acid;
H-$\gamma^4$-DiHhIle-OH (4S,6S)-4-Amino-6-methyl-octanoic acid;
H-$\gamma^4$-DiHhLeu-OH (4S)-4-Amino-7-methyl-ocatanoic acid;
H-$\gamma^4$-DiHhNle-OH (4S)-4-Amino-nonanoic acid;
H-$\gamma^4$-DiHhLys-OH (4S)-4,9-Diamino-nonanoic acid;
H-$\gamma^4$-DiHhMet-OH (4R)-4-Amino-7-methylthioheptanoic acid;
H-$\gamma^4$-DiHhPhe-OH (4S)-4-Amino-6-phenyl-hexanoic acid;
H-$\gamma^4$-DiHhSer-OH (4R)-4-Amino-6-hydroxy-hexanoic acid;
H-$\gamma^4$-DiHhThr-OH (4R,6R)-4-Amino-6-hydroxy-heptanoic acid:
H-$\gamma^4$-DiHhTrp-OH (4S)-4-Amino-6-(indol-3'-yl)-hexanoic acid;
H-$\gamma^4$-DiHhTyr-OH (4S)-4-Amino-6-(4'-hydroxyphenyl)-hexaoic acid;
H-$\gamma^4$-DiHhCha-OH (4R)-4-Amino-5-cyclohexyl-pentanoic acid;
H-$\gamma^4$-DihBpa-OH (4R)-4-Amino-5-(4'-benzoylphenyl)-pentanoic acid;
H-$\gamma^4$-DiHOctG-OH (4S)-4-Amino-doderanoic acid;
H-$\gamma^4$-DiHNle-OH (4S)-4-Amino-octanoic acid;
H-$\gamma^4$-DiHTic-OH (3R)-1',2',3',4'-Tetrahydroisoquinoline-3'-yl-3-propionic acid;
H-$\gamma^4$-DiHTiq-OH (1'R)-1',2',3',4'-Tetrahydroisoquinoline-1'-yl-3-propionic acid;
H-$\gamma^4$-DiHOic-OH (2'S,3'aS,7'aS)-1'-Octahydro-1H-indole-2'-yl-3-propionic acid;
H-$\gamma^4$-DiH4AmPyrr1-OH (2'R,4'S)-4'-Amino-pyrrolidine-2'-yl-3-propionic acid;
H-$\gamma^4$-DiH4AmPyrr2-OH (2'R,4'R)-4'-Amino-pyrrolidine-2'-yl-3-propionic acid;
H-$\gamma^4$-DiH4PhePyrr1-OH (2'R,4'R)-4'-Phenyl-pyrrolidine-2'-yl-3-propionic acid;
H-$\gamma^4$-DiH4PhePyrr2-OH (2'R,4'S)-4'-Phenyl-pyrrolidine-2'-yl-3-propionic acid
H-$\gamma^4$-DiH5PhePyrr1-OH (2'S,5'R)-5'-Phenyl-pyrrolidine-2'-yl-3-propionic acid;
H-$\gamma^4$-DiH5PhePyrr2-OH (2'S,5'S)-5'-Phenyl-pyrrolidine-2'-yl-3-propionic acid
H-$\gamma^4$-DiH4Hyp1-OH (2'R,4'S)-4'-Hydroxy-pyrrolidine-2'-yl-2-propionic acid;
H-$\gamma^4$-DiH4Hyp2-OH (2'R,4'R)-4'-Hydroxy-pyrrolidine-2'-yl-3-propionic acid;
H-$\gamma^4$-DiH4Mp1-OH (2'R,4'S)-4'-Mercapto-pyrrolidine-2'-yl-3-propionic acid;
H-$\gamma^4$-DiH4Mp2-OH (2'R,4'R)-4'-Mercapto-pyrrolidine-2'-yl-3-propionic acid;
H-$\gamma^4$-DiHPip-OH (2'S)-Piperidine-2'-yl-3-propionic acid;
H-$\gamma^4$-DiHPro-OH (2'S)-Pyrrolidine-2'-yl-3-propionic acid;
(AEt)G N-(2-Aminoethyl)glycine;
(APr)G N-(3-Amino-n-propyl)glycine;
(ABu)G N-(4-Amino-n-butyl)glycine;
(APe)G N-(5-Amino-n-pentyl)glycine;
(GuEt)G N-(2-Guanidinoethyl)glycine;
(GuPr)G N-(3-Guanidino-n-propyl)glycine;
(GuBu)G N-(4-Guanidino-n-butyl)glycine;
(GuPe)G N-(5-Guanidino-n-pentyl)glycine;
($PEG_3$-$NH_2$) N—[$H_2N$—$(CH_2)_3$—$(OCH_2$—$CH_2)_2$—O $(CH_2)_3$]glycine;
(Me)G N-Methylglycine;
(Et)G N-Ethylglycine;

(Bu)G N-Butylglycine;
(Pe)G N-Pentylglycine;
(Ip)G N-Isopropylglycine;
(2MePr)G N-(2-Methylpropyl)glycine;
(3MeBu)G N-(3-Methylbutyl)glyecine;
(1MePr)G (1S)-N-(1-Methylpropyl)glycine;
(2MeBu)G (2S)-N-(2-Methylbutyl)glycine;
(MthEt)G N-(Methylthioethyl)glycine;
(MthPr)G N-(Methylthiopropyl)glycine;
(Ben)G N(Benzyl)glycine;
(PhEt)G N-(2-Phenylethyl)glycine;
(HphMe)G N-([4-hydroxyphenyl]methyl)glycine;
(HphEt)G N-(2-[4'-hydroxyphenyl]ethyl)glycine
(ImMe)G N-(Imidazol-5-yl-methyl)glycine;
(ImEt)G N-(2-(Imidazol-5'-yl)ethyl)glycine;
(InMe)G N-(Indol-2-yl-methyl)glycine;
(InEt)G N-(2-(Indol-2'-yl)ethyl)glycine;
(CboMe)G N-(Carboxymethyl)glycine;
(CboEt)G N-(2-Carboxyethyl)glycine;
(CboPr)G N-(3-Carboxypropyl)glycine;
(CbaMe)G N-(Carbamoylmethyl)glycine;
(CbaEt)G N-(2-Carbamoylethyl)glycine;
(CbaPr)G N-(3-Carbarmoylpropyl)glycine;
(HyEt)G N-(2-Hydroxyethyl)glycine
(HyPr)G (2R)-N-(2-Hydroxypropyl)glycine;or
(Mcet)G N-(2-Mercaptoethyl)glycine.

7. Compounds according to claim 2, selected from:

(2S,11S,19aS)-2-(acetylamino)-15-fluoro-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)-N-[2-(dimethylamino)ethyl]-15-fluoro-2-{[2-(1H-indol-3-yl)acetyl]amino}-7,12-dimethyl-5,8,13-trioxo-2,3,6,7,8,9,10,11,12,13,19,19a-dodecahydro-1H,5H-pyrrolo[2,1-c]-[1,4,7,12] benzoxatriazacyclopentadecine-11-carboxamide; (2S,11S,19aS)-15-fluoro-2-{[2-(1H-indol-3-yl)acetyl] amino}-N-[2-(1H-indol-3-yl)ethyl]-7,12-dimethyl-5,8,13-trioxo-2,3,6,7,8, 9,10,11,12,13,19,19a-dodecahydro-1H,5H-pyrrolo[2,1-c][1,4,7,12]-benzoxatriazacyclopentadecine-11-carboxamide; (2S,11S,19aS)-2-{[2-(dimethylamino)acetyl]amino}-15-fluoro-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c]-[1,4,7,12] benzoxatriazacyclopentadecine-11-carboxamide;

tert-butyl N-[(2S,11S,19aS)-15-fluoro-11-({[2-(1H-indol-3-yl)ethyl]amino}carbonyl)-7,12-dimethyl-5,8,13-trioxo-2,3,6,7,8,9,10,11,12,13,19,19a-dodecahydro-1H,5H-pyrrolo[2,1-c]-[1,4,7,12] benzoxatriazacyclopentadecin-2-yl]carbamate; (2S,11S,19aS)-N-[2-(dimethylamino)ethyl]-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c]-[1,4,7,12] benzoxatriazacyclopentadecine-11-carboxamide;

benzyl N-[(4S,6S,10S)-14-methyl-6-{[2-(2-naphthyl) acetyl]amino}-9,15-dioxo-2-oxa-8,14-diazatricyclo [14.3.1.$0^{4,8}$]icosa-1(20),16,18-trien-10-yl]carbamate;

benzyl N-[(4S,6S,13S)-6-{[2-(1H-indol-3-yl)acetyl] amino}-11,15-dimethyl-9,12,16-trioxo-2-oxa-8,11,15-triazatricyclo[15.3.1.$0^{4,8}$]henicosa-1(21),17,19-trien-13-yl]carbamate;

N-[(4S,6S,13S)-6-{[2-(1H-indol-3-yl)acetyl]amino}-11,15-dimethyl-9,12,16-trioxo-2-oxa-8,11,15-triazatricyclo[15.3.1.$0^{4,8}$]henicosa-1(21),17,19-trien-13-yl]decanamide.

8. A pharmaceutical composition containing a compound or a mixture of compounds according to any claim 1 and at least one therapeutically inert excipient.

9. A composition according to claim 8 suitable for oral, topical, transdermal, injection, buccal, transmucosal, pulmonary or inhalation administration, particularly in form of tablets, dragees, capsules, solutions, liquids, gels, plaster, creams, ointments, syrup, slurries, suspensions, spray, nebulizer or suppositories.

10. The use of compounds according to claim 1, having agonistic or antagonistic activity on the motilin receptor (MR receptor), on the serotonin receptor of subtype 5-$HT_{2B}$ (5-$HT_{2B}$ receptor), on the prostaglandin F2α receptor (FP receptor), on the purinoreceptor $P2Y_1$, on the voltage-gated potassium channel $K_v$1.3; or on the canonical (β-catenin-dependent) Wnt pathway.

11. Compounds selected from:

(2S,11S,19aS)-N-[2-(dimethylamino)ethyl]-15-fluoro-7,12-dimethyl-2-{[(1-naphthylamino)carbonyl]amino}-5,8,13-trioxo-2,3,6,7,8,9,10,11,12,13,19,19a-dodecahydro-1H,5H-pyrrolo[2,1-c][1,4,7,12] benzoxatriazacyclopentadecine-11-carboxamide;

(2S,11S,19aS)-N-(2-aminoethyl)-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c][1,4,7,12] benzoxatriazacyclopentadecine-11-carboxamide;

(2S,11S,19aS)-N-(2-{[amino(imino)methyl] amino}ethyl)-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)-15-fluoro-7,12-dimethyl-2-{[2-(1-naphthyl)acetyl]amino}-5,8,13-trioxo-N-[2-(2-pyridinylamino)ethyl]-2,3,6,7,8,9,10,11,12,13,19,19a-dodecahydro-1H,5H-pyrrolo[2,1-c][1,4,7,12] benzoxatriazacyclopentadecine-11-carboxamide;

(2S,11S,19aS)-N-[2-(dimethylamino)ethyl]-15-fluoro-7,12-dimethyl-2-{[2-(1-naphthyl)ethyl]amino}-5,8,13-trioxo-2,3,6,7,8,9,10,11,12,13,19,19a-dodecahydro-1H,5H-pyrrolo[2,1-c][1,4,7,12] benzoxatriazacyclopentadecine-11-carboxamide;

(2S,11S,19aS)-N-[2-(acetylamino)ethyl]-15-fluoro-7,12-dimethyl-2-[2-(1-naphthyl)acetyl]amino-5,8,13-trioxo-2,3,6,7,8,9,10,11,12,13,19,19a-dodecahydro-1H,5H-pyrrolo[2,1-c][1,4,7,12] benzoxatriazacyclopentadecine-11-carboxamide;

(2S,11S,19aS)-N-[2-(dimethylamino)ethyl]-15-fluoro-7,12-dimethyl-2-{[2-(2-naphthyl)acetyl]amino}-5,8,13-trioxo-2,3,6,7,8,9,10,11,12,13,19,19a-dodecahydro-1H,5H-pyrrolo[2,1-c][1,4,7,12] benzoxatriazacyclopentadecine-11-carboxamide;

(2S,11S,19aS)-N-[2-(dimethylamino)ethyl]-15-fluoro-7,12-dimethyl-5,8,13-trioxo-2-(2-[3-(trifluoromethyl) phenyl]acetylamino)-2,3,6,7,8,9,10,11,12,13,19,19a-dodecahydro-1H,5H-pyrrolo[2,1-c][1,4,7,12] benzoxatriazacyclopentadecine-11-carboxamide;

(2S,11S,19aS)-N-[2-(dimethylamino)ethyl]-15-fluoro-2-[2-(3-methoxyphenyl)acetyl]amino-7,12-dimethyl-5,8,13-trioxo-2,3,6,7,8,9,10,11,12,13,19,19a-dodecahydro-1H,5H-pyrrolo[2,1-c][1,4,7,12] benzoxatriazacyclopentadecine-11-carboxamide;

(2S,1S,19aS)-N-[3-(dimethylamino)propyl]-15-fluoro-7,12-dimethyl-2-[2-(1-naphthyl)acetyl]amino-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)-15-fluoro-7,12-dimethyl-2-[2-(1-naphthyl)acetyl]amino-5,8,13-trioxo-N-(3-pyridinylmethyl)-2,3,6,7,8,9,10,11,12,13,19,19a-dodecahydro-1H,5H-pyrrolo[2,1-c][1,4,7,12]-benzoxatriazacyclopentadecine-11-carboxamide;

N-[(4S,6S,10S)-14-methyl-6-[2-(2-naphthyl)acetyl]amino-9,15-dioxo-2-oxa-8,14-diazatricyclo[14.3.1.$0^{4,8}$]icosa-1(20),16,18-trien-10-yl]decanamide;

N-[(4S,6S,10)-14-methyl-10-{[2-(2-naphthyl)acetyl]amino}-9,15-dioxo-2-oxa-8,14-diazatricyclo[14.3.1.$0^{4,8}$]icosa-1(20),16,18-trien-6-yl]-2-(2-naphthyl)acetamide;

N-[(4S,6S,10S)-14-methyl-6-[2-(2-naphthyl)acetyl]amino-9,15-dioxo-2-oxa-8,14-diazatricyclo[14.3.1.$0^{4,8}$]icosa-1(20),16,18-trien-10-yl]-2-(1-naphthyl)acetamide;

N-[(4S,6S,10S)-14-methyl-9,15-dioxo-10-[(3-toluidinocarbonyl)amino]-2-oxa-8,14-diazatricyclo[14.3.1.$0^{4,8}$]icosa-1(20),16,18-trien-6-yl]-2-(2-naphthyl)acetamide;

N-[(4S,6S,10S)-10-([3-(dimethylamino)anilino]carbonylamino)-14-methyl-9,15-dioxo-2-oxa-8,14-diazatricyclo[14.3.1.$0^{4,8}$]icosa-1(20),16,18-trien-6-yl]-2-(2-naphthyl)acetamide;

N-[(4S,6S,10S)-6-({[3-(dimethylamino)anilino]carbonyl}amino)-14-methyl-9,15-dioxo-2-oxa-8,14-diazatricyclo[14.3.1.$0^{4,8}$]icosa-1(20),16,18-trien-10-yl]-2-(2-naphthyl)acetamide;

N-[(4S,6S,10S)-14-methyl-9,15-dioxo-6-[(3-phenylpropanoyl)amino]-2-oxa-8,14-diazatricyclo[14.3.1.$0^{4,8}$]icosa-1(20),16,18-trien-10-yl]decanamide;

N-[(4S,6S,10S)-14-methyl-6-[(3-morpholinobenzoyl)amino]-9,15-dioxo-2-oxa-8,14-diazatricyclo[14.3.1.$0^{4,8}$]icosa-1(20),16,18-trien-10-yl]decanamide;

N-[(4S,6S,10S)-6-({[3-(dimethylamino)anilino]carbonyl}amino)-14-methyl-9,15-dioxo-2-oxa-8,14-diazatricyclo[14.3.1.$0^{4,8}$]icosa-1(20),16,18-trien-10-yl]decanamide;

N-[(4S,6S,10S)-6-({[3-(dimethylamino)anilino]carbonyl}amino)-14-methyl-9,15-dioxo-2-oxa-8,14-diazatricyclo[14.3.1.$0^{4,8}$]icosa-1(20),16,18-trien-10-yl]-2-(1-naphthyl)acetamide;

N-[(4S,6S,10S)-6-{[(3-methoxyanilino)carbonyl]amino}-14-methyl-9,15-dioxo-2-oxa-8,14-diazatricyclo[14.3.1.$0^{4,8}$]icosa-1(20),16,18-trien-10-yl]-2-(2-naphthyl)acetamide;

N-[(4S,6S,10S)-14-methyl-9,15-dioxo-6-{[2-(3-phenoxyphenyl)acetyl]amino}-2-oxa-8,14-diazatricyclo[14.3.1.$0^{4,8}$]icosa-1(20),16,18-trien-10-yl]decanamide;

N-[(4S,6S,10S)-14-methyl-6-{[2-(2-naphthyl)acetyl]amino}-9,15-dioxo-2-oxa-8,14-diazatricyclo[14.3.1.$0^{4,8}$]icosa-1(20),16,18-trien-10-yl]-6-phenylhexanamide;

N-[(4S,6S,10S)-14-methyl-6-{[2-(2-naphthyl)acetyl]amino}-9,15-dioxo-2-oxa-8,14-diazatricyclo[14.3.1.$0^{4,8}$]icosa-1(20),16,18-trien-10-yl]-5-phenoxypentanamide;

(E)-N-[(4S,6S,10S)-14-methyl-6-[2-(2-naphthyl)acetyl]amino-9,15-dioxo-2-oxa-8,14-diazatricyclo[14.3.1.$0^{4,8}$]icosa-1(20),16,18-trien-10-yl]-3-decanamide;

N-[(4S,6S,10S)-14-methyl-6-{[2-(1-naphthyl)acetyl]amino}-9,15-dioxo-2-oxa-8,14-diazatricyclo[14.3.1.$0^{4,8}$]icosa-1(20),16,18-trien-10-yl]decanamide;

6-(benzyloxy)-N-[(4S,6S6S,10S)-14-methyl-6-[2-(2-naphthyl)acetyl]amino-9,15-dioxo-2-oxa-8,14-diazatricyclo[14.3.1.$0^{4,8}$]icosa-1(20),16,18-trien-10-yl]hexanamide;

2-[1,1'-biphenyl]-4-yl-N-[(4S,6S,10S)-14-methyl-6-{[2-(2-naphthyl)acetyl]amino}-9,15-dioxo-2-oxa-8,14-diazatricyclo[14.3.1.$0^{4,8}$]icosa-1(20),16,18-trien-10-yl]acetamide;

N-[(4S,6S,10S)-14-methyl-6-{[2-(2-naphthyl)acetyl]amino}-9,15-dioxo-2-oxa-8,14-diazatricyclo[14.3.1.$0^{4,8}$]icosa-1(20),16,18-trien-10-yl]-3,3-diphenylpropanamide;

6-(benzyloxy)-N-[(4S,6S,10S)-14-methyl-9,15-dioxo-10-[(6-phenylhexanoyl)amino]-2-oxa-8,14-diazatricyclo[14.3.1.$0^{4,8}$]icosa-1(20),16,18-trien-6-yl]hexanamide;

2-[1,1'-biphenyl]-3-yl-N-[(4S,6S,10S)-6-([3-(dimethylamino)anilino]carbonylamino)-14-methyl-9,15-dioxo-2-oxa-8,14-diazatricyclo[14.3.1.$0^{4,8}$]icosa-1(20),16,18-trien-10-yl]acetamide;

2-[1,1'-biphenyl]-4-yl-N-[(4S,6S,10S)-6-([3-(dimethylamino)anilino]carbonylamino)-14-methyl-9,15-dioxo-2-oxa-8,14-diazatricyclo[14.3.1.$0^{4,8}$]icosa-1(20),16,18-trien-10-yl]acetamide;

N-[(4S,6S,10S)-10-[([1,1'-biphenyl]-4-ylsulfonyl)amino]-14-methyl-9,15-dioxo-2-oxa-8,14-diazatricyclo[14.3.1.$0^{4,8}$]icosa-1(20),16,18-trien-6-yl]-2-(2-naphthyl)acetamide;

N-[(4S,6S,10S)-6-{[(3-fluoroanilino)carbonyl]amino}-14-methyl-9,15-dioxo-2-oxa-8,14-diazatricyclo[14.3.1.$0^{4,8}$]icosa-1(20),16,18-trien-10-yl]-2-(2-naphthyl)acetamide;

N-[(4S,6S,10S)-6-({[4-(dimethylamino)anilino]carbonyl}amino)-14-methyl-9,15-dioxo-2-oxa-8,14-diazatricyclo[14.3.1.$0^{4,8}$]icosa-1(20),16,18-trien-10-yl]-2-(2-naphthyl)acetamide;

phenyl N-[(4S,6S,10S)-14-methyl-10-{[2-(2-naphthyl)acetyl]amino}-9,15-dioxo-2-oxa-8,14-diazatricyclo[14.3.1.$0^{4,8}$]icosa-1(20),16,18-trien-6-yl]carbamate;

N-[(4S,6S,10S)-14-methyl-9,15-dioxo-6-[2-(7-quinolinyl)acetyl]amino-2-oxa-8,14-diazatricyclo[14.3.1.$0^{4,8}$]icosa-1(20),16,18-trien-10-yl]-2-(2-naphthyl)acetamide;

N-[(4S,6S,105)-14-methyl-9,15-dioxo-6-{[2-(3-phenoxyphenyl)acetyl]amino}-2-oxa-8,14-diazatricyclo[14.3.1.$0^{4,8}$]icosa-1(20),16,18-trien-10-yl]-2-(2-naphthyl)acetamide;

N-[(4S,6S,10S)-14-methyl-10-{[2-(2-naphthyl)acetyl]amino}-9,15-dioxo-2-oxa-8,14-diazatricyclo[14.3.1.$0^{4,8}$]icosa-1(20),16,18-trien-6-yl]decanamide;

N-[(4S,6S,10S)-14-methyl-10-{[2-(1-naphthyl)acetyl]amino}-9,15-dioxo-2-oxa-8,14-diazatricyclo[14.3.1.$0^{4,8}$]icosa-1(20),16,18-trien-6-yl]decanamide;

N-[(4S,6S,10S)-14-methyl-10-{[2-(1-naphthyl)acetyl]amino}-9,15-dioxo-2-oxa-8,14-diazatricyclo[14.3.1.$0^{4,8}$]icosa-1(20),16,18-trien-6-yl]hexanamide;

2-[1,1'-biphenyl]-4-yl-N-[(4S,6S,10S)-14-methyl-10-{[2-(1-naphthyl)acetyl]amino}-9,15-dioxo-2-oxa-8,14-diazatricyclo[14.3.1.$0^{4,8}$]icosa-1(20),16,18-trien-6-yl]acetamide;

N-[(4S,6S,10S)-10-[(2-[1,1'-biphenyl]-4-ylacetyl)amino]-14-methyl-9,15-dioxo-2-oxa-8,14-diazatricyclo[14.3.1.$0^{4,8}$]icosa-1(20),16,18-trien-6-yl]-2,2-diphenylacetamide;

N-[(4S,6S,10S)-6-[(2-[1,1'-biphenyl]-4-ylacetyl)amino]-14-methyl-9,15-dioxo-2-oxa-8,14-diazatricyclo[$14.3.1.0^{4,8}$]icosa-1(20),16,18-trien-10-yl]-2,2-diphenylacetamide;

N-[(4S,6S,10S)-6-[(2,2-diphenylacetyl)amino]-14-methyl-9,15-dioxo-2-oxa-8,14-diazatricyclo[$14.3.1.0^{4,8}$]icosa-1(20),16,18-trien-10-yl]decanamide;

N-[(4S,6S,10S)-14-methyl-10-{[2-(1-naphthyl)acetyl]amino}-9,15-dioxo-2-oxa-8,14-diazatricyclo[$14.3.1.0^{4,8}$]icosa-1(20),16,18-trien-6-yl]-2,2-diphenylacetamide;

N-[(4S,6S,100S)-6-[(3,3-diphenylpropanoyl)amino]-14-methyl-9,15-dioxo-2-oxa-8,14-diazatricyclo[$14.3.1.0^{4,8}$]icosa-1(20),16,18-trien-10-yl]decanamide;

2-[1,1'-biphenyl]-4-yl-N-[(4S,6S,10S)-10-[(2-[1,1'-biphenyl]-4-ylacetyl)amino]-14-methyl-9,15-dioxo-2-oxa-8,14-diazatricyclo[$14.3.1.0^{4,8}$]icosa-1(20),16,18-trien-6-yl]acetamide;

N-[(4S,6S,10S)-6-({[3-(dimethylamino)anilino]carbonyl}amino)-14-methyl-9,15-dioxo-2-oxa-8,14-diazatricyclo[$14.3.1.0^{4,8}$]icosa-1(20),16,18-trien-10-yl]-3,3-dimethylbutanamide;

N-[(4S,6S,10S)-6-({[3-(dimethylamino)anilino]carbonyl}amino)-9,15-dioxo-2-oxa-8,14-diazatricyclo[$14.3.1.0^{4,8}$]icosa-1(20),16,18-trien-10-yl]-2-(2-naphthyl)acetamide;

benzyl N-[(4S,6S,10S)-6-{[2-(2-naphthyl)acetyl]amino}-9,15-dioxo-2-oxa-8,14-diazatricyclo[$14.3.1.0^{4,8}$]icosa-1(20),16,18-trien-10-yl]carbamate;

N-[(4S,6S,10S)-6-{[2-(2-naphthyl)acetyl]amino}-9,15-dioxo-2-oxa-8,14-diazatricyclo[$14.3.1.0^{4,8}$]icosa-1(20),16,18-trien-10-yl]decanamide;

(4S,6R,15S)-11,16-dimethyl-N-(2-naphthylmethyl)-9,12,17-trioxo-6-{[3-(4-pyridinyl)propanoyl]amino}-2-thia-8,11,16-triazatricyclo[$16.3.1.0^{4,8}$]docosa-1(22),18,20-triene-15-carboxamide;

tert-butyl N-[(4S,6R,15S)-11,16-dimethyl-15-{[(2-naphthylmethyl)amino]carbonyl}-9,12,17-trioxo-2-thia-8,11,16-triazatricyclo[$16.3.1.0^{4,8}$]docosa-1(22),18,20-trien-6-yl]carbamate;

(4S,6R,15S)-11,16-dimethyl-N-(2-naphthylmethyl)-9,12,17-trioxo-6-(pentanoylamino)-2-thia-8,11,16-triazatricyclo[$16.3.1.0^{4,8}$]docosa-1(22),18,20-triene-15-carboxamide;

(4S,6R,15S)-6-(acetylamino)-11,16-dimethyl-N-(2-naphthylmethyl)-9,12,17-trioxo-2-thia-8,11,16-triazatricyclo[$16.3.1.0^{4,8}$]docosa-1(22),18,20-triene-15-carboxamide;

(2S,11S,19aS)-15-fluoro-7,12-dimethyl-2-(1-naphthoylamino)-N-(2-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)-15-fluoro-7,12-dimethyl-2-[2-(2-naphthyl)acetyl]amino-N-(1-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)-2-[(3-chlorobenzoyl)amino]-15-fluoro-7,12-dimethyl-N-(1-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)-N-[2-(dimethylamino)ethyl]15-fluoro-2-{[2-(1H-indol-3-yl)acetyl]amino}7,12-dimethyl-5,8,13-trioxo-2,3,6,7,8,9,10,11,12,13,19,19a-dodecahydro- 1H,5H-pyrrolo[2,1-c][1,4,7,12]benzoxatriazacyclopentadecine-11-carboxamide;

(2S,11S,19aS)-15-fluoro-2{[2-(1H-indol-3-yl)acetyl]amino}-N-[2-(1H-indol-3-yl)ethyl]-7,12-dimethhyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)-N-[2-(dimethylamino)ethyl]-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)-N-[3-(dimethylamino)propyl]-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

benzyl N-(4S,6S,10S)-14-methyl-6-{[2-(2-naphthyl)acetyl]amino}-9,15-dioxo-2-oxa-8,14-diazatricyclo[$14.3.1.0^{4,8}$icosa-1(20),16,18-trien-10-yl]carbamate;

benzyl N-(4S,6S,13S)-6-{[2-(1H-indol-3-yl)acetyl]amino}-11,15-dimethyl-9,12,16-trioxo-2-oxa-8,11,15-triazatricyclo[$15.3.1.0^{4,8}$henicosa-1(21),17,19-trien-13-yl]carbamate;

N-[(4S,6S,13S)-6-{[2-(1H-indol-3yl)acetyl]amino}-11,15dimethyl-9,12,16-trioxo-2-oxa-8,11,15-triazatricyclo[$15.3.1.0^{4,8}$]henicosa-1(21),17,19-trien-13-yl]decanamide;

N-[(4S,6S,10S)-6-{[2-(2-naphthyl)acetyl]amino}-9,15-dioxo-2-oxa-8,14-diazatricyclo[$14.3.1.0^{4,8}$]icosa-1(20),16,18-trien-10-yl]-decanamide;

(2S,11S,19aS)-2-(acetylamino)-15-flouro-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

(2S,11S,19aS)-2-{[2-(dimethylamino)acetyl]amino}-15-flouro-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide;

tert-butyl N-[(2S,11S,19aS)-15-flouro-11-({[2-(1H-indol-3-yl)ethyl]amino}carbonyl)-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl]carbamate;

benzyl N-(4S,6S,10S)-13-methyl-9,14-dioxo-6-(pentanoylamino)-2-oxa-8,13-diazatricyclo[$13.3.1.0^{4,8}$nonadeca-1(19),15,17-trien-10-yl]carbamate;

benzyl N-(4S,6S,10S)-13-methyl-6-{[2-(2-naphthyl)acetyl]amino}-9,14-dioxo-2-oxa-8,13-diazatricyclo[$13.3.1.0^{4,8}$nonadeca-1(19),15,17-trien-10-yl]carbamate;

N-(4S,6S,10S)-13-methyl-9,14-dioxo-10-{[3-(4-pyridinyl)propanoyl]amino}-2-oxa-8,13-diazatricyclo[$13.3.1.0^{4,8}$nonadeca-1(19),15,17-trien-6-yl]pentanamide;

N-(4S,6S,10S)-13-methyl-9,14-dioxo-6-(pentanoylamino)-2-oxa-8,13-diazatricyclo[$13.3.1.0^{4,8}$nonadeca-1(19),15,17-trien-10-yl]-2-naphthamide;

N-(4S,6S,10S)-13-methyl-6-{[2-(2-naphthyl)acetyl]amino}-9,14-dioxo-2-oxa-8,13-diazatricyclo[$13.3.1.0^{4,8}$nonadeca-1(19),15,17-trien-10-yl]-2-(1-naphthyl)acetamide.

* * * * *